United States Patent
Kaila et al.

(10) Patent No.: US 12,252,488 B2
(45) Date of Patent: Mar. 18, 2025

(54) HPK1 ANTAGONISTS AND USES THEREOF

(71) Applicant: Nimbus Saturn, Inc., Cambridge, MA (US)

(72) Inventors: Neelu Kaila, Lexington, MA (US); Ian Linney, Saffron Walden (GB); Stuart Ward, Saffron Walden (GB); Grant Wishart, Saffron Walden (GB); Benjamin Whittaker, Saffron Walden (GB); William Sinko, Roslindale, MA (US); Shawn Watts, Portland, OR (US); Mark Anthony Ashwell, Carlisle, MA (US); Byron Scott Delabarre, Arlington, MA (US)

(73) Assignee: Nimbus Saturn, Inc., Boston, MA (US)

( * ) Notice: Subject to any disclaimer, the term of this patent is extended or adjusted under 35 U.S.C. 154(b) by 0 days.

(21) Appl. No.: 17/650,732

(22) Filed: Feb. 11, 2022

(65) Prior Publication Data

US 2023/0096641 A1    Mar. 30, 2023

Related U.S. Application Data

(60) Provisional application No. 63/148,857, filed on Feb. 12, 2021.

(51) Int. Cl.
| | | |
|---|---|---|
| *C07D 471/04* | (2006.01) | |
| *C07D 401/14* | (2006.01) | |
| *C07D 453/06* | (2006.01) | |
| *C07D 519/00* | (2006.01) | |

(52) U.S. Cl.
CPC ......... *C07D 471/04* (2013.01); *C07D 401/14* (2013.01); *C07D 453/06* (2013.01); *C07D 519/00* (2013.01)

(58) Field of Classification Search
CPC .. C07D 471/04; C07D 401/14; C07D 453/06; C07D 519/00
See application file for complete search history.

(56) References Cited

U.S. PATENT DOCUMENTS

| | | | |
|---|---|---|---|
| 2,475,569 A | 7/1949 | Halley | |
| 4,650,750 A | 3/1987 | Giese | |
| 4,709,016 A | 11/1987 | Giese | |
| 5,360,819 A | 11/1994 | Giese | |
| 5,516,931 A | 5/1996 | Giese et al. | |
| 5,602,273 A | 2/1997 | Giese et al. | |
| 5,604,104 A | 2/1997 | Giese et al. | |
| 5,610,020 A | 3/1997 | Giese et al. | |
| 5,650,270 A | 7/1997 | Giese et al. | |
| 7,081,449 B2 | 7/2006 | Pietrzkowski et al. | |
| 7,390,799 B2 | 6/2008 | Bruncko et al. | |
| 8,138,347 B2 | 3/2012 | Knight et al. | |
| 8,546,370 B2* | 10/2013 | Okram ................ | A61P 31/18 514/183 |
| 8,796,313 B2 | 8/2014 | Dudash et al. | |
| 8,906,682 B2 | 12/2014 | June et al. | |
| 8,969,565 B2* | 3/2015 | Bi ........................ | A61P 21/00 546/121 |
| 11,021,481 B2 | 6/2021 | Kaila et al. | |
| 11,028,085 B2 | 6/2021 | Kaila et al. | |
| 11,034,694 B2 | 6/2021 | Kaila et al. | |
| 11,078,201 B2* | 8/2021 | Kaila ................ | C07D 401/14 |
| 11,548,890 B1* | 1/2023 | Kaila ................ | C07D 519/00 |
| 2006/0287370 A1 | 12/2006 | Curtin et al. | |
| 2010/0179153 A1* | 7/2010 | Mattes ................ | A61P 5/24 546/141 |
| 2011/0245247 A1 | 10/2011 | Braje et al. | |
| 2014/0171429 A1* | 6/2014 | Vasudevan ........ | C07D 401/12 546/122 |
| 2017/0226129 A1 | 8/2017 | Yu et al. | |
| 2018/0127396 A1 | 5/2018 | Li et al. | |
| 2018/0141951 A1 | 5/2018 | Arikawa et al. | |
| 2018/0179221 A1 | 6/2018 | Sampson et al. | |
| 2018/0282328 A1 | 10/2018 | Chan et al. | |
| 2019/0256520 A1 | 8/2019 | Sokolsky et al. | |
| 2020/0038378 A1 | 2/2020 | Crew et al. | |
| 2021/0078996 A1 | 3/2021 | Kaila et al. | |
| 2021/0078997 A1 | 3/2021 | Kaila et al. | |
| 2021/0078998 A1* | 3/2021 | Kaila ................ | C07D 495/04 |
| 2021/0087189 A1* | 3/2021 | Kaila ................ | C07D 495/04 |
| 2021/0087190 A1* | 3/2021 | Kaila ................ | C07D 471/04 |

FOREIGN PATENT DOCUMENTS

| | | |
|---|---|---|
| CA | 2988721 A1 | 6/2018 |
| CN | 111961035 | * 11/2020 |
| EP | 1477472 B1 | 1/2009 |
| EP | 2108642 A1 | 10/2009 |
| WO | WO-2001042246 A2 | 6/2001 |
| WO | WO-2002088112 A1 | 11/2002 |
| WO | WO-2003063794 A2 | 8/2003 |

(Continued)

OTHER PUBLICATIONS

Stupnikova; Khimiya Geterotsiklicheskikh Soedinenii 1983, 115-118 (English Translation, pp. 103-106). (Year: 1983).*
Bozdag; Bioorganic & Medicinal Chemistry 2017, 25, 677-683. (Year: 2017).*
Mishra; J. Med. Chem. 2021, 64, 1545-1557. https://doi.org/10.1021/acs.jmedchem.0c01700 (Year: 2021).*
Hensbergen; Tetrahedron Letters 2015, 56, 6478-6483, with supplemental information, 24 pages. http://dx.doi.org/10.1016/j.tetlet 2015.10.008 (Year: 2015).*
Jin; Bioorg. Med. Chem. Lett. 2006, 16, 5864-5869. https://doi.org/10.1016/j.bmcl.2006.08.058 (Year: 2006).*

(Continued)

*Primary Examiner* — Daniel R Carcanague
(74) *Attorney, Agent, or Firm* — Dechert LLP; Andrea L. C. Reid; Todd Macklin

(57) ABSTRACT

The present invention provides compounds, compositions thereof, and methods of using the same for the inhibition of HPK1, and the treatment of HPK1-mediated disorders.

22 Claims, No Drawings

(56) References Cited

FOREIGN PATENT DOCUMENTS

| | | | |
|---|---|---|---|
| WO | WO-2004019973 A1 | 3/2004 | |
| WO | WO-2004089925 A1 | 10/2004 | |
| WO | WO-2004106328 A1 | 12/2004 | |
| WO | WO-2005007623 A2 | 1/2005 | |
| WO | WO-2005113554 A2 | 12/2005 | |
| WO | WO-2006029879 A2 | 3/2006 | |
| WO | WO-2006078846 A1 | 7/2006 | |
| WO | WO-2006105021 A2 | 10/2006 | |
| WO | WO-2006122806 A2 | 11/2006 | |
| WO | WO-2007005874 A2 | 1/2007 | |
| WO | WO-2007016176 A2 | 2/2007 | |
| WO | WO-2007044729 A2 | 4/2007 | |
| WO | WO-2007053452 A1 | 5/2007 | |
| WO | WO-2007070514 A1 | 6/2007 | |
| WO | WO-2007084786 A1 | 7/2007 | |
| WO | WO-2007129161 A2 | 11/2007 | |
| WO | WO-2020089026 A2 | 1/2008 | |
| WO | WO-2008039218 A2 | 4/2008 | |
| WO | WO-2008109943 A1 | 9/2008 | |
| WO | WO-2008118802 A1 | 10/2008 | |
| WO | WO-2008132601 A1 | 11/2008 | |
| WO | WO-2009009116 A2 | 1/2009 | |
| WO | WO-2009044273 A2 | 4/2009 | |
| WO | WO-2009073620 A2 | 6/2009 | |
| WO | WO-2009074812 A1 | 6/2009 | |
| WO | WO-2009114512 A1 | 9/2009 | |
| WO | WO-2009156652 A1 | 12/2009 | |
| WO | WO-2010019570 A2 | 2/2010 | |
| WO | WO-2010077634 A1 | 7/2010 | |
| WO | WO-2011014515 A1 | 2/2011 | |
| WO | WO-2011014795 A2 | 2/2011 | |
| WO | WO-2011028683 A1 | 3/2011 | |
| WO | WO-2011056652 A1 | 5/2011 | |
| WO | WO-2011070024 A1 | 6/2011 | |
| WO | WO-2011090760 A1 | 7/2011 | |
| WO | WO-2011107553 A1 | 9/2011 | |
| WO | WO-2011109400 A2 | 9/2011 | |
| WO | WO-2011131407 A1 | 10/2011 | |
| WO | WO-2011140249 A2 | 11/2011 | |
| WO | WO-2012032433 A1 | 3/2012 | |
| WO | WO-2012142237 A1 | 10/2012 | |
| WO | WO-2012145493 A1 | 10/2012 | |
| WO | WO-2013079174 A1 | 6/2013 | |
| WO | WO-2013086397 A1 | 6/2013 | |
| WO | WO-2013087699 A1 | 6/2013 | |
| WO | WO-2013119716 A1 | 8/2013 | |
| WO | WO-2013132044 A1 | 9/2013 | |
| WO | WO-2013169264 A1 | 11/2013 | |
| WO | WO-2014008218 A1 | 1/2014 | |
| WO | WO-2014036357 A1 | 3/2014 | |
| WO | WO-2014074660 A1 | 5/2014 | |
| WO | WO-2014074661 A1 | 5/2014 | |
| WO | WO-2015089143 A1 | 6/2015 | |
| WO | WO-2015131080 A1 | 9/2015 | |
| WO | WO-2016106106 A2 | 6/2016 | |
| WO | WO-2018183964 A1 | 10/2018 | |
| WO | WO-2019070742 A1 * | 4/2019 | ........... C07D 401/14 |
| WO | WO-2019238424 A1 * | 12/2019 | ........... A61K 31/437 |
| WO | WO-2020106307 A1 | 5/2020 | |
| WO | WO-2021000935 A1 | 1/2021 | |
| WO | WO-2021050964 A1 | 3/2021 | |

OTHER PUBLICATIONS

Zhao; Bioorg. Med. Chem. Lett. 2020, 30, 127496. https://doi.org/10.1016/j.bmcl.2020.127496 (Year: 2020).*

Chemical Abstracts STN Registry Database, Record for RN 2578859-71-7, "5-[2-(1-Methyl-1H-pyrazol-4-yl)ethynyl]-4(3H)-quinazolinone", Entered STN Jan. 29, 2021. (Year: 2021).*

Chemical Abstracts STN Registry Database, Record for RN 2398890-74-7, "3,4-Dihydro-N-(2-methylpropyl)-N-[(1-methyl-1H-pyrazol-4-yl)methyl]-4-oxo-5-quinazolinecarboxamide", Entered STN Jan. 3, 2020. (Year: 2020).*

Baker; The Journal of Organic Chemistry 1952, 17, 164-176. https://doi.org/10.1021/jo01135a017 (Year: 1952).*

Lu; Bioorg. Med. Chem. Lett. 2014, 24, 2555-2559. https://doi.org/10.1016/j.bmcl.2014.03.086 (Year: 2014).*

Wang; Adv. Synth. Catal. 2017, 359, 4411-4416. https://doi.org/10.1002/adsc.201700899 (Year: 2017).*

Adams et al., "Big opportunities for small molecules in immuno-oncology," Cancer Therapy. 2015; 14: 603-622.

Berge et al., "Pharmaceutical salts," J. Pharmaceutical Sciences 1977; 66(1):1-19.

Deguest et al., "One-Pot Synthesis of 2,3-Dihydro-pyrrolopyridinones Using in Situ Generated Formimines," Organic Letters. 2006; 8(25):5889-92.

Di Bartolo et al. A novel pathway down-modulating T cell activation involves HPK-1-dependent recruitment of 14-3-3 proteins on SLP-76, J Exp Med. 2007; 204(3): 681-691.

Hu et al., "Human HPK1, a novel human hematopoietic progenitor kinase that activates the JNK/SAPK kinase cascade," Genes Dev. 1996; 10(18): 2251-64.

Ikegami et al., "The expression of prostaglandin E receptors EP2 and EP4 and their different regulation by lipopolysaccharide in C3H/HeN peritoneal macrophages," J Immunol. 2001; 166(7): 4689-96.

Kiefer et al., "HPK1, a hematopoietic protein kinase activating the SAPK/JNK pathway," EMBO J. 1996; 15(24): 7013-25.

Lasserre et al., "Release of serine/threonine-phosphorylated adaptors from signaling microclusters down-regulates T cell activation," J Cell Biol. 2011; 195(5): 839-853.

Liou et al., "HPK1 is activated by lymphocyte antigen receptors and negatively regulates AP-1," Immunity. 2000; 12(4): 399-408.

Okazaki et al., "A rheostat for immune responses: the unique properties of PD-1 and their advantages for clinical application," Nat. Immunol. 2013; 14(12): 1212-1218.

PCT International Search Report from PCT/US2020/050524 dated Oct. 31, 2020.

PCT International Search Report from PCT/US2022/070627 dated Jun. 6, 2022.

PCT International Search Report from PCT/US2022/070970 dated Jul. 14, 2022.

PCT International Search Report from PCT/US2022/071403 dated Jun. 6, 2022.

Pubchem-CID-14005627, Modify Date: Feb. 9, 2007.

PubChem-SID-369999312, Modify Date: May 28, 2018.

PubChem-SID-132639281, Modify Date: May 31, 2019.

Ramirez et al "Defining causative factors contributing in the activation of hedgehog signaling in diffuse large B-cell lymphoma" Leuk. Res. (2012), published online Jul. 17.

Ross et al., "Bispecific T cell engager (BITER) antibody constructs can mediate bystander tumor cell killing," PLoS ONE. 2017; 12(8): e0183390.

Rostovtsev et al., "A stepwise huisgen cycloaddition process: copper(I)-catalyzed regioselective "ligation" of azides and terminal alkynes," Angew. Chem. Int. Ed., 2002, vol. 41, pp. 2596-2599.

Shui et al., "Hematopoietic progenitor kinase 1 negatively regulates T cell receptor signaling and T cell-mediated immune responses," Nat Immunol. 2007; 8(1): 84-91.

Sun et al., "Carbohydrate and protein immobilization onto solid surfaces by sequential Diels-Alder and azide-alkyne cycloadditions," Bioconjugate Chem., 2006, vol. 17, No. 1, pp. 52-57.

Toogood, "Small molecule immuno-oncology therapeutic agents," Bioorganic & Medicinal Chemistry Letters. 2018; 28(3): 319-329.

Wang et al., "Activation of the hematopoietic progenitor kinase-1 (HPK1)-dependent, stress-activated c-Jun N-terminal kinase (JNK) pathway by transforming growth factor beta (TGF-beta)-activated kinase (TAK1), a kinase mediator of TGF beta signal transduction," J Biol Chem. 1997; 272(36): 22771-5.

Wang et al., "Down-regulation of B cell receptor signaling by hematopoietic progenitor kinase 1 (HPK1)-mediated phosphorylation and ubiquitination of activated B cell linker protein (BLNK)," J Biol Chem. 2012; 287(14): 11037-48.

Zhou et al., "Hematopoietic progenitor kinase 1 is a component of transforming growth factor beta-induced c-Jun N-terminal kinase signaling cascade," J Biol Chem. 1999; 274(19): 13133-8.

(56) References Cited

OTHER PUBLICATIONS

Zou et al., "PD-L1 (B7-H1) and PD-1 pathway blockade for cancer therapy: Mechanisms, response biomarkers, and combinations," Sci. Transl. Med. 2016; 8(328): 1-14.

* cited by examiner

HPK1 ANTAGONISTS AND USES THEREOF

CROSS-REFERENCE TO RELATED APPLICATIONS

This application claims the benefit of U.S. Provisional Application No. 63/148,857, filed on Feb. 12, 2021, the contents of which is hereby incorporated by reference.

TECHNICAL FIELD OF THE INVENTION

The present invention relates to compounds and methods useful for antagonizing hematopoietic progenitor kinase 1 (HPK1). The invention also provides pharmaceutically acceptable compositions comprising compounds of the present invention and methods of using said compositions in the treatment of various disorders.

BACKGROUND OF THE INVENTION

The hematopoietic progenitor kinase 1 (HPK1), otherwise known as mitogen activated protein kinase kinase kinase kinase 1 (MAP4K1), is a hematopoietic cell-restricted member of the Ste20 serine/threonine kinase super family. The MAP4Ks family includes MAP4K1/HPK1, MAP4K2/GCK, MAP4K3/GLK, MAP4K4/HGK, MAP4K5/KHS, and MAP4K6/MINK. HPK1 is a tissue-specific upstream activator of the MEKK/JNK/SAPK signaling pathway.

HPK1 is of particular interest because it is predominantly expressed in hematopoietic cells such as T cells, B cells, macrophages, dendritic cells, neutrophils, and mast cells (Hu, M. C., et al., Genes Dev, 1996. 10(18): p. 2251-64; Kiefer, F., et al., EMBO J, 1996. 15(24): p. 7013-25). HPK1 kinase activity has been shown to be induced upon activation of T cell receptors (TCR) (Liou, J., et al., Immunity, 2000. 12(4): p. 399-408), B cell receptors (BCR) (Liou, J., et al., Immunity, 2000. 12(4): p. 399-408), transforming growth factor receptor (TGF-PR) (Wang, W., et al., J Biol Chem, 1997. 272(36): p. 22771-5; Zhou, G., et al., J Biol Chem, 1999. 274(19): p. 13133-8), or Gs-coupled PGE2 receptors (EP2 and EP4) (Ikegami, R., et al., J Immunol, 2001. 166(7): p. 4689-96). As such, HPK1 regulates diverse functions of various immune cells. HPK1 is also an example of a negative regulator of dendritic cell activation, and T and B cell responses that can be targeted to enhance anti-tumor immunity. HPK1 is expressed predominantly by hematopoietic cells, including early progenitors. In T cells, it is believed that HPK1 negatively regulates T cell activation by reducing the persistence of signaling microclusters by phosphorylating SLP76 at Ser376 (Di Bartolo et al. (2007) JEM 204:681-691) and Gads at Thr254, which leads to the recruitment of 14-3-3 proteins that bind to the phosphorylated SLP76 and Gads, releasing the SLP76-Gads-14-3-3 complex from LAT-containing microclusters (Lasserre et al. (2011) J Cell Biol 195(5):839-853). HPK1 can also become activated in response to prostaglandin E2, which is often secreted by tumors, contributing to the escape of tumor cells from the immune system.

HPK1 is important in regulating the functions of various immune cells and it has been implicated in autoimmune diseases and anti-tumor immunity (Shui, J. W., et al., Nat Immunol, 2007. 8(1): p. 84-91; Wang, X., et al., J Biol Chem, 2012. 287(14): p. 11037-48).

SUMMARY OF THE INVENTION

It has now been found that compounds of this invention, and pharmaceutically acceptable compositions thereof, are effective as antagonists of HPK1. In certain embodiments, the invention provides for compounds of the formulae presented herein.

Compounds of the present invention, and pharmaceutically acceptable compositions thereof, are useful for treating a variety of diseases, disorders or conditions, associated with regulation of signaling pathways implicating HPK1 kinases. Such diseases, disorders, or conditions include those described herein.

Compounds provided by this invention are also useful for the study of HPK1 enzymes in biological and pathological phenomena; the study of intracellular signal transduction pathways occurring in bodily tissues; and the comparative evaluation of new HPK1 inhibitors or other regulators of kinases, signaling pathways, and cytokine levels in vitro or in vivo.

DETAILED DESCRIPTION OF CERTAIN EMBODIMENTS

1. General Description of Certain Embodiments of the Invention

In certain aspects, the present invention provides a compound of formula I:

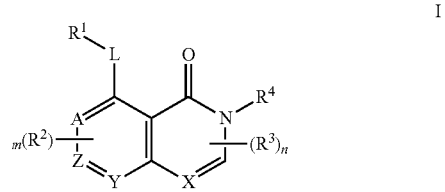

or a pharmaceutically acceptable salt thereof, wherein each of X, Y, Z, A, L, $R^1$, $R^2$, $R^3$, $R^4$, m, and n is as defined below and described in embodiments herein, both singly and in combination.

In some embodiments, the present invention provides a pharmaceutical composition comprising a compound provided herein, and a pharmaceutically acceptable carrier, adjuvant, or diluent.

In some embodiments, the present invention provides a method of treating a HPK1-mediated disease, disorder, or condition comprising administering to a patient in need thereof, a a compound provided herein, or a pharmaceutically acceptable salt thereof.

2. Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

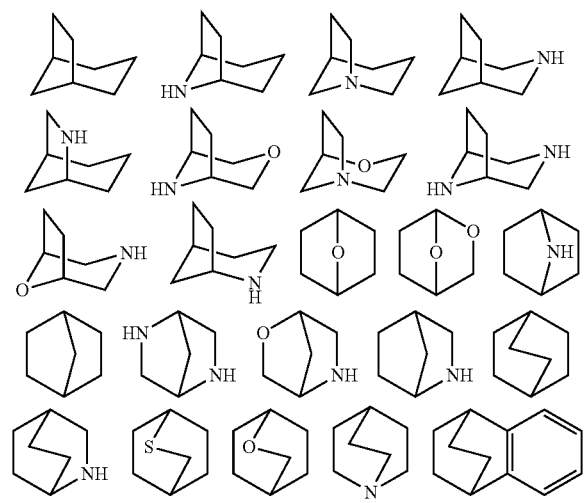

-continued

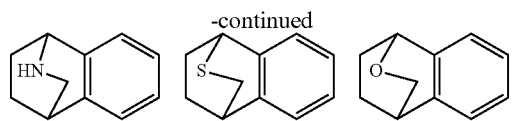

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^-$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —$(CH_2)_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where unless otherwise specified, the radical or point of attachment is on the heteroaromatic ring or on one of the rings to which the heteroaromatic ring is fused. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, and tetrahydroisoquinolinyl. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, 2-oxa-6-azaspiro[3.3]heptane, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —N(R°)C(NR°)N(R°)$_2$; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR°; —SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; —SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^•$, -(haloR$^•$), —(CH$_2$)$_{0-2}$OH, —(CH$_2$)$_{0-2}$OR$^•$, —(CH$_2$)$_{0-2}$CH(OR$^•$)$_2$; —O(haloR$^•$), —CN, —N$_3$, —(CH$_2$)$_{0-2}$C(O)R$^•$, —(CH$_2$)$_{0-2}$C(O)OH, —(CH$_2$)$_{0-2}$C(O)OR$^•$, —(CH$_2$)$_{0-2}$SR$^•$, —(CH$_2$)$_{0-2}$SH, —(CH$_2$)$_{0-2}$NH$_2$, —(CH$_2$)$_{0-2}$NHR$^•$, —(CH$_2$)$_{0-2}$NR$^•_2$, —NO$_2$, —SiR$^•_3$, —OSiR$^•_3$, —C(O)SR$^•$, —(C$_{1-4}$ straight or branched alkylene)C(O)OR$^•$, or —SSR$^•$ wherein each R$^•$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R•, -(haloR•), —OH, —OR•, —O(haloR•), —CN, —C(O)OH, —C(O)OR•, —NH$_2$, —NHR•, —NR•$_2$, or —NO$_2$, wherein each R• is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^†$, —NR$^†_2$, —C(O)R$^†$, —C(O)OR$^†$, —C(O)C(O)R$^†$, —C(O)CH$_2$C(O)R$^†$, —S(O)$_2$R$^†$, —S(O)$_2$NR$^†_2$, —C(S)NR$^†_2$, —C(NH)NR$^†_2$, or —N(R$^†$)S(O)$_2$R$^†$; wherein each R$^†$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R are independently halogen, —R•, -(haloR•), —OH, —OR•, —O(haloR•), —CN, —C(O)OH, —C(O)OR•, —NH$_2$, —NHR•, —NR•$_2$, or —NO$_2$, wherein each R• is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference.

Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention. In certain embodiments, a warhead moiety, R$^1$, of a provided compound comprises one or more deuterium atoms. In certain embodiments, Ring B of a provided compound may be substituted with one or more deuterium atoms.

As used herein, a "HPK1 antagonist" or a "HPK1 inhibitor" is a molecule that reduces, inhibits, or otherwise diminishes one or more of the biological activities of HPK1 (e.g., serine/threonine kinase activity, recruitment to the TCR complex upon TCR activation, interaction with a protein binding partner, such as SLP76). Antagonism using the HPK1 antagonist does not necessarily indicate a total elimination of the HPK1 activity. Instead, the activity could decrease by a statistically significant amount including, for example, a decrease of at least about 5%, 10%, 15%, 20%, 25%, 30%, 35%, 40%, 45%, 50%, 55%, 60%, 65%, 70%, 75%, 80%, 85%, 95% or 100% of the activity of HPK1 compared to an appropriate control. In some embodiments, the HPK1 antagonist reduces, inhibits, or otherwise diminishes the serine/threonine kinase activity of HPK1. In some of these embodiments, the HPK1 antagonist reduces, inhibits, or otherwise diminishes the HPK1-mediated phosphorylation of SLP76 and/or Gads. The presently disclosed compounds bind directly to HPK1 and inhibit its kinase activity.

By "specific antagonist" is intended an agent that reduces, inhibits, or otherwise diminishes the activity of a defined target greater than that of an unrelated target. For example, a HPK1 specific antagonist reduces at least one biological activity of HPK1 by an amount that is statistically greater than the inhibitory effect of the antagonist on any other protein (e.g., other serine/threonine kinases). In some embodiments, the $IC_{50}$ of the antagonist for the target is about 90%, 80%, 70%, 60%, 50%, 40%, 30%, 20%, 10%, 5%, 1%, 0.1%, 0.01%, 0.001% or less of the $IC_{50}$ of the antagonist for a non-target. The presently disclosed compounds may or may not be a specific HPK1 antagonist. A specific HPK1 antagonist reduces the biological activity of HPK1 by an amount that is statistically greater than the inhibitory effect of the antagonist on any other protein (e.g., other serine/threonine kinases). In certain embodiments, the HPK1 antagonist specifically inhibits the serine/threonine kinase activity of HPK1. In some of these embodiments, the $IC_{50}$ of the HPK1 antagonist for IPK1 is about 90%, 80%, 70%, 60%, 50%, 40%, 30%, 20%, 10%, 0.1%, 0.01%, 0.001%, or less of the $IC_{50}$ of the HPK1 antagonist for another serine/threonine or other type of kinase (e.g., tyrosine kinase).

A compound of the present invention may be tethered to a detectable moiety. It will be appreciated that such compounds are useful as imaging agents. One of ordinary skill in the art will recognize that a detectable moiety may be attached to a provided compound via a suitable substituent. As used herein, the term "suitable substituent" refers to a moiety that is capable of covalent attachment to a detectable moiety. Such moieties are well known to one of ordinary skill in the art and include groups containing, e.g., a carboxylate moiety, an amino moiety, a thiol moiety, or a hydroxyl moiety, to name but a few. It will be appreciated that such moieties may be directly attached to a provided compound or via a tethering group, such as a bivalent saturated or unsaturated hydrocarbon chain. In some embodiments, such moieties may be attached via click chemistry. In some embodiments, such moieties may be attached via a 1,3-cycloaddition of an azide with an alkyne, optionally in the presence of a copper catalyst. Methods of using click chemistry are known in the art and include those described by Rostovtsev et al., Angew. Chem. Int. Ed. 2002, 41, 2596-99 and Sun et al., Bioconjugate Chem., 2006, 17, 52-57.

As used herein, the term "detectable moiety" is used interchangeably with the term "label" and relates to any moiety capable of being detected, e.g., primary labels and secondary labels. Primary labels, such as radioisotopes (e.g., tritium, $^{32}P$, $^{33}P$, $^{35}S$, or $^{14}C$), mass-tags, and fluorescent labels are signal generating reporter groups which can be detected without further modifications. Detectable moieties also include luminescent and phosphorescent groups.

The term "secondary label" as used herein refers to moieties such as biotin and various protein antigens that require the presence of a second intermediate for production of a detectable signal. For biotin, the secondary intermediate may include streptavidin-enzyme conjugates. For antigen labels, secondary intermediates may include antibody-enzyme conjugates. Some fluorescent groups act as secondary labels because they transfer energy to another group in the process of nonradiative fluorescent resonance energy transfer (FRET), and the second group produces the detected signal.

The terms "fluorescent label", "fluorescent dye", and "fluorophore" as used herein refer to moieties that absorb light energy at a defined excitation wavelength and emit light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red, Texas Red-X.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-Methoxytetrafluorobenzyl)oxy]phenyl]-3-methylglyceronyl]isonipecotic Acid, 4'-[2,3,5,6-Tetrafluoro-4-(pentafluorophenoxyl)]methyl acetophenone, and their derivatives. The synthesis and utility of these mass-tags is described in U.S. Pat. Nos. 4,650,750, 4,709,016, 5,360, 8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) may also be used as mass-tags.

The terms "measurable affinity" and "measurably inhibit," as used herein, means a measurable change in a HPK1 protein kinase activity between a sample comprising a compound of the present invention, or composition thereof, and a HPK1 protein kinase, and an equivalent sample comprising an HPK1 protein kinase, in the absence of said compound, or composition thereof.

3. Description of Exemplary Embodiments

As described above, in certain embodiments, the present invention provides a compound of formula I:

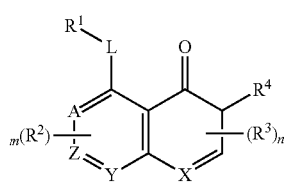

I or a pharmaceutically acceptable salt thereof, wherein:

X is N or CR$^3$;

Y is N or CR$^2$;

Z is N or CR$^2$;

A is N or CR$^2$;

L is a covalent bond, —O—, —S—, —NR—, —S(O)$_2$—, —S(O)$_2$NR—, —S(O)—, —S(O)NR—, —C(O)—, —C(O)O—, —C(O)NR—, —C(O)N(R)O—, —OC(O)—, —OC(O)NR—, —N(R)C(O)O—, —N(R)C(O)—, —N(R)S(O)$_2$—; or L is a C$_{1-4}$ bivalent saturated or unsaturated, straight or branched hydrocarbon chain wherein one or two methylene units of the chain are optionally and independently replaced by —C(R)$_2$—, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)— or —S(O)$_2$—;

R$^1$ is selected from H; C$_{1-6}$ aliphatic; phenyl; a 3-7 membered saturated or partially unsaturated monocyclic carbocyclic ring; a 5-6 membered monocyclic heteroaryl ring having 1-4 heteroatoms independently selected from nitrogen, oxygen, and sulfur; and a 3-7 membered saturated or partially unsaturated monocyclic heterocyclic ring having 1-2 heteroatoms independently selected from nitrogen, oxygen, and sulfur; each of which is substituted with q instances of R$^C$;

each R$^2$ is independently selected from H; C$_{1-6}$ aliphatic; phenyl; a 3-7 membered saturated or partially unsaturated monocyclic carbocyclic ring; a 5-6 membered monocyclic heteroaryl ring having 1-4 heteroatoms independently selected from nitrogen, oxygen, and sulfur; a 3-7 membered saturated or partially unsaturated monocyclic heterocyclic ring having 1-2 heteroatoms independently selected from nitrogen, oxygen, and sulfur; a 5-8 membered saturated or partially unsaturated bridged bicyclic ring having 0-3 heteroatoms independently selected from nitrogen, oxygen, and sulfur; and a 6-11 membered saturated, partially unsaturated, or unsaturated fused, bridged, or spiro bicyclic ring having 0-3 heteroatoms independently selected from nitrogen, oxygen, and sulfur; each of which is substituted with r instances of R$^D$; or R$^2$ is halogen, —CN, —NO$_2$, —OR, —SR, —NR$_2$, —S(O)$_2$R, —S(O)(NR)R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)R, —N(R)C(O)OR, —N(R)C(O)NR$_2$, —N(R)C(NR)NR$_2$, —N(R)S(O)$_2$NR$_2$, —N(R)S(O)$_2$R, or —P(O)R$^2$;

each R$^3$ is independently selected from H; C$_{1-6}$ aliphatic; phenyl; a 3-7 membered saturated or partially unsaturated monocyclic carbocyclic ring; a 5-6 membered monocyclic heteroaryl ring having 1-4 heteroatoms independently selected from nitrogen, oxygen, and sulfur; and a 3-7 membered saturated or partially unsaturated monocyclic heterocyclic ring having 1-2 heteroatoms independently selected from nitrogen, oxygen, and sulfur; each of which is substituted with s instances of R$^E$; or R$^3$ is halogen, —CN, —NO$_2$, —OR, —SR, —NR$_2$, —S(O)$_2$R, —S(O)(NR)R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)R, —N(R)C(O)OR, —N(R)C(O)NR$_2$, —N(R)C(NR)NR$_2$, —N(R)S(O)$_2$NR$_2$, —N(R)S(O)$_2$R, or —P(O)R$^2$;

R$^4$ is H or C$_{1-6}$ aliphatic; which is substituted with t instances of R$^F$;

each instance of R$^C$, R$^D$, R$^E$, and R$^F$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)NR$_2$, —N(R)S(O)$_2$NR$_2$, —N(R)S(O)$_2$R, —N=S(O)R$_2$, —S(NR)(O)R, —N(R)S(O)R, —N(R)CN, —P(O)(R)NR$_2$, —P(O)(R)OR or —P(O)R$_2$; or each instance of R$^C$, R$^D$, R$^E$, and R$^F$ is independently an optionally substituted group selected from C$_{1-6}$ aliphatic; phenyl; naphthalenyl; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, phosphorous, silicon and sulfur; a 5-6 membered monocyclic heteroaryl ring having 1-4 heteroatoms independently selected from nitrogen, oxygen, and sulfur; an 8-10 membered bicyclic heteroaryl ring having 1-5 heteroatoms independently selected from nitrogen, oxygen, and sulfur; a 5-8 membered saturated or partially unsaturated bridged bicyclic ring having 0-3 heteroatoms independently selected from nitrogen, oxygen, and sulfur; a 6-10 membered saturated or partially unsaturated spirocyclic ring having 0-3 heteroatoms independently selected from nitrogen, oxygen, and sulfur; or a 6-11 membered saturated or partially unsaturated bicyclic heterocyclic ring having 1-2 heteroatoms independently selected from nitrogen, oxygen, and sulfur; each of which is substituted with u instances of R;

each R is independently hydrogen, —CN, halogen, or an optionally substituted group selected from C$_{1-6}$ aliphatic; phenyl; naphthalenyl; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, and sulfur; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 7-12 membered saturated or partially unsaturated bicyclic heterocyclic ring having 1-4 heteroatoms independently selected from nitrogen, oxygen, and sulfur; a 5-8 membered saturated or partially unsaturated bridged bicyclic ring having 0-3 heteroatoms independently selected from nitrogen, oxygen, and sulfur; a 6-10 membered saturated or partially unsaturated spirocyclic ring having 0-3 heteroatoms independently selected from nitrogen, oxygen, and sulfur; a 6-11 membered saturated or partially unsaturated bicyclic heterocyclic ring having 1-2 heteroatoms independently selected from nitrogen, oxygen, and sulfur; or:

two R groups on the same nitrogen are taken together with the nitrogen to form an optionally substituted 4-7 membered monocyclic saturated, partially unsaturated, or heteroaryl ring having, in addition to the nitrogen, 0-3 heteroatoms independently selected from nitrogen, oxygen, and sulfur; an 8-10 membered bicyclic heteroaryl ring having 1-4 heteroatoms independently selected from nitrogen, oxygen, and sulfur; a 7-12 membered saturated or partially unsaturated bicyclic heterocyclic ring having 1-4 heteroatoms independently selected from nitrogen, oxygen, and sulfur;

m is 1, 2, or 3;

n is 0, 1, or 2;

each of q, r, s, and t is independently 0, 1, 2, 3, or 4; and u is 0, 1, 2, 3, or 4.

In one embodiment, X is $CR^3$; Y is N or $CR^2$; Z is N or $CR^2$; and A is N or $CR^2$.

In certain embodiments, X is $CR^3$; Y is $CR^2$; Z is N; and A is $CR^2$.

In certain embodiments, X is $CR^3$; Y is N; Z is $CR^2$; and A is $CR^2$.

In certain embodiments, X is $CR^3$; Y is $CR^2$; Z is $CR^2$; and A is $CR^2$.

In certain embodiments, X is $CR^3$; Y is $CR^2$; Z is $CR^2$; and A is N.

In certain embodiments, X is $CR^3$; Y is N; Z is $CR^2$; and A is N.

In another embodiment, X is N; Y is N or $CR^2$; Z is N or $CR^2$; and A is N or $CR^2$.

In certain embodiments, X is N; Y is $CR^2$; Z is N; and A is $CR^2$.

In certain embodiments, X is N; Y is N; Z is $CR^2$; and A is $CR^2$.

In certain embodiments, X is N; Y is $CR^2$; Z is $CR^2$; and A is $CR^2$.

In certain embodiments, X is N; Y is $CR^2$; Z is $CR^2$; and A is N.

In certain embodiments, X is N; Y is N; Z is $CR^2$; and A is N.

In certain embodiments, L is a covalent bond, —O—, —S—, —NR—, —S(O)$_2$—, —S(O)$_2$NR—, —S(O)—, —S(O)NR—, —C(O)—, —C(O)O—, —C(O)NR—, —C(O)N(R)O—, —OC(O)—, —OC(O)NR—, —N(R)C(O)O—, —N(R)C(O)—, —N(R)C(O)NR—, —N(R)C(NR)NR—, —N(R)NR—, —N(R)S(O)$_2$NR—, or —N(R)S(O)$_2$—.

In some embodiments, L is a covalent bond.

In certain embodiments, L is —O—, —S—, —NR—, —S(O)$_2$—, —S(O)$_2$NR—, —S(O)—, —S(O)NR—, —C(O)—, —C(O)O—, —C(O)NR—, —C(O)N(R)O—, —OC(O)—, —OC(O)NR—, —N(R)C(O)O—, —N(R)C(O)—, —N(R)C(O)NR—, —N(R)C(NR)NR—, —N(R)NR—, —N(R)S(O)$_2$NR—, or —N(R)S(O)$_2$—.

In certain embodiments, L is —NR—, —C(O)—, —C(O)O—, —C(O)NR—, —C(O)N(R)O—, —OC(O)—, —OC(O)NR—, —N(R)C(O)O—, —N(R)C(O)—, —N(R)C(O)NR—, —N(R)C(NR)NR—, or —N(R)NR—.

In certain embodiments, L is —NR—. In certain embodiments, L is —NH—.

In some embodiments, L is selected from those depicted in Table 1, below.

In some embodiments, $R^1$ is H.

In some embodiments, $R^1$ is $C_{1-6}$ aliphatic which is substituted with q instances of $R^C$; phenyl which is substituted with q instances of $R^C$; a 3-7 membered saturated or partially unsaturated monocyclic carbocyclic ring, which is substituted with q instances of $R^C$; a 5-6 membered monocyclic heteroaryl ring having 1-4 heteroatoms independently selected from nitrogen, oxygen, and sulfur, which is substituted with q instances of $R^C$; a 3-7 membered saturated or partially unsaturated monocyclic heterocyclic ring having 1-2 heteroatoms independently selected from nitrogen, oxygen, and sulfur, which is substituted with q instances of $R^C$.

In some embodiments, $R^1$ is phenyl or a 5-6 membered monocyclic heteroaryl ring having 1-4 heteroatoms independently selected from nitrogen, oxygen, and sulfur, each of which is substituted with q instances of $R^C$.

In certain embodiments, $R^1$ is —H, -Et, -i-Pr, s-Bu, straight chain or branched pentyl, cyclopropyl, cyclobutyl, cyclopentyl, cyclohexyl, phenyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; 1,2,5oxadiazolyl, 1,3,4-oxadiazolyl, oxazolidinyl, oxazolyl, oxazolidinyl, oxetanyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydropyranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, oxetanyl, azetidinyl, or xanthenyl; each of which is substituted by q instances of $R^C$.

In certain embodiments, $R^1$ is cyclopropyl, cyclobutyl, cyclopentyl, cyclohexyl, phenyl, furanyl, furazanyl, imidazolidinyl, imidazolinyl, imidazolyl, isothiazolyl, isoxazolyl, morpholinyl, oxadiazolyl, 1,2,3-oxadiazolyl, 1,2,4-oxadiazolyl; 1,2,5oxadiazolyl, 1,3,4-oxadiazolyl, oxazolidinyl, oxazolyl, oxazolidinyl, oxetanyl, pyrimidinyl, piperazinyl, piperidinyl, pyranyl, pyrazinyl, pyrazolidinyl, pyrazolinyl, pyrazolyl, pyridazinyl, pyridinyl, pyridyl, pyrimidinyl, pyrrolidinyl, pyrrolinyl, 2H-pyrrolyl, pyrrolyl, tetrahydrofuranyl, tetrahydropyranyl, thiazolyl, thienyl, triazinyl, 1,2,3-triazolyl, 1,2,4-triazolyl, 1,2,5-triazolyl, 1,3,4-triazolyl, oxetanyl, azetidinyl, or xanthenyl; each of which is substituted by q instances of $R^C$.

In certain embodiments, $R^1$ is phenyl, furanyl, furazanyl, imidazolidinyl, imidazolinyl, imidazolyl, isothiazolyl, isoxazolyl, oxadiazolyl, 1,2,3-oxadiazolyl, 1,2,4-oxadiazolyl; 1,2,5-oxadiazolyl, 1,3,4-oxadiazolyl, oxazolidinyl, oxazolyl, oxazolidinyl, oxetanyl, pyrimidinyl, pyranyl, pyrazinyl, pyrazolidinyl, pyrazolinyl, pyrazolyl, pyridazinyl, pyridinyl, pyridyl, pyrimidinyl, pyrrolidinyl, pyrrolinyl, 2H-pyrrolyl, pyrrolyl, thiazolyl, thienyl, triazinyl, 1,2,3-triazolyl, 1,2,4-triazolyl, or 1,2,5-triazolyl, 1,3,4-triazolyl; each of which is substituted by q instances of $R^C$.

In certain embodiments, $R^1$ is phenyl, pyrazolyl, or pyridinyl; each of which is substituted by q instances of $R^C$.

In certain embodiments, $R^1$ is phenyl, pyrazolyl, or pyridinyl; each of which is substituted by q instances of $R^C$; wherein each $R^C$ is independently halogen, —CN, —OR, —S(O)$_2$R, —C(O)NR$_2$, or each instance of $R^C$ is independently an optionally substituted group selected from $C_{1-6}$ aliphatic; a 5-10 membered saturated or partially unsaturated bridged bicyclic ring having 0-3 heteroatoms independently selected from nitrogen, oxygen, and sulfur; a 6-12 membered saturated or partially unsaturated spirocyclic ring having 0-3 heteroatoms independently selected from nitrogen, oxygen, and sulfur; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, phosphorous, silicon and sulfur; or two $R^C$ groups together with the atoms to which each is attached, forms a bridged, fused, or spiro 5-6 membered aryl ring, a 3-7 membered saturated or partially unsaturated monocyclic carbocyclic ring, a 3-7 membered saturated or partially unsaturated monocyclic heterocyclic ring having 1-2 heteroatoms independently selected from nitrogen, oxygen, phosphorous, silicon and sulfur; wherein or each instance of $R^C$ is independently optionally substituted by R and $R^D$.

In certain embodiments, $R^1$ is

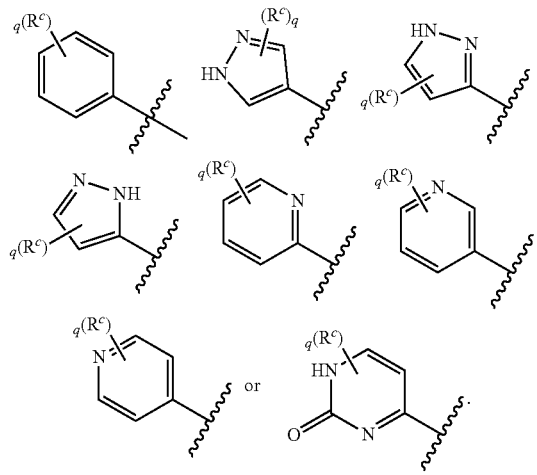

In certain embodiments, $R^1$ is

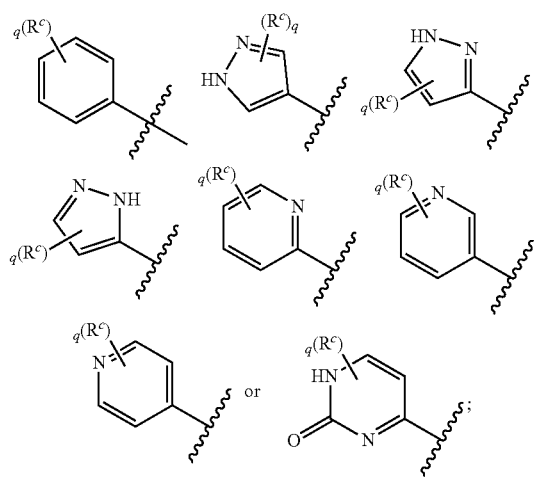

wherein each instance of $R^C$ is independently halogen, —CN, —OR, —S(O)$_2$R, —S(O)NR$_2$, —C(O)NR$_2$, an optionally substituted group selected from C$_{1-6}$ aliphatic; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, phosphorous, silicon and sulfur; a 5-8 membered saturated or partially unsaturated bridged bicyclic ring having 0-3 heteroatoms independently selected from nitrogen, oxygen, and sulfur; a 6-10 membered saturated or partially unsaturated spirocyclic ring having 0-3 heteroatoms independently selected from nitrogen, oxygen, and sulfur; or a 6-11 membered saturated or partially unsaturated bicyclic heterocyclic ring having 1-2 heteroatoms independently selected from nitrogen, oxygen, and sulfur; each of which is substituted with r instances of R and s instances of $R^D$.

In certain embodiments, $R^1$ is

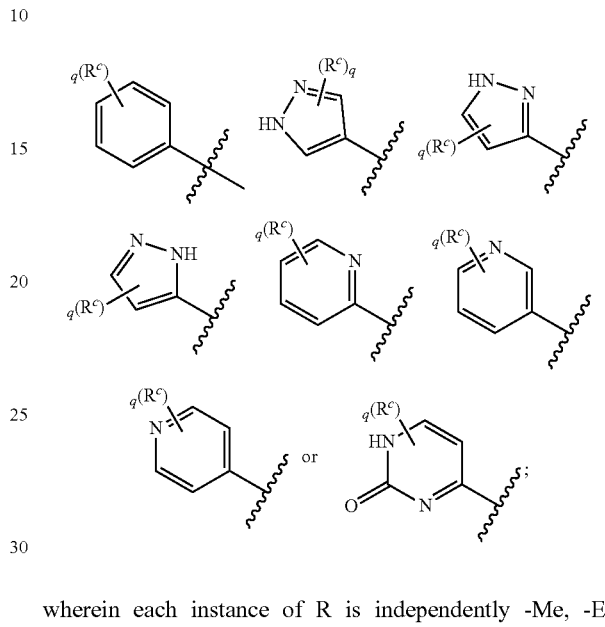

wherein each instance of R is independently -Me, -Et, —CH$_2$N(CH$_3$)$_2$, —CN, —CH$_2$CN, —F, —OMe, —S(O)$_2$Me, —CH$_2$S(O)$_2$Me

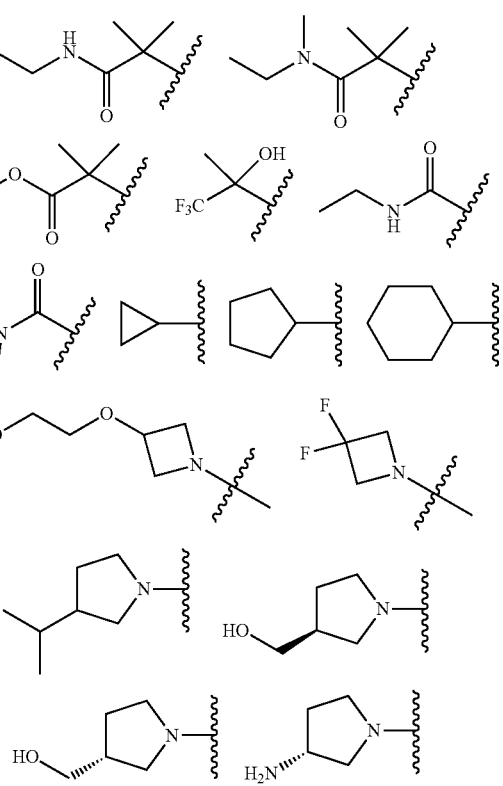

-continued
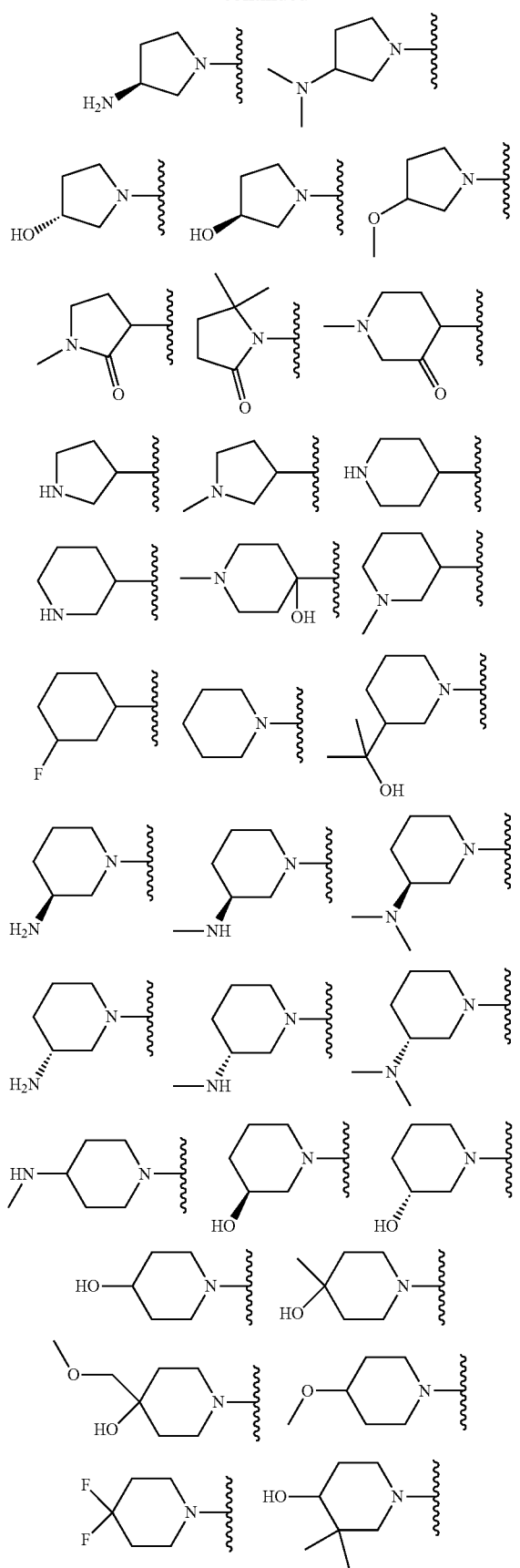
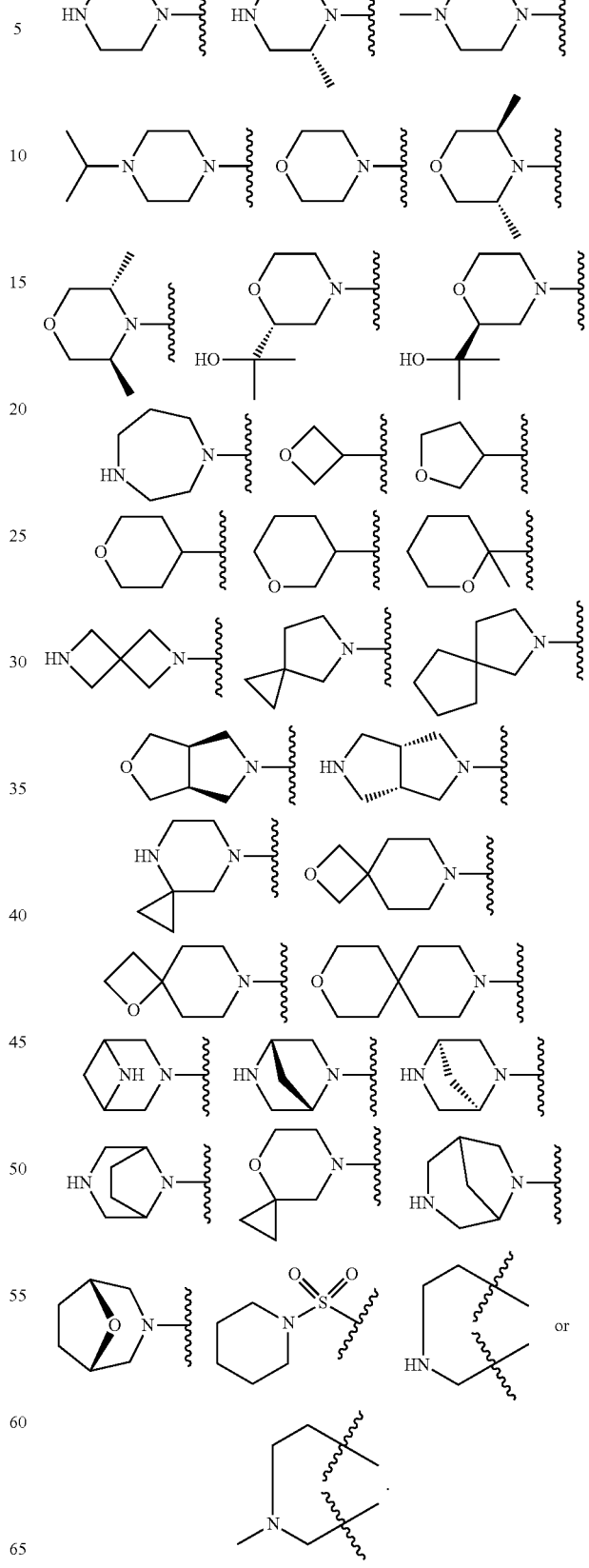

In certain embodiments, R[1] is
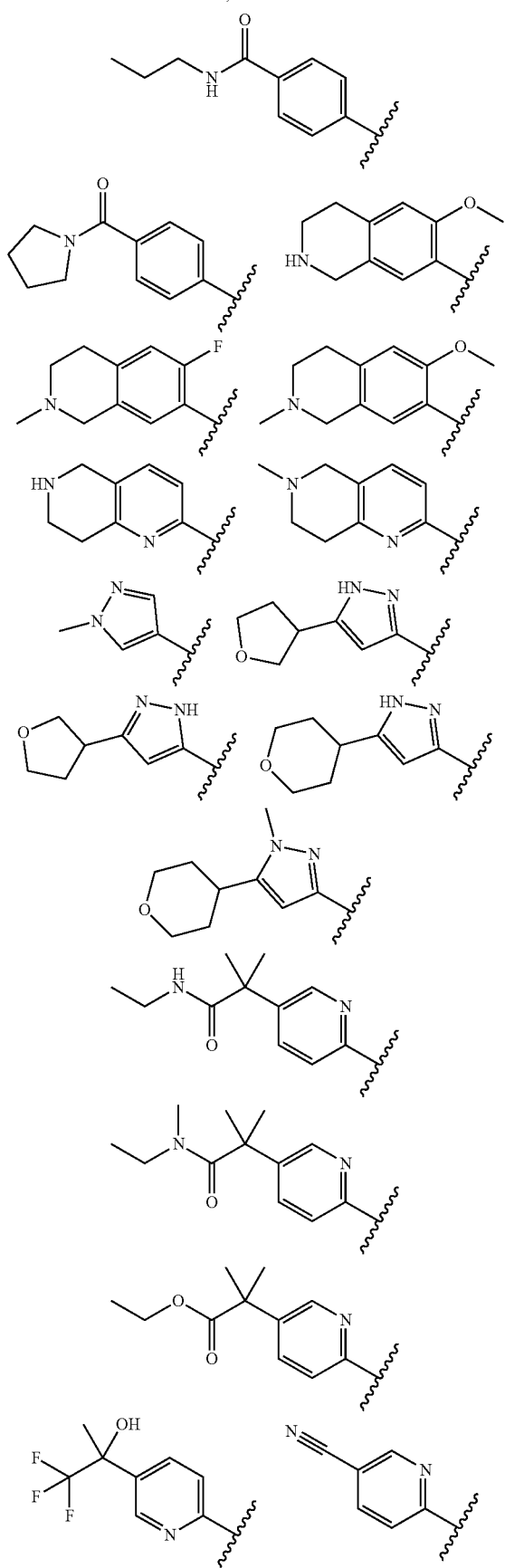
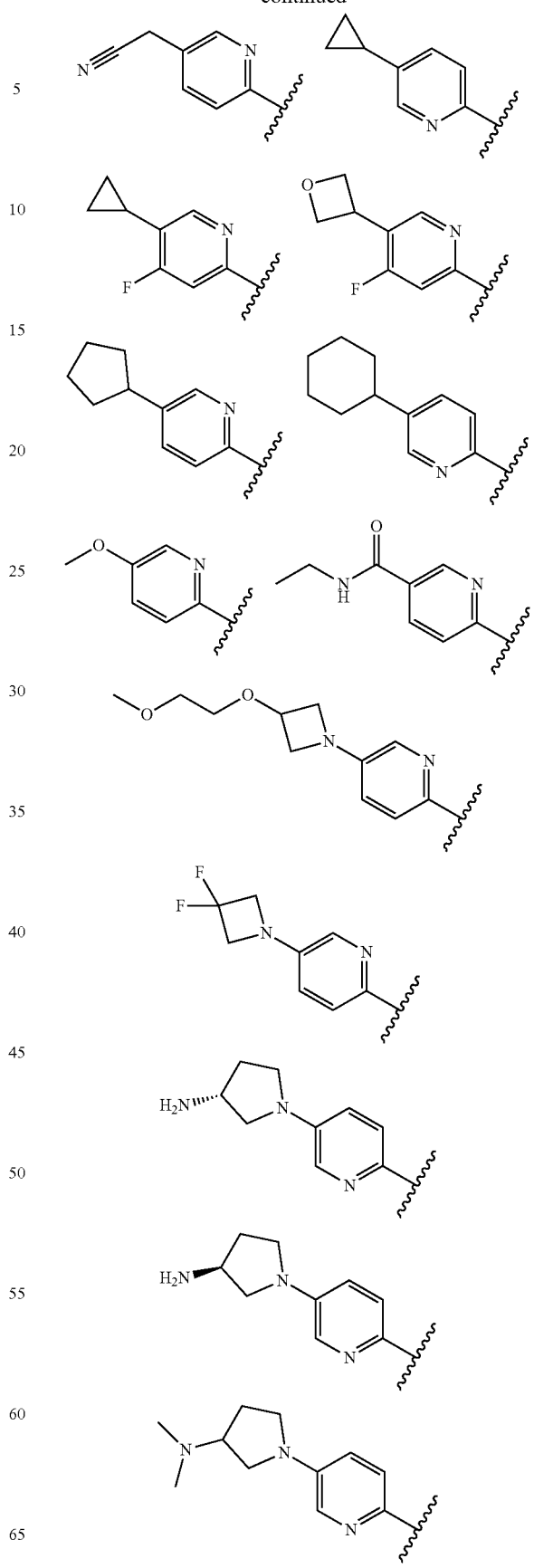

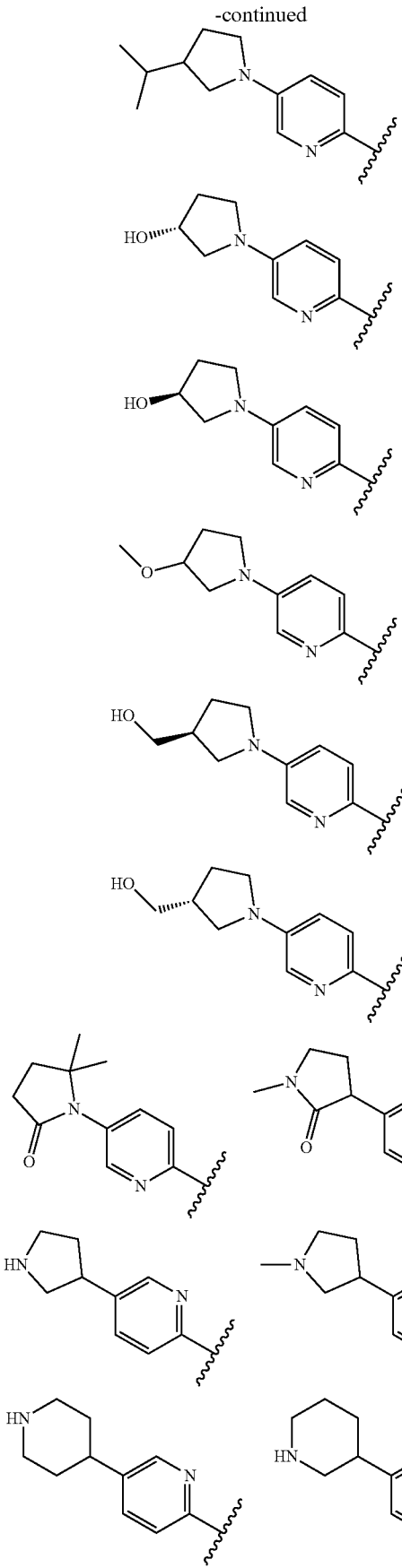
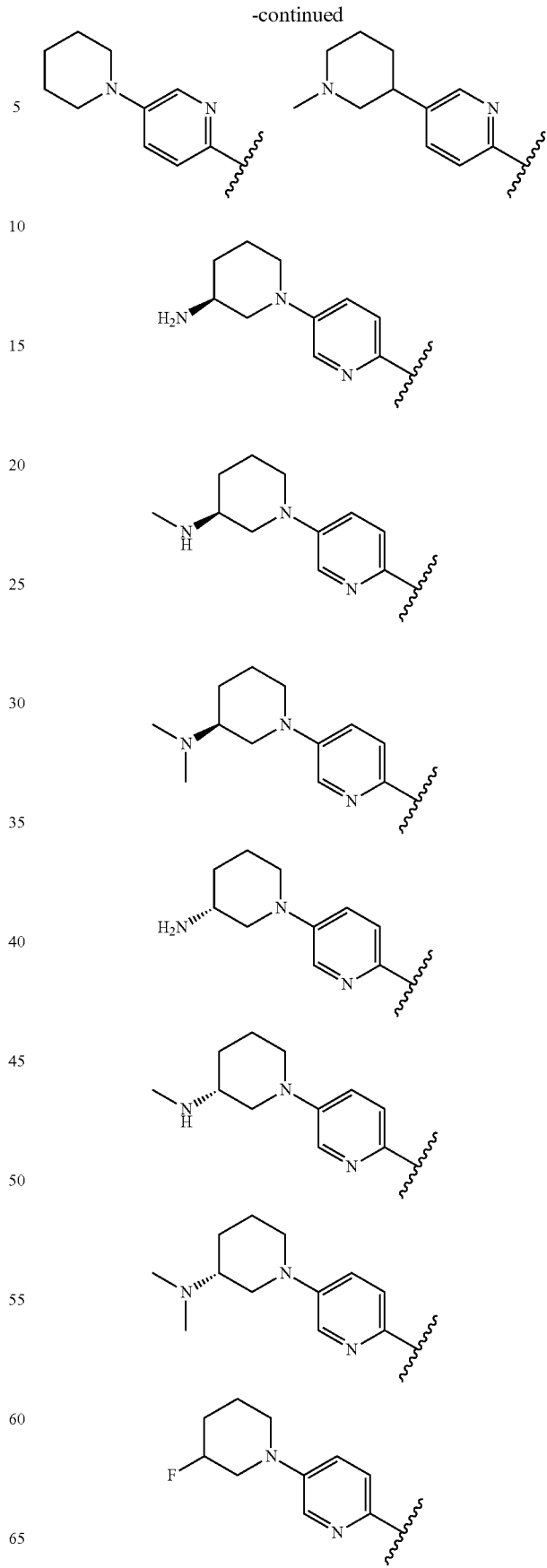

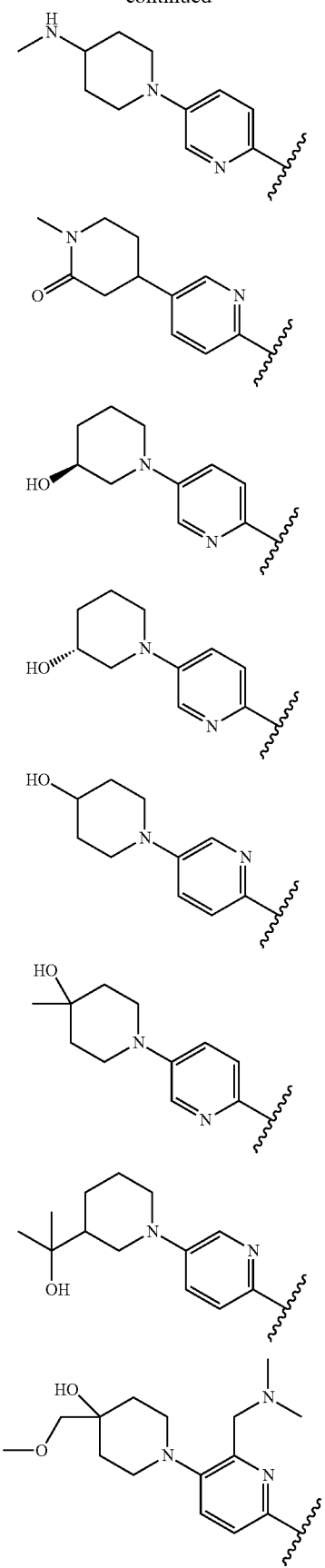
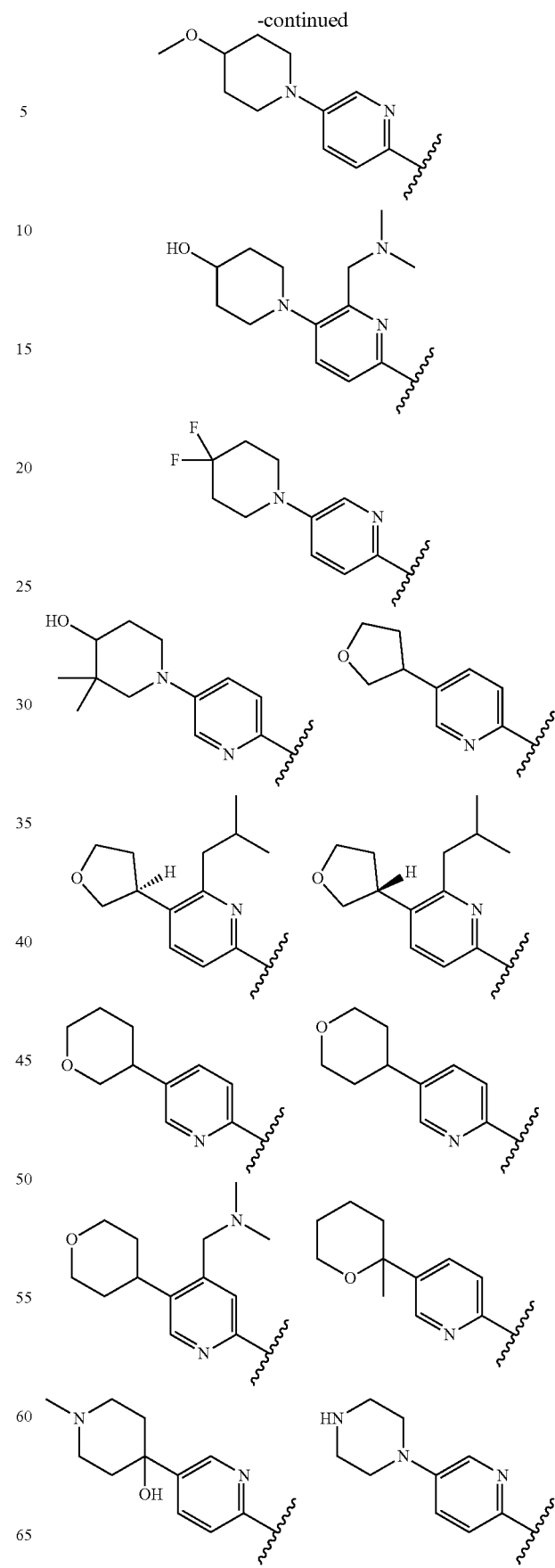

-continued
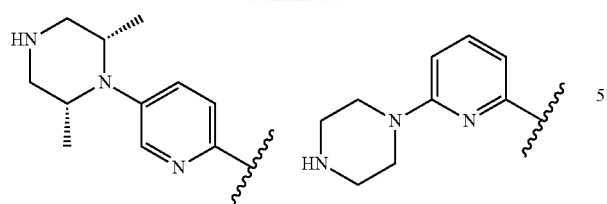
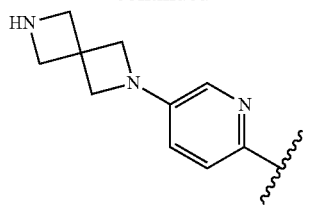
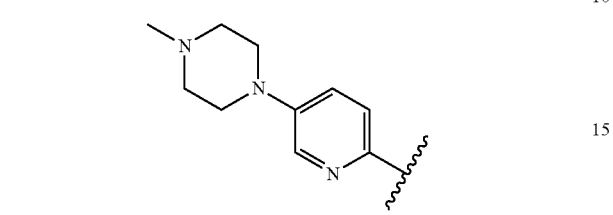
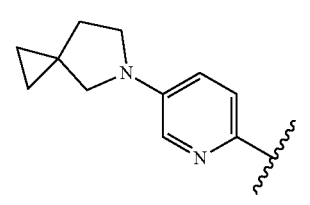
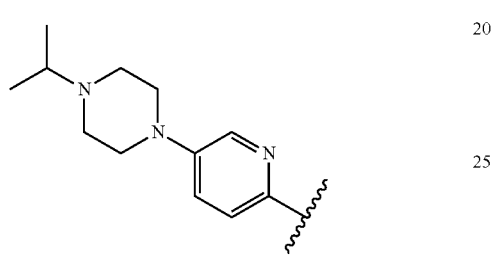
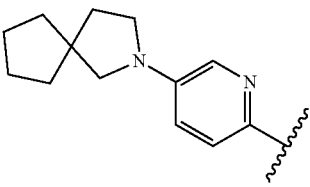
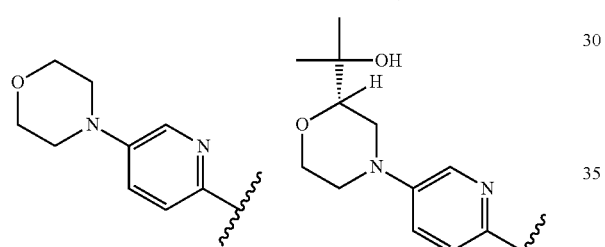
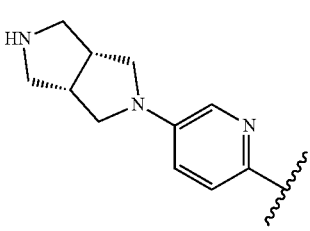
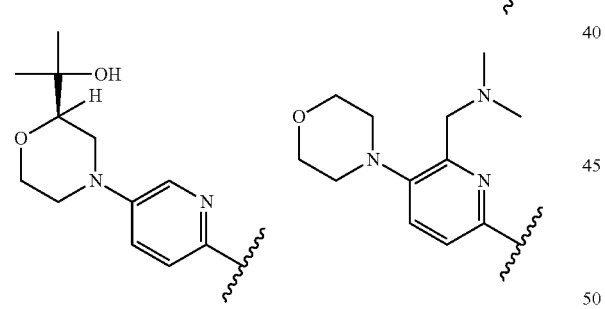
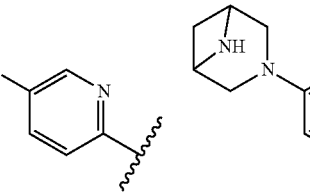
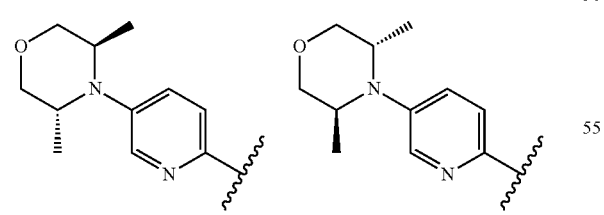
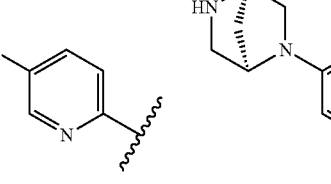
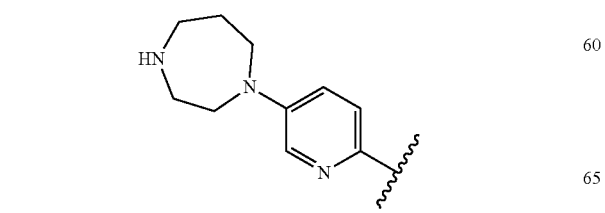
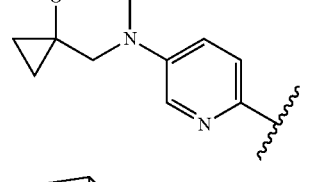
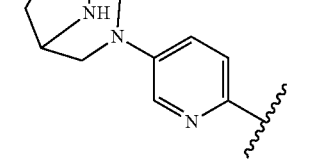

-continued

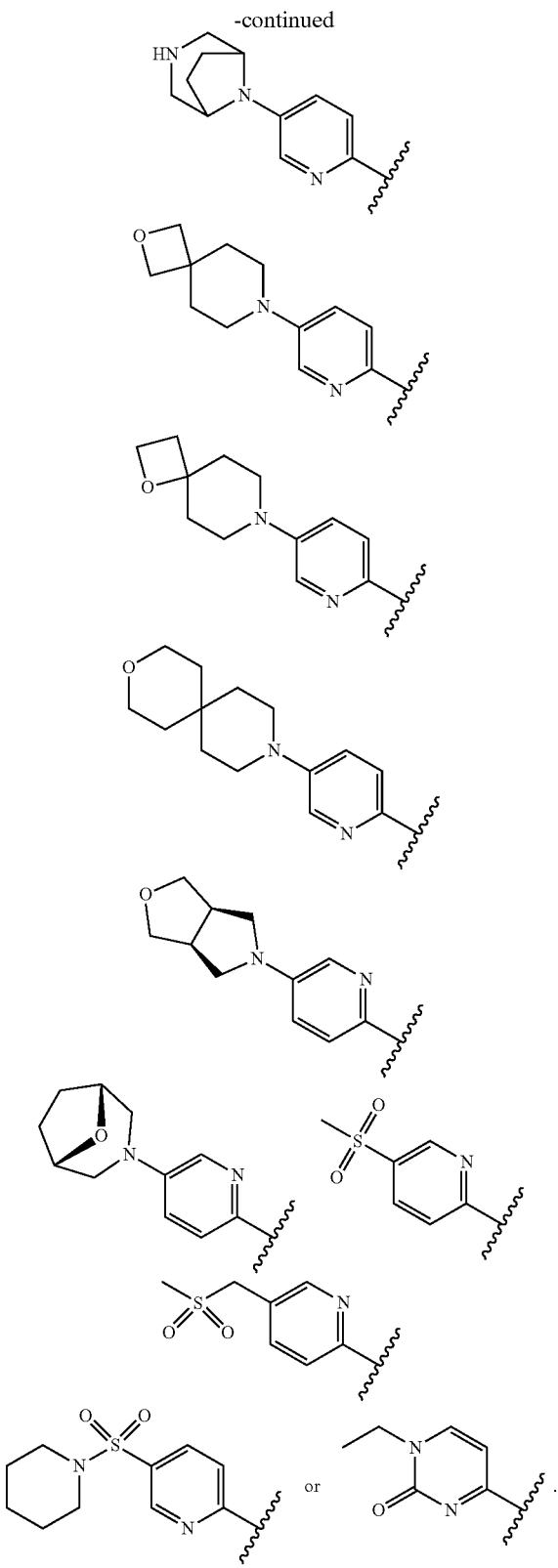

In some embodiments, $R^1$ is selected from those depicted in Table 1, below.

In some embodiments, each $R^2$ is independently H.

In some embodiments, each $R^2$ is independently $R^2$ is selected from $C_{1-6}$ aliphatic; phenyl; a 3-7 membered saturated or partially unsaturated monocyclic carbocyclic ring; a 5-6 membered monocyclic heteroaryl ring having 1-4 heteroatoms independently selected from nitrogen, oxygen, and sulfur; and a 3-7 membered saturated or partially unsaturated monocyclic heterocyclic ring having 1-2 heteroatoms independently selected from nitrogen, oxygen, and sulfur; each of which is substituted with r instances of $R^D$.

In some embodiments, each $R^2$ is independently selected from $C_{2-6}$ aliphatic; phenyl; a 3-7 membered saturated or partially unsaturated monocyclic carbocyclic ring; a 5-6 membered monocyclic heteroaryl ring having 1-4 heteroatoms independently selected from nitrogen, oxygen, and sulfur; a 3-7 membered saturated or partially unsaturated monocyclic heterocyclic ring having 1-2 heteroatoms independently selected from nitrogen, oxygen, and sulfur; each of which is substituted with r instances of $R^D$.

In some embodiments, each $R^2$ is independently $C_{2-6}$ aliphatic substituted with r instances of $R^D$.

In some embodiments, each $R^2$ is independently phenyl substituted with r instances of $R^D$.

In some embodiments, each $R^2$ is independently a 3-7 membered saturated or partially unsaturated monocyclic carbocyclic ring substituted with r instances of $R^D$.

In some embodiments, each $R^2$ is independently a 5-6 membered monocyclic heteroaryl ring having 1-4 heteroatoms independently selected from nitrogen, oxygen, and sulfur; substituted with r instances of $R^D$.

In some embodiments, each $R^2$ is independently a 3-7 membered saturated or partially unsaturated monocyclic heterocyclic ring having 1-2 heteroatoms independently selected from nitrogen, oxygen, and sulfur; substituted with r instances of $R^D$.

In certain embodiments, each $R^2$ is independently —H, -Et, -i-Pr, s-Bu, straight chain or branched pentyl, cyclopropyl, cyclobutyl, cyclopentyl, cyclohexyl, phenyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; 1,2,5oxadiazolyl, 1,3,4-oxadiazolyl, oxazolidinyl, oxazolyl, oxazolidinyl, oxetanyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydropyranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, oxetanyl, azetidinyl, or xanthenyl; each of which is substituted by r instances of $R^D$.

In certain embodiments, each $R^2$ is independently —H, -Et, -i-Pr, s-Bu, straight chain or branched pentyl, cyclopropyl, cyclobutyl, cyclopentyl, cyclohexyl, phenyl, furanyl, furazanyl, imidazolidinyl, imidazolinyl, imidazolyl, isothiazolyl, isoxazolyl, morpholinyl, oxadiazolyl, 1,2,3-oxadiazolyl, 1,2,4-oxadiazolyl; 1,2,5oxadiazolyl, 1,3,4-oxadiazolyl, oxazolidinyl, oxazolyl, oxazolidinyl, oxetanyl, pyrimidinyl, piperazinyl, piperidinyl, pyranyl, pyrazinyl, pyrazolidinyl, pyrazolinyl, pyrazolyl, pyridazinyl, pyridinyl, pyridyl, pyrimidinyl, pyrrolidinyl, pyrrolinyl, 2H-pyrrolyl, pyrrolyl, tetrahydrofuranyl, tetrahydropyranyl, thiazolyl, thienyl, triazinyl, 1,2,3-triazolyl, 1,2,4-triazolyl, 1,2,5-triazolyl, 1,3,4-triazolyl, oxetanyl, azetidinyl, or xanthenyl; wherein each instance of $R^D$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)NR$_2$, —N(R)S(O)$_2$NR$_2$, —N(R)S(O)$_2$R, —N=S(O)R$_2$, —S(NR)(O)R, —N(R)S(O)R, —N(R)CN, —P(O)(R)NR$_2$, —P(O)(R)OR or —P(O)R$_2$; or each instance of $R^D$ is independently an optionally substituted group selected from $C_{1-6}$ aliphatic; phenyl; naphthalenyl; an 8-10 membered bicyclic heteroaryl ring having 1-5 heteroatoms independently selected from nitrogen, oxygen, and sulfur; a 5-8 membered saturated or partially unsaturated bridged bicyclic ring having 0-3 heteroatoms independently selected from nitrogen, oxygen, and sulfur; a 6-10 membered saturated or partially unsaturated spirocyclic ring having 0-3 heteroatoms independently selected from nitrogen, oxygen, and sulfur; a 6-11 membered saturated or partially unsaturated bicyclic heterocyclic ring having 1-2 heteroatoms independently selected from nitrogen, oxygen, and sulfur; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, phosphorous, silicon and sulfur; and a 5-6 membered monocyclic heteroaryl ring having 1-4 heteroatoms independently selected from nitrogen, oxygen, and sulfur; or two $R^D$ groups together with the atoms to which each is attached, forms a bridged, fused, or spiro 5-6 membered aryl ring, a 3-7 membered saturated or partially unsaturated monocyclic carbocyclic ring, a 3-7 membered saturated or partially unsaturated monocyclic heterocyclic ring having 1-2 heteroatoms independently selected from nitrogen, oxygen, phosphorous, silicon and sulfur; and a 5-6 membered monocyclic heteroaryl ring having 1-4 heteroatoms independently selected from nitrogen, oxygen, and sulfur; wherein each instance of $R^D$ is independently optionally substituted by u instances of R.

In certain embodiments, each $R^2$ is independently —H, -Et, -i-Pr, s-Bu, straight chain or branched pentyl, cyclopropyl, cyclobutyl, cyclopentyl, cyclohexyl, phenyl, oxetanyl, piperazinyl, piperidinyl, pyrrolidinyl, tetrahydropyranyl, azetidinyl; each of which is substituted by r instances of $R^D$.

In certain embodiments, each $R^2$ is independently —H, -Et, -i-Pr, s-Bu, straight chain or branched pentyl, cyclopropyl, cyclobutyl, cyclopentyl, cyclohexyl, phenyl, oxetanyl, piperazinyl, piperidinyl, pyrrolidinyl, tetrahydropyranyl, azetidinyl; each of which is substituted by each of which is substituted by r instances of $R^D$; wherein each $R^D$ is independently oxo, halogen, —CN, —OR, —C(O)R, —C(O)OR, —C(O)NR$_2$, —N(R)C(O)R; or each instance of $R^D$ is independently an optionally substituted group selected from $C_{1-6}$ aliphatic; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, phosphorous, silicon and sulfur; and a 5-6 membered monocyclic heteroaryl ring having 1-4 heteroatoms independently selected from nitrogen, oxygen, and sulfur; or two $R^D$ groups together with the atoms to which each is attached, forms a bridged, fused, or spiro 5-6 membered aryl ring, a 3-7 membered saturated or partially unsaturated monocyclic carbocyclic ring, a 3-7 membered saturated or partially unsaturated monocyclic heterocyclic ring having 1-2 heteroatoms independently selected from nitrogen, oxygen, phosphorous, silicon and sulfur; and a 5-6 membered monocyclic heteroaryl ring having 1-4 heteroatoms independently selected from nitrogen, oxygen, and sulfur; wherein each instance of $R^D$ is independently optionally substituted by u instances of R.

In some embodiments, each $R^2$ is independently a 6-11 membered saturated, partially unsaturated, or unsaturated fused, bridged, or spiro bicyclic ring having 0-3 heteroatoms independently selected from nitrogen, oxygen, and sulfur; each of which is substituted with r instances of $R^D$.

In certain embodiments, each $R^2$ is independently a 7-10-membered fused bicyclic ring having 1-3 nitrogen atoms; each of which is substituted by each of which is substituted by r instances of $R^D$.

In certain embodiments, each $R^2$ is independently a 9-membered fused bicyclic ring having 1-3 nitrogen atoms; each of which is substituted by each of which is substituted by r instances of $R^D$; wherein each $R^D$ is independently halogen, —CN, —OR, —C(O)NR$_2$, —NR$_2$; or each instance of $R^D$ is independently an optionally substituted group selected from $C_{1-6}$ aliphatic; phenyl; a 3-7 membered saturated or partially unsaturated monocyclic heterocyclic ring having 1-2 heteroatoms independently selected from nitrogen, oxygen, phosphorous, silicon and sulfur; and a 6-11 membered saturated or partially unsaturated fused, bridged, or spiro bicyclic heterocyclic ring having 1-3 heteroatoms independently selected from nitrogen, oxygen, and sulfur; wherein each instance of $R^D$ is independently optionally substituted by u instances of R.

In certain embodiments, each $R^2$ is independently —H,

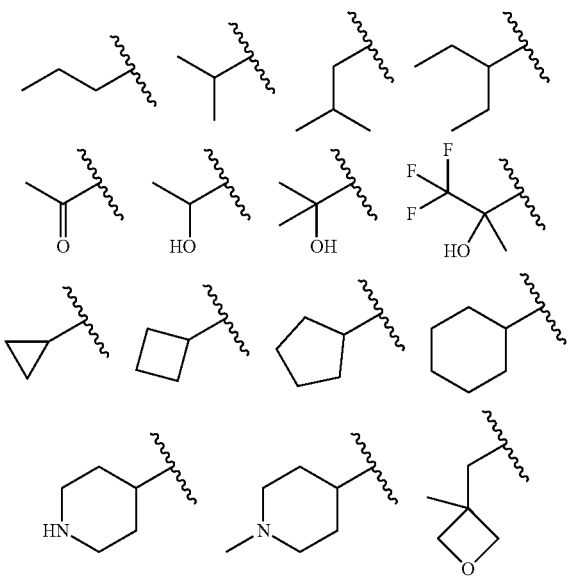

-continued
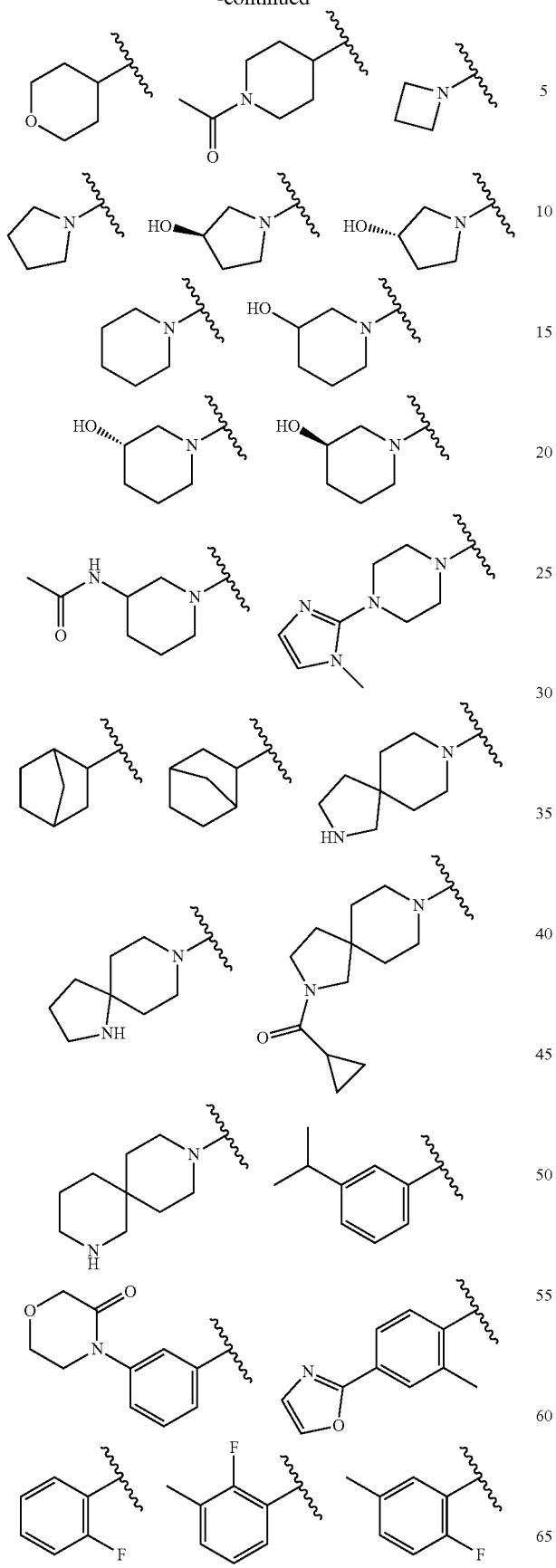
-continued
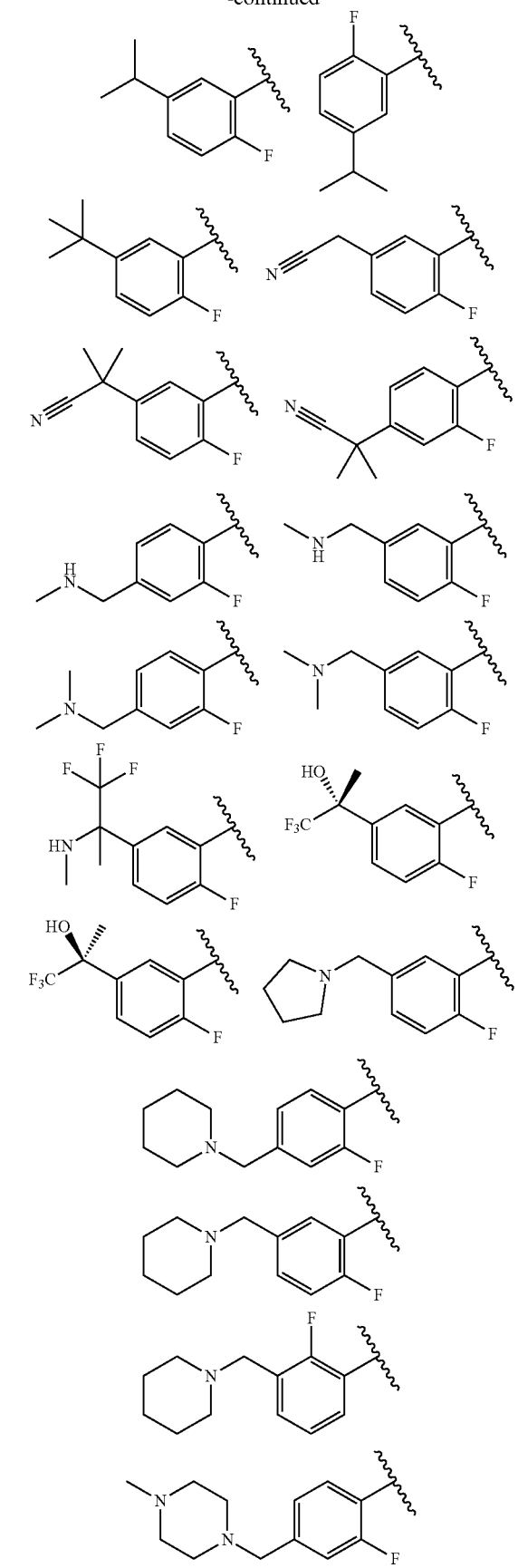

-continued
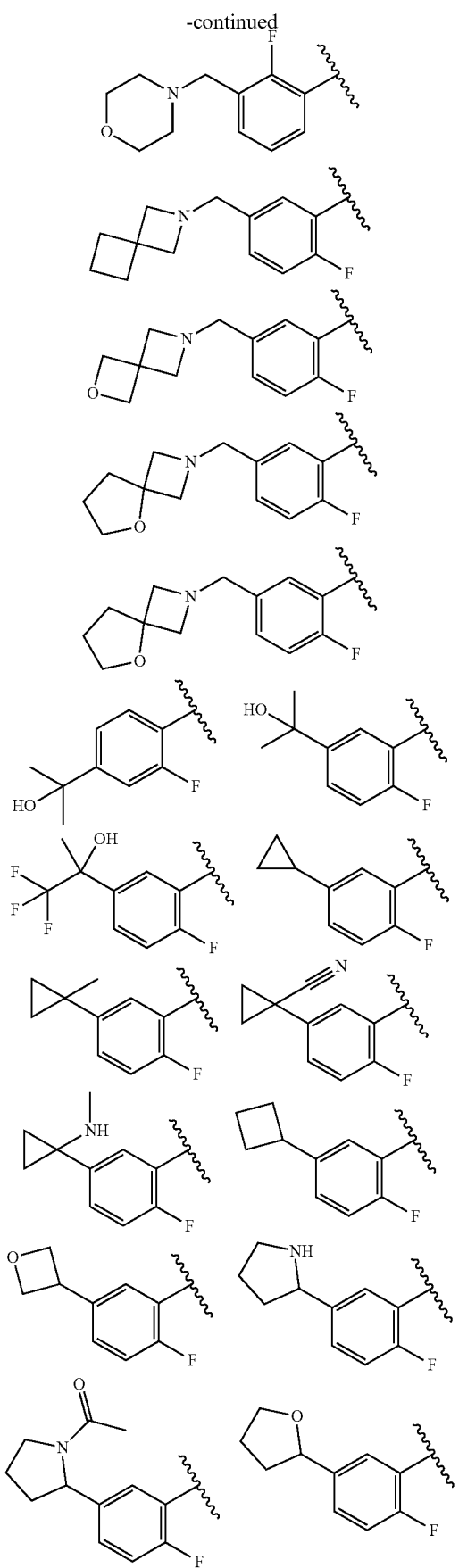
-continued
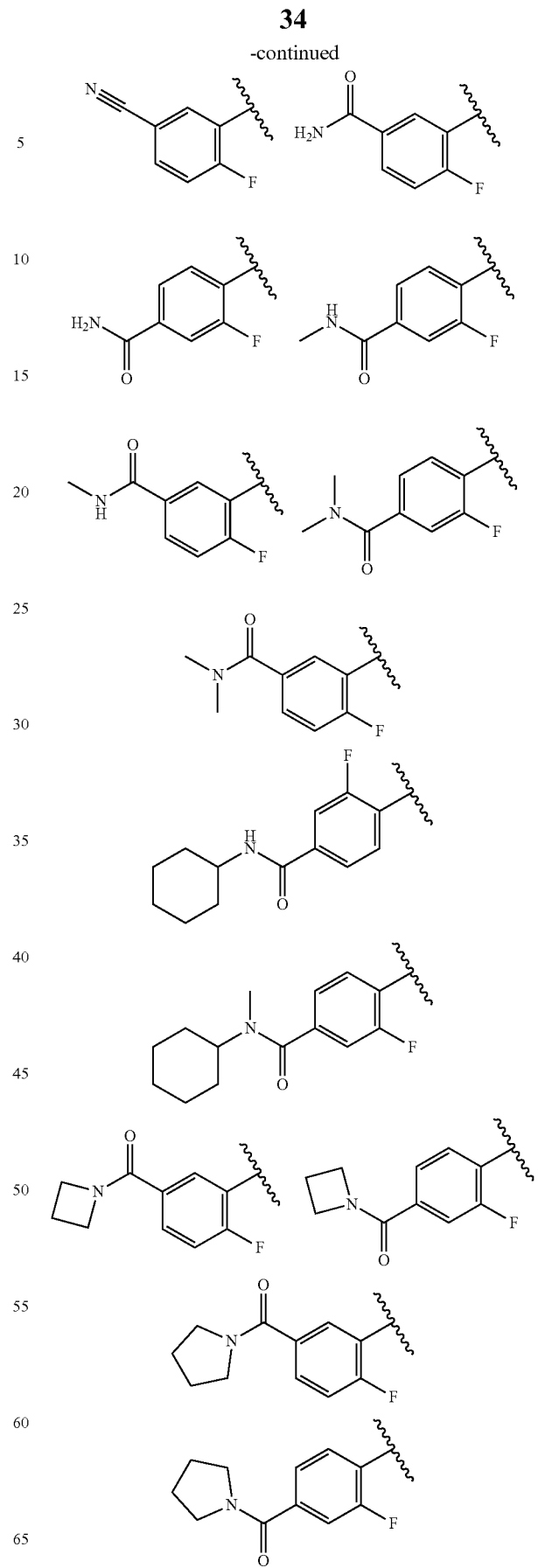

-continued
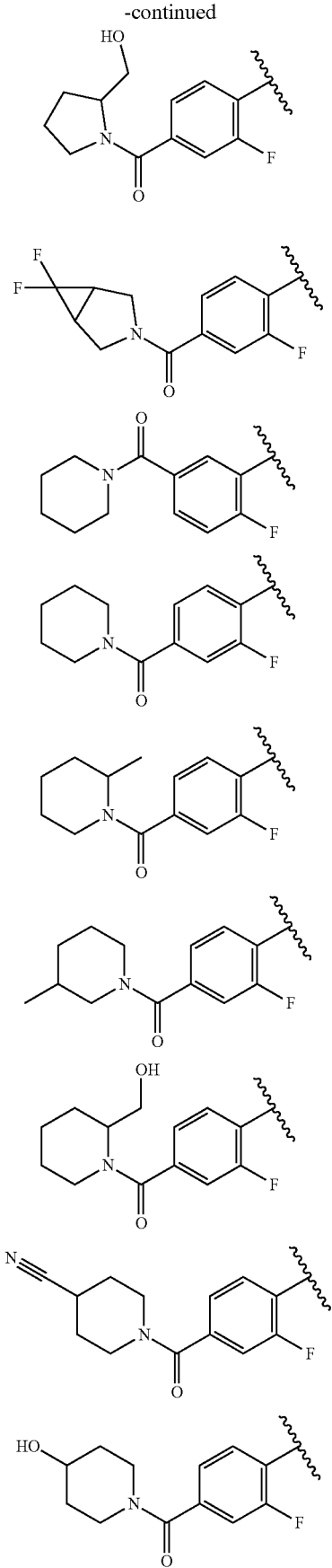
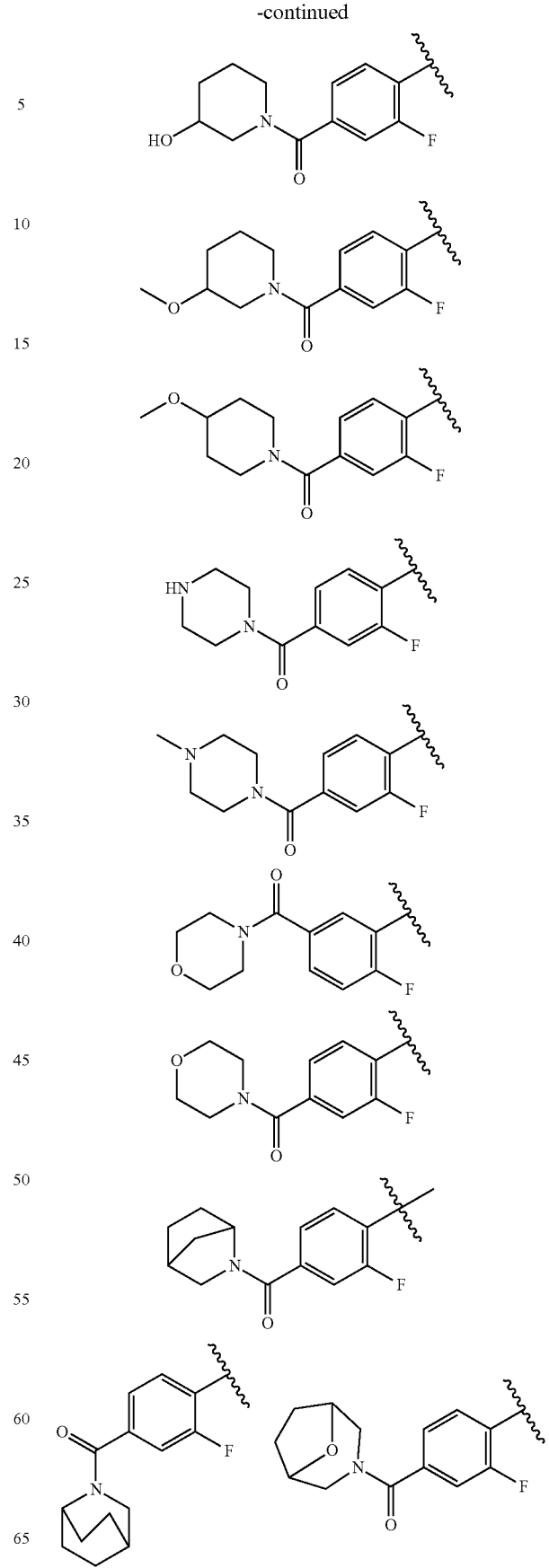

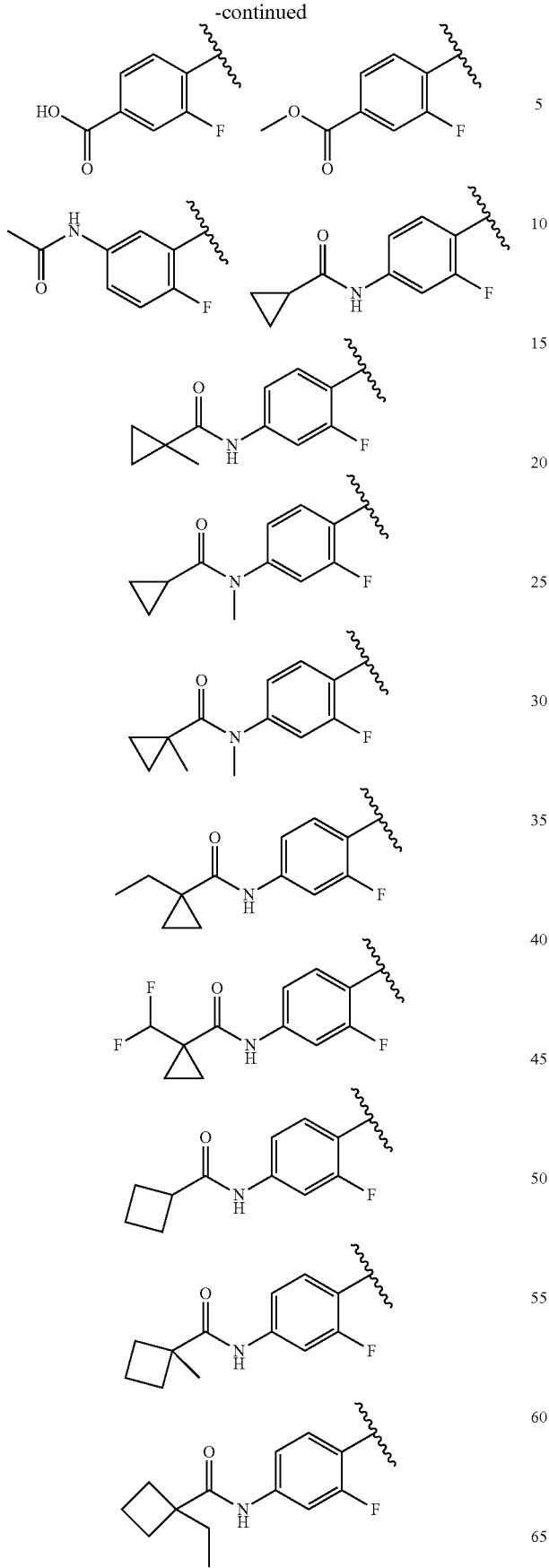
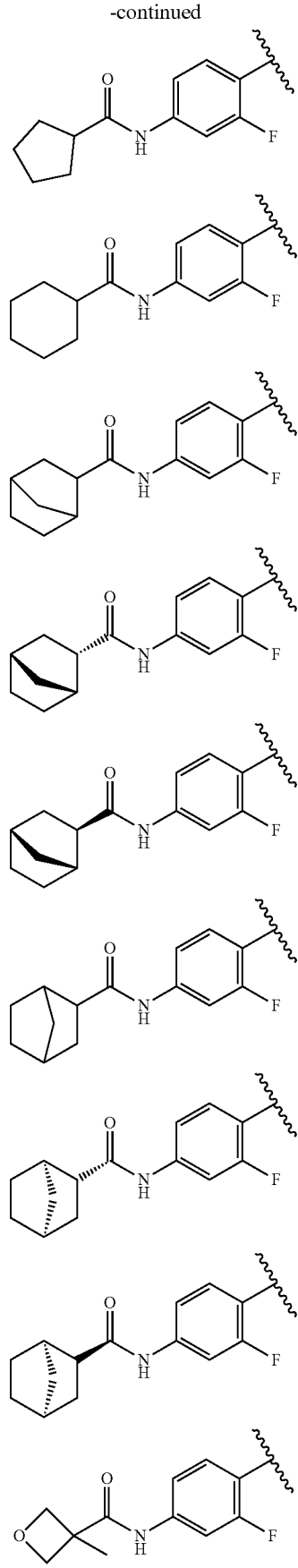

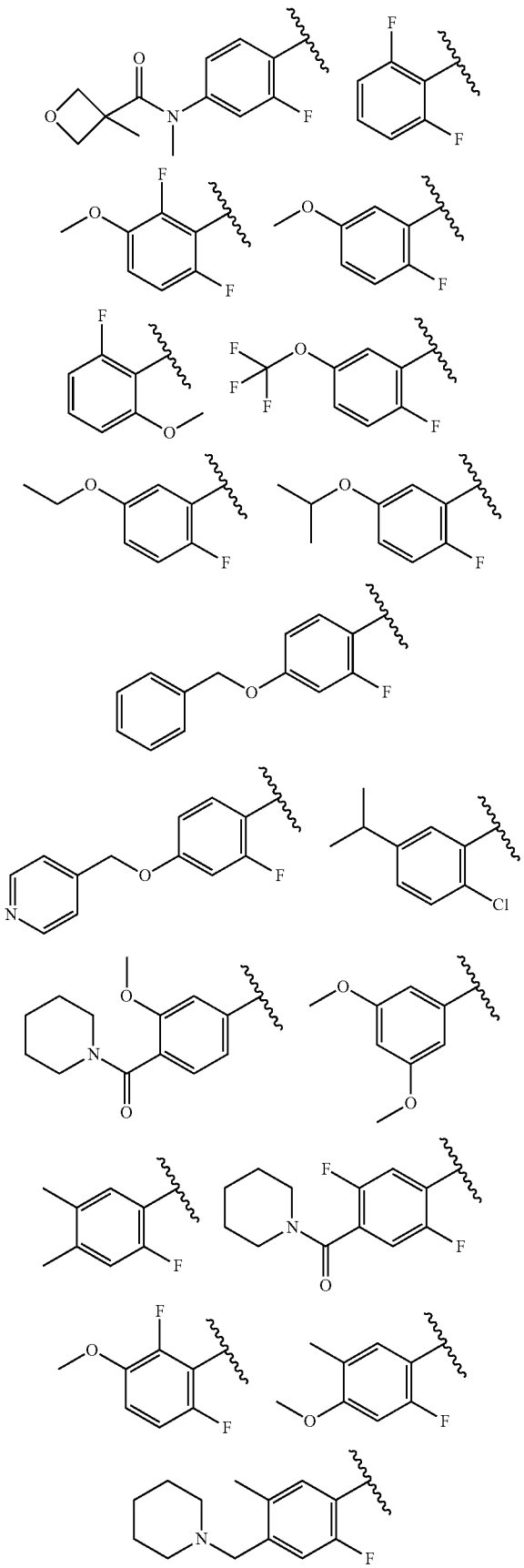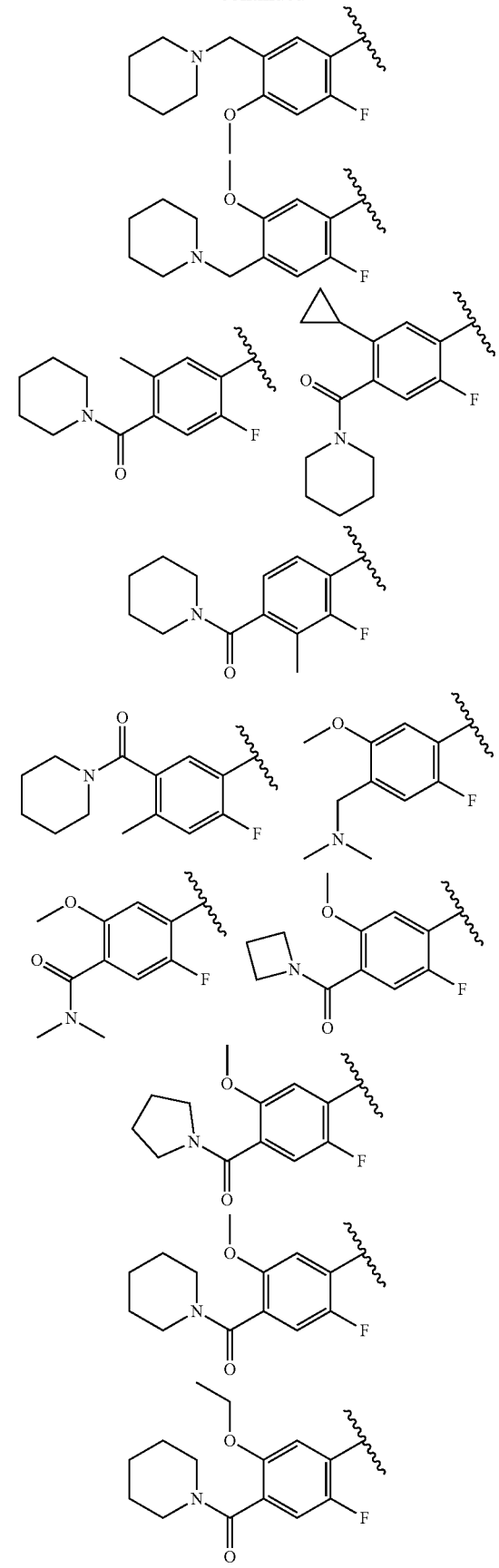

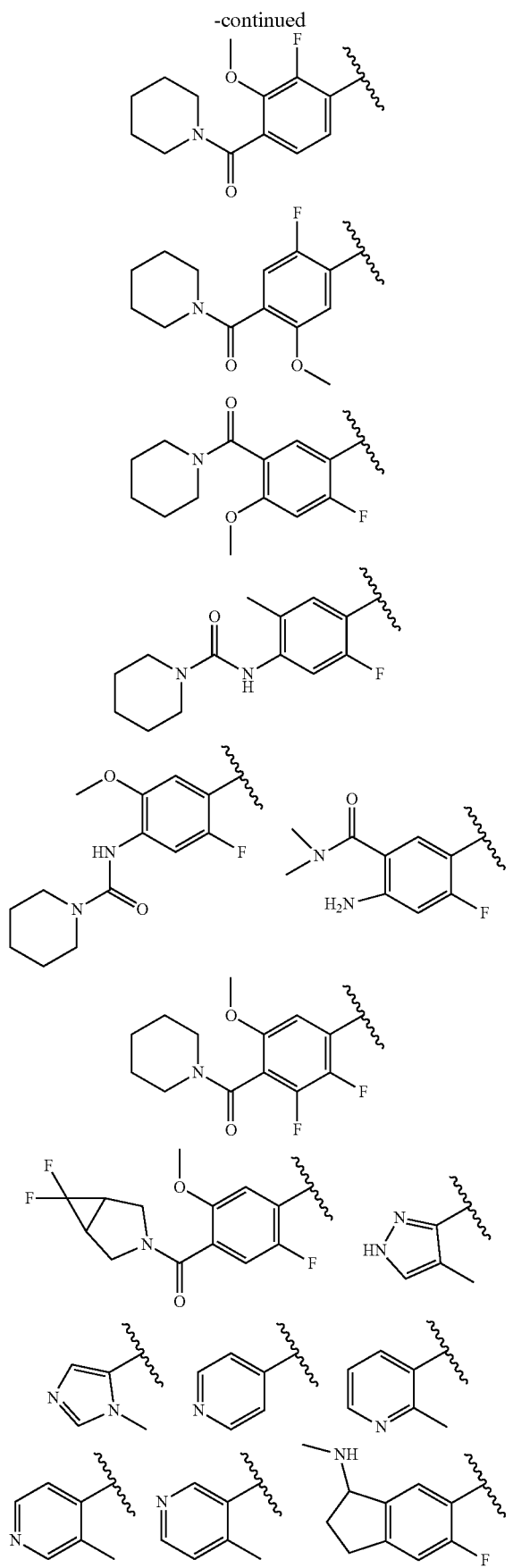
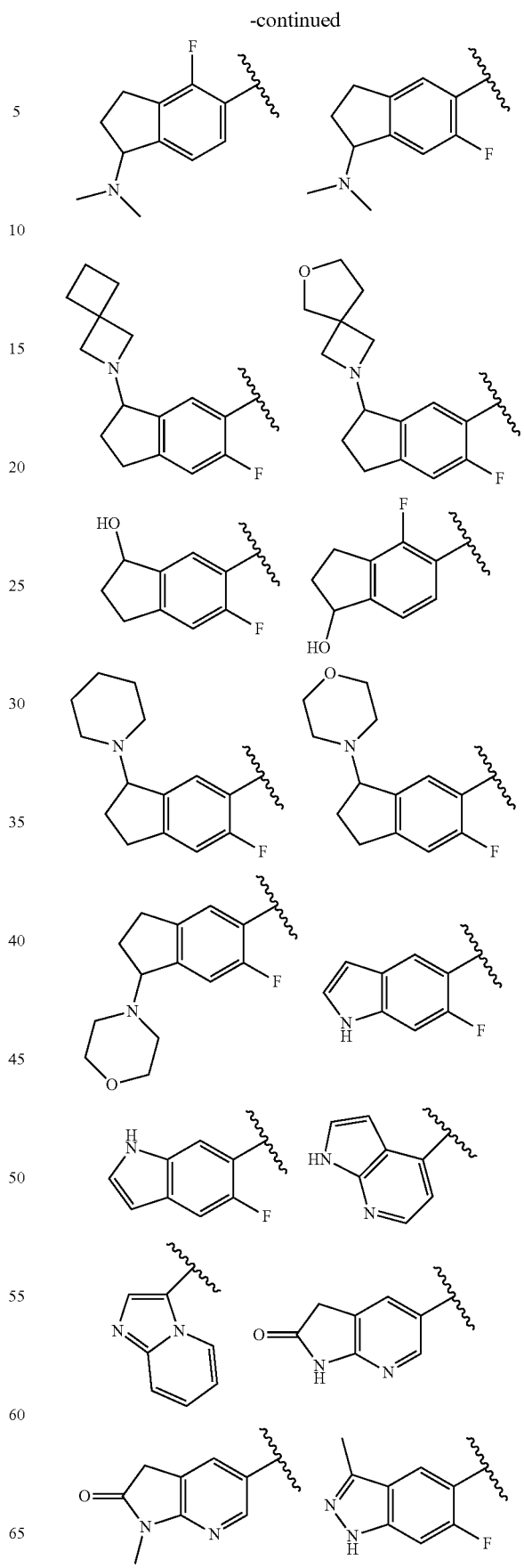

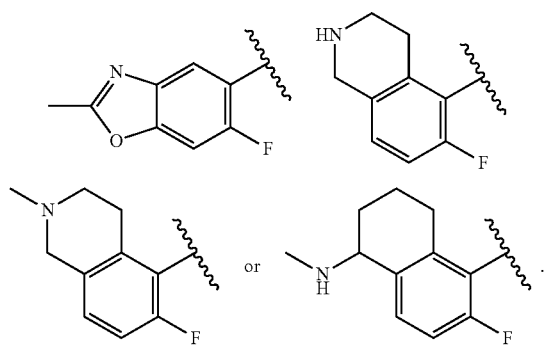
In certain embodiments, each $R^2$ is independently
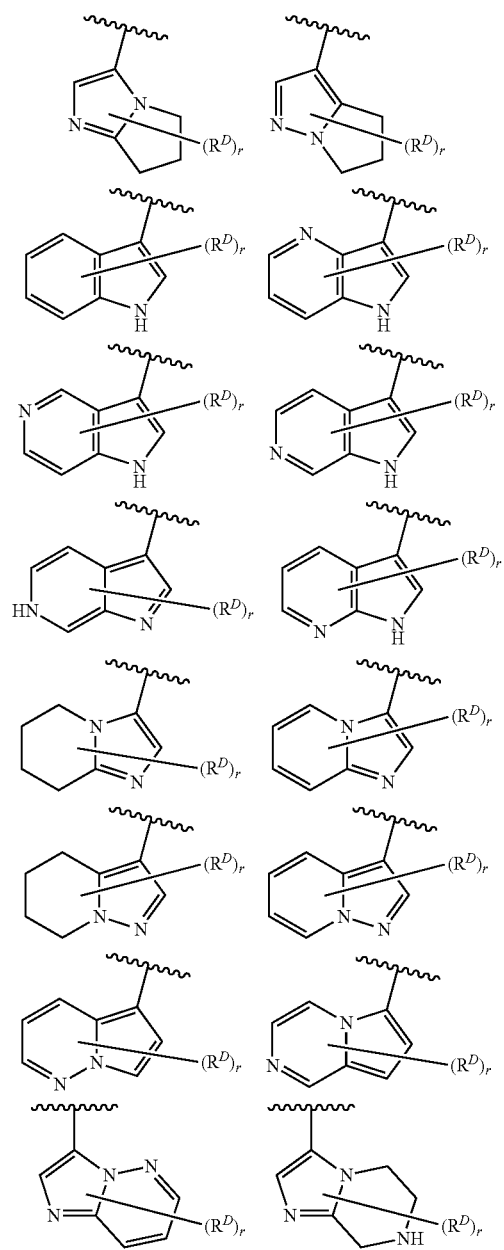
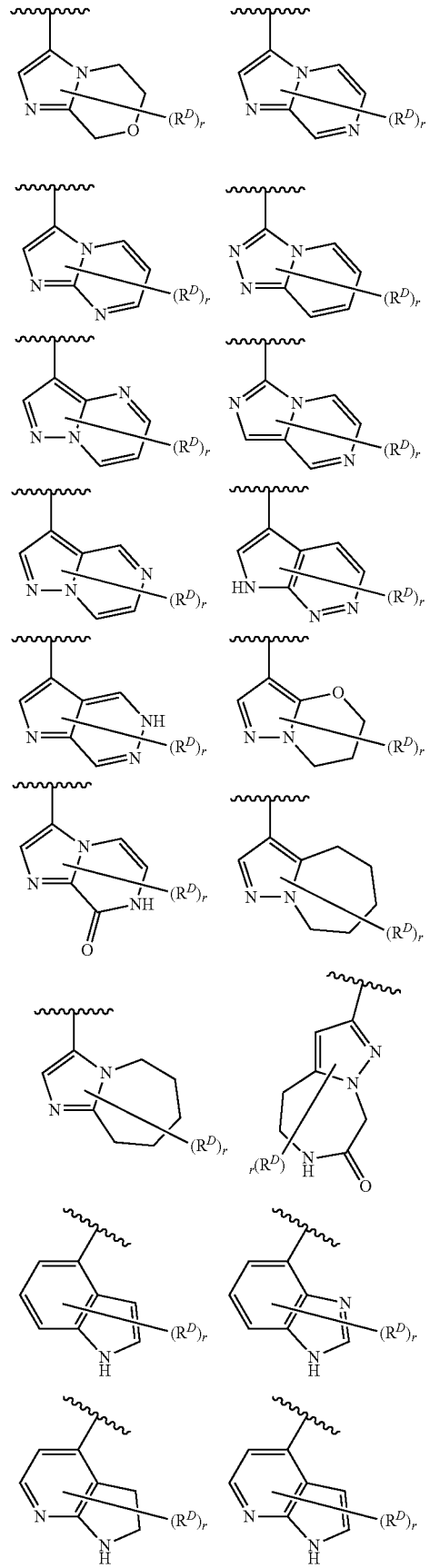

-continued
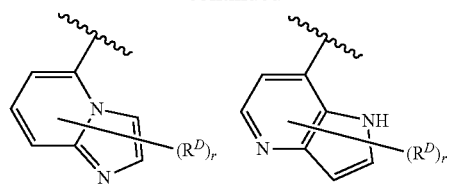
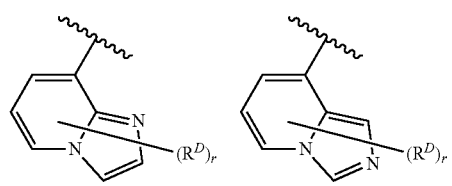
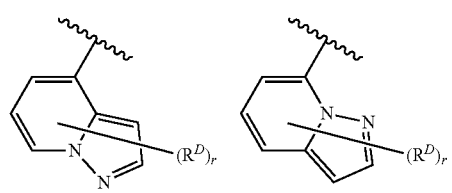
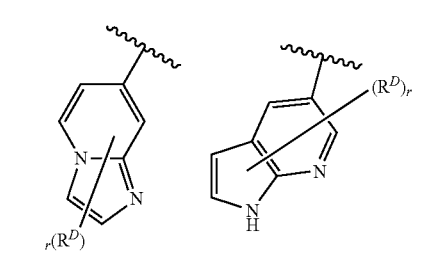
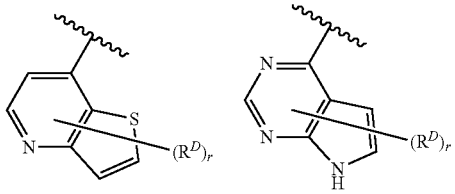
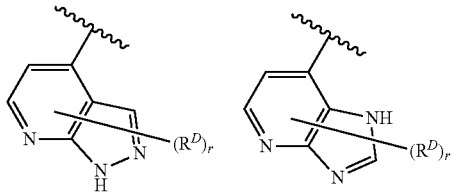
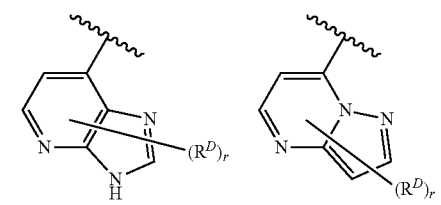
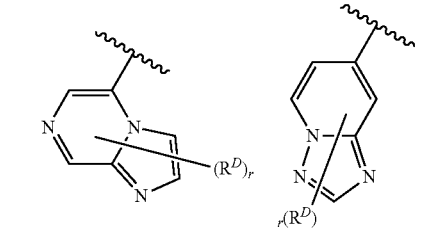
-continued
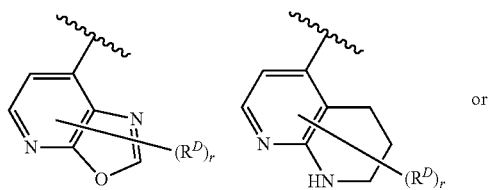
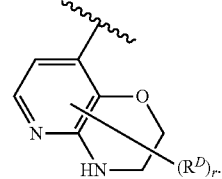
In certain embodiments, each $R^2$ is independently
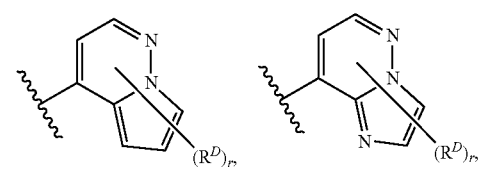
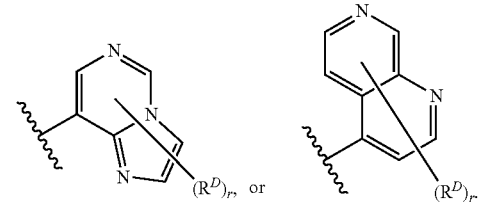
In certain embodiments, each $R^2$ is independently
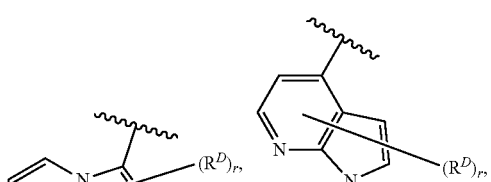
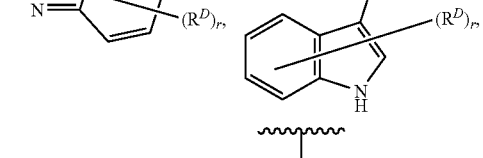
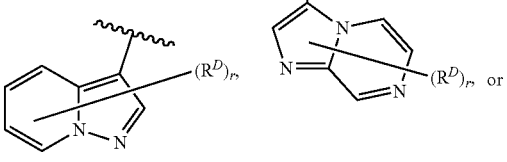

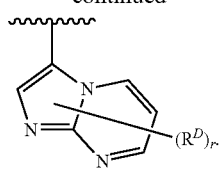
In certain embodiments, each $R^2$ together with its $R^D$ substituents is independently
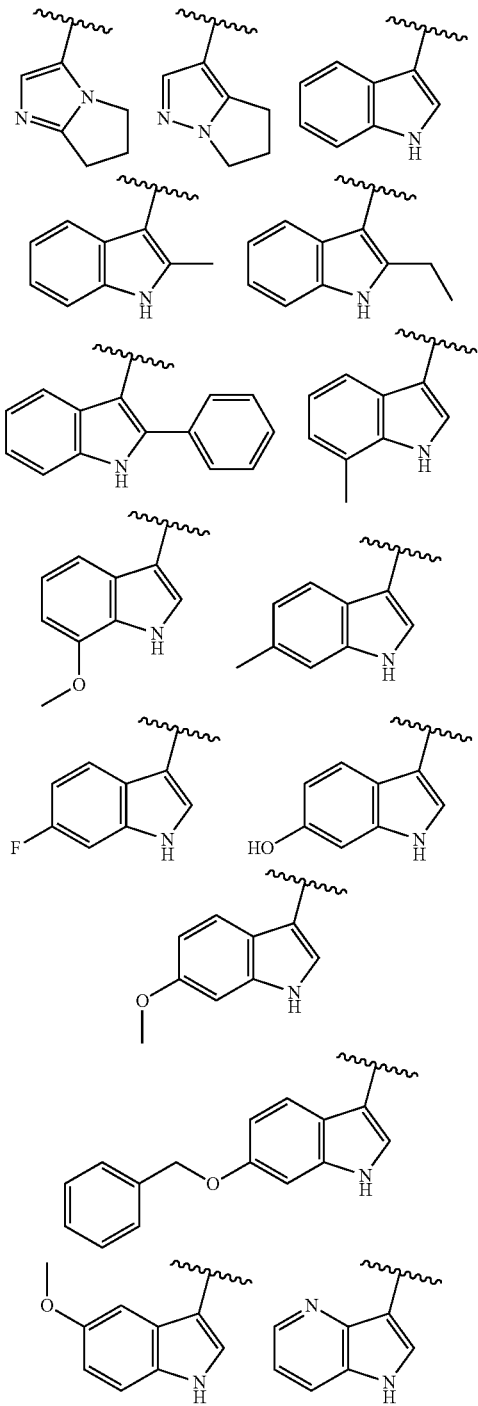
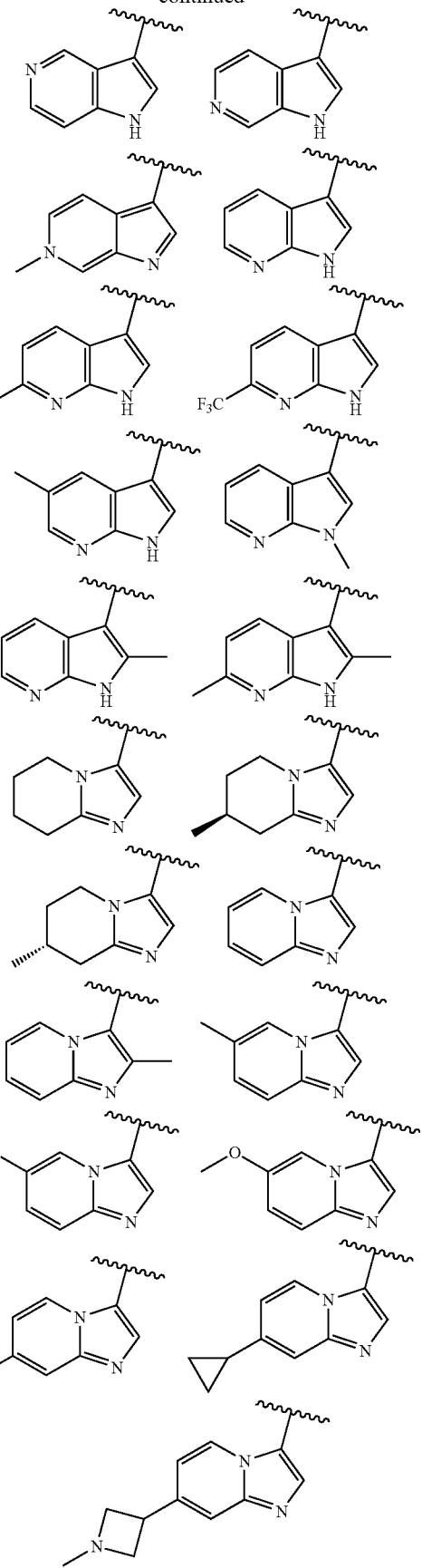

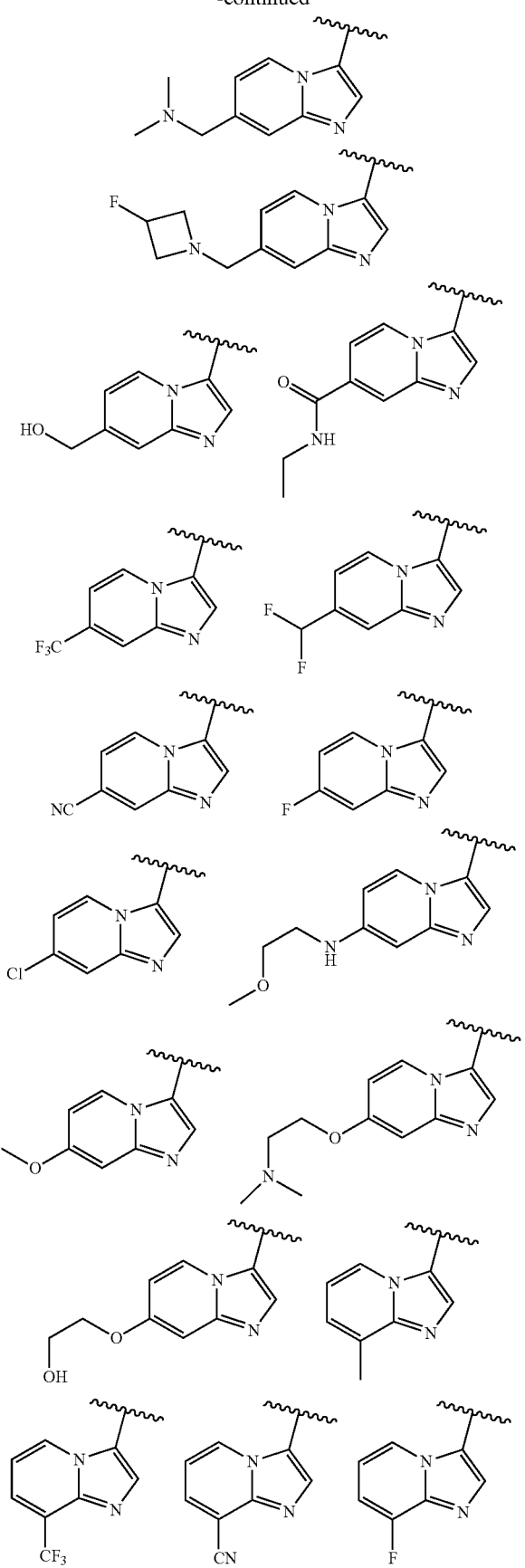
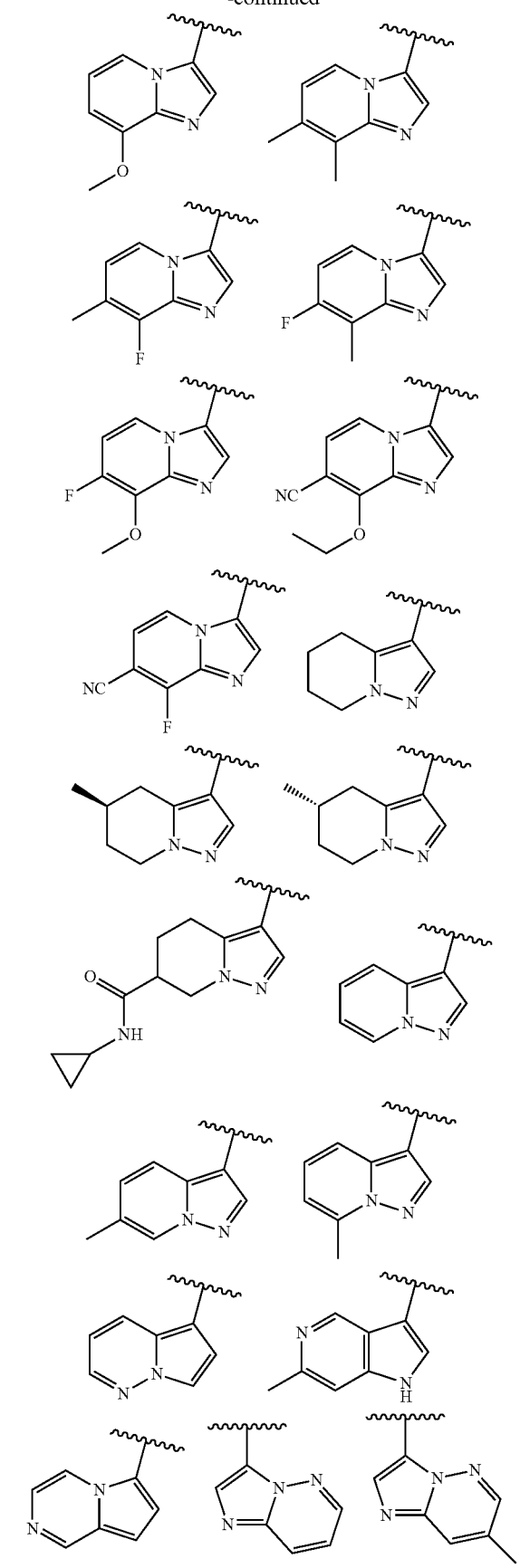

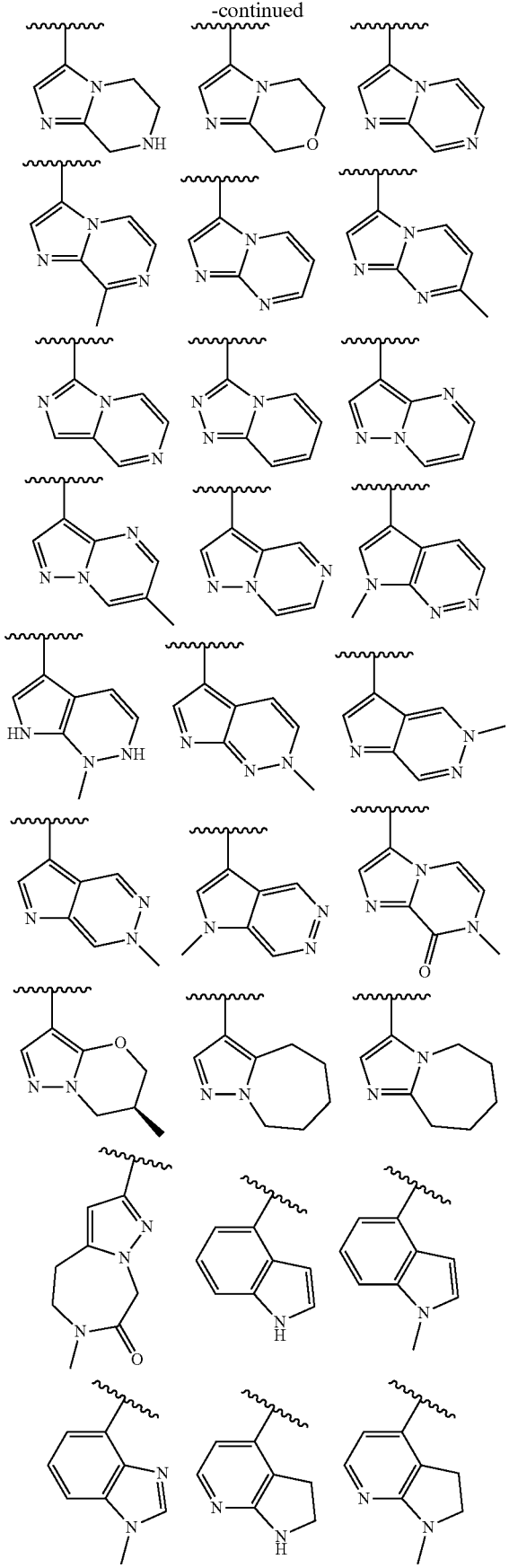
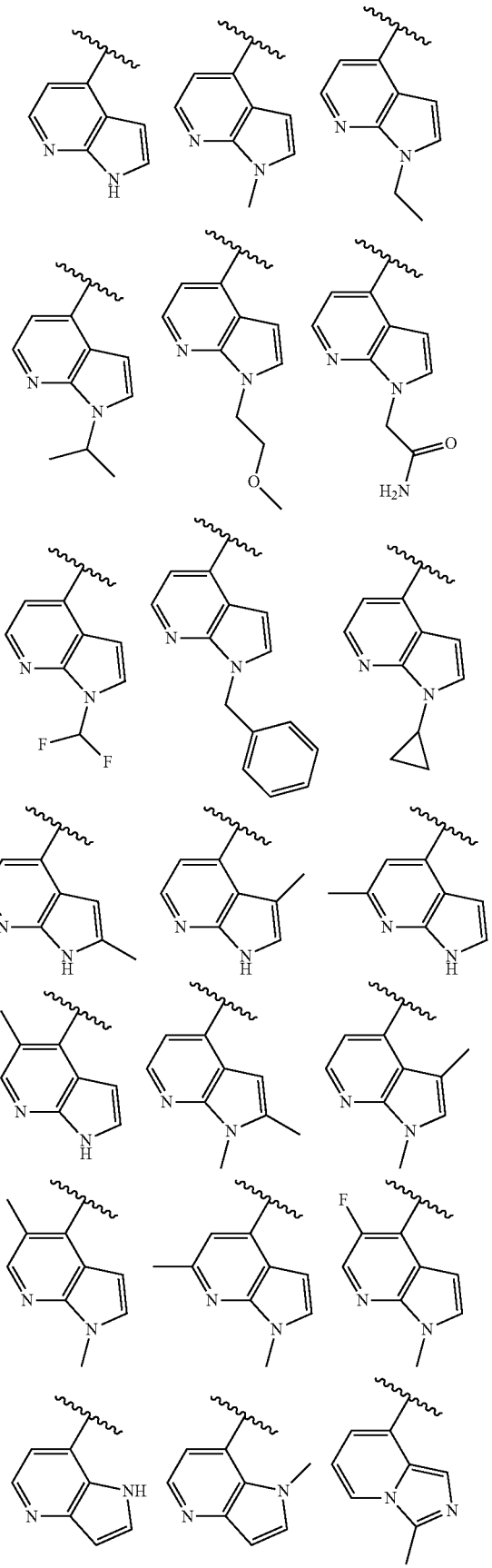

-continued

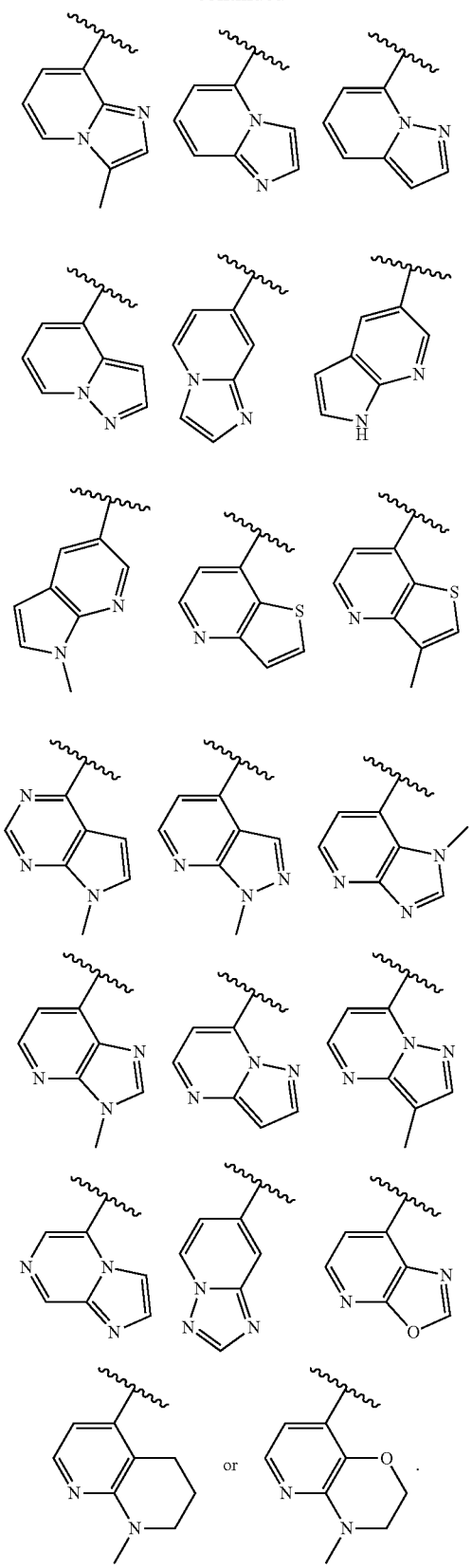
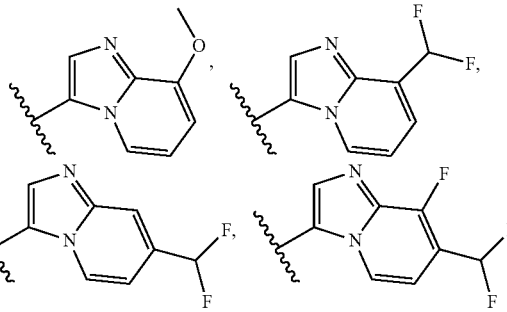
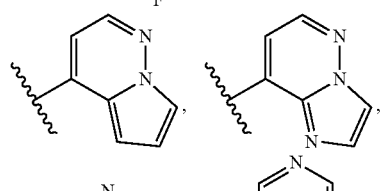
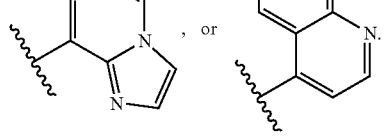

In certain embodiments, each R² together with its RP substituents is independently In some embodiments, each R² is independently selected from those depicted in Table 1, below.

In certain embodiments, each R³ is independently —H.

In certain embodiments, each R³ is independently —C₁₋₆ aliphatic, or -Phenyl; each of which is substituted with s instances of R^E; or each R³ is independently —CN, halogen, —OR, —SR, —NR₂, —S(O)₂R, —S(O)(NR)R, —S(O)₂NR₂, —S(O)R, —S(O)NR₂, —C(O)R, —C(O)OR, —C(O)NR₂, —C(O)N(R)OR, —OC(O)R, —OC(O)NR₂, —N(R)C(O)R, —N(R)C(O)OR, —N(R)C(O)NR₂, —N(R)C(NR)NR₂, —N(R)S(O)₂NR₂, or —N(R)S(O)₂R.

In certain embodiments, each R³ is independently —H, C₁₋₆ aliphatic, or -Phenyl; each of which is substituted with s instances of R^E; or each R³ is independently —CN, halogen, —OR, —SR, —NR₂, —S(O)₂R, —S(O)(NR)R, —S(O)₂NR₂, —S(O)R, —S(O)NR₂, —C(O)R, —C(O)OR, —C(O)NR₂, —C(O)N(R)OR, —OC(O)R, —OC(O)NR₂, —N(R)C(O)R, —N(R)C(O)OR, —N(R)C(O)NR₂, —N(R)C(NR)NR₂, —N(R)S(O)₂NR₂, or —N(R)S(O)₂R.

In certain embodiments, each R³ is independently —H, C₁₋₆ aliphatic, or -Phenyl; each of which is substituted with s instances of R^E; or each R³ is independently —CN, halogen, —OR, —NR₂, —C(O)R, —C(O)OR, —C(O)NR₂, —C(O)N(R)OR, —OC(O)R, —OC(O)NR₂, —N(R)C(O)R, —N(R)C(O)OR, —N(R)C(O)NR₂, —N(R)C(NR)NR₂, —N(R)S(O)₂NR₂, or —N(R)S(O)₂R.

In certain embodiments, each R³ is independently —H, C₁₋₆ aliphatic, or -Phenyl; each of which is substituted with s instances of R^E; or each R³ is independently —CN, halogen, —OR, —NR₂, —C(O)R, —C(O)OR, —C(O)NR₂, —C(O)N(R)OR, —OC(O)R, —OC(O)NR₂, —N(R)C(O)R, —N(R)C(O)OR, —N(R)C(O)NR₂, or —N(R)C(NR)NR₂.

In certain embodiments, each R³ is independently —H, C₁₋₆ aliphatic, or -Phenyl; each of which is substituted with s instances of $R^E$; or each $R^3$ is independently —CN, halogen, —C(O)R, —C(O)OR, —C(O)NR$_2$, or —C(O)N(R)OR.

In certain embodiments, each $R^3$ is independently —H, -Me, -Et, or -Phenyl; each of which is substituted with s instances of $R^E$; or each $R^3$ is independently —CN, halogen, or —C(O)OR.

In some embodiments, each $R^3$ is independently —H, -Me, -Et, —CN, —Br,

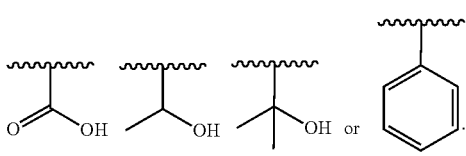

In some embodiments, each $R^3$ is independently selected from those depicted in Table 1, below.

In some embodiments, $R^4$ is H.

In some embodiments, $R^4$ is $C_{1-6}$ aliphatic which is substituted with t instances of R.

In some embodiments, $R^4$ is selected from those depicted in Table 1, below.

In some embodiments, each instance of $R^C$, $R^D$, $R^E$, and $R^F$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)NR$_2$, —N(R)S(O)$_2$NR$_2$, —N(R)S(O)$_2$R, —N=S(O)R$_2$, —S(NR)(O)R, —N(R)S(O)R, —N(R)CN, —P(O)(R)NR$_2$, —P(O)(R)OR or —P(O)R$_2$; or each instance of $R^C$, $R^D$, $R^E$, and $R^F$, is independently an optionally substituted group selected from $C_{1-6}$ aliphatic; phenyl; naphthalenyl; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, phosphorous, silicon and sulfur; or a 5-6 membered monocyclic heteroaryl ring having 1-4 heteroatoms independently selected from nitrogen, oxygen, and sulfur; an 8-10 membered bicyclic heteroaryl ring having 1-5 heteroatoms independently selected from nitrogen, oxygen, and sulfur; a 5-8 membered saturated or partially unsaturated bridged bicyclic ring having 0-3 heteroatoms independently selected from nitrogen, oxygen, and sulfur; a 6-10 membered saturated or partially unsaturated spirocyclic ring having 0-3 heteroatoms independently selected from nitrogen, oxygen, and sulfur; or a 6-11 membered saturated or partially unsaturated bicyclic heterocyclic ring having 1-2 heteroatoms independently selected from nitrogen, oxygen, and sulfur.

In some embodiments, each instance of $R^C$, $R^D$, $R^E$, and $R^F$ is oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)NR$_2$, —N(R)S(O)$_2$NR$_2$, —N(R)S(O)$_2$R, —N=S(O)R$_2$, —S(NR)(O)R, —N(R)S(O)R, —N(R)CN, —P(O)(R)NR$_2$, —P(O)(R)OR or —P(O)R$_2$.

In some embodiments, each instance of $R^C$, $R^D$, $R^E$, and $R^F$ is an optionally substituted group selected from $C_{1-6}$ aliphatic; phenyl; naphthalenyl; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, phosphorous, silicon and sulfur; or a 5-6 membered monocyclic heteroaryl ring having 1-4 heteroatoms independently selected from nitrogen, oxygen, and sulfur; an 8-10 membered bicyclic heteroaryl ring having 1-5 heteroatoms independently selected from nitrogen, oxygen, and sulfur; a 5-8 membered saturated or partially unsaturated bridged bicyclic ring having 0-3 heteroatoms independently selected from nitrogen, oxygen, and sulfur; a 6-10 membered saturated or partially unsaturated spirocyclic ring having 0-3 heteroatoms independently selected from nitrogen, oxygen, and sulfur; or a 6-11 membered saturated or partially unsaturated bicyclic heterocyclic ring having 1-2 heteroatoms independently selected from nitrogen, oxygen, and sulfur.

In some embodiments, each instance of $R^C$, $R^D$, $R^E$, and $R^F$ is selected from those depicted in Table 1, below.

As defined generally above, each R is independently hydrogen, or an optionally substituted group selected from $C_{1-6}$ aliphatic; phenyl; naphthalenyl; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, and sulfur; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 7-12 membered saturated or partially unsaturated bicyclic heterocyclic ring having 1-4 heteroatoms independently selected from nitrogen, oxygen, and sulfur; a 5-8 membered saturated or partially unsaturated bridged bicyclic ring having 0-3 heteroatoms independently selected from nitrogen, oxygen, and sulfur; a 6-10 membered saturated or partially unsaturated spirocyclic ring having 0-3 heteroatoms independently selected from nitrogen, oxygen, and sulfur; a 6-11 membered saturated or partially unsaturated bicyclic heterocyclic ring having 1-2 heteroatoms independently selected from nitrogen, oxygen, and sulfur; or:

two R groups on the same nitrogen are taken together with the nitrogen to form an optionally substituted 4-7 membered monocyclic saturated, partially unsaturated, or heteroaryl ring having, in addition to the nitrogen, 0-3 heteroatoms independently selected from nitrogen, oxygen, and sulfur; an 8-10 membered bicyclic heteroaryl ring having 1-4 heteroatoms independently selected from nitrogen, oxygen, and sulfur; a 7-12 membered saturated or partially unsaturated bicyclic heterocyclic ring having 1-4 heteroatoms independently selected from nitrogen, oxygen, and sulfur.

In some embodiments, R is selected from those depicted in Table 1, below.

As defined generally above, m is 1, 2, or 3. In some embodiments, m is 1. In some embodiments, m is 2. In some embodiments, m is 3.

In some embodiments, m is selected from those depicted in Table 1, below.

As defined generally above, n is 0, 1, or 2. In some embodiments, n is 0. In some embodiments, n is 1. In some embodiments, n is 2.

In some embodiments, n is selected from those depicted in Table 1, below.

As defined generally above, q is 0, 1, 2, 3, or 4. In some embodiments, q is 0. In some embodiments, q is 1, 2, 3, or 4. In some embodiments, q is 1. In some embodiments, q is 2. In some embodiments, q is 3. In some embodiments, q is 4.

In some embodiments, q is selected from those depicted in Table 1, below.

As defined generally above, r is 0, 1, 2, 3, or 4. In some embodiments, r is 0. In some embodiments, r is 1, 2, 3, or 4. In some embodiments, r is 1. In some embodiments, r is 2. In some embodiments, r is 3. In some embodiments, r is 4.

In some embodiments, r is selected from those depicted in Table 1, below.

As defined generally above, s is 0, 1, 2, 3, or 4. In some embodiments, s is 0. In some embodiments, s is 1, 2, 3, or 4. In some embodiments, s is 1. In some embodiments, s is 2. In some embodiments, s is 3. In some embodiments, s is 4.

In some embodiments, s is selected from those depicted in Table 1, below.

As defined generally above, t is 0, 1, 2, 3, or 4. In some embodiments, t is 0. In some embodiments, t is 1, 2, 3, or 4. In some embodiments, t is 1. In some embodiments, t is 2. In some embodiments, t is 3. In some embodiments, t is 4.

In some embodiments, t is selected from those depicted in Table 1, below.

As defined generally above, u is 0, 1, 2, 3, or 4. In some embodiments, u is 0. In some embodiments, u is 1, 2, 3, or 4. In some embodiments, u is 1. In some embodiments, u is 2. In some embodiments, u is 3. In some embodiments, u is 4.

In some embodiments, u is selected from those depicted in Table 1, below.

In some embodiments, the present invention provides a compound of formula II, III, IV, V, VI, VII, VIII, IX, X, or XI:

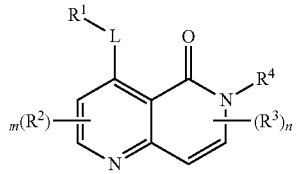

II

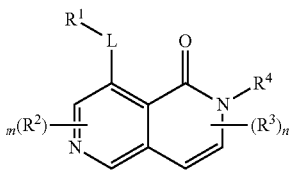

III

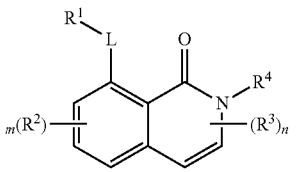

IV

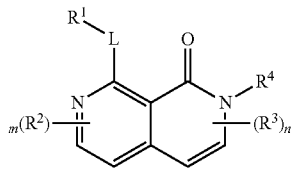

V

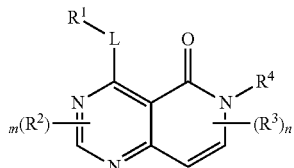

VI

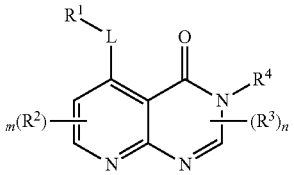

VII

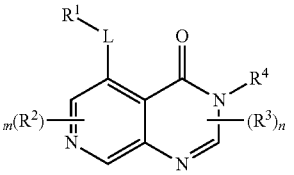

VIII

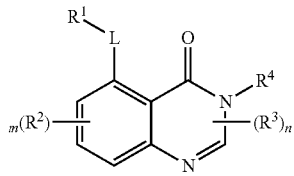

IX

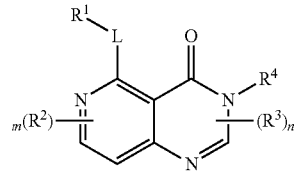

X

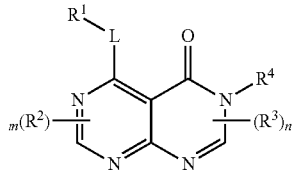

XI or a pharmaceutically acceptable salt thereof, wherein each of L, $R^1$, $R^2$, $R^3$, $R^4$, m and n is as defined above and described in embodiments herein, both singly and in combination.

In some embodiments, the present invention provides a compound of formula II-a, III-a, IV-a, V-a, VI-a, VII-a, VIII-a, IX-a, X-a or XI-a:

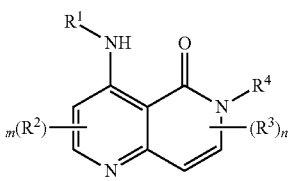

II-a

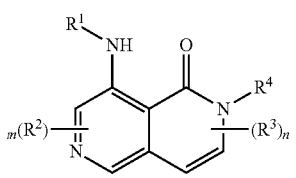
III-a
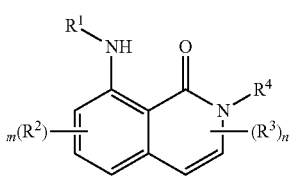
IV-a
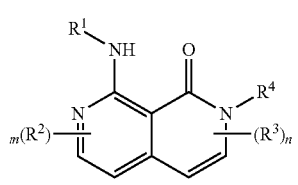
V-a
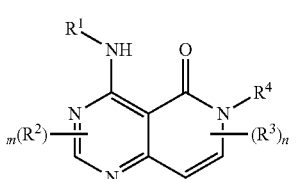
VI-a
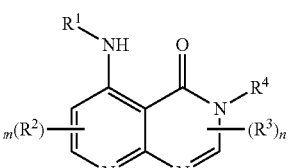
VII-a
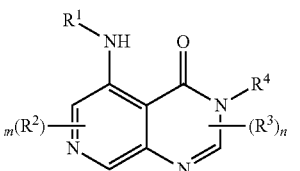
VIII-a
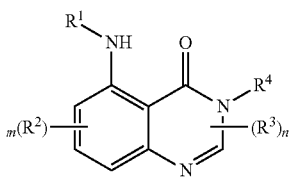
IX-a
X-a
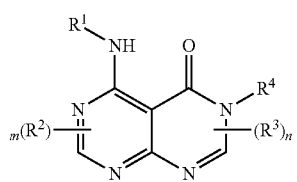
XI-a
or a pharmaceutically acceptable salt thereof, wherein each of $R^1$, $R^2$, $R^3$, $R^4$, m and n is as defined above and described in embodiments herein, both singly and in combination.
In some embodiments, the present invention provides a compound of formula II-b, III-b, IV-b, V-b, VI-b, VII-b, VIII-b, IX-b, X-b, or XI-b:
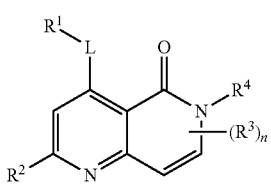
II-b
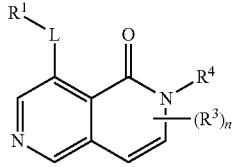
III-b
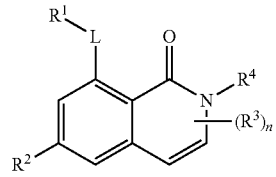
IV-b
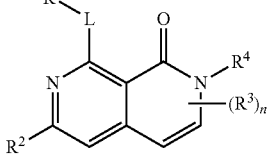
V-b
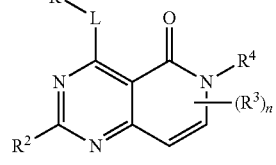
VI-b
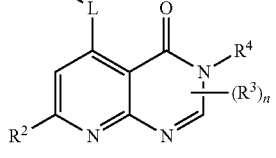
VII-b

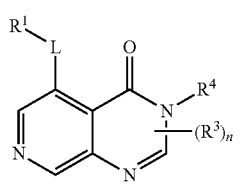
VIII-b
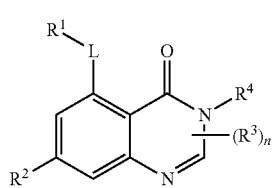
IX-b
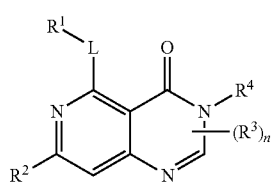
X-b
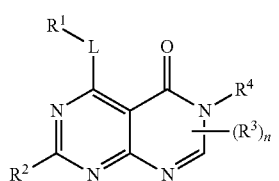
XI-b
or a pharmaceutically acceptable salt thereof, wherein each of L, $R^1$, $R^2$, $R^3$, $R^4$, and m is as defined above and described in embodiments herein, both singly and in combination.
In some embodiments, the present invention provides a compound of formula II-c, III-c, IV-c, V-c, VI-c, VII-c, VIII-c, IX-c, X-c, or XI-c:
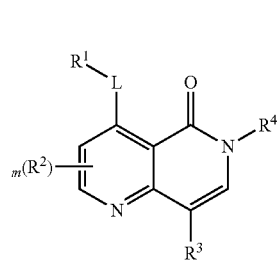
II-c
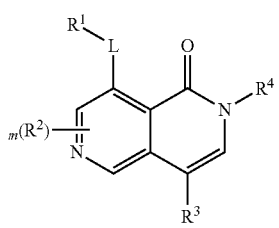
III-c
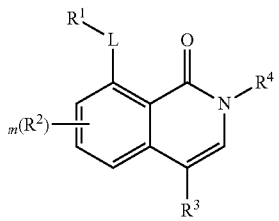
IV-c
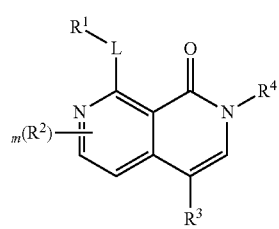
V-c
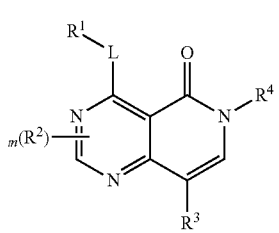
VI-c
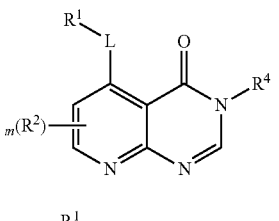
VII-c
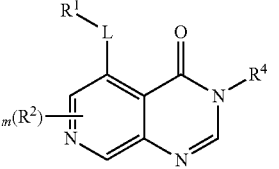
VIII-c
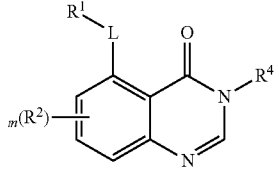
IX-c
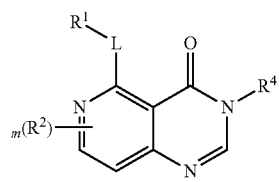
X-c
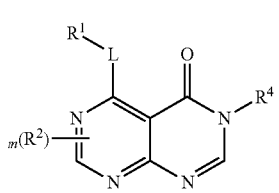
XI-c or a pharmaceutically acceptable salt thereof, wherein each of L, $R^1$, $R^2$, $R^3$, $R^4$, and m is as defined above and described in embodiments herein, both singly and in combination.
Exemplary compounds of the invention are set forth in Table 1, below.
TABLE 1
Selected Compounds
| STRUCTURE | STRUCTURE |
|---|---|
| I-1 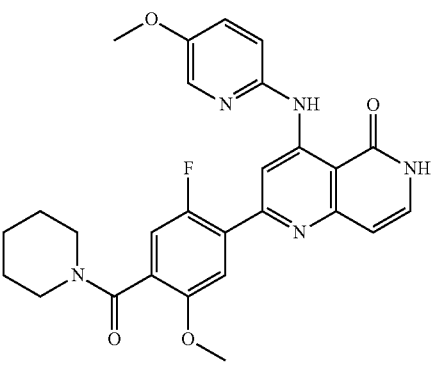 [SMILES: COc1ccc(Nc2cc(-c3cc(OC)c(C(=O)N4CCCCC4)cc3F)nc3cc[nH]c(=O)c23)nc1] | I-2 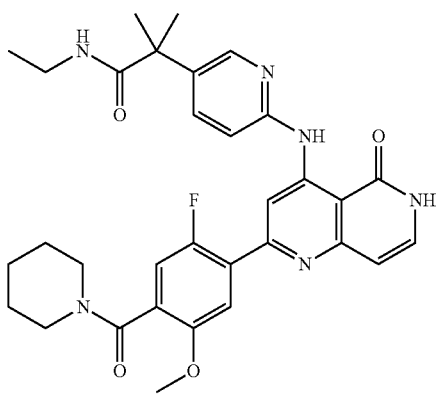 [SMILES: CCNC(=O)C(C)(C)c1ccc(Nc2cc(-c3cc(OC)c(C(=O)N4CCCCC4)cc3F)nc3cc[nH]c(=O)c23)nc1] |
| I-3 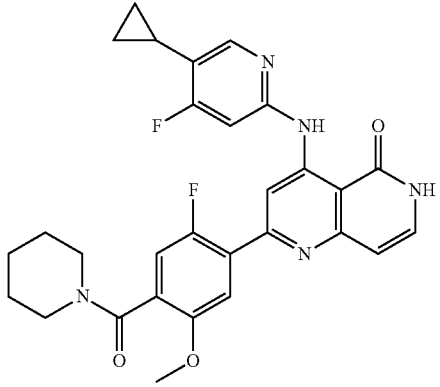 [SMILES: COc1cc(-c2cc(Nc3cc(F)c(C4CC4)cn3)c3c(=O)[nH]ccc3n2)c(F)cc1C(=O)N1CCCCC1] | I-4 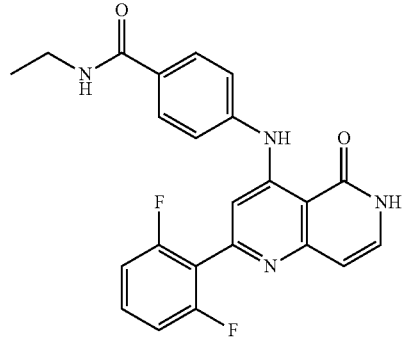 [SMILES: CCNC(=O)c1ccc(Nc2cc(-c3c(F)cccc3F)nc3cc[nH]c(=O)c23)cc1] |
| I-5 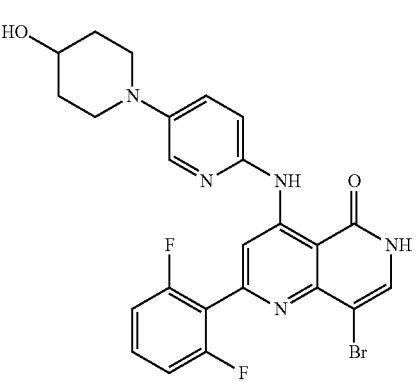 | I-6 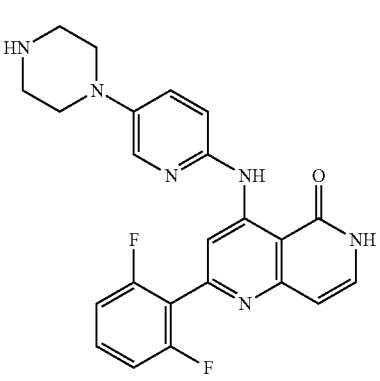 [SMILES: O=c1[nH]ccc2nc(-c3c(F)cccc3F)cc(Nc3ccc(N4CCNCC4)cn3)c12] |

TABLE 1-continued
Selected Compounds
| STRUCTURE | STRUCTURE |
|---|---|
| I-7 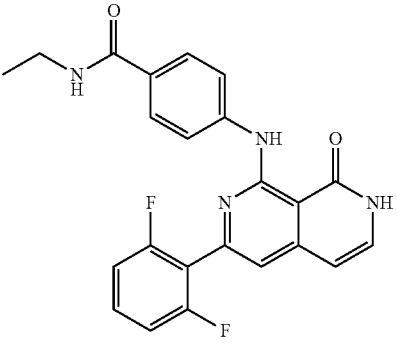 [SMILES: CCNC(=O)c1ccc(Nc2nc(-c3c(F)cccc3F)cc3cc[nH]c(=O)c23)cc1] | I-8 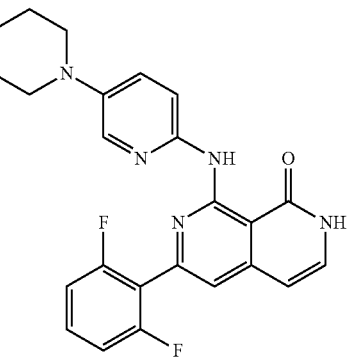 |
| I-9 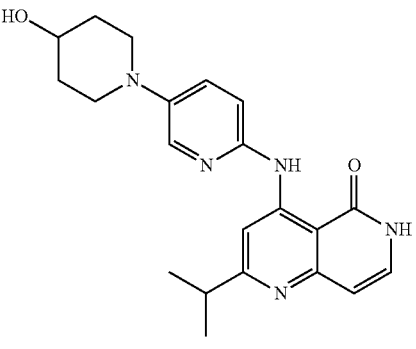 [SMILES: CC(C)c1cc(Nc2ccc(N3CCC(O)CC3)cn2)c2c(=O)[nH]ccc2n1] | I-10 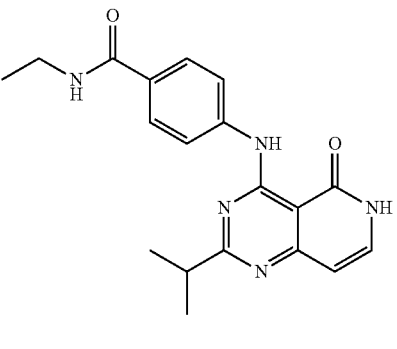 [SMILES: CCNC(=O)c1ccc(Nc2nc(C(C)C)nc3cc[nH]c(=O)c23)cc1] |
| I-11 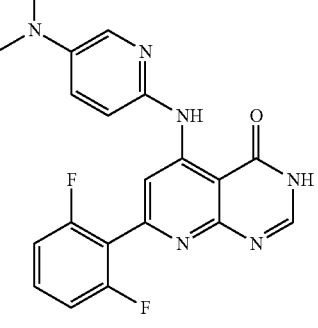 | I-12 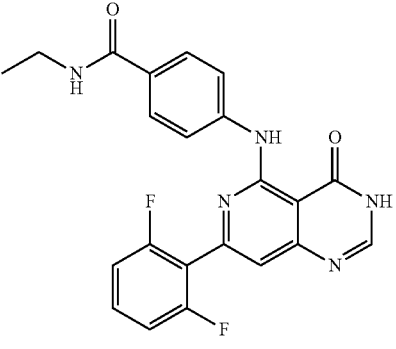 |
| I-13 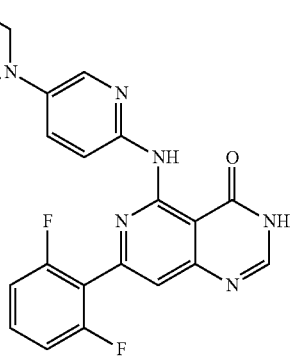 | I-14 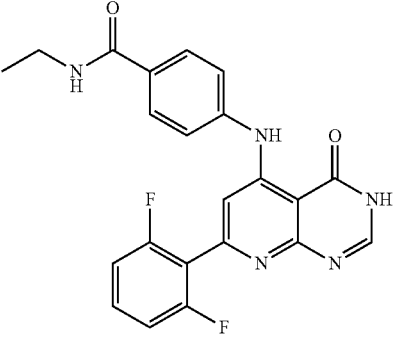 [SMILES: CCNC(=O)c1ccc(Nc2cc(-c3c(F)cccc3F)nc3nc[nH]c(=O)c23)cc1] |

TABLE 1-continued

Selected Compounds

| ID | STRUCTURE | ID | STRUCTURE |
|---|---|---|---|
| I-15 | (chemical structure) | I-16 | (chemical structure) |
| I-17 | (chemical structure) | I-18 | (chemical structure) |
| I-19 | (chemical structure) | I-20 | (chemical structure) |
| I-21 | (chemical structure) | I-22 | (chemical structure) |

TABLE 1-continued

Selected Compounds

| STRUCTURE | STRUCTURE |
| --- | --- |
| I-23 | I-24 |
| I-25 | I-26 |
| I-27 | I-28 |
| I-29 | I-30 |

TABLE 1-continued
Selected Compounds
| STRUCTURE | STRUCTURE |
|---|---|
| I-31 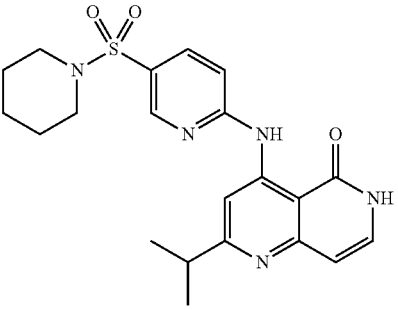 [SMILES: CC(C)c1cc(Nc2ccc(S(=O)(=O)N3CCCCC3)cn2)c2c(=O)[nH]ccc2n1] | I-32 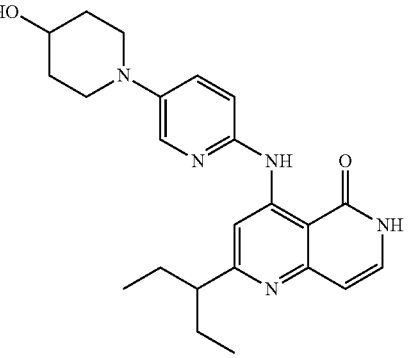 |
| I-33 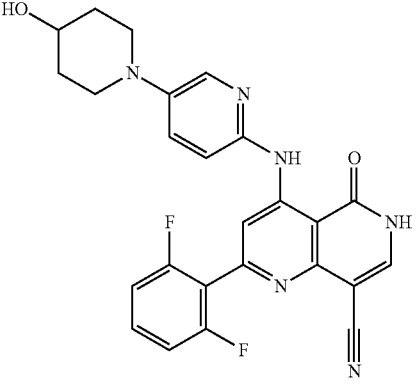 | I-34 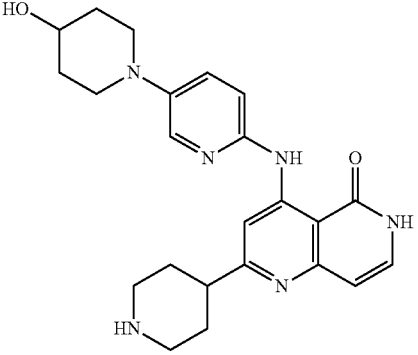 [SMILES: O=c1[nH]ccc2nc(C3CCNCC3)cc(Nc3ccc(N4CCC(O)CC4)cn3)c12] |
| I-35 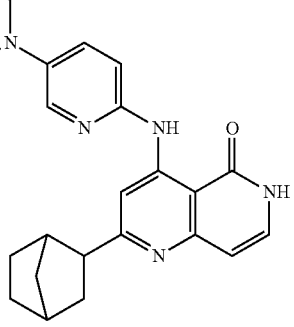 | I-36 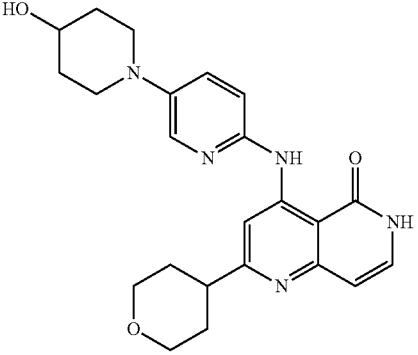 |
| I-37 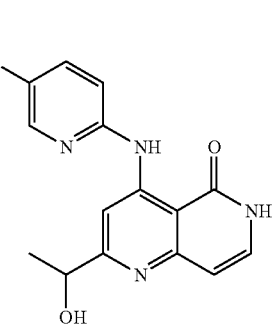 | I-38 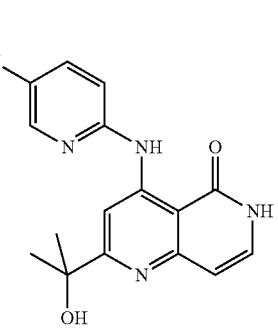 |

TABLE 1-continued

Selected Compounds

| STRUCTURE | STRUCTURE |
|---|---|
| I-39 | I-40 |
| I-41 | I-42 |
| I-43 | I-44 |

TABLE 1-continued

Selected Compounds

| STRUCTURE | STRUCTURE |
|---|---|
| I-45 | I-46 |
| I-47 | I-48 |
| I-49 | I-50 |

TABLE 1-continued

Selected Compounds

| STRUCTURE | STRUCTURE |
|---|---|
| I-51 | I-52 |
| I-53 | I-54 |
| I-55 | I-56 |

TABLE 1-continued

Selected Compounds

| STRUCTURE | STRUCTURE |
|---|---|
| I-57 | I-58 |
| I-59 | I-60 |
| I-61 | I-62 |

TABLE 1-continued

Selected Compounds

| | STRUCTURE | | STRUCTURE |
|---|---|---|---|
| I-63 | 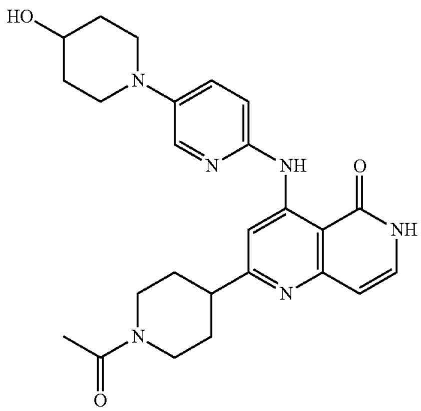 [SMILES: CC(=O)N1CCC(c2cc(Nc3ccc(N4CCC(O)CC4)cn3)c3c(=O)[nH]ccc3n2)CC1] | I-64 | 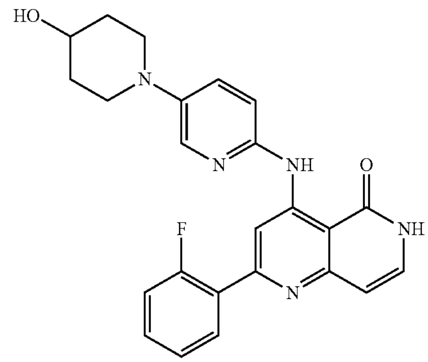 |
| I-65 | 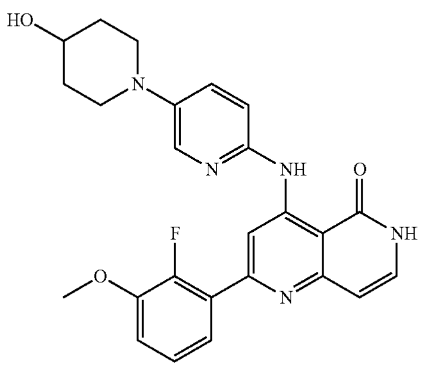 | I-66 | 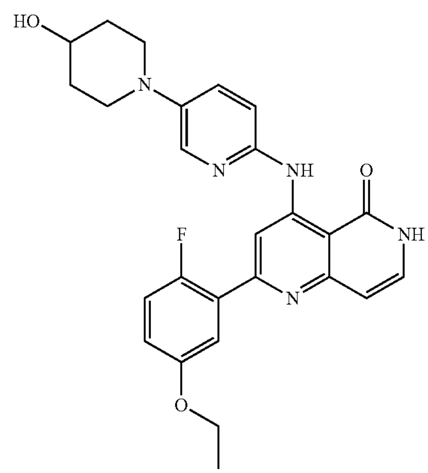 |
| I-67 | 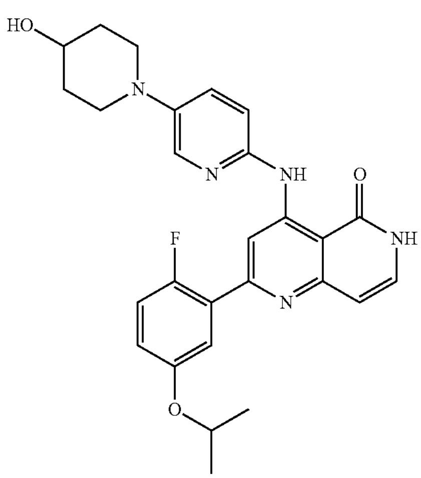 | I-68 | 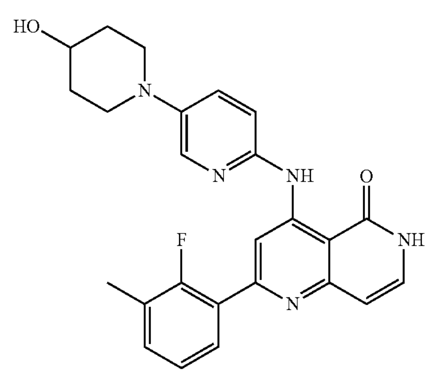 |

TABLE 1-continued

Selected Compounds

| | STRUCTURE | | STRUCTURE |
|---|---|---|---|
| I-69 | 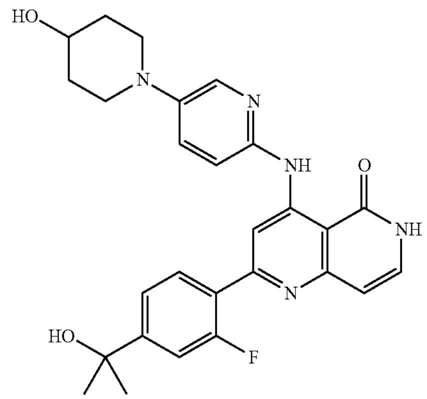 [SMILES: CC(C)(O)c1ccc(-c2cc(Nc3ccc(N4CCC(O)CC4)cn3)c3c(=O)[nH]ccc3n2)c(F)c1] | I-70 | 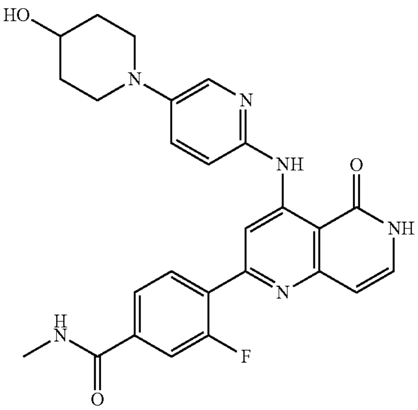 [SMILES: CNC(=O)c1ccc(-c2cc(Nc3ccc(N4CCC(O)CC4)cn3)c3c(=O)[nH]ccc3n2)c(F)c1] |
| I-71 | 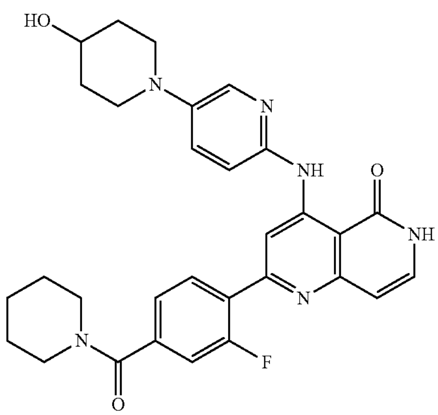 [SMILES: O=C(c1ccc(-c2cc(Nc3ccc(N4CCC(O)CC4)cn3)c3c(=O)[nH]ccc3n2)c(F)c1)N1CCCCC1] | I-72 | 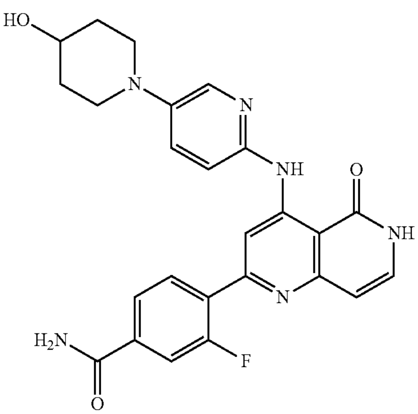 [SMILES: NC(=O)c1ccc(-c2cc(Nc3ccc(N4CCC(O)CC4)cn3)c3c(=O)[nH]ccc3n2)c(F)c1] |
| I-73 | 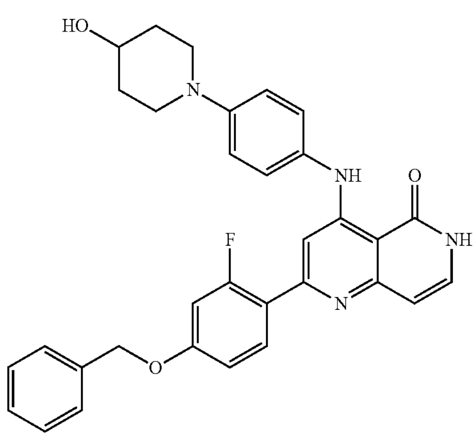 [SMILES: O=c1[nH]ccc2nc(-c3ccc(OCc4ccccc4)cc3F)cc(Nc3ccc(N4CCC(O)CC4)cc3)c12] | I-74 | 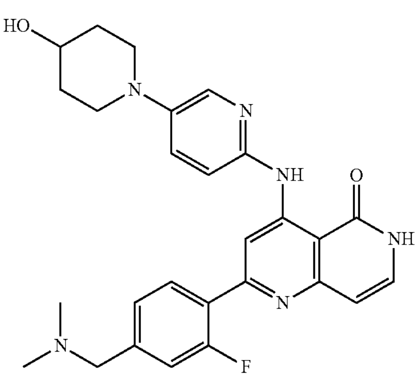 [SMILES: CN(C)Cc1ccc(-c2cc(Nc3ccc(N4CCC(O)CC4)cn3)c3c(=O)[nH]ccc3n2)c(F)c1] |

TABLE 1-continued

Selected Compounds

| STRUCTURE | STRUCTURE |
| --- | --- |
| I-75 | I-76 |
| I-77 | I-78 |
| I-79 | I-80 |

TABLE 1-continued

Selected Compounds

| STRUCTURE | STRUCTURE |
| --- | --- |
| I-81 | I-82 |
| I-83 | I-84 |
| I-85 | I-86 |
| I-87 | I-88 |

TABLE 1-continued

Selected Compounds

| | STRUCTURE | | STRUCTURE |
|---|---|---|---|
| I-89 | | I-90 | |
| I-91 | | I-92 | |
| I-93 | | I-94 | |

TABLE 1-continued

Selected Compounds

| STRUCTURE | STRUCTURE |
|---|---|
| I-95 | I-96 |
| I-97 | I-98 |
| I-99 | I-100 |

TABLE 1-continued

Selected Compounds

| STRUCTURE | STRUCTURE |
| --- | --- |
| I-101 | I-102 |
| I-103 | I-104 |
| I-105 | I-106 |

TABLE 1-continued
Selected Compounds
| STRUCTURE | STRUCTURE |
|---|---|
| I-107 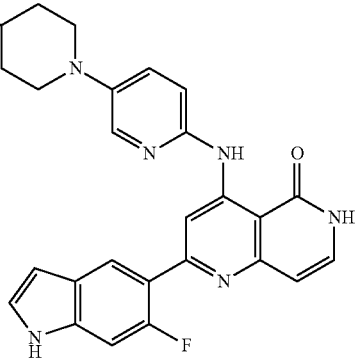 | I-108 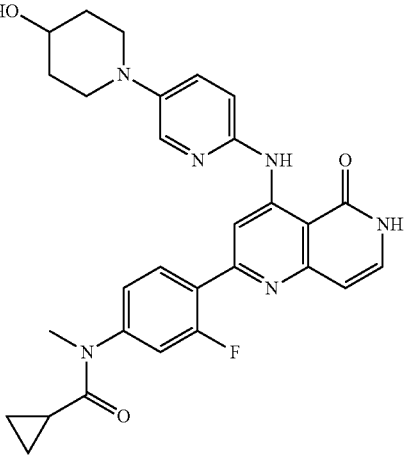 |
| I-109 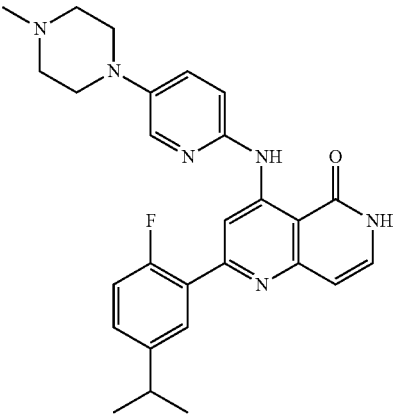 [SMILES: CC(C)c1ccc(F)c(-c2cc(Nc3ccc(N4CCN(C)CC4)cn3)c3c(=O)[nH]ccc3n2)c1] | I-110 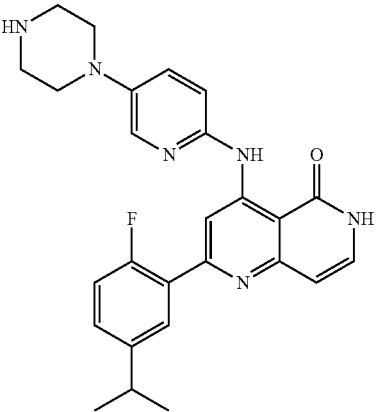 [SMILES: CC(C)c1ccc(F)c(-c2cc(Nc3ccc(N4CCNCC4)cn3)c3c(=O)[nH]ccc3n2)c1] |
| I-111 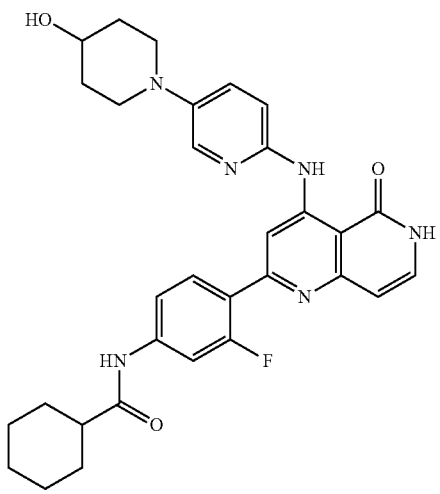 [SMILES: O=C(Nc1ccc(-c2cc(Nc3ccc(N4CCC(O)CC4)cn3)c3c(=O)[nH]ccc3n2)c(F)c1)C1CCCCC1] | I-112 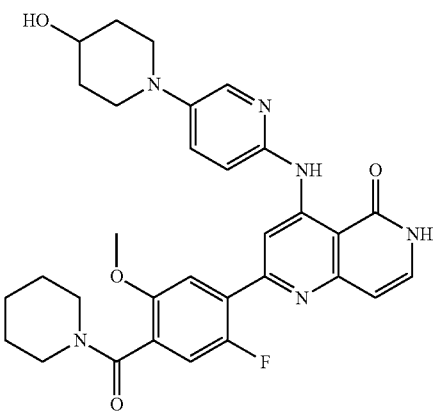 [SMILES: COc1cc(-c2cc(Nc3ccc(N4CCC(O)CC4)cn3)c3c(=O)[nH]ccc3n2)c(F)cc1C(=O)N1CCCCC1] |

TABLE 1-continued

Selected Compounds

| STRUCTURE | STRUCTURE |
|---|---|
| I-113 | I-114 |
| I-115 | I-116 |
| I-117 | I-118 |

TABLE 1-continued
Selected Compounds
| STRUCTURE | STRUCTURE |
|---|---|
| I-119 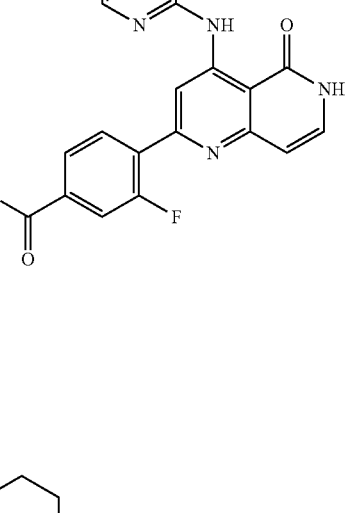 | I-120 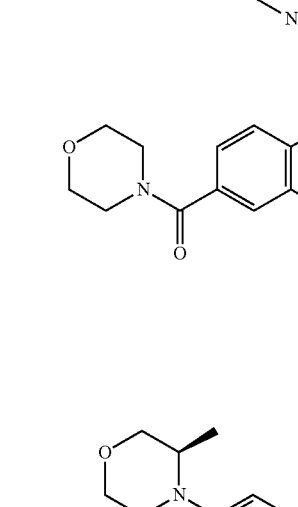 |
| I-121 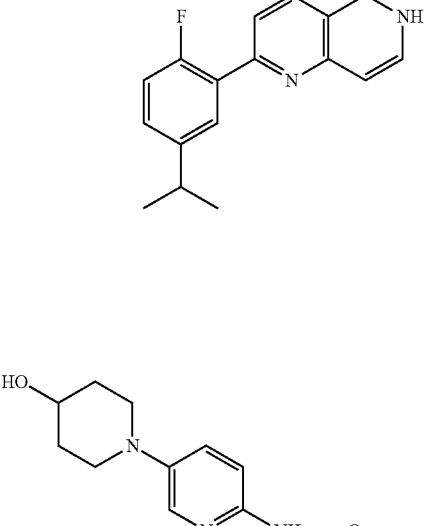 | I-122 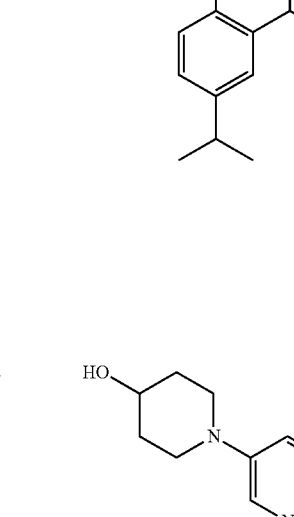 |
| I-123 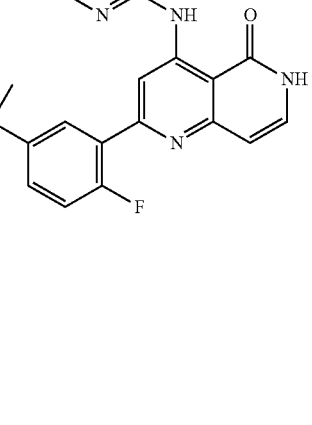 | I-124 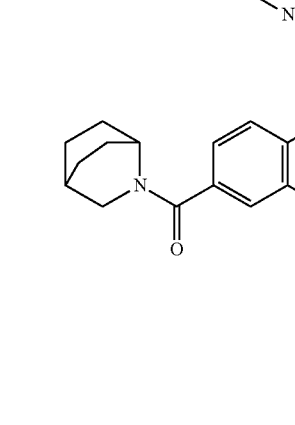 |

TABLE 1-continued
Selected Compounds
| STRUCTURE | STRUCTURE |
|---|---|
| I-125 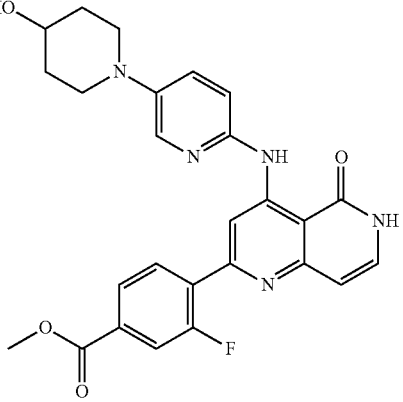 | I-126 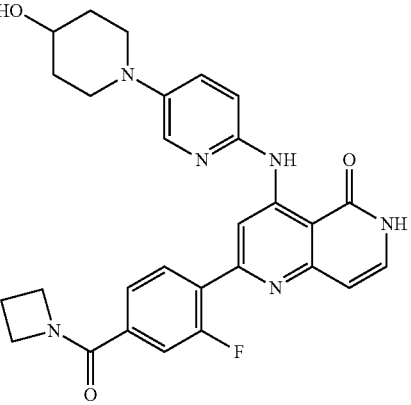 |
| I-127 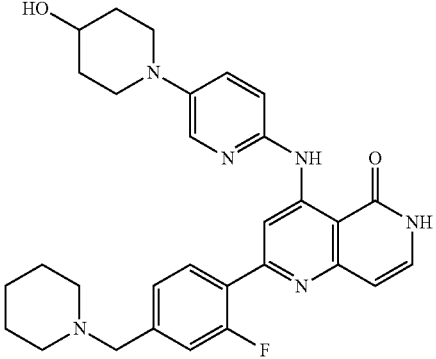 [SMILES: O=c1[nH]ccc2nc(-c3ccc(CN4CCCCC4)cc3F)cc(Nc3ccc(N4CCC(O)CC4)cn3)c12] | I-128 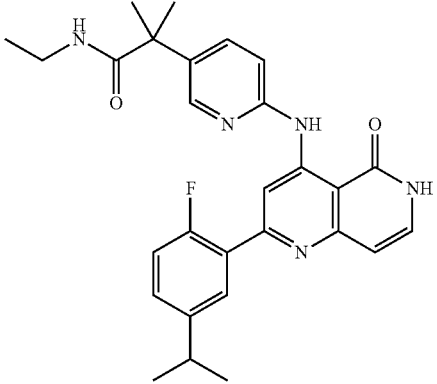 [SMILES: CCNC(=O)C(C)(C)c1ccc(Nc2cc(-c3cc(C(C)C)ccc3F)nc3cc[nH]c(=O)c23)nc1] |
| I-129 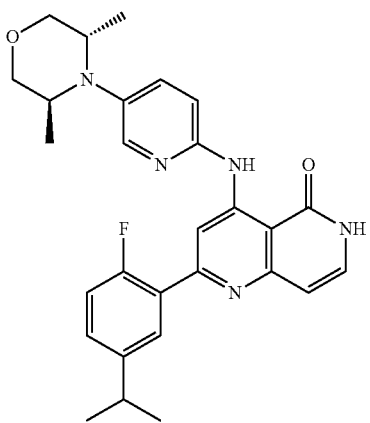 [SMILES: CC(C)c1ccc(F)c(-c2cc(Nc3ccc(N4[C@@H](C)COC[C@@H]4C)cn3)c3c(=O)[nH]ccc3n2)c1] | I-130 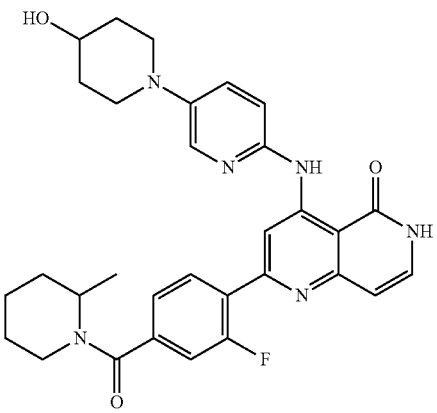 [SMILES: CC1CCCCN1C(=O)c1ccc(-c2cc(Nc3ccc(N4CCC(O)CC4)cn3)c3c(=O)[nH]ccc3n2)c(F)c1] |

TABLE 1-continued

Selected Compounds

| STRUCTURE | STRUCTURE |
|---|---|
| I-131 | I-132 |
| I-133 | I-134 |
| I-135 | I-136 |

TABLE 1-continued

Selected Compounds

| | STRUCTURE | | STRUCTURE |
|---|---|---|---|
| I-137 | 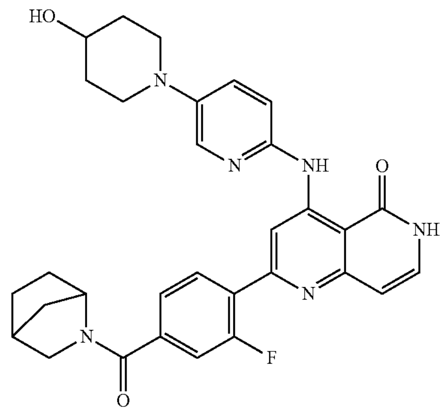 [SMILES: O=C(c1ccc(-c2cc(Nc3ccc(N4CCC(O)CC4)cn3)c3c(=O)[nH]ccc3n2)c(F)c1)N1CC2CCC1C2] | I-138 | 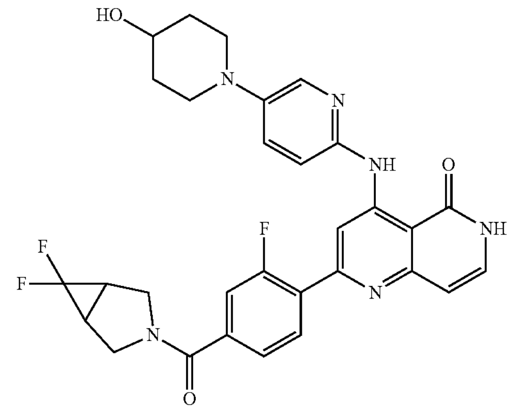 [SMILES: O=C(c1ccc(-c2cc(Nc3ccc(N4CCC(O)CC4)cn3)c3c(=O)[nH]ccc3n2)c(F)c1)N1CC2C(C1)C2(F)F] |
| I-139 | 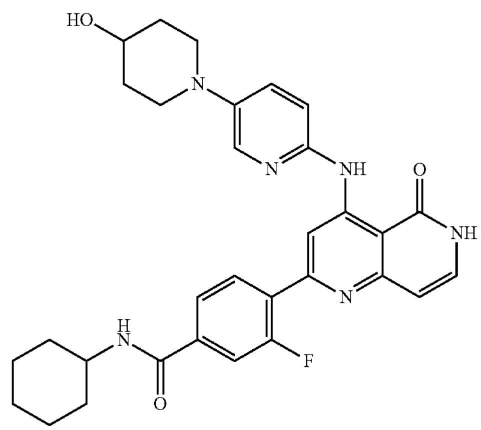 [SMILES: O=C(NC1CCCCC1)c1ccc(-c2cc(Nc3ccc(N4CCC(O)CC4)cn3)c3c(=O)[nH]ccc3n2)c(F)c1] | I-140 | 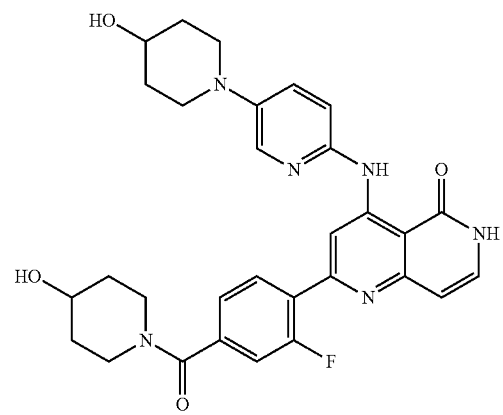 [SMILES: O=C(c1ccc(-c2cc(Nc3ccc(N4CCC(O)CC4)cn3)c3c(=O)[nH]ccc3n2)c(F)c1)N1CCC(O)CC1] |
| I-141 | 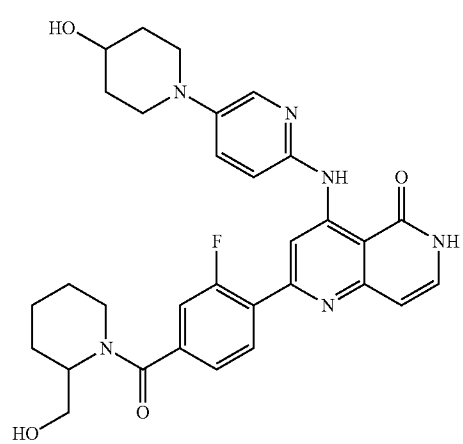 | I-142 | 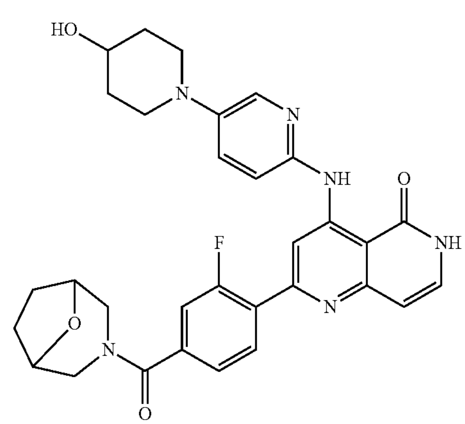 [SMILES: O=C(c1ccc(-c2cc(Nc3ccc(N4CCC(O)CC4)cn3)c3c(=O)[nH]ccc3n2)c(F)c1)N1CC2CCC(C1)O2] |

TABLE 1-continued

Selected Compounds

| STRUCTURE | STRUCTURE |
|---|---|
| I-143 | I-144 |
| I-145 | I-146 |
| I-147 | I-148 |

TABLE 1-continued

Selected Compounds

| STRUCTURE | STRUCTURE |
| --- | --- |
| I-149 | I-150 |
| I-151 | I-152 |
| I-153 | I-154 |

TABLE 1-continued

Selected Compounds

| STRUCTURE | STRUCTURE |
|---|---|
| I-155 | I-156 |
| I-157 | I-158 |
| I-159 | I-160 |

TABLE 1-continued
Selected Compounds
| STRUCTURE | STRUCTURE |
|---|---|
| I-161 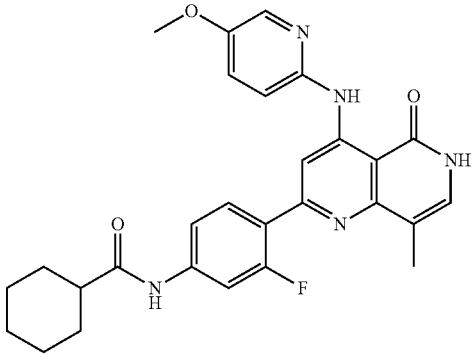 [SMILES: COc1ccc(Nc2cc(-c3ccc(NC(=O)C4CCCCC4)cc3F)nc3c(C)c[nH]c(=O)c23)nc1] | I-162 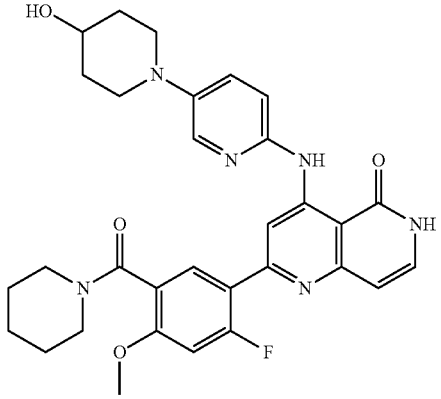 [SMILES: COc1cc(F)c(-c2cc(Nc3ccc(N4CCC(O)CC4)cn3)c3c(=O)[nH]ccc3n2)cc1C(=O)N1CCCCC1] |
| I-163 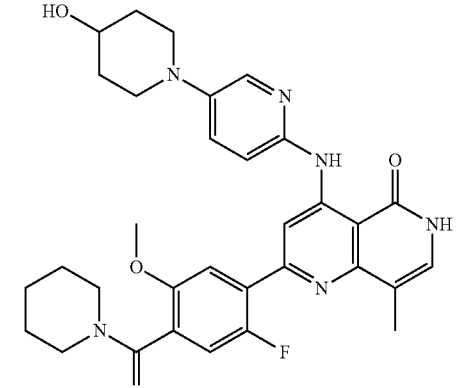 | I-164 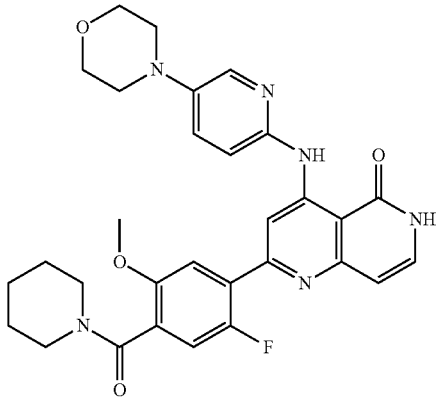 [SMILES: COc1cc(-c2cc(Nc3ccc(N4CCOCC4)cn3)c3c(=O)[nH]ccc3n2)c(F)cc1C(=O)N1CCCCC1] |
| I-165 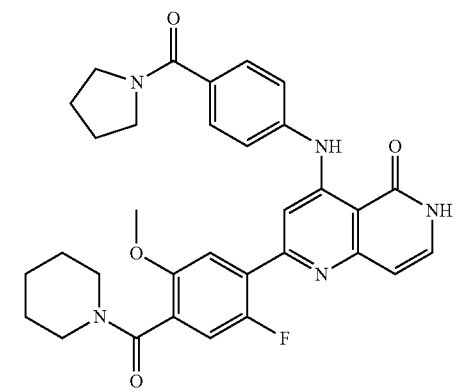 [SMILES: COc1cc(-c2cc(Nc3ccc(C(=O)N4CCCC4)cc3)c3c(=O)[nH]ccc3n2)c(F)cc1C(=O)N1CCCCC1] | I-166 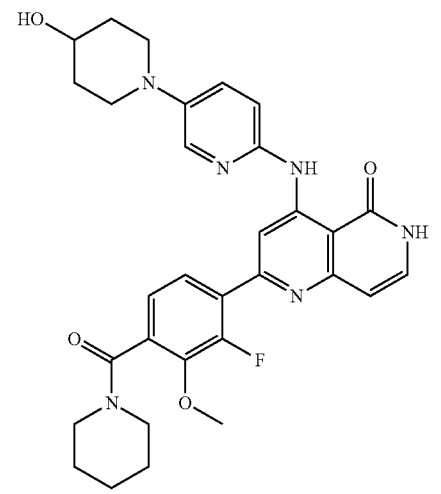 [SMILES: COc1c(C(=O)N2CCCCC2)ccc(-c2cc(Nc3ccc(N4CCC(O)CC4)cn3)c3c(=O)[nH]ccc3n2)c1F] |

TABLE 1-continued
Selected Compounds
| STRUCTURE | STRUCTURE |
|---|---|
| I-167 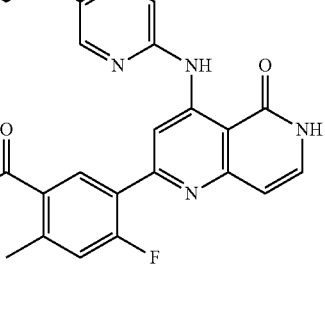 | I-168 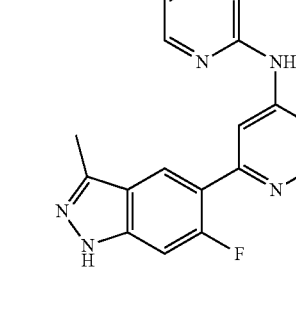 |
| I-169 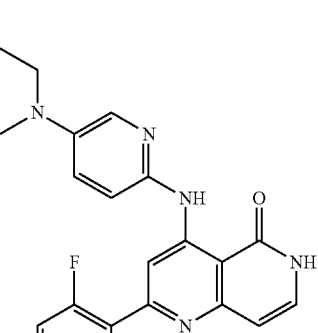 | I-170 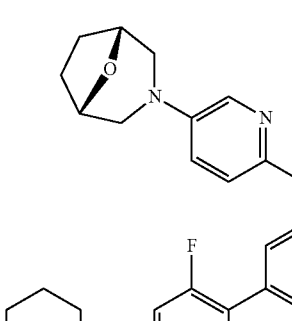 |
| I-171 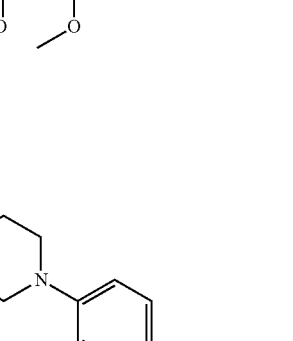 | I-172 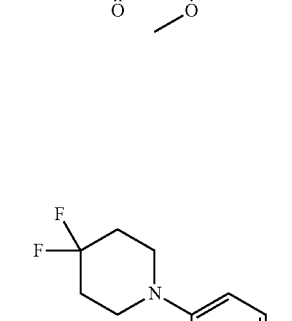 |

TABLE 1-continued
Selected Compounds
| STRUCTURE | STRUCTURE |
|---|---|
| I-173 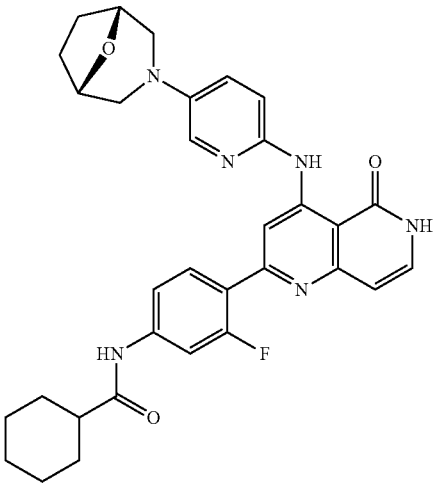 [SMILES: O=C(Nc1ccc(-c2cc(Nc3ccc(N4C[C@H]5CC[C@@H](C4)O5)cn3)c3c(=O)[nH]ccc3n2)c(F)c1)C1CCCCC1] | I-174 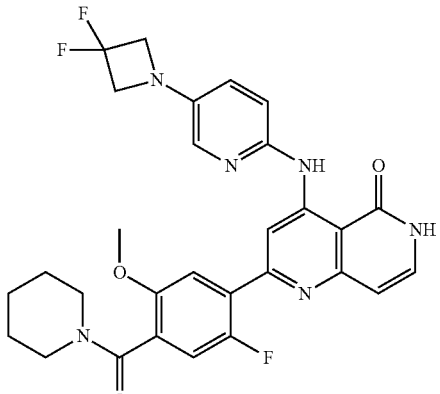 |
| I-175 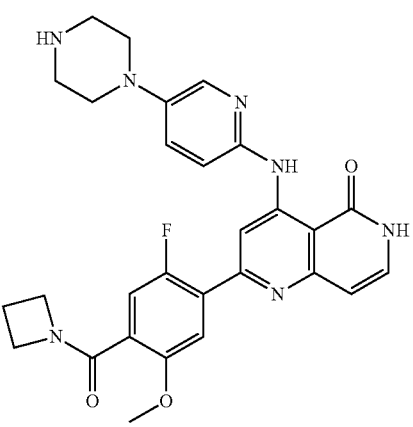 [SMILES: COc1cc(-c2cc(Nc3ccc(N4CCNCC4)cn3)c3c(=O)[nH]ccc3n2)c(F)cc1C(=O)N1CCC1] | I-176 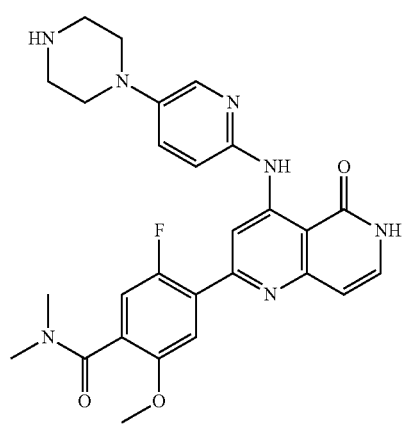 [SMILES: COc1cc(-c2cc(Nc3ccc(N4CCNCC4)cn3)c3c(=O)[nH]ccc3n2)c(F)cc1C(=O)N(C)C] |
| I-177 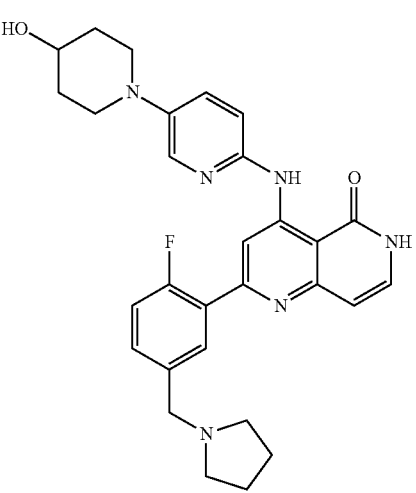 [SMILES: O=c1[nH]ccc2nc(-c3cc(CN4CCCC4)ccc3F)cc(Nc3ccc(N4CCC(O)CC4)cn3)c12] | I-178 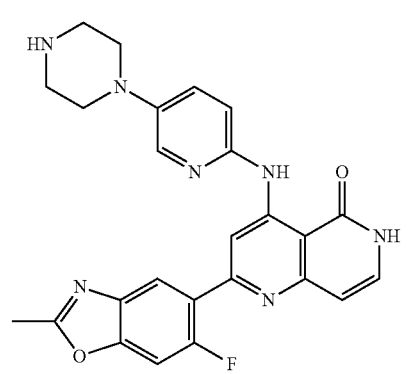 [SMILES: Cc1nc2cc(-c3cc(Nc4ccc(N5CCNCC5)cn4)c4c(=O)[nH]ccc4n3)c(F)cc2o1] |

TABLE 1-continued
Selected Compounds
| STRUCTURE | STRUCTURE |
|---|---|
| I-179 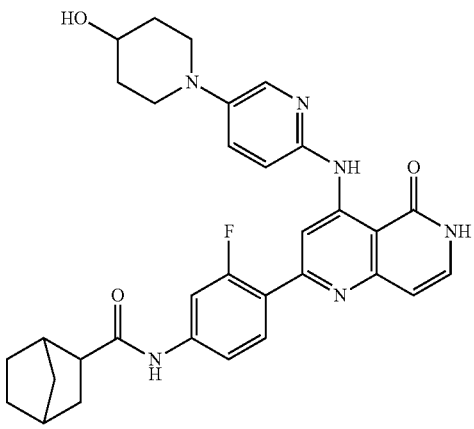 [SMILES: O=C(Nc1ccc(-c2cc(Nc3ccc(N4CCC(O)CC4)cn3)c3c(=O)[nH]ccc3n2)c(F)c1)C1CC2CCC1C2] | I-180 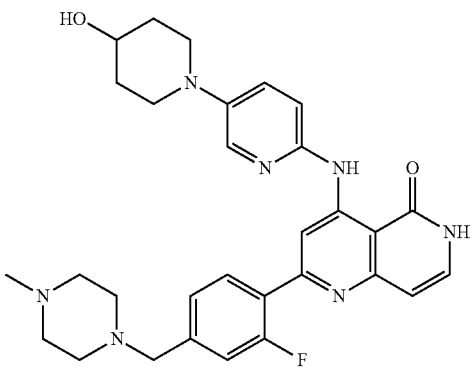 [SMILES: CN1CCN(Cc2ccc(-c3cc(Nc4ccc(N5CCC(O)CC5)cn4)c4c(=O)[nH]ccc4n3)c(F)c2)CC1] |
| I-181 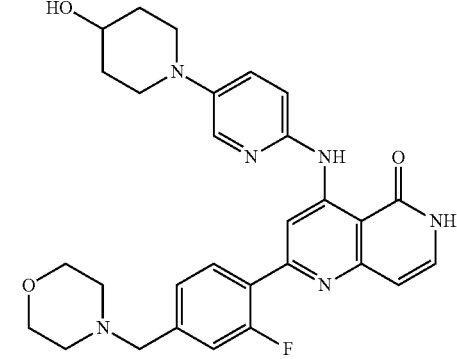 [SMILES: O=c1[nH]ccc2nc(-c3ccc(CN4CCOCC4)cc3F)cc(Nc3ccc(N4CCC(O)CC4)cn3)c12] | I-182 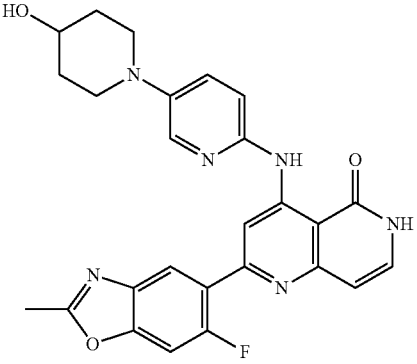 [SMILES: Cc1nc2cc(-c3cc(Nc4ccc(N5CCC(O)CC5)cn4)c4c(=O)[nH]ccc4n3)c(F)cc2o1] |
| I-183 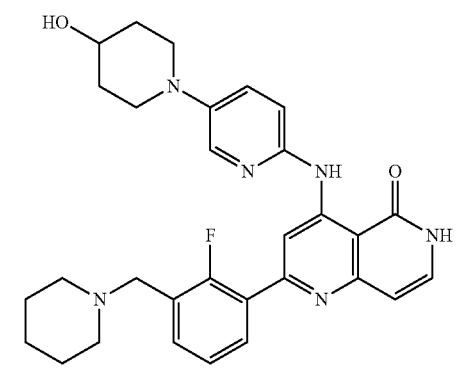 [SMILES: O=c1[nH]ccc2nc(-c3cccc(CN4CCCCC4)c3F)cc(Nc3ccc(N4CCC(O)CC4)cn3)c12] | I-184 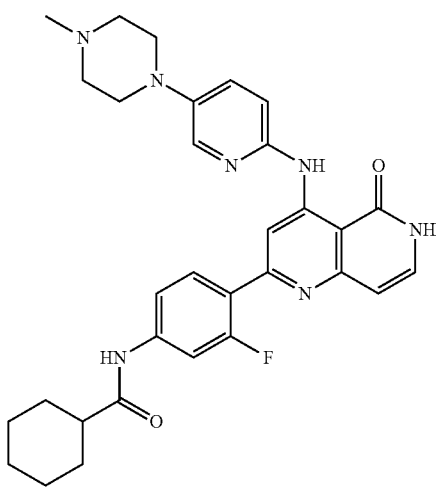 [SMILES: CN1CCN(c2ccc(Nc3cc(-c4ccc(NC(=O)C5CCCCC5)cc4F)nc4cc[nH]c(=O)c34)nc2)CC1] |

TABLE 1-continued
Selected Compounds
| STRUCTURE | STRUCTURE |
|---|---|
| I-185 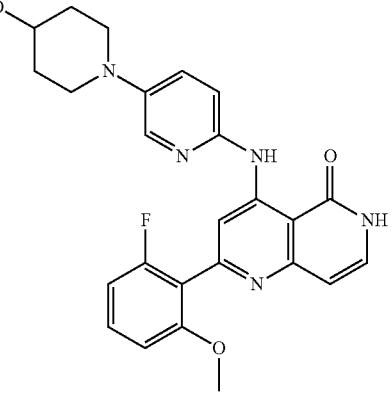 | I-186 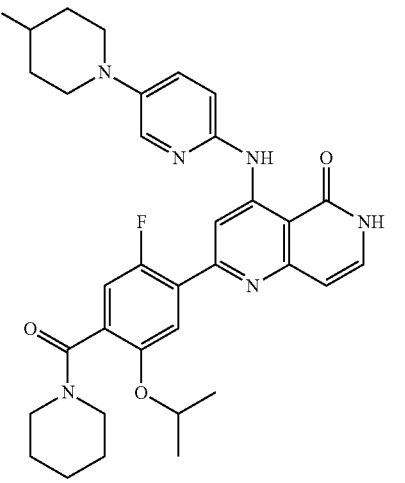 |
| I-187 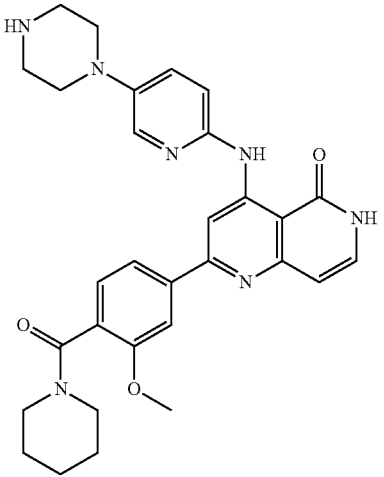 | I-188 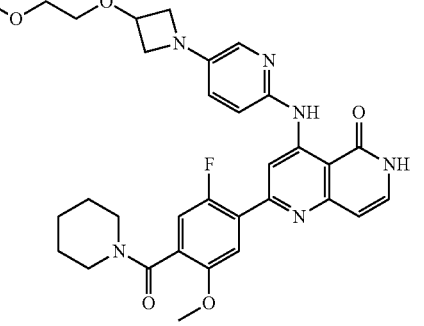 |
| I-189 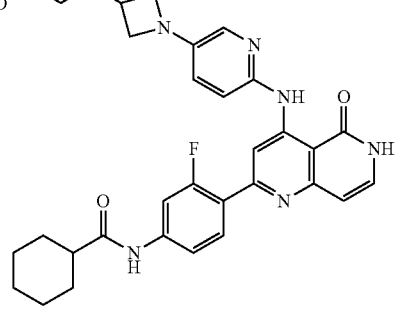 | I-190 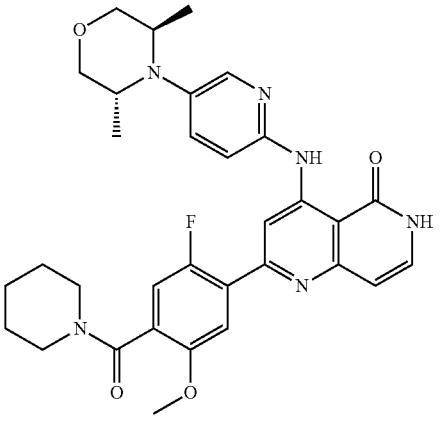 [SMILES: COc1cc(-c2cc(Nc3ccc(N4[C@H](C)COC[C@H]4C)cn3)c3c(=O)[nH]ccc3n2)c(F)cc1C(=O)N1CCCCC1] |

TABLE 1-continued
Selected Compounds
| STRUCTURE | STRUCTURE |
|---|---|
| I-191 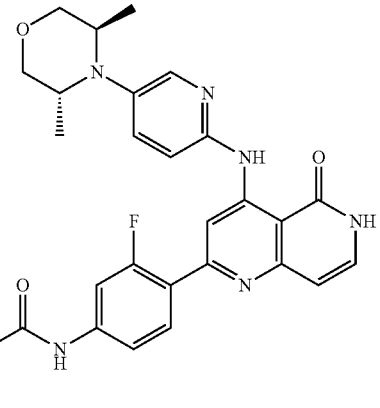 | I-192 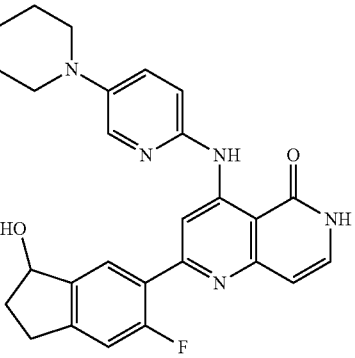 |
| I-193 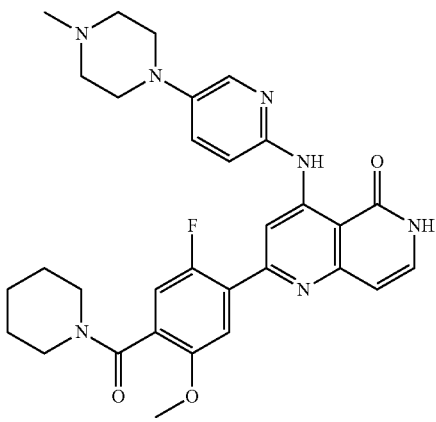 [SMILES: COc1cc(-c2cc(Nc3ccc(N4CCN(C)CC4)cn3)c3c(=O)[nH]ccc3n2)c(F)cc1C(=O)N1CCCCC1] | I-194 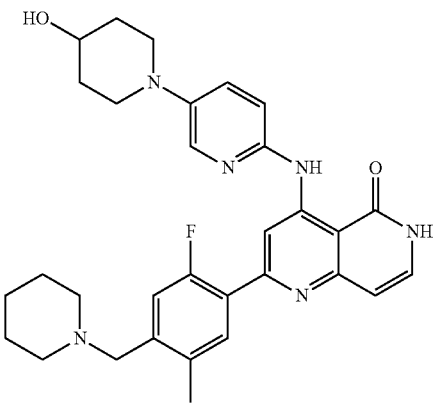 [SMILES: Cc1cc(-c2cc(Nc3ccc(N4CCC(O)CC4)cn3)c3c(=O)[nH]ccc3n2)c(F)cc1CN1CCCCC1] |
| I-195 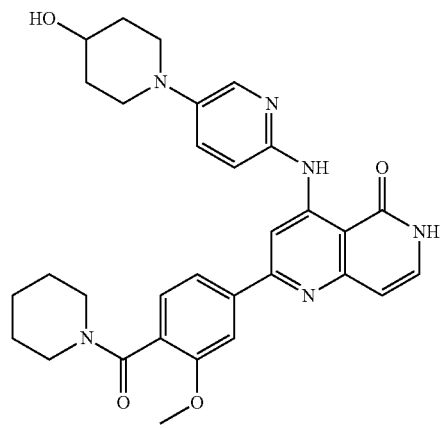 [SMILES: COc1cc(-c2cc(Nc3ccc(N4CCC(O)CC4)cn3)c3c(=O)[nH]ccc3n2)ccc1C(=O)N1CCCCC1] | I-196 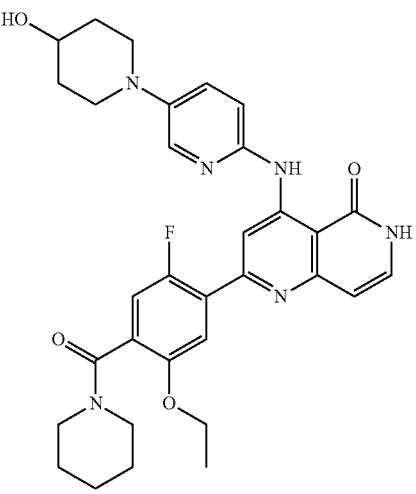 |

TABLE 1-continued
Selected Compounds
| STRUCTURE | STRUCTURE |
|---|---|
| I-197 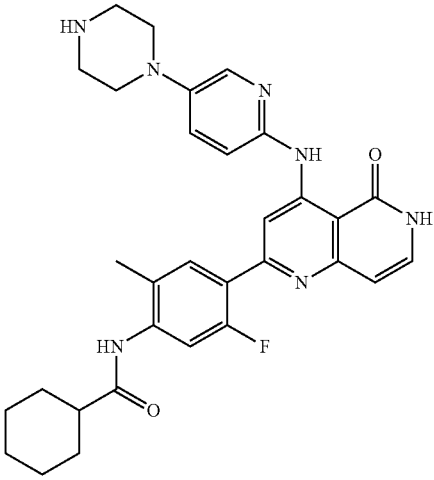 [SMILES: Cc1cc(-c2cc(Nc3ccc(N4CCNCC4)cn3)c3c(=O)[nH]ccc3n2)c(F)cc1NC(=O)C1CCCCC1] | I-198 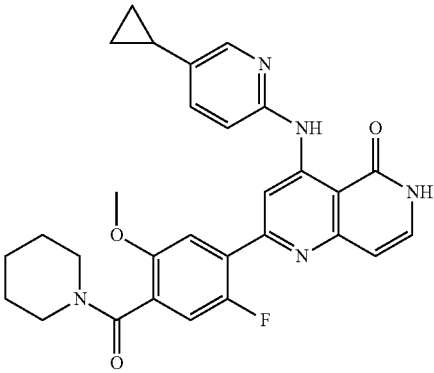 [SMILES: COc1cc(-c2cc(Nc3ccc(C4CC4)cn3)c3c(=O)[nH]ccc3n2)c(F)cc1C(=O)N1CCCCC1] |
| I-199 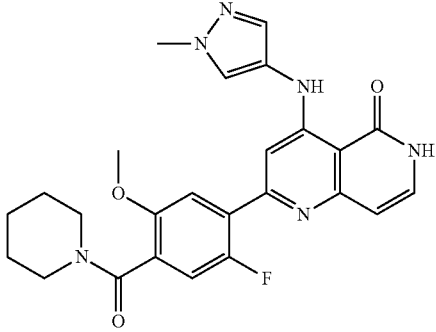 [SMILES: COc1cc(-c2cc(Nc3cnn(C)c3)c3c(=O)[nH]ccc3n2)c(F)cc1C(=O)N1CCCCC1] | I-200 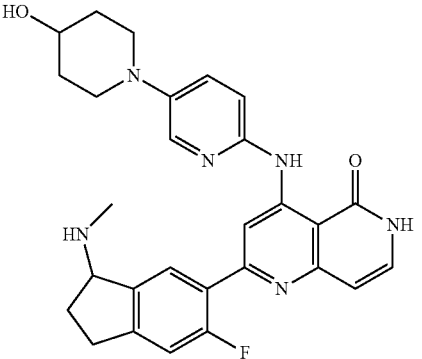 [SMILES: CNC1CCc2cc(F)c(-c3cc(Nc4ccc(N5CCC(O)CC5)cn4)c4c(=O)[nH]ccc4n3)cc21] |
| I-201 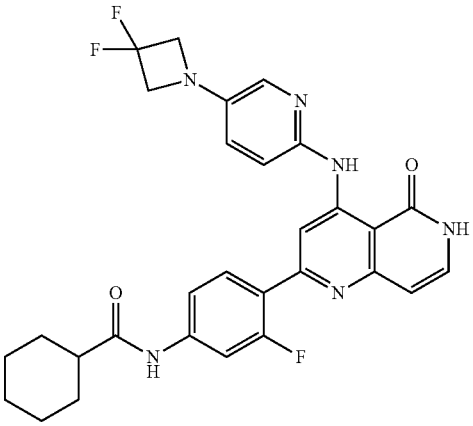 [SMILES: O=C(Nc1ccc(-c2cc(Nc3ccc(N4CC(F)(F)C4)cn3)c3c(=O)[nH]ccc3n2)c(F)c1)C1CCCCC1] | I-202 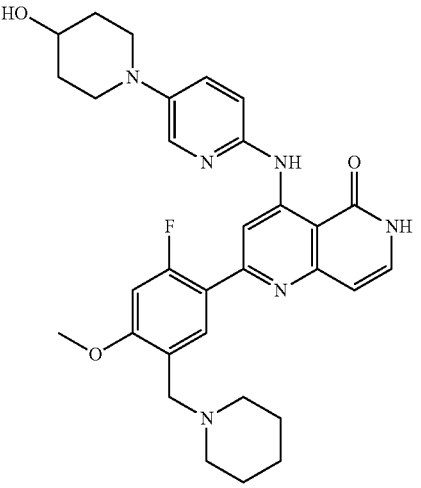 [SMILES: COc1cc(F)c(-c2cc(Nc3ccc(N4CCC(O)CC4)cn3)c3c(=O)[nH]ccc3n2)cc1CN1CCCCC1] |

TABLE 1-continued
Selected Compounds
| STRUCTURE | STRUCTURE |
|---|---|
| I-203 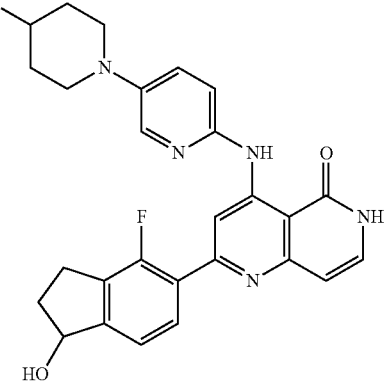 | I-204 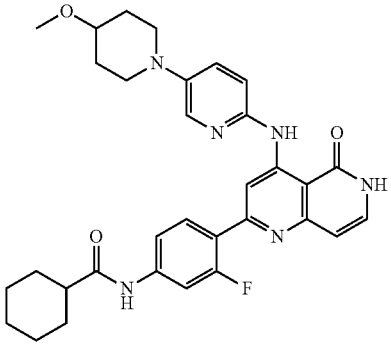 [SMILES: COC1CCN(c2ccc(Nc3cc(-c4ccc(NC(=O)C5CCCCC5)cc4F)nc4cc[nH]c(=O)c34)nc2)CC1] |
| I-205 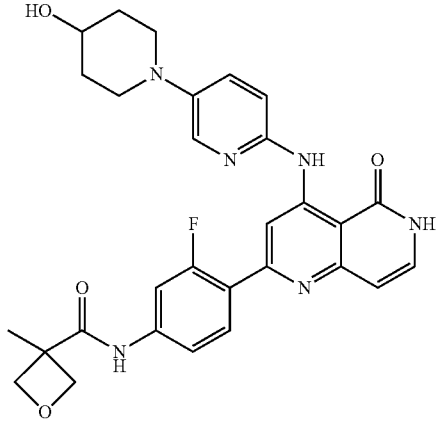 [SMILES: CC1(C(=O)Nc2ccc(-c3cc(Nc4ccc(N5CCC(O)CC5)cn4)c4c(=O)[nH]ccc4n3)c(F)c2)COC1] | I-206 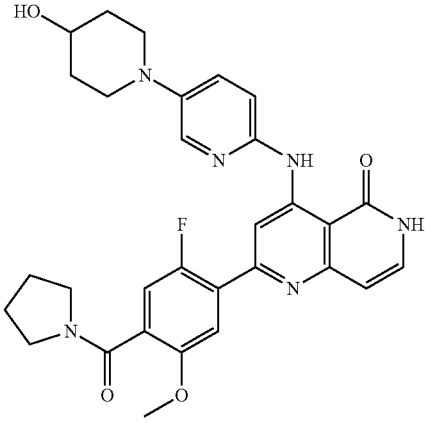 [SMILES: COc1cc(-c2cc(Nc3ccc(N4CCC(O)CC4)cn3)c3c(=O)[nH]ccc3n2)c(F)cc1C(=O)N1CCCC1] |
| I-207 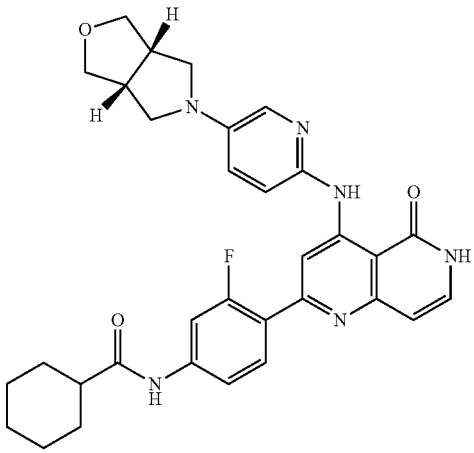 [SMILES: O=C(Nc1ccc(-c2cc(Nc3ccc(N4C[C@H]5COC[C@H]5C4)cn3)c3c(=O)[nH]ccc3n2)c(F)c1)C1CCCCC1] | I-208 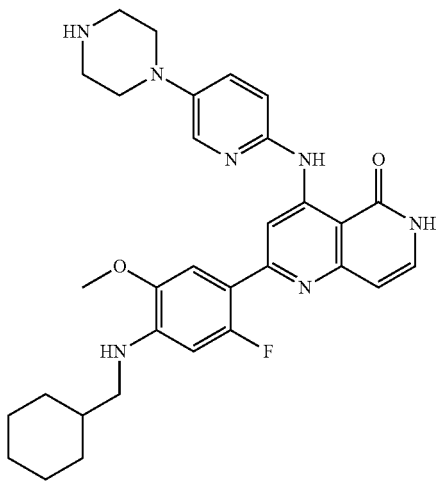 [SMILES: COc1cc(-c2cc(Nc3ccc(N4CCNCC4)cn3)c3c(=O)[nH]ccc3n2)c(F)cc1NCC1CCCCC1] |

TABLE 1-continued

Selected Compounds

| STRUCTURE | STRUCTURE |
|---|---|
| I-209 | I-210 |
| I-211 | I-212 |
| I-213 | I-214 |

TABLE 1-continued
Selected Compounds
| STRUCTURE | STRUCTURE |
|---|---|
| I-215 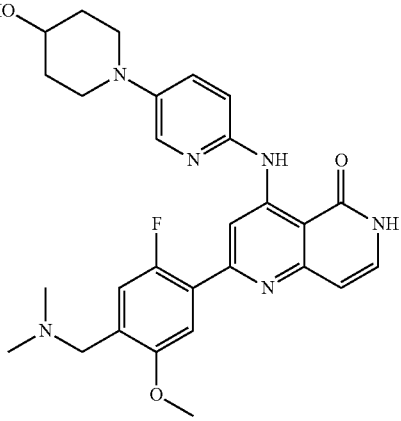 | I-216 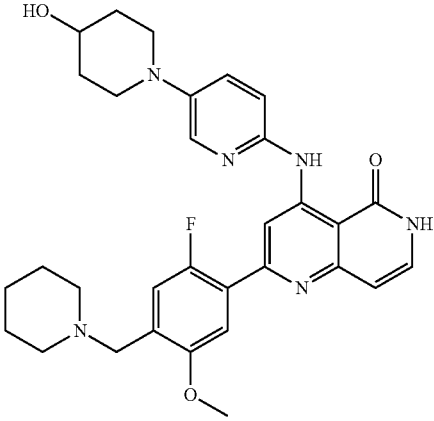 [SMILES: COc1cc(-c2cc(Nc3ccc(N4CCC(O)CC4)cn3)c3c(=O)[nH]ccc3n2)c(F)cc1CN1CCCCC1] |
| I-217 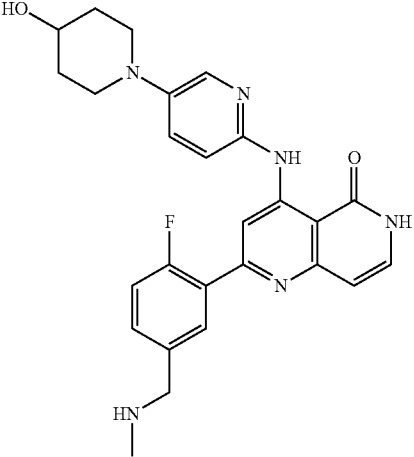 [SMILES: CNCc1ccc(F)c(-c2cc(Nc3ccc(N4CCC(O)CC4)cn3)c3c(=O)[nH]ccc3n2)c1] | I-218 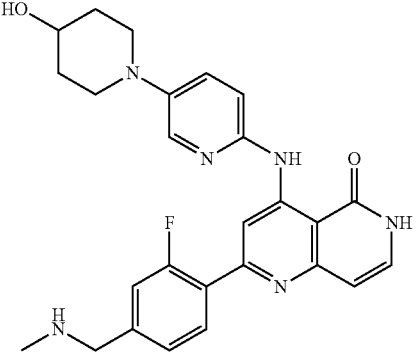 [SMILES: CNCc1ccc(-c2cc(Nc3ccc(N4CCC(O)CC4)cn3)c3c(=O)[nH]ccc3n2)c(F)c1] |
| I-219 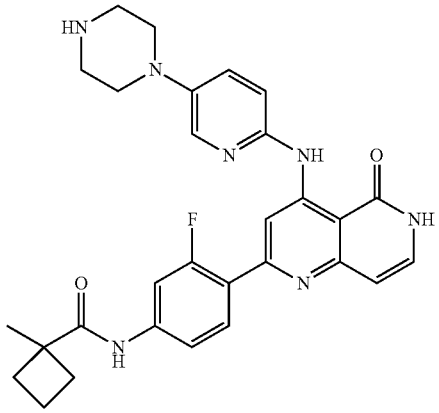 [SMILES: CC1(C(=O)Nc2ccc(-c3cc(Nc4ccc(N5CCNCC5)cn4)c4c(=O)[nH]ccc4n3)c(F)c2)CCC1] | I-220 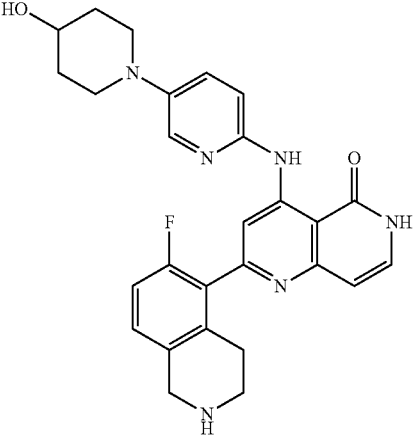 [SMILES: O=c1[nH]ccc2nc(-c3c(F)ccc4c3CCNC4)cc(Nc3ccc(N4CCC(O)CC4)cn3)c12] |

TABLE 1-continued

Selected Compounds

| STRUCTURE | STRUCTURE |
|---|---|
| I-221 | I-222 |
| I-223 | I-224 |
| I-225 | I-226 |

TABLE 1-continued

Selected Compounds

| STRUCTURE | STRUCTURE |
|---|---|
| I-227 | I-228 |
| I-229 | I-230 |
| I-231 | I-232 |

TABLE 1-continued
Selected Compounds
| STRUCTURE | STRUCTURE |
|---|---|
| I-233 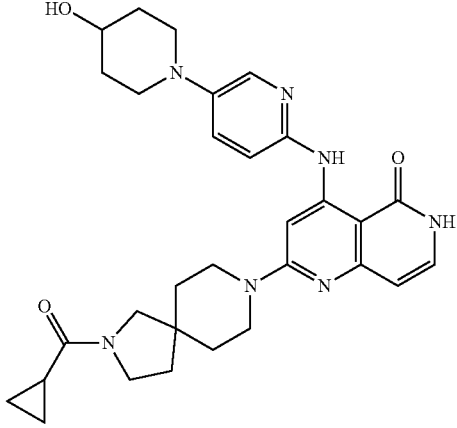 [SMILES: O=C(C1CC1)N1CCC2(CCN(c3cc(Nc4ccc(N5CCC(O)CC5)cn4)c4c(=O)[nH]ccc4n3)CC2)C1] | I-234 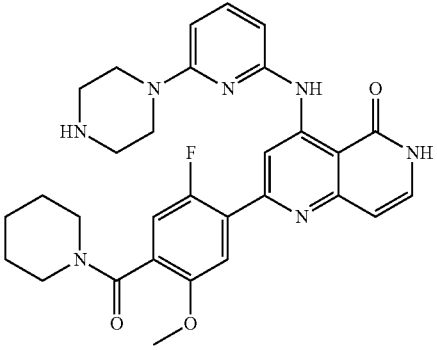 [SMILES: COc1cc(-c2cc(Nc3cccc(N4CCNCC4)n3)c3c(=O)[nH]ccc3n2)c(F)cc1C(=O)N1CCCCC1] |
| I-235 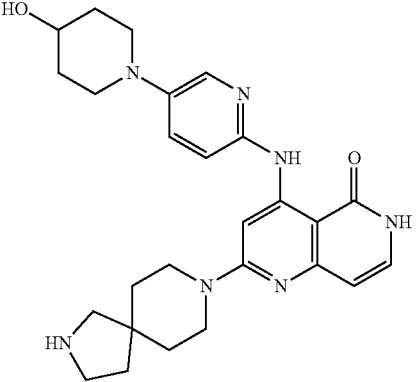 [SMILES: O=c1[nH]ccc2nc(N3CCC4(CCNC4)CC3)cc(Nc3ccc(N4CCC(O)CC4)cn3)c12] | I-236 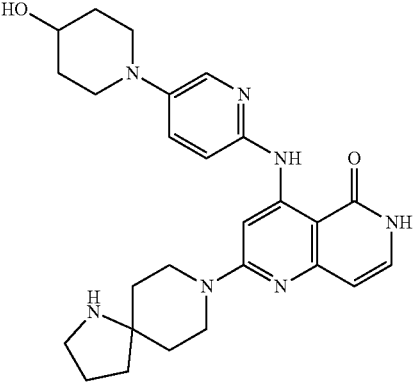 [SMILES: O=c1[nH]ccc2nc(N3CCC4(CCCN4)CC3)cc(Nc3ccc(N4CCC(O)CC4)cn3)c12] |
| I-237 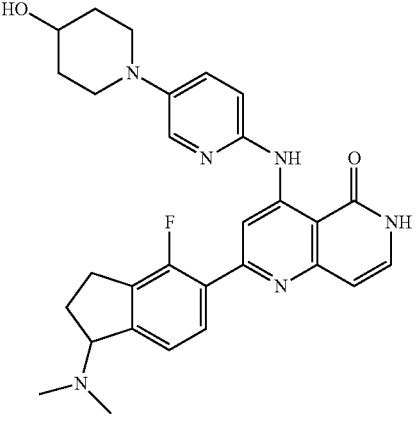 [SMILES: CN(C)C1CCc2c1ccc(-c1cc(Nc3ccc(N4CCC(O)CC4)cn3)c3c(=O)[nH]ccc3n1)c2F] | I-238 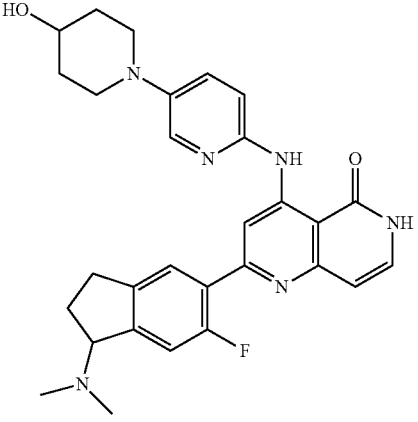 [SMILES: CN(C)C1CCc2cc(-c3cc(Nc4ccc(N5CCC(O)CC5)cn4)c4c(=O)[nH]ccc4n3)c(F)cc21] |

TABLE 1-continued

Selected Compounds

| STRUCTURE | STRUCTURE |
|---|---|
| I-239 | I-240 |
| I-241 | I-242 |
| I-243 | I-244 |

TABLE 1-continued
Selected Compounds
| STRUCTURE | STRUCTURE |
|---|---|
| I-245 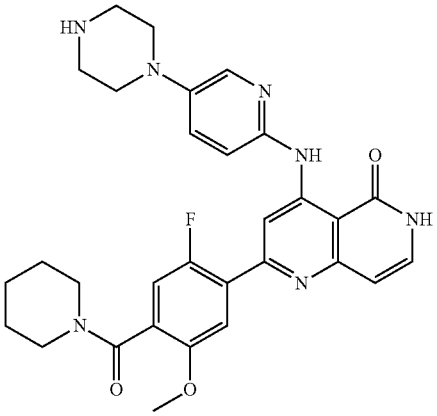 [SMILES: COc1cc(-c2cc(Nc3ccc(N4CCNCC4)cn3)c3c(=O)[nH]ccc3n2)c(F)cc1C(=O)N1CCCCC1] | I-246 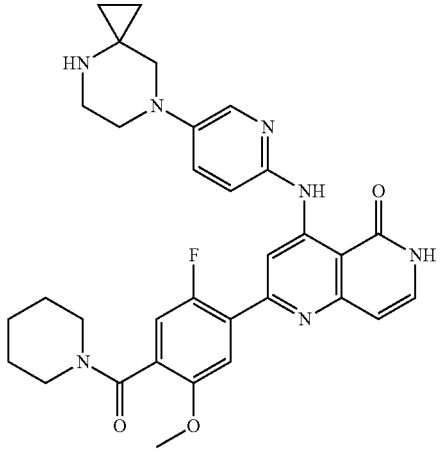 [SMILES: COc1cc(-c2cc(Nc3ccc(N4CCNC5(CC5)C4)cn3)c3c(=O)[nH]ccc3n2)c(F)cc1C(=O)N1CCCCC1] |
| I-247 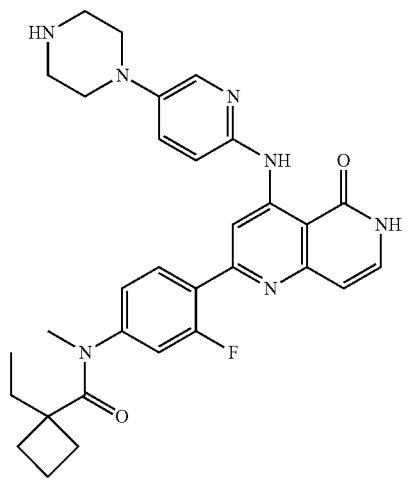 [SMILES: CCC1(C(=O)N(C)c2ccc(-c3cc(Nc4ccc(N5CCNCC5)cn4)c4c(=O)[nH]ccc4n3)c(F)c2)CCC1] | I-248 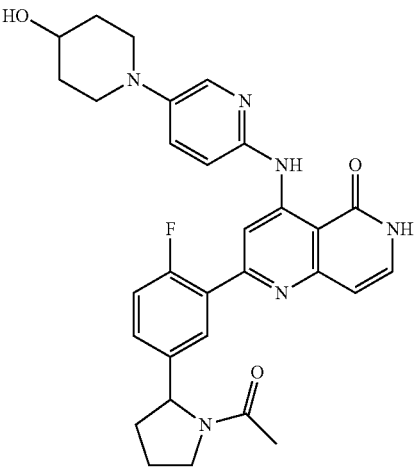 [SMILES: CC(=O)N1CCCC1c1ccc(F)c(-c2cc(Nc3ccc(N4CCC(O)CC4)cn3)c3c(=O)[nH]ccc3n2)c1] |
| I-249 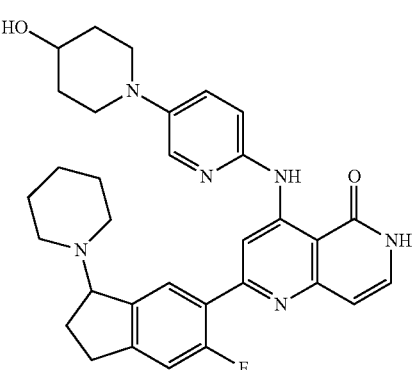 | I-250 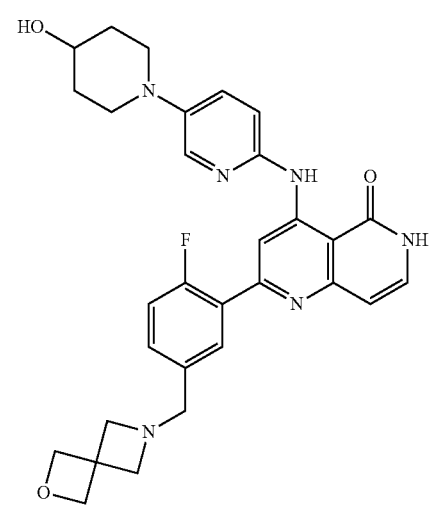 [SMILES: O=c1[nH]ccc2nc(-c3cc(CN4CC5(COC5)C4)ccc3F)cc(Nc3ccc(N4CCC(O)CC4)cn3)c12] |

TABLE 1-continued

Selected Compounds

| STRUCTURE | STRUCTURE |
|---|---|
| I-251 (structure) | I-252 (structure) |
| I-253 (structure) | I-254 (structure) |
| I-255 (structure) | I-256 (structure) |

TABLE 1-continued

Selected Compounds

| STRUCTURE | STRUCTURE |
|---|---|
| I-257 | I-258 |
| I-259 | I-260 |
| I-261 | I-262 |

TABLE 1-continued
Selected Compounds
| STRUCTURE | STRUCTURE |
|---|---|
| I-263 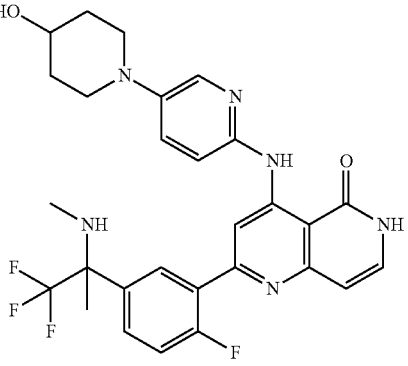 | I-264 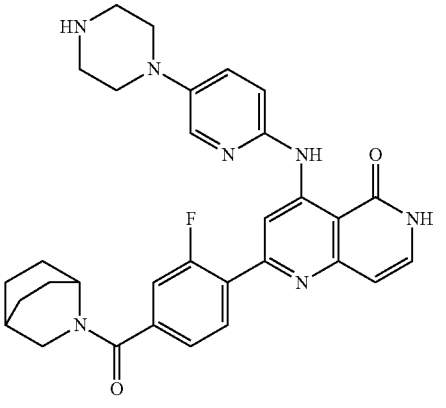 [SMILES: O=C(c1ccc(-c2cc(Nc3ccc(N4CCNCC4)cn3)c3c(=O)[nH]ccc3n2)c(F)c1)N1CC2CCC1CC2] |
| I-265 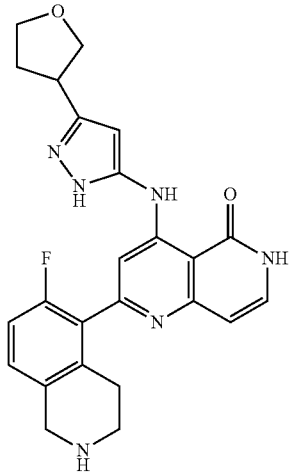 [SMILES: O=c1[nH]ccc2nc(-c3c(F)ccc4c3CCNC4)cc(Nc3cc(C4CCOC4)n[nH]3)c12] | I-266 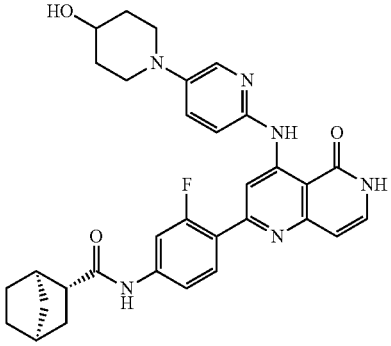 [SMILES: O=C(Nc1ccc(-c2cc(Nc3ccc(N4CCC(O)CC4)cn3)c3c(=O)[nH]ccc3n2)c(F)c1)[C@@H]1C[C@H]2CC[C@@H]1C2] |
| I-267 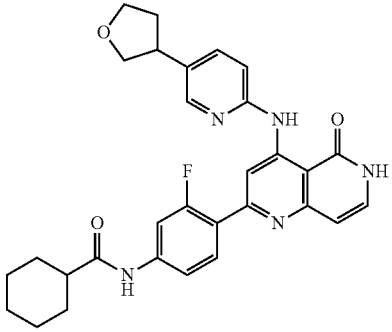 [SMILES: O=C(Nc1ccc(-c2cc(Nc3ccc(C4CCOC4)cn3)c3c(=O)[nH]ccc3n2)c(F)c1)C1CCCCC1] | I-268 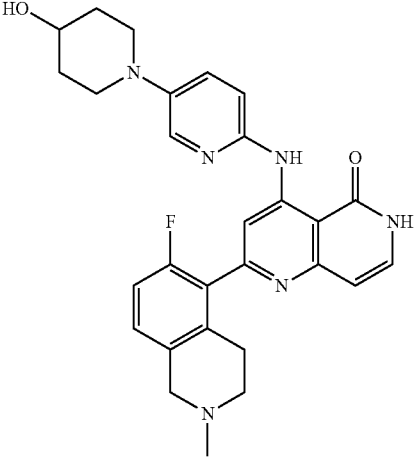 [SMILES: CN1CCc2c(ccc(F)c2-c2cc(Nc3ccc(N4CCC(O)CC4)cn3)c3c(=O)[nH]ccc3n2)C1] |

TABLE 1-continued

Selected Compounds

| STRUCTURE | STRUCTURE |
| --- | --- |
| I-269 | I-270 |
| I-271 | I-272 |
| I-273 arbitrarily assigned | I-274 arbitrarily assigned |

TABLE 1-continued

Selected Compounds

| | STRUCTURE | | STRUCTURE |
|---|---|---|---|
| I-275 | 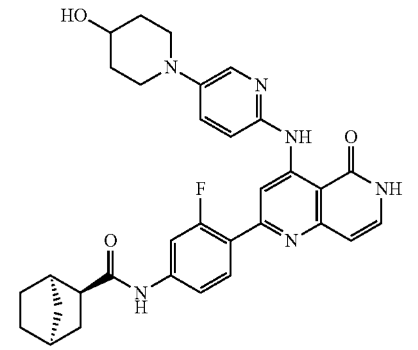 [SMILES: O=C(Nc1ccc(-c2cc(Nc3ccc(N4CCC(O)CC4)cn3)c3c(=O)[nH]ccc3n2)c(F)c1)[C@H]1C[C@H]2CC[C@@H]1C2] | I-276 | 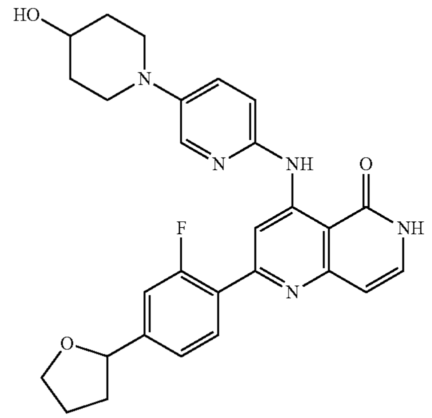 [SMILES: O=c1[nH]ccc2nc(-c3ccc(C4CCCO4)cc3F)cc(Nc3ccc(N4CCC(O)CC4)cn3)c12] |
| I-277 | 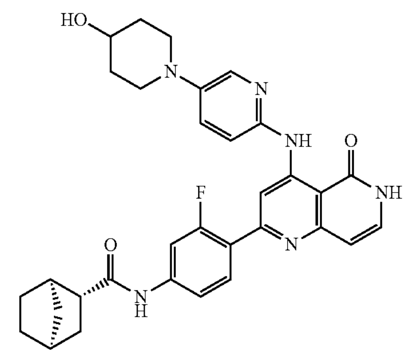 | I-278 | 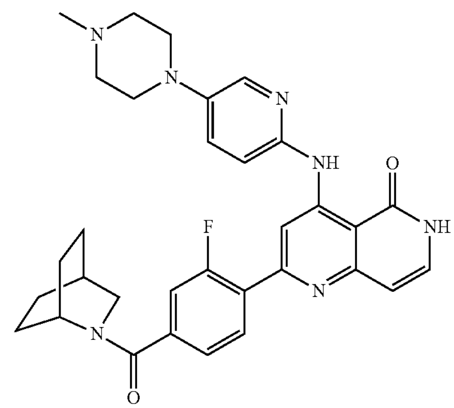 [SMILES: CN1CCN(c2ccc(Nc3cc(-c4ccc(C(=O)N5CC6CCC5CC6)cc4F)nc4cc[nH]c(=O)c34)nc2)CC1] |
| I-279 | 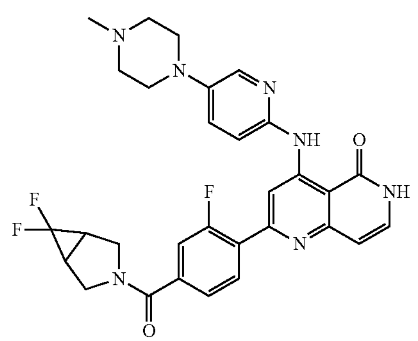 [SMILES: CN1CCN(c2ccc(Nc3cc(-c4ccc(C(=O)N5CC6C(C5)C6(F)F)cc4F)nc4cc[nH]c(=O)c34)nc2)CC1] | I-280 | 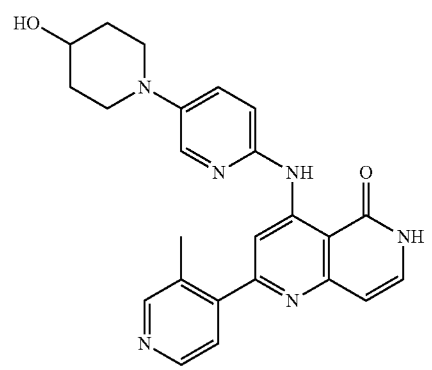 [SMILES: Cc1cnccc1-c1cc(Nc2ccc(N3CCC(O)CC3)cn2)c2c(=O)[nH]ccc2n1] |
| I-281 | 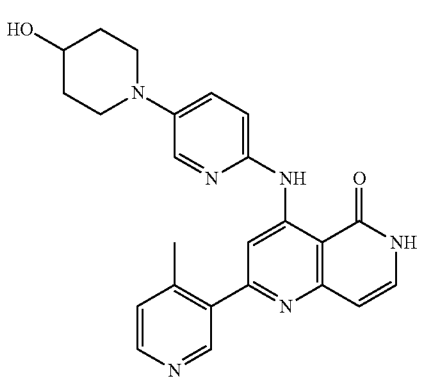 [SMILES: Cc1ccncc1-c1cc(Nc2ccc(N3CCC(O)CC3)cn2)c2c(=O)[nH]ccc2n1] | I-282 | 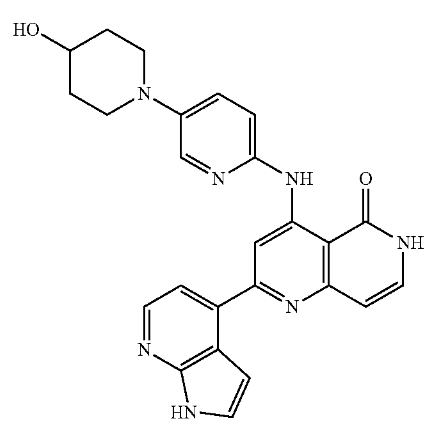 [SMILES: O=c1[nH]ccc2nc(-c3ccnc4[nH]ccc34)cc(Nc3ccc(N4CCC(O)CC4)cn3)c12] |

TABLE 1-continued

Selected Compounds

| STRUCTURE | STRUCTURE |
|---|---|
| I-283 | I-284 |
| I-285 | I-286 |
| I-287 | I-288 |

TABLE 1-continued

Selected Compounds

| STRUCTURE | STRUCTURE |
|---|---|
| I-289 | I-290 |
| I-291 | I-292 |
| I-293 | I-294 |
| I-295 | I-296 |

TABLE 1-continued
Selected Compounds
| STRUCTURE | STRUCTURE |
|---|---|
| I-297 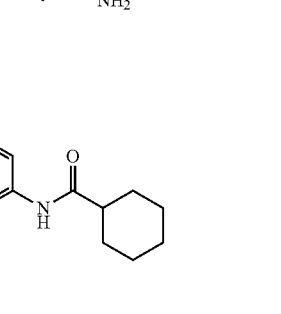 | I-298 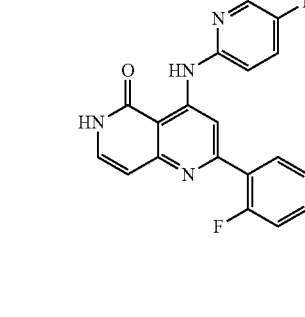 |
| I-299 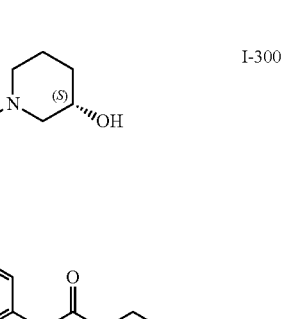 | I-300 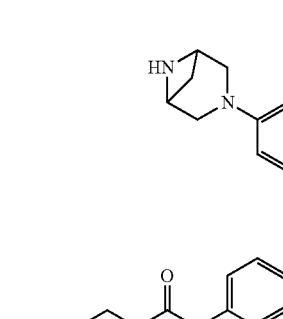 |
| I-301 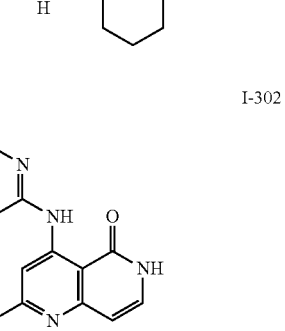 | I-302 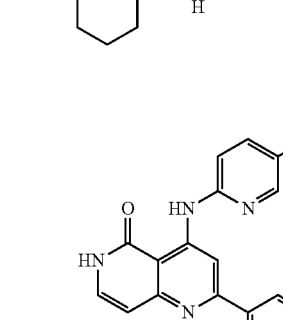 |
| I-303 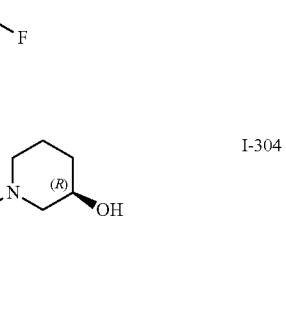 | I-304 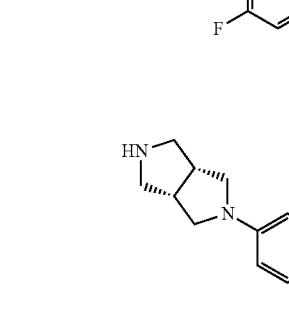 |

TABLE 1-continued

Selected Compounds

| STRUCTURE | STRUCTURE |
|---|---|
| I-305 | I-306 |
| I-307 | I-308 |
| I-309 | I-310 |
| I-311 | I-312 |

TABLE 1-continued

Selected Compounds

| STRUCTURE | STRUCTURE |
|---|---|
| I-313 | I-314 |
| I-315 | I-316 |
| I-317 | I-318 |
| I-319 | I-320 |

TABLE 1-continued

Selected Compounds

| STRUCTURE | STRUCTURE |
| --- | --- |
| I-321 | I-322 |
| I-323 | I-324 |
| I-325 | I-326 |
| I-327 | I-328 |

TABLE 1-continued

Selected Compounds

| ID | STRUCTURE | ID | STRUCTURE |
|---|---|---|---|
| I-329 | | I-330 | |
| I-331 | | I-332 | |
| I-333 | | I-334 | |
| I-335 | | I-336 | |

TABLE 1-continued
Selected Compounds
| STRUCTURE | STRUCTURE |
|---|---|
| I-337 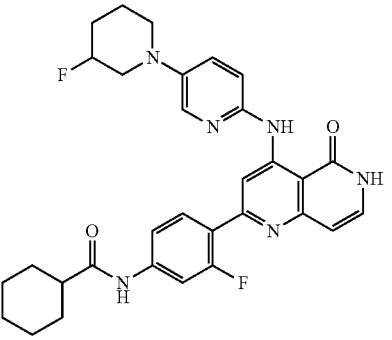 [SMILES: O=C(Nc1ccc(-c2cc(Nc3ccc(N4CCCC(F)C4)cn3)c3c(=O)[nH]ccc3n2)c(F)c1)C1CCCCC1] | I-338 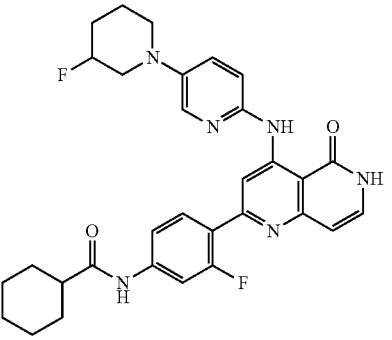 [SMILES: O=C(Nc1ccc(-c2cc(Nc3ccc(N4CCCC(F)C4)cn3)c3c(=O)[nH]ccc3n2)c(F)c1)C1CCCCC1] |
| I-339 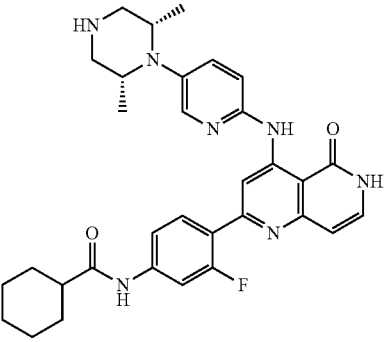 [SMILES: C[C@@H]1CNC[C@H](C)N1c1ccc(Nc2cc(-c3ccc(NC(=O)C4CCCCC4)cc3F)nc3cc[nH]c(=O)c23)nc1] | I-340 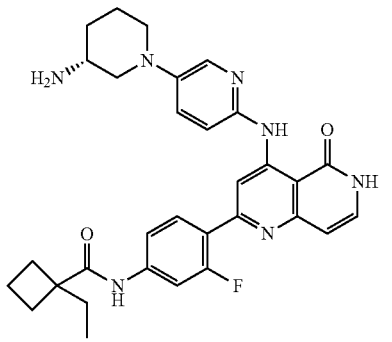 [SMILES: CCC1(C(=O)Nc2ccc(-c3cc(Nc4ccc(N5CCC[C@@H](N)C5)cn4)c4c(=O)[nH]ccc4n3)c(F)c2)CCC1] |
| I-341 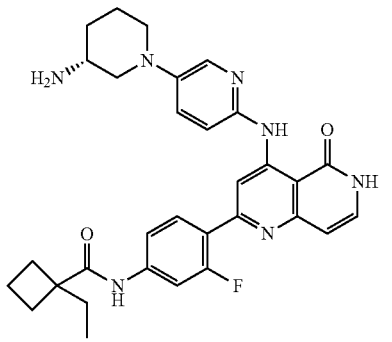 [SMILES: CCC1(C(=O)Nc2ccc(-c3cc(Nc4ccc(N5CCC[C@@H](N)C5)cn4)c4c(=O)[nH]ccc4n3)c(F)c2)CCC1] | I-342 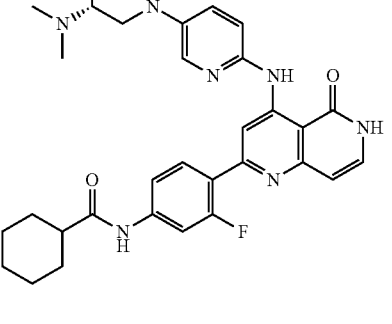 |
| I-343 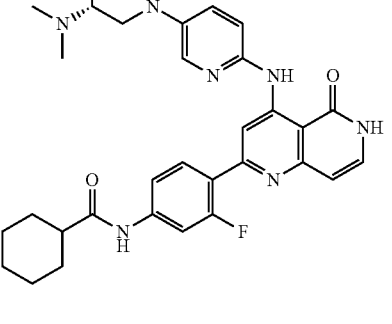 | I-344 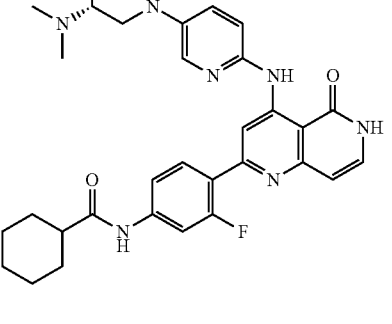 |

TABLE 1-continued
Selected Compounds
| STRUCTURE | STRUCTURE |
|---|---|
| I-345 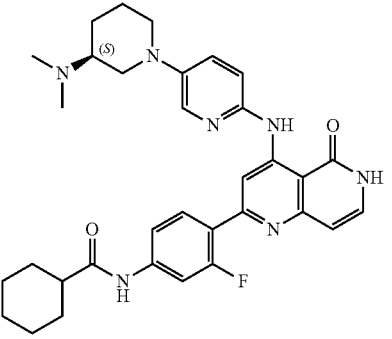 | I-346 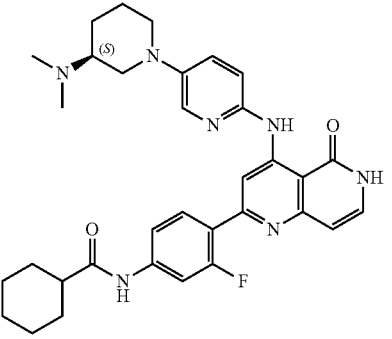 |
| I-347 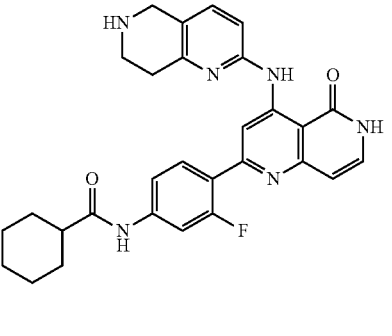 [SMILES: O=C(Nc1ccc(-c2cc(Nc3ccc4c(n3)CCNC4)c3c(=O)[nH]ccc3n2)c(F)c1)C1CCCCC1] | I-348 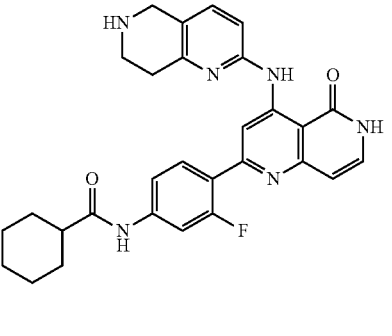 [SMILES: O=C(Nc1ccc(-c2cc(Nc3ccc4c(n3)CCNC4)c3c(=O)[nH]ccc3n2)c(F)c1)C1CCCCC1] |
| I-349 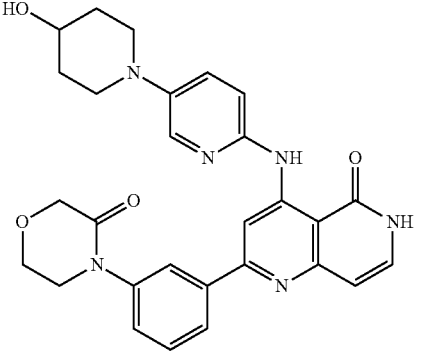 [SMILES: O=C1COCCN1c1cccc(-c2cc(Nc3ccc(N4CCC(O)CC4)cn3)c3c(=O)[nH]ccc3n2)c1] | I-350 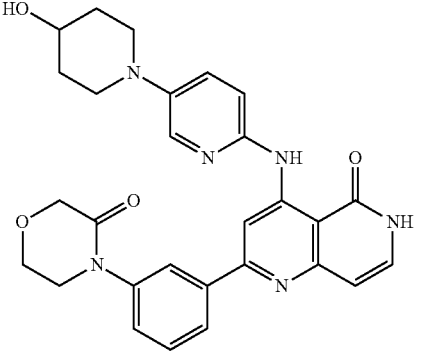 [SMILES: O=C1COCCN1c1cccc(-c2cc(Nc3ccc(N4CCC(O)CC4)cn3)c3c(=O)[nH]ccc3n2)c1] |
| I-351 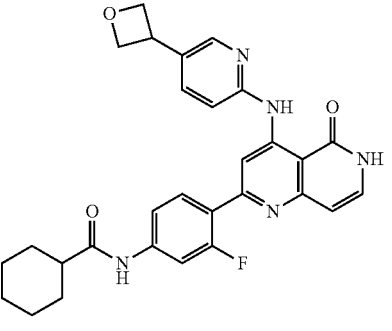 [SMILES: O=C(Nc1ccc(-c2cc(Nc3ccc(C4COC4)cn3)c3c(=O)[nH]ccc3n2)c(F)c1)C1CCCCC1] | I-352 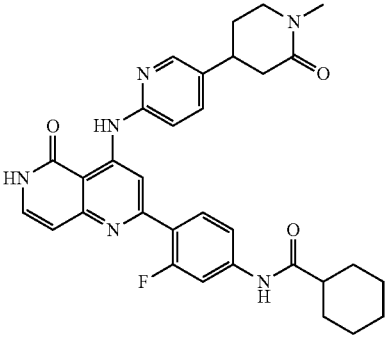 |

TABLE 1-continued

Selected Compounds

| STRUCTURE | | STRUCTURE | |
|---|---|---|---|
| I-353 | | I-354 | |
| I-355 | | I-356 | |
| I-357 | | I-358 | |

TABLE 1-continued

Selected Compounds

| STRUCTURE | STRUCTURE |
|---|---|
| I-359 | I-360 |
| I-361 | I-362 |
| I-363 | I-364 |

TABLE 1-continued

Selected Compounds

| STRUCTURE | STRUCTURE |
|---|---|
| I-365  | I-366  |
| I-367 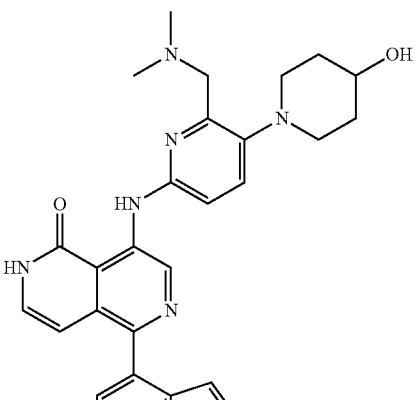 | I-368 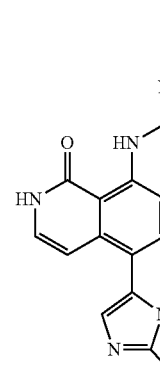 |
| I-369 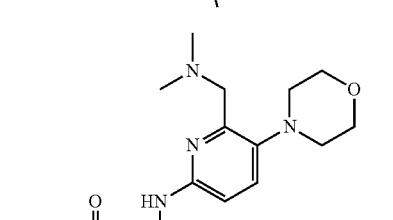 | I-370 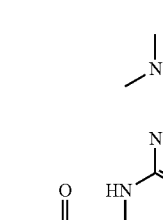 |

In some embodiments, the present invention provides a compound set forth in Table 1, above, or a pharmaceutically acceptable salt thereof. In some embodiments, the present invention provides a compound set forth in Table 1, above. In some embodiments, the present invention provides a pharmaceutical composition comprising a compound set forth in Table 1 above, or a pharmaceutically acceptable salt thereof, together with a pharmaceutically acceptable carrier, excipient, or diluent.

In some embodiments, the present invention provides a compound of formula I as defined above, or a pharmaceutically acceptable salt thereof, or a pharmaceutical composition comprising a compound of formula I as defined above, or a pharmaceutically acceptable salt thereof, and a pharmaceutically acceptable carrier, adjuvant, or vehicle for use as a medicament.

In some embodiments, the invention also provides compounds of formula I described herein or pharmaceutical compositions described herein for use in a method for inhibiting HPK1 as described herein, in a method for enhancing an immune response in a subject in need thereof as described herein and/or in a method for treating a HPK1-dependent disorder as described herein.

In some embodiments, the invention also provides compounds of formula I described herein or pharmaceutical compositions described herein for use in a method for inhibiting HPK1 as described herein.

In some embodiments, the invention also provides compounds of formula I described herein or pharmaceutical compositions described herein for use in a method for enhancing an immune response in a subject in need thereof as described herein.

In some embodiments, the invention also provides compounds of formula I described herein or pharmaceutical compositions described herein for use in a method for treating a HPK1-dependent disorder as described herein.

In some embodiments, the invention also provides the use of a compound of formula I described herein or a pharmaceutical composition described herein for the manufacture of a medicament for inhibiting HPK1, a medicament for enhancing an immune response in a subject in need thereof and/or a medicament for treating a HPK1-dependent disorder.

In some embodiments, the invention also provides the use of a compound of formula I described herein or a pharmaceutical composition described herein for the manufacture of a medicament for inhibiting HPK1.

In some embodiments, the invention also provides the use of a compound of formula I described herein or a pharmaceutical composition described herein for the manufacture of a medicament for enhancing an immune response in a subject in need thereof.

In some embodiments, the invention also provides the use of a compound of formula I described herein or a pharmaceutical composition described herein for the manufacture of a medicament treating a HPK1-dependent disorder.

In some embodiments, the invention also provides the use of compounds of formula I described herein or pharmaceutical compositions described herein in a method for inhibiting HPK1 as described herein, in a method for enhancing an immune response in a subject in need thereof as described herein and/or in a method for treating a HPK1-dependent disorder as described herein.

In some embodiments, the invention also provides the use of compounds of formula I described herein or pharmaceutical compositions described herein in a method for inhibiting HPK1 as described herein.

In some embodiments, the invention also provides the use of compounds of formula I described herein or pharmaceutical compositions described herein in a method for enhancing an immune response in a subject in need thereof as described herein.

In some embodiments, the invention also provides the use of compounds of formula I described herein or pharmaceutical compositions described herein in a method for treating a HPK1-dependent disorder as described herein.

As defined generally above, each hydrogen bound to carbon can be optionally and independently replaced by deuterium.

In some embodiments, a hydrogen bound to carbon is replaced by deuterium.

4. General Methods of Providing the Present Compounds

The compounds of this invention may be prepared or isolated in general by synthetic and/or semi-synthetic methods known to those skilled in the art for analogous compounds and by methods described in detail in the Examples, herein.

5. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit HPK1, or a mutant thereof, in a biological sample or in a patient. In certain embodiments, the amount of compound in compositions of this invention is such that is effective to measurably inhibit HPK1, or a mutant thereof, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of HPK1, or a mutant thereof.

The subject matter disclosed herein includes prodrugs, metabolites, derivatives, and pharmaceutically acceptable salts of compounds of the invention. Metabolites include compounds produced by a process comprising contacting a compound of the invention with a mammal for a period of time sufficient to yield a metabolic product thereof. If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like. If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

A compound of the invention can be in the form of a "prodrug," which includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", J. Pharm. Sci. 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionic acid esters), lower alkenyl esters, di-lower alkylamino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Prodrugs which are converted to active forms through other mechanisms in vivo are also included. In aspects, the compounds of the invention are prodrugs of any of the formulae herein.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

The compounds and compositions described herein are generally useful for the inhibition of kinase activity of one or more enzymes. In some embodiments the kinase inhibited by the compounds and methods of the invention is HPK1.

The presently disclosed compounds find use in inhibiting the activity of the enzyme HPK1. HPK1 is a member of the germinal center kinase subfamily of Ste20-related serine/threonine kinases. HPK1 functions as a MAP4K by phosphorylating and activating MAP3K proteins, including MEKK1, MLK3 and TAK1, leading to the activation of the MAPK Jnk.

In one embodiment, the subject matter disclosed herein is directed to a method of inhibiting HPK1, the method comprising contacting HPK1 with an effective amount of a compound of the invention or a pharmaceutical composition described herein.

In certain embodiments, the subject matter disclosed herein is directed to a method for enhancing an immune response in a subject in need thereof, wherein the method comprises administering to the subject an effective amount of a compound of the invention or a pharmaceutical composition described herein. In certain aspects of this embodiment, the T cells in the subject have at least one of enhanced priming, enhanced activation, enhanced migration, enhanced proliferation, enhanced survival, and enhanced cytolytic activity relative to prior to the administration of the compound or pharmaceutical composition. In certain aspects of this embodiment, the T cell activation is characterized by an elevated frequency of γ-IFN+CD8 T cells or enhanced levels of IL-2 or granzyme B production by T cells relative to prior to administration of the compound or pharmaceutical composition. In certain aspects of this embodiment, the number of T cells is elevated relative to prior to administration of the compound or pharmaceutical composition. In certain aspects of this embodiment, the T cell is an antigen-specific CD8 T cell. In certain aspects of this embodiment, the antigen presenting cells in the subject have enhanced maturation and activation relative prior to the administration of the compound or pharmaceutical composition. In certain aspects of this embodiment, the antigen presenting cells are dendritic cells. In certain aspects of this embodiment, the maturation of the antigen presenting cells is characterized by increased frequency of CD83+ dendritic cells. In certain aspects of this embodiment, the activation of the antigen presenting cells is characterized by elevated expression of CD80 and CD86 on dendritic cells.

The presently disclosed compounds bind directly to HPK1 and inhibit its kinase activity. In some embodiments, the presently disclosed compounds reduce, inhibit, or otherwise diminish the HPK1-mediated phosphorylation of SLP76 and/or Gads.

The presently disclosed compounds may or may not be a specific HPK1 antagonist. A specific HPK1 antagonist reduces the biological activity of HPK1 by an amount that is statistically greater than the inhibitory effect of the antagonist on any other protein (e.g., other serine/threonine kinases). In certain embodiments, the presently disclosed compounds specifically inhibit the serine/threonine kinase activity of HPK1. In some of these embodiments, the $IC_{50}$ of the HPK1 antagonist for HPK1 is about 90%, 80%, 70%, 60%, 50%, 40%, 30%, 20%, 10%, 0.1%, 0.01%, 0.001%, or less of the $IC_{50}$ of the HPK1 antagonist for another serine/threonine kinase or other type of kinase (e.g., tyrosine kinase).

The presently disclosed compounds can be used in a method for inhibiting HPK1. Such methods comprise contacting HPK1 with an effective amount of a presently disclosed compound. By "contact" is intended bringing the compound within close enough proximity to an isolated HPK1 enzyme or a cell expressing HPK1 (e.g., T cell, B cell, dendritic cell) such that the compound is able to bind to and inhibit the activity of HPK1. The compound can be contacted with HPK1 in vitro or in vivo via administration of the compound to a subject.

Any method known in the art to measure the kinase activity of HPK1 may be used to determine if HPK1 has been inhibited, including in vitro kinase assays, immunoblots with antibodies specific for phosphorylated targets of HPK1, such as SLP76 and Gads, or the measurement of a downstream biological effect of HPK1 kinase activity, such as the recruitment of 14-3-3 proteins to phosphorylated SLP7 and Gads, release of the SLP76-Gads-14-3-3 complex from LAT-containing microclusters, or T or B cell activation.

The presently disclosed compounds can be used to treat a HPK1-dependent disorder. As used herein, a "HPK1-dependent disorder" is a pathological condition in which HPK1 activity is necessary for the genesis or maintenance of the pathological condition. In some embodiments, the HPK1-dependent disorder is cancer.

The presently disclosed compounds also find use in enhancing an immune response in a subject in need thereof. Such methods comprise administering an effective amount of a compound of the invention.

As used herein, "enhancing an immune response" refers to an improvement in any immunogenic response to an antigen. Non-limiting examples of improvements in an immunogenic response to an antigen include enhanced maturation or migration of dendritic cells, enhanced activation of T cells (e.g., CD4 T cells, CD8 T cells), enhanced T cell (e.g., CD4 T cell, CD8 T cell) proliferation, enhanced B cell proliferation, increased survival of T cells and/or B cells, improved antigen presentation by antigen presenting cells (e.g., dendritic cells), improved antigen clearance, increase in production of cytokines by T cells (e.g., interleukin-2), increased resistance to prostaglandin E2-induced immune suppression, and enhanced priming and/or cytolytic activity of CD8 T cells.

In some embodiments, the CD8 T cells in the subject have enhanced priming, activation, proliferation and/or cytolytic activity relative to prior to the administration of the compound of the invention or a pharmaceutically acceptable salt, prodrug, metabolite, or derivative thereof. In some embodiments, the CD8 T cell priming is characterized by elevated CD44 expression and/or enhanced cytolytic activity in CD8 T cells. In some embodiments, the CD8 T cell activation is characterized by an elevated frequency of $\gamma$-IFN$^+$ CD8 T cells. In some embodiments, the CD8 T cell is an antigen-specific T-cell.

In some embodiments, the antigen presenting cells in the subject have enhanced maturation and activation relative to prior to the administration of the compound of the invention or a pharmaceutically acceptable salt, prodrug, metabolite, or derivative thereof. In some embodiments, the antigen presenting cells are dendritic cells. In some embodiments, the maturation of the antigen presenting cells is characterized by an increased frequency of CD83$^+$dendritic cells. In some embodiments, the activation of the antigen presenting cells is characterized by elevated expression of CD80 and CD86 on dendritic cells.

In some embodiments, the serum levels of cytokine IL-10 and/or chemokine IL-8, a human homolog of murine KC, in the subject are reduced relative to prior to the administration of the compound of Formula I or Ia or a pharmaceutically acceptable salt, prodrug, metabolite, or derivative thereof.

Engagement of the TCR leads to HPK1 activation, which functions as a negative regulator of TCR-induced AP-1 response pathway. It is believed that HPK1 negatively regulates T cell activation by reducing the persistence of signaling microclusters by phosphorylating SLP76 at Ser376 (Di Bartolo et al. (2007) JEM 204:681-691) and Gads at Thr254, which leads to the recruitment of 14-3-3 proteins that bind to the phosphorylated SLP76 and Gads, releasing the SLP76-Gads-14-3-3 complex from LAT-containing microclusters, which leads to T cell dysfunction, including anergy and exhaustion (Lasserre et al. (2011) J Cell Biol 195(5):839-853).

In some embodiments, administration of a compound of the invention or a pharmaceutically acceptable salt, prodrug, metabolite, or derivative thereof to a subject results in an enhancement of T cell function.

Accordingly, the presently disclosed compounds of the invention or pharmaceutically acceptable salts, prodrugs, metabolites, or derivatives thereof are useful in treating T cell dysfunctional disorders. A "T cell dysfunctional disorder" is a disorder or condition of T cells characterized by decreased responsiveness to antigenic stimulation. In a particular embodiment, a T cell dysfunctional disorder is a disorder that is specifically associated with increased kinase activity of HPK1. In another embodiment, a T cell dysfunctional disorder is one in which T cells are anergic or have decreased ability to secrete cytokines, proliferate, or execute cytolytic activity. In a specific aspect, the decreased responsiveness results in ineffective control of a pathogen or tumor expressing an immunogen. Examples of T cell dysfunctional disorders characterized by T-cell dysfunction include unresolved acute infection, chronic infection and tumor immunity.

Thus, the presently disclosed compounds can be used in treating conditions where enhanced immunogenicity is desired, such as increasing tumor immunogenicity for the treatment of cancer.

The term "dysfunction" in the context of immune dysfunction, refers to a state of reduced immune responsiveness to antigenic stimulation. The term includes the common elements of both exhaustion and/or anergy in which antigen recognition may occur, but the ensuing immune response is ineffective to control infection or tumor growth.

The term "dysfunctional", as used herein, also includes refractory or unresponsive to antigen recognition, specifically, impaired capacity to translate antigen recognition into downstream T-cell effector functions, such as proliferation, cytokine production (e.g., IL-2, $\gamma$-IFN) and/or target cell killing.

The term "anergy" refers to the state of unresponsiveness to antigen stimulation resulting from incomplete or insufficient signals delivered through the T-cell receptor (e.g. increase in intracellular Ca$^{+2}$ in the absence of ras-activation). T cell anergy can also result upon stimulation with antigen in the absence of co-stimulation, resulting in the cell becoming refractory to subsequent activation by the antigen even in the context of costimulation. The unresponsive state can often be overridden by the presence of Interleukin-2. Anergic T-cells do not undergo clonal expansion and/or acquire effector functions.

The term "exhaustion" refers to T cell exhaustion as a state of T cell dysfunction that arises from sustained TCR signaling that occurs during many chronic infections and cancer. It is distinguished from anergy in that it arises not through incomplete or deficient signaling, but from sustained signaling. It is defined by poor effector function, sustained expression of inhibitory receptors and a transcriptional state distinct from that of functional effector or memory T cells. Exhaustion prevents optimal control of infection and tumors. Exhaustion can result from both extrinsic negative regulatory pathways (e.g., immunoregulatory cytokines) as well as cell intrinsic negative regulatory (costimulatory) pathways (PD-1, B7-H3, B7-H4, etc.).

"Immunogenicity" refers to the ability of a particular substance to provoke an immune response. Tumors are immunogenic and enhancing tumor immunogenicity aids in the clearance of the tumor cells by the immune response.

"Enhancing T cell function" means to induce, cause or stimulate a T cell to have a sustained or amplified biological function, or renew or reactivate exhausted or inactive T cells. Examples of enhancing T cell function include: increased secretion of cytokines (e.g., γ-interferon, IL-2, IL-12, and TNFα), increased proliferation, increased antigen responsiveness (e.g., viral, pathogen, or tumor clearance) relative to such levels before the intervention, and increased effector granule production by CD8 T cells, such as granzyme B. In one embodiment, the level of enhancement is as least 50%, alternatively 60%, 70%, 80%, 90%, 100%, 120%, 150%, 200%. The manner of measuring this enhancement is known to one of ordinary skill in the art.

"Tumor immunity" refers to the process in which tumors evade immune recognition and clearance. Thus, as a therapeutic concept, tumor immunity is "treated" when such evasion is attenuated, and the tumors are recognized and attacked by the immune system. Examples of tumor recognition include tumor binding, tumor shrinkage and tumor clearance.

The present disclosure provides methods of modulating (e.g., inhibiting) HPK1 activity, said method comprising administering to a patient a compound provided herein, or a pharmaceutically acceptable salt thereof.

In one aspect, provided herein is a method for treating of cancer in a subject in need thereof comprising administering to the subject an effective amount of a compound of the invention or a pharmaceutically acceptable salt, prodrug, metabolite, or derivative thereof.

In the methods described herein, a compound of the invention or a pharmaceutical composition thereof is administered to a subject that has cancer.

In certain embodiments, the subject matter disclosed herein is directed to a method for treating a HPK1-dependent disorder, the method comprising administering to a subject in need thereof an effective amount of a compound of the invention or a pharmaceutical composition described herein. In certain aspects of this embodiment, the HPK1-dependent disorder is a cancer. In certain aspects of this embodiment, the cancer comprises at least one cancer selected from the group consisting of colorectal cancer, melanoma, non-small cell lung cancer, ovarian cancer, breast cancer, pancreatic cancer, a hematological malignancy, and a renal cell carcinoma. In certain aspects of this embodiment, the cancer has elevated levels of T-cell infiltration. In certain aspects of this embodiment, the cancer cells in the subject selectively have elevated expression of MHC class I antigen expression relative to prior to the administration of the compound or composition.

In some embodiments, the invention provides a pharmaceutical composition comprising an effective amount of a compound of the invention, or a pharmaceutically acceptable salt, hydrate, solvate, or prodrug thereof, and a pharmaceutically acceptable carrier.

In certain aspects, the invention provides a method of treating cell proliferation disorders, including cancers, benign papillomatosis, gestational trophoblastic diseases, and benign neoplastic diseases, such as skin papilloma (warts) and genital papilloma.

In one aspect, the invention provides a method of treating a cell proliferation disorder in a subject, comprising administering a therapeutically effective amount of a compound of the invention, or a pharmaceutically acceptable salt, hydrate, solvate, or prodrug thereof, to the subject.

In certain embodiments, the cell proliferation disorder is cancer.

Examples of cancers that are treatable using the compounds of the present disclosure include, but are not limited to, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, endometrial cancer, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or urethra, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers.

In some embodiments, cancers that are treatable using the compounds of the present disclosure include, but are not limited to, solid tumors (e.g., prostate cancer, colon cancer, esophageal cancer, endometrial cancer, ovarian cancer, uterine cancer, renal cancer, hepatic cancer, pancreatic cancer, gastric cancer, breast cancer, lung cancer, cancers of the head and neck, thyroid cancer, glioblastoma, sarcoma, bladder cancer, etc.), hematological cancers (e.g., lymphoma, leukemia such as acute lymphoblastic leukemia (ALL), acute myelogenous leukemia (AML), chronic lymphocytic leukemia (CLL), chronic myelogenous leukemia (CML), DLBCL, mantle cell lymphoma, Non-Hodgkin lymphoma (including relapsed or refractory NHL and recurrent follicular), Hodgkin lymphoma or multiple myeloma) and combinations of said cancers.

In certain embodiments, the cancer is brain cancer, leukemia, skin cancer, prostate cancer, thyroid cancer, colon cancer, lung cancer or sarcoma. In another embodiment the cancer is selected from the group consisting of glioma, glioblastoma multiforme, paraganglioma, suprantentorial primordial neuroectodermal tumors, acute myeloid leukemia, myelodysplastic syndrome, chronic myelogenous leukemia, melanoma, breast, prostate, thyroid, colon, lung, central chondrosarcoma, central and periosteal chondroma tumors, fibrosarcoma, and cholangiocarcinoma.

In certain embodiments, the cancer is selected from brain and spinal cancers, cancers of the head and neck, leukemia and cancers of the blood, skin cancers, cancers of the reproductive system, cancers of the gastrointestinal system, liver and bile duct cancers, kidney and bladder cancers, bone cancers, lung cancers, malignant mesothelioma, sarcomas, lymphomas, glandular cancers, thyroid cancers, heart tumors, germ cell tumors, malignant neuroendocrine (carcinoid) tumors, midline tract cancers, and cancers of unknown primary (cancers in which a metastasized cancer is found but the original cancer site is not known). In particular embodiments, the cancer is present in an adult patient; in additional embodiments, the cancer is present in a pediatric patient. In particular embodiments, the cancer is AIDS-related.

In a further embodiment, the cancer is selected from brain and spinal cancers. In particular embodiments, the cancer is selected from the group consisting of anaplastic astrocytomas, glioblastomas, astrocytomas, and estheosioneuroblastomas (olfactory blastomas). In particular embodiments, the brain cancer is selected from the group consisting of astrocytic tumor (e.g., pilocytic astrocytoma, subependymal giant-cell astrocytoma, diffuse astrocytoma, pleomorphic xanthoastrocytoma, anaplastic astrocytoma, astrocytoma, giant cell glioblastoma, glioblastoma, secondary glioblastoma, primary adult glioblastoma, and primary pediatric glioblastoma), oligodendroglial tumor (e.g., oligodendroglioma, and anaplastic oligodendroglioma), oligoastrocytic tumor (e.g., oligoastrocytoma, and anaplastic oligoastrocytoma), ependymoma (e.g., myxopapillary ependymoma, and anaplastic ependymoma); medulloblastoma, primitive neuroectodermal tumor, schwannoma, meningioma, atypical meningioma, anaplastic meningioma, pituitary adenoma, brain stem glioma, cerebellar astrocytoma, cerebral astorcytoma/malignant glioma, visual pathway and hypothalmic glioma, and primary central nervous system lymphoma. In specific instances of these embodiments, the brain cancer is selected from the group consisting of glioma, glioblastoma multiforme, paraganglioma, and suprantentorial primordial neuroectodermal tumors (sPNET).

In specific embodiments, the cancer is selected from cancers of the head and neck, including nasopharyngeal cancers, nasal cavity and paranasal sinus cancers, hypopharyngeal cancers, oral cavity cancers (e.g., squamous cell carcinomas, lymphomas, and sarcomas), lip cancers, oropharyngeal cancers, salivary gland tumors, cancers of the larynx (e.g., laryngeal squamous cell carcinomas, rhabdomyosarcomas), and cancers of the eye or ocular cancers. In particular embodiments, the ocular cancer is selected from the group consisting of intraocular melanoma and retinoblastoma.

In specific embodiments, the cancer is selected from leukemia and cancers of the blood. In particular embodiments, the cancer is selected from the group consisting of myeloproliferative neoplasms, myelodysplastic syndromes, myelodysplastic/myeloproliferative neoplasms, acute myeloid leukemia (AML), myelodysplastic syndrome (MDS), chronic myelogenous leukemia (CMIL), myeloproliferative neoplasm (MPN), post-MPN AML, post-MDS AML, del(5q)-associated high risk MDS or AML, blast-phase chronic myelogenous leukemia, angioimmunoblastic lymphoma, acute lymphoblastic leukemia, Langerans cell histiocytosis, hairy cell leukemia, and plasma cell neoplasms including plasmacytomas and multiple myelomas. Leukemias referenced herein may be acute or chronic.

In specific embodiments, the cancer is selected from skin cancers. In particular embodiments, the skin cancer is selected from the group consisting of melanoma, squamous cell cancers, and basal cell cancers.

In specific embodiments, the cancer is selected from cancers of the reproductive system. In particular embodiments, the cancer is selected from the group consisting of breast cancers, cervical cancers, vaginal cancers, ovarian cancers, prostate cancers, penile cancers, and testicular cancers. In specific instances of these embodiments, the cancer is a breast cancer selected from the group consisting of ductal carcinomas and phyllodes tumors. In specific instances of these embodiments, the breast cancer may be male breast cancer or female breast cancer. In specific instances of these embodiments, the cancer is a cervical cancer selected from the group consisting of squamous cell carcinomas and adenocarcinomas. In specific instances of these embodiments, the cancer is an ovarian cancer selected from the group consisting of epithelial cancers.

In specific embodiments, the cancer is selected from cancers of the gastrointestinal system. In particular embodiments, the cancer is selected from the group consisting of esophageal cancers, gastric cancers (also known as stomach cancers), gastrointestinal carcinoid tumors, pancreatic cancers, gallbladder cancers, colorectal cancers, and anal cancer. In instances of these embodiments, the cancer is selected from the group consisting of esophageal squamous cell carcinomas, esophageal adenocarcinomas, gastric adenocarcinomas, gastrointestinal carcinoid tumors, gastrointestinal stromal tumors, gastric lymphomas, gastrointestinal lymphomas, solid pseudopapillary tumors of the pancreas, pancreatoblastoma, islet cell tumors, pancreatic carcinomas including acinar cell carcinomas and ductal adenocarcinomas, gallbladder adenocarcinomas, colorectal adenocarcinomas, and anal squamous cell carcinomas.

In specific embodiments, the cancer is selected from liver and bile duct cancers. In particular embodiments, the cancer is liver cancer (hepatocellular carcinoma). In particular embodiments, the cancer is bile duct cancer (cholangiocarcinoma); in instances of these embodiments, the bile duct cancer is selected from the group consisting of intrahepatic cholangiocarcinoma and extrahepatic cholangiocarcinoma.

In specific embodiments, the cancer is selected from kidney and bladder cancers. In particular embodiments, the cancer is a kidney cancer selected from the group consisting of renal cell cancer, Wilms tumors, and transitional cell cancers. In particular embodiments, the cancer is a bladder cancer selected from the group consisting of urethelial carcinoma (a transitional cell carcinoma), squamous cell carcinomas, and adenocarcinomas.

In specific embodiments, the cancer is selected from bone cancers. In particular embodiments, the bone cancer is selected from the group consisting of osteosarcoma, malignant fibrous histiocytoma of bone, Ewing sarcoma, and chordoma.

In specific embodiments, the cancer is selected from lung cancers. In particular embodiments, the lung cancer is selected from the group consisting of non-small cell lung cancer, small cell lung cancers, bronchial tumors, and pleuropulmonary blastomas.

In specific embodiments, the cancer is selected from malignant mesothelioma. In particular embodiments, the cancer is selected from the group consisting of epithelial mesothelioma and sarcomatoids.

In specific embodiments, the cancer is selected from sarcomas. In particular embodiments, the sarcoma is selected from the group consisting of central chondrosarcoma, central and periosteal chondroma, fibrosarcoma, clear cell sarcoma of tendon sheaths, and Kaposi's sarcoma.

In specific embodiments, the cancer is selected from lymphomas. In particular embodiments, the cancer is selected from the group consisting of Hodgkin lymphoma (e.g., Reed-Sternberg cells), non-Hodgkin lymphoma (e.g., diffuse large B-cell lymphoma, follicular lymphoma, mycosis fungoides, Sezary syndrome, primary central nervous system lymphoma), cutaneous T-cell lymphomas, and primary central nervous system lymphomas.

In specific embodiments, the cancer is selected from glandular cancers. In particular embodiments, the cancer is selected from the group consisting of adrenocortical cancer, pheochromocytomas, paragangliomas, pituitary tumors, thymoma, and thymic carcinomas.

In specific embodiments, the cancer is selected from thyroid cancers. In particular embodiments, the thyroid cancer is selected from the group consisting of medullary thyroid carcinomas, papillary thyroid carcinomas, and follicular thyroid carcinomas.

In specific embodiments, the cancer is selected from germ cell tumors. In particular embodiments, the cancer is selected from the group consisting of malignant extracranial germ cell tumors and malignant extragonadal germ cell tumors. In specific instances of these embodiments, the malignant extragonadal germ cell tumors are selected from the group consisting of nonseminomas and seminomas.

In specific embodiments, the cancer is selected from heart tumors. In particular embodiments, the heart tumor is selected from the group consisting of malignant teratoma, lymphoma, rhabdomyosacroma, angiosarcoma, chondrosarcoma, infantile fibrosarcoma, and synovial sarcoma.

In specific embodiments, the cell-proliferation disorder is selected from benign papillomatosis, benign neoplastic diseases and gestational trophoblastic diseases. In particular embodiments, the benign neoplastic disease is selected from skin papilloma (warts) and genital papilloma. In particular embodiments, the gestational trophoblastic disease is selected from the group consisting of hydatidiform moles, and gestational trophoblastic neoplasia (e.g., invasive moles, choriocarcinomas, placental-site trophoblastic tumors, and epithelioid trophoblastic tumors).

In some embodiments, the subject has melanoma. The melanoma may be at early stage or at late stage. In some embodiments, the subject has colorectal cancer. The colorectal cancer may be at early stage or at late stage. In some embodiments, the subject has non-small cell lung cancer. The non-small cell lung cancer may be at early stage or at late stage. In some embodiments, the subject has pancreatic cancer. The pancreatic cancer may be at early stage or late state. In some embodiments, the subject has a hematological malignancy. The hematological malignancy may be at early stage or late stage. In some embodiments, the subject has ovarian cancer. The ovarian cancer may be at early stage or at late stage. In some embodiments, the subject has breast cancer. The breast cancer may be at early stage or at late stage. In some embodiments, the subject has renal cell carcinoma. The renal cell carcinoma may be at early stage or at late stage. In some embodiments, the cancer has elevated levels of T-cell infiltration.

In some embodiments, cancers treatable with compounds of the present disclosure include melanoma (e.g., metastatic malignant melanoma), renal cancer (e.g. clear cell carcinoma), prostate cancer (e.g. hormone refractory prostate adenocarcinoma), breast cancer, triple-negative breast cancer, colon cancer and lung cancer (e.g. non-small cell lung cancer and small cell lung cancer). Additionally, the disclosure includes refractory or recurrent malignancies whose growth may be inhibited using the compounds of the disclosure.

In some embodiments, diseases and indications that are treatable using the compounds of the present disclosure include, but are not limited to hematological cancers, sarcomas, lung cancers, gastrointestinal cancers, genitourinary tract cancers, liver cancers, bone cancers, nervous system cancers, gynecological cancers, and skin cancers.

Exemplary hematological cancers include lymphomas and leukemias such as acute lymphoblastic leukemia (ALL), acute myelogenous leukemia (AML), acute promyelocytic leukemia (APL), chronic lymphocytic leukemia (CLL), chronic myelogenous leukemia (CML), diffuse large B-cell lymphoma (DLBCL), mantle cell lymphoma, Non-Hodgkin lymphoma (including relapsed or refractory NHL and recurrent follicular), Hodgkin lymphoma, myeloproliferative diseases (e.g., primary myelofibrosis (PMF), polycythemia vera (PV), essential thrombocytosis (ET)), myelodysplasia syndrome (MDS), T-cell acute lymphoblastic lymphoma (T-ALL), multiple myeloma, cutaneous T-cell lymphoma, Waldenstrom's Macroglubulinemia, hairy cell lymphoma, chronic myelogenic lymphoma and Burkitt's lymphoma.

Exemplary sarcomas include chondrosarcoma, Ewing's sarcoma, osteosarcoma, rhabdomyosarcoma, angiosarcoma, fibrosarcoma, liposarcoma, myxoma, rhabdomyoma, rhabdosarcoma, fibroma, lipoma, harmatoma, and teratoma.

Exemplary lung cancers include non-small cell lung cancer (NSCLC), small cell lung cancer, bronchogenic carcinoma (squamous cell, undifferentiated small cell, undifferentiated large cell, adenocarcinoma), alveolar (bronchiolar) carcinoma, bronchial adenoma, chondromatous hamartoma, and mesothelioma.

Exemplary gastrointestinal cancers include cancers of the esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), and colorectal cancer.

Exemplary genitourinary tract cancers include cancers of the kidney (adenocarcinoma, Wilm's tumor [nephroblastoma]), bladder and urethra (squamous cell carcinoma, transitional cell carcinoma, adenocarcinoma), prostate (adenocarcinoma, sarcoma), and testis (seminoma, teratoma, embryonal carcinoma, teratocarcinoma, choriocarcinoma, sarcoma, interstitial cell carcinoma, fibroma, fibroadenoma, adenomatoid tumors, lipoma).

Exemplary liver cancers include hepatoma (hepatocellular carcinoma), cholangiocarcinoma, hepatoblastoma, angiosarcoma, hepatocellular adenoma, and hemangioma.

Exemplary bone cancers include, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors Exemplary nervous system cancers include cancers of the skull (osteoma, hemangioma, granuloma, xanthoma, osteitis deformans), meninges (meningioma, meningiosarcoma, gliomatosis), brain (astrocytoma, meduoblastoma, glioma, ependymoma, germinoma (pinealoma), glioblastoma, glioblastoma multiform, oligodendroglioma, schwannoma, retinoblastoma, congenital tumors), and spinal cord (neurofibroma, meningioma, glioma, sarcoma), as well as neuroblastoma and Lhermitte-Duclos disease.

Exemplary gynecological cancers include cancers of the uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

Exemplary skin cancers include melanoma, basal cell carcinoma, squamous cell carcinoma, Kaposi's sarcoma, Merkel cell skin cancer, moles dysplastic nevi, lipoma, angioma, dermatofibroma, and keloids. In some embodiments, diseases and indications that are treatable using the compounds of the present disclosure include, but are not limited to, sickle cell disease (e.g., sickle cell anemia), triple-negative breast cancer (TNBC), myelodysplastic syndromes, testicular cancer, bile duct cancer, esophageal cancer, and urothelial carcinoma.

Exemplary head and neck cancers include glioblastoma, melanoma, rhabdosarcoma, lymphosarcoma, osteosarcoma, squamous cell carcinomas, adenocarcinomas, oral cancer, laryngeal cancer, nasopharyngeal cancer, nasal and paranasal cancers, thyroid and parathyroid cancers.

In some embodiments, HPK1 inhibitors may be used to treat tumors producing PGE2 (e.g. Cox-2 overexpressing tumors) and/or adenosine (CD73 and CD39 over-expressing tumors). Overexpression of Cox-2 has been detected in a number of tumors, such as colorectal, breast, pancreatic and lung cancers, where it correlates with a poor prognosis. Overexpression of COX-2 has been reported in hematological cancer models such as RAJI (Burkitt's lymphoma) and U937 (acute promonocytic leukemia) as well as in patient's blast cells. CD73 is up-regulated in various human carcinomas including those of colon, lung, pancreas and ovary. Importantly, higher expression levels of CD73 are associated with tumor neovascularization, invasiveness, and metastasis and with shorter patient survival time in breast cancer.

In some embodiments, the compounds of the invention are useful in preventing or reducing the risk of developing any of the diseases referred to herein; e.g., preventing or reducing the risk of developing a disease, condition or disorder in an individual who may be predisposed to the disease, condition or disorder but does not yet experience or display the pathology or symptomatology of the disease.

The presently disclosed compounds may be administered in any suitable manner known in the art. In some embodiments, the compound of the invention or a pharmaceutically acceptable salt, prodrug, metabolite, or derivative thereof is administered intravenously, intramuscularly, subcutaneously, topically, orally, transdermally, intraperitoneally, intraorbitally, by implantation, by inhalation, intrathecally, intraventricularly, intratumorally, or intranasally.

In some embodiments, the HPK1 antagonist is administered continuously. In other embodiments, the HPK1 antagonist is administered intermittently. Moreover, treatment of a subject with an effective amount of a HPK1 antagonist can include a single treatment or can include a series of treatments.

It is understood that appropriate doses of the active compound depends upon a number of factors within the knowledge of the ordinarily skilled physician or veterinarian. The dose(s) of the active compound will vary, for example, depending upon the age, body weight, general health, gender, and diet of the subject, the time of administration, the route of administration, the rate of excretion, and any drug combination.

It will also be appreciated that the effective dosage of a compound of the invention or a pharmaceutically acceptable salt, prodrug, metabolite, or derivative thereof used for treatment may increase or decrease over the course of a particular treatment. Changes in dosage may result and become apparent from the results of diagnostic assays.

In some embodiments, the HPK1 antagonist is administered to the subject at a dose of between about 0.001 µg/kg and about 1000 mg/kg, including but not limited to about 0.001 µg/kg, 0.01 µg/kg, 0.05 µg/kg, 0.1 µg/kg, 0.5 µg/kg, 1 µg/kg, 10 µg/kg, 25 µg/kg, 50 µg/kg, 100 µg/kg, 250 µg/kg, 500 µg/kg, 1 mg/kg, 5 mg/kg, 10 mg/kg, 25 mg/kg, 50 mg/kg, 100 mg/kg, and 200 mg/kg.

In the methods described herein, the method can further comprise administering a chemotherapeutic agent to the subject. In certain aspects of this embodiment, the chemotherapeutic agent is administered to the subject simultaneously with the compound or the composition. In certain aspects of this embodiment, the chemotherapeutic agent is administered to the subject prior to administration of the compound or the composition. In certain aspects of this embodiment, the chemotherapeutic agent is administered to the subject after administration of the compound or the composition.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

The term "administration" or "administering" includes routes of introducing the compound(s) to a subject to perform their intended function. Examples of routes of administration which can be used include injection (subcutaneous, intravenous, parenterally, intraperitoneally, intrathecal), topical, oral, inhalation, rectal and transdermal.

The term "effective amount" includes an amount effective, at dosages and for periods of time necessary, to achieve the desired result. An effective amount of compound may vary according to factors such as the disease state, age, and weight of the subject, and the ability of the compound to elicit a desired response in the subject. Dosage regimens may be adjusted to provide the optimum therapeutic response.

The phrases "systemic administration," "administered systemically", "peripheral administration" and "administered peripherally" as used herein mean the administration of a compound(s), drug or other material, such that it enters the patient's system and, thus, is subject to metabolism and other like processes.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The term "subject" refers to animals such as mammals, including, but not limited to, primates (e.g., humans), cows, sheep, goats, horses, dogs, cats, rabbits, rats, mice and the like. In certain embodiments, the subject is a human.

Combination Therapies

Depending upon the particular condition, or disease, to be treated, additional therapeutic agents, which are normally administered to treat that condition, may be administered in combination with compounds and compositions of this invention. As used herein, additional therapeutic agents that are normally administered to treat a particular disease, or condition, are known as "appropriate for the disease, or condition, being treated."

In certain embodiments, a provided combination, or composition thereof, is administered in combination with another therapeutic agent.

Examples of agents the combinations of this invention may also be combined with include, without limitation: treatments for Alzheimer's Disease such as Aricept® and Excelon®; treatments for HIV such as ritonavir; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents that prolong or improve pharmacokinetics such as cytochrome P450 inhibitors (i.e., inhibitors of metabolic breakdown) and CYP3A4 inhibitors (e.g., ketokenozole and ritonavir), and agents for treating immunodeficiency disorders such as gamma globulin.

In certain embodiments, combination therapies of the present invention, or a pharmaceutically acceptable composition thereof, are administered in combination with a monoclonal antibody or an siRNA therapeutic.

Those additional agents may be administered separately from a provided combination therapy, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a combination of the present invention may be administered with another therapeutic agent simultaneously or sequentially in separate unit dosage forms or together in a single unit dosage form.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In one embodiment, the present invention provides a composition comprising a compound of formula I and one or more additional therapeutic agents. The therapeutic agent may be administered together with a compound of formula I, or may be administered prior to or following administration of a compound of formula I. Suitable therapeutic agents are described in further detail below. In certain embodiments, a compound of formula I may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours before the therapeutic agent. In other embodiments, a compound of formula I may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours following the therapeutic agent.

In another embodiment, the present invention provides a method of treating an inflammatory disease, disorder or condition by administering to a patient in need thereof a compound of formula I and one or more additional therapeutic agents. Such additional therapeutic agents may be small molecules or recombinant biologic agents and include, for example, acetaminophen, non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol, febuxostat (Uloric®), sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), canakinumab (Ilaris®), anti-Jak inhibitors such as tofacitinib, antibodies such as rituximab (Rituxan®), "anti-T-cell" agents such as abatacept (Orencia®), "anti-IL-6" agents such as tocilizumab (Actemra®), diclofenac, cortisone, hyaluronic acid (Synvisc® or Hyalgan®), monoclonal antibodies such as tanezumab, anticoagulants such as heparin (Calcinparine® or Liquaemin®) and warfarin (Coumadin®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot®, anticholinergics or antispasmodics such as dicyclomine (Bentyl®), Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as beclomethasone dipropionate (Beclovent®, Qvar®, and Vanceril®), triamcinolone acetonide (Azmacort®), mometasone (Asthmanex®), budesonide (Pulmocort®), and flunisolide (Aerobid®), Afviar®, Symbicort®, Dulera®, cromolyn sodium (Intal®), methylxanthines such as theophylline (Theo-Dur®, Theolair®, Slo-Bid®, Uniphyl®, Theo-24®) and aminophylline, IgE antibodies such as omalizumab (Xolair®), nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), doxorubicin (Hydrodaunorubicin®), vincristine (Oncovin®), bortezomib (Velcade®), and dexamethasone (Decadron®) in combination with lenalidomide (Revlimid®), or any combination(s) thereof.

In another embodiment, the present invention provides a method of treating rheumatoid arthritis comprising administering to a patient in need thereof a compound of formula I and one or more additional therapeutic agents selected from non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), antibodies such as rituximab (Rituxan®), "anti-T-cell" agents such as abatacept (Orencia®) and "anti-IL-6" agents such as tocilizumab (Actemra®).

In some embodiments, the present invention provides a method of treating osteoarthritis comprising administering to a patient in need thereof a compound of formula I and one or more additional therapeutic agents selected from acetaminophen, non-steroidal anti-inflammatory drugs (NSAIDS) such as aspirin, ibuprofen, naproxen, etodolac (Lodine®) and celecoxib, diclofenac, cortisone, hyaluronic acid (Synvisc® or Hyalgan®) and monoclonal antibodies such as tanezumab.

In some embodiments, the present invention provides a method of treating cutaneous lupus erythematosus or systemic lupus erythematosus comprising administering to a patient in need thereof a compound of formula I and one or more additional therapeutic agents selected from acetaminophen, non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, antimalarials such as hydroxychloroquine (Plaquenil®) and chloroquine (Aralen®), cyclophosphamide (Cytoxan®), methotrexate (Rheumatrex®), azathioprine (Imuran®) and anticoagulants such as heparin (Calcinparine® or Liquaemin®) and warfarin (Coumadin®).

In some embodiments, the present invention provides a method of treating Crohn's disease, ulcerative colitis, or inflammatory bowel disease comprising administering to a patient in need thereof a compound of formula I and one or more additional therapeutic agents selected from mesalamine (Asacol®) sulfasalazine (Azulfidine®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot® and anticholinergics or antispasmodics such as dicyclomine (Bentyl®), anti-TNF therapies, steroids, and antibiotics such as Flagyl or ciprofloxacin.

In some embodiments, the present invention provides a method of treating asthma comprising administering to a patient in need thereof a compound of formula I and one or more additional therapeutic agents selected from Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, cromolyn sodium (Intal®), methylxanthines such as theophylline (Theo-Dur®, Theolair®, Slo-Bid®, Uniphyl®, Theo-24®) and aminophylline, and IgE antibodies such as omalizumab (Xolair®).

In some embodiments, the present invention provides a method of treating COPD comprising administering to a patient in need thereof a compound of formula I and one or more additional therapeutic agents selected from beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), methylxanthines such as theophylline (Theo-Dur®, Theolair®, Slo-Bid®, Uniphyl®, Theo-24®) and aminophylline, inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, In another embodiment, the present invention provides a method of treating a hematological malignancy comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a PI3K inhibitor, a SYK inhibitor, and combinations thereof.

In another embodiment, the present invention provides a method of treating a solid tumor comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a PI3K inhibitor, a SYK inhibitor, and combinations thereof.

In another embodiment, the present invention provides a method of treating a hematological malignancy comprising administering to a patient in need thereof a compound of formula I and a Hedgehog (Hh) signaling pathway inhibitor. In some embodiments, the hematological malignancy is DLBCL (Ramirez et al "Defining causative factors contributing in the activation of hedgehog signaling in diffuse large B-cell lymphoma" Leuk. Res. (2012), published online July 17, and incorporated herein by reference in its entirety).

In another embodiment, the present invention provides a method of treating diffuse large B-cell lymphoma (DLBCL) comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, and combinations thereof.

In another embodiment, the present invention provides a method of treating multiple myeloma comprising administering to a patient in need thereof a compound of formula I and one or more additional therapeutic agents selected from bortezomib (Velcade®), and dexamethasone (Decadron®), a hedgehog signaling inhibitor, a BTK inhibitor, a JAK/pan-JAK inhibitor, a TYK2 inhibitor, a PI3K inhibitor, a SYK inhibitor in combination with lenalidomide (Revlimid®).

In another embodiment, the present invention provides a method of treating or lessening the severity of a disease comprising administering to a patient in need thereof a compound of formula I and a BTK inhibitor, wherein the disease is selected from inflammatory bowel disease, arthritis, cutaneous lupus erythematosus, systemic lupus erythematosus (SLE), vasculitis, idiopathic thrombocytopenic purpura (ITP), rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, autoimmune thyroiditis, Sjogren's syndrome, multiple sclerosis, systemic sclerosis, Lyme neuroborreliosis, Guillain-Barre syndrome, acute disseminated encephalomyelitis, Addison's disease, opsoclonus-myoclonus syndrome, ankylosing spondylosis, antiphospholipid antibody syndrome, aplastic anemia, autoimmune hepatitis, autoimmune gastritis, pernicious anemia, celiac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, membranous glomerulonephropathy, endometriosis, interstitial cystitis, pemphigus vulgaris, bullous pemphigoid, neuromyotonia, scleroderma, vulvodynia, a hyperproliferative disease, rejection of transplanted organs or tissues, Acquired Immunodeficiency Syndrome (AIDS, also known as HIV), type 1 diabetes, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis, asthma, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis, B-cell proliferative disorder, e.g., diffuse large B cell lymphoma, follicular lymphoma, chronic lymphocytic lymphoma, chronic lymphocytic leukemia, acute lymphocytic leukemia, B-cell prolymphocytic leukemia, lymphoplasmacytic lymphoma/Waldenstrom macroglobulinemia, splenic marginal zone lymphoma, multiple myeloma (also known as plasma cell myeloma), non-Hodgkin's lymphoma, Hodgkin's lymphoma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt lymphoma/leukemia, or lymphomatoid granulomatosis, breast cancer, prostate cancer, or cancer of the mast cells (e.g., mastocytoma, mast cell leukemia, mast cell sarcoma, systemic mastocytosis), bone cancer, colorectal cancer, pancreatic cancer, diseases of the bone and joints including, without limitation, rheumatoid arthritis, seronegative spondyloarthropathies (including ankylosing spondylitis, psoriatic arthritis and Reiter's disease), Behcet's disease, Sjogren's syndrome, systemic sclerosis, osteoporosis, bone cancer, bone metastasis, a thromboembolic disorder, (e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, deep venous thrombosis), inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, diabetes, septic shock, cutaneous lupus erythematosus, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, scleraderma, mycosis fungoides, acute inflammatory responses (such as acute respiratory distress syndrome and ischemia/reperfusion injury), and Graves' disease.

In another embodiment, the present invention provides a method of treating or lessening the severity of a disease comprising administering to a patient in need thereof a compound of formula I and a PI3K inhibitor, wherein the disease is selected from a cancer, a neurodegenerative disorder, an angiogenic disorder, a viral disease, an autoimmune disease, an inflammatory disorder, a hormone-related disease, conditions associated with organ transplantation, immunodeficiency disorders, a destructive bone disorder, a proliferative disorder, an infectious disease, a condition associated with cell death, thrombin-induced platelet aggregation, chronic myelogenous leukemia (CML), chronic lymphocytic leukemia (CLL), liver disease, pathologic immune conditions involving T cell activation, a cardiovascular disorder, and a CNS disorder.

In another embodiment, the present invention provides a method of treating or lessening the severity of a disease comprising administering to a patient in need thereof a compound of formula I and a PI3K inhibitor, wherein the disease is selected from benign or malignant tumor, carcinoma or solid tumor of the brain, kidney (e.g., renal cell carcinoma (RCC)), liver, adrenal gland, bladder, breast, stomach, gastric tumors, ovaries, colon, rectum, prostate, pancreas, lung, vagina, endometrium, cervix, testis, genitourinary tract, esophagus, larynx, skin, bone or thyroid, sarcoma, glioblastomas, neuroblastomas, multiple myeloma or gastrointestinal cancer, especially colon carcinoma or colorectal adenoma or a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, (including, for example, non-Hodgkin's Lymphoma (NHL) and Hodgkin's lymphoma (also termed Hodgkin's or Hodgkin's disease)), a mammary carcinoma, follicular carcinoma, undifferentiated carcinoma, papillary carcinoma, seminoma, melanoma, or a leukemia, diseases include Cowden syndrome, Lhermitte-Dudos disease and Bannayan-Zonana syndrome, or diseases in which the PI3K/PKB pathway is aberrantly activated, asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection, acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy, bronchitis of whatever type or genesis including, but not limited to, acute, arachidic, catarrhal, croupus, chronic or phthinoid bronchitis, pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis, Loffler's syndrome, eosinophilic, pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction, psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), cutaneous lupus erythematosus, systemic lupus erythematosus, rheumatoid arthritis, polychondritis, scleredoma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy, restenosis, cardiomegaly, atherosclerosis, myocardial infarction, ischemic stroke and congestive heart failure, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia.

In some embodiments the present invention provides a method of treating or lessening the severity of a disease comprising administering to a patient in need thereof a compound of formula I and a Bcl-2 inhibitor, wherein the disease is an inflammatory disorder, an autoimmune disorder, a proliferative disorder, an endocrine disorder, a neurological disorder, or a disorder associated with transplantation. In some embodiments, the disorder is a proliferative disorder, lupus, or lupus nephritis. In some embodiments, the proliferative disorder is chronic lymphocytic leukemia, diffuse large B-cell lymphoma, Hodgkin's disease, small-cell lung cancer, non-small-cell lung cancer, myelodysplastic syndrome, lymphoma, a hematological neoplasm, or solid tumor.

In some embodiments, the present invention provides a method of treating or lessening the severity of a disease, comprising administering to a patient in need thereof a HPK1 binding compound. In some embodiments, the disease is an autoimmune disorder, an inflammatory disorder, a proliferative disorder, an endocrine disorder, a neurological disorder, or a disorder associated with transplantation. In some embodiments the HPK1 binding compound is a compound of formula I.

The compounds and compositions, according to the method of the present invention, may be administered using any amount and any route of administration effective for treating or lessening the severity of an autoimmune disorder, an inflammatory disorder, a proliferative disorder, an endocrine disorder, a neurological disorder, or a disorder associated with transplantation. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting protein kinase activity in a biological sample comprising the step of contacting said biological sample with a compound of this invention, or a composition comprising said compound.

According to another embodiment, the invention relates to a method of inhibiting HPK1, or a mutant thereof, activity in a biological sample comprising the step of contacting said biological sample with a compound of this invention, or a composition comprising said compound. In certain embodiments, the invention relates to a method of irreversibly inhibiting HPK1, or a mutant thereof, activity in a biological sample comprising the step of contacting said biological sample with a compound of this invention, or a composition comprising said compound.

In another embodiment, the invention provides a method of selectively inhibiting HPK1 over one or more kinases.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of HPK1 (or a mutant thereof) activity in a biological sample is useful for a variety of purposes that are known to one of skill in the art. Examples of such purposes include, but are not limited to, blood transfusion, organ-transplantation, biological specimen storage, and biological assays.

Another embodiment of the present invention relates to a method of inhibiting protein kinase activity in a patient comprising the step of administering to said patient a compound of the present invention, or a composition comprising said compound.

According to another embodiment, the invention relates to a method of inhibiting activity of HPK1, or a mutant thereof, in a patient comprising the step of administering to said patient a compound of the present invention, or a composition comprising said compound. According to certain embodiments, the invention relates to a method of reversibly or irreversibly inhibiting one or more of HPK1, or a mutant thereof, activity in a patient comprising the step of administering to said patient a compound of the present invention, or a composition comprising said compound. In other embodiments, the present invention provides a method for treating a disorder mediated by HPK1, or a mutant thereof, in a patient in need thereof, comprising the step of administering to said patient a compound according to the present invention or pharmaceutically acceptable composition thereof. Such disorders are described in detail herein.

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

A compound of the current invention may also be used to advantage in combination with other therapeutic compounds. In some embodiments, the other therapeutic compounds are antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZD6244 from AstraZeneca, PD181461 from Pfizer and leucovorin. The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™ Letrozole is marketed under the trade names Femara™ or Femar™. Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™. Raloxifene hydrochloride is marketed under the trade name Evista™. Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™). The term "gonadorelin agonist" as used herein includes, but is not limited to abarelix, goserelin and goserelin acetate. Goserelin can be administered under the trade name Zoladex™.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g. in the form as it is marketed, e.g. under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™) daunorubicin, epirubicin, idarubicin and nemorubicin, the anthraquinones mitoxantrone and losoxantrone, and the podophillotoxines etoposide and teniposide. Etoposide is marketed under the trade name Etopophos™. Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed. under the trade name Zavedos™. Mitoxantrone is marketed under the trade name Novantron.

The term "microtubule active agent" relates to microtubule stabilizing, microtubule destabilizing compounds and microtublin polymerization inhibitors including, but not limited to taxanes, such as paclitaxel and docetaxel; vinca alkaloids, such as vinblastine or vinblastine sulfate, vincristine or vincristine sulfate, and vinorelbine; discodermolides; cochicine and epothilones and derivatives thereof. Paclitaxel is marketed under the trade name Taxol™ Docetaxel is marketed under the trade name Taxotere™. Vinblastine sulfate is marketed under the trade name Vinblastin R.P™. Vincristine sulfate is marketed under the trade name Farmistin™

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™.

The term "platin compound" as used herein includes, but is not limited to, carboplatin, cis-platin, cisplatinum and oxaliplatin. Carboplatin can be administered, e.g., in the form as it is marketed, e.g. under the trademark Carboplat™. Oxaliplatin can be administered, e.g., in the form as it is marketed, e.g. under the trademark Eloxatin™.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the AxI receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, PI3K, SYK, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; llmofosine; RO 318220 and RO 320432; GO 6976; lsis 3521; LY333531/LY379196; isochinoline compounds; FTIs; PD184352 or QAN697 (a P13K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5- dihydroxyphenyl)methyl]amino}-benzoic acid adamantyl ester; NSC 680410, adaphostin); 1) compounds targeting, decreasing or inhibiting the activity of the epidermal growth factor family of receptor tyrosine kinases (EGFR1 ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, CI-1033, EKB-569, GW-2016, E1.1, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PI3Kβ, PI3K-C2α, PI3K-C2β, PI3K-C2γ, Vps34, p110-α, p110-β, p110-γ, p110-δ, p85-α, p85-β, p55-γ, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib.

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof; see WO2008118802), navitoclax (and analogs thereof, see U.S. Pat. No. 7,390,799), NH-1 (Shenayng Pharmaceutical University), obatoclax (and analogs thereof, see WO2004106328), S—001 (Gloria Pharmaceuticals), TW series compounds (Univ. of Michigan), and venetoclax.

In some embodiments the Bcl-2 inhibitor is a small molecule therapeutic. In some embodiments the Bcl-2 inhibitor is a peptidomimetic.

Further examples of BTK inhibitory compounds, and conditions treatable by such compounds in combination with compounds of this invention can be found in WO2008039218 and WO2011090760, the entirety of which are incorporated herein by reference.

Further examples of SYK inhibitory compounds, and conditions treatable by such compounds in combination with compounds of this invention can be found in WO2003063794, WO2005007623, and WO2006078846, the entirety of which are incorporated herein by reference.

Further examples of PI3K inhibitory compounds, and conditions treatable by such compounds in combination with compounds of this invention can be found in WO2004019973, WO2004089925, WO2007016176, U.S. Pat. No. 8,138,347, WO2002088112, WO2007084786, WO2007129161, WO2006122806, WO2005113554, and WO2007044729 the entirety of which are incorporated herein by reference.

Further examples of JAK inhibitory compounds, and conditions treatable by such compounds in combination with compounds of this invention can be found in WO2009114512, WO2008109943, WO2007053452, WO2000142246, and WO2007070514, the entirety of which are incorporated herein by reference.

Further anti-angiogenic compounds include compounds having another mechanism for their activity, e.g. unrelated to protein or lipid kinase inhibition e.g. thalidomide (Thalomid™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g. inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™. Pamidronic acid is marketed under the trade name Aredia™. Alendronic acid is marketed under the trade name Fosamax™. Ibandronic acid is marketed under the trade name Bondranat™. Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zarnestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™) and MLLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; ALK inhibitors, which are compounds which target, decrease or inhibit anaplastic lymphoma kinase, and Bcl-2 inhibitors.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino,17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PR064553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412. In some embodiments, the present invention provides a method of treating AML associated with an ITD and/or D835Y mutation, comprising administering a compound of the present invention together with a one or more FLT3 inhibitors. In some embodiments, the FLT3 inhibitors are selected from quizartinib (AC220), a staurosporine derivative (e.g. midostaurin or lestaurtinib), sorafenib, tandutinib, LY-2401401, LS-104, EB-10, famitinib, NOV-110302, NMS-P948, AST-487, G-749, SB-1317, 5-209, SC-110219, AKN-028, fedratinib, tozasertib, and sunitinib. In some embodiments, the FLT3 inhibitors are selected from quizartinib, midostaurin, lestaurtinib, sorafenib, and sunitinib.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl]phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., $4^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; Angiostatin™; Endostatin™; anthranilic acid amides; ZD4190; ZD6474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The compounds of the invention are also useful as co-therapeutic compounds for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. A compound of the invention may be mixed with the other drug substance in a fixed pharmaceutical composition or it may be administered separately, before, simultaneously with or after the other drug substance. Accordingly the invention includes a combination of a compound of the invention as hereinbefore described with an anti-inflammatory, bronchodilatory, antihistamine or anti-tussive drug substance, said compound of the invention and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate; non-steroidal glucocorticoid receptor agonists; LTB4 antagonists such LY293111, CGS025019C, CP-195543, SC-53228, BIIL 284, ONO 4057, SB 209247; LTD4 antagonists such as montelukast and zafirlukast; PDE4 inhibitors such cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo); A2a agonists; A2b antagonists; and beta-2 adrenoceptor agonists such as albuterol (salbutamol), metaproterenol, terbutaline, salmeterol fenoterol, procaterol, and especially, formoterol and pharmaceutically acceptable salts thereof. Suitable bronchodilatory drugs include anticholinergic or antimuscarinic compounds, in particular ipratropium bromide, oxitropium bromide, tiotropium salts and CHF 4226 (Chiesi), and glycopyrrolate.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine.

Other useful combinations of compounds of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, and Takeda antagonists such as N-[[4-[[[6,7-dihydro-2-(4-methylphenyl)-5H-benzo-cyclohepten-8-yl]carbonyl]amino]phenyl]-methyl] tetrahydro-N,N-dimethyl-2H-pyran-4-aminium chloride (TAK-770).

The structure of the active compounds identified by code numbers, generic or trade names may be taken from the actual edition of the standard compendium "The Merck Index" or from databases, e.g. Patents International (e.g. IMS World Publications).

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 µg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of this invention are another embodiment of the present invention.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein. Additional compounds of the invention were prepared by methods substantially similar to those described herein in the Examples and methods known to one skilled in the art.

Preparation of Intermediates

Method CA1—Preparation of 2-(6-aminopyridin-3-yl)-N-ethyl-2-methylpropanamide (CA1)

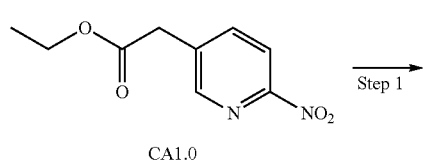

CA1.0

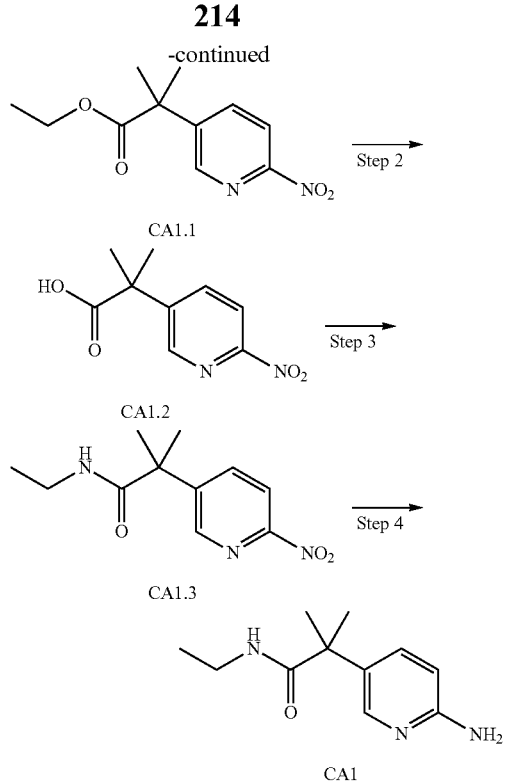

Step 1: Ethyl 2-methyl-2-(6-nitropyridin-3-yl)propanoate (CA1.1)

A solution of ethyl-2-(6-nitropyridin-3-yl)acetate (CA1.0) (980 mg, 4.6 mmol) in DMF (20 mL) at 0° C. was treated with sodium hydride (60% dispersion in mineral oil, 196 mg, 4.8 mmol). The mixture was stirred for 5 minutes, and then iodomethane (0.316 mL, 5.0 mmol) was added dropwise. After a further 2 h an additional portion of sodium hydride (60% dispersion in mineral oil, 196 mg, 4.8 mmol) was added, followed by iodomethane (0.316 mL, 5.0 mmol) 5 minutes later. The mixture was stirred at RT for 18 h, quenched with water (30 mL) and extracted into EtOAc (2×30 mL). The combined extracts were washed with brine (30 mL), dried over Na2SO4, filtered, and concentrated in vacuo. The residue was purified by column chromatography (0-50% gradient elution EtOAc in cyclohexane) to afford the title compound (CA1.1) (758 mg, 68%) as a yellow oil. $^1$H NMR (400 MHz, CDCl3): δ 8.63 (s, 1H), 8.22 (d, J=8.4 Hz, 1H), 7.99 (d, J=8.2 Hz, 1H), 4.16 (q, J=7.2 Hz, 2H), 1.67 (s, 6H), 1.20 (t, J=7.2 Hz, 3H)

Step 2: 2-Methyl-2-(6-nitropyridin-3-yl)propanoic Acid (CA1.2)

A solution of ethyl 2-methyl-2-(6-nitropyridin-3-yl)propanoate (CA1.1) (750 mg, 3.1 mmol) in methanol-water (14 mL, 1:1) was treated with lithium hydroxide monohydrate (198 mg, 4.7 mmol), and the mixture was stirred at RT overnight. The pH was adjusted to ~5 using 1M aqueous HCl solution, and the mixture was extracted with 9:1 DCM-MeOH (3×25 mL). The combined organic extracts were dried over Na2SO4, filtered, and concentrated in vacuo to give the title compound as a crude, off white solid (CA1.2) (423 mg, 63%). $^1$H NMR (400 MHz, DMSO): δ 12.87 (s, 1H), 8.67 (d, J=1.8 Hz, 1H), 8.28 (d, J=8.6 Hz, 1H), 8.19 (dd, J=2.4, 8.5 Hz, 1H), 1.59 (s, 6H).

Step 3: N-Ethyl-2-methyl-2-(6-nitropyridin-3-yl) propenamide (CA1.3)

To a suspension of 2-methyl-2-(6-nitropyridin-3-yl)propanoic acid (CA1.2) (430 mg, 2.0 mmol) in THF (5 mL) was added 1-hydroxybenzotriazole (359 mg, 2.6 mmol) and N-(3-Dimethylaminopropyl)-N'-ethylcarbodiimide hydrochloride (510 mg, 2.6 mmol). The mixture was stirred for 10 minutes at RT. DIPEA (1.069 mL, 6.1 mmol) and ethylamine (2M solution in THF, 2.04 mL. 4.0 mmol) were added and the reaction was stirred overnight at RT. The reaction was diluted with EtOAc (20 mL) and the organic phase was washed with water (15 mL) and brine (15 mL). The organic phase was dried (MgSO$_4$), filtered and concentrated in vacuo. The residue was purified by column chromatography (0-100% gradient elution EtOAc in cyclohexane) to afford the title compound (CA1.3) (375 mg, 77%) as a pale yellow oil. $^1$H NMR (400 MHz, DMSO): δ 8.58 (d, J=2.0 Hz, 1H), 8.27 (d, J=7.8 Hz, 1H), 8.10 (dd, J=2.4, 8.5 Hz, 1H), 7.60 (dd, J=6.2, 6.2 Hz, 1H), 3.11-3.03 (m, 2H), 1.53 (s, 6H), 0.97 (dd, J=7.2, 7.2 Hz, 3H).

Step 4: 2-(6-Aminopyridin-3-yl)-N-ethyl-2-methyl-propanamide (CA1)

N-Ethyl-2-methyl-2-(6-nitropyridin-3-yl)propenamide (CA1.3) (375 mg, 1.5 mmol) dissolved in methanol (5 mL) was added 10% Palladium on charcoal (35 mg). After hydrogenating under a hydrogen atmosphere overnight, the mixture was filtered through celite and the solvent was removed under vacuum to yield the title compound (CA1) (320 mg, 96%) as a pale yellow oil, which was used without further purification. $^1$H NMR (400 MHz, DMSO): δ 7.83 (d, J=2.0 Hz, 1H), 7.26 (dd, J=2.5, 8.6 Hz, 2H), 6.38 (d, J=8.1 Hz, 1H), 5.74 (s, 2H), 3.05-3.01 (m, 2H), 1.36 (s, 6H), 0.93 (t, J=7.0 Hz, 3H).

Method CA2—Preparation of 2-(6-aminopyridin-3-yl)-N-ethyl-N,2-dimethylpropanamide (CA2)

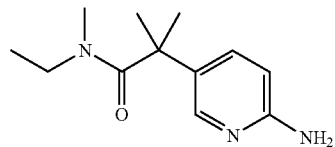
(CA2)

Intermediate CA2 was synthesised following Method CA1, but using N-methylethanamine for Step 3. The crude product was used without further purification or characterisation.

Method CA3—Preparation of 5-(3-(2-methoxyethoxy)azetidin-1-yl)pyridin-2-amine (CA3)

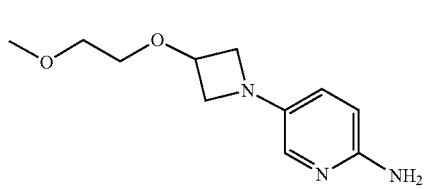
(CA3)

Intermediate CA3 was prepared according to methods described in WO2015131080, but using 3-(2-methoxyethoxy)azetidine. $^1$H NMR (400 MHz, CDCl3) δ 7.40 (d, J=2.3 Hz, 1H), 6.74 (dd, J=3.0, 8.6 Hz, 1H), 6.47-6.43 (m, 1H), 4.50-4.42 (m, 1H), 4.11-4.01 (m, 2H), 3.65 (t, J=6.3 Hz, 2H), 3.60-3.54 (m, 4H), 3.40-3.38 (m, 3H). 2H Exchangeable protons not observed.

Method PA1—Preparation of 1-(6-aminopyridin-3-yl)piperidin-4-ol (PA1)

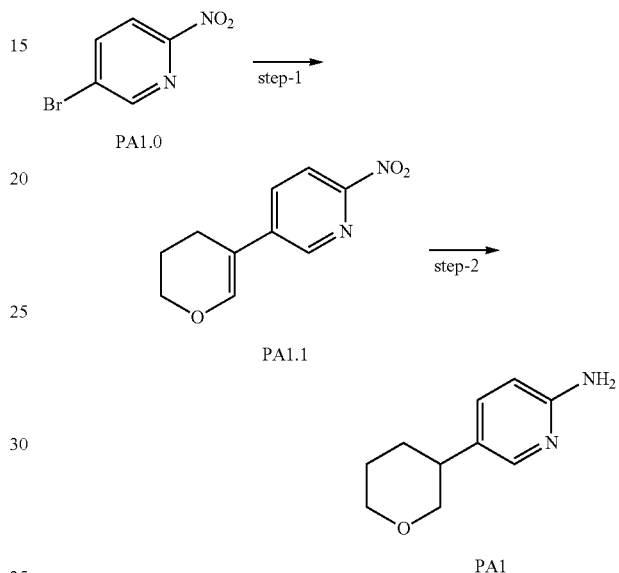

Step 1. 5-(3,4-dihydro-2H-pyran-5-yl)-2-nitropyridine (PA1.1)

To a stirred solution of 3,4-Dihydro-2H-pyran-5-ylboronic acid, pinacol ester (0.217 g, 1.06 mmol, 1.0 eq) in THF (4.5 mL) and water (0.5 mL) were added 5-bromo-2-nitropyridine (0.336 g, 1.60 mmol, 1.5 eq), S-phos (0.043 g, 0.106 mmol, 0.1 eq) and potassium phosphate (0.680 g, 3.206 mmol, 3.0 eq). After degassing under argon atmosphere for 5 minutes, palladium acetate (0.011 g, 0.053 mmol, 0.05 eq) was added and the reaction mixture was degassed again under argon atmosphere for 10 minutes. After stirring at 60° C. for 1 h, the reaction mixture was quenched with water (50 ml) and extracted with ethyl acetate (50 ml×3). The combined organic layer was washed with brine solution (25 ml), dried over sodium sulphate and concentrated under reduced pressure. The residue was purified by column chromatography eluting with 19% ethyl acetate in n-hexane to afford pure PA1.1 (0.140 g, 63.51%). MS(ES): m/z 206.20 [M+H]$^+$.

Step 2. 1-(6-aminopyridin-3-yl)piperidin-4-ol (PA1)

To a suspension of palladium hydroxide (0.03 g) in methanol (3 mL) was added a solution of 5-(3,4-dihydro-2H-pyran-5-yl)-2-nitropyridine (PA1.1) (0.140 g, 0.678 mmol, 1.0 eq) in methanol (3 mL) under nitrogen atmosphere. Hydrogen gas was bubbled into the reaction mixture for 1 h. After completion of reaction, the reaction mixture was filtered through celite, washed with methanol. The filtrate was concentrated under reduced pressure to afford pure PA1 (0.095 g, 78.45%). MS(ES): m/z 178.24 [M+H]+, 1H NMR (400 MHz, DMSO-d6) δ 7.77 (s, 1H), 7.28-7.25 (dd, J=2 Hz, 8.4 Hz, 1H), 6.37 (d, J=8.4, 1H), 5.72 (s, 2H), 3.94 (s, 2H), 3.84 (d, 12.4 Hz, 1H), 3.72 (d, J=8.4 Hz, 1H), 3.2 (t, J=11.4, 1H), 1.82 (s, 1H), 1.62 (s, 3H).

Method PA2—Preparation of 5-(2-methyltetrahydro-2H-pyran-2-yl)pyridin-2-amine (PA2)

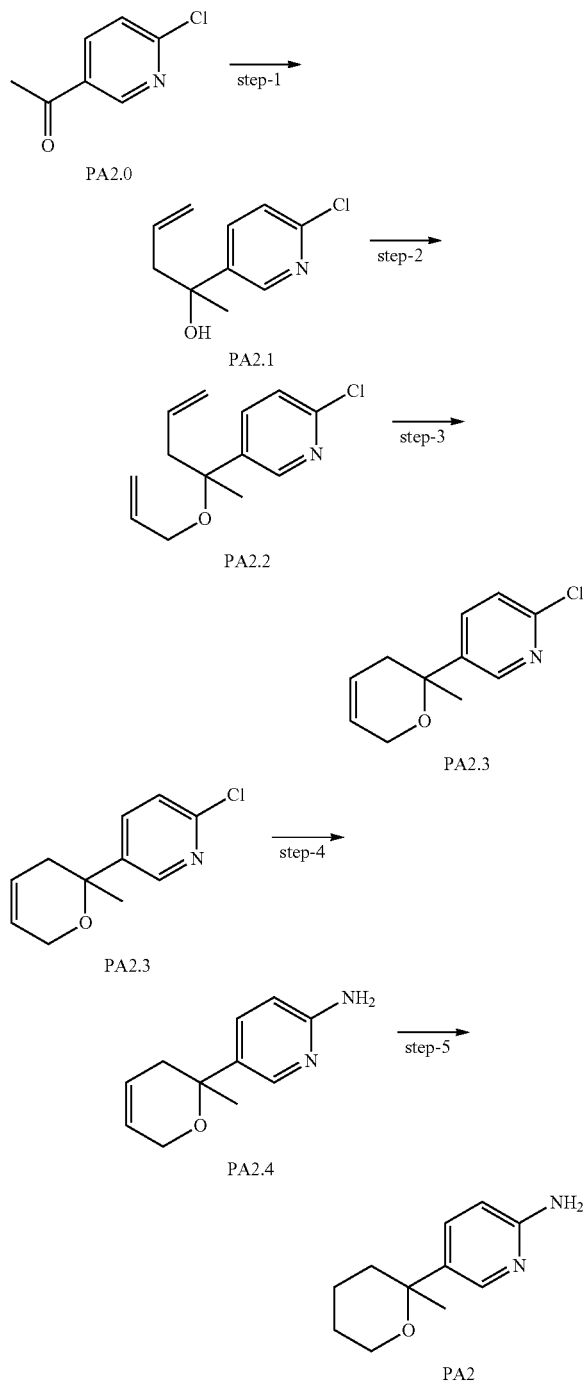

Step 1. 2-(6-chloropyridin-3-yl)pent-4-en-2-ol (PA2.1)

To a stirred solution of 1-(6-chloropyridin-3-yl)ethan-1-one PA2.0 (1.2 g, 7.71 mmol, 1.0 eq) dissolved in THF (12 mL) and cooled to −78° C. was added allyl magnesium bromide (in ether) (11.56 mL, 11.56 mmol, 1.5 eq). After stirring for 30 minutes at −78° C., the reaction mixture was quenched with water (50 ml) and ammonium chloride solution (10 ml) and extracted with ethyl acetate (50 ml×3). The combined organic layer was washed with brine solution (50 ml), dried over sodium sulphate and concentrated under reduced pressure. The residue was purified by column chromatography eluting with 15% ethyl acetate in n-hexane to afford pure PA2.1 (1.31 g, 85.93%). MS(ES): m/z 197.66 [M+H]+.

Step 2. 5-(2-(allyloxy)pent-4-en-2-yl)-2-chloropyridine (PA2.2)

To a stirred solution of 2-(6-chloropyridin-3-yl)pent-4-en-2-ol PA2.1 (1.31 g, 6.6 mmol, 1.0 eq) dissolved in THF (5 mL) at 0° C. was added sodium hydride (0.792 g, 19.8 mmol, 3.0 eq). After stirring at 0° C. for 10 minutes, allyl bromide (2.0 g, 16.5 mmol, 2.5 eq) was added slowly to the reaction mixture. After stirring at 0° C. for 15 minutes, the reaction mixture was heated to reflux for 6 h. After completion of reaction, the reaction mixture was quenched with cold 0.5N Hydrochloric acid solution (100 ml) and extracted with ethyl acetate (50 ml×3). The combined organic layer was washed with brine solution (50 ml), dried over sodium sulphate and concentrated under reduced pressure. The residue was purified by column chromatography eluting with 8% ethyl acetate in n-hexane to afford pure PA2.2 (1.05 g, 66.64%). MS(ES): m/z 237.73 [M+H]+.

Step 3. 2-chloro-5-(2-methyl-3,6-dihydro-2H-pyran-2-yl)pyridine (PA2.3)

To a stirred solution of 5-(2-(allyloxy)pent-4-en-2-yl)-2-chloropyridine PA2.2 (0.5 g, 2.1 mmol, 1.0 eq) in DCM (5 mL) was added Grubbs catalyst (0.021 g, 0.025 mmol, 0.012 eq). After stirring at RT for 45 minutes, the solvent was concentrated under reduced pressure. The residue was purified by column chromatography eluting with 15% ethyl acetate in n-hexane to afford pure PA2.3 (0.4 g, 90.70%). MS(ES): m/z 209.67 [M+H]+.

Step 4. 2-chloro-5-(2-methyl-3,6-dihydro-2H-pyran-2-yl)pyridine (PA2.4)

To a stirred solution of 2-chloro-5-(2-methyl-3,6-dihydro-2H-pyran-2-yl)pyridine (0.4 g, 1.9 mmol, 1.0 eq), tris(dibenzylideneacetone)dipalladium(0) (0.174 g, 0.19 mmol, 0.1 eq) and (2-biphenyl)dicyclohexylphosphine (0.134 g, 0.38 mmol, 0.2 eq) in 1,4-dioxane (5 mL) degassed with argon for 30 minutes was added lithium hexamethyl disilazide (5.7 mL, 5.7 mmol, 3.0 eq). After heating at 70° C. for 3 h, the reaction mixture was poured into water (50 ml) and extracted with ethyl acetate (50 ml×3). The combined organic layer was washed with brine solution (50 ml), dried over sodium sulphate and concentrated under reduced pressure. The residue was purified by column chromatography eluting with 2.5% methanol in DCM to afford pure PA2.4 (0.255 g, 70.26%). MS(ES): m/z 190.25 [M+H]+.

Step 5. 5-(2-methyltetrahydro-2H-pyran-2-yl)pyridin-2-amine (PA2)

To a suspension of 10% Pd/C (0.050 g) in methanol (3 mL) was added a solution of 2-chloro-5-(2-methyl-3,6-dihydro-2H-pyran-2-yl)pyridine PA2.4 (0.250 g, 1.3 mmol, 1.0 eq) in methanol (3 mL). H$_2$ (gas) was bubbled into the reaction mixture for 1 h. After completion of reaction, the reaction mixture was filtered through celite and washed with methanol (30 ml). The filtrate was concentrated under reduced pressure to afford pure PA2 (0.220 g, 54.42%). MS(ES): m/z 192.26 [M+H]$^+$, LCMS purity: 97.40%, HPLC purity: 96.52%.

Method PA4—Preparation of tert-butyl 3-(6-aminopyridin-3-yl)-3,6-diazabicyclo[3.1.1]heptane-6-carboxylate (PA4)

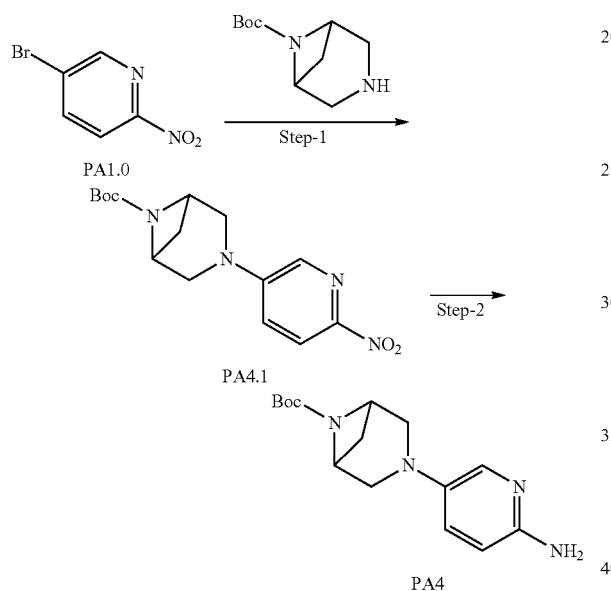

Step 1. tert-butyl 3-(6-nitropyridin-3-yl)-3,6-diazabicyclo[3.1.1]heptane-6-carboxylate (PA4.1)

To a solution of 5-bromo-2-nitropyridine (1.1 g, 5.42 mmol, 1.0 eq) into 1,4-dioxane (10 mL), tert-butyl 3,6-diazabicyclo[3.1.1]heptane-6-carboxylate (1.18 g, 5.96 mmol, 1.1 eq) and potassium carbonate (2.24 g, 16.26 mmol, 3.0 eq) degassed with nitrogen gas for 10 min were added 4,5-Bis(diphenylphosphino)-9,9-dimethylxanthene (0.62 g, 1.08 mmol, 0.2 eq) and Tris(dibenzylideneacetone)dipalladium (0.49 g, 0.542 mmol, 0.1 eq). After stirring at 120° C. for 5 h, the reaction mixture was diluted with water (100 ml) and extracted into ethylacetate (100 ml×3). The combined organic layer was washed with brine solution (50 ml), dried over sodium sulphate and concentrated under reduced pressure. The residue was purified using combi-flash silica eluting with 7% methanol/DCM to afford material as tert-butyl 3-(6-nitropyridin-3-yl)-3,6-diazabicyclo[3.1.1]heptane-6-carboxylate PA4.1 (1 g, Yield-57.03%). MS(ES): m/z 321.35 [M+H]+.

Step 2. tert-butyl 3-(6-aminopyridin-3-yl)-3,6-diazabicyclo[3.1.1]heptane-6-carboxylate (PA4)

To a suspension of 10% Pd/C (0.050 g) in methanol (3 mL) was added a solution of tert-butyl 3-(6-nitropyridin-3-yl)-3,6-diazabicyclo[3.1.1]heptane-6-carboxylate (0.850 g, 2.65 mmol, 1.0 eq) in methanol (3 mL). After bubbling hydrogen gas through solution for 1 h, the reaction mixture was filtered through Celite which washed with MeOH. The filtrate was concentrated under reduced pressure to afford crude PA4 (0.900 g, 55.16%). MS(ES): m/z 291.37[M+H]+.

Method PA9—Preparation of tert-butyl 3-(6-aminopyridin-3-yl)-3,6-diazabicyclo[3.1.1]heptane-6-carboxylate (PA9)

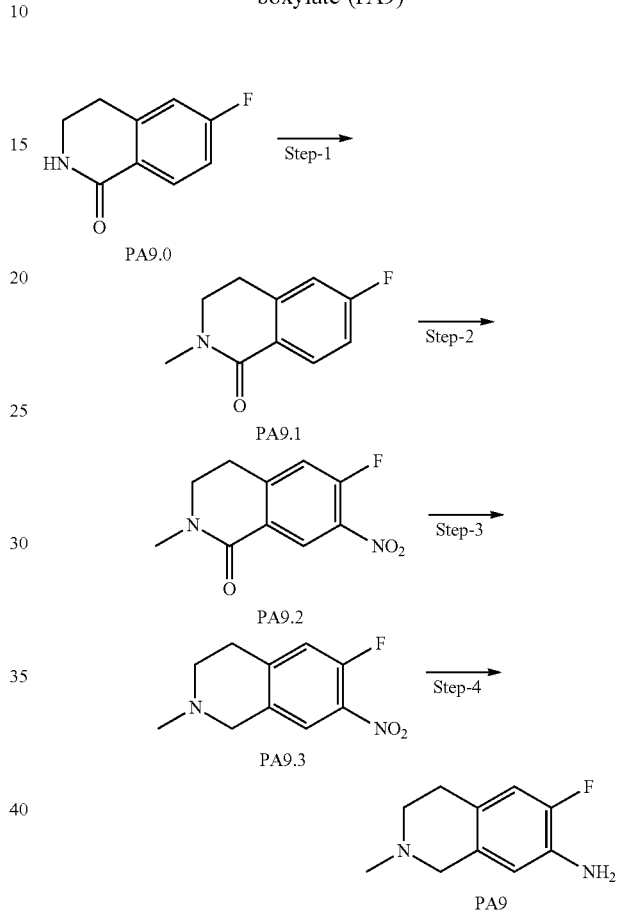

Step 1. 6-fluoro-2-methyl-3,4-dihydroisoquinolin-1(2H)-one (PA9.1)

To a solution of 6-fluoro-3,4-dihydroisoquinolin-1(2H)-one PA9.0 (2.5 g, 15.13 mmol, 1.0 eq) in dry THF (130 mL) at 0° C. was added sodium hydride (60% in mineral oil) (1.2 g, 30.27 mmol, 2.0 eq). After stirring for 30 min, Methyl iodide (4.3 g, 30.27 mmol, 2.0 eq) was added. After stirring at RT for 1 h, the reaction mixture was diluted with saturated sodium bicarbonate solution (100 ml) and extracted with ethyl acetate (50 ml×3). The combined organic layer was washed with brine solution (50 ml), dried over sodium sulphate and concentrated under reduced pressure to afford PA9.1 (3.07 g, Quantitative yield) MS (ES): m/z 180.2 [M+H]$^+$ Step 2. 6-fluoro-2-methyl-7-nitro-3,4-dihydroisoquinolin-1(2H)-one (PA9.2)

To a solution of 6-fluoro-2-methyl-3,4-dihydroisoquinolin-1(2H)-one PA9.1 (2.9 g, 16.201 mmol, 1.0 eq) dissolved into concentrated sulphuric acid (25 mL) at RT was added potassium nitrate (1.44 g, 17.821 mmol, 1.1 eq). After stirring for 2 h at RT, the reaction mixture was poured into ice water and stirred for 10 min. The solid was filtered, washed with water and dried under high vacuum to afford PA9.2 (3.1 g, 85.44%) MS (ES): m/z 225 [M+H]+

Step 3. 6-fluoro-2-methyl-7-nitro-1,2,3,4-tetrahydroisoquinoline (PA9.3)

To a solution of 6-fluoro-2-methyl-7-nitro-3,4-dihydroisoquinolin-1(2H)-one PA9.2 (3.0 g, 13.392 mmol, 1.0 eq) dissolved into dry THF (80 mL) at 0° C. was added borane-THF complex (0.9 molar) (22 ml, 20.089 mmol, 1.5 eq). After stirring for 2 h at 80° C., the reaction mixture was cooled to RT and diluted water (100 ml). The aqueous layer was extracted with ethyl acetate (50 ml×3). The combined organic layer was washed with brine solution (50 ml), dried over sodium sulphate and concentrated under reduced pressure. The residue was purified using combi-flash silica eluting with 5% methanol/DCM to afford PA9.3 (0.8 g, 28.44%) MS (ES): m/z 211.2 [M+H]+

Step 4. 6-fluoro-2-methyl-1,2,3,4-tetrahydroisoquinolin-7-amine (PA9)

To a suspension of 10% Pd/C (158 mg, 0.2% W/Wq) in methanol (3 mL) was added a solution of 6-fluoro-2-methyl-7-nitro-1,2,3,4-tetrahydroisoquinoline PA9.3 (0.79 g, 3.761 mmol, 1.0 eq) in methanol (30 mL). After purging Hydrogen gas through solution for 1 h, the reaction mixture was filtered through Celite which was washed with MeOH. The filtrate was concentrated under reduced pressure to afford crude PA9 (0.56 g, 82.68%) MS (ES): m/z 181.3 [M+H]+

Method PA28—Preparation of 3-(6-aminopyridin-3-yl)-1-methylpyrrolidin-2-one (PA28)

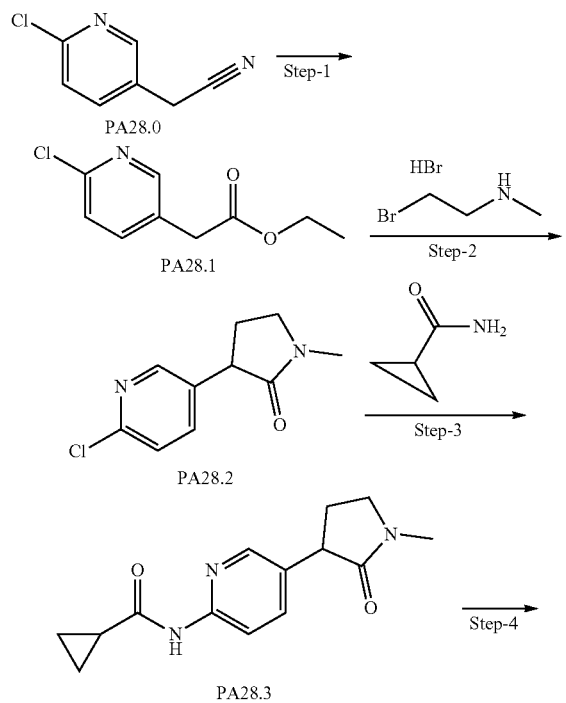

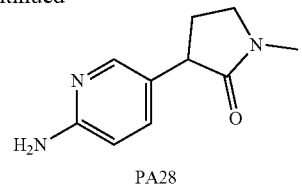

Step 1. 6-fluoro-2-methyl-1,2,3,4-tetrahydroisoquinolin-7-amine (PA28.1)

To a Solution of 2-(6-chloropyridin-3-yl)acetonitrile PA28.0 (8 g, 52.4 mmol, 1.0 eq) in Ethanol (40 ml) at 0° C. was added dropwise sulfuric acid (15 ml). After stirring at 100° C. for 3 h, the reaction mixture was poured into ice cold water (300 ml) and extracted with ethyl acetate (50 ml×3). The combined organic layers were dried over sodium sulphate and concentrated under reduced pressure to afford crude material PA28.1 which was directly used for next step without further purification (8 g, 76.4%). MS(ES): m/z 200.30 [M+H]+.

Step 2. 3-(6-chloropyridin-3-yl)-1-methylpyrrolidin-2-one (PA28.2)

To a solution of 6-fluoro-2-methyl-1,2,3,4-tetrahydroisoquinolin-7-amine PA28.1 (1.0 g, 5.025 mmol, 1.0 eq) dissolved in DMSO (10 ml) at 10° C. was added sodium hydride (0.603 g, 25.12 mmol, 3.0 eq). After stirring for 20 minute at same temperature, 2-bromo-N-methylethan-1-amine (1.3 g, 6.030 mmol, 1.2 eq) was added. After stirring at RT for 1 h, the reaction mixture was poured into ice cold water (50 ml) and extracted with ethyl acetate (50 ml×3). The combined organic layers were dried over sodium sulphate and concentrated under reduced pressure to afford crude material PA28.2 (0.258 g, 24.48%) MS(ES): m/z 211.30[M+H]+.

Step 3. N-(5-(1-methyl-2-oxopyrrolidin-3-yl)pyridin-2-yl)cyclopropanecarboxamide (PA28.3)

Reaction of step-3 was carried out following the representative procedure described in Method PA4 (Step-1) using 3-(6-chloropyridin-3-yl)-1-methylpyrrolidin-2-one PA28.2 and cyclopropanecarboxamide to afford PA28.3 (0.80 g, Yield-64.99%). MS(ES): m/z 260.61 [M+H]+

Step 4. 3-(6-aminopyridin-3-yl)-1-methylpyrrolidin-2-one (PA28)

To a solution of N-(5-(1-methyl-2-oxopyrrolidin-3-yl)pyridin-2-yl)cyclopropanecarboxamide (0.500 g, 1.93 mmol, 1.0 eq) in MeOH (7 mL) was added a solution of 5N sodium hydroxide (2.31 ml, 56.0 mmol, 6 eq). After stirring at 60° C. for 16 h, the reaction mixture was poured into ice cold water (100 ml) and extracted with 10% chloroform/isopropyl alcohol (100 ml×3). The combined organic layers were dried over sodium sulphate and concentrated under reduced pressure. The residue was further purified by diethyl ether solvent trituration (20 ml×2) to afford pure PA28 (0.250 g, 67.80%). MS(ES): m/z 192.51 [M+H]+

223

Method PA29 and PA30—Preparation of (S)-5-(3-(dimethylamino)piperidin-1-yl)pyridin-2-amine (PA29) & (R)-5-(3-(dimethylamino)piperidin-1-yl)pyridin-2-amine (PA30)

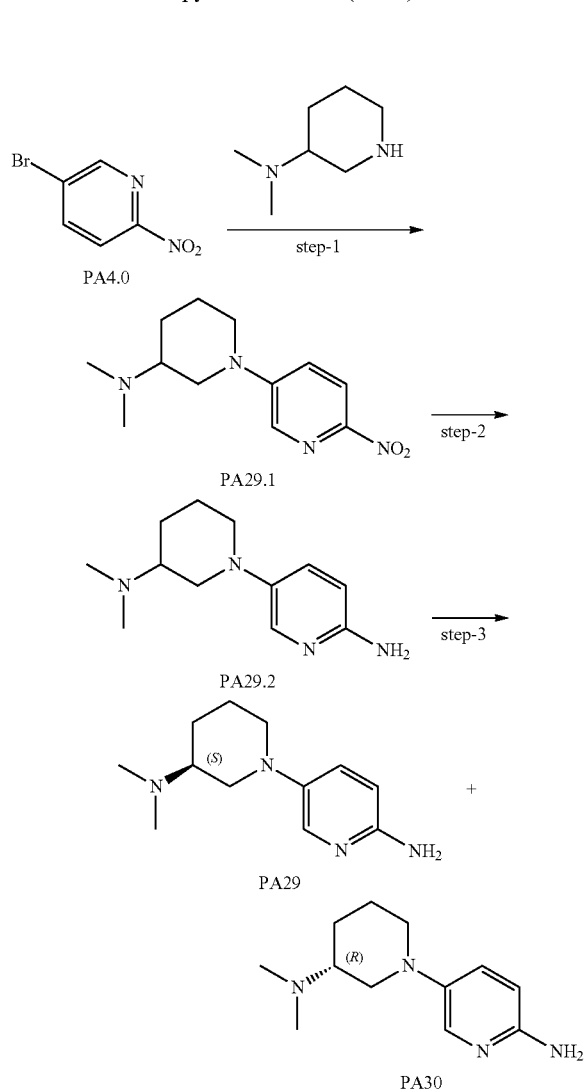

Step 1 & Step 2. 5-(3-(dimethylamino)piperidin-1-yl)pyridin-2-amine (PA29.2)

Reaction was carried out following representative procedure outlined in Method PA4 to afford PA29.2 (0.980 g, 45.15%). MS(ES): m/z 221.35 [M+H].

Step 3. (S)-5-(3-(dimethylamino)piperidin-1-yl)pyridin-2-amine (PA29) & (R)-5-(3-(dimethylamino)piperidin-1-yl)pyridin-2-amine (PA30)

Compounds 29.2 (980 mg racemate) were separated by Chiral SFC in Shimadzu LC-20AP and UV detector with CHIRALPAK IC (250×21.0) mm, 5 micron column at flowrate of 20 ml/min using Mobile phase (A) 0.1% DEA IN n-Hexane and (B) 0.1% DEA in Propane 2-ol:Acetonitrile (70:30) to afford pure compounds PA29 (350 mg) and PA30 (351 mg). Stereochemistry arbitrarily assign.

224

Method PA31—Preparation of 5-(oxetan-3-yl)pyridin-2-amine (PA31)

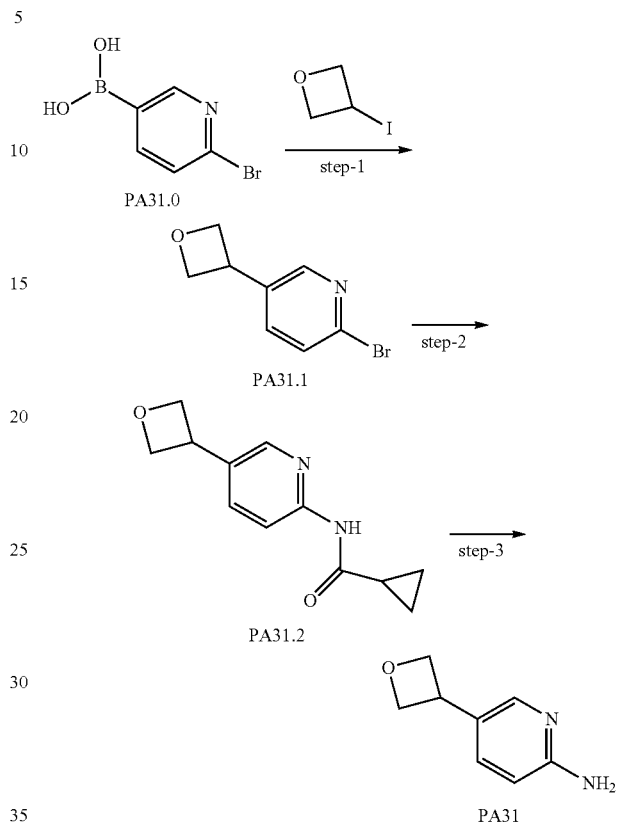

Step 1. 2-bromo-5-(oxetan-3-yl)pyridine (PA32.1)

To a solution of (6-bromopyridin-3-yl)boronic acid (1.10 g, 5.44 mmol, 1 eq), nickel iodide (51 mg, 0.16 mmol, 0.2 eq), trans-2-aminocyclohexanol hydrochloride (24.73 mg, 0.16 mmol, 0.1 eq) in 2-propanol (5 mL) was added sodium bis(trimethylsilyl)amide (1.0 g, 5.44 mmol, 1 eq). After stirring under nitrogen for 10 minutes, a solution of 3-iodooxetane (0.5 g, 2.7 mmol) in 2-propanol (2 mL) was added. After stirring in a sealed vial at 80° C. for 16 h, the reaction was filtered through celite which was washed with ethanol. The filtrate was concentrated and the residue purified by flash chromatography on silica gel (10-100% ethyl acetate in hexanes) to afford the title compound PA32.1 (0.28 g, 26%). MS(ES) m/z 215.87 [M+2+H]+

Step 2 & Step 3. 5-(oxetan-3-yl)pyridin-2-amine (PA31)

Reaction of step-2 & 3 was carried out following the representative procedure described in Method PA28 (Step-3 & 4) using 2-bromo-5-(oxetan-3-yl)pyridine (PA32.1) and cyclopropanecarboxamide to afford PA31 (0.15 g, Yield-76.36%). MS(ES): m/z 151.2 [M+H]+

Method PA32—Preparation of 3-(6-aminopyridin-3-yl)-1-methylpyrrolidin-2-one (PA32)

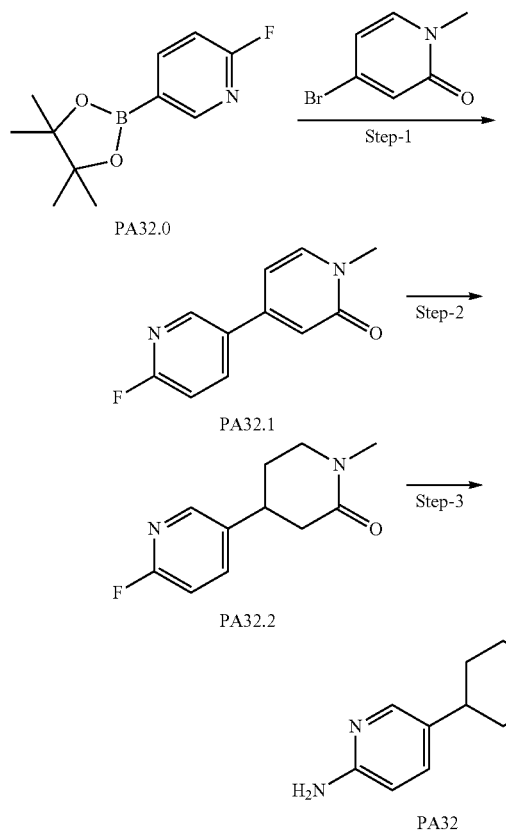

Step 1. 6-fluoro-1'-methyl-[3,4'-bipyridin]-2'(1'H)-one (PA32.1)

To a solution of 2-fluoro-5-(4,4,5,5-tetramethyl-1,3,2-dioxaborolan-2-yl)pyridine (2.0 g, 0.0089 mol, 1.0 eq) and 4-bromo-1-methylpyridin-2(1H)-one (1.3 g, 0.0074 mol, 0.8 eq) in 1, 2-dimethoxyethane (10 ml) and water (2 ml) were added Na$_2$CO$_3$ (2.8 g, 0.0267 mol, 3.0 eq) and [1,1'-Bis(diphenylphosphino)ferrocene]dichloropalladium(II)catalyst (0.36 g, 0.0004 mol, 0.05 eq). After stirring at 120° C. in microwave for 30 minutes, the reaction mixture was diluted with water (60 ml) and extracted with ethyl acetate (50 ml×3). The combined organic layer was dried over sodium sulphate and concentrated under reduced pressure. The residue was purified using combi-flash silica eluting with 3% methanol in DCM to afford PA32.1 (1.4 g, 76.46%) MS (ES): m/z 205.3 [M+H]$^+$

Step 2. 4-(6-fluoropyridin-3-yl)-1-methylpiperidin-2-one (PA32.2)

To a suspension of 10% Pd/C (558 mg, 0.5% W/Wq) in methanol (3 mL) was added a solution of 6-fluoro-1'-methyl-[3,4'-bipyridin]-2'(1'H)-one PA32.1 (1.0 g, 0.0049 mol, 1.0 eq) in methanol (30 mL). After bubbling hydrogen gas through solution for 1 h, the reaction mixture was filtered through Celite. The filtrate was concentrated under reduced pressure to afford crude PA32.2 (1.0 g, 98.06%) MS (ES): m/z 209.2 [M+H]$^+$

Step 3. 4-(6-aminopyridin-3-yl)-1-methylpiperidin-2-one (PA32)

A solution of 4-(6-fluoropyridin-3-yl)-1-methylpiperidin-2-one PA32.2 (0.850 g, 0.00048 mol, 1.0 eq) in aq. ammonia (40 mL) in a steel bomb (remaining 40% head space) was heated at 150° C. (100 psi) for 20 h. The reaction mixture was poured into water (50 ml) and extracted with ethyl acetate (50 ml×3). The combined organic layer was dried over sodium sulphate and concentrated under reduced pressure. The residue was purified using combi-flash silica eluting with 6.2% methanol in DCM to afford PA32 (0.220 g, 26.26%) MS (ES): m/z 206.3 [M+H]$^+$

Method PA35—Preparation of 5-cyclopentyl-6-((dimethylamino)methyl)pyridin-2-amine (Intermediate PA35)

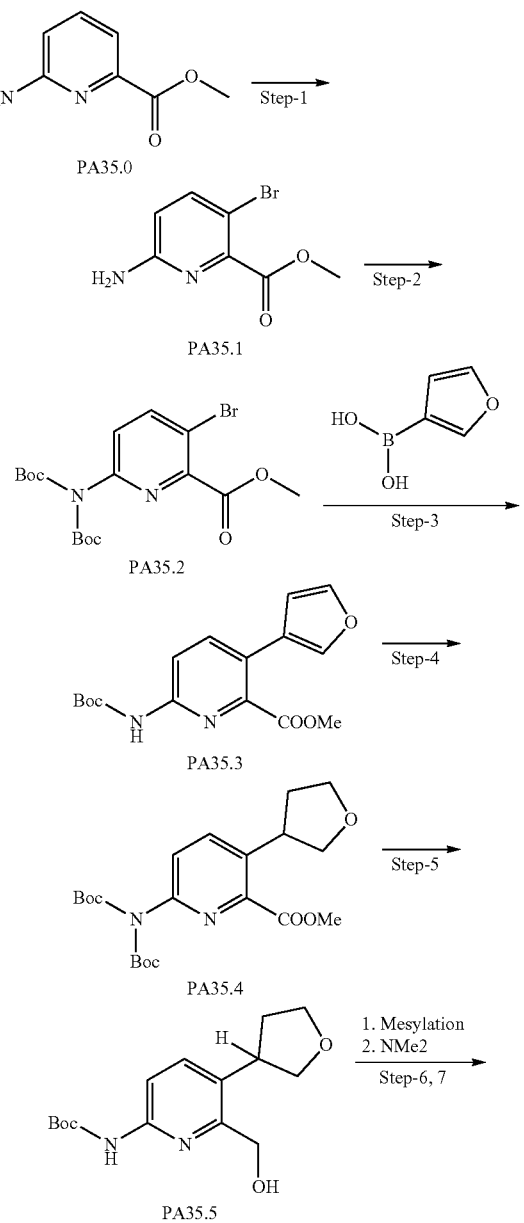

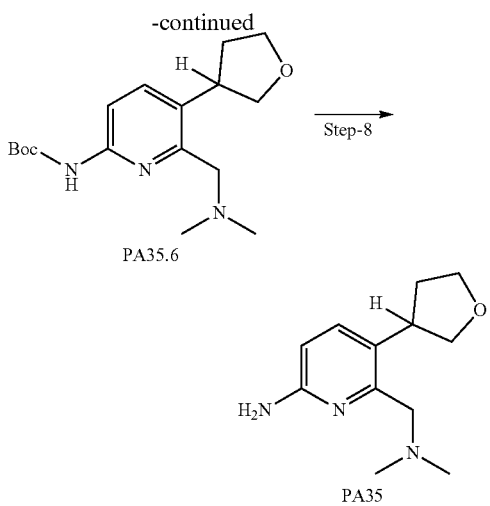

PA35.6

PA35

Step 1. methyl 6-amino-3-bromopicolinate (PA35.1)

To a solution of PA35.0 (500 g, 3289.4 mmol, 1.0 eq) in acetonitrile (12.5 L) was added portionwise N-bromo succinamide (644 g, 3618.4 mmol, 1.1 eq) at RT over 30 min. After stirring at RT for 30 min, the reaction mixture was quenched with 10% $Na_2S_2O_3$ solution in water (3.0 L) and concentrated to remove acetonitrile. The residue was diluted with 10% $Na_2S_2O_3$ solution in water (20 L) and extracted with 50% ethyl acetate in hexanes (10 L×5). The combined organic layers were dried over sodium sulphate and concentrated under reduced pressure. The crude material was triturated with 25% ethyl acetate in hexanes to afford pure PA35.1 (methyl 6-amino-3-bromopicolinate). (57.07% yield). MS (ES): m/z 231-233 [M+2]$^+$, $^1$H NMR (400 MHz, CDCL3): δ 7.66 (d, 1H), 6.53 (d, 1H), 4.68 (S, 2H), 3.98 (s, 3H). Note: other region isomer (methyl 6-amino-5-bromopicolinate) also form and can be separated via silica purification. Required regio-isomer confirmed by 1H NMR and NOE analysis.

Step 2. methyl 3-bromo-6-(bis(tert-butoxycarbonyl) amino)picolinate (PA35.2)

To a solution of PA35.1 (1100 g, 4782.6 mmol, 1.0 eq) in THF (20 L) were added dimethyl amino pyridine (116.7 g, 956.5 mmol, 0.2 eq) and Boc anhydride (2502 g, 11478.2 mmol, 2.4 eq). After stirring at 75° C. for 1.5 h, the solvent was evaporated and the residue was diluted with brine solution and extracted by ethyl acetate (2×10 L). The combined organic layer dried over sodium sulphate and concentrated under vacuum. The residue was purified by column chromatography eluting with 5% ethyl acetate in hexane. The isolated material was triturated with hexanes (4 L) to afford PA35.2 (1700 g, 82.79%) as white solid. MS (ES): m/z 431-433 [M+2]$^+$. $^1$H NMR (400 MHz, DMSO): δ 8.32 (d, 1H), 7.61 (d, 1H), 3.90 (s, 3H), 1.40 (s, 18H).

Step 3. methyl 6-(bis(tert-butoxycarbonyl)amino)-3-(furan-3-yl)picolinate (PA35.3)

To a solution of PA35.2 (730 g, 1693.7 mmol, 1.0 eq) and furan boronic acid (379 g, 3387.4 mmol, 2 eq) and potassium phosphate tribasic (Sigma, 1078.3 g, 5086.2 mmol, 3.0 eq) suspended in 1-4 dioxane (5.85 L) and water (1.46 L) and degassed with flow of nitrogen for 20 min was added Dikis (59.5 g, 84.8 mmol, 0.05 eq). After stirring at 120° C. for 15 min, the reaction was cooled to RT. The organic layer was collected, filtered through celite bed and concentrated under reduced pressure. The residue was purified by silica gel chromatography eluting with 6.0% to 10% ethyl acetate/hexanes. The isolated material was triturated by n-pentane to afford PA35.3 (84 yield) as a cream colored solid. MS(ES): m/z 418 [M+1]$^+$ $^1$H NMR (400 MHz, DMSO): δ 8.12 (d, 1H), 8.00 (d, 1H), 7.81 (s, 1H), 7.61 (s, 1H), 6.70 (S, 1H), 3.83 (S, 3H), 1.41 (s, 18H)

Step 4. methyl 6-(bis(tert-butoxycarbonyl)amino)-3-(furan-3-yl)picolinate (PA35.4)

To a solution of PA35.4 (191 g, 456.9 mmol, 1.0 eq) in methanol (1140 mL) and THE (955 mL) were added ammonium formate (115.1 g, 182.5 mmol, 4.0 eq), acetic acid (133.7 ml, 0.7V) and 20% WET palladium hydroxide on carbon (133.7 g, 1:0.7 W/W). After stirring under an atmosphere of hydrogen gas for 24 h at RT, the reaction mixture was combined with 6 other batches on the same scale prepared by an identical method. The combined reaction mixture was then filtered through Celite bad, and the filtrate was concentrated under reduced pressure. The residue was neutralized with sat. $NaHCO_3$ (10 L) solution and extracted by DCM (10 L×3) to afford PA35.4 (1251 g, 92.6%). MS(ES): m/z 423 [M+1]$^+$ $^1$H NMR (400 MHz, DMSO): δ 8.01 (d, 1H), 7.58 (d, 1H), 3.99 (t, 2H), 3.87 (S, 3H), 3.71 (m, 2H), 3.60 (m, 1H), 2.31 (m, 1H) 1.91 (d, 1H), 1.4 (S, 18H).

Step 5. tert-butyl (6-(hydroxymethyl)-5-(THF-3-yl) pyridin-2-yl) carbamate (PA35.5)

To a solution of PA35.4 (250 g, 592.4 mmol, 1.0 eq) in ethanol (2500 mL) was added portionwise with sodium borohydride (135 g, 355.4 mmol, 6 eq). After stirring at 60° C. for 2 h, the reaction was concentrated under reduced pressure, diluted with water (10 L), and extracted by DCM (4×10 L). The combined organic layer was washed with brine (10 L), dried with $Na_2SO_4$, filtered and concentrated under reduced pressure. The residue was combined with 4 other batches on the same scale prepared by an identical method to afford PA35.5 (640 g, 73.49%), as colorless gummy liquid which turned into white solid at RT after 2 days. MS(ES): m/z 295.0 [M+1]$^+$ $^1$H NMR (400 MHz, DMSO): δ 7.81 (d, 1H), 7.67 (d, 1H), 7.2 (d, 1H), 5.22 (d, 1H), 4.55 (t, 1H), 3.99 (s, 3H), 3.77 (m, 3H), 3.55 (m, 2H), 2.28 (d, 2H), 1.87 (d, 1H), 1.41 (s, 9H)

Step 6 & 7. tert-butyl (6-((dimethylamino)methyl)-5-(THF-3-yl) pyri din-2-yl)carbamate (PA35.6)

To a solution of PA35.5 (440 g, 149.6 mmol, 1.0 eq) in DCM (6.5 L) was added dropwise diisopropyl ethyl amine (581.4 g, 448.9 mmol, 3.0 eq) at 0° C. After stirring for 20 min. mesyl chloride (257.04 g, 2244 mmol, 1.5 eq) was added at 0° C. After stirring at 0° C. to RT for 2 h, the reaction mixture was quenched with DM water (1 L) and extracted by DCM (3×2 L). The combined organic layer was washed with brine (10 L), passed through a $Na_2SO_4$ frit, and concentrated under reduced pressure to afford mesylated intermediate. The mesylated intermediate was combined with 1 other batch (on the 200 g scale) prepared by an identical method. (700 g-crude, 86.44%), as light yellow liquid. MS(ES): m/z 373.35 [M+1]$^+$.

To a solution of mesylated intermediate (350 g, 940.0 mmol, 1.0 eq) in MeCN (3.5 L) at RT were added dropwise diisopropylethylamine (529.23 g, 423.0 mmol, 4.5 eq) followed by dimethylamine hydrochloride (152.41 g, 1880.0 mmol, 2.0 eq). After stirring at 90° C. for 3 h, the reaction mixture was concentrated to remove acetonitrile, quenched in DM water (1500 mL) and extracted by DCM (3×3 L). The combined organic layer was washed with brine (10 L), dried with Na2SO4 and concentrated under reduced pressure to afford PA35.6. The product was combined with 1 other batches on the same scale prepared by an identical method. (700 g, quantitative yield), as brown semi solid. MS(ES): m/z 322.39 [M+1]$^+$, $^1$H NMR (400 MHz, DMSO): δ 9.61 (S, 1H), 7.67 (S, 2H), 3.96-3.94 (t, 2H, J=7.6), 3.78-3.77 (d, 2H, J=4 HZ), 3.57 (S, 1H), 3.54 (s, 1H), 2.26-2.25 (t, 1H), 2.1 (S, 6H), 1.86 (S, 1H), 1.45 (s, 9H)

Step 8. 5-cyclopentyl-6-((dimethylamino)methyl)pyridin-2-amine (PA35)

To a solution of PA35.6 (700 g, 2180.7 mmol, 1.0 eq) in DCM (5.0 L) was added trifluoroacetic acid (2.1 L, 3 v) at 0° C. After stirring at 70° C. for 2 h, the reaction mixture was concentrated, diluted in DM water (2 L) and washed with heptane. The collected aqueous layer was neutralized with 10% NaOH solution and then extracted by 15% MeOH in DCM (4×3.0 L). The combined organic layers were dried over sodium sulphate and concentrated under reduced pressure. The residue was triturated by 20% ethyl acetate in hexanes and then diethylether to afford pure PA35 as light brown solid. (330 g, 68.47%). MS (ES): m/z 222.30 [M+1]$^+$, $^1$H NMR (400 MHz, DMSO-d6) δ 7.33 (d, J=8.4 Hz, 1H), 6.36 (d, J=8.5 Hz, 1H), 5.71 (s, 1H), 3.96-3.85 (m, 1H), 3.72 (dq, J=31.0, 7.7 Hz, 1H), 3.46-3.34 (m, 1H), 3.35 (s, 1H), 3.30 (d, J=11.9 Hz, 0H), 2.19 (td, J=7.8, 4.2 Hz, 0H), 2.14 (s, 3H), 1.79 (dq, J=12.2, 8.0 Hz, 1H).

Method PA37—Preparation of 6-((dimethylamino)methyl)-5-(tetrahydro-2H-pyran-4-yl)pyridin-2-amine (PA37)

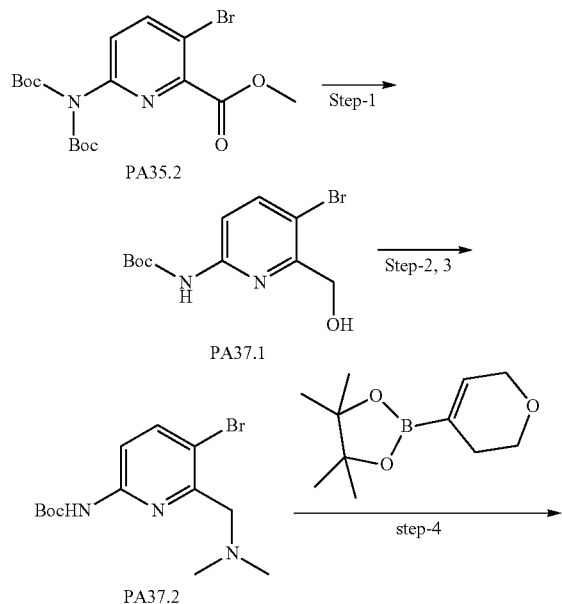

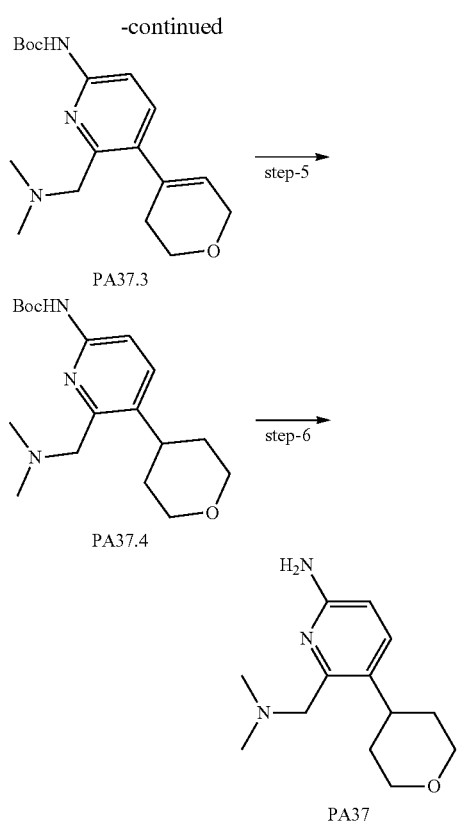

Step 1. tert-butyl (5-bromo-6-(hydroxymethyl)pyridin-2-yl) carbamate (PA37.1)

To a solution of PA35.2 (50 g, 116.27 mmol, 1.0 eq) in ethanol (200 mL) was added portionwise with sodium borohydride (26.3 g, 697.6 mmol, 6 eq). After stirring at 70° C. for 2 h, the reaction was concentrated under reduced pressure, diluted carefully with water (200 mL) and extracted into DCM (3×150 mL). The combined organic layer was washed with brine (100 mL), passed through a hydrophobic filter, and concentrated under reduced pressure to afford PA37.1 (27 g, 79%), as white solid. MS(ES): m/z 395 [M+1]$^+$ $^1$H NMR (400 MHz, DMSO): δ 7.81 (d, 1H), 7.67 (d, 1H), 7.2 (d, 1H), 5.22 (d, 1H), 4.55 (t, 1H), 3.99 (s, 3H), 3.77 (m, 3H), 3.55 (m, 2H), 2.28 (d, 2H), 1.87 (d, 1H), 1.41 (s, 19H)

Step 2, 3. tert-butyl (5-bromo-6-((dimethylamino)methyl)pyridin-2-yl)carbamate (PA37.2)

To a solution of the PA37.1 (22.2 g, 73.2 mmol, 1.0 eq) and N—N diisopropyl ethylamine (33.3 g, 256.3 mmol, 3.5 eq) in DCM (200 mL) at 0° C. was added methane sulfonyl chloride (12.5 g, 109.8 mmol, 1.5 eq). After stirring for 30 min, the reaction was quenched with water (100 mL) and extracted with ethyl acetate (3×40 mL). The combined organic layer was washed with brine, passed through a hydrophobic filter, and concentrated under reduced pressure. To the mesylate intermediate dissolved in acetonitrile (200 mL) were added Dimethyl amine (15 g, 183.0 mmol, 2.5 eq) and N—N diisopropyl ethylamine (33.3 g, 256.3 mmol, 3.5 eq). After stirring at 70° C. for 1 h, the reaction was quenched with water (100 mL) and extracted into ethyl acetate (3×40 mL). The combined organic layer was washed with brine, passed through a hydrophobic filter, and concentrated under reduced pressure. The residue was purified by silica gel chromatography eluting with 50% ethyl acetate/hexane to afford PA37.2 (17.0 g, 94.3%). MS(ES): m/z 330 [M+H]$^+$

Step 3. tert-butyl (5-(3,6-dihydro-2H-pyran-4-yl)-6-((dimethylamino) methyl) pyridin-2-yl)carbamate (PA37.3)

To a solution of PA37.2 (50 g, 151.5 mmol, 1.0 eq) in 1,4-Dioxane:water (400 mL:100 mL) with 2-(3,6-dihydro-2H-pyran-4-yl)-4,4,5,5-tetramethyl-1,3,2-dioxaborolane (47.7 g, 227.2 mmol, 1.5 eq) and potassium phosphate tribasic (96.3 g, 454.5 mmol, 3.0 eq) degassed with N$_2$ for 15 min was added X-phosPdG2 (11.9 g, 15.1 mmol, 0.1 eq). After stirring at 140° C. for 4 h, the reaction mixture was cooled to RT, diluted with water (1 L) and extracted with ethyl acetate (2×2 L). The combined organic extracts were wash with brine (1 L), dried over Na$_2$SO$_4$, filtered, and concentrated under reduced pressure. The residue was purified by column chromatography eluting with 2% methanol in DCM to afford PA37.3 (40 g, 79%), MS(ES): m/z 334.2 [M+H]$^+$

Step 4. tert-butyl (6-((dimethylamino)methyl)-5-(tetrahydro-2H-pyran-4-yl) pyridin-2-yl)carbamate (PA37.4)

To a suspension of palladium hydroxide (130 g) in methanol (600 ml) and THE (40 ml), was added Intermediate PA37.3 (130 g, 1.0 eq). Hydrogen gas was purged through reaction mixture for 4 h at RT. After completion of reaction, the reaction mixture was filtered through celite-bed which was washed with methanol. The filtrate was concentrated under reduced pressure to afford PA37.4 (120 g, 91.75%). MS (ES): m/z 336.2 [M+H]$^+$

Step 5. 6-((dimethylamino)methyl)-5-(tetrahydro-2H-pyran-4-yl)pyridin-2-amine (PA37)

To a solution of Intermediate PA37.4 (120 g, 356.9 mmol, 1.0 eq) in DCM (1.2 L), was add trifluoroacetic acid (360 mL) dropwise. After stirring at 55° C. for 2 h, the reaction mixture was neutralized with saturated sodium hydroxide solution and extracted with 10% methanol in DCM (4×10 L). The combined organic layer was concentrated under reduced pressure to afford PA37 (66 g, 78.40%). MS(ES): m/z 236.1 [M+H]$^+$

Method PA39—Preparation of 2-(1-(6-aminopyridin-3-yl)piperidin-3-yl)propan-2-ol (PA39)

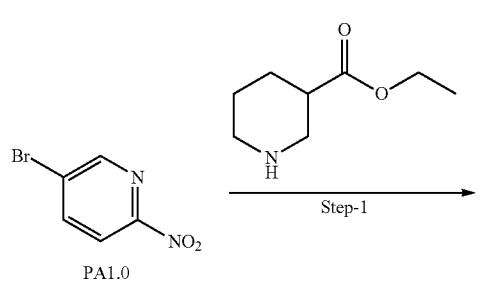

PA1.0

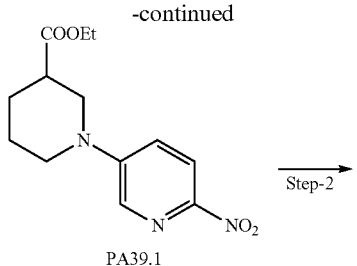

PA39.1

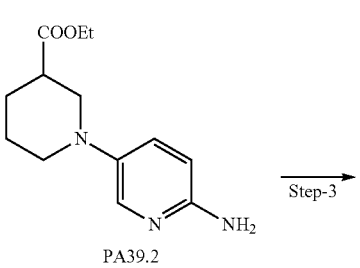

PA39.2

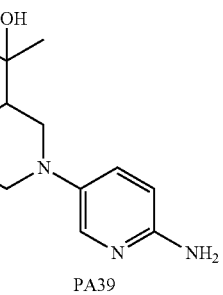

PA39

Step-1 & Step 2. ethyl 1-(6-aminopyridin-3-yl)piperidine-3-carboxylate (PA39.2)

Ethyl 1-(6-aminopyridin-3-yl)piperidine-3-carboxylate (PA39.2) was prepared in a similar fashion to that described in method PA4 (1.2 g, 89.62%). MS(ES): m/z 250.15 [M+H]

Step 3. 2-(1-(6-aminopyridin-3-yl)piperidin-3-yl)propan-2-ol (PA39)

To a solution of ethyl 1-(6-aminopyridin-3-yl)piperidine-3-carboxylate (PA39.2) (2.0 g, 8.03 mmol, 1.0 eq) in THE (15 mL) was added a solution of methyl magnesium bromide (3N in THF, 20 mL) dropwise at 0° C. After stirring at RT for 1 h, the reaction mixture was quenched with ice cool water (100 mL) and filtered on celite bed. The filtrate was extracted with ethyl acetate (100 mL×3) and the combine organic layer washed with brine (100 mL) and concentrated under reduced pressure. The residue was purified by column chromatography (0-80% gradient elution EtOAc in Hexanes) to afford PA39 (0.200 g, 10.60%). MS(ES): m/z 236.17 [M+H]$^+$

Method PA40—Preparation of 1-(6-amino-2-((dimethylamino)methyl)pyridin-3-yl) piperidin-4-ol (PA40)

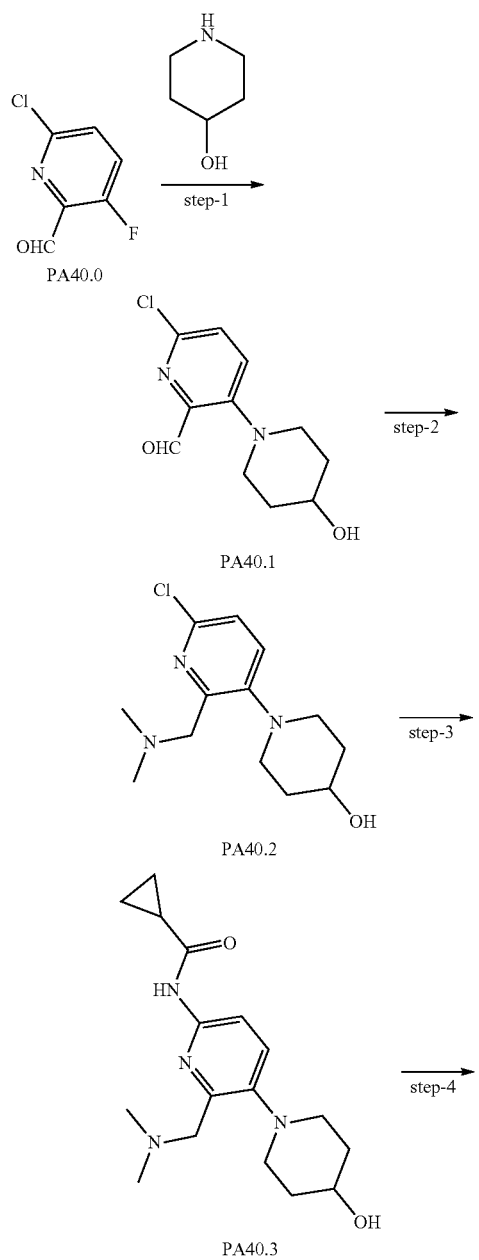

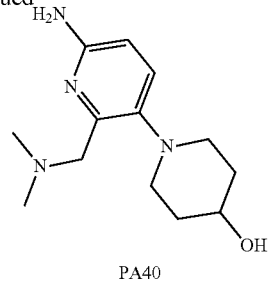

PA40

Step 1. 6-chloro-3-(4-hydroxypiperidin-1-yl)picolinaldehyde (PA40.1)

To a solution of PA40.0 (1.0 g, 6.28 mmol, 1.0 eq) and piperidin-4-ol (1.0 g, 10.04 mmol, 1.6 eq) N,N-dimethylformamide (10 mL) was added potassium carbonate (2.6 g, 18.84 mmol, 3.0 eq). After stirring at 100° C. for 1 h, the reaction mixture was cooled to RT, diluted with ice cold water (100 mL) and extracted with ethyl acetate (3×40 mL). The combined organic extracts were washed with brine (80 mL), dried over $Na_2SO_4$, filtered, and concentrated under reduced pressure. The residue was purified by column chromatography eluting with 30% ethyl acetate in hexane to afford PA40.1 (1.2 g, 79.54%), MS(ES): m/z 241.07 $[M+H]^+$

Step 2. 1-(6-chloro-2-((dimethylamino)methyl)pyridin-3-yl)piperidin-4-ol (PA40.2)

To a cooled solution of PA40.1 (1.2 g, 5.00 mmol, 1.0 eq) in 1,2-dichloroethane (20 ml) was added acetic acid (2.4 ml) at 0° C. The reaction was bubbled with dimethylamine gas for 30 min before adding portionwise sodium triacetoxyborohydride (7.4 g, 35 mmol, 7.0 eq). After stirring at RT for 16 h, the reaction mixture was diluted with ice cold water (100 mL) and extracted with DCM (4×40 mL). The combined organic extracts were washed with brine (90 mL), dried over Na2SO4, filtered, and concentrated under reduced pressure. The residue was purified by column chromatography eluting with 3.0% gradient of methanol in DCM to afford PA40.2 (0.450 g, 33.46%), MS(ES): m/z 270.2 $[M+H]^+$

Step 3 & Step 4. 5-(oxetan-3-yl)pyridin-2-amine (PA40)

Reaction of step-3 & 4 was carried out following the representative procedure described in Method PA28 (Step-3 & 4) using PA40.2 and cyclopropanecarboxamide to afford PA40 (0.3 g, 64%). MS(ES): m/z 251.35 [M+H]+

The following anilines intermediates were prepared according to any of Intermediate Methods PA1-PA40 as described above.

| # | STRUCTURE | Method | # | STRUCTURE | Method |
|---|---|---|---|---|---|
| PA3 | 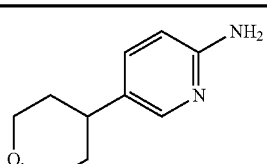 | 5-(tetrahydro-2H-pyran-4-yl)pyridin-2-amine (same as PA1) | PA5 | 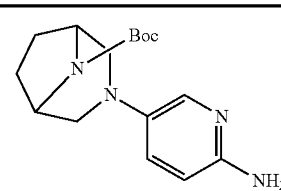 | tert-butyl 3-(6-aminopyridin-3-yl)-3,8-diazabicyclo[3.2.1]octane-8-carboxylate (same as PA4) |

-continued

| # | STRUCTURE | Method | # | STRUCTURE | Method |
|---|---|---|---|---|---|
| PA6 | 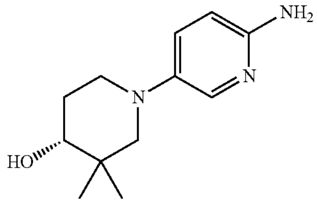 [SMILES: CC1(C)CN(c2ccc(N)nc2)CC[C@H]1O] | (R)-1-(6-aminopyridin-3-yl)-3,3-dimethyl-piperidin-4-ol (same as PA4) | PA7 | 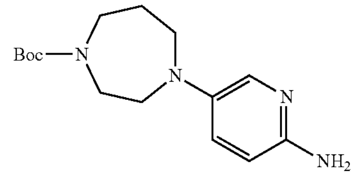 [SMILES: CC(C)(C)OC(=O)N1CCCN(c2ccc(N)nc2)CC1] | tert-butyl 4-(6-aminopyridin-3-yl)-1,4-diazepane-1-carboxylate (same as PA4) |
| PA8 | 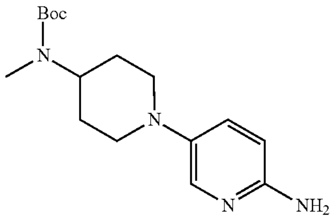 [SMILES: CN(C(=O)OC(C)(C)C)C1CCN(c2ccc(N)nc2)CC1] | tert-butyl (1-(6-aminopyridin-3-yl)piperidin-4-yl)(methyl)carbamate (same as PA4) | PA10 | 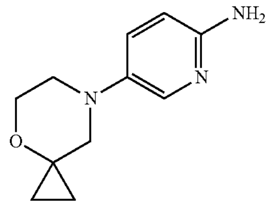 [SMILES: Nc1ccc(N2CCOC3(CC3)C2)cn1] | 5-(4-oxa-7-azaspiro[2.5]octan-7-yl)pyridin-2-amine (same as PA4) |
| PA11 | 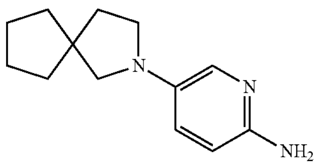 [SMILES: Nc1ccc(N2CCC3(CCCC3)C2)cn1] | 5-(2-azaspiro[4.4]nonan-2-yl)pyridin-2-amine (same as PA4) | PA12 | 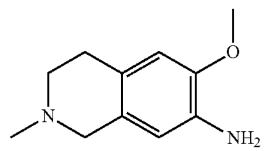 | 6-methoxy-2-methyl-1,2,3,4-tetrahydro-isoquinollin-7-amine (same as PA9) |
| PA13 | 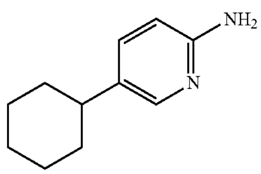 [SMILES: Nc1ccc(C2CCCCC2)cn1] | 5-cyclohexyl-pyridin-2-amine (same as PA1) | PA14 | 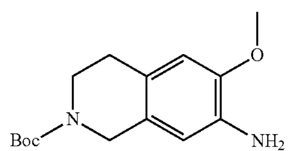 | tert-butyl 7-amino-6-methoxy-3,4-dihydro-isoquinoline-2(1H)-carboxylate (same as PA9) |
| PA15 | 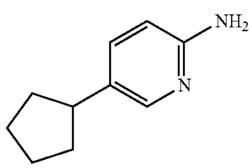 [SMILES: Nc1ccc(C2CCCC2)cn1] | 5-cyclopentyl-pyridin-2-amine (same as PA1) | PA16 | 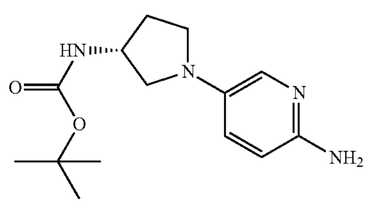 [SMILES: CC(C)(C)OC(=O)N[C@@H]1CCN(c2ccc(N)nc2)C1] | tert-butyl (R)-(1-(6-aminopyridin-3-yl)pyrrolidin-3-yl)carbamate (same as PA4) |
| PA17 | 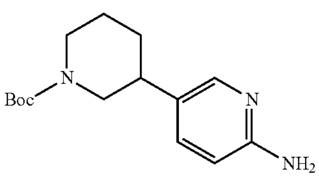 [SMILES: CC(C)(C)OC(=O)N1CCCC(c2ccc(N)nc2)C1] | tert-butyl 3-(6-aminopyridin-3-yl)piperidine-1-carboxylate (same as PA1) | PA18 | 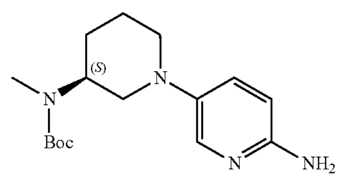 | tert-butyl (S)-(1-(6-aminopyridin-3-yl)piperidin-3-yl)(methyl)carbamate (same as PA4) |
| PA19 | 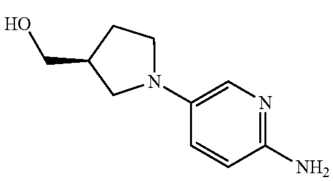 [SMILES: Nc1ccc(N2CC[C@H](CO)C2)cn1] | (S)-(1-(6-aminopyridin-3-yl)pyrrolidin-3-yl)methanol (same as PA4) | PA20 | 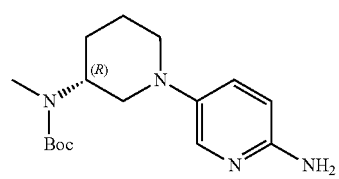 | tert-butyl (R)-(1-(6-aminopyridin-3-yl)piperidin-3-yl)(methyl)carbamate (same as PA4) |
| PA21 | 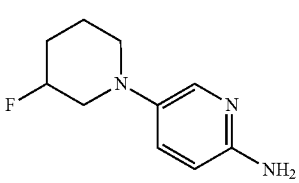 [SMILES: Nc1ccc(N2CCCC(F)C2)cn1] | 5-(3-fluoropiperidin-1-yl)pyridin-2-amine (same as PA4) | PA22 | 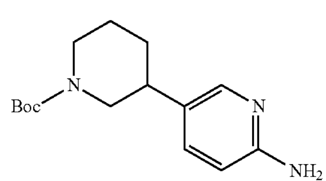 [SMILES: CC(C)(C)OC(=O)N1CCCC(c2ccc(N)nc2)C1] | tert-butyl 3-(6-aminopyridin-3-yl)piperidine-1-carboxylate (same as PA1) |

-continued

| # | STRUCTURE | Method | # | STRUCTURE | Method |
|---|---|---|---|---|---|
| PA23 | 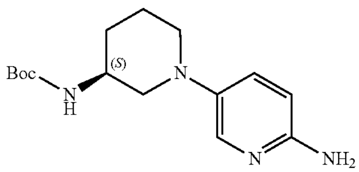 | tert-butyl (S)-(1-(6-aminopyridin-3-yl)piperidin-3-yl)carbamate (same as PA4) | PA24 | 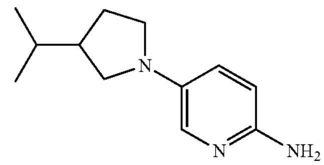 | 5-(3-isopropyl-pyrrolidin-1-yl)pyridin-2-amine (same as PA4) |
| PA25 | 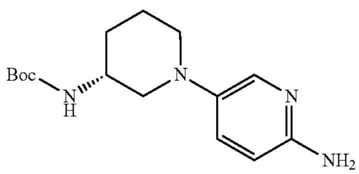 [SMILES: CC(C)(C)OC(=O)N[C@@H]1CCCN(c2ccc(N)nc2)C1] | tert-butyl (R)-(1-(6-aminopyridin-3-yl)piperidin-3-yl)carbamate (same as PA4) | PA26 | 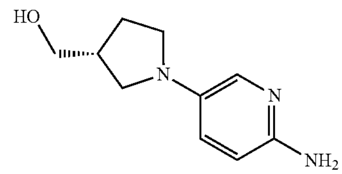 [SMILES: Nc1ccc(N2CC[C@@H](CO)C2)cn1] | (R)-(1-(6-aminopyridin-3-yl)pyrrolidin-3-yl)methanol (same as PA4) |
| PA27 | 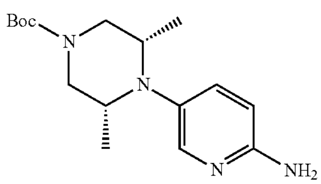 [SMILES: C[C@@H]1CN(C(=O)OC(C)(C)C)C[C@H](C)N1c1ccc(N)nc1] | tert-butyl (3S,5R)-4-(6-aminopyridin-3-yl)-3,5-dimethylpiperazine-1-carboxylate (same as PA4) | PA33 | 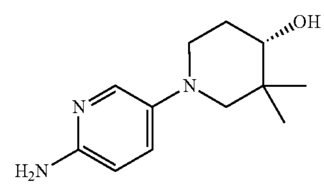 [SMILES: CC1(C)CN(c2ccc(N)nc2)CC[C@@H]1O] | (S)-1-(6-aminopyridin-3-yl)-3,3-dimethylpiperidin-4-ol (same as PA4) |
| PA34 | 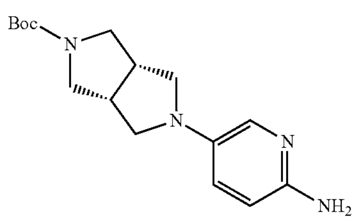 [SMILES: CC(C)(C)OC(=O)N1C[C@@H]2CN(c3ccc(N)nc3)C[C@@H]2C1] | tert-butyl (3aR,6aS)-5-(6-aminopyridin-3-yl)hexahydropyrrolo[3,4-c]pyrrole-2(1H)-carboxylate (same as PA4) | PA36 | 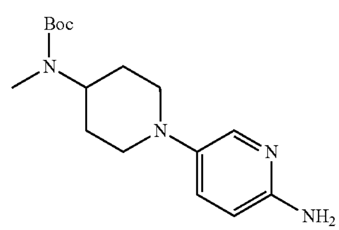 [SMILES: CN(C(=O)OC(C)(C)C)C1CCN(c2ccc(N)nc2)CC1] | tert-butyl (1-(6-aminopyridin-3-yl)piperidin-4-yl)(methyl)carbamate (same as PA4) |
| PA38 | 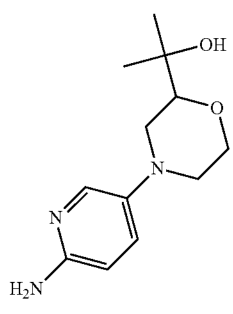 [SMILES: CC(C)(O)C1CN(c2ccc(N)nc2)CCO1] | 2-(4-(6-aminopyridin-3-yl)morpholin-2-yl)propan-2-ol (using PA4) | PA41 | 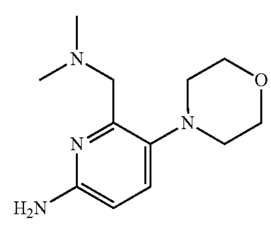 | 6-((dimethylamino)methyl)-5-morpholino-pyridin-2-amine (using PA40) |
| PA42 | 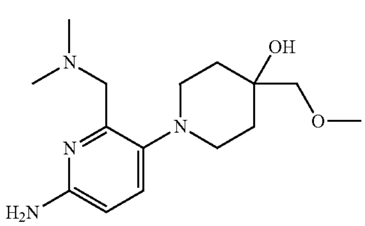 [SMILES: COCC1(O)CCN(c2ccc(N)nc2CN(C)C)CC1] | 1-(6-amino-2-((dimethylamino)methyl)pyridin-3-yl)-4-(methoxymethyl)piperidin-4-ol (same as PA40) | | | |

Method CB1—Preparation of 5-fluoro-2-methoxy-4-(4,4,5,5-tetramethyl-1,3,2-dioxaborolan-2-yl)phenyl)(piperidin-1-yl)methanone (CB1)

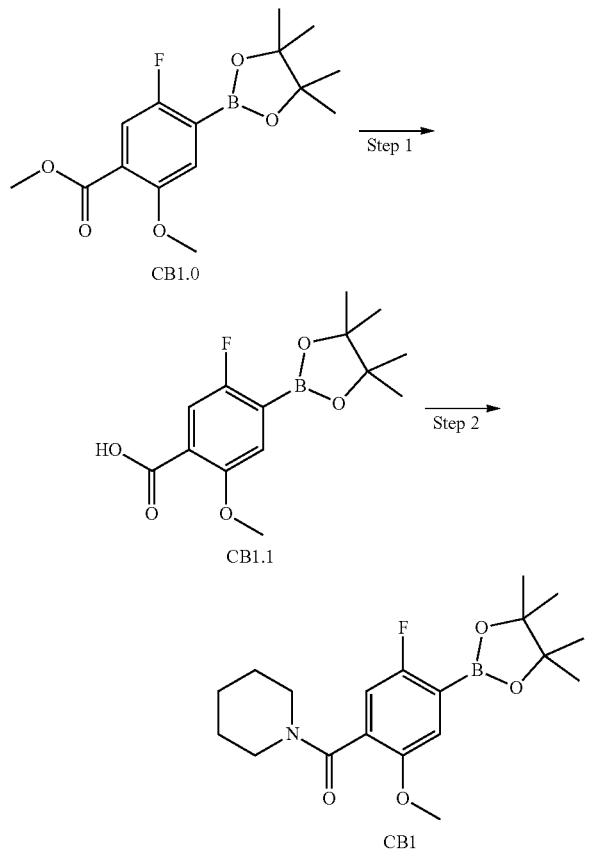

Step 1. 5-Fluoro-2-methoxy-4-(4,4,5,5-tetramethyl-1,3,2-dioxaborolan-2-yl)benzoic acid (CB1.1)

To a solution of methyl 5-fluoro-2-methoxy-4-(4,4,5,5-tetramethyl-1,3,2-dioxaborolan-2-yl)benzoate (CB 1.0) (2.0 g, 6.45 mmol) in THF (60 mL) was added LiOH (2M, 7.1 mL, 14.2 mmol). After stirring at RT for 16 h, the organic solvent was removed under reduced pressure, and the residual material was neutralized with aqueous 2M HCl (20 mL), diluted with brine (10 mL), and then extracted into ethyl acetate (3×50 mL). The combined organic layer were washed with brine (40 mL), passed through a hydrophobic frit and concentrated under reduced pressure to afford product (CB 1.1) (1.66 g, 87%) as a white solid, which was used without further purification. m/z=297.1 [M+H]$^+$, $^1$H NMR (400 MHz, CDCl$_3$): δ 10.83 (brs, 1H), 7.85 (d, J=8.7 Hz, 1H), 7.38 (d, J=4.0 Hz, 1H), 4.13 (s, 3H), 1.40 (s, 2H).

Step 2. 5-Fluoro-2-methoxy-4-(4,4,5,5-tetramethyl-1,3,2-dioxaborolan-2-yl)phenyl)(piperidin-1-yl)methanone (CB1)

To a solution of (CB1.1) (1.66 g, 5.61 mmol) in THF (25 mL) were added hydroxybenzotriazole (0.98 g, 7.29 mmol) and EDC hydrochloride (1.40 g, 7.29 mmol). After stirring at RT for 1 h, N, N-diisopropylethylamine (2.9 mL, 16.8 mmol) and piperidine (0.66 mL, 6.73 mmol) were sequentially added. After stirring at RT for 22 h, the organic solvent was evaporated under reduced pressure, diluted with water (40 mL) and extracted with DCM (2×40 mL). The combined organic layer was passed through a hydrophobic frit and concentrated under reduced pressure. The resulting foam was dissolved in DCM (10 mL) and product was precipitated by addition of diethyl ether. The solvent was removed under reduced pressure to afford crude (CB1) (2.07 g, quant.) as an off-white solid, which was used without further purification. m/z=364.2 [M+H]$^+$, $^1$H NMR (400 MHz, CDCl$_3$): δ 7.18 (d, J=4.2 Hz, 1H), 6.92 (d, J=8.1 Hz, 1H), 3.85 (s, 3H), 3.82-3.64 (m, 4H), 1.56-1.41 (m, 4H), 1.36 (s, 12H), 1.33-1.25 (m, 2H).

Method CB2—Preparation of N-(3-fluoro-4-(4,4,5,5-tetramethyl-1,3,2-dioxaborolan-2-yl)phenyl)-N-methylcyclopropanecarboxamide (CB2)

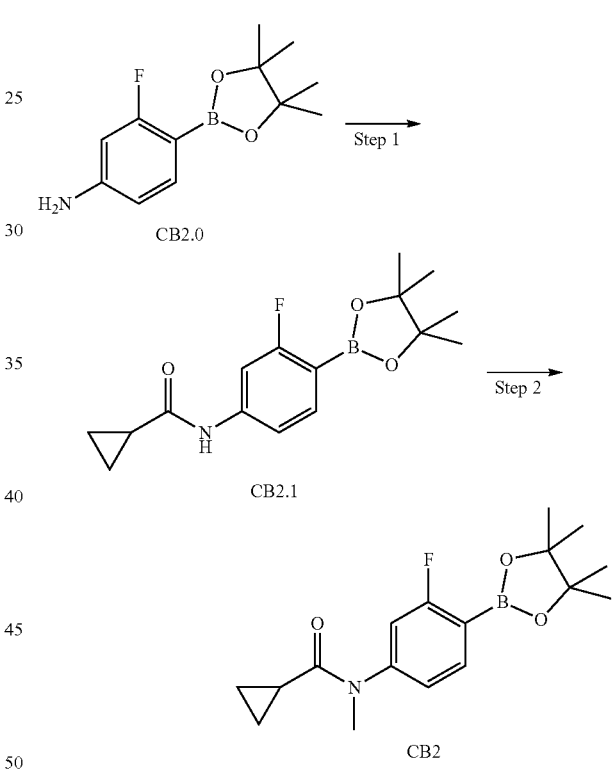

Step 1. N-(3-fluoro-4-(4,4,5,5-tetramethyl-1,3,2-dioxaborolan-2-yl)phenyl)cyclopropanecarboxamide (CB2.1)

To a solution of 3-fluoro-4-(4,4,5,5-tetramethyl-1,3,2-dioxaborolan-2-yl)aniline (CB2.0) (600 mg, 2.53 mmol), in dry DCM (12.0 mL) were added cyclopropanecarbonyl chloride (0.24 mL, 2.66 mmol) and N,N-diisopropylethylamine (0.88 mL, 5.06 mmol). After stirring at rt for 2 h, the reaction was quenched with 2M HCl (20 mL) and extracted with DCM (3×10 mL). The combined organic layer was washed with brine (20 mL), passed through a hydrophobic frit and concentrated under reduced pressure to afford crude product (CB2.1) (650 mg, 85%) as a white solid, which was used without further purification. m/z=306.1 [M+H]$^+$. $^1$H NMR (400 MHz, CDCl₃): δ 7.61-7.55 (m, 1H), 7.47 (d, J=1.6 Hz, 1H), 7.25 (s, 1H), 7.18 (d, J=1.6 Hz, 1H), 1.54-1.50 (m, 1H), 1.38-1.30 (m, 12H), 1.88-1.83 (m, 2H), 0.75-0.69 (m, 2H).

Step 2. N-(3-fluoro-4-(4,4,5,5-tetramethyl-1,3,2-dioxaborolan-2-yl)phenyl)-N-methylcyclopropanecarboxamide (CB2)

To a solution of N-(3-fluoro-4-(4,4,5,5-tetramethyl-1,3,2-dioxaborolan-2-yl)phenyl)cyclopropanecarboxamide (CB2.1) (650 mg, 2.13 mmol) in dry THF (6.0 mL), and methyl iodide (0.65 mL, 3.62 mmol) was added sodium hydride (60% in mineral oil, 145 mg, 3.62 mmol) portionwise. After stirring at RT for 4 h, the reaction was [cautiously!] quenched with dropwise water (1.0 mL) and extracted with EtOAc (2×5 mL). The combined organic layer were dried over anhydrous MgSO₄ and concentrated under reduced pressure. The residue was purified by silica gel chromatography (eluting 0-100% EtOAc in iso-hexane) to afford the title compound (CB2) (390 mg, 57%) as an off-white solid. m/z=320.2 [M+H]⁺, ¹H NMR (400 MHz, CDCl₃): δ 8.75 (s, 1H), 8.08 (d, J=1.6 Hz, 1H), 8.02 (d, J=1.6 Hz, 1H), 3.28 (s, 3H), 2.54 (s, 1H), 1.68-1.60 (m, 12H), 0.88-0.83 (m, 2H), 0.75-0.69 (m, 2H).

Method CB3—Preparation of 2-(2-fluoro-4-methoxy-5-methylphenyl)-4,4,5,5-tetramethyl-1,3,2-dioxaborolane (CB3)

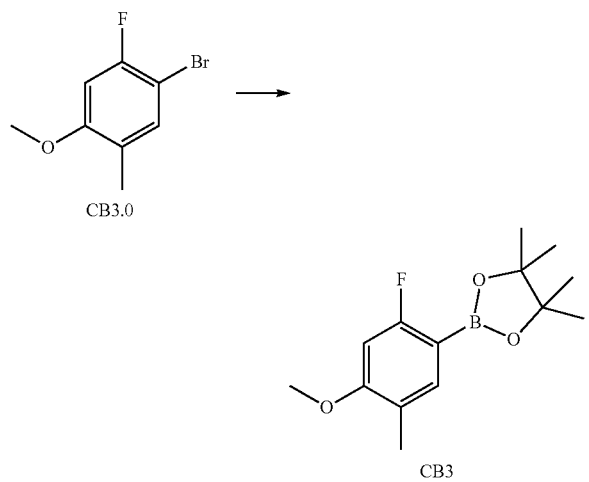

To a mixture of 1-bromo-2-fluoro-4-methoxy-5-methylbenzene (CB3.0) (500 mg, 2.28 mmol), bis(pinacolato)diboron (696 mg, 2.74 mmol), and potassium acetate (560 mg, 5.71 mmol) in 1,4-dioxane (10 mL) was added [1,1'-bis(diphenylphosphino)ferrocene]dichloropalladium(II), complex with DCM (186 mg, 0.23 mmol). After degassing with nitrogen, the mixture was heated at 100° C. for 6 h. The cooled mixture was diluted with EtOAc. The organic solution was collected, washed with water and brine, dried over Na₂SO₄ and concentrated in vacuo. The residue was purified by silica gel chromatography (gradient 0-50% EtOAc in iso-hexane) to afford the title compound (CB3) (539 mg, 89%) as a light brown solid.

Method CB4—Preparation of 5-fluoro-N,N-dimethyl-6-(4,4,5,5-tetramethyl-1,3,2-dioxaborolan-2-yl)-2,3-dihydro-1H-inden-1-amine (CB4)

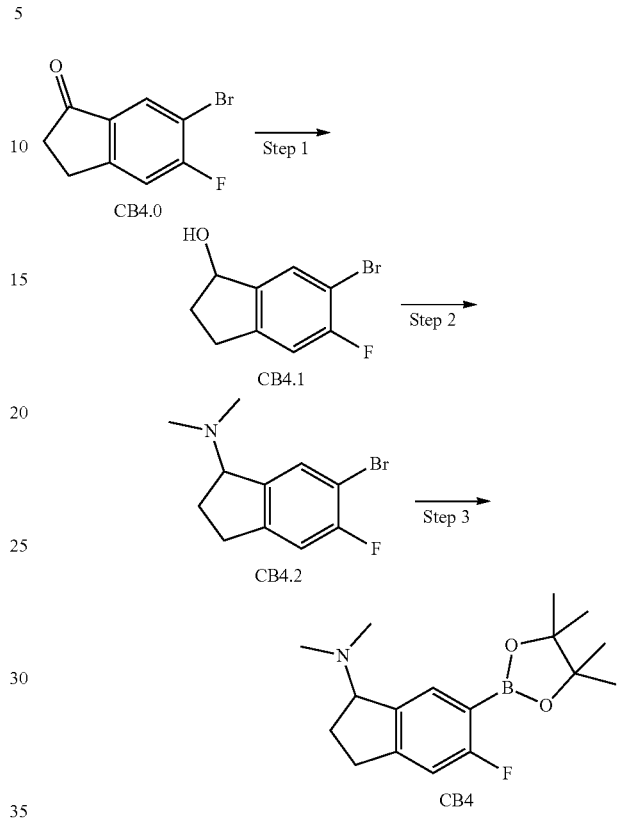

Step 1: 6-Bromo-5-fluoro-2,3-dihydro-1H-inden-1-ol (CB4.1)

To a solution of 6-bromo-5-fluoro-2,3-dihydro-1H-inden-1-one (CB4.0) (300 mg, 1.3 mmol) in methanol (3.0 mL) was added sodium borohydride (141 mg, 3.9 mmol). After stirring at RT for 30 mins, the mixture was diluted with DCM (20 mL) and washed with saturated aqueous NaHCO₃ (15 mL). The organic layer was passed through a hydrophobic frit and evaporated under reduced pressure to afford the desired product (CB4.1) (307 mg, quant.) as an off-white solid which was used in the next step without further purification. m/z=231.9 [M+H]⁺, ¹H NMR (400 MHz, CDCl₃): δ 7.56 (d, J=6.3 Hz, 1H), 7.02-6.97 (m, 1H), 5.25-5.16 (m, 1H), 3.06-2.96 (m, 1H), 2.83-2.72 (m, 1H), 2.58-2.47 (m, 1H), 2.04-1.94 (m, 1H), 1.78 (d, J=6.8 Hz, 1H).

Step 2: 6-Bromo-5-fluoro-N,N-dimethyl-2,3-dihydro-1H-inden-1-amine (CB4.2)

To a solution of 6-bromo-5-fluoro-2,3-dihydro-1H-inden-1-ol (CB4.1) (307 mg, 3.9 mmol) in THF (12 mL) and triethylamine (0.94 mL, 5.1 mmol) at −15° C. was added methanesulfonyl chloride (200 μL, 2.6 mmol) dropwise. After stirring for 3 h at −15° C., dimethylamine solution (2M in THF, 7.8 mL, 15.5 mmol) was added. After stirring overnight warming to RT, the reaction mixture was filtered, and the solvent was evaporated under reduced pressure. The crude product was passed through an SCX cartridge (loaded with DCM, washed with 10% MeOH in DCM eluting with 10% 7N methanolic ammonia in DCM). The solvent was evaporated under reduced pressure to afford the desired product (CB4.2) (310 mg, 92%) as a red-brown oil which was used in the next step without further purification. m/z=259.1 [M+H]+, $^1$H NMR (400 MHz, CDCl$_3$): δ 7.51 (d, J=6.7 Hz, 1H), 6.97-6.94 (m, 1H), 4.26 (t, J=6.8 Hz, 1H), 2.93-2.72 (m, 2H), 2.23 (s, 6H), 2.12-2.03 (m, 2H).

Step 3: 5-Fluoro-N,N-dimethyl-6-(4,4,5,5-tetramethyl-1,3,2-dioxaborolan-2-yl)-2,3-dihydro-1H-inden-1-amine (CB4)

To a large carousel tube was charged with 6-bromo-5-fluoro-N,N-dimethyl-2,3-dihydro-1H-inden-1-amine (CB4.2) (310 mg, 1.2 mmol), bis(pinacolato)diboron (475 mg, 1.8 mmol) and potassium acetate (354 mg, 3.6 mmol) in dioxane (10 mL) was added [1,1'-bis(diphenylphosphino)ferrocene]dichloropalladium(II), complex with DCM (44 mg, 0.06 mmol). The tube was sealed and heated with stirring at 110° C. for 3 h. The reaction mixture was allowed to cool to RT and the compound (CB4) was taken forwards to the next step without further purification. m/z=306.2 [M+H]+.

Method CB5—4-((3-Fluoro-4-(4,4,5,5-tetramethyl-1,3,2-dioxaborolan-2-yl)phenoxy)methyl)pyridine (CB5)

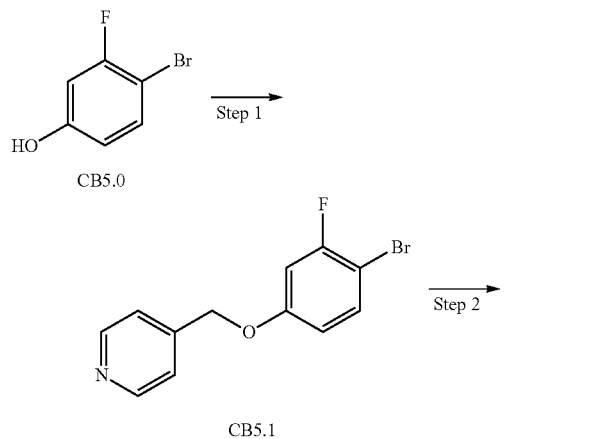

Step 1:
4-((4-bromo-3-fluorophenoxy)methyl)pyridine (CB5.1)

To a solution of 4-bromo-3-fluorophenol (CB5.0) (1.00 g, 5.24 mmol) in DMF (8 mL) were added 4-(bromomethyl) pyridine (1.59 g, 6.28 mmol) and potassium carbonate (1.81 g, 13.1 mmol). After stirring at RT overnight, the reaction mixture was diluted with ethyl acetate and washed with water (three times) and brine. The organic layer was dried over Na$_2$SO$_4$, filtered, and concentrated under reduced pressure. The crude material was purified by silica gel chromatography eluting with 0-100% EtOAc in DCM to afford the desired product (CB5.1) (162 mg, 11%) as a white solid. m/z=283.9 [M+H]+, $^1$H NMR (400 MHz, CDCl3): δ 8.63 (d, J=6.1 Hz, 2H), 7.45-7.38 (m, 1H), 7.32 (d, J=5.8 Hz, 2H), 6.73 (dd, J=2.4, 8.4 Hz, 1H), 6.67 (dd, J=2.3, 11.0 Hz, 1H), 5.09 (s, 2H).

Step 2: 4-((3-fluoro-4-(4,4,5,5-tetramethyl-1,3,2-dioxaborolan-2-yl)phenoxy)methyl)pyridine (CB5)

A mixture of 4-((4-bromo-3-fluorophenoxy)methyl)pyridine (CB5.1) (155 mg, 0.55 mmol), bis(pinacolato)diboron (167 mg, 0.66 mmol), [1,1'-bis(diphenylphosphino)ferrocene]dichloropalladium(II) complex with DCM (45 mg, 0.05 mmol) and potassium acetate (135 mg, 1.37 mmol) in 1,4-dioxane (10 mL) was degassed and purged with nitrogen. After heating to 100° C. for 6 h, the reaction mixture was then cooled to RT, diluted with EtOAc and washed with water, and brine. The organic layer was dried over Na$_2$SO$_4$, filtered, and concentrated under reduced pressure. The crude material was purified by silica gel chromatography using 0-100% EtOAc in DCM to afford CB5 (179 mg, 99%) as an orange-brown residue. m/z=330.0 [M+H]+, $^1$H NMR (400 MHz, CDCl3): δ 8.62 (d, J=6.1 Hz, 2H), 7.70-7.65 (m, 1H), 7.34 (d, J=5.8 Hz, 2H), 6.74 (dd, J=2.4, 8.4 Hz, 1H), 6.63 (dd, J=2.3, 11.0 Hz, 1H), 5.10 (s, 2H), 1.35-1.24 (m, 12H).

Method CB6—2-(5-Cyclobutyl-2-fluorophenyl)-4,4,5,5-tetramethyl-1,3,2-dioxaborolane (CB6)

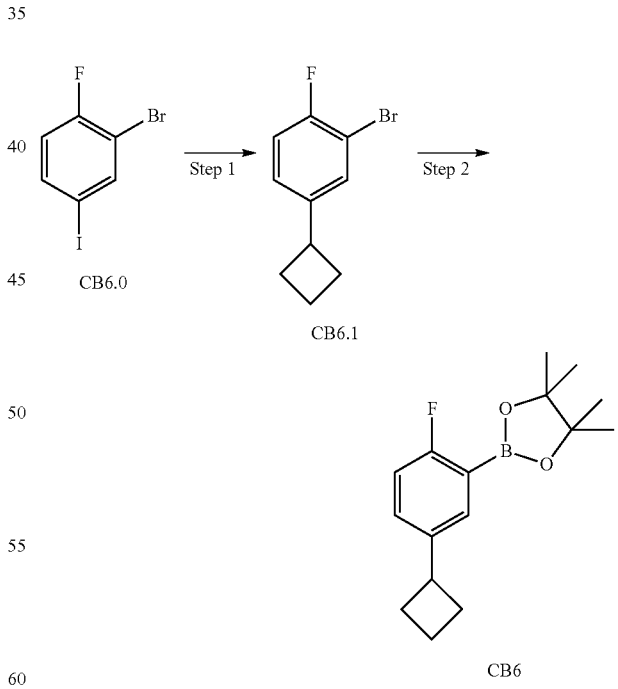

Step 1: 2-bromo-4-cyclobutyl-1-fluorobenzene (CB6.1)

A solution of 2-bromo-1-fluoro-4-iodobenzene (CB6.0) (600 mg, 1.99 mmol), Xantphos palladacycle Gen. 3 (95 mg, 0.10 mmol) and Xantphos (58 mg, 0.10 mmol) in THF (10 mL) was degassed and purged with nitrogen. Following addition of cyclobutylzinc bromide (0.5 M, 5.2 mL, 2.59 mmol), the reaction was heated to 50° C. for 7 h. After standing at RT for 3 days, the reaction mixture was quenched with saturated aqueous ammonium chloride and extracted into EtOAc (two times). The combined organic layer was washed with brine, dried over Na$_2$SO$_4$ and concentrated under reduced pressure. The crude material was purified by silica gel chromatography eluting with 0-20% EtOAc in iso-hexane to afford CB6.1 (385 mg, 84%) as a colourless oil. $^1$H NMR (400 MHz, CDCl3): δ 7.37 (dd, J=1.8, 6.6 Hz, 1H), 7.12-7.06 (m, 1H), 7.02 (dd, J=8.5, 8.5 Hz, 1H), 3.54-3.43 (m, 1H), 2.39-2.30 (m, 2H), 2.15-1.96 (m, 4H).

Step 2: 2-(5-cyclobutyl-2-fluorophenyl)-4,4,5,5-tetramethyl-1,3,2-dioxaborolane (CB6)

A mixture of 2-bromo-4-cyclobutyl-1-fluorobenzene (CB6.1) (378 mg, 1.65 mmol), bis(pinacolato)diboron (503 mg, 1.98 mmol), [1,1'-bis(diphenylphosphino)ferrocene]dichloropalladium(II), complex with DCM (135 mg, 0.17 mmol) and potassium acetate (405 mg, 4.12 mmol) in 1,4-dioxane (10 mL) was degassed and purged with nitrogen. After heating to 100° C. for 6 h, the reaction mixture was cooled to RT, diluted with EtOAc and washed with water, and brine. The organic layer was dried over Na$_2$SO$_4$, filtered, and concentrated under reduced pressure. The crude material was purified by silica gel chromatography using 0-40% EtOAc in iso-hexane to afford CB6 (286 mg, 63%) as a pale yellow oil. $^1$H NMR (400 MHz, CDCl3): δ 7.53 (dd, J=2.4, 5.6 Hz, 1H), 6.95 (dd, J=8.8, 8.8 Hz, 1H), 3.57-3.46 (m, 1H), 2.37-2.28 (m, 2H), 2.18-1.95 (m, 3H), 1.89-1.83 (m, 1H), 1.36 (s, 12H).

Method CB7—2-(2-Fluoro-5-(1-methylcyclopropyl)phenyl)-4,4,5,5-tetramethyl-1,3,2-dioxaborolane (CB7)

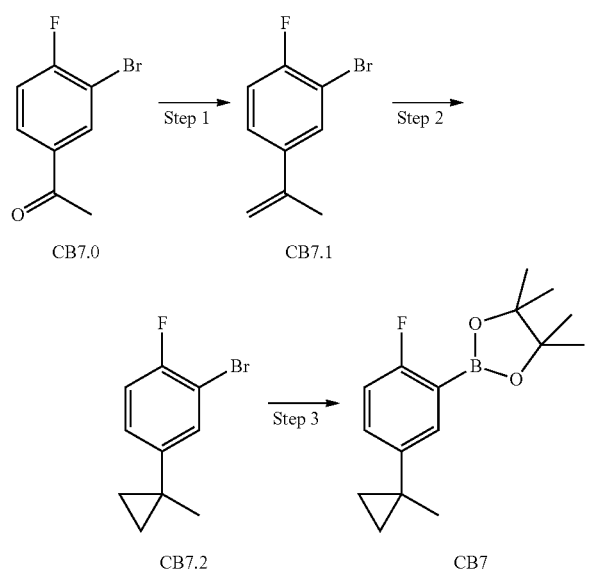

Step 1: 2-bromo-1-fluoro-4-(prop-1-en-2-yl)benzene (CB7.1)

A suspension of methyltriphenylphosphonium bromide (1.73 g, 4.84 mmol) in THF (10 mL) was cooled to 0° C., then treated portionwise with potassium tert-butoxide (0.57 g, 5.07 mmol). After stirring at 0° C. for 2 h, the reaction was treated with the dropwise addition of a solution of 1-(3-bromo-4-fluorophenyl)ethan-1-one (CB7.0) (1.00 g, 4.61 mmol) in THF (5 mL). After warming to RT and stirring at RT overnight, the reaction mixture was quenched with 1M aqueous HCl and extracted into EtOAc (two times). The combined organic layer was washed with brine, dried over Na$_2$SO$_4$, filtered, and concentrated under reduced pressure. The crude material was purified by silica gel chromatography using 0-20% EtOAc in iso-hexane to afford CB7.1 (352 mg, 36%) as a colourless oil. $^1$H NMR (400 MHz, CDCl3): δ 7.63 (dd, J=2.4, 6.7 Hz, 1H), 7.38-7.34 (m, 1H), 7.06 (dd, J=8.5, 8.5 Hz, 1H), 5.31 (s, 1H), 5.10 (s, 1H), 2.11 (s, 3H).

Step 2: 2-bromo-1-fluoro-4-(1-methylcyclopropyl)benzene (CB7.2)

A solution of diethylzinc (1.0 M in hexanes, 1.95 mL, 1.95 mmol) in DCM (5 mL) was placed under an atmosphere of nitrogen and cooled to −15° C. The solution was treated with dropwise addition of a solution of dibutylphosphate (0.39 mL, 1.95 mmol) in DCM (4 mL). After stirring at −15° C. for 15 min, the reaction was then treated with diiodomethane (0.16 mL. 1.95 mmol). After stirring for 30 min at −15° C., a solution of 2-bromo-1-fluoro-4-(prop-1-en-2-yl)benzene (CB7.1) (350 mg, 1.63 mmol) in DCM (4 mL) was added. After warming to RT and stirring for 18 hr, the reaction mixture was quenched with saturated aqueous ammonium chloride and extracted into EtOAc (two times). The combined organic layer was washed with brine, dried over Na2SO4 and concentrated under reduced pressure. The crude material was purified by silica gel chromatography using 0-30% EtOAc in iso-hexane to afford CB7.2 (311 mg, 67%) as a colourless oil. $^1$H NMR (400 MHz, CDCl3): δ 7.36 (ddd, J=2.2, 4.7, 8.5 Hz, 1H), 7.17-7.10 (m, 2H), 2.11 (s, 3H), 0.84-0.78 (m, 4H).

Step 3: 2-(2-fluoro-5-(1-methylcyclopropyl)phenyl)-4,4,5,5-tetramethyl-1,3,2-dioxaborolane (CB7)

A mixture of 2-bromo-1-fluoro-4-(1-methylcyclopropyl)benzene (CB7.2) (310 mg, 1.35 mmol), bis(pinacolato)diboron (412 mg, 1.62 mmol), [1,1'-bis(diphenylphosphino)ferrocene]dichloropalladium(II) complex with DCM (111 mg, 0.14 mmol) and potassium acetate (332 mg, 3.38 mmol) in 1,4-dioxane (10 mL) was degassed and purged with nitrogen. After heating to 100° C. for 5 h, the reaction mixture was cooled to RT, diluted with EtOAc and washed with water and brine. The organic layer was dried over Na$_2$SO$_4$, filtered, and concentrated under reduced pressure. The crude material was purified by silica gel chromatography using 0-50% EtOAc in iso-hexane to afford CB7 (357 mg) as an orange residue, which was used in the subsequent step without further purification.

Method CB8—1,1,1-Trifluoro-2-(4-fluoro-3-(4,4,5,5-tetramethyl-1,3,2-dioxaborolan-2-yl)phenyl)propan-2-ol (CB8)

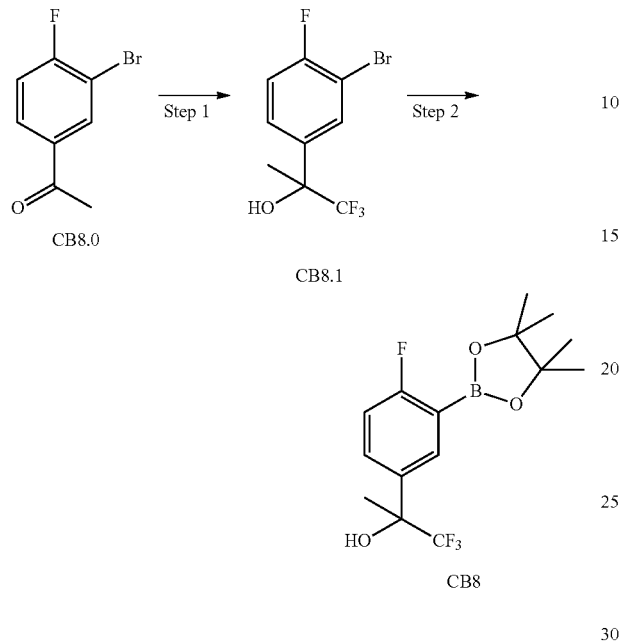

Step 1: 2-(3-bromo-4-fluorophenyl)-1,1,1-trifluoropropan-2-ol (CB8.1)

A solution of 1-(3-bromo-4-fluorophenyl)ethan-1-one (CB8.0) (1.00 g, 4.61 mmol) and trimethyl(trifluoromethyl)silane (1.4 mL, 9.22 mmol) in THF (15 mL) was treated with dropwise addition of tetrabutylammonium fluoride (1.0 M, 6.9 mL, 6.91 mmol). After stirring at RT overnight, the reaction mixture was quenched with saturated aqueous ammonium chloride and extracted into EtOAc (two times). The combined organic layer was washed with brine, dried over Na2SO4 and concentrated under reduced pressure. The crude material was purified by silica gel chromatography using 0-50% EtOAc in iso-hexane to afford CB8.1 (1.39 g, quant.) as a pale yellow oil. $^1$H NMR (400 MHz, DMSO): δ 12.42 (s, 1H), 8.69 (s, 1H), 8.05 (dd, J=1.9, 7.5 Hz, 1H), 7.99 (d, J=2.8 Hz, 1H), 7.65-7.58 (m, 1H), 7.40 (dd, J=2.9, 9.0 Hz, 1H), 7.35 (d, J=7.6 Hz, 2H), 2.43 (s, 6H).

Step 2: 1,1,1-trifluoro-2-(4-fluoro-3-(4,4,5,5-tetramethyl-1,3,2-dioxaborolan-2-yl)phenyl)propan-2-ol (CB8)

A mixture of 2-(3-bromo-4-fluorophenyl)-1,1,1-trifluoropropan-2-ol (CB8.1) (521 mg, 1.82 mmol), bis(pinacolato)diboron (553 mg, 2.18 mmol), [1,1'-bis(diphenylphosphino)ferrocene]dichloropalladium(II) complex with DCM (148 mg, 0.18 mmol) and potassium acetate (445 mg, 4.54 mmol) in 1,4-dioxane (10 mL) was degassed and purged with nitrogen. After heating to 100° C. for 5 h, the reaction mixture was cooled to RT, diluted with EtOAc and washed with water, and brine. The organic layer was dried over Na$_2$SO$_4$, filtered, and concentrated under reduced pressure. The crude material was purified by silica gel chromatography using 0-10% MeOH in DCM to afford CB8 (348 mg) as an orange residue, which was used the subsequent step without analysis.

Method CB9—(2-Ethoxy-5-fluoro-4-(4,4,5,5-tetramethyl-1,3,2-dioxaborolan-2-yl)phenyl)(piperidin-1-yl)methanone (CB9)

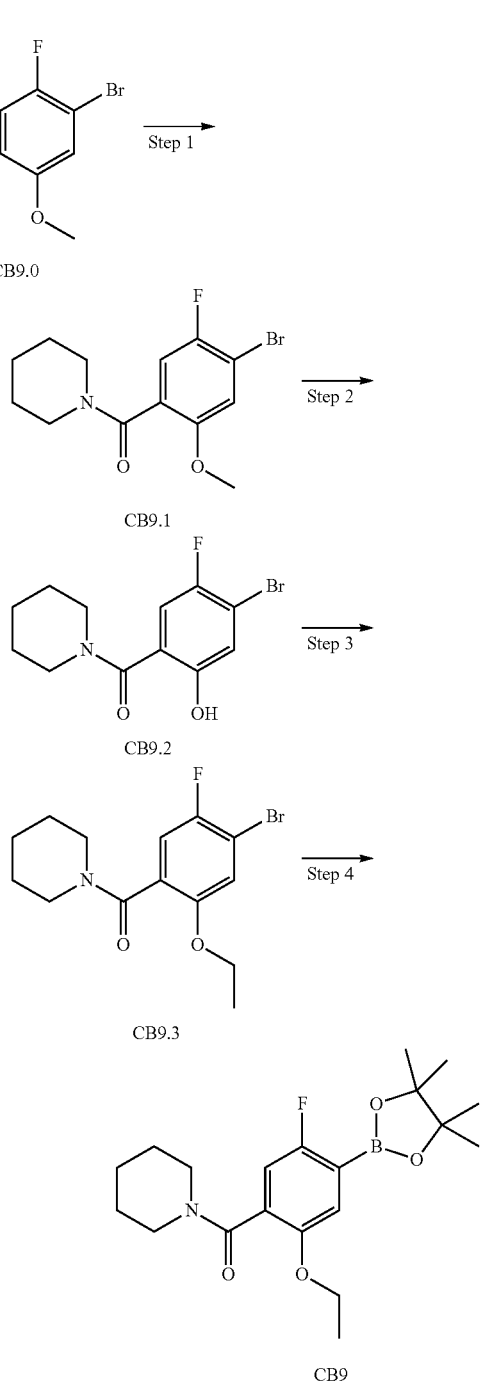

Step 1: (4-bromo-5-fluoro-2-methoxyphenyl)(piperidin-1-yl)methanone (CB9.1)

A solution of 4-bromo-5-fluoro-2-methoxybenzoic acid (CB9.0) (215 mg, 0.82 mmol) in THF (5 mL) was treated with HOBt (144 mg, 1.06 mmol) and EDC hydrochloride (204 mg, 1.06 mmol). After stirring at RT for 1 hr, the reaction mixture was treated with DIPEA (0.43 mL, 2.45 mmol) and piperidine (0.10 mL, 0.98 mmol). After stirring at RT for 3 days, the reaction mixture was quenched with saturated aqueous sodium bicarbonate and diluted with DCM. The organic layer was separated, passed through a hydrophobic frit and concentrated under reduced pressure to afford CB9.1 (250 mg, 93%). m/z=318.0 [M+H]+, $^1$H NMR (400 MHz, CDCl3): δ 7.07-7.00 (m, 2H), 3.81 (s, 3H), 3.78-3.61 (m, 4H), 3.21-3.14 (m, 2H), 1.53-1.41 (m, 4H).

Step 2: (4-bromo-5-fluoro-2-hydroxyphenyl)(piperidin-1-yl)methanone (CB9.2)

A solution of (4-bromo-5-fluoro-2-methoxyphenyl)(piperidin-1-yl)methanone (CB9.1) (500 mg, 1.58 mmol) in DCM (30 mL) was cooled to −78° C., and treated with boron tribromide (1.0 M in DCM, 4.7 mL, 4.74 mmol). After stirring at −78° C. for 2 h, the reaction was quenched with water and neutralized with saturated aqueous sodium bicarbonate. The organic layer was separated, passed through a hydrophobic frit and concentrated under reduced pressure to afford CB9.2 (450 mg, 94%) as a tan solid. m/z=304.0 [M+H]+, $^1$H NMR (400 MHz, CDCl3): δ 7.37 (d, J=5.8 Hz, 1H), 6.97 (d, J=8.1 Hz, 1H), 3.58 (dd, J=5.2, 5.2 Hz, 4H), 3.21-3.14 (m, 2H), 1.53-1.41 (m, 4H).

Step 3: (4-bromo-2-ethoxy-5-fluorophenyl)(piperidin-1-yl)methanone (CB9.3)

To a solution of (4-bromo-5-fluoro-2-hydroxyphenyl)(piperidin-1-yl)methanone (CB9.2) (220 mg, 0.73 mmol) in DMF (5 mL) were added potassium carbonate (1.00 g, 7.28 mmol) and bromoethane (0.12 mL, 1.60 mmol). After stirring at 60° C. for 3 h, the reaction was cooled to RT and filtered. The filtrate was concentrated under reduced pressure to afford crude CB9.3 (250 mg), which was used in the subsequent step without further purification. m/z=332.0 [M+H]+, $^1$H NMR (400 MHz, CDCl3): δ 7.06-7.00 (m, 2H), 4.08-3.96 (m, 2H), 3.75-3.62 (m, 3H), 3.23-3.09 (m, 4H), 1.89 (s, 2H), 1.45-1.35 (m, 4H).

Step 4: (2-ethoxy-5-fluoro-4-(4,4,5,5-tetramethyl-1,3,2-dioxaborolan-2-yl)phenyl)(piperidin-1-yl)methanone (CB9)

A mixture of (4-bromo-2-ethoxy-5-fluorophenyl)(piperidin-1-yl)methanone (CB9.3) (250 mg, 0.76 mmol), bis(pinacolato)diboron (211 mg, 0.83 mmol), [1,1'-bis(diphenylphosphino)ferrocene]dichloropalladium(II) complex with DCM (28 mg, 0.04 mmol) and potassium acetate (223 mg, 2.27 mmol) in 1,4-dioxane (10 mL) was degassed and purged with nitrogen. After stirring at 110° C. overnight, the reaction mixture was cooled to RT, quenched with saturated aqueous ammonium chloride and filtered. The filtrate was extracted into DCM, and the organic layer was passed through a hydrophobic frit and concentrated under reduced pressure to afford crude CB9, which was used in the subsequent step without further purification. m/z=378.3 [M+H]+.

Method CB10—(2,3-Difluoro-5-methoxy-4-(piperidine-1-carbonyl)phenyl)boronic acid (CB10)

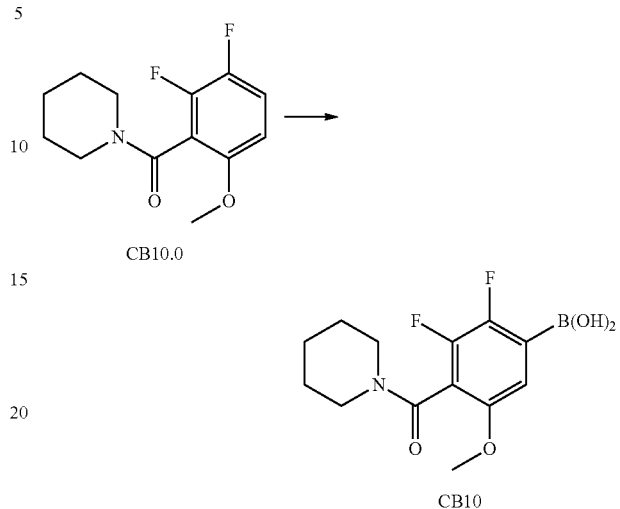

A solution of (2,3-difluoro-6-methoxyphenyl)(piperidin-1-yl)methanone (CB10.0) (2.30 g, 9.01 mmol) in THF (40 mL) was degassed and purged with nitrogen, cooled to −78° C., and then treated with dropwise addition of n-butyllithium (2.50 M in hexanes, 3.6 mL, 9.01 mmol). After stirring at −78° C. for 30 min, trimethylborate (1.2 mL, 10.8 mmol) was added dropwise. After stirring for 16 h warming to RT, the reaction was quenched with 1M aqueous HCl (40 mL), and extracted into EtOAc (3×50 mL). The combined organic layer was washed with brine (40 mL), dried over MgSO4, filtered, and concentrated under reduced pressure to afford CB10 (2.76 g, quant.) as an off-white solid. m/z=299.9 [M+H]+, $^1$H NMR (400 MHz, CDCl3): δ 7.04 (s, 1H), 5.13-5.05 (m, 2H), 3.84 (s, 3H), 3.82-3.76 (m, 1H), 3.71-3.67 (m, 1H), 3.21 (q, J=5.1 Hz, 2H), 1.67-1.63 (m, 4H), 1.25 (s, 2H).

Method CB11—1-(2-(4-fluoro-3-(4,4,5,5-tetramethyl-1,3,2-dioxaborolan-2-yl)phenyl)pyrrolidin-1-yl)ethan-1-one (CB11)

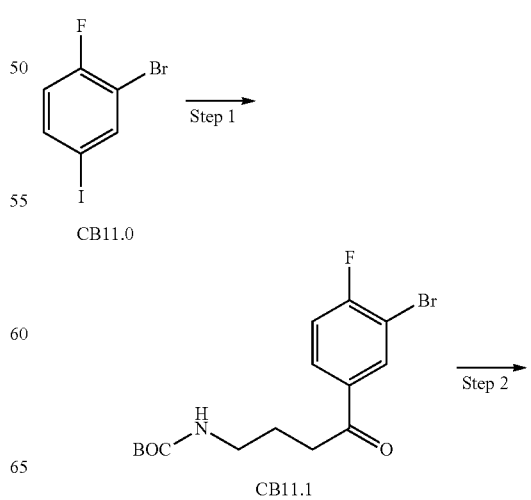

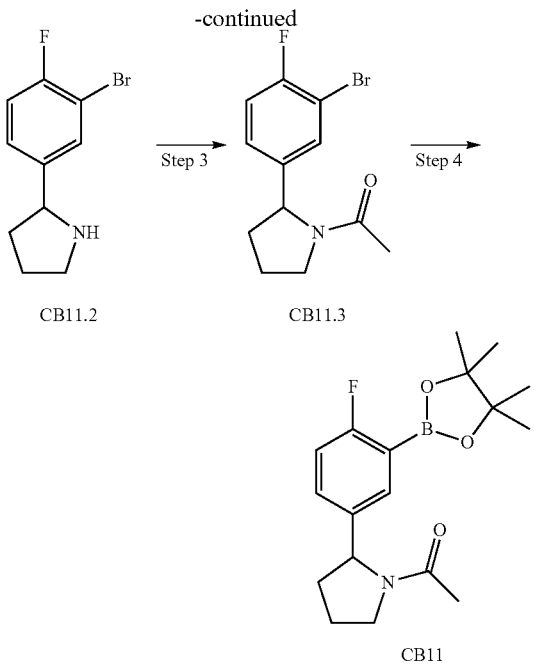

Step 1: tert-butyl (4-(3-bromo-4-fluorophenyl)-4-oxobutyl)carbamate (CB11.1)

A solution of 2-bromo-1-fluoro-4-iodobenzene (CB11.0) (3.00 g, 9.97 mmol) in THF (75 mL) was cooled to −40° C. and treated with dropwise addition of isopropylmagnesium chloride (2.0 M, 5.0 mL, 9.97 mmol). After stirring at −40° C. for 1 hr and then cooling to −78° C., tert-butyl 2-oxopyrrolidine-1-carboxylate (1.85 g, 9.97 mmol) was added. After warming to RT over 90 minutes, the reaction was quenched with saturated aqueous ammonium chloride and extracted into EtOAc. The organic layer was washed with brine, passed through a hydrophobic frit and concentrated under reduced pressure. The crude material was purified by silica gel chromatography using 0-60% EtOAc in cyclohexane to afford CB11.1 (1.50 g, 42%) as a tan oil, which solidified on standing. m/z=362.2 [M+H]+, $^1$H NMR (400 MHz, CDCl3): δ 8.18 (dd, J=1.8, 6.6 Hz, 1H), 7.94-7.89 (m, 1H), 7.19 (dd, J=8.3, 8.3 Hz, 1H), 4.70-4.59 (m, 1H), 3.26-3.22 (m, 2H), 2.98 (dd, J=7.1, 7.1 Hz, 2H), 1.99-1.88 (m, 2H), 1.27-1.14 (m, 9H).

Step 2: 2-(3-bromo-4-fluorophenyl)pyrrolidine (CB11.2)

To a solution of tert-butyl (4-(3-bromo-4-fluorophenyl)-4-oxobutyl)carbamate (CB11.1) (1.50 g, 4.16 mmol) in DCM (15 mL) was added trifluoroacetic acid (15 mL, 196 mmol). After stirring at RT for 30 min, the solvent was removed under reduced pressure. The crude residue was taken up in THF (30 mL) and treated with trimethylamine (0.70 mL, 5.00 mmol), followed by sodium triacetoxyborohydride (2.65 g, 12.5 mmol). After 2 h, sodium cyanoborohydride (392 mg, 6.24 mmol) was added. After stirring for 30 min, the reaction was quenched with saturated aqueous sodium bicarbonate, and extracted into EtOAc. The organic layer was separated, passed through a hydrophobic frit and concentrated under reduced pressure to afford CB11.2 as an oil, which was used in the subsequent step without further purification. m/z=246.1 [M+H]+.

Step 3: 1-(2-(3-bromo-4-fluorophenyl)pyrrolidin-1-yl)ethan-1-one (CB11.3)

To a solution of 2-(3-bromo-4-fluorophenyl)pyrrolidine (CB11.2) (510 mg, 2.0 mmol) in THF (20 mL) and triethylamine (350 mL, 2.5 mmol) was added acetyl chloride (220 mL, 3.1 mmol). After stirring at RT for 4 h, the reaction was quenched with saturated NaHCO$_3$ solution and extracted with ethyl acetate. The organic layer was washed with brine, dried (MgSO$_4$), filtered, and concentrated under reduced pressure. The crude residue was purified by silica gel chromatography using 0-60% ethyl acetate to afford CB11.3 (310 mg, 52%) as a colourless clear oil. $^1$H NMR (400 MHz, CDCl3) 7.38-7.28 (1H, m), 7.12-7.02 (2H, m), 5.14-4.86 (1H, m), 3.77-3.57 (2H, m), 2.46-2.21 (1H, m), 2.13 (3H, s), 2.01-1.85 (3H, m).

Step 4: 1-(2-(4-fluoro-3-(4,4,5,5-tetramethyl-1,3,2-dioxaborolan-2-yl)phenyl)pyrrolidin-1-yl)ethan-1-one (CB11)

The desired product was prepared following representative procedure outlined in Method CB3 using 1-(2-(3-bromo-4-fluorophenyl)pyrrolidin-1-yl)ethan-1-one (CB11.3) to give the crude product (CB11) as a red-brown oil which was used in the subsequent step without further purification.

Method CB12—6-(4-Fluoro-3-(4,4,5,5-tetramethyl-1,3,2-dioxaborolan-2-yl)benzyl)-2-oxa-6-azaspiro[3.3]heptane (CB12)

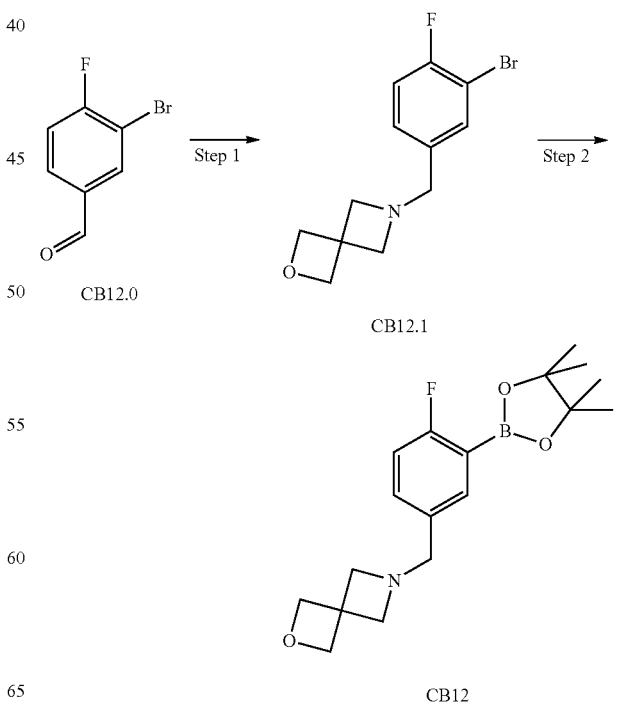

Step 1: 6-(3-bromo-4-fluorobenzyl)-2-oxa-6-azaspiro[3.3]heptane (CB12.1)

To a solution of 3-bromo-4-fluorobenzaldehyde (CB12.0) (250 mg, 1.23 mmol) in 2-propanol (10 mL) were added with 2-oxa-6-azaspiro[3.3]heptane (244 mg, 2.46 mmol) and titanium (IV) isopropoxide (0.53 mL, 1.79 mmol). After stirring at RT overnight, the reaction was then treated with sodium borohydride (47 mg, 1.23 mmol). After stirring at RT for 1 hr, the reaction was quenched with 6 M aqueous HCl, stirred at RT for 2 h and neutralize to pH~10 with 4 M aqueous NaOH. The reaction mixture was extracted into diethyl ether, and the organic layer was dried with MgSO4, filtered and concentrated under reduced pressure. The crude material was loaded onto an SCX cartridge and eluted with 10% (7N NH$_3$ in MeOH) in DCM to afford CB12.1 (234 mg, 66%) as a colourless oil. m/z=288.0 [M+H]+, $^1$H NMR (400 MHz, CDCl3): δ 7.48-7.43 (m, 1H), 7.16-7.11 (m, 1H), 7.05 (dd, J=8.3, 8.3 Hz, 1H), 4.74 (s, 4H), 3.47 (s, 2H), 3.35 (s, 4H).

Step 2: 6-(4-fluoro-3-(4,4,5,5-tetramethyl-1,3,2-dioxaborolan-2-yl)benzyl)-2-oxa-6-azaspiro[3.3]heptane (CB12)

To a degassed solution of 6-(3-bromo-4-fluorobenzyl)-2-oxa-6-azaspiro[3.3]heptane (CB12.1) (234 mg, 0.82 mmol) in 1,4-dioxane (5 mL) in a large carousel tube were added bis(pinacolato)diboron (311 mg, 1.23 mmol), potassium acetate (241 mg, 2.45 mmol) and [1,1'-bis(diphenylphosphino)ferrocene]dichloropalladium(II) (30 mg, 0.04 mmol). The reaction mixture was degassed and purged with nitrogen. After stirring the sealed tube at 115° C. for 3 h, the reaction mixture was allowed to cool to RT and the compound (CB12) was taken forwards to the next step without further purification.

Method CB13—1,1,1-Trifluoro-2-(4-fluoro-3-(4,4,5,5-tetramethyl-1,3,2-dioxaborolan-2-yl)phenyl)-N,N-dimethylpropan-2-amine (CB13)

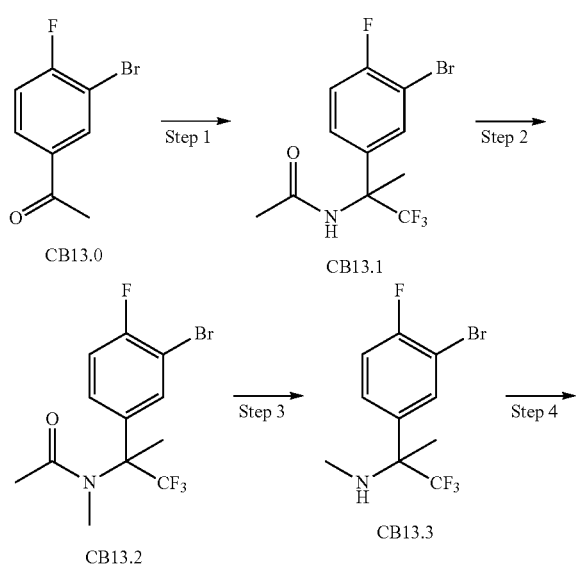

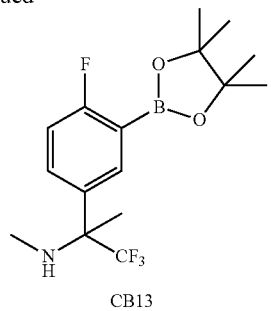

Step 1: N-(2-(3-bromo-4-fluorophenyl)-1,1,1-trifluoropropan-2-yl)acetamide (CB13.1)

A solution of 1-(3-bromo-4-fluorophenyl)ethan-1-one (CB13.0) (1.00 g, 4.61 mmol) in THF (15 mL) was placed under an atmosphere of nitrogen, then treated with trimethyl (trifluoromethyl)silane (0.82 mL, 5.53 mmol) and tetrabutylammonium fluoride (1 M in THF, 0.23 mL. 0.23 mmol). After stirring at RT for 24 h, the reaction mixture was then charged with further trimethyl(trifluoromethyl)silane (0.82 mL, 5.53 mmol). After stirring at RT for 2 h, the solvent was evaporated under reduced pressure, and the crude residue was taken up in acetonitrile (10 mL). The solution was treated with sulfuric acid (1.0 mL, 18.8 mmol) and heated to 80° C. for 24 h. The reaction mixture was cooled to RT, neutralised by dropwise addition of saturated aqueous sodium bicarbonate and extracted into DCM (3×20 mL). The combined organic layer was washed with brine (30 mL), passed through a hydrophobic frit and concentrated under reduced pressure. The crude material was purified by silica gel chromatography using 0-60% EtOAc in cyclohexane to afford CB13.1 (275 mg, 18%) as a white solid. m/z=329.9 [M+H]+, $^1$H NMR (400 MHz, CDCl3): δ 7.60 (d, J=4.8 Hz, 1H), 7.39-7.33 (m, 1H), 7.11 (dd, J=8.5, 8.5 Hz, 1H), 6.05 (s, 1H), 2.05 (d, J=19.7 Hz, 6H).

Step 2: N-(2-(3-bromo-4-fluorophenyl)-1,1,1-trifluoropropan-2-yl)-N-methylacetamide (CB13.2)

To a suspension of sodium hydride (60 wt % dispersion in mineral oil, 34 mg, 0.84 mmol) in DMF (3 mL) was added N-(2-(3-bromo-4-fluorophenyl)-1,1,1-trifluoropropan-2-yl) acetamide (CB13.1) (250 mg, 0.76 mmol). After stirring at RT for 2 h, iodomethane (0.05 mL, 0.84 mmol) was added. After heating at 85° C. for 16 h, the reaction was cooled to RT and quenched with 4% aqueous lithium chloride (10 mL). The mixture was extracted in DCM (3×15 mL), and the combined organic layer was washed with brine (20 mL), passed through a hydrophobic frit, and concentrated under reduced pressure. The crude material was purified by silica gel chromatography using 0-60% EtOAc in cyclohexane to afford CB13.2 (120 mg, 46%) as a colourless oil. m/z=343.9 [M+H]+, $^1$H NMR (400 MHz, CDCl3): δ 7.50 (d, J=5.1 Hz, 1H), 7.08 (dd, J=8.3, 8.3 Hz, 2H), 3.16 (s, 3H), 2.10 (s, 3H), 1.54 (s, 3H).

Step 3: 2-(3-bromo-4-fluorophenyl)-1,1,1-trifluoro-N-methylpropan-2-amine (CB13.3)

A solution of N-(2-(3-bromo-4-fluorophenyl)-1,1,1-trifluoropropan-2-yl)-N-methylacetamide (CB13.2) (115 mg, 0.34 mmol) in ethanol (2 mL) and water (0.2 mL) was treated with aqueous hydrochloric acid (11 M, 0.15 mL, 1.68 mmol). After stirring at 100° C. for 4 days, the reaction was cooled to RT and the solvent was removed under reduced pressure to afford CB13.3 (89 mg, 88%) as a white solid, which was used in the subsequent step without further purification. m/z=302.0 [M+H]+.

Step 4: 1,1,1-trifluoro-2-(4-fluoro-3-(4,4,5,5-tetramethyl-1,3,2-dioxaborolan-2-yl)phenyl)-N-methylpropan-2-amine (CB13)

A mixture of 2-(3-bromo-4-fluorophenyl)-1,1,1-trifluoro-N-methylpropan-2-amine (CB13.3) (89 mg, 0.30 mmol), bis(pinacolato)diboron (90 mg, 0.36 mmol), [1,1'-bis(diphenylphosphino)ferrocene]dichloropalladium(II) complex with DCM (12 mg, 0.01 mmol) and potassium acetate (87 mg, 0.89 mmol) in 1,4-dioxane (4 mL) was degassed and purged with nitrogen. After stirring at 100° C. for 2.5 h, the reaction was cooled to RT, filtered through a Celite® pad (2.5 g), and eluted with DCM. The filtrate was concentrated under reduced pressure to afford crude CB13, which was used in the subsequent step without further purification.

Method CB14—(2-Cyclopropyl-5-fluoro-4-(4,4,5,5-tetramethyl-1,3,2-dioxaborolan-2-yl)phenyl)(piperidin-1-yl)methanone (CB14)

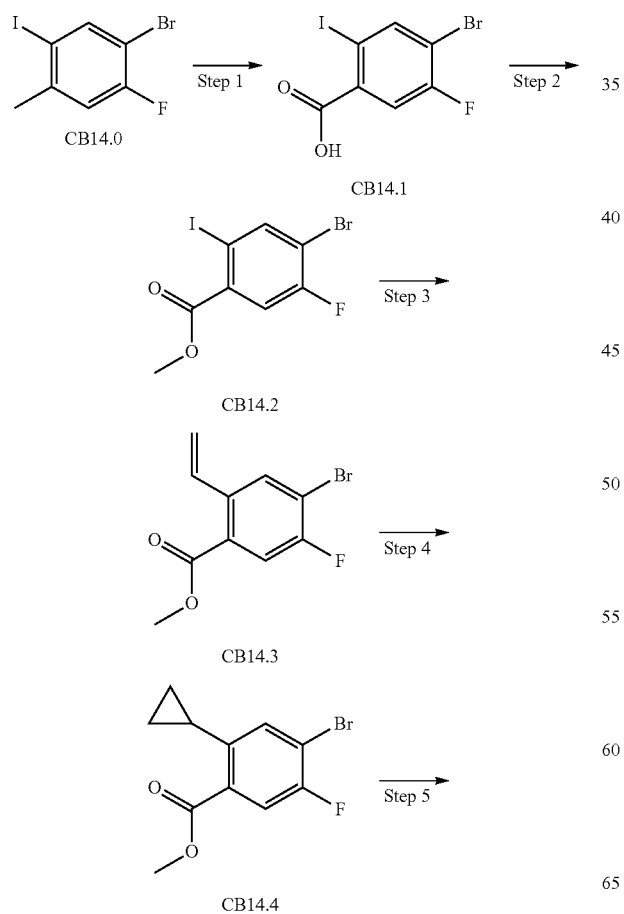

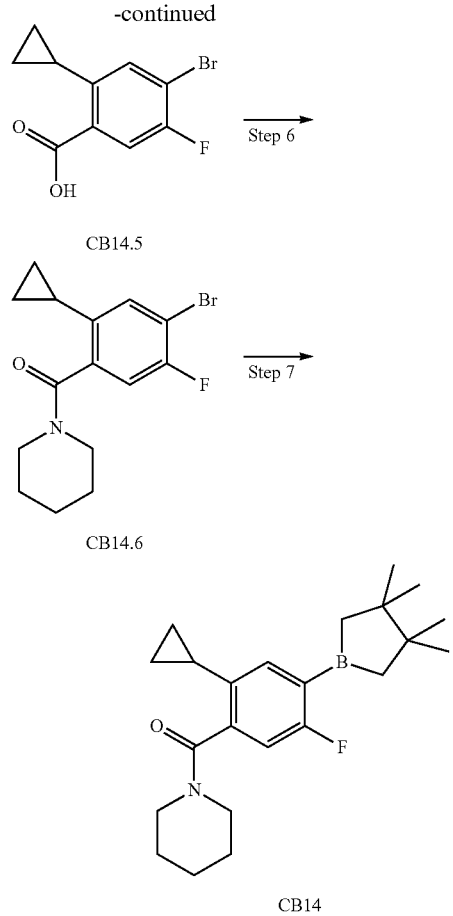

Step 1: 4-bromo-5-fluoro-2-iodobenzoic acid (CB14.1)

Potassium permanganate (5.02 g, 31.8 mmol) was added to a solution of 4-bromo-5-fluoro-2-iodotoluene (CB14.0) (1.00 g, 3.18 mmol) in water (12 mL) and pyridine (8 mL). After stirring at 100° C. overnight, the reaction was allowed to reach RT, filtered onto a Celite pad and washed with water (20 mL). The aqueous layer was washed with EtOAc (2×15 mL) then acidified with HCl 2N until pH~1. The cloudy suspension was extracted with EtOAc (2×15 mL. The combined organic extracts were washed with water (20 mL) and brine (20 mL), dried over MgSO4, filtered and concentrated under reduced pressure. The desired product (CB14.1) was isolated as a white solid and used for next step without further purification (520 mg, 47%). m/z=344.9 [M+H]+, $^1$H NMR (400 MHz, DMSO): δ 12.6 (s, 1H), 8.37 (d, J=6.8 Hz, 1H), 7.76 (d, J=9.3 Hz, 1H).

Step 2: methyl 4-bromo-5-fluoro-2-iodobenzoate (CB14.2)

Sulfuric acid (0.04 mL, 0.754 mmol) was added to a solution of (CB14.1) (0.52 gr, 1.51 mmol) in MeOH (0.8 mL). After stirring at 65° C. overnight, the reaction was quenched with saturated aqueous NaHCO₃ (10 mL) and extracted with EtOAc (3×8 mL). The organic solvent was evaporated under reduced pressure to yield the desired compound (CB14.2) as a crystal solid (420 mg, 78%).

m/z=358.9 [M+H]+, ¹H NMR (400 MHz, CDCl3): δ 8.20 (d, J=6.6 Hz, 1H), 7.62 (d, J=8.8 Hz, 1H), 3.90 (s, 3H).

Step 3: methyl 4-bromo-5-fluoro-2-vinylbenzoate (CB14.3)

A degassed solution of (CB14.2) (500 mg, 1.39 mmol), potassium vinyltrifluoroborate (220 mg, 1.16 mmol), cesium carbonate (910 mg, 2.79 mmol) and [1,1'-bis(diphenylphosphino)ferrocene]dichloropalladium(II) (100 mg, 0.14 mmol) in 1,4-dioxane (20 mL) and water (2 mL) was stirred at 100° C. overnight. After cooling to RT, the reaction mixture was filtered through a Celite pad and solvent evaporated. The crude was purified by silica gel chromatography eluting with 0-60% EtOAc in cyclohexane to afford the title compound (CB14.3) (200 mg, 56%) as a clear solid. m/z=259.1 [M+H]+, ¹H NMR (400 MHz, CDCl3): δ 7.76 (d, J=6.6 Hz, 1H), 7.65 (d, J=9.1 Hz, 1H), 7.39 (d, J=6.6 Hz, 1H), 5.60 (d, J=17.4 Hz, 1H), 5.38 (d, J=11.1 Hz, 1H), 3.90 (s, 3H).

Step 4: methyl 4-bromo-2-cyclopropyl-5-fluorobenzoate (CB14.4)

A degassed solution of diethylzinc (1.5 mL, 1.54 mmol) in dry DCM (2 mL) at 0° C. was treated with a degassed solution of TFA (0.12 mL, 1.54 mmol) in dry DCM (1 mL). After stirring at 0° C. for 20 mins, diiodomethane (0.12 mL, 1.54 mmol) in dry DCM (2 mL) was added. After stirring at 0° C. for 20 mins, a solution of (CB14.3) (200 mg, 0.777 mmol) in dry DCM (1 mL) was added. After stirring at rt for 120 mins, the reaction was quenched with NH₄Cl (5 mL). The organic phase was collected, concentrated and purified on silica gel (eluting 0-70% EtOAc in cyclohexane) to afford the title compound (CB14.4) (200 mg, 95%) as a clear solid. m/z=273.1 [M+H]+, ¹H NMR (400 MHz, CDCl3): δ 7.56 (d, J=8.8 Hz, 1H), 7.20 (d, J=6.6 Hz, 1H), 3.91 (s, 3H), 2.65-2.53 (m, 1H), 1.04-0.95 (m, 2H), 0.64 (q, J=5.4 Hz, 2H).

Step 5: 4-bromo-2-cyclopropyl-5-fluorobenzoic acid (CB14.5)

To a solution of (CB14.4) (200 mg, 0.732 mmol) in dry THF (10 mL) was added LiOH (2M in water, 0.81 mL, 1.61 mmol). After stirring at rt overnight, the resulting precipitate was collected and used for next step without further purification. m/z=259.1 [M+H]+.

Step 6: (4-bromo-2-cyclopropyl-5-fluorophenyl)(piperidin-1-yl)methanone (CB14.6)

To a stirred solution of (CB14.5) (120 mg, 0.463 mmol) in dry THF (5 mL) were added 1-hydroxybenzotriazole (81 mg, 0.60 mmol), N-(3-dimethylaminopropyl)-N'-ethylcarbodiimide hydrochloride (115 mg, 0.60 mmol). After stirring at rt for 1 h, DIPEA (0.24 mL, 1.39 mmol) and piperidine (0.05 mL, 0.55 mmol) were added. After stirring at rt for 3 h, the solvent was removed under reduced pressure. The crude residue was purified by silica gel chromatography eluting 0-60% EtOAc in cyclohexane to afford the title compound (CB14.6) (74 mg, 49%) as a clear oil. m/z=326.2 [M+H]+, ¹H NMR (400 MHz, CDCl3): δ 7.06 (d, J=6.3 Hz, 1H), 6.93 (d, J=8.1 Hz, 1H), 3.79-3.61 (m, 2H), 3.20 (dd, J=5.4, 5.4 Hz, 2H), 1.92-1.79 (m, 1H), 1.67 (t, J=11.6 Hz, 4H), 1.50 (d, J=4.3 Hz, 4H), 1.01-0.75 (m, 2H).

Step 7: (2-cyclopropyl-5-fluoro-4-(4,4,5,5-tetramethyl-1,3,2-dioxaborolan-2-yl)phenyl)(piperidin-1-yl)methanone (CB14)

To a mixture of (CB 14.6) (74 mg, 0.23 mmol), Bis(pinacolato)diboron (69 mg, 0.27 mmol) and potassium acetate (67 mg, 0.68 mmol) in 1,4-dioxane (4 mL) under an atmosphere of N₂ was added [1,1'-bis(diphenylphosphino)ferrocene]dichloropalladium(II) complex with DCM (9.3 mg, 0.01 mmol). After stirring at 100° C. for 3.5 h, the reaction was cooled to RT, filtered through Celite and extracted with DCM (2×10 mL). The combined organic layer was concentrated in vacuo to afford product (CB 14) which was used for the next step without further purification (81 mg, 95%), m/z=373.2 [M+H]+.

The following boronate intermediates were prepared according to any of Intermediate Methods CB 1-CB 14 as described above.

| Intermediate CB | Structure | Representative Synthetic Method |
|---|---|---|
| CB15 | 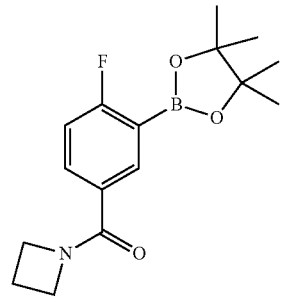 [SMILES: CC1(C)OB(c2cc(C(=O)N3CCC3)ccc2F)OC1(C)C] | Method CB1 using 4-fluoro-3-(4,4,5,5-tetramethyl-1,3,2-dioxaborolan-2-yl)benzoic acid and azetidine (Step 2) |

-continued

| Intermediate CB | Structure | Representative Synthetic Method |
|---|---|---|
| CB16 | 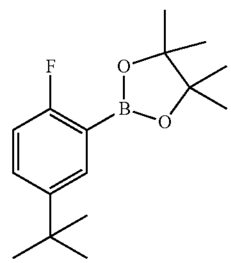 [SMILES: CC(C)(C)c1ccc(F)c(B2OC(C)(C)C(C)(C)O2)c1] | Method CB3 using 2-bromo-4-(tert-butyl)-1-fluorobenzene |
| CB17 | 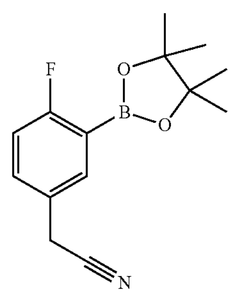 [SMILES: CC1(C)OB(c2cc(CC#N)ccc2F)OC1(C)C] | Method CB3 using 2-(3-bromo-4-fluorophenyl)acetonitrile |
| CB18 | 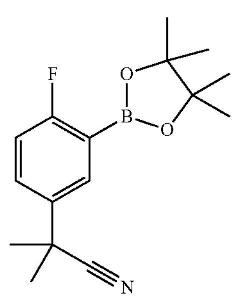 [SMILES: CC(C)(C#N)c1ccc(F)c(B2OC(C)(C)C(C)(C)O2)c1] | Method CB3 using 2-(3-bromo-4-fluorophenyl)-2-methylpropanenitrile |
| CB19 | 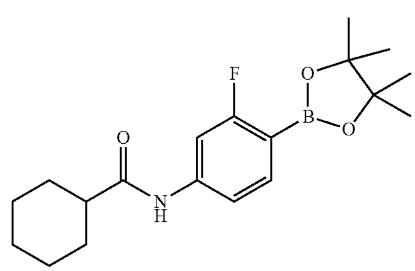 [SMILES: CC1(C)OB(c2ccc(NC(=O)C3CCCCC3)cc2F)OC1(C)C] | Method CB2 using 3-fluoro-4-(4,4,5,5-tetramethyl-1,3,2-dioxaborolan-2-yl)aniline and cyclohexanecarbonyl chloride (Step 1) |
| CB20 | 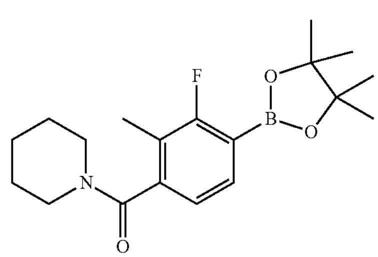 [SMILES: Cc1c(C(=O)N2CCCCC2)ccc(B2OC(C)(C)C(C)(C)O2)c1F] | Method CB14 using 4-bromo-3-fluoro-2-methylbenzoic acid and piperidine (Step 6 and 7) |

| Intermediate CB | Structure | Representative Synthetic Method |
|---|---|---|
| CB21 | 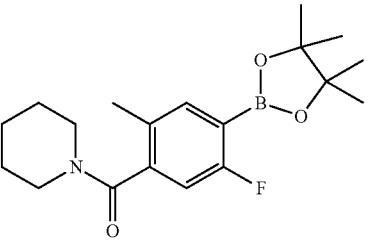 [SMILES: Cc1cc(B2OC(C)(C)C(C)(C)O2)c(F)cc1C(=O)N1CCCCC1] | Method CB14 using 4-bromo-5-fluoro-2-methylbenzoic acid and piperidine (Step 6 and 7) |
| CB22 | 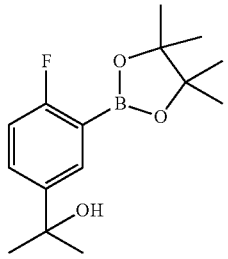 [SMILES: CC(C)(O)c1ccc(F)c(B2OC(C)(C)C(C)(C)O2)c1] | Method CB3 using 2-(3-bromo-4-fluorophenyl)propan-2-ol |
| CB23 | 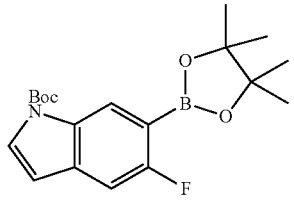 [SMILES: CC(C)(C)OC(=O)n1ccc2cc(F)c(B3OC(C)(C)C(C)(C)O3)cc21] | Method CB3 using tert-butyl 6-bromo-5-fluoro-1H-indole-1-carboxylate |
| CB24 | 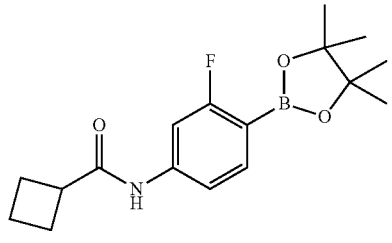 [SMILES: CC1(C)OB(c2ccc(NC(=O)C3CCC3)cc2F)OC1(C)C] | Method CB2 using 3-fluoro-4-(4,4,5,5-tetramethyl-1,3,2-dioxaborolan-2-yl)aniline and cyclobutanecarbonyl chloride (Step 1) |
| CB25 | 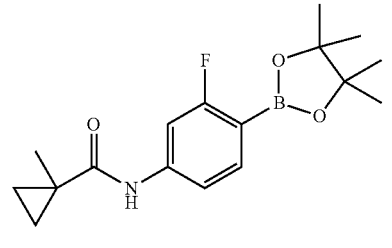 [SMILES: CC1(C(=O)Nc2ccc(B3OC(C)(C)C(C)(C)O3)c(F)c2)CC1] | Method CB2 using 3-fluoro-4-(4,4,5,5-tetramethyl-1,3,2-dioxaborolan-2-yl)aniline and 1-methylcyclopropane-1-carbonyl chloride (Step 1) |
| CB26 | 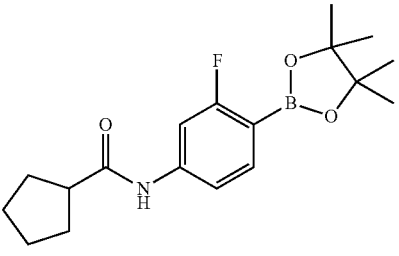 [SMILES: CC1(C)OB(c2ccc(NC(=O)C3CCCC3)cc2F)OC1(C)C] | Method CB2 using 3-fluoro-4-(4,4,5,5-tetramethyl-1,3,2-dioxaborolan-2-yl)aniline and cyclopentanecarbonyl chloride (Step 1) |

-continued

| Intermediate CB | Structure | Representative Synthetic Method |
|---|---|---|
| CB27 | 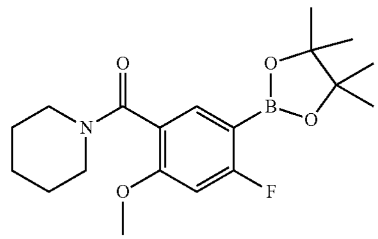 [SMILES: COc1cc(F)c(B2OC(C)(C)C(C)(C)O2)cc1C(=O)N1CCCCC1] | Method CB14 using 5-bromo-4-fluoro-2-methoxybenzoic acid and piperidine (Step 6 and 7) |
| CB28 | 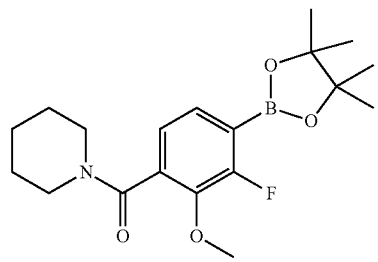 [SMILES: COc1c(C(=O)N2CCCCC2)ccc(B2OC(C)(C)C(C)(C)O2)c1F] | Method CB14 using 4-bromo-3-fluoro-2-methoxybenzoic acid and piperidine (Step 6 and 7) |
| CB29 | 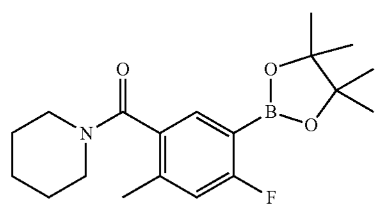 [SMILES: Cc1cc(F)c(B2OC(C)(C)C(C)(C)O2)cc1C(=O)N1CCCCC1] | Method CB14 using 5-bromo-4-fluoro-2-methylbenzoic acid and piperidine (Step 6 and 7) |
| CB30 | 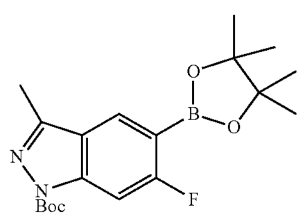 [SMILES: Cc1nn(C(=O)OC(C)(C)C)c2cc(F)c(B3OC(C)(C)C(C)(C)O3)cc12] | Method CB3 using tert-butyl 5-bromo-6-fluoro-3-methyl-1H-indazole-1-carboxylate |
| CB31 | 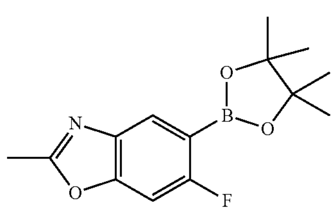 | Method CB3 using 5-bromo-6-fluoro-2-methylbenzo[d]oxazole |
| CB32 | 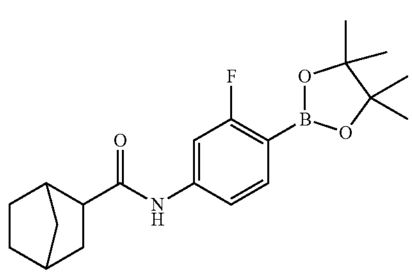 [SMILES: CC1(C)OB(c2ccc(NC(=O)C3CC4CCC3C4)cc2F)OC1(C)C] | Method CB2 using 3-fluoro-4-(4,4,5,5-tetramethyl-1,3,2-dioxaborolan-2-yl)aniline and bicyclo[2.2.1]heptane-2-carbonyl chloride |

-continued

| Intermediate CB | Structure | Representative Synthetic Method |
|---|---|---|
| CB33 | 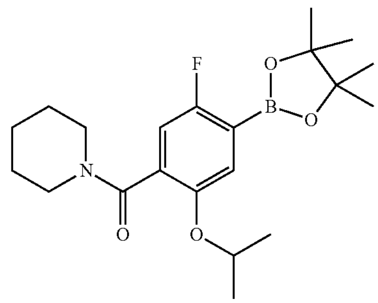 [SMILES: CC(C)Oc1cc(B2OC(C)(C)C(C)(C)O2)c(F)cc1C(=O)N1CCCCC1] | Method CB9 using 2-iodopropane |
| CB34 | 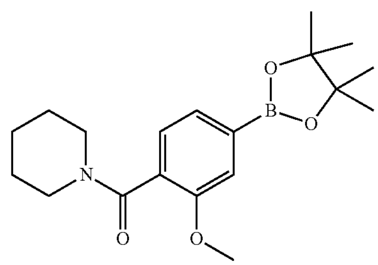 [SMILES: COc1cc(B2OC(C)(C)C(C)(C)O2)ccc1C(=O)N1CCCCC1] | Method CB1 using methyl 2-methoxy-4-(4,4,5,5-tetramethyl-1,3,2-dioxaborolan-2-yl)benzoate and piperidine (Step 2) |
| CB35 | 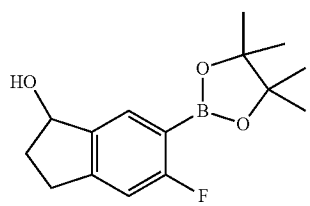 [SMILES: CC1(C)OB(c2cc3c(cc2F)CCC3O)OC1(C)C] | Method CB3 using CB4.1 |
| CB36 | 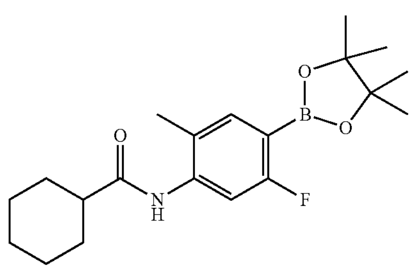 [SMILES: Cc1cc(B2OC(C)(C)C(C)(C)O2)c(F)cc1NC(=O)C1CCCCC1] | Method CB2 using 5-fluoro-2-methyl-4-(4,4,5,5-tetramethyl-1,3,2-dioxaborolan-2-yl)aniline and cyclohexanecarbonyl chloride (Step 1) |
| CB37 | 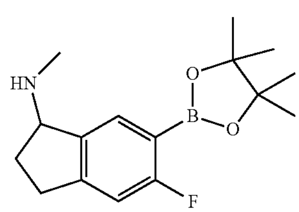 [SMILES: CNC1CCc2cc(F)c(B3OC(C)(C)C(C)(C)O3)cc21] | Method CB4 using methylamine (Step 2) |
| CB38 | 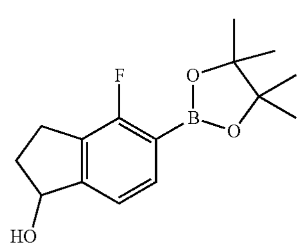 [SMILES: CC1(C)OB(c2ccc3c(c2F)CCC3O)OC1(C)C] | Method CB3 using 5-bromo-4-fluoro-2,3-dihydro-1H-inden-1-ol |

-continued

| Intermediate CB | Structure | Representative Synthetic Method |
|---|---|---|
| CB39 | 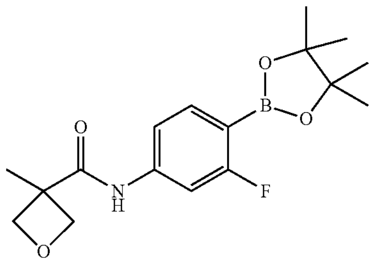 | Method CB2 using 3-fluoro-4-(4,4,5,5-tetramethyl-1,3,2-dioxaborolan-2-yl)aniline and 3-methyloxetane-3-carbonyl chloride (Step 1) |
| CB40 | 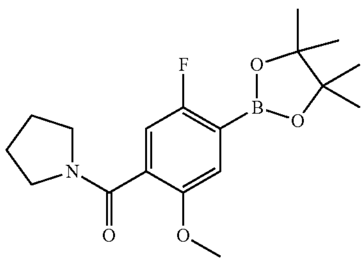 [SMILES: COc1cc(B2OC(C)(C)C(C)(C)O2)c(F)cc1C(=O)N1CCCC1] | Method CB1 using methyl 5-fluoro-2-methoxy-4-(4,4,5,5-tetramethyl-1,3,2-dioxaborolan-2-yl)benzoate and pyrrolidine |
| CB41 | 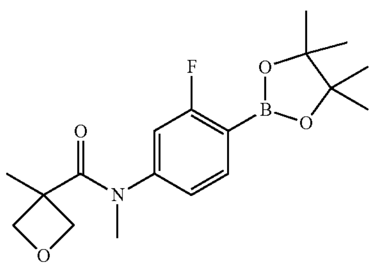 | Method CB2 using 3-fluoro-4-(4,4,5,5-tetramethyl-1,3,2-dioxaborolan-2-yl)aniline and 3-methyloxetane-3-carbonyl chloride (Step 1) |
| CB42 | 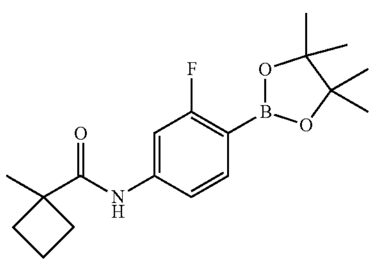 | Method CB2 using 3-fluoro-4-(4,4,5,5-tetramethyl-1,3,2-dioxaborolan-2-yl)aniline and 1-methylcyclobutane-1-carbonyl chloride (Step 1) |
| CB43 | 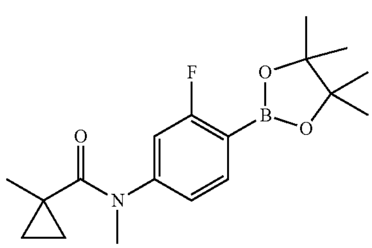 | Method CB2 using 3-fluoro-4-(4,4,5,5-tetramethyl-1,3,2-dioxaborolan-2-yl)aniline and 1-methylcyclopropane-1-carbonyl chloride (Step 1) |
| CB44 | 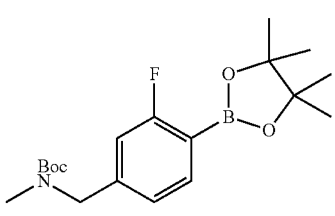 | Method CB3 using tert-butyl (4-bromo-3-fluorobenzyl)(methyl)carbamate |

| Intermediate CB | Structure | Representative Synthetic Method |
|---|---|---|
| CB45 | 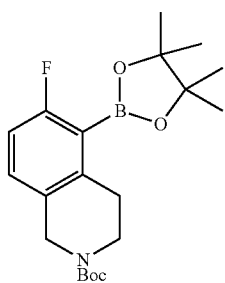 [SMILES: CC(C)(C)OC(=O)N1CCc2c(ccc(F)c2B2OC(C)(C)C(C)(C)O2)C1] | Method CB3 using tert-butyl 5-bromo-6-fluoro-3,4-dihydroisoquinoline-2(1H)-carboxylate |
| CB46 | 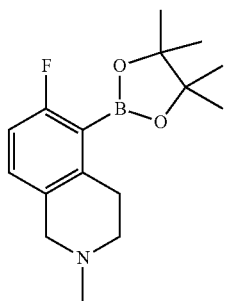 [SMILES: CN1CCc2c(ccc(F)c2B2OC(C)(C)C(C)(C)O2)C1] | Method CB3 using 5-bromo-6-fluoro-2-methyl-1,2,3,4-tetrahydroisoquinoline |
| CB47 | 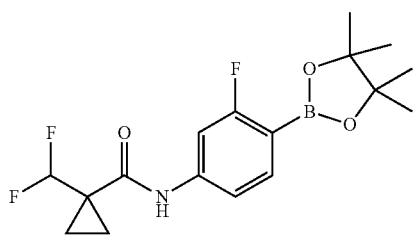 [SMILES: CC1(C)OB(c2ccc(NC(=O)C3(C(F)F)CC3)cc2F)OC1(C)C] | Method CB2 using 3-fluoro-4-(4,4,5,5-tetramethyl-1,3,2-dioxaborolan-2-yl)aniline and 1-(difluoromethyl)cyclopropane-1-carbonyl chloride |
| CB48 | 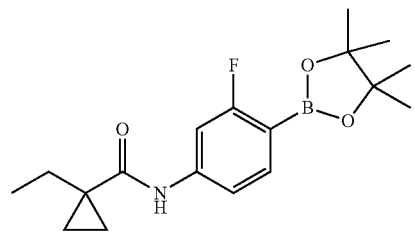 [SMILES: CCC1(C(=O)Nc2ccc(B3OC(C)(C)C(C)(C)O3)c(F)c2)CC1] | Method CB2 using 3-fluoro-4-(4,4,5,5-tetramethyl-1,3,2-dioxaborolan-2-yl)aniline and 1-ethylcyclopropane-1-carbonyl chloride |
| CB49 | 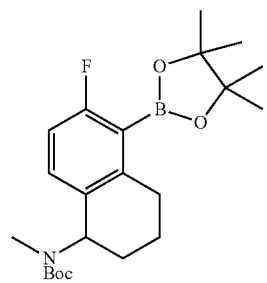 | Method CB3 using tert-butyl (5-bromo-6-fluoro-1,2,3,4-tetrahydronaphthalen-1-yl)(methyl)carbamate |

-continued

| Intermediate CB | Structure | Representative Synthetic Method |
|---|---|---|
| CB50 | 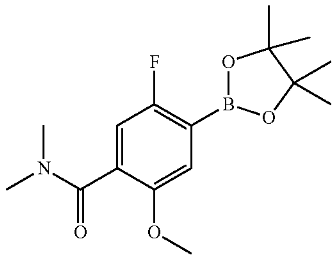 | Method CB1 using methyl 5-fluoro-2-methoxy-4-(4,4,5,5-tetramethyl-1,3,2-dioxaborolan-2-yl)benzoate and dimethylamine |
| CB51 | 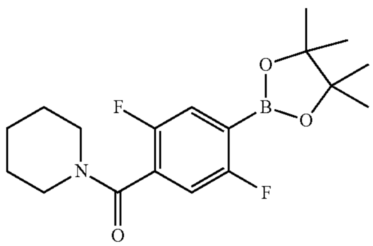 | Method CB14 using 4-bromo-2,5-difluorobenzoic acid and piperidine (Step 6 and 7) |
| CB52 | 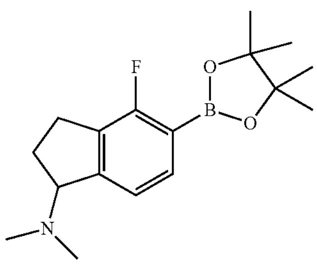 | Method CB4 using 5-bromo-4-fluoro-2,3-dihydro-1H-inden-1-ol |
| CB53 | 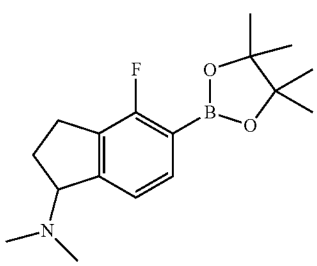 | Method CB4 using 5-bromo-6-fluoro-2,3-dihydro-1H-inden-1-ol |
| CB54 | 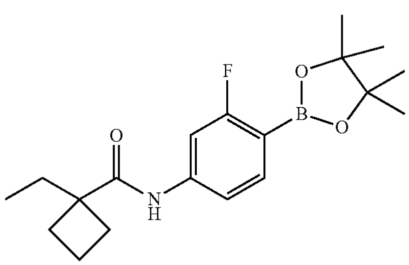 [SMILES: CCC1(C(=O)Nc2ccc(B3OC(C)(C)C(C)(C)O3)c(F)c2)CCC1] | Method CB2 using 3-fluoro-4-(4,4,5,5-tetramethyl-1,3,2-dioxaborolan-2-yl)aniline and 1-ethylcyclobutane-1-carbonyl chloride |
| CB55 | 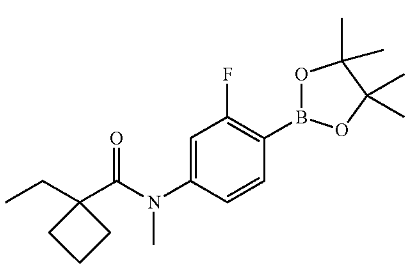 [SMILES: CCC1(C(=O)N(C)c2ccc(B3OC(C)(C)C(C)(C)O3)c(F)c2)CCC1] | Method CB2 using 3-fluoro-4-(4,4,5,5-tetramethyl-1,3,2-dioxaborolan-2-yl)aniline and 1-ethylcyclobutane-1-carbonyl chloride |

-continued
| Intermediate CB | Structure | Representative Synthetic Method |
|---|---|---|
| CB56 | 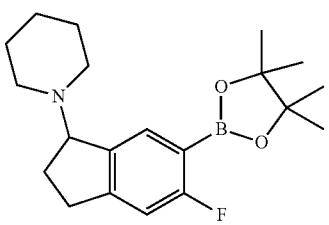 [SMILES: CC1(C)OB(c2cc3c(cc2F)CCC3N2CCCCC2)OC1(C)C] | Method CB4 using piperidine (Step 2) |
| CB57 | 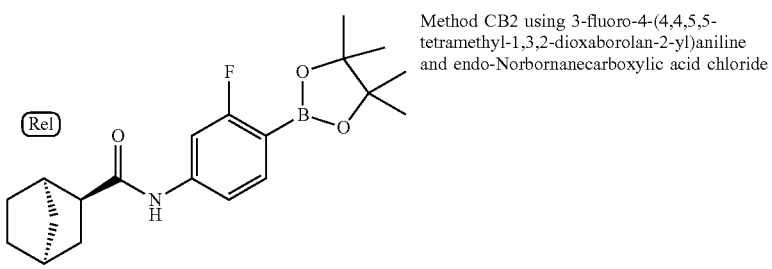 | Method CB2 using 3-fluoro-4-(4,4,5,5-tetramethyl-1,3,2-dioxaborolan-2-yl)aniline and endo-Norbornanecarboxylic acid chloride |
| CB58 | 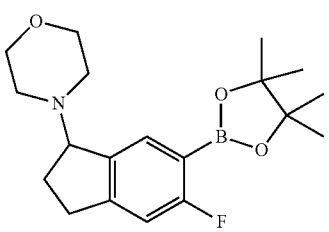 [SMILES: CC1(C)OB(c2cc3c(cc2F)CCC3N2CCOCC2)OC1(C)C] | Method CB4 using morpholine (Step 2) |
| CB59 | 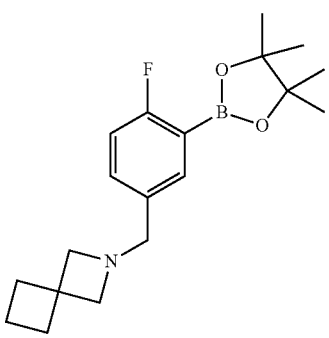 [SMILES: CC1(C)OB(c2cc(CN3CC4(CCC4)C3)ccc2F)OC1(C)C] | Method CB12 using 2-azaspiro[3.3]heptane (Step 1) |
| CB60 | 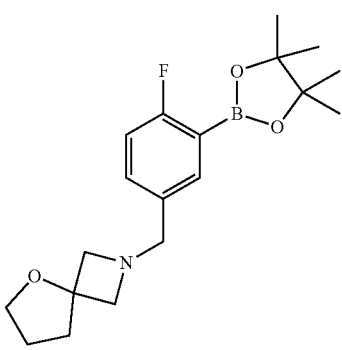 [SMILES: CC1(C)OB(c2cc(CN3CC4(CCCO4)C3)ccc2F)OC1(C)C] | Method CB12 using 5-oxa-2-azaspiro[3.4]octane (Step 1) |

| Intermediate CB | Structure | Representative Synthetic Method |
|---|---|---|
| CB61 | 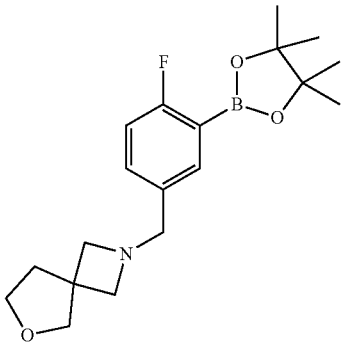 [SMILES: CC1(C)OB(c2cc(CN3CC4(CCOC4)C3)ccc2F)OC1(C)C] | Method CB12 using 6-oxa-2-azaspiro[3.4]octane (Step 1) |
| CB62 | 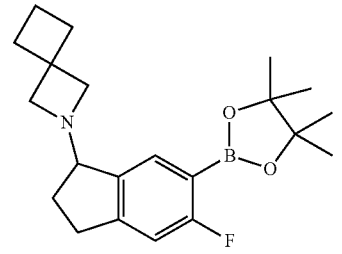 [SMILES: CC1(C)OB(c2cc3c(cc2F)CCC3N2CC3(CCC3)C2)OC1(C)C] | Method CB4 using 2-azaspiro[3.3]heptane (Step 2) |
| CB63 | 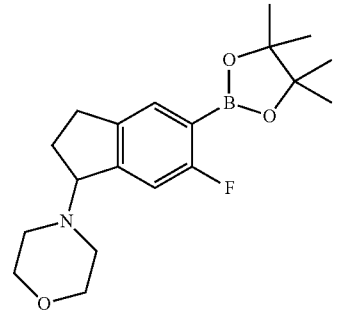 [SMILES: CC1(C)OB(c2cc3c(cc2F)C(N2CCOCC2)CC3)OC1(C)C] | Method CB4 using 5-bromo-6-fluoro-2,3-dihydro-1H-inden-1-ol and morpholine (Step 2) |
| CB64 | 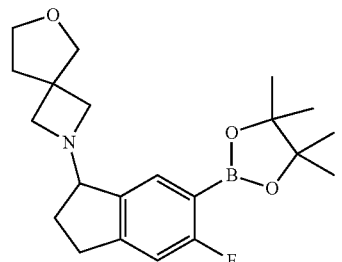 | Method CB4 using 6-oxa-2-azaspiro[3.4]octane (Step 2) |
| CB65 | 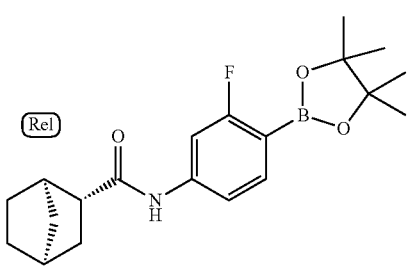 [SMILES: CC1(C)OB(c2ccc(NC(=O)[C@@H]3C[C@H]4CC[C@@H]3C4)cc2F)OC1(C)C] | Method CB2 using 3-fluoro-4-(4,4,5,5-tetramethyl-1,3,2-dioxaborolan-2-yl)aniline and exo-Norbornanecarboxylic acid chloride |

-continued

| Intermediate CB | Structure | Representative Synthetic Method |
|---|---|---|
| CB66 | 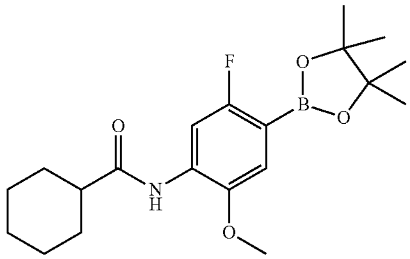 [SMILES: COc1cc(B2OC(C)(C)C(C)(C)O2)c(F)cc1NC(=O)C1CCCCC1] | Method CB2 using 5-fluoro-2-methoxy-4-(4,4,5,5-tetramethyl-1,3,2-dioxaborolan-2-yl)aniline cyclohexanecarbonyl chloride (Step 1) |
| CB67 | 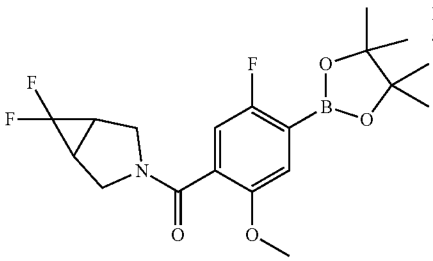 | Method CB1 using 6,6-difluoro-3-azabicyclo[3.1.0]hexane (Step 2) |
| CB68 | 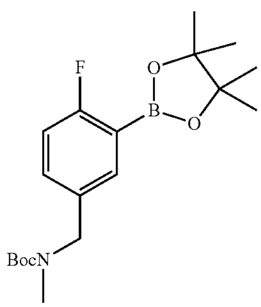 [SMILES: CN(Cc1ccc(F)c(B2OC(C)(C)C(C)(C)O2)c1)C(=O)OC(C)(C)C] | Method CB12 using methylamine (Step 1) |
| CB69 | 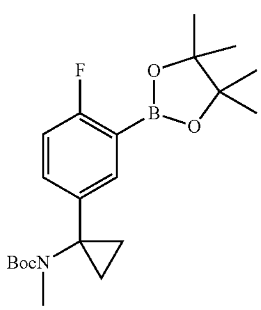 [SMILES: CN(C(=O)OC(C)(C)C)C1(c2ccc(F)c(B3OC(C)(C)C(C)(C)O3)c2)CC1] | Method CB3 using tert-butyl (1-(3-bromo-4-fluorophenyl)cyclopropyl)(methyl)carbamate |
| CB70 | 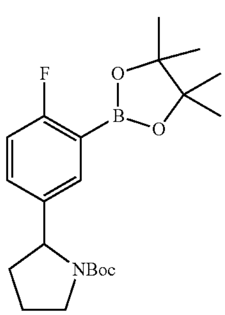 [SMILES: CC(C)(C)OC(=O)N1CCCC1c1ccc(F)c(B2OC(C)(C)C(C)(C)O2)c1] | Method CB3 using tert-butyl 2-(3-bromo-4-fluorophenyl)pyrrolidine-1-carboxylate |

Method PB1—Preparation of N-(3-fluoro-4-(4,4,5,5-tetramethyl-1,3,2-dioxaborolan-2-yl)phenyl)cyclohexanecarboxamide (PB1)

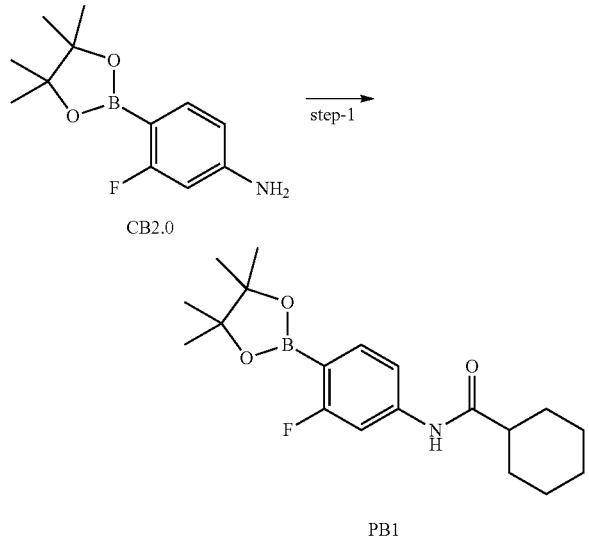

Step 1. of N-(3-fluoro-4-(4,4,5,5-tetramethyl-1,3,2-dioxaborolan-2-yl)phenyl)cyclohexanecarboxamide (PB1)

To a solution of 3-fluoro-4-(4,4,5,5-tetramethyl-1,3,2-dioxaborolan-2-yl)aniline (CB2.0) (10 g, 0.0421 mol, 1.0 eq) in DCM (60 mL) and diisopropyl ethyl amine (15 ml) was added cyclohexanecarbonyl chloride (509 ml, 0.08435 mol, 2.0 eq). After stirring at RT for 16 h, the reaction mixture was diluted with DCM (500 ml), and washed with saturated sodiumbicarbonate (300 ml) and then water (300 ml). The combined organic layer was washed with brine (100 ml), dried over sodium sulphate and concentrated under reduced pressure to afford crude material was purified by trituration using diethyl ether (2×30 ml) to afford title compound PB1 (12.5 g, 85.35%). MS (ES): m/z 348.2 [M+H]$^+$.

Method PB2—Preparation of 4-(3-(4,4,5,5-tetramethyl-1,3,2-dioxaborolan-2-yl)phenyl)morpholin-3-one (PB2)

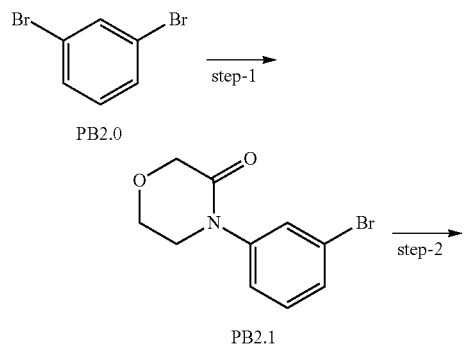

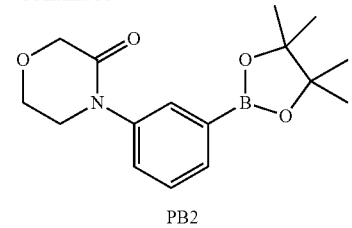

Step 1. 4-(3-bromophenyl)morpholin-3-one (PB2.1)

To a solution of morpholin-3-one (1 g, 9.90 mmol, 1.0 eq) in 1,4-dioxane (100 mL), 1,3-dibromobenzene PB2.0 (2.6 g, 11.4 mmol, 1.1 eq) was added at room temperature. The reaction mixture was degassed for 10 min under argon atmosphere followed by addition of Cesium carbonate (6.2 g, 19.8 mmol, 2.0 eq), (palladium acetate) Pd(OAc)$_2$ (0.21 g, 0.99 mmol, 0.1 eq) and 4,5-Bis(diphenylphosphino)-9,9-dimethylxanthene (xanthphos) (0.8 g, 7.5 mmol, 0.1 eq). The reaction mixture was heated at 100° C. for 16 h in three parallel reaction. After completion of reaction, reaction mixture was cooled to room temperature, combined, filtered, and concentrated under reduced pressure. The crude product was passed through flash chromatography eluting with 0-30% Ethylacetate in Hexane. The solvent was evaporated under reduced pressure to afford the desired product (PB2.1) (3.0 g, 39.48%). MS (ES): m/z 258.1 [M+2H]$^+$

Step 2. 6-4-(3-(4,4,5,5-tetramethyl-1,3,2-dioxaborolan-2-yl)phenyl)morpholin-3-one (PB2)

To a solution of 4-(3-bromophenyl)morpholin-3-one (PB2.1) (3.0 g, 11.7 mmol, 1.0 eq) in 1,4-dioxane (30 mL) was added bis(pinacolato)diborane (3.5 g, 14.0 mmol, 1.2 eq). The reaction mixture was degassed for 10 min under argon atmosphere followed by addition of potassium acetate (3.4 g, 35.1 mmol, 3.0 eq) and [1,1'-Bis (diphenyl phosphino) ferrocene] palladium(II) dichloride (Pd(dppf)Cl$_2$) (0.85 g, 1.17 mmol, 0.1 eq). After stirring at 100° C. for 4 h, the reaction mixture was cooled to RT, filtered, and concentrated under reduced pressure. The crude product was passed through flash chromatography product eluting with 10-80% ethyl acetate in hexane. The solvent was evaporated under reduced pressure to afford the desired product PB2 (3.2 g, Yield: 90.11%). MS (ES): m/z 304.1 [M+H]$^+$

Method PB3—Preparation of 6-amino-2-fluoro-N,N-dimethyl-3-(4,4,5,5-tetramethyl-1,3,2-dioxaborolan-2-yl)benzamide (PB3)

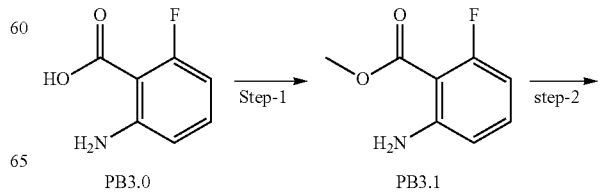

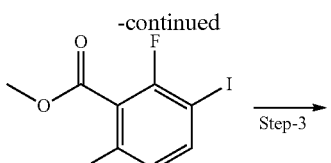

PB3.2

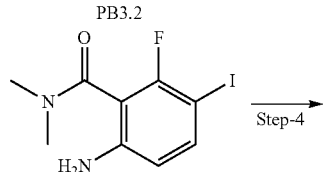

PB3.3

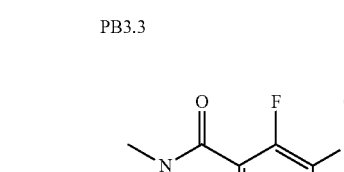

PB3

Step 1. methyl 2-amino-6-fluorobenzoate (PB3.1)

To a solution of 2-amino-6-fluorobenzoic acid (2 g, 12.892 mmol, 1.0 eq) in DCM (20 mL) and methanol (5 mL) at 0° C. was added (trimethylsilyl)diazomethane (0.6M) (22 mL, 12.9 mmol, 1.0 eq) under nitrogen atmosphere. After stirring at RT for 3 h, the reaction mixture was quenched slowly by acetic acid till bubbling stop. The reaction mixture was diluted with DCM (50 ml) and washed with saturated sodium bicarbonate solution (50 ml). The combined organic layer was dried over sodium sulphate and concentrate under vacuum. The residue was purified by flash column chromatography eluting at 2% ethyl acetate in hexane to afford PB3.1 (2.1 g, 96.29%) MS (ES): m/z 170.1 [M+H]$^+$

Step 2. methyl 6-amino-2-fluoro-3-bromobenzoate (PB3.2)

To a solution of methyl 2-amino-6-fluorobenzoic acid PB3.1 (2.1 g, 12.416 mmol, 1.0 eq) in ethanol (20 mL) were added silver sulfate (2.1 g, 14.899 mmol, 1.2 eq) and bromine in ethanol (2.98 g, 18.62 mmol, 1.5 eq) dropwise at 0° C. After stirring at RT for 3 h, the reaction mixture was quenched with sodium thiosulphate and ethyl acetate (100 ml). The mixture was filtered through a celite bed and the combined organic layer was dried over sodium sulphate, filtered and concentrated under vacuum. The residue was purified by flash column chromatography eluting with 4% ethyl acetate in hexane to afford PB3.2 (1.5 g, 48.71%) MS (ES): m/z 249.1 [M+H]$^+$

Step 3. 6-amino-2-fluoro-3-bromo-N,N-dimethylbenzamide (PB3.3)

To a solution of methyl 6-amino-3-bromo 2-fluorobenzoate PB3.2 (1.4 g, 5.645 mmol, 1.0 eq) in toluene (10 mL) was added dimethyl amine (2.0 M in THF) (4.8 ml, 9.596 mmol, 1.7 eq) was added trimethyl aluminum (2.0 M in THF) (4.8 ml, 9.596 mmol, 1.7 eq)f. After stirring at RT for 16 h. the reaction mixture was quenched with cold water (100 ml) and ethyl acetate (150 ml). The mixture was filtered through a celite bed and the combined organic layer was dried over sodium sulphate, filtered and concentrate under vacuum. The residue was purified by flash column chromatography eluting with 75% ethyl acetate in hexane to afford PB3.3 (0.45 g, 30.54%) MS (ES): m/z 262.1 [M+H]$^+$

Step 4. 6-amino-2-fluoro-N,N-dimethyl-3-(4,4,5,5-tetramethyl-1,3,2-dioxaborolan-2-yl)benzamide (PB3)

To a solution of methyl 6-amino-3-bromo 2-fluoro n,n-dimethylbenzamidefluorobenzoate PB3.3 (0.4 g, 1.532 mmol, 1.0 eq) in 1,4-dioxane (8 mL) were added bispinacolatodiboron (1.17 g, 4.597 mmol, 3.0 eq) and potassium acetate (0.45 g, 4.597 mmol, 3.0 eq). After stirring degassing with argon gas for 15 min, Chloro(2-dicyclohexylphosphino-2',4',6'-triisopropyl-1,1'-biphenyl)[2-(2'-amino-1,1'-biphenyl)] palladium(II) (xphos PdG$_2$) (0.12 g, 0.153 mmol, 0.1 eq) was added at RT. After stirring at 120° C. for 2.5 h, the reaction mixture was quenched by water (50 ml). The aqueous layer was washed with ethyl acetate (100 ml×3). The combined organic layer dried over sodium sulphate and concentrate under vacuum. The residue was purified by flash Colum chromatography eluting at 2% methanol in DCM to afford PB3 (0.4 g, 84.73%) MS (ES): m/z 309.1 [M+H]$^+$ Method PB4—Preparation of 1-ethyl-N-(3-fluoro-4-(4,4,5,5-tetramethyl-1,3,2-dioxaborolan-2-yl)phenyl)cyclobutane-1-carboxamide (PB4)

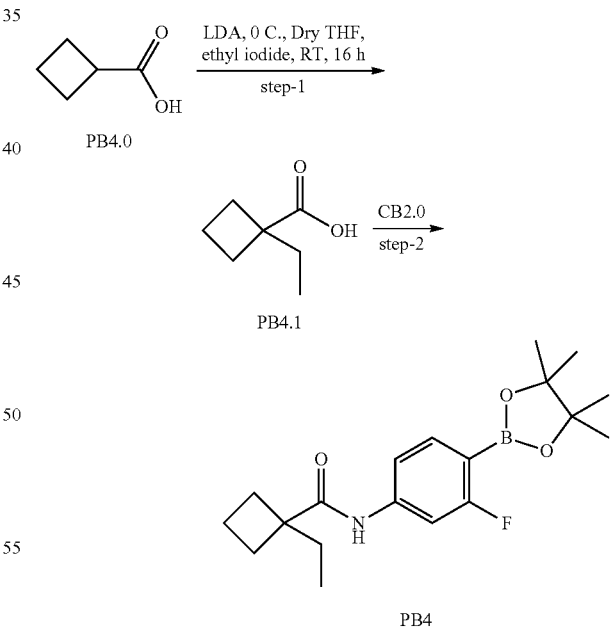

Step 1. 1-ethylcyclobutane-1-carboxylic acid (PB4.1)

To a stirred solution of cyclobutanecarboxylic acid (1 g, 5.0 mmol, 1 eq) in dry THF was added lithium diisopropylamide (2M in THF) (10 mL, 20.00 mmol, 2.0 eq) at 0° C. under argon atmosphere. After stirring at 0° C. for 2 h, Ethyl iodide (1.7 g, 11 mmol, 1.1 eq) was added. After stirring at RT for 16 h, the reaction mixture was poured into water (50 ml), extracted with ethyl acetate (50 ml×3). The combined organic layer was washed with brine solution (30 ml), dried over sodium sulphate and concentrated under reduced pressure to afford PB4.1, which was used as such for next step without purification. (1.2 g, 100%). $^1$H NMR (DMSO-$d_6$, 400 MHZ): 12.08 (s, 1H), 1.82 (m, 4H), 1.60 (m, 2H), 1.48 (q, 2H), 0.94 (t, 3H).

Step 2. 1-ethyl-N-(3-fluoro-4-(4,4,5,5-tetramethyl-1,3,2-dioxaborolan-2-yl)phenyl)cyclobutane-1-carboxamide (PB4)

To a stirred solution of PB4.1 (1.2 g, 9.375 mmol, 1.2 eq) in THF was added phosphorous oxychloride and pyridine at 0° C. After stirring at 0° C. for 20 mins, a solution of 3-fluoro-4-(4,4,5,5-tetramethyl-1,3,2-dioxaborolan-2-yl)aniline (CB2.0) (2.554 g, 7.812 mmol, 1.0 eq) in THF was added dropwise. After stirring at RT for 1 h, the reaction mixture was poured into to water (100 ml), neutralized with sodium bicarbonate and extracted with ethyl acetate (100 ml×3). The combined organic layer was washed with brine solution (50 ml), dried over sodium sulphate and concentrated under reduced pressure. The residue was purified by combi flash chromatography eluting with 9% ethyl acetate in hexane to afford pure PB4. (0.350 g, 10.75%). MS(ES): m/z 348.24 [M+H]+.

Preparation of Compounds of the Invention

Example 1: Method A—Preparation of 2-(2-fluoro-5-methoxyphenyl)-4-((5-(4-hydroxypiperidin-1-yl)pyridin-2-yl)amino)-1,6-naphthyridin-5(6H)-one (I-42)

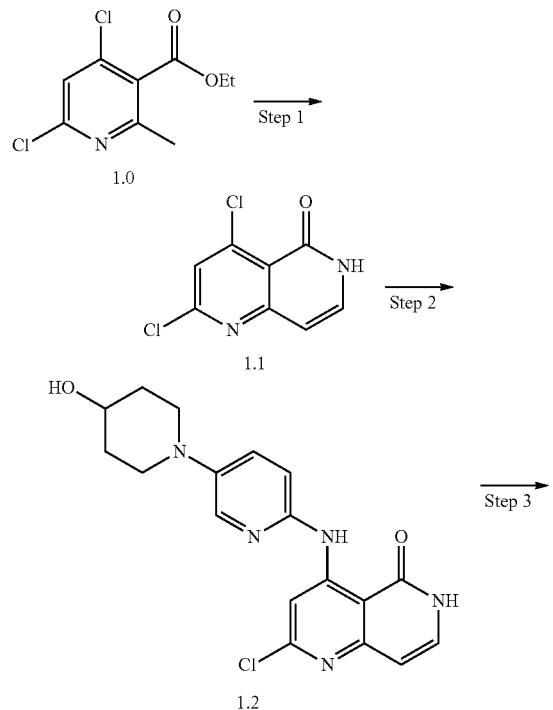

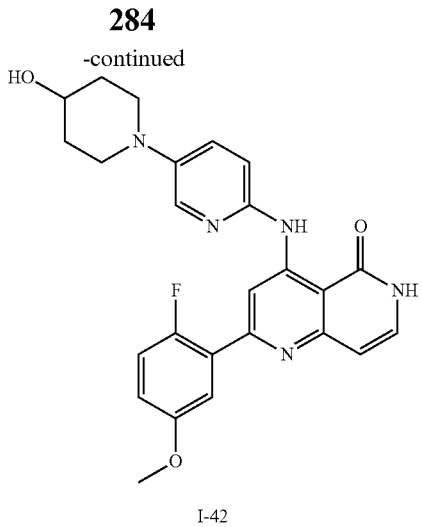

I-42

Step 1: 2,4-dichloro-1,6-naphthyridin-5(6H)-one (1.1)

To a solution of ethyl 4,6-dichloro-2-methylnicotinate (1.0) (20 g, 85.4 mmol) in tert-butanol (200 mL) were added 1,3,5-triazine (13.8 g, 170.8 mmol) and potassium tert-butoxide (19.1 g, 170.8 mmol). After stirring at 90° C. for 1 h, the mixture was cooled to RT and evaporated under reduced pressure. The resulting residue was diluted with water (300 mL) and then acidified to ~pH 5 using aqueous 2M HCl solution. After stirring the resulting suspension at RT for 1 h, the solid was collected by filtration and washed with water. The crude solid was suspended in 4:1 DCM:acetonitrile (250 mL) and stirred for 20 minutes. The solid was collected by filtration and washed with 1:1 DCM:diethyl ether (100 mL). Residual water was removed from the solid via azeotropic distillation with toluene (200 mL). Compound (1.1) was obtained as a brown solid (9.43 g, 51%) which was used without further purification. m/z=215.9 [M+H]+, $^1$H NMR (400 MHz, DMSO): δ 11.82 (s, 1H), 7.75 (s, 1H), 7.60 (t, J=5.9 Hz, 1H), 6.59 (d, J=7.1 Hz, 1H).

Step 2. 2-Chloro-4-((5-(4-hydroxypiperidin-1-yl)pyridin-2-yl)amino)-1,6-naphthyridin-5(6H)-one (1.2)

To 10-20 mL microwave tube charged with 2,4-dichloro-1,6-naphthyridin-5(6H)-one (1.1) (1.61 g, 7.5 mmol) in n-butanol (12.0 mL) and N,N-diisopropylethylamine (2.6 mL, 15 mmol) was added 1-(6-aminopyridin-3-yl)piperidin-4-ol (preparation described in WO2015131080, 1.59 g, 8.25 mmol). After heating in a Biotage Initiator® microwave at 160° C. for 6 h, the precipitate was isolated by filtration and washed sequentially with ethyl acetate (15 mL) and diethyl ether (40 mL). The reaction was carried out three times in parallel, at the same scale, and combined to yield crude product (1.2) (5.02 g, 60%) as a brown solid which was used without further purification. m/z=372.5 [M+H]+, $^1$H NMR (400 MHz, DMSO): δ 12.57 (s, 1H), 11.90 (d, J=3.8 Hz, 1H), 8.43 (s, 1H), 8.20-8.15 (m, 1H), 7.53 (d, J=6.6 Hz, 2H), 7.07-7.02 (m, 1H), 6.53 (d, J=7.1 Hz, 1H), 4.76-4.72 (m, 1H), 3.70 (dd, J=3.4, 4.2 Hz, 1H), 3.61 (s, 2H), 2.98-2.88 (m, 2H), 1.89-1.87 (m, 2H), 1.57-1.50 (m, 2H).

Step 3—2-(2-fluoro-5-methoxyphenyl)-4-((5-(4-hydroxypiperidin-1-yl)pyridin-2-yl)amino)-1,6-naphthyridin-5(6H)-one (I-42)

A 2-5 mL microwave vial charged with 2-chloro-4-((5-(4-hydroxypiperidin-1-yl)pyridin-2-yl)amino)-1,6-naphthyridin-5(6H)-one (1.2) (100 mg, 0.269 mmol), 2-fluoro-5-methoxyphenyl boronic acid (69 mg, 0.403 mmol) in dioxane (4.0 mL), water (0.5 mL) and $K_3PO_4$ (228 mg, 1.08 mmol) was added XPhos Pd G2 catalyst (21 mg, 0.027 mmol). The mixture was degassed, purged with $N_2$ and heated at 150° C. for 45 minutes in a Biotage Initiator® microwave. The mixture was loaded onto Biotage—ISOLUTE® HM-N cartridge and purified by silica gel chromatography (eluting 0-20% MeOH in DCM). The isolated yellow residue was treated with $Et_2O$, collected by filtration, washed with $Et_2O$, dried at 40° C. under vacuum to yield the title compound (I-42) (81 mg, 65%) as a yellow solid. m/z=462 [M+H]$^+$, $^1$H NMR (400 MHz, DMSO): δ 12.42 (s, 1H), 11.68-11.62 (m, 1H), 8.72 (d, J=1.4 Hz, 1H), 8.07 (d, J=3.0 Hz, 1H), 7.50-7.46 (m, 2H), 7.42 (d, J=7.3 Hz, 1H), 7.29 (dd, J=9.0, 10.5 Hz, 1H), 7.11-7.01 (m, 2H), 6.60 (d, J=7.3 Hz, 1H), 4.70 (d, J=4.3 Hz, 1H), 3.83 (s, 3H), 3.68-3.61 (m, 1H), 3.57-3.49 (m, 2H), 2.92-2.83 (m, 2H), 1.88-1.80 (m, 2H), 1.56-1.45 (m, 2H).

Example 2: Method B—Preparation of 2-(2,6-difluoro-3-methoxyphenyl)-4-((5-(4-hydroxypiperidin-1-yl)pyridin-2-yl)amino)-1,6-naphthyridin-5(6H)-one (I-92)

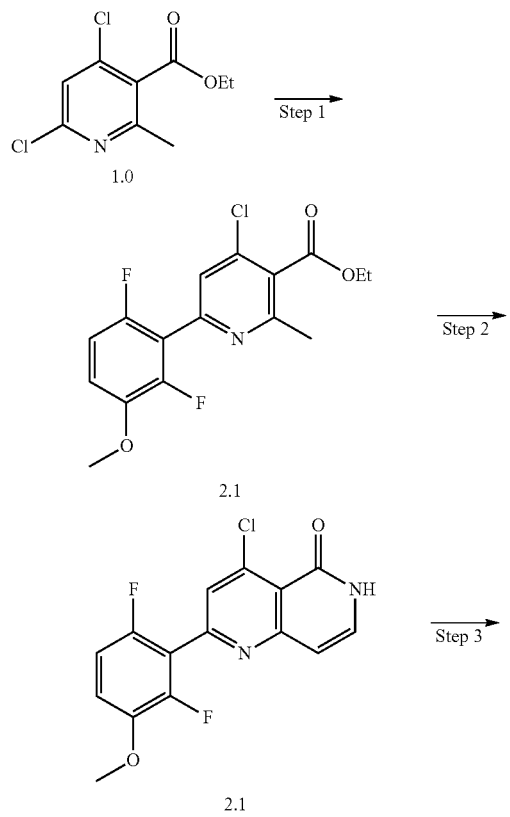

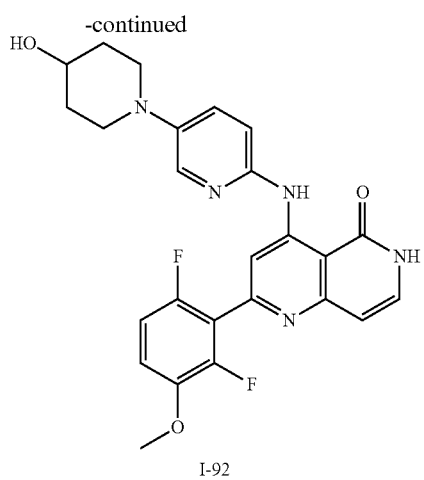

I-92

Step 1: Ethyl 4-chloro-6-(2,6-difluoro-3-methoxyphenyl)-2-methylnicotinate (2.1)

To a solution of 2,6-difluoro-3-methoxy-bromobenzene (838 mg, 3.76 mmol) in dry THF (5 mL) under a nitrogen atmosphere at −78° C. was treated dropwise with isopropylmagnesium chloride lithium chloride complex solution (1.3M in THF, 4.2 mL, 5.40 mmol). After stirring at −78° C. for 40 min, zinc chloride (2M in THF, 5.6 mL, 11.28 mmol) was added dropwise. After warming to 0° C. for 20 min, the organo-zinc suspension was added to a degassed and nitrogen purged mixture of ethyl 4,6-dichloro-2-methylnicotinate (1.0) (550 mg, 2.35 mmol) and Pd(PPh$_3$)$_4$ (272 mg, 0.235 mmol) in THF (7 mL). After stirring at RT overnight, the reaction was quenched with sat. NH$_4$Cl and extracted into EtOAc (2×). The combined organic phase was washed with brine, dried over Na2SO4, filtered, and concentrated in vacuo. The residue was purified by silica gel column chromatography (0-60% EtOAc in cyclohexane gradient elution) to afford the title compound (2.1) (745 mg, 93%) as a colourless oil. $^1$H NMR (400 MHz, CDCl3): δ 7.39 (s, 1H), 7.02-6.90 (m, 2H), 4.49 (q, J=7.2 Hz, 2H), 3.90 (s, 3H), 2.63 (s, 3H), 1.44 (dd, J=7.2, 7.2 Hz, 3H).

Step 2: 4-Chloro-2-(2,6-difluoro-3-methoxyphenyl)-1,6-naphthyridin-5(6H)-one (2.2)

Reaction was carried out following representative procedure outlined in Example 1, Method A, Step 1, to give the product (2.2) $^1$H NMR (400 MHz, DMSO): δ 11.67-11.67 (m, 1H), 7.76 (s, 1H), 7.53 (d, J=7.3 Hz, 1H), 7.41-7.33 (m, 1H), 7.27-7.19 (m, 1H), 6.63 (d, J=7.3 Hz, 1H), 3.90 (s, 3H).

Step 3: 2-(2,6-Difluoro-3-methoxyphenyl)-4-((5-(4-hydroxypiperidin-1-yl)pyridin-2-yl)amino)-1,6-naphthyridin-5(6H)-one (I-92)

Reaction was carried out following representative procedure outlined in Example 1, Step 2, to give the product (I-92) $^1$H NMR (400 MHz, DMSO): δ 12.45 (s, 1H), 11.64 (s, 1H), 8.35 (s, 1H), 7.97 (d, J=2.8 Hz, 1H), 7.41-7.33 (m, 2H), 7.27-7.18 (m, 1H), 7.10 (dd, J=9.0, 9.0 Hz, 1H), 6.92 (d, J=9.1 Hz, 1H), 6.47 (d, J=7.3 Hz, 1H), 4.60 (d, J=4.0 Hz, 1H), 3.82 (s, 3H), 3.60-3.50 (m, 2H), 3.15-3.08 (m, 1H), 2.82-2.73 (m, 2H), 1.72 (d, J=9.6 Hz, 2H), 1.46-1.34 (m, 2H).

Example 3: Method C—Preparation of 4-((1-ethyl-2-oxo-1,2-dihydropyrimidin-4-yl)amino)-2-(2-fluoro-5-methoxy-4-(piperidine-1-carbonyl)phenyl)-1,6-naphthyridin-5(6H)-one (1-228)

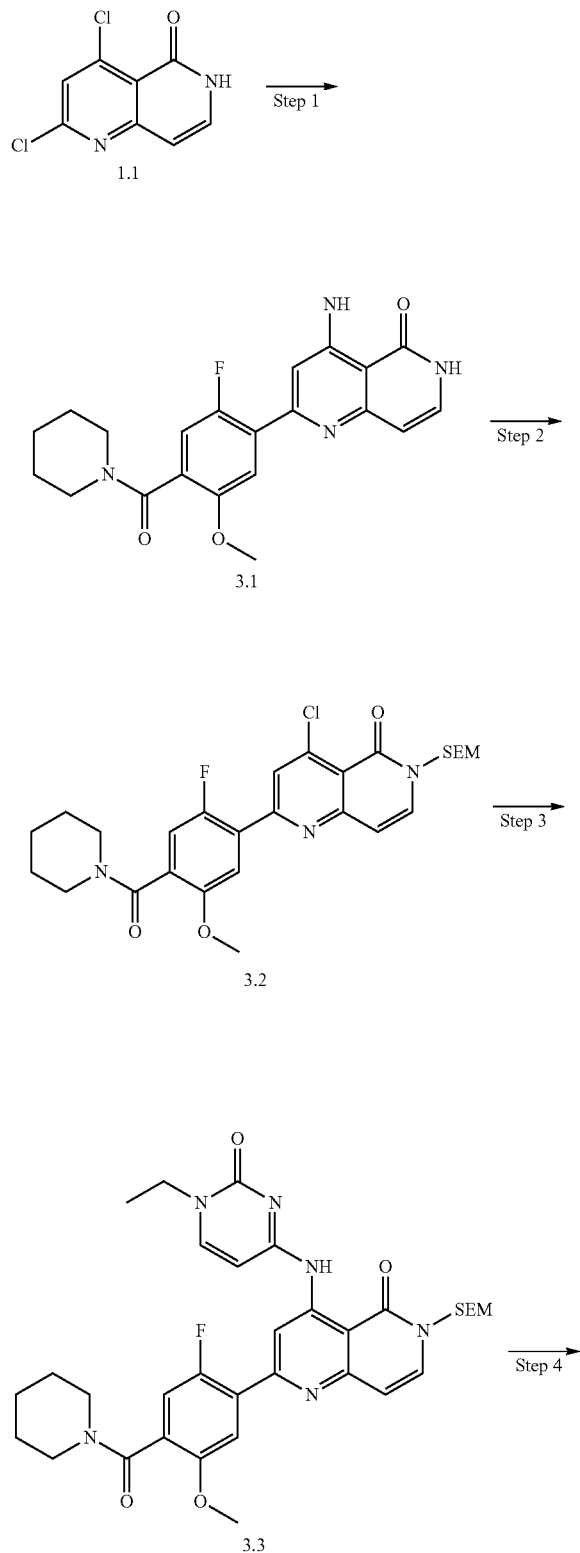

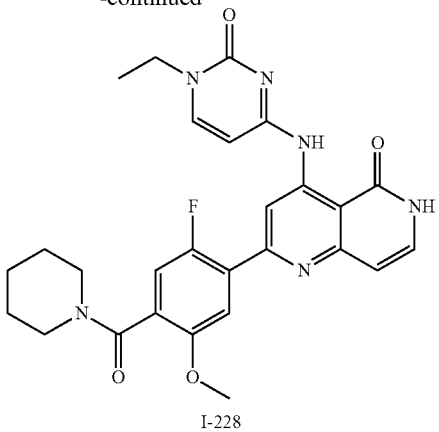

I-228

Step 1. 4-Chloro-2-(2-fluoro-5-methoxy-4-(piperidine-1-carbonyl)phenyl)-1,6-naphthyridin-5(6H)-one (3.1)

To a mixture of 2,4-dichloro-1,6-naphthyridin-5(6H)-one (1.1) (250 mg, 1.16 mmol), (5-fluoro-2-methoxy-4-(4,4,5,5-tetramethyl-1,3,2-dioxaborolan-2-yl)phenyl)(piperidin-1-yl)methanone (CB1) (422 mg, 1.16 mmol) and tetrakis(triphenylphosphine)palladium (134 mg, 10 mol %) under an atmosphere of nitrogen in DME (5.0 mL) was added a solution of potassium carbonate (2M in H$_2$O, 1.3 mL, 2.56 mmol). The reaction mixture was purged with flow of nitrogen for 5 min, then heated in a Biotage Initiator microwave at 100° C. for 1 h. The crude reaction mixture was cooled to RT and filtered through a Celite® pad (2.5 g), flushing with DCM. The filtrate was concentrated under reduced pressure and purified by silica gel column chromatography (0-15% MeOH/DCM gradient elution) to afford (3.1) (381 mg, 63% yield, 80% purity) which was taken forwards to the next step without further purification. m/z=416.7 [M+H]$^+$.

Step 2. 4-Chloro-2-(2-fluoro-5-methoxy-4-(piperidine-1-carbonyl)phenyl)-6-((2-(trimethylsilyl)ethoxy)methyl)-1,6-naphthyridin-5(6H)-one (3.2)

To a mixture of 4-chloro-2-(2-fluoro-5-methoxy-4-(piperidine-1-carbonyl)phenyl)-1,6-naphthyridin-5(6H)-one (3.1) (200 mg, 0.48 mmol) and 2-(trimethylsilyl)ethoxymethyl chloride (0.34 mL, 1.92 mmol) in THF (5.0 mL) degassed with flow of nitrogen for 5 min was added 1,8-diazabicyclo[5.4.0]undec-7-ene (0.36 mL, 2.40 mmol). After stirring at RT for 16 h, the solvent was removed under reduced pressure, diluted with water (15 mL) and extracted with DCM (2×15 mL). The combined organic layer were washed with brine (15 mL), passed through a hydrophobic frit and concentrated under reduced pressure. The crude material was purified by silica gel chromatography using 0-20% MeOH/DCM to afford (3.2) (234 mg, 89% yield, 84% purity) as a yellow oil with 16% unreacted (3.1) co-eluting. The compound was taken forwards to the next step without further purification. m/z=546.9 [M+H]$^+$.

Step 3. 4-((1-Ethyl-2-oxo-1,2-dihydropyrimidin-4-yl)amino)-2-(2-fluoro-5-methoxy-4-(piperidine-1-carbonyl)phenyl)-6-((2-(trimethylsilyl)ethoxy)methyl)-1,6-naphthyridin-5(6H)-one (3.3)

To a mixture of 4-amino-1-ethylpyrimidin-2(1H)-one (42 mg, 0.30 mmol), Xantphos (23 mg, 0.04 mmol) and cesium carbonate (92 mg, 0.28 mmol) in 1,4-dioxane (2.5 mL) was added 4-chloro-2-(2-fluoro-5-methoxy-4-(piperidine-1-carbonyl)phenyl)-6-((2-(trimethylsilyl)ethoxy)methyl)-1,6-naphthyridin-5(6H)-one (3.2) (110 mg, 0.20 mmol). The reaction mixture was stirred at RT degassing with flow of nitrogen for 10 min, treated with palladium(II) acetate (4.5 mg, 0.02 mmol) degassing for a further 5 min, and then heated at 100° C. for 16 h. The crude material was filtered over a pad of Celite® (2.5 g frit), eluted with 5% MeOH/DCM, then passed down a silica gel column with 0-20% MeOH/DCM to afford the title compound (3.3) (88 mg, 67% yield, 62% purity) which was used without further purification. m/z=649.2 [M+H]$^+$.

Step 4. 4-((1-Ethyl-2-oxo-1,2-dihydropyrimidin-4-yl)amino)-2-(2-fluoro-5-methoxy-4-(piperidine-1-carbonyl)phenyl)-1,6-naphthyridin-5(6H)-one (I-228)

A solution of crude 4-((1-ethyl-2-oxo-1,2-dihydropyrimidin-4-yl)amino)-2-(2-fluoro-5-methoxy-4-(piperidine-1-carbonyl)phenyl)-6-((2-(trimethylsilyl)ethoxy)methyl)-1,6-naphthyridin-5(6H)-one (3.3) (88 mg, 0.14 mmol) in DCM (1.0 mL) was treated dropwise with trifluoroacetic acid (0.50 mL). After stirring at RT for 16 h, the solvent was removed under reduced pressure. The crude material was neutralized with saturated aqueous sodium bicarbonate (5 mL) and extracted into DCM (3×5 mL). The combined organic layers were washed with brine (10 mL), passed through a hydrophobic frit and concentrated under reduced pressure. The crude material was purified by preparative HPLC to afford 4-((1-ethyl-2-oxo-1,2-dihydropyrimidin-4-yl)amino)-2-(2-fluoro-5-methoxy-4-(piperidine-1-carbonyl)phenyl)-1,6-naphthyridin-5(6H)-one (I-228) (23 mg, 33%) as a white solid. m/z=519.7 [M+H]$^+$, $^1$H NMR (400 MHz, DMSO): δ 12.98 (s, 1H), 11.94 (s, 1H), 9.35 (s, 1H), 8.01 (d, J=7.1 Hz, 1H), 7.58-7.49 (m, 2H), 7.27 (d, J=10.1 Hz, 1H), 6.73 (d, J=7.3 Hz, 1H), 6.13 (d, J=7.1 Hz, 1H), 3.86 (s, 3H), 3.81 (q, J=7.0 Hz, 2H), 3.66-3.54 (m, 2H), 3.19-3.13 (m, 2H), 1.61-1.56 (m, 4H), 1.48-1.44 (m, 2H), 1.22 (t, J=7.1 Hz, 3H).

Example 4: Method D—Preparation of 2-(4-((Dimethylamino)methyl)-2-fluoro-5-methoxyphenyl)-4-((5-(4-hydroxypiperidin-1-yl)pyridin-2-yl)amino)-1,6-naphthyridin-5(6H)-one (I-215)

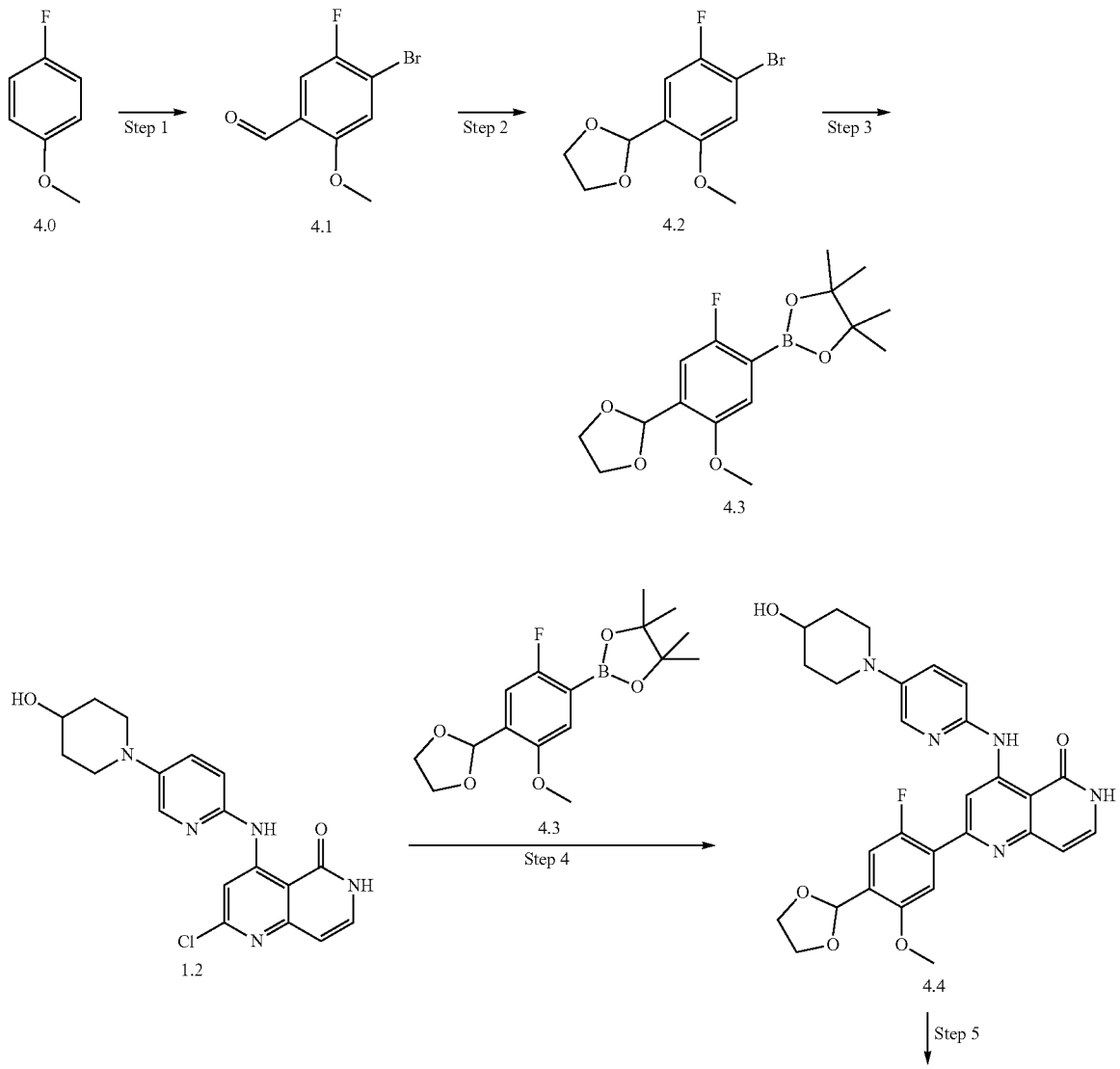

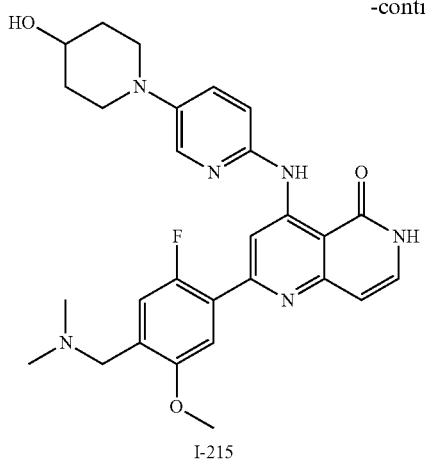

I-215

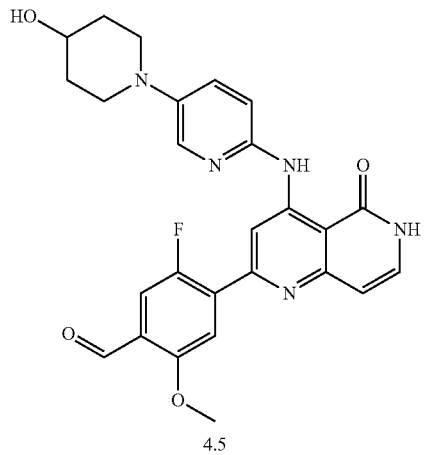

4.5

← Step 6

Step 1: 4-Bromo-5-fluoro-2-methoxybenzaldehyde (4.1)

To a solution of 2-bromo-1-fluoro-4-methoxybenzene (4.0) (2.65 g, 12.93 mmol) in DCM (45 mL) at 0° C. under a nitrogen atmosphere was added dropwise titanium (IV) chloride (1M in DCM, 12.93 mL, 19.93 mmol). After 15 min, dichloromethyl methyl ether (1.4 mL, 15.51 mmol) and an additional portion of titanium (IV) chloride (1M in DCM, 12.93 mL, 19.93 mmol) were added. After stirring at 0° C. for 3 h, the reaction was quenched by pouring onto ice/water and extracted into DCM (3×). The combined extracts were washed with water and brine, dried over Na2SO4 and concentrated in vacuo to afford the title compound (4.1) (3.69 g) as a yellow/orange solid which used as is in the next step.

Step 2: 2-(4-Bromo-5-fluoro-2-methoxyphenyl)-1,3-dioxolane (4.2)

A mixture of 4-bromo-5-fluoro-2-methoxybenzaldehyde (4.1) (3.01 g, 12.93 mmol), ethylene glycol (1.4 mL, 25.86 mmol) and p-toluene sulfonic acid monohydrate (250 mg, 1.29 mmol) in toluene (30 mL) was heated at reflux (Dean-Stark) for 18 h. The mixture was diluted with EtOAc, washed with sat. NaHCO$_3$, water and brine, dried over Na$_2$SO$_4$ and concentrated in vacuo. The residue was purified by silica gel chromatography using 0-50% EtOAc in isohexane to afford the title compound (4.2) (1.91 g, 53%) as a pale yellow oil. $^1$H NMR (400 MHz, CDCl3): δ 7.31 (d, J=8.6 Hz, 1H), 7.04 (d, J=5.1 Hz, 1H), 6.06 (s, 1H), 4.14-3.99 (m, 4H), 3.85 (s, 3H).

Step 3: 2-(4-(1,3-Dioxolan-2-yl)-2-fluoro-5-methoxyphenyl)-4,4,5,5-tetramethyl-1,3,2-dioxaborolane (4.3)

Reaction was carried out following the representative procedure described in Method CB3 using 2-(4-bromo-5-fluoro-2-methoxyphenyl)-1,3-dioxolane (4.2), to give product (4.3) $^1$H NMR (400 MHz, CDCl3): δ 7.23-7.17 (m, 1H), 6.12 (s, 1H), 4.14-4.01 (m, 4H), 3.91-3.86 (m, 2H), 1.38-1.34 (m, 9H), 1.29-1.25 (m, 6H).

Step 4: 2-(4-(1,3-Dioxolan-2-yl)-2-fluoro-5-methoxyphenyl)-4-((5-(4-hydroxypiperidin-1-yl)pyridin-2-yl)amino)-1,6-naphthyridin-5(6H)-one (4.4)

Reaction was carried out following the representative procedure described in Example 1, Method A, step 3 using 2-chloro-4-((5-(4-hydroxypiperidin-1-yl)pyridin-2-yl)amino)-1,6-naphthyridin-5(6H)-one (1.2) and 2-(4-(1,3-dioxolan-2-yl)-2-fluoro-5-methoxyphenyl)-4,4,5,5-tetramethyl-1,3,2-dioxaborolane (4.3), to give product (4.4). $^1$H NMR (400 MHz, DMSO): δ 12.47 (s, 1H), 11.73-11.68 (m, 1H), 8.77 (s, 1H), 8.11 (d, J=2.5 Hz, 1H), 7.60 (d, J=6.1 Hz, 1H), 7.52 (dd, J=2.9, 9.0 Hz, 1H), 7.47 (d, J=7.3 Hz, 1H), 7.38 (s, 1H), 7.07 (d, J=8.8 Hz, 1H), 6.66 (d, J=7.3 Hz, 1H), 6.08 (s, 1H), 4.74 (d, J=4.0 Hz, 1H), 4.14 (dd, J=6.8, 6.8 Hz, 2H), 4.03-3.91 (m, 4H), 3.72-3.66 (m, 1H), 3.59-3.52 (m, 2H), 3.01-2.83 (m, 3H), 1.88 (d, J=9.9 Hz, 2H), 1.60-1.50 (m, 2H).

Step 5: 5-Fluoro-4-(4-((5-(4-hydroxypiperidin-1-yl)pyridin-2-yl)amino)-5-oxo-5,6-dihydro-1,6-naphthyridin-2-yl)-2-methoxybenzaldehyde (4.5)

A mixture of 2-(4-(1,3-dioxolan-2-yl)-2-fluoro-5-methoxyphenyl)-4-((5-(4-hydroxypiperidin-1-yl)pyridin-2-yl)amino)-1,6-naphthyridin-5(6H)-one (4.4) (240 mg, 0.450 mmol) and HCl (4N in 1,4-dioxane, 4 mL, 16 mmol) in THF (10 mL) was heated at 50° C. for 2 h. The cooled mixture was neutralized with sat. NaHCO$_3$ and extracted into EtOAc (×2). The combined extracts were washed with brine, dried over Na$_2$SO$_4$, filtered and concentrated in vacuo to afford the title compound (4.5) (194 mg, 88%) as an orange solid which was used in the next step without purification.

Step 6: 2-(4-((Dimethylamino)methyl)-2-fluoro-5-methoxyphenyl)-4-((5-(4-hydroxypiperidin-1-yl)pyridin-2-yl)amino)-1,6-naphthyridin-5(6H)-one (I-215)

To a mixture at RT of 5-fluoro-4-(4-((5-(4-hydroxypiperidin-1-yl)pyridin-2-yl)amino)-5-oxo-5,6-dihydro-1,6-naphthyridin-2-yl)-2-methoxybenzaldehyde (4.5) (90 mg, 0.184 mmol), dimethylamine (370 μL, 0.735 mmol) in DCM (5 mL) and MeOH (1 mL) was added sodium triacetoxy borohydride (58 mg, 0.276 mmol) After stirring for 18 h, the mixture was filtered over a pad of Celite® and the filtrate passed through an SCX cartridge (eluted with MeOH followed 7N methanolic ammonia). The crude material was purified by preparative HPLC, to afford 2-(4-((dimethylamino)methyl)-2-fluoro-5-methoxyphenyl)-4-((5-(4-hydroxypiperidin-1-yl)pyridin-2-yl)amino)-1,6-naphthyridin-5(6H)-one (I-215) (23 mg, 24%) as a yellow solid. m/z=519.2 [M+H]$^+$, $^1$H NMR (400 MHz, DMSO): δ 12.41 (s, 1H), 11.66 (d, J=5.5 Hz, 1H), 8.73 (d, J=1.3 Hz, 1H), 8.23 (s, 1H), 8.08 (d, J=3.0 Hz, 1H), 7.53 (d, J=6.4 Hz, 1H), 7.48 (dd, J=3.1, 9.0 Hz, 1H), 7.44-7.40 (m, 1H), 7.03 (d, J=8.8 Hz, 1H), 6.61 (d, J=7.3 Hz, 1H), 3.86 (s, 4H), 3.68-3.60 (m, 2H), 3.57-3.49 (m, 3H), 2.92-2.83 (m, 2H), 2.23 (s, 6H), 1.88-1.80 (m, 2H), 1.56-1.45 (m, 2H).

Example 5: Method E—Preparation of 2-(3-hydroxy-1-piperidyl)-4-[[5-(4-hydroxy-1-piperidyl)-2-pyridyl]amino]-6H-1,6-naphthyridin-5-one (I-50)

Step 1. 2-Chloro-4-((5-(4-hydroxypiperidin-1-yl)pyridin-2-yl)amino)-1,6-naphthyridin-5(6H)-one (1.2)

Reaction was carried out following procedure outlined in Example 1, Method A, Step 2.

Step 2. 2-(3-hydroxy-1-piperidyl)-4-[[5-(4-hydroxy-1-piperidyl)-2-pyridyl]amino]-6H-1,6-naphthyridin-5-one (I-50)

To a reaction tube charged with 2-chloro-4-((5-(4-hydroxypiperidin-1-yl)pyridin-2-yl)amino)-1,6-naphthyridin-5(6H)-one (1.2) (200 mg, 0.58 mmol), 3-hydroxypiperidine (65 mg, 0.64 mmol), potassium carbonate (149 mg, 1.0 mmol) and Xantphos (62 mg, 0.10 mmol) in dioxane (8 mL) purged with N$_2$ was added Bis(dibenzylideneacetone)palladium(0) (31 mg, 0.05 mmol). After stirring at 125° C. for 8 h, the reaction mixture was allowed to cool to RT and filtered through celite. The solvent was removed in vacuo to leave a crude residue which was purified by preparative HPLC to afford 2-(3-hydroxy-1-piperidyl)-4-[[5-(4-hydroxy-1-piperidyl)-2-pyridyl]amino]-6H-1,6-naphthyridin-5-one (I-50) (16 mg, 7%) as a yellow solid. m/z=437 [M+H]$^+$, $^1$H NMR (400 MHz, DMSO) δ 12.25 (s, 1H), 11.15 (s, 1H), 8.04 (s, 1H), 7.92 (s, 1H), 7.47-7.41 (m, 1H), 7.21 (s, 1H), 6.92-6.87 (m, 1H), 6.22 (d, J=6.9 Hz, 1H), 4.30 (d, J=11.8 Hz, 1H), 4.14-4.06 (m, 1H), 3.62-3.50 (m, 4H), 3.04-2.98 (m, 1H), 2.89-2.79 (m, 3H), 1.94-1.75 (m, 4H), 1.55-1.41 (m, 4H).

Example 6: Method F—Preparation of 2-[2-fluoro-4-(pyrrolidine-1-carbonyl)phenyl]-4-[[5-(4-hydroxy-1-piperidyl)-2-pyridyl]amino]-6H-1,6-naphthyridin-5-one (I-115)

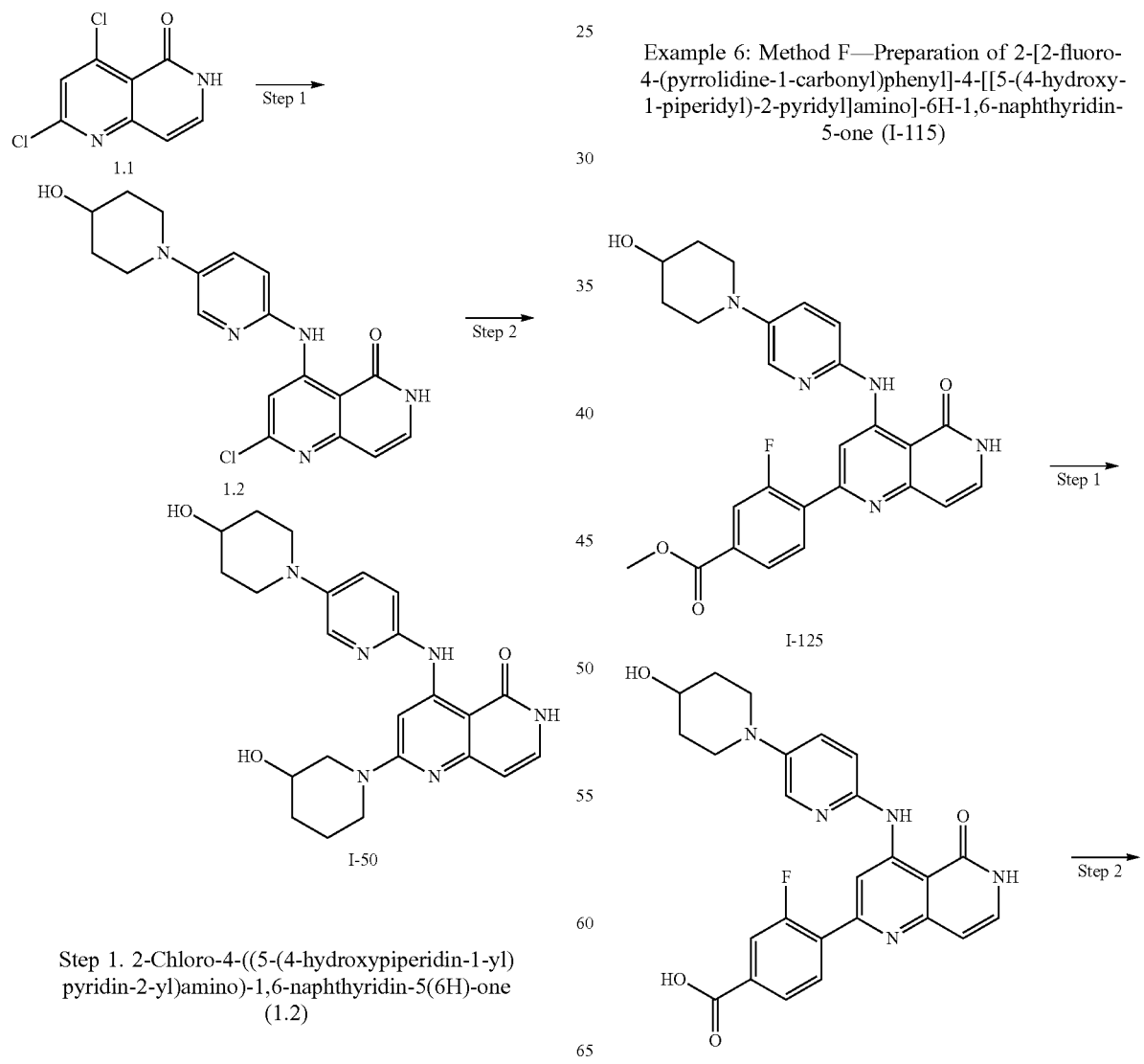

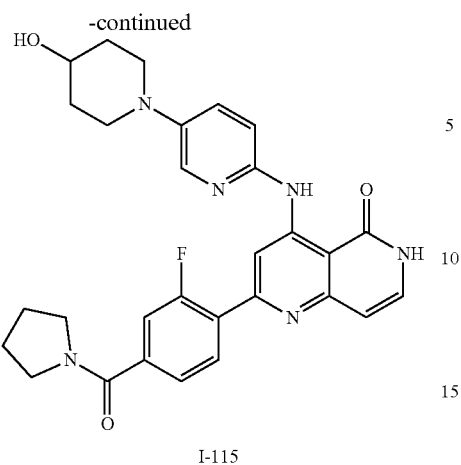

I-115

Step 1. 3-Fluoro-4-[4-[[5-(4-hydroxy-1-piperidyl)-2-pyridyl]amino]-5-oxo-6H-1,6-naphthyridin-2-yl]benzoic Acid (I-134)

To a mixture of Methyl 3-fluoro-4-[4-[[5-(4-hydroxy-1-piperidyl)-2-pyridyl]amino]-5-oxo-6H-1,6-naphthyridin-2-yl]benzoate (I-125) (1.43 g, 2.92 mmol) dissolved in THF (20 mL) and water (5 mL) was added Lithium hydroxide monohydrate (200 mg, 4.67 mmol). After stirring at RT overnight. 4M HCl in dioxane (10 mL) was added and the mixture was evaporated to dryness. The residue was dried via azeotropic distillation with dioxane (2×100 mL) to yield the crude product (I-134) (2.78 g) as a colourless gum-solid. The crude residue was used in the next step without further purification (assumed to be HCl salt, plus residual LiCl). 45 mg of crude product was further purified by preparative HPLC, to afford pure 3-fluoro-4-[4-[[5-(4-hydroxy-1-piperidyl)-2-pyridyl]amino]-5-oxo-6H-1,6-naphthyridin-2-yl]benzoic acid (I-134) as a white solid. m/z=476 [M+H]$^+$, $^1$H NMR (400 MHz, DMSO): δ 13.47-13.46 (m, 1H), 12.50 (s, 1H), 11.72 (d, J=5.3 Hz, 1H), 8.80 (s, 1H), 8.17-8.09 (m, 2H), 7.95 (dd, J=1.3, 8.1 Hz, 1H), 7.86 (s, 1H), 7.55-7.44 (m, 2H), 7.08 (d, J=9.1 Hz, 1H), 6.65 (d, J=6.6 Hz, 1H), 4.73-4.67 (m, 1H), 3.73-3.66 (m, 1H), 3.61-3.53 (m, 2H), 2.95-2.87 (m, 2H), 1.89 (dd, J=3.5, 8.8 Hz, 2H), 1.60-1.49 (m, 2H).

Step 2. Preparation of 2-[2-fluoro-4-(pyrrolidine-1-carbonyl)phenyl]-4-[[5-(4-hydroxy-1-piperidyl)-2-pyridyl]amino]-6H-1,6-naphthyridin-5-one (I-115)

To crude 3-fluoro-4-[4-[[5-(4-hydroxy-1-piperidyl)-2-pyridyl]amino]-5-oxo-6H-1,6-naphthyridin-2-yl]benzoic acid (I-134) (94 mg, assumed 0.19 mmol) dissolved in DMF (900 μL) were added DIPEA (138 μL, 0.79 mmol), pyrrolidine (50 μL, 0.59 mmol) and a solution of HOPO (33 mg, 0.29 mmol), and EDCl.HCl (51 mg, 0.26 mmol) in DMF (300 μL). After stirring at RT overnight, the reaction mixture was diluted with DCM (6 mL) and washed with water (3 mL). The organic phase was collected and the aqueous phase was washed with more DCM. The combined organic phases were passed through a hydrophobic separator and the solvent was removed in vacuo to leave a crude residue which was purified by preparative HPLC to afford 2-[2-fluoro-4-(pyrrolidine-1-carbonyl)phenyl]-4-[[5-(4-hydroxy-1-piperidyl)-2-pyridyl]amino]-6H-1,6-naphthyridin-5-one (I-115) (12 mg, 12%) as a yellow solid. m/z=529 [M+H]$^+$, $^1$H NMR (400 MHz, DMSO): δ 12.49 (s, 1H), 11.73 (s, 1H), 8.79 (s, 1H), 8.13-8.04 (m, 2H), 7.57-7.50 (m, 3H), 7.47 (d, J=7.1 Hz, 1H), 7.08 (d, J=8.8 Hz, 1H), 6.64 (d, J=7.3 Hz, 1H), 4.74 (d, J=1.3 Hz, 1H), 3.68 (d, J=1.3 Hz, 1H), 3.61-3.46 (m, 6H), 2.95-2.87 (m, 2H), 1.98-1.86 (m, 6H), 1.60-1.49 (m, 2H).

Example 7: Method G—Preparation of 2-(6-fluoro-1,2,3,4-tetrahydroisoquinolin-5-yl)-4-[(5-tetrahydropyran-4-yl-1H-pyrazol-3-yl)amino]-6H-1,6-naphthyridin-5-one (I-285)

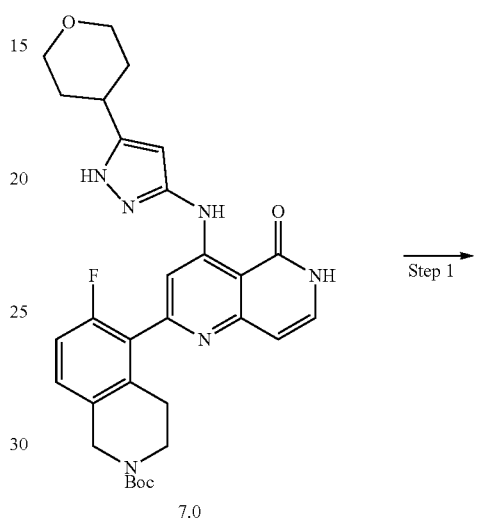

7.0

→ Step 1

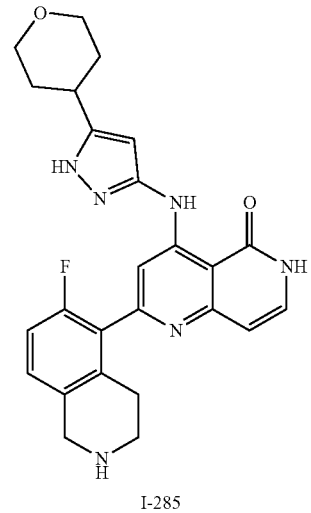

I-285

To a solution of tert-Butyl 6-fluoro-5-(5-oxo-4-((5-(tetrahydro-2H-pyran-4-yl)-1H-pyrazol-3-yl)amino)-5,6-dihydro-1,6-naphthyridin-2-yl)-3,4-dihydroisoquinoline-2(1H)-carboxylate (7.0) (77 mg, 0.13 mmol) in (2 mL) was added trifluoroacetic acid (0.5 mL). After stirring at RT for 3 h, the mixture was concentrated in vacuo and the resulting residue was purified by preparative HPLC to afford 2-(6-fluoro-1,2,3,4-tetrahydroisoquinolin-5-yl)-4-[(5-tetrahydropyran-4-yl-1H-pyrazol-3-yl)amino]-6H-1,6-naphthyridin-5-one (I-285) (47 mg, 74%) as a yellow solid. m/z=461

[M+H]+, 1H NMR (400 MHz, DMSO): δ 12.02 (s, 1H), 8.29 (s, 1H), 7.82 (s, 1H), 7.45 (d, J=7.3 Hz, 1H), 7.39 (dd, J=5.7, 8.7 Hz, 1H), 7.29 (dd, J=8.8, 8.8 Hz, 1H), 6.59 (d, J=7.3 Hz, 1H), 5.99 (s, 1H), 4.32 (s, 2H), 3.45 (dd, J=9.9, 11.6 Hz, 2H), 2.95-2.88 (m, 1H), 2.81 (dd, J=5.7, 5.7 Hz, 4H), 1.83 (dd, J=1.8, 12.9 Hz, 4H), 1.70-1.58 (m, 4H).

Example 8: Method H—Preparation of 2-(2,6-difluorophenyl)-8-(1-hydroxyethyl)-4-[[5-(4-hydroxy-1-piperidyl)-2-pyridyl]amino]-6H-1,6-naphthyridin-5-one (I-15) and 2-(2,6-difluorophenyl)-8-(1-hydroxy-1-methyl-ethyl)-4-[[5-(4-hydroxy-1-piperidyl)-2-pyridyl]amino]-6H-1,6-naphthyridin-5-one (I-16)

by filtration and was purified by trituration with the minimum of methanol to give pure product (8.1) (450 mg, 47%) as an off-white solid. 1H NMR (400 MHz, DMSO) 12.02-12.02 (1H, m), 8.01-7.94 (2H, m), 7.75-7.66 (1H, m), 7.36 (2H, t, J=8.1 Hz).

Step 2. 8-bromo-2-(2,6-difluorophenyl)-4-[[5-(4-hydroxy-1-piperidyl)-2-pyridyl]amino]-6H-1,6-naphthyridin-5-one (I-5)

Reaction was carried out following procedure outlined in Example 1, Method A, Step 2 using 8-bromo-4-chloro-2-(2,

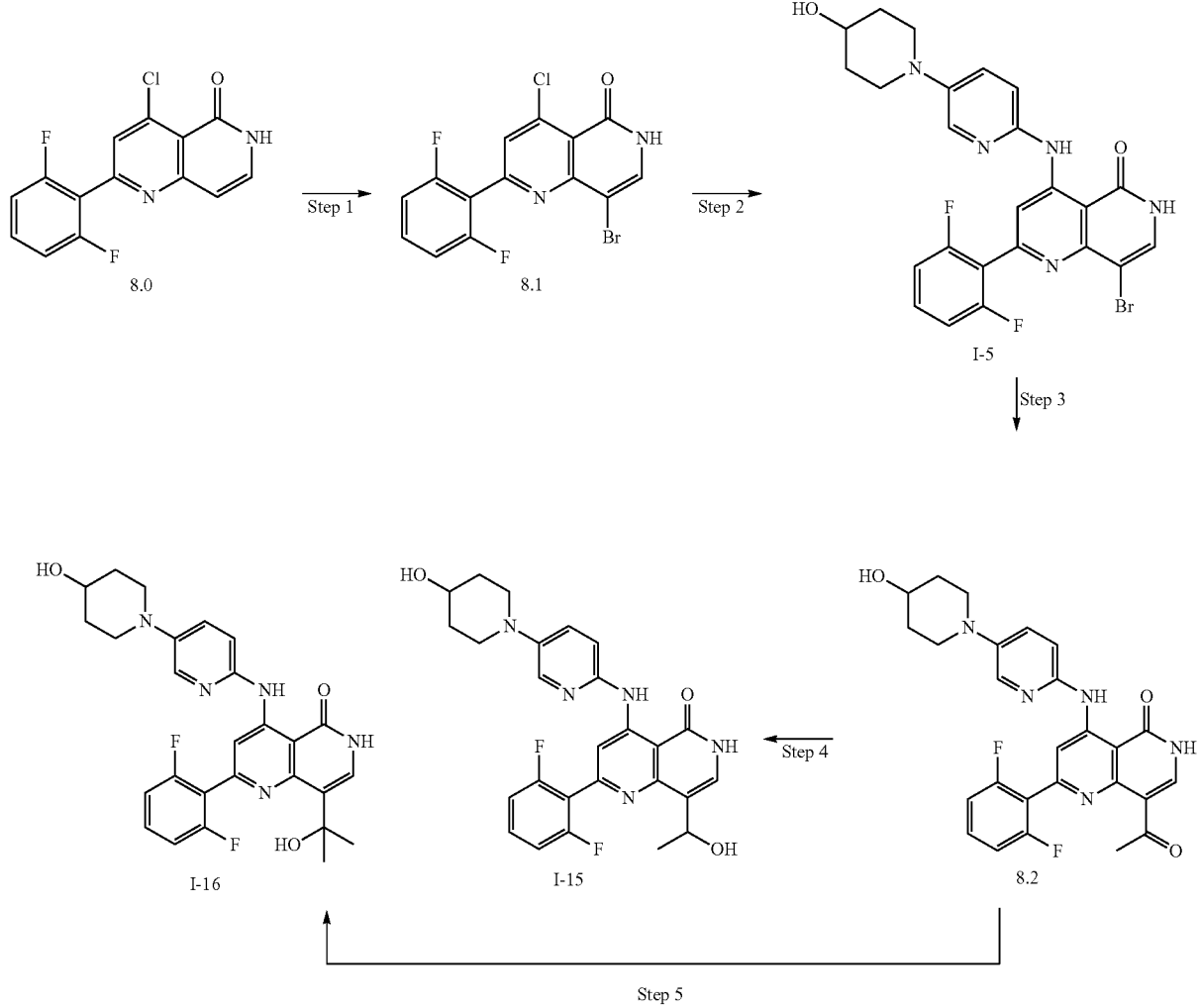

Step 1. 8-bromo-4-chloro-2-(2,6-difluorophenyl)-1,6-naphthyridin-5(6H)-one (8.1)

To a solution of 4-Chloro-2-(2,6-difluorophenyl)-1,6-naphthyridin-5(6H)-one (8.0, prepared according to Method B step 1 and 2 from 2,6-difluorobromobenzene and ethyl 4,6-dichloro-2-methylnicotinate) (750 mg, 2.5 mmol) dissolved in DMF (10 mL) was added N-Bromosuccinimide (460 mg, 2.5 mmol). After stirring at RT for 1 h, the solvent was removed in vacuo and DCM was added to the residue to encourage product precipitation. The solid was collected 6-difluorophenyl)-1,6-naphthyridin-5(6H)-one (8.1) and 1-(6-aminopyridin-3-yl)piperidin-4-ol to give the desired product (I-5) as a yellow solid. m/z=528 [M+H]+, 1H NMR (400 MHz, DMSO) δ 12.65 (s, 1H), 12.13-12.09 (m, 1H), 8.60 (s, 1H), 8.11 (d, J=2.5 Hz, 1H), 7.91 (s, 1H), 7.69-7.60 (m, 1H), 7.52 (dd, J=2.9, 9.0 Hz, 1H), 7.32 (dd, J=8.0, 8.0 Hz, 2H), 7.07 (d, J=8.8 Hz, 1H), 4.73 (d, J=4.3 Hz, 1H), 3.70-3.65 (m, 1H), 3.56 (d, J=12.6 Hz, 2H), 2.95-2.86 (m, 2H), 1.90-1.84 (m, 2H), 1.58-1.46 (m, 2H).

Step 3. 8-acetyl-2-(2,6-difluorophenyl)-4-((5-(4-hydroxypiperidin-1-yl)pyridin-2-yl)amino)-1,6-naphthyridin-5(6H)-one (8.2)

To a solution of 8-Bromo-2-(2,6-difluorophenyl)-4-[[5-(4-hydroxy-1-piperidyl)-2-pyridyl]amino]-6H-1,6-naphthyridin-5-one (I-5) (75 mg, 0.14 mmol) dissolved in DMF (1 mL) and purged with nitrogen for 20 minutes were added tributyl(1-ethoxyvinyl)tin (67 mg, 0.18 mmol) and tetrakis(triphenylphosphine)palladium(0) (16 mg, 0.01 mmol). After stirring at 80° C. for 48 h, the mixture was diluted with water (6 mL) and extracted with DCM (3×3 mL). The combined organic phases were washed with water (4 mL) and then passed through a hydrophobic separator. The solvent was removed in vacuo and the crude residue was purified by column chromatography eluting with 0-20% methanol in DCM to afford pure 8.2 (40 mg, 57%) as an off-white solid. $^1$H NMR (400 MHz, DMSO) 12.48 (1H, s), 12.26 (1H, s), 8.60 (1H, s), 8.13-8.08 (1H, m), 7.91 (1H, s), 7.68-7.59 (1H, m), 7.55-7.49 (1H, m), 7.36-7.29 (2H, m), 7.11-7.03 (1H, m), 4.73 (1H, d, J=4.0 Hz), 3.71-3.65 (1H, m), 3.63-3.53 (2H, m), 2.95-2.88 (2H, m), 2.74-2.72 (3H, m), 1.90-1.80 (2H, m), 1.57-1.47 (2H, m).

Step 4. 2-(2,6-difluorophenyl)-8-(1-hydroxyethyl)-4-[[5-(4-hydroxy-1-piperidyl)-2-pyridyl]amino]-6H-1,6-naphthyridin-5-one (I-15)

To a solution of 8-Acetyl-2-(2,6-difluorophenyl)-4-((5-(4-hydroxypiperidin-1-yl)pyridin-2-yl)amino)-1,6-naphthyridin-5(6H)-one (8.2) (40 mg, 0.08 mmol) in ethanol (0.6 mL) was added sodium borohydride (31 mg, 0.81 mmol). After stirring at RT for 1 h, the reaction was quenched with saturated aqueous ammonium chloride solution (1 mL), stirred for 10 minutes, and extracted with ethyl acetate (3×3 mL). The combined organic phases were dried (MgSO$_4$), filtered and evaporated in vacuo to give a crude product which was purified by preparative HPLC to afford (I-15) (16 mg, 42%) as a yellow solid. m/z=494 [M+H]$^+$, $^1$H NMR (400 MHz, MeOD) δ 8.44 (s, 1H), 8.09 (d, J=2.9 Hz, 1H), 7.56-7.48 (m, 2H), 7.38 (s, 1H), 7.14 (dd, J=8.2, 8.2 Hz, 2H), 7.07 (d, J=8.8 Hz, 1H), 5.23 (q, J=6.3 Hz, 1H), 3.82-3.74 (m, 1H), 3.62-3.54 (m, 2H), 2.98-2.90 (m, 2H), 2.03-1.97 (m, 2H), 1.73-1.63 (m, 2H), 1.56 (d, J=6.4 Hz, 3H). 3 Exchangeable protons not observed.

Step 5. 2-(2,6-difluorophenyl)-8-(1-hydroxy-1-methyl-ethyl)-4-[[5-(4-hydroxy-1-piperidyl)-2-pyridyl]amino]-6H-1,6-naphthyridin-5-one (I-16)

To a solution of 8-Acetyl-2-(2,6-difluorophenyl)-4-((5-(4-hydroxypiperidin-1-yl)pyridin-2-yl)amino)-1,6-naphthyridin-5(6H)-one (8.2) (73 mg, 0.14 mmol) dissolved in THF (3 mL) at 0° C. under a nitrogen atmosphere was added Methylmagnesium bromide (297 μL, 3M solution in diethylether, 0.89 mmol) drop-wise. After stirring for 25 minutes, the reaction was quenched with saturated aqueous ammonium chloride solution (2 mL) and diluted with water (5 mL). The mixture was extracted with DCM (3×5 mL) and the combined organic extracts were passed through a phase separator, and concentrated in vacuo to give a crude product which was purified by preparative HPLC to afford pure (I-16) (17 mg, 23%) as a yellow solid. m/z=508 [M+H]$^+$, $^1$H NMR (400 MHz, MeOD) δ 12.51 (s, 1H), 8.48 (td, J=1.3, 11.9 Hz, 2H), 8.11 (d, J=2.9 Hz, 1H), 7.57-7.49 (m, 2H), 7.36 (s, 1H), 7.16 (dd, J=8.3, 8.3 Hz, 2H), 7.08 (dd, J=1.6, 8.8 Hz, 1H), 3.83-3.75 (m, 1H), 3.63-3.56 (m, 2H), 2.99- 2.91 (m, 2H), 2.03-1.98 (m, 2H), 1.74-1.67 (m, 2H), 1.65 (s, 6H). 2 Exchangeable Protons not observed.

Example 9: Method I—Preparation of 2-(2,6-difluorophenyl)-4-[[5-(4-hydroxy-1-piperidyl)-2-pyridyl]amino]-5-oxo-6H-1,6-naphthyridine-8-carbonitrile (I-33) and 2-(2,6-difluorophenyl)-4-[[5-(4-hydroxy-1-piperidyl)-2-pyridyl]amino]-5-oxo-6H-1,6-naphthyridine-8-carboxylic Acid (I-39)

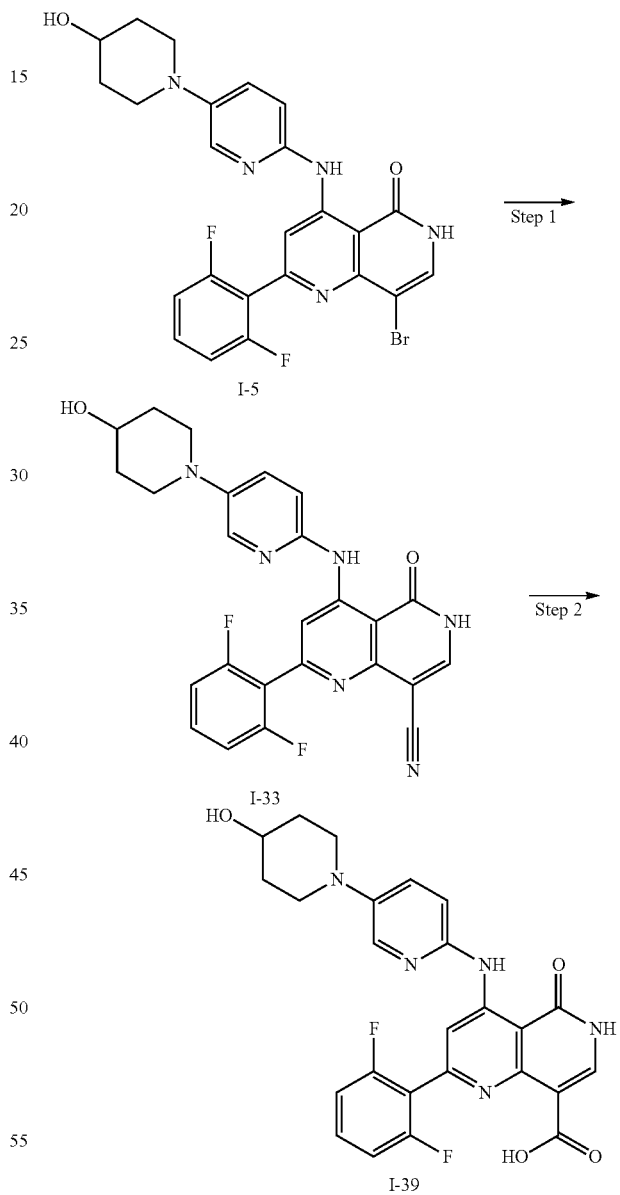

Step 1. 2-(2,6-difluorophenyl)-4-[[5-(4-hydroxy-1-piperidyl)-2-pyridyl]amino]-5-oxo-6H-1,6-naphthyridine-8-carbonitrile (I-33)

A microwave tube was charged with 8-bromo-2-(2,6-difluorophenyl)-4-[[5-(4-hydroxy-1-piperidyl)-2-pyridyl]amino]-6H-1,6-naphthyridin-5-one (I-5) (200 mg, 0.37 mmol), copper (I) cyanide (68 mg, 0.75 mmol) and DMF (2 mL). After stirring at 175° C. for 3 h in a microwave, the reaction mixture was cooled to RT and evaporated in vacuo to give a crude product which was purified by preparative HPLC to afford pure I-33 (9 mg, 5%) as a yellow solid. m/z=475 [M+H]+, 1H NMR (400 MHz, DMSO) δ 12.62-12.57 (m, 1H), 8.54 (s, 1H), 8.40 (s, 1H), 8.10 (d, J=2.5 Hz, 1H), 7.69-7.60 (m, 1H), 7.51 (dd, J=2.7, 9.0 Hz, 1H), 7.32 (dd, J=8.0, 8.0 Hz, 2H), 7.07 (d, J=9.1 Hz, 1H), 4.73-4.72 (m, 1H), 3.70-3.64 (m, 1H), 3.56 (d, J=12.1 Hz, 2H), 2.90 (dd, J=10.0, 10.0 Hz, 2H), 1.84 (d, J=9.6 Hz, 2H), 1.58-1.48 (m, 2H). One Exchangeable proton not observed

Step 2. 2-(2,6-difluorophenyl)-4-[[5-(4-hydroxy-1-piperidyl)-2-pyridyl]amino]-5-oxo-6H-1,6-naphthyridine-8-carboxylic Acid (I-39)

To a reaction tube charged with 2-(2,6-difluorophenyl)-4-[[5-(4-hydroxy-1-piperidyl)-2-pyridyl]amino]-5-oxo-6H-1,6-naphthyridine-8-carbonitrile (I-33) (70 mg, 0.14 mmol) in water (1.5 mL) and dioxane (2 mL) were added concentrated sulfuric acid (168 µL, 3.09 mmol). After stirring at 115° C. for 24 h, the pH of the reaction mixture was adjusted to pH 8 using NaHCO3 (insolubles formed). The mixture was diluted with ethyl acetate and filtered through a celite pad, washing with methanol and DMF. The filtrate was evaporated in vacuo to give a crude product which was purified by preparative HPLC to afford I-39 (10 mg, 14%) as a yellow solid. m/z=494 [M+H]+, 1H NMR (400 MHz, DMSO) δ 12.83-12.77 (m, 1H), 8.65 (s, 1H), 8.38 (s, 1H), 8.15 (d, J=2.8 Hz, 1H), 7.75-7.67 (m, 1H), 7.54 (dd, J=2.8, 8.8 Hz, 1H), 7.40 (dd, J=8.3, 8.3 Hz, 2H), 7.15 (d, J=8.8 Hz, 1H), 4.74 (s, 1H), 4.08 (s, 1H), 3.72-3.67 (m, 1H), 3.60 (dd, J=4.4, 8.2 Hz, 2H), 2.98-2.91 (m, 2H), 1.87 (dd, J=3.2, 12.8 Hz, 2H), 1.58-1.47 (m, 2H). 1 Exchangeable proton not observed

Example 10. Method J—Preparation of 2-(2,6-difluorophenyl)-4-[[5-(4-hydroxy-1-piperidyl)-2-pyridyl]amino]-8-methyl-6H-1,6-naphthyridin-5-one (I-25)

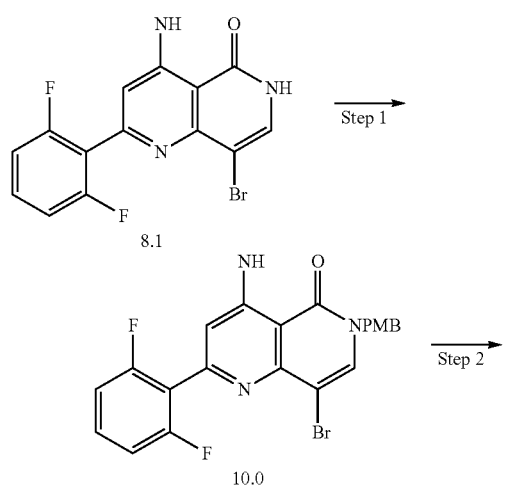

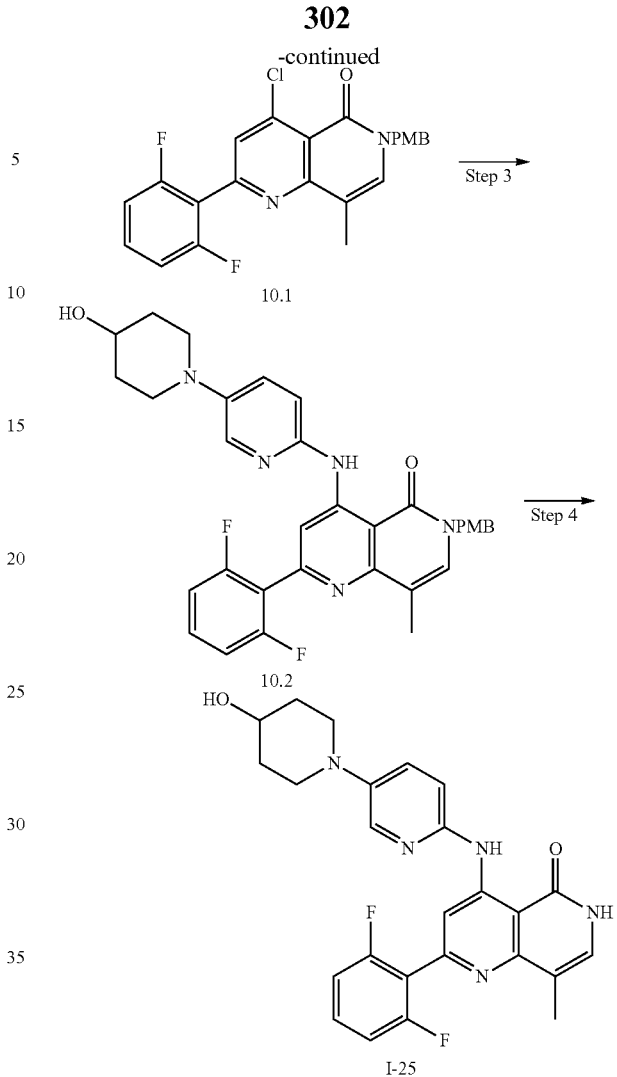

Step 1. 8-bromo-4-chloro-2-(2,6-difluorophenyl)-6-(4-methoxybenzyl)-1,6-naphthyridin-5(6H)-one (10.0)

To a solution of 8-Bromo-4-chloro-2-(2,6-difluorophenyl)-1,6-naphthyridin-5(6H)-one (8.1) (460 mg, 1.24 mmol) dissolved in DMF (10 mL) were added Potassium iodide (51 mg, 0.31 mmol), potassium carbonate (210 mg, 1.55 mmol) and 4-methoxybenzyl chloride (200 µL, 1.49 mmol). After stirring at RT for 2 h, the reaction mixture was diluted with water (20 mL) and a precipitate formed. The solid was collected by filtration and dried to give the desired product (10.0) (550 mg, 90%) as an off white solid. 1H NMR (400 MHz, DMSO) 8.56 (1H, s), 7.99 (1H, s), 7.75-7.66 (1H, m), 7.45-7.33 (4H, m), 7.00-6.95 (2H, m), 5.16 (2H, s), 3.80-3.78 (3H, m).

Step 2. 4-chloro-2-(2,6-difluorophenyl)-6-(4-methoxybenzyl)-8-methyl-1,6-naphthyridin-5(6H)-one (10.1)

To a carousel tube with 8-bromo-4-chloro-2-(2,6-difluorophenyl)-6-(4-methoxybenzyl)-1,6-naphthyridin-5(6H)-one (10.0) (150 mg, 0.30 mmol), methylboronic acid (21 mg, 0.35 mmol) and cesium carbonate (298 mg, 0.91 mmol)

in dioxane (1.5 mL) and water (0.15 mL) purged with nitrogen was added [1,1'-Bis(diphenylphosphino)ferrocene]dichloropalladium(II), complex with DCM (30 mg, 0.03 mmol), After stirring at 100° C. overnight, the reaction mixture was diluted water (10 mL) and brine (2 mL) and extracted with ethyl acetate (2×20 mL). The combined organic phases were dried (MgSO$_4$), filtered and the solvent was removed in vacuo to give a crude product which was purified by column chromatography eluting with 0-20% ethyl acetate in DCM to afford pure (10.1) (44 mg, 34%) as a yellow solid. $^1$H NMR (400 MHz, CDCl3) 7.59 (1H, s), 7.44-7.35 (1H, m), 7.35-7.22 (3H, m), 7.06-6.99 (2H, m), 6.91-6.85 (2H, m), 5.14-5.10 (2H, m), 3.81-3.79 (3H, m), 2.30-2.28 (3H, m).

Step 3. 2-(2,6-difluorophenyl)-4-((5-(4-hydroxypiperidin-1-yl)pyridin-2-yl)amino)-6-(4-methoxybenzyl)-8-methyl-1,6-naphthyridin-5(6H)-one (10.2)

Reaction was carried out following procedure outlined in Example 1, Method A, Step 2 using 4-chloro-2-(2,6-difluorophenyl)-6-(4-methoxybenzyl)-8-methyl-1,6-naphthyridin-5(6H)-one (10.1) and 1-(6-aminopyridin-3-yl)piperidin-4-ol to give the desired crude product (10.2) as a yellow solid which was used directly in the next step.

Step 4. 2-(2,6-difluorophenyl)-4-[[5-(4-hydroxy-1-piperidyl)-2-pyridyl]amino]-8-methyl-6H-1,6-naphthyridin-5-one (I-25)

A microwave tube was charged with 2-(2,6-difluorophenyl)-4-((5-(4-hydroxypiperidin-1-yl)pyridin-2-yl)amino)-6-(4-methoxybenzyl)-8-methyl-1,6-naphthyridin-5(6H)-one (10.2) (57 mg, 0.09 mmol) and TFA (1 mL). The tube was sealed and the reaction was heated at 165° C. for 4 h. The reaction solvent was removed in vacuo to give a crude product which was diluted in DCM (1 mL), methanol (2 mL) and 1M methanolic ammonia (4 mL) [caution!] and stirred for 1 h at RT before re-evaporating to dryness. The residue was purified by preparative HPLC to afford pure (I-25) (10 mg, 22%) as a yellow solid. m/z=464 [M+H]$^+$, $^1$H NMR (400 MHz, DMSO) δ 12.78 (s, 1H), 11.63 (s, 1H), 8.55 (s, 1H), 8.09 (d, J=2.8 Hz, 1H), 7.67-7.58 (m, 1H), 7.51 (dd, J=2.9, 9.0 Hz, 1H), 7.37 (s, 1H), 7.31 (dd, J=8.0, 8.0 Hz, 2H), 7.04 (d, J=8.8 Hz, 1H), 4.73 (s, 1H), 3.70-3.65 (m, 1H), 3.54 (d, J=12.9 Hz, 2H), 2.94-2.85 (m, 2H), 2.21 (s, 3H), 1.90-1.84 (m, 2H), 1.58-1.47 (m, 2H).

Example 11. Method K—Preparation of 2-(2,6-difluorophenyl)-8-ethyl-4-((5-(4-hydroxypiperidin-1-yl)pyridin-2-yl)amino)-1,6-naphthyridin-5(6H)-one (I-49)

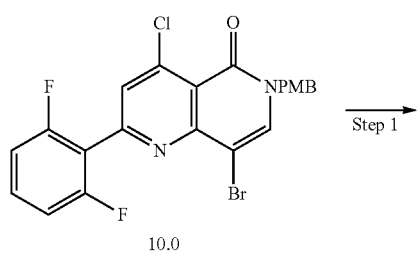

10.0

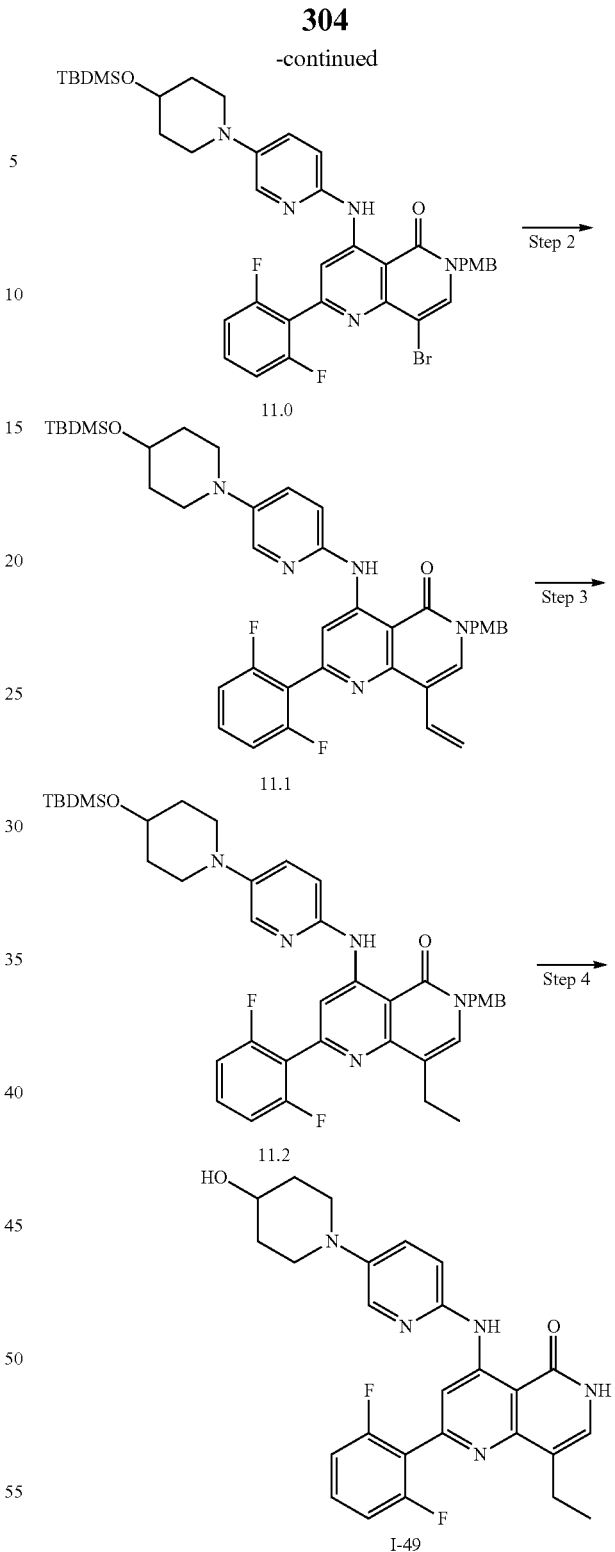

Step 1. 8-bromo-4-((5-(4-((tert-butyldimethylsilyl)oxy)piperidin-1-yl)pyridin-2-yl)amino)-2-(2,6-difluorophenyl)-6-(4-methoxybenzyl)-1,6-naphthyridin-5(6H)-one (11.0)

Reaction was carried out following procedure outlined in Example 1, Method A, Step 2 using 8-bromo-4-chloro-2-(2,6-difluorophenyl)-6-(4-methoxybenzyl)-1,6-naphthyridin-5

(6H)-one (10.0) and 5-(4-((tert-butyldimethylsilyl)oxy)piperidin-1-yl)pyridin-2-amine to give the desired crude product (11.0) as a yellow solid which was used in next step without further purification.

Step 2. 4-((5-(4-((tert-butyldimethylsilyl)oxy)piperidin-1-yl)pyridin-2-yl)amino)-2-(2,6-difluorophenyl)-6-(4-methoxybenzyl)-8-vinyl-1,6-naphthyridin-5(6H)-one (11.1)

Reaction was carried out following procedure outlined in Example 10. Method J, Step 2 using 8-bromo-4-((5-(4-((tert-butyldimethylsilyl)oxy)piperidin-1-yl)pyridin-2-yl)amino)-2-(2,6-difluorophenyl)-6-(4-methoxybenzyl)-1,6-naphthyridin-5(6H)-one (11.0) and vinylboronic acid pinacol ester to give the desired product (11.1) as a yellow solid at purity of 75%. The product was used in the next step without further purification.

Step 3. 4-((5-(4-((tert-butyldimethylsilyl)oxy)piperidin-1-yl)pyridin-2-yl)amino)-2-(2,6-difluorophenyl)-8-ethyl-6-(4-methoxybenzyl)-1,6-naphthyridin-5(6H)-one (11.2)

A solution of 4-((5-(4-((tert-butyldimethylsilyl)oxy)piperidin-1-yl)pyridin-2-yl)amino)-2-(2,6-difluorophenyl)-6-(4-methoxybenzyl)-8-vinyl-1,6-naphthyridin-5(6H)-one (11.1) (117 mg, 0.16 mmol) in methanol (20 mL) was passed through a H-Cube® using a 10% Pd/C cartridge (RT, atmospheric pressure). The solvent was removed in vacuo to give a crude product which was purified by column chromatography eluting with 0-100% diethyl ether in DCM to give the desired product (11.2) (53 mg, 45%) as a yellow solid. $^1$H NMR (400 MHz, CDCl3) 12.51-12.47 (1H, m), 8.49 (1H, s), 7.98-7.95 (1H, m), 7.30-7.23 (1H, m), 7.22-7.18 (2H, m), 7.01-6.98 (1H, m), 6.91 (4H, q, J=7.7 Hz), 6.82 (2H, d, J=8.6 Hz), 5.06 (2H, s), 3.84-3.78 (1H, m), 3.75-3.71 (3H, m), 3.35-3.28 (2H, m), 2.96-2.88 (2H, m), 2.75-2.64 (2H, m), 1.84-1.76 (2H, m), 1.65-1.59 (2H, m), 0.84-0.81 (12H, m), 0.00 (6H, s).

Step 4. 2-(2,6-difluorophenyl)-8-ethyl-4-((5-(4-hydroxypiperidin-1-yl)pyridin-2-yl)amino)-1,6-naphthyridin-5(6H)-one (I-49)

Reaction was carried out following procedure outlined in Example 10. Method J, Step 4 using 4-((5-(4-((tert-butyldimethylsilyl)oxy)piperidin-1-yl)pyridin-2-yl)amino)-2-(2,6-difluorophenyl)-8-ethyl-6-(4-methoxybenzyl)-1,6-naphthyridin-5(6H)-one (11.2). The crude residue was purified by preparative HPLC to afford pure (I-49) (8 mg, 24%) as a yellow solid. m/z=478 [M+H]$^+$, $^1$H NMR (400 MHz, DMSO) δ 12.78 (s, 1H), 11.71-11.65 (m, 1H), 8.60-8.53 (m, 1H), 8.09 (d, J=2.8 Hz, 1H), 7.67-7.57 (m, 1H), 7.51 (dd, J=2.8, 9.1 Hz, 1H), 7.35-7.27 (m, 3H), 7.06-7.02 (m, 1H), 4.72 (s, 1H), 3.72-3.63 (m, 1H), 3.59-3.51 (m, 2H), 2.93-2.87 (m, 2H), 2.71 (q, J=7.2 Hz, 2H), 1.86 (d, J=9.6 Hz, 2H), 1.58-1.47 (m, 2H), 1.22 (t, J=7.5 Hz, 3H).

Example 12. Method L—Preparation of 4-[[5-(4-hydroxy-1-piperidyl)-2-pyridyl]amino]-2-isopropyl-8-methyl-6H-1,6-naphthyridin-5-one (I-89) and 4-[[5-(4-hydroxy-1-piperidyl)-2-pyridyl]amino]-8-methyl-6H-1,6-naphthyridin-5-one (I-90)

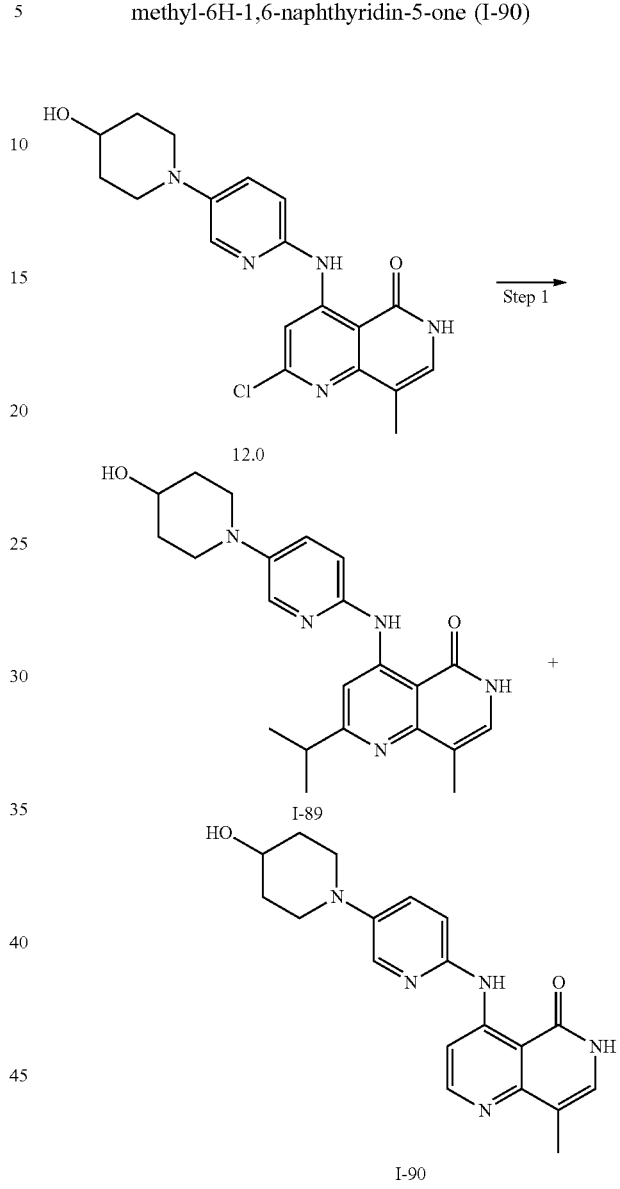

Step 1. 4-[[5-(4-hydroxy-1-piperidyl)-2-pyridyl]amino]-2-isopropyl-8-methyl-6H-1,6-naphthyridin-5-one (I-89) and 4-[[5-(4-hydroxy-1-piperidyl)-2-pyridyl]amino]-8-methyl-6H-1,6-naphthyridin-5-one (I-90)

2-chloro-4-((5-(4-hydroxypiperidin-1-yl)pyridin-2-yl)amino)-8-methyl-1,6-naphthyridin-5(6H)-one (12.0) (100 mg, 0.25 mmol, prepared following procedure outlined in Example 1, Method A using ethyl 4,6-dichloro-2-ethylnicotinate) and iron III acetylacetonate (18 mg, 0.05 mmol) dissolved in THF (3 mL) and NMP (1 mL). The mixture was cooled to −45° C. and isopropylmagnesium chloride (1.9 mL, 3.89 mmol, 2M in THF) was added dropwise over 15 minutes. The reaction was stirred at −10° C. for 1 h, then at RT for 1.5 h. The reaction was cooled to −15° C. and then quenched using saturated aqueous ammonium chloride (5 mL). The mixture was allowed to warm to RT, diluted with water (5 mL), and extracted with ethyl acetate (2×25 mL). The combined organic extracts were passed through a Isolute phase separator and the solvent was removed in vacuo to give a crude product which was purified by preparative HPLC to afford pure 4-[[5-(4-hydroxy-1-piperidyl)-2-pyridyl]amino]-2-isopropyl-8-methyl-6H-1,6-naphthyridin-5-one (I-89) (10 mg, 10%) as a yellow solid. m/z=394 [M+H]$^+$, $^1$H NMR (400 MHz, DMSO) δ 12.54 (s, 1H), 11.39 (s, 1H), 8.28 (s, 1H), 8.13 (d, J=3.0 Hz, 1H), 7.51 (dd, J=2.8, 8.8 Hz, 1H), 7.27 (s, 1H), 7.01 (d, J=8.8 Hz, 1H), 4.74 (d, J=4.0 Hz, 1H), 3.72-3.66 (m, 1H), 3.58-3.52 (m, 2H), 3.05-2.97 (m, 1H), 2.96-2.88 (m, 2H), 2.25 (s, 3H), 1.93-1.87 (m, 2H), 1.61-1.50 (m, 2H), 1.32 (d, J=7.1 Hz, 6H); and 4-[[5-(4-hydroxy-1-piperidyl)-2-pyridyl]amino]-8-methyl-6H-1,6-naphthyridin-5-one (I-90) (17 mg, 19%) as a yellow solid. m/z=352 [M+H]$^+$, $^1$H NMR (400 MHz, DMSO) δ 12.62 (s, 1H), 11.51 (d, J=4.7 Hz, 1H), 8.55 (d, J=5.8 Hz, 1H), 8.32 (d, J=6.0 Hz, 1H), 8.12 (d, J=2.8 Hz, 1H), 7.51 (dd, J=2.8, 8.8 Hz, 1H), 7.30 (d, J=4.8 Hz, 1H), 7.03 (d, J=8.8 Hz, 1H), 4.77 (s, 1H), 3.72-3.65 (m, 1H), 3.59-3.51 (m, 2H), 2.94-2.87 (m, 2H), 2.24 (s, 3H), 1.87 (dd, J=4.5, 7.9 Hz, 2H), 1.61-1.50 (m, 2H).

Example 13: Method M—Preparation of 2-acetyl-4-[[5-(4-hydroxy-1-piperidyl)-2-pyridyl]amino]-6H-1,6-naphthyridin-5-one (I-47), 2-(1-hydroxyethyl)-4-[[5-(4-hydroxy-1-piperidyl)-2-pyridyl]amino]-6H-1,6-naphthyridin-5-one (I-37), 2-(1-hydroxy-1-methyl-ethyl)-4-[[5-(4-hydroxy-1-piperidyl)-2-pyridyl]amino]-6H-1,6-naphthyridin-5-one (I-38) and 4-[[5-(4-hydroxy-1-piperidyl)-2-pyridyl]amino]-2-(2,2,2-trifluoro-1-hydroxy-1-methyl-ethyl)-6H-1,6-naphthyridin-5-one (I-77)

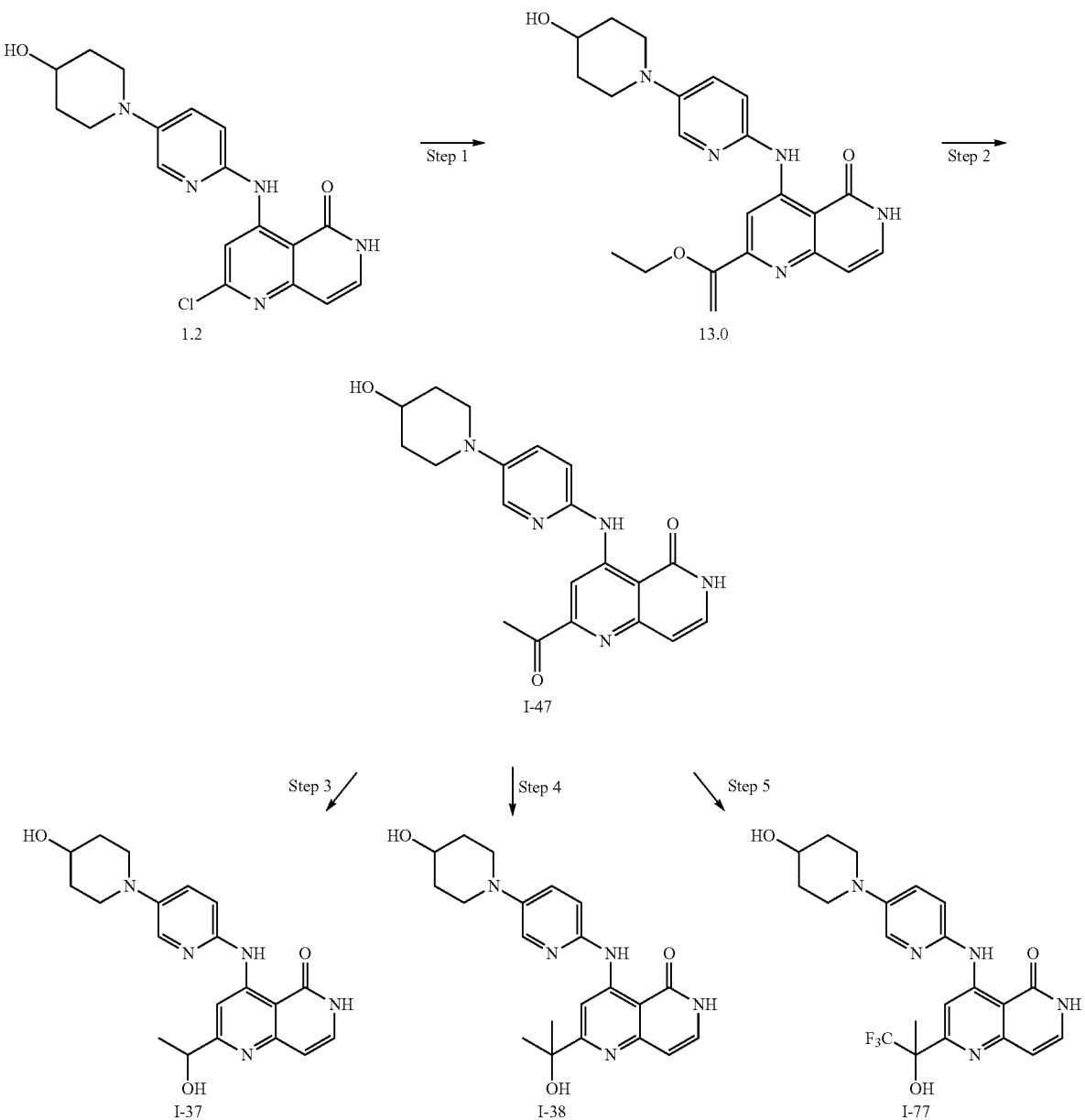

Step 1. 2-(1-ethoxyvinyl)-4-((5-(4-hydroxypiperi-din-1-yl)pyridin-2-yl)amino)-1,6-naphthyridin-5(6H)-one (13.0)

Reaction was carried out following procedure outlined in Example 8. Method H, Step 3 using 2-chloro-4-((5-(4-hydroxypiperidin-1l-yl)pyridin-2-yl)amino)-1,6-naphthyridin-5(6H)-one (1.2) and tributyl(1-ethoxyvinyl)tin to give the desired product (13.0) as a yellow solid. $^1$H NMR (400 MHz, DMSO) 12.33 (1H, s), 11.56-11.52 (1H, m), 8.58 (1H, s), 8.08 (1H, d, J=3.0 Hz), 7.50-7.46 (1H, m), 7.36 (1H, dd, J=5.8, 7.2 Hz), 7.02-6.99 (1H, m), 6.52-6.49 (1H, m), 5.47 (1H, d, J=1.1 Hz), 4.72-4.70 (1H, m), 4.49 (1H, s), 3.95 (2H, q, J=7.0 Hz), 3.68-3.62 (1H, m), 3.57-3.49 (2H, m), 2.92-2.84 (2H, m), 1.89-1.81 (2H, m), 1.57-1.46 (2H, m), 1.42-1.37 (3H, m).

Step 2. 2-acetyl-4-[[5-(4-hydroxy-1-piperidyl)-2-pyridyl]amino]-6H-1,6-naphthyridin-5-one (I-47)

To a solution of 2-(1-ethoxyvinyl)-4-((5-(4-hydroxypiperidin-1l-yl)pyridin-2-yl)amino)-1,6-naphthyridin-5(6H)-one (13.0) (191 mg, 0.46 mmol) dissolved in THF (5 mL) was added 4M HCl solution (5 mL). After stirring at RT overnight, the mixture was concentrated under vacuum and the residue was partitioned between aqueous NaHCO$_3$ and ethyl acetate. The organic phase was collected and washed with brine, dried (Na$_2$SO$_4$) and the solvent was removed in vacuo to afford (I-47) (158 mg, 88%) as an orange solid. m/z=380 [M+H]$^+$, $^1$H NMR (400 MHz, DMSO) δ 12.46 (s, 1H), 11.78 (s, 1H), 8.71 (s, 1H), 8.15-8.10 (m, 1H), 7.53-7.42 (m, 2H), 7.02 (d, J=8.8 Hz, 1H), 6.63 (d, J=7.3 Hz, 1H), 4.71 (s, 1H), 3.71-3.49 (m, 3H), 2.96-2.84 (m, 2H), 2.65 (s, 3H), 1.85 (s, 2H), 1.53 (t, J=9.3 Hz, 2H).

Step 3. 2-(1-hydroxyethyl)-4-[[5-(4-hydroxy-1-piperidyl)-2-pyridyl]amino]-6H-1,6-naphthyridin-5-one (I-37)

Reaction was carried out following procedure outlined in Example 8: Method H, step 4 using 2-acetyl-4-[[5-(4-hydroxy-1-piperidyl)-2-pyridyl]amino]-6H-1,6-naphthyridin-5-one (I-47) to afford (I-37) as a yellow solid. m/z=382 [M+H]$^+$, $^1$H NMR (400 MHz, DMSO) δ 12.32 (s, 1H), 11.53 (d, J=5.0 Hz, 1H), 8.29 (s, 1H), 8.22 (s, 1H), 8.09 (d, J=3.0 Hz, 1H), 7.48 (dd, J=3.1, 9.0 Hz, 1H), 7.35 (dd, J=5.5, 7.0 Hz, 1H), 7.02 (d, J=8.9 Hz, 1H), 6.48 (d, J=7.3 Hz, 1H), 5.36 (s, 1H), 4.65 (q, J=6.5 Hz, 1H), 3.69-3.51 (m, 3H), 2.93-2.84 (m, 2H), 1.89-1.81 (m, 2H), 1.57-1.46 (m, 2H), 1.37 (d, J=6.7 Hz, 3H).

Step 4. 2-(1-hydroxy-1-methyl-ethyl)-4-[[5-(4-hydroxy-1-piperidyl)-2-pyridyl]amino]-6H-1,6-naphthyridin-5-one (I-38)

Reaction was carried out following procedure outlined in Example 8: Method H, step 5 using 2-acetyl-4-[[5-(4-hydroxy-1-piperidyl)-2-pyridyl]amino]-6H-1,6-naphthyridin-5-one (I-47) to afford (I-38) as a yellow solid. m/z=396 [M+H]$^+$, $^1$H NMR (400 MHz, DMSO) δ 12.32 (s, 1H), 11.59-11.54 (m, 1H), 8.44 (s, 1H), 8.13 (d, J=2.5 Hz, 1H), 7.51 (dd, J=2.9, 9.0 Hz, 1H), 7.38 (d, J=7.3 Hz, 1H), 7.10-7.05 (m, 1H), 6.53 (d, J=7.3 Hz, 1H), 5.26 (s, 1H), 4.75 (d, J=3.8 Hz, 1H), 3.74-3.67 (m, 1H), 3.61-3.53 (m, 2H), 2.97-2.88 (m, 2H), 1.93-1.87 (m, 2H), 1.62-1.52 (m, 2H), 1.50 (s, 6H).

Step 5. 4-[[5-(4-hydroxy-1-piperidyl)-2-pyridyl]amino]-2-(2,2,2-trifluoro-1-hydroxy-1-methyl-ethyl)-6H-1,6-naphthyridin-5-one (I-77)

Reaction was carried out following procedure outlined in Method CB8, step 1 using 2-acetyl-4-[[5-(4-hydroxy-1-piperidyl)-2-pyridyl]amino]-6H-1,6-naphthyridin-5-one (I-47) to afford (I-77) as a yellow solid. m/z=450 [M+H]$^+$, $^1$H NMR (400 MHz, DMSO) δ 12.43 (s, 1H), 11.71 (s, 1H), 8.64 (s, 1H), 8.14 (d, J=2.8 Hz, 1H), 7.53 (dd, J=2.9, 9.0 Hz, 1H), 7.45 (d, J=7.3 Hz, 1H), 7.06 (d, J=8.8 Hz, 1H), 6.75 (s, 1H), 6.58 (d, J=7.1 Hz, 1H), 4.74 (d, J=4.3 Hz, 1H), 3.73-3.67 (m, 1H), 3.63-3.55 (m, 2H), 2.98-2.90 (m, 2H), 1.88 (d, J=9.9 Hz, 2H), 1.75 (s, 3H), 1.61-1.49 (m, 2H).

Example 14: Method N—Preparation of 4-[[5-(4-hydroxy-1-piperidyl)-2-pyridyl]amino]-2-tetrahydropyran-4-yl-6H-1,6-naphthyridin-5-one (I-36)

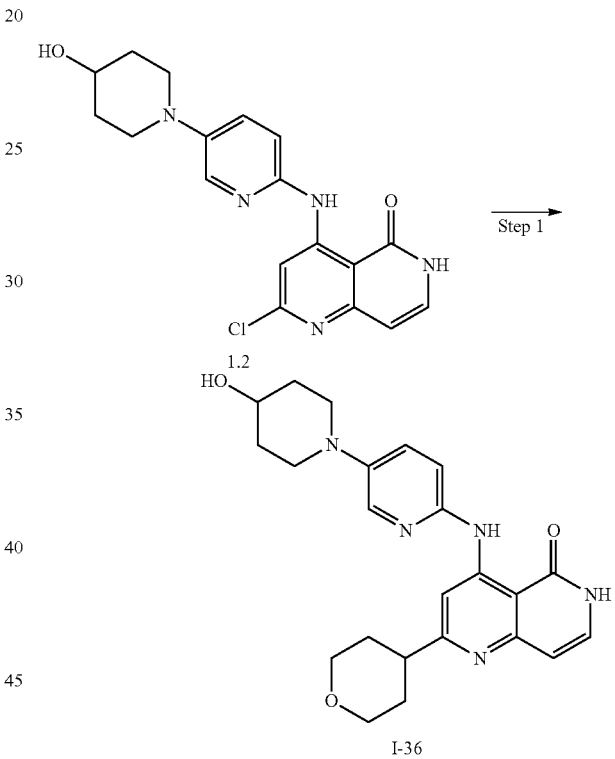

I-36

To a microwave tube charged with 2-chloro-4-((5-(4-hydroxypiperidin-1-yl)pyridin-2-yl)amino)-1,6-naphthyridin-5(6H)-one (1.2) (70 mg, 0.18 mmol) in THF (2 mL) was added RuPhos Pd G2 (15 mg, 0.018 mmol). The mixture was purged with nitrogen for 5 minutes and then (tetrahydro-2H-pyran-4-yl)zinc bromide (0.6 M in THF, 3 mL, 1.8 mmol) was added. After stirring at 120° C. for 1 h, the reaction mixture was dry loaded onto silica and was purified by column chromatography eluting with 0-20% 7N methanolic ammonia in DCM to give a crude residue which was further purified by preparative HPLC to afford pure (I-36) (19 mg, 24%) as a yellow solid. m/z=422 [M+H]$^+$, $^1$H NMR (400 MHz, DMSO) δ 12.33 (s, 1H), 11.56-11.50 (m, 1H), 8.21 (s, 1H), 8.10 (d, J=3.0 Hz, 1H), 7.47 (dd, J=3.1, 9.0 Hz, 1H), 7.35 (dd, J=5.5, 7.0 Hz, 1H), 6.99 (d, J=8.9 Hz, 1H), 6.49 (d, J=7.2 Hz, 1H), 4.72 (s, 1H), 4.00-3.94 (m, 2H), 3.69-3.61 (m, 1H), 3.57-3.42 (m, 4H), 2.92-2.82 (m, 3H), 1.88-1.75 (m, 6H), 1.57-1.46 (m, 2H).

Example 15: Method O—Preparation of 2-(1-acetyl-4-piperidyl)-4-[[5-(4-hydroxy-1-piperidyl)-2-pyridyl]amino]-6H-1,6-naphthyridin-5-one (I-63) and 4-[[5-(4-hydroxy-1-piperidyl)-2-pyridyl]amino]-2-(1-methyl-4-piperidyl)-6H-1,6-naphthyridin-5-one (I-75)

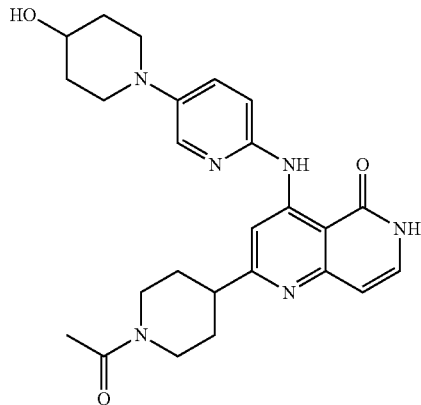
I-63

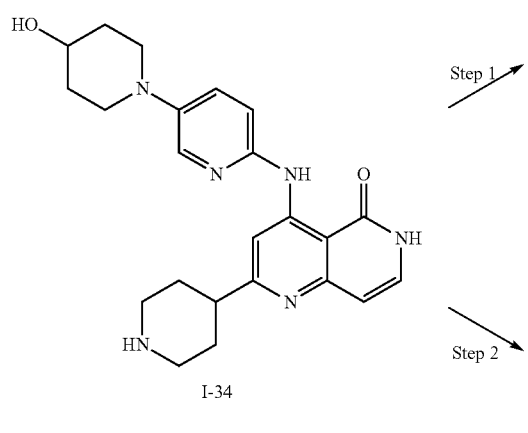
I-34

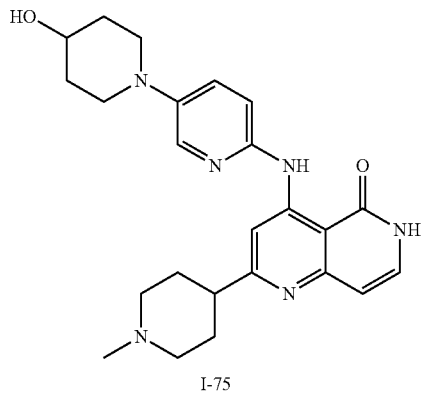
I-75

Step 1. 2-(1-acetyl-4-piperidyl)-4-[[5-(4-hydroxy-1-piperidyl)-2-pyridyl]amino]-6H-1,6-naphthyridin-5-one (I-63)

To a solution of 4-[[5-(4-hydroxy-1-piperidyl)-2-pyridyl]amino]-2-(4-piperidyl)-6H-1,6-naphthyridin-5-one (I-34) (80 mg, 0.19 mmol) in DCM (5 mL) at 0° C. was added acetic anhydride (0.1 mL). After stirring at RT overnight, the reaction was quenched with 2 drops of 2N HCl solution and diluted with water (5 mL). The mixture was passed through an Isolute hydrophobic filter and the organic layer was evaporated in vacuo to give a crude residue which was purified by preparative HPLC to afford pure (I-63) (7 mg, 8%) as a yellow solid. m/z=463 [M+H]$^+$, $^1$H NMR (400 MHz, DMSO) δ 12.34 (s, 1H), 11.55 (d, J=2.3 Hz, 1H), 8.37-8.31 (m, 1H), 8.11 (d, J=6.5 Hz, 1H), 8.06 (d, J=3.3 Hz, 1H), 7.46 (dd, J=3.0, 9.0 Hz, 1H), 7.34 (d, J=7.3 Hz, 1H), 7.00 (d, J=8.8 Hz, 1H), 6.52 (d, J=7.3 Hz, 1H), 4.52-4.47 (m, 1H), 3.95-3.91 (m, 1H), 3.68-3.61 (m, 1H), 3.54-3.46 (m, 2H), 3.18-3.10 (m, 1H), 2.89-2.80 (m, 3H), 2.68-2.60 (m, 1H), 2.04 (s, 3H), 1.89-1.80 (m, 4H), 1.71-1.44 (m, 4H). (1 eq. formate salt, 1 exchangeable proton not observed).

Step 2. 4-[[5-(4-hydroxy-1-piperidyl)-2-pyridyl]amino]-2-(1-methyl-4-piperidyl)-6H-1,6-naphthyridin-5-one (I-75)

To a solution of 4-[[5-(4-hydroxy-1-piperidyl)-2-pyridyl]amino]-2-(4-piperidyl)-6H-1,6-naphthyridin-5-one (I-34) (30 mg, 0.07 mmol) in methanol (5 mL) with a drop of acetic acid were added 37% formaldehyde solution (11 μL, 0.14 mmol) and sodium cyanoborohydride (5 mg, 0.07 mmol). After stirring at RT overnight, the mixture was evaporated in vacuo to give a crude residue which was purified by preparative HPLC to afford pure (I-75) (17 mg, 54%) as a yellow solid. m/z=435 [M+H]$^+$, $^1$H NMR (400 MHz, DMSO) δ 13.08 (s, 1H), 12.49 (s, 1H), 9.71-9.70 (m, 1H), 8.32-8.28 (m, 1H), 8.15-8.13 (m, 1H), 7.77 (s, 1H), 7.58-7.53 (m, 1H), 7.26-7.20 (m, 1H), 6.70 (s, 1H), 3.73-3.56 (m, 5H), 3.17-3.08 (m, 3H), 3.02-2.94 (m, 2H), 2.87 (s, 3H), 2.24-2.20 (m, 2H), 2.01-1.82 (m, 4H), 1.55-1.45 (m, 2H). (1 eq. formate salt, 1 exchangeable proton not observed).

Example 16: Method P—Preparation of 2-(2,8-diazaspiro[4.5]decan-8-yl)-4-[[5-(4-hydroxy-1-piperidyl)-2-pyridyl]amino]-6H-1,6-naphthyridin-5-one (I-235) and 2-[2-(cyclopropanecarbonyl)-2,8-diazaspiro[4.5]decan-8-yl]-4-[[5-(4-hydroxy-1-piperidyl)-2-pyridyl]amino]-6H-1,6-naphthyridin-5-one (I-233)

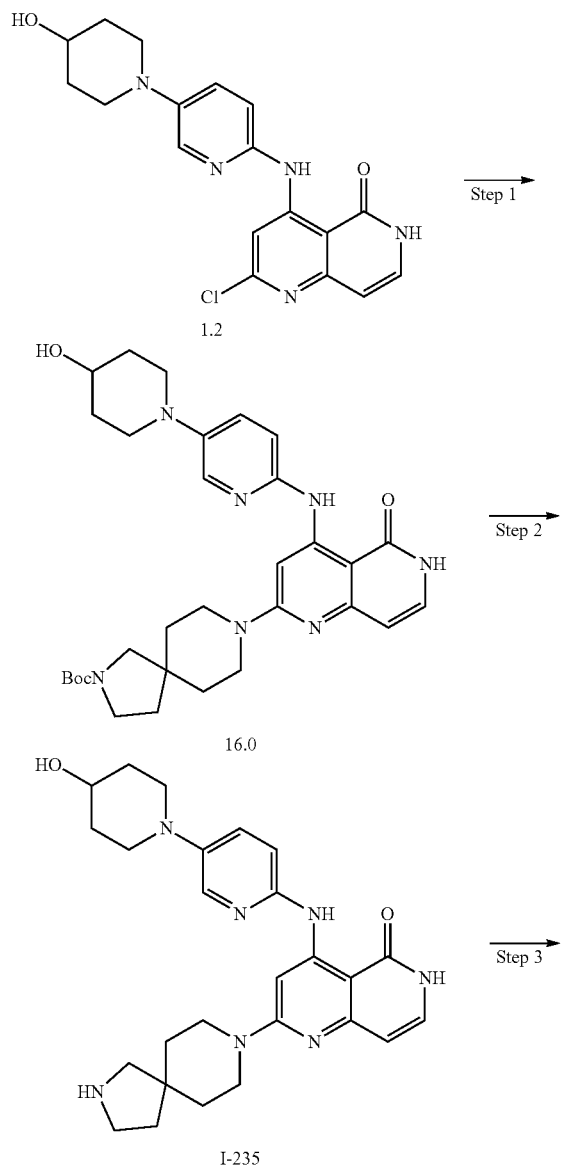

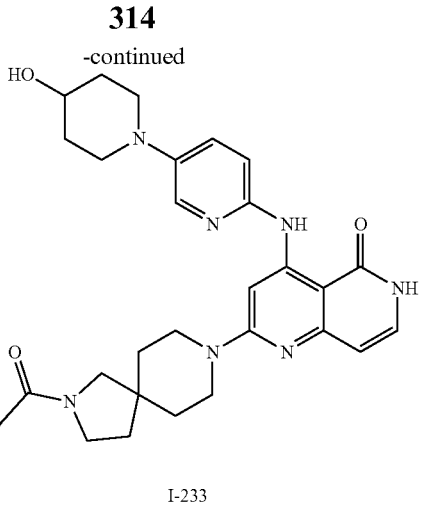

I-233

Step 1. tert-butyl 8-(4-((5-(4-hydroxypiperidin-1-yl)pyridin-2-yl)amino)-5-oxo-5,6-dihydro-1,6-naphthyridin-2-yl)-2,8-diazaspiro[4.5]decane-2-carboxylate (16.0)

A reaction tube was charged with 2-chloro-4-((5-(4-hydroxypiperidin-1-yl)pyridin-2-yl)amino)-1,6-naphthyridin-5(6H)-one (1.2) (250 mg, 0.67 mmol), tert-butyl 2,8-diazaspiro[4.5]decane-2-carboxylate (323 mg, 1.34 mmol) in DMSO (6 mL). After stirring sealed at 120° C. overnight, the reaction mixture was diluted with ethyl acetate and washed with brine. The organic layer was dried (MgSO$_4$), filtered, and the solvent was evaporated in vacuo to give a crude residue which was purified by column chromatography eluting with 0-100% ethyl acetate in hexane to afford 16.0 (300 mg) at about 80% purity which was used in the next step without further purification.

Step 2. 2-(2,8-diazaspiro[4.5]decan-8-yl)-4-[[5-(4-hydroxy-1-piperidyl)-2-pyridyl]amino]-6H-1,6-naphthyridin-5-one (I-235)

Reaction was carried out following procedure outlined in Example 7, Method G using tert-butyl 8-(4-((5-(4-hydroxypiperidin-1-yl)pyridin-2-yl)amino)-5-oxo-5,6-dihydro-1,6-naphthyridin-2-yl)-2,8-diazaspiro[4.5]decane-2-carboxylate (16.0) to afford I-235 as a yellow gum. m/z=476 [M+H]$^+$, $^1$H NMR (400 MHz, DMSO) δ 12.31 (s, 1H), 11.21 (s, 1H), 8.43 (s, 1H), 8.08 (d, J=2.5 Hz, 1H), 7.99 (s, 1H), 7.48 (dd, J=2.5, 8.8 Hz, 1H), 7.26 (d, J=7.3 Hz, 1H), 6.93 (d, J=8.8 Hz, 1H), 6.28 (d, J=7.3 Hz, 1H), 4.75 (s, 1H), 3.75-3.49 (m, 6H), 3.23 (s, 1H), 3.19 (t, J=7.0 Hz, 2H), 2.97 (s, 2H), 2.90 (t, J=11.2 Hz, 2H), 1.90-1.77 (m, 4H), 1.66-1.51 (m, 6H). (1 eq. formate salt, 1 exchangeable proton not observed)

Step 3. 2-[2-(cyclopropanecarbonyl)-2,8-diazaspiro[4.5]decan-8-yl]-4-[[5-(4-hydroxy-1-piperidyl)-2-pyridyl]amino]-6H-1,6-naphthyridin-5-one (I-233)

Reaction was carried out following procedure outlined in Method CB2, step 1 using 2-(2,8-diazaspiro[4.5]decan-8-yl)-4-[[5-(4-hydroxy-1-piperidyl)-2-pyridyl]amino]-6H-1,6-naphthyridin-5-one (I-235) and cyclopropanecarbonyl chloride to afford I-233 as a yellow solid. m/z=544 [M+H]$^+$, $^1$H NMR (400 MHz, DMSO) δ 12.26 (d, J=2.6 Hz, 1H), 11.15 (s, 1H), 8.04 (dd, J=2.4, 2.4 Hz, 1H), 7.97 (d, J=4.9

Hz, 1H), 7.44 (dd, J=3.0, 8.9 Hz, 1H), 7.25-7.19 (m, 1H), 6.90 (d, J=9.0 Hz, 1H), 6.24 (dd, J=1.6, 7.2 Hz, 1H), 4.71-4.70 (m, 1H), 3.78-3.41 (m, 10H), 3.26 (s, 1H), 2.89-2.80 (m, 2H), 1.92-1.75 (m, 5H), 1.63-1.46 (m, 6H), 0.76-0.70 (m, 4H).

Example 17: Method Q—Preparation of 4-[[3-(2,6-difluorophenyl)-8-oxo-7H-2,7-naphthyridin-1-yl]amino]-N-ethyl-benzamide (I-7)

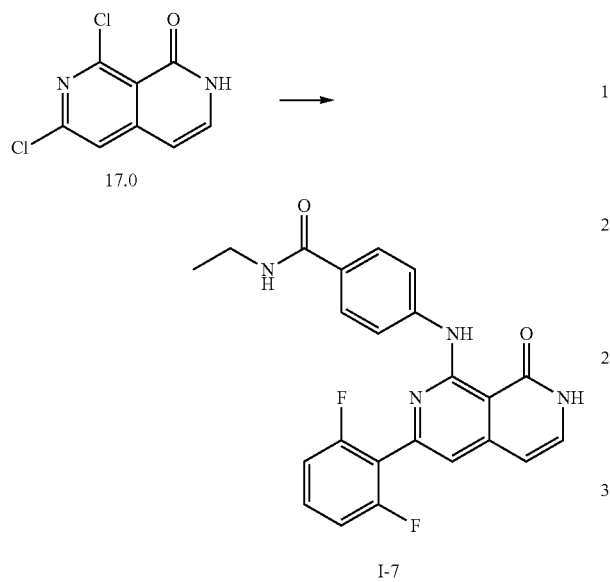

The title compound was prepared from 6,8-dichloro-2,7-naphthyridin-1(2H)-one (17.0) according to procedures described in Tett Lett, 2013 54(15), pg 2014 and WO2012097683 using 4-amino-N-ethylbenzamide and 2-bromo-1,3-difluorobenzene to afford I-7. m/z=421 [M+H]+, $^1$H NMR (400 MHz, DMSO) δ 12.25 (s, 1H), 11.99 (s, 1H), 8.30 (dd, J=5.5, 5.5 Hz, 1H), 7.89 (d, J=8.9 Hz, 2H), 7.82 (d, J=8.8 Hz, 2H), 7.64-7.56 (m, 1H), 7.51 (d, J=6.9 Hz, 1H), 7.31 (dd, J=8.2, 8.2 Hz, 2H), 7.19 (s, 1H), 6.63 (d, J=7.0 Hz, 1H), 3.32-3.23 (m, 2H), 1.12 (t, J=7.2 Hz, 3H).

Example 18: Method R—Preparation of 7-(2,6-difluorophenyl)-5-[[5-(4-hydroxy-1-piperidyl)-2-pyridyl]amino]-3H-pyrido[2,3-d]pyrimidin-4-one (I-11)

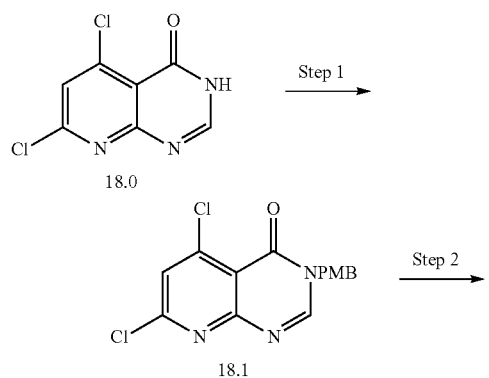

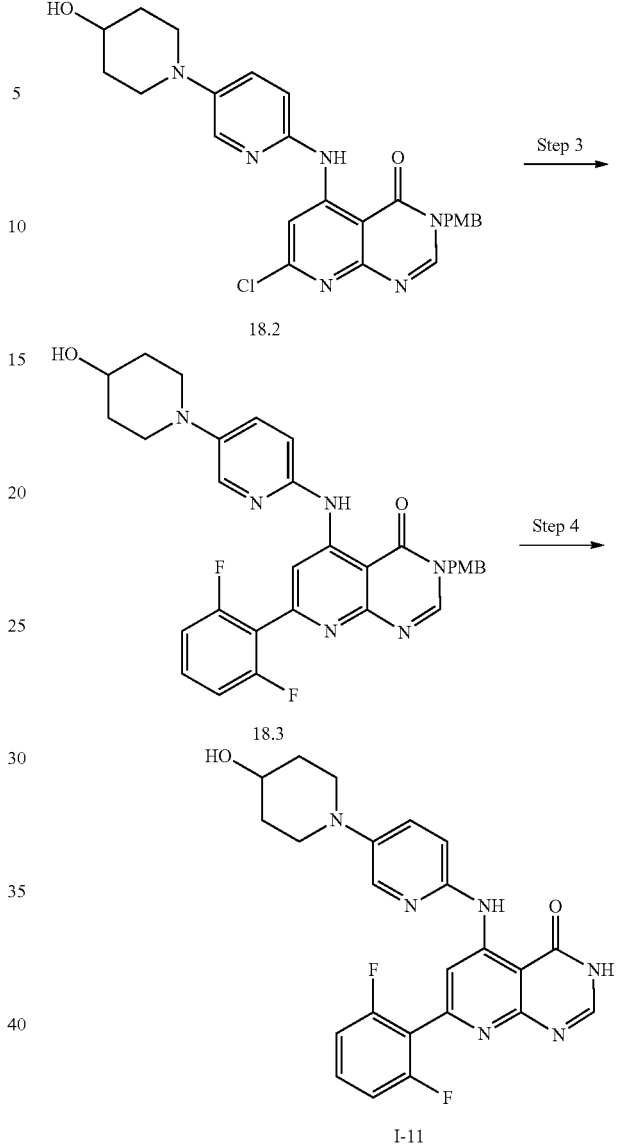

Step 1. 5,7-dichloro-3-(4-methoxybenzyl)pyrido[2,3-d]pyrimidin-4(3H)-one (18.1)

Reaction was carried out following procedure outlined in Example 10, Method J, step 1 using 5,7-dichloropyrido[2,3-d]pyrimidin-4(3H)-one (18.0) (described in WO2012097683) to afford 18.1 as a yellow solid. $^1$H NMR (400 MHz, DMSO) 8.95-8.93 (1H, m), 7.91-7.89 (1H, m), 7.45-7.39 (2H, m), 6.99-6.93 (2H, m), 5.15-5.12 (2H, m), 3.79-3.77 (3H, m).

Step 2. 7-chloro-5-((5-(4-hydroxypiperidin-1-yl)pyridin-2-yl)amino)-3-(4-methoxybenzyl)pyrido[2,3-d]pyrimidin-4(3H)-one (18.2)

Reaction was carried out following procedure outlined in Example 1, Method A, Step 2 using 5,7-dichloro-3-(4-methoxybenzyl)pyrido[2,3-d]pyrimidin-4(3H)-one (18.1) and 1-(6-aminopyridin-3-yl)piperidin-4-ol to afford 18.2 as a brown solid. $^1$H NMR (400 MHz, DMSO) 11.78-11.75

(1H, m), 8.83 (1H, s), 8.48-8.46 (1H, m), 8.20-8.16 (1H, m), 7.52 (1H, q, J=3.8 Hz), 7.42 (2H, d, J=8.6 Hz), 7.14-7.09 (1H, m), 7.01-6.95 (2H, m), 5.20-5.16 (2H, m), 4.77-4.73 (1H, m), 3.78 (3H, s), 3.74-3.68 (1H, m), 3.62-3.54 (2H, m), 2.97-2.91 (2H, m), 1.88 (2H, d, J=14.0 Hz), 1.57-1.48 (2H, m).

Step 3. 7-(2,6-difluorophenyl)-5-((5-(4-hydroxypiperidin-1-yl)pyridin-2-yl)amino)-3-(4-methoxybenzyl)pyrido[2,3-d]pyrimidin-4(3H)-one (18.3)

To a carousel tube charged with 7-chloro-5-((5-(4-hydroxypiperidin-1-yl)pyridin-2-yl)amino)-3-(4-methoxybenzyl)pyrido[2,3-d]pyrimidin-4(3H)-one (18.2) (140 mg, 0.28 mmol), 2,6-difluorophenyltributyltin (229 mg, 0.56 mmol) and dioxane (2 mL) purged with N₂ were added. Copper I iodide (11 mg, 0.05 mmol) and bis(triphenylphosphine) palladium chloride (20 mg, 0.02 mmol). After stirring sealed at 120° C. overnight, the reaction was cooled and filtered through celite. The volatiles were removed under reduced pressure and the crude residue was purified by trituration with diethyl ether to afford 18.3 (120 mg, 74%) as a brown solid. ¹H NMR (400 MHz, DMSO) 11.80 (1H, s), 8.84-8.80 (1H, m), 8.54-8.52 (1H, m), 8.12-8.08 (1H, m), 7.67-7.59 (1H, m), 7.53-7.40 (3H, m), 7.31 (2H, t, J=8.0 Hz), 7.15-7.09 (1H, m), 7.02-6.95 (2H, m), 5.23-5.19 (2H, m), 4.72 (1H, d, J=4.0 Hz), 3.80-3.77 (3H, m), 3.69-3.62 (1H, m), 3.56 (2H, d, J=12.6 Hz), 2.94-2.86 (2H, m), 1.87-1.85 (2H, m), 1.55-1.47 (2H, m).

Step 4. 7-(2,6-difluorophenyl)-5-[[5-(4-hydroxy-1-piperidyl)-2-pyridyl]amino]-3H-pyrido[2,3-d]pyrimidin-4-one (I-11)

Reaction was carried out following procedure outlined in Example 10. Method J, step 4 using 7-(2,6-difluorophenyl)-5-((5-(4-hydroxypiperidin-1-yl)pyridin-2-yl)amino)-3-(4-methoxybenzyl)pyrido[2,3-d]pyrimidin-4(3H)-one (18.3) to give I-11 as a yellow solid. m/z=451 [M+H]⁺, ¹H NMR (400 MHz, DMSO) δ 11.87-11.82 (m, 1H), 8.38 (s, 1H), 8.22 (s, 1H), 7.98 (d, J=2.8 Hz, 1H), 7.55-7.46 (m, 1H), 7.39 (dd, J=2.9, 9.0 Hz, 1H), 7.19 (dd, J=8.0, 8.0 Hz, 2H), 6.96 (d, J=8.8 Hz, 1H), 4.60-4.60 (m, 1H), 3.59-3.51 (m, 1H), 3.48-3.39 (m, 3H), 2.83-2.74 (m, 2H), 1.75-1.71 (m, 2H), 1.45-1.33 (m, 2H).

Example 19: Method S—Preparation of 4-[[7-(2,6-difluorophenyl)-4-oxo-3H-pyrido[4,3-d]pyrimidin-5-yl]amino]-N-ethyl-benzamide (I-12)

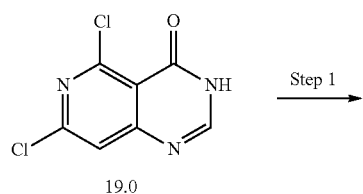

19.0

Step 1

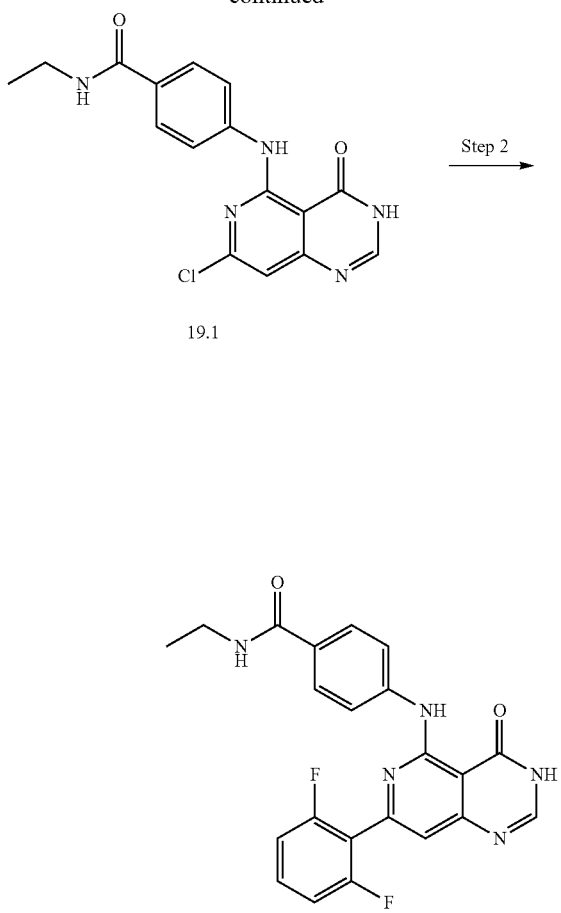

19.1

I-12

Step 1. 6-((7-chloro-4-oxo-3,4-dihydropyrido[4,3-d]pyrimidin-5-yl)amino)-N-ethylnicotinamide (19.1)

Reaction was carried out following procedure outlined in Example 1, Method A, Step 2 using 5,7-dichloropyrido[4,3-d]pyrimidin-4(3H)-one (19.0) and 4-amino-N-ethylbenzamide to afford (19.1) to afford 19.1 as a brown solid. ¹H NMR (400 MHz, DMSO) 13.01-12.99 (1H, m), 11.56-11.50 (1H, m), 8.43 (1H, t, J=5.4 Hz), 8.36 (1H, s), 7.96-7.85 (4H, m), 7.04-7.02 (1H, m), 3.36-3.30 (2H, m), 1.21-1.14 (3H, m).

Step 2. 4-[[7-(2,6-difluorophenyl)-4-oxo-3H-pyrido[4,3-d]pyrimidin-5-yl]amino]-N-ethyl-benzamide (I-12)

Reaction was carried out following procedure outlined in Example 18: Method R, step 3 using 6-((7-chloro-4-oxo-3,4-dihydropyrido[4,3-d]pyrimidin-5-yl)amino)-N-ethylnicotinamide (19.1) to afford I-12 as a white solid. m/z=422 [M+H]⁺, ¹H NMR (400 MHz, DMSO) δ 11.67 (s, 1H), 8.25-8.20 (m, 2H), 7.81 (d, J=8.3 Hz, 2H), 7.74 (d, J=8.3 Hz, 2H), 7.57-7.48 (m, 1H), 7.22 (dd, J=8.1, 8.1 Hz, 2H), 7.02 (s, 1H), 3.19 (q, J=6.7 Hz, 2H), 1.04 (dd, J=6.8, 6.8 Hz, 3H). One NH resonance not observed

Example 20: Method T—Preparation of N-ethyl-4-[(2-isopropyl-5-oxo-6H-pyrido[4,3-d]pyrimidin-4-yl)amino]benzamide (I-10)

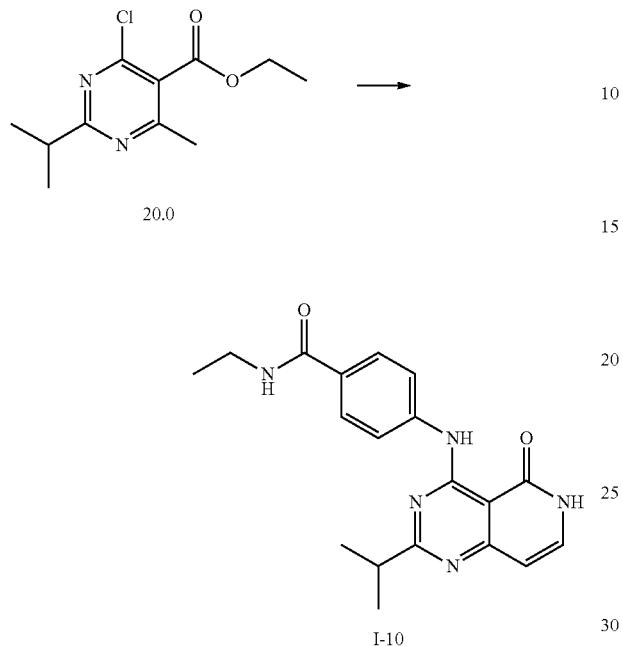

The title compounds was prepared from ethyl 4-chloro-2-isopropyl-6-methylpyrimidine-5-carboxylate (20.0) according to procedures described in KR2016035411 using 4-amino-N-ethylbenzamide to afford I-10 as a yellow solid. m/z=352 [M+H]+, 1H NMR (400 MHz, DMSO) δ 12.13 (s, 1H), 12.00 (s, 1H), 8.41 (dd, J=5.4, 5.4 Hz, 1H), 7.98 (d, J=8.9 Hz, 2H), 7.91 (d, J=8.8 Hz, 2H), 7.62 (d, J=7.2 Hz, 1H), 6.48 (d, J=7.2 Hz, 1H), 3.32-3.26 (m, 2H), 3.09-2.99 (m, 1H), 1.33 (d, J=6.9 Hz, 6H), 1.14 (dd, J=7.2, 7.2 Hz, 3H).

Example 21: Method U—Preparation of 5-[[5-(4-hydroxy-1-piperidyl)-2-pyridyl]amino]-7-isopropyl-3H-pyrido[2,3-d]pyrimidin-4-one (I-59) and 5-[[5-(4-hydroxy-1-piperidyl)-2-pyridyl]amino]-7-propyl-3H-pyrido[2,3-d]pyrimidin-4-one (I-60)

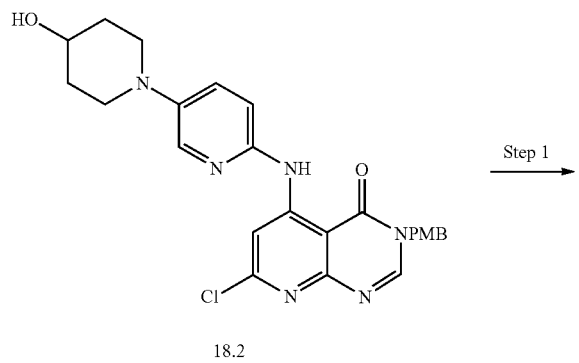

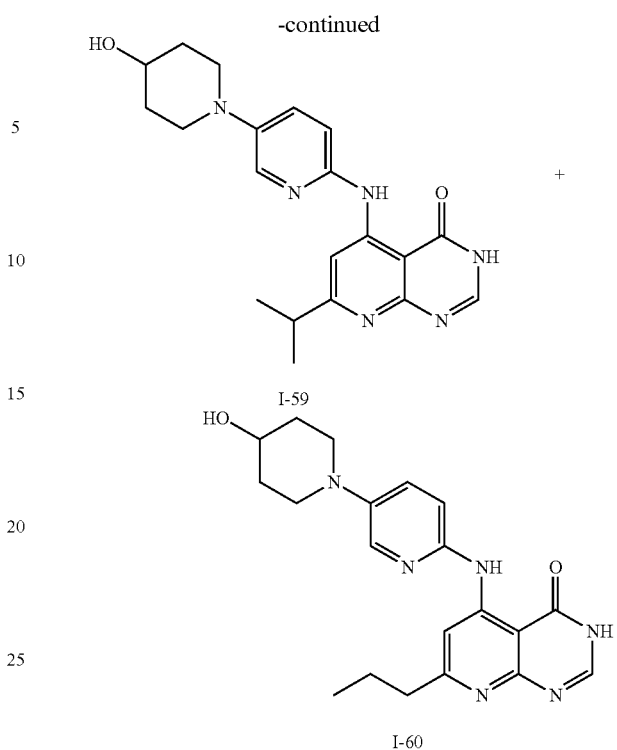

Step 1. 5-[[5-(4-hydroxy-1-piperidyl)-2-pyridyl]amino]-7-isopropyl-3H-pyrido[2,3-d]pyrimidin-4-one (I-59) and 5-[[5-(4-hydroxy-1-piperidyl)-2-pyridyl]amino]-7-propyl-3H-pyrido[2,3-d]pyrimidin-4-one (I-60)

To a microwave tube charged with 7-chloro-5-((5-(4-hydroxypiperidin-1-yl)pyridin-2-yl)amino)-3-(4-methoxybenzyl)pyrido[2,3-d]pyrimidin-4(3H)-one (18.2) (100 mg, 0.2 mmol), Tetrakis(triphenylphosphine)palladium(0) (23 mg, 0.02 mmol) in THF (2 mL) was added 2-propylzinc bromide (0.5 M solution in THF, 4.1 mL, 2.03 mmol). After stirring sealed at 120° C. for 1 h the reaction was combined with a duplicate reaction and quenched with addition of methanol (1 mL) and diluted with DCM. The mixture was absorbed directly onto silica and purified by column chromatography eluting with 0-10% methanol in DCM to afford 5-((5-(4-hydroxypiperidin-1-yl)pyridin-2-yl)amino)-7-isopropyl-3-(4-methoxybenzyl)pyrido[2,3-d]pyrimidin-4(3H)-one (200 mg) at about 80% purity which was sed in the next step without further purification.

Crude 5-((5-(4-hydroxypiperidin-1-yl)pyridin-2-yl)amino)-7-isopropyl-3-(4-methoxybenzyl)pyrido[2,3-d]pyrimidin-4(3H)-one (200 mg) was dissolved in TFA (5 mL). After stirring at reflux for 4 h, the reaction solvent was removed in vacuo to give a crude product which was diluted in DCM (1 mL), methanol (2 mL) and 1M methanolic ammonia (4 mL) [caution!] and stirred for 1 h at RT before re-evaporating to dryness. The residue was purified by preparative HPLC to afford product as a mixture of isomers (I-59 and I-60). The isomers were subsequently separated via preparative SFC to give (I-59) (4 mg, 3%) and (I-60) (7 mg, 6%) both as a yellow solid. I-59: m/z=381 [M+H]+, 1H NMR (400 MHz, DMSO) δ 12.06-11.99 (m, 1H), 8.26 (s, 1H), 8.21 (s, 1H), 8.14 (d, J=2.8 Hz, 1H), 7.51 (dd, J=2.9, 9.0 Hz, 1H), 7.05 (d, J=9.1 Hz, 1H), 4.74 (s, 1H), 3.72-3.66

(m, 1H), 3.62-3.53 (m, 2H), 3.02-2.88 (m, 3H), 1.93-1.87 (m, 2H), 1.61-1.50 (m, 2H), 1.30 (d, J=7.1 Hz, 6H). 1 Exchangeable proton not observed. I-60 (7 mg, 6%) as a yellow solid. m/z=381 [M+H]+, $^1$H NMR (400 MHz, DMSO) δ 12.55 (s, 1H), 11.78 (s, 1H), 8.27 (s, 1H), 8.18-8.13 (m, 2H), 7.51 (dd, J=2.9, 9.0 Hz, 1H), 7.07 (d, J=8.8 Hz, 1H), 4.74 (d, J=3.5 Hz, 1H), 3.71-3.67 (m, 1H), 3.62-3.53 (m, 2H), 2.97-2.87 (m, 2H), 2.70 (dd, J=7.6, 7.6 Hz, 2H), 1.93-1.87 (m, 2H), 1.76 (dd, J=7.3, 14.9 Hz, 2H), 1.61-1.49 (m, 2H), 0.99 (dd, J=7.5, 7.5 Hz, 3H).

Example 22: Method AP—Preparation of 6-(2-fluoro-5-isopropylphenyl)-8-((5-(4-hydroxypiperidin-1-yl)pyridin-2-yl)amino)isoquinolin-1(2H)-one (I-288)

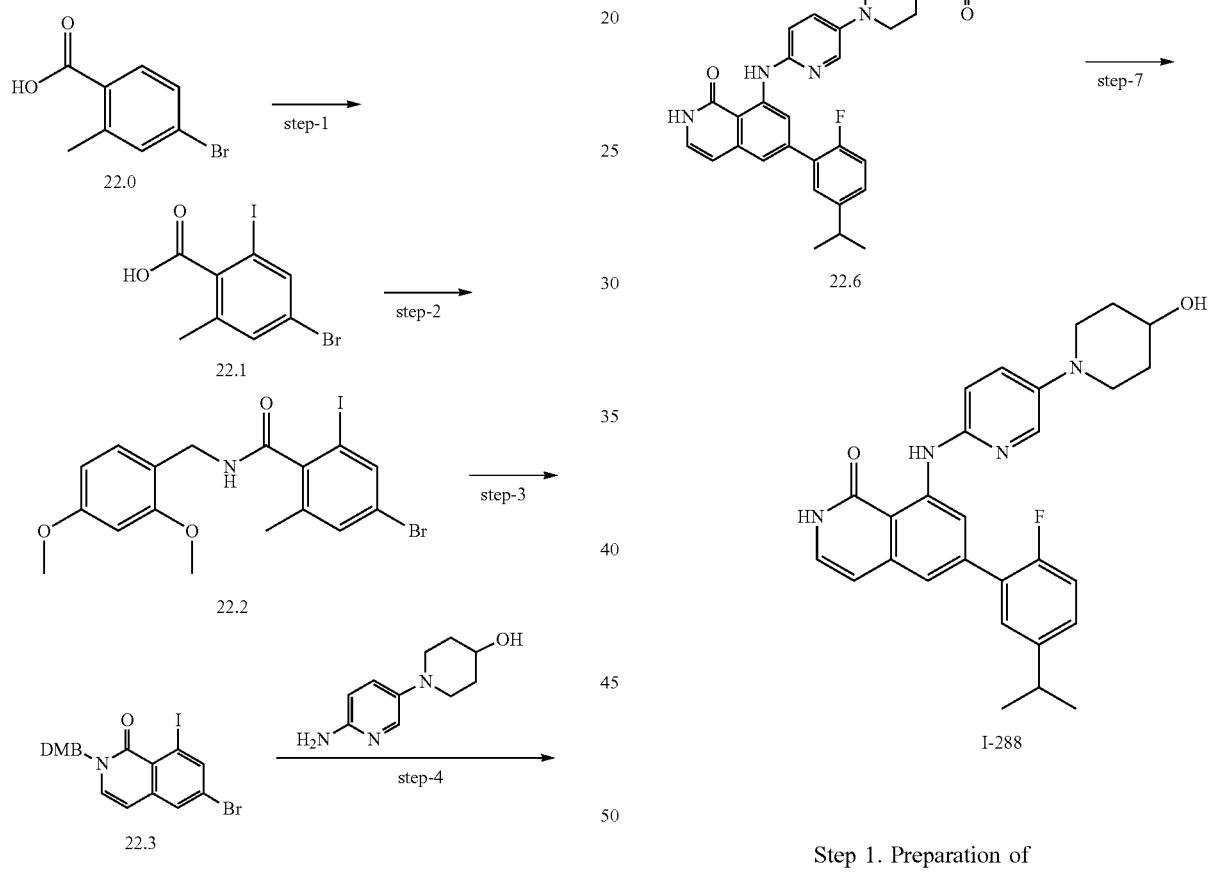

Step 1. Preparation of 4-bromo-2-iodo-6-methylbenzoic acid (22.1)

To a stir solution of 4-bromo-2-methylbenzoic acid (22.0) (15 g, 69.7 mmol, 1.0 eq) and iodobenzene diacetate (44.93 g, 139.5 mmol, 2.0 eq) in N,N-dimethylformamide (150 ml) at RT were added palladium(II) acetate (0.78 g, 3.48 mmol, 0.05 eq) followed by iodine (17.7 g, 69.7 mmol, 1.0 eq). After stirring at 100° C. for 16 h, the reaction mixture was transferred into an ice cold water (500 ml) and extracted with ethyl acetate (200 ml×3). The combined organic layer was dried over sodium sulphate and concentrated under reduced pressure. The residue was purified by column chromatography eluting with 20% ethyl acetate in hexane to afford 22.1. (11.25 g, 47.31%). MS (ES): m/z 341.84 [M+H]+.

Step 2. 4-bromo-N-(2,4-dimethoxybenzyl)-2-iodo-6-methylbenzamide (22.2)

To a solution of 4-bromo-2-iodo-6-methylbenzoic acid (22.1) (5 g, 14.70 mmol, 1.0 eq) in THF (10 mL) at RT were added N,N-Diisopropylethylamine, (5.6 g, 44.10 mmol, 3.0 eq) and Bromo-tris-pyrrolidino-phosphonium hexafluorophosphate (12.3 g, 26.46 mmol, 1.8). After stirring at RT for 30 min, 2,4 dimethoxy benzylamine (3.2 g, 19.11 mmol, 1.3 eq) was added. After stirring at RT for 16 h, the reaction mixture was transferred into water (300 ml) and extracted with ethyl acetate (200 ml×3). The combined organic layer was washed with brine solution, dried over sodium sulphate and concentrated under reduced pressure. The residue was purified by column chromatography eluting with 35% ethyl acetate in hexane to afford 22.2 (6.5 g, 90.43%). MS (ES): m/z 492.72 [M+H]$^+$.

Step 3. 6-bromo-2-(3,4-dimethylbenzyl)-8-iodoisoquinolin-1(2H)-one (22.3)

To a solution of 4-bromo-N-(2,4-dimethoxybenzyl)-2-iodo-6-methylbenzamide (22.2) (2.5 g, 5.10 mmol, 1.0 eq) in THF (50 mL) was added lithium diisopropylamide 2.5M in THF (7.6 ml, 15.306 mmol, 3 eq) at −78° C. After stirring at −78° C. for 30 min, N,N dimethylformamide (1.49 g, 20.40 mmol, 4 eq) was added. After stirring at −78° C. for 1 h, the reaction mixture was acidified by using Hydrochloric acid and extracted with ethyl acetate (100 ml×3). The combined organic layer was dried over with sodium sulphate and concentrated under reduced pressure. The residue was purified by column chromatography eluting with 12% ethyl acetate in hexane to afford 22.3 (1.5 g, 62.82%). MS (ES): m/z 500.85 [M+H]$^+$.

Step 4. 6-bromo-2-(3,4-dimethylbenzyl)-8-((5-(4-hydroxypiperidin-1-yl)pyridin-2-yl)amino)isoquinolin-1(2H)-one (22.4)

To a solution of 6-bromo-2-(3,4-dimethylbenzyl)-8-iodo-isoquinolin-1(2H)-one (22.3) (0.7 g, 1.40 mmol, 1.0 eq) in 1,4-dioxane (15 mL) were added 1-(6-aminopyridin-3-yl)piperidin-4-ol (0.325 g, 1.68 mmol, 1.2 eq) and cesium carbonate (1.36 g, 4.20 mmol, 3.0 eq). After degassing for 10 min. under argon atmosphere, tris(dibenzylideneacetone)dipalladium(0) (0.064 g, 0.07 mmol, 0.05 eq) and 4,5-Bis(diphenylphosphino)-9,9-dimethylxanthene (0.08 g, 0.070 mmol, 0.1 eq) were added and again degassed for 5 min. After stirring at 140° C. for 1 h in microwave, the reaction mixture was cooled to RT, transferred into water (100 ml) and extracted with ethyl acetate (100 ml×3). The combined organic layer was washed with brine solution, dried over sodium sulphate and concentrated under reduced pressure. The residue was purified by combi-flash using 75-80% ethyl acetate in hexane to afford 22.4 (0.250 g, 31.34%). MS(ES): m/z 566.25 [M+H]$^+$.

Step 5. 2-(3,4-dimethylbenzyl)-6-(2-fluoro-5-isopropylphenyl)-8-((5-(4-hydroxypiperidin-1-yl)pyridin-2-yl)amino)isoquinolin-1(2H)-one (22.5)

To a solution of 6-bromo-2-(3,4-dimethylbenzyl)-8-((5-(4-hydroxypiperidin-1-yl)pyridin-2-yl)amino)isoquinolin-1(2H)-one (22.4) (0.1 g, 0.17 mmol, 1.0 eq) and (2-fluoro-5-isopropylphenyl)boronic acid (0.038 g, 0.21 mmol, 1.2 eq) in 1,4-dioxane (5 mL) and water (1 ml), was added potassium phosphate (0.75 g, 0.35 mmol, 2 eq. After degassing for 10 min under argon, [1,1'-Bis(diphenylphosphino)ferrocene]dichloropalladium(II) (0.07 g, 0.008 mmol, 0.05 eq) was added. After stirring at 110° C. for 1 h in microwave, the reaction mixture was diluted with water (50 ml) and extracted with ethylacetate (100 ml×3). The combined organic layer was washed with brine solution, dried over sodium sulphate and concentrated under reduced pressure. The residue was purified by combi-flash column chromatography eluting with 65% ethyl acetate in hexane to afford 22.5 (0.1 g, 90.30%). MS (ES): m/z 624.24 [M+H]$^+$

Step 6. 1-(6-((6-(2-fluoro-5-isopropylphenyl)-1-oxo-1,2-dihydroisoquinolin-8-yl)amino)pyridin-3-yl)piperidin-4-yl 2,2,2-trifluoroacetate (22.6)

To a solution of 2-(3,4-dimethylbenzyl)-6-(2-fluoro-5-isopropylphenyl)-8-((5-(4-hydroxypiperidin-1-yl)pyridin-2-yl)amino)isoquinolin-1(2H)-one (22.5) (0.07 g, 0.11 mmol, 1.0 eq) in DCM (2 mL) at RT was added trifluoroaceticacid (1.4 ml). After stirring at 55° C. for 16 h, the reaction mixture was evaporated in vacuum to afford 22.6 (0.07 g, quantitative) which was used in the next step without further purification MS (ES): m/z 569.65 [M+H]$^+$.

Step 7. 6-(2-fluoro-5-isopropylphenyl)-8-((5-(4-hydroxypiperidin-1-yl)pyridin-2-yl)amino)isoquinolin-1(2H)-one (I-288)

To a solution of 1-(6-((6-(2-fluoro-5-isopropylphenyl)-1-oxo-1,2-dihydroisoquinolin-8-yl)amino)pyridin-3-yl)piperidin-4-yl 2,2,2-trifluoroacetate (22.6) (0.07 g, 0.123 mmol, 1.0 eq) in THF (3 mL) at RT was added sodium hydroxide (0.014 g, 0.36 mmol, 3.0 eq). After stirring at RT for 2 h, the reaction was concentrated in vacuum. The residue was purified by prep HPLC using column: SUNFIRE C18 (250*19) mm 5u, mobile phase: 0.1% Trifluoroacetic acid in water/acetonitrile as buffer, flow 15 ml/min, gradient 0-40% over 25 min. The desired fractions were lyophilized to afford TFA salt. The salt was dissolved in methanol (3 ml) and neutralized with tetralkyl ammonium carbonate polymer-bound (basic resin) to afford the free base of 22 (0.025 g, 42.97%) MS (ES): 473.87 m/z [M+H]+, LCMS purity: 100%, HPLC purity: 95.07% 1H NMR (400 MHz, DMSO-d6) δ 1.26 (d, J=7.0 Hz, 6H), 1.58 (s, 2H), 1.88 (s, 2H), 2.95-3.03 (m, 2H), 3.52 (s, 2H), 3.69 (s, 1H), 6.63 (d, J=6.9 Hz, 1H), 7.08 (s, 1H), 7.17-7.32 (m, 3H), 7.35 (s, 1H), 7.43 (d, J=7.3 Hz, 1H), 7.67 (s, 1H), 8.10 (s, 1H), 8.61 (s, 1H), 11.48 (s, 1H), 12.47 (s, 1H).

Example 23: Method BP—Preparation of N-(3-fluoro-4-(4-(((6-fluoro-2-methyl-1,2,3,4-tetrahydroisoquinolin-7-yl)amino)-5-oxo-5,6-dihydro-1,6-naphthyridin-2-yl)phenyl) cyclohexanecarboxamide (I-312)
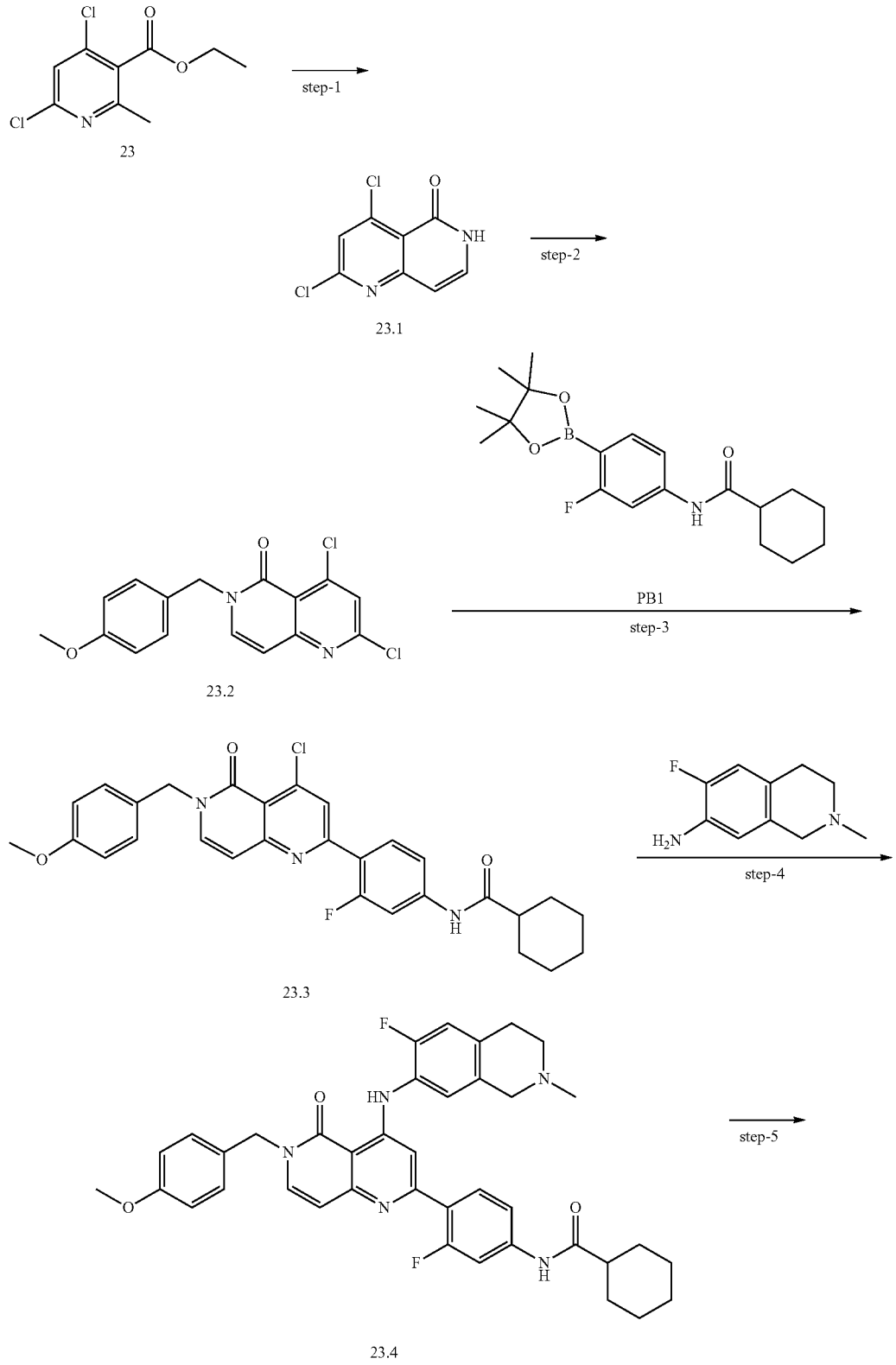

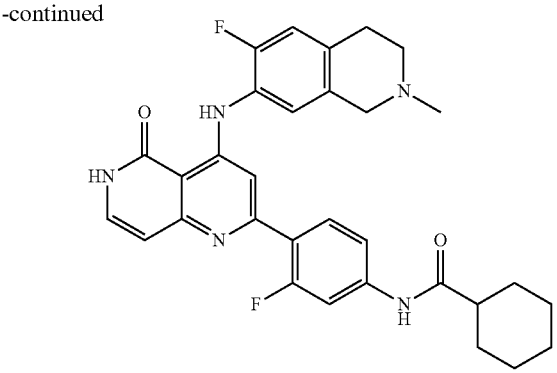

I-312

Step 1. Preparation of 2,4-dichloro-1,6-naphthyridin-5(6H)-one (23.1)

To a solution of ethyl 4,6-dichloro-2-methylnicotinate 23.0 (25.0 g, 0.1068 mol, 1.0 eq) in t-Butanol (200 mL) were added potassium ter-butoxide (23.79 g, 0.2136 mol, 2.0 eq) and 1,3,5 triazine (16.25 g, 0.216 mol, 2.0 eq). After stirring at 90° C. for 1 h, the reaction mixture was concentrated under reduced pressure. The residue was dissolve in ice water and acidified with 1N Hydrochloric acid to pH 2-3. After stirring at RT for 1 h, reaction mixture was filtered and washed with water (300 ml). Additional product was extracted from aqueous layer using DCM (500 ml×3) to afford crude material which was concentrated and then azeotrope by toluene (100 ml) to afford 23.1 (18.5 g, Yield: 80.55%). MS (ES): m/z 216 [M+H]$^+$.

Step 2. 2,4-dichloro-6-(4-methoxybenzyl)-1,6-naphthyridin-5(6H)-one (23.2)

To a solution of 2,4-dichloro-1,6-naphthyridin-5(6H)-one (23.1) (10.0 g, 0.0465 mol, 1.0 eq) in N,N, Dimethyl formamide (40 mL) was added cesium carbonate (30.23 g, 0.093 mol, 2.0 eq). After stirring at RT for 30 min, 1-(chloromethyl)-4-methoxybenzene (7.25 g, 0.0465 mol, 1.0 eq) was added. After stirring at RT for 4 h, the reaction mixture was diluted with cold water (100 ml) whereby a solid precipitated from solution. The solid was filtered and washed with water (50 ml) and hexane (50 ml). The solid was dried under reduced pressure to afford 23.2 (9.98 g, Yield: 64.03%). MS (ES): m/z 316.18 [M+H]$^+$.

Step 3. N-(4-(4-chloro-6-(4-methoxybenzyl)-5-oxo-5,6-dihydro-1,6-naphthyridin-2-yl)-3-fluorophenyl)cyclohexanecarboxamide (23.3)

To a solution of 2,4-dichloro-6-(4-methoxybenzyl)-1,6-naphthyridin-5(6H)-one 23.1 (11.5 g, 0.0344 mol, 1.0 eq) and N-(3-fluoro-4-(4,4,5,5-tetramethyl-1,3,2-dioxaborolan-2-yl)phenyl)cyclohexanecarboxamide (11.91 g, 0.0344 mol, 1.0 eq) in 1,2 Dimethoxy ethane (160 ml) and water (40 ml) was added potassium phosphate (21.89 g, 0.1032 mol, 3.0 eq). After degassing with argon gas for 20 min, tetrakis(triphenylphosphine)palladium(0) (1.98 g, 0.0017 mol, 0.05 eq) was added. After stirring at 100° C. for 16 h, the reaction mixture was transferred to water (500 ml) and extracted with ethylacetate (500 ml×2). The combined organic layer was dried over sodium sulphate and concentrated under reduced pressure. The residue was purified by column chromatography eluting at 25% ethylacetate in hexane to afford 23.3 (5.2 g, Yield: 28.03%). MS (ES): m/z 521.00[M+H]$^+$.

Step 4. N-(3-fluoro-4-(4-(((6-fluoro-2-methyl-1,2,3,4-tetrahydroisoquinolin-7-yl)amino)-6-(4-methoxybenzyl)-5-oxo-5,6-dihydro-1,6-naphthyridin-2-yl)phenyl) cyclo hexanecarboxamide (23.4)

To a solution of N-(4-(4-chloro-6-(4-methoxybenzyl)-5-oxo-5,6-dihydro-1,6-naphthyridin-2-yl)-3-fluorophenyl)cyclohexane carboxamide 23.3 (0.30 g, 0.576 mmol, 1.0 eq) in 1,4-dioxane (5 mL) were added 6-fluoro-2-methyl-1,2,3,4-tetrahydroisoquinolin-7-amine (PA9) (0.11 g, 0.634 mmol, 1.1 eq) and potassium carbonate (0.22 g, 1.728 mmol, 3.0 eq). After degassing with nitrogen gas for 10 min, 4,5-Bis(diphenylphosphino)-9,9-dimethylxanthene (0.10 g, 0.115 mmol, 0.2 eq) and Tris(dibenzylideneacetone)dipalladium(0.033 g, 0.057 mmol, 0.1 eq) were added under nitrogen gas atmosphere. After stirring at 120° C. for 16 h, the reaction mixture was diluted with water (100 ml) and extracted into ethylacetate (100 ml×3). The combined organic layer was washed with brine solution (100 ml), dried over sodium sulphate and concentrated under reduced pressure. The residue was purified using combi-flash silica eluting at 7% methanol/DCM to afford 23.4 (0.15 g, 39.17%) MS (ES): m/z 664.6 [M+H]$^+$

Step 5. N-(3-fluoro-4-(4-(((6-fluoro-2-methyl-1,2,3,4-tetrahydroisoquinolin-7-yl)amino)-5-oxo-5,6-dihydro-1,6-naphthyridin-2-yl)phenyl)cyclohexanecarboxamide (I-312)

To a solution of N-(3-fluoro-4-(4-(((6-fluoro-2-methyl-1,2,3,4-tetrahydroisoquinolin-7-yl)amino)-6-(4-methoxybenzyl)-5-oxo-5,6-dihydro-1,6-naphthyridin-2-yl) phenyl) cyclo hexane carboxamide 23.4 (0.14 g, 0.211 mmol, 1.0 eq) in DCM (4 mL) at RT were added triflic acid (0.54 g, 3.625 mmol, 17.1 eq) and trifluoro acetic acid (0.55 g, 4.853 mmol, 23.0 eq). After stirring at RT for 30 min, the reaction mixture was concentrated under reduced pressure. The residue was purified via preparative HPLC purified using: SUNFIRE C18 (150*19) mm 5p column with mobile phase: (A) 0.1% Trifluoroacetic acid (TFA) in water and (B) acetonitrile, flowrate at 13 ml/min, gradient 0-34% over 23 min to afford after lyophilization I-312 TFA salt. The salt was dissolved into methanol (3 ml) and neutralized with tetralkyl ammonium carbonate polymer-bound (basic resin) to isolate the free base of I-312 (0.042 g, 36.63%) MS (ES): 542.99 m/z [M−H]+, LCMS purity: 98.66%, HPLC purity: 99.43%, 1H NMR (400 MHz, DMSO-d6) δ 1.15-1.28 (m, 4H), 1.35-1.41 (m, 2H), 1.63-1.82 (m, 5H), 2.36 (d, J=12.9 Hz, 1H), 2.43 (s, 2H), 2.74 (s, 2H), 2.88 (s, 2H), 3.60 (s, 2H), 6.56 (d, J=7.3 Hz, 1H), 7.04 (s, 1H), 7.19 (d, J=11.2 Hz, 1H), 7.32 (d, J=8.0 Hz, 1H), 7.42 (d, J=7.7 Hz, 2H), 7.72 (d, J=14.6 Hz, 1H), 7.93-8.06 (m, 1H), 10.23 (s, 1H), 11.38 (s, 1H), 11.62 (s, 1H).

Example 24: Method CP—Preparation of N-(3-fluoro-4-(4-((5-(4-hydroxy-4-methylpiperidin-1-yl)pyridin-2-yl)amino)-5-oxo-5,6-dihydro-1,6-naphthyridin-2-yl)phenyl)cyclohexanecarboxamide (I-294)

Step 1. 2-chloro-4-((5-(4-hydroxy-4-methylpiperidin-1-yl)pyridin-2-yl)amino)-1,6-naphthyridin-5(6H)-one (24.1)

To the stirred solution of 2,4-dichloro-1,6-naphthyridin-5(6H)-one (1.2) (0.50 g, 2.325 mmol, 1.5 eq) and 1-(6-aminopyridin-3-yl)-4-methylpiperidin-4-ol (0.53 g, 2.558 mmol, 1.1 eq) in tert-butanol (10 ml) was added di-isopropylethylamine (0.60 g, 4.650 mmol, 2.0 eq). After heating in microwave for 6 h at 150° C., the reaction mixture was diluted with water (50 ml) and extracted with ethyl acetate (100 ml×2). The combined organic layer was washed with brine solution (50 ml), dried over sodium sulphate and concentrated under reduced pressure. The residue was puri-

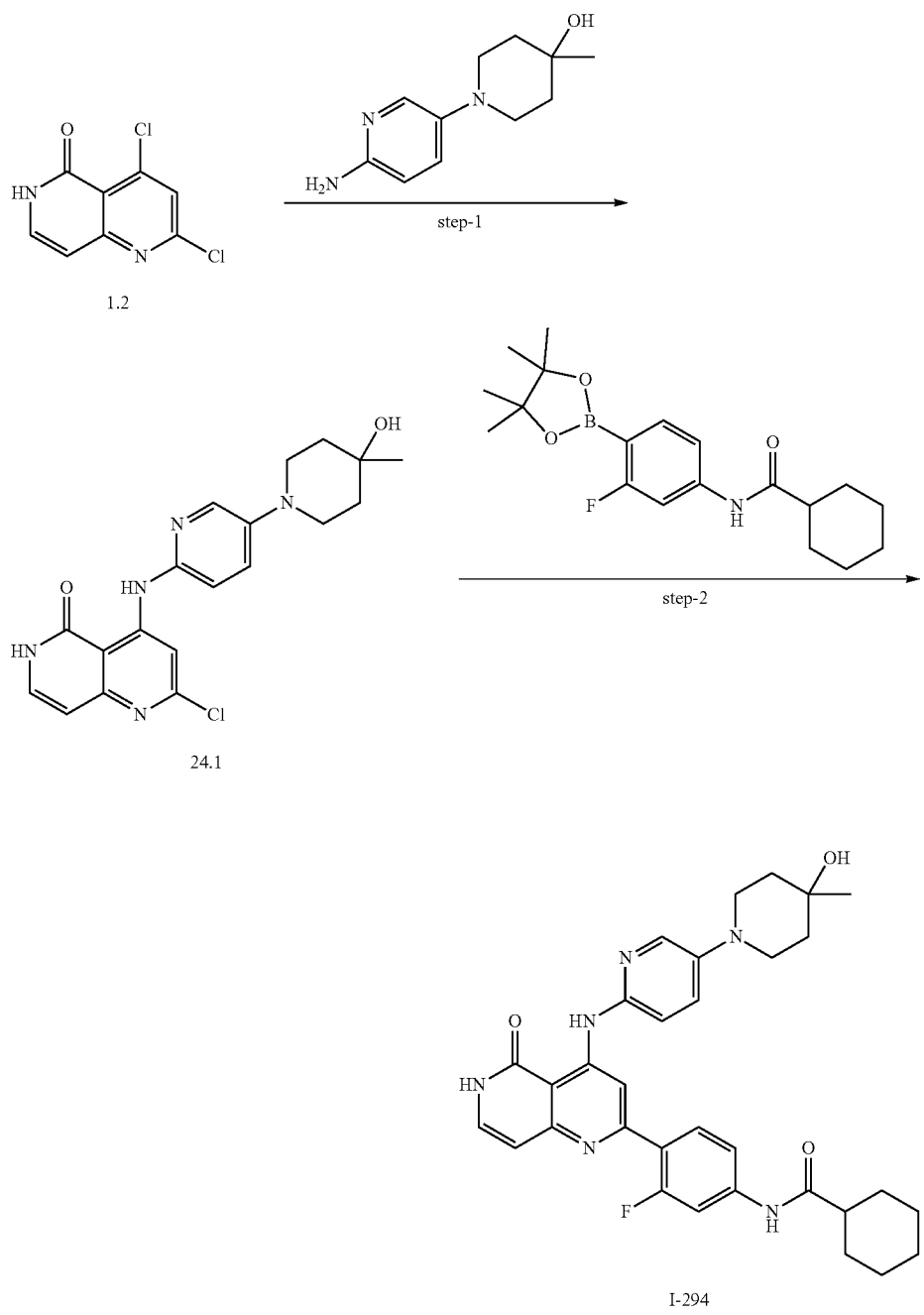

fied via preparative HPLC using X-SELECT PHENYL HEXYL (150*19) mm, 5μ. Column flow at 15.0 ml/min with Mobile phase (A) 0.1% Formic acid in Water and (B) 100% Acetonitrile with a gradient of solvent B 0-43% over 18 min to afford 24.1 (0.11 g, 12.26%) MS (ES): m/z 387.2 [M+H]+

Step 2. N-(3-fluoro-4-(4-((5-(4-hydroxy-4-methylpi-peridin-1-yl)pyridin-2-yl)amino)-5-oxo-5,6-dihydro-1,6-naphthyridin-2-yl)phenyl)cyclohexanecarboxam-ide (I-294)

To a solution of 2-chloro-4-((5-(4-hydroxy-4-methylpip-eridin-1-yl)pyridin-2-yl)amino)-1,6-naphthyridin-5(6H)-one 24.1 (0.10 g, 0.261 mmol, 1.0 eq) and N-(3-fluoro-4-(4,4,5,5-tetramethyl-1,3,2-dioxaborolan-2-yl)phenyl) cyclohexanecarboxamide (0.13 g, 0.392 mmol, 1.5 eq) in 1,4-dioxane (6.0 ml) and water (1.0 ml) at RT was added potassium phosphate tribasic (0.39 g, 1.831 mmol, 7.0 eq). After degassing using argon gas for 20 mins, X-Phos ami-nobiphenyl palladium chloride precatalyst (0.020 g, 0.0261 mmol, 0.1 eq) was added. After stirring at 150° C. for 20 mins in microwave, the reaction mixture was transferred into water (25 ml) and extracted with ethyl acetate (50 ml×3). The combined organic layer was washed with brine solution (25 ml), dried over sodium sulphate and concentrated under reduced pressure. The residue was purified by column chromatography using Redisep gold column eluting with 15% methanol in DCM to afford I-294 (0.10 g, 67.61%) MS (ES): 556.82 m/z [M+H]+, LCMS purity: 95.09%, HPLC purity: 95.73% 1H NMR (400 MHz, DMSO-d6) δ 1.18 (s, 3H), 1.22-1.34 (m, 3H), 1.37-1.51 (m, 2H), 1.59 (s, 4H), 1.59 (d, J=11.4 Hz, 1H), 1.68 (d, J=10.6 Hz, 1H), 1.79 (d, J=11.7 Hz, 2H), 1.85 (d, J=12.7 Hz, 1H), 2.40-2.35 (m, 2H), 3.14 (s, 2H), 3.08-3.19 (m, 1H), 3.32 (d, J=11.3 Hz, 2H), 4.35 (s, 1H), 6.58 (d, J=7.3 Hz, 1H), 7.03 (d, J=8.9 Hz, 1H), 7.37-7.53 (m, 3H), 7.72-7.81 (m, 1H), 8.01 (t, J=8.8 Hz, 1H), 8.09 (d, J=3.1 Hz, 1H), 8.74 (s, 1H), 10.25 (s, 1H), 11.65 (s, 1H), 12.39 (s, 1H).

Example 25: Method DP—Preparation of N-(3-fluoro-4-(4-((5-(1-methylpiperidin-3-yl)pyridin-2-yl) amino)-5-oxo-5,6-dihydro-1,6-naphthyridin-2-yl) phenyl) cyclohexane carboxamide (I-337)

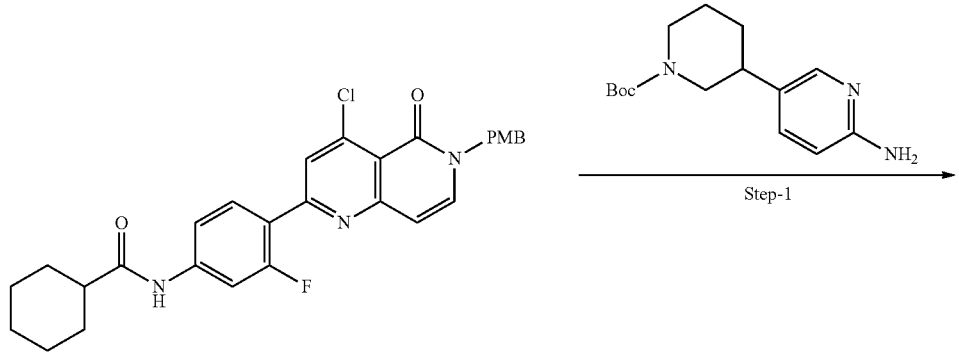

23.3

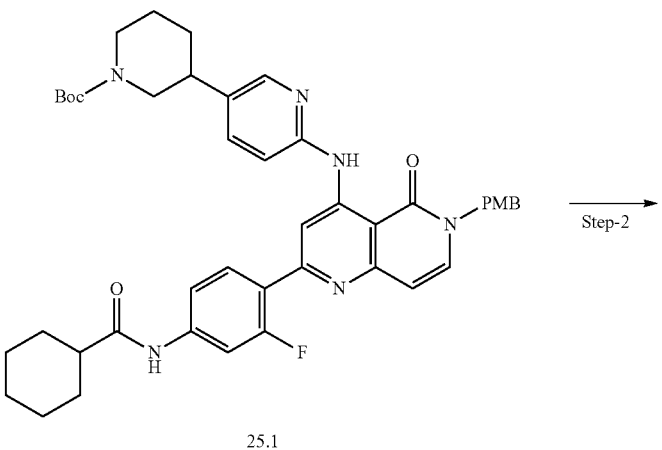

25.1

-continued

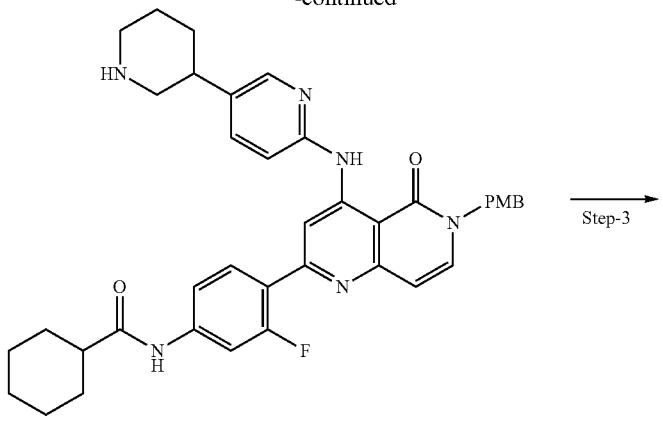
25.2

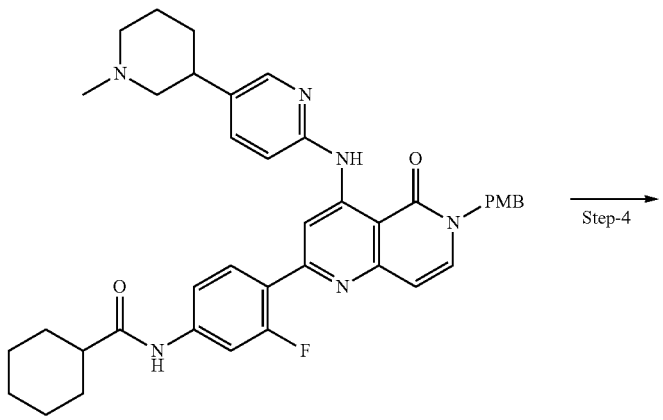
25.3

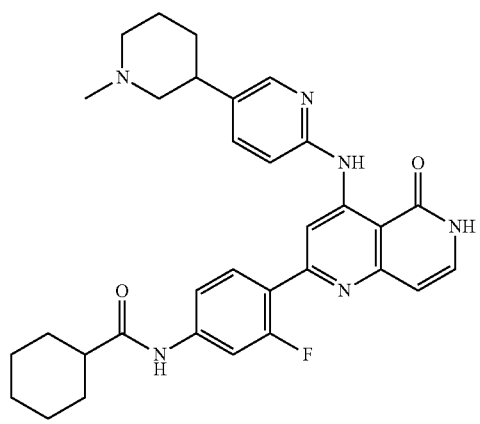
I-337

Step 1. tert-butyl 3-(6-((2-(4-(cyclohexanecarboxamido)-2-fluorophenyl)-6-(4-methoxybenzyl)-5-oxo-5,6-dihydro-1,6-naphthyridin-4-yl)amino)pyridin-3-yl)piperidine-1-carboxylate (25.1)

To a solution of N-(4-(4-chloro-6-(4-methoxybenzyl)-5-oxo-5,6-dihydro-1,6-naphthyridin-2-yl)-3-fluorophenyl) cyclohexane carboxamide 23.3 (0.50 g, 0.96 mmol, 1.0 eq) in 1,4-dioxane (5.0 ml) were added tert-butyl 3-(6-aminopyridin-3-yl)piperidine-1-carboxylate (0.26 g, 0.96 mmol, 1.0 eq) and cesium carbonate (0.93 g, 2.8 mmol, 3.0 eq). After degassing for 10 min. under argon atmosphere, tris (dibenzylideneacetone)dipalladium(0) (0.087 g, 0.09 mmol, 0.1 eq) and 4,5-Bis(diphenylphosphino)-9,9-dimethylxanthene (0.111 g, 0.19 mmol, 0.2 eq) were added and again degassed for 5 min. After stirring at 1H10C for 1 h, the reaction mixture was transferred in water (100 ml) and extracted with ethyl acetate (100 ml×3). The combined organic layer was washed with brine solution (100 ml), dried over sodium sulphate and concentrated under reduced pressure. The residue was purified by combi flash eluting with 35-40% ethyl acetate in hexane to afford 25.1 (0.5 g, Yield: 68.34%). MS(ES): m/z 761.94 [M+H]$^+$.

Step 2. N-(3-fluoro-4-(6-(4-methoxybenzyl)-5-oxo-4-((5-(piperidin-3-yl)pyridin-2-yl)amino)-5,6-dihydro-1,6-naphthyridin-2-yl)phenyl)cyclohexanecarboxamide (25.2)

To a solution of tert-butyl 3-(6-((2-(4-(cyclohexanecarboxamido)-2-fluorophenyl)-6-(4-methoxybenzyl)-5-oxo-5,6-dihydro-1,6-naphthyridin-4-yl)amino)pyridin-3-yl)piperidine-1-carboxylate 25.1 (0.24 g, 0.31 mmol, 1.0 eq) in DCM (2 mL) at 0° C. was added trifluoroacetic acid (1 mL). After stirring at RT for 15 min, the reaction mixture was poured in water (50 ml), neutralized with saturated sodium bicarbonate solution (15 ml) and extracted with DCM (50 ml×3). The combined organic layer was dried over sodium sulphate and concentrated under reduced pressure. The residue was purified by trituration using diethyl ether (10 ml×2) to afford 25.2 (0.14 g, 67.17%). MS(ES): m/z 661.7 [M+H]$^+$.

Step 3. N-(3-fluoro-4-(6-(4-methoxybenzyl)-4-((5-(1-methylpiperidin-3-yl)pyridin-2-yl)amino)-5-oxo-5,6-dihydro-1,6-naphthyridin-2-yl)phenyl) cyclo hexane carboxamide (25.3)

To a solution of N-(3-fluoro-4-(6-(4-methoxybenzyl)-5-oxo-4-((5-(piperidin-3-yl)pyridin-2-yl)amino)-5,6-dihydro-1,6-naphthyridin-2-yl)phenyl)cyclohexanecarboxamide (25.2) (0.14 g, 0.21 mmol, 1.0 eq) in methanol (2 mL) were added p-formaldehyde (0.019 g, 0.63 mmol, 3.0 eq), anhydrous zinc chloride (0.043 g, 0.31 mmol, 1.5 eq) and triethylamine (0.85 mL, 0.63 mmol, 3.0 eq). After stirring at 60° C. for 2 h, the reaction mixture was cooled to RT and sodium cyanoborohydride (0.033 g, 0.53 mmol, 2.5 eq) was added. After stirring overnight, the reaction mixture was transferred into water (100 ml) and extracted with ethyl acetate (100 ml×3). The combined organic layer was washed with brine solution, dried over sodium sulphate and concentrated under reduced pressure. The residue was purified by combi flash eluting with 2-3% methanol in DCM to afford 25.3 (0.1 g, 69.94%). MS(ES): m/z 675.8 [M+H]$^+$.

Step 4. N-(3-fluoro-4-(4-((5-(1-methylpiperidin-3-yl)pyridin-2-yl)amino)-5-oxo-5,6-dihydro-1,6-naphthyridin-2-yl)phenyl)cyclohexanecarboxamide (I-337)

To a solution of N-(3-fluoro-4-(6-(4-methoxybenzyl)-4-((5-(1-methylpiperidin-3-yl)pyridin-2-yl)amino)-5-oxo-5,6-dihydro-1,6-naphthyridin-2-yl)phenyl) cyclo hexane carboxamide (25.3) (0.1 g, 0.14 mmol, 1.0 eq) in DCM (1.0 mL) at 0° C. was added triflic acid (0.6 mL). After stirring at RT for 0.5 h, the reaction mixture was poured in water (50 ml), neutralized with saturated bicarbonate solution (15 ml) and extracted with DCM (50 ml×3). The combined organic layer was dried over sodium sulphate and concentrated under reduced pressure. The residue was purified via prep HPLC using X-SELECT PHENYL HEXYL (150*19) mm, 5p column mobile with mobile phase (A): 0.1% formic acid in water/acetonitrile and (B) acetonitrile, flowrate 15 ml/min, gradient 0-22% over 16 min. The desired fractions were lyophilized to afford formate salt of I-337. The salt was dissolved into methanol (3 ml) and neutralized with tetralkyl ammonium carbonate polymer-bound (basic resin) to afford the free base of I-337 (0.025 g, 30.42%). MS (ES): 555.8 m/z [M+H]+, LCMS purity: 100%, HPLC purity: 100%, $^1$H NMR (400 MHz, DMSO-d$_6$) δ 1.25-1.30 (m, 5H), 1.39-1.51 (m, 3H), 1.69-1.77 (m, 2H), 1.78-1.86 (m, 6H), 2.40 (s, 3H), 2.87-3.01 (s, 3H), 6.62 (d, J=7.2 Hz, 1H), 7.08 (d, J=8.5 Hz, 1H), 7.40-7.50 (m, 2H), 7.71-7.81 (m, 2H), 8.01-8.05 (m, 1H), 8.32 (s, 1H), 9.06 (s, 1H), 10.26 (s, 1H), 11.71 (d, J=6.0 Hz, 1H), 12.69 (s, 1H).

Example 26: Method EP—Preparation of N-(4-(4-((5-(cyanomethyl)pyridin-2-yl)amino)-5-oxo-5,6-dihydro-1,6-naphthyridin-2-yl)-3-fluorophenyl)cyclohexanecarboxamide (I-353)

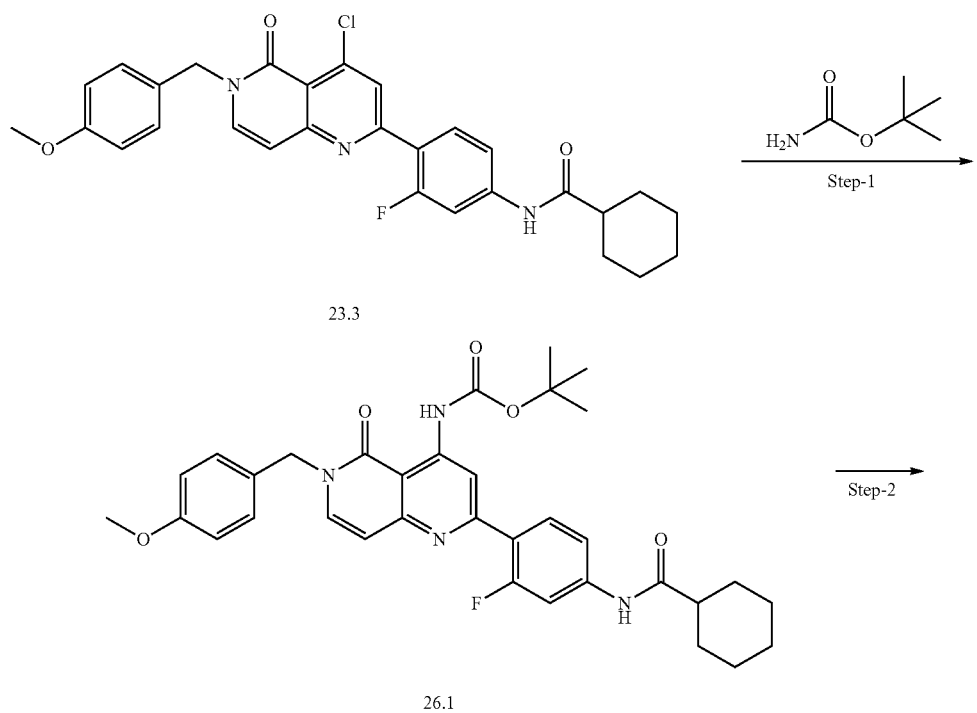

-continued

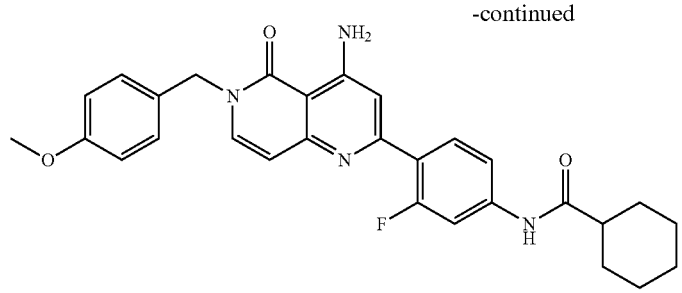
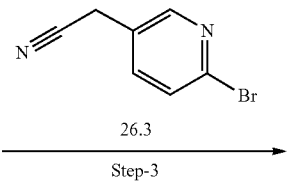

26.3
Step-3

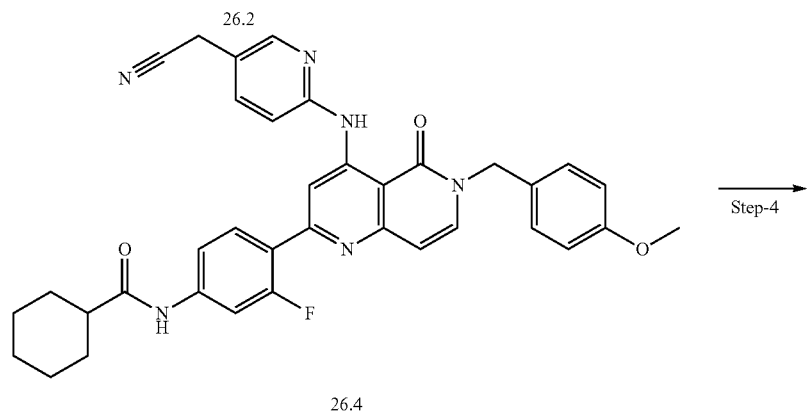

Step-4

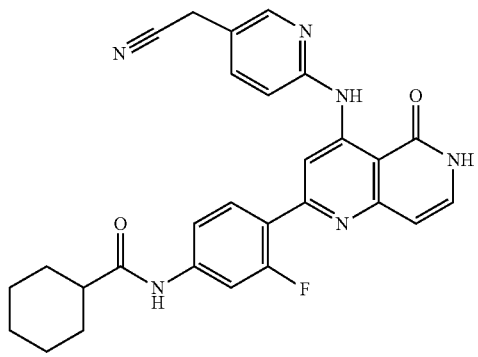

I-353

Step 1. tert-butyl (2-(4-(cyclohexanecarboxamido)-2-fluorophenyl)-6-(4-methoxybenzyl)-5-oxo-5,6-dihydro-1,6-naphthyridin-4-yl)carbamate (26.1)

Reaction was carried out following the representative procedure described in Method BP (Step-4) using N-(4-(4-amino-6-(4-methoxybenzyl)-5-oxo-5,6-dihydro-1,6-naphthyridin-2-yl)-3-fluorophenyl)cyclohexanecarboxamide (23.3) and tert-butyl carbamate. (1.0 g, 86.57%) MS (ES): m/z 601.7 [M+H]$^+$.

Step 2. N-(4-(4-amino-6-(4-methoxybenzyl)-5-oxo-5,6-dihydro-1,6-naphthyridin-2-yl)-3-fluorophenyl)cyclohexanecarboxamide (26.2)

To a solution of tert-butyl (2-(4-(cyclohexanecarboxamido)-2-fluorophenyl)-6-(4-methoxybenzyl)-5-oxo-5,6-dihydro-1,6-naphthyridin-4-yl)carbamate (26.1) (1.0 g, 0.00161 mol, 1.0 eq) in DCM (5.0 ml) at 0° C. was added methyl sulphonic acid (2.0 ml). After stirring at RT for 30 minute, the reaction mixture was poured into saturated NaHCO$_3$ solution (50 ml) and extracted with ethyl acetate (100 ml×3). The combined organic layer was dried over sodium sulphate and concentrated under reduced pressure to afford 26.2 (800 mg, 96%) MS (ES): m/z 501.5 [M+H]$^+$ Step 3. N-(4-(4-((5-(cyanomethyl)pyridin-2-yl)amino)-6-(4-methoxybenzyl)-5-oxo-5,6-dihydro-1,6-naphthyridin-2-yl)-3-fluorophenyl)cyclohexanecarboxamide (26.3)

Reaction was carried out following the representative procedure described in Method BP (Step-4) using N-(4-(4-chloro-6-(4-methoxybenzyl)-5-oxo-5,6-dihydro-1,6-naphthyridin-2-yl)-3-fluorophenyl)cyclohexanecarboxamide (26.2) and 2-(6-bromopyridin-3-yl)acetonitrile to afford (26.3) (0.060 g, 37.46%) MS (ES): m/z 617.7 [M+H]$^+$.

Step 4. N-(4-(4-((5-(cyanomethyl)pyridin-2-yl)amino)-5-oxo-5,6-dihydro-1,6-naphthyridin-2-yl)-3-fluorophenyl)cyclohexanecarboxamide (I-353)

Reaction was carried out following the representative procedure described in Method DP (Step-4) to afford I-353 (30 mg, 62.10%) MS (ES): m/z 597.39 [M+H]$^+$. $^1$H NMR (DMSO-d$_6$, 400 MHZ): 13.26 (s, 1H), 12.41 (s, 1H), 10.40

(s, 1H), 8.96 (s, 1H), 8.45 (s, 1H), 7.89-7.85 (m, 3H), 7.47 (s, 1H), 7.55 (d, J=8.0 Hz, 1H), 7.34 (s, 1H), 6.77 (d, J=72 Hz, 1H), 4.21 (s, 2H), 2.42-2.36 (m, 1H), 1.87-1.77 (m, 4H), 1.69-1.67 (m, 1H), 1.48-1.39 (m, 2H), 1.34-1.25 (m, 4H).

Example 27: Method FP—Preparation of (R)-8-((6-((dimethylamino)methyl)-5-(THF-3-yl)pyridin-2-yl)amino)-5-(7-fluoroimidazo[1,2-a]pyridin-3-yl)isoquinolin-1(2H)-one (I-356) and (S)-8-((6-((dimethylamino)methyl)-5-(THF-3-yl)pyridin-2-yl)amino)-5-(7-fluoroimidazo[1,2-a]pyridin-3-yl)isoquinolin-1(2H)-one (I-357)

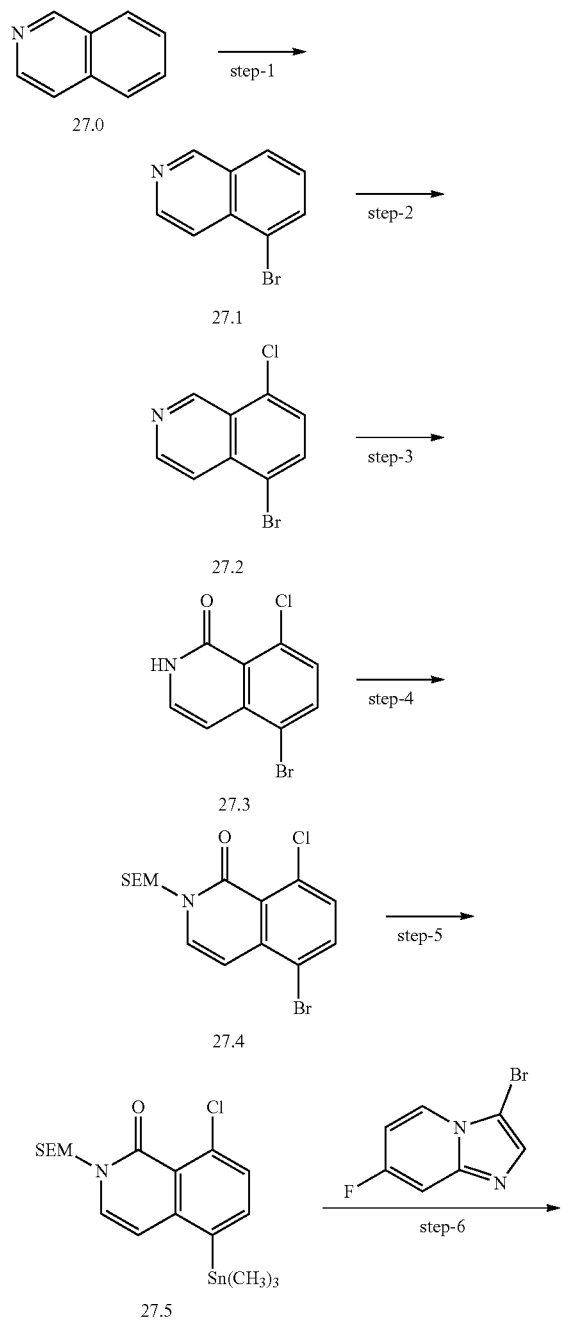

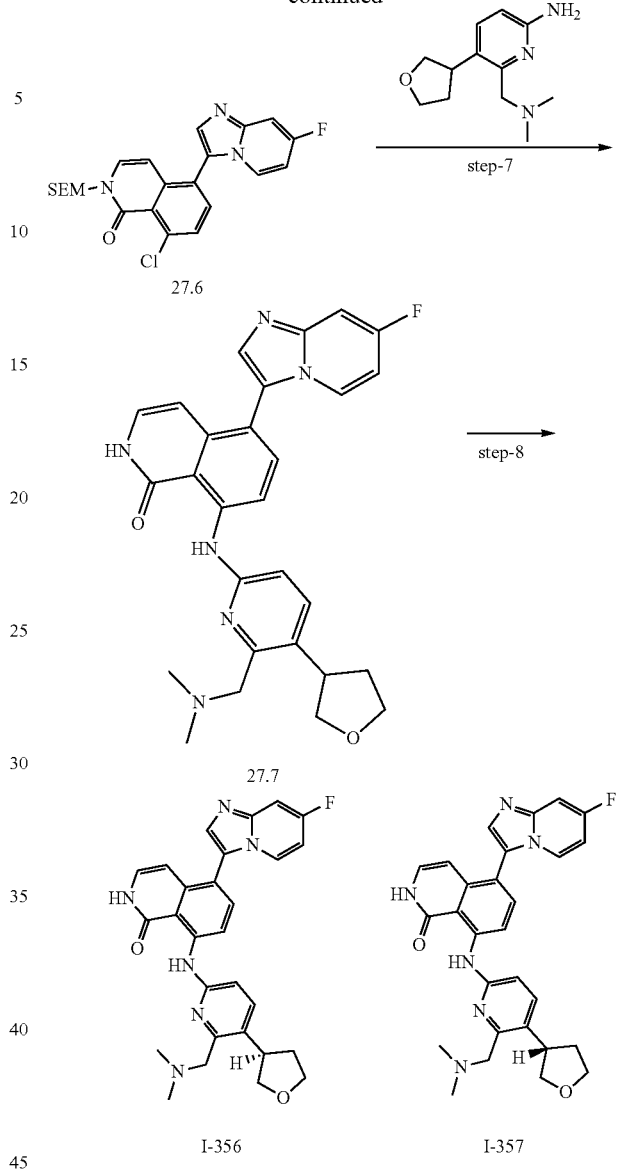

Step 1. 5-bromoisoquinoline (27.1)

To a solution of isoquinoline (27.0) (20.0 g, 0.1550 mol, 1.0 eq) in $H_2SO_4$ (120.0 ml) at 0° C. was added of N-bromosuccinamide (30.35 g, 0.465 mol, 3.0 eq). After stirring at RT for 1.5 h, the reaction mixture was poured into water (500 ml), neutralized with concentrated ammonium hydroxide, and extracted with DCM (100 ml×3). The combined organic layer was dried over sodium sulphate and concentrated under reduced pressure to afford 27.1 (20.5 g, 99%) MS (ES): m/z 208.97 [M+H]$^+$ Step 2. 5-bromo-8-chloroisoquinoline (27.2)

To a solution of 5-bromoisoquinoline (27.1) (20.5 g, 0.0985 mol, 1.0 eq) in $H_2SO_4$ (5.0 ml) at 0° C. was added N-Chlorosuccinamide (19.75 g, 1.5 eq). After stirring at 80° C. for 2 h, the reaction mixture was poured into water (50 ml), neutralized with concentrated ammonium hydroxide, and extracted with ethyl acetate (100 ml×3). The combined organic layer was dried over sodium sulphate and concentrated under reduced pressure to afford 27.2 (18.5, 96%) MS (ES): m/z 243.93 [M+H]$^+$

Step 3. 5-bromo-8-chloroisoquinolin-1(2H)-one (27.3)

To a solution of 5-bromo-8-chloroisoquinoline (27.2) (18.0 g, 0.0743 mol, 1.0 eq) in DCM (15.0 ml) at 0° C. was added m-CPBA (19.23 g, 0.1114, 1.5 eq). After stirring at RT for 3 h, the reaction mixture was poured into saturated NaHCO$_3$ solution (200 ml) and extracted with ethyl acetate (100 ml×3). The combined organic layer was dried over sodium sulphate and concentrated under reduced pressure to give crude (15 g) material which was dissolved into acetic anhydride (200 ml). After stirring at 100° C. for 1 h, 2N NaOH (150 ml) was added. After stirring at 110° C. for 1 h, the reaction mixture was poured into water (200 ml) and extracted with ethyl acetate (100 ml×3). The combined organic layer was dried over sodium sulphate and concentrated under reduced pressure. The residue was purified by combi flash eluting with 20-30% ethyl acetate in hexane to afford 27.3 (7 g, 60.94%). MS(ES): m/z 258.9 [M+H]$^+$.

Step 4. 5-bromo-8-chloro-2-((2-(trimethylsilyl)ethoxy)methyl)isoquinolin-1(2H)-one (27.4)

To a solution of 5-bromo-8-chloroisoquinolin-1(2H)-one (27.3) (7.0 g, 0.026 mol, 1.0 eq) in THF (70 ml) at 0° C. were added DBU (20.4 g, 0.13, 5 eq) and 2-(Trimethylsilyl)ethoxymethyl chloride (17.8 g, 0.010, 4 eq). After stirring at RT for 1.5 h, the reaction mixture poured into water (100 ml) and extracted with ethyl acetate (50 ml×3). The combined organic layer was dried over sodium sulphate and concentrated under reduced pressure. The residue was purified by combi flash eluting with 60-70% ethyl acetate in hexane to afford 27.4 (4.0 g, 96%). MS(ES): m/z 389 [M+H]$^+$.

Step 5. 8-chloro-2-((2-(trimethylsilyl)ethoxy)methyl)-5-(trimethylstannyl) iso quinolin-1(2H)-one (27.5)

To a solution of 5-bromo-8-chloro-2-((2-(trimethylsilyl)ethoxy)methyl)isoquinolin-1(2H)-one (27.4) (4.0 g, 0.0102 mol, 1.0 eq) in toluene (5 ml) was added hexamethylditine (5.0 g, 0.0153, 1.5 eq). After degassing for 10 min. under argon atmosphere, Bis(triphenylphosphine)palladium chloride (0.715 g, 0.00102 mol, 0.1 eq) was added and again degassed for 5 min. After stirring at 110° C. for 4 h, the reaction mixture was transferred in water (30 ml) and extracted with ethyl acetate (40 ml×3). The combined organic layer was washed with brine solution (100 ml), dried over sodium sulphate and concentrated under reduced pressure. The residue was purified by combiflash eluting with 2% ethyl acetate in hexane to afford 27.5 (3.8 g, Yield: 68.34%). MS(ES): m/z 473.06 [M+H]$^+$.

Step 6. 8-chloro-5-(7-fluoroimidazol[1,2-a]pyridine-3-yl)-2-((2-(tri methylsilyl)ethoxy)methyl)isoquinolin-1(2H)-one (27.6)

To a solution of 8-chloro-2-((2-(trimethylsilyl)ethoxy)methyl)-5-(trimethylstannyl) isoquinolin-1(2H)-one (27.5) (3.5 g, 0.0074 mol, 1.0 eq) in dioxane was added 3-bromo-7-fluoroimidazo[1,2-a]pyridine (1.9 g, 0.0088 mol, 1.2 eq). After degassing for 15 min. under argon atmosphere, tetrakis (0.85 g, 0.00074 mol, 0.1 eq) and CuI (0.14 g, 0.00074 mol, 0.1 eq) were added. After stirring at 110° C. for 2 h, the reaction mixture was transferred in water (50 ml) and extracted by ethyl acetate (50 ml×3). The combined organic layer was washed with brine solution (100 ml), dried over sodium sulphate and concentrated under reduced pressure. The residue was purified by combiflash eluting with 25% ethyl acetate in hexane to afford 27.6 (1.9 g, Yield: 64%) MS(ES): m/z 444.13 [M+H]$^+$.

Step 7. 8-((6-((dimethylamino)methyl)-5-(THF-3-yl) pyridine-2-yl)amino)-5-(7-fluoroimidazol[1,2-a] pyridine-3-yl)isoquinolin-1(2H)-one (27.7)

To a solution of 8-chloro-5-(7-fluoroimidazol[1,2-a]pyridine-3-yl)-2-((2-(trimethylsilyl)ethoxy)methyl)isoquinolin-1(2H)-one (27.6) (1.9 g, 0.00428 mol, 1.0 eq) in dioxane (1.5 ml) were added 6-((dimethylamino)methyl)-5-(THF-3-yl)pyridin-2-amine (0.94 g, 0.00428 mol. 1.0 eq) and K$_2$CO$_3$ (1.7 g, 0.0128 mol, 3.0 eq). After degassing for 15 min. under argon atmosphere, 4,5-Bis(diphenylphosphino)-9,9-dimethylxanthene (xanthphos) (0.24 g, 0.428 mmol, 0.1 eq) and Tris(dibenzylideneacetone)dipalladium (Pd$_2$(dba)$_3$) (0.39 g, 0.428 mmol, 0.1 eq) were added. After stirring at 110° C. for 2 h, the reaction mixture was transferred into water (50 ml) and extracted by ethyl acetate (50 ml×3). The combined organic layer was washed with brine solution (100 ml), dried over sodium sulphate and concentrated under reduced pressure. The residue was purified by combiflash eluting with 4% DCM in methanol to afford 27.7 (900 mg, Yield: 45%) MS(ES): m/z 499.2 [M+H]+.

Step 8. (R)-8-((6-((dimethylamino)methyl)-5-(THF-3-yl)pyridin-2-yl)amino)-5-(7-fluoroimidazo[1,2-a] pyridin-3-yl)isoquinolin-1(2H)-one (I-356) and (S)-8-((6-((dimethylamino)methyl)-5-(THF-3-yl) pyridin-2-yl)amino)-5-(7-fluoroimidazo[1,2-a] pyridin-3-yl)isoquinolin-1(2H)-one (I-357)

27.7 (100 mg racemic) was separated by Chiral SFC in Shimadzu LC-20AP and UV detector. The column used was CHIRALPAK IC (250×21.0) mm, 5 micron, column flow was 20 ml/min. Mobile phase were used (A) 0.1% DEA IN n-Hexane (B) 0.1% DEA IN Propane 2-ol: Acetonitrile (70:30) to afford I-356 (25 mg) and I-357 (28 mg). stereochemistry was arbitrarily assigned. I-356: MS(ES): m/z=500.2 [M+H]+, 1H NMR (400 MHz, DMSO-d6) δ 12.81 (s, 1H), 11.61 (d, J=6.0 Hz, 1H), 8.89 (d, J=8.7 Hz, 1H), 7.93 (dd, J=7.5, 5.8 Hz, 1H), 7.77-7.63 (m, 3H), 7.55 (dd, J=10.2, 2.6 Hz, 1H), 7.15 (dd, J=7.3, 5.8 Hz, 1H), 7.01-6.88 (m, 2H), 5.89 (dd, J=7.3, 1.3 Hz, 1H), 4.05-3.93 (m, 2H), 3.81 (q, J=7.7 Hz, 2H), 3.54 (dd, J=8.2, 6.8 Hz, 1H), 2.36-2.18 (m, 6H), 1.90 (dq, J=12.1, 7.7 Hz, 1H). I-357: MS(ES): m/z=500.2 [M+H]+, 1H NMR (400 MHz, DMSO-d6) δ 12.81 (s, 1H), 11.63 (d, J=5.8 Hz, 1H), 8.80 (s, 1H), 7.93 (dd, J=7.6, 5.8 Hz, 1H), 7.77-7.63 (m, 3H), 7.56 (dd, J=10.1, 2.6 Hz, 1H), 7.23-7.11 (m, 1H), 7.02 (d, J=8.3 Hz, 1H), 6.93 (td, J=7.6, 2.6 Hz, 1H), 5.97-5.81 (m, 1H), 4.15-3.93 (m, 3H), 3.82 (q, J=7.7 Hz, 2H), 3.73 (s, 1H), 3.55 (t, J=7.6 Hz, 1H), 3.49 (t, J=5.3 Hz, 1H), 3.42 (t, J=5.2 Hz, 1H), 2.31 (s, 2H), 1.96-1.86 (m, 1H), 1.25 (d, J=8.0 Hz, 1H).

Example 28: Method GP—Preparation of 8-((5-(4-methylpiperazin-1-yl)pyridine-2-yl)amino)-5-(pyridine-4-yl)isoquinolin-1(2H)-one (I-358)

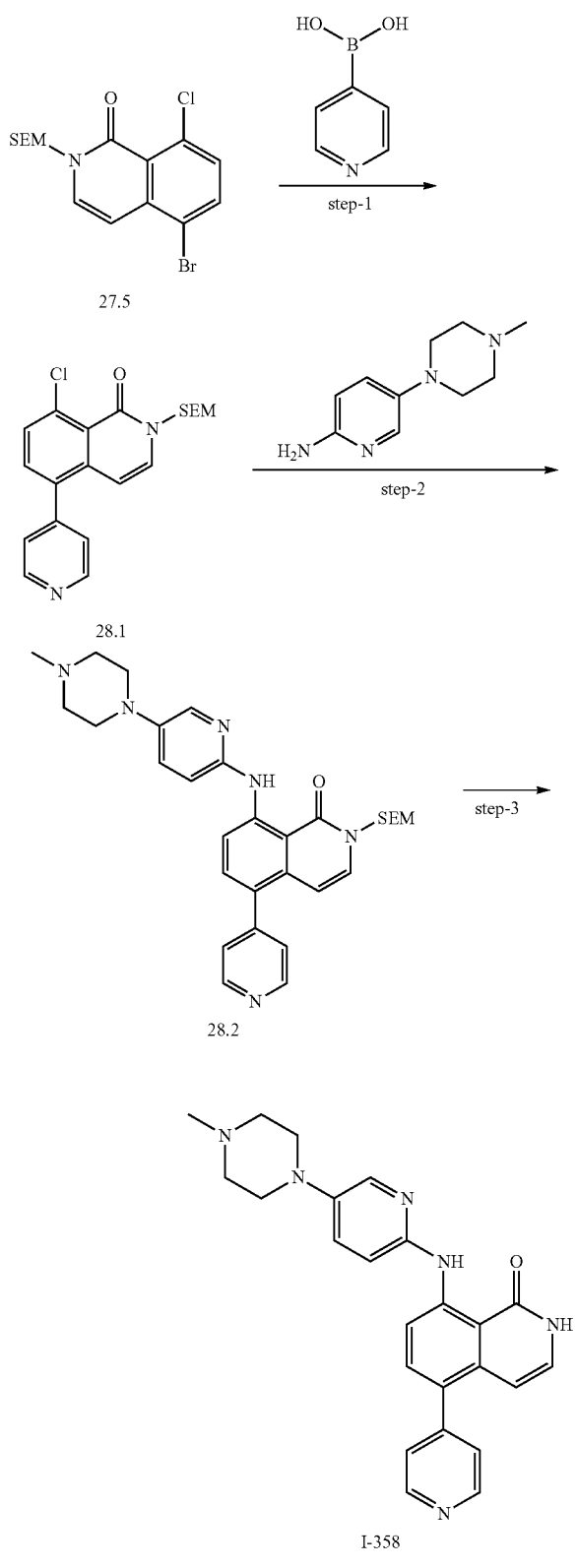

Step 1. 8-chloro-5-(pyridin-4-yl)-2-((2-(trimethylsilyl) ethoxy) methyl) iso quinolin-1(2H)-one (28.1)

To a solution of 5-bromo-8-chloro-2-((2-(trimethylsilyl)ethoxy)methyl)isoquinolin-1(2H)-one (27.5) (1.0 g, 2.57 mmol, 1.0 eq) and pyridin-4-ylboronic acid (0.75 g, 3.08 mmol, 1.2) in 1,4 dioxane (8 ml) and water (2 ml) was added potassium carbonate (1.06 g, 7.771 mmol, 3.0 eq). After degassing for 15 min. under argon atmosphere, [1,1'-Bis(diphenyl phosphino) ferrocene]palladium(II) dichloride DCM complex (Pd(dppf)Cl$_2$).dcm (0.205 g, 0.257 mmol, 0.1 eq) was added. After stirring at 110° C. for 1 hr, the reaction mixture was transferred into water (200 ml) and extracted with ethyl acetate (100 ml×3). The combined organic layer was washed with brine solution (100 ml), dried over sodium sulphate and concentrated under reduced pressure. The residue was purified by combiflash eluting with 4% DCM in methanol to afford 28.1 (700 mg, Yield: 60%) MS(ES): m/z 387.12 [M+H]+.

Step 2. 8-((5-(4-methylpiperazin-1-yl)pyridin-2-yl)amino)-5-(pyridin-4-yl)-2-((2-(trimethylsilyl)ethoxy)methyl)isoquinolin-1(2H)-one (28.2)

To a solution of 8-chloro-5-(pyridin-4-yl)-2-((2-(trimethylsilyl)ethoxy)methyl)isoquinolin-1(2H)-one (28.1) (0.7 g, 1.813 mmol, 1.0 eq) and 5-(4-methylpiperazin-1-yl)pyridin-2-amine (0.383 g, 1.99 mmol, 1.1 eq) in toluene (7 ml) was added K$_2$CO$_3$ (0.750 g, 5.43 mmol, 3.0 eq). After degassing for 15 min. under argon atmosphere, 4,5-Bis(diphenylphosphino)-9,9-dimethylxanthene (xanthphos) (0.104 g, 0.181 mmol, 0.1 eq) and Tris(dibenzylideneacetone)dipalladium (Pd$_2$(dba)$_3$) (0.165 g, 0.181 mmol, 0.1 eq) were added. After stirring at 110° C. for 2 h, the reaction mixture was transferred into water (200 ml) and extracted with ethyl acetate (100 ml×3). The combined organic layer was washed with brine solution (100 ml), dried over sodium sulphate and concentrated under reduced pressure. The residue was purified by combiflash eluting with 4% DCM in methanol to afford 28.2 (300 mg, Yield: 30.28%) MS(ES): m/z 543.28 [M+H]+.

Step 3. 8-((5-(4-methylpiperazin-1-yl)pyridin-2-yl)amino)-5-(pyridin-4-yl)isoquinolin-1(2H)-one (I-358)

To a solution of 8-((5-(4-methylpiperazin-1-yl)pyridin-2-yl)amino)-5-(pyridin-4-yl)-2-((2-(trimethylsilyl)ethoxy)methyl)isoquinolin-1(2H)-one (28.2) (300 mg, 0.777 mmol, 1.0 eq) in DCM (2 ml) at 0° C. was added 4M HCl in 1, 4 Dioxane (8 ml). After stirring at RT for 1 h, the reaction mixture was transferred into water (50 ml), neutralized with sodium bicarbonate and extracted with DCM (40 ml×3). The combined organic layer was washed with brine solution (50 ml), dried over sodium sulphate and concentrated under reduced pressure. The residue was purified by trituration with diethyl ether/pentane to afford I-358 (200 mg, 87% Yield). MS(ES): m/z 413.2 [M+H]+. 1H NMR (400 MHz, DMSO-d6) δ 12.51 (s, 1H), 8.70-8.54 (m, 3H), 8.00 (d, J=3.0 Hz, 1H), 7.54 (d, J=8.7 Hz, 1H), 7.50-7.39 (m, 3H), 7.17 (d, J=7.4 Hz, 1H), 6.96 (d, J=8.9 Hz, 1H), 6.47 (d, J=7.5 Hz, 1H), 3.13 (t, J=5.0 Hz, 4H), 2.5 (s, 4H, merged in DMSO peak), 2.26 (s, 3H).

345

Example 29: Method HP—Preparation of 5-(1-methyl-1H-imidazol-5-yl)-8-((5-(piperazin-1-yl)pyridin-2-yl)amino)isoquinolin-1(2H)-one (I-366)

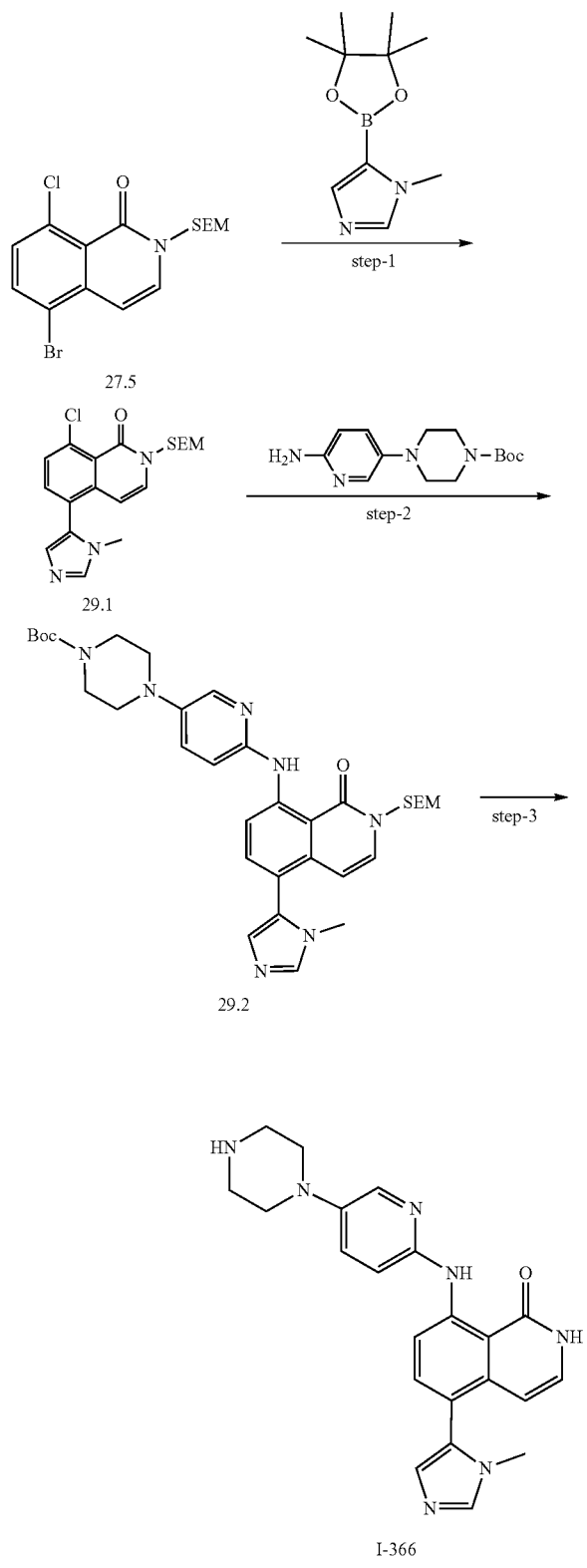

346

Step 1. 8-chloro-5-(1-methyl-1H-imidazol-5-yl)-2-((2-(trimethyl silyl) ethoxy) methyl)isoquinolin-1(2H)-one (29.1)

Reaction was carried out following the representative procedure described in Method GP (Step-1) using 5-bromo-8-chloro-2-((2-(trimethylsilyl)ethoxy)methyl)isoquinolin-1(2H)-one 27.5 and 1-methyl-5-(4,4,5,5-tetramethyl-1,3,2-dioxaborolan-2-yl)-1H-imidazole to afford 29.1 (1.4 g, 51.87% Yield) MS(ES): m/z 391.2 [M+H]$^+$ Step 2 & 3. 5-(1-methyl-1H-imidazol-5-yl)-8-((5-(piperazin-1-yl)pyridin-2-yl)amino)isoquinolin-1(2H)-one (I-366)

Reaction of step-2 & 3 was carried out following the representative procedure described in Method GP (Step-2 and 3) using 8-chloro-5-(1-methyl-1H-imidazol-5-yl)-2-((2-(trimethylsilyl)ethoxy)methyl)isoquinolin-1(2H)-one 29.1 and tert-butyl 4-(6-aminopyridin-3-yl)piperazine-1-carboxylate followed by 2-(Trimethylsilyl)ethoxymethyl (SEM) group deprotection to afford I-366 (0.8 g, 53.87% Yield) MS(ES): m/z 402.2 [M+H]$^+$ 1H NMR (400 MHz, DMSO-d6) δ 12.52 (s, 1H), 11.50 (s, 1H), 8.60 (d, J=8.7 Hz, 1H), 8.27 (s, 1H), 8.01 (d, J=3.0 Hz, 1H), 7.76 (s, 1H), 7.51-7.43 (m, 2H), 7.15 (d, J=5.7 Hz, 1H), 6.93 (d, J=8.9 Hz, 1H), 6.91 (td, J=7.5, 2.7 Hz, 1H), 6.14 (d, J=7.2 Hz, 1H), 3.36 (s, 3H), 3.26 (s, 4H), 3.17 (s, 4H).

Example 30: Method IP—Preparation of 8-((6-((dimethylamino)methyl)-5-(4-hydroxypiperidin-1-yl)pyridin-2-yl)amino)-5-(1-methyl-1H-pyrrolo[2,3-b]pyridin-4-yl)-2,6-naphthyridin-1(2H)-one (I-361)

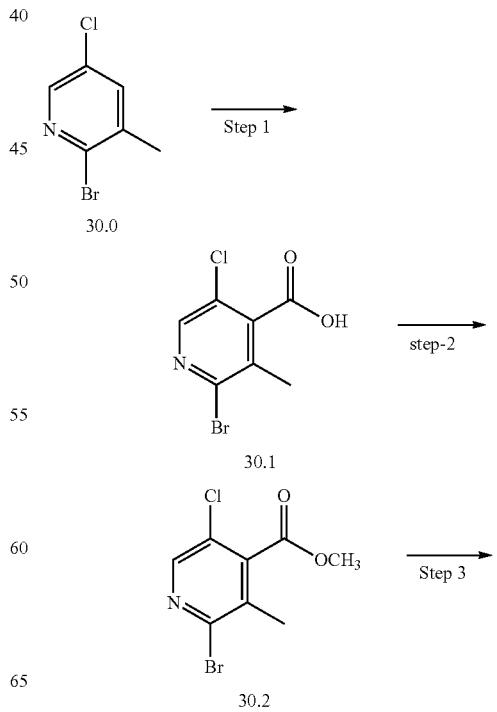

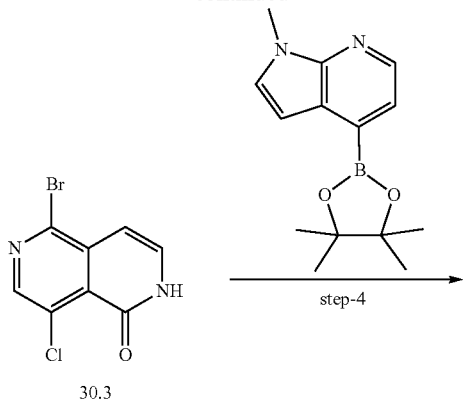

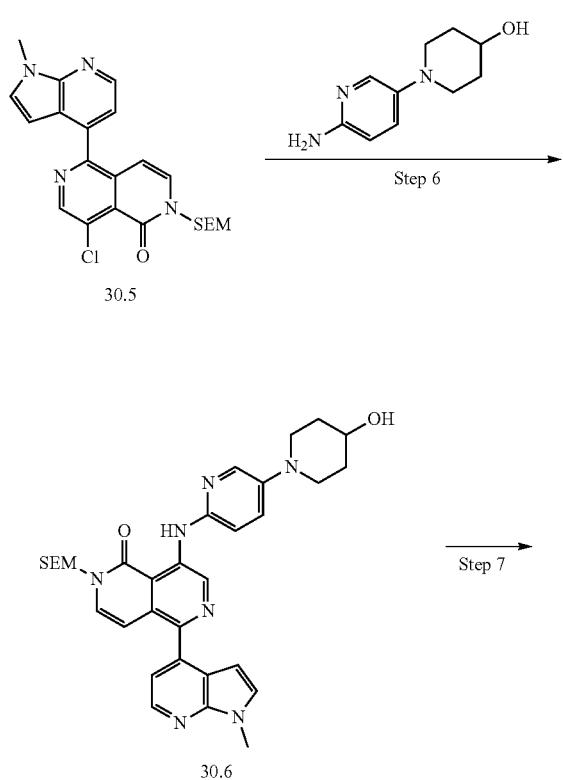

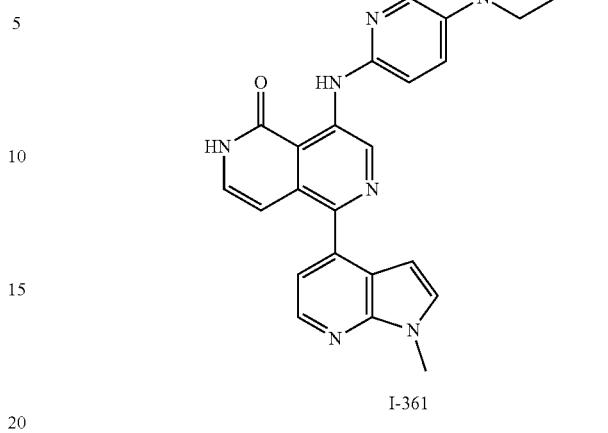

Step 1. 2-bromo-5-chloro-3-methylisonicotinic acid (30.1)

To a solution of 2-bromo-5-chloro-3-methylpyridine (30.0) (2.5 g, 12.13 mmol) in THF (25 mL) at −78° C. was added 2M Lithium diisopropylamide (LDA) in THF (2M, 9.1 mL, 18.15 mmol) dropwise under nitrogen atmosphere. After completion of addition of LDA, the reaction mixture was purged the $CO_2$ gas at −78° C. for 1 h. After warming to 0° C., the reaction mixture was diluted with ethylacetate (25 ml) and then water (25 ml). The aqueous layer was extracted with ethylacetate (2×100 ml). The aqueous layer neutralized with citric acid and then extracted with ethyl acetate (4×150 ml). The combined organic layer was dried over sodium sulphate and concentrated under reduced pressure to afford 2-bromo-5-chloro-3-methylisonicotinic acid (30.1) (1.7 g, 56%), which was used without further purification. MS(ES): m/z=251.4 $[M+H]^+$.

Step 2. methyl 2-bromo-5-chloro-3-methylisonicotinate (30.2)

To a solution of (30.1) (3 g, 12 mmol, 1.0 eq) in dimethylformamide (30 ml) under nitrogen atmosphere were added potassium carbonate (3.31 g, 24 mmol, 2.0 eq) and by Methyliodide (2.04 g, 14.5 mmol, 1.1 eq). After stirring at RT for 3 h, the reaction mixture was diluted with water (100 ml) and extracted with ethylacetate (3×150 ml). The combined organic layer was dried over sodium sulphate and concentrated under reduced pressure. The residue was purified by combiflash silicagel eluting with 5 to 10% ethylacetate in hexane to afford 30.2 (1.5 g, 47% yield) MS(ES): m/z=265.5 $[M+H]^+$ Step 3. 5-bromo-8-chloro-2,6-naphthyridin-1(2H)-one (30.3)

To a solution of methyl 2-bromo-5-chloro-3-methylisonicotinate (30.2) (1.5 g, 5.68 mmol, 1.0 eq) in NMP (15 ml) at 0° C. was added 1,3,5 Triazine (0.92 g, 11.36 mmol, 2.0 eq) dropwise. After warming to RT, potassium tertiary butoxide (1.2 g, 11.36 mmol, 2.0 eq) was added. After stirring at 110° C. for 1 h, the reaction mixture was transferred to water (100 ml) and extracted with ethyl acetate (50 ml×3). The combined organic layer was washed with brine solution (100 ml), dried over sodium sulphate and concentrated under reduced pressure. The residue was triturated with ether to afford 30.3 (1.0 g, 68% Yield). MS(ES): m/z 260.0 [M+H]$^+$.

Step 4. 8-chloro-5-(1-methyl-1H-pyrrolo[2,3-b]pyridin-4-yl)-2,6-naphthyridin-1(2H)-one (9.4)

To a solution 5-bromo-8-chloro-2,6-naphthyridin-1(2H)-one (30.3) (1.0 g, 3.84 mmol, 1.0 eq) and 1-methyl-4-(4,4,5,5-tetramethyl-1,3,2-dioxaborolan-2-yl)-1H-pyrrolo[2,3-b]pyridine (1.0 g, 4.2 mmol, 1.1 eq) in dioxane (10 ml) and water (2 ml) was added potassium phosphate (2.4 g, 11.5 mmol, 3.0 eq). After degassing for 15 mins under argon atmosphere, [1,1'-Bis (diphenyl phosphino) ferrocene] palladium(II) dichloride. DCM complex (Pd(dppf)Cl$_2$).dcm (0.31 g, 0.384 mmol, 0.1 eq) was added. After stirring at 90° C. for 1 h, the reaction mixture was transferred into water (100 ml) and extracted with ethyl acetate (50 ml×3). The combined organic layer was washed with brine solution (100 ml), dried over sodium sulphate, and concentrated under reduced pressure. The residue was purified by combiflash eluting with 100% ethyl acetate to afford 30.4 (0.8 g, 66.8% Yield). MS(ES): m/z 311.0 [M+H]$^+$.

Step 5. 8-chloro-5-(1-methyl-1H-pyrrolo[2,3-b]pyridin-4-yl)-2-((2-(trimethyl silyl) ethoxy)methyl)-2,6-naphthyridin-1(2H)-one (30.5)

To a solution of 8-chloro-5-(1-methyl-1H-pyrrolo[2,3-b]pyridin-4-yl)-2,6-naphthyridin-1(2H)-one (30.4) (0.8 g, 2.58 mmol, 1.0 eq) in THF (8 ml) was added DBU (0.16 g, 12.9 mmol, 5.0 eq). After stirring at RT for 20 mins, 2-(Trimethylsilyl)ethoxymethyl chloride (1.71 g, 10.32 mmol, 4.0 eq) was added at 0° C. After stirring at RT for 3 h, the reaction mixture was transferred into water (100 ml) and extracted with ethyl acetate (50 ml×3). The combined organic layer was washed with brine solution (100 ml), dried over sodium sulphate and concentrated under reduced pressure. The residue was purified using combiflash eluting in 50% ethyl acetate in aexane to afford 30.5 (1.0 g, 88% yield) MS(ES): m/z 442.0 [M+H]$^+$.

Step 6. 8-((5-(4-hydroxypiperidin-1-yl)pyridin-2-yl)amino)-5-(1-methyl-1H-pyrrolo[2,3-b]pyridin-4-yl)-2-((2-(trimethylsilyl)ethoxy)methyl)-2,6-naphthyridin-1(2H)-one (30.6)

To a solution of 8-chloro-5-(1-methyl-1H-pyrrolo[2,3-b]pyridin-4-yl)-2-((2-(trimethylsilyl)ethoxy)methyl)-2,6-naphthyridin-1(2H)-one (30.5) (1.0 g, 2.26 mmol, 1.0 eq) in dioxane (10 ml) were added 1-(6-aminopyridin-3-yl)piperidin-4-ol (0.48 g, 2.48 mmol, 1.1 eq) and cesium carbonate (2.2 g, 6.78 mmol, 3.0 eq). After degassing for 15 min. under argon atmosphere, 4,5-Bis(diphenylphosphino)-9,9-dimethylxanthene (xanthphos) (0.150 g, 0.26 mmol, 0.1 eq) and Chloro(2-dicyclohexylphosphino-2',4',6'-triisopropyl-1,1'-biphenyl)[2-(2'-amino-1,1'-biphenyl)]palladium(II) (xphos PdG$_2$) (0.204 g, 0.26 mmol, 0.1 eq) were added. After stirring at 110° C. for 16 h, the reaction mixture was transferred into water (100 ml) and extracted in DCM (50 ml×3). The combined organic layer was washed with brine solution, dried over sodium sulphate and concentrated under reduced pressure. The reside was purified using combiflash eluting with 15% methanol in DCM to afford 30.6 (0.8 g, 59% Yield) MS(ES): m/z 598.0 [M+H]$^+$.

Step 7. 8-((5-(4-hydroxypiperidin-1-yl)pyridin-2-yl)amino)-5-(1-methyl-1H-pyrrolo[2,3-b]pyridin-4-yl)-2,6-naphthyridin-1(2H)-one (I-361)

To a solution of 8-((5-(4-hydroxypiperidin-1-yl)pyridin-2-yl)amino)-5-(1-methyl-1H-pyrrolo[2,3-b]pyridin-4-yl)-2-((2-(trimethylsilyl)ethoxy)methyl)-2,6-naphthyridin-1(2H)-one (30.6) (0.8 g, 1.0 eq) in DCM (10 ml) at 0° C. was added 4M HCl in dioxane (10 ml) portionwise. After stirring at RT for 2 h, the reaction mixture was neutralized with aqueous NaHCO$_3$ and extracted with 10% methanol in DCM (50 ml×3). The combined organic layer was dried over sodium sulphate and concentrated under reduced pressure. The residue was purified using combiflash eluting with 15% Methanol in DCM to afford I-361 (0.43 g, 69% yield). MS(ES): m/z 468.0 [M+H]$^+$. 1H NMR (400 MHz, DMSO-d6) δ 11.41 (s, 1H), 9.33 (s, 1H), 8.32-8.07 (m, 2H), 8.04 (d, J=3.1 Hz, 1H), 7.97-7.77 (m, 2H), 7.51-7.37 (m, 2H), 7.32 (t, J=6.4 Hz, 1H), 7.18 (d, J=7.4 Hz, 1H), 6.92 (d, J=4.9 Hz, 1H), 6.07 (d, J=3.5 Hz, 1H), 4.70 (s, 1H), 3.84 (s, 3H), 3.71-3.58 (m, 1H), 3.49 (dd, J=11.2, 6.2 Hz, 2H), 2.93-2.76 (m, 2H), 1.97-1.75 (m, 2H), 1.51 (q, J=11.1, 9.7 Hz, 2H).

Example 31: Method JP—Preparation of 8-((6-((dimethylamino)methyl)-5-morpholinopyridin-2-yl)amino)-5-(1-methyl-1H-pyrrolo[2,3-b]pyridin-4-yl)-2,6-naphthyridin-1(2H)-one (I-369)

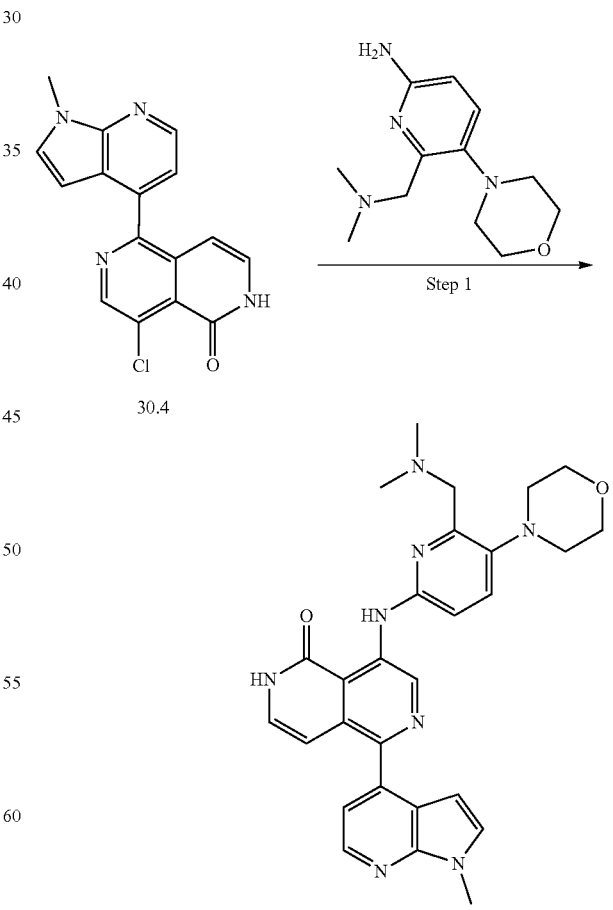

Reaction was carried out following the representative procedure described in Method IP (Step-6) using 8-chloro-5-(1-methyl-1H-pyrrolo[2,3-b]pyridin-4-yl)-2,6-naphthyridin-1(2H)-one 30.4 and 6-((dimethylamino)methyl)-5-morpholinopyridin-2-amine to afford I-369 (0.8 g, 53.87% Yield) MS(ES): m/z 511.2.0 [M+H]+. 1H NMR (400 MHz, DMSO-d6) δ 9.40 (s, 1H), 8.24 (d, J=4.9 Hz, 1H), 7.91-7.74 (m, 2H), 7.45 (dd, J=8.2, 4.9 Hz, 2H), 6.97 (dd, J=16.2, 6.1 Hz, 2H), 4.51 (s, 1H), 3.86 (s, 2H), 3.81-3.74 (m, 2H), 2.95 (s, 2H), 2.85 (t, J=4.5 Hz, 2H).

Example 32: The Compounds of the Invention

The compounds of the invention were made according to the procedures outlined above with known literature/commercially available boronates and anilines or with listed intermediates. In the case where the reagents are written out, they are known literature/commercially available.

TABLE 2

| I-# | STRUCTURE | NAME | LCMS | HNMR | Method SM |
|---|---|---|---|---|---|
| I-1 | 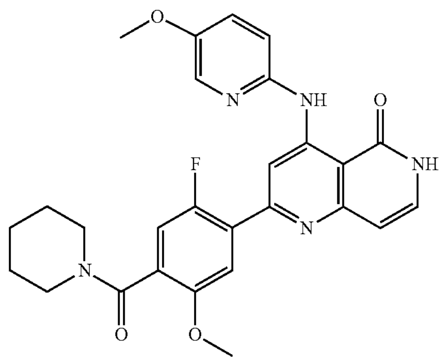 [SMILES: COc1ccc(Nc2cc(-c3cc(OC)c(C(=O)N4CCCCC4)cc3F)nc3cc[nH]c(=O)c23)nc1] | 2-[2-fluoro-5-methoxy-4-(piperidine-1-carbonyl)phenyl]-4-[(5-methoxy-2-pyridyl)amino]-6H-1,6-naphthyridin-5-one | Method AcHSS C18, m/z = 504 [M + H]+, Ret. time = 3.39 min. | $^1$H NMR (400 MHz, DMSO): δ 12.55 (s, 1H), 11.72 (s, 1 H), 8.78 (s, 1 H), 8.12 (d, J = 3.0 Hz, 1 H), 7.57 (d, J = 6.1 Hz, 1 H), 7.49-7.42 (m, 2 H), 7.25 (s, 1 H), 7.12 (d, J = 8.8 Hz, 1 H), 6.62 (d, J = 7.3 Hz, 1 H), 3.85 (s, 3 H), 3.82 (s, 3 H), 3.65-3.55 (m, 2 H), 3.18-3.14 (m, 2 H), 1.62-1.54 (m, 4 H), 1.47-1.41 (m, 2 H). | A 5-methoxy pyridin-2-amine CB1 |
| I-2 | 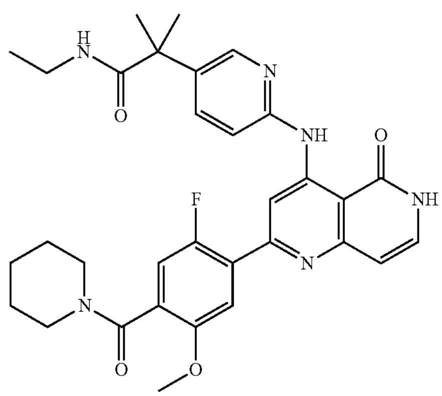 [SMILES: CCNC(=O)C(C)(C)c1ccc(Nc2cc(-c3cc(OC)c(C(=O)N4CCCCC4)cc3F)nc3cc[nH]c(=O)c23)nc1] | N-ethyl-2-[6-[[2-[2-fluoro-5-methoxy-4-(piperidine-1-carbonyl)phenyl]-5-oxo-6H-1,6-naphthyridin-4-yl]amino]-3-pyridyl]-2-methyl-propanamide | Method BicarbB EHC18, m/z = 587 [M + H]+, Ret. time = 4.08 min. | $^1$H NMR (400 MHz, DMSO): δ 12.75 (s, 1 H), 11.78 (s, 1 H), 9.09 (s, 1 H), 8.32 (d, J = 1.8 Hz, 1 H), 7.67 (dd, J = 2.3, 8.6 Hz, 1 H), 7.59 (d, J = 6.1 Hz, 1 H), 7.45 (d, J = 6.8 Hz, 2 H), 7.26 (d, J = 8.3 Hz, 1 H), 7.06 (d, J = 8.3 Hz, 1 H), 6.64 (d, J = 7.3 Hz, 1 H), 3.86 (s, 3 H), 3.62-3.55 (m, 2 H), 3.20-3.15 (m, 2 H), 3.10-3.00 (m, 4 H), 1.60 (dd, J = 4.8, 20.7 Hz, 4 H), 1.47 (s, 6 H), 0.95 (dd, J = 7.2, 7.2 Hz, 3 H). | A CA1 CB1 |
| I-3 | 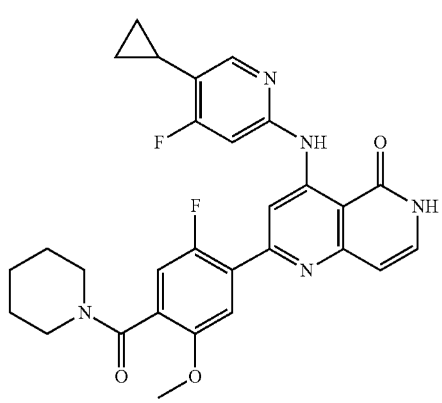 [SMILES: COc1cc(-c2cc(Nc3cc(F)c(C4CC4)cn3)c3c(=O)[nH]ccc3n2)c(F)cc1C(=O)N1CCCCC1] | 4-[(5-cyclopropyl-4-fluoro-2-pyridyl)amino]-2-[2-fluoro-5-methoxy-4-(piperidine-1-carbonyl)phenyl]-6H-1,6-naphthyridin-5-one | Method BicarbB EHC18, m/z = 532 [M + H]+, Ret. time = 5.09 min. | $^1$H NMR (400 MHz, DMSO): δ 12.78 (s, 1 H), 11.79-11.77 (m, 1 H), 8.98 (d, J = 1.4 Hz, 1 H), 8.16 (d, J = 6.0 Hz, 1 H), 7.57 (d, J = 6.0 Hz, 1 H), 7.48 (d, J = 7.3 Hz, 1 H), 7.27 (d, J = 7.3 Hz, 1 H), 7.05 (d, J = 7.3 Hz, 1 H), 6.66 (d, J = 7.3 Hz, 1 H), 3.87 (s, 3 H) 3.67-3.56 (m, 2 H), 3.17 (dd, J = 5.4, 5.4 Hz, 2 H), 1.98-1.90 (m, 1 H), 1.65-1.45 (m, 6 H), 0.99-0.93 (m, 2 H), 0.86-0.81 (m, 2 H). | A 5-cyclopropyl-4-fluoro-pyridin-2-amine CB1 |

TABLE 2-continued

| I-# | STRUCTURE | NAME | LCMS | HNMR | Method SM |
|---|---|---|---|---|---|
| I-4 | 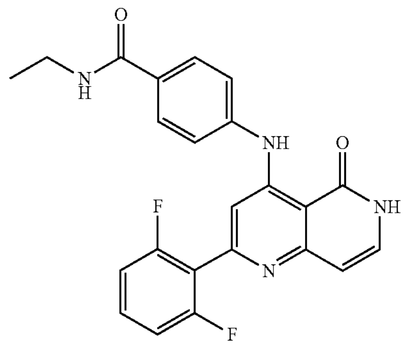 [SMILES: CCNC(=O)c1ccc(Nc2cc(-c3c(F)cccc3F)nc3cc[nH]c(=O)c23)cc1] | 4-[[2-(2,6-difluoro-phenyl)-5-oxo-6H-1,6-naphthyridin-4-yl]amino]-N-ethyl-benzamide | Method 10cm_Bicarb_AQ, m/z = 421 [M + H]+, Ret time = 2.87 min. | $^1$H NMR (400 MHz, DMSO) δ 11.92 (s, 1H), 11.79 (s, 1H), 8.47 (dd, J = 5.4, 5.4 Hz, 1H), 7.94 (d, J = 8.6 Hz, 2H), 7.63-7.54 (m, 1H), 7.52-7.46 (m, 3H), 7.26 (dd, J = 8.1, 8.1 Hz, 2H), 7.11 (s, 1H), 6.60 (d, J = 7.1 Hz, 1H), 3.32 (q, J = 7.2 Hz, 2H), 1.16 (t, J = 7.2 Hz, 3H). | B 4-amino-N-ethyl-benzamide 2-bromo-1,3-difluoro benzene |
| I-5 | 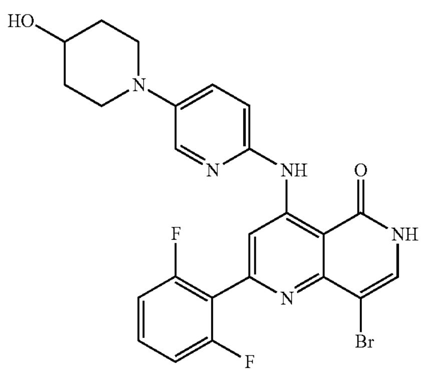 [SMILES: O=c1[nH]cc(Br)c2nc(-c3c(F)cccc3F)cc(Nc3ccc(N4CCC(O)CC4)cn3)c12] | 8-bromo-2-(2,6-difluoro-phenyl)-4-[[5-(4-hydroxy-1-piperidyl)-2-pyridyl]amino]-6H-1,6-naphthyridin-5-one | Method 10cm_Formic_AQ, m/z = 528 [M + H]+, Ret. time = 3.02 min. | $^1$H NMR (400 MHz, DMSO) δ 12.65 (s, 1H), 12.13-12.09 (m, 1H), 8.60 (s, 1H), 8.11 (d, J = 2.5 Hz, 1H), 7.19 (s, 1H), 7.69-7.06 (m, 1H), 7.52 (dd, J = 2.9, 9.0 Hz, 1H), 7.32 (dd, J = 8.0, 8.0 Hz, 2H), 7.07 (d, J = 8.8 Hz, 1H), 4.73 (d, J = 4.3 Hz, 1H), 3.70-3.65 (m, 1H), 3.56 (d, J = 12.6 Hz, 2H), 2.95-2.86 (m, 2H), 1.90-1.84 (m, 2H), 1.58-1.46 (m, 2H). | H 1-(6-amino-pyridin-3-yl)piperidin-4-ol 2-bromo-1,3-difluoro benzene |
| I-6 | 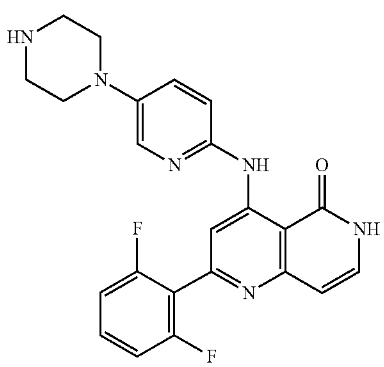 [SMILES: O=c1[nH]ccc2nc(-c3c(F)cccc3F)cc(Nc3ccc(N4CCNCC4)cn3)c12] | 2-(2,6-difluoro-phenyl)-4-[(5-piperazin-1-yl-2-pyridyl)amino]-6H-1,6-naphthyridin-5-one | Method 10cm_Bicarb_AQ, m/z = 435 [M + H]+, Ret. time = 2.67 min. | $^1$H NMR (400 MHz, DMSO) δ 12.59 (s, 1H), 8.50 (s, 1H), 8.07 (d, J = 2.8 Hz, 1H), 7.67-7.57 (m, 1H), 7.52-7.46 (m, 2H), 7.30 (dd, J = 8.0, 8.0 Hz, 2H), 7.06 (d, J = 8.8 Hz, 1H), 6.60 (d, J = 7.3 Hz, 1H), 3.08 (dd, J = 4.7, 4.7 Hz, 4H), 2.87 (dd, J = 4.8, 4.8 Hz, 4H). | B and G tert-butyl 4-(6-amino-pyridin-3-yl)piperazine-1-carboxylate 2-bromo-1,3-difluoro benzene |
| I-7 | 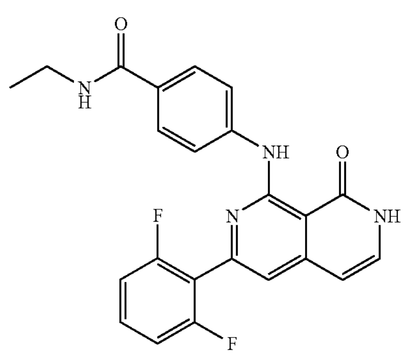 [SMILES: CCNC(=O)c1ccc(Nc2nc(-c3c(F)cccc3F)cc3cc[nH]c(=O)c23)cc1] | 4-[[3-(2,6-difluoro-phenyl)-8-oxo-7H-2,7-naphthyridin-1-yl]amino]-N-ethyl-benzamide | Method 10cm_Bicarb_AQ, m/z = 421 [M + H]+, Ret. time = 3.14 min. | $^1$H NMR (400 MHz, DMSO) δ 12.25 (s, 1H), 11.99 (s, 1H), 8.30 (dd, J = 5.5, 5.5 Hz, 1H), 7.89 (d, J = 8.9 Hz, 2H), 7.82 (d, J = 8.8 Hz, 2H), 7.64-7.56 (m, 1H), 7.51 (d, J = 6.9 Hz, 1H), 7.31 (dd, J = 8.2, 8.2 Hz, 2H), 7.19 (s, 1H), 6.63 (d, J = 7.0 Hz, 1H), 3.32-3.23 (m, 2H), 1.12 (t, J = 7.2 Hz, 3H). | Q 4-amino-N-ethyl-benzamide 2-bromo-1,3-difluoro-benzene |

TABLE 2-continued

| I-# | STRUCTURE | NAME | LCMS | HNMR | Method SM |
|---|---|---|---|---|---|
| I-8 | (structure) | 6-(2,6-difluoro-phenyl)-8-[[5-(4-hydroxy-1-piperidyl)-2-pyridyl]amino]-2H-2,7-naphthyridin-1-one | Method 10cm_Formic_AQ, m/z = 450 [M + H]+, Ret. time = 2.65 min. | $^1$H NMR (400 MHz, DMSO) δ 12.10 (s, 1H), 11.83-11.83 (m, 1H), 8.28 (d, J = 9.0 Hz, 1H), 7.94 (d, J = 2.9 Hz, 1H), 7.55-7.46 (m, 1H), 7.40 (d, J = 7.0 Hz, 1H), 7.30 (dd, J = 3.0, 9.2 Hz, 1H), 7.21 (dd, J = 8.2, 8.2 Hz, 2H), 7.02 (s, 1H), 6.50 (d, J = 7.0 Hz, 1H), 4.60 (d, J = 3.6 Hz, 1H), 3.56-3.51 (m, 1H), 3.41 (dd, J = 3.9, 8.3 Hz, 2H), 2.78-2.70 (m, 2H), 1.78-1.70 (m, 2H), 1.46-1.35 (m, 2H). | Q 1-(6-amino-pyridin-3-yl)piperidin-4-ol 2-bromo-1,3-difluoro benzene |
| I-9 | (structure) | 4-[[5-(4-hydroxy-1-piperidyl)-2-pyridyl]amino]-2-isopropyl-6H-1,6-naphthyridin-5-one | Method 10cm_Formic_AQ, m/z = 380 [M + H]+, Ret. time = 2.4 min. | $^1$H NMR (400 MHz, DMSO) δ 12.32 (s, 1H), 11.50 (d, H = 3.8 Hz, 1H), 8.19 (s, 1H), 8.10 (d, J = 3.0 Hz, 1H), 7.47 (dd, J = 2.9, 9.0 Hz, 1H), 7.34 (dd, J = 6.3, 6.3 Hz, 1H), 6.99 (d, J = 8.8 Hz, 1H), 6.49 (d, J = 7.1 Hz, 1H), 4.71 (d, J = 4.0 Hz, 1H), 3.69-3.62 (m, 1H), 3.57-3.48 (m, 2H), 2.97-2.83 (m, 3H), 1.85 (dd, J = 3.3, 12.9 Hz, 2H), 1.57-1.46 (m, 2H), 1.26 (d, J = 6.8 Hz, 6H). | B 1-(6-amino-pyridin-3-yl)piperidin-4-ol 2-Propylzinc bromide |
| I-10 | (structure) | N-ethyl-4-[(2-isopropyl-5-oxo-6H-pyrido[4,3-d]pyrimidin-4-yl)amino]benzamide | Method 10cm_Bicarb_AQ, m/z = 352 [M + H]+, Ret. time = 2.87 min. | $^1$H NMR (400 MHz, DMSO) δ 12.13 (s, 1H), 12.00 (s, 1H), 8.41 (dd, J = 5.4, 5.4 Hz, 1H), 7.98 (d, J = 8.9 Hz, 2H) 7.91 (d, J = 8.8 Hz, 2H), 7.62 (d, J = 7.2 Hz, 1H), 6.48 (d, J = 7.2 Hz, 1H), 3.32-3.26 (m, 2H), 3.09-2.99 (m, 1H), 1.33 (d, J = 6.9 Hz, 6H), 1.14 (dd, J = 7.2, 7.2 Hz, 3H). | T 4-amino-N-ethyl-benzamide |
| I-11 | (structure) | 7-(2,6-difluoro-phenyl)-5-[[5-(4-hydroxy-1-piperidyl)-2-pyridyl]amino]-3H-pyrido[2,3-d]pyrimidin-4-one | Method 10cm_Formic_AQ, m/z = 451 [M + H]+, Ret. time = 2.49 min. | $^1$H NMR (400 MHz, DMSO) δ 11.87-11.82 (m, 1H), 8.38 (s, 1H), 8.22 (s, 1H), 7.98 (d, J = 7.8 Hz, 1H), 7.55-7.46 (m, 1H), 7.39 (dd, J = 2.9, 9.0 Hz, 1H), 7.19 (dd, J = 8.0, 8.0 Hz, 2H), 6.96 (d, J = 8.8 Hz, 1H), 4.60-4.60 (m, 1H), 3.59-3.51 (m, 1H), 3.48-3.39 (m, 3H), 2.83-2.74 (m, 2H), 1.75-1.71 (m, 2H), 1.45-1.33 (m, 2H). | R 1-(6-amino-pyridin-3-yl)piperidin-4-ol 2,6-difluoro phenyl-tributyltin |

TABLE 2-continued

| I-# | STRUCTURE | NAME | LCMS | HNMR | Method SM |
|---|---|---|---|---|---|
| I-12 | 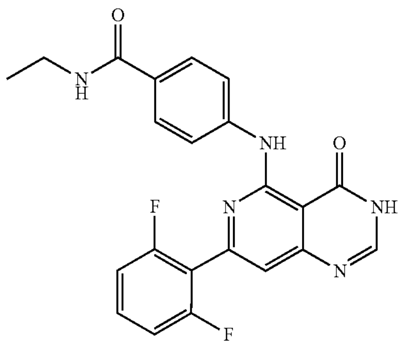 [SMILES: CCNC(=O)c1ccc(Nc2nc(-c3c(F)cccc3F)cc3nc[nH]c(=O)c23)cc1] | 4-[[7-(2,6-difluoro-phenyl)-4-oxo-3H-pyrido[4,3-d]pyrimidin-5-yl]amino]-N-ethyl-benzamide | Method 10cm_Bicarb_AQ, m/z = 422 [M + H]+, Ret. time = 2.9 min. | ¹H NMR (400 MHz, DMSO) δ 11.67 (s, 1H), 8.25-8.20 (m, 2H), 7.81 (d, J = 8.3 Hz, 2H), 7.74 (d, J = 8.3 Hz, 2H), 7.57-7.48 (m, 1H), 7.22 (dd, J = 8.1, 8.1 Hz, 2H), 7.02 (s, 1H), 3.19 (q, J = 6.7 Hz, 2H), 1.04 (dd, J = 6.8, 6.8 Hz, 3H). One NH resonance not observed. | S 4-amino-N-ethyl-benzamide 2,6-difluoro phenyl-tributyltin |
| I-13 | 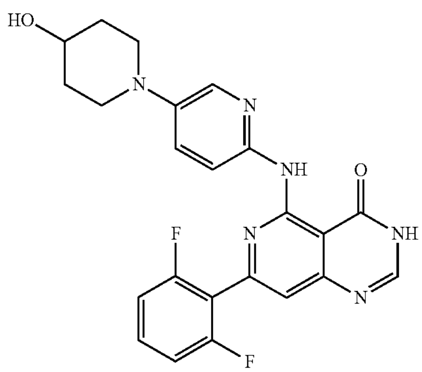 [SMILES: O=c1[nH]cnc2cc(-c3c(F)cccc3F)nc(Nc3ccc(N4CCC(O)CC4)cn3)c12] | 7-(2,6-difluoro-phenyl)-5-[[5-(4-hydroxy-1-piperidyl)-2-pyridyl]amino]-3H-pyrido[4,3-d]pyrimidin-4-one | Method 10cm_Formic_AQ, m/z = 451 [M + H]+, Ret. time = 2.56 min. | ¹H NMR (400 MHz, DMSO) δ 12.80-12.79 (m, 1H), 11.41 (s, 1H), 8.29-8.22 (m, 2H), 7.97-7.95 (m, 1H), 7.57-7.48 (m, 1H), 7.32 (dd, J = 2.4, 9.2 Hz, 1H), 7.22 (dd, J = 8.2, 8.2 Hz, 2H), 6.98 (s, 1H), 4.60 (d, J = 4.0 Hz, 1H), 3.58-3.50 (m, 1H), 3.45-3.37 (m, 2H), 2.74 (dd, J = 10.0, 10.0 Hz, 2H), 1.78-1.72 (m, 2H), 1.46-1.35 (m, 2H). | S 1-(6-amino-pyridin-3-yl)piperidin-4-ol 2,6-difluoro phenyl-tributyltin |
| I-14 | 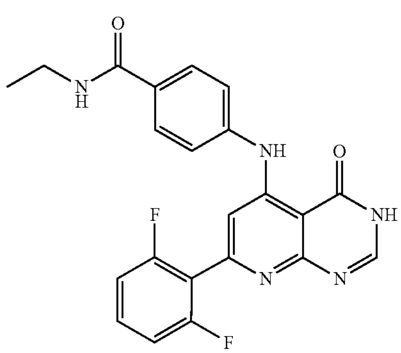 | 4-[[7-(2,6-difluoro-phenyl)-4-oxo-3H-pyrido[2,3-d]pyrimidin-5-yl]amino]-N-ethyl-benzamide | Method 10cm_Formic_AQ, m/z = 422 [M + H]+, Ret. time = 2.55 min. | ¹H NMR (400 MHz, DMSO) δ 12.65 (s, 1H), 11.11 (s, 1H), 8.39-8.33 (m, 1H), 8.23-8.20 (m, 1H), 7.83 (d, J = 8.6 Hz, 2H), 7.53-7.43 (m, 1H), 7.38 (d J = 8.3 Hz, 2H), 7.15 (dd, J = 8.1, 8.1 Hz, 2H), 7.03 (s, 1H), 3.20 (q, J = 6.7 Hz, 2H), 1.04 (dd, J = 7.2, 7.2 Hz, 3H). | R 4-amino-N-ethyl-benzamide 2,6-difluoro phenyl-tributyltin |
| I-15 | 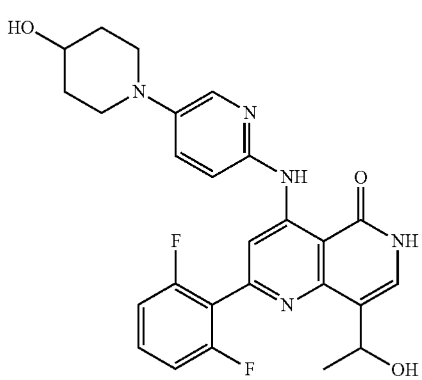 [SMILES: CC(O)c1c[nH]c(=O)c2c(Nc3ccc(N4CCC(O)CC4)cn3)cc(-c3c(F)cccc3F)nc12] | 2-(2,6-difluoro-phenyl)-8-(1-hydroxy-ethyl)-4-[[5-(4-hydroxy-1-piperidyl)-2-pyridyl]amino]-6H-1,6-naphthyridin-5-one | Method 10cm_Formic_AQ, m/z = 494 [M + H]+, Ret. time = 2.66 min. | ¹H NMR (400 MHz, MeOD) δ 8.44 (s, 1H), 8.09 (d, J = 2.9 Hz, 1H), 7.56-7.48 (m, 2H), 7.38 (s, 1H), 7.14 (dd, J = 8.2, 8.2 Hz, 2H), 7.07 (d, J = 8.8 Hz, 1H), 5.23 (q, J = 6.3 Hz, 1H), 3.82-3.74 (m, 1H), 3.62-3.54 (m, 2H), 2.98-2.90 (m, 2H), 2.03-1.97 (m, 2H), 1.73-1.63 (m, 2H), 1.56 (d, J = 6.4 Hz, 3H). 3 Exchangable protons not observed | H 1-(6-amino-pyridin-3-yl) piperidin-4-ol 2-bromo-1,3-difluoro benzene |

TABLE 2-continued

| I-# | STRUCTURE | NAME | LCMS | HNMR | Method SM |
|---|---|---|---|---|---|
| I-16 | 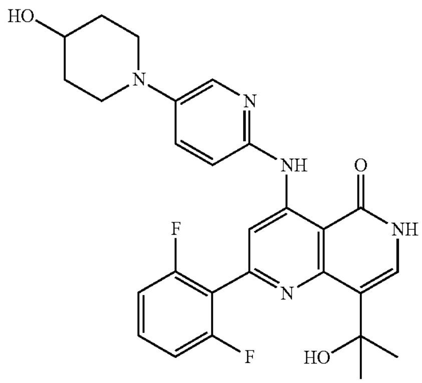 [SMILES: CC(C)(O)c1c[nH]c(=O)c2c(Nc3ccc(N4CCC(O)CC4)cn3)cc(-c3c(F)cccc3F)nc12] | 2-(2,6-difluoro-phenyl)-8-(1-hydroxy-1-methyl-ethyl)-4-[[5-(4-hydroxy-1-piperidyl)-2-pyridyl]amino]-6H-1,6-naphthyridin-5-one | Method 10cm_Formic_AQ, m/z = 508 [M + H]+, Ret. time = 2.71 min. | $^1$H NMR (400 MHz, MeOD) δ 12.51 (s, 1H), 8.48 (td, J = 1.3, 11.9 Hz, 2H), 8.11 (d, J = 2.9 Hz, 1H), 7.57-7.49 (m, 2H), 7.36 (s, 1H), 7.16 (dd, J = 8.3, 8.3 Hz, 2H), 7.08 (dd, J = 1.6, 8.8 Hz, 1H), 3.83-3.75 (m, 1H), 3.63-3.56 (m, 2H), 2.99-2.91 (m, 2H), 2.03-1.98 (m, 2H), 1.74-1.67 (m, 2H), 1.65 (s, 6H). 2 Exchangable Protons not observed | H 1-(6-amino-pyridin-3-yl)piperidin-4-ol 2-bromo-1,3-difluoro benzene |
| I-17 | 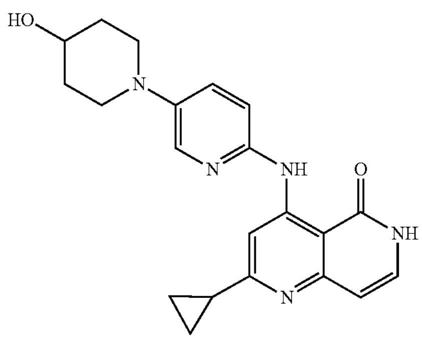 [SMILES: O=c1[nH]ccc2nc(C3CC3)cc(Nc3ccc(N4CCC(O)CC4)cn3)c12] | 2-cyclopropyl-4-[[5-(4-hydroxy-1-piperidyl)-2-pyridyl]amino]-6H-1,6-naphthyridin-5-one | Method 10cm_Bicarb_AQ, m/z = 378 [M + H]+, Ret. time = 2.8 min. | $^1$H NMR (400 MHz, DMSO) δ 12.78 (s, 1H), 11.63 (s, 1H), 8.55 (s, 1H), 8.09 (d, J = 2.8 Hz, 1H), 7.67-7.58 (m, 1H), 7.51 (dd, J = 2.9, 9.0 Hz, 1H), 7.37 (s, 1H), 7.31 (dd, J = 8.0, 8.0 Hz, 2H), 7.04 (d, J = 8.8 Hz, 1H), 4.73 (s, 1H), 3.70-3.65 (m, 1H), 3.54 (d, J = 12.9 Hz, 2H), 2.94-2.85 (m, 2H), 2.21 (s, 3H), 1.90-1.84 (m, 2H), 1.58-1.47 (m, 2H). | B 1-(6-amino-pyridin-3-yl)piperidin-4-ol Cyclo-propylzinc bromide |
| I-18 | 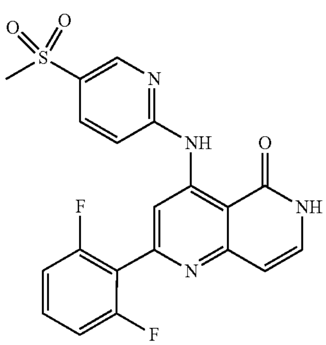 [SMILES: CS(=O)(=O)c1ccc(Nc2cc(-c3c(F)cccc3F)nc3cc[nH]c(=O)c23)nc1] | 2-(2,6-difluoro-phenyl)-4-[(5-methyl-sulfonyl-2-pyridyl)amino]-6H-1,6-naphthyridin-5-one | Method 10cm_Bicarb_AQ, m/z = 429 [M + H]+, Ret. time = 2.99 min. | $^1$H NMR (400 MHz, DMSO) δ 13.29 (s, 1H), 11.95-11.89 (m, 1H), 8.78 (s, 1H), 8.75 (d, J = 2.5 Hz, 1H), 8.12 (dd, J = 2.6, 8.7 Hz, 1H), 7.58-7.49 (m, 1H), 7.45 (d, J = 7.3 Hz, 1H), 7.24-7.19 (m, 3H), 6.60 (d, J = 7.3 Hz, 1H), 3.20 (s, 3H). | B 5-(methyl-sulfonyl)pyridin-2-amine 2-bromo-1,3-difluoro benzene |
| I-19 | 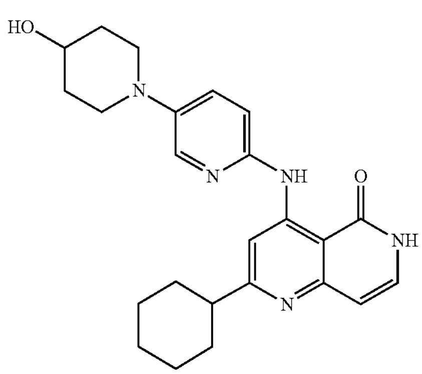 [SMILES: O=c1[nH]ccc2nc(C3CCCCC3)cc(Nc3ccc(N4CCC(O)CC4)cn3)c12] | 2-cyclohexyl-4-[[5-(4-hydroxy-1-piperidyl)-2-pyridyl]amino]-6H-1,6-naphthyridin-5-one | Method 10cm_Bicarb_AQ, m/z = 420 [M + H]+, Ret. time = 3.02 min. | $^1$H NMR (400 MHz, DMSO) δ 12.31 (s, 1H), 11.52-11.45 (m, 1H), 8.16 (s, 1H), 8.10 (d, J = 3.0 Hz, 1H), 7.46 (dd, J = 3.1, 9.0 Hz, 1H), 7.33 (d, J = 7.3 Hz, 1H), 6.98 (d, J = 8.9 Hz, 1H), 6.48 (d, J = 7.3 Hz, 1H), 4.71 (d, J = 4.1 Hz, 1H), 3.68-3.61 (m, 1H), 3.56-3.49 (m, 2H), 2.91-2.83 (m, 2H), 2.64-2.55 (m, 1H), 1.87-1.68 (m, 6H), 1.58-1.24 (m, 6H). | B 1-(6-amino-pyridin-3-yl)piperidin-4-ol Cyclo-hexylzinc bromide |

TABLE 2-continued

| I-# | STRUCTURE | NAME | LCMS | HNMR | Method SM |
|---|---|---|---|---|---|
| I-20 | 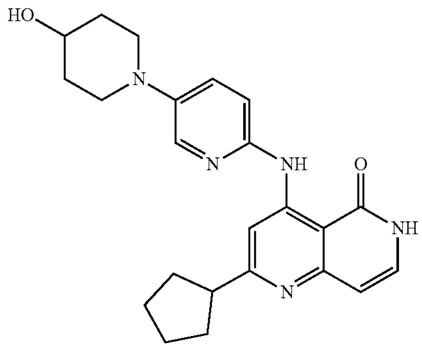 [SMILES: O=c1[nH]ccc2nc(C3CCCC3)cc(Nc3ccc(N4CCC(O)CC4)cn3)c12] | 2-cyclopentyl-4-[[5-(4-hydroxy-1-piperidyl)-2-pyridyl]amino]-6H-1,6-naphthyridin-5-one | Method 10cm_Bicarb_AQ, m/z = 406 [M + H]+, Ret. time = 2.92 min. | $^1$H NMR (400 MHz, DMSO) δ 12.30 (s, 1H), 11.49 (s, 1H), 8.20 (s, 1H), 8.08 (d, J = 3.0 Hz, 1H), 7.46 (dd, J = 3.1, 9.0 Hz, 1H), 7.33 (d, J = 7.3 Hz, 1H), 6.98 (d, J = 8.9 Hz, 1H), 6.47 (d, J = 7.3 Hz, 1H), 4.70 (d, J = 4.1 Hz, 1H), 3.68-3.61 (m, 1H), 3.56-3.48 (m, 2H), 3.14-3.04 (m, 1H), 2.91-2.83 (m, 2H), 2.02-1.94 (m, 2H), 1.89-1.75 (m, 6H), 1.75-1.64 (m, 2H), 1.57-1.46 (m, 2H). | B 1-(6-amino-pyridin-3-yl)piperidin-4-ol Cyclopentylzinc bromide |
| I-21 | 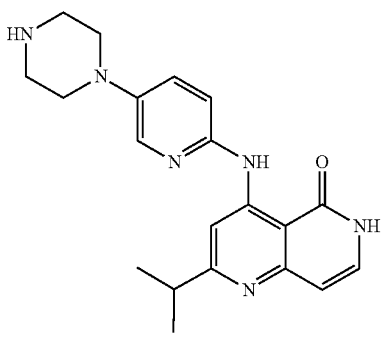 [SMILES: CC(C)c1cc(Nc2ccc(N3CCNCC3)cn2)c2c(=O)[nH]ccc2n1] | 2-isopropyl-4-[(5-piperazin-1-yl-2-pyridyl)amino]-6H-1,6-naphthyridin-5-one | Method 10cm_Formic_AQ, m/z = 365 [M + H]+, Ret. time = 2.1 min. | $^1$H NMR (400 MHz, DMSO) δ 12.33 (s, 1H), 11.51-11.50 (m, 1H), 8.20 (s, 1H), 8.07 (d, J = 2.9 Hz, 1H), 7.45 (dd, J = 3.1, 8.9 Hz, 1H), 7.34 (d, J = 7.3 Hz, 1H), 7.00 (d, J = 8.9 Hz, 1H), 6.49 (d, J = 7.3 Hz, 1H), 3.08-3.04 (m, 4H), 3.00-2.98 (m, 1H), 2.88-2.84 (m, 4H), 1.26 (d, J = 6.9 Hz, 6H). | B and G tert-butyl 4-(6-amino-pyridin-3-yl)piperazine-1-carboxylate 2-Propylzinc bromide |
| I-22 | 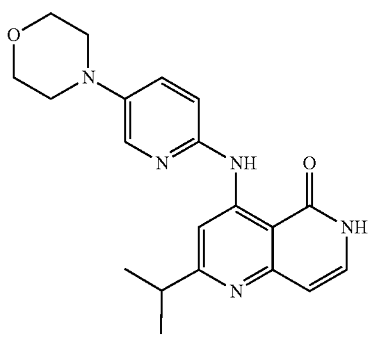 [SMILES: CC(C)c1cc(Nc2ccc(N3CCOCC3)cn2)c2c(=O)[nH]ccc2n1] | 2-isopropyl-4-[(5-morpholino-2-pyridyl)amino]-6H-1,6-naphthyridin-5-one | Method 10cm_Bicarb_AQ, m/z = 366 [M + H]+, Ret. time = 2.96 min. | $^1$H NMR (400 MHz, DMSO) δ 12.36 (s, 1H), 11.51 (s, 1H), 8.23 (s, 1H), 8.11 (d, J = 3.0 Hz, 1H), 7.48 (dd, J = 3.1, 9.0 Hz, 1H), 7.34 (d, J = 7.3 Hz, 1H), 7.02 (d, J = 8.8 Hz, 1H), 6.50 (d, J = 7.3 Hz, 1H), 3.79-3.75 (m, 4H), 3.16-3.12 (m, 4H), 3.00-2.89 (m, 1H), 1.26 (d, J = 6.9 Hz, 6H). | B 5-morpholino-pyridin-2-amine 2-Propylzinc bromide |
| I-23 | 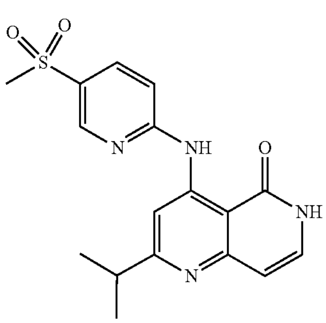 [SMILES: CC(C)c1cc(Nc2ccc(S(C)(=O)=O)cn2)c2c(=O)[nH]ccc2n1] | 2-isopropyl-4-[(5-methylsulfonyl-2-pyridyl)amino]-6H-1,6-naphthyridin-5-one | Method 10cm_Bicarb_AQ, m/z = 359 [M + H]+, Ret. time = 2.9 min. | $^1$H NMR (400 MHz, DMSO) δ 13.21 (s, 1H), 11.81-11.74 (m, 1H), 8.88 (d, J = 2.5 Hz, 1H), 8.65 (s, 1H), 8.18 (dd, J = 2.5, 8.8 Hz, 1H), 7.43 (d, J = 7.3 Hz, 1H), 7.23 (d, J = 8.5 Hz, 1H), 6.61 (d, J = 7.3 Hz, 1H), 3.30 (s, 3H), 3.11-3.00 (m, 1H), 1.30 (d, J = 6.9 Hz, 6H). | B 5-(methylsulfonyl)pyridin-2-amine 2-Propylzinc bromide |

TABLE 2-continued

| I-# | STRUCTURE | NAME | LCMS | HNMR | Method SM |
|---|---|---|---|---|---|
| I-24 | 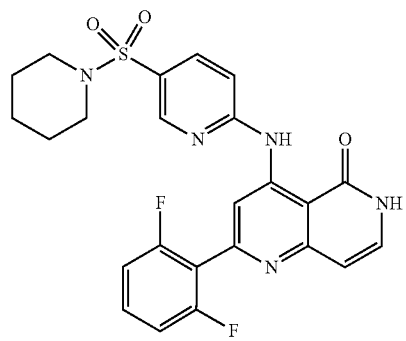 [SMILES: O=c1[nH]ccc2nc(-c3c(F)cccc3F)cc(Nc3ccc(S(=O)(=O)N4CCCCC4)cn3)c12] | 2-(2,6-difluoro-phenyl)-4-[[5-(1-piperidyl-sulfonyl)-2-pyridyl]amino]-6H-1,6-naphthyridin-5-one | Method 10cm_Bicarb_AQ, m/z = 498 [M + H]+, Ret. time = 3.36 min. | ¹H NMR (400 MHz, DMSO) δ 13.29 (s, 1H), 11.93 (s, 1H), 8.77 (s, 1H), 8.58 (d, J = 2.4 Hz, 1H), 7.94 (dd, J = 2.5, 8.8 Hz, 1H), 7.58-7.49 (m, 1H), 7.45 (d, J = 7.2 Hz, 1H), 7.24-7.17 (m, 3H), 6.59 (d, J = 7.3 Hz, 1H), 2.85 (dd, J = 5.3, 5.3 Hz, 4H), 1.50-1.43 (m, 4H), 1.30 (d, J = 4.0 Hz, 2H). | B 5-(piperidin-1-ylsulfonyl)pyridin-2-amine 2-bromo-1,3-difluorobenzene |
| I-25 | 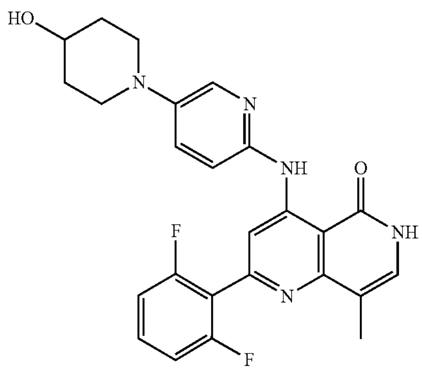 [SMILES: Cc1c[nH]c(=O)c2c(Nc3ccc(N4CCC(O)CC4)cn3)cc(-c3c(F)cccc3F)nc12] | 2-(2,6-difluoro-phenyl)-4-[[5-(4-hydroxy-1-piperidyl)-2-pyridyl]amino]-8-methyl-6H-1,6-naphthyridin-5-one | Method 10cm_Formic_AQ, m/z = 464 [M + H]+, Ret. time = 2.63 min. | ¹H NMR (400 MHz, DMSO) δ 12.78 (s, 1H), 11.63 (s, 1H), 8.55 (s, 1H), 8.09 (d, J = 2.8 Hz, 1H), 7.67-7.58 (m, 1H), 7.51 (dd, J = 2.9, 9.0 Hz, 1H), 7.37 (s, 1H), 7.31 (dd, J = 8.0, 8.0 Hz, 2H), 7.04 (d, J = 8.8 Hz, 1H), 4.73 (s, 1H), 3.70-3.65 (m, 1H), 3.54 (d, J = 12.9 Hz, 2H), 2.94-2.85 (m, 2H), 2.21 (s, 3H), 1.90-1.84 (m, 2H), 1.58-1.47 (m, 2H). | J 1-(6-amino-pyridin-3-yl)piperidin-4-ol 2-bromo-1,3-difluorobenzene |
| I-26 | 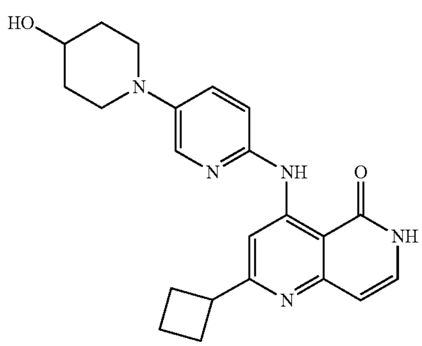 [SMILES: O=c1[nH]ccc2nc(C3CCC3)cc(Nc3ccc(N4CCC(O)CC4)cn3)c12] | 2-cyclobutyl-4-[[5-(4-hydroxy-1-piperidyl)-2-pyridyl]amino]-6H-1,6-naphthyridin-5-one | Method 10cm_Formic_AQ, m/z = 392 [M + H]+, Ret. time = 2.43 min. | ¹H NMR (400 MHz, DMSO) δ 12.32 (s, 1H), 11.51 (s, 1H), 8.14 (s, 1H), 8.08 (d, J = 3.0 Hz, 1H), 7.46 (dd, J = 3.1, 9.0 Hz, 1H), 7.34 (d, J = 7.3 Hz, 1H), 6.98 (d, J = 8.9 Hz, 1H) 6.51 (d, J = 7.3 Hz, 1H), 4.71 (d, J = 4.0 Hz, 1H), 3.68-3.48 (m, 4H), 2.91-2.83 (m, 2H), 2.36-2.25 (m, 4H), 2.10-1.98 (m, 1H), 1.89-1.81 (m, 3H), 1.57-1.46 (m, 2H). | B 1-(6-amino-pyridin-3-yl)piperidin-4-ol Cyclo-butylzinc bromide |
| I-27 | 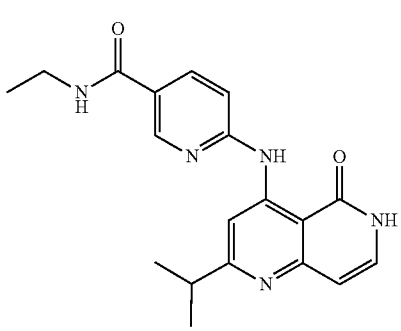 [SMILES: CCNC(=O)c1ccc(Nc2cc(C(C)C)nc3cc[nH]c(=O)c23)nc1] | N-ethyl-6-[(2-isopropyl-5-oxo-6H-1,6-naphthyridin-4-yl)amino]pyridine-3-carboxamide | Method 10cm_Bicarb_AQ, m/z = 352.246 [M + H]+, Ret. time = 2.83 min. | ¹H NMR (400 MHz, DMSO) δ 12.93 (s, 1H), 11.70 (d, J = 5.3 Hz, 1H), 8.89 (d, J = 2.1 Hz, 1H), 8.63 (s, 1H), 8.51 (dd, J = 5.5, 5.5 Hz, 1H), 8.19-8.5 (m, 1H), 7.42-7.38 (m, 1H), 7.11 (d, J = 8.3 Hz, 1H), 6.57 (d, J = 7.0 Hz, 1H), 3.09-2.97 (m, 1H), 1.30 (d, J = 6.8 Hz, 6H), 1.15 (t, J = 7.3 Hz, 3H). | B 6-amino-N-ethyl-nicotinamide 2-Propylzinc bromide |

TABLE 2-continued

| I-# | STRUCTURE | NAME | LCMS | HNMR | Method SM |
|---|---|---|---|---|---|
| I-28 | 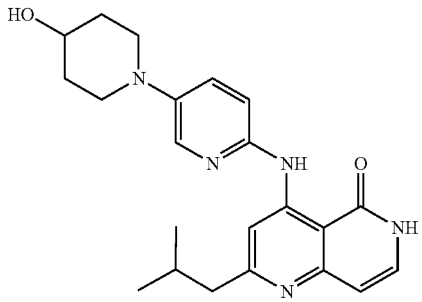 [SMILES: CC(C)Cc1cc(Nc2ccc(N3CCC(O)CC3)cn2)c2c(=O)[nH]ccc2n1] | 4-[[5-(4-hydroxy-1-piperidyl)-2-pyridyl]amino]-2-isobutyl-6H-1,6-naphthyridin-5-one | Method 10cm_Formic_AQ, m/z = 394 [M + H]+, Ret. time = 2.48 min. | $^1$H NMR (400 MHz, DMSO) δ 12.30 (s, 1H), 11.53 (d, J = 4.6 Hz, 1H), 8.11-8.07 (m, 2H), 7.46 (dd, J = 3.1, 9.0 Hz, 1H), 7.36-7.31 (m, 1H), 6.98 (d, J = 8.9 Hz, 1H), 6.48 (d, J = 7.3 Hz, 1H), 4.70 (s, 1H), 3.69-3.62 (m, 1H), 3.57-3.48 (m, 2H), 2.91-2.83 (m, 2H), 2.55 (d, J = 7.2 Hz, 2H), 2.16-2.07 (m, 1H), 1.88-1.81 (m, 2H), 1.56-1.46 (m, 2H), 0.92 (d, J = 6.6 Hz, 6H). | B 1-(6-amino-pyridin-3-yl)piperidin-4-ol t-butylzinc bromide |
| I-29 | 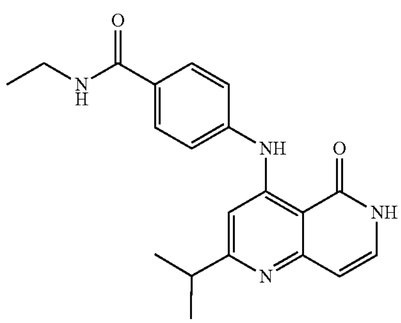 [SMILES: CCNC(=O)c1ccc(Nc2cc(C(C)C)nc3cc[nH]c(=O)c23)cc1] | N-ethyl-4-[(2-isopropyl-5-oxo-6H-1,6-naphthyridin-4-yl)amino]benzamide | Method 10cm_Bicarb_AQ, m/z = 351 [M + H]+, Ret. time = 2.91 min. | $^1$H NMR (400 MHz, DMSO) δ 11.65 (s, 1H), 11.45-11.43 (m, 1H), 8.37 (dd, J = 5.5, 5.5 Hz, 1H), 7.84 (d, J =8.7 Hz, 2H), 7.35 (d, J = 8.7 Hz, 2H), 7.27 (dd, J = 4.5, 7.0 Hz, 1H), 6.85 (s, 1H), 6.41 (d, J = 7.3 Hz, 1H), 3.24-3.18 (m, 2H), 2.88-2.80 (m, 1H), 1.13 (d, J = 6.9 Hz, 6H), 1.06 (t, J = 7.2 Hz, 3H). | B 4-amino-N-ethyl-benzamide 2-Propylzinc bromide |
| I-30 | 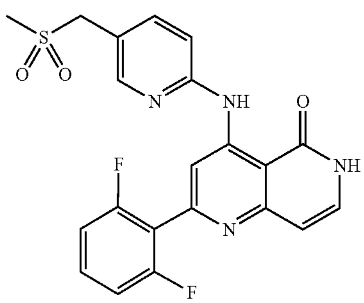 [SMILES: CS(=O)(=O)Cc1ccc(Nc2cc(-c3c(F)cccc3F)nc3cc[nH]c(=O)c23)nc1] | 2-(2,6-difluoro-phenyl)-4-[[5-(methyl-sulfonyl-methyl)-2-pyridyl]amino]-6H-1,6-naphthyridin-5-one | Method 10cm_Formic_AQ, m/z = 443 [M + H]+, Ret. time = 2.5 min. | $^1$H NMR (400 MHz, DMSO) δ 12.98 (s, 1H), 11.92-11.85 (m, 1H), 8.77 (s, 1H), 8.35 (d, J = 2.1 Hz, 1H), 7.81 (dd, J = 2.4, 8.4 Hz, 1H), 7.64 7.56 (m, 1H), 7.49 (d, J = 7.3 Hz, 1H), 7.28 (dd, J = 8.0, 8.0 Hz, 2H), 7.16 (d, J = 8.4 Hz, 1H), 6.63 (d, J = 7.3 Hz, 1H), 4.50 (s, 2H), 2.95 (s, 3H). | B 5-((methyl-sulfonyl)methyl)pyridin-2-amine 2-bromo-1,3-difluoro benzene |
| I-31 | 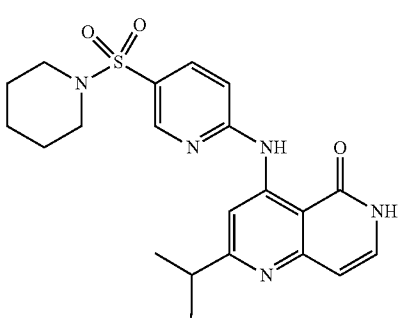 [SMILES: CC(C)c1cc(Nc2ccc(S(=O)(=O)N3CCCCC3)cn2)c2c(=O)[nH]ccc2n1] | 2-isopropyl-4-[[5-(1-piperidyl-sulfonyl)-2-pyridyl]amino]-6H-1,6-naphthyridin-5-one | Method 10cm_Formic_AQ, m/z = 428 [M + H]+, Ret. time = 2.79 min. | $^1$H NMR (400 MHz, DMSO) δ 13.19 (s, 1H), 11.80-11.73 (m, 1H), 8.71 (d, J = 2.4 Hz, 1H), 8.64 (s, 1H), 8.00 (dd, J = 2.5, 8.8 Hz, 1H), 7.43 (d, J = 7.3 Hz, 1H), 7.21 (d, J = 8.8 Hz, 1H), 6.61 (d, J = 7.3 Hz, 1H), 3.11-3.00 (m, 1H), 2.96 (dd, J = 5.3, 5.3 Hz, 4H), 1.62-1.53 (m, 4H), 1.45-1.36 (m, 2H), 1.30 (d, J = 6.9 Hz, 6H). | B 5-(piperidin-1-ylsulfonyl)pyridin-2-amine 2-Propylzinc bromide |

TABLE 2-continued

| I-# | STRUCTURE | NAME | LCMS | HNMR | Method SM |
|---|---|---|---|---|---|
| I-32 | 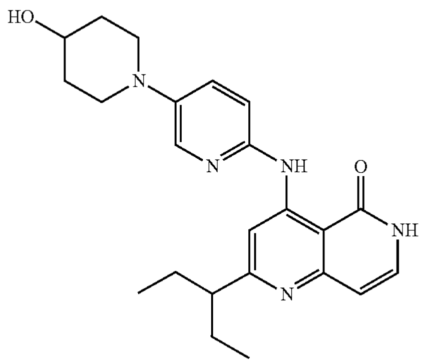 [SMILES: CCC(CC)c1cc(Nc2ccc(N3CCC(O)CC3)cn2)c2c(=O)[nH]ccc2n1] | 2-(1-ethylpropyl)-4-[[5-(4-hydroxy-1-piperidyl)-2-pyridyl]amino]-6H-1,6-naphthyridin-5-one | Method 10cm_Formic_AQ, m/z = 408 [M + H]+, Ret. time = 2.52 min. | $^1$H NMR (400 MHz, DMSO) δ 12.32 (s, 1H), 11.50 (d, J = 4.8 Hz, 1H), 8.13 (s, 1H), 8.09 (d, J = 3.1 Hz, 1H), 7.47 (dd, J = 3.1, 9.0 Hz, 1H), 7.35-7.30 (m, 1H), 6.97 (d, J = 8.9 Hz, 1H), 6.50 (d, J = 7.2 Hz, 1H), 4.71 (s, 1H), 3.69-3.61 (m, 1H), 3.57-3.48 (m, 2H), 2.91-2.83 (m, 2H), 2.49-2.40 (m, 1H), 1.88-1.80 (m, 2H), 1.73-1.48 (m, 6H), 0.77 (dd, J = 7.4, 7.4 Hz, 6H). | B 1-(6-amino-pyridin-3-yl)piperidyl-4-ol pentan-3-ylzinc bromide |
| I-33 | 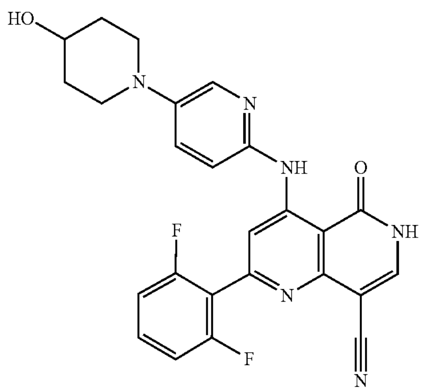 [SMILES: N#Cc1c[nH]c(=O)c2c(Nc3ccc(N4CCC(O)CC4)cn3)cc(-c3c(F)cccc3F)nc12] | 2-(2,6-difluoro-phenyl)-4-[[5-(4-hydroxy-1-piperidyl)-2-pyridyl]amino]-5-oxo-6H-1,6-naphthyridin-8-carbonitrile | Method 10cm_Formic_AQ, m/z = 475 [M + H]+, Ret. time = 2.93 min. | $^1$H NMR (400 MHz, DMSO) δ 12.62-12.57 (m, 1H), 8.54 (s, 1H), 8.40 (s, 1H), 8.10 (d, J = 2.5 Hz, 1H), 7.69-7.60 (m, 1H), 7.51 (dd, J = 2.7, 9.0 Hz, 1H), 7.32 (dd, J = 8.0, 8.0 Hz, 2H), 7.07 (d, J = 9.1 Hz, 1H), 4.73-4.72 (m, 1H), 3.70-3.64 (m, 1H), 3.56 (d, J = 12.1 Hz, 2H), 2.90 (dd, J = 10.0, 10.0 Hz, 2H), 1.84 (d, J = 9.6 Hz, 2H), 1.58-1.48 (m, 2H). One Exchangable proton no observed | I 1-(6-amino-pyridin-3-yl)piperidin-4-ol 2-bromo-1,3-difluoro benzene |
| I-34 | 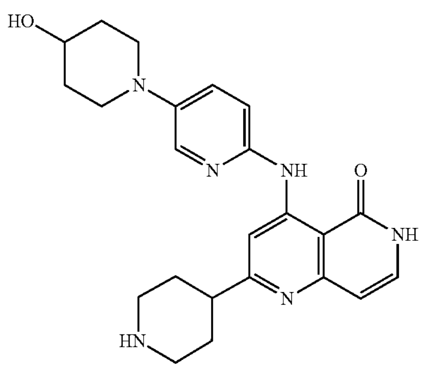 [SMILES: O=c1[nH]ccc2nc(C3CCNCC3)cc(Nc3ccc(N4CCC(O)CC4)cn3)c12] | 4-[[5-(4-hydroxy-1-piperidyl)-2-pyridyl]amino]-2-(4-piperidyl)-6H-1,6-naphthyridin-5-one | Method 10cm_Formic AQ, m/z = 421 [M + H]+, Ret. time = 2.07 min. | $^1$H NMR (400 MHz, DMSO) δ 12.34 (s, 1H), 8.17 (s, 1H), 8.10 (d, J = 3.0 Hz, 1H), 7.47 (dd, J = 3.0, 9.0 Hz, 1H), 7.34 (d, J = 7.3 Hz, 1H), 6.98 (d, J = 8.9 Hz, 1H), 6.47 (d, J = 7.3 Hz, 1H), 4.71 (s, 1H), 3.68-3.62 (m, 1H), 3.56-3.50 (m, 2H), 3.03 (dd, J = 3.1, 8.8 Hz, 2H), 2.92-2.83 (m, 2H), 2.71-2.58 (m, 5H), 1.88-1.84 (m, 2H), 1.76-1.46 (m, 6H). | B and G 1-(6-amino-pyridin-3-yl)piperidin-4-ol (1-(tert-butoxy-carbonyl)piperidin-4-yl)zinc bromide |
| I-35 | 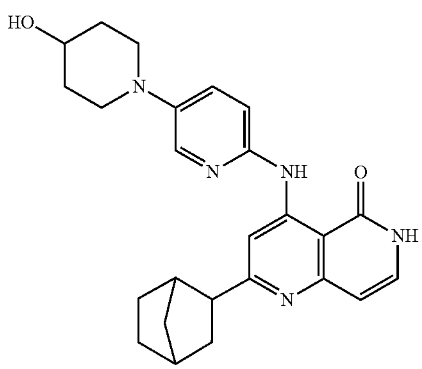 [SMILES: O=c1[nH]ccc2nc(C3CC4CCC3C4)cc(Nc3ccc(N4CCC(O)CC4)cn3)c12] | 4-[[5-(4-hydroxy-1-piperidyl)-2-pyridyl]amino]-2-norbornan-2-yl-6H-1,6-naphthyridin-5-one | Method 10cm_Formic_AQ, m/z = 432 [M + H]+, Ret. time = 2.61 min. | $^1$H NMR (400 MHz, DMSO) δ 12.27 (s, 1H), 11.49-11.47 (m, 1H), 8.19 (s, 1H), 8.08 (d, J = 3.0 Hz, 1H), 7.46 (dd, J = 3.1, 9.0 Hz, 1H), 7.34-7.31 (m, 1H), 6.99-6.96 (m, 1H), 6.48 (d, J = 7.3 Hz, 1H), 4.71 (d, J = 4.0 Hz, 1H), 3.69-3.61 (m, 1H), 3.56-3.48 (m, 2H), 2.92-2.83 (m, 2H), 2.77 (dd, J = 5.4, 8.8 Hz, 1H), 2.41-2.32 (m, 2H), 2.08-2.00 (m, 1H), 1.89-1.81 (m, 2H), 1.74 (d, J = 9.4 Hz, 1H), 1.64-1.46 (m, 5H), 1.42-1.35 (m, 1H), 1.34-1.23 (m, 1H), 1.12 (d, J = 9.9 Hz, 1H). | B 1-(6-amino-pyridin-3-yl)piperidin-4-ol Exo-2-norborn-ylzinc bromide |

TABLE 2-continued

| I-# | STRUCTURE | NAME | LCMS | HNMR | Method SM |
|---|---|---|---|---|---|
| I-36 | 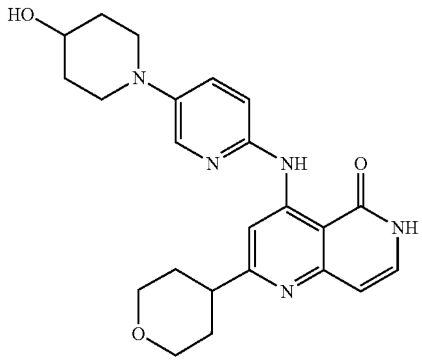 [SMILES: O=c1[nH]ccc2nc(C3CCOCC3)cc(Nc3ccc(N4CCC(O)CC4)cn3)c12] | 4-[[5-(4-hydroxy-1-piperidyl)-2-pyridyl]amino]-2-tetrahydropyran-4-yl-6H-1,6-naphthyridin-5-one | Method 10cm_Formic_AQ, m/z = 422 [M + H]+, time = 2.32 min. | $^1$H NMR (400 MHz, DMSO) δ 12.33 (s, 1H), 11.56-11.50 (m, 1H), 8.21 (s, 1H), 8.10 (d, J = 3.0 Hz, 1H), 7.47 (dd, J = 3.1, 9.0 Hz, 1H), 7.35 (dd, J = 5.5, 7.0 Hz, 1H), 6.99 (d, J = 8.9 Hz, 1H), 6.49 (d, J = 7.2 Hz, 1H), 4.72 (s, 1H), 4.00-3.94 (m, 2H), 3.69-3.61 (m, 1H), 3.57-3.42 (m, 4H), 2.92-2.82 (m, 3H), 1.88-1.75 (m, 6H), 1.57-1.46 (m, 2H). | N 1-(6-aminopyridin-3-yl)piperidin-4-ol (tetrahydro-2H-pyran-4-yl)zinc bromide |
| I-37 | 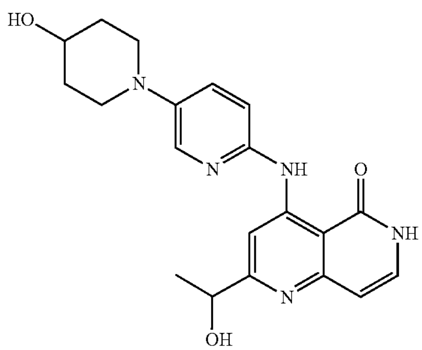 [SMILES: CC(O)c1cc(Nc2ccc(N3CCC(O)CC3)cn2)c2c(=O)[nH]ccc2n1] | 2-(1-hydroxyethyl)-4-[[5-(4-hydroxy-1-piperidyl)-2-pyridyl]amino]-6H-1,6-naphthyridin-5-one | Method 10cm_Bicarb_AQ, m/z = 382 [M + H]+, Ret. time = 2.56 min. | $^1$H NMR (400 MHz, DMSO) δ 12.32 (s, 1H), 11.53 (d, J = 5.0 Hz, 1H), 8.29 (s, 1H), 8.22 (s, 1H), 8.09 (d, J = 3.0 Hz, 1H), 7.48 (dd, J = 3.1, 9.0 Hz, 1H), 7.35 (dd, J = 5.5, 7.0 Hz, 1H), 7.02 (d, J = 8.9 Hz, 1H), 6.48 (d, J = 7.3 Hz, 1H), 5.36 (s, 1H), 4.65 (q, J = 6.5 Hz, 1H), 3.69-3.51 (m, 3H), 2.93-2.84 (m, 2H), 1.89-1.81 (m, 2H), 1.57-1.46 (m, 2H), 1.37 (d, J = 6.7 Hz, 3H). | M 1-(6-aminopyridin-3-yl)piperidin-4-ol |
| I-38 | 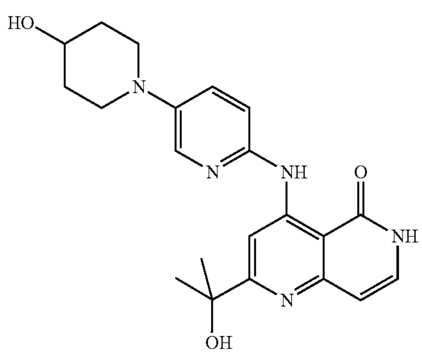 [SMILES: CC(C)(O)c1cc(Nc2ccc(N3CCC(O)CC3)cn2)c2c(=O)[nH]ccc2n1] | 2-(1-hydroxy-1-methyl-ethyl)-4-[[5-(4-hydroxy-1-piperidyl)-2-pyridyl]amino]-6H-1,6-naphthyridin 5-one | Method 10cm_Formic_AQ, m/z = 396 [M + H]+, Ret. time = 2.29 min. | $^1$H NMR (400 MHz, DMSO) δ 12.32 (s, 1H), 11.59-11.54 (m, 1H), 8.44 (s, 1H), 8.13 (d, J = 2.5 Hz, 1H), 7.51 (dd, J = 2.9, 9.0 Hz, 1H), 7.38 (d, J = 7.3 Hz, 1H), 7.10-7.05 (m, 1H), 6.53 (d, J = 7.3 Hz, 1H), 5.26 (s, 1H), 4.75 (d, J = 3.8 Hz, 1H), 3.74-3.67 (m, 1H), 3.61-3.53 (m, 2H), 2.97-2.88 (m, 2H), 1.93-1.87 (m, 2H), 1.62-1.52 (m, 2H), 1.50 (s, 6H). | M 1-(6-aminopyridin-3-yl)piperidin-4-ol |
| I-39 | 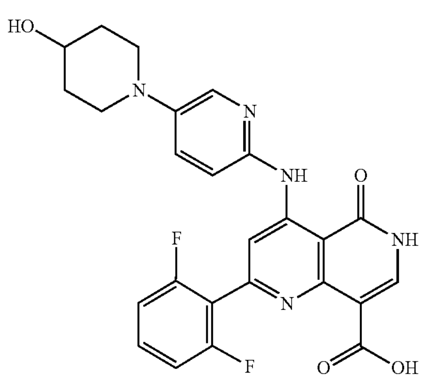 [SMILES: O=C(O)c1c[nH]c(=O)c2c(Nc3ccc(N4CCC(O)CC4)cn3)cc(-c3c(F)cccc3F)nc12] | 2-(2,6-difluorophenyl)-4-[[5-(4-hydroxy-1-piperidyl)-2-pyridyl]amino]-5-oxo-6H-1,6-naphthyridine-8-carboxylic acid | Method 10cm_Formic_AQ, m/z = 494 [M + H]+, Ret. time = 2.68 min. | $^1$H NMR (400 MHz, DMSO) δ 12.83-12.77 (m, 1H), 8.65 (s, 1H), 8.38 (s, 1H), 8.15 (d, J = 2.8 Hz, 1H), 7.75-7.67 (m, 1H), 7.54 (dd, J = 2.8, 8.8 Hz, 1H), 7.40 (dd, J = 8.3, 8.3 Hz, 2H), 7.15 (d, J = 8.8 Hz, 1H), 4.74 (s, 1H), 4.08 (s, 1H), 3.72-3.67 (m, 1H), 3.60 (dd, J = 4.4, 8.2 Hz, 2H), 2.98-2.91 (m, 2H), 1.87 (dd, J = 3.2, 12.8 Hz, 2H), 1.58-1.47 (m, 2H). 1 Exchangable proton not observed | I 1-(6-aminopyridin-3-yl)piperidin-4-ol 2-bromo-1,3-difluorobenzene |

TABLE 2-continued

| I-# | STRUCTURE | NAME | LCMS | HNMR | Method SM |
|---|---|---|---|---|---|
| I-40 | (structure) | 4-[[5-(4-hydroxy-1-piperidyl)-2-pyridyl]amino]-2-norbornan-2-yl-6H-1,6-naphthyridin-5-one | Method 10cm_Formic_AQ, m/z = 432 [M + H]+, Ret. time = 2.6 min. | $^1$H NMR (400 MHz, DMSO) δ 12.27 (s, 1H), 11.51-11.48 (m, 1H), 8.27 (s, 1H), 8.08 (d, J = 3.0 Hz, 1H), 7.49-7.44 (m, 1H), 7.33 (d, J = 7.3 Hz, 1H), 6.98 (d, J = 9.0 Hz, 1H), 6.50-6.48 (m, 1H), 4.71 (d, J = 4.0 Hz, 1H), 3.68-3.61 (m, 1H), 3.56-3.48 (m, 2H), 3.30-3.24 (m, 1H), 2.91-2.83 (m, 2H), 2.35-2.30 (m, 1H), 1.93-1.79 (m, 4H), 1.62-1.37 (m, 6H), 1.31-1.20 (m, 3H). | B 1-(6-aminopyridin-3-yl)piperidin-4-ol Exo-2-norbornylzinc bromide |
| I-41 | (structure) | 2-(2-fluoro-2-methyl-phenyl)-4-[[5-(4-hydroxy-1-piperidyl)-2-pyridyl]amino]-6H-1,6-naphthyridin-5-one | Method 10cm_Bicarb_AQ, m/z = 446 [M + H]+, Ret. time = 3.01 min. | $^1$H NMR (400 MHz, DMSO): δ 12.42 (s, 1 H), 11.65 (d, J = 5.4 Hz, 1 H), 8.69 (d, J = 1.6 Hz, 1 H), 8.07 (d, J = 3.0 Hz, 1 H), 7.76 (dd, J = 2.0, 7.4 Hz, 1 H), 7.48 (dd, J = 3.1, 9.0 Hz, 1 H), 7.44-7.39 (m, 1 H), 7.34-7.30 (m, 1 H), 7.26-7.20 (m, 1 H), 7.02 (d, J = 8.9 Hz, 1 H), 6.60 (d, J = 7.2 Hz, 1 H), 4.70 (brs, 1 H), 3.68-3.60 (m, 1 H), 3.58-3.48 (m, 2 H), 2.92-2.83 (m, 2 H), 2.38 (s, 3 H), 1.88-1.80 (m, 2 H), 1.56-1.45 (m, 2 H). | B 1-(6-aminopyridin-3-yl)piperidin-4-ol 2-bromo-1-fluoro-4-methyl-benzene |
| I-42 | (structure) | 2-(2-fluoro-5-methoxy-phenyl)-4-[[5-(4-hydroxy-1-piperidyl)-2-pyridyl]amino]-6H-1,6-naphthyridin-5-one | Method 10cm_Formic_AQ, m/z = 462 [M + H]+, Ret. time = 2.53 min. | $^1$H NMR (400 MHz, DMSO): δ 12.42 (s, 1 H), 11.68-11.62 (m, 1 H), 8.72 (d, J = 1.4 Hz, 1 H), 8.07 (d, J = 3.0 Hz, 1 H), 7.50-7.46 (m, 2 H), 7.42 (d, J = 7.3 Hz, 1 H), 7.29 (dd, J = 9.0, 10.5 Hz, 1 H), 7.11-7.01 (m, 2 H), 6.60 (d, J = 7.3 Hz, 1 H), 4.70 (d, J = 4.3 Hz, 1 H), 3.83 (s, 3 H), 3.68-3.61 (m, 1 H), 3.57-3.49 (m, 2 H), 2.92-2.83 (m, 2 H), 1.88-1.80 (m, 2 H), 1.56-1.45 (m, 2 H). | A 1-(6-aminopyridin-3-yl)piperidin-4-ol (2-fluoro-5-methoxyphenyl)boronic acid |

TABLE 2-continued

| I-# | STRUCTURE | NAME | LCMS | HNMR | Method SM |
|---|---|---|---|---|---|
| I-43 | 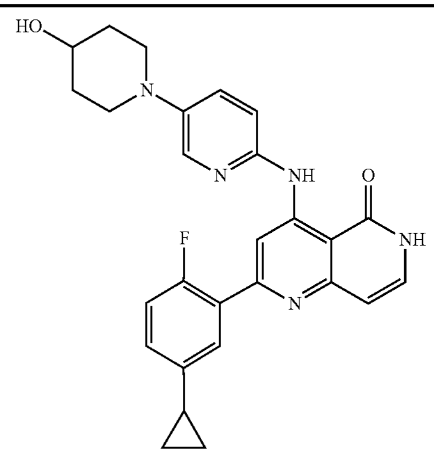 | 2-(5-cyclopropyl-2-fluoro-phenyl)-4-[[5-(4-hydroxy-1-piperidyl)-2-pyridyl]amino]-6H-1,6-naphthyridin-5-one | Method 10cm_Formic_AQ, m/z = 0 [M + H]+, Ret. time = 2.67 min. | $^1$H NMR (400 MHz, DMSO): δ 12.42 (s, 1 H), 11.65 (s, 1 H), 8.67 (d, J = 1.6 Hz, 1 H), 8.07 (d, J = 3.0 Hz, 1 H), 7.67 (d, J = 2.3, 7.4 Hz, 1 H), 7.48 (dd, J = 3.1, 9.0 Hz, 1 H), 7.42 (d, J = 7.4 Hz, 1 H), 7.24 (d, J = 7.4 Hz, 1 H), 7.21-7.18 (m, 1 H), 7.02 (d, J = 8.9 Hz, 1 H), 6.61 (d, J = 7.3 Hz, 1 H), 4.70 (d, J = 4.1 Hz, 1 H), 3.67-3.61 (m, 1 H), 3.57-3.48 (m, 2 H), 2.91-2.83 (m, 2 H), 2.08-2.00 (m, 1 H), 1.88-1.80 (m, 2 H), 1.56-1.44 (m, 2 H), 1.02-0.96 (m, 2 H), 0.73-0.68 (m, 2 H). | A 1-(6-aminopyridin-3-yl)piperidin-4-ol (5-cyclopropyl-2-fluorophenyl)boronic acid |
| I-44 | 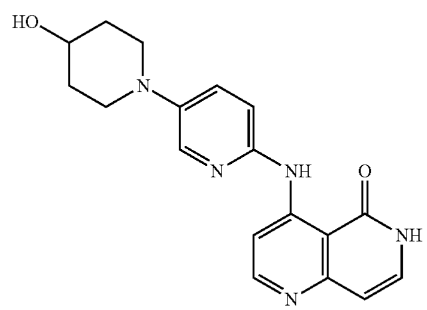 [SMILES: O=c1[nH]ccc2nccc(Nc3ccc(N4CCC(O)CC4)cn3)c12] | 4-[[5-(4-hydroxy-1-piperidyl)-2-pyridyl]amino]-6H-1,6-naphthyridin-5-one | Method 10cm_Formic_AQ, m/z = 338 [M + H]+, Ret. time = 2.22 min. | $^1$H NMR (400 MHz, DMSO) δ 8.38 (d, J = 6.0 Hz, 1H), 8.19 (s, 1H), 8.15 (d, J = 5.8 Hz, 1H), 8.05 (d, J = 2.9 Hz, 1H), 7.46 (dd, J = 3.0, 9.0 Hz, 1H), 7.38 (d, J = 7.3 Hz, 1H), 7.03 (d, J = 8.9 Hz, 1H), 6.55 (d, J = 7.4 Hz, 1H), 3.68-3.60 (m, 1H), 3.54-3.46 (m, 2H), 2.89-2.81 (m, 2H), 1.87-1.80 (m, 2H), 1.54-1.44 (m, 2H). (1 eq. formate salt, 3 exchangable proton not observed) | A (by product) 1-(6-aminopyridin-3-yl)piperidin-4-ol Bis(pinacolato)diboron |
| I-45 | 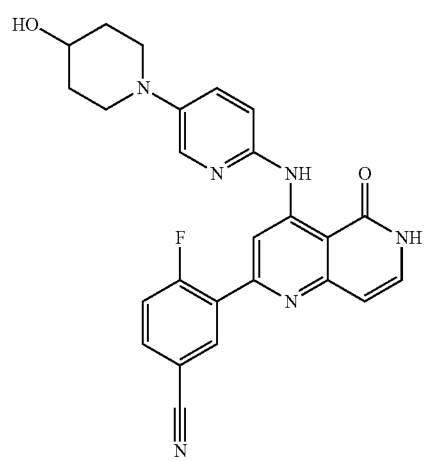 [SMILES: N#Cc1ccc(F)c(-c2cc(Nc3ccc(N4CCC(O)CC4)cn3)c3c(=O)[nH]ccc3n2)c1] | 4-fluoro-3-[4-[[5-(4-hydroxy-1-piperidyl)-2-pyridyl]amino]-5-oxo-6H-1,6-naphthyridin-2-yl]benzonitrile | Method 10cm_Formic_AQ, m/z = 457 [M + H]+, Ret. time = 2.5 min. | $^1$H NMR (400 MHz, DMSO) δ 12.42 (s, 1 H), 11.65 (s, 1 H), 8.67 (d, J = 1.6 Hz, 1 H), 8.07 (d, J = 3.0 Hz, 1 H), 7.67 (dd, J = 2.3, 7.4 Hz, 1 H), 7.48 (dd, J = 3.1, 9.0 Hz, 1 H), 7.42 (d, J = 7.4 Hz, 1 H), 7.24 (d, J = 7.4 Hz, 1 H), 7.21-7.18 (m, 1 H), 7.02 (d, J = 8.9 Hz, 1 H), 6.61 (d, J = 7.3 Hz, 1 H), 4.70 (d, J = 4.1 Hz, 1 H), 3.67-3.61 (m, 1 H), 3.57-3.48 (m, 2 H), 2.91-2.83 (m, 2 H), 1.88-1.80 (m, 2 H), 1.56-1.44 (m, 2 H). | A 1-(6-aminopyridin-3-yl)piperidin-4-ol (5-Cyano-2-fluorophenyl)boronic acid |
| I-46 | 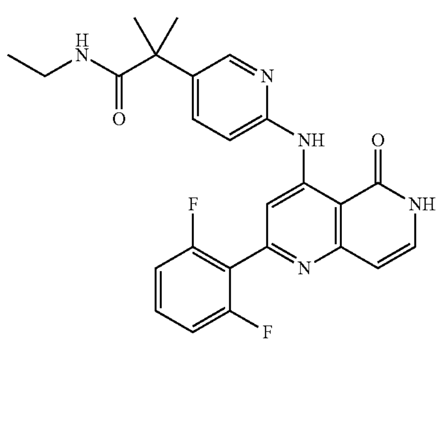 [SMILES: CCNC(=O)C(C)(C)c1ccc(Nc2cc(-c3c(F)cccc3F)nc3cc[nH]c(=O)c23)nc1] | 2-[6-[[2-(2,6-difluorophenyl)-5-oxo-6H-1,6-naphthyridin-4-yl]amino]-3-pyridyl]-N-ethyl-2-methyl-propanamide | Method 10cm_Formic_AQ, m/z = 464 [M + H]+, Ret. time = 2.67 min. | $^1$H NMR (400 MHz, DMSO) δ 12.89 (s, 1H), 11.84 (d, J = 1.0 Hz, 1H), 8.80 (s, 1H), 8.36 (d, J = 2.3 Hz, 1H), 7.71 (dd, J = 2.5, 8.6 Hz, 1H), 7.68-7.59 (m, 1H), 7.52 (d, J = 7.3 Hz, 1H), 7.45 (dd, J = 5.3, 5.3 Hz, 1H), 7.32 (dd, J = 8.0, 8.0 Hz, 2H), 7.11 (d, J = 8.6 Hz, 1H), 6.65 (d, J = 7.1 Hz, 1H), 3.14-3.05 (m, 2H), 1.50 (s, 6H), 1.00 (t, J = 7.2 Hz, 3H). | B CA1 2-bromo-1,3-difluorobenzene |

TABLE 2-continued

| I-# | STRUCTURE | NAME | LCMS | HNMR | Method SM |
|---|---|---|---|---|---|
| I-47 | 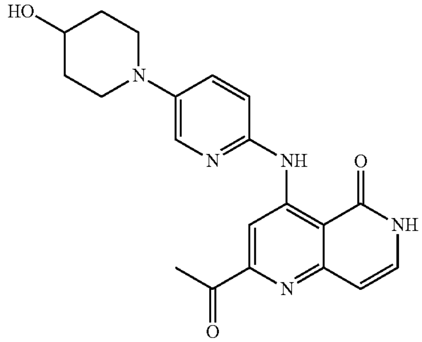 [SMILES: CC(=O)c1cc(Nc2ccc(N3CCC(O)CC3)cn2)c2c(=O)[nH]ccc2n1] | 2-acetyl-4-[[5-(4-hydroxy-1-piperidyl)-2-pyridyl]amino]-6H-1,6-naphthyridin-5-one | Method 10cm_Formic_AQ, m/z = 380 [M + H]+, Ret. time = 2.33 min. | ¹H NMR (400 MHz, DMSO) δ 12.46 (s, 1H), 11.78 (s, 1H), 8.71 (s, 1H), 8.15-8.10 (m, 1H), 7.53-7.42 (m, 2H), 7.02 (d, J = 8.8 Hz, 1H), 6.63 (d, J = 7.3 Hz, 1H), 4.71 (s, 1H), 3.71-3.49 (m, 3H), 2.96-2.84 (m, 2H), 2.65 (s, 3H), 1.85 (s, 2H), 1.53 (t, J = 9.3 Hz, 2H). | M 1-(6-amino-pyridin-3-yl)piperidin-4-ol |
| I-48 | 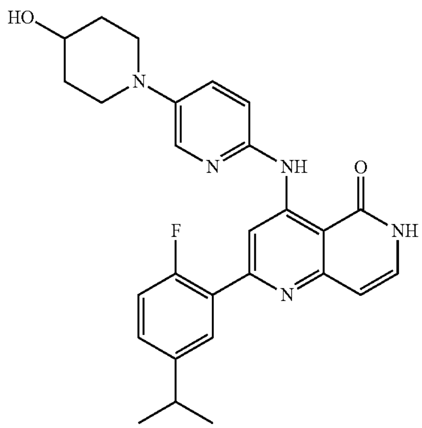 [SMILES: CC(C)c1ccc(F)c(-c2cc(Nc3ccc(N4CCC(O)CC4)cn3)c3c(=O)[nH]ccc3n2)c1] | 2-(2-fluoro-5-isopropyl-phenyl)-4-[[5-(4-hydroxy-1-piperidyl)-2-pyridyl]amino]-6H-1,6-naphthyridin-5-one | Method 10cm_Formic_AQ, m/z = 474 [M + H]+, Ret. time = 2.75 min. | ¹H NMR (400 MHz, DMSO): δ 12.42 (s, 1 H), 11.68-11.62 (m, 1 H), 8.68 (d, J = 1.6 Hz, 1 H), 8.06 (d, J = 3.0 Hz, 1 H), 7.78 (dd, J = 2.4, 7.5 Hz, 1 H), 7.48 (dd, J = 3.1, 9.0 Hz, 1 H), 7.43-7.38 (m, 2 H), 7.27 (dd, J = 8.5, 11.0 Hz, 1 H), 7.03 (d, J = 8.9 Hz, 1 H), 6.61 (d, J = 7.3 Hz, 1 H), 4.70 (d, J = 4.1 Hz, 1 H), 3.67-3.61 (m, 1 H), 3.56-3.48 (m, 2 H), 3.06-2.95 (m, 1 H), 2.91-2.83 (m, 2 H), 1.88-1.80 (m, 2 H), 1.55-1.44 (m, 2 H), 1.26 (d, J = 6.9 Hz, 6 H). | A 1-(6-amino-pyridin-3-yl)piperidin-4-ol [2-Fluoro-5-(propan-2-yl)phenyl]boronic acid |
| I-49 | 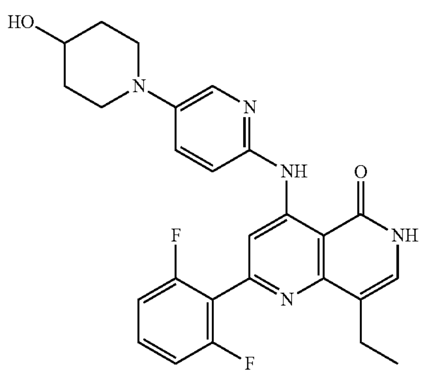 [SMILES: CCc1c[nH]c(=O)c2c(Nc3ccc(N4CCC(O)CC4)cn3)cc(-c3c(F)cccc3F)nc12] | 2-(2,6-difluoro-phenyl)-8-ethyl-4-[[5-(4-hydroxy-1-piperidyl)-2-pyridyl]amino]-6H-1,6-naphthyridin-5-one | Method 10cm_Formic_AQ, m/z 478 [M + H]+, Ret. time = 2.8 min. | ¹H NMR (400 MHz, DMSO) δ 12.78 (s, 1H), 11.71-11.65 (m, 1H), 8.60-8.53 (m, 1H), 8.09 (d, J = 2.8 Hz, 1H), 7.67-7.57 (m, 1H), 7.51 (dd, J = 2.8, 9.1 Hz, 1H), 7.35-7.27 (m, 3H), 7.06-7.02 (m, 1H), 4.72 (s, 1H), 3.72-3.63 (m, 1H), 3.59-3.51 (m, 2H), 2.93-2.87 (m, 2H), 2.71 (q, J = 7.2 Hz, 2H), 1.86 (d, J = 9.6 Hz, 2H), 1.58-1.47 (m, 2H), 1.22 (t, J = 7.5 Hz, 3H). | K 1-(6-amino-pyridin-3-yl)piperidin-4-ol 2-bromo-1,3-difluoro benzene |
| I-50 | 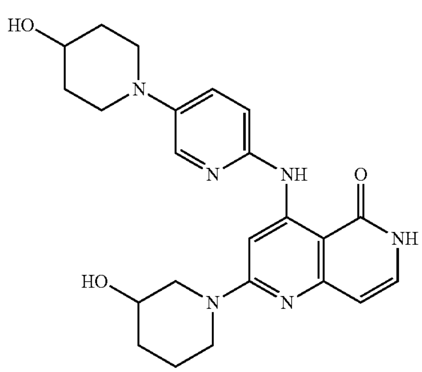 [SMILES: O=c1[nH]ccc2nc(N3CCCC(O)C3)cc(Nc3ccc(N4CCC(O)CC4)cn3)c12] | 2-(3-hydroxy-1-piperidyl)-4-[[5-(4-hydroxy-1-piperidyl)-2-pyridyl]amino]-6H-1,6-naphthyridin-5-one | Method 10cm_Formic_AQ, m/z = 437 [M + H]+, Ret. time = 2.32 min. | ¹H NMR (400 MHz, DMSO) δ 12.25 (s, 1H), 11.15 (s, 1H), 8.04 (s, 1H), 7.92 (s, 1H), 7.47-7.41 (m, 1H), 7.21 (s, 1H), 6.92-6.87 (m, 1H), 6.22 (d, J = 6.9 Hz, 1H), 4.30 (d, J = 11.8 Hz, 1H), 4.14-4.06 (m, 1H), 3.62-3.50 (m, 4H), 3.04-2.98 (m, 1H), 2.89-2.79 (m, 3H), 1.94-1.75 (m, 4H), 1.55-1.41 (m, 4H). | E 1-(6-amino-pyridin-3-yl)piperidin-4-ol 3-hydroxy-piperidine |

TABLE 2-continued

| I-# | STRUCTURE | NAME | LCMS | HNMR | Method SM |
|---|---|---|---|---|---|
| I-51 | 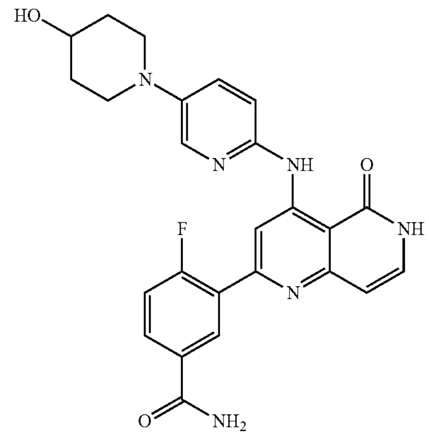 [SMILES: NC(=O)c1ccc(F)c(-c2cc(Nc3ccc(N4CCC(O)CC4)cn3)c3c(=O)[nH]ccc3n2)c1] | 4-fluoro-3-[4-[[5-(4-hydroxy-1-piperidyl)-2-pyridyl]amino]-5-oxo-6H-1,6-naphthyridin-2-yl]benzamide | Method 10cm_Formic_AQ, m/z = 475 [M + H]+, Ret. time = 2.35 min. | ¹H NMR (400 MHz, DMSO): δ 12.47 (s, 1 H), 11.67 (s, 1 H), 8.73 (d, J = 1.6 Hz, 1 H), 8.47 (dd, J = 2.4, 7.5 Hz, 1 H), 8.13 (s, 1 H), 8.09-8.00 (m, 2 H), 7.51-7.42 (m, 4 H), 7.04 (d, J = 8.9 Hz, 1 H), 6.64 (d, J = 7.3 Hz, 1 H), 4.70 (d, J = 4.3 Hz, 1 H), 3.68-3.61 (m, 1 H), 3.57-3.49 (m, 2 H), 2.92-2.83 (m, 2 H), 1.88-1.80 (m, 2 H), 1.56-1.45 (m, 2 H). | A 1-(6-amino-pyridin-3-yl)piperidin-4-ol 5-Carbamoyl-2-fluoro-phenyl-boronic acid |
| I-52 | 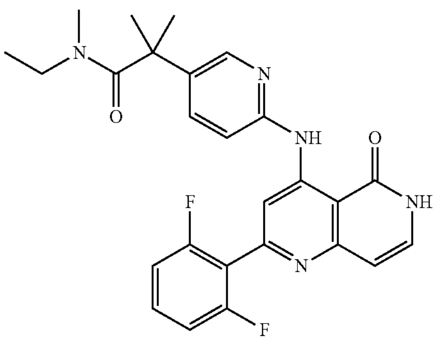 [SMILES: CCN(C)C(=O)C(C)(C)c1ccc(Nc2cc(-c3c(F)cccc3F)nc3cc[nH]c(=O)c23)nc1] | 2-[6-[[2-(2,6-difluoro-phenyl)-5-oxo-6H-1,6-naphthyridin-4-yl]amino]-3-pyridyl]-N-ethyl-N,2-dimethyl-propanamide | Method 10cm_Bicarb_AQ, m/z = 478 [M + H]+, Ret. time = 3.3 min. | ¹H NMR (400 MHz, DMSO) δ 12.73 (s, 1H), 11.50-11.47 (m, 1H), 8.60 (s, 1H), 8.21 (d, J = 2.5 Hz, 1H), 7.56-7.50 (m, 2H), 7.39 (d, J = 7.3 Hz, 1H), 7.19 (dd, J = 8.0, 8.0 Hz, 2H), 7.07 (d, J = 8.5 Hz, 1H), 6.57 (d, J = 7.3 Hz, 1H), 3.19-3.13 (m, 2H), 2.60 (s, 3H), 1.46 (s, 6H), 0.89 (dd, J = 7.0, 7.0 Hz, 3H). | B CA2 2-bromo-1,3-difluoro benzene |
| I-53 | 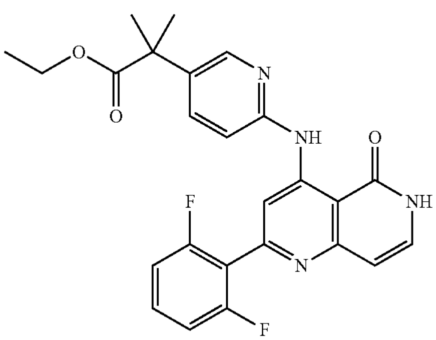 [SMILES: CCOC(=O)C(C)(C)c1ccc(Nc2cc(-c3c(F)cccc3F)nc3cc[nH]c(=O)c23)nc1] | ethyl 2-[6-[[2-(2,6-difluoro-phenyl)-5-oxo-6H-1,6-naphthyridin-4-yl]amino]-3-pyridyl]-2-methyl-propanoate | Method 10cm_Bicarb_AQ, m/z = 465 [M + H]+, Ret. time = 3.56 min. | ¹H NMR (400 MHz, DMSO) δ 12.92 (s, 1H), 11.87 (s, 1H), 8.80 (s, 1H), 8.39 (d, J = 2.3 Hz, 1H), 7.78 (dd, J = 2.5, 8.6 Hz, 1H), 7.67-7.60 (m, 1H), 7.52 (d, J = 7.3 Hz, 1H), 7.32 (dd, J = 8.0, 8.0 Hz, 2H), 7.12 (d, J = 8.6 Hz, 1H), 6.65 (d, J = 7.1 Hz, 1H), 4.12 (q, J = 7.1 Hz, 2H), 1.57 (s, 6H), 1.17 (dd, J = 7.1, 7.1 Hz, 3H). | B CA1.1 2-bromo-1,3-difluoro benzene |
| I-54 | 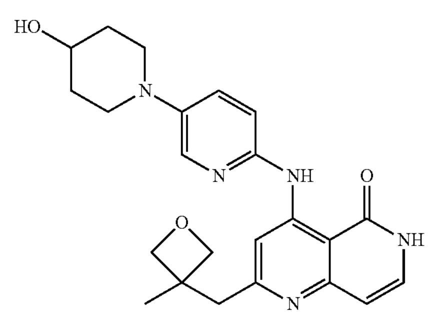 [SMILES: CC1(Cc2cc(Nc3ccc(N4CCC(O)CC4)cn3)c3c(=O)[nH]ccc3n2)COC1] | 4-[[5-(4-hydroxy-1-piperidyl)-2-pyridyl]amino]-2-[(3-methyl-oxetan-3-yl)methyl]-6H-1,6-naphthyridin-5-one | Method 10cm_Formic_AQ, m/z = 422 [M + H]+, Time = 2.38 min. | ¹H NMR (400 MHz, DMSO) δ 15.30 (s, 1H), 8.38 (s, 1H), 8.16 (d, J = 3.1 Hz, 1H), 8.14 (s, 1H), 8.03 (d, J = 6.3 Hz, 1H), 7.52 (dd, J = 3.1, 9.0 Hz, 1H), 7.10 (d, J = 8.9 Hz, 1H), 6.42 (d, J = 6.3 Hz, 1H), 4.26 (d, J = 11.7 Hz, 2H), 4.01 (d, J = 11.7 Hz, 2H), 3.72-3.64 (m, 1H), 3.63-3.55 (m, 2H), 3.24 (d, J = 17.9 Hz, 1H), 3.05 (d, J = 18.3 Hz, 1H), 2.99-2.91 (m, 2H), 1.89-1.80 (m, 2H), 1.55-1.45 (m, 2H), 1.20 (s, 3H). (1 eq. formate salt, 2 exchangable proton not observed) | N 1-(6-amino-pyridin-3-yl)piperidin-4-ol ((3-methyl-oxetan-3-yl)methyl) zinc bromide |

TABLE 2-continued

| I-# | STRUCTURE | NAME | LCMS | HNMR | Method SM |
|---|---|---|---|---|---|
| I-55 | 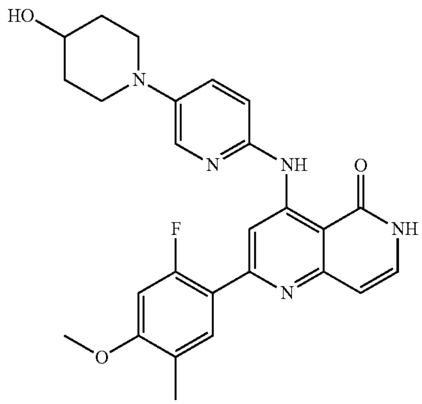 [SMILES: COc1cc(F)c(-c2cc(Nc3ccc(N4CCC(O)CC4)cn3)c3c(=O)[nH]ccc3n2)cc1C] | 2-(2-fluoro-4-methoxy-5-methyl-phenyl)-4-[[5-(4-hydroxy-1-piperidyl)-2-pyridyl]amino]-6H-1,6-naphthyridin-5-one | Method 10cm_Formic_AQ, m/z = 476 [M + H]+, Ret. time = 2.64 min. | $^1$H NMR (400 MHz, DMSO): δ 12.36 (s, 1 H), 11.59 (s, 1 H), 8.70 (d, J = 1.1 Hz, 1 H), 8.07 (d, J = 3.0 Hz, 1 H), 7.83 (d, J = 8.9 Hz, 1 H), 7.48 (dd, J = 3.1, 9.0 Hz, 1 H), 7.39 (d, J = 7.3 Hz, 1 H), 7.02 (d, J = 8.9 Hz, 1 H), 6.98 (s, 1 H), 6.59 (d, J = 7.3 Hz, 1 H), 4.70 (d, J = 4.3 Hz, 1 H), 3.89 (s, 3 H), 3.68-3.61 (m, 1 H), 3.57-3.49 (m, 2 H), 2.92-2.84 (m, 2 H), 2.20 (s, 3 H), 1.88-1.81 (m, 2 H), 1.56-1.45 (m, 2 H). | A 1-(6-amino-pyridin-3-yl)piperidin-4-ol CB3 |
| I-56 | 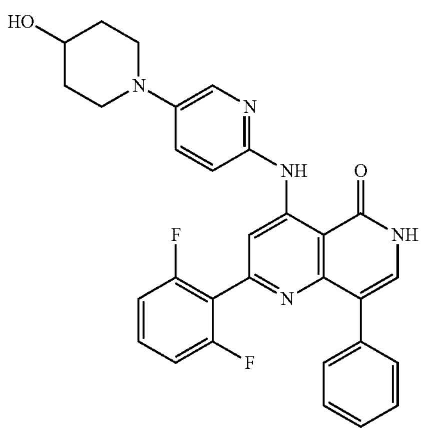 [SMILES: O=c1[nH]cc(-c2ccccc2)c2nc(-c3c(F)cccc3F)cc(Nc3ccc(N4CCC(O)CC4)cn3)c12] | 2-(2,6-difluoro-phenyl)-4-[[5-(4-hydroxy-1-piperidyl)-2-pyridyl]amino]-8-phenyl]-6H-1,6-naphthyridin-5-one | Method 10cm_Formic_AQ, m/z = 526 [M + H]+, Ret. time = 2.96 min. | $^1$H NMR (400 MHz, DMSO) δ 12.79 (s, 1H), 12.06 (s, 1H), 8.59 (s, 1H), 8.11 (d, J = 2.5 Hz, 1H), 7.67-7.49 (m, 5H), 7.44-7.24 (m, 5H), 7.08 (d, J = 8.8 Hz, 1H), 4.73 (s, 1H), 3.69-3.64 (m, 1H), 3.56 (d, J = 12.6 Hz, 2H), 2.95-2.88 (m, 2H), 1.86 (d, J = 9.6 Hz, 2H), 1.58-1.48 (m, 2H). | J 1-(6-amino-pyridin-3-yl)piperidin-4-ol Phenyl boronic acid (step 2) |
| I-57 | 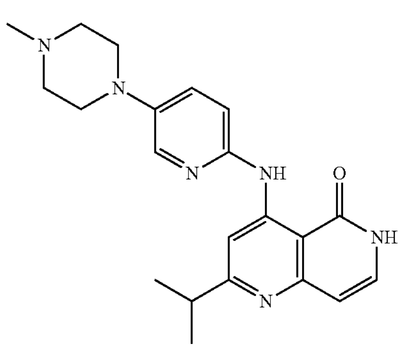 [SMILES: CC(C)c1cc(Nc2ccc(N3CCN(C)CC3)cn2)c2c(=O)[nH]ccc2n1] | 2-isopropyl-4-[[5-(4-methyl-piperazin-1-yl)-2-pyridyl]amino]-6H-1,6-naphthyridin-5-one | Method 10cm_Formic_AQ, m/z = 379 [M + H]+, Ret. time = 2.14 min. | $^1$H NMR (400 MHz, DMSO) δ 8.16 (d, J = 6.3 Hz, 1H), 8.07 (d, J = 2.7 Hz, 1H), 7.67-7.54 (m, 2H), 7.47 (dd, J = 3.1, 9.0 Hz, 1H), 7.34 (d, J = 7.7 Hz, 1H), 7.02 (d, J = 8.5 Hz, 1H), 6.54 (d, J = 7.3 Hz, 1H), 3.20-3.16 (m, 4H), 2.96-2.88 (m, 1H), 2.60-2.56 (m, 4H), 2.28 (s, 3H), 1.23 (d, J = 6.9 Hz, 6H). | B 5-(4-methyl-piperazin-1-yl)pyridin-2-amine 2-Propylzinc bromide |

TABLE 2-continued

| I-# | STRUCTURE | NAME | LCMS | HNMR | Method SM |
|---|---|---|---|---|---|
| I-58 | 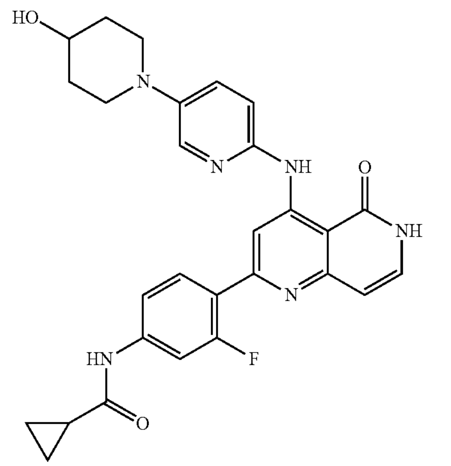 [SMILES: O=C(Nc1ccc(-c2cc(Nc3ccc(N4CCC(O)CC4)cn3)c3c(=O)[nH]ccc3n2)c(F)c1)C1CC1] | N-[3-fluoro-4-[4-[[5-(4-hydroxy-1-piperidyl)-2-pyridyl]amino]-5-oxo-6H-1,6-naphthyridin-2-yl]phenyl]cyclopropane-carboxamide | Method 10cm_Bicarb_AQ, m/z = 515 [M + H]+, Ret. time = 3.01 min. | ¹H NMR (400 MHz, DMSO): δ 12.38 (s, 1 H), 11.61 (d, J = 4.4 Hz, 1 H), 10.60 (s, 1 H), 8.73 (s, 1 H), 8.08 (d, J = 3.0 Hz, 1 H), 8.01 (dd, J = 8.8, 8.8 Hz, 1 H), 7.79-7.69 (m, 1 H), 7.50-7.37 (m, 3 H), 7.02 (d, J = 8.9 Hz, 1 H), 6.58 (d, J = 7.2 Hz, 1 H), 4.70 (d, J = 4.1 Hz, 1 H), 3.68-3.60 (m, 1 H), 3.58-3.51 (m, 2 H), 2.92-2.83 (m, 2 H), 1.88-1.82 (m, 3 H), 1.57-1.45 (m, 2 H), 0.89-0.84 (m, 4 H). | A 1-(6-amino-pyridin-3-yl)piperidin-4-ol CB2.1 |
| I-59 | 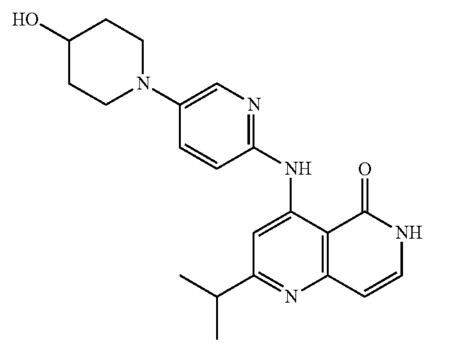 [SMILES: CC(C)c1cc(Nc2ccc(N3CCC(O)CC3)cn2)c2c(=O)[nH]ccc2n1] | 5-[[5-(4-hydroxy-1-piperidyl)-2-pyridyl]amino]-7-isopropyl-3H-pyrido[2,3-d]pyrimidin-4-one | Method 10cm_Formic_AQ, m/z = 381 [M + H]+, Ret. time = 2.38 min. | ¹H NMR (400 MHz, DMSO) δ 12.06-11.99 (m, 1H), 8.26 (s, 1H), 8.21 (s, 1H), 8.14 (d, J = 2.8 Hz, 1H), 7.51 (dd, J = 2.9, 9.0 Hz, 1H), 7.05 (d, J = 9.1 Hz, 1H), 4.74 (s, 1H), 3.72-3.66 (m, 1H), 3.62-3.53 (m, 2H), 3.02-2.88 (m, 3H), 1.93-1.87 (m, 2H), 1.61-1.50 (m, 2H), 1.30 (d, J = 7.1 Hz, 6H). 1-Exchangable proton not observed | U 1-(6-amino-pyridin-3-yl)piperidin-4-ol |
| I-60 | 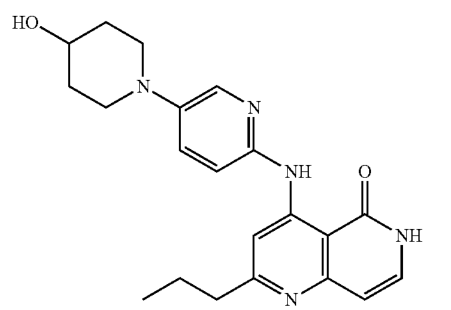 [SMILES: CCCc1cc(Nc2ccc(N3CCC(O)CC3)cn2)c2c(=O)[nH]ccc2n1] | 5-[[5-(4-hydroxy-1-piperidyl)-2-pyridyl]amino]-7-propyl-3H-pyrido[2,3-d]pyrimidin-4-one | Method 10cm_Formic_AQ, m/z = 381 [M + H]+, Ret. time = 2.39 min. | ¹H NMR (400 MHz, DMSO) δ 12.55 (s, 1H), 11.78 (s, 1H), 8.27 (s, 1H), 8.18-8.13 (m, 2H), 7.51 (dd, J = 2.9, 9.0 Hz, 1H), 7.07 (d, J = 8.8 Hz, 1H), 4.74 (d, J = 3.5 Hz, 1H), 3.71-3.67 (m, 1H), 3.62-3.53 (m, 2H), 2.97-2.87 (m, 2H), 2.70 (dd, J = 7.6, 7.6 Hz, 2H), 1.93-1.87 (m, 2H), 1.76 (dd, J = 7.3, 14.9 Hz, 2H), 1.61-1.49 (m, 2H), 0.99 (dd, J = 7.5, 7.5 Hz, 3H). | U 1-(6-amino-pyridin-3-yl)piperidin-4-ol |
| I-61 | 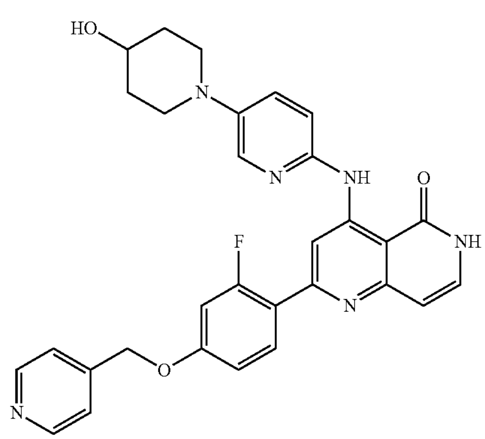 [SMILES: O=c1[nH]ccc2nc(-c3ccc(OCc4ccncc4)cc3F)cc(Nc3ccc(N4CCC(O)CC4)cn3)c12] | 2-[2-fluoro-4-(4-pyridyl-methoxy)phenyl]-4-[[5-(4-hydroxy-1-piperidyl)-2-pyridyl]amino]-6H-1,6-naphthyridin-5-one | Method 10cm_Formic_AQ, m/z = 539 [M + H]+, Ret. time = 2.34 min. | ¹H NMR (400 MHz, DMSO): δ 12.39 (s, 1 H), 11.61 (s, 1 H), 8.71 (d, J = 1.0 Hz, 1 H), 8.63-8.61 (m, 2 H), 8.07 (d, J = 3.0 Hz, 1 H), 8.01 (dd, J = 9.2, 9.2 Hz, 1 H), 7.50-7.45 (m, 3 H), 7.40 (d, J = 7.3 Hz, 1 H), 7.09 (d, J = 7.3 Hz, 1 H), 7.07-7.00 (m, 2 H), 6.57 (d, J = 7.3 Hz, 1 H), 5.32 (s, 2 H), 4.71 (d, J = 4.1 Hz, 1 H), 3.68-3.61 (m, 1 H), 3.57-3.49 (m, 2 H), 2.92-2.83 (m, 2 H), 1.88-1.80 (m, 2 H), 1.56-1.45 (m, 2 H). | A 1-(6-amino-pyridin-3-yl)piperidin-4-ol CB5 |

TABLE 2-continued

| I-# | STRUCTURE | NAME | LCMS | HNMR | Method SM |
|---|---|---|---|---|---|
| I-62 | 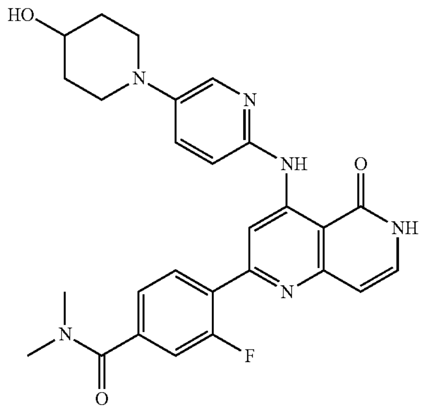 [SMILES: CN(C)C(=O)c1ccc(-c2cc(Nc3ccc(N4CCC(O)CC4)cn3)c3c(=O)[nH]ccc3n2)c(F)c1] | 3-fluoro-4-[4-[[5-(4-hydroxy-1-piperidyl)-2-pyridyl]amino]-5-oxo-6H-1,6-naphthyridin-2-yl]-N,N-dimethyl-benzamdie | Method 10cm_Bicarb_AQ, m/z = 503 [M + H]+, Ret. time = 2.84 min. | ¹H NMR (400 MHz, DMSO): δ 12.49 (s, 1 H), 11.71 (s, 1 H), 8.80 (s, 1 H), 8.12 (d, J = 2.5 Hz, 1 H), 8.07 (dd, J = 7.8, 7.8 Hz, 1 H), 7.52 (dd, J = 2.8, 8.8 Hz, 1 H), 7.50-7.40 (m, 3 H), 7.08 (d, J = 9.1 Hz, 1 H), 6.64 (d, J = 7.3 Hz, 1 H), 4.74 (d, J = 4.0 Hz, 1 H), 3.72-3.66 (m, 1 H), 3.56 (d, J = 12.4 Hz, 2 H), 3.07 (s, 3 H), 3.02 (s, 3 H), 2.92 (dd, J = 10.0, 10.0 Hz, 2 H), 1.88 (d, J = 9.6 Hz, 2 H), 1.59-1.49 (m, 2 H). | A 1-(6-amino-pyridin-3-yl)piperidin-4-ol (4-(dimethyl-carbamoyl)-2-fluoro-phenyl)boronic acid |
| I-63 | 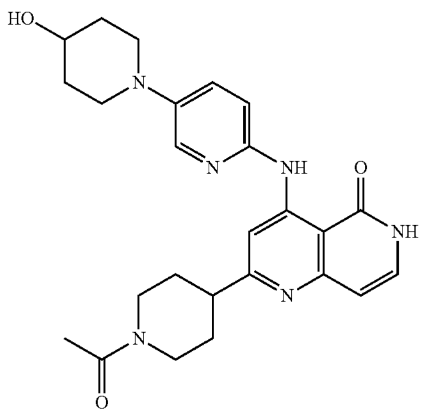 [SMILES: CC(=O)N1CCC(c2cc(Nc3ccc(N4CCC(O)CC4)cn3)c3c(=O)[nH]ccc3n2)CC1] | 2-(1-acetyl-4-piperidyl)-4-[[5-(4-hydroxy-1-piperidyl)-2-pyridyl]amino]-6H-1,6-naphthyridin-5-one | Method 10cm_Formic_AQ, m/z = 463 [M + H]+, Ret. time = 2.31 min. | ¹H NMR (400 MHz, DMSO) δ 12.34 (s, 1H), 11.55 (d, J = 2.3 Hz, 1H), 8.37-8.31 (m, 1H), 8.11 (d, J = 6.5 Hz, 1H), 8.06 (d, J = 3.3 Hz, 1H), 7.46 (dd, J = 3.0, 9.0 Hz, 1H), 7.34 (d, J = 7.3 Hz, 1H), 7.00 (d, J = 8.8 Hz, 1H), 6.52 (d, J = 7.3 Hz, 1H), 4.52-4.47 (m, 1H), 3.95-3.91 (m, 1H), 3.68-3.61 (m, 1H), 3.54-3.46 (m, 2H), 3.18-3.10 (m, 1H), 2.89-2.80 (m, 3H), 2.68-2.60 (m, 1H), 2.04 (s, 3H), 1.89-1.80 (m, 4H), 1.71-1.44 (m, 4H). (1 eq. formate salt, 1 exchangable proton not observed) | O 1-(6-amino-pyridin-3-yl)piperidin-4-ol (1-(tert-butoxy-carbonyl)piperidin-4-yl)zinc bromide |
| I-64 | 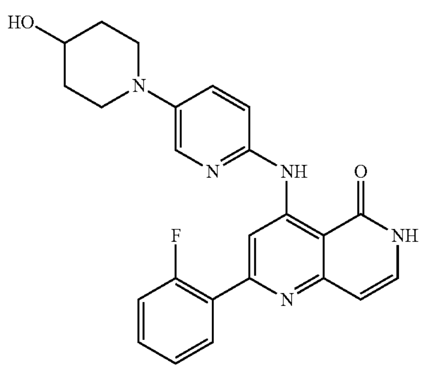 [SMILES: O=c1[nH]ccc2nc(-c3ccccc3F)cc(Nc3ccc(N4CCC(O)CC4)cn3)c12] | 2-(2-fluoro-phenyl)-4-[[5-(4-hydroxy-1-piperidyl)-2-pyridyl]amino]-6H-1,6-naphthyridin-5-one | Method 10cm_Bicarb_AQ, m/z = 432 [M + H]+, Ret. time = 3.09 min. | ¹H NMR (400 MHz, DMSO): δ 12.47 (s, 1 H), 11.69 (s, 1 H), 8.76 (s, 1 H), 8.11 (d, J = 2.8 Hz, 1 H), 8.01 (dd, J = 7.2, 7.2 Hz, 1 H), 7.62-7.46 (m, 2 H) 7.44-7.36 (m, 2 H), 7.07 (d, J = 8.8 Hz, 1 H), 6.63 (d, J = 7.3 Hz, 1 H), 4.74 (d, J = 4.0 Hz, 1 H), 3.73-3.66 (m, 1 H), 3.57 (d, J = 12.4 Hz, 2 H), 2.92 (dd, J = 10.0, 10.0 Hz, 2 H), 1.92-1.84 (m, 2 H), 1.60-1.48 (m, 2 H), 1.14 (dd, J = 6.9, 6.9 Hz, 1 H). | A 1-(6-amino-pyridin-3-yl)piperidin-4-ol 2-Fluoro-phenyl-boronic acid |
| I-65 | 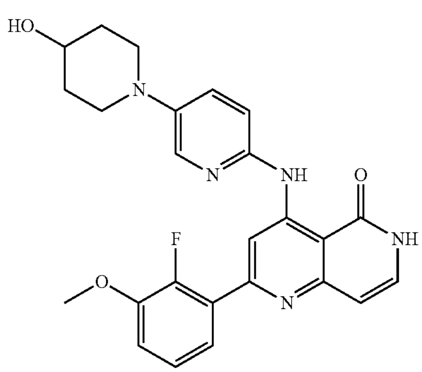 [SMILES: COc1cccc(-c2cc(Nc3ccc(N4CCC(O)CC4)cn3)c3c(=O)[nH]ccc3n2)c1F] | 2-(2-fluoro-3-methoxy-phenyl)-4-[[5-(4-hydroxy-1-piperidyl)-2-pyridyl]amino]-6H-1,6-naphthyridin-5-one | Method 10cm_Bicarb_AQ, m/z = 462 [M + H]+, Ret. time = 3.05 min. | ¹H NMR (400 MHz, DMSO): δ 12.46 (s, 1 H), 11.68 (s, 1 H), 8.69 (s, 1 H), 8.11 (d, J = 2.5 Hz, 1 H), 7.76 (dd, J = 7.1, 7.1 Hz, 1 H), 7.52 (dd, J = 2.9 9.0 Hz, 1 H), 7.44 (dd, J = 7.1, 7.1 Hz, 2 H), 7.27 (dd, J = 7.6, 7.6 Hz, 1 H), 7.07 (d, J = 8.8 Hz, 1 H), 6.62 (d, J = 7.1 Hz, 1 H), 4.73 (d, J = 4.0 Hz, 1 H), 4.38 (s, 3 H), 3.73-3.65 (m, 1 H), 3.60-3.52 (m, 2 H), 2.91 (dd, J = 9.9, 9.9 Hz, 2 H), 1.89 (d, J = 9.3 Hz, 2H), 1.60-1.48 (m, 2 H). | A 1-(6-amino-pyridin-3-yl)piperidin-4-ol 2-Fluoro-3-methoxy phenyl boronic acid |

TABLE 2-continued

| I-# | STRUCTURE | NAME | LCMS | HNMR | Method SM |
|---|---|---|---|---|---|
| I-66 | 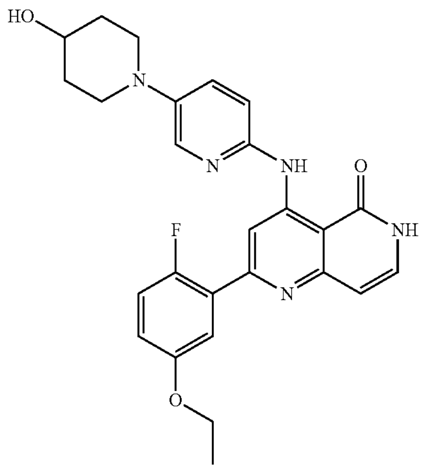 [SMILES: CCOc1ccc(F)c(-c2cc(Nc3ccc(N4CCC(O)CC4)cn3)c3c(=O)[nH]ccc3n2)c1] | 2-(5-ethoxy-2-fluoro-phenyl)-4-[[5-(4-hydroxy-1-piperidyl)-2-pyridyl]amino]-6H-1,6-naphthyridin-5-one | Method 10cm_Bicarb_AQ, m/z = 476 [M + H]+, Ret. time = 3.22 min. | $^1$H NMR (400 MHz, DMSO): δ 12.46 (s, 1 H), 11.68 (s, 1 H), 8.76 (s, 1 H), 8.11 (d, J = 2.8 Hz, 1 H), 7.55-7.48 (m, 2 H), 7.46 (d, J = 7.3 Hz, 1 H), 7.32 (d, J = 9.3 Hz, 1 H), 7.14-7.04 (m, 2 H), 6.64 (d, J = 7.3 Hz, 1 H), 4.73 (d, J = 3.8 Hz, 1 H), 4.12 (q, J = 6.9 Hz, 2 H), 3.73-3.64 (m, 1 H), 3.57 (d, J = 12.6 Hz, 2 H), 2.91 (dd, J = 10.0, 10.0 Hz, 2 H), 1.89 (d, J = 9.3 Hz, 2 H), 1.60-1.50 (m, 2 H), 1.40 (dd, J = 6.9, 6.9 Hz, 3 H). | A 1-(6-amino-pyridin-3-yl) piperidin-4-ol 5-ethoxy-2-fluoro-phenyl-boronic acid |
| I-67 | 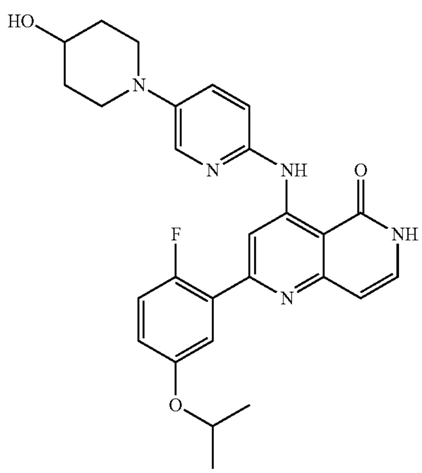 [SMILES: CC(C)Oc1ccc(F)c(-c2cc(Nc3ccc(N4CCC(O)CC4)cn3)c3c(=O)[nH]ccc3n2)c1] | 2-(2-fluoro-5-isopropoxy-phenyl)-4-[[5-(4-hydroxy-1-piperidyl)-2-pyridyl]amino]-6H-1,6-naphthyridin-5-one | Method 10cm_Bicarb_AQ, m/z = 490 [M + H]+, Ret. time = 3.31 min. | $^1$H NMR (400 MHz, DMSO): δ 12.46 (s, 1 H), 11.68 (s, 1 H), 8.76 (s, 1 H), 8.11 (d, J = 2.5 Hz, 1 H), 7.55-7.43 (m, 3 H), 7.31 (d, J = 9.3 Hz, 1 H), 7.14-7.05 (m, 2 H), 6.64 (d, J = 7.1 Hz, 1 H), 4.75-4.63 (m, 2 H), 3.73-3.66 (m, 1 H), 3.61-3.53 (m, 2 H), 2.96-2.87 (m, 2 H), 1.88 (d, J = 9.3 Hz, 2 H), 1.60-1.48 (m, 2 H), 1.34 (d, J = 5.8 Hz, 6 H). | A 1-(6-amino-pyridin-3-yl) piperidin-4-ol (2-fluoro-5-isopropoxy-phenyl) boronic acid |
| I-68 | 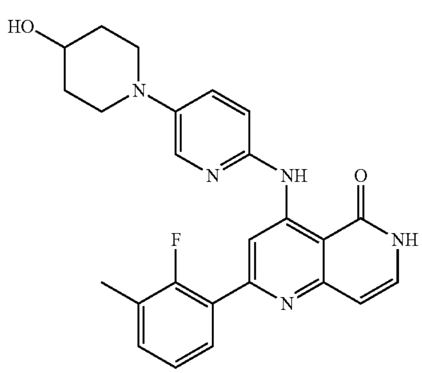 [SMILES: Cc1cccc(-c2cc(Nc3ccc(N4CCC(O)CC4)cn3)c3c(=O)[nH]ccc3n2)c1F] | 2-(2-fluoro-3-methyl-phenyl)-4-[[5-(4-hydroxy-1-piperidyl)-2-pyridyl]amino]-6H-1,6-naphthyridin-5-one | Method 10cm_Formic_AQ, m/z = 446 [M + H]+, Ret. time = 2.68 min. | $^1$H NMR (400 MHz, DMSO): δ 12.46 (s, 1 H), 11.68 (s, 1 H), 8.69 (s, 1 H), 8.11 (d, J = 2.5 Hz, 1 H), 7.76 (dd, J = 7.1, 7.1 Hz, 1 H), 7.52 (dd, J = 2.9, 9.0 Hz, 1 H), 7.44 (dd, J = 7.1, 7.1 Hz, 2 H), 7.27 (dd, J = 7.6, 7.6 Hz, 1 H), 7.07 (d, J = 8.8 Hz, 1 H), 6.62 (d, J = 7.1 Hz, 1 H), 4.73 (d, J = 4.0 Hz, 1 H), 3.73-3.65 (m, 1 H), 3.60-3.52 (m, 2 H), 2.91 (dd, J = 9.9, 9.9 Hz, 2 H), 2.38 (s, 3 H), 1.89 (d, J = 9.3 Hz, 2 H), 1.60-1.48 (m, 2 H). | A 1-(6-amino-pyridin-3-yl) piperidin-4-ol 2-Fluoro-3-methyl-phenyl boronic acid |

TABLE 2-continued

| I-# | STRUCTURE | NAME | LCMS | HNMR | Method SM |
|---|---|---|---|---|---|
| I-69 | 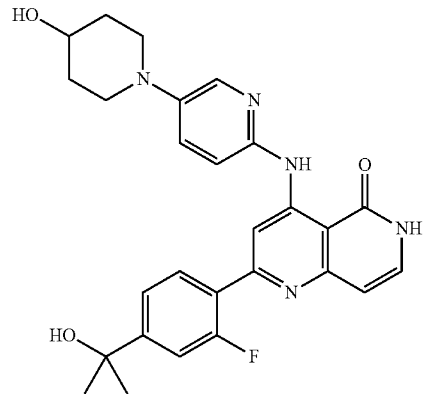 [SMILES: CC(C)(O)c1ccc(-c2cc(Nc3ccc(N4CCC(O)CC4)cn3)c3c(=O)[nH]ccc3n2)c(F)c1] | 2-[2-fluoro-4-(1-hydroxy-1-methyl-ethyl)phenyl]-4-[[5-(4-hydroxy-1-piperidyl)-2-pyridyl]amino]-6H-1,6-naphthyridin-5-one | Method 10cm_Formic_AQ, m/z = 490 [M + H]+, Ret. time = 2.63 min. | $^1$H NMR (400 MHz, DMSO): δ 12.48 (s, 1 H), 11.66 (d, J = 5.3 Hz, 1 H), 8.89 (s, 1 H), 8.20 (d, J = 2.8 Hz, 1 H), 7.89 (dd, J = 1.4, 8.2 Hz, 1 H), 7.86-7.78 (m, 2 H), 7.53 (dd, J = 3.0, 8.8 Hz, 1 H), 7.49-7.42 (m, 1 H), 7.09 (d, J = 8.8 Hz, 1 H), 6.66-6.63 (m, 1 H), 5.42 (s, 1 H), 4.75 (d, J = 4.0 Hz, 1 H), 3.73-3.66 (m, 1 H), 3.63-3.57 (m, 2 H), 2.97-2.89 (m, 2 H), 1.90 (dd, J = 3.2, 12.8 Hz, 2 H), 1.58 (s, 6 H), 1.56-1.52 (m, 2 H). | A 1-(6-amino-pyridin-3-yl)piperidin-4-ol 2-(3-fluoro-4-(4,4,5,5-tetramethyl-1,3,2-dioxa-borolan-2-yl)phenyl)propan-2-ol |
| I-70 | 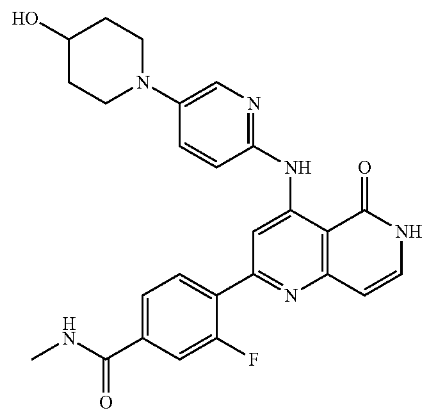 [SMILES: CNC(=O)c1ccc(-c2cc(Nc3ccc(N4CCC(O)CC4)cn3)c3c(=O)[nH]ccc3n2)c(F)c1] | 3-fluoro-4-[4-[[5-(4-hydroxy-1-piperidyl)-2-pyridyl]amino]-5-oxo-6H-1,6-naphthyridin-2-yl]-N-methyl-benzamide | Method 10cm_Formic_AQ, m/z = 489 [M + H]+, Ret. time = 2.48 min. | $^1$H NMR (400 MHz, DMSO): δ 12.50 (s, 1 H), 11.74-11.67 (m, 1 H), 8.79 (s, 1 H), 8.69 (d, J = 4.5 Hz, 1 H), 8.13-8.07 (m, 2 H), 7.86 (d, J = 8.3 Hz, 1 H), 7.80 (s, 1 H), 7.55-7.45 (m, 2 H), 7.08 (d, J = 8.8 Hz, 1 H), 6.65 (d, J = 7.3 Hz, 1 H), 4.74 (d, J = 1.5 Hz, 1 H), 3.68 (d, J = 2.5 Hz, 1 H), 3.57 (d, J = 12.4 Hz, 2 H), 2.96 (d, J = 12.4 Hz, 2 H), 2.94-2.86 (m, 3 H), 1.88 (d, J = 9.6 Hz, 2 H), 1.60-1.49 (m, 2 H). | A 1-(6-amino-pyridin-3-yl)piperidin-4-ol (2-fluoro-4-(methyl-carbamoyl)phenyl)boronic acid |
| I-71 | 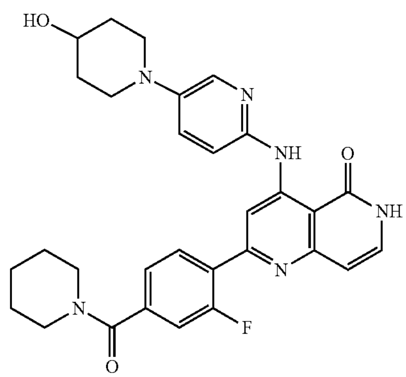 [SMILES: O=C(c1ccc(-c2cc(Nc3ccc(N4CCC(O)CC4)cn3)c3c(=O)[nH]ccc3n2)c(F)c1)N1CCCCC1] | 2-[2-fluoro-4-(piperidine-1-carbonyl)phenyl]-4-[[5-(4-hydroxy-1-piperidyl)-2-pyridyl]amino]-6H-1,6-naphthyridin 5-one | Method 10cm_Formic_AQ, m/z = 543 [M + H]+, Ret. time = 2.68 min. | $^1$H NMR (400 MHz, DMSO): δ 12.49 (s, 1 H), 11.74-11.69 (m, 1 H), 8.79 (s, 1 H), 8.12 (d, J = 2.5 Hz, 1 H), 8.07 (dd, J = 7.8, 7.8 Hz, 1 H), 7.52 (dd, J = 2.9, 9.0 Hz, 1 H), 7.47 (d, J = 7.3 Hz, 1 H), 7.42-7.37 (m, 2 H), 7.08 (d, J = 8.8 Hz, 1 H), 6.63 (d, J = 7.1 Hz, 1 H), 4.74 (d, J = 4.0 Hz, 1 H), 3.72-3.63 (m, 3 H), 3.61-3.53 (m, 2 H), 2.92 (dd, J = 9.9, 9.9 Hz, 2 H), 1.89-1.86 (m, 2 H), 1.73-1.50 (m, 10 H). | A 1-(6-amino-pyridin-3-yl)piperidin-4-ol (2-fluoro-4-(piperidine-1-carbonyl)phenyl)boronic acid |
| I-72 | 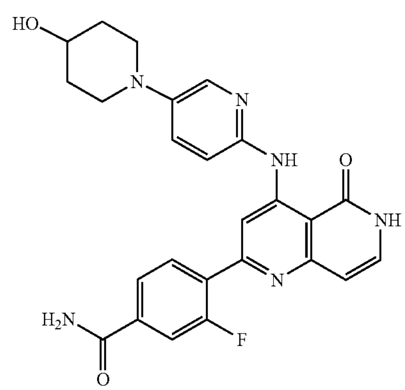 [SMILES: NC(=O)c1ccc(-c2cc(Nc3ccc(N4CCC(O)CC4)cn3)c3c(=O)[nH]ccc3n2)c(F)c1] | 3-fluoro-4-[4-[[5-(4-hydroxy-1-piperidyl)-2-pyridyl]amino]-5-oxo-6H-1,6-naphthyridin-2-yl]benzamide | Method 10cm_Formic_AQ, m/z = 475 [M + H]+, Ret. time = 2.71 min. | $^1$H NMR (400 MHz, DMSO): δ 12.32 (s, 1 H), 11.62 (s, 1 H), 10.90 (s, 1 H), 8.97 (s, 1 H), 8.13 (d, J = 2.8 Hz, 1 H), 7.95-7.87 (m, 2 H), 7.65-7.58 (m, 1 H), 7.56-7.47 (m, 2 H), 7.42 (d, J = 7.3 Hz, 1 H), 7.13 (d, J = 8.8 Hz, 1 H), 6.47 (d, J = 7.3 Hz, 1 H), 4.74 (s, 1 H), 3.69 (s, 1 H), 3.61-3.55 (m, 2 H), 2.98-2.89 (m, 2 H), 1.94-1.88 (m, 2 H), 1.62-1.50 (m, 2 H). | A 1-(6-amino-pyridin-3-yl)piperidin-4-ol (4-carbamoyl-2-fluoro-phenyl)boronic acid |

TABLE 2-continued

| I-# | STRUCTURE | NAME | LCMS | HNMR | Method SM |
|---|---|---|---|---|---|
| I-73 | 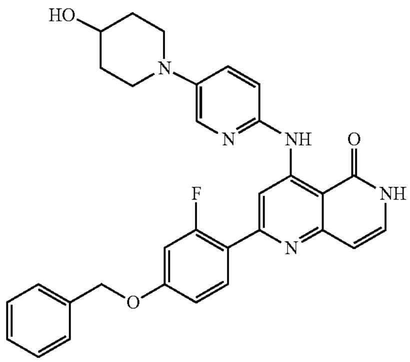 [SMILES: O=c1[nH]ccc2nc(-c3ccc(OCc4ccccc4)cc3F)cc(Nc3ccc(N4CCC(O)CC4)cn3)c12] | 2-(4-benzyloxy-2-fluoro-phenyl)-4-[[5-(4-hydroxy-1-piperidyl)-2-pyridyl]amino]-6H-1,6-naphthyridin-5-one | Method 10cm_Formic_AQ, m/z = 538 [M + H]+, Ret. time = 2.83 min. | $^1$H NMR (400 MHz, DMSO): δ 12.43 (s, 1 H), 11.61 (s, 1 H), 8.81 (s, 1 H), 8.16 (d, J = 3.0 Hz, 1 H), 7.86 (d, J = 8.7 Hz, 1 H), 7.53-7.38 (m, 9 H), 7.04 (d, J = 8.9 Hz, 1 H), 6.59 (d, J = 7.3 Hz, 1 H), 5.29 (s, 2 H), 4.72 (d, J = 4.1 Hz, 1 H), 3.69-3.62 (m, 1 H), 3.59-3.51 (m, 2 H), 2.94-2.85 (m, 2 H), 1.90-1.82 (m, 2 H), 1.58-1.47 (m, 2 H). | A 1-(6-amino-pyridin-3-yl)piperidin-4-ol 4-benzyloxy-2-fluoro-phenyl-boronic acid |
| I-74 | 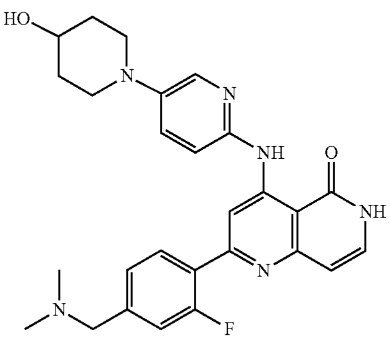 [SMILES: CN(C)Cc1ccc(-c2cc(Nc3ccc(N4CCC(O)CC4)cn3)c3c(=O)[nH]ccc3n2)c(F)c1] | 2-[4-[(dimethyl-amino)methyl]-2-fluoro-phenyl]-4-[[5-(4-hydroxy-1-piperidyl)-2-pyridyl]amino]-6H-1,6-naphthyridin-5-one | Method 10cm_Formic_AQ, m/z = 489 [M + H]+, Ret. time = 2.3 min. | $^1$H NMR (400 MHz, DMSO): δ 12.45 (s, 1 H), 11.68 (d, J = 5.6 Hz, 1 H), 8.75 (s, 1 H), 8.11 (d, J = 2.5 Hz, 1 H), 7.97 (dd, J = 8.1, 8.1 Hz, 1 H), 7.52 (dd, J = 2.8, 9.1 Hz, 1 H), 7.45 (dd, J = 6.4, 6.4 Hz, 1 H), 7.32 (d, J = 8.8 Hz, 1 H), 7.07 (d, J = 8.8 Hz, 1 H), 6.62 (d, J = 7.1 Hz, 1 H), 4.74 (d, J = 4.0 Hz, 1 H), 3.72-3.65 (m, 1 H), 3.61-3.51 (m, 5 H), 2.96-2.87 (m, 2 H), 2.25 (s, 6 H), 1.88 (d, J = 9.9 Hz, 2 H), 1.60-1.49 (m, 2 H). | A 1-(6-amino-pyridin-3-yl)piperidin-4-ol 1-(3-fluoro-4-(4,4,5,5-tetramethyl-1,3,2-dioxa-borolan-2-yl)phenyl)-N,N-dimethyl |
| I-75 | 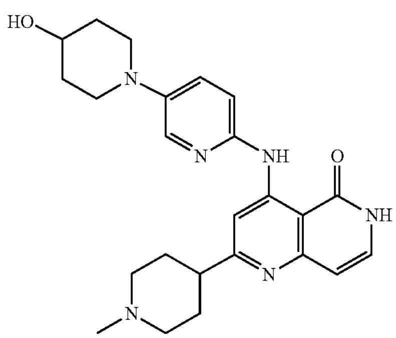 [SMILES: CN1CCC(c2cc(Nc3ccc(N4CCC(O)CC4)cn3)c3c(=O)[nH]ccc3n2)CC1] | 4-[[5-(4-hydroxy-1-piperidyl)-2-pyridyl]amino]-2-(1-methyl-4-piperidyl)-6H-1,6-naphthyridin-5-one | Method 10cm_Formic_AQ, m/z = 435 [M + H]+, Ret. time = 2.11 min. | $^1$H NMR (400 MHz, DMSO) δ 13.08 (s, 1H), 12.49 (s, 1H), 9.71-9.70 (m, 1H), 8.32-8.28 (m, 1H), 8.15-8.13 (m, 1H), 7.77 (s, 1H), 7.58-7.53 (m, 1H), 7.26-7.20 (m, 1H), 6.70 (s, 1H), 3.73-3.56 (m, 5H), 3.17-3.08 (m, 3H), 3.02-2.94 (m, 2H), 2.87 (s, 3H), 2.24-2.20 (m, 2H), 2.01-1.82 (m, 4H), 1.55-1.45 (m, 2H). (1 eq. formate salt, 1 exchangable proton not observed) | O 1-(6-amino-pyridin-3-yl)piperidin-4-ol (1-(tert-butoxy-carbonyl)piperidin-4-yl)zinc bromide |
| I-76 | 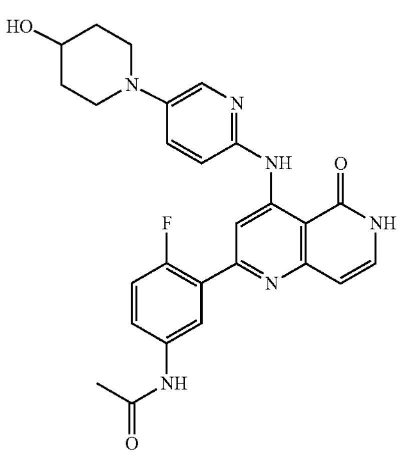 [SMILES: CC(=O)Nc1ccc(F)c(-c2cc(Nc3ccc(N4CCC(O)CC4)cn3)c3c(=O)[nH]ccc3n2)c1] | N-[4-fluoro-3-[4-[[5-(4-hydroxy-1-piperidyl)-2-pyridyl]amino]-5-oxo-6H-1,6-naphthyridin-2-yl]phenyl]acetamide | Method 10cm_Formic_AQ, m/z = 489 [M + H]+, Ret. time = 2.39 min. | $^1$H NMR (400 MHz, DMSO): δ 12.47 (s, 1 H), 11.70 (s, 1 H), 10.18 (s, 1 H), 8.76 (s, 1 H), 8.16-8.10 (m, 2 H), 7.88-7.83 (m, 1 H), 7.52 (dd, J = 2.8, 8.8 Hz, 1 H), 7.47 (d, J = 7.3 Hz, 1 H), 7.33 (dd, J = 9.2, 10.5 Hz, 1 H), 7.07 (d, J = 9.1 Hz, 1 H), 6.62 (d, J = 7.3 Hz, 1 H), 4.74 (d, J = 4.3 Hz, 1 H), 3.72-3.66 (m, 1 H), 3.57 (d, J = 12.6 Hz, 2 H), 2.95-2.87 (m, 2 H), 2.11 (s, 3 H), 1.92-1.86 (m, 2 H), 1.60-1.48 (m, 2 H). | A 1-(6-amino-pyridin-3-yl)piperidin-4-ol N-(4-fluoro-3-(4,4,5,5-tetramethyl-1,3,2-dioxa-borolan-2-yl)phenyl)acetamide |

TABLE 2-continued

| I-# | STRUCTURE | NAME | LCMS | HNMR | Method SM |
|---|---|---|---|---|---|
| I-77 | 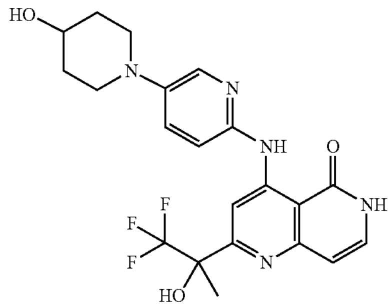 [SMILES: CC(O)(c1cc(Nc2ccc(N3CCC(O)CC3)cn2)c2c(=O)[nH]ccc2n1)C(F)(F)F] | 4-[[5-(4-hydroxy-1-piperidyl)-2-pyridyl]amino]-2-(2,2,2-trifluoro-1-hydroxy-1-methyl-ethyl)-6H-1,6-naphthyridin-5-one | Method 10cm_Formic_AQ, m/z = 450 [M + H]+, Ret. time = 2.48 min. | $^1$H NMR (400 MHz, DMSO) δ 12.43 (s, 1H), 11.71 (s, 1H), 8.64 (s, 1H), 8.14 (d, J = 2.8 Hz, 1H), 7.53 (dd, J = 2.9, 9.0 Hz, 1H), 7.45 (d, J = 7.3 Hz, 1H), 7.06 (d, J = 8.8 Hz, 1H), 6.75 (s, 1H), 6.58 (d, J = 7.1 Hz, 1H), 4.74 (d, J = 4.3 Hz, 1H), 3.73-3.67 (m, 1H), 3.63-3.55 (m, 2H), 2.98-2.90 (m, 2H), 1.88 (d, J = 9.9 Hz, 2H), 1.75 (s, 3H), 1.61-1.49 (m, 2H). | M 1-(6-amino-pyridin-3-yl)piperidin-4-ol |
| I-78 | 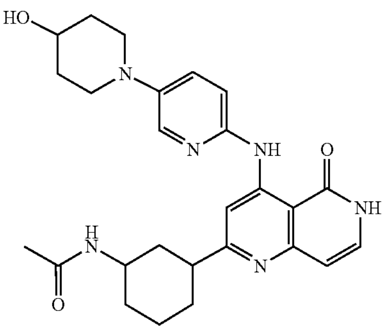 [SMILES: CC(=O)NC1CCCC(c2cc(Nc3ccc(N4CCC(O)CC4)cn3)c3c(=O)[nH]ccc3n2)C1] | N-[1-[4-[[5-(4-hydroxy-1-piperidyl)-2-pyridyl]amino]-5-oxo-6H-1,6-naphthyridin-2-yl]-3-piperidyl]acetamide | Method 10cm_Formic_AQ, m/z = 478 [M + H]+, Ret. time = 2.27 min. | $^1$H NMR (400 MHz, DMSO) δ 12.24 (s, 1H), 11.15 (d, J = 5.4 Hz, 1H), 8.02-7.97 (m, 2H), 7.81 (d, J = 5.4 Hz, 1H), 7.43 (dd, J = 2.9, 9.0 Hz, 1H), 7.22 (d, J = 7.4 Hz, 1H), 6.93 (d, J = 9.0 Hz, 1H), 6.28 (d, J = 7.3 Hz, 1H), 4.69 (s, 1H), 4.18-4.14 (m, 1H), 3.99 (1H, d, J = 13.7 Hz), 3.67-3.59 (m, 2H), 3.48-3.42 (m, 2H), 3.22-3.16 (m, 1H), 2.99 (dd, J = 9.0, 12.6 Hz, 1H), 2.85-2.77 (m, 2H), 1.82-1.80 (m, 7H), 1.55-1.44 (m, 4H). | E 1-(6-amino-pyridin-3-yl)piperidin-4-ol N-(piperidin-3-yl)acetamide (Step 2) |
| I-79 | 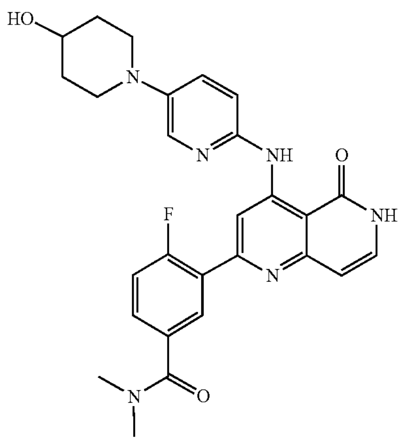 [SMILES: CN(C)C(=O)c1ccc(F)c(-c2cc(Nc3ccc(N4CCC(O)CC4)cn3)c3c(=O)[nH]ccc3n2)c1] | 4-fluoro-3-[4-[[5-(4-hydroxy-1-piperidyl)-2-pyridyl]amino]-5-oxo-6H-1,6-naphthyridin-2-yl]-N,N-dimethyl-benzamide | Method 10cm_Formic_AQ, m/z = 503 [M + H]+, Ret. time = 2.4 min. | $^1$H NMR (400 MHz, DMSO): δ 12.49 (s, 1 H), 11.68 (s, 1 H), 8.81 (s, 1 H), 8.11 (d, J = 2.8 Hz, 1 H), 8.06 (dd, J = 1.8, 7.3 Hz, 1 H), 7.66-7.61 (m, 1 H), 7.55-7.43 (m, 3 H), 7.08 (d, J = 9.1 Hz, 1 H), 6.65 (d, J = 7.3 Hz, 1 H), 4.74 (d, J = 4.3 Hz, 1 H), 3.72-3.66 (m, 1 H), 3.62-3.53 (m, 2 H), 3.04 (d, J = 12.9 Hz, 6 H), 2.92 (dd, J = 10.0, 10.0 Hz, 2 H), 1.88 (d, J = 9.6 Hz, 2 H), 1.60-1.49 (m, 2 H). | A 1-(6-amino-pyridin-3-yl)piperidin-4-ol (5-dimethyl-carbamoyl)-2-fluoro-phenyl)boronic acid |
| I-80 | 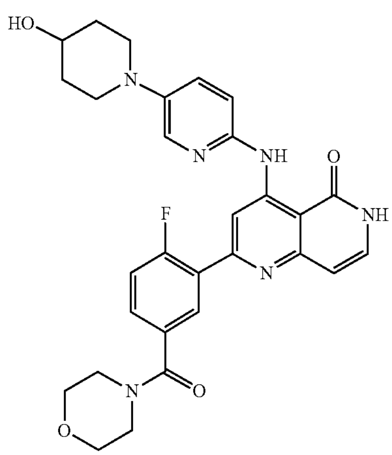 [SMILES: O=C(c1ccc(F)c(-c2cc(Nc3ccc(N4CCC(O)CC4)cn3)c3c(=O)[nH]ccc3n2)c1)N1CCOCC1] | 2-[2-fluoro-5-(morpholine-4-carbonyl)phenyl]-4-[[5-(4-hydroxy-1-piperidyl)-2-pyridyl]amino]-6H-1,6-naphthyridin-5-one | Method 10cm_Formic_AQ, m/z = 545 [M + H]+, Ret. time = 2.39 min. | $^1$H NMR (400 MHz, DMSO) δ 12.37 (s, 1H), 11.60 (s, 1H), 8.69 (s, 1H), 8.00-7.93 (m, 2H), 7.54-7.49 (m, 1H), 7.43-7.32 (m, 3H), 6.96 (d, J = 9.1 Hz, 1H), 6.53 (d, J = 7.3 Hz, 1H), 4.62 (d, J = 3.8 Hz, 1H), 3.56 (d, J = 3.8 Hz, 6H), 3.54-3.38 (m, 5H), 2.83-2.75 (m, 2H), 1.75 (d, J = 9.9 Hz, 2H), 1.48-1.36 (m, 2H). | A 1-(6-amino-pyridin-3-yl)piperidin-4-ol (2-fluoro-5-morpholine-4-carbonyl)phenyl)boronic acid |

TABLE 2-continued

| I-# | STRUCTURE | NAME | LCMS | HNMR | Method SM |
|---|---|---|---|---|---|
| I-81 | 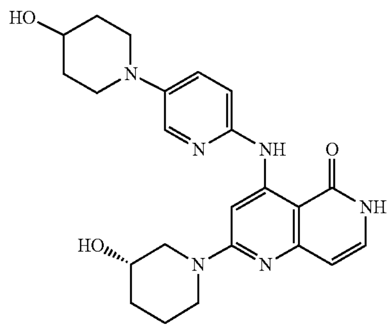 [SMILES: O=c1[nH]ccc2nc(N3CCC[C@H](O)C3)cc(Nc3ccc(N4CCC(O)CC4)cn3)c12] | 2-[(3S)-3-hydroxy-1-piperidyl]-4-[[5-(4-hydroxy-1-piperidyl)-2-pyridyl]amino]-6H-1,6-naphthyridin-5-one | Method 10cm_Formic_AQ, m/z = 437 [M + H]+, Ret. time = 2.26 min. | $^1$H NMR (400 MHz, DMSO) δ 12.26 (s, 1H), 11.14 (d, J = 5.6 Hz, 1H), 8.04 (d, J = 3.0 Hz, 1H), 7.92 (s, 1H), 7.44 (dd, J = 3.1, 9.0 Hz, 1H), 7.21 (dd, J = 6.0, 7.1 Hz, 1H), 6.89 (d, J = 8.9 Hz, 1H), 6.23 (dd, J = 0.7, 7.2 Hz, 1H), 4.94-4.71 (m, 2H), 4.32-4.26 (m, 1H), 4.12 (d, J = 12.9 Hz, 1H), 3.67-3.60 (m, 1H), 3.53-3.47 (m, 3H), 3.05-2.98 (m, 1H), 2.89-2.78 (m, 3H), 1.95-1.73 (m, 4H), 1.56-1.38 (m, 4H). | E 1-(6-amino-pyridin-3-yl)piperidin-4-ol (S)-piperidin-3-ol (Step 2) |
| I-82 | 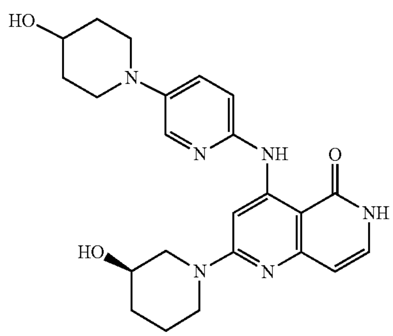 [SMILES: O=c1[nH]ccc2nc(N3CCC[C@@H](O)C3)cc(Nc3ccc(N4CCC(O)CC4)cn3)c12] | 2-[(3R)-3-hydroxy-1-piperidyl]-4-[[5-(4-hydroxy-1-piperidyl)-2-pyridyl]amino]-6H-1,6-naphthyridin-5-one | Method 10cm_Formic_AQ, m/z = 437 [M + H]+, Ret. time = 2.27 min. | $^1$H NMR (400 MHz, DMSO) δ 12.26 (s, 1H), 11.14 (d, J = 5.6 Hz, 1H), 8.29 (1H, s), 8.04 (d, J = 3.0 Hz, 1H), 7.92 (s, 1H), 7.44 (dd, J = 3.1, 9.0 Hz, 1H), 7.21 (dd, J = 6.0, 7.1 Hz, 1H), 6.91-6.87 (m, 1H), 6.23-6.21 (m, 1H), 4.83-4.83 (m, 2H), 4.32-4.26 (m, 1H), 4.12 (d, J = 12.4 Hz, 1H), 3.67-3.60 (m, 1H), 3.53-3.48 (m, 3H), 3.06-2.98 (m, 1H), 2.89-2.78 (m, 3H), 1.94-1.75 (m, 4H), 1.57-1.38 (m, 4H). (1 eq formate salt) | E 1-(6-amino-pyridin-3-yl)piperidin-4-ol (R)-piperidin-3-ol (Step 2) |
| I-83 | 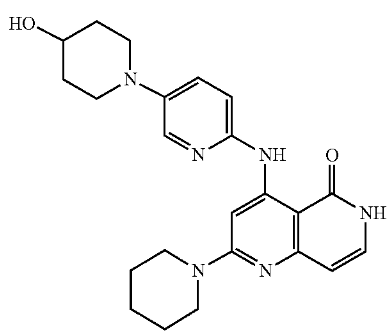 [SMILES: O=c1[nH]ccc2nc(N3CCCCC3)cc(Nc3ccc(N4CCC(O)CC4)cn3)c12] | 4-[[5-(4-hydroxy-1-piperidyl)-2-pyridyl]amino]-2-(1-piperidyl)-6H-1,6-naphthyridin-5-one | Method 10cm_Formic_AQ, m/z = 421 [M + H]+, Ret. time = 2.45 min. | $^1$H NMR (400 MHz, DMSO) δ 12.26 (s, 1H), 11.12 (d, J = 5.9 Hz, 1H), 8.05 (d, J = 2.9 Hz, 1H), 7.93 (s, 1H), 7.44 (dd, J = 3.3, 9.0 Hz 1H), 7.21 (dd, J = 6.0, 6.8 Hz, 1H), 6.89 (d, J = 8.8 Hz, 1H), 6.23 (d, J = 7.5 Hz, 1H), 4.69 (d, J = 4.1 Hz, 1H), 3.67-3.59 (m, 5H), 3.53-3.45 (m, 2H), 2.88-2.80 (m, 2H), 1.88-1.80 (m, 2H), 1.68-1.47 (m, 8H). | E 1-(6-amino-pyridin-3-yl)piperidin-4-ol piperidine (Step 2) |
| I-84 | 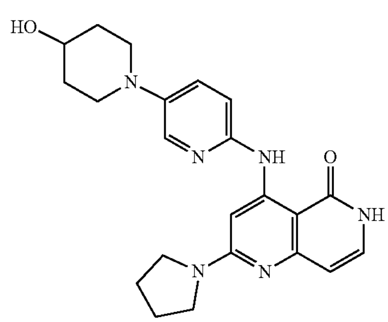 [SMILES: O=c1[nH]ccc2nc(N3CCCC3)cc(Nc3ccc(N4CCC(O)CC4)cn3)c12] | 4-[[5-(4-hydroxy-1-piperidyl)-2-pyridyl]amino]-2-pyrrolidin-yl-6H-1,6-naphthyridin-5-one | Method 10cm_Formic_AQ, m/z = 407 [M + H]+, Ret. time = 2.38 min. | $^1$H NMR (400 MHz, DMSO) δ 12.28 (s, 1H), 11.08 (s, 1H), 8.03 (d, J = 3.0 Hz, 1H), 7.55 (s, 1H), 7.43 (dd, J = 3.1, 9.0 Hz, 1H), 7.20 (d, J = 7.3 Hz, 1H), 6.93-6.90 (m, 1H), 6.23 (d, J = 7.3 Hz, 1H), 4.70 (d, J = 4.3 Hz, 1H), 3.68-3.60 (m, 1H), 3.52-3.43 (m, 6H), 2.88-2.80 (m, 2H), 1.97-1.94 (m, 4H), 1.88-1.80 (m, 2H), 1.56-1.46 (m, 2H). | E 1-(6-amino-pyridin-3-yl)piperidin-4-ol pyrrolidine (Step 2) |

TABLE 2-continued

| I-# | STRUCTURE | NAME | LCMS | HNMR | Method SM |
|---|---|---|---|---|---|
| I-85 | 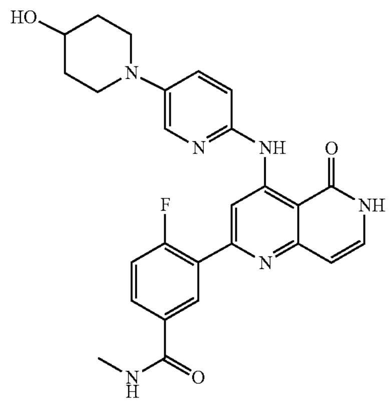 [SMILES: CNC(=O)c1ccc(F)c(-c2cc(Nc3ccc(N4CCC(O)CC4)cn3)c3c(=O)[nH]ccc3n2)c1] | 4-fluoro-3-[4-[[5-(4-hydroxy-1-piperidyl)-2-pyridyl]amino]-5-oxo-6H-1,6-naphthyridin-2-yl]-N-methyl-benzamide | Method 10cm_Formic_AQ, m/z = 489 [M + H]+, Ret. time = 2.36 min. | $^1$H NMR (400 MHz, DMSO): δ 12.38 (s, 1 H), 11.66-11.59 (m, 1 H), 8.65 (s, 1 H), 8.51 (d, J = 4.3 Hz, 1 H), 8.35 (dd, J = 1.9, 7.2 Hz, 1 H), 7.99 (d, J = 2.8 Hz, 1 H), 7.93-7.87 (m, 1 H), 7.43-7.33 (m, 3 H), 6.95 (d, J = 8.8 Hz, 1 H), 6.55 (d, J = 7.3 Hz, 1 H), 4.62-4.62 (m, 1 H), 3.59-3.53 (m, 1 H), 3.49-3.40 (m, 2 H), 2.81-2.71 (m, 2 H), 2.75-2.69 (m, 3 H), 1.75 (dd, J = 8.7, 8.7 Hz, 2 H), 1.48-1.36 (m, 2 H). | A 1-(6-amino-pyridin-3-yl)piperidin-4-ol (2-fluoro-5-(methyl-carbamoyl)phenyl)boronic acid |
| I-86 | 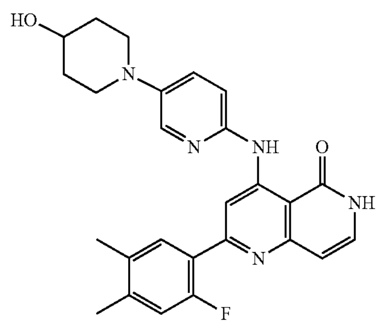 [SMILES: Cc1cc(F)c(-c2cc(Nc3ccc(N4CCC(O)CC4)cn3)c3c(=O)[nH]ccc3n2)cc1C] | 2-(2-fluoro-4,5-dimethyl-phenyl)-4-[[5-(4-hydroxy-1-piperidyl)-2-pyridyl]amino]-6H-1,6-naphthyridin-5-one | Method 10cm_Formic_AQ, m/z = 460 [M + H]+, Ret. time = 2.65 min. | $^1$H NMR (400 MHz, DMSO): δ 12.39 (s, 1 H), 11.62 (d, J = 1.8 Hz, 1 H), 8.68 (d, J = 1.4 Hz, 1 H), 8.07 (d, J = 3.0 Hz, 1 H), 7.77-7.74 (m, 1 H), 7.50-7.38 (m, 2 H), 7.14 (d, J = 12.3 Hz, 1 H), 7.04-7.00 (m, 1 H), 6.59 (d, J = 7.3 Hz, 1 H), 4.70 (d, J = 3.5 Hz, 1 H), 3.67-3.63 (m, 1 H), 3.57-3.49 (m, 2 H), 2.91-2.83 (m, 2 H), 2.31-2.28 (m, 6 H), 1.87-1.80 (m, 2 H), 1.56-1.45 (m, 2 H), | A 1-(6-amino-pyridin-3-yl)piperidin-4-ol 2-(2-fluoro-4,5-dimethyl-phenyl)-4,4,5,5-tetramethyl-1,3,2-dioxa-borolane |
| I-87 | 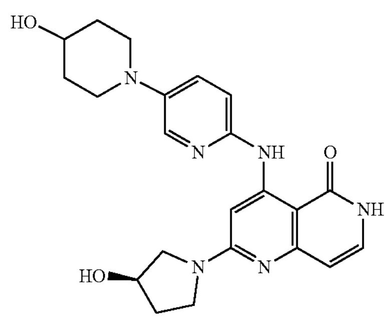 [SMILES: O=c1[nH]ccc2nc(N3CC[C@@H](O)C3)cc(Nc3ccc(N4CCC(O)CC4)cn3)c12] | 4-[[5-(4-hydroxy-1-piperidyl)-2-pyridyl]amino]-2-[(3R)-3-hydroxy-pyrrolidin-1-yl]-6H-1,6-naphthyridin-5-one | Method 10cm_Formic_AQ, m/z = 423 [M + H]+, Ret. time = 2.26 min. | $^1$H NMR (400 MHz, DMSO) δ 12.29 (s, 1H), 11.10 (d, J = 5.5 Hz, 1H), 8.40 (s, 1H), 8.03 (d, J = 3.0 Hz, 1H), 7.54 (s, 1H), 7.44 (dd, J = 3.1, 9.0 Hz, 1H), 7.20 (dd, J = 6.0, 7.2 Hz, 1H), 6.92 (d, J = 9.0 Hz, 1H), 6.24 (d, J = 6.3 Hz, 1H), 4.92 (s, 1H), 4.40 (s, 1H), 3.67-3.45 (m, 8H), 2.89-2.80 (m, 2H), 2.08-1.98 (m, 1H), 1.93-1.81 (m, 3H), 1.57-1.46 (m, 2H). (1 eq. formate salt) | E 1-(6-amino-pyridin-3-yl)piperidin-4-ol (R)-pyrrolidin-3-ol (Step 2) |
| I-88 | 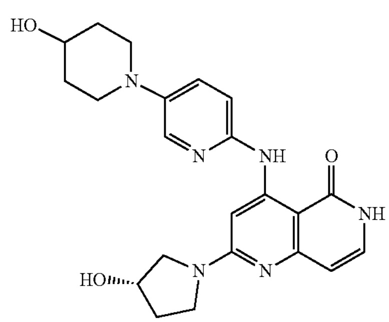 [SMILES: O=c1[nH]ccc2nc(N3CC[C@H](O)C3)cc(Nc3ccc(N4CCC(O)CC4)cn3)c12] | 4-[[5-(4-hydroxy-1-piperidyl)-2-pyridyl]amino]-2-[(3S)-3-hydroxy-pyrrolidin-1-yl]-6H-1,6-naphthyridin-5-one | Method 10cm_Formic_AQ, m/z = 423 [M + H]+, Ret. time = 2.27 min. | $^1$H NMR (400 MHz, DMSO) δ 12.29 (s, 1H), 11.09 (d, J = 5.5 Hz, 1H), 8.29 (s, 1H), 8.03 (d, J = 3.0 Hz, 1H), 7.54 (s, 1H), 7.44 (dd, J = 3.1, 9.0 Hz, 1H), 7.20 (dd, J = 6.0, 7.2 Hz, 1H), 6.91 (d, J = 8.9 Hz, 1H), 6.24 (dd, J = 1.4, 7.3 Hz, 1H), 4.96 (s, 1H), 4.40 (s, 1H), 3.67-3.43 (m, 8H), 2.88-2.80 (m, 2H), 2.09-2.00 (m, 1H), 1.93-1.81 (m, 3H), 1.57-1.46 (m, 2H). (1 eq. formate salt) | E 1-(6-amino-pyridin-3-yl)piperidin-4-ol (S)-pyrrolidin-3-ol (Step 2) |

TABLE 2-continued

| I-# | STRUCTURE | NAME | LCMS | HNMR | Method SM |
|---|---|---|---|---|---|
| I-89 | (structure) | 4-[[5-(4-hydroxy-1-piperidyl)-2-pyridyl]amino]-2-isopropyl-8-methyl-6H-1,6-naphthyridin-5-one | Method 10cm_Formic_AQ, m/z = 394 [M + H]+, Ret. time = 2.43 min. | $^1$H NMR (400 MHz, DMSO) δ 12.54 (s, 1H), 11.39 (s, 1H), 8.28 (s, 1H), 8.13 (d, J = 3.0 Hz, 1H), 7.51 (dd, J = 2.8, 2.8 Hz, 1H), 7.27 (s, 1H), 7.01 (d, J = 8.8 Hz, 1H), 4.74 (d, J = 4.0 Hz, 1H), 3.72-3.66 (m, 1H), 3.58-3.52 (m, 2H), 3.05-2.97 (m, 1H), 2.96-2.88 (m, 2H), 2.25 (s, 3H), 1.93-1.87 (m, 2H), 1.61-1.50 (m, 2H), 1.32 (d, J = 7.1 Hz, 6H). | L 1-(6-amino-pyridin-3-yl)piperidin-4-ol isopropyl-magnesium chloride |
| I-90 | (structure) | 4-[[5-(4-hydroxy-1-piperidyl)-2-pyridyl]amino]-8-methyl-6H-1,6-naphthyridin-5-one | Method 10cm_Formic_AQ, m/z = 352 [M + H]+, Ret. time = 2.24 min. | $^1$H NMR (400 MHz, DMSO) δ 12.62 (s, 1H), 11.51 (d, J = 4.7 Hz, 1H), 8.55 (d, J = 5.8 Hz, 1H), 8.32 (d, J = 6.0 Hz, 1H), 8.12 (d, J = 2.8 Hz, 1H), 7.51 (dd, J = 2.8, 8.8 Hz, 1H), 7.30 (d, J = 4.8 Hz, 1H), 7.03 (d, J = 8.8 Hz, 1H), 4.77 (s, 1H), 3.72-3.65 (m, 1H), 3.59-3.51 (m, 2H), 2.94-2.87 (m, 2H), 2.24 (s, 3H), 1.87 (dd, J = 4.5, 7.9 Hz, 2H), 1.61-1.50 (m, 2H). | L 1-(6-amino-pyridin-3-yl)piperidin-4-ol |
| I-91 | (structure) | 2-(2,6-difluoro-3-methoxy-phenyl)-4-[(5-piperazin-1-yl-2-pyridyl)amino]-6H-1,6-naphthyridin-5-one | Method 10cm_Formic_AQ, m/z = 0 [M + H]+, Ret. time = 2.2 min. | $^1$H NMR (400 MHz, DMSO): δ 12.59 (s, 1 H), 11.70 (brs, 1 H), 8.49 (s, 1 H), 8.08 (d, J = 2.5 Hz, 1 H), 7.53-7.46 (m, 2 H), 7.40-7.31 (m, 1 H), 7.23 (dd, J = 9.1, 9.1 Hz, 1 H), 7.06 (d, J = 8.8 Hz, 1 H), 6.60 (d, J = 7.3 Hz, 1 H), 3.94 (s, 3 H), 3.12-3.08 (m, 4 H), 3.08-3.06 (m, 1 H), 2.88 (dd, J = 4.9, 4.9 Hz, 4 H). | B and G tert-butyl 4-(6-amino-pyridin-3-yl)piperazine-carboxylate 2-bromo-1,3-difluoro-4-methoxy |
| I-92 | (structure) | 2-(2,6-difluoro-3-methoxy-phenyl)-4-[[5-(4-hydroxy-1-piperidyl)-2-pyridyl]amino]-6H-1,6-naphthyridin-5-one | Method 10cm_Bicarb_AQ, m/z = 480 [M + H]+, Ret. time = 2.84 min. | $^1$H NMR (400 MHz, DMSO): δ 12.45 (s, 1 H), 11.64 (s, 1 H), 8.35 (s, 1 H), 7.97 (d, J = 2.8 Hz, 1 H), 7.41-7.33 (m, 2 H), 7.27-7.18 (m, 1 H), 7.10 (dd, J = 9.0, 9.0 Hz, 1 H), 6.92 (d, J = 9.1 Hz, 1 H), 6.47 (d, J = 7.3 Hz, 1 H), 4.60 (d, J = 4.0 Hz, 1 H), 3.82 (s, 3 H), 3.60-3.50 (m, 2 H), 3.15-3.08 (m, 1 H), 2.82-2.73 (m, 2 H), 1.72 (d, J = 9.6 Hz, 2 H), 1.46-1.34 (m, 2 H). | B 1-(6-amino-pyridin-3-yl)piperidin-4-ol 2-bromo-1,3-difluoro-4-methoxy benzene |

TABLE 2-continued

| I-# | STRUCTURE | NAME | LCMS | HNMR | Method SM |
|---|---|---|---|---|---|
| I-93 | | 2-[2-fluoro-5-(pyrrolidine-1-carbonyl)phenyl]-4-[[5-(4-hydroxy-1-piperidyl)-2-pyridyl]amino]-6H-1,6-naphthyridin-5-one | Method 10cm_Formic_AQ, m/z = 529 [M + H]+, Ret. time = 2.48 min. | $^1$H NMR (400 MHz, DMSO): δ 12.98-12.98 (m, 1 H), 12.32-12.31 (m, 1 H), 8.57 (s, 1 H), 8.09-8.01 (m, 2 H), 7.86-7.82 (m, 1 H), 7.66 (s, 1 H), 7.52-7.43 (m, 2 H), 7.13 (d, J = 8.9 Hz, 1 H), 6.65 (d, J = 7.2 Hz, 1 H), 4.29 (dd, J = 7.5, 7.5 Hz, 2 H), 4.01 (dd, J = 7.5, 7.5 Hz, 2 H), 3.60-3.46 (m, 6 H), 2.92-2.82 (m, 2 H), 2.27-2.17 (m, 2 H), 1.79-1.70 (m, 2 H), 1.46-1.35 (m, 2 H). | A 1-(6-amino-pyridin-3-yl)piperidin-4-ol (2-fluoro-5-(pyrrolidine-1-carbonyl)phenyl)boronic acid |
| I-94 | 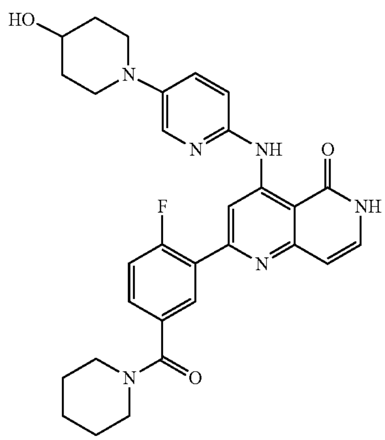 [SMILES: O=C(c1ccc(F)c(-c2cc(Nc3ccc(N4CCC(O)CC4)cn3)c3c(=O)[nH]ccc3n2)c1)N1CCCCC1] | 2-[2-fluoro-5-(piperidine-1-carbonyl)phenyl]-4-[[5-(4-hydroxy-1-piperidyl)-2-pyridyl]amino]-6H-1,6-naphthyridin-5-one | Method 10cm_Formic_AQ, m/z = 543 [M + H]+, Ret. time = 2.55 min. | $^1$H NMR (400 MHz, DMSO): δ 12.98-12.98 (m, 1 H), 12.32-12.31 (m, 1 H), 8.57 (s, 1 H), 8.09-8.01 (m, 2 H), 7.86-7.82 (m, 1 H), 7.66 (s, 1 H), 7.52-7.43 (m, 2 H), 7.13 (d, J = 8.9 Hz, 1 H), 6.65 (d, J = 7.2 Hz, 1 H), 4.29 (dd, J = 7.5, 7.5 Hz, 4 H), 4.01 (dd, J = 7.5, 7.5 Hz, 4 H), 3.67-3.54 (m, 4 H), 2.92-2.82 (m, 2 H), 2.27-2.17 (m, 2 H), 1.79-1.70 (m, 2 H), 1.46-1.35 (m, 2H). | A 1-(6-amino-pyridin-3-yl)piperidin-4-ol (2-fluoro-5-(piperidine-1-carbonyl)phenyl)boronic acid |
| I-95 | 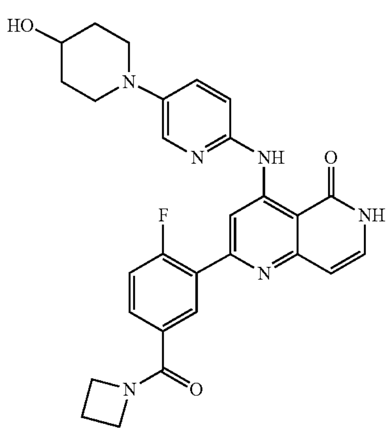 [SMILES: O=C(c1ccc(F)c(-c2cc(Nc3ccc(N4CCC(O)CC4)cn3)c3c(=O)[nH]ccc3n2)c1)N1CCC1] | 2-[5-(azetidine-1-carbonyl)-2-fluoro-phenyl]-4-[[5-(4-hydroxy-1-piperidyl)-2-pyridyl]amino]-6H-1,6-naphthyridin-5-one | Method 10cm_Formic_AQ, m/z = 515 [M + H]+, Ret. time = 2.43 min. | $^1$H NMR (400 MHz, DMSO): δ 12.43 (s, 1 H), 11.60-11.60 (m, 1 H), 8.68 (s, 1 H), 7.99 (d, J = 2.5 Hz, 1 H), 7.91 (dd, J = 1.9, 7.2 Hz, 1 H), 7.50-7.43 (m, 1 H), 7.43-7.31 (m, 3 H), 6.95 (d, J = 9.1 Hz, 1 H), 6.52 (d, J = 7.3 Hz, 1 H), 4.65-4.58 (m, 1 H), 3.62-3.50 (m, 2 H), 3.49-3.40 (m, 3 H), 2.84-2.77 (m, 2 H), 1.76 (d, J = 10.1 Hz, 2 H), 1.56 (s, 2 H), 1.46-1.38 (m, 4 H). | A 1-(6-amino-pyridin-3-yl)piperidin-4-ol CB15 |

TABLE 2-continued

| I-# | STRUCTURE | NAME | LCMS | HNMR | Method SM |
|---|---|---|---|---|---|
| I-96 | 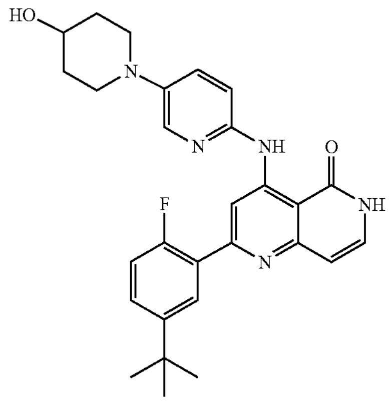 [SMILES: CC(C)(C)c1ccc(F)c(-c2cc(Nc3ccc(N4CCC(O)CC4)cn3)c3c(=O)[nH]ccc3n2)c1] | 2-(5-tert-butyl-2-fluoro-phenyl)-4-[[5-(4-hydroxy-1-piperidyl)-2-pyridyl]amino]-6H-1,6-naphthyridin-5-one | Method 10cm_Bicarb_AQ, m/z = 488 [M + H]+, Ret. time = 3.37 min. | $^1$H NMR (400 MHz, DMSO): δ 12.42 (s, 1 H), 11.65-11.65 (m, 1 H), 8.68 (d, J = 1.8 Hz, 1 H), 8.06 (d J = 3.0 Hz, 1 H), 7.92 (dd, J = 2.6, 7.5 Hz, 1 H), 7.58-7.53 (m, 1 H), 7.48 (dd, J = 3.1, 9.0 Hz, 1 H), 7.42 (d, J = 7.3 Hz, 1 H), 7.27 (dd, J = 8.7, 10.9 Hz, 1 H), 7.03 (d, J = 8.9 Hz, 1 H), 6.61 (d, J = 7.3 Hz, 1 H), 4.70 (d, J = 4.0 Hz, 1 H), 3.68-3.61 (m, 1 H), 3.56-3.48 (m, 2 H), 2.91-2.83 (m, 2 H), 1.88-1.80 (m, 2 H), 1.55-1.45 (m, 2 H), 1.35 (s, 9 H). | A 1-(6-amino-pyridin-3-yl) piperidin-4-ol CB16 |
| I-97 | 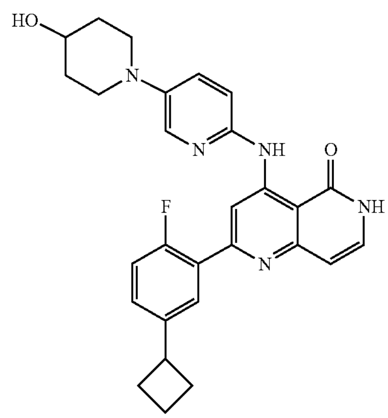 [SMILES: O=c1[nH]ccc2nc(-c3cc(C4CCC4)ccc3F)cc(Nc3ccc(N4CCC(O)CC4)cn3)c12] | 2-(5-cyclobutyl-2-fluoro-phenyl)-4-[[5-(4-hydroxy-1-piperidyl)-2-pyridyl]amino]-6H-naphthyridin-5-one | Method 10cm_Bicarb_AQ, m/z = 486 [M + H]+, Ret. time = 3.38 min. | $^1$H NMR (400 MHz, DMSO): δ 12.46 (s, 1 H), 11.69 (s, 1 H), 8.73 (s, 1 H), 8.10 (d, J = 2.8 Hz, 1 H), 7.79 (dd, J = 1.9, 7.5 Hz, 1 H), 7.52 (dd, J = 3.0, 8.8 Hz, 1 H), 7.49-7.41 (m, 2 H), 7.31 (dd, J = 8.6, 10.9 Hz, 1 H), 7.07 (d, J = 8.8 Hz, 1 H), 6.65 (d, J = 7.1 Hz, 1 H), 4.77-4.70 (m, 1 H), 3.70-3.52 (m, 4 H), 2.95-2.86 (m, 2 H), 2.43-2.33 (m, 2 H), 2.21-1.99 (m, 3 H), 1.93-1.83 (m, 3 H), 1.60-1.48 (m, 2 H). | A 1-(6-amino-pyridin-3-yl) piperidin-4-ol CB6 |
| I-98 | 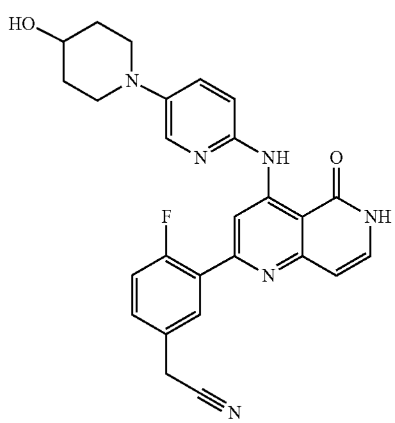 [SMILES: N#CCc1ccc(F)c(-c2cc(Nc3ccc(N4CCC(O)CC4)cn3)c3c(=O)[nH]ccc3n2)c1] | 2-[4-fluoro-3-[4-[[5-(4-hydroxy-1-piperidyl)-2-pyridyl]amino]-5-oxo-6H-1,6-naphthyridin-2-yl]phenyl]acetonitrile | Method 10cm_Formic_AQ, m/z = 471 [M + H]+, Ret. time = 2.47 min. | $^1$H NMR (400 MHz, DMSO): δ 12.36 (s, 1 H), 11.59 (s, 1 H), 8.66 (s, 1 H), 7.99 (d, J = 2.5 Hz, 1 H), 7.89 (dd, J = 1.9, 6.9 Hz, 1 H), 7.44-7.37 (m, 2 H), 7.37-7.29 (m, 2 H), 6.95 (d, J = 9.1 Hz, 1 H), 6.52 (d, J = 7.3 Hz, 1 H), 4.62 (d, J = 4.0 Hz, 1 H), 4.08 (s, 2 H), 3.61-3.54 (m, 1 H), 3.51-3.40 (m, 2 H), 2.84-2.75 (m, 2 H), 1.76 (d, J = 9.3 Hz, 2 H), 1.48-1.36 (m, 2 H). | A 1-(6-amino-pyridin-3-yl) piperidin-4-ol CB17 |

TABLE 2-continued

| I-# | STRUCTURE | NAME | LCMS | HNMR | Method SM |
|---|---|---|---|---|---|
| I-99 | 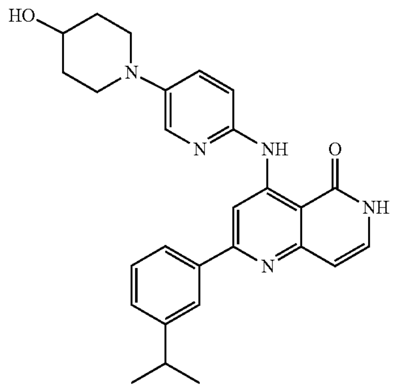 [SMILES: CC(C)c1cccc(-c2cc(Nc3ccc(N4CCC(O)CC4)cn3)c3c(=O)[nH]ccc3n2)c1] | 4-[[5-(4-hydroxy-1-piperidyl)-2-pyridyl]amino]-2-(3-isopropyl-phenyl)-6H-1,6-naphthyridin-5-one | Method 10cm_Formic_AQ, m/z = 456 [M + H]+, Ret. time = 2.73 min. | $^1$H NMR (400 MHz, DMSO): δ 12.54 (s, 1 H), 11.64 (d, J = 4.8 Hz, 1 H), 8.90 (s, 1 H), 8.18 (d, J = 2.8 Hz, 1 H), 8.01 (s, 1 H), 7.89 (d, J = 7.3 Hz, 1 H), 7.56-7.42 (m, 4 H), 7.08 (d, J = 8.8 Hz, 1 H), 6.66 (d, J = 7.1 Hz, 1 H), 4.80 (brs, 1 H), 3.72-3.66 (m, 1 H), 3.62-3.53 (m, 2 H), 3.12-3.03 (m, 1 H), 2.97-2.88 (m, 2 H), 1.90 (d, J = 9.3 Hz, 2 H), 1.62-1.50 (m, 2 H), 1.33 (d, J = 6.8 Hz, 6 H). | A 1-(6-amino-pyridin-3-yl)piperidin-4-ol 3-isopropyl-benzene boronic acid |
| I-100 | 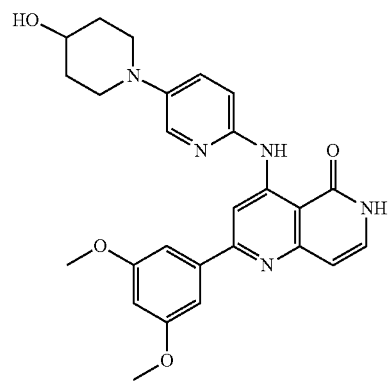 [SMILES: COc1cc(OC)cc(-c2cc(Nc3ccc(N4CCC(O)CC4)cn3)c3c(=O)[nH]ccc3n2)c1] | 2-(3,5-dimethoxyphenyl)-4-[[5-(4-hydroxy-1-piperidyl)-2-pyridyl]amino]-6H-1,6-naphthyridin-5-one | Method 10cm_Formic_AQ, m/z = 474 [M + H]+, Ret. time = 2.58 min. | $^1$H NMR (400 MHz, DMSO): δ 12.40 (s, 1 H), 8.81-8.78 (m, 1 H), 8.13 (d, J = 3.0 Hz, 1 H), 7.49 (dd, J = 2.9, 9.0 Hz, 1 H), 7.40 (d, J = 7.4 Hz, 1 H), 7.17 (dd, J = 2.4, 2.4 Hz, 2 H), 7.04 (d, J = 8.9 Hz, 1 H), 6.67-6.62 (m, 2 H), 3.84 (s, 3 H), 3.67-3.63 (m, 2 H), 3.62-3.40 (m, 6 H), 2.91-2.83 (m, 2 H), 1.86-1.83 (m, 2 H), 1.56-1.46 (m, 2 H). | A 1-(6-amino-pyridin-3-yl)piperidin-4-ol 3,5-dimethoxy-phenyl-boronic acid |
| I-101 | 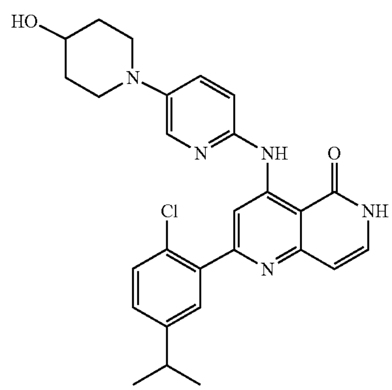 | 2-(2-chloro-5-isopropyl-phenyl)-4-[[5-(4-hydroxy-1-piperidyl)-2-pyridyl]amino]-6H-1,6-naphthyridin-5-one | Method 10cm_Formic_AQ, m/z = 490 [M + H]+, Ret. time = 2.75 min. | $^1$H NMR (400 MHz, DMSO): δ 12.47 (s, 1 H), 11.69 (d, J = 5.1 Hz, 1 H), 8.49 (s, 1 H), 8.04 (d, J = 3.0 Hz, 1 H), 7.51-7.35 (m, 6 H), 7.01 (d, J = 8.9 Hz, 1 H), 6.58 (d, J = 7.3 Hz, 1 H), 3.67-3.58 (m, 1 H), 3.54-3.46 (m, 2 H), 3.04-2.92 (m, 1 H), 2.89-2.80 (m, 2 H), 1.86-1.78 (m, 2 H), 1.53-1.42 (m, 2 H), 1.24 (d, J = 6.9 Hz, 6 H). | A 1-(6-amino-pyridin-3-yl)piperidin-4-ol 5-isopropyl-2-chloro-phenyl-boronic acid |
| I-102 | 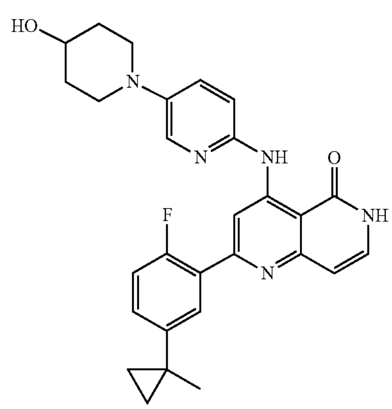 [SMILES: CC1(c2ccc(F)c(-c3cc(Nc4ccc(N5CCC(O)CC5)cn4)c4c(=O)[nH]ccc4n3)c2)CC1] | 2-[2-fluoro-5-(1-methylcyclopropyl)phenyl]-4-[[5-(4-hydroxy-1-piperidyl)-2-pyridyl]amino]-6H-1,6-naphthyridin-5-one | Method 10cm_Formic_AQ, m/z = 486 [M + H]+, Ret. time = 2.92 min. | $^1$H NMR (400 MHz, DMSO): δ 12.46 (s, 1 H), 11.73-11.65 (m, 1 H), 8.71 (s, 1 H), 8.10 (d, J = 2.8 Hz, 1 H), 7.84 (dd, J = 2.3, 7.3 Hz, 1 H), 7.51 (dd, J = 3.0, 8.8 Hz, 1 H), 7.48-7.37 (m, 2 H), 7.29 (dd, J = 8.7, 10.7 Hz, 1 H), 7.06 (d, J = 8.8 Hz, 1 H), 6.65 (d, J = 7.1 Hz, 1 H), 4.73 (d, J = 3.0 Hz, 1 H), 3.69 (d, J = 3.3 Hz, 1 H), 3.60-3.52 (m, 2 H), 2.96-2.88 (m, 2 H), 1.89 (d, J = 9.3 Hz, 2 H), 1.60-1.49 (m, 2 H), 1.46 (s, 3 H), 0.93-0.89 (m, 2 H), 0.86-0.80 (m, 2 H). | A 1-(6-amino-pyridin-3-yl)piperidin-4-ol CB7 |

TABLE 2-continued

| I-# | STRUCTURE | NAME | LCMS | HNMR | Method SM |
|---|---|---|---|---|---|
| I-103 | 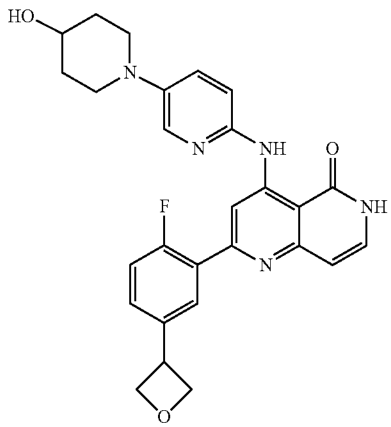 [SMILES: O=c1[nH]ccc2nc(-c3cc(C4COC4)ccc3F)cc(Nc3ccc(N4CCC(O)CC4)cn3)c12] | 2-[2-fluoro-5-(oxetan-3-yl)phenyl]-4-[[5-(4-hydroxy-1-piperidyl)-2-pyridyl]amino]-6H-1,6-naphthyridin-5-one | Method 10cm_Bicarb_AQ, m/z = 488 [M + H]+, Ret. time = 2.8 min. | ¹H NMR (400 MHz, DMSO): δ 12.30 (s, 1 H), 11.51-11.50 (m, 1 H), 8.59 (s, 1 H), 7.94 (d, J = 2.5 Hz, 1 H), 7.81 (dd, J = 2.0, 7.3 Hz, 1 H), 7.51-7.44 (m, 1 H), 7.35 (dd, J = 2.8, 8.8 Hz, 1 H), 7.32-7.20 (m, 2 H), 6.90 (d, J = 8.8 Hz, 1 H), 6.49 (d, J = 7.3 Hz, 1 H), 4.86 (dd, J = 6.1, 8.3 Hz, 2 H), 4.61-4.50 (m, 3 H), 4.29-4.19 (m, 1 H), 3.58-3.47 (m, 1 H), 3.47-3.32 (m, 2 H), 2.75 (dd, J = 9.9, 9.9 Hz, 2 H), 1.69 (dd, J = 8.5, 8.5 Hz, 2 H), 1.43-1.32 (m, 2 H). | A 1-(6-amino-pyridin-3-yl)piperidin-4-ol 2-(2-fluoro-5-(oxetan-3-yl)phenyl)-4,4,5,5-tetramethyl-1,3,2-dioxa-borolane |
| I-104 | 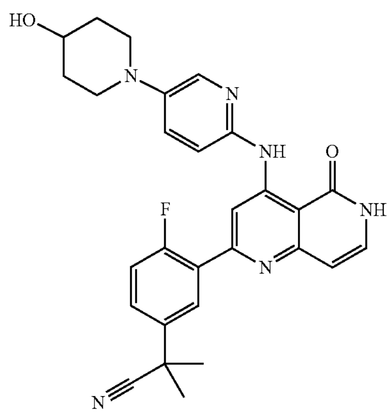 [SMILES: CC(C)(C#N)c1ccc(F)c(-c2cc(Nc3ccc(N4CCC(O)CC4)cn3)c3c(=O)[nH]ccc3n2)c1] | 2-[4-fluoro-3-[4-[[5-(4-hydroxy-1-piperidyl)-2-pyridyl]amino]-5-oxo-6H-1,6-naphthyridin-2-yl]phenyl]-2-methyl-propane-nitrile | Method 10cm_Formic_AQ, m/z = 499 [M + H]+, Ret. time = 2.58 min. | ¹H NMR (400 MHz, DMSO): δ 12.49 (s, 1 H), 11.72 (s, 1 H), 8.77 (d, J = 1.3 Hz, 1 H), 8.16-8.08 (m, 2 H), 7.76-7.69 (m, 1 H), 7.55-7.46 (m, 3 H), 7.07 (d, J = 8.8 Hz 1 H), 6.65 (d, J = 7.1 Hz, 1 H), 4.73 (d, J = 3.5 Hz, 1 H), 3.68 (dd, J = 4.3, 8.1 Hz, 1 H), 3.61-3.52 (m, 2 H), 2.96-2.86 (m, 2 H), 1.90-1.83 (m, 2 H), 1.80 (s, 6 H), 1.60-1.48 (m, 2 H). | A 1-(6-amino-pyridin-3-yl)piperidin-4-ol CB18 |
| I-105 | 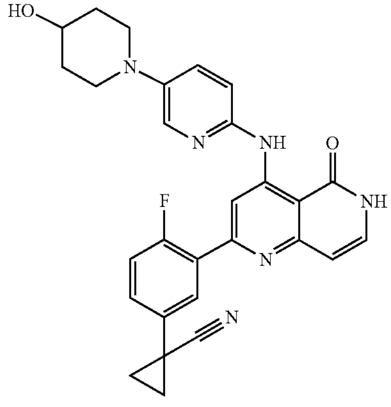 [SMILES: N#CC1(c2ccc(F)c(-c3cc(Nc4ccc(N5CCC(O)CC5)cn4)c4c(=O)[nH]ccc4n3)c2)CC1] | 1-[4-fluoro-3-[4-[[5-(4-hydroxy-1-piperidyl)-2-pyridyl]amino]-5-oxo-6H-1,6-naphthyridin-2-yl]phenyl]cyclo-propane-carbonitrile | Method 10cm_Bicarb_AQ, m/z = 497 [M + H]+, Ret. time = 2.96 min. | ¹H NMR (400 MHz, DMSO): δ 12.37 (s, 1 H), 11.60 (s, 1 H), 8.64 (d, J = 1.0 Hz, 1 H), 7.98 (d, J = 2.8 Hz, 1 H), 7.89 (dd, J = 2.4, 6.9 Hz, 1 H), 7.43-7.32 (m, 3 H), 7.30 (d, J = 8.8 Hz, 1 H), 6.95 (d, J = 8.8 Hz, 1 H), 6.54 (d, J = 7.3 Hz, 1 H), 4.61 (d, J = 3.5 Hz, 1 H), 3.59-3.51 (m, 1 H), 3.50-3.37 (m, 2 H), 2.84-2.72 (m, 2 H), 1.80-1.67 (m, 4 H), 1.52-1.39 (m, 4 H). | A 1-(6-amino-pyridin-3-yl)piperidin-4-ol (5-(1-cyanocyclo-propyl)-2-fluoro-phenyl)boronic acid |

TABLE 2-continued

| I-# | STRUCTURE | NAME | LCMS | HNMR | Method SM |
|---|---|---|---|---|---|
| I-106 | 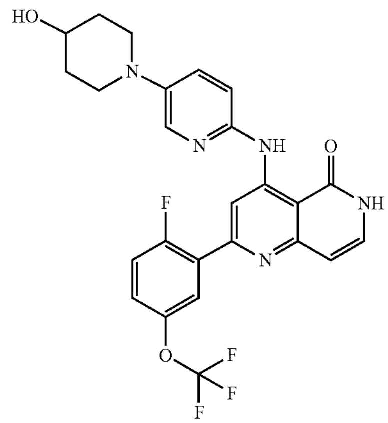 [SMILES: O=c1[nH]ccc2nc(-c3cc(OC(F)(F)F)ccc3F)cc(Nc3ccc(N4CCC(O)CC4)cn3)c12] | 2-[2-fluoro-5-(trifluoromethoxy)phenyl]-4-[[5-(4-hydroxy-1-piperidyl)-2-pyridyl]amino]-6H-1,6-naphthyridin-5-one | Method 10cm_Bicarb_AQ, m/z = 516 [M + H]+, Ret. time = 3.28 min. | $^{1}$H NMR (400 MHz, DMSO): δ 12.40 (s, 1 H), 11.64-11.63 (m, 1 H), 8.72 (s, 1 H), 7.99 (d, J = 2.5 Hz, 1 H), 7.89 (d, J = 3.3 Hz, 1 H), 7.49 (d, J = 3.3 Hz, 1 H), 7.47-7.33 (m, 3 H), 6.96 (d, J = 9.1 Hz, 1 H), 6.53 (d, J = 7.3 Hz, 1 H), 4.66-4.62 (m, 1 H), 3.55 (d, J = 3.3 Hz, 1 H), 3.50-3.37 (m, 2 H), 2.83-2.74 (m, 2 H), 1.77 (d, J = 9.6 Hz, 2 H), 1.48-1.36 (m, 2 H). | A 1-(6-aminopyridin-3-yl)piperidin-4-ol (2-fluoro-5-(trifluoromethoxy)phenyl)boronic acid |
| I-107 | 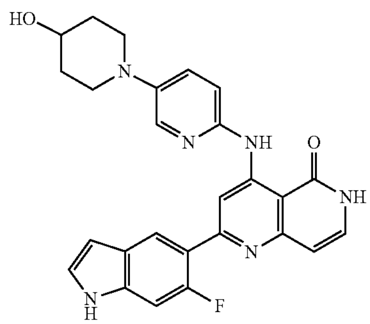 [SMILES: O=c1[nH]ccc2nc(-c3cc4cc[nH]c4cc3F)cc(Nc3ccc(N4CCC(O)CC4)cn3)c12] | 2-(6-fluoro-1H-indol-5-yl)-4-[[5-(4-hydroxy-1-piperidyl)-2-pyridyl]amino]-6H-1,6-naphthyridin-5-one | Method 10cm_Formic_AQ, m/z = 471 [M + H]+, Ret. time = 2.48 min. | $^{1}$H NMR (400 MHz, DMSO): δ 12.37 (s, 1 H), 11.58 (d, J = 3.9 Hz, 1 H), 11.29 (s, 1 H), 8.70 (d, J = 1.9 Hz, 1 H), 8.16 (d, J = 7.8 Hz, 1 H), 8.07 (d, J = 3.0 Hz, 1 H), 7.48 (dd, J = 3.1, 9.0 Hz, 1 H), 7.43-7.38 (m, 2 H), 7.30 (d, J = 8.9 Hz, 1 H), 7.03 (d, J = 8.9 Hz, 1 H), 6.62-6.54 (m, 2 H), 4.70 (d, J = 4.1 Hz, 1 H), 2.91-2.83 (m, 2 H), 1.87-1.81 (m, 5 H), 1.56-1.45 (m, 2 H). | A and G 1-(6-aminopyridin-3-yl)piperidin-4-ol tert-butyl 6-fluoro-5-(4,4,5,5-tetramethyl-1,3,2-dioxaborolan-2-yl)-1H-indole-1-carboxylate |
| I-108 | 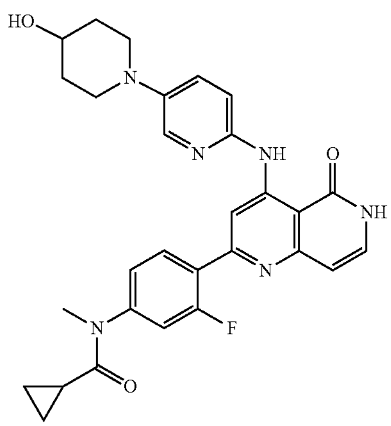 [SMILES: CN(C(=O)C1CC1)c1ccc(-c2cc(Nc3ccc(N4CCC(O)CC4)cn3)c3c(=O)[nH]ccc3n2)c(F)c1] | N-[3-fluoro-4-[4-[[5-(4-hydroxy-1-piperidyl)-2-pyridyl]amino]-5-oxo-6H-1,6-naphthyridin-2-yl]phenyl]-N-methyl-cyclopropane-carboxamide | Method 10cm_Formic_AQ, m/z = 529 [M + H]+, Ret. time = 2.51 min. | $^{1}$H NMR (400 MHz, DMSO): δ 12.45 (s, 1 H), 11.68-11.68 (m, 1 H), 8.75 (d, J = 1.6 Hz, 1 H), 8.08-8.02 (m, 2 H), 7.52-7.47 (m, 2 H), 7.46-7.37 (m, 2 H), 7.04 (d, J = 8.9 Hz, 1 H), 6.59 (d, J = 7.3 Hz, 1 H), 3.67-3.45 (m, 2 H), 3.28 (s, 3 H), 2.92-2.84 (m, 2 H), 2.54 (s, 1 H), 1.88-1.80 (m, 2 H), 1.58-1.45 (m, 4 H), 0.88-0.83 (m, 2 H), 0.75-0.69 (m, 2 H). | A 1-(6-aminopyridin-3-yl)piperidin-4-ol CB2 |
| I-109 | 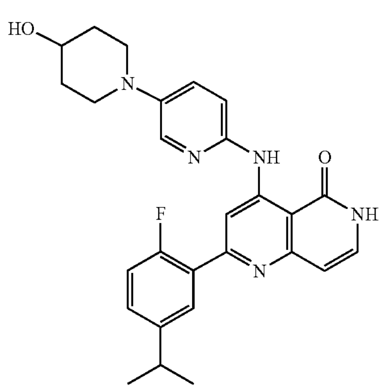 [SMILES: CC(C)c1ccc(F)c(-c2cc(Nc3ccc(N4CCC(O)CC4)cn3)c3c(=O)[nH]ccc3n2)c1] | 2-(2-fluoro-5-isopropylphenyl)-4-[[5-(4-methylpiperazin-1-yl)-2-pyridyl]amino]-6H-1,6-naphthyridin-5-one | Method 10cm_Formic_AQ, m/z = 473 [M + H]+, Ret. time = 2.37 min. | $^{1}$H NMR (400 MHz, DMSO): δ 12.40 (s, 1 H), 8.68 (s, 1 H), 8.05 (d, J = 2.6 Hz, 1 H), 7.76 (d, J = 7.7 Hz, 1 H), 7.48 (dd, J = 3.1, 9.0 Hz, 1 H), 7.43-7.37 (m, 2 H), 7.29-7.23 (m, 1 H), 7.04 (d, J = 8.9 Hz, 1 H), 6.63 (d, J = 7.3 Hz, 1 H), 3.46-3.42 (m, 1 H), 3.15 (dd, J = 4.7, 4.7 Hz, 4 H), 3.04-2.96 (m, 1 H), 2.47 (dd, J = 4.9, 4.9 Hz, 4 H), 2.23 (s, 3 H), 1.25 (d, J = 6.9 Hz, 6 H). | A 5-(4-methyl-piperazin-1-yl)pyridin-2-amine 2-fluoro-5-isopropyl-phenylboronic acid |

TABLE 2-continued

| I-# | STRUCTURE | NAME | LCMS | HNMR | Method SM |
|---|---|---|---|---|---|
| I-110 | 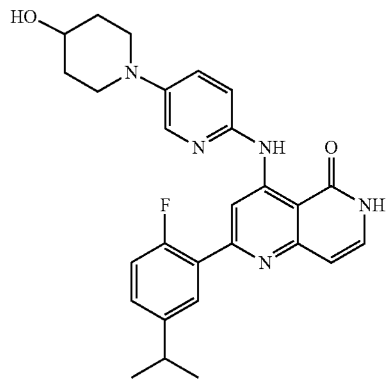 | 2-(2-fluoro-5-isopropyl-phenyl)-4-[(5-piperazin-1-yl-2-pyridyl)amino]-6H-1,6-naphthyridin-5-one | Method 10cm_Formic_AQ, m/z = 459 [M + H]+, Ret. time = 2.34 min. | ¹H NMR (400 MHz, DMSO): δ 12.37 (s, 1 H), 8.61 (s, 1 H), 7.95 (d, J = 2.5 Hz, 1 H), 7.70 (dd, J = 2.1, 7.5 Hz, 1 H), 7.41-7.30 (m, 3 H), 7.22-7.14 (m, 1 H), 6.95 (d, J = 8.8 Hz, 1 H), 6.53 (d, J = 7.3 Hz, 1 H), 3.01-2.95 (m, 6 H), 2.94-2.89 (m, 1 H), 2.76 (dd, J = 4.5, 4.5 Hz, 4 H), 1.17 (d, J = 6.8 Hz, 6 H). | A and G tert-butyl 4-(6-amino-pyridin-3-yl)piperazine-1-carboxylate 2-fluoro-5-isopropyl-phenyl-boronic acid |
| I-111 | 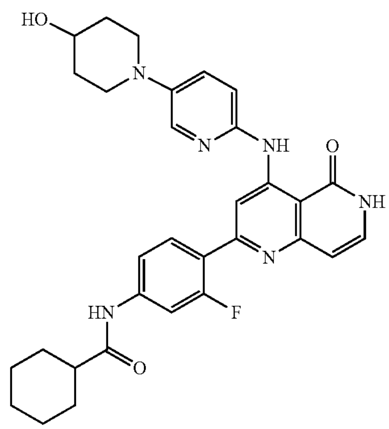 [SMILES: O=C(Nc1ccc(-c2cc(Nc3ccc(N4CCC(O)CC4)cn3)c3c(=O)[nH]ccc3n2)c(F)c1)C1CCCCC1] | N-[3-fluoro-4-[4-[[5-(4-hydroxy-1-piperidyl)-2-pyridyl]amino]-5-oxo-6H-1,6-naphthyridin-2-yl]phenyl]cyclohexane carboxamide | Method BicarbB EHC18, m/z = 557.3 [M + H]+, Ret. time = 4.09 min. | ¹H NMR (400 MHz, DMSO): δ 12.38 (s, 1H), 11.61 (d, J = 1.5 Hz, 1H), 10.22 (s, 1H), 8.73 (d, J = 1.0 Hz, 1H), 8.09-7.98 (m, 2H), 7.76 (dd, J = 1.9, 14.3 Hz, 1H), 7.50-7.39 (m, 3H), 7.04-7.01 (m, 1H), 6.59-6.56 (m, 1H), 4.70 (s, 1H), 3.69-3.61 (m, 1H), 3.56-3.50 (m, 2H), 2.92-2.84 (m, 4H), 2.41-2.33 (m, 1H), 1.87-1.75 (m, 4H), 1.56-1.19 (m, 8H). | A 1-(6-amino-pyridin-3-yl)piperidin-4-ol CB19 |
| I-112 | 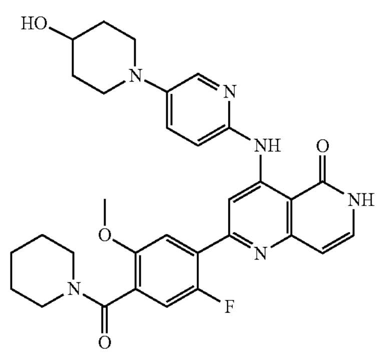 | 2-[2-fluoro-5-methoxy-4-(piperidine-1-carbonyl)phenyl]-4-[[5-(4-hydroxy-1-piperidyl)-2-pyridyl]amino]-6H-1,6-naphthyridin-5-one | Method 10cm_Formic_AQ, m/z = 573 [M + H]+, Ret. time = 2.6 min. | ¹H NMR (400 MHz, DMSO) δ 12.47 (s, 1 H), 11.68-11.65 (m, 1 H), 8.74 (d, J = 1.5 Hz, 1 H), 8.08 (d, J = 2.9 Hz, 1 H), 7.58 (d, J = 6.0 Hz, 1 H), 7.50-7.42 (m, 2 H), 7.24 (d, J = 10.4 Hz, 1 H), 7.05-7.02 (m, 1 H), 6.61 (d, J = 7.3 Hz, 1 H), 4.70 (d, J = 4.3 Hz, 1 H), 3.87-3.86 (m, 3 H), 3.68-3.50 (m, 5 H), 3.20-3.14 (m, 2 H), 2.91-2.84 (m, 2 H), 1.88-1.81 (m, 2 H), 1.64-1.45 (m, 8 H). | A 1-(6-amino-pyridin-3-yl)piperidin-4-ol CB1 |
| I-113 | 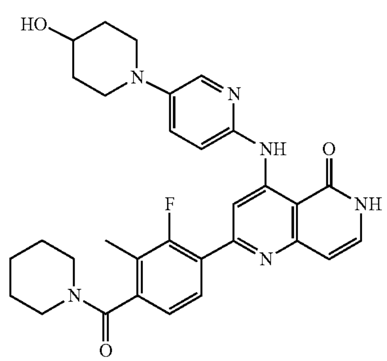 [SMILES: Cc1c(C(=O)N2CCCCC2)ccc(-c2cc(Nc3ccc(N4CCC(O)CC4)cn3)c3c(=O)[nH]ccc3n2)c1F] | 2-[2-fluoro-3-methyl-4-(piperidine-1-carbonyl)phenyl]-4-[[5-(4-hydroxy-1-piperidyl)-2-pyridyl]amino]-6H-1,6-naphthyridin-5-one | Method 10cm_Bicarb_AQ, m/z = 557 [M + H]+, Ret. time = 2.95 min. | ¹H NMR (400 MHz, DMSO): δ 12.28 (s, 1 H), 11.51-11.49 (m, 1 H), 8.52 (s, 1 H), 7.92 (d, J = 2.8 Hz, 1 H), 7.62 (dd, J = 7.6, 7.6 Hz, 1 H), 7.34-7.24 (m, 2 H), 6.99 (d, J = 7.8 Hz, 1 H), 6.87 (d, J = 8.8 Hz, 1 H), 6.43-6.37 (m, 1 H), 4.53 (d, J = 4.3 Hz, 1 H), 3.52-3.46 (m, 3 H), 3.38-3.35 (m, 2 H), 3.06-3.00 (m, 2 H), 2.74-2.67 (m, 2 H), 2.06 (d, J = 1.5 Hz, 3 H), 1.69-1.65 (m, 2 H), 1.48-1.43 (m, 4 H), 1.33 (dd, J = 10.0, 13.0 Hz, 4 H). | A 1-(6-amino-pyridin-3-yl)piperidin-4-ol CB20 |

TABLE 2-continued

| I-# | STRUCTURE | NAME | LCMS | HNMR | Method SM |
|---|---|---|---|---|---|
| I-114 | 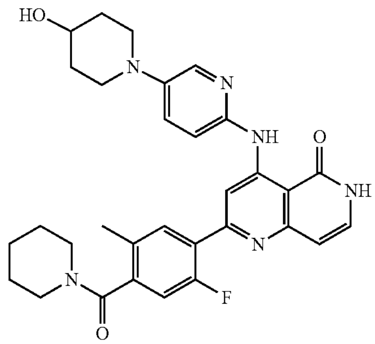 [SMILES: Cc1cc(-c2cc(Nc3ccc(N4CCC(O)CC4)cn3)c3c(=O)[nH]ccc3n2)c(F)cc1C(=O)N1CCCCC1] | 2-[2-fluoro-5-methyl-4-(piperidine-1-carbonyl)phenyl]-4-[[5-(4-hydroxy-1-piperidyl)-2-pyridyl]amino]-6H-1,6-naphthyridin-5-one | Method 10cm_Formic_AQ, m/z = 557 [M + H]+, Ret. time = 2.59 min. | $^1$H NMR (400 MHz, DMSO): δ 12.45 (s, 1 H), 8.76-8.72 (m, 1 H), 8.11 (d, J = 2.8 Hz, 1 H), 7.87 (d, J = 7.6 Hz, 1 H), 7.52 (dd, J = 2.8, 2.8 Hz, 1 H), 7.46 (d, J = 7.3 Hz, 1 H), 7.26 (s, 1 H), 7.07 (d, J = 8.8 Hz, 1 H), 6.65 (d, J = 7.3 Hz, 1 H), 3.73-3.63 (m, 3 H), 3.57 (d, J = 12.4 Hz, 3 H), 3.02 (dd, J = 5.3, 5.3 Hz, 2 H), 2.96-2.87 (m, 2 H), 2.60 (s, 1 H), 2.30 (s, 3 H), 1.91-1.86 (m, 2 H), 1.67-1.63 (m, 4 H), 1.59-1.48 (m, 4 H). | A 1-(6-amino-pyridin-3-yl)piperidin-4-ol CB21 |
| I-115 | 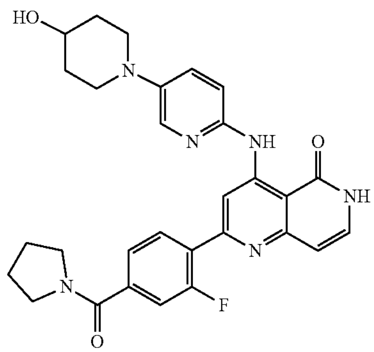 [SMILES: O=C(c1ccc(-c2cc(Nc3ccc(N4CCC(O)CC4)cn3)c3c(=O)[nH]ccc3n2)c(F)c1)N1CCCC1] | 2-[2-fluoro-4-(pyrrolidine-1-carbonyl)phenyl]-4-[[5-(4-hydroxy-1-piperidyl)-2-pyridyl]amino]-6H-1,6-naphthyridin-5-one | Method 10cm_Formic_AQ, m/z = 529 [M + H]+, Ret. time = 2.46 min. | $^1$H NMR (400 MHz, DMSO): δ 12.49 (s, 1 H), 11.73 (s, 1 H), 8.79 (s, 1 H), 8.13-8.04 (m, 2 H), 7.57-7.50 (m, 3 H), 7.47 (d, J = 7.1 Hz, 1 H), 7.08 (d, J = 8.8 Hz, 1 H), 6.64 (d, J = 7.3 Hz, 1 H), 4.74 (d, J = 1.3 Hz, 1 H), 3.68 (d, J = 1.3 Hz, 1 H), 3.61-3.46 (m, 6 H), 2.95-2.87 (m, 2 H), 1.98-1.86 (m, 6 H), 1.60-1.49 (m, 2 H). | F 1-(6-amino-pyridin-3-yl)piperidin-4-ol |
| I-116 | 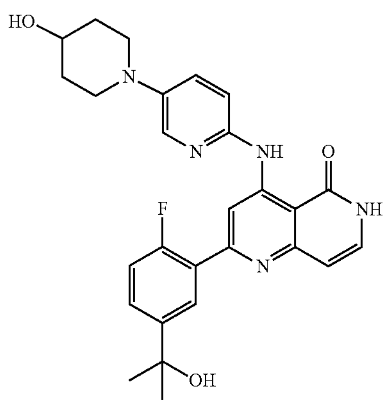 [SMILES: CC(C)(O)c1ccc(F)c(-c2cc(Nc3ccc(N4CCC(O)CC4)cn3)c3c(=O)[nH]ccc3n2)c1] | 2-[2-fluoro-5-(1-hydroxy-1-methyl-ethyl)phenyl]-4-[[5-(4-hydroxy-1-piperidyl)-2-pyridyl]amino]-6H-1,6-naphthyridin-5-one | Method 10cm_Formic_AQ, m/z = 490 [M + H]+, Ret. time = 2.48 min. | $^1$H NMR (400 MHz, DMSO): δ 12.33 (s, 1 H), 11.56 (d, J = 4.5 Hz 1 H), 8.59 (s, 1 H), 7.96 (dd, J = 2.7, 10.5 Hz, 2 H), 7.52-7.45 (m, 1 H), 7.40 (dd, J = 2.9, 9.0 Hz, 1 H), 7.33 (dd, J = 6.3, 6.3 Hz, 1 H), 7.18 (dd, J = 8.8, 10.9 Hz, 1 H), 6.94 (d, J = 8.8 Hz, 1 H), 6.52 (d, J = 7.3 Hz, 1 H), 5.09 (s, 1 H), 4.61-4.58 (m, 1 H), 3.60-3.54 (m, 1 H), 3.25 (s, 2 H), 2.82-2.72 (m, 2 H), 1.77 (d, J = 9.6 Hz, 2 H), 1.51-1.40 (m, 8 H). | A 1-(6-amino-pyridin-3-yl)piperidin-4-ol CB22 |
| I-117 | 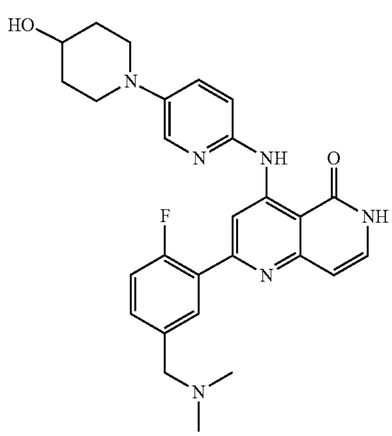 [SMILES: CN(C)Cc1ccc(F)c(-c2cc(Nc3ccc(N4CCC(O)CC4)cn3)c3c(=O)[nH]ccc3n2)c1] | 2-[5-[(dimethyl-amino)methyl]-2-fluoro-phenyl]-4-[[5-(4-hydroxy-1-piperidyl)-2-pyridyl]amino]-6H-1,6-naphthyridin-5-one | Method 10cm_Formic_AQ, m/z = 489 [M + H]+, Ret. time = 2.21 min. | $^1$H NMR (400 MHz, DMSO): δ 12.46 (s, 1 H), 11.69 (s, 1 H), 8.75 (s, 1 H), 8.10 (d, J = 2.5 Hz, 1 H), 7.93-7.89 (m, 1 H), 7.52 (dd, J = 2.9, 9.0 Hz, 1 H), 7.46 (d, J = 7.3 Hz, 2 H), 7.37-7.30 (m, 1 H), 7.07 (d, J = 8.8 Hz, 1 H), 6.65 (d, J = 7.3 Hz, 1 H), 4.74 (d, J = 4.0 Hz, 1 H), 3.73-3.65 (m, 1 H), 3.61-3.52 (m, 2 H), 3.49 (s, 2 H), 2.94-2.86 (m, 2 H), 2.22 (s, 6 H), 1.88 (d, J = 9.3 Hz, 2 H), 1.60-1.49 (m, 2 H). | A 1-(6-amino-pyridin-3-yl)piperidin-4-ol 1-(4-fluoro-3-(4,4,5,5-tetramethyl-1,3,2-dioxa-borolan-2-yl)phenyl)-N,N-dimethyl methanamine |

TABLE 2-continued

| I-# | STRUCTURE | NAME | LCMS | HNMR | Method SM |
|---|---|---|---|---|---|
| I-118 | 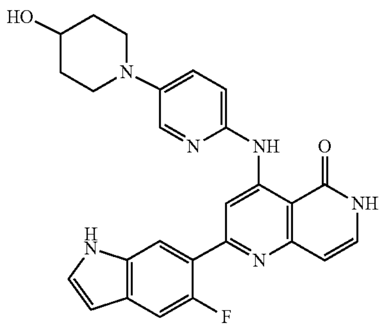 [SMILES: O=c1[nH]ccc2nc(-c3cc4[nH]ccc4cc3F)cc(Nc3ccc(N4CCC(O)CC4)cn3)c12] | 2-(5-fluoro-1H-indol-6-yl)-4-[[5-(4-hydroxy-1-piperidyl)-2-pyridyl]amino]-6H-1,6-naphthyridin-5-one | Method 10cm_Formic_AQ, m/z = 471 [M + H]+, Ret. time = 2.56 min. | $^1$H NMR (400 MHz, DMSO): δ 12.37 (s, 1 H), 11.59-11.59 (m, 1 H), 11.36 (s, 1 H), 8.76 (d, J = 1.6 Hz, 1 H), 8.10-8.07 (m, 2 H), 7.56 (dd, J = 2.8, 2.8 Hz, 1 H), 7.51-7.45 (m, 2 H), 7.43-7.39 (m, 1 H), 7.04 (d, J = 8.8 Hz, 1 H), 6.60 (d, J = 7.2 Hz, 1 H), 6.50 (dd, J = 2.5, 2.5 Hz, 1 H), 4.70 (d, J = 4.3 Hz, 1 H), 3.67-3.61 (m, 1 H), 3.57-3.50 (m, 2 H), 2.92-2.84 (m, 2 H), 1.87-1.81 (m, 2 H), 1.56-1.46 (m, 2 H). | A and G 1-(6-amino-pyridin-3-yl)piperidin-4-ol CB23 |
| I-119 | 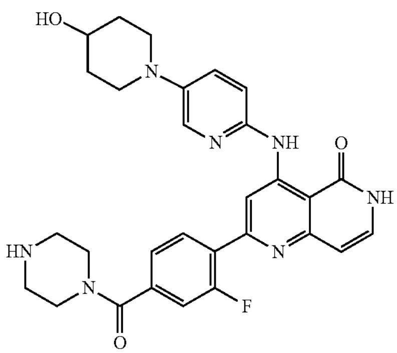 [SMILES: O=C(c1ccc(-c2cc(Nc3ccc(N4CCC(O)CC4)cn3)c3c(=O)[nH]ccc3n2)c(F)c1)N1CCNCC1] | 2-[2-fluoro-4-(piperazine-1-carbonyl)phenyl]-4-[[5-(4-hydroxy-1-piperidyl)-2-pyridyl]amino]-6H-1,6-naphthyridin-5-one | Method 10cm_Formic_AQ, m/z = 544 [M + H]+, Ret. time = 2.18 min. | $^1$H NMR (400 MHz, DMSO): δ 12.51 (s, 1 H), 11.72-11.68 (m, 1 H), 8.79 (s, 1 H), 8.12 (d, J = 2.5 Hz, 1 H), 8.06 (dd, J = 7.7, 7.7 Hz, 1 H), 7.53 (dd, J = 2.7, 9.0 Hz, 1 H), 7.50-7.44 (m, 1 H), 7.43-7.38 (m, 2 H), 7.07 (d, J = 8.8 Hz, 1 H), 6.63 (d, J = 7.3 Hz, 1 H), 4.73 (d, J = 2.0 Hz, 1 H), 3.68 (s, 1 H), 3.56 (dd, J = 4.7, 8.0 Hz, 4 H), 3.34 (s, 3 H), 2.92 (dd, J = 10.0, 10.0 Hz, 2 H), 2.80 (s, 2 H), 2.72 (s, 2 H), 1.89-1.86 (m, 2 H), 1.59-1.50 (m, 2 H). | F and G 1-(6-amino-pyridin-3-yl)piperidin-4-ol tert-butyl piperazine-1-carboxylate (step 2) |
| I-120 | 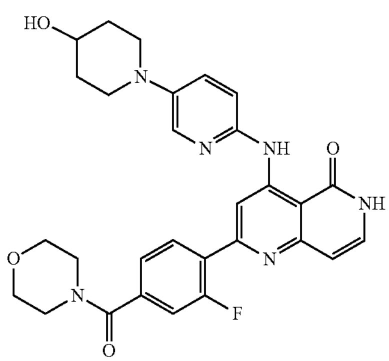 [SMILES: O=C(c1ccc(-c2cc(Nc3ccc(N4CCC(O)CC4)cn3)c3c(=O)[nH]ccc3n2)c(F)c1)N1CCOCC1] | 2-[2-fluoro-4-(morpholine-4-carbonyl)phenyl]-4-[[5-(4-hydroxy-1-piperidyl)-2-pyridyl]amino-6H-1,6-naphthyridin-5-one | Method 10cm_Formic_ACE-AR_AQ, m/z = 545 [M + H]+, Ret. time = 2.53 min. | $^1$H NMR (400 MHz, DMSO): δ 12.09 (s, 1 H), 11.72 (s, 1 H), 8.78 (s, 1 H), 8.13-8.04 (m, 2 H), 7.55-7.43 (m, 4 H), 7.07 (d, J = 8.8 Hz, 1 H), 6.63 (d, J = 7.3 Hz, 1 H), 4.75-4.74 (brs, 1 H), 3.77-3.61 (m, 8 H), 3.60-3.53 (m, 3 H), 2.96-2.87 (m, 2 H), 1.89-1.86 (m, 2 H), 1.60-1.48 (m, 2 H). | F 1-(6-amino-pyridin-3-yl)piperidin-4-ol Morpholine (step 2) |
| I-121 | 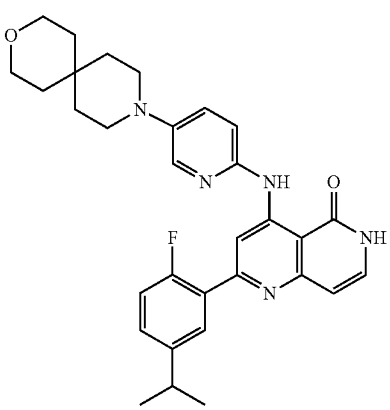 [SMILES: CC(C)c1ccc(F)c(-c2cc(Nc3ccc(N4CCC5(CCOCC5)CC4)cn3)c3c(=O)[nH]ccc3n2)c1] | 2-(2-fluoro-5-isopropyl-phenyl)-4-[[5-(3-oxa-9-azaspiro[5.5]undecan-9-yl)-2-pyridyl]amino]-6H-1,6-naphthyridin-5-one | Method 10cm_Formic_AQ, m/z = 528 [M + H]+, Ret. time = 3.06 min. | $^1$H NMR (400 MHz, DMSO): δ 12.28 (s, 1 H), 8.56 (s, 1 H), 7.98 (d, J = 2.5 Hz, 1 H), 7.68 (d, J = 7.1 Hz, 1 H), 7.39 (dd, J = 2.9, 9.0 Hz, 1 H), 7.32 (dd, J = 7.3, 7.3 Hz, 2 H), 7.17 (dd, J = 8.6, 10.9 Hz, 1 H), 6.95 (d, J = 8.8 Hz, 1 H), 6.54 (d, J = 7.3 Hz, 1 H), 3.49 (dd, J = 5.1, 5.1 Hz, 4 H), 3.36-3.32 (m, 1 H), 3.07 (dd, J = 5.4, 5.4 Hz, 4 H), 2.95-2.86 (m, 1 H), 1.53 (dd, J = 5.2, 5.2 Hz, 4 H), 1.38 (dd, J = 4.9, 4.9 Hz, 4 H), 1.16 (d, J = 6.8 Hz, 6 H). | A 5-(3-oxa-9-azaspiro[5.5]undecan-9-yl)pyridin-2-amine 2-fluoro-5-isopropyl-phenyl-boronic acid |

TABLE 2-continued

| I-# | STRUCTURE | NAME | LCMS | HNMR | Method SM |
|---|---|---|---|---|---|
| I-122 | 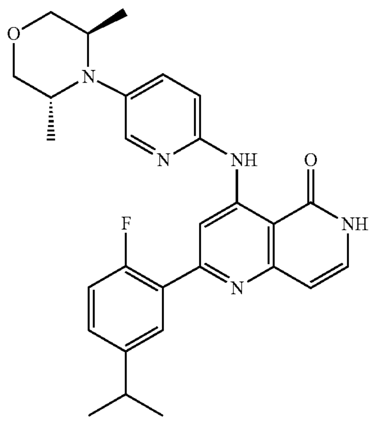 [SMILES: CC(C)c1ccc(F)c(-c2cc(Nc3ccc(N4[C@H](C)COC[C@H]4C)cn3)c3c(=O)[nH]ccc3n2)c1] | 4-[[5-[(3R,5R)-3,5-dimethyl-morpholin-4-yl]-2-pyridyl]amino]-2-(2-fluoro-5-isopropyl-phenyl)-6H-1,6-naphthyridin-5-one | Method 10cm_Formic_AQ, m/z = 488 [M + H]+, Ret. time = 3.01 min. | ¹H NMR (400 MHz, DMSO): δ 12.63 (s, 1 H), 8.90 (s, 1 H), 8.12 (d, J = 2.5 Hz, 1 H), 7.81 (dd, J = 1.9, 7.7 Hz, 1 H), 7.56 (dd, J = 2.5, 8.8 Hz, 1 H), 7.49-7.44 (m, 2 H), 7.35-7.28 (m, 1 H), 7.12 (d, J = 8.8 Hz, 1 H), 6.70 (d, J = 7.3 Hz, 1 H), 3.87 (dd, J = 2.4, 10.7 Hz, 2 H), 3.48-3.41 (m, 4 H), 3.08-2.99 (m, 1 H), 2.39 (s, 1 H), 1.28 (d, J = 7.1 Hz, 6 H), 0.89 (d, J = 6.3 Hz, 6 H). | A 5-((3R,5R)-3,5-dimethyl morpholino) pyridin-2-amine 2-fluoro-5-isopropyl-phenyl-boronic acid |
| I-123 | 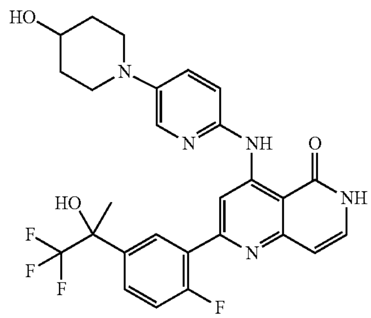 [SMILES: CC(O)(c1ccc(F)c(-c2cc(Nc3ccc(N4CCC(O)CC4)cn3)c3c(=O)[nH]ccc3n2)c1)C(F)(F)F] | 2-[2-fluoro-5-(2,2,2-trifluoro-1-hydroxy-1-methyl-ethyl) phenyl]-4-[[5-(4-hydroxy-1-piperidyl)-2-pyridyl] amino]-6H-1,6-naphthyridin-5-one | Method 10cm_Formic_AQ, m/z = 544 [M + H]+, Ret. time = 2.59 min. | ¹H NMR (400 MHz, DMSO): δ 12.35 (s, 1 H), 11.58 (d, J = 5.3 Hz, 1 H), 8.64 (s, 1 H), 8.12 (d, J = 6.3 Hz, 1 H), 7.98 (d, J = 2.3 Hz, 1 H), 7.63 (d, J = 3.8 Hz, 1 H), 7.43-7.27 (m, 3 H), 6.95 (d, J = 8.8 Hz, 1 H), 6.71 (s, 1 H), 6.53 (d, J = 7.3 Hz, 1 H), 4.61 (d, J = 4.0 Hz, 1 H), 3.61-3.51 (m, 1 H), 3.25 (s, 2 H), 2.79 (dd, J = 10.1, 10.1 Hz, 2 H), 1.76 (d, J = 9.6 Hz, 2 H), 1.67 (s, 3 H), 1.46-1.36 (m, 2 H). | A 1-(6-amino-pyridin-3-yl) piperidin-4-ol CB8 |
| I-124 | 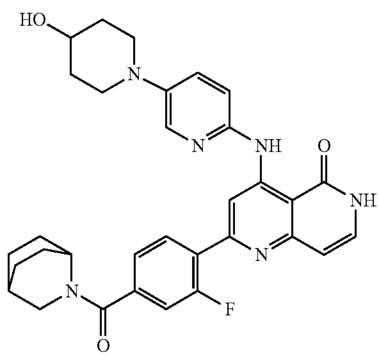 [SMILES: O=C(c1ccc(-c2cc(Nc3ccc(N4CCC(O)CC4)cn3)c3c(=O)[nH]ccc3n2)c(F)c1)N1CC2CCC1CC2] | 2-[4-(3-azabicyclo [2.2.2] octane-3-carbonyl)-2-fluoro-phenyl]-4-[[5-(4-hydroxy-1-piperidyl)-2-pyridyl] amino]-6H-1,6-naphthyridin-5-one | Method 10cm_Formic_AQ, m/z = 569 [M + H]+, Ret. time = 2.62 min. | ¹H NMR (400 MHz, DMSO): δ 12.37 (s, 1 H), 11.60 (s, 1 H), 8.66 (s, 1 H), 8.00-7.97 (m, 1 H), 7.93 (dd, J = 8.0, 8.0 Hz, 1 H), 7.43-7.32 (m, 2 H), 7.26 (d, J = 7.8 Hz, 1 H), 6.95 (d, J = 8.8 Hz, 1 H), 6.54-6.48 (m, 1 H), 3.59-3.53 (m, 1 H), 3.31-3.24 (m, 1 H), 2.79 (dd, J = 9.9, 9.9 Hz, 2 H), 2.43 (s, 6 H), 1.97-1.90 (m, 1 H), 1.76-1.70 (m, 4 H), 1.63-1.49 (m, 6 H), 1.42 (q, J = 9.2 Hz, 2 H). | F 1-(6-amino-pyridin-3-yl) piperidin-4-ol 2-azabicyclo [2.2.2] octane (step 2) |
| I-125 | 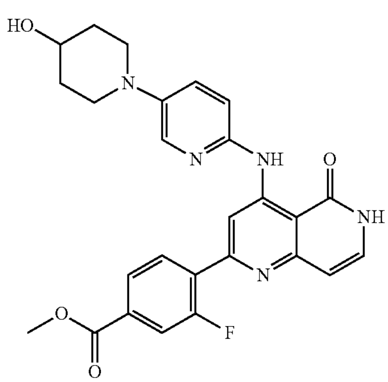 [SMILES: COC(=O)c1ccc(-c2cc(Nc3ccc(N4CCC(O)CC4)cn3)c3c(=O)[nH]ccc3n2)c(F)c1] | methyl 3-fluoro-4-[4-[[5-(4-hydroxy-1-piperidyl)-2-pyridyl]amino]-5-oxo-6H-1,6-naphthyridin-2-yl]benzoate | Method 10cm_Formic_AQ, m/z = 490 [M + H]+, Ret. time = 2.55 min. | ¹H NMR (400 MHz, DMSO): δ 12.51 (s, 1 H), 11.76-11.71 (m, 1 H), 8.81 (s, 1 H), 8.71 (dd, J = 8.0, 8.0 Hz, 1 H), 8.11 (d, J = 2.3 Hz, 1 H), 7.98 (d, J = 8.1 Hz, 1 H), 7.87 (s, 1 H), 7.55-7.45 (m, 2 H), 7.08 (d, J = 8.8 Hz, 1 H), 6.65 (d, J = 7.3 Hz, 1 H), 4.74 (d, J = 3.8 Hz, 1 H), 3.97 (s, 3 H), 3.72-3.66 (m, 1 H), 3.57 (d, J = 12.1 Hz, 2 H), 2.92 (dd, J = 10.1, 10.1 Hz, 2 H), 1.87 (d, J = 10.1 Hz, 2 H), 1.60-1.49 (m, 2 H). | A 1-(6-amino-pyridin-3-yl) piperidin-4-ol methyl 3-fluoro-4-(4,4,5,5-tetramethyl-1,3,2-dioxa-borolan-2-yl)benzoate |

TABLE 2-continued

| I-# | STRUCTURE | NAME | LCMS | HNMR | Method SM |
|---|---|---|---|---|---|
| I-126 | 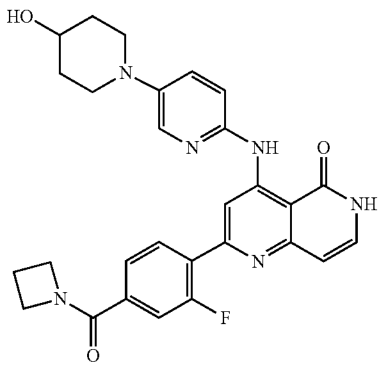 [SMILES: O=C(c1ccc(-c2cc(Nc3ccc(N4CCC(O)CC4)cn3)c3c(=O)[nH]ccc3n2)c(F)c1)N1CCC1] | 2-[4-(azetidine-1-carbonyl)-2-fluoro-phenyl]-4-[[5-(4-hydroxy-1-piperidyl)-2-pyridyl]amino]-6H-1,6-naphthyridin-5-one | Method 10cm_FormicAQ, m/z = 515 [M + H]+, Ret. time = 2.41 min. | ¹H NMR (400 MHz, DMSO): δ 12.38 (s, 1 H), 11.60 (s, 1 H), 8.66 (s, 1 H), 8.01-7.93 (m, 2 H), 7.54-7.47 (m, 1 H), 7.40 (dd, J = 2.9, 9.0 Hz, 1 H), 7.39-7.36 (m, 1 H), 7.35 (d, J = 7.3 Hz, 1 H), 6.95 (d, J = 8.8 Hz, 1 H), 6.51 (d, J = 7.1 Hz, 1 H), 4.61 (d, J = 4.0 Hz, 1 H), 4.31 (dd, J = 7.5, 7.5 Hz, 2 H), 4.06-3.98 (m, 2 H), 3.60-3.53 (m, 1 H), 3.52-3.46 (m, 2 H), 2.83-2.75 (m, 2 H), 2.28-2.18 (m, 2 H), 1.78-1.75 (m, 2 H), 1.48-1.36 (m, 2 H). | F 1-(6-amino-pyridin-3-yl)piperidin-4-ol Azetidine (step 2) |
| I-127 | 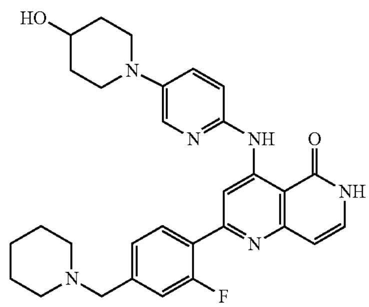 [SMILES: O=c1[nH]ccc2nc(-c3ccc(CN4CCCCC4)cc3F)cc(Nc3ccc(N4CCC(O)CC4)cn3)c12] | 2-[2-fluoro-4-(1-piperidyl-methylethyl)phenyl]-4-[[5-(4-hydroxy-1-piperidyl)-2-pyridyl]amino]-6H-1,6-naphthyridin-5-one | Method 10cm_Formic_AQ, m/z = 265.347 [M + H]+, Ret. time = 2.23 min. | ¹H NMR (400 MHz, DMSO): δ 12.45 (s, 1 H), 11.66 (d, J = 4.8 Hz, 1 H), 8.74 (s, 1 H), 8.11 (d, J = 2.8 Hz, 1 H), 7.96 (dd, J = 8.0, 8.0 Hz, 1 H), 7.52 (dd, J = 2.9, 9.0 Hz, 1 H), 7.48-7.42 (m, 1 H), 7.32 (d, J = 8.3 Hz, 1 H), 7.06 (d, J = 8.8 Hz, 1 H), 6.62 (d, J = 6.6 Hz, 1 H), 4.73 (d, J = 4.0 Hz, 1 H), 3.73-3.65 (m, 1 H), 3.61-3.52 (m, 4 H), 2.96-2.87 (m, 2 H), 2.42 (s, 4 H), 1.89-1.84 (m, 2 H), 1.57-1.46 (m, 9 H). | A 1-(6-amino-pyridin-3-yl)piperidin-4-ol 1-(3-fluoro-4-(4,4,5,5-tetramethyl-1,3,2-dioxa-borolan-2-yl)benzyl)piperidine |
| I-128 | 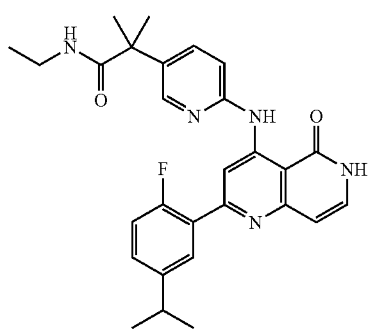 [SMILES: CCNC(=O)C(C)(C)c1ccc(Nc2cc(-c3cc(C(C)C)ccc3F)nc3cc[nH]c(=O)c23)nc1] | N-ethyl-2-[6-[[2-(2-fluoro-5-isopropyl-phenyl)-5-oxo-6H-1,6-naphthyridin-4-yl]amino]-3-pyridyl]-2-methyl-propanamide | Method 10cm_Formic_AQ, m/z = 488 [M + H]+, Ret. time = 2.9 min. | ¹H NMR (400 MHz, DMSO): δ 12.75 (s, 1 H), 11.74 (s, 1 H), 9.05 (d, J = 1.6 Hz, 1 H), 8.32 (d, J = 2.5 Hz, 1 H), 7.81 (dd, J = 2.4, 7.5 Hz, 1 H), 7.68 (dd, J = 2.6, 8.5 Hz, 1 H), 7.48-7.41 (m, 3 H), 7.30 (dd, J = 8.4, 11.0 Hz, 1 H), 7.07 (d, J = 8.8 Hz, 1 H), 6.66 (d, J = 7.3 Hz, 1 H), 3.11-2.99 (m, 3 H), 1.48 (s, 6 H), 1.26 (d, J = 6.9 Hz, 6 H), 0.97 (dd, J = 7.2, 7.2 Hz, 3 H). | A CA1 2-fluoro-5-isopropyl-phenyl-boronic acid |
| I-129 | 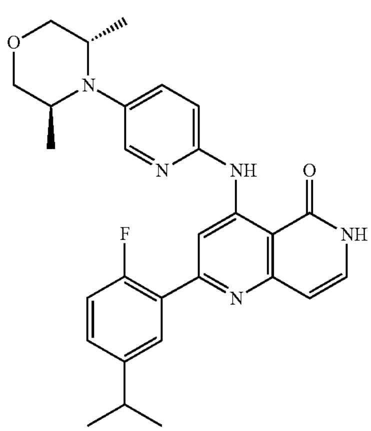 [SMILES: CC(C)c1ccc(F)c(-c2cc(Nc3ccc(N4[C@@H](C)COC[C@@H]4C)cn3)c3c(=O)[nH]ccc3n2)c1] | 4-[[5-[(3S,5S)-3,5-dimethyl-morpholin-4-yl]-2-pyridyl]amino]-2-(2-fluoro-5-isopropyl-phenyl)-6H-1,6-naphthyridin-5-one | Method 10cm_Formic_AQ, m/z = 488 [M + H]+, Ret. time = 3.03 min. | ¹H NMR (400 MHz, DMSO): δ 12.65 (s, 1 H), 11.70 (s, 1 H), 8.87 (d, J = 1.6 Hz, 1 H), 8.10 (d, J = 2.8 Hz, 1 H), 7.79 (dd, J = 2.4, 7.5 Hz, 1 H), 7.53 (dd, J = 2.7, 8.7 Hz, 1 H), 7.46-7.39 (m, 2 H), 7.28 (dd, J = 8.5, 11.0 Hz, 1 H), 7.08 (d, J = 8.7 Hz, 1 H), 6.64 (d, J = 7.3 Hz, 1 H), 3.84 (dd, J = 3.1, 10.7 Hz, 2 H), 3.53-3.39 (m, 4 H), 3.05-2.97 (m, 1 H), 1.26 (d, J = 6.9 Hz, 6 H), 0.87 (d, J = 6.3 Hz, 6 H). | A 5-((3S,5S)-3,5-dimethyl-morpholino)pyridin-2-amine 2-fluoro-5-isopropyl-phenyl-boronic acid |

TABLE 2-continued

| I-# | STRUCTURE | NAME | LCMS | HNMR | Method SM |
|---|---|---|---|---|---|
| I-130 | 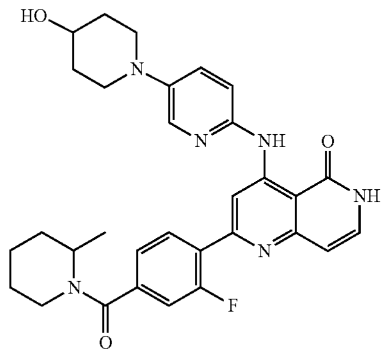 [SMILES: CC1CCCCN1C(=O)c1ccc(-c2cc(Nc3ccc(N4CCC(O)CC4)cn3)c3c(=O)[nH]ccc3n2)c(F)c1] | 2-[2-fluoro-4-(2-methyl-piperidine-1-carbonyl)phenyl]-4-[[5-(4-hydroxy-1-piperidyl)-2-pyridyl]amino]-6H-1,6-naphthyridin-5-one | Method 10cm_Formic_AQ, m/z = 557 [M + H]+, Ret. time = 2.62 min. | $^1$H NMR (400 MHz, DMSO): δ 12.51 (s, 1 H), 11.75-11.70 (m, 1 H), 8.78 (s, 1 H), 8.12 (d, J = 2.8 Hz, 1 H), 8.06 (dd, J = 7.8, 7.8 Hz, 1 H), 7.52 (dd, J = 2.8, 2.8 Hz, 1 H), 7.47 (d, J = 7.3 Hz, 1 H), 7.41-7.34 (m, 2 H), 7.07 (d, J = 8.8 Hz, 1 H), 6.63 (d, J = 7.3 Hz, 1 H), 4.72 (d, J = 1.3 Hz, 1 H), 3.68 (s, 1 H), 3.61-3.54 (m, 2 H), 3.12-3.08 (m, 2 H), 2.14 (s, 1 H), 1.90-1.84 (m, 2 H), 1.71-1.43 (m, 9 H), 1.26 (d, J = 6.8 Hz, 3 H). | F 1-(6-amino-pyridin-3-yl)piperidin-4-ol 2-methyl-piperidine (step 2) |
| I-131 | 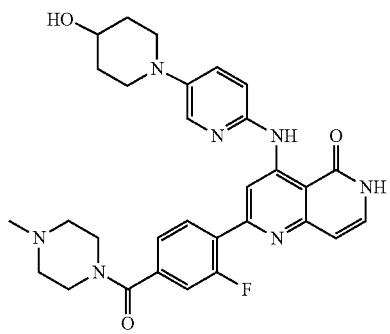 [SMILES: CN1CCN(C(=O)c2ccc(-c3cc(Nc4ccc(N5CCC(O)CC5)cn4)c4c(=O)[nH]ccc4n3)c(F)c2)CC1] | 2-[2-fluoro-4-(4-methyl-piperazine-1-carbonyl)phenyl]-4-[[5-(4-hydroxy-1-piperidyl)-2-pyridyl]amino]-6H-1,6-naphthyridin-5-one | Method 10cm_Formic_AQ, m/z = 558 [M + H]+, Ret. time = 2.17 min. | $^1$H NMR (400 MHz, DMSO): δ 12.49 (s, 1 H), 11.71 (d, J = 5.3 Hz, 1 H), 8.78 (s, 1 H), 8.20 (s, 2 H), 8.13-8.03 (m, 2 H), 7.55-7.44 (m, 3 H), 7.44-7.38 (m, 2 H), 7.07 (d, J = 8.8 Hz, 1 H), 6.63 (d, J = 7.3 Hz, 1 H), 3.61-3.55 (m, 3 H), 3.43-3.42 (m, 2 H), 2.96-2.87 (m, 2 H), 2.43 (s, 2 H), 2.38 (s, 2 H), 2.27 (s, 3 H), 1.90-1.83 (m, 2 H), 1.60-1.48 (m, 2 H). | F 1-(6-amino-pyridin-3-yl)piperidin-4-ol 1-methyl-piperazine (step 2) |
| I-132 | 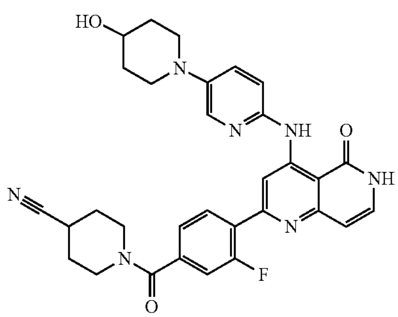 [SMILES: N#CC1CCN(C(=O)c2ccc(-c3cc(Nc4ccc(N5CCC(O)CC5)cn4)c4c(=O)[nH]ccc4n3)c(F)c2)CC1] | 1-[3-fluoro-4-[4-[[5-(4-hydroxy-1-piperidyl)-2-pyridyl]amino]-5-oxo-6H-1,6-naphthyridin-2-yl]benzoyl]piperidine-4-carbonitrile | Method 10cm_Formic_AQ, m/z = 568 [M + H]+, Ret. time = 2.45 min. | $^1$H NMR (400 MHz, DMSO): δ 12.49 (s, 1 H), 11.70 (s, 1 H), 8.78 (s, 1 H), 8.13-8.04 (m, 2 H), 7.55-7.39 (m, 4 H), 7.44 (d, J = 8.1 Hz, 1 H), 7.08 (d, J = 9.1 Hz, 1 H), 6.63 (d, J = 7.3 Hz, 1 H), 3.98-3.98 (m, 1 H), 3.72-3.66 (m, 2 H), 3.62-3.55 (m, 2 H), 3.26-3.19 (m, 2 H), 2.97-2.87 (m, 2 H), 2.04-1.99 (m, 2 H), 1.92-1.86 (m, 5 H), 1.60-1.49 (m, 2 H). | F 1-(6-amino-pyridin-3-yl)piperidin-4-ol Piperidine-4-carbonitrile (step 2) |
| I-133 | 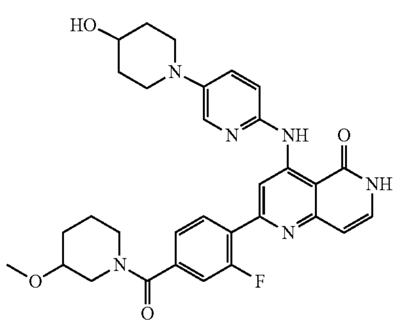 [SMILES: COC1CCCN(C(=O)c2ccc(-c3cc(Nc4ccc(N5CCC(O)CC5)cn4)c4c(=O)[nH]ccc4n3)c(F)c2)C1] | 2-[2-fluoro-4-(3-methoxy-piperidine-1-carbonyl)phenyl]-4-[[5-(4-hydroxy-1-piperidyl)-2-pyridyl]amino]-6H-1,6-naphthyridin-5-one | Method 10cm_Formic_AQ, m/z = 573 [M + H]+, Ret. time = 2.49 min. | $^1$H NMR (400 MHz, DMSO): δ 12.49 (s, 1 H), 11.71 (d, J = 4.3 Hz, 1 H), 8.79 (s, 1 H), 8.14-8.05 (m, 2 H), 7.55-7.45 (m, 1 H), 7.43 (s, 6 H), 7.40 (s, 1 H), 7.08 (d, J = 8.8 Hz, 1 H), 6.63 (d, J = 7.1 Hz, 1 H), 3.71-3.66 (m, 1 H), 3.57 (d, J = 12.6 Hz, 1 H), 3.56-3.20 (m, 4 H), 3.17 (s, 1 H), 2.96-2.87 (m, 2 H), 1.89-1.83 (m, 3 H), 1.76 (s, 2 H), 1.60-1.49 (m, 4 H). | F 1-(6-amino-pyridin-3-yl)piperidin-4-ol 3-methoxy-piperidine (step 2) |

TABLE 2-continued

| I-# | STRUCTURE | NAME | LCMS | HNMR | Method SM |
|---|---|---|---|---|---|
| I-134 | 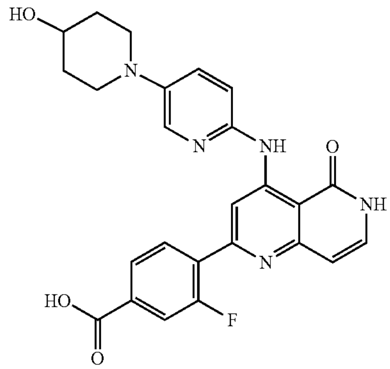 | 3-fluoro-4-[4-[[5-(4-hydroxy-1-piperidyl)-2-pyridyl]amino]-5-oxo-6H-1,6-naphthyridin-2-yl]benzoic acid | Method 10cm_Formic_AQ, m/z = 476 [M + H]+, Ret. time = 2.38 min. | $^1$H NMR (400 MHz, DMSO): δ 13.47-13.46 (m, 1 H), 12.50 (s, 1 H), 11.72 (d, J = 5.3 Hz, 1 H), 8.80 (s, 1 H), 8.17-8.09 (m, 2 H), 7.95 (dd, J = 1.3, 8.1 Hz, 1 H), 7.86 (s, 1 H), 7.55-7.44 (m, 2 H), 7.08 (d, J = 9.1 Hz, 1 H), 6.65 (d, J = 6.6 Hz, 1 H), 4.73-4.67 (m, 1 H), 3.73-3.66 (m, 1 H), 3.61-3.53 (m, 2 H), 2.95-2.87 (m, 2 H), 1.89 (dd, J = 3.5, 8.8 Hz, 2 H), 1.60-1.49 (m, 2 H). | F 1-(6-amino-pyridin-3-yl)piperidin-4-ol |
| I-135 | 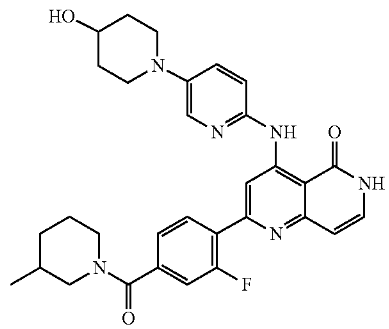 | 2-[2-fluoro-4-(3-methyl-piperidine-1-carbonyl)phenyl]-4-[[5-(4-hydroxy-1-piperidyl)-2-pyridyl]amino]-6H-1,6-naphthyridin-5-one | Method 10cm_Formic_AQ, m/z = 577 [M + H]+, Ret. time = 2.64 min. | $^1$H NMR (400 MHz, DMSO): δ 12.49 (s, 1 H), 11.73 (d, J = 2.8 Hz, 1 H), 8.79 (s, 1 H), 8.23 (s, 1 H), 8.12 (d, J = 2.8 Hz, 1 H), 8.07 (dd, J = 8.0, 8.0 Hz, 1 H), 7.55-7.45 (m, 2 H), 7.43 (s, 1 H), 7.42-7.37 (m, 1 H), 7.07 (d, J = 8.8 Hz, 1 H), 6.63 (d, J = 7.3 Hz, 1 H), 4.69-4.68 (m, 1 H), 4.35 (s, 1 H), 3.72-3.65 (m, 1 H), 3.12-3.04 (m, 1 H), 2.95-2.87 (m, 3 H), 2.82-2.80 (m, 1 H), 1.92-1.86 (m, 2 H), 1.66 (s, 1 H), 1.60-1.48 (m, 2 H), 1.29-1.19 (m, 2 H), 1.02-0.95 (s, 2 H), 0.93-0.89 (m, 2 H), 0.88-0.83 (m, 2 H). | F 1-(6-amino-pyridin-3-yl)piperidin-4-ol 3-methyl-piperidine (step 2) |
| I-136 | 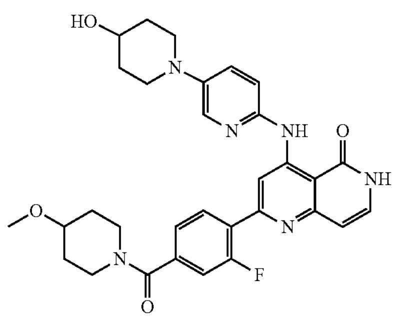 [SMILES: COC1CCN(C(=O)c2ccc(-c3cc(Nc4ccc(N5CCC(O)CC5)cn4)c4c(=O)[nH]ccc4n3)c(F)c2)CC1] | 2-[2-fluoro-4-(4-methoxy-piperidine-1-carbonyl)phenyl]-4-[[5-(4-hydroxy-1-piperidyl)-2-pyridyl]amino]-6H-1,6-naphthyridin-5-one | Method 10cm_Formic_AQ, m/z = 573 [M + H]+, Ret. time = 2.47 min. | $^1$H NMR (400 MHz, DMSO): δ 12.49 (s, 1 H), 11.72 (s, 1 H), 8.79 (s, 1 H), 8.12 (d, J = 2.8 Hz, 1 H), 8.07 (dd, J = 8.0, 8.0 Hz, 1 H), 7.55-7.45 (m, 2 H), 7.45-7.38 (m, 1 H), 7.08 (d, J = 9.1 Hz, 1 H), 6.63 (d, J = 7.3 Hz, 1 H), 4.74-4.74 (m, 1 H), 3.98-3.94 (m, 1 H), 3.71-3.65 (m, 1 H), 3.61-3.51 (m, 4 H), 3.50-3.39 (m, 4 H), 3.29 (s, 1 H), 3.22 (s, 1 H), 2.96-2.87 (m, 2 H), 1.88-1.87 (m, 4 H), 1.58-1.48 (m, 4 H). | F 1-(6-amino-pyridin-3-yl)piperidin-4-ol 4-methoxy-piperidine (step 2) |
| I-137 | 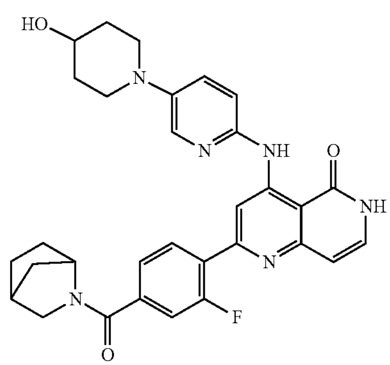 [SMILES: O=C(c1ccc(-c2cc(Nc3ccc(N4CCC(O)CC4)cn3)c3c(=O)[nH]ccc3n2)c(F)c1)N1CC2CCC1C2] | 2-[4-(3-azabicyclo[2.2.1]heptane-3-carbonyl)-2-fluoro-phenyl]-4-[[5-(4-hydroxy-1-piperidyl)-2-pyridyl]amino]-6H-1,6-naphthyridin-5-one | Method 10cm_Bicarb_AQ, m/z = 555 [M + H]+, Ret. time = 2.9 min. | $^1$H NMR (400 MHz, DMSO): δ 12.49 (s, 1 H), 11.71-11.71 (m, 1 H), 8.79 (d, J = 6.8 Hz, 1 H), 8.22 (s, 1 H), 8.14-8.07 (m, 2 H), 7.56-7.50 (m, 2 H), 7.50-7.43 (m, 2 H), 7.08 (d, J = 8.8 Hz, 1 H), 6.64 (d, J = 7.3 Hz, 1 H), 4.59 (s, 1 H), 4.13 (s, 1 H), 3.72-3.65 (m, 1 H), 3.52-3.41 (m, 1 H), 3.18-3.06 (m, 2 H), 2.95-2.89 (m, 2 H), 2.68 (s, 1 H), 1.89-1.66 (m, 6 H), 1.58-1.42 (m, 4 H). | F 1-(6-amino-pyridin-3-yl)piperidin-4-ol 2-azabicyclo[2.2.1]heptane (step 2) |

TABLE 2-continued

| I-# | STRUCTURE | NAME | LCMS | HNMR | Method SM |
|---|---|---|---|---|---|
| I-138 | 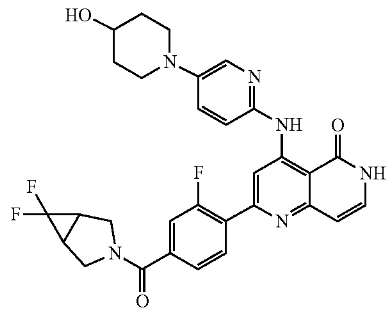 [SMILES: O=C(c1ccc(-c2cc(Nc3ccc(N4CCC(O)CC4)cn3)c3c(=O)[nH]ccc3n2)c(F)c1)N1CC2C(C1)C2(F)F] | 2-[4-(6,6-difluoro-3-azabicyclo[3.1.0]hexane-3-carbonyl)-2-fluoro-phenyl]-4-[[5-(4-hydroxy-1-piperidyl)-2-pyridyl]amino]-6H-1,6-naphthyridin-5-one | Method 10cm_Formic_AQ, m/z = 577 [M + H]+, Ret. time = 2.53 min. | $^1$H NMR (400 MHz, DMSO): δ 12.49 (s, 1 H), 11.73 (s, 1 H), 8.79 (s, 1 H), 8.13-8.04 (m, 2 H), 7.56-7.47 (m, 3 H), 7.38-7.33 (m, 1 H), 7.07 (d, J = 8.8 Hz, 1 H), 6.64 (d, J = 7.3 Hz, 1 H), 4.73-4.73 (m, 1 H), 4.18 (dd, J = 12.5, 12.5 Hz, 1 H), 3.83-3.66 (m, 2 H), 3.61-3.53 (m, 2 H), 3.22 (s, 2 H), 2.96-2.89 (m, 2 H), 2.70-2.59 (m, 2 H), 1.90-1.84 (m, 2 H), 1.60-1.49 (m, 2 H). | F 1-(6-amino-pyridin-3-yl)piperidin-4-ol 6,6-difluoro-3-azabicyclo[3.1.0]hexane |
| I-139 | 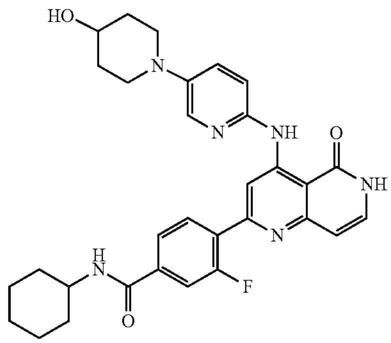 [SMILES: O=C(NC1CCCCC1)c1ccc(-c2cc(Nc3ccc(N4CCC(O)CC4)cn3)c3c(=O)[nH]ccc3n2)c(F)c1] | N-cyclohexyl-3-fluoro-4-[4-[[5-(4-hydroxy-1-piperidyl)-2-pyridyl]amino]-5-oxo-6H-1,6-naphthyridin-2-yl]benzamide | Method 10cm_Formic_AQ, m/z = 557 [M + H]+, Ret. time = 2.7 min. | $^1$H NMR (400 MHz, DMSO): δ 12.48 (s, 1 H), 11.70 (s, 1 H), 8.79 (s, 1 H), 8.43 (d, J = 7.8 Hz, 1 H), 8.12-8.05 (m, 2 H), 7.90-7.84 (m, 1 H), 7.52 (dd, J = 3.0, 8.8 Hz, 1 H), 7.48-7.47 (m, 1 H), 7.08 (d, J = 8.8 Hz, 1 H), 6.65 (d, J = 7.3 Hz, 1 H), 4.74-4.72 (m, 1 H), 3.88-3.81 (m, 1 H), 3.71-3.66 (m, 1 H), 3.59-3.52 (m, 2 H), 2.97-2.87 (m, 2 H), 1.94-1.87 (m, 4 H), 1.82 (s, 2 H), 1.69-1.66 (m, 2 H), 1.59-1.49 (m, 2 H), 1.41-1.36 (m, 4 H), 1.22-1.18 (m, 1 H). | F 1-(6-amino-pyridin-3-yl)piperidin-4-ol Cyclohexyl-amino (step 2) |
| I-140 | 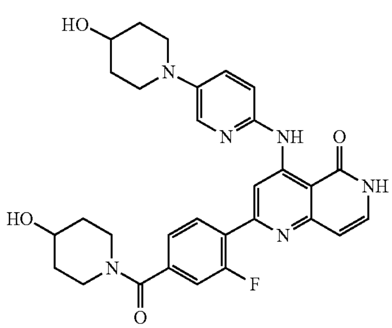 [SMILES: O=C(c1ccc(-c2cc(Nc3ccc(N4CCC(O)CC4)cn3)c3c(=O)[nH]ccc3n2)c(F)c1)N1CCC(O)CC1] | 2-[2-fluoro-4-(4-hydroxy-piperidine-1-carbonyl)phenyl]-4-[[5-(4-hydroxy-1-piperidyl)-2-pyridyl]amino]-6H-1,6-naphthyridin-5-one | Method 10cm_Formic_AQ, m/z = 559 [M + H]+, Ret. time = 2.34 min. | $^1$H NMR (400 MHz, DMSO): δ 12.49 (s, 1 H), 11.72-11.68 (m, 1 H), 8.79 (s, 1 H), 8.12 (d, J = 2.8 Hz, 1 H), 8.07 (dd, J = 7.8, 7.8 Hz, 1 H), 7.52 (dd, J = 2.9, 8.7 Hz, 1 H), 7.49-7.44 (m, 2 H), 7.43-7.38 (m, 2 H), 7.08 (d, J = 9.1 Hz, 1 H), 6.63 (d, J = 7.3 Hz, 1 H), 4.04-4.02 (m, 1 H), 3.85-3.78 (m, 1 H), 3.72-3.66 (m, 1 H), 3.62-3.55 (m, 3 H), 3.22 (s, 2 H), 2.95-2.87 (m, 2 H), 1.89-1.82 (m, 4 H), 1.59-1.51 (m, 3 H), 1.42-1.41 (m, 2 H). | F 1-(6-amino-pyridin-3-yl)piperidin-4-ol 4-hydroxy-piperidine (step 2) |
| I-141 | 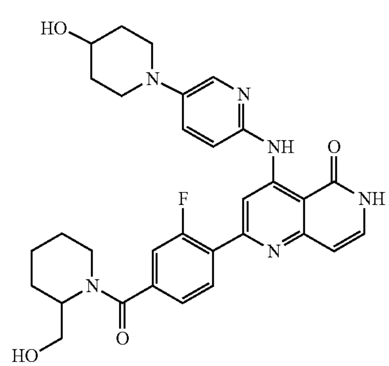 [SMILES: O=C(c1ccc(-c2cc(Nc3ccc(N4CCC(O)CC4)cn3)c3c(=O)[nH]ccc3n2)c(F)c1)N1CCCCC1CO] | 2-[2-fluoro-4-[2-(hydroxy-methyl)piperidine-1-carbonyl]phenyl]-4-[[5-(4-hydroxy-1-piperidyl)-2-pyridyl]amino]-6H-1,6-naphthyridin-5-one | Method 10cm_Formic_AQ, m/z = 573 [M + H]+, Ret. time = 2.45 min. | $^1$H NMR (400 MHz, DMSO): δ 12.44 (s, 1 H), 11.67-11.64 (m, 1 H), 8.73 (s, 1 H), 8.07 (d, J = 2.8 Hz, 1 H), 7.99 (dd, J = 8.0, 8.0 Hz, 1 H), 7.47 (dd, J = 2.8, 8.8 Hz, 1 H), 7.42 (d, J = 5.6 Hz, 1 H), 7.35 (d, J = 7.6 Hz, 2 H), 7.02 (d, J = 8.8 Hz, 1 H), 6.58 (d, J = 7.3 Hz, 1 H), 4.37-4.37 (m, 1 H), 3.88-3.60 (m, 2 H), 3.52 (dd, J = 5.3, 7.6 Hz, 2 H), 3.17 (s, 2 H), 2.89-2.82 (m, 2 H), 1.84-1.81 (m, 4 H), 1.61-1.44 (m, 9 H). | F 1-(6-amino-pyridin-3-yl)piperidin-4-ol 2-piperidine-methanol (step 2) |

TABLE 2-continued

| I-# | STRUCTURE | NAME | LCMS | HNMR | Method SM |
|---|---|---|---|---|---|
| I-142 | 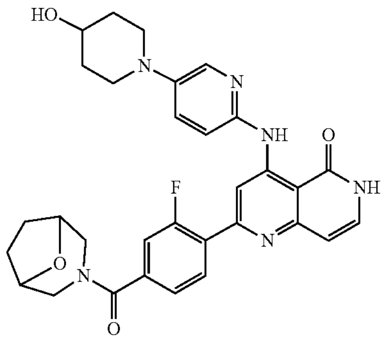 [SMILES: O=C(c1ccc(-c2cc(Nc3ccc(N4CCC(O)CC4)cn3)c3c(=O)[nH]ccc3n2)c(F)c1)N1CC2CCC(C1)O2] | 2-[2-fluoro-4-(8-oxa-3-azabicyclo[3.2.1]octane-3-carbonyl)phenyl]-4-[[5-(4-hydroxy-1-piperidyl)-2-pyridyl]amino]-6H-naphthyridin-5-one | Method 10cm_Formic_AQ, m/z = 571 [M + H]+, Ret. time = 2.43 min. | $^1$H NMR (400 MHz, DMSO): δ 12.46 (s, 1 H), 11.67 (d, J = 4.0 Hz, 1 H), 8.75 (d, J = 1.6 Hz, 1 H), 8.08-8.00 (m, 2 H), 7.51-7.36 (m, 4 H), 7.04 (d, J = 8.9 Hz, 1 H), 6.59 (d, J = 7.3 Hz, 1 H), 4.26-4.18 (m, 3 H), 3.68-3.60 (m, 1H), 3.57-3.51 (m, 2 H), 3.49-3.23 (m, 4 H), 3.05-2.98 (m, 1 H), 2.92-2.84 (m, 2 H), 1.88-1.82 (m, 4 H), 1.74 (d, J = 2.0 Hz, 1 H), 1.55-1.45 (m, 2 H). | F 1-(6-amino-pyridin-3-yl)piperidin-4-ol 8-oxa-3-azabicyclo[3.2.1]octane (step 2) |
| I-143 | 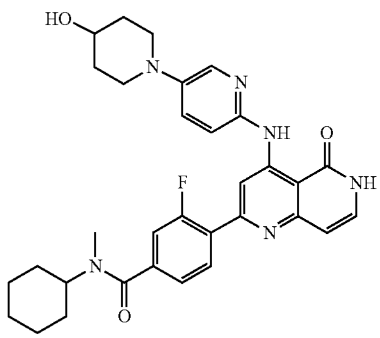 [SMILES: CN(C(=O)c1ccc(-c2cc(Nc3ccc(N4CCC(O)CC4)cn3)c3c(=O)[nH]ccc3n2)c(F)c1)C1CCCCC1] | N-cyclohexyl-3-fluoro-4-[4-[[5-(4-hydroxy-1-piperidyl)-2-pyridyl]amino]-5-oxo-6H-1,6-naphthyridin-2-yl]-N-methyl-benzamide | Method 10cm_Formic_AQ, m/z = 571 [M + H]+, Ret. time = 2.68 min. | $^1$H NMR (400 MHz, DMSO): δ 12.50 (s, 1 H), 11.71 (s, 1 H), 8.80 (s, 1 H), 8.12-8.11 (m, 1 H), 8.09-8.06 (m, 1 H), 7.55-7.45 (m, 1 H), 7.43 (s, 1 H), 7.38 (s, 1 H), 7.08 (d, J = 8.8 Hz, 1 H), 6.64 (d, J = 7.3 Hz, 1 H), 4.73 (d, J = 3.5 Hz, 1 H), 3.69 (dd, J = 3.5, 8.1 Hz, 1 H), 3.61-3.53 (m, 2 H), 3.23 (s, 1 H), 2.97-2.85 (m, 4 H), 1.92-1.84 (m, 3 H), 1.76-1.71 (m, 4 H), 1.59-1.50 (m, 5 H), 1.40-1.39 (m, 2 H), 1.15-1.09 (m, 2 H). | F 1-(6-amino-pyridin-3-yl)piperidin-4-ol N-methyl-cyclohexyl-amine (step 2) |
| I-144 | 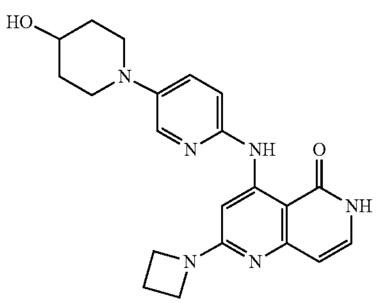 [SMILES: O=c1[nH]ccc2nc(N3CCC3)cc(Nc3ccc(N4CCC(O)CC4)cn3)c12] | 2-(azetidin-1-yl)-4-[[5-(4-hydroxy-1-piperidyl)-2-pyridyl]amino]-6H-1,6-naphthyridin-5-one | Method 10cm_Formic_AQ, m/z = 393 [M + H]+, Ret. time = 2.32 min. | $^1$H NMR (400 MHz, DMSO) δ 12.34 (s, 1H), 11.16 (d, J = 4.1 Hz, 1H), 8.29 (s, 1H), 8.01 (d, J = 3.0 Hz, 1H), 7.44 (dd, J = 3.1, 9.0 Hz, 1H), 7.29 (s, 1H), 7.24-7.19 (m, 1H), 6.90 (d, J = 8.9 Hz, 1H), 6.24 (d, J = 7.3 Hz, 1H), 4.73 (s, 1H), 4.04 (t, J = 7.4 Hz, 4H), 3.67-3.59 (m, 1H), 3.51-3.46 (m, 2H), 2.88-2.80 (m, 2H), 2.38-2.29 (m, 2H), 1.88-1.80 (m, 2H), 1.56-1.46 (m, 2H). (1 eq formate salt) | E 1-(6-amino-pyridin-3-yl)piperidin 4-ol Azetidine (step 2) |
| I-145 | 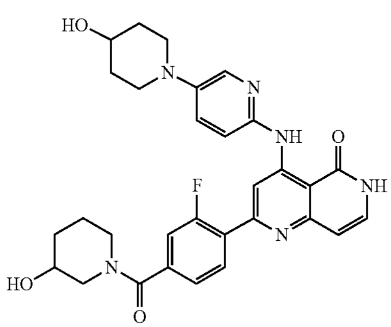 [SMILES: O=C(c1ccc(-c2cc(Nc3ccc(N4CCC(O)CC4)cn3)c3c(=O)[nH]ccc3n2)c(F)c1)N1CCCC(O)C1] | 2-[2-fluoro-4-(3-hydroxy-piperidine-1-carbonyl)phenyl]-4-[[5-(4-hydroxy-1-piperidyl)-2-pyridyl]amino]-6H-1,6-naphthyridin-5-one | Method 10cm_Formic_AQ, m/z = 559 [M + H]+, Ret. time = 2.38 min. | $^1$H NMR (400 MHz, DMSO): δ 12.36 (s, 1 H), 11.58 (d, J = 1.3 Hz, 1 H), 8.65 (s, 1 H), 8.18 (s, 1 H), 7.98 (d, J = 2.8 Hz, 1 H), 7.92 (dd, J = 7.7, 7.7 Hz, 1 H), 7.39 (dd, J = 2.9, 9.0 Hz, 1 H), 7.32 (s, 1 H), 7.30-7.27 (m, 1 H), 6.94 (d, J = 9.1 Hz, 1 H), 6.49 (d, J = 7.1 Hz, 1 H), 3.57-3.51 (m, 2 H), 3.35 (s, 1 H), 3.29-3.24 (m, 4 H), 3.08 (s, 2 H), 2.99-2.98 (m, 1 H), 2.79 (dd, J = 9.9, 9.9 Hz, 2 H), 1.78-1.73 (m, 4 H), 1.44-1.33 (m, 4 H). | F 1-(6-amino-pyridin-3-yl)piperidin-4-ol 3 hydroxy-piperidine (step 2) |

TABLE 2-continued

| I-# | STRUCTURE | NAME | LCMS | HNMR | Method SM |
|---|---|---|---|---|---|
| I-146 | 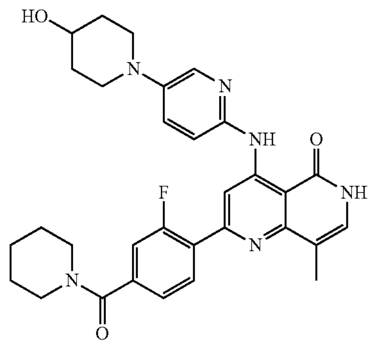 [SMILES: Cc1c[nH]c(=O)c2c(Nc3ccc(N4CCC(O)CC4)cn3)cc(-c3ccc(C(=O)N4CCCCC4)cc3F)nc12] | 2-[2-fluoro-4-(piperidine-1-carbonyl)phenyl]-4-[[5-(4-hydroxy-1-piperidyl)-2-pyridyl]amino]-8-methyl-6H-1,6-naphthyridin-5-one | Method 10cm_Bicarb_AQ, m/z = 557 [M + H]+, Ret. time = 3.17 min. | $^1$H NMR (400 MHz, DMSO): δ 12.68 (s, 1 H), 11.57-11.57 (m, 1 H), 8.88 (s, 1 H), 8.18 (dd, J = 7.8, 7.8 Hz, 1 H), 8.12 (d, J = 2.5 Hz, 1 H), 7.52 (dd, J = 2.8, 9.1 Hz, 1 H), 7.45 (s, 1 H), 7.41 (d, J = 6.8 Hz, 1 H), 7.37-7.36 (m, 1 H), 7.07 (d, J = 9.1 Hz, 1 H), 4.74 (s, 1 H), 3.68-3.66 (m, 3 H), 3.58 (d, J = 12.4 Hz, 3 H), 2.96-2.87 (m, 2 H), 2.60-2.30 (m, 3 H), 1.92-1.87 (m, 2 H), 1.67 (s, 3 H), 1.59-1.50 (m, 6 H). | A 2-chloro-4-((5-(4-hydroxypiperidin-1-yl)pyridin-2-yl)amino)-8-methyl-1,6-naphthyridin-5(6H)-one (12.0) (2-fluoro-4-(piperidine-1-carbonyl)phenyl) boronic acid |
| I-147 | 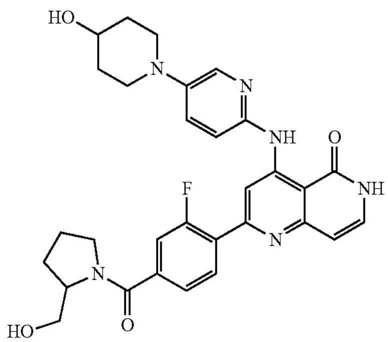 [SMILES: O=C(c1ccc(-c2cc(Nc3ccc(N4CCC(O)CC4)cn3)c3c(=O)[nH]ccc3n2)c(F)c1)N1CCCC1CO] | 2-[2-fluoro-4-[2-(hydroxymethyl)pyrrolidine-1-carbonyl]phenyl]-4-[[5-(4-hydroxy-1-piperidyl)-2-pyridyl]amino]-6H-1,6-naphthyridin-5-one | Method 10cm_Formic_AQ, m/z = 559 [M + H]+, Ret. time = 2.4 min. | $^1$H NMR (400 MHz, DMSO): δ 12.49 (s, 1 H), 11.73-11.71 (m, 1 H), 8.79 (s, 1 H), 8.14-8.12 (m, 1 H), 8.06 (dd, J = 7.8, 7.8 Hz, 1 H), 7.53 (dd, J = 2.3, 8.6 Hz, 3 H), 7.47 (d, J = 7.3 Hz, 1 H), 7.08 (d, J = 9.1 Hz, 1 H), 6.64 (d, J = 7.3 Hz, 1 H), 4.89-4.88 (m, 1 H), 4.23-4.17 (m, 1 H), 3.39 (dd, J = 5.4, 15.8 Hz, 4 H), 3.22 (s, 1 H), 3.18 (s, 2 H), 2.97-2.88 (m, 2 H), 2.13 (s, 1 H), 2.03-1.96 (m, 3 H), 1.91-1.86 (m, 2 H), 1.78 (s, 1 H), 1.59-1.49 (m, 2 H). | A 1-(6-aminopyridin-3-yl)piperidin-4-ol pyrrolidin-2-yl-methanol (step 2) |
| I-148 | 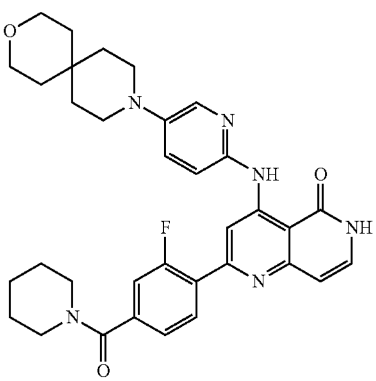 [SMILES: O=C(c1ccc(-c2cc(Nc3ccc(N4CCC5(CCOCC5)CC4)cn3)c3c(=O)[nH]ccc3n2)c(F)c1)N1CCCCC1] | 2-[2-fluoro-4-(piperidine-1-carbonyl)phenyl]-4-[[5-(3-oxa-9-azaspiro[5.5]undecan-9-yl)-2-pyridyl]amino]-6H-naphthyridin-5-one | Method 10cm_Formic_AQ, m/z = 597 [M + H]+, Ret. time = 2.86 min. | $^1$H NMR (400 MHz, DMSO): δ 12.48 (s, 1 H), 11.73-11.67 (m, 1 H), 8.78 (s, 1 H), 8.12 (d, J = 2.8 Hz, 1H), 8.06 (dd, J = 7.8, 7.8 Hz, 1 H), 7.52 (dd, J = 2.7, 9.0 Hz, 1 H), 7.47 (d, J = 7.3 Hz, 1 H), 7.42-7.36 (m, 2 H), 7.08 (d, J = 9.1 Hz, 1 H), 6.63 (d, J = 7.1 Hz, 1 H), 3.73-3.60 (m, 7 H), 3.21 (dd, J = 5.3, 5.3 Hz, 4 H), 1.68 (dd, J = 5.2, 5.2 Hz, 9 H), 1.51 (dd, J = 5.1, 5.1 Hz, 6 H). | A 5-(3-oxa-9-azaspiro[5.5]undecan-9-yl)pyridin-2-amine (2-fluoro-4-(piperidine-1-carbonyl)phenyl) boronic acid |
| I-149 | 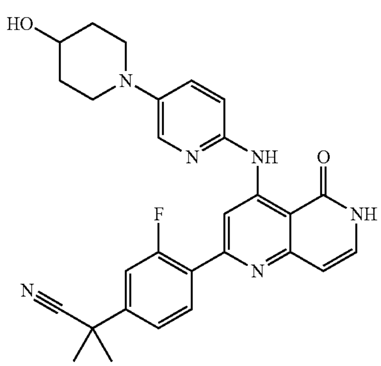 [SMILES: CC(C)(C#N)c1ccc(-c2cc(Nc3ccc(N4CCC(O)CC4)cn3)c3c(=O)[nH]ccc3n2)c(F)c1] | 2-[3-fluoro-4-[4-[[5-(4-hydroxy-1-piperidyl)-2-pyridyl]amino]-5-oxo-6H-1,6-naphthyridin-2-yl]phenyl]-2-methyl-propanenitrile | Method 10cm_Formic_AQ, m/z = 499 [M + H]+, Ret. time = 2.6 min. | $^1$H NMR (400 MHz, DMSO): δ 12.45 (s, 1 H), 11.69 (s, 1 H), 8.74 (d, J = 1.6 Hz, 1 H), 8.07 (d, J = 3.0 Hz, 1 H), 8.01 (dd, J = 8.3, 8.3 Hz, 1 H), 7.55-7.46 (m, 3 H), 7.43 (d, J = 7.3 Hz, 1 H), 7.03 (d, J = 8.9 Hz, 1 H), 6.59 (d, J = 7.3 Hz, 1 H), 4.72 (d, J = 4.1 Hz, 1 H), 3.68-3.58 (m, 1 H), 3.57-3.49 (m, 2 H), 2.91-2.83 (m, 2 H), 1.87-1.79 (m, 2 H), 1.76 (s, 6 H), 1.55-1.44 (m, 2 H). | A 1-(6-aminopyridin-3-yl)piperidin-4-ol (4-(2-cyanopropan-2-yl)-2-fluorophenyl) boronic acid |

TABLE 2-continued

| I-# | STRUCTURE | NAME | LCMS | HNMR | Method SM |
|---|---|---|---|---|---|
| I-150 | 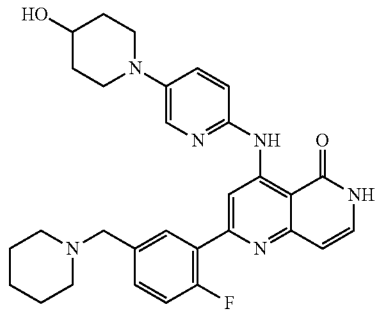 [SMILES: O=c1[nH]ccc2nc(-c3cc(CN4CCCCC4)ccc3F)cc(Nc3ccc(N4CCC(O)CC4)cn3)c12] | 2-[2-fluoro-5-(1-piperidyl-methyl)phenyl]-4-[[5-(4-hydroxy-1-piperidyl)-2-pyridyl]amino]-6H-1,6-naphthyridin-5-one | Method 10cm_Formic_AQ, m/z = 529 [M + H]+, Ret. time = 2.24 min. | ¹H NMR (400 MHz, DMSO): δ 12.42 (s, 1 H), 11.68-11.65 (m, 1 H), 8.71 (d, J = 1.5 Hz, 1 H), 8.06 (d, J = 3.0 Hz, 1 H), 7.85 (dd, J = 2.3, 7.7 Hz, 1 H), 7.48 (dd, J = 3.1, 9.0 Hz, 1 H), 7.44-7.39 (m, 2 H), 7.28 (dd, J = 8.4, 11.0 Hz, 1 H), 7.03 (d, J = 8.9 Hz, 1 H), 6.61 (d, J = 7.3 Hz, 1 H), 4.70 (d, J = 3.9 Hz, 1 H), 3.68-3.06 (m, 1 H), 3.55-3.49 (m, 2 H), 3.48 (s, 2 H), 2.91-2.83 (m, 2 H), 2.39-2.31 (m, 4 H), 1.88-1.80 (m, 2 H), 1.54-1.36 (m, 8 H). | A 1-(6-amino-pyridin-3-yl)piperidin-4-ol 1-(4-fluoro-3-(4,4,5,5-tetramethyl-1,3,2-dioxa-borolan-2-yl)benzyl)piperidine |
| I-151 | 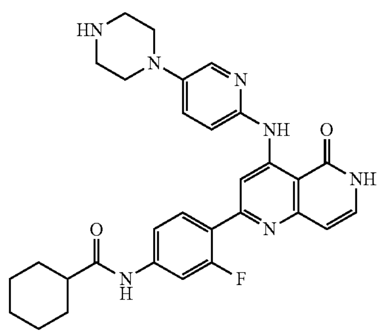 [SMILES: O=C(Nc1ccc(-c2cc(Nc3ccc(N4CCNCC4)cn3)c3c(=O)[nH]ccc3n2)c(F)c1)C1CCCCC1] | N-[3-fluoro-4-[5-oxo-4-[(5-piperazin-1-yl-2-pyridyl)amino]-6H-1,6-naphthyridin-2-yl]phenyl]cyclohexane-carboxamide | Method 10cm_Formic_AQ, m/z = 0 [M + H]+, Ret. time = 2.42 min. | ¹H NMR (400 MHz, DMSO): δ 12.46 (s, 1 H), 11.64-11.64 (m, 1 H), 10.23 (s, 1 H), 8.80 (s, 1 H), 8.22 (s, 1 H), 8.11 (d, J = 3.0 Hz, 1 H), 8.01 (dd, J = 8.8, 8.8 Hz, 1 H), 7.52 (dd, J = 3.1, 9.0 Hz, 1 H), 7.47-7.40 (m, 2 H), 7.07 (d, J = 8.9 Hz, 1 H), 6.59 (d, J = 7.3 Hz, 1 H), 3.29-3.23 (m, 6 H), 2.42-2.33 (m, 1 H), 1.86-1.76 (m, 6 H), 1.67 (d, J = 11.2 Hz, 1 H), 1.48-1.18 (m, 6 H). | A and G tert-butyl 4-(6-amino-pyridin-3-yl)piperazine-1-carboxy-late CB19 |
| I-152 | 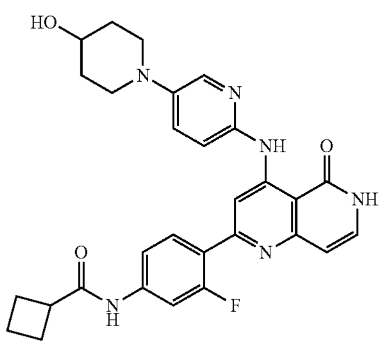 [SMILES: O=C(Nc1ccc(-c2cc(Nc3ccc(N4CCC(O)CC4)cn3)c3c(=O)[nH]ccc3n2)c(F)c1)C1CCC1] | N-[3-fluoro-4-[4-[[5-(4-hydroxy-1-piperidyl)-2-pyridyl]amino]-5-oxo-6H-1,6-naphthyridin-2-yl]phenyl]cyclobutane-carboxamide | Method 10cm_Formic_AQ, m/z = 529 [M + H]+, Ret. time = 2.61 min. | ¹H NMR (400 MHz, DMSO): δ 12.38 (s, 1 H), 11.61 (d, J = 4.6 Hz, 1 H), 10.13 (s, 1 H), 8.73 (s, 1 H), 8.23 (s, 1 H), 8.08 (d, J = 3.0 Hz, 1 H), 8.01 (dd, J = 8.8, 8.8 Hz, 1 H), 7.79 (d, J = 1.9 Hz, 1 H), 7.76 (d, J = 2.0 Hz, 1 H), 7.50-7.38 (m, 2 H), 7.02 (d, J = 8.9 Hz, 1 H), 6.57 (d, J = 7.3 Hz, 1 H), 3.68-3.61 (m, 1 H), 3.57-3.49 (m, 2 H), 3.42-3.12 (m, 6 H), 2.92-2.83 (m, 2 H), 2.35-2.10 (m, 2 H), 2.02-1.83 (m, 1 H), 1.57-1.46 (m, 2 H). | A 1-(6-amino-pyridin-3-yl)piperidin-4-ol CB24 |
| I-153 | 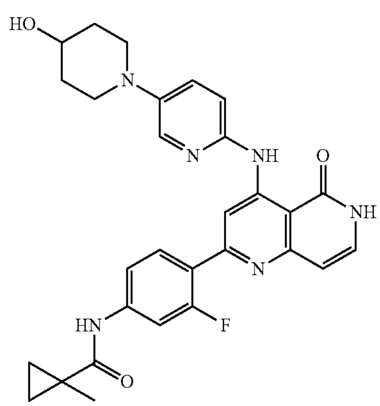 [SMILES: CC1(C(=O)Nc2ccc(-c3cc(Nc4ccc(N5CCC(O)CC5)cn4)c4c(=O)[nH]ccc4n3)c(F)c2)CC1] | N-[3-fluoro-4-[4-[[5-(4-hydroxy-1-piperidyl)-2-pyridyl]amino]-5-oxo-6H-1,6-naphthyridin-2-yl]phenyl]-1-methyl-cyclopropane-carboxamide | Method 10cm_Formic_AQ, m/z = 529 [M + H]+, Ret. time = 2.61 min. | ¹H NMR (400 MHz, DMSO): δ 12.39 (s, 1 H), 11.63 (d, J = 4.8 Hz, 1 H), 9.52 (s, 1 H), 8.72 (s, 1 H), 8.08 (d, J = 3.0 Hz, 1 H), 8.00 (dd, J = 8.9, 8.9 Hz, 1 H), 7.80-7.76 (m, 1 H), 7.61 (dd, J = 2.1, 8.7 Hz, 1 H), 7.48 (dd, J = 3.1, 9.0 Hz, 1 H), 7.43-7.38 (m, 1 H), 7.03 (d, J = 9.0 Hz, 1 H), 6.58 (d, J = 7.3 Hz, 1 H), 3.69-3.60 (m, 1 H), 3.57-3.49 (m, 2 H), 2.92-2.83 (m, 2 H), 1.88-1.80 (m, 2 H), 1.56-1.46 (m, 3 H), 1.45 (s, 3 H), 1.18-1.13 (m, 2 H), 0.72-0.68 (m, 2 H). | A 1-(6-amino-pyridin-3-yl)piperidin-4-ol CB25 |

TABLE 2-continued

| I-# | STRUCTURE | NAME | LCMS | HNMR | Method SM |
|---|---|---|---|---|---|
| I-154 | 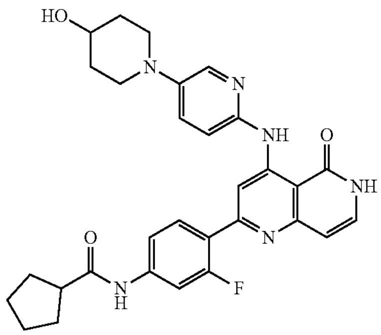 [SMILES: O=C(Nc1ccc(-c2cc(Nc3ccc(N4CCC(O)CC4)cn3)c3c(=O)[nH]ccc3n2)c(F)c1)C1CCCC1] | N-[3-fluoro-4-[4-[[5-(4-hydroxy-1-piperidyl)-2-pyridyl]amino]-5-oxo-6H-1,6-naphthyridin-2-yl]phenyl]cyclopentane carboxamide | Method 10cm_Formic_AQ, m/z = 543 [M + H]+, Ret. time = 2.69 min. | $^1$H NMR (400 MHz, DMSO): δ 12.43 (s, 1 H), 11.62 (s, 1 H), 10.27 (s, 1 H), 8.72 (s, 1 H), 8.08 (d, J = 3.0 Hz, 1 H), 8.01 (dd, J = 8.8, 8.8 Hz, 1 H), 7.78 (d, J = 1.9 Hz, 1 H), 7.75 (d, J = 2.0 Hz, 1 H), 7.50-7.44 (m, 2 H), 7.41 (d, J = 7.3 Hz, 1 H), 7.02 (d, J = 8.9 Hz, 1 H), 6.57 (d, J = 7.3 Hz, 1 H), 4.70 (d, J = 4.1 Hz, 1 H), 3.67-3.61 (m, 1 H), 3.57-3.50 (m, 2 H), 3.18 (d, J = 5.1 Hz, 1 H), 2.92-2.80 (m, 3 H), 1.92-1.69 (m, 5 H), 1.63-1.46 (m, 5 H). | A 1-(6-amino-pyridin-3-yl)piperidin-4-ol CB26 |
| I-155 | 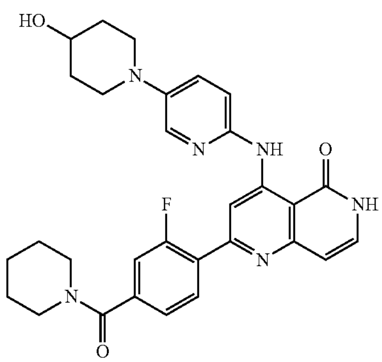 [SMILES: O=C(c1ccc(-c2cc(Nc3ccc(N4CCC(O)CC4)cn3)c3c(=O)[nH]ccc3n2)c(F)c1)N1CCCCC1] | 2-[2-fluoro-4-(piperidine-1-carbonyl)phenyl]-4-[(5-morpholino-2-pyridyl)amino]-6H-1,6-naphthyridin-5-one | Method 10cm_Bicarb_AQ, m/z = 529 [M + H]+, Ret. time = 3.12 min. | $^1$H NMR (400 MHz, DMSO): δ 12.51 (s, 1 H), 11.69 (s, 1 H), 8.79 (d, J = 1.5 Hz, 1 H), 8.09 (d, J = 3.0 Hz, 1 H), 8.03 (dd, J = 7.8, 7.8 Hz, 1 H), 7.51 (dd, J = 3.1, 9.0 Hz, 1 H), 7.44 (d, J = 7.3 Hz, 1 H), 7.38-7.34 (m, 2 H), 7.08 (d, J = 9.0 Hz, 1 H), 6.60 (d, J = 7.3 Hz, 1 H), 3.78-3.74 (m, 4 H), 3.70-3.56 (m, 2 H), 3.15 (dd, J = 4.8, 4.8 Hz, 4 H), 1.62-1.62 (m, 8 H). | A 5-morpholino-pyridin-2-amine (2-fluoro-4-(piperidine-1-carbonyl)phenyl)boronic acid |
| I-156 | 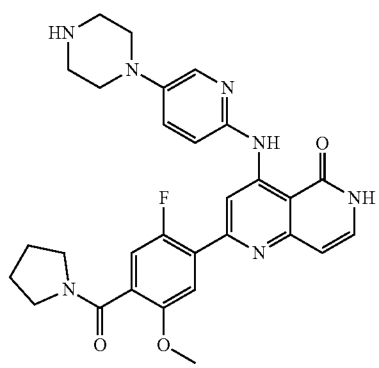 [SMILES: COc1cc(-c2cc(Nc3ccc(N4CCNCC4)cn3)c3c(=O)[nH]ccc3n2)c(F)cc1C(=O)N1CCCC1] | 2-[2-fluoro-5-methoxy-4-(pyrrolidine-1-carbonyl)phenyl]-4-[(5-piperazin-1-yl-2-pyridyl)amino]-6H-1,6-naphthyridin-5-one | Method 10cm_Formic_AQ, m/z = 544 [M + H]+, Ret. time = 2.25 min. | $^1$H NMR (400 MHz, DMSO): δ 12.51 (s, 1 H), 11.88 (s, 1 H), 8.81 (s, 1 H), 8.12-8.09 (m, 1 H), 7.63 (d, J = 5.8 Hz, 1 H), 7.54-7.46 (m, 2 H), 7.30 (d, J = 8.8 Hz, 1 H), 7.09 (d, J = 8.8 Hz, 1 H), 6.66 (d, J = 7.3 Hz, 1 H), 3.92 (s, 3 H), 3.51 (dd, J = 6.1, 6.8 Hz, 2 H), 3.24 (dd, J = 6.3, 6.3 Hz, 2 H), 3.10 (dd, J = 5.1, 5.1 Hz, 4 H), 2.88 (dd, J = 5.2, 5.2 Hz, 4 H), 1.96-1.84 (m, 5 H). | F and G tert-butyl 4-(6-amino-pyridin-3-yl)piperazine-1-carboxylate pyrrolidine (step 2) |
| I-157 | 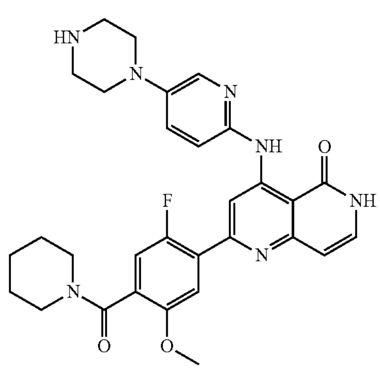 [SMILES: COc1cc(-c2cc(Nc3ccc(N4CCNCC4)cn3)c3c(=O)[nH]ccc3n2)c(F)cc1C(=O)N1CCCCC1] | 2-[2-fluoro-5-methoxy-4-(piperidine-1-carbonyl)phenyl]-4-[(5-piperazin-1-yl]-2-pyridyl)amino]-6H-1,6-naphthyridin-5-one | Method 10cm_Formic_AQ, m/z = 558 [M + H]+, Ret. time = 2.31 min. | $^1$H NMR (400 MHz, DMSO): δ 12.54 (s, 1 H), 11.77-11.77 (m, 1 H), 8.82 (s, 1 H), 8.33 (s, 1 H), 8.15-8.10 (m, 1 H), 7.61 (d, J = 6.1 Hz, 1 H), 7.56-7.46 (m, 2 H), 7.30 (s, 1 H), 7.10 (d, J = 8.8 Hz, 1 H), 6.66 (d, J = 7.3 Hz, 1 H), 3.91 (s, 3 H), 3.25-3.17 (m, 4 H), 3.01-2.94 (m, 4 H), 2.47-2.47 (m, 2 H), 2.39-2.36 (m, 1 H), 1.70-1.60 (m, 4 H), 1.53-1.47 (m, 3 H). | F and G tert-butyl 4-(6-aminopyridin-3-yl)piperazine-1-carboxylate piperidine (step 2) |

TABLE 2-continued

| I-# | STRUCTURE | NAME | LCMS | HNMR | Method SM |
|---|---|---|---|---|---|
| I-158 | 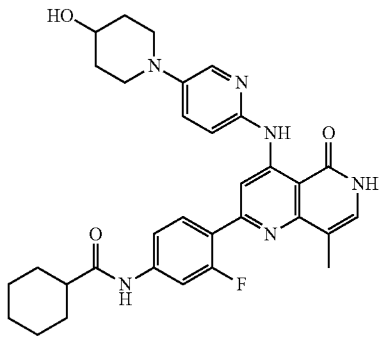 [SMILES: Cc1c[nH]c(=O)c2c(Nc3ccc(N4CCC(O)CC4)cn3)cc(-c3ccc(NC(=O)C4CCCCC4)cc3F)nc12] | N-[3-fluoro-4-[4-[[5-(4-hydroxy-1-piperidyl)-2-pyridyl]amino]-8-methyl-5-oxo-6H-1,6-naphthyridin-2-yl]phenyl]cyclohexane carboxamide | Method AcHSS C18, m/z = 571 [M + H]+, Ret. time = 3.61 min. | $^1$H NMR (400 MHz, DMSO): δ 12.61 (s, 1 H), 11.54-11.50 (m, 1 H), 10.28 (s, 1 H), 8.86 (s, 1 H), 8.19-8.11 (m, 2 H), 7.55-7.48 (m, 2 H), 7.36-7.32 (m, 1 H), 7.05 (d, J = 8.8 Hz, 1 H), 4.76 (d, J = 4.3 Hz, 1 H), 3.71-3.67 (m, 1 H), 3.60-3.55 (m, 2 H), 2.94-2.87 (m, 2 H), 2.42 (dd, J = 11.7, 15.0 Hz, 2 H), 2.31 (s, 3 H), 1.92-1.80 (m, 6 H), 1.73 (s, 1 H), 1.57-1.44 (m, 4 H), 1.36-1.26 (m, 3 H). | A 2-chloro-4-((5-(4-hydroxy piperidin-1-yl)pyridin-2-yl)amino)-8-methyl-1,6-naphthyridin-5(6H)-one (12.0) CB19 |
| I-159 | 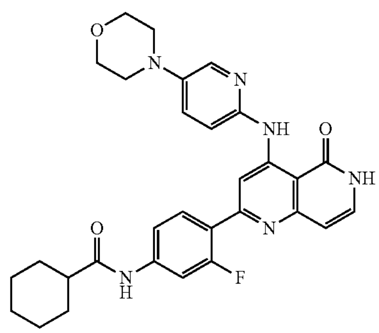 [SMILES: O=C(Nc1ccc(-c2cc(Nc3ccc(N4CCOCC4)cn3)c3c(=O)[nH]ccc3n2)c(F)c1)C1CCCCC1] | N-[3-fluoro-4-[4-[(5-morpholino-2-pyridyl)amino]-5-oxo-6H-1,6-naphthyridin-2-yl]phenyl]cyclohexane carboxamide | Method BicarbB EHC18, m/z = 543 [M + H]+, Ret. time = 4.57 min. | $^1$H NMR (400 MHz, DMSO): δ 12.48 (s, 1 H), 11.68 (s, 1 H), 10.27 (s, 1 H), 8.82 (s, 1 H), 8.13 (d, J = 2.5 Hz, 1 H), 8.05 (dd, J = 8.7, 8.7 Hz, 1 H), 7.56-7.48 (m, 2 H), 7.45 (d, J = 7.1 Hz, 1 H), 7.10 (d, J = 9.1 Hz, 1 H), 6.62 (d, J = 7.1 Hz, 1 H), 3.84-3.78 (m, 4 H), 3.19 (dd, J = 4.5, 4.5 Hz, 4 H), 2.45-2.38 (m, 1 H), 1.91-1.79 (m, 4 H), 1.74-1.70 (m, 1 H), 1.52-1.23 (m, 6 H). | A 5-morpholino-pyridin-2-amine CB19 |
| I-160 | 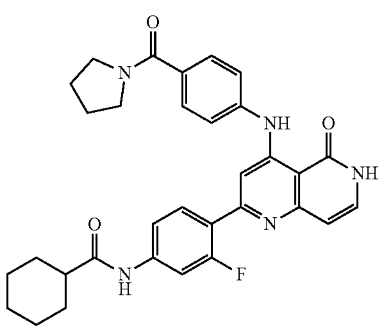 [SMILES: O=C(Nc1ccc(-c2cc(Nc3ccc(C(=O)N4CCCC4)cc3)c3c(=O)[nH]ccc3n2)c(F)c1)C1CCCCC1] | N-[3-fluoro-4-[5-oxo-4-[4-(pyrrolidine-1-carbonyl)anilino]-6H-1,6-naphthyridin-2-yl]phenyl]cyclohexane carboxamide | Method BicarbB EHC18, m/z = 554 [M + H]+, Ret. time = 4.49 min. | $^1$H NMR (400 MHz, DMSO): δ 11.80 (s, 1 H), 11.69 (d, J = 1.3 Hz, 1 H), 10.26 (s, 1 H), 8.07 (dd, J = 9.0, 9.0 Hz, 1 H), 7.79-7.77 (m, 1 H), 7.74 (d, J = 1.8 Hz, 1 H), 7.68 (d, J = 8.3 Hz, 2 H), 7.51-7.45 (m, 4 H), 6.62 (d, J = 7.3 Hz, 1 H), 3.52 (s, 4 H), 1.94-1.93 (m, 1 H), 1.92-1.87 (m, 6 H), 1.86-1.80 (m, 2 H), 1.72-1.69 (m, 1 H), 1.51-1.41 (m, 2 H), 1.35-1.25 (m, 3 H). | A (4-amino-phenyl)(pyrrolidin-1-yl)methanone CB19 |
| I-161 | 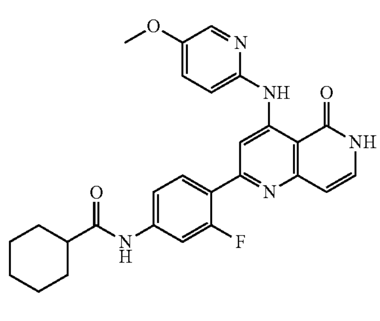 [SMILES: COc1ccc(Nc2cc(-c3ccc(NC(=O)C4CCCCC4)cc3F)nc3cc[nH]c(=O)c23)nc1] | N-[3-fluoro-4-[4-[(5-methoxy-2-pyridyl)amino]-5-oxo-6H-1,6-naphthyridin-2-yl]phenyl]cyclohexane carboxamide | Method AcHSS C18, m/z = 488 [M + H]+, Ret. time = 3.81 min. | $^1$H NMR (400 MHz, DMSO): δ 12.55 (s, 1 H), 11.72 (s, 1 H), 10.29 (s, 1 H), 8.84 (s, 1 H), 8.17 (d, J = 2.8 Hz, 1 H), 8.05 (dd, J = 8.8, 8.8 Hz, 1 H), 7.83 (d, J = 1.3 Hz, 1 H), 7.55-7.45 (m, 3 H), 7.17 (d, J = 8.8 Hz, 1 H), 6.64 (d, J = 7.3 Hz, 1 H), 3.89 (s, 3 H), 2.72 (s, 1 H), 2.44-2.38 (m, 1 H), 1.84 (dd, J = 11.7, 24.6 Hz, 4 H), 1.73-1.70 (m, 1 H), 1.52-1.26 (m, 4 H). | A 5-methoxy pyridin-2-amine CB19 |

TABLE 2-continued

| I-# | STRUCTURE | NAME | LCMS | HNMR | Method SM |
|-----|-----------|------|------|------|-----------|
| I-162 | 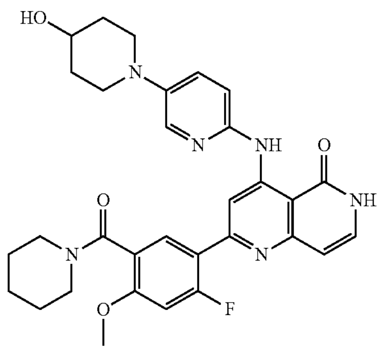 [SMILES: COc1cc(F)c(-c2cc(Nc3ccc(N4CCC(O)CC4)cn3)c3c(=O)[nH]ccc3n2)cc1C(=O)N1CCCCC1] | 2-[2-fluoro-5-methoxy-4-(piperidine-1-carbonyl)phenyl]-4-[[5-(4-hydroxy-1-piperidyl)-2-pyridyl]amino]-6H-1,6-naphthyridin-5-one | Method AcHSS C18, m/z = 573 [M + H]+, Ret. time = 2.92 min. | $^1$H NMR (400 MHz, DMSO): δ 12.44 (s, 1 H), 11.67 (s, 1 H), 8.81 (s, 1 H), 8.10 (d, J = 2.8 Hz, 1 H), 7.92 (d, J = 8.8 Hz, 1 H), 7.53 (dd, J = 2.9, 9.0 Hz, 1 H), 7.46 (d, J = 5.6 Hz, 1 H), 7.07 (d, J = 9.1 Hz, 1 H), 6.64 (d, J = 7.3 Hz, 1 H), 4.77 (d, J = 4.3 Hz, 1 H), 3.94 (s, 3 H), 3.70-3.53 (m, 6 H), 3.21 (s, 2 H), 2.96-2.89 (m, 2 H), 1.90-1.84 (m, 2 H), 1.65-1.45 (m, 8 H). | A 1-(6-aminopyridin-3-yl)piperidin-4-ol CB27 |
| I-163 | 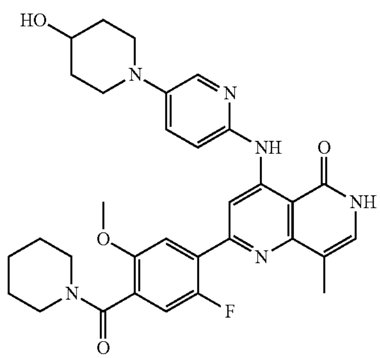 [SMILES: COc1cc(-c2cc(Nc3ccc(N4CCC(O)CC4)cn3)c3c(=O)[nH]cc(C)c3n2)c(F)cc1C(=O)N1CCCCC1] | 2-[2-fluoro-5-methoxy-4-(piperidine-1-carbonyl)phenyl]-4-[[5-(4-hydroxy-1-piperidyl)-2-pyridyl]amino]-8-methyl-6H-1,6-naphthyridin-5-one | Method AcHSS C18, m/z = 587 [M + H]+, Ret. time = 3.32 min. | $^1$H NMR (400 MHz, DMSO): δ 12.68 (s, 1 H), 11.59 (s, 1 H), 8.89 (s, 1 H), 8.12 (d, J = 2.5 Hz, 1 H), 7.78 (d, J = 6.1 Hz, 1 H), 7.53 (dd, J = 2.9, 9.0 Hz, 1 H), 7.37 (s, 1 H), 7.06 (d, J = 8.8 Hz, 1 H), 4.76 (d, J = 4.0 Hz, 1 H), 3.91 (s, 3 H), 3.70-3.53 (m, 6 H), 3.25-3.21 (m, 2 H), 2.94-2.88 (m, 2 H), 2.32 (s, 3 H), 1.88 (d, J = 9.3 Hz, 2 H), 1.67-1.50 (m, 8 H). | A 2-chloro-4-((5-(4-hydroxypiperidin-1-yl)pyridin-2-yl)amino)-8-methyl-1,6-naphthyridin-5(6H)-one (12.0) CB1 |
| I-164 | 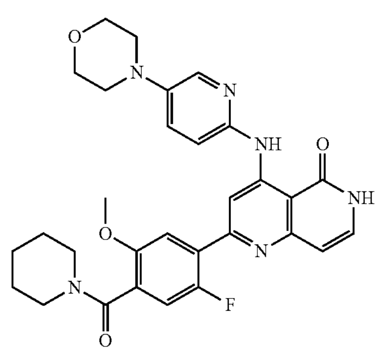 [SMILES: COc1cc(-c2cc(Nc3ccc(N4CCOCC4)cn3)c3c(=O)[nH]ccc3n2)c(F)cc1C(=O)N1CCCCC1] | 2-[2-fluoro-5-methoxy-4-(piperidine-1-carbonyl)phenyl]-4-[(5-morpholino-2-pyridyl)amino]-6H-1,6-naphthyridin-5-one | Method AcHSS C18, m/z = 559.2 [M + H]+, Ret. time = 3.39 min. | $^1$H NMR (400 MHz, DMSO): δ 12.54 (s, 1 H), 11.73-11.71 (m, 1 H), 8.83 (s, 1 H), 8.13 (d, J = 2.5 Hz, 1 H), 7.61 (d, J = 6.1 Hz, 1 H), 7.54 (dd, J = 2.8, 8.8 Hz, 1 H), 7.48 (d, J = 7.3 Hz, 1 H), 7.29 (d, J = 9.1 Hz, 1 H), 7.11 (d, J = 9.1 Hz, 1 H), 6.66 (d, J = 7.3 Hz, 1 H), 3.91 (s, 3 H), 3.80 (dd, J = 4.5, 4.5 Hz, 4 H), 3.71-3.59 (m, 2 H), 3.23-3.15 (m, 6 H), 1.70-1.50 (m, 6 H). | A 5-morpholinopyridin-2-amine CB1 |
| I-165 | 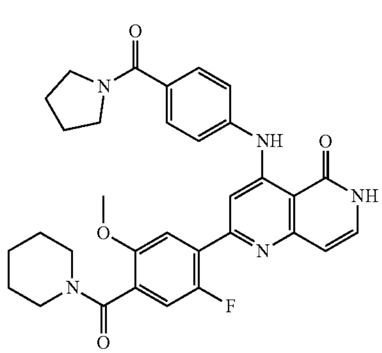 [SMILES: COc1cc(-c2cc(Nc3ccc(C(=O)N4CCCC4)cc3)c3c(=O)[nH]ccc3n2)c(F)cc1C(=O)N1CCCCC1] | 2-[2-fluoro-5-methoxy-4-(piperidine-1-carbonyl)phenyl]-4-[4-(pyrrolidine-1-carbonyl)amino]-6H-1,6-naphthyridin-5-one | Method BicarbB EHC18, m/z = 571 [M + H]+, Ret. time = 3.98 min. | $^1$H NMR (400 MHz, DMSO): δ 11.79 (s, 1 H), 11.73 (s, 1 H), 7.64-7.57 (m, 2 H), 7.46-7.39 (m, 4 H), 7.19 (d, J = 7.1 Hz, 1 H), 6.60 (d, J = 7.1 Hz, 1 H), 3.84 (s, 3 H), 3.65-3.53 (m, 2 H), 3.46 (dd, J = 10.1, 10.1 Hz, 4 H), 3.12 (dd, J = 6.1, 6.1 Hz, 2 H), 2.07 (s, 1 H), 1.85-1.84 (m, 4 H), 1.54 (dd, J = 4.4, 21.3 Hz, 4 H), 1.45 (d, J = 5.3 Hz, 2 H). | A (4-aminophenyl)(pyrrolidin-1-yl)methanone CB1 |

TABLE 2-continued

| I-# | STRUCTURE | NAME | LCMS | HNMR | Method SM |
|---|---|---|---|---|---|
| I-166 | 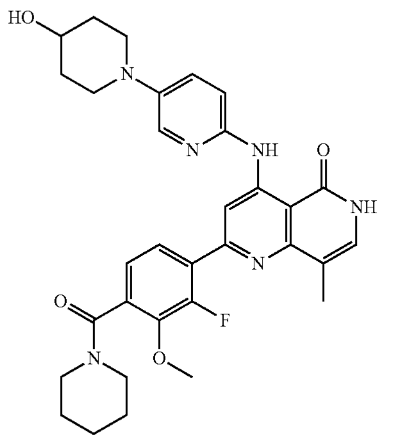 | 2-[2-fluoro-3-methoxy-4-(piperidine-1-carbonyl)phenyl]-4-[[5-(4-hydroxy-1-piperidyl)-2-pyridyl]amino]-6H-1,6-naphthyridin-5-one | Method AcHSS C18, m/z 573.3 [M + H]+, Ret. time = 2.95 min. | $^1$H NMR (400 MHz, DMSO): δ 12.47 (s, 1 H), 11.70-11.70 (m, 1 H), 8.71 (d, J = 1.5 Hz, 1 H), 8.09 (d, J = 2.9 Hz, 1 H), 7.67-7.63 (m, 1 H), 7.49 (dd, J = 3.1, 9.0 Hz, 1 H), 7.44 (d, J = 7.3 Hz, 1 H), 7.17 (d, J = 8.0 Hz, 1 H), 7.04 (d, J = 8.9 Hz, 1 H), 6.59 (d, J = 7.3 Hz, 1 H), 3.90 (s, 3 H), 3.72-3.49 (m, 5 H), 3.21 (dd, J = 5.5, 5.5 Hz, 3 H), 2.92-2.83 (m, 2 H), 1.88-1.80 (m, 2 H), 1.65-1.45 (m, 8 H). | A 1-(6-amino-pyridin-3-yl)piperidin-4-ol CB28 |
| I-167 | 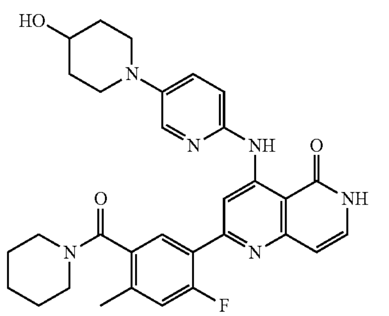 [SMILES: Cc1cc(F)c(-c2cc(Nc3ccc(N4CCC(O)CC4)cn3)c3c(=O)[nH]ccc3n2)cc1C(=O)N1CCCCC1] | 2-[2-fluoro-4-methyl-5-(piperidine-1-carbonyl)phenyl]-4-[[5-(4-hydroxy-1-piperidyl)-2-pyridyl]amino]-6H-1,6-naphthyridin-5-one | Method AcHSS C18, m/z = 557 [M + H]+, Ret. time = 2.95 min. | $^1$H NMR (400 MHz, DMSO): δ 12.44 (s, 1 H), 11.67-11.65 (m, 1 H), 8.75 (s, 1 H), 8.06 (d, J = 3.0 Hz, 1 H), 7.79 (d, J = 8.0 Hz 1 H), 7.49 (dd, J = 3.1, 9.0 Hz, 1 H), 7.42 (d, J = 7.3 Hz, 1 H), 7.04 (d, J = 8.9 Hz, 1 H), 6.60 (d, J = 7.3 Hz, 1 H), 4.70 (d, J = 4.3 Hz, 1 H), 3.68-3.49 (m, 6 H), 3.18 (dd, J = 5.3, 5.3 Hz, 2 H), 2.92-2.84 (m, 2 H), 2.30 (s, 3 H), 1.87-1.81 (m, 2 H), 1.64-1.43 (m, 8 H). | A 1-(6-amino-pyridin-3-yl)piperidin-4-ol CB29 |
| I-168 | 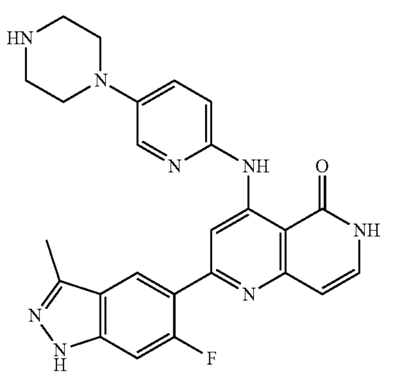 [SMILES: Cc1n[nH]c2cc(F)c(-c3cc(Nc4ccc(N5CCNCC5)cn4)c4c(=O)[nH]ccc4n3)cc12] | 2-(6-fluoro-3-methyl-1H-indazol-5-yl)-4-[[5-piperazin-1-yl-2-pyridyl]amino]-6H-1,6-naphthyridin-5-one | Method AcHSS C18, m/z = 471 [M + H]+, Ret. time = 1.92 min. | $^1$H NMR (400 MHz, DMSO): δ 12.89-12.80 (m, 1 H), 12.48 (s, 1 H), 11.71-11.59 (m, 1 H), 8.76-8.75 (m, 1 H), 8.30-8.27 (m, 1 H), 8.21 (s, 1 H), 8.10-8.08 (m, 1 H), 7.51 (dd, J = 3.1, 9.0 Hz, 1 H), 7.45-7.37 (m, 2 H), 7.09-7.06 (m, 1 H), 6.66-6.63 (m, 1 H), 3.85 (s, 3 H), 3.25-3.20 (m, 4 H), 3.06 (t, J = 5.0 Hz, 4 H). | A and G tert-butyl 4-(6-amino-pyridin-3-yl)piperazine-1-carboxylate CB30 |
| I-169 | 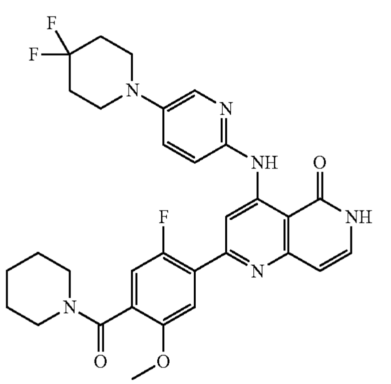 [SMILES: COc1cc(-c2cc(Nc3ccc(N4CCC(F)(F)CC4)cn3)c3c(=O)[nH]ccc3n2)c(F)cc1C(=O)N1CCCCC1] | 4-[[5-(4,4-difluoro-1-piperidyl)-2-pyridyl]amino]-2-[2-fluoro-5-methoxy-4-(piperidine-1-carbonyl)phenyl]-6H-1,6-naphthyridin-5-one | Method AcHSS C18, m/z = 593 [M + H]+, Ret. time = 3.85 min. | $^1$H NMR (400 MHz, DMSO): δ 12.56 (s, 1 H), 11.76-11.71 (m, 1 H), 8.84 (s, 1 H), 8.20 (d, J = 2.8 Hz, 1 H), 7.64-7.58 (m, 2 H), 7.47 (d, J = 6.6 Hz, 1 H), 7.27 (s, 1 H), 7.11 (d, J = 8.8 Hz, 1 H), 6.66 (d, J = 7.1 Hz, 1 H), 3.91 (s, 3 H), 3.89 (s, 1 H), 3.68-3.62 (m, 3 H), 3.21 (s, 3 H), 2.19-2.09 (m, 4 H), 1.64 (dd, J = 4.4, 20.8 Hz, 4 H), 1.52-1.49 (m, 3 H). | A 5-(4,4-difluoro-piperidin-1-yl)pyridin-2-amine CB1 |

TABLE 2-continued

| I-# | STRUCTURE | NAME | LCMS | HNMR | Method SM |
|---|---|---|---|---|---|
| I-170 | 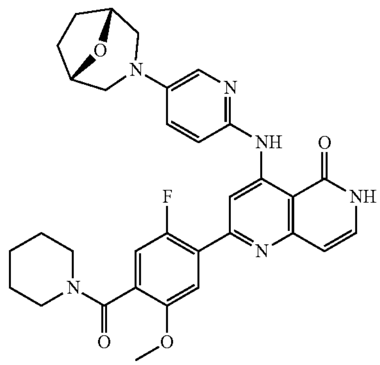 [SMILES: COc1cc(-c2cc(Nc3ccc(N4C[C@H]5CC[C@@H](C4)O5)cn3)c3c(=O)[nH]ccc3n2)c(F)cc1C(=O)N1CCCCC1] | 2-[2-fluoro-5-methoxy-4-(piperidine-1-carbonyl)phenyl]-4-[[5-[(1R,5S)-8-oxa-3-azabicyclo[3.2.1]octan-3-yl]-2-pyridyl]amino]-6H-1,6-naphthyridin-5-one | Method AcHSS C18, m/z = 585.3 [M + H]+, Ret. time = 3.45 min. | $^1$H NMR (400 MHz, DMSO): δ 12.46 (s, 1 H), 11.72 (s, 1 H), 8.76 (s, 1 H), 8.04 (d, J = 2.5 Hz, 1 H), 7.62 (d, J = 6.1 Hz, 1 H), 7.50-7.41 (m, 2 H), 7.28 (d, J = 8.8 Hz, 1 H), 7.09 (d, J = 8.8 Hz, 1 H), 6.65 (d, J = 7.1 Hz, 1 H), 4.51-4.45 (m, 2 H), 3.91 (s, 3 H), 3.70-3.62 (m, 2 H), 3.47 (d, J = 10.6 Hz, 2 H), 3.22-3.17 (m, 2 H), 2.87 (d, J = 9.6 Hz, 2 H), 1.91 (s, 4 H), 1.67-1.60 (m, 4 H), 1.53-1.47 (m, 2 H). | A 5-((1R,5S)-8-oxa-3-azabicyclo[3.2.1]octan-3-yl)pyridin-2-amine CB1 |
| I-171 | 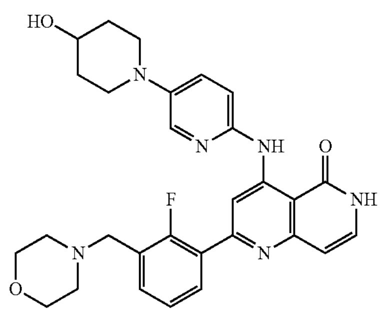 [SMILES: O=c1[nH]ccc2nc(-c3cccc(CN4CCOCC4)c3F)cc(Nc3ccc(N4CCC(O)CC4)cn3)c12] | 2-[2-fluoro-3-(morpholinomethyl)phenyl]-4-[[5-(4-hydroxy-1-piperidyl)-2-pyridyl]amino]-6H-1,6-naphthyridin-5-one | Method AcHSS C18, m/z = 531 [M + H]+, Ret. time = 1.98 min. | $^1$H NMR (400 MHz, DMSO): δ 12.42 (s, 1 H), 11.66 (d, J = 5.3 Hz, 1 H), 8.63 (d, J = 1.5 Hz, 1 H), 8.22 (s, 1 H), 8.06 (d, J = 3.0 Hz, 1 H), 7.81-7.76 (m, 1 H), 7.56-7.46 (m, 2 H), 7.44-7.40 (m, 1 H), 7.32 (dd, J = 7.6, 7.6 Hz, 1 H), 7.03 (d, J = 8.9 Hz, 1 H), 6.58 (d, J = 7.0 Hz, 1 H), 3.51-3.78 (m, 6 H), 3.57-3.48 (m, 2 H), 2.91-2.83 (m, 2 H), 2.70-2.55 (m, 1 H), 2.44 (d, J = 4.3, 4.3 Hz, 4 H), 1.87-1.80 (m, 2 H), 1.56-1.45 (m, 2 H). | A 1-(6-amino-pyridin-3-yl)piperidin-4-ol 4-(2-fluoro-3-(4,4,5,5-tetramethyl-1,3,2-dioxaborolan-2-yl)benzyl)morpholine |
| I-172 | 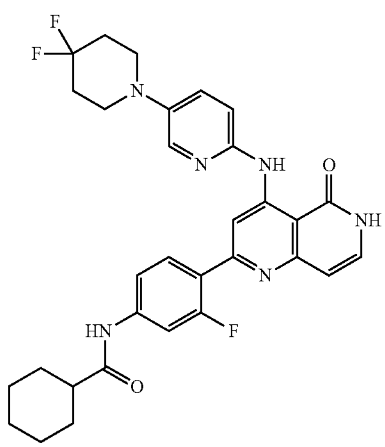 [SMILES: O=C(Nc1ccc(-c2cc(Nc3ccc(N4CCC(F)(F)CC4)cn3)c3c(=O)[nH]ccc3n2)c(F)c1)C1CCCCC1] | N-[4-[4-[[5-(4,4-difluoro-1-piperidyl)-2-pyridyl]amino]-5-oxo-6H-1,6-naphthyridin-2-yl]-3-fluorophenyl]cyclohexane-carboxamide | Method AcHSS C18, m/z = 577 [M + H]+, Ret. time = 4.2 min. | $^1$H NMR (400 MHz, DMSO): δ 12.43 (s, 1 H), 10.23 (s, 1 H), 8.78 (s, 1 H), 8.15 (d, J = 2.5 Hz, 1 H), 7.99 (dd, J = 8.5, 8.5 Hz, 1 H), 7.75 (d, J = 8.9 Hz, 1 H), 7.56 (dd, J = 2.9, 8.8 Hz, 1 H), 7.46 (d, J = 8.5 Hz, 1 H), 7.41 (d, J = 7.3 Hz, 1 H), 7.06 (d, J = 8.9 Hz, 1 H), 6.60 (d, J = 7.3 Hz, 1 H), 3.34 (dd, J = 5.6, 5.6 Hz, 4 H), 2.40-2.34 (m, 4 H), 2.14-2.04 (m, 4 H), 1.85-1.76 (m, 4 H), 1.66 (s, 2 H), 1.45-1.39 (m, 2 H). | A 5-(4,4-difluoro-piperidin-1-yl)pyridin-2-amine CB19 |

| I-# | STRUCTURE | NAME | LCMS | HNMR | Method SM |
|---|---|---|---|---|---|
| I-173 | 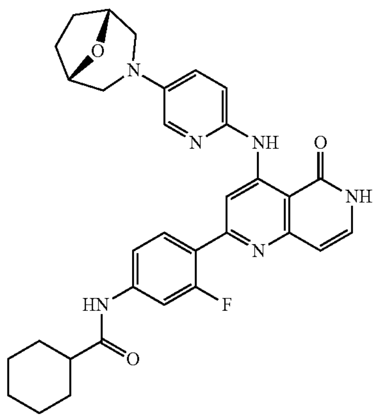 [SMILES: O=C(Nc1ccc(-c2cc(Nc3ccc(N4C[C@H]5CC[C@@H](C4)O5)cn3)c3c(=O)[nH]ccc3n2)c(F)c1)C1CCCCC1] | N-[3-fluoro-4-[4-[[5-[(1R,5S)-8-oxa-3-azabicyclo[3.2.1]octan-3-yl]-2-pyridyl]amino]-5-oxo-6H-1,6-naphthyridin-2-yl]phenyl]-cyclohexane-carboxamide | Method BicarbB EHC18, m/z = 569.3 [M + H]+, Ret. time = 4.82 min. | $^1$H NMR (400 MHz, DMSO): δ 12.36 (s, 1 H), 11.61 (d, J = 4.6 Hz, 1 H), 10.21 (s, 1 H), 8.71 (s, 1 H), 8.03-7.97 (m, 2 H), 7.75 (dd, J = 2.0, 8.7 Hz, 1 H), 7.46 (dd, J = 2.0, 8.7 Hz, 1 H), 7.39 (dd, J = 3.1, 8.8 Hz, 2 H), 7.04 (d, J = 9.0 Hz, 1 H), 6.57 (d, J = 7.3 Hz, 1 H), 4.46-4.43 (m, 2 H), 3.45-3.38 (m, 2 H), 2.85 (dd, J = 2.3, 11.2 Hz, 2 H), 2.42-2.34 (m, 2 H), 1.89-1.75 (m, 6 H), 1.69 (d, J = 11.2 Hz, 1 H), 1.48-1.19 (m, 6 H). | A 5-((1R,5S)-8-oxa-3-azabicyclo[3.2.1]octan-3-yl)pyridin-2-amine CB19 |
| I-174 | 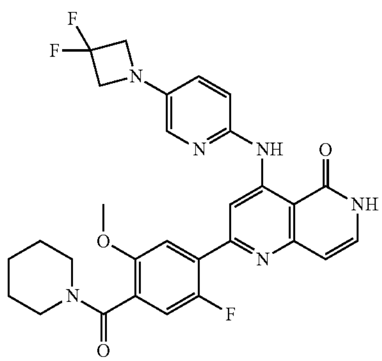 [SMILES: COc1cc(-c2cc(Nc3ccc(N4CC(F)(F)C4)cn3)c3c(=O)[nH]ccc3n2)c(F)cc1C(=O)N1CCCCC1] | 4-[[5-(3,3-difluoro-azetidin-1-yl)-2-pyridyl]amino]-2-[2-fluoro-5-methoxy-4-(piperidine-1-carbonyl)phenyl]-6H-1,6-naphthyridin-5-one | Method AcHSS C18, m/z = 565 [M + H]+, Ret. time = 3.66 min. | $^1$H NMR (400 MHz, DMSO): δ 12.48 (s, 1 H), 11.68 (d, J = 1.5 Hz, 1 H), 8.77 (s, 1 H), 7.79 (d, J = 2.0 Hz, 1 H), 7.58 (d, J = 5.8 Hz, 1 H), 7.42 (d, J = 7.1 Hz, 1 H), 7.25 (dd, J = 2.9, 8.5 Hz, 1 H), 7.14 (dd, J = 2.9, 8.5 Hz, 1 H), 7.08 (d, J = 8.6 Hz, 1 H), 6.61 (d, J = 7.3 Hz, 1 H), 4.33 (dd, J = 12.3, 12.3 Hz, 4 H), 3.85 (s, 3 H), 3.64-3.54 (m, 2 H), 3.15 (s, 2 H), 1.62-1.54 (m, 4 H), 1.48-1.43 (m, 2 H). | A 5-(3,3-difluoro-azetidin-1-yl)pyridin-2-amine CB1 |
| I-175 | 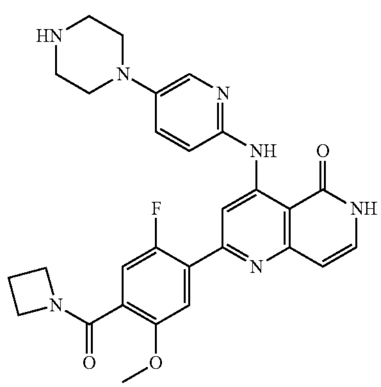 [SMILES: COc1cc(-c2cc(Nc3ccc(N4CCNCC4)cn3)c3c(=O)[nH]ccc3n2)c(F)cc1C(=O)N1CCC1] | 2-[4-(azetidine-1-carbonyl)-2-fluoro-5-methoxy-phenyl]-4-[(5-piperazin-1-yl-2-pyridyl)amino]-6H-1,6-naphthyridin-5-one | Method AcHSS C18, m/z = 530 [M + H]+, Ret. time = 1.99 min. | $^1$H NMR (400 MHz, DMSO): δ 12.45 (s, 1 H), 8.74 (s, 1 H), 8.05 (d, J = 2.8 Hz, 1 H), 7.58 (d, J = 6.1 Hz, 1 H), 7.48-7.40 (m, 2 H), 7.29 (d, J = 8.8 Hz, 1 H), 7.03 (d, J = 8.8 Hz, 1 H), 6.60 (d, J = 7.3 Hz, 1 H), 4.05-3.92 (m, 4 H), 3.88 (s, 3 H), 3.19 (s, 1 H), 3.07 (dd, J = 4.5, 4.5 Hz, 4 H), 2.86 (dd, J = 4.9, 4.9 Hz, 4 H), 2.33-2.20 (m, 3 H). | F and G tert-butyl 4-(6-amino-pyridin-3-yl)piperazine-1-carboxylate azetidine (step 2) |
| I-176 | 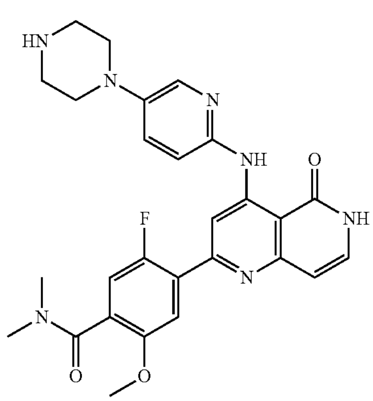 [SMILES: COc1cc(-c2cc(Nc3ccc(N4CCNCC4)cn3)c3c(=O)[nH]ccc3n2)c(F)cc1C(=O)N(C)C] | 5-fluoro-2-methoxy-N,N-dimethyl-4-[5-oxo-4-[(5-piperazin-1-yl-2-pyridyl)amino]-6H-1,6-naphthyridin-2-yl]benzamide | Method AcHSS C18, m/z = 518 [M + H]+, Ret. time = 1.97 min. | $^1$H NMR (400 MHz, DMSO): δ 12.44 (s, 1 H), 8.75 (s, 1 H), 8.05 (d, J = 2.8 Hz, 1 H), 7.58 (d, J = 5.8 Hz, 1 H), 7.48-7.40 (m, 2 H), 7.24 (d, J = 8.8 Hz, 1 H), 7.03 (d, J = 8.8 Hz, 1 H), 6.61 (d, J = 7.1 Hz, 1 H), 3.86 (s, 3 H), 3.23-3.13 (m, 2 H), 3.07 (dd, J = 4.4, 4.4 Hz, 4 H), 2.99 (s, 3 H), 2.86 (dd, J = 4.4, 4.4 Hz, 4 H), 2.82 (s, 3 H). | F and G tert-butyl 4-(6-amino-pyridin-3-yl)piperazine-1-carboxylate dimethyl amine (step 2) |

TABLE 2-continued

| I-# | STRUCTURE | NAME | LCMS | HNMR | Method SM |
|---|---|---|---|---|---|
| I-177 | 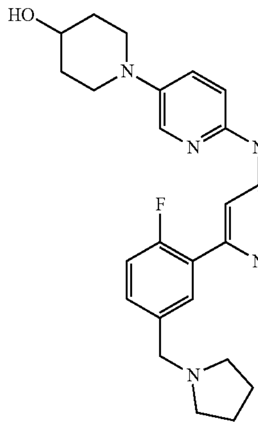 | 2-[2-fluoro-5-(pyrrolidin-1-ylmethyl)phenyl]-4-[[5-(4-hydroxy-1-piperidyl)-2-pyridyl]amino]-6H-1,6-naphthyridin-5-one | Method AcHSS C18, m/z = 515 [M + H]+, Ret. time = 2.06 min. | $^1$H NMR (400 MHz, DMSO): δ 12.45 (s, 1 H), 8.71 (d, J = 1.6 Hz, 1 H), 8.06 (d, J = 3.0 Hz, 1 H), 7.87 (dd, J = 2.3, 7.7 Hz, 1 H), 7.50-7.41 (m, 3 H), 7.28 (dd, J = 8.4, 11.2 Hz, 1 H), 7.03 (d, J = 8.9 Hz, 1 H), 6.61 (d, J = 7.2 Hz, 1 H), 4.71-4.70 (m, 1 H), 3.64 (s, 3 H), 3.57-3.48 (m, 2 H), 2.91-2.83 (m, 2 H), 2.49-2.41 (m, 5 H), 1.88-1.80 (m, 2 H), 1.73-1.68 (m, 4 H), 1.56-1.45 (m, 2 H). | A 1-amino-pyridin-3-yl) piperidin-4-ol 1-(4-fluoro-3-(4,4,5,5-tetramethyl-1,3,2-dioxa-borolan-2-yl)benzyl) pyrrolidine |
| I-178 | 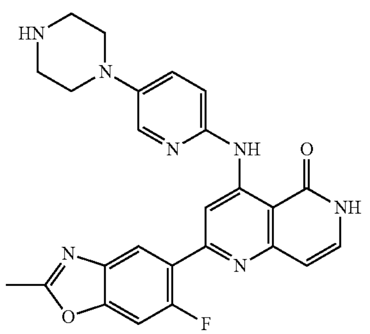 [SMILES: Cc1nc2cc(-c3cc(Nc4ccc(N5CCNCC5)cn4)c4c(=O)[nH]ccc4n3)c(F)cc2o1] | 2-(6-fluoro-2-methyl-1,3-benzoxazol-5-yl)-4-[(5-piperazin-1-yl-2-pyridyl)amino]-6H-1,6-naphthyridin-5-one | Method AcHSS C18, m/z = 472 [M + H]+, Ret. time = 2.02 min. | $^1$H NMR (400 MHz, DMSO): δ 12.50 (s, 1 H), 8.77 (d, J = 2.0 Hz, 1 H), 8.22-8.14 (m, 2 H), 8.08 (d, J = 3.0 Hz, 1 H), 7.83 (d, J = 10.4 Hz, 1 H), 7.52-7.42 (m, 2 H), 7.09-7.05 (m, 1 H), 6.64-6.62 (m, 1 H), 3.32 (br, 1 H), 3.19-3.14 (m, 4 H), 3.01-2.96 (m, 4 H), 2.67-2.66 (m, 3 H). | A and G tert-butyl 4-(6-amino-pyridin-3-yl) piperazine-1-carboxylate CB31 |
| I-179 | 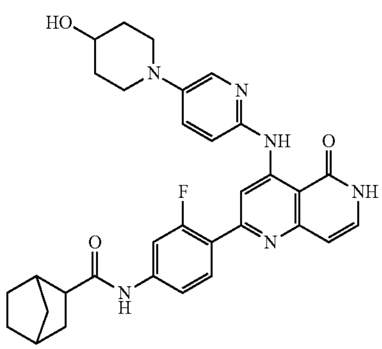 [SMILES: O=C(Nc1ccc(-c2cc(Nc3ccc(N4CCC(O)CC4)cn3)c3c(=O)[nH]ccc3n2)c(F)c1)C1CC2CCC1C2] | N-[3-fluoro-4-[4-[[5-(4-hydroxy-1-piperidyl)-2-pyridyl]amino]-5-oxo-6H-1,6-naphthyridin-2-yl]phenyl]norbornane-2-carboxamide | Method AcHSS C18, m/z = 569.3 [M + H]+, Ret. time = 3.46 min. | $^1$H NMR (400 MHz, DMSO): δ 12.36 (s, 1 H), 11.59 (d, J = 5.3 Hz, 1 H), 10.16 (s, 1 H), 8.71 (s, 1 H), 8.17 (s, 1 H), 8.06 (d, J = 2.5 Hz, 1 H), 8.02-7.94 (m, 1 H), 7.77-7.71 (m, 1 H), 7.49-7.43 (m, 2 H), 7.38 (dd, J = 6.6, 6.6 Hz, 1 H), 7.01 (d, J = 9.1 Hz, 1 H), 6.56 (d, J = 7.3 Hz, 1 H), 4.68-4.68 (m, 1 H), 3.66-3.60 (m, 1 H), 2.87 (dd, J = 9.7, 9.7 Hz, 3 H), 2.43 (d, J = 13.6 Hz, 1 H), 2.28-2.22 (m, 2 H), 1.87-1.81 (m, 2 H), 1.69-1.65 (m, 2 H), 1.58-1.22 (m, 8 H). | A 1-(6-amino-pyridin-3-yl) piperidin-4-ol CB32 |
| I-180 | 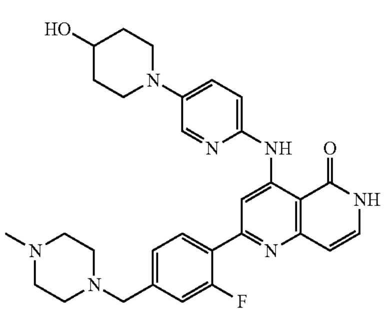 [SMILES: CN1CCN(Cc2ccc(-c3cc(Nc4ccc(N5CCC(O)CC5)cn4)c4c(=O)[nH]ccc4n3)c(F)c2)CC1] | 2-[2-fluoro-4-[(4-methyl-piperazin-1-yl)methyl]phenyl]-4-[[5-(4-hydroxy-1-piperidyl)-2-pyridyl]amino]-6H-1,6-naphthyridin-5-one | Method AcHSS C18, m/z = 544.3 [M + H]+, Ret. time = 2.22 min. | $^1$H NMR (400 MHz, DMSO): δ 12.43 (s, 1 H), 11.67 (s, 1 H), 8.46 (s, 1 H), 8.11 (d, J = 2.3 Hz, 1 H), 7.60-7.54 (m, 1 H), 7.50 (dd, J = 2.8, 8.8 Hz, 1 H), 7.45 (d, J = 7.1 Hz, 1 H), 7.32-7.25 (m, 2 H), 7.06 (d, J = 8.8 Hz, 1 H), 6.58 (d, J = 7.3 Hz, 1 H), 4.73 (d, J = 3.8 Hz, 1 H), 3.71-3.64 (m, 1 H), 3.37 (s, 3 H), 2.89 (dd, J = 10.0, 10.0 Hz, 2 H), 2.34-2.28 (m, 4 H), 2.15-2.14 (m, 4 H), 2.07 (s, 3 H), 1.88-1.86 (m, 3 H), 1.59-1.47 (m, 2 H). | A 1-(6-amino-pyridin-3-yl) piperidin-4-ol 1-(3-fluoro-4-(4,4,5,5-tetramethyl-1,3,2-dioxa-borolan-2-yl)benzyl)-4-methyl-piperazine |

TABLE 2-continued

| I-# | STRUCTURE | NAME | LCMS | HNMR | Method SM |
|---|---|---|---|---|---|
| I-181 | 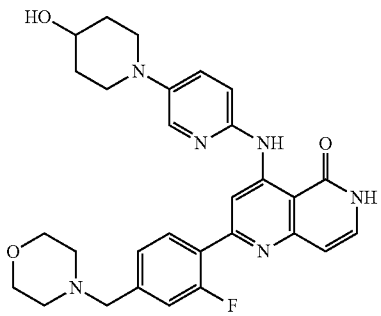 [SMILES: O=c1[nH]ccc2nc(-c3ccc(CN4CCOCC4)cc3F)cc(Nc3ccc(N4CCC(O)CC4)cn3)c12] | 2-[2-fluoro-4-(morpholino-methyl)phenyl]-4-[[5-(4-hydroxy-1-piperidyl)-2-pyridyl]amino]-6H-1,6-naphthyridin-5-one | Method BicarbB EHC18, m/z = 531 [M + H]+, Ret. time = 3.41 min. | $^1$H NMR (400 MHz, DMSO): δ 12.46 (s, 1 H), 11.67 (s, 1 H), 8.75 (s, 1 H), 8.11 (d, J = 2.5 Hz, 1 H), 7.97 (dd, J = 8.1, 8.1 Hz, 1 H), 7.52 (dd, J = 2.8, 8.8 Hz, 1 H), 7.45 (d, J = 7.1 Hz, 1 H), 7.34 (d, J = 7.3 Hz, 1 H), 7.06 (d, J = 9.1 Hz, 1 H), 6.62 (d, J = 7.3 Hz, 1 H), 4.74 (d, J = 3.5 Hz, 1 H), 3.63 (s, 4 H), 3.66-3.53 (m, 6 H), 2.91 (dd, J = 9.9, 9.9 Hz, 2 H), 2.45 (s, 4 H), 1.88 (d, J = 10.1 Hz, 2 H), 1.60-1.49 (m, 2 H). | A 1-(6-amino-pyridin-3-yl) piperidin-4-ol 4-(3-fluoro-4-(4,4,5,5-tetramethyl-1,3,2-dioxa-borolan-2-yl)benzyl) morpholine |
| I-182 | 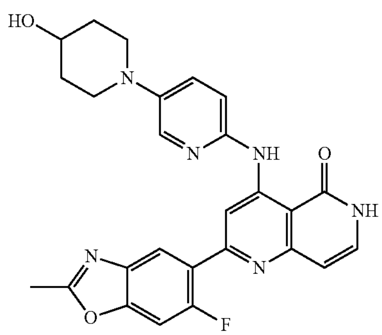 [SMILES: Cc1nc2cc(-c3cc(Nc4ccc(N5CCC(O)CC5)cn4)c4c(=O)[nH]ccc4n3)c(F)cc2o1] | 2-(6-fluoro-2-methyl-1,3-benzoxazol-5-yl)-4-[[5-(4-hydroxy-1-piperidyl)-2-pyridyl]amino]-6H-1,6-naphthyridin-5-one | Method AcHSS C18, m/z = 487.2 [M + H]+, Ret. time = 2.66 min. | $^1$H NMR (400 MHz, DMSO): δ 12.47 (s, 1 H), 11.72-11.66 (m, 1 H), 8.73 (d, J = 2.0 Hz, 1 H), 8.14 (d, J = 7.0 Hz, 1 H), 8.07 (d, J = 3.0 Hz, 1 H), 7.83 (d, J = 10.4 Hz, 1 H), 7.50-7.42 (m, 2 H), 7.05-7.02 (m, 1 H), 6.62 (d, J = 7.3 Hz, 1 H), 4.69 (d, J = 3.1 Hz, 1 H), 3.67-3.63 (m, 1 H), 3.57-3.49 (m, 2 H), 2.91-2.83 (m, 2 H), 2.67 (s, 3 H), 1.86-1.81 (m, 2 H), 1.55-1.45 (m, 2 H). | A 1-(6-amino-pyridin-3-yl) piperidin-4ol CB31 |
| I-183 | 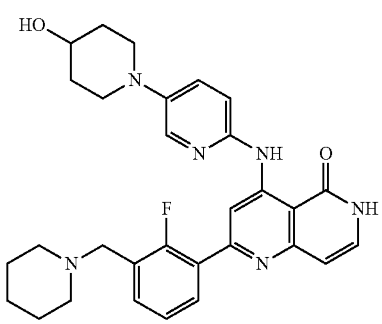 [SMILES: O=c1[nH]ccc2nc(-c3cccc(CN4CCCCC4)c3F)cc(Nc3ccc(N4CCC(O)CC4)cn3)c12] | 2-[2-fluoro-3-(1-piperidyl-methyl)phenyl]-4-[[5-(4-hydroxy-1-piperidyl)-2-pyridyl]amino]-6H-1,6-naphthyridin-5-one | Method AcHSS C18, m/z = 529 [M + H]+, Ret. time = 2.03 min. | $^1$H NMR (400 MHz, DMSO): δ 12.42 (s, 1 H), 11.68-11.64 (m, 1 H), 8.63 (d, J = 1.5 Hz, 1 H), 8.22 (s, 1 H), 8.06 (d, J = 3.0 Hz, 1 H), 7.79-7.74 (m, 1 H), 7.54-7.39 (m, 3 H), 7.31 (t, J = 7.6 Hz, 1 H), 7.05-7.01 (m, 1 H), 6.58 (d, J = 7.3 Hz, 1 H), 3.50 (d, J = 9.3 Hz, 2 H), 2.91-2.83 (m, 2 H), 2.44-2.37 (m, 6 H), 1.87-1.79 (m, 2 H), 1.55-1.38 (m, 9 H). | A 1-(6-amino-pyridin-3-yl) piperidin-4-ol 1-(2-fluoro-3-(4,4,5,5-tetramethyl-1,3,2-dioxa-borolan-2-yl)benzyl) piperidine |
| I-184 | 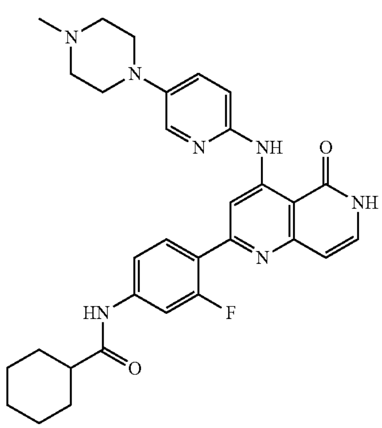 [SMILES: CN1CCN(c2ccc(Nc3cc(-c4ccc(NC(=O)C5CCCCC5)cc4F)nc4cc[nH]c(=O)c34)nc2)CC1] | N-[3-fluoro-4-[4-[[5-(4-methyl-piperazin-1-yl)-2-pyridyl]amino]-5-oxo-6H-1,6-naphthyridin-2-yl]phenyl]cyclohexane carboxamide | Method AcHSS C18, m/z = 556.3 [M + H]+, Ret. time = 2.59 min. | $^1$H NMR (400 MHz, DMSO): δ 12.40 (s, 1 H), 11.62 (d, J = 5.8 Hz, 1 H), 10.22 (s, 1 H), 8.75 (s, 1 H), 8.08 (d, J = 3.0 Hz, 1 H), 8.01 (dd, J = 8.8, 8.8 Hz, 1 H), 7.77 (d, J = 1.9 Hz, 1 H), 7.51-7.44 (m, 1 H), 7.43-7.38 (m, 1 H), 7.04 (d, J = 8.9 Hz, 1 H), 6.58 (d, J = 6.9 Hz, 1 H), 3.17 (dd, J = 5.0, 5.0 Hz, 4 H), 2.50-2.45 (m, 3 H), 2.42-2.34 (m, 2 H), 2.24 (s, 3 H), 1.86-1.77 (m, 4 H), 1.68 (d, J = 11.0 Hz, 1 H), 1.49-1.18 (m, 6 H). | A 5-(4-methyl-piperazin-1-yl) pyridin-2-amine CB19 |

TABLE 2-continued

| I-# | STRUCTURE | NAME | LCMS | HNMR | Method SM |
|---|---|---|---|---|---|
| I-185 | 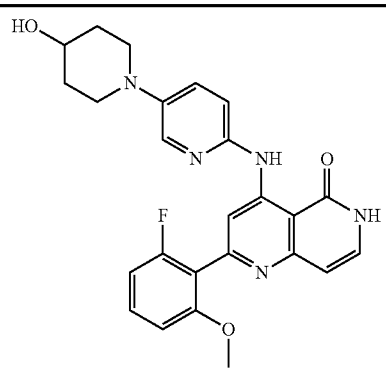 | 2-(2-fluoro-6-methoxy-phenyl)-4-[[5-(4-hydroxy-1-piperidyl)-2-pyridyl]amino]-6H-1,6-naphthyridin-5-one | Method AcHSS C18, m/z = 462 [M + H]+, Ret. time = 2.75 min. | $^1$H NMR (400 MHz, DMSO): δ 12.47 (s, 1 H), 11.66 (d, J = 5.6 Hz, 1 H), 8.31 (s, 1 H), 8.18 (s, 1 H), 8.04 (d, J = 3.0 Hz, 1 H), 7.50-7.38 (m, 2 H), 7.02-6.90 (m, 2 H), 6.53 (d, J = 7.0 Hz, 1 H), 4.69-4.68 (m, 1 H), 3.75 (s, 3 H), 3.66-3.56 (m, 2 H), 3.53-3.46 (m, 3 H), 3.18 (s, 1 H), 2.88-2.80 (m, 2 H), 1.85-1.78 (m, 2 H), 1.53-1.42 (m, 2 H). | A 1-(6-amino-pyridin-3-yl)piperidin-4-ol (2-fluoro-6-methoxy phenyl) boronic acid |
| I-186 | 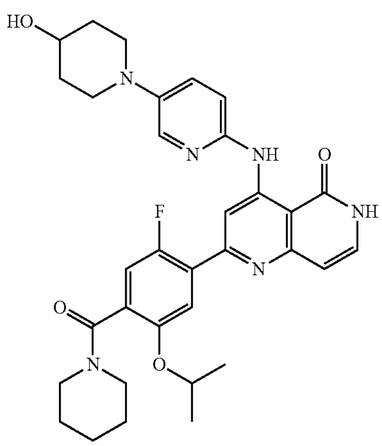 [SMILES: CC(C)Oc1cc(-c2cc(Nc3ccc(N4CCC(O)CC4)cn3)c3c(=O)[nH]ccc3n2)c(F)cc1C(=O)N1CCCCC1] | 2-[2-fluoro-5-isopropoxy-4-(piperidine-1-carbonyl)phenyl]-4-[[5-(4-hydroxy-1-piperidyl)-2-pyridyl]amino]-6H-1,6-naphthyridin-5-one | Method AcHSS C18, m/z = 601.3 [M + H]+, Ret. time = 3.25 min. | $^1$H NMR (400 MHz, DMSO): δ 12.44 (s, 1 H), 11.67 (d, J = 4.1 Hz, 1 H), 8.74 (d, J = 1.4 Hz, 1 H), 8.07 (d, J = 3.0 Hz, 1 H), 7.56 (d, J = 6.1 Hz, 1 H), 7.51-7.40 (m, 2 H), 7.21 (d, J = 8.9 Hz, 1 H), 7.04 (d, J = 8.9 Hz, 1 H), 6.60 (d, J = 7.3 Hz, 1 H), 4.70-4.62 (m, 1 H), 3.67-3.49 (m, 6 H), 3.23-3.16 (m, 2 H), 2.92-2.83 (m, 2 H), 1.88-1.80 (m, 2 H), 1.62-1.45 (m, 8 H), 1.29 (dd, J = 5.9, 17.1 Hz, 6 H). | A 1-(6-amino-pyridin-3-yl)piperidin-4-ol CB33 |
| I-187 | 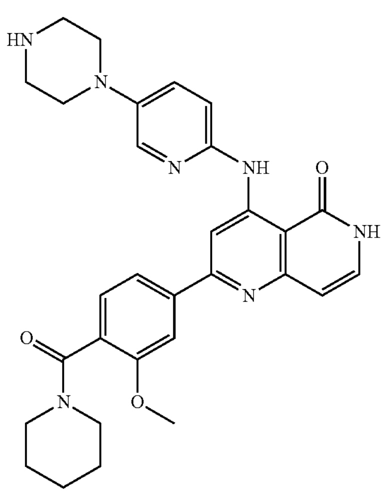 [SMILES: COc1cc(-c2cc(Nc3ccc(N4CCNCC4)cn3)c3c(=O)[nH]ccc3n2)ccc1C(=O)N1CCCCC1] | 2-[3-methoxy-4-(piperidine-1-carbonyl)phenyl]-4-[(5-piperazin-1-yl-2-pyridyl)amino]-6H-1,6-naphthyridin-5-one | Method BicarbB EHC18, m/z = 540 [M + H]+, Ret. time = 3.4 min. | $^1$H NMR (400 MHz, DMSO): δ 12.47 (s, 1 H), 8.90 (s, 1 H), 8.13 (d, J = 3.0 Hz, 1 H), 7.75 (s, 1 H), 7.65-7.62 (m, 1 H), 7.48 (dd, J = 3.1, 9.0 Hz, 1 H), 7.43 (d, J = 7.3 Hz, 1 H), 7.31 (d, J = 7.8 Hz, 1 H), 7.07 (d, J = 8.9 Hz, 1 H), 6.63 (d, J = 7.3 Hz, 1 H), 3.92 (s, 3 H), 3.67 (d, J = 5.5 Hz, 1 H), 3.59-3.58 (m, 1 H), 3.30 (d, J = 3.9 Hz, 2 H), 3.18-3.05 (m, 6 H), 2.86 (dd, J = 4.8, 4.8 Hz, 4 H), 1.63-1.57 (m, 4 H), 1.43-1.42 (m, 2 H). | A and G tert-butyl 4-(6-amino-pyridin-3-yl)piperazine-1-carboxylate CB34 |

TABLE 2-continued

| I-# | STRUCTURE | NAME | LCMS | HNMR | Method SM |
|---|---|---|---|---|---|
| I-188 | 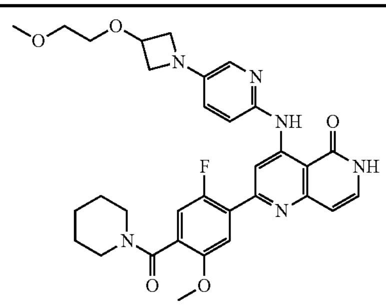 | 2-[2-fluoro-5-methoxy-4-(piperidine-1-carbonyl)phenyl]-4-[[5-[3-(2-methoxyethoxy)azetidin-1-yl]-2-pyridyl]amino]-6H-1,6-naphthyridin-5-one | Method AcHSS C18, m/z = 603.3 [M + H]+, Ret. time = 3.39 min. | ¹H NMR (400 MHz, DMSO): δ 12.43 (s, 1 H), 11.70 (d, J = 5.1 Hz, 1 H), 8.72 (s, 1 H), 7.71 (d, J = 2.0 Hz, 1 H), 7.63 (d, J = 5.8 Hz, 1 H), 7.47 (dd, J = 6.7, 6.7 Hz, 1 H), 7.29 (d, J = 7.1 Hz, 1 H), 7.08-7.05 (m, 1 H), 6.65 (d, J = 7.1 Hz, 1 H), 4.52-4.47 (m, 1 H), 4.16 (dd, J = 6.9, 6.9 Hz, 4 H), 3.91 (s, 3 H), 3.61-3.47 (m, 4 H), 3.34 (d, J = 20.5 Hz, 4 H), 3.21 (dd, J = 4.8, 4.8 Hz, 4 H), 1.67-1.60 (m, 4 H), 1.52-1.50 (m, 2 H). | A CA3 CB1 |
| I-189 | 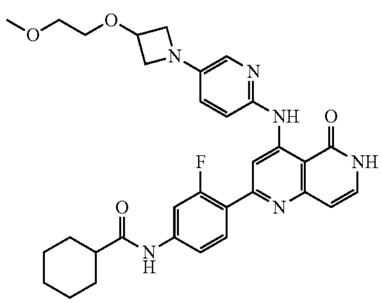 [SMILES: COCCOC1CN(c2ccc(Nc3cc(-c4ccc(NC(=O)C5CCCCC5)cc4F)nc4cc[nH]c(=O)c34)nc2)C1] | N-[3-fluoro-4-[4-[[5-[3-(2-methoxyethoxy)azetidin-1-yl]-2-pyridyl]amino]-5-oxo-6H-1,6-naphthyridin-2-yl]phenyl]cyclohexanecarboxamide | Method AcHSS C18, m/z = 587.3 [M + H]+, Ret. time = 3.8 min. | ¹H NMR (400 MHz, DMSO): δ 12..31 (s, 1 H), 11.57 (d, J = 5.8 Hz, 1 H), 10.19 (s, 1 H), 8.64 (s, 1 H), 7.99 (dd, J = 9.0, 9.0 Hz, 1 H), 7.75 (d, J = 1.5 Hz, 1 H), 7.66 (d, J = 1.5 Hz, 1 H), 7.45 (d, J = 9.1 Hz, 1 H), 7.38 (dd, J = 6.6, 6.6 Hz, 1 H), 7.01 (s, 1 H), 6.55 (d, J = 7.6 Hz, 1 H), 4.48-4.42 (m, 1 H), 4.11 (dd, J = 7.2, 7.2 Hz, 2 H), 3.64 (dd, J = 4.5, 7.8 Hz, 2 H), 3.55-3.44 (m, 4 H), 3.27-3.19 (m, 4 H), 2.40-2.32 (m, 1 H), 1.85-1.75 (m, 4 H), 1.68 (s, 1 H), 1.47-1.37 (m, 2 H), 1.33-1.21 (m, 4 H). | A CA3 CB19 |
| I-190 | 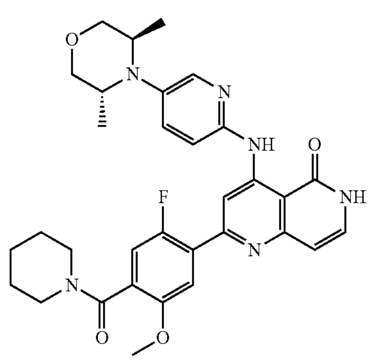 [SMILES: COc1cc(-c2cc(Nc3ccc(N4[C@H](C)COC[C@H]4C)cn3)c3c(=O)[nH]ccc3n2)c(F)cc1C(=O)N1CCCCC1] | 4-[[5-[(3R,5R)-3,5-dimethylmorpholin-4-yl]-2-pyridyl]amino]-2-[2-fluoro-5-methoxy-4-(piperidine-1-carbonyl)phenyl]-6H-1,6-naphthyridin-5-one | Method BicarbB EHC18, m/z = 587.3 [M + H]+, Ret. time = 4.48 min. | ¹H NMR (400 MHz, DMSO): δ 12.64 (s, 1 H), 11.72-11.72 (m, 1 H), 8.92 (s, 1 H), 8.10 (d, J = 2.0 Hz, 1 H), 7.57 (d, J = 5.8 Hz, 1 H), 7.51 (dd, J = 2.1, 8.7 Hz, 1 H), 7.45-7.43 (m, 1 H), 7.24 (d, J = 8.8 Hz, 1 H), 7.07 (d, J = 8.8 Hz, 1 H), 6.62 (d, J = 7.3 Hz, 1 H), 3.86 (s, 3 H), 3.81 (dd, J = 2.5, 10.9 Hz, 2 H), 3.64-3.57 (m, 2 H), 3.52-3.37 (m, 4 H), 3.16 (dd, J = 5.3, 5.3 Hz, 2 H), 1.61-1.54 (m, 4 H), 1.47-1.42 (m, 2 H), 0.85 (d, J = 6.1 Hz, 6 H). | A 5-((3R,5R)-3,5-dimethyl morpholino)pyridin-2-amine CB1 |
| I-191 | 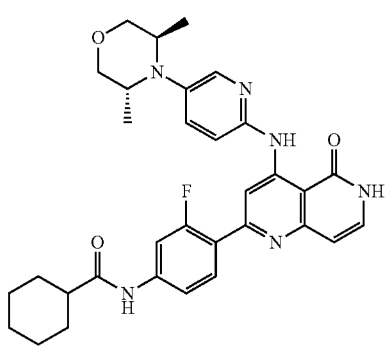 [SMILES: C[C@@H]1COC[C@@H](C)N1c1ccc(Nc2cc(-c3ccc(NC(=O)C4CCCCC4)cc3F)nc3cc[nH]c(=O)c23)nc1] | N-[4-[4-[[5-[(3R,5R)-3,5-dimethylmorpholin-4-yl]-2-pyridyl]amino]-5-oxo-6H-1,6-naphthyridin-2-yl]-3-fluorophenyl]cyclohexanecarboxamide | Method BicarbB EHC18, m/z = 571.3 [M + H]+, Ret. time = 4.98 min. | ¹H NMR (400 MHz, DMSO): δ 12.58 (s, 1 H), 11.65-11.63 (m, 1 H), 10.21 (s, 1 H), 8.91 (s, 1 H), 8.10 (d, J = 1.8 Hz, 1 H), 8.00 (dd, J = 9.2, 9.2 Hz, 1H), 7.77 (dd, J = 2.4, 9.0 Hz, 1 H), 7.51 (dd, J = 2.4, 9.0 Hz, 1 H), 7.47-7.39 (m, 2 H), 7.06 (d, J = 8.3 Hz, 1 H), 6.59 (d, J = 7.3 Hz, 1 H), 3.83 (dd, J = 2.1, 10.2 Hz, 2 H), 3.52-3.49 (m, 2 H), 3.41 (dd, J = 5.8, 10.6 Hz, 2 H), 2.36-2.32 (m, 2 H), 1.85-1.75 (m, 4 H), 1.44-1.38 (m, 2 H), 1.30-1.24 (m, 3 H), 0.86 (d, J = 6.1 Hz, 6 H). | A 5-((3R,5R)-3,5-dimethyl morpholino)pyridin-2-amine CB19 |

TABLE 2-continued

| I-# | STRUCTURE | NAME | LCMS | HNMR | Method SM |
|---|---|---|---|---|---|
| I-192 | 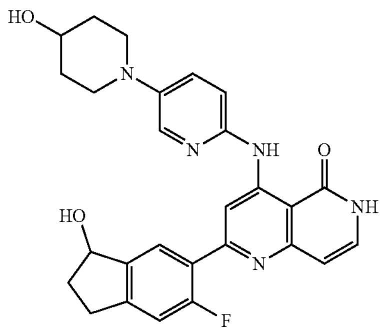 [SMILES: O=c1[nH]ccc2nc(-c3cc4c(cc3F)CCC4O)cc(Nc3ccc(N4CCC(O)CC4)cn3)c12] | 2-(6-fluoro-3-hydroxy-indan-5-yl)-4-[[5-(4-hydroxy-1-piperidyl)-2-pyridyl]amino]-6H-1,6-naphthyridin-5-one | Method AcHSS C18, m/z = 488 [M + H]+, Ret. time = 2.63 min. | $^1$H NMR (400 MHz, DMSO): δ 12.44 (s, 1 H), 11.68 (d, J = 3.5 Hz, 1 H), 8.73 (s, 1 H), 8.10 (d, J = 2.8 Hz, 1 H), 7.97 (d, J = 7.3 Hz, 1 H), 7.52 (dd, J = 2.9, 9.0 Hz, 1 H), 7.45 (dd, J = 5.6, 5.6 Hz, 1 H), 7.25 (d, J = 9.1 Hz, 1 H), 7.07 (d, J = 9.1 Hz, 1 H), 6.64 (d, J = 7.3 Hz, 1 H), 5.45-5.38 (m, 1 H), 5.14 (dd, J = 5.8, 5.8 Hz, 1 H), 4.78-4.69 (m, 1 H), 3.71-3.65 (m, 1 H), 3.41-3.35 (m, 2 H), 3.08-2.99 (m, 1 H), 2.94-2.81 (m, 3 H), 2.49-2.40 (m, 1 H), 1.94-1.83 (m, 3 H), 1.60-1.49 (m, 2 H). | A 1-(6-amino-pyridin-3-yl)piperidin-4-ol CB35 |
| I-193 | 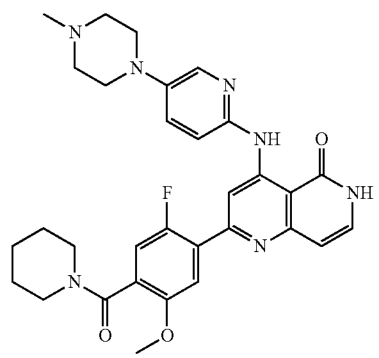 [SMILES: COc1cc(-c2cc(Nc3ccc(N4CCN(C)CC4)cn3)c3c(=O)[nH]ccc3n2)c(F)cc1C(=O)N1CCCCC1] | 2-[2-fluoro-5-methoxy-4-(piperidine-1-carbonyl)phenyl]-4-[[5-(4-methyl-piperazin-1-yl)-2-pyridyl]amino]-6H-napthyridin-5-one | Method BicarbB ECH18, m/z = 572 [M + H]+, Ret. time = 4.19 min. | $^1$H NMR (400 MHz, DMSO): δ 12.51 (s, 1H), 11.72 (s, 1H), 8.80 (s, 1H), 8.12 (d, J = 3.0 Hz, 1H), 7.62 (d, J = 6.1 Hz, 1H), 7.53 (dd, J = 2.8, 9.1 Hz, 1H), 7.50-7.45 (m, 1H), 7.28 (d, J = 10.4 Hz, 1H), 7.09 (d, J = 9.1 Hz, 1H), 6.66 (d, J = 7.3 Hz, 1H), 3.91 (s, 3H), 3.70-3.60 (m, 2H), 3.24-3.18 (m, 6H), 2.60-2.40 (m, 4H), 2.28 (s, 3H), 1.69-1.60 (m, 4H), 1.52-1.47 (m, 2H). | A 5-(4-methyl-piperazin-1-yl)pyridin-2-amine CB1 |
| I-194 | 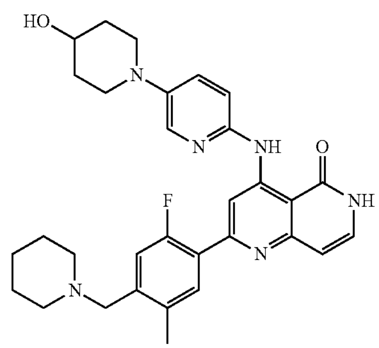 [SMILES: Cc1cc(-c2cc(Nc3ccc(N4CCC(O)CC4)cn3)c3c(=O)[nH]ccc3n2)c(F)cc1CN1CCCCC1] | 2-[2-fluoro-5-methyl-4-(1-piperidyl-methyl)phenyl]-4-[[5-(4-hydroxy-1-piperidyl)-2-pyridyl]amino]-6H-1,6-naphthyridin-5-one | Method BicarbB EHC18, m/z = 543 [M + H]+, Ret. time = 4.85 min. | $^1$H NMR (400 MHz, DMSO): δ 12.41 (s, 1 H), 11.64 (d, J = 5.4 Hz, 1 H), 8.70 (d, J = 1.3 Hz, 1 H), 8.07 (d, J = 3.0 Hz, 1 H), 7.74 (d, J = 7.8 Hz, 1 H), 7.47 (dd, J = 3.1, 9.0 Hz, 1 H), 7.43-7.39 (m, 1 H), 7.21 (d, J = 8.9 Hz, 1 H), 7.02 (d, J = 8.9 Hz, 1 H), 6.59 (d, J = 7.2 Hz, 1 H), 3.68-3.60 (m, 1 H), 3.57-3.48 (m, 2 H), 2.91-2.83 (m, 2 H), 2.43-2.36 (m, 6 H), 2.35 (s, 3 H), 1.87-1.79 (m, 2 H), 1.56-1.38 (m, 9 H). | D 1-(6-amino-pyridin-3-yl)piperidin-4-ol 4-Bromo-5-fluoro-2-methyl-benzalde-hyde Piperidine (step 6) |
| I-195 | 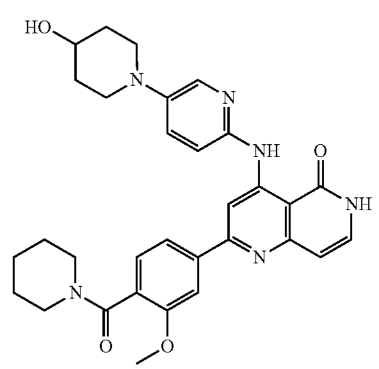 [SMILES: COc1cc(-c2cc(Nc3ccc(N4CCC(O)CC4)cn3)c3c(=O)[nH]ccc3n2)ccc1C(=O)N1CCCCC1] | 4-[[5-(4-hydroxy-1-piperidyl)-2-pyridyl]amino]-2-[3-methoxy-4-(piperidine-1-carbonyl)phenyl]-6H-1,6-naphthyridin-5-one | Method BicarbB EHC18, m/z = 555 [M + H]+, Ret. time = 3.64 min. | $^1$H NMR (400 MHz, DMSO): δ 12.44 (s, 1 H), 11.62 (d, J = 5.3 Hz, 1 H), 8.87 (s, 1 H), 8.14 (d, J = 1.3 Hz, 1 H), 7.73 (s, 1 H), 7.61 (d, J = 7.6 Hz, 1 H), 7.48 (dd, J = 2.0, 9.1 Hz, 1 H), 7.41 (dd, J = 6.6, 6.6 Hz, 1 H), 7.30 (d, J = 7.8 Hz, 1 H), 7.04 (d, J = 8.3 Hz, 1 H), 6.61 (d, J = 7.1 Hz, 1 H), 4.69 (d, J = 3.5 Hz, 1 H), 3.91 (s, 3 H), 3.67-3.64 (m, 2 H), 3.55-3.50 (m, 3 H), 3.13 (s, 2 H), 2.91-2.82 (m, 2 H), 1.86-1.82 (m, 2 H), 1.61-1.53 (m, 6 H), 1.49-1.47 (m, 2 H). | A 1-(6-amino-pyridin-3-yl)piperidin-4-ol CB34 |

TABLE 2-continued

| I-# | STRUCTURE | NAME | LCMS | HNMR | Method SM |
|---|---|---|---|---|---|
| I-196 | 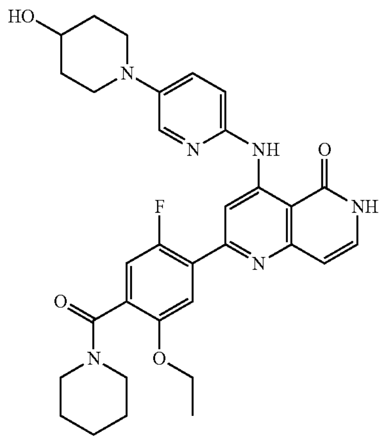 [SMILES: CCOc1cc(-c2cc(Nc3ccc(N4CCC(O)CC4)cn3)c3c(=O)[nH]ccc3n2)c(F)cc1C(=O)N1CCCCC1] | 2-[5-ethoxy-2-fluoro-4-(piperidine-1-carbonyl)phenyl]-4-[[5-(4-hydroxy-1-piperidyl)-2-pyridyl]amino]-6H-1,6-naphthyridin-5-one | Method AcHSS C18, m/z = 587.3 [M + H]+, Ret. time = 3.1 min. | $^1$H NMR (400 MHz, DMSO): δ 12.29 (s, 1 H), 11.52 (s, 1 H), 8.59 (s, 1 H), 7.92 (d, J = 2.3 Hz, 1 H), 7.41 (d, J = 5.8 Hz, 1 H), 7.33 (dd, J = 2.4, 8.7 Hz, 1 H), 7.27 (d, J = 6.1 Hz, 1 H), 6.88 (d, J = 8.8 Hz, 1 H), 6.45 (d, J = 7.1 Hz, 1 H), 4.54 (s, 1 H), 3.99 (q, J = 6.7 Hz, 2 H), 3.43-3.37 (m, 3 H), 3.18 (s, 3 H), 3.02 (s, 2 H), 2.75-2.68 (m, 2H), 1.69 (d, J = 9.6 Hz, 2 H), 1.47 (s, 2 H), 1.42-1.30 (m, 6 H), 1.19 (dd, J = 6.9, 6.9 Hz, 3 H). | A 1-(6-amino-pyridin-3-yl)piperidin-4-ol CB9 |
| I-197 | 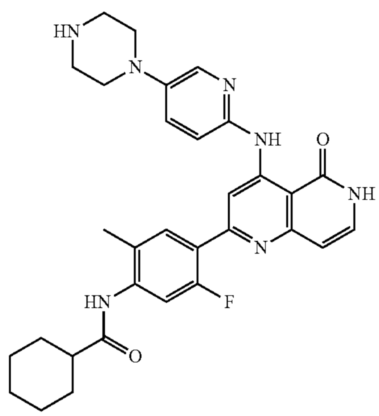 [SMILES: Cc1cc(-c2cc(Nc3ccc(N4CCNCC4)cn3)c3c(=O)[nH]ccc3n2)c(F)cc1NC(=O)C1CCCCC1] | N-[5-fluoro-2-methyl-4-[5-oxo-4-[(5-piperazin-1-yl-2-pyridyl)amino]-6H-1,6-naphthyridin-2-yl]phenyl]cyclohexanecarboxamide | Method AcHSS C18, m/z = 556.2 [M + H]+, Ret. time = 2.61 min. | $^1$H NMR (400 MHz, DMSO): δ 12.46 (s, 1 H), 11.69-11.65 (m, 1 H), 9.32 (s, 1 H), 8.78 (s, 1 H), 8.27 (s, 1 H), 8.12 (d, J = 2.3 Hz, 1 H), 7.87 (d, J = 8.6 Hz, 1 H), 7.67 (d, J = 7.6 Hz, 1 H), 7.56-7.49 (m, 1 H), 7.46 (d, J = 7.6 Hz, 1 H), 7.08 (d, J = 8.8 Hz, 1 H), 6.64 (d, J = 7.3 Hz, 1 H), 3.17 (s, 4 H), 2.98-2.95 (m, 4 H), 2.33 (s, 3 H), 1.86 (dd, J = 12.4, 32.1 Hz, 4 H), 1.74-1.69 (m, 2 H), 1.54-1.44 (m, 2 H), 1.37-1.27 (m, 3 H). | A and G tert-butyl 4-(6-amino-pyridin-3-yl)piperazine-1-carboxylate CB36 |
| I-198 | 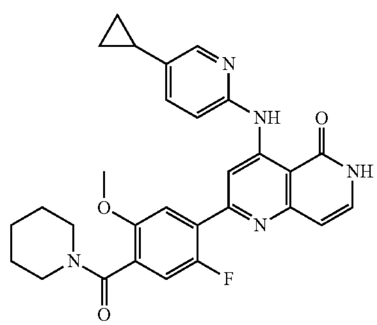 [SMILES: COc1cc(-c2cc(Nc3ccc(C4CC4)cn3)c3c(=O)[nH]ccc3n2)c(F)cc1C(=O)N1CCCCC1] | 4-[(5-cyclopropyl-2-pyridyl)amino]-2-[2-fluoro-5-methoxy-4-(piperidine-1-carbonyl)phenyl]-6H-1,6-naphthyridin-5-one | Method BicarbB EHC18, m/z = 514 [M + H]+, Ret. time = 4.85 min. | $^1$H NMR (400 MHz, DMSO): δ 12.71 (s, 1 H), 11.80-11.79 (m, 1 H), 9.02 (s, 1 H), 8.28 (d, J = 1.5 Hz, 1 H), 7.63 (d, J = 5.8 Hz, 1 H), 7.54-7.47 (m, 1 H), 7.31 (d, J = 8.3 Hz, 1 H), 7.07 (d, J = 8.3 Hz, 1 H), 6.69 (d, J = 7.3 Hz, 1 H), 3.91 (s, 3 H), 3.70-3.63 (m, 2 H), 3.21 (dd, J = 5.7, 5.7 Hz, 2 H), 2.03-1.95 (m, 2 H), 1.67-1.61 (m, 4 H), 1.53 (d, J = 5.3 Hz, 2 H), 1.03-0.98 (m, 2 H), 0.77 (dd, J = 4.9, 4.9 Hz, 2 H). | A 5-cyclopropyl-pyridin-2-amine CB1 |
| I-199 | 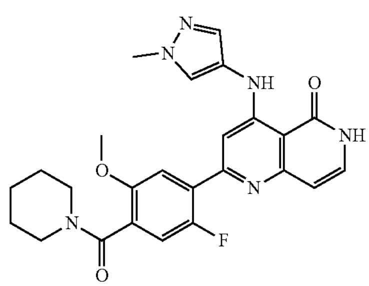 [SMILES: COc1cc(-c2cc(Nc3cnn(C)c3)c3c(=O)[nH]ccc3n2)c(F)cc1C(=O)N1CCCCC1] | 2-[2-fluoro-5-methoxy-4-(piperidine-1-carbonyl)phenyl]-4-[(1-methylpyrazol-4-yl)amino]-6H-1,6-naphthyridin-5-one | Method BicarbB EHC18, m/z = 477 [M + H]+, Ret. time = 3.56 min. | $^1$H NMR (400 MHz, DMSO): δ 11.42 (d, J = 4.0 Hz, 1 H), 10.86 (s, 1 H), 7.75 (s, 1 H), 7.38 (d, J = 3.8 Hz, 2 H), 7.22 (dd, J = 6.2, 6.2 Hz, 1 H), 7.02 (d, J = 7.3 Hz, 1 H), 6.87 (s, 1 H), 6.38 (d, J = 7.3 Hz, 1 H), 3.68 (d, J = 6.3 Hz, 6 H), 3.13-3.11 (m, 1 H), 2.96 (dd, J = 5.6, 5.6 Hz, 3 H), 1.42 (dd, J = 4.7, 21.6 Hz, 4 H), 1.28 (s, 2 H). | A 1-methyl-1H-pyrazol-4-amine CB1 |

TABLE 2-continued

| I-# | STRUCTURE | NAME | LCMS | HNMR | Method SM |
|---|---|---|---|---|---|
| I-200 | 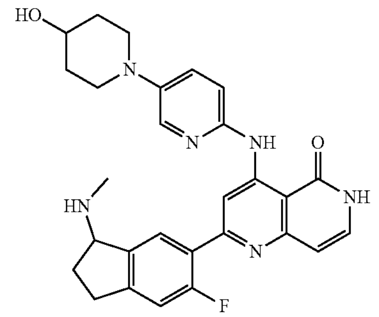 [SMILES: CNC1CCc2cc(F)c(-c3cc(Nc4ccc(N5CCC(O)CC5)cn4)c4c(=O)[nH]ccc4n3)cc21] | 2-[6-fluoro-3-(methyl-amino)indan-5-yl]-4-[[5-(4-hydroxy-1-piperidyl)-2-pyridyl]amino]-6H-1,6-naphthyridin-5-one | Method AcHSS C18, m/z = 501 [M + H]+, Ret. time = 2.08 min. | $^1$H NMR (400 MHz, DMSO): δ 12.44 (s, 1 H), 8.72 (s, 1 H), 8.10 (d, J = 2.5 Hz, 1 H), 7.99 (d, J = 7.3 Hz, 1 H), 7.52 (dd, J = 2.7, 9.0 Hz, 1 H), 7.45 (d, J = 7.3 Hz, 1 H), 7.06 (d, J = 9.1 Hz, 1 H), 6.63 (d, J = 7.3 Hz, 1 H), 4.74-4.74 (m, 1 H), 4.26 (dd, J = 4.8, 6.8 Hz, 1 H), 3.68 (d, J = 1.8 Hz, 1 H), 3.56 (d, J = 12.4 Hz, 2 H), 3.11-3.02 (m, 1 H), 2.94-2.85 (m, 4 H), 2.44 (s, 4 H), 1.98-1.88 (m, 5 H), 1.61-1.50 (m, 2 H). | A 1-(6-amino-pyridin-3-yl) piperidin-4-ol CB37 |
| I-201 | 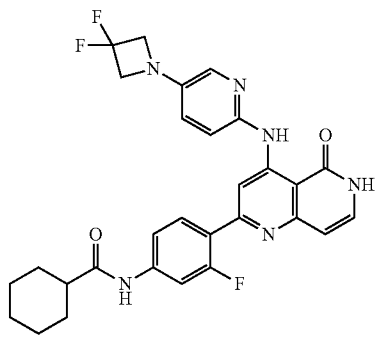 [SMILES: O=C(Nc1ccc(-c2cc(Nc3ccc(N4CC(F)(F)C4)cn3)c3c(=O)[nH]ccc3n2)c(F)c1)C1CCCCC1] | N-[4-[4-[[5-(3,3-difluoro-azetidin-1-yl)-2-pyridyl]amino]-5-oxo-6H-1,6-naphthyridin-2-yl]-3-fluoro-phenyl]cyclohexane-carboxamide | Method BicarbB EHC18, m/z = 549 [M + H]+, Ret. time = 5.01 min. | $^1$H NMR (400 MHz, DMSO): δ 12.45 (s, 1 H), 11.63 (s, 1 H), 10.22 (s, 1 H), 8.76 (d, J = 1.0 Hz, 1 H), 8.05-7.99 (m, 1 H), 7.82-7.73 (m, 2 H), 7.48-7.39 (m, 2 H), 7.17-7.07 (m, 2 H), 6.58 (d, J = 7.3 Hz, 1 H), 4.35 (t, J = 12.2 Hz, 4 H), 2.42-2.33 (m, 1 H), 2.09 (s, 1 H), 1.86-1.77 (m, 4 H), 1.68 (d, J = 10.9 Hz, 1 H), 1.49-1.19 (m, 4 H). | A 5-(3,3-difluoro azetidin-1-yl) pyridin-2-amine CB19 |
| I-202 | 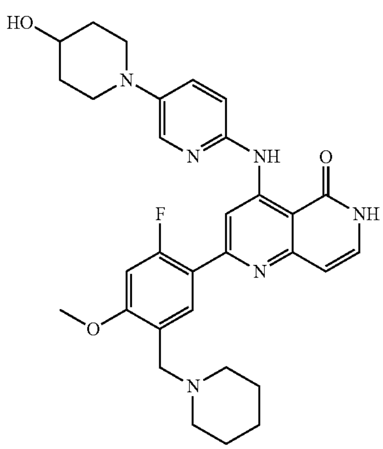 [SMILES: COc1cc(F)c(-c2cc(Nc3ccc(N4CCC(O)CC4)cn3)c3c(=O)[nH]ccc3n2)cc1CN1CCCCC1] | 2-[2-fluoro-4-methoxy-5-(1-piperidyl-methyl)phenyl]-4-[[5-(4-hydroxy-1-piperidyl)-1-2-pyridyl]amino]-6H-1,6-naphthyridin-5-one | Method AcHSS C18, m/z = 559.3 [M + H]+, Ret. time = 2.2 min. | $^1$H NMR (400 MHz, DMSO): δ 12.37 (s, 1 H), 11.61 (d, J = 5.5 Hz, 1 H), 8.71 (s, 1 H), 8.21 (s, 1 H), 8.05 (d, J = 3.0 Hz, 1 H), 7.99 (d, J = 9.4 Hz, 1 H), 7.48 (dd, J = 3.1, 9.0 Hz, 1 H), 7.42-7.38 (m, 1 H), 7.04-7.01 (m, 2 H), 6.58 (d, J = 7.3 Hz, 1 H), 3.87 (s, 4 H), 3.69-3.61 (m, 3 H), 3.32 (s, 1 H), 2.92-2.83 (m, 2 H), 2.41 (s, 4 H), 1.88-1.80 (m, 2 H), 1.56-1.36 (m, 8 H). | D 1-(6-amino-pyridin-3-yl) piperidin-4-ol 5-Bromo-4-fluoro-2-methoxy benz-aldehyde Piperidine (Step 6) |
| I-203 | 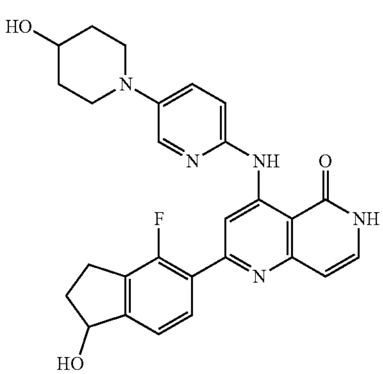 [SMILES: O=c1[nH]ccc2nc(-c3ccc4c(c3F)CCC4O)cc(Nc3ccc(N4CCC(O)CC4)cn3)c12] | 2-(4-fluoro-1-hydroxy-indan-5-yl)-4-[[5-(4-hydroxy-1-piperidyl)-2-pyridyl]amino]-6H-1,6-naphthyridin-5-one | Method AcHSS C18, m/z = 488 [M + H]+, Ret. time = 2.59 min. | $^1$H NMR (400 MHz, DMSO): δ 12.27 (s, 1 H), 11.50 (d, J = 5.1 Hz, 1 H), 8.53 (s, 1 H), 7.94 (d, J = 2.8 Hz, 1 H), 7.68 (dd, J = 7.3, 7.3 Hz, 1 H), 7.34 (dd, J = 28.9, 9.1 Hz, 1 H), 7.28 (dd, J = 6.3, 6.3 Hz, 1 H), 7.17 (d, J = 7.8 Hz, 1 H), 6.89 (d, J = 9.1 Hz, 1 H), 6.45 (d, J = 7.1 Hz, 1 H), 5.01 (dd, J = 6.6, 6.6 Hz, 1 H), 3.54-3.48 (m, 1 H), 2.91 (ddd, J = 3.7, 8.8, 15.9 Hz, 1 H), 2.79-2.63 (m, 3 H), 2.38-2.33 (m, 5 H), 1.81-1.69 (m, 3 H), 1.43-1.31 (m, 2 H). | A 1-(6-amino-pyridin-3-yl) piperidin-4-ol CB38 |

TABLE 2-continued

| I-# | STRUCTURE | NAME | LCMS | HNMR | Method SM |
|---|---|---|---|---|---|
| I-204 | 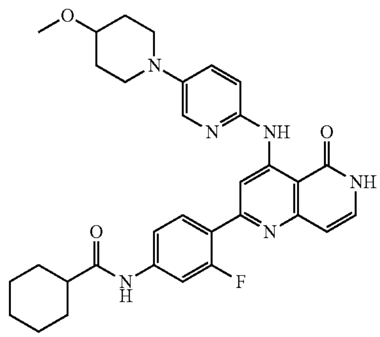 [SMILES: COC1CCN(c2ccc(Nc3cc(-c4ccc(NC(=O)C5CCCCC5)cc4F)nc4cc[nH]c(=O)c34)nc2)CC1] | N-[3-fluoro-4-[4-[[5-(4-methoxy-1-piperidyl)-2-pyridyl]amino]-5-oxo-6H-1,6-naphthyridin-2-yl]phenyl]cyclohexane carboxamide | Method AcHSS C18, m/z = 571 [M + H]+, Ret. time = 3.96 min. | $^1$H NMR (400 MHz, DMSO): δ 12.39 (s, 1 H), 11.61 (d, J = 5.0 Hz, 1 H), 10.22 (s, 1 H), 8.74 (s, 1 H), 8.09 (d, J = 3.0 Hz, 1 H), 8.00 (dd, J = 8.8, 8.8 Hz, 1 H), 7.76 (d, J = 7.4 Hz, 1 H), 7.51-7.44 (m, 2 H), 7.40 (dd, J = 6.0, 7.2 Hz, 1 H), 7.03 (d, J = 8.9 Hz, 1 H), 6.57 (d, J = 7.4 Hz, 1 H), 3.53-3.46 (m, 2 H), 3.42-3.24 (m, 3 H), 2.97-2.89 (m, 2 H), 2.42-2.34 (m, 2 H), 1.99-1.92 (m, 2 H), 1.86-1.76 (m, 4 H), 1.69 (s, 1 H), 1.61-1.51 (m, 2 H), 1.35-1.16 (m, 3 H). | A 5-(4-methoxy piperidin-1-yl)pyridin-2-amine CB19 |
| I-205 | 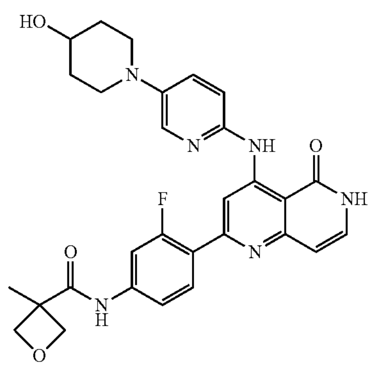 [SMILES: CC1(C(=O)Nc2ccc(-c3cc(Nc4ccc(N5CCC(O)CC5)cn4)c4c(=O)[nH]ccc4n3)c(F)c2)COC1] | N-[3-fluoro-4-[4-[[5-(4-hydroxy-1-piperidyl)-2-pyridyl]amino]-5-oxo-6H-1,6-naphthyridin-2-yl]phenyl]-3-methyl-oxetane-3-carboxamide | Method AcHSS C18, m/z = 545 [M + H]+, Ret. time = 2.64 min. | $^1$H NMR (400 MHz, DMSO): δ 12.43 (s, 1 H), 11.65 (s, 1 H), 10.18 (s, 1 H), 8.78 (s, 1 H), 8.14-8.05 (m, 2 H), 7.57-7.53 (m, 1 H), 7.83 (d, J = 7.3 Hz, 1 H), 7.50 (s, 1 H), 7.45 (d, J = 7.3 Hz, 1 H), 7.07 (d, J = 9.1 Hz, 1 H), 6.62 (d, J = 7.3 Hz, 1 H), 4.91 (d, J = 6.1 Hz, 2 H), 4.74 (d, J = 4.0 Hz, 1 H), 4.43 (d, J = 6.1 Hz, 2 H), 3.73-3.65 (m, 1 H), 3.57 (d, J = 12.6 Hz, 2 H), 2.97-2.87 (m, 2 H), 1.88 (d, J = 9.3 Hz, 2 H), 1.69 (s, 3 H), 1.59-1.49 (m, 2 H). | A 1-(6-amino-pyridin-3-yl)piperidin-4-ol CB39 |
| I-206 | 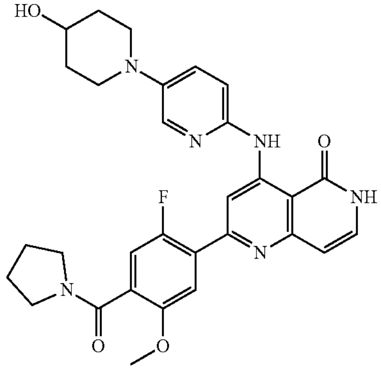 [SMILES: COc1cc(-c2cc(Nc3ccc(N4CCC(O)CC4)cn3)c3c(=O)[nH]ccc3n2)c(F)cc1C(=O)N1CCCC1] | 2-[2-fluoro-5-methoxy-4-(pyrrolidine-1-carbonyl)phenyl]-4-[[5-(4-hydroxy-1-piperidyl)-2-pyridyl]amino]-6H-naphthyridin-5-one | Method AcHSS C18, m/z = 559 [M + H]+, Ret. time = 2.7 min. | $^1$H NMR (400 MHz, DMSO): δ 12.43 (s, 1 H), 11.67 (s, 1 H), 8.73 (s, 1 H), 8.06 (d, J = 2.8 Hz, 1 H), 7.58 (d, J = 6.1 Hz, 1 H), 7.49-7.39 (m, 2 H), 7.24 (d, J = 8.8 Hz, 1 H), 7.02 (d, J = 8.8 Hz, 1 H), 6.60 (d, J = 7.3 Hz, 1 H), 4.73-4.63 (m, 1 H), 3.86 (s, 3 H), 3.67-3.60 (m, 1 H), 3.55-3.42 (m, 4 H), 3.19 (dd, J = 6.3, 6.3 Hz, 2 H), 2.91-2.82 (m, 2 H), 1.90-1.77 (m, 6 H), 1.54-1.43 (m, 2 H). | A 1-(6-amino-pyridin-3-yl)piperidin-4-ol CB40 |

TABLE 2-continued

| I-# | STRUCTURE | NAME | LCMS | HNMR | Method SM |
|---|---|---|---|---|---|
| I-207 | 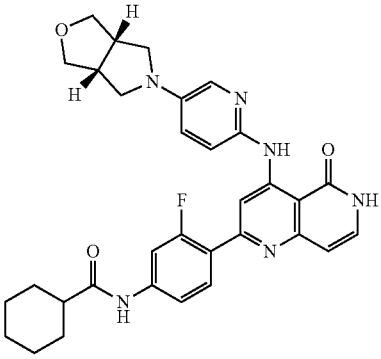 [SMILES: O=C(Nc1ccc(-c2cc(Nc3ccc(N4C[C@H]5COC[C@H]5C4)cn3)c3c(=O)[nH]ccc3n2)c(F)c1)C1CCCCC1] | N-[4-[4-[[5-[(3aS,6aS)-1,3,3a,4,6,6a-hexahydro-furo[3,4-c]pyrrol-5-yl]-2-pyridyl]amino]-5-oxo-6H-1,6-naphthyridin-2-yl]-3-fluoro-phenyl]cyclohexane-carboxamide | Method AcHSS C18, m/z = 569 [M + H]+, Ret. time = 3.8 min. | $^1$H NMR (400 MHz, DMSO): δ 12.27 (s, 1 H), 11.58-11.56 (m, 1 H), 10.21 (s, 1 H), 8.60 (s, 1 H), 7.99 (dd, J = 8.7, 8.7 Hz, 1 H), 7.82 (d, J = 2.5 Hz, 1 H), 7.74 (dd, J = 8.7, 8.7 Hz, 1 H), 7.44 (dd, J = 1.6, 8.7 Hz, 1 H), 7.38 (d, J = 7.1 Hz, 1 H), 7.18 (dd, J = 2.9, 9.0 Hz, 1 H), 7.03 (d, J = 8.8 Hz, 1 H), 6.55 (d, J = 7.3 Hz, 1 H), 3.90-3.83 (m, 2 H), 3.54 (dd, J = 3.0, 8.6 Hz, 2 H), 3.25-3.17 (m, 2 H), 3.00 (s, 2 H), 2.39-2.32 (m, 2 H), 1.81 (dd, J = 12.4, 24.0 Hz, 4 H), 1.66 (d, J = 10.6 Hz, 1 H), 1.47-1.36 (m, 2 H), 1.33-1.18 (m, 4 H). | A 5-((3aR,6aS)-tetrahydro-1H-furo[3,4-c]pyrrol-5(3H)-yl)pyridin-2-amine CB19 |
| I-208 | 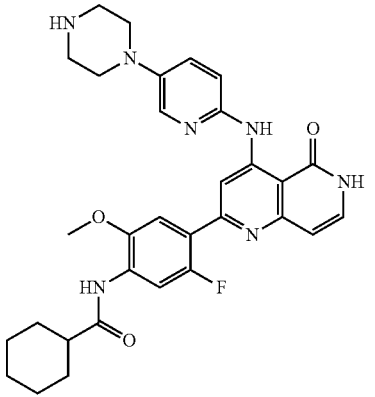 [SMILES: COc1cc(-c2cc(Nc3ccc(N4CCNCC4)cn3)c3c(=O)[nH]ccc3n2)c(F)cc1NC(=O)C1CCCCC1] | N-[5-fluoro-2-methoxy-4-[5-oxo-4-[(5-piperazin-1-yl-2-pyridyl)amino]-6H-1,6-naphthyridin-2-yl]phenyl]cyclohexane carboxamide | Method AcHSS C18, m/z = 572 [M + H]+, Ret. time = 2.77 min. | $^1$H NMR (400 MHz, DMSO): δ 12.42 (s, 1 H), 9.29 (s, 1 H), 8.80 (s, 1 H), 8.23 (s, 1 H), 8.14 (d, J = 7.2 Hz, 1 H), 8.08 (d, J = 3.0 Hz, 1 H), 7.66 (d, J = 7.2 Hz, 1 H), 7.49 (dd, J = 3.0, 9.0 Hz, 1 H), 7.42 (d, J = 7.3 Hz, 1 H), 7.05 (d, J = 8.9 Hz, 1 H), 6.61 (d, J = 7.3 Hz, 1 H), 3.94 (s, 3 H), 3.15 (dd, J = 5.0, 5.0 Hz, 4 H), 2.95 (dd, J = 4.9, 4.9 Hz, 4 H), 2.71-2.62 (m, 1 H), 1.84-1.73 (m, 4 H), 1.67 (d, J = 11.2 Hz, 1 H), 1.46-1.17 (m, 6 H). | A and G tert-butyl 4-(6-amino-pyridin-3-yl)piperazine-1-carboxylate CB66 |
| I-209 | 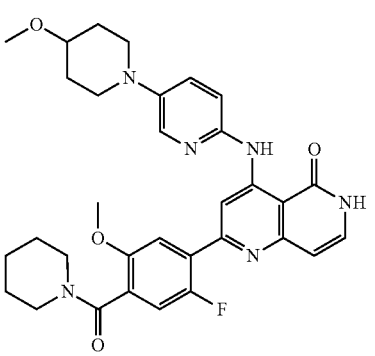 [SMILES: COc1cc(-c2cc(Nc3ccc(N4CCC(OC)CC4)cn3)c3c(=O)[nH]ccc3n2)c(F)cc1C(=O)N1CCCCC1] | 2-[2-fluoro-5-methoxy-4-(piperidine-1-carbonyl)phenyl]-4-[[5-(4-methoxy-1-piperidyl)-2-pyridyl]amino]-6H-1,6-naphthyridin-5-one | Method BicarbB ECH18, m/z = 587.3 [M + H]+, Ret. time = 4.4 min. | $^1$H NMR (400 MHz, DMSO): δ 12.46 (s, 1 H), 11.73-11.68 (m, 1 H), 8.75 (d, J = 1.4 Hz, 1 H), 8.09 (d, J = 3.0 Hz, 1 H), 7.58 (d, J = 6.0 Hz, 1 H), 7.49 (dd, J = 3.1, 9.0 Hz, 1 H), 7.44 (d, J = 6.9 Hz, 1 H), 7.24 (d, J = 8.9 Hz, 1 H), 7.04 (d, J = 8.9 Hz, 1 H), 6.61 (d, J = 7.3 Hz, 1 H), 3.87 (s, 3 H), 3.66-3.56 (m, 2 H), 3.53-3.45 (m, 2 H), 3.43-3.30 (m, 3 H), 3.17 (dd, J = 5.6, 5.6 Hz, 2 H), 2.96-2.88 (m, 2 H), 1.99-1.91 (m, 2 H), 1.65-1.44 (m, 9 H). | A 5-(4-methoxy-piperidin-1-yl)pyridin-2-amine CB1 |

TABLE 2-continued

| I-# | STRUCTURE | NAME | LCMS | HNMR | Method SM |
|---|---|---|---|---|---|
| I-210 | 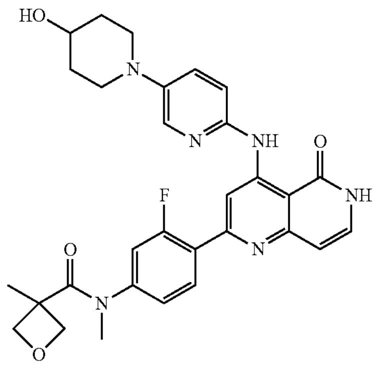 [SMILES: CN(C(=O)C1(C)COC1)c1ccc(-c2cc(Nc3ccc(N4CCC(O)CC4)cn3)c3c(=O)[nH]ccc3n2)c(F)c1] | N-[3-fluoro-4-[4-[[5-(4-hydroxy-1-piperidyl)-2-pyridyl]amino]-5-oxo-6H-1,6-naphthyridin-2-yl]phenyl]-N,3-dimethyl-oxetane-3-carboxamide | Method AcHSS C18, m/z = 559.2 [M + H]+, Ret. time = 2.57 min. | ¹H NMR (400 MHz, DMSO): δ 12.50 (s, 1 H), 11.70-11.70 (m, 1 H), 8.79 (s, 1 H), 8.14-8.04 (m, 2 H), 7.57-7.49 (m, 2 H), 7.47 (d, J = 7.3 Hz, 1 H), 7.40 (d, J = 8.1 Hz, 1 H), 7.07 (d, J = 8.8 Hz, 1 H), 6.63 (d, J = 7.3 Hz, 1 H), 4.89-4.81 (m, 2 H), 4.77-4.74 (m, 1 H), 4.01-4.01 (m, 2 H), 3.69 (s, 1 H), 3.57 (d, J = 12.1 Hz, 2 H), 3.21 (s, 3 H), 2.92 (dd, J = 10.0, 10.0 Hz, 2 H), 1.88 (d, J = 9.3 Hz, 2 H), 1.71 (s, 3 H), 1.60-1.48 (m, 2 H). | A 1-(6-amino-pyridin-3-yl) piperidin-4-ol CB41 |
| I-211 | 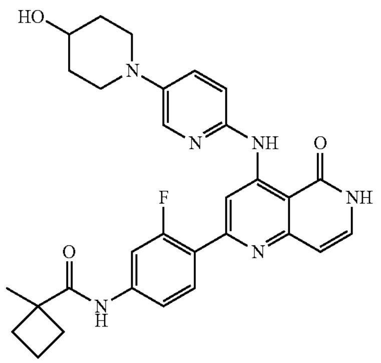 [SMILES: CC1(C(=O)Nc2ccc(-c3cc(Nc4ccc(N5CCC(O)CC5)cn4)c4c(=O)[nH]ccc4n3)c(F)c2)CCC1] | N-[3-fluoro-4-[4-[[5-(4-hydroxy-1-piperidyl)-2-pyridyl]amino]-5-oxo-6H-1,6-naphthyridin-2-yl]phenyl]-1-methyl-cyclobutane-carboxamide | Method AcHSS C18, m/z = 543 [M + H]+, Ret. time = 3.15 min. | ¹H NMR (400 MHz, DMSO): δ 12.43 (s, 1 H), 11.68-11.65 (m, 1 H), 9.78 (s, 1 H), 8.77 (s, 1 H), 8.12 (d, J = 2.5 Hz, 1 H), 8.05 (dd, J = 8.8, 8.8 Hz, 1 H), 7.86 (d, J = 8.6 Hz, 1 H), 7.61 (d, J = 8.6 Hz, 1 H), 7.52 (dd, J = 2.7, 9.0 Hz, 1 H), 7.44 (d, J = 7.1 Hz, 1 H), 7.07 (d, J = 9.1 Hz, 1 H), 6.62 (d, J = 7.1 Hz, 1 H), 4.74 (d, J = 3.8 Hz, 1 H), 3.69 (dd, J = 4.0, 7.8 Hz, 1 H), 3.62-3.52 (m, 2 H), 2.92 (dd, J = 10.1, 10.1 Hz, 2 H), 2.53-2.46 (m, 2 H), 2.03-1.84 (m, 5 H), 1.82-1.71 (m, 1 H), 1.53 (s, 5 H). | A 1-(6-amino-pyridin-3-yl) piperidin-4-ol CB42 |
| I-212 | 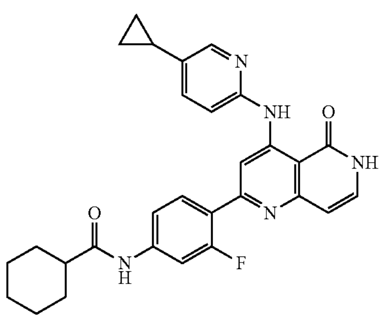 [SMILES: O=C(Nc1ccc(-c2cc(Nc3ccc(C4CC4)cn3)c3c(=O)[nH]ccc3n2)c(F)c1)C1CCCCC1] | N-[4-[4-[(5-cyclopropyl-2-pyridyl)amino]-5-oxo-6H-1,6-naphthyridin-2-yl]-3-fluoro-phenyl]cyclohexane-carboxamide | Method AcHSS C18, m/z = 498 [M + H]+, Ret. time = 4.25 min. | ¹H NMR (400 MHz, DMSO): δ 12.64 (s, 1 H), 12.57 (s, 1 H), 11.93-11.89 (m, 1 H), 8.54 (s, 1 H), 8.43 (s, 1 H), 8.18 (d, J = 2.5 Hz, 1 H), 8.13-8.08 (m, 1 H), 7.55-7.49 (m, 1 H), 7.12-7.09 (m, 1 H), 7.05 (d, J = 9.1 Hz, 1 H), 6.53 (d, J = 7.1 Hz, 1 H), 4.75 (s, 1 H), 4.08 (d, J = 7.3 Hz, 1 H), 3.70-3.68 (m, 2 H), 3.61-3.56 (m, 2 H), 3.27 (s, 2 H), 2.93 (dd, J = 9.7, 9.7 Hz, 2 H), 2.04 (s, 1 H), 1.90-1.85 (m, 2 H), 1.59-1.48 (m, 2 H), 1.35-1.21 (m, 2 H). | A 5-cyclopropyl-pyridin-2-amine CB19 |
| I-213 | 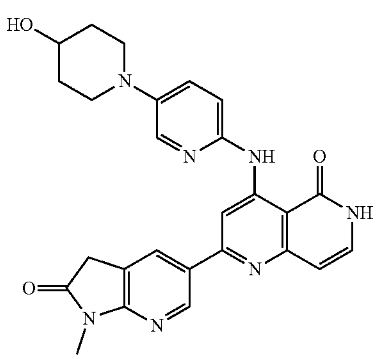 [SMILES: CN1C(=O)Cc2cc(-c3cc(Nc4ccc(N5CCC(O)CC5)cn4)c4c(=O)[nH]ccc4n3)cnc21] | 4-[[5-(4-hydroxy-1-piperidyl)-2-pyridyl]amino]-2-(1-methyl-2-oxo-3H-pyrrolo[2,3-b]pyridin-5-yl)-6H-1,6-naphthyridin-5-one | Method AcHSS C18, m/z = 484 [M + H]+, Ret. time = 2.4 min. | ¹H NMR (400 MHz, DMSO): δ 12.48 (s, 1 H), 11.68 (s, 1 H), 8.90 (s, 2 H), 8.31 (s, 1 H), 8.21 (d, J = 2.5 Hz, 1 H), 7.53 (dd, J = 2.9, 9.0 Hz, 1 H), 7.45 (d, J = 7.3 Hz, 1 H), 7.08 (d, J = 9.1 Hz, 1 H), 6.63 (d, J = 7.3 Hz, 1 H), 4.76-4.76 (m, 1 H), 3.77 (s, 2 H), 3.74-3.67 (m, 1 H), 3.60 (d, J = 12.4 Hz, 2 H), 3.25 (s, 3 H), 2.98-2.91 (m, 2 H), 1.91-1.88 (m, 2 H), 1.62-1.53 (m, 2 H). | A 1-(6-amino-pyridin-3-yl) piperidin-4-ol 1-methyl-5-(4,4,5,5-tetramethyl-1,3,2-dioxa-borolan-2-yl)-1,3-dihydro-2H-pyrrolo[2,3-b]pyridin-2-one |

TABLE 2-continued

| I-# | STRUCTURE | NAME | LCMS | HNMR | Method SM |
|---|---|---|---|---|---|
| I-214 | 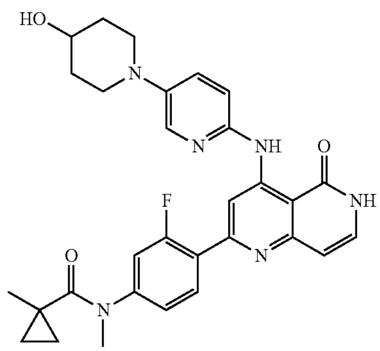 [SMILES: CN(C(=O)C1(C)CC1)c1ccc(-c2cc(Nc3ccc(N4CCC(O)CC4)cn3)c3c(=O)[nH]ccc3n2)c(F)c1] | N-[3-fluoro-4-[4-[[5-(4-hydroxy-1-piperidyl)-2-pyridyl]amino]-5-oxo-6H-1,6-naphthyridin-2-yl]phenyl]-N,1-dimethyl-cyclopropane-carboxamide | Method AcHSS C18, m/z = 543.2 [M + H]+, Ret. time = 2.88 min. | $^1$H NMR (400 MHz, DMSO): δ 13.18-13.13 (m, 1 H), 12.52-12.51 (m, 1 H), 8.67 (s, 1 H), 8.21 (d, J = 2.3 Hz, 1 H), 7.94 (dd, J = 8.5, 8.5 Hz, 1 H), 7.84-7.79 (m, 1 H), 7.68 (d, J = 8.8 Hz, 1 H), 7.61-7.50 (m, 1 H), 7.26 (d, J = 8.8 Hz, 1 H), 6.79 (d, J = 7.1 Hz, 1 H), 3.74-3.69 (m, 1 H), 3.66-3.60 (m, 2 H), 3.00 (dd, J = 10.4, 10.4 Hz, 2 H), 1.89-1.83 (m, 2 H), 1.58-1.47 (m, 2 H), 1.20-1.03 (m, 8 H), 0.60 (dd, J = 5.4, 5.4 Hz, 4 H). | A 1-(6-amino-pyridin-3-yl) piperidin-4-ol CB43 |
| I-215 | 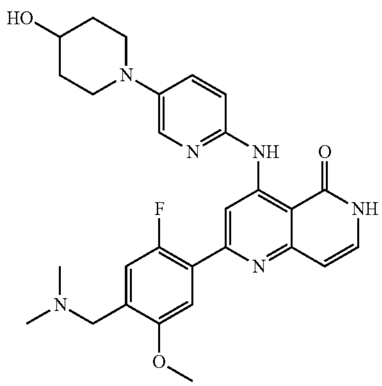 [SMILES: COc1cc(-c2cc(Nc3ccc(N4CCC(O)CC4)cn3)c3c(=O)[nH]ccc3n2)c(F)cc1CN(C)C] | 2-[4-[(dimethyl-amino) methyl]-2-fluoro-5-methoxy-phenyl]-4-[[5-(4-hydroxy-1-piperidyl)-2-pyridyl]amino]-6H-1,6-naphthyridin-5-one | Method AcHSS C18, m/z = 519.2 [M + H]+, Ret. time = 2.05 min. | $^1$H NMR (400 MHz, DMSO): δ 12.41 (s, 1 H), 11.66 (d, J = 5.5 Hz, 1 H), 8.73 (d, J = 1.3 Hz, 1 H), 8.23 (s, 1 H), 8.08 (d, J = 3.0 Hz, 1 H), 7.53 (d, J = 6.4 Hz, 1 H), 7.48 (dd, J = 3.1, 9.0 Hz, 1 H), 7.44-7.40 (m, 1 H), 7.03 (d, J = 8.8 Hz, 1 H), 6.61 (d, J = 7.3 Hz, 1 H), 3.86 (s, 4 H), 3.68-3.60 (m, 2 H), 3.57-3.49 (m, 3 H), 2.92-2.83 (m, 2 H), 2.23 (s, 6 H), 1.88-1.80 (m, 2 H), 1.56-1.45 (m, 2 H). | D 1-(6-amino-pyridin-3-yl) piperidin-4-ol |
| I-216 | 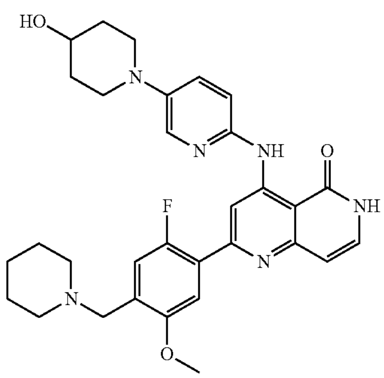 [SMILES: COc1cc(-c2cc(Nc3ccc(N4CCC(O)CC4)cn3)c3c(=O)[nH]ccc3n2)c(F)cc1CN1CCCCC1] | 2-[2-fluoro-5-methoxy-4-(1-piperidyl-methyl) phenyl]-4-[[5-(4-hydroxy-1-piperidyl)-2-pyridyl]amino]-6H-1,6-naphthyridin-5-one | Method AcHSS C18, m/z = 559.3 [M + H]+, Ret. time = 2.18 min. | $^1$H NMR (400 MHz, DMSO): δ 12.45 (s, 1 H), 11.69 (d, J = 4.5 Hz, 1 H), 8.78 (s, 1 H), 8.21 (s, 1 H), 8.12 (d, J = 2.3 Hz, 1 H), 7.57 (d, J = 6.3 Hz, 1 H), 7.52 (dd, J = 2.8, 2.8 Hz, 1 H), 7.49-7.43 (m, 1 H), 7.31 (d, J = 8.8 Hz, 1 H), 7.06 (d, J = 8.8 Hz, 1 H), 6.64 (d, J = 7.3 Hz, 1 H), 3.89 (s, 3 H), 3.73-3.64 (m, 2 H), 2.91 (dd, J = 10.1, 10.1 Hz, 2 H), 2.53-2.33 (m, 6 H), 1.88 (d, J = 10.4 Hz, 2 H), 1.64-1.42 (m, 9 H). | D 1-(6-amino-pyridin-3-yl) piperidin-4-ol Piperidine (Step 6) |
| I-217 | 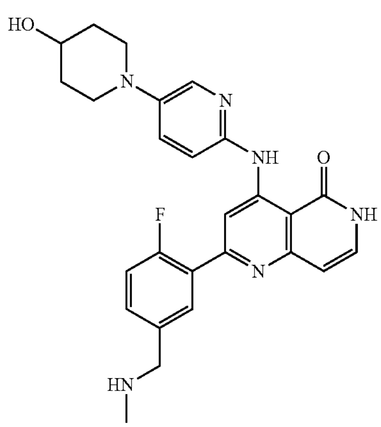 [SMILES: CNCc1ccc(F)c(-c2cc(Nc3ccc(N4CCC(O)CC4)cn3)c3c(=O)[nH]ccc3n2)c1] | 2-[2-fluoro-5-(methyl-amino-methyl) phenyl]-4-[[5-(4-hydroxy-1-piperidyl)-2-pyridyl]amino]-6H-1,6-naphthyridin-5-one | Method AcHSS C18, m/z = 238 [M + H]+, Ret. time = 2 min. | $^1$H NMR (400 MHz, DMSO): δ 12.47 (s, 1 H), 8.75 (s, 1 H), 8.34 (s, 1 H), 8.11 (d, J = 2.5 Hz, 1 H), 7.98 (d, J = 7.3 Hz, 1 H), 7.55-7.51 (m, 2 H), 7.47 (d, J = 7.3 Hz, 1 H), 7.39-7.33 (m, 1 H), 7.07 (d, J = 8.8 Hz, 1 H), 6.64 (d, J = 7.3 Hz, 1 H), 3.84 (s, 3 H), 3.71-3.65 (m, 2 H), 3.22-3.21 (m, 1 H), 2.96-2.88 (m, 2 H), 2.38 (s, 3 H), 2.14 (s, 1 H), 1.88 (d, J = 8.3 Hz, 2 H), 1.58-1.50 (m, 2 H). | A and G 1-(6-amino-pyridin-3-yl) piperidin-4-ol CB68 |

TABLE 2-continued

| I-# | STRUCTURE | NAME | LCMS | HNMR | Method SM |
|---|---|---|---|---|---|
| I-218 | 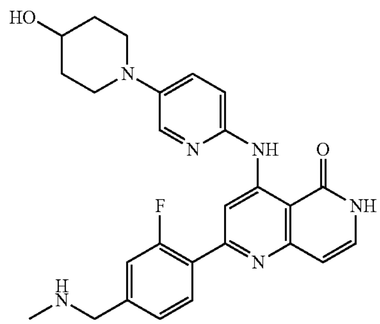 [SMILES: CNCc1ccc(-c2cc(Nc3ccc(N4CCC(O)CC4)cn3)c3c(=O)[nH]ccc3n2)c(F)c1] | 2-[2-fluoro-4-(methyl-amino-methyl)phenyl]-4-[[5-(4-hydroxy-1-piperidyl)-2-pyridyl]amino]-6H-naphthyridin-5-one | Method AcHSS C18, m/z = 475 [M + H]+, Ret. time = 1.94 min. | $^1$H NMR (400 MHz, DMSO): δ 12.46 (s, 1 H), 8.74 (s, 1 H), 8.11 (d, J = 2.4 Hz, 1 H), 7.95 (dd, J = 7.9, 7.9 Hz, 1 H), 7.52 (dd, J = 2.6, 8.7 Hz, 1 H), 7.45 (d, J = 7.3 Hz, 1 H), 7.36-7.29 (m, 2 H), 7.06 (d, J = 8.9 Hz, 1 H), 6.62 (d, J = 7.3 Hz, 1 H), 4.76-4.75 (m, 1 H), 3.76 (s, 2 H), 3.72-3.67 (m, 1 H), 3.57 (d, J = 12.6 Hz, 4 H), 2.91 (dd, J = 9.9, 9.9 Hz, 2 H), 2.34 (s, 3 H), 1.90-1.86 (m, 2 H), 1.60-1.50 (m, 2 H). | A and G 1-(6-amino-pyridin-3-yl)piperidin-4-ol CB44 |
| I-219 | 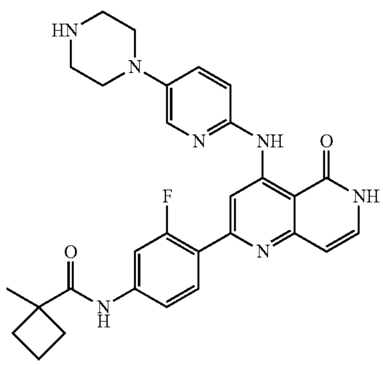 [SMILES: CC1(C(=O)Nc2ccc(-c3cc(Nc4ccc(N5CCNCC5)cn4)c4c(=O)[nH]ccc4n3)c(F)c2)CCC1] | N-[3-fluoro-4-[5-oxo-4-[(5-piperazin-1-yl-2-pyridyl)amino]-6H-1,6-naphthyridin-2-yl]phenyl]-1-methyl-cyclobutane-carboxamide | Method AcHSS C18, m/z = 528 [M + H]+, Ret. time = 2.35 min. | $^1$H NMR (400 MHz, DMSO): δ 12.40 (s, 1 H), 9.75 (s, 1 H), 8.75 (s, 1 H), 8.07-7.99 (m, 2 H), 7.80 (d, J = 7.3 Hz, 1 H), 7.57 (dd, J = 2.0, 8.7 Hz, 1 H), 7.47 (dd, J = 3.1, 9.0 Hz, 1 H), 7.41 (d, J = 7.3 Hz, 1 H), 7.04 (d, J = 8.9 Hz, 1 H), 6.58 (d, J = 7.3 Hz, 1 H), 3.10-3.05 (m, 4 H), 2.88-2.83 (m, 4 H), 2.49-2.41 (m, 4 H), 2.01-1.83 (m, 3 H), 1.78-1.69 (m, 1 H), 1.48 (s, 3 H). | A and G tert-butyl 4-(6-amino-pyridin-3-yl)piperazine-1-carboxylate CB42 |
| I-220 | 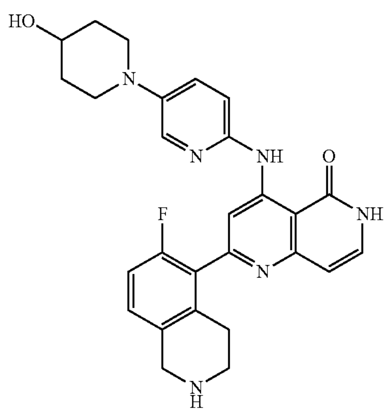 [SMILES: O=c1[nH]ccc2nc(-c3c(F)ccc4c3CCNC4)cc(Nc3ccc(N4CCC(O)CC4)cn3)c12] | 2-(6-fluoro-1,2,3,4-tetrahydro-isoquinolin-5-yl)-4-[[5-(4-hydroxy-1-piperidyl)-2-pyridyl]amino]-6H-1,6-naphthyridin-5-one | Method BicarbB EHC18, m/z = 487 [M + H]+, Ret. time = 2.79 min. | $^1$H NMR (400 MHz, DMSO): δ 12.52 (s, 1 H), 8.33 (s, 1 H), 8.04 (d, J = 3.0 Hz, 1 H), 7.48-7.40 (m, 2 H), 7.18-7.05 (m, 2 H), 7.00-6.97 (m, 1 H), 6.53 (d, J = 7.3 Hz, 1 H), 4.69-4.66 (m, 1 H), 3.90-3.87 (m, 2 H), 3.65-3.62 (m, 2 H), 2.89-2.80 (m, 6 H), 2.68 (dd, J = 1.7, 3.7 Hz, 1 H), 2.18-2.12 (m, 2H), 1.84-1.78 (m, 2 H), 1.53-1.43 (m, 2 H). | A and G 1-(6-amino-pyridin-3-yl)piperidin-4-ol CB45 |
| I-221 | 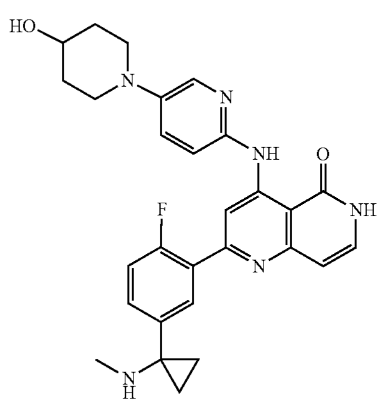 [SMILES: CNC1(c2ccc(F)c(-c3cc(Nc4ccc(N5CCC(O)CC5)cn4)c4c(=O)[nH]ccc4n3)c2)CC1] | 2-[2-fluoro-5-[1-(methyl-amino)cyclopropyl]phenyl]-4-[[5-(4-hydroxy-1-piperidyl)-2-pyridyl]amino]-6H-1,6-naphthyridin-5-one | Method AcHSS C18, m/z = 501 [M + H]+, Ret. time = 2.12 min. | $^1$H NMR (400 MHz, DMSO): δ 9.90 (s, 1 H), 8.79 (s, 1 H), 8.58 (d, J = 8.5 Hz, 1 H), 8.39 (d, J = 6.9 Hz, 1 H), 8.05 (d, J = 2.9 Hz, 1 H), 7.85 (s, 1 H), 7.70 (dd, J = 8.8, 16.9 Hz, 2 H), 7.49 (dd, J = 3.0, 9.0 Hz, 1 H), 7.34-7.30 (m, 1 H), 7.01 (d, J = 8.9 Hz, 1 H), 6.95 (dd, J = 6.3, 6.3 Hz, 1 H), 4.40 (s, 2 H), 3.43-3.21 (m, 6 H), 3.18 (s, 2 H), 2.94 (s, 4 H), 2.57 (s, 3 H). | A and G 1-(6-amino-pyridin-3-yl)piperidin-4-ol CB69 |

TABLE 2-continued

| I-# | STRUCTURE | NAME | LCMS | HNMR | Method SM |
|---|---|---|---|---|---|
| I-222 | 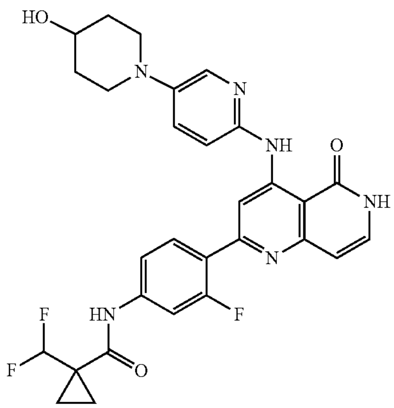 [SMILES: O=C(Nc1ccc(-c2cc(Nc3ccc(N4CCC(O)CC4)cn3)c3c(=O)[nH]ccc3n2)c(F)c1)C1(C(F)F)CC1] | 1-(difluoro-methyl)-N-[3-fluoro-[4-[4-[[5-(4-hydroxy-1-piperidyl)-2-pyridyl]amino]-5-oxo-6H-1,6-naphthyridin-2-yl]phenyl]cyclopropane-carboxamide | Method AcHSS C18, m/z 565 [M + H]+, Ret. time = 3.08 min. | $^1$H NMR (400 MHz, DMSO): δ 12.46 (s, 1 H), 8.77 (s, 1 H), 8.12 (d, J = 2.5 Hz, 1 H), 8.06 (dd, J = 8.8, 8.8 Hz, 1 H), 7.79 (dd, J = 7.2, 7.2 Hz, 1 H), 7.60 (d, J = 8.3 Hz, 1 H), 7.52 (dd, J = 2.9, 9.0 Hz, 1 H), 7.45 (d, J = 7.3 Hz, 1 H), 7.07 (d, J = 8.8 Hz, 1 H), 6.66-6.60 (m, 2 H), 4.74 (d, J = 4.0 Hz, 1 H), 3.70-3.66 (m, 2 H), 3.60-3.53 (m, 2 H), 2.95-2.87 (m, 2 H), 2.73 (s, 1 H), 1.88 (d, J = 8.6 Hz, 2 H), 1.55 (q, J = 9.0 Hz, 2 H), 1.44 (s, 2 H), 1.24-1.18 (m, 2 H). | A 1-(6-amino-pyridin-3-yl)piperidin-4-ol CB47 |
| I-223 | 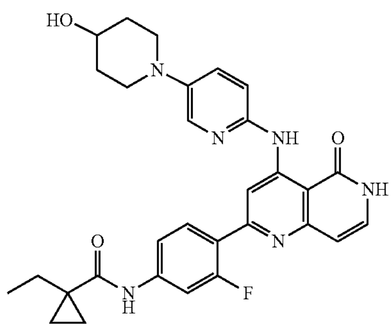 [SMILES: CCC1(C(=O)Nc2ccc(-c3cc(Nc4ccc(N5CCC(O)CC5)cn4)c4c(=O)[nH]ccc4n3)c(F)c2)CC1] | 1-ethyl-N-[3-fluoro-4-[4-[[5-(4-hydroxy-1-piperidyl)-2-pyridyl]amino]-5-oxo-6H-1,6-naphthyridin-2-yl]phenyl]cyclopropane-carboxamide | Method AcHSS C18, m/z = 543 [M + H]+, Ret. time = 3.13 min. | $^1$H NMR (400 MHz, DMSO): δ 12.42 (s, 1 H), 11.65 (d, J = 4.5 Hz, 1 H), 9.65 (s, 1 H), 8.76 (s, 1 H), 8.12 (d, J = 2.8 Hz, 1 H), 8.03 (dd, J = 9.0, 9.0 Hz, 1 H), 7.82 (d, J = 8.8 Hz, 1 H), 7.63 (dd, J = 1.5, 8.6 Hz, 1 H), 7.52 (dd, J = 2.9, 9.0 Hz, 1 H), 7.44 (dd, J = 6.4, 6.4 Hz, 1 H), 7.07 (d, J = 8.8 Hz, 1 H), 6.62 (d, J = 7.3 Hz, 1 H), 4.74-4.74 (m, 1 H), 3.72-3.66 (m, 1 H), 3.61-3.53 (m, 2 H), 2.97-2.87 (m, 2 H), 1.92-1.87 (m, 2 H), 1.78 (q, J = 7.2 Hz, 2 H), 1.60-1.49 (m, 2 H), 1.18-1.14 (m, 2 H), 1.01 (dd, J = 7.3, 7.3 Hz, 3 H), 0.76-0.71 (m, 2 H). | A 1-(6-amino-pyridin-3-yl)piperidin-4-ol CB48 |
| I-224 | 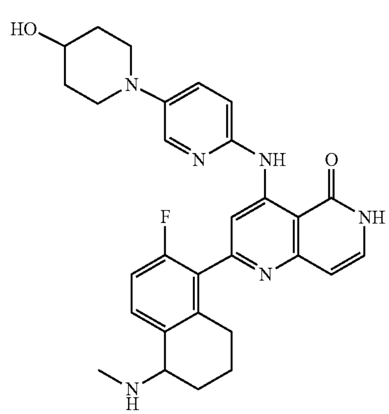 [SMILES: CNC1CCCc2c1ccc(F)c2-c1cc(Nc2ccc(N3CCC(O)CC3)cn2)c2c(=O)[nH]ccc2n1] | 2-[6-fluoro-1-(methyl-amino)tetralin-5-yl]-4-[[5-(4-hydroxy-1-piperidyl)-2-pyridyl]amino]-6H-1,6-naphthyridin-5-one | Method AcHSS C18, m/z = 515.2 [M + H]+, Ret. time = 2.04 min. | $^1$H NMR (400 MHz, DMSO) δ $^1$H NMR (400 MHz, DMSO): δ 12.52 (s, 1 H), 8.31 (s, 1 H), 8.05-8.03 (m, 1 H), 7.53-7.39 (m, 2 H), 7.18-7.05 (m, 2 H), 7.00-6.96 (m, 1 H), 6.54-6.52 (m, 1 H), 4.69-4.66 (m, 1 H), 3.64-3.60 (m, 2 H), 2.88-2.80 (m, 2 H), 2.68 (dd, J = 1.7, 3.7 Hz, 1 H), 2.35-2.34 (m, 6 H), 2.18-2.12 (m, 1 H), 1.83-1.72 (m, 3 H), 1.57-1.42 (m, 4 H), 1.27-1.23 (m, 2 H). | A and G 1-(6-amino-pyridin-3-yl)piperidin-4-ol CB49 |

TABLE 2-continued

| I-# | STRUCTURE | NAME | LCMS | HNMR | Method SM |
|---|---|---|---|---|---|
| I-225 | 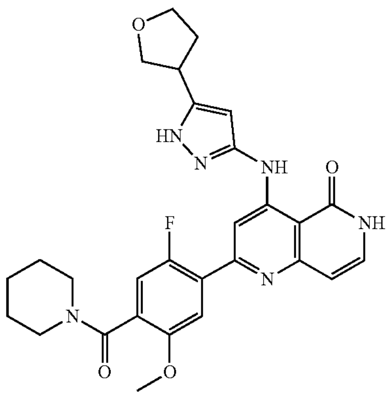 [SMILES: COc1cc(-c2cc(Nc3cc(C4CCOC4)[nH]n3)c3c(=O)[nH]ccc3n2)c(F)cc1C(=O)N1CCCCC1] | 2-[2-fluoro-5-methoxy-4-(piperidine-1-carbonyl)phenyl]-4-[(5-THF-3-yl-1H-pyrazol-3-yl)amino]-6H-1,6-naphthyridin-5-one | Method AcHSS C18, m/z = 533 [M + H]+, Ret. time = 2.99 min. | $^1$H NMR (400 MHz, DMSO) δ $^1$H NMR (400 MHz, DMSO): δ 12.46-12.41 (m, 1 H), 12.03-12.00 (m, 1 H), 11.65 (d, J = 5.3 Hz, 1 H), 8.30-8.28 (m, 1 H), 7.61 (d, J = 6.0 Hz, 1 H), 7.42 (dd, J = 5.9, 7.0 Hz, 1 H), 7.26-7.23 (m, 1 H), 6.60 (d, J = 7.2 Hz, 1 H), 6.05 (s, 1 H), 4.01 (t, J = 7.7 Hz, 1 H), 3.87-3.86 (m, 4 H), 3.66-3.56 (m, 2 H), 3.49-3.42 (m, 3 H), 3.18-3.13 (m, 2 H), 2.35-1.96 (m, 2 H), 2.05-1.96 (m, 2 H), 1.64-1.56 (m, 2 H), 1.50-1.43 (m, 2 H). | A 5-(THF-3-yl)-1H-pyrazol-3-amine CB1 |
| I-226 | 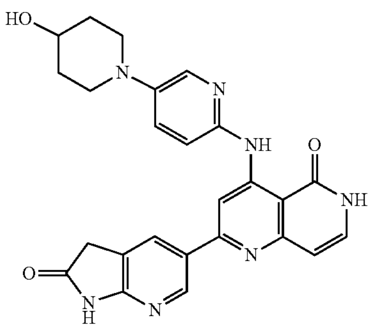 [SMILES: O=C1Cc2cc(-c3cc(Nc4ccc(N5CCC(O)CC5)cn4)c4c(=O)[nH]ccc4n3)cnc2N1] | 4-[[5-(4-hydroxy-1-piperidyl)-2-pyridyl]amino]-2-(2-oxo-1,3-dihydropyrrolo[2,3-b]pyridin-5-yl)-6H-1,6-naphthyridin-5-one | Method AcHSS C18, m/z = 470 [M + H]+, Ret. time = 2.23 min. | $^1$H NMR (400 MHz, DMSO): δ 12.45 (s, 1 H), 11.62 (d, J = 4.4 Hz, 1 H), 11.24 (s, 1 H), 8.82 (s, 1 H), 8.79 (d, J = 2.0 Hz, 1 H), 8.23 (d, J = 1.6 Hz, 1 H), 8.17 (d, J = 2.9 Hz, 1 H), 7.50 (dd, J = 3.1, 9.0 Hz, 1 H), 7.41 (dd, J = 5.2, 6.8 Hz, 1 H), 7.05 (d, J = 8.9 Hz, 1 H), 6.59 (d, J = 7.3 Hz, 1 H), 4.72 (d, J = 1.6 Hz, 1 H), 3.68 (s, 2 H), 3.66 (s, 1 H), 3.57-3.51 (m, 2 H), 2.94-2.85 (m, 2 H), 1.92-1.83 (m, 2 H), 1.58-1.47 (m, 2 H). | A 1-(6-aminopyridin-3-yl)piperidin-4-ol 5-(4,4,5,5-tetramethyl-1,3,2-dioxaborolan-2-yl)-1,3-dihydro-2H-pyrrolo[2,3-b]pyridin-2-one |
| I-227 | 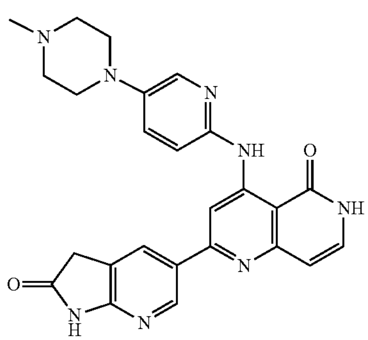 [SMILES: CN1CCN(c2ccc(Nc3cc(-c4cnc5c(c4)CC(=O)N5)nc4cc[nH]c(=O)c34)nc2)CC1] | 4-[[5-(4-methylpiperazin-1-yl)-2-pyridyl]amino]-2-(2-oxo-1,3-dihydropyrrolo[2,3-b]pyridin-5-yl)-6H-1,6-naphthyridin-5-one | Method AcHSS C18, m/z = 469 [M + H]+, Ret. time = 1.76 min. | $^1$H NMR (400 MHz, DMSO): δ 12.46 (s, 1 H), 11.6 (s, 1 H), 11.3 (s, 1 H), 8.84 (d, J = 5.3 Hz, 1 H), 8.79 (d, J = 2.1 Hz, 1 H), 8.23 (d, J = 2.1 Hz, 1 H), 8.16 (d, J = 3.0 Hz, 1 H), 7.50 (dd, J = 3.0, 8.9 Hz, 1 H), 7.42 (d, J = 7.3 Hz, 1 H), 7.07 (d, J = 8.9 Hz, 1 H), 6.60 (d, J = 7.3 Hz, 1 H), 3.42-3.36 (m, 2 H), 3.18 (dd, J = 4.9, 4.9 Hz, 4 H), 2.48 (d, J = 5.0 Hz, 4 H), 2.25 (s, 3 H). | A 5-(4-methylpiperazin-1-yl)pyridin-2-amine 5-(4,4,5,5-tetramethyl-1,3,2-dioxaborolan-2-yl)-1,3-dihydro-2H-pyrrolo[2,3-b]pyridin-2-one |
| I-228 | 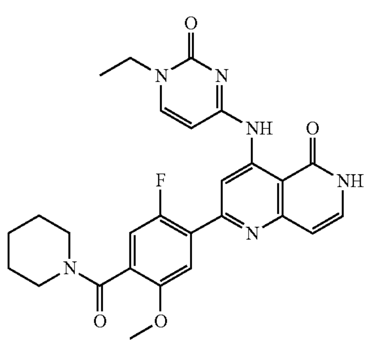 [SMILES: CCn1ccc(Nc2cc(-c3cc(OC)c(C(=O)N4CCCCC4)cc3F)nc3cc[nH]c(=O)c23)nc1=O] | 4-[(1-ethyl-2-oxopyrimidin-4-yl)amino]-2-[2-fluoro-5-methoxy-4-(piperidine-1-carbonyl)phenyl]-6H-1,6-naphthyridin-5-one | Method BicarbB EHC18, m/z = 519 [M + H]+, Ret. time = 3.49 min. | $^1$H NMR (400 MHz, DMSO): δ 12.98 (s, 1H), 11.94 (s, 1H), 9.35 (s, 1H), 8.01 (d, J = 7.1 Hz, 1H), 7.58-7.49 (m, 2H), 7.27 (d, J = 10.1 Hz, 1H), 6.73 (d, J = 7.3 Hz, 1H), 6.13 (d, J = 7.1 Hz, 1H), 3.86 (s, 3H), 3.81 (q, J = 7.0 Hz, 2H), 3.66-3.54 (m, 2H), 3.19-3.13 (m, 2H), 1.61-1.56 (m, 4H), 1.48-1.44 (m, 2H), 1.22 (t, J = 7.1 Hz, 3H). | C 4-amino-1-ethylpyrimidin-2(1H)-one CB1 |

TABLE 2-continued

| I-# | STRUCTURE | NAME | LCMS | HNMR | Method SM |
|---|---|---|---|---|---|
| I-229 | 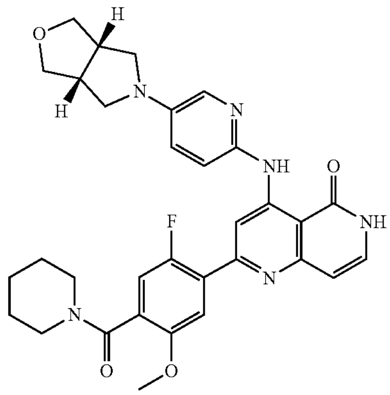 [SMILES: COc1cc(-c2cc(Nc3ccc(N4C[C@H]5COC[C@H]5C4)cn3)c3c(=O)[nH]ccc3n2)c(F)cc1C(=O)N1CCCCC1] | 4-[[5-[(3aR,6aS)-1,3,3a,4,6,6a-hexahydrofuro[3,4-c]pyrrol-5-yl]-2-pyridyl]amino]-2-[2-fluoro-5-methoxy-4-(piperidine-1-carbonyl)phenyl]-6H-1,6-naphthyridin-5-one | Method AcHSS C18, m/z = 585 [M + H]+, Ret. time = 3.38 min. | $^1$H NMR (400 MHz, DMSO): δ 12.35-12.32 (m, 1 H), 11.64 (d, J = 1.5 Hz, 1 H), 8.62 (s, 1 H), 7.82 (d, J = 2.5 Hz, 1 H), 7.56 (d, J = 6.1 Hz, 1 H), 7.41 (d, J = 6.8 Hz, 1 H), 7.22-7.15 (m, 2 H), 7.04 (d, J = 8.8 Hz, 1 H), 6.59 (d, J = 7.3 Hz, 2 H), 3.85 (s, 3 H), 3.62-3.51 (m, 5 H), 3.24-3.14 (m, 6 H), 3.00 (d, J = 1.5 Hz, 2 H), 1.65-1.54 (m, 4 H), 1.45 (d, J = 5.6 Hz, 2 H). | A 5-((3aR,6aS)-tetrahydro-1H-furo[3,4-c]pyrrol-5(3H)-yl)pyridin-2-amine CB1 |
| I-230 | 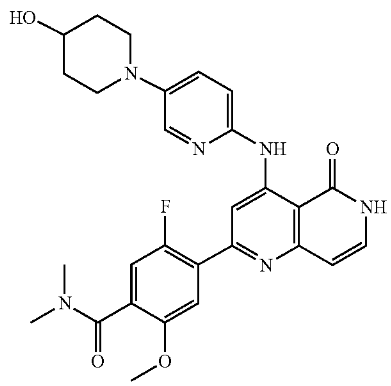 [SMILES: COc1cc(-c2cc(Nc3ccc(N4CCC(O)CC4)cn3)c3c(=O)[nH]ccc3n2)c(F)cc1C(=O)N(C)C] | 5-fluoro-4-[4-[[5-(4-hydroxy-1-piperidyl)-2-pyridyl]amino]-5-oxo-6H-1,6-naphthyridin-2-yl]-2-methoxy-N,N-dimethyl-benzamide | Method AcHSS C18, m/z = 533 [M + H]+, Ret. time = 2.59 min. | $^1$H NMR (400 MHz, DMSO): δ 12.43 (s, 1 H), 11.67 (s, 1 H), 8.73 (s, 1 H), 8.06 (d, J = 2.8 Hz, 1 H), 7.58 (d, J = 5.8 Hz, 1 H), 7.49-7.39 (m, 2 H), 7.22 (d, J = 9.1 Hz, 1 H), 7.02 (d, J = 9.1 Hz, 1 H), 6.60 (d, J = 7.3 Hz, 1 H), 3.86 (s, 3 H), 3.66-3.60 (m, 1 H), 3.56-3.49 (m, 2 H), 2.99 (s, 3 H), 2.87 (d, J = 10.1 Hz, 2 H), 2.82 (s, 4 H), 1.82 (d, J = 9.6 Hz, 2 H), 1.54-1.43 (m, 2 H). | A 1-(6-amino-pyridin-3-yl)piperidin-4-ol CB50 |
| I-231 | 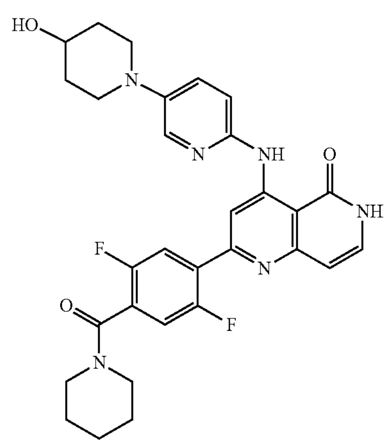 [SMILES: O=C(c1cc(F)c(-c2cc(Nc3ccc(N4CCC(O)CC4)cn3)c3c(=O)[nH]ccc3n2)cc1F)N1CCCCC1] | 2-[2,5-difluoro-4-(piperidine-1-carbonyl)phenyl]-4-[[5-(4-hydroxy-1-piperidyl)-2-pyridyl]amino]-6H-1,6-naphthyridin-5-one | Method AcHSS C18, m/z = 561 [M + H]+, Ret. time = 3 min. | $^1$H NMR (400 MHz, DMSO): δ 12.49 (s, 1 H), 11.76-11.64 (m, 1 H), 8.80 (d, J = 1.3 Hz, 1 H), 8.08 (d, J = 3.0 Hz, 1 H), 7.88 (dd, J = 6.0, 9.7 Hz, 1H), 7.52-7.43 (m, 3 H), 7.06-7.03 (m, 1 H), 6.60 (d, J = 7.3 Hz, 1 H), 4.70 (d, J = 4.1 Hz, 1 H), 3.66-3.58 (m, 3 H), 3.56-3.50 (m, 2 H), 2.92-2.84 (m, 2 H), 1.88-1.81 (m, 2 H), 1.68-1.46 (m, 10 H). | A 1-(6-amino-pyridin-3-yl)piperidin-4-ol CB51 |

TABLE 2-continued

| I-# | STRUCTURE | NAME | LCMS | HNMR | Method SM |
|---|---|---|---|---|---|
| I-232 | 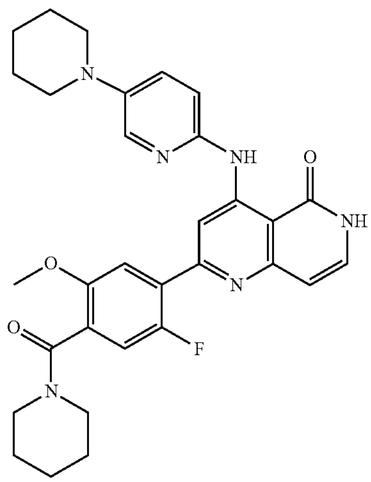 [SMILES: COc1cc(-c2cc(Nc3ccc(N4CCCCC4)cn3)c3c(=O)[nH]ccc3n2)c(F)cc1C(=O)N1CCCCC1] | 2-[2-fluoro-5-methoxy-4-(piperidine-1-carbonyl)phenyl]-4-[[5-(1-piperidyl)-2-pyridyl]amino]-6H-1,6-naphthyridin-5-one | Method AcHSS C18, m/z = 557 [M + H]+, Ret. time = 3.98 min. | $^1$H NMR (400 MHz, DMSO): δ 12.43 (s, 1 H), 8.74 (s, 1 H), 8.07 (d, J = 2.9 Hz, 1 H), 7.57 (d, J = 6.0 Hz, 1 H), 7.50-7.42 (m, 2 H), 7.24 (d, J = 8.9 Hz, 1 H), 7.04 (d, J = 8.9 Hz, 1 H), 6.62 (d, J = 7.3 Hz, 1 H), 3.87 (s, 3 H), 3.66-3.56 (m, 2 H), 3.19-3.12 (m, 6 H), 1.67-1.45 (m, 12 H). | A 5-(piperidin-1-yl)pyridin-2-amine CB1 |
| I-233 | 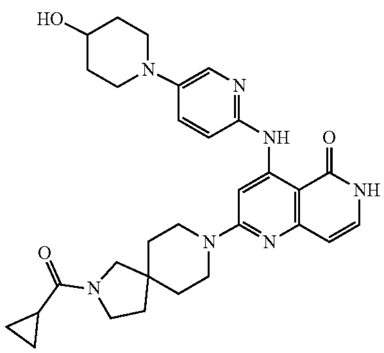 [SMILES: O=C(C1CC1)N1CCC2(CCN(c3cc(Nc4ccc(N5CCC(O)CC5)cn4)c4c(=O)[nH]ccc4n3)CC2)C1] | 2-[2-(cyclopropylcarbonyl)-2,8-diazaspiro[4.5]decan-8-yl]-4-[[5-(4-hydroxy-1-piperidyl)-2-pyridyl]amino]-6H-1,6-naphthyridin-5-one | Method AcHSS C18, m/z = 544.3 [M + H]+, Ret. time = 2.57 min. | $^1$H NMR (400 MHz, DMSO) δ 12.26 (d, J = 2.6 Hz, 1H), 11.15 (s, 1H), 8.04 (dd, J = 2.4, 2.4 Hz, 1H), 7.97 (d, J = 4.9 Hz, 1H), 7.44 (dd, J = 3.0, 8.9 Hz, 1H), 7.25-7.19 (m, 1H), 6.90 (d, J = 9.0 Hz, 1H), 6.24 (dd, J = 1.6, 7.2 Hz, 1H), 4.71-4.70 (m, 1H), 3.78-3.41 (m, 10H), 3.26 (s, 1H), 2.89-2.80 (m, 2H), 1.92-1.75 (m, 5H), 1.63-1.46 (m, 6H), 0.76-0.70 (m, 4H). | P 1-(6-amino-pyridin-3-yl)piperidin-4-ol tert-butyl 2,8-diazaspiro[4.5]decane-2-carboxylate |
| I-234 | 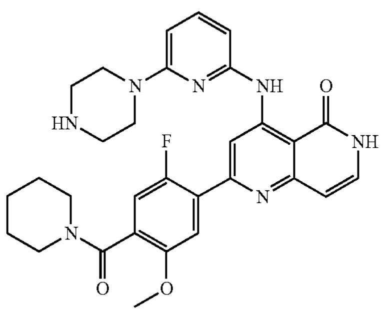 [SMILES: COc1cc(-c2cc(Nc3cccc(N4CCNCC4)n3)c3c(=O)[nH]ccc3n2)c(F)cc1C(=O)N1CCCCC1] | 2-[2-fluoro-5-methoxy-4-(piperidine-1-carbonyl)phenyl]-4-[(6-piperazin-1-yl-2-pyridyl)amino]-6H-1,6-naphthyridin-5-one | Method AcHSS C18, m/z = 558 [M + H]+, Ret. time = 2.43 min. | $^1$H NMR (400 MHz, MeOD) δ 9.00 (d, J = 2.3 Hz, 1 H), 7.44-7.38 (m, 2 H), 7.28 (d, J = 7.3 Hz, 1 H), 7.11-7.05 (m, 1 H), 6.61 (d, J = 7.3 Hz, 1 H), 6.32 (d, J = 8.3 Hz, 1 H), 6.22 (d, J = 7.6 Hz, 1 H), 3.83 (s, 3 H), 3.63 (d, J = 4.8 Hz, 2 H), 3.44-3.37 (m, 4 H), 2.79 (dd, J = 4.9, 4.9 Hz, 4 H), 2.61-2.57 (m, 1 H), 1.62-1.55 (m, 6 H), 1.53-1.44 (m, 4 H). | A and G tert-butyl 4-(6-amino-pyridin-2-yl)piperazine-1-carboxylate CB1 |
| I-235 | 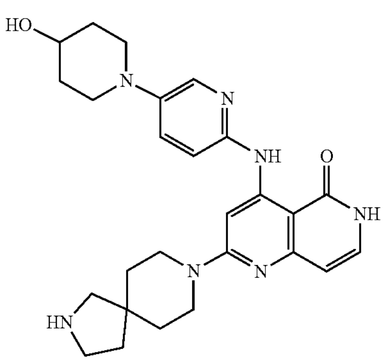 [SMILES: O=c1[nH]ccc2nc(N3CCC4(CCNC4)CC3)cc(Nc3ccc(N4CCC(O)CC4)cn3)c12] | 2-(2,8-diazaspiro[4.5]decan-8-yl)-4-[[5-(4-hydroxy-1-piperidyl)-2-pyridyl]amino]-6H-naphthyridin-5-one | Method AcHSS C18, m/z = 476 [M + H]+, Ret. time = 1.85 min. | $^1$H NMR (400 MHz, DMSO) δ 12.31 (s, 1H), 11.21 (s, 1H), 8.43 (s, 1H), 8.08 (d, J = 2.5 Hz, 1H), 7.99 (s, 1H), 7.48 (dd, J = 2.5, 8.8 Hz, 1H), 7.26 (d, J = 7.3 Hz, 1H), 6.93 (d, J = 8.8 Hz, 1H), 6.28 (d, J = 7.3 Hz, 1H), 4.75 (s, 1H), 3.75-3.49 (m, 6H), 3.23 (s, 1H), 3.19 (t, J = 7.0 Hz, 2H), 2.97 (s, 2H), 2.90 (t, J = 11.2 Hz, 2H), 1.90-1.77 (m, 4H), 1.66-1.51 (m, 6H). (1 eq. formate salt, 1 exchangable proton not observed) | P 1-(6-amino-pyridin-3-yl)piperidin-4-ol tert-butyl 2,8-diazaspiro[4.5]decane-2-carboxylate |

TABLE 2-continued

| I-# | STRUCTURE | NAME | LCMS | HNMR | Method SM |
|---|---|---|---|---|---|
| I-236 | 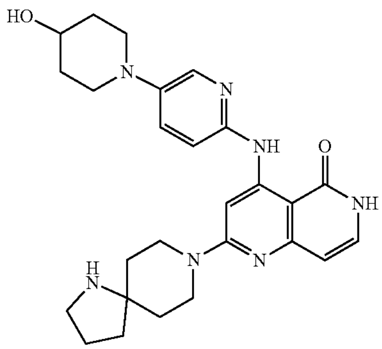 [SMILES: O=c1[nH]ccc2nc(N3CCC4(CCCN4)CC3)cc(Nc3ccc(N4CCC(O)CC4)cn3)c12] | 2-(1,8-diazaspiro[4.5]decan-8-yl)-4-[[5-(4-hydroxy-1-piperidyl)-2-pyridyl]amino]-6H-1,6-naphthyridin-5-one | Method AcHSS C18, m/z = 476 [M + H]+, Ret. time = 1.89 min. | $^1$H NMR (400 MHz, DMSO) δ 12.29 (s, 1H), 11.16 (s, 1H), 8.08 (d, J = 2.3 Hz, 1H), 7.98 (s, 1H), 7.48 (dd, J = 2.8, 8.8 Hz, 1H), 7.25 (d, J = 7.3 Hz, 1H), 6.93 (d, J = 8.8 Hz, 1H), 6.27 (d, J = 7.1 Hz, 1H), 4.73 (d, J = 4.0 Hz, 1H), 3.76-3.65 (m, 5H), 3.52 (d, J = 12.1 Hz, 2H), 2.93-2.86 (m, 4H), 1.92-1.85 (m, 2H), 1.79-1.72 (m, 2H), 1.61-1.55 (m, 9H). | P 1-(6-amino-pyridin-3-yl)piperidin-4-ol tert-butyl 1,8-diaza-spiro[4.5]decane-1-carboxylate |
| I-237 | 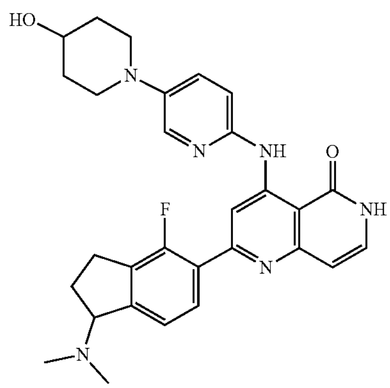 [SMILES: CN(C)C1CCc2c1ccc(-c1cc(Nc3ccc(N4CCC(O)CC4)cn3)c3c(=O)[nH]ccc3n1)c2F] | 2-[1-(dimethyl-amino)-4-fluoro-indan-5-yl]-4-[[5-(4-hydroxy-1-piperidyl)-2-pyridyl]amino]-6H-1,6-naphthyridin-5-one | Method AcHSS C18, m/z = 515 [M + H]+, Ret. time = 2.07 min. | $^1$H NMR (400 MHz, DMSO): δ 12.45 (s, 1 H), 11.66 (d, J = 1.3 Hz, 1 H), 8.71 (s, 1 H), 8.11 (d, J = 2.5 Hz, 1 H), 7.62 (d, J = 7.1 Hz, 1 H), 7.42 (dd, J = 2.9, 9.0 Hz, 1 H), 7.35 (d, J = 7.3 Hz, 1 H), 7.18 (d, J = 8.8 Hz, 1 H), 7.06 (d, J = 8.8 Hz, 1 H), 6.62 (d, J = 7.3 Hz, 1 H), 4.74 (d, J = 4.0 Hz, 1 H), 4.30 (dd, J = 7.1, 7.1 Hz, 1 H), 3.71-3.66 (m, 1 H), 3.61-3.52 (m, 2 H), 3.01-2.84 (m, 4 H), 2.24 (s, 6 H), 2.11 (q, J = 7.3 Hz, 2 H), 1.88 (d, J = 9.1 Hz, 2 H), 1.60-1.49 (m, 2 H). | A 1-(6-amino-pyridin-3-yl)piperidin-4-ol CB52 |
| I-238 | 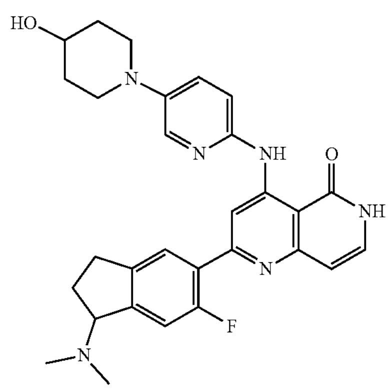 [SMILES: CN(C)C1CCc2cc(-c3cc(Nc4ccc(N5CCC(O)CC5)cn4)c4c(=O)[nH]ccc4n3)c(F)cc21] | 2-[1-(dimethyl-amino)-6-fluoro-indan-5-yl]-4-[[5-(4-hydroxy-1-piperidyl)-2-pyridyl]amino]-6H-1,6-naphthyridin-5-one | Method AcHSS C18, m/z = 515 [M + H]+, Ret. time = 2.03 min. | $^1$H NMR (400 MHz, DMSO): δ 12.45 (s, 1 H), 11.66 (d, J = 1.3 Hz, 1 H), 8.71 (s, 1 H), 8.11 (d, J = 2.5 Hz, 1 H), 7.82 (d, J = 7.1 Hz, 1 H), 7.52 (dd, J = 2.9, 9.0 Hz, 1 H), 7.45 (d, J = 7.3 Hz, 1 H), 7.18 (d, J = 8.8 Hz, 1 H), 7.06 (d, J = 8.8 Hz, 1 H), 6.62 (d, J = 7.3 Hz, 1 H), 4.74 (d, J = 4.0 Hz, 1 H), 4.39 (dd, J = 7.1, 7.1 Hz, 1 H), 3.71-3.66 (m, 1 H), 3.61-3.52 (m, 2 H), 3.01-2.84 (m, 4 H), 2.24 (s, 6 H), 2.11 (q, J = 7.3 Hz, 2 H), 1.88 (d, J = 9.1 Hz, 2 H), 1.60-1.49 (m, 2 H). | A 1-(6-amino-pyridin-3-yl)piperidin-4-ol CB53 |
| I-239 | 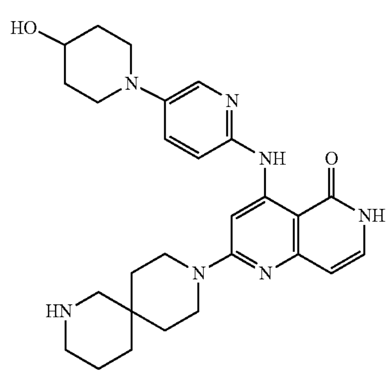 [SMILES: O=c1[nH]ccc2nc(N3CCC4(CCCNC4)CC3)cc(Nc3ccc(N4CCC(O)CC4)cn3)c12] | 2-(2,9-diazaspiro[5.5]undecan-9-yl)-4-[[5-(4-hydroxy-1-piperidyl)-2-pyridyl]amino]-6H-1,6-naphthyridin-5-one | Method AcHSS C18, m/z = 490 [M + H]+, Ret. time = 1.97 min. | $^1$H NMR (400 MHz, DMSO) 12.25 (1H, s), 11.11 (1H, s), 8.04 (1H, d, J = 3.0 Hz), 7.92 (1H, s), 7.44 (1H, dd, J = 3.1, 9.0 Hz), 7.21 (1H, d, J = 7.3 Hz), 6.89 (1H, d, J = 8.9 Hz), 6.23 (1H, d, J = 7.3 Hz), 4.70 (1H, d, J = 4.3 Hz), 3.70-3.46 (8H, m), 2.89-2.80 (2H, m), 2.69-2.66 (2H, m), 2.59-2.56 (2H, m), 1.88-1.81 (2H, m), 1.56-1.43 (10H, m). | P 1-(6-amino-pyridin-3-yl)piperidin-4-ol tert-butyl 2,9-diazaspiro[5.5]undecane-2-carboxylate |

TABLE 2-continued

| I-# | STRUCTURE | NAME | LCMS | HNMR | Method SM |
|---|---|---|---|---|---|
| I-240 | 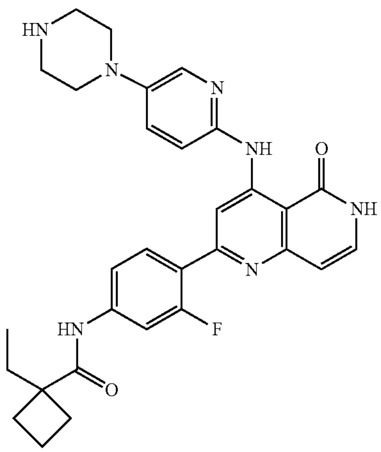 [SMILES: CCC1(C(=O)Nc2ccc(-c3cc(Nc4ccc(N5CCNCC5)cn4)c4c(=O)[nH]ccc4n3)c(F)c2)CCC1] | 1-ethyl-N-[3-fluoro-4-[5-oxo-4-[(5-piperazin-1-yl-2-pyridyl)amino]-6H-1,6-naphthyridin-2-yl]phenyl]cyclobutane carboxamide | Method AcHSS C18, m/z = 542 [M + H]+, Ret. time = 2.5 min. | $^1$H NMR (400 MHz, DMSO): δ 12.43 (s, 1 H), 9.76 (s, 1 H), 8.78 (s, 1 H), 8.10 (d, J = 2.5 Hz, 1 H), 8.04 (dd, J = 8.8, 8.8 Hz, 1 H), 7.86 (d, J = 7.3 Hz, 1 H), 7.64-7.58 (m, 1 H), 7.51 (dd, J = 2.9, 9.0 Hz, 1 H), 7.45 (d, J = 7.3 Hz, 1 H), 7.08 (d, J = 8.8 Hz, 1 H), 6.62 (d, J = 7.3 Hz, 1 H), 3.11 (dd, J = 4.7, 4.7 Hz, 4 H), 2.89 (dd, J = 4.7, 4.7 Hz, 4 H), 2.49-2.38 (m, 3 H), 1.98-1.90 (m, 6 H), 1.83-1.73 (m, 1 H), 0.83 (dd, J = 7.3, 7.3 Hz, 3 H). | A and G tert-butyl 4-(6-amino-pyridin-3-yl)piperazine-1-carboxylate CB54 |
| I-241 | 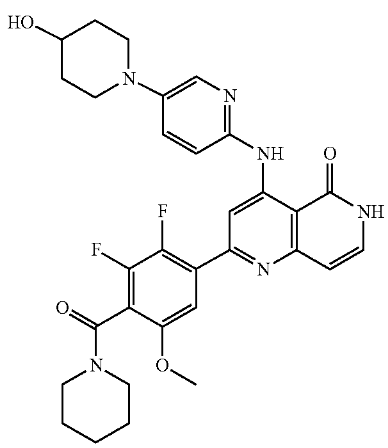 [SMILES: COc1cc(-c2cc(Nc3ccc(N4CCC(O)CC4)cn3)c3c(=O)[nH]ccc3n2)c(F)c(F)c1C(=O)N1CCCCC1] | 2-[2,3-difluoro-5-methoxy-4-(piperidine-1-carbonyl)phenyl]-4-[[5-(4-hydroxy-1-piperidyl)-2-pyridyl]amino]-6H-1,6-naphthyridin-5-one | Method AcHSS C18, m/z = 591 [M + H]+, Ret. time = 3.1 min. | $^1$H NMR (400 MHz, DMSO): δ 12.48 (s, 1 H), 11.71 (s, 1 H), 8.77 (d, J = 1.4 Hz, 1 H), 8.10 (d, J = 3.0 Hz, 1 H), 7.51-7.43 (m, 2 H), 7.40 (dd, J = 1.6, 5.0 Hz, 1 H), 7.04 (d, J = 8.9 Hz, 1 H), 6.61 (d, J = 7.3 Hz, 1 H), 4.71 (d, J = 4.1 Hz, 1 H), 3.89 (s, 3 H), 3.69-3.59 (m, 2 H), 3.58-3.50 (m, 3 H), 3.24-3.22 (m, 2 H), 2.92-2.48 (m, 2 H), 1.88-1.80 (m, 2 H), 1.67-1.54 (m, 4 H), 1.52-1.44 (m, 4 H). | A 1-(6-amino-pyridin-3-yl)piperidin-4-ol CB10 |
| I-242 | 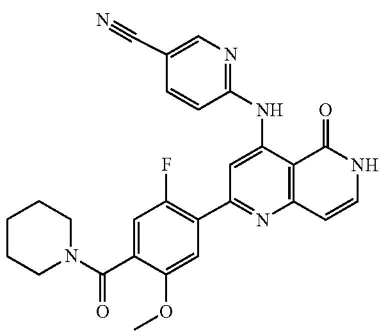 [SMILES: COc1cc(-c2cc(Nc3ccc(C#N)cn3)c3c(=O)[nH]ccc3n2)c(F)cc1C(=O)N1CCCCC1] | 6-[[2-[2-fluoro-5-methoxy-4-(piperidine-1-carbonyl)phenyl]-5-oxo-6H-1,6-naphthyridin-4-yl]amino]pyridine-3-carbonitrile | Method BicarbB EHC18, m/z = 499 [M + H]+, Ret. time = 4.34 min. | $^1$H NMR (400 MHz, DMSO): δ 13.29 (s, 1 H), 11.97 (s, 1 H), 9.15 (s, 1 H), 8.89 (s, 1 H), 8.24-8.20 (m, 1 H), 7.64 (d, J = 5.8 Hz, 1 H), 7.56 (d, J = 7.3 Hz, 1 H), 7.32-7.25 (m, 2 H), 6.76 (d, J = 7.3 Hz, 1 H), 3.92 (s, 3 H), 3.71-3.61 (m, 2 H), 3.22 (dd, J = 5.4, 5.4 Hz, 2 H), 1.75-1.44 (m, 6 H). | A 6-aminonico-tinonitrile CB1 |

TABLE 2-continued

| I-# | STRUCTURE | NAME | LCMS | HNMR | Method SM |
|---|---|---|---|---|---|
| I-243 | 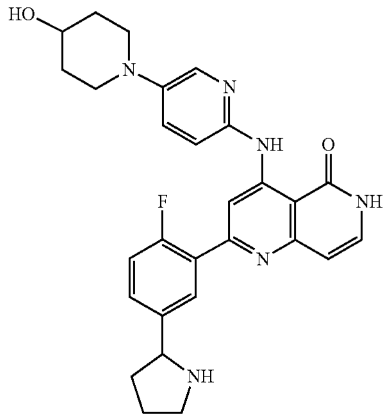 [SMILES: O=c1[nH]ccc2nc(-c3cc(C4CCCN4)ccc3F)cc(Nc3ccc(N4CCC(O)CC4)cn3)c12] | 2-(2-fluoro-5-pyrrolidin-2-yl-phenyl)-4-[[5-(4-hydroxy-1-piperidyl)-2-pyridyl]amino]-6H-1,6-naphthyridin-5-one | Method AcHSS C18, m/z = 501 [M + H]+, Ret. time = 2.09 min. | ¹H NMR (400 MHz, DMSO): δ 12.4 (s, 1 H), 11.97 (s, 1 H), 8.72 (d, J = 1.5 Hz, 1 H), 8.23 (s, 1 H), 8.06 (d, J = 2.9 Hz, 1 H), 8.01 (dd, J = 2.1, 7.4 Hz, 1 H), 7.60-7.57 (m, 1 H), 7.48 (dd, J = 3.1, 9.0 Hz, 1 H), 7.45-7.38 (m, 2 H), 7.03 (d, J = 8.8 Hz, 1 H), 6.61 (d, J = 7.3 Hz, 1 H), 3.67-3.60 (m, 1 H), 3.55-3.49 (m, 2 H), 3.23-3.12 (m, 2 H), 2.91-2.83 (m, 2 H), 2.35-2.29 (m, 2 H), 1.94-1.79 (m, 6 H), 1.54-1.45 (m, 2 H). | A and G 1-(6-amino-pyridin-3-yl)piperidin-4-ol CB70 |
| I-244 | 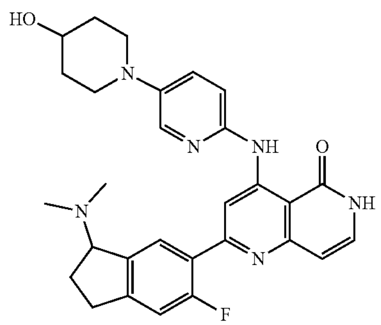 [SMILES: CN(C)C1CCc2cc(F)c(-c3cc(Nc4ccc(N5CCC(O)CC5)cn4)c4c(=O)[nH]ccc4n3)cc21] | 2-[3-(dimethyl-amino)-6-fluoro-indan-5-yl]-4-[[5-(4-hydroxy-1-piperidyl)-2-pyridyl]amino]-6H-1,6-naphthyridin-5-one | Method AcHSS C18, m/z = 515.2 [M + H]+, Ret. time = 2.12 min. | ¹H NMR (400 MHz, DMSO) δ 12.43 (s, 1H), 11.69-11.66 (m, 1H), 8.75 (s, 1H), 8.10 (d, J = 2.5 Hz, 1H), 7.90 (d, J = 7.3 Hz, 1H), 7.52 (dd, J = 2.9, 9.0 Hz, 1H), 7.46 (d, J = 3.0 Hz, 1H), 7.24 (d, J = 8.8 Hz, 1H), 7.06 (d, J = 8.8 Hz, 1H), 6.64 (d, J = 7.3 Hz, 1H), 4.77-4.74 (m, 1H), 4.35 (dd, J = 6.4, 6.4 Hz, 1H), 3.72-3.68 (m, 1H), 3.57 (d, J = 12.1 Hz, 2H), 3.01-2.88 (m, 4H), 2.21 (s, 6H), 2.16-2.04 (m, 2H), 1.90-1.86 (m, 2H), 1.60-1.49 (m, 2H). | A 1-(6-amino-pyridin-3-yl)piperidin-4-ol CB4 |
| I-245 | 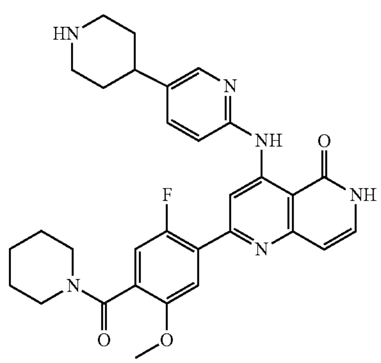 [SMILES: COc1cc(-c2cc(Nc3ccc(C4CCNCC4)cn3)c3c(=O)[nH]ccc3n2)c(F)cc1C(=O)N1CCCCC1] | 2-[2-fluoro-5-methoxy-4-(piperidine-1-carbonyl)phenyl]-4-[[5-(4-piperidyl)-2-pyridyl]amino]-6H-1,6-naphthyridin-5-one | Method AcHSS C18, m/z = 557 [M + H]+, Ret. time = 2.41 min. | ¹H NMR (400 MHz, DMSO): δ 12.75 (s, 1 H), 9.06 (s, 1 H), 8.32 (s, 1 H), 7.72 (dd, J = 2.1, 8.5 Hz, 1 H), 7.64 (d, J = 5.8 Hz, 1 H), 7.51 (d, J = 7.3 Hz, 1 H), 7.12 (d, J = 8.6 Hz, 1 H), 6.69 (d, J = 7.3 Hz, 1 H), 3.92 (s, 3 H), 3.69-3.60 (m, 2 H), 3.22 (s, 2 H), 3.11 (d, J = 12.1 Hz, 2 H), 2.67 (dd, J = 10.2, 12.0 Hz, 2 H), 1.78 (dd, J = 11.6, 11.6 Hz, 2 H), 1.70-1.51 (m, 9 H), 1.29 (s, 2 H), 0.93-0.82 (m, 1 H). | A and G tert-butyl 4-(6-amino-pyridin-3-yl)piperidine-1-carboxylate CB1 |
| I-246 | 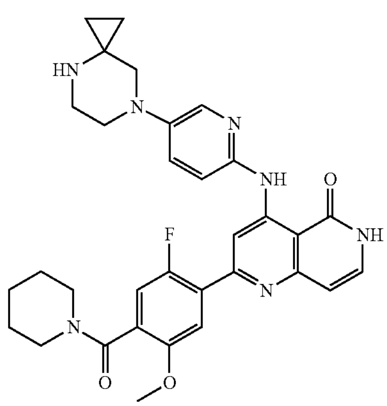 [SMILES: COc1cc(-c2cc(Nc3ccc(N4CCNC5(CC5)C4)cn3)c3c(=O)[nH]ccc3n2)c(F)cc1C(=O)N1CCCCC1] | 4-[[5-(4,7-diazaspiro[2.5]octan-7-yl)-2-pyridyl]amino]-2-[2-fluoro-5-methoxy-4-(piperidine-1-carbonyl)phenyl]-6H-1,6-naphthyridin-5-one | Method AcHSS C18, m/z = 584 [M + H]+, Ret. time = 2.39 min. | ¹H NMR (400 MHz, DMSO): δ 12.75 (s, 1 H), 9.07 (s, 1 H), 8.33-8.30 (m, 1 H), 7.73 (d, J = 8.3 Hz, 1 H), 7.64 (d, J = 6.1 Hz, 1 H), 7.50 (d, J = 7.3 Hz, 1 H), 7.30 (d, J = 8.3 Hz, 1 H), 7.12 (d, J = 8.3 Hz, 1 H), 6.69 (d, J = 7.3 Hz, 1 H), 3.92 (s, 3 H), 3.69-3.62 (m, 2 H), 3.21 (d, J = 4.5 Hz, 2 H), 3.12 (d, J = 11.4 Hz, 2 H), 2.73-2.65 (m, 2 H), 1.77 (d, J = 12.6 Hz, 2 H), 1.67-1.57 (m, 6 H), 1.51 (d, J = 5.1 Hz, 3 H), 1.32-1.27 (m, 2 H), 0.90 (dd, J = 4.3, 12.4 Hz, 1 H). | A and G tert-butyl 7-(6-amino-pyridin-3-yl)-4,7-diazaspiro[2.5]octane-4-carboxylate CB1 |

TABLE 2-continued

| I-# | STRUCTURE | NAME | LCMS | HNMR | Method SM |
|---|---|---|---|---|---|
| I-247 | 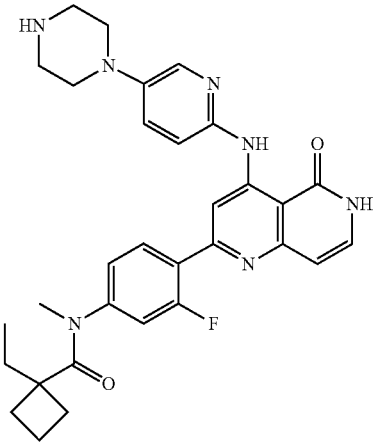 [SMILES: CCC1(C(=O)N(C)c2ccc(-c3cc(Nc4ccc(N5CCNCC5)cn4)c4c(=O)[nH]ccc4n3)c(F)c2)CCC1] | 1-ethyl-N-[3-fluoro-4-[5-oxo-4-[(5-piperazin-1-yl-2-pyridyl)amino]-6H-1,6-naphthyridin-2-yl]phenyl]-N-methyl-cyclobutane-carboxamide | Method AcHSS C18, m/z = 556.3 [M + H]+, Ret. time = 2.47 min. | $^1$H NMR (400 MHz, DMSO): δ 12.46 (s, 1 H), 8.78 (s, 1 H), 8.26 (d, J = 2.0 Hz, 1 H), 8.09 (d, J = 3.1 Hz, 1 H), 7.98 (dd, J = 8.4, 8.4 Hz, 1 H), 7.51 (dd, J = 2.1, 9.0 Hz, 1 H), 7.43 (d, J = 7.3 Hz, 1 H), 7.39 (d, J = 8.3 Hz, 1 H), 7.30 (d, J = 8.3 Hz, 1 H), 7.07 (d, J = 8.9 Hz, 1 H), 6.62 (d, J = 7.2 Hz, 1 H), 3.49-3.39 (m, 4 H), 3.20 (s, 2 H), 3.03 (s, 4 H), 2.69 (dd, J = 1.8, 1.8 Hz, 1 H), 2.62 (s, 1 H), 2.46 (d, J = 10.3 Hz, 2 H), 2.34 (dd, J = 1.8, 1.8 Hz, 2 H), 1.84 (s, 2 H), 1.63 (s, 2 H), 0.85 (dd, J = 7.3, 7.3 Hz, 3 H). | A and G tert-butyl 4-(6-amino-pyridin-3-yl)piperazine-1-carboxylate CB55 |
| I-248 | 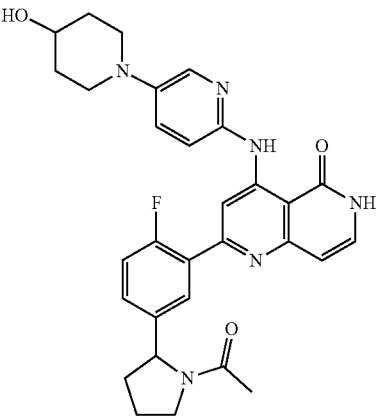 [SMILES: CC(=O)N1CCCC1c1ccc(F)c(-c2cc(Nc3ccc(N4CCC(O)CC4)cn3)c3c(=O)[nH]ccc3n2)c1] | 2-[5-(1-acetyl-pyrrolidin-2-yl)-2-fluoro-phenyl]-4-[[5-(4-hydroxy-1-piperidyl)-2-pyridyl]amino]-6H-1,6-naphthyridin-5-one | Method AcHSS C18, m/z = 543.2 [M + H]+, Ret. time = 2.7 min. | $^1$H NMR (400 MHz, DMSO): δ 12.37 (d, J = 4.0 Hz, 1 H), 8.69 (d, J = 2.9 Hz, 1 H), 8.05 (d, J = 2.9 Hz, 1 H), 7.74 (d, J = 7.0 Hz, 1 H), 7.66 (d, J = 6.8 Hz, 1 H), 7.47 (dd, J = 2.9, 9.0 Hz, 1 H), 7.41 (d, J = 7.3 Hz, 1 H), 7.36-7.22 (m, 2 H), 7.03 (d, J = 8.9 Hz, 1 H), 6.63 (dd, J = 3.6, 7.3 Hz, 1 H), 5.16 (d, J = 8.0 Hz, 1 H), 5.06 (dd, J = 2.2, 7.8 Hz, 1 H), 3.79-3.74 (m, 1 H), 3.53-3.47 (m, 3 H), 2.89-2.82 (m, 2 H), 2.41-2.22 (m, 2 H), 2.04 (s, 2 H), 1.93-1.89 (m, 1 H), 1.82 (dd, J = 3.5, 6.8 Hz, 3 H), 1.75 (s, 2 H), 1.54-1.44 (m, 2 H). | A 1-(6-amino-pyridin-3-yl)piperidin-4-ol CB11 |
| I-249 | 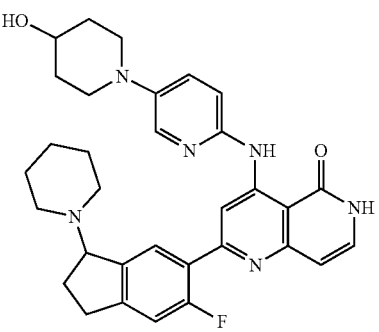 [SMILES: O=c1[nH]ccc2nc(-c3cc4c(cc3F)CCC4N3CCCCC3)cc(Nc3ccc(N4CCC(O)CC4)cn3)c12] | 2-[6-fluoro-3-(1-piperidyl)indan-5-yl]-4-[[5-(4-hydroxy-1-piperidyl)-2-pyridyl]amino]-6H-naphthyridin-5-one | Method AcHSS C18, m/z = 555.3 [M + H]+, Ret. time = 2.23 min. | $^1$H NMR (400 MHz, DMSO): δ 12.40 (s, 1 H), 11.63 (s, 1 H), 8.70 (d, J = 1.5 Hz, 1 H), 8.05 (d, J = 3.0 Hz, 1 H), 7.80 (d, J = 7.4 Hz, 1 H), 7.48 (dd, J = 3.0, 9.0 Hz, 1 H), 7.41 (d, J = 7.3 Hz, 1 H), 7.20 (d, J = 8.9 Hz, 1 H), 7.03 (d, J = 8.9 Hz, 1 H), 6.60 (d, J = 7.3 Hz, 1 H), 4.70 (d, J = 4.1 Hz, 1 H), 4.31 (dd, J = 6.9, 6.9 Hz, 1 H), 3.68-3.61 (m, 1 H), 3.55-3.50 (m, 2 H), 2.95-2.83 (m, 4 H), 2.40-2.32 (m, 3 H), 2.15-2.00 (m, 3 H), 1.87-1.81 (m, 2 H), 1.56-1.38 (m, 8 H). | A 1-(6-amino-pyridin-3-yl)piperidin-4-ol CB56 |

TABLE 2-continued

| I-# | STRUCTURE | NAME | LCMS | HNMR | Method SM |
|---|---|---|---|---|---|
| I-250 | 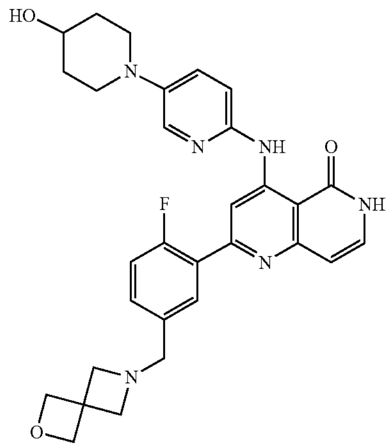 [SMILES: O=c1[nH]ccc2nc(-c3cc(CN4CC5(COC5)C4)ccc3F)cc(Nc3ccc(N4CCC(O)CC4)cn3)c12] | 2-[2-fluoro-5-(2-oxa-6-azaspiro[3.3]heptan-6-ylmethyl)phenyl]-4-[[5-(4-hydroxy-1-piperidyl)-2-pyridyl]amino]-6H-1,6-naphthyridin-5-one | Method AcHSS C18, m/z = 543 [M + H]+, Ret. time = 2.04 min. | $^1$H NMR (400 MHz, DMSO): δ 12.43 (s, 1 H), 11.66 (s, 1 H), 8.71 (d, J = 1.6 Hz, 1 H), 8.07 (d, J = 3.0 Hz, 1 H), 7.81 (dd, J = 2.3, 7.7 Hz, 1 H), 7.48 (dd, J = 3.1, 9.0 Hz, 1 H), 7.42 (d, J = 7.3 Hz, 1 H), 7.40-7.35 (m, 1 H), 7.31-7.25 (m, 1 H), 7.03 (d, J = 8.8 Hz, 1 H), 6.61 (d, J = 7.3 Hz, 1 H), 4.70 (d, J = 4.3 Hz, 1 H), 4.62 (s, 4 H), 3.67-3.60 (m, 1 H), 3.57-3.50 (m, 4 H), 3.32 (s, 4 H), 2.91-2.83 (m, 2 H), 1.88-1.80 (m, 2 H), 1.55-1.45 (m, 2 H). | A 1-(6-amino-pyridin-3-yl)piperidin-4-ol CB12 |
| I-251 | 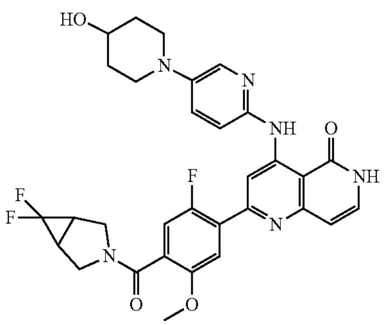 [SMILES: COc1cc(-c2cc(Nc3ccc(N4CCC(O)CC4)cn3)c3c(=O)[nH]ccc3n2)c(F)cc1C(=O)N1CC2C(C1)C2(F)F] | 2-[4-(6,6-difluoro-3-azabicyclo[3.1.0]hexane-3-carbonyl)-2-fluoro-5-methoxy-phenyl]-4-[[5-(4-hydroxy-1-piperidyl)-2-pyridyl]amino]-6H-1,6-naphthyridin-5-one | Method BicarbB EHC18, m/z = 607 [M + H]+, Ret. time = 3.81 min. | $^1$H NMR (400 MHz, DMSO): δ 12.38 (s, 1 H), 8.70 (d, J = 5.6 Hz, 1 H), 8.19 (s, 1 H), 8.04 (d, J = 2.5 Hz, 1 H), 7.56 (d, J = 6.1 Hz, 1 H), 7.48-7.39 (m, 2 H), 7.18 (d, J = 8.8 Hz, 1 H), 7.01 (d, J = 8.8 Hz, 1 H), 6.62 (d, J = 7.1 Hz, 1 H), 3.96 (d, J = 12.6 Hz, 1 H), 3.95-3.80 (m, 6 H), 3.75-3.57 (m, 3 H), 3.49-3.41 (m, 3 H), 2.89-2.81 (m, 2 H), 2.65-2.53 (m, 2 H), 1.86-1.79 (m, 2 H), 1.53-1.41 (m, 2 H). | A 1-(6-amino-pyridin-3-yl)piperidin-4-ol CB67 |
| I-252 | 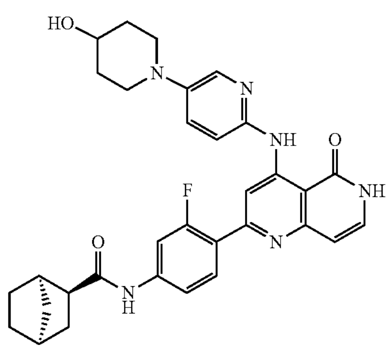 [SMILES: O=C(Nc1ccc(-c2cc(Nc3ccc(N4CCC(O)CC4)cn3)c3c(=O)[nH]ccc3n2)c(F)c1)[C@H]1C[C@H]2CC[C@@H]1C2] | (1R,2S,4S)-N-[3-fluoro-4-[4-[[5-(4-hydroxy-1-piperidyl)-2-pyridyl]amino]-5-oxo-6H-1,6-naphthyridin-2-yl]phenyl]norbornane-2-carboxamide Racemic | Method BicarbB EHC18, m/z = 569 [M + H]+, Ret. time = 4.28 min. | $^1$H NMR (400 MHz, DMSO): δ 12.36 (s, 1 H), 11.59 (d, J = 5.6 Hz, 1 H), 10.17 (s, 1 H), 8.71 (s, 1 H), 8.06 (d, J = 2.5 Hz, 1 H), 7.98 (dd, J = 8.8, 8.8 Hz, 1 H), 7.46 (dd, J = 3.3, 8.6 Hz, 1 H), 7.38 (dd, J = 6.4, 6.4 Hz, 1 H), 7.01 (d, J = 9.1 Hz, 1 H), 6.56 (d, J = 7.1 Hz, 1 H), 3.67-3.60 (m, 1 H), 2.86 (dd, J = 9.7, 9.7 Hz, 4 H), 1.83 (d, J = 9.9 Hz, 4 H), 1.71-1.66 (m, 1 H), 1.60-1.41 (m, 6 H), 1.38-1.23 (m, 6 H). | A 1-(6-amino-pyridin-3-yl)piperidin-4-ol CB57 |
| I-253 | 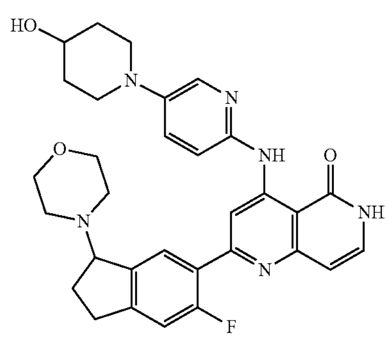 [SMILES: O=c1[nH]ccc2nc(-c3cc4c(cc3F)CCC4N3CCOCC3)cc(Nc3ccc(N4CCC(O)CC4)cn3)c12] | 2-(6-fluoro-3-morpholino-indan-5-yl)-4-[[5-(4-hydroxy-1-piperidyl)-2-pyridyl]amino]-6H-1,6-naphthyridin-5-one | Method AcHSS C18, m/z = 557 [M + H]+, Ret. time = 2.14 min. | $^1$H NMR (400 MHz, DMSO): δ 12.37 (s, 1 H), 8.69 (s, 1 H), 8.29 (d, J = 8.4 Hz, 1 H), 8.03 (d, J = 1.0 Hz, 1 H), 7.84-7.81 (m, 1 H), 7.48 (d, J = 9.2 Hz, 1 H), 7.42-7.39 (m, 1 H), 7.21 (d, J = 8.9 Hz, 1 H), 7.03 (d, J = 8.9 Hz, 1 H), 6.62 (d, J = 7.3 Hz, 1 H), 4.30 (d, J = 5.0 Hz, 1 H), 3.43 (s, 6 H), 2.99-2.81 (m, 6 H), 2.38 (s, 3 H), 2.15-2.07 (m, 2 H), 1.83 (dd, J = 2.9, 12.6 Hz, 2 H), 1.53-1.45 (m, 3 H). | A 1-(6-amino-pyridin-3-yl)piperidin-4-ol CB58 |

TABLE 2-continued

| I-# | STRUCTURE | NAME | LCMS | HNMR | Method SM |
|---|---|---|---|---|---|
| I-254 | 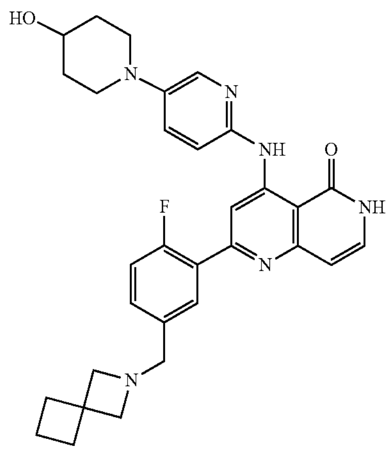 [SMILES: O=c1[nH]ccc2nc(-c3cc(CN4CC5(CCC5)C4)ccc3F)cc(Nc3ccc(N4CCC(O)CC4)cn3)c12] | 2-[5-(2-azaspiro[3.3]heptan-2-ylmethyl)-2-fluoro-phenyl]-4-[[5-(4-hydroxy-1-piperidyl)-2-pyridyl]amino]-6H-1,6-naphthyridin-5-one | Method AcHSS C18, m/z = 541 [M + H]+, Ret. time = 2.22 min. | $^1$H NMR (400 MHz, DMSO): δ 12.43 (s, 1 H), 11.66 (s, 1 H), 8.70 (d, J = 1.5 Hz, 1 H), 8.07 (d, J = 3.0 Hz, 1 H), 7.81 (dd, J = 2.2, 7.6 Hz, 1 H), 7.48 (dd, J = 3.1, 9.0 Hz, 1 H), 7.44-7.35 (m, 2 H), 7.30-7.24 (m, 1 H), 7.03 (d, J = 9.0 Hz, 1 H), 6.61 (d, J = 7.3 Hz, 1 H), 4.70 (d, J = 4.1 Hz, 1 H), 3.67-3.61 (m, 2 H), 3.55 (s, 3 H), 3.51 (dd, J = 4.3, 4.3 Hz, 2 H), 3.12 (s, 2 H), 2.91-2.83 (m, 2 H), 2.05 (dd, J = 7.6, 7.6 Hz, 4 H), 1.87-1.73 (m, 4 H), 1.55-1.45 (m, 2 H). | A 1-(6-amino-pyridin-3-yl)piperidin-4-ol CB59 |
| I-255 | 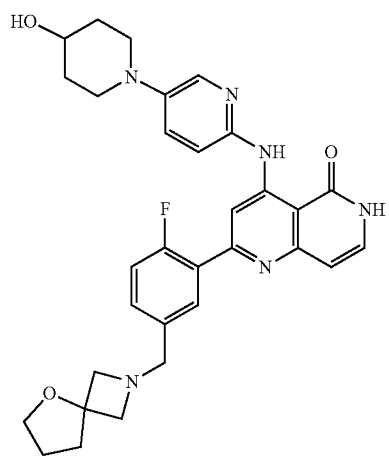 [SMILES: O=c1[nH]ccc2nc(-c3cc(CN4CC5(CCCO5)C4)ccc3F)cc(Nc3ccc(N4CCC(O)CC4)cn3)c12] | 2-[2-fluoro-5-(5-oxa-2-azaspiro[3.4]octan-2-ylmethyl)phenyl]-4-[[5-(4-hydroxy-1-piperidyl)-2-pyridyl]amino]-6H-1,6-naphthyridin-5-one | Method BicarbB EHC18, m/z = 557.2 [M + H]+, Ret. time = 3.82 min. | $^1$H NMR (400 MHz, DMSO): δ 12.46-12.42 (m, 1 H), 8.71 (d, J = 1.5 Hz, 1 H), 8.06 (d, J = 3.0 Hz, 1H), 7.83 (dd, J = 2.2, 7.7 Hz, 1 H), 7.48 (dd, J = 3.1, 9.0 Hz, 1 H), 7.44-7.38 (m, 2 H), 7.28 (dd, J = 8.5, 11.1 Hz, 1 H), 7.03 (d, J = 8.9 Hz, 1 H), 6.61 (d, J = 7.3 Hz, 1 H), 4.70 (d, J = 4.3 Hz, 1 H), 3.69-3.63 (m, 6 H), 3.55-3.50 (m, 2 H), 3.32-3.26 (m, 2 H), 3.05 (d, J = 8.2 Hz, 2 H), 2.91-2.83 (m, 2 H), 2.02 (dd, J = 7.2, 7.2 Hz, 2H), 1.86-1.79 (m, 4 H), 1.55-1.46 (m, 2 H). | A 1-(6-amino-pyridin-3-yl)piperidin-4-ol CB60 |
| I-256 | 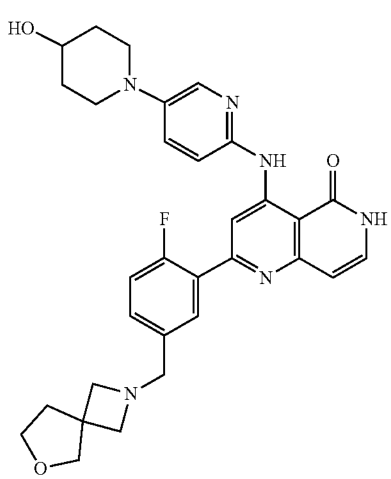 [SMILES: O=c1[nH]ccc2nc(-c3cc(CN4CC5(CCOC5)C4)ccc3F)cc(Nc3ccc(N4CCC(O)CC4)cn3)c12] | 2-[2-fluoro-5-(6-oxa-2-azaspiro[3.4]octan-2-ylmethyl)phenyl]-4-[[5-(4-hydroxy-1-piperidyl)-2-pyridyl]amino]-6H-1,6-naphthyridin-5-one | Method BicarbB EHC18, m/z = 557 [M + H]+, Ret. time = 3.7 min. | $^1$H NMR (400 MHz, DMSO): δ 12.46 (s, 1 H), 11.70 (d, J = 5.1 Hz, 1 H), 8.74 (s, 1 H), 8.23 (s, 1 H), 8.10 (d, J = 2.8 Hz, 1 H), 7.88 (dd, J = 1.6, 7.2 Hz, 1 H), 7.54-7.43 (m, 3 H), 7.36-7.29 (m, 1 H), 7.07 (d, J = 8.8 Hz, 1 H), 6.65 (d, J = 7.3 Hz, 1 H), 3.71-3.64 (m, 6 H), 3.60-3.52 (m, 2 H), 3.27-3.21 (m, 4 H), 2.94-2.86 (m, 2 H), 2.14-2.03 (m, 3 H), 1.92-1.86 (m, 2 H), 1.60-1.48 (m, 2 H). | A 1-(6-amino-pyridin-yl)piperidin-4-ol CB61 |

TABLE 2-continued

| I-# | STRUCTURE | NAME | LCMS | HNMR | Method SM |
|---|---|---|---|---|---|
| I-257 | 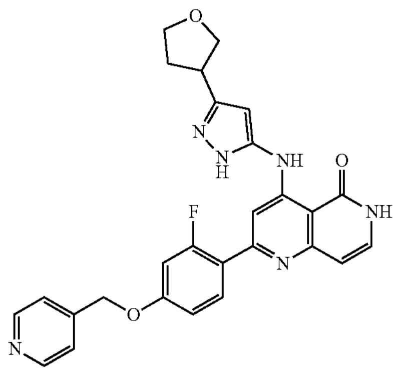 [SMILES: O=c1[nH]ccc2nc(-c3ccc(OCc4ccncc4)cc3F)cc(Nc3cc(C4CCOC4)n[nH]3)c12] | 2-[2-fluoro-4-(4-pyridyl-methoxy)phenyl]-4-[(3-THF-3-yl-1H-pyrazol-5-yl)amino]-6H-1,6-naphthyridin-5-one | Method AcHSS C18, m/z = 499 [M + H]+, Ret. time = 2.25 min. | $^1$H NMR (400 MHz, DMSO): δ 12.44 (d, J = 1.1 Hz, 1 H), 11.96 (s, 1 H), 11.59 (d, J = 4.3 Hz, 1 H), 8.62 (d, J = 5.6 Hz, 2 H), 8.25 (s, 1 H), 8.01 (dd, J = 8.9, 8.9 Hz, 1 H), 7.48 (d, J = 6.0 Hz, 2 H), 7.42-7.37 (m, 1 H), 7.09 (d, J = 7.3 Hz, 1 H), 7.08-7.02 (m, 1 H), 6.56 (d, J = 7.3 Hz, 1 H), 6.04 (d, J = 2.0 Hz, 1 H), 5.31 (s, 2 H), 4.02 (dd, J = 7.8, 7.8 Hz, 1 H), 3.92-3.77 (m, 2 H), 3.63 (dd, J = 7.7, 7.7 Hz, 1 H), 3.49-3.40 (m, 1 H), 2.35-2.55 (m, 1 H), 2.01 (ddd, J = 7.2, 12.2, 15.0 Hz, 1 H). | A 5-(THF-3-yl)-1H-pyrazol-3-amine CB5 |
| I-258 | 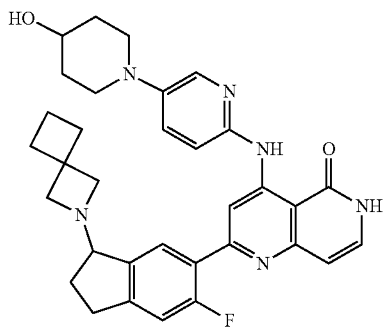 [SMILES: O=c1[nH]ccc2nc(-c3cc4c(cc3F)CCC4N3CC4(CCC4)C3)cc(Nc3ccc(N4CCC(O)CC4)cn3)c12] | 2-[3-(2-azaspiro[3.3]heptan-2-yl)-6-fluoro-indan-5-yl]-4-[[5-(4-hydroxy-1-piperidyl)-2-pyridyl]amino]-6H-1,6-naphthyridin-5-one | Method AcHSS C18, m/z = 567.3 [M + H]+, Ret. time = 2.39 min. | $^1$H NMR (400 MHz, DMSO): δ 12.40 (s, 1 H), 11.67 (d, J = 5.1 Hz, 1 H), 8.68 (d, J = 1.4 Hz, 1 H), 8.37 (s, 1 H), 8.06 (d, J = 3.0 Hz, 1 H), 7.77 (d, J = 7.4 Hz, 1 H), 7.48 (dd, J = 3.1, 9.0 Hz, 1 H), 7.44-7.39 (m, 1 H), 7.03 (d, J = 9.0 Hz, 1 H), 6.60 (d, J = 7.2 Hz, 1 H), 3.76 (dd, J = 2.9, 6.6 Hz, 2 H), 3.67-3.60 (m, 4 H), 3.25 (d, J = 6.3 Hz, 2 H), 3.12 (d, J = 6.1 Hz, 3 H), 3.03-2.77 (m, 4 H), 2.56 (s, 1 H), 2.11-2.06 (m, 1 H), 2.04 (dd, J = 7.6, 7.6 Hz, 2 H), 1.89-1.73 (m, 4 H), 1.56-1.45 (m, 2 H). | A 1-(6-amino-pyridin-3-yl)piperidin-4-ol CB62 |
| I-259 | 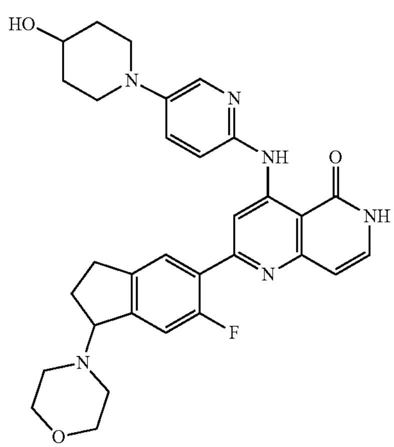 [SMILES: O=c1[nH]ccc2nc(-c3cc4c(cc3F)C(N3CCOCC3)CC4)cc(Nc3ccc(N4CCC(O)CC4)cn3)c12] | 2-(6-fluoro-1-morphoino-indan-5-yl)-4-[[5-(4-hydroxy-1-piperidy)-2-pyridy]amino]-6H-1,6-naphthyridin-5-one | Method AcHSS C18, m/z = 557 [M + H]+, Ret. time = 2.07 min. | $^1$H NMR (400 MHz, DMSO): δ 12.47 (s, 1 H), 11.70 (brs, 1 H), 8.71 (s, 1 H), 8.11 (d, J = 2.8 Hz, 1 H), 7.82 (d, J = 7.3 Hz, 1 H), 7.52 (dd, J = 2.9, 9.0 Hz, 1 H), 7.45 (d, J = 7.3 Hz, 1 H), 7.21 (d, J = 8.8 Hz, 1 H), 7.06 (d, J = 8.8 Hz, 1 H), 6.62 (d, J = 7.3 Hz, 1 H), 4.74 (d, J = 3.8 Hz, 1 H), 4.39 (dd, J = 7.1, 7.1 Hz, 1 H), 3.68-3.62 (m, 6 H), 3.60-3.54 (m, 3 H), 2.99-2.85 (m, 4 H), 2.47-2.42 (m, 2 H), 2.21-2.12 (m, 2 H), 1.90-1.84 (m, 2 H), 1.59-1.49 (m, 2 H). | A 1-(6-amino-pyridin-3-yl)piperidin-4-o CB63 |

TABLE 2-continued

| I-# | STRUCTURE | NAME | LCMS | HNMR | Method SM |
|---|---|---|---|---|---|
| I-260 | 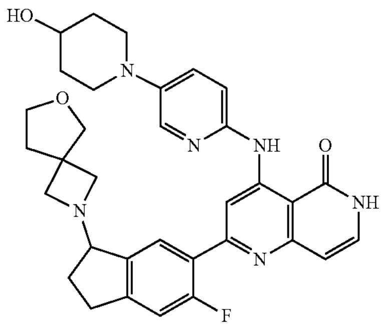 [SMILES: O=c1[nH]ccc2nc(-c3cc4c(cc3F)CCC4N3CC4(CCOC4)C3)cc(Nc3ccc(N4CCC(O)CC4)cn3)c12] | 2-[6-fluoro-3-(6-oxa-2-azaspiro[3.4]octan-2-yl)indan-5-yl]-4-[[5-(4-hydroxy-1-piperidyl)-2-pyridyl]amino]-6H-1,6-naphthyridin-5-one | Method AcHSS C18, m/z = 583 [M + H]+, Ret. time = 2.13 min. | $^1$H NMR (400 MHz, DMSO): δ 12.45 (s, 1 H), 8.72 (s, 1 H), 11.79 (S, 1 H), 8.08 (d, J = 2.8 Hz, 1 H), 7.83 (d, J = 7.3 Hz, 1 H), 7.52 (dd, J = 3.0, 8.8 Hz, 1 H), 7.45 (d, J = 7.1 Hz, 1 H), 7.22 (d, J = 8.8 Hz, 1 H), 7.06 (d, J = 8.8 Hz, 1 H), 6.63 (d, J = 7.3 Hz, 1 H), 4.73 (d, J = 3.5 Hz, 1 H), 3.89 (dd, J = 2.5, 6.3 Hz, 1 H), 3.75-3.64 (m, 6 H), 3.60-3.53 (m, 2 H), 3.22 (d, J = 7.6 Hz, 2 H), 3.20 (dd, J = 6.3, 6.3 Hz, 2 H), 3.10-3.00 (m, 1 H), 2.95-2.85 (m, 3 H), 2.15-2.00 (m, 3 H), 1.97-1.83 (m, 3 H), 1.60-1.49 (m, 2 H). | A 1-(6-aminopyridin-3-yl)piperidin-4-ol CB64 |
| I-261 | 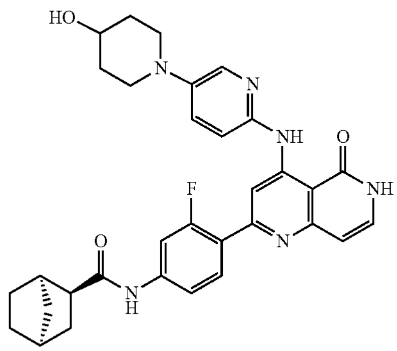 [SMILES: O=C(Nc1ccc(-c2cc(Nc3ccc(N4CCC(O)CC4)cn3)c3c(=O)[nH]ccc3n2)c(F)c1)[C@H]1C[C@H]2CC[C@@H]1C2] | (1R,2S,4S)-N-[3-fluoro-4-[4-[[5-(4-hydroxy-1-piperidyl)-2-pyridyl]amino]-5-oxo-6H-1,6-naphthyridin-2-yl]phenyl]norbornane-2-carboxamide Isomer 1 separated by SFC | Method AcHSS C18, m/z = 569 [M + H]+, Ret. time = 3.5 min. | $^1$H NMR (400 MHz, DMSO): δ 11.16 (s, 1 H), 9.67 (s, 1 H), 8.43-8.40 (m, 1 H), 7.97 (d, J = 2.9 Hz, 1 H), 7.43 (dd, J = 3.0, 9.0 Hz, 1 H), 7.39-7.35 (m, 2 H), 7.15 (d, J = 7.9 Hz, 1 H), 7.07 (dd, J = 7.2, 7.2 Hz, 1 H), 6.98-6.94 (m, 2 H), 4.14-4.14 (m, 2 H), 3.63 (s, 2 H), 3.10 (dd, J = 4.9, 4.9 Hz, 4 H), 2.69-2.64 (m, 2 H), 2.48 (dd, J = 4.8, 4.8 Hz, 4 H), 2.23 (s, 3 H), 2.09 (s, 2 H), 1.22 (dd, J = 7.6, 7.6 Hz, 3 H). | A 1-(6-aminopyridin-3-yl)piperidin-4-ol CB57 |
| I-262 | 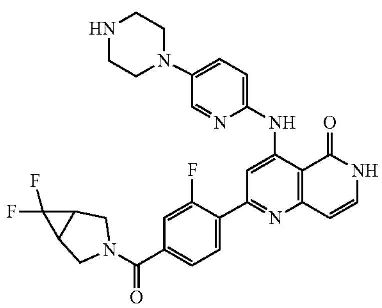 [SMILES: O=C(c1ccc(-c2cc(Nc3ccc(N4CCNCC4)cn3)c3c(=O)[nH]ccc3n2)c(F)c1)N1CC2C(C1)C2(F)F] | 2-[4-(6,6-difluoro-3-azabicyclo[3.1.0]hexane-3-carbonyl)-2-fluorophenyl]-4-[(5-piperazin-1-yl-2-pyridyl)amino]-6H-1,6-naphthyridin-5-one | Method AcHSS C18, m/z = 562 [M + H]+, Ret. time = 2.16 min. | $^1$H NMR (400 MHz, DMSO): δ 12.52 (s, 1 H), 8.84-8.80 (m, 1 H), 8.14 (d, J = 2.5 Hz, 1 H), 8.03 (dd, J = 7.8, 7.8 Hz, 1 H), 7.57 (dd, J = 2.8, 9.1 Hz, 1 H), 7.48-7.44 (m, 3 H), 7.13 (d, J = 8.8 Hz, 1 H), 6.68 (d, J = 7.3 Hz, 1 H), 5.72 (s, 1 H), 4.17 (d, J = 12.9 Hz, 1 H), 4.02-3.94 (m, 2 H), 3.67 (d, J = 11.4 Hz, 2 H), 3.40-3.36 (m, 4 H), 3.24 (dd, J = 5.3, 5.3 Hz, 4 H), 2.66-2.59 (m, 2 H). | F and G tert-butyl 4-(6-aminopyridin-3-yl)piperazine-1-carboxylate 6,6-difluoro-3-azabicyclo[3.1.0]hexane (step 2) |
| I-263 | 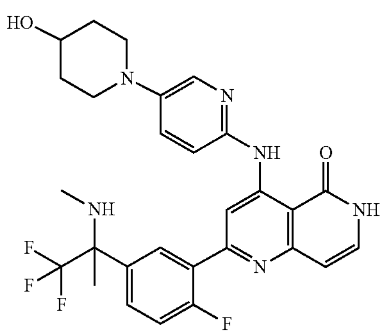 [SMILES: CNC(C)(c1ccc(F)c(-c2cc(Nc3ccc(N4CCC(O)CC4)cn3)c3c(=O)[nH]ccc3n2)c1)C(F)(F)F] | 2-[2-fluoro-5-[2,2,2-trifluoro-1-methyl-1-(methylamino)ethyl]phenyl]-4-[[5-(4-hydroxy-1-piperidyl)-2-pyridyl]amino]-6H-1,6-naphthyridin-5-one | Method AcHSS C18, m/z = 557 [M + H]+, Ret. time = 2.73 min. | $^1$H NMR (400 MHz, DMSO): δ 12.48 (s, 1 H), 11.7 (brs, 1 H), 8.77 (s, 1 H), 8.24 (d, J = 5.6 Hz, 1 H), 8.11 (d, J = 2.5 Hz, 1 H), 7.77-7.74 (m, 1 H), 7.53 (dd, J = 2.9, 9.0 Hz, 1 H), 7.50-7.40 (m, 2 H), 7.08 (d, J = 8.8 Hz, 1 H), 6.85 (s, 1 H), 6.66 (d, J = 7.3 Hz, 1 H), 4.74 (d, J = 4.0 Hz, 1 H), 3.71-3.65 (m, 1 H), 3.57 (d, J = 12.4 Hz, 2 H), 2.97-2.89 (m, 2 H), 2.15 (s, 3 H), 1.89 (d, J = 9.1 Hz, 2 H), 1.80 (s, 3 H), 1.61-1.50 (m, 2 H). | A 1-(6-aminopyridin-3-yl)piperidin-4-ol CB13 |

TABLE 2-continued

| I-# | STRUCTURE | NAME | LCMS | HNMR | Method SM |
|---|---|---|---|---|---|
| I-264 | 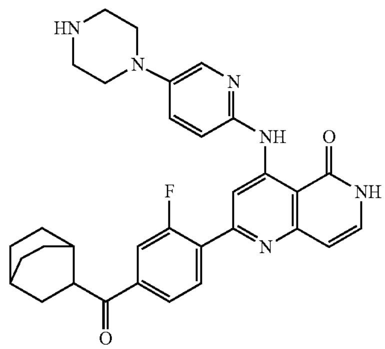 [SMILES: O=C(c1ccc(-c2cc(Nc3ccc(N4CCNCC4)cn3)c3c(=O)[nH]ccc3n2)c(F)c1)C1CC2CCC1CC2] | 2-[4-(3-azabicyclo[2.2.2]octane-3-carbonyl)-2-fluoro-phenyl]-4-[(5-piperazin-1-yl-2-pyridyl)amino]-6H-1,6-naphthyridin-5-one | Method AcHSS C18, m/z = 554 [M + H]+, Ret. time = 2.34 min. | ¹H NMR (400 MHz, DMSO): δ 12.51 (s, 1 H), 11.80 (brs, 1 H), 8.80 (s, 1 H), 8.12-8.04 (m, 2 H), 7.54-7.45 (m, 3 H), 7.39 (d, J = 7.8 Hz, 1 H), 7.09 (d, J = 9.1 Hz, 1 H), 6.66-6.61 (m, 1 H), 3.62-3.57 (m, 1 H), 3.52 (s, 2 H), 3.45-3.41 (m, 1 H), 3.16-3.10 (m, 4 H), 2.92 (dd, J = 4.5, 4.5 Hz, 4 H), 2.06 (s, 1 H), 1.91-1.86 (m, 2 H), 1.75-1.63 (m, 6 H). | F and G tert-butyl 4-(6-amino-pyridin-3-yl)piperazine-1-carboxylate 2-azabicyclo[2.2.2]octane (step 2) |
| I-265 | 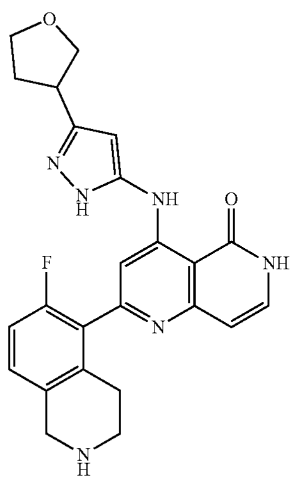 [SMILES: O=c1[nH]ccc2nc(-c3c(F)ccc4c3CCNC4)cc(Nc3cc(C4CCOC4)n[nH]3)c12] | 2-(6-fluoro-1,2,3,4-tetrahydro-isoquinolin-5-yl)-4-[(3-THF-3-yl-1H-pyrazol-5-yl)amino]-6H-1,6-naphthyridin-5-one | Method AcHSS C18, m/z = 447 [M + H]+, Ret. time = 2 min. | ¹H NMR (400 MHz, DMSO): δ 12.32 (s, 1 H), 12.03 (s, 1 H), 7.80 (s, 1 H), 7.40 (d, J = 7.3 Hz, 1 H), 7.14 (dd, J = 5.8, 8.5 Hz, 1 H), 7.07 (dd, J = 8.9, 8.9 Hz, 1 H), 6.51 (d, J = 7.3 Hz, 1 H), 6.02-6.00 (m, 1 H), 3.99 (dd, J = 7.8, 7.8 Hz, 1 H), 3.88-3.77 (m, 4 H), 3.60 (dd, J = 7.6, 7.6 Hz, 1 H), 3.47-3.38 (m, 1 H), 2.84 (dd, J = 6.0, 6.0 Hz, 2 H), 2.70-2.67 (m, 1 H), 2.45 (dd, J = 5.5, 5.5 Hz, 2 H), 2.36-2.23 (m, 2 H), 2.02-1.93 (m, 1 H). | A and G 5-(THF-3-yl)-1H-pyrazol-3-amine CB45 |
| I-266 | 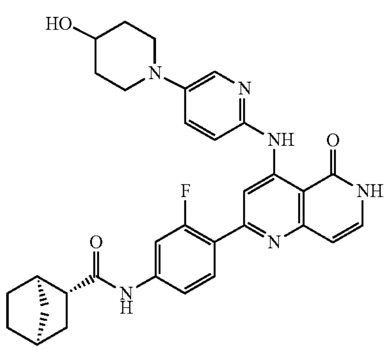 [SMILES: O=C(Nc1ccc(-c2cc(Nc3ccc(N4CCC(O)CC4)cn3)c3c(=O)[nH]ccc3n2)c(F)c1)[C@@H]1C[C@H]2CC[C@@H]1C2] | (1R,2R,4S)-N-[3-fluoro-4-[4-[[5-(4-hydroxy-1-piperidyl)-2-pyridyl]amino]-5-oxo-6H-1,6-naphthyridin-2-yl]phenyl]norbornane-2-carboxamide Racemic | Method AcHSS C18, m/z = 570 [M + H]+, Ret. time = 3.49 min. | ¹H NMR (400 MHz, DMSO): δ 12.42 (s, 1 H), 11.64 (d, J = 5.3 Hz, 1 H), 10.30 (s, 1 H), 8.76 (s, 1 H), 8.12 (d, J = 2.8 Hz, 1 H), 8.04 (dd, J = 8.8, 8.8 Hz, 1 H), 7.78-7.75 (m, 1 H), 7.55-7.47 (m, 2 H), 7.44 (dd, J = 6.6, 6.6 Hz, 1 H), 7.07 (d, J = 8.8 Hz, 1 H), 6.61 (d, J = 6.6 Hz, 1 H), 4.75-4.71 (m, 1 H), 3.71-3.66 (m, 1 H), 3.59-3.55 (m, 2 H), 2.95-2.89 (m, 2 H), 2.49 (d, J = 13.1 Hz, 1 H), 2.39-2.33 (m, 1 H), 1.95-1.85 (m, 3 H), 1.60-1.25 (m, 8 H), 1.17-1.14 (m, 1 H), 0.96-0.92 (m, 1 H). | A 1-(6-amino-pyridin-3-yl)piperidin-4-ol CB65 |

TABLE 2-continued

| I-# | STRUCTURE | NAME | LCMS | HNMR | Method SM |
|---|---|---|---|---|---|
| I-267 | 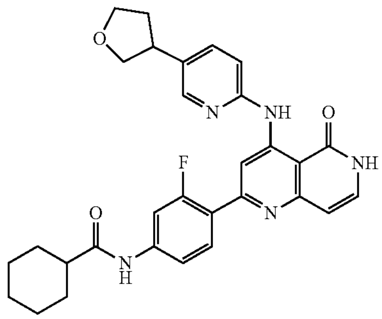 [SMILES: O=C(Nc1ccc(-c2cc(Nc3ccc(C4CCOC4)cn3)c3c(=O)[nH]ccc3n2)c(F)c1)C1CCCCC1] | N-[3-fluoro-4-[5-oxo-4-[(5-THF-3-yl-2-pyridyl)amino]-6H-1,6-naphthyridin-2-yl]phenyl]cyclohexane carboxamide Isomer 2 separated by SFC | Method BicarbB EHC18, m/z = 528 [M + H]+, Ret. time = 4.79 min. | $^1$H NMR (400 MHz, DMSO): δ 12.84 (s, 1 H), 11.73 (s, 1 H), 10.28 (s, 1 H), 9.07 (s, 1 H), 8.35 (d, J = 1.8 Hz, 1 H), 8.06 (dd, J = 8.8, 8.8 Hz, 1 H), 7.82-7.74 (m, 2 H), 7.54-7.46 (m, 2 H), 7.11 (d, J = 8.3 Hz, 1 H), 6.65 (d, J = 7.3 Hz, 1 H), 4.11-3.98 (m, 2 H), 3.86 (q, J = 7.8 Hz, 1 H), 3.61 (dd, J = 7.8, 7.8 Hz, 1 H), 3.50-3.41 (m, 1 H), 2.46-2.33 (m, 1 H), 2.04-1.79 (m, 5 H), 1.73 (d, J = 11.1 Hz, 1 H), 1.53-1.23 (m, 6 H). | A 5-(THF-3-yl)pyridin-2-amine CB19 |
| I-268 | 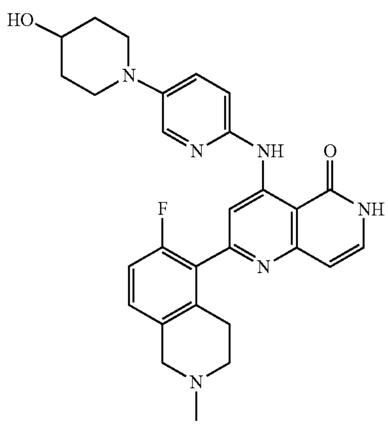 [SMILES: CN1CCc2c(ccc(F)c2-c2cc(Nc3ccc(N4CCC(O)CC4)cn3)c3c(=O)[nH]ccc3n2)C1] | 2-(6-fluoro-2-methyl-3,4-dihydro-1H-isoquinolin-5-yl)-4-[[5-(4-hydroxy-1-piperidyl)-2-pyridyl]amino]-6H-1,6-naphthyridin-5-one | Method AcHSS C18, m/z = 501 [M + H]+, Ret. time = 2.06 min. | $^1$H NMR (400 MHz, DMSO): δ 12.56 (s, 1 H), 11.72 (s, 1 H), 8.37 (s, 1 H), 8.08 (d, J = 2.8 Hz, 1 H), 7.52-7.43 (m, 2 H), 7.23 (dd, J = 5.8, 8.6 Hz, 1 H), 7.15 (dd, J = 9.0, 9.0 Hz, 1 H), 7.02 (d, J = 8.8 Hz, 1 H), 6.58 (d, J = 7.3 Hz, 1 H), 4.71 (d, J = 4.0 Hz, 1 H), 3.70-3.63 (m, 1 H), 3.54-3.42 (m, 2 H), 3.36 (s, 2 H), 2.93-2.83 (m, 2 H), 2.67-2.59 (m, 2 H), 2.36 (s, 3 H), 1.85 (d, J = 9.9 Hz, 2 H), 1.57-1.46 (m, 4 H). | A 1-(6-amino-pyridin-3-yl)piperidin-4-ol CB46 |
| I-269 | 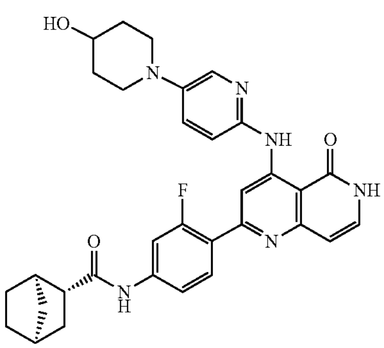 [SMILES: O=C(Nc1ccc(-c2cc(Nc3ccc(N4CCC(O)CC4)cn3)c3c(=O)[nH]ccc3n2)c(F)c1)[C@@H]1C[C@H]2CC[C@@H]1C2] | (1R,2R,4S)-N-[3-fluoro-4-[4-[[5-(4-hydroxy-1-piperidyl)-2-pyridyl]amino]-5-oxo-6H-1,6-naphthyridin-2-yl]phenyl]norbornane-2-carboxamide Isomer 1 separated by SFC | Method BicarbB EHC18, m/z = 569 [M + H]+, Ret. time = 4.35 min. | $^1$H NMR (400 MHz, DMSO): δ 12.48-12.48 (m, 1 H), 10.33 (s, 1 H), 8.75 (s, 1 H), 8.13 (d, J = 2.8 Hz, 1 H), 8.04-7.99 (m, 1 H), 7.82 (s, 1 H), 7.55-7.48 (m, 3 H), 7.09 (d, J = 8.6 Hz, 1 H), 6.64 (d, J = 7.3 Hz, 1 H), 4.78-4.71 (m, 1 H), 3.69 (dd, J = 4.3, 4.3 Hz, 1 H), 3.58 (d, J = 12.9 Hz, 2 H), 2.93 (dd, J = 9.9, 9.9 Hz, 2 H), 2.51-2.45 (m, 2 H), 2.39-2.31 (m, 2 H), 1.96-1.84 (m, 3 H), 1.60-1.51 (m, 4 H), 1.51-1.23 (m, 4 H), 1.16 (d, J = 9.1 Hz, 1 H). | A 1-(6-amino-pyridin-3-yl)piperidin-4-ol CB65 |

TABLE 2-continued

| I-# | NAME | LCMS | HNMR | Method SM |
|---|---|---|---|---|
| I-270 | 2-[5-cyclopropyl-2-fluoro-4-(piperidine-1-carbonyl)phenyl]-4-[[5-(4-hydroxy-1-piperidyl)-2-pyridyl]amino]-6H-naphthyridin-5-one | Method BicarbB EHC18, m/z = 583 [M + H]+, Ret. time = 4.23 min. | $^1$H NMR (400 MHz, DMSO): δ 12.47 (s, 1 H), 11.70 (s, 1 H), 8.72 (s, 1 H), 8.11 (d, J = 2.8 Hz, 1 H), 7.54-7.45 (m, 3 H), 7.23 (d, J = 8.8 Hz, 1 H), 7.06 (d, J = 8.8 Hz, 1 H), 6.64 (d, J = 7.1 Hz, 1 H), 4.74-4.73 (m, 1 H), 3.74-3.66 (m, 3 H), 3.57 (d, J = 12.6 Hz, 2 H), 3.25 (dd, J = 4.9, 4.9 Hz, 2 H), 2.96-2.86 (m, 2 H), 1.94-1.86 (m, 3 H), 1.65 (dd, J = 4.5, 5.3 Hz, 4 H), 1.58-1.50 (m, 4 H), 1.01 (d, J = 8.3 Hz, 2 H), 0.89-0.83 (m, 1 H), 0.69-0.65 (m, 1 H). | A 1-(6-amino-pyridin-3-yl)piperidin-4-ol CB14 |
| I-271 | 4-[[5-(4-hydroxy-1-piperidyl)-2-pyridyl]amino]-2-[4-(1-methyl-imidazol-2-yl)piperazin-1-yl]-6H-1,6-naphthyridin-5-one | Method AcHSS C18, m/z = 502 [M + H]+, Ret. time = 1.9 min. | $^1$H NMR (400 MHz, DMSO) δ 12.34 (s, 1H), 11.24 (d, J = 4.8 Hz, 1H), 8.11-8.08 (m, 1H), 8.01 (s, 1H), 7.49 (dd, J = 2.8, 9.1 Hz, 1H), 7.29 (t, J = 6.6 Hz, 1H), 6.98-6.94 (m, 2H), 6.67 (d, J = 1.0 Hz, 1H), 6.31 (d, J = 6.8 Hz, 1H), 4.74-4.73 (m, 1H), 3.84-3.77 (m, 4H), 3.71-3.64 (m, 1H), 3.57-3.52 (m, 5H), 3.14-3.08 (m, 4H), 2.92-2.85 (m, 2H), 1.90-1.84 (m, 2H), 1.61-1.50 (m, 2H). | E 1-(6-amino-pyridin-3-yl)piperidin-4-ol 1-(1-methyl-1H-imidazol-2-yl)piperazine |
| I-272 | N-[3-fluoro-4-[5-oxo-4-[(5-THF-3-yl-2-pyridyl)amino]-6H-1,6-naphthyridin-2-yl]phenyl]cyclohexane carboxamide Isomer 1 separated by SFC | Method BicarbB EHC18, m/z = 528 [M + H]+, Ret. time = 4.79 min. | $^1$H NMR (400 MHz, DMSO): δ 12.76 (s, 1 H), 11.73 (s, 1 H), 10.26 (s, 1 H), 9.08 (s, 1 H), 8.36 (d, J = 2.0 Hz, 1 H), 8.07 (dd, J = 8.8, 8.8 Hz, 1 H), 7.82-7.74 (m, 2 H), 7.54-7.45 (m, 2 H), 7.11 (d, J = 8.3 Hz, 1 H), 6.65 (d, J = 7.1 Hz, 1 H), 4.12-3.98 (m, 2 H), 3.87 (q, J = 7.8 Hz, 1 H), 3.61 (dd, J = 7.8, 7.8 Hz, 1 H), 3.50-3.41 (m, 1 H), 2.46-2.33 (m, 2 H), 1.99 (ddd, J = 8.1, 12.3, 16.0 Hz, 1 H), 1.93-1.79 (m, 3 H), 1.73 (d, J = 11.1 Hz, 1 H), 1.53-1.22 (m, 6 H). | A 5-(THF-3-yl)pyridin-2-amine CB19 |

TABLE 2-continued

| I-# | STRUCTURE | NAME | LCMS | HNMR | Method SM |
|---|---|---|---|---|---|
| I-273 | 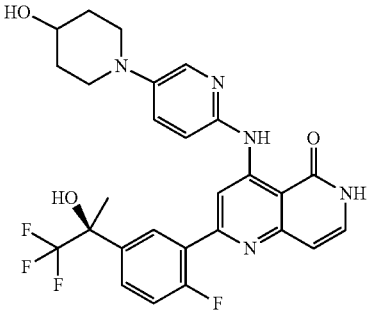 arbitrarily assigned | 2-(2-fluoro-5-(1,1,1-tifluoro-2-hydroxy-propan-2-yl)phenyl)-4-((5-(4-hydroxy-piperidin-1-yl)pyridin-2-yl)amino)-1,6-naphthyridin-5(6H)-one Isomer 2 separated by SFC | Method AcHSS C18, m/z = 544 [M + H]+, Ret. time = 2.95 min. | ¹H NMR (400 MHz, DMSO): δ 12.50 (s, 1 H), 11.46-11.44 (m, 1 H), 8.77 (s, 1 H), 8.27-8.22 (m, 1 H), 8.11 (d, J = 2.5 Hz, 1 H), 7.76-7.72 (m, 1 H), 7.53 (dd, J = 2.8, 8.8 Hz, 1 H), 7.48 (d, J = 7.3 Hz, 1 H), 7.45-7.40 (m, 1 H), 7.08 (d, J = 8.8 Hz, 1 H), 6.85-6.82 (m, 1 H), 6.65 (d, J = 7.3 Hz, 1 H), 4.73 (d, J = 2.5 Hz, 1 H), 3.69 (d, J = 2.5 Hz, 1 H), 3.57 (d, J = 12.4 Hz, 2 H), 2.97-2.89 (m, 2 H), 1.93-1.84 (m, 2 H), 1.80 (s, 3 H), 1.61-1.49 (m, 2 H). | A 1-(6-amino-pyridin-3-yl) piperidin-4-ol CB8 |
| I-274 | 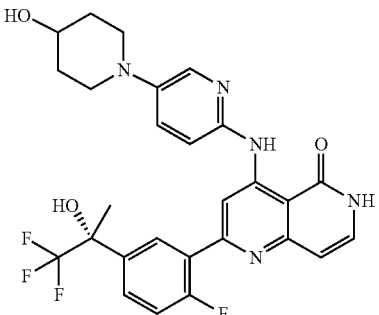 arbitrarily assigned | 2-(2-fluoro-5-(1,1,1-hydroxy-propan-2-yl)phenyl)-4-((5-(4-hydroxy-piperidin-1-y)pyridin-2-yl)amino)-1,6-naphthyridin-5(6H)-one Isomer 1 separated by SFC | Method BicarbB EHC18, m/z = 544 [M + H]+, Ret. time = 3.72 min. | ¹H NMR (400 MHz, DMSO): δ 12.48 (s, 1 H), 11.7 (brs, 1 H), 8.77 (s, 1 H), 8.24 (d, J = 5.6 Hz, 1 H), 8.11 (d, J = 2.5 Hz, 1 H), 7.77-7.74 (m, 1 H), 7.53 (dd, J = 2.9, 9.0 Hz, 1 H), 7.50-7.40 (m, 2 H), 7.08 (d, J = 8.8 Hz, 1 H), 6.85 (s, 1 H), 6.66 (d, J = 7.3 Hz, 1 H), 4.74 (d, J = 4.0 Hz, 1 H), 3.71-3.65 (m, 1 H), 3.57 (d, J = 12.4 Hz, 2 H), 2.97-2.89 (m, 2 H), 1.89 (d, J = 9.1 Hz, 2 H), 1.80 (s, 3 H), 1.61-1.50 (m, 2 H). | A 1-(6-amino-pyridin-3-yl) piperidin-4-ol CB8 |
| I-275 | 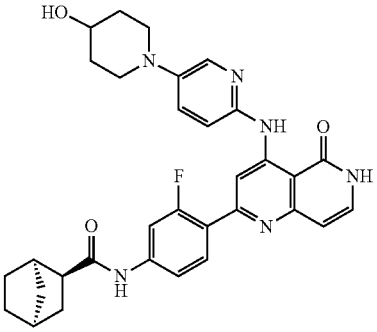 [SMILES: O=C(Nc1ccc(-c2cc(Nc3ccc(N4CCC(O)CC4)cn3)c3c(=O)[nH]ccc3n2)c(F)c1)[C@H]1C[C@H]2CC[C@@H]1C2] | (1R,2S,4S)-N-[3-fluoro-4-[4-[[5-(4-hydroxy-1-piperidyl)-2-pyridyl]amino]-5-oxo-6H-1,6-naphthyridin-2-yl]phenyl]norbornane-2-carboxamide Isomer 2 separated by SFC | Method AcHSS C18, m/z = 569.3 [M + H]+, Ret. time = 3.54 min. | ¹H NMR (400 MHz, DMSO): δ 12.42 (s, 1 H), 11.64 (d, J = 5.3 Hz, 1 H), 10.22 (s, 1 H), 8.76 (s, 1 H), 8.27 (s, 1 H), 8.12 (d, J = 2.8 Hz, 1 H), 8.03 (dd, J = 8.8, 8.8 Hz, 1 H), 7.82 (d, J = 1.5 Hz, 1 H), 7.55-7.49 (m, 2 H), 7.44 (dd, J = 6.3, 6.3 Hz, 1 H), 7.06 (d, J = 8.8 Hz, 1 H), 6.61 (d, J = 7.1 Hz, 1 H), 4.73-4.73 (m, 1 H), 3.72-3.66 (m, 2 H), 3.60-3.55 (m, 2 H), 3.22 (s, 1 H), 2.96-2.89 (m, 3 H), 2.67-2.49 (m, 2 H), 1.91-1.87 (m, 2 H), 1.77-1.71 (m, 1 H), 1.65-1.51 (m, 2 H), 1.43-1.32 (m, 2 H), 1.30 (s, 2 H). | A 1-(6-amino-pyridin-3-yl) piperidin-4-ol CB57 |
| I-276 | 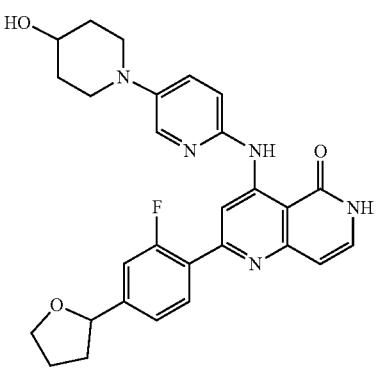 [SMILES: O=c1[nH]ccc2nc(-c3ccc(C4CCCO4)cc3F)cc(Nc3ccc(N4CCC(O)CC4)cn3)c12] | 2-(2-fluoro-4-THF-2-yl-phenyl)-4-[[5-(4-hydroxy-1-piperidyl)-2-pyridyl]amino]-6H-1,6-naphthyridin-5-one | Method AcHSS C18, m/z = 502 [M + H]+, Ret. time = 3.05 min. | ¹H NMR (400 MHz, DMSO): δ 12.84 (s, 1 H), 11.73 (s, 1 H), 10.28 (s, 1 H), 9.07 (s, 1 H), 8.35 (d, J = 1.8 Hz, 1 H), 8.06 (dd, J = 8.8, 8.8 Hz, 1 H), 7.82-7.74 (m, 2 H), 7.54-7.46 (m, 2 H), 7.11 (d, J = 8.3 Hz, 1 H), 6.65 (d, J = 7.3 Hz, 1 H), 4.11-3.98 (m, 2 H), 3.86 (q, J = 7.8 Hz, 1 H), 3.61 (dd, J = 7.8, 7.8 Hz, 1 H), 3.50-3.41 (m, 1 H), 2.46-2.33 (m, 1 H), 2.04-1.79 (m, 3 H), 1.73 (d, J = 11.1 Hz, 1 H), 1.53-1.23 (m, 6 H). | A 1-(6-amino-pyridin-4-ol 2-[2-fluoro-4-(tetrahydro-2-furanyl) phenyl]-4,4,5,5-tetramethyl-1,3,2-Dioxa-borolane |

TABLE 2-continued

| I-# | STRUCTURE | NAME | LCMS | HNMR | Method SM |
|---|---|---|---|---|---|
| I-277 | 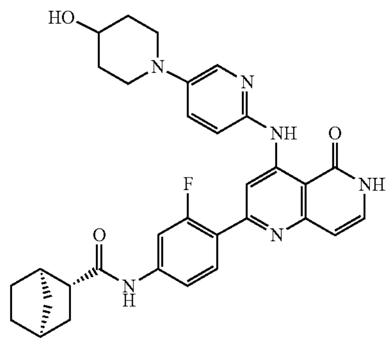 [SMILES: O=C(Nc1ccc(-c2cc(Nc3ccc(N4CCC(O)CC4)cn3)c3c(=O)[nH]ccc3n2)c(F)c1)[C@@H]1C[C@H]2CC[C@@H]1C2] | (1R,2R,4S)-N-[3-fluoro-4-[4-[[5-(4-hydroxy-1-piperidyl)-2-pyridyl]amino]-5-oxo-6H-1,6-naphthyridin-2-yl]phenyl]norbornane-2-carboxamide Isomer 2 separated by SFC | Method AcHSS C18, m/z = 569 [M + H]+, Ret. time = 3.53 min. | $^1$H NMR (400 MHz, DMSO): δ 12.47 (s, 1 H), 11.70 (s, 1 H), 10.33-10.30 (m, 1 H), 8.76 (s, 1 H), 8.12 (d, J = 3.0 Hz, 1 H), 8.06-8.01 (m, 1 H), 7.81-7.76 (m, 1 H), 7.55-7.49 (m, 2 H), 7.45 (d, J = 7.3 Hz, 1 H), 7.06 (d, J = 9.1 Hz, 1 H), 6.61 (d, J = 7.3 Hz, 1 H), 4.74-4.72 (m, 1 H), 3.68-3.66 (m, 1 H), 3.59-3.54 (m, 2 H), 2.95-2.89 (m, 1 H), 2.39-2.33 (m, 2 H), 1.94-1.84 (m, 3 H), 1.59-1.51 (m, 4 H), 1.47-1.44 (m, 2 H), 1.38-1.25 (m, 3 H), 1.16 (d, J = 9.1 Hz, 2 H). | A 1-(6-amino-pyridin-3-yl) piperidin-4-ol CB65 |
| I-278 | 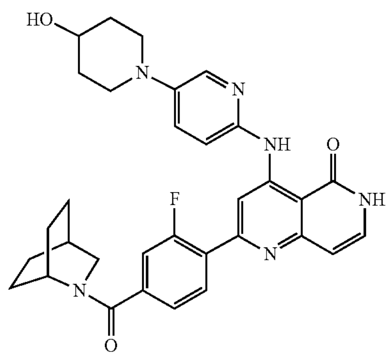 [SMILES: O=C(c1ccc(-c2cc(Nc3ccc(N4CCC(O)CC4)cn3)c3c(=O)[nH]ccc3n2)c(F)c1)N1CC2CCC1CC2] | 2-[4-(3-azabicyclo [2.2.2] octane-3-carbonyl)-2-fluoro-phenyl]-4-[[5-(4-methyl-piperazin-1-yl)-2-pyridyl]amino]-6H-1,6-naphthyridin 5-one | Method AcHSS C18, m/z = 568 [M + H]+, Ret. time = 2.39 min. | $^1$H NMR (400 MHz, DMSO) δ 12.48 (s, 1H), 11.71 (d, J = 5.4 Hz, 1H), 8.77 (d, J = 1.4 Hz, 1H), 8.26 (s, 1H), 8.09-8.00 (m, 2H), 7.52-7.33 (m, 2H), 7.07-7.04 (m, 1H), 6.62-6.58 (m, 1H), 3.48 (d, J = 2.1 Hz, 2H), 3.38 (d, J = 2.0 Hz, 1H), 3.19-3.13 (m, 4H), 2.50-2.44 (m, 4H), 2.25-2.23 (m, 3H), 2.04-2.02 (m, 1H), 1.90-1.84 (m, 2H), 1.69-1.63 (m, 6H). | F 1-methyl-piperazine 2-azabicyclo [2.2.2] octane (step 2) |
| I-279 | 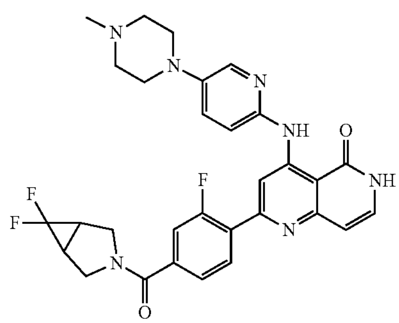 [SMILES: CN1CCN(c2ccc(Nc3cc(-c4ccc(C(=O)N5CC6C(C5)C6(F)F)cc4F)nc4cc[nH]c(=O)c34)nc2)CC1] | 2-[4-(6,6-difluoro-3-azabicyclo [3.1.0] hexane-3-carbonyl)-2-fluoro-phenyl]-4-[[5-(4-methyl-piperazin-1-yl)-2-pyridyl]amino]-6H-1,6-naphthyridin-5-one | Method AcHSS C18, m/z = 576 [M + H]+, Ret. time = 2.23 min. | $^1$H NMR (400 MHz, DMSO) 12.49-12.47 (m, 1H), 11.71-11.68 (m, 1H), 8.78 (d, J = 1.5 Hz, 1H), 8.08-8.01 (m, 2H), 7.52-7.42 (m, 4H), 7.07-7.04 (m, 1H), 6.60 (d, J = 7.3 Hz, 1H), 4.15 (d, J = 12.8 Hz, 1H), 4.02-3.95 (m, 1H), 3.79-3.64 (m, 2H), 3.20-3.14 (m, 4H), 2.69-2.55 (m, 2H), 2.48 (t, J = 5.0 Hz, 4H), 2.24 (s, 3H). | F 1-methyl-piperazine 6,6-difluoro-3-azabicyclo [3.1.0] hexane (step 2) |
| I-280 | 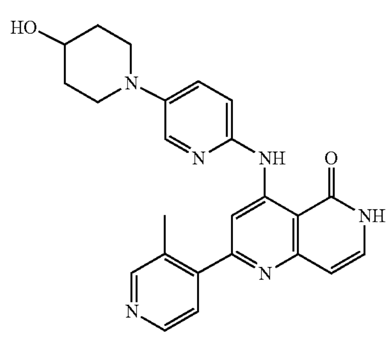 [SMILES: Cc1cnccc1-c1cc(Nc2ccc(N3CCC(O)CC3)cn2)c2c(=O)[nH]ccc2n1] | 4-[[5-(4-hydroxy-1-piperidyl)-2-pyridyl]amino]-2-(3-methyl-4-pyridyl)-6H-1,6-naphthyridin-5-one | Method AcHSS C18, m/z = 429 [M + H]+, Ret. time = 2.18 min. | $^1$H NMR (400 MHz, DMSO): δ 12.54 (s, 1 H), 11.73 (d, J = 4.3 Hz, 1 H), 8.60 (s, 1 H), 8.59-8.53 (m, 2 H), 8.10 (d, J = 2.8 Hz, 1 H), 7.54-7.44 (m, 3 H), 7.06 (d, J = 8.8 Hz, 1 H), 6.61 (d, J = 7.1 Hz, 1 H), 4.73 (d, J = 4.0 Hz, 1 H), 3.71-3.64 (m, 1 H), 3.59-3.51 (m, 2 H), 2.94-2.85 (m, 2 H), 2.42 (s, 3 H), 1.91-1.82 (m, 2 H), 1.58-1.48 (m, 2 H). | A 1-(6-amino-pyridin-3-yl) piperidin-4-ol (3-methyl-pyridin-3-yl) boronic acid |

TABLE 2-continued

| I-# | STRUCTURE | NAME | LCMS | HNMR | Method SM |
|---|---|---|---|---|---|
| I-281 | 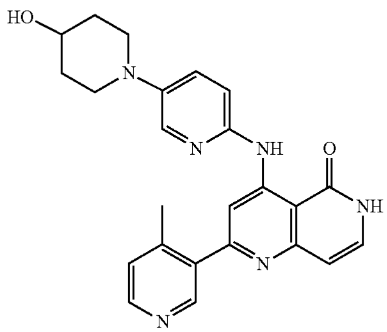 [SMILES: Cc1ccncc1-c1cc(Nc2ccc(N3CCC(O)CC3)cn2)c2c(=O)[nH]ccc2n1] | 4-[[5-(4-hydroxy-1-piperidyl)-2-pyridyl]amino]-2-(4-methyl-3-pyridyl)-6H-1,6-naphthyridin-5-one | Method AcHSS C18, m/z = 429 [M + H]+, Ret. time = 2.2 min. | $^1$H NMR (400 MHz, DMSO): δ 12.55 (s, 1 H), 11.71-11.65 (m, 1 H), 8.62 (s, 1 H), 8.57-8.52 (m, 2 H), 8.11 (d, J = 2.8 Hz, 1 H), 7.54-7.45 (m, 2 H), 7.42 (d, J = 5.1 Hz, 1 H), 7.06 (d, J = 9.1 Hz, 1 H), 6.61 (d, J = 7.3 Hz, 1 H), 4.73-4.72 (m, 1 H), 3.67 (s, 1 H), 3.57-3.50 (m, 2 H), 2.94-2.86 (m, 2 H), 2.46 (s, 3 H), 1.86 (dd, J = 2.9, 12.0 Hz, 2 H), 1.59-1.48 (m, 2 H). | A 1-(6-amino-pyridin-3-yl)piperidin-4-ol (4-methyl-pyridin-3-yl)boronic acid |
| I-282 | 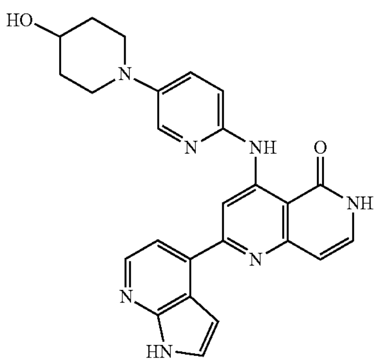 [SMILES: O=c1[nH]ccc2nc(-c3ccnc4[nH]ccc34)cc(Nc3ccc(N4CCC(O)CC4)cn3)c12] | 4-[[5-(4-hydroxy-1-piperidyl)-2-pyridyl]amino]-2-(1H-pyrrolo[2,3-b]pyridin-4-yl)-6H-1,6-naphthyridin-5-one | Method AcHSS C18, m/z = 454 [M + H]+, Ret. time = 3.44 min. | $^1$H NMR (400 MHz, DMSO): δ 12.28 (s, 1 H), 11.54-11.53 (m, 1 H), 9.70 (s, 1 H), 8.43-8.40 (m, 2 H), 8.08-8.03 (m, 2 H), 7.48 (dd, J = 3.2, 9.0 Hz, 1 H), 7.35 (d, J = 7.1 Hz, 1 H), 7.24-7.15 (m, 2 H), 6.71 (d, J = 3.8 Hz, 1 H), 6.47 (d, J = 7.3 Hz, 1 H), 4.64 (d, J = 4.3 Hz, 1 H), 3.66-3.35 (m, 3 H), 2.88-2.79 (m, 2 H), 1.82-1.75 (m, 2 H), 1.51-1.41 (m, 2 H). | A 1-(6-amino-pyridin-3-yl)piperidin-4-ol 4-(4,4,5,5-tetramethyl-1,3,2-dioxa-borolan-2-yl)-1H-pyrrolo[2,3-b]pyridine |
| I-283 | 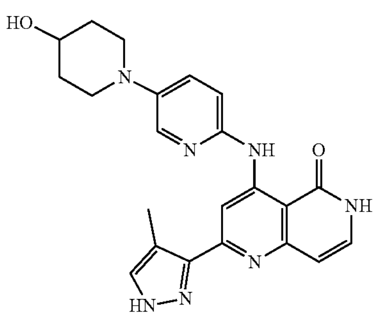 [SMILES: Cc1c[nH]nc1-c1cc(Nc2ccc(N3CCC(O)CC3)cn2)c2c(=O)[nH]ccc2n1] | 4-[[5-(4-hydroxy-1-piperidyl)-2-pyridyl]amino]-2-(4-methyl-1H-pyrazol-3-yl)-6H-1,6-naphthyridin-5-one | Method AcHSS C18, m/z = 418 [M + H]+, Ret. time = 2.49 min. | $^1$H NMR (400 MHz, DMSO): δ 12.75 (s, 1 H), 12.23-12.23 (m, 1 H), 11.46-11.45 (m, 1 H), 8.67 (s, 1 H), 8.01 (d, J = 2.8 Hz, 1 H), 7.54-7.52 (m, 1 H), 7.40 (dd, J = 3.0, 9.1 Hz, 1 H), 7.29 (dd, J = 6.1, 6.1 Hz, 1 H), 6.94 (d, J = 8.8 Hz, 1 H), 6.46 (d, J = 7.3 Hz, 1 H), 4.62 (d, J = 4.0 Hz, 1 H), 3.60-3.53 (m, 1 H), 3.24 (s, 2 H), 2.84-2.76 (m, 2 H), 2.33 (s, 3 H), 1.80-1.73 (m, 2 H), 1.49-1.38 (m, 2 H). | A 1-(6-amino-pyridin-3-yl)piperidin-4-ol 1-BOC-4-Methyl-pyrazole-3-boronic acid pinacol ester |
| I-284 | 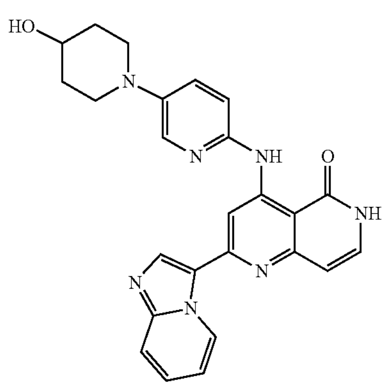 [SMILES: O=c1[nH]ccc2nc(-c3cnc4ccccn34)cc(Nc3ccc(N4CCC(O)CC4)cn3)c12] | 4-[[5-(4-hydroxy-1-piperidy)-2-pyridyl]amino]-2-imidazo[1,2-a]pyridin-3-yl-6H-1,6-naphthyridin-5-one | Method AcHSS C18, m/z = 454 [M + H]+, Ret. time = 2.37 min. | $^1$H NMR (400 MHz, DMSO): δ 12.43 (s, 1 H), 11.65 (d, J = 5.0 Hz, 1 H), 10.21 (d, J = 7.0 Hz, 1 H), 8.92 (s, 1 H), 8.35 (s, 1 H), 8.21 (d, J = 3.0 Hz, 1 H), 7.77 (d, J = 9.0 Hz, 1 H), 7.51-7.42 (m, 3 H), 7.18-7.15 (m, 1 H), 7.04 (d, J = 8.9 Hz, 1 H), 6.71 (d, J = 7.2 Hz, 1 H), 4.72 (d, J = 4.3 Hz, 1 H), 3.70-3.63 (m, 1 H), 3.59-3.51 (m, 2 H), 2.94-2.86 (m, 2 H), 1.91-1.82 (m, 2 H), 1.59-1.48 (m, 2 H). | A 1-(6-amino-pyridin-3-yl)piperidin-4-ol 3-(4,4,5,5-tetramethyl-1,3,2-dioxa-borolan-2-yl)imidazo[1,2-a]pyridine |

TABLE 2-continued

| I-# | STRUCTURE | NAME | LCMS | HNMR | Method SM |
|---|---|---|---|---|---|
| I-285 | 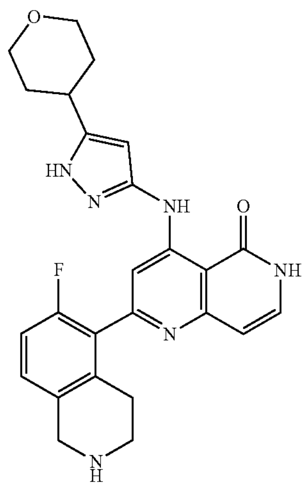 [SMILES: O=c1[nH]ccc2nc(-c3c(F)ccc4c3CCNC4)cc(Nc3cc(C4CCOCC4)[nH]n3)c12] | 2-(6-fluoro-1,2,3,4-tetrahydro-isoquinolin-5-yl)-4-[(5-tetrahydro-pyran-4-yl-1H-pyrazol-3-yl)amino]-6H-1,6-naphthyridin-5-one | Method AcHSS C18, m/z = 461 [M + H]+, Ret. time = 2.07 min. | $^1$H NMR (400 MHz, DMSO): δ 12.02 (s, 1 H), 8.29 (s, 1 H), 7.82 (s, 1 H), 7.45 (d, J = 7.3 Hz, 1 H), 7.39 (dd, J = 5.7, 8.7 Hz, 1 H), 7.29 (dd, J = 8.8, 8.8 Hz, 1 H), 6.59 (d, J = 7.3 Hz, 1 H), 5.99 (s, 1 H), 4.32 (s, 2 H), 3.45 (dd, J = 9.9, 11.6 Hz, 2 H), 2.95-2.88 (m, 1 H), 2.81 (dd, J = 5.7, 5.7 Hz, 4 H), 1.83 (dd, J = 1.8, 12.9 Hz, 4 H), 1.70-1.58 (m, 4 H). | A and G 5-(tetrahydro-2H-pyran-4-yl)-1H-pyrazol-3-amine CB45 |
| I-286 | 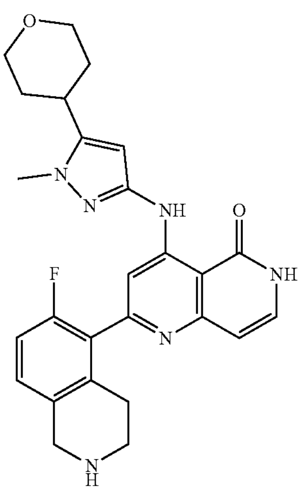 [SMILES: Cn1nc(Nc2cc(-c3c(F)ccc4c3CCNC4)nc3cc[nH]c(=O)c23)cc1C1CCOCC1] | 2-(6-fluoro-1,2,3,4-tetrahydro-isoquinolin-5-yl)-4-[(1-methyl-5-tetrahydro-pyran-4-yl-pyrazol-3-yl)amino]-6H-1,6-naphthyridin-5-one | Method AcHSS C18, m/z = 475 [M + H]+, Ret. time = 2.17 min. | $^1$H NMR (400 MHz, DMSO): δ 8.36 (s, 1 H), 7.73 (d, J = 3.5 Hz, 1 H), 7.45 (d, J = 7.3 Hz, 1 H), 7.35 (dd, J = 5.8, 8.6 Hz, 1 H), 7.26 (dd, J = 9.1, 9.1 Hz, 1 H), 6.58 (d, J = 7.3 Hz, 1 H), 6.00 (s, 1 H), 4.22 (s, 2 H), 3.93 (dd, J = 3.5, 11.1 Hz, 2 H), 3.72 (s, 3 H), 3.49 (dd, J = 10.1, 11.9 Hz, 2 H), 3.20 (dd, J = 6.2, 6.2 Hz, 2 H), 3.02-2.93 (m, 1 H), 2.74 (dd, J = 5.2, 5.2 Hz, 2 H), 1.79 (dd, J = 2.1, 13.0 Hz, 2 H), 1.67-1.55 (m, 4 H). | A and G 1-methyl-5-(tetrahydro-2H-pyran-4-yl)-1H-pyrazol-3-amine CB45 |
| I-287 | 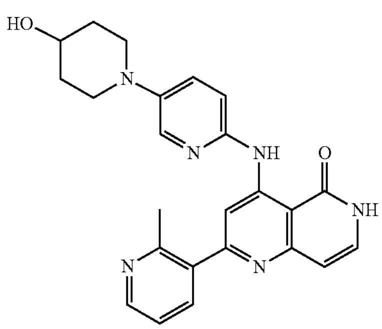 | 4-[[5-(4-hydroxy-1-piperidyl)-2-pyridyl]amino]-2-(2-methyl-3-pyridyl)-6H-1,6-naphthyridin-5-one | Method AcHSS C18, m/z = 429 [M + H]+, Ret. time = 2.14 min. | $^1$H NMR (400 MHz, DMSO) δ 12.53 (s, 1H), 11.71 (s, 1H), 8.58 (dd, J = 1.8, 4.8 Hz, 1H), 8.53 (s, 1H), 8.11 (d, J = 3.0 Hz, 1H), 7.87 (dd, J = 1.8, 7.6 Hz, 1H), 7.51 (dd, J = 3.1, 9.1 Hz, 1H), 7.46 (d, J = 7.5 Hz, 1H), 7.40 (dd, J = 4.8, 7.8 Hz, 1H), 7.06 (d, J = 8.8 Hz, 1H), 6.61 (d, J = 7.1 Hz, 1H), 4.73 (d, J = 3.8 Hz, 1H), 3.71-3.64 (m, 1H), 3.58-3.50 (m, 2H), 2.94-2.85 (m, 2H), 2.61 (s, 3H), 1.90-1.83 (m, 2H), 1.58-1.47 (m, 2H). | A 1-(6-amino-pyridin-3-yl) piperidin-4ol (2-methyl-piperidin-3-yl) boronic acid |

TABLE 2-continued

| I-# | STRUCTURE | NAME | LCMS | HNMR | Method SM |
|---|---|---|---|---|---|
| I-288 | 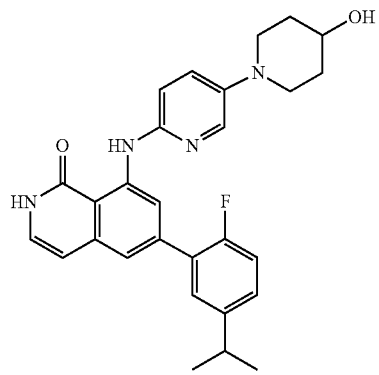 [SMILES: CC(C)c1ccc(F)c(-c2cc(Nc3ccc(N4CCC(O)CC4)cn3)c3c(=O)[nH]ccc3c2)c1] | 6-(2-fluoro-5-isopropyl-phenyl)-8-((5-(4-hydroxy-piperidin-1-yl)pyridin-2-yl)amino)isoquinolin-1(2H)-one | Method: C3, m/z = 473.87 [M + H]+, Ret. time = 1.7 min. | 1H NMR (400 MHz, DMSO-d6) δ 1.26 (d, J = 7.0 Hz, 6H), 1.58 (s, 2H), 1.88 (s, 2H), 2.95-3.03 (m, 2H), 3.52 (s, 2H), 3.69 (s, 1H), 6.63 (d, J = 6.9 Hz, 1H), 7.08 (s, 1H), 7.17-7.32 (m, 3H), 7.35 (s, 1H), 7.43 (d, J = 7.3 Hz, 1H), 7.67 (s, 1H), 8.10 (s, 1H), 8.61 (s, 1H), 11.48 (s, 1H), 12.47 (s, 1H). | AP 1-(6-amino-pyridin-3-yl)piperidin-4-ol (2-fluoro-5-isopropyl-phenyl)boronic acid |
| I-289 | 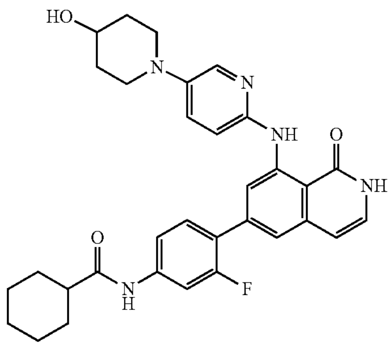 [SMILES: O=C(Nc1ccc(-c2cc(Nc3ccc(N4CCC(O)CC4)cn3)c3c(=O)[nH]ccc3c2)c(F)c1)C1CCCCC1] | N-(3-fluoro-4-(8-((5-(4-hydroxy-piperidin-1-yl)pyridin-2-y)amino)-1-oxo-1,2-dihydro-isoquinolin-6-yl)phenyl)cyclohexane carboxamide | Method: C3, m/z = 556.96 [M + H]+, Ret. time = 1.59 min. | 1H NMR (400 MHz, DMSO-d6) δ 1.27-1.32 (dt, J = 24.0, 11.9 Hz, 4H), 1.43 (q, J = 11.7 Hz, 2H), 1.57 (s, 2H), 1.67 (d, J = 10.7 Hz, 1H), 1.76 (s, 3H), 1.84 (s, 3H), 2.36 (s, 1H), 3.00 (s, 2H), 3.51 (d, J = 11.7 Hz, 2H), 3.68 (s, 2H), 6.61 (d, J = 7.1 Hz, 1H), 7.06 (d, J = 8.8 Hz, 1H), 7.20 (d, J = 4.3 Hz, 2H), 7.45 (d, J = 8.8 Hz, 1H), 7.54 (t, J = 8.6 Hz, 1H), 7.65 (s, 1H), 7.76 (d, J = 13.4 Hz, 1H), 8.10 (s, 1H), 8.59 (s, 1H), 10.19 (s, 1H), 11.45 (d, J = 5.6 Hz, 1H), 12.43 (s, 1H). | AP 1-(6-amino-pyridin-3-yl)piperidin-4-ol PB1 |
| I-290 | 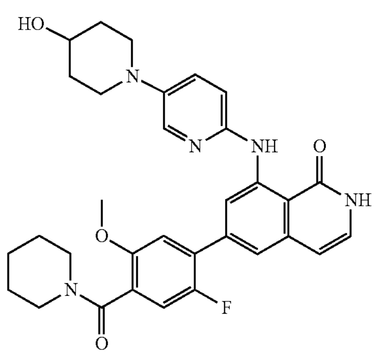 [SMILES: COc1cc(-c2cc(Nc3ccc(N4CCC(O)CC4)cn3)c3c(=O)[nH]ccc3c2)c(F)cc1C(=O)N1CCCCC1] | 6-(2-fluoro-5-methoxy-4-(piperidine-1-carbonyl)phenyl)-8-((5-(4-hydroxy-piperidin-1-yl)pyridin-2-yl)amino)isoquinolin-1(2H)-one | Method: C3, m/z = 572.58 [M + H]+, Ret. time = 1.49 min. | 1H NMR (400 MHz, DMSO-d6) δ 1.48 (s, 2H), 1.56 (s, 4H), 1.63 (s, 2H), 1.85 (s, 2H), 2.56 (s, 3H), 2.93 (s, 2H), 3.18 (t, J = 5.5 Hz, 2H), 3.51 (s, 2H), 3.66 (s, 4H), 3.87 (s, 3H), 6.62 (d, J = 7.0 Hz, 1H), 7.00 (d, J = 11.7 Hz, 1H), 7.18-7.28 (m, 4H), 7.57 (s, 1H), 8.07 (s, 1H), 8.70 (s, 1H), 11.49 (s, 1H), 12.42 (s, 1H) | AP 1-(6-amino-pyridin-3-yl)piperidin-4-ol CB1 |
| I-291 | 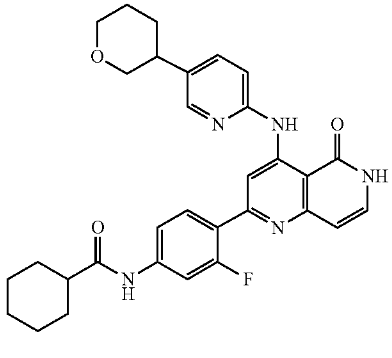 [SMILES: O=C(Nc1ccc(-c2cc(Nc3ccc(C4CCCOC4)cn3)c3c(=O)[nH]ccc3n2)c(F)c1)C1CCCCC1] | N-(3-fluoro-4-(5-oxo-4-((5-(tetrahydro-2H-pyran-3-yl)pyridin-2-yl)amino)-5,6-dihydro-1,6-naphthyridin-2-yl)phenyl)cyclohexane carboxamide | Method: C3, m/z = 542.50 [M + H]+, Ret. time = 1.74 min. | 1H NMR (400 MHz, DMSO-d6) δ 1.16-1.37 (m, 2H), 1.43 (q, J = 12.1, 11.3 Hz, 2H), 1.66 (s, 3H), 1.63-1.71 (m, 4H), 1.74-1.89 (m, 2H), 2.32-2.4 (m, 2H), 2.86 (t, J = 10.8 Hz, 1H), 3.35-3.43 (m, 2H), 3.86 (s, 2H), 6.78 (d, J = 7.4 Hz, 1H), 7.29 (d, J = 8.4 Hz, 1H), 7.53-7.66 (m, 1H), 7.79-7.93 (m, 4H), 8.42 (d, J = 2.3 Hz, 1H), 8.92 (s, 1H), 10.44 (s, 1H), 12.54 (s, 1H), 13.31 (s, 1H). | BP AP1 PB1 |

| I-# | STRUCTURE | NAME | LCMS | HNMR | Method SM |
|---|---|---|---|---|---|
| I-292 | 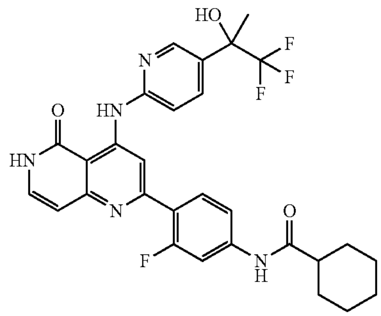 [SMILES: CC(O)(c1ccc(Nc2cc(-c3ccc(NC(=O)C4CCCCC4)cc3F)nc3cc[nH]c(=O)c23)nc1)C(F)(F)F] | N-(3-fluoro-5-(5-oxo-4-((5-(1,1,1-trifluoro-2-hydroxy-propan-2-yl)pyridin-2-yl)amino)-5,6-dihydro-1,6-naphthyridin-2-yl)phenyl)cyclohexane carboxamide | Method: C3, m/z = 570.68 [M + H]+, Ret. time = 1.66 min. | 1H NMR (400 MHz, DMSO-d6) δ 1.35 (ddq, J = 61.7, 23.8, 12.0 Hz, 4H), 1.48 (q, 2H), 1.68 (d, J = 11.3 Hz, 1H), 1.71 (s, 3H), 1.76 (s, 2H), 1.86 (d, J = 12.6 Hz, 2H), 6.75 (d, J = 7.3 Hz, 1H), 6.87 (s, 1H), 7.28 (d, J = 8.5 Hz, 1H), 7.55 (d, J = 9.2 Hz, 1H), 7.70 (s, 1H), 7.82-7.98 (m, 1H), 8.06 (d, J = 8.6 Hz, 1H), 8.64 (s, 1H), 9.08 (s, 1H), 10.38 (s, 1H), 12.29 (s, 1H), 13.23 (s, 1H). | BP 2-(4-amino-phenyl)-1,1,1-trifluoro-propan-2-ol PB1 |
| I-293 | 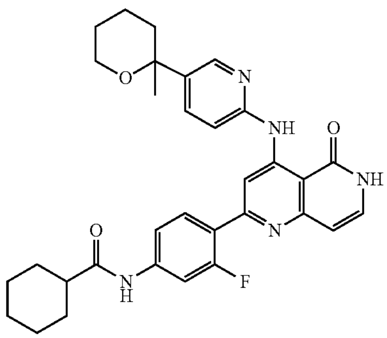 [SMILES: CC1(c2ccc(Nc3cc(-c4ccc(NC(=O)C5CCCCC5)cc4F)nc4cc[nH]c(=O)c34)nc2)CCCCO1] | N-(3-fluoro-4-(4-((5-(2-methyl-tetrahydro-2H-pyran-2-yl)pyridin-2-yl)amino)-5-oxo-5,6-dihydro-1,6-naphthyridin-2-yl)phenyl)cyclohexane carboxamide | Method: C3, m/z = 556.82 [M + H]+, Ret. time = 1.76 min. | 1H NMR (400 MHz, DMSO-d6) δ 0.87 (q, J = 7.1 Hz, 2H), 1.26 (d, J = 13.5 Hz, 5H), 1.40 (d, J = 34.7 Hz, 3H), 1.52 (s, 4H), 1.67 (s, 2H), 1.81 (dd, J = 25.3, 12.1 Hz, 4H), 2.24 (d, J = 12.7 Hz, 1H), 3.69 (d, J = 11.5 Hz, 1H), 6.61 (d, J = 7.2 Hz, 1H), 7.09 (d, J = 8.5 Hz, 1H), 7.45 (dd, J = 18.2, 8.0 Hz, 2H), 7.73-7.82 (m, 2H), 8.02 (t, J = 8.8 Hz, 1H), 8.38 (d, J = 2.4 Hz, 1H), 9.11 (s, 1H), 10.25 (s, 1H), 11.72 (d, J = 5.8 Hz, 1H), 12.75 (s, 1H). | BP PA2 PB1 |
| I-294 | 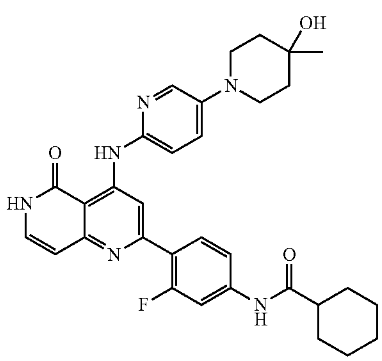 [SMILES: CC1(O)CCN(c2ccc(Nc3cc(-c4ccc(NC(=O)C5CCCCC5)cc4F)nc4cc[nH]c(=O)c34)nc2)CC1] | N-(3-fluoro-4-(4-((5-(4-hydroxy-4-methyl-piperidin-1-yl)pyridin-2-yl)amino)-5-oxo-5,6-dihydro-1,6-naphthyridin-2-yl)phenyl)cyclohexane carboxamide | Method: C3, m/z = 571.55 [M + H]+, Ret. time = 1.64 min. | 1H NMR (400 MHz, DMSO-d6) δ 1.18 (s, 3H), 1.22-1.34 (m, 3H), 1.37-1.51 (m, 2H), 1.59 (s, 4H), 1.59 (d, J = 11.4 Hz, 1H), 1.68 (d, J = 10.6 Hz, 1H), 1.79 (d, J = 11.7 Hz, 2H), 1.85 (d, J = 12.7 Hz, 1H), 2.40-2.35 (m, 2H), 3.14 (s, 2H), 3.08-3.19 (m, 1H), 3.32 (d, J = 11.3 Hz, 2H), 4.35 (s, 1H), 6.58 (d, J = 7.3 Hz, 1H), 7.03 (d, J = 8.9 Hz, 1H), 7.37-7.53 (m, 3H), 7.27-7.81 (m, 1H), 8.01 (t, J = 8.8 Hz, 1H), 8.09 (d, J = 3.1 Hz, 1H), 8.74 (s, 1H), 10.25 (s, 1H), 11.65 (s, 1H), 12.39 (s, 1H). | CP 1-(6-amino-pyridin-3-yl)-4-methyl-piperidin-4-ol PB1 |
| I-295 | 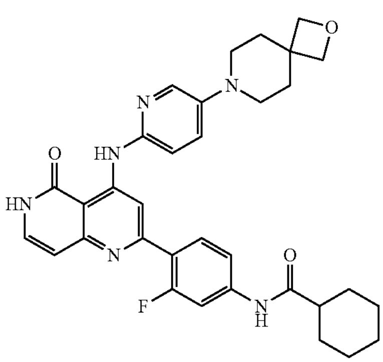 [SMILES: O=C(Nc1ccc(-c2cc(Nc3ccc(N4CCC5(CC4)COC5)cn3)c3c(=O)[nH]ccc3n2)c(F)c1)C1CCCCC1] | N-(4-(4-((5-(2-oxa-7-azaspiro[3.5]nonan-7-yl)pyridin-2-yl)amino)-5-oxo-5,6-dihydro-1,6-naphthyridin-2-yl)-3-fluoro-phenyl)cyclohexane-carboxamide | Method: C3, m/z = 583.98 [M + H]+, Ret. time = 1.37 min. | 1H NMR (400 MHz, DMSO-d6) δ 1.24 (s, 1H), 1.25-1.36 (m, 3H), 1.43 (d, J = 12.5 Hz, 2H), 1.77 (s, 1H), 1.80-1.92 (m, 3H), 3.17 (s, 3H), 3.71 (s, 2H), 3.86 (s, 2H), 3.98 (s, 2H), 4.39 (s, 2H), 5.23 (s, 1H), 6.67 (d, J = 7.2 Hz, 1H), 7.35 (d, J = 8.9 Hz, 1H), 7.42-7.53 (m, 2H), 7.83 (d, J = 14.1 Hz, 1H), 8.06 (t, J = 8.9 Hz, 1H), 8.21-8.28 (m, 1H), 8.85 (d, J = 2.9 Hz, 1H), 9.18 (s, 1H), 10.29 (s, 1H), 11.85 (s, 1H), 13.11 9s, 1H). | BP 5-(2-oxa-7-azaspiro[3.5]nonan-7-yl)pyridin-2-amine PB1 |

| I-# | STRUCTURE | NAME | LCMS | HNMR | Method SM |
|---|---|---|---|---|---|
| I-296 | 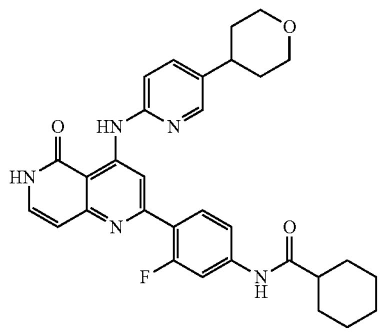 [SMILES: O=C(Nc1ccc(-c2cc(Nc3ccc(C4CCOCC4)cn3)c3c(=O)[nH]ccc3n2)c(F)c1)C1CCCCC1] | N-(3-fluoro-4-(5-oxa-4-((5-(tetrahydro-2H-pyran-4-yl)pyridin-2-yl)amino)-5,6-dihydro-1,6-naphthyridin-2-yl)phenyl)cyclohexane carboxamide | Method: C3, m/z = 542.88 [M + H]+, Ret. time = 1.58 min. | 1H NMR (400 MHz, DMSO-d6) δ 1.24 (s, 2H), 1.25-1.37 (m, 2H), 1.43 (q, J = 12.1, 11.5 Hz, 2H), 1.65-1.88 (m, 6H), 2.37 (dd, J = 13.5, 10.2 Hz, 1H), 2.78 (s, 1H), 3.39-3.50 (m, 2H), 3.92-4.00 (m, 2H), 6.63 (d, J = 7.3 Hz, 1H), 7.09 (d, J = 8.5 Hz, 1H), 7.48 (d, J = 8.7 Hz, 2H), 7.69-7.83 (m, 2H), 7.99 (t, J = 8.8 Hz, 1H), 8.31 (d, J = 2.4 Hz, 1H), 9.01 (s, 1H), 10.27 (s, 1H), 11.80 (s, 1H), 12.75 (s, 1H). | BP 5-(tetrahydro-2H-pyran-4-yl)pyridin-2-amine PB1 |
| I-297 | 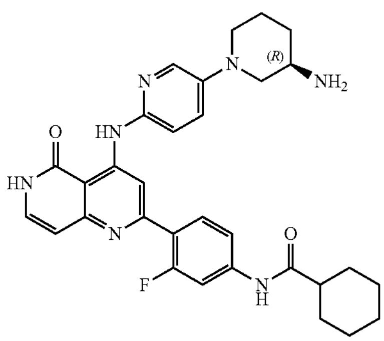 | (R)-N-(4-(4-((5-(3-amino-piperidin-1-yl)pyridin-2-yl)amino)-5-oxo-5,6-dihydro-1,6-naphthyridin-2-yl)-3-fluorophenyl)cyclohexane-carboxamide | Method: J, m/z = 556.3 [M + H]+, Ret. time = 4.35 min. | 1H NMR (400 MHz, DMSO-d6) δ 1.23-1.33 (m, 8H), 1.37-1.48 (m, 1H), 1.68 (d, J = 13.4 Hz, 1H), 1.80 (s, 4H), 1.85 (d, J = 15.0 Hz, 2H), 2.85 (d, J = 9.4 Hz, 1H), 3.08 (s, 1H), 3.49-3.60 (m, 2H), 6.59 (d, J = 7.3 Hz, 1H), 7.07 (d, J = 9.2 Hz, 1H), 7.38-7.51 (m, 2H), 7.79 (d, J = 14.2 Hz, 1H), 8.00-8.12 (m, 2H), 8.80 (s, 1H), 10.25 (s, 1H), 12.44 (s, 1H). | BP tert-butyl (R)-(1-(6-amino-pyridin-3-yl)piperidin-3-yl)carbamate PB1 |
| I-298 | 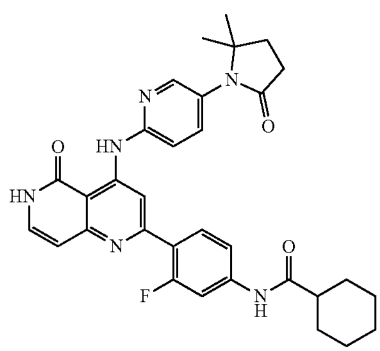 [SMILES: CC1(C)CCC(=O)N1c1ccc(Nc2cc(-c3ccc(NC(=O)C4CCCCC4)cc3F)nc3cc[nH]c(=O)c23)nc1] | N-(4-(4-((5-(2,2-dimethyl-5-oxo-pyrrolidin-1-yl)pyridin-2-yl)amino)-5-oxo-5,6-dihydro-1,6-naphthyridin-2-yl)-3-fluorophenyl)cyclohexane-carboxamide | Method: C3, m/z = 569.73 [M + H]+, Ret. time = 1.57 min. | 1H NMR (400 MHz, DMSO-d6) δ 1.23 (s 6H), 1.22-1.38 (m, 4H), 1.44 (q, J = 12.1 Hz, 2H), 1.68 (d, J = 11.9 Hz, 1H), 1.82 (dd, J = 26.6, 12.2 Hz, 4H), 2.03 (t, J = 7.9 Hz, 2H), 2.40 (d, J = 11.7 Hz, 1H), 6.71 (d, J = 7.1 Hz, 1H), 7.27 (s, 1H), 7.52 (d, J = 8.6 Hz, 1H), 7.57-7.69 (m, 1H), 7.83 (d, J = 14.0 Hz, 1H), 7.99 (d, J = 8.8 Hz, 1H), 8.21 (s, 1H), 9.06 (s, 1H), 10.33 (s, 1H), 12.08 (s, 1H), 13.12 (s, 1H). | BP 1-(6-amino-pyridin-3-yl)-5,5-dimethyl pyrrolidin-2-one PB1 |
| I-299 | 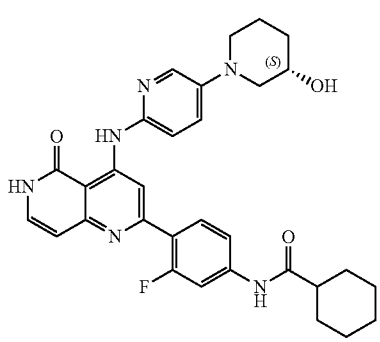 | (S)-N-(3-fluoro-4-(4-((5-(3-hydroxy-piperidin-1-yl)pyridin-2-yl)amino)-5-oxo-5,6-dihydro-1,6-naphthyridin-2-yl)phenyl)cyclohexane carboxamide | Method: C3, m/z = 557.5 [M + H]+, Ret. time = 1.59 min. | 1H NMR (400 MHz, DMSO-d6) δ 1.25-1.31 (m, 5H), 1.39 (q, J = 12.2 Hz, 2H), 1.57 (s, 1H), 1.68 (d, J = 11.1 Hz, 1H), 1.77-1.81 (m, 5H), 2.34 (t, J = 12 Hz, 1H), 2.58 (dd, J = 11.4, 8.5 Hz, 1H), 2.72 (t, J = 11.9 Hz, 1H), 3.47 (d, J = 11.8 Hz, 1H), 3.53-3.66 (m, 2H), 4.86 (d, J = 4.6 Hz, 1H), 6.58 (d, J = 7.4 Hz, 1H), 7.05 (t, J = 11.9 Hz, 1H), 7.39-7.50 (m, 3H), 7.77 (d, J = 14.2 Hz, 1H), 7.96-8.09 (m, 2H), 8.74 (s, 1H), 10.24 (s, 1H), 11.66 (s, 1H), 12.42 (s, 1H). | BP (S)-1-(6-amino-pyridin-3-yl)piperidin-3-ol PB1 |

TABLE 2-continued

| I-# | STRUCTURE | NAME | LCMS | HNMR | Method SM |
|---|---|---|---|---|---|
| I-300 | 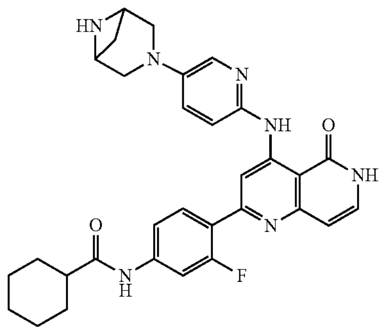 [SMILES: O=C(Nc1ccc(-c2cc(Nc3ccc(N4CC5CC(C4)N5)cn3)c3c(=O)[nH]ccc3n2)c(F)c1)C1CCCCC1] | N-(4-(4-((5-(3,6-diazabicyclo[3.1.1]heptan-3-yl)pyridin-2-yl)amino)-5-oxo-5,6-dihydro-1,6-naphthyridin-2-yl)-3-fluorophenyl)cyclohexane carboxamide | Method: C3, m/z = 554.88 [M + H]+, Ret. time = 1.34 min. | 1H NMR (400 MHz, DMSO-d6) δ 0.87 (s, 1H), 1.22-1.31 (m, 4H), 1.43 (d, J = 12.0 Hz, 2H), 1.56 (s, 1H), 1.74-1.85 (m, 2H), 1.83-1.94 (m, 2H), 2.35-2.38 (m, 2H), 2.88 (s, 1H), 3.71 (d, J = 11.5 Hz, 1H), 3.84 (d, J = 11.6 Hz, 1H), 4.44 (s, 2H), 6.58 (d, J = 7.2 Hz, 1H), 6.84 (s, 1H), 7.09 (s, 1H), 7.15 (d, J = 8.7 Hz, 1H), 7.34 (d, J = 8.9 Hz, 1H), 7.39-7.49 (m, 2H), 7.79 (d, J = 14.4 Hz, 1H), 7.97-8.07 (m, 1H), 8.65 (s, 1H), 10.28 (s, 1H), 11.64 (s, 1H), 12.33 (s, 1H) | BP PA4 PB1 |
| I-301 | 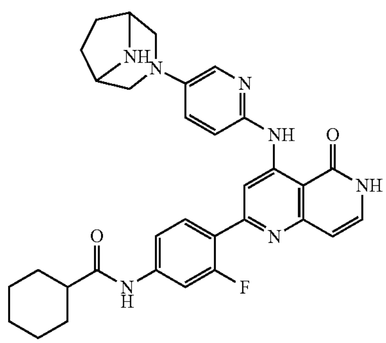 [SMILES: O=C(Nc1ccc(-c2cc(Nc3ccc(N4CC5CCC(C4)N5)cn3)c3c(=O)[nH]ccc3n2)c(F)c1)C1CCCCC1] | N-(4-(4-((5-(3,8-diazabicyclo[3.2.1]octan-3-yl)pyridin-2-yl)amino)-5-oxo-5,6-dihydro-1,6-naphthyridin-2-yl)-3-fluorophenyl)cyclohexane carboxamide | Method: H, m/z = 568 [M + H]+, Ret. time = 3.71 min. | 1H NMR (400 MHz, DMSO-d6) δ 1.16-1.36 (m, 4H), 1.43 (q, J = 11.7, 11.2 Hz, 2H), 1.58-1.88 (m, 8H), 2.26-2.39 (m, 2H), 2.72-2.87 (m, 2H), 3.50 (s, 4H), 4.24 (s, 1H), 6.53 (d, J = 7.1 Hz, 1H), 6.99 (d, J = 9.0 Hz, 1H), 7.33 (dt, J = 9.0, 5.0 Hz, 1H), 7.44 (dd, J = 10.0, 8.0 Hz, 2H), 7.74 (dd, J = 14.2, 2.4 Hz, 1H), 7.90-8.02 (m, 2H), 8.62 (d, J = 3.8 Hz, 1H), 10.24 (s, 1H), 11.59 (s, 1H), 12.64 (s, 1H). | BP PA5 PB1 |
| I-302 | 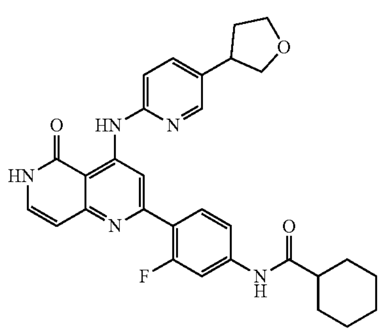 [SMILES: O=C(Nc1ccc(-c2cc(Nc3ccc(C4CCOC4)cn3)c3c(=O)[nH]ccc3n2)c(F)c1)C1CCCCC1] | N-(3-fluoro-4-(5-oxo-4-((5-(THF-3-yl)pyridin-2-yl)amino)-5,6-dihydro-1,6-naphthyridin-2-yl)phenyl)cyclohexane carboxamide | Method: C3, m/z = 528.82 [M + H]+, Ret. time = 1.57 min. | 1H NMR (400 MHz, DMSO-d6) δ 1.17-1.29 (m, 3H), 1.37-1.43 (m, 2H), 1.67 (d, J = 11.3 Hz, 1H), 1.81 (dd, J = 25.6 12.3 Hz, 1H), 1.87-2.02 (m, 4H), 2.34 (ddd, J = 12.3, 8.4, 4.5 Hz, 2H), 3.41 (q, J = 7.8 Hz, 1H), 3.56 (t, J = 7.9 Hz, 1H), 3.81 (q, J = 7.8 Hz, 1H), 3.92-4.08 (m, 2H), 6.61 (d, J = 7.2 Hz, 1H), 7.07 (d, J = 8.4 Hz, 1H), 7.39-7.50 (m, 2H), 7.68-7.82 (m, 2H), 8.02 (t, J = 8.8 Hz, 1H), 8.31 (d, J = 2.5 Hz, 1H), 9.04 (s, 1H), 10.24 (s, 1H), 11.72 (s, 1H), 12.69 (s, 1H) | BP PA3 PB1 |

TABLE 2-continued

| I-# | STRUCTURE | NAME | LCMS | HNMR | Method SM |
|---|---|---|---|---|---|
| I-303 | 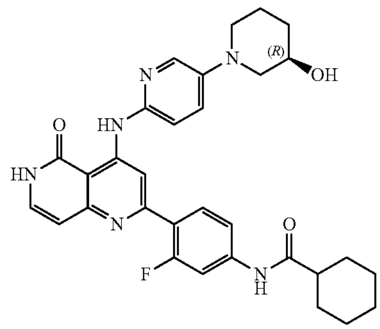 | (R)-N-(3-fluoro-4-(4-((5-(3-hydroxy-piperidin-1-yl)pyridin-2-yl)amino)-5-oxo-5,6-dihydro-1,6-naphthyridin-2-yl)phenyl)cyclohexane carboxamide | Method: C3, m/z = 558.38 [M + H]+, Ret. time = 1.54 min. | 1H NMR (400 MHz, DMSO-d6) δ 1.16-1.41 (m, 4H), 1.43 (d, J = 11.9 Hz, 2H), 1.55 (d, J = 12.0 Hz, 1H), 1.67 (d, J = 11.0 Hz, 1H), 1.73-1.93 (m, 5H), 2.32-2.38 (m, 1H), 2.470-2.58 (m, 2H), 2.67-2.72 (m, 1H), 3.34-3.46 (m, 1H), 3.54-3.61 (m, 2H), 4.84 (s, 1H), 6.57 (d, J = 7.2 Hz, 1H), 7.02 (d, J = 8.9 Hz, 1H), 7.37-7.45 (m, 3H), 7.75 (dd, J = 14.2, 2.0 Hz, 1H), 7.95-8.04 (m, 2H), 8.72 (s, 1H), 10.22 (s, 1H), 11.62 (d, J = 5.7 Hz, 1H), 12.37 (s, 1H) | BP (R)-1-(6-amino-pyridin-3-yl)piperidin-3-ol PB1 |
| I-304 | 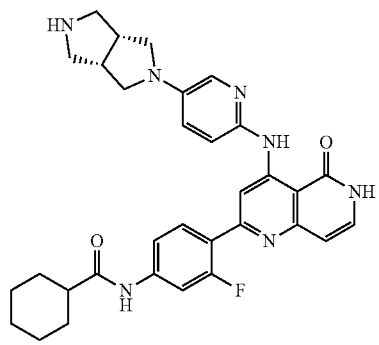 [SMILES: O=C(Nc1ccc(-c2cc(Nc3ccc(N4C[C@H]5CNC[C@H]5C4)cn3)c3c(=O)[nH]ccc3n2)c(F)c1)C1CCCCC1] | N-(3-fluoro-4-(4-((5-((3aR,6aS)-hexahydro-pyrano[3,4-c]pyrrol-2(1H)-yl)pyridin-2-yl)amino)-5-oxo-5,6-dihydro-1,6-naphthyridin-2-yl)phenyl)cyclohexane-carboxamide | Method: C3, m/z = 568.2 [M + H]+, Ret. time = 1.64 min. | 1H NMR (400 MHz, DMSO-d6) δ 1.26 (dq, J = 22.8, 12.1, 11.6 Hz, 3H), 1.42 (q, J = 12.11, 11.5 Hz, 2H), 1.67 (d, J = 11.7 Hz, 1H), 1.80 (dd, J = 24.4, 12.2 Hz, 4H), 2.32-2.38 (m, 1H), 2.96 (d, J = 10.8 Hz, 2H), 3.04 (s, 2H), 6.56 (d, J = 7.3 Hz, 1H), 7.06 (d, J = 8.8 Hz, 1H), 7.21 (dd, J = 8.8, 3.0 Hz, 1H), 7.36-7.47 (m, 2H), 7.77 (dd, J = 14.3, 2.0 Hz, 1H), 7.85 (d, J = 3.0 Hz, 1H), 8.01 (t, J = 8.8 Hz, 1H), 8.28 (s, 1H), 8.64 (s, 1H), 10.25 (s, 1H), 12.30 (s, 1H). | BP PA34 PB1 |
| I-305 | 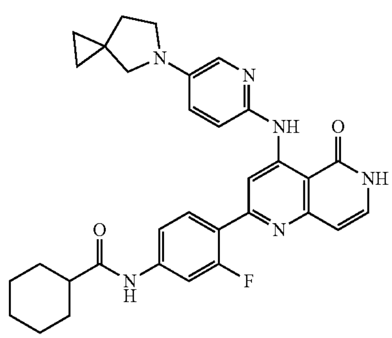 [SMILES: O=C(Nc1ccc(-c2cc(Nc3ccc(N4CCC5(CC5)C4)cn3)c3c(=O)[nH]ccc3n2)c(F)c1)C1CCCCC1] | N-(4-(4-((5-(5-azaspiro[2.4]heptan-5-yl)pyridin-2-yl)amino)-5-oxo-5,6-dihydro-1,6-naphthyridin-2-yl)-3-fluorophenyl)cyclohexane-carboxamide | Method: C3, m/z = 554.13 [M + H]+, Ret. time = 1.90 min. | 1H NMR (400 MHz, DMSO-d6) δ 0.66 (d, J = 8.2 Hz, 3H), 1.23-1.34 (m, 4H), 1.37-1.48 (m, 2H), 1.69 (s, 1H), 1.77-1.85 (m, 4H), 1.94 (t, J = 6.7 Hz, 2H), 2.34-2.40 (m, 1H), 3.22 (s, 2H), 3.45 (t, J = 6.7 Hz, 2H), 6.56 (d, J = 7.3 Hz, 1H), 7.06 (s, 1H), 7.39-7.46 (m, 2H), 7.75 (d, J = 14.1 Hz, 2H), 8.01 (t, J = 8.8 Hz, 1H), 8.22 (s, 1H), 8.54 (s, 1H), 10.23 (s, 1H), 11.60 (s, 1H), 12.22 (s, 1H). | BP 5-(5-azaspiro[2.4]heptan-5-yl)pyridin-2-amine PB1 |
| I-306 | 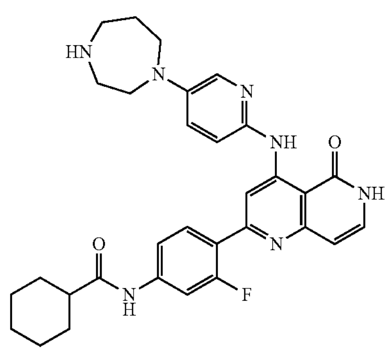 [SMILES: O=C(Nc1ccc(-c2cc(Nc3ccc(N4CCCNCC4)cn3)c3c(=O)[nH]ccc3n2)c(F)c1)C1CCCCC1] | N-(4-(4-((5-(1,4-diazepan-1-yl)pyridin-2-yl)amino)-5-oxo-5,6-dihydro-1,6-naphthyridin-2-yl)-2-fluorophenyl)cyclohexane-carboxamide | Method: J, m/z = 556.2 [M + H]+, Ret. time = 3.37 min. | 1H NMR (400 MHz, DMSO-d6) δ 1.19-1.32 (m, 3H), 1.39-1.44 (m, 2H), 1.69 (s, 1H), 1.77-1.86 (m, 3H), 2.08 (s, 1H), 2.38 (s, 1H), 3.18 (s, 2H), 3.29 (s, 2H), 3.57 (t, J = 6.1 Hz, 3H), 3.77 (t, J = 6.1 Hz, 3H), 6.75 (d, J = 7.5 Hz, 1H), 7.25 (d, J = 9.4 Hz, 1H), 7.41 (s, 1H), 7.55 (d, J = 8.9 Hz, 1H), 7.85 (dd, J = 28.7, 11.5 Hz, 2H), 8.07 (d, J = 3.0 Hz, 1H), 8.60 (d, J = 5.7 Hz, 1H), 8.77 (s, 1H), 10.44 (s, 1H), 12.44 (s, 1H), 13.05 (s, 1H). | BP PA7 PB1 |

TABLE 2-continued

| I-# | STRUCTURE | NAME | LCMS | HNMR | Method SM |
|---|---|---|---|---|---|
| I-307 | 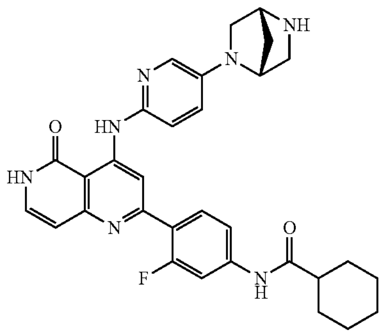 [SMILES: O=C(Nc1ccc(-c2cc(Nc3ccc(N4C[C@H]5C[C@@H]4CN5)cn3)c3c(=O)[nH]ccc3n2)c(F)c1)C1CCCCC1] | Exemple25: N-(4-(4-((5-((1R,4R)-2,5-diazaspiro[2.2.1]heptan-2-yl)pyridin-2-yl)amino)-5-oxo-5,6-dihydro-1,6-naphthyridin-2-yl)-3-fluorophenyl)cyclohexane-carboxamide | Method: C3, m/z = 554.2 [M + H]+, Ret. time = 1.65 min. | 1H NMR (400 MHz, DMSO-d6) δ 1.25 (q, J = 12.1, 11.4 Hz, 3H), 1.35-1.46 (m, 2H), 1.67 (d, J = 11.2 Hz, 1H), 1.75-1.90 (m, 5H), 2.34-2.37 (m, 3H), 2.96 (q, J = 10.3 Hz, 2H), 3.06 (d, J = 9.3 Hz, 1H), 3.56 (d, J = 8.8 Hz, 1H), 3.90 (s, 1H), 4.49 (s, 1H), 6.55 (d, J = 7.3 Hz, 1H), 7.03 (d, J = 8.9 Hz, 1H), 7.15 (dd, J = 8.8, 3.0 Hz, 1H), 7.39 (d, J = 7.3 Hz, 1H), 7.46 (d, J = 9.0 Hz, 1H), 7.72-7.79 (m, 2H), 7.99 (t, J = 8.8 Hz, 1H), 8.60 (s, 1H), 10.30 (s, 1H), 11.60 (s, 1H), 12.27 (s, 1H) | BP tert-butyl (1R,4R)-5-(6-aminopyridin-3-yl)-2,5-diazabicyclo[2.2.1]heptane-2-carboxylate PB1 |
| I-308 | 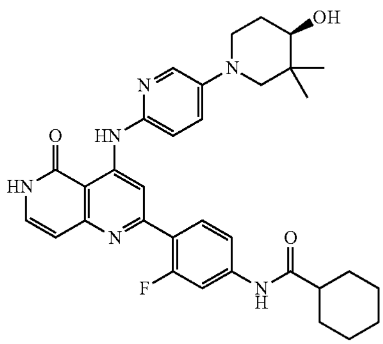 [SMILES: CC1(C)CN(c2ccc(Nc3cc(-c4ccc(NC(=O)C5CCCCC5)cc4F)nc4cc[nH]c(=O)c34)nc2)CC[C@H]1O] | (R)-N-(3-fluoro-4-(4-((5-(4-hydroxy-3,3-dimethyl-piperidin-1-yl)pyridin-2-yl)amino)-5-oxo-5,6-dihydro-1,6-naphthyridin-2-yl)phenyl)cyclohexane carboxamide | Method: C3, m/z = 586.19 [M + H]+, Ret. time = 1.60 min. | 1H NMR (400 MHz, DMSO-d6) δ 0.94 (d, J = 7.6 Hz, 6H), 1.26 (dq, J = 23.2, 12.3 Hz, 3H), 1.43 (q, J = 11.6, 11.1 Hz, 2H), 1.61-1.67 (m, 2H), 1.71-1.84 (m, 4H), 2.32-2.38 (m, 1H), 2.50-5.54 (m, 2H), 2.74-2.81 (m, 1H), 3.16-3.25 (m, 2H), 3.47 (d, J = 12.3 Hz, 1H), 4.63 (d, J = 4.6 Hz, 1H), 6.56 (d, J = 7.2 Hz, 1H), 7.00 (d, J = 8.9 Hz, 1H), 7.37-7.45 (m, 3H), 7.75 (dd, J = 14.3, 2.0 Hz, 1H), 7.95-8.04 (m, 2H), 8.73 (s, 1H), 10.22 (s, 1H), 11.61 (d, J = 5.8 Hz, 1H), 12.37 (s, 1H). | BP PA6 PB1 |
| I-309 | 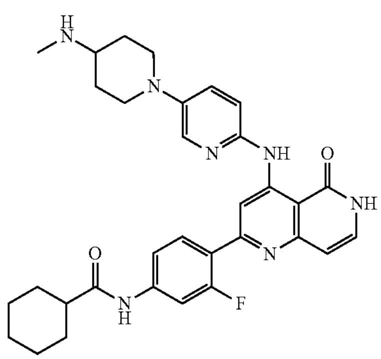 [SMILES: CNC1CCN(c2ccc(Nc3cc(-c4ccc(NC(=O)C5CCCCC5)cc4F)nc4cc[nH]c(=O)c34)nc2)CC1] | N-(3-fluoro-4-(4-((5-(4-(methylamino)piperidin-1-yl)pyridin-2-yl)amino)-5-oxo-5,6-dihydro-1,6-naphthyridin-2-yl)phenyl)cyclohexane carboxamide | Method: C3, m/z = 570.88 [M + H]+, Ret. time = 1.35 min. | 1H NMR (400 MHz, DMSO-d6) δ 1.11-1.32 (m, 3H), 1.37-1.46 (m, 2H), 1.49-1.60 (m, 2H), 1.67 (d, J = 11.1 Hz, 1H), 1.75-1.84 (m, 4H), 2.01 (d, J = 12.3 Hz, 2H), 2.33-2.38 (m, 2H), 2.75 (t, J = 11.9 Hz, 3H), 2.97 (s, 2H), 3.76 (d, J = 12.5 Hz, 2H), 6.57 (d, J = 7.3 Hz, 1H), 7.04 (d, J = 8.9 Hz, 1H), 7.37-7.47 (m, 2H), 7.51 (dd, J = 8.9, 3.1 Hz, 1H), 7.78 (dd, J = 14.3, 2.0 Hz, 1H), 8.00 (t, J = 8.9 Hz, 1H), 8.10 (d, J = 3.1 Hz, 1H), 8.77 (s, 1H), 10.24 (s, 1H), 12.42 (s, 1H) | BP PA8 PB1 |
| I-310 | 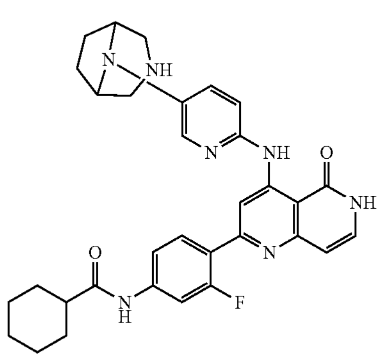 [SMILES: O=C(Nc1ccc(-c2cc(Nc3ccc(N4C5CCC4CNC5)cn3)c3c(=O)[nH]ccc3n2)c(F)c1)C1CCCCC1] | N-(4-(4-((5-(3,8-diazaspiro[3.2.1]octan-8-yl)pyridin-2-yl)amino)-5-oxo-5,6-dihydro-1,6-naphthyridin-2-yl)-3-fluorophenyl)cyclohexane-carboxamide | Method: C3, m/z = 568.2 [M + H]+, Ret. time = 1.69 min. | 1H NMR (400 MHz, DMSO-d6) δ 1.22-1.34 (m, 3H), 1.38-1.47 (m, 2H), 1.66-1.69 (m, 1H), 1.77-1.86 (m, 4H), 2.04-2.09 (m, 4H), 2.37 (d, J = 12.3 Hz, 1H), 3.04-3.14 (m, 4H), 4.51 (s, 2H), 6.74 (s, 1H), 7.28 (s, 1H), 7.53 (d, J = 8.9 Hz, 2H), 7.87 (d, J = 13.4 Hz, 2H), 8.19 (s, 1H), 8.72 (s, 1H), 8.99 (s, 1H), 10.41 (s, 1H), 12.37 (s, 1H), 13.04 (s, 1H) | BP tert-butyl 8-(6-aminopyridin-3-yl)-3,8-diazaspiro[3.2.1]octane-3-carboxylate PB1 |

TABLE 2-continued

| I-# | STRUCTURE | NAME | LCMS | HNMR | Method SM |
|---|---|---|---|---|---|
| I-311 | 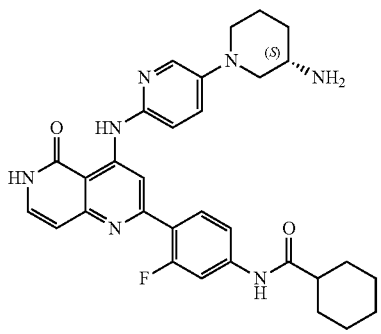 | (S)-N-(4-(4-((5-(3-amino-piperidin-1-yl)pyridin-2-yl)amino)-5-oxo-5,6-dihydro-1,6-naphthyridin-2-yl)-3-fluorophenyl)cyclohexane-carboxamide | Method: C3, m/z = 556.5 [M + H]+, Ret. time = 1.47 min. | 1H NMR (400 MHz, DMSO-d6) δ 1.17-1.32 (m, 3H), 1.37-1.45 (m, 3H), 1.60-1.75 (m, 2H), 1.80-1.88 (m, 7H), 2.37 (dd, J = 13.3, 9.9 Hz, 1H), 2.88 (q, J = 8.1 Hz, 2H), 3.20 (dt, J = 8.1 Hz, 2H), 3.20 (dt, J = 11.0, 5.4 Hz, 2H), 6.58 (d, J = 7.3 Hz, 1H), 7.07 (d, J = 8.8 Hz, 1H), 7.39-7.47 (m, 3H), 7.77 (d, J = 14.2 Hz, 1H), 7.96-8.11 (m, 2H), 8.32 (s, 1H), 8.80 (s, 1H), 10.28 (s, 1H), 12.44 (s, 1H) | BP tert-butyl (S)-(1-(6-amino-pyridin-3-yl) piperidin-3-yl) carbamate PB1 |
| I-312 | 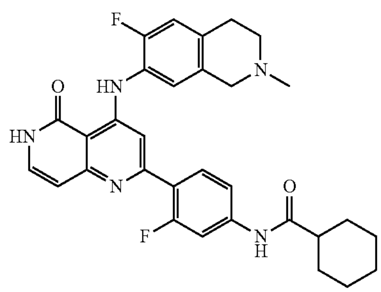 [SMILES: CN1CCc2cc(F)c(Nc3cc(-c4ccc(NC(=O)C5CCCCC5)cc4F)nc4cc[nH]c(=O)c34)cc2C1] | N-(3-fluoro-4-(4-((6-fluoro-2-methyl-1,2,3,4-tetrahydro-isoquinolin-7-yl)amino)-5-oxo-5,6-dihydro-1,6-naphthyridin-2-yl)phenyl)cyclohexane-carboxamide | Method: C3, m/z = 542.99 [M + H]+, Ret. time = 1.39 min. | 1H NMR (400 MHz, DMSO-d6) δ 1.15-1.28 (m, 4H), 1.35-1.41 (m, 2H), 1.63-1.82 (m, 5H), 2.36 (d, J = 12.9 Hz, 1H), 2.43 (s, 2H), 2.74 (s, 2H), 2.88 (s, 2H), 3.60 (s, 2H), 6.56 (d, J = 7.3 Hz, 1H), 7.04 (s, 1H), 7.19 (d, J = 11.2 Hz, 1H), 7.32 (d, J = 8.0 Hz, 1H), 7.42 (d, J = 7.7 Hz, 2H), 7.72 (d, J = 14.6 Hz, 1H), 7.93-8.06 (m, 1H), 10.23 (s, 1H), 11.38 (s, 1H), 11.62 (s, 1H) | BP PA9 PB1 |
| I-313 | 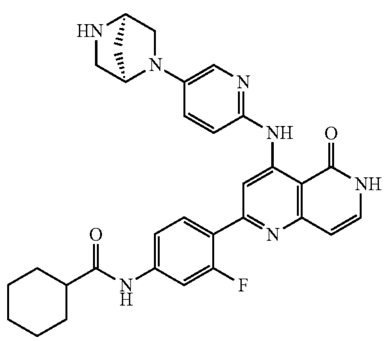 [SMILES: O=C(Nc1ccc(-c2cc(Nc3ccc(N4C[C@H]5C[C@@H]4CN5)cn3)c3c(=O)[nH]ccc3n2)c(F)c1)C1CCCCC1] | N-(4-(4-((5-((1R,4R)-2,5-diazabicyclo[2.2.1]heptan-2-yl)pyridin-2-yl)amino)-5-oxo-5,6-dihydro-1,6-naphthyridin-2-yl)-3-fluorophenyl)cyclohexane-carboxamide | Method: C3, m/z = 554.2 [M + H]+, Ret. time = 1.65 min. | 1H NMR (400 MHz, DMSO-d6) δ 1.19-1.33 (m, 3H), 1.39-1.47 (m, 2H), 1.67 (d, J = 9.8 Hz, 2H), 1.78-1.85 (m, 5H), 2.34-2.40 (m, 1H), 2.55 (s, 1H), 2.78-2.96 (m, 3H), 3.52-3.54 (m, 1H), 3.62 (s, 1H), 4.40 (s, 1H), 6.56 (d, J = 7.3 Hz, 1H), 7.02 (d, J = 8.8 Hz, 1H), 7.11 (dd, J = 8.8, 3.0 Hz, 1H), 7.36-7.49 (m, 2H), 7.76 (dd, J = 17.7, 2.7 Hz, 2H), 8.00 (t, J = 8.8 Hz, 1H), 8.58 (s, 1H), 10.23 (s, 1H), 11.62 (s, 1H), 12.24 (s, 1H). | BP tert-butyl (1R,4R)-5-(6-amino-pyridin-3-yl)-2,5-diaza-bicyclo[2.2.1]heptane-2-carboxylate PB1 |
| I-314 | 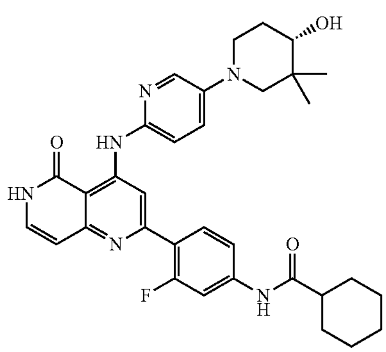 [SMILES: CC1(C)CN(c2ccc(Nc3cc(-c4ccc(NC(=O)C5CCCCC5)cc4F)nc4cc[nH]c(=O)c34)nc2)CC[C@@H]1O] | (S)-N-(3-fluoro-4-(4-((5-(4-hydroxy-3,3-dimethyl-piperidin-1-yl)pyridin-2-yl)amino)-5-oxo-5,6-dihydro-1,6-naphthyridin-2-yl)phenyl)cyclohexane-carboxamide | Method: C3, m/z = 585.93 [M + H]+, Ret. time = 1.56 min. | 1H NMR (400 MHz, DMSO-d6) δ 0.94 (s, 3H), 0.96 (s, 3H), 1.13-1.31 (m, 3H), 1.39-1.48 (m, 2H), 1.66-1.68 (m, 2H), 1.74-1.86 (m, 4H), 2.34-2.40 (m, 3H), 2.75 (t, J = 11.9 Hz, 1H), 3.18-3.26 (m, 2H), 3.46-3.49 (m, 1H), 4.64 (s, 1H), 6.57 (d, J = 7.3 Hz, 1H), 7.04 (d, J = 8.9 Hz, 1H), 7.37-7.47 (m, 3H), 7.74-3.77 (m, 1H), 7.98-8.05 (m, 2H), 8.73 (s, 1H), 10.24 (s, 1H), 11.62 (s, 1H), 12.42 (s, 1H) | BP PA33 PB1 |

TABLE 2-continued

| I-# | STRUCTURE | NAME | LCMS | HNMR | Method SM |
|---|---|---|---|---|---|
| I-315 | 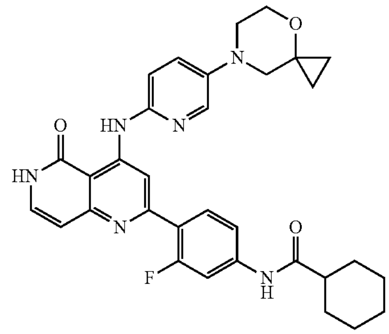 [SMILES: O=C(Nc1ccc(-c2cc(Nc3ccc(N4CCOC5(CC5)C4)cn3)c3c(=O)[nH]ccc3n2)c(F)c1)C1CCCCC1] | N-(4-(4-((5-(4-oxa-7-azaspiro[2.5]octan-7-yl)pyridin-2-yl)amino)-5-oxo-5,6-dihydro-1,6-naphthyridin-2-yl)-3-fluorophenyl)cyclohexane-carboxamide | Method: F, m/z = 569.3 [M + H]+, Ret. time = 7.44 min. | 1H NMR (400 MHz, DMSO-d6) δ 0.61-0.76 (m, 4H), 1.17-1.26 (m, 3H), 1.32 (ddt, J = 60.4, 23.0 12.1 Hz, 2H), 1.80 (dd, J = 24.7, 12.3 Hz, 4H), 3.11-3.24 (m, 4H), 3.81 (d, J = 9.6 Hz, 2H), 6.57 (d, J = 7.2 Hz, 1H), 7.05 (d, J = 9.0 Hz, 1H), 7.36-7.47 (m, 1H), 7.47 (dd, J = 9.1, 2.8 Hz, 2H), 7.75 (dd, J = 14.3, 2.0 Hz, 1H), 7.95-8.09 (m, 2H), 8.79 (s, 1H), 10.23 (s, 1H), 11.63 (d, J = 5.4 Hz, 1H), 12.42 (s, 1H) | BP PA10 PB1 |
| I-316 | 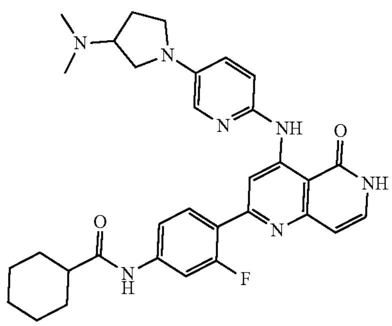 | N-(4-(4-((5-(3-(dimethyl-amino)pyrrolidin-1-yl)pyridin-2-yl)amino)-5-oxo-5,6-dihydro-1,6-naphthyridin-2-yl)-3-fluorophenyl)cyclohexane-carboxamide | Method: F, m/z = 570.3 [M + H]+, Ret. time = 6.56 min. | 1H NMR (400 MHz, DMSO-d6) δ 1.16-1.33 (m, 4H), 1.40 (dd, J = 24.7, 13.3 Hz, 2H), 1.68 (d, J = 11.6 Hz, 2H), 1.81 (dd, J = 24.7, 12.0 Hz, 4H), 2.24 (s, 1H), 2.40 (s, 6H), 3.22-3.34 (m, 2H), 3.49 (dt, J = 31.6, 8.6 Hz, 2H), 6.56 (d, J = 7.2 Hz, 1H), 7.02-7.16 (m, 2H), 7.35-7.49 (m, 2H), 7.72-7.82 (m, 1H), 8.01 (t, J = 8.9 Hz, 1H), 8.60 (s, 1H), 10.24 (s, 1H), 11.60 (d, J = 5.9 Hz, 1H), 12.26 (s, 1H). | BP 5-(3-(dimethyl-amino)pyrrolidin-1-yl)pyridin-2-amine PB1 |
| I-317 | 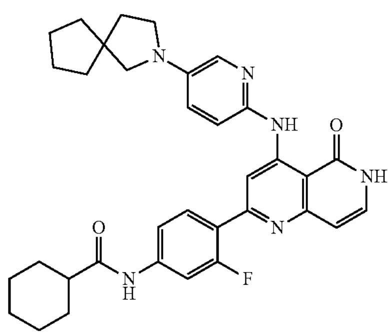 [SMILES: O=C(Nc1ccc(-c2cc(Nc3ccc(N4CCC5(CCCC5)C4)cn3)c3c(=O)[nH]ccc3n2)c(F)c1)C1CCCCC1] | N-(4-(4-((5-(2-azaspiro[4.4]nonan-2-yl)pyridin-2-yl)amino)-5-oxo-5,6-dihydro-1,6-naphthyridin-2-yl)-3-fluorophenyl)cyclohexane-carboxamide | Method: H, m/z = 581.45 [M + H]+, Ret. time = 5.77 min. | 1H NMR (400 MHz, DMSO-d6) δ 1.26 (h, J = 11.7 Hz, 3H), 1.43 (q, J = 11.8 Hz, 2H), 1.63 (dd, J = 31.2, 6.7 Hz, 9H), 1.74-1.92 (m, 7H), 2.39 (d, J = 12.1 Hz, 1H), 3.16 (s, 3H), 6.55 (d, J = 7.3 Hz, 1H), 7.03 (s, 2H), 7.35-7.49 (m, 2H), 7.74 (d, J = 17.6 Hz, 2H), 8.00 (t, J = 8.8 Hz, 1H), 8.53 (s, 1H), 10.23 (s, 1H), 11.58 (d, J = 5.9 Hz, 1H), 12.19 (s, 1H). | BP PA11 PB1 |
| I-318 | 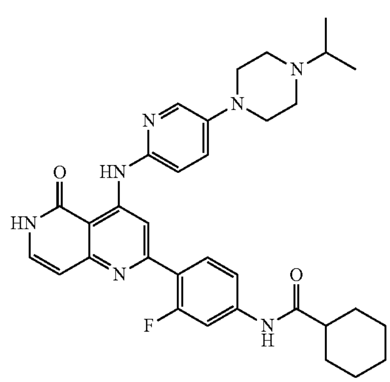 [SMILES: CC(C)N1CCN(c2ccc(Nc3cc(-c4ccc(NC(=O)C5CCCCC5)cc4F)nc4cc[nH]c(=O)c34)nc2)CC1] | N-(3-fluoro-4-(4-((5-(4-isopropyl-piperazin-1-yl)pyridin-2-yl)amino)-5-oxo-5,6-dihydro-1,6-naphthyridin-2-yl)phenyl)cyclohexane carboxamide | Method: H, m/z = 584.40 [M + H]+, Ret. time = 4.27 min. | 1H NMR (400 MHz, DMSO-d6) δ 1.09-1.31 (m, 10H), 1.39-1.48 (dd, 4H), 1.68 (d, 2H), 1.77-1.86 (m, 5H), 2.37 (m, 2H), 3.14 (s, 4H), 6.59 (d, J = 7.4 Hz, 1H), 7.06 (d, J = 9.0 Hz, 1H), 7.40-7.50 (m, 3H), 7.78 (d, J = 14.3 Hz, 1H), 8.01 (t, J = 8.8 Hz, 1H), 8.11 (s, 1H), 8.80 (s, 1H), 10.25 (s, 1H), 11.65 (d, J = 5.8 Hz, 1H), 12.46 (s, 1H) | BP 5-(4-isopropyl-piperazin-yl)pyridin-2-amine PB1 |

TABLE 2-continued

| I-# | STRUCTURE | NAME | LCMS | HNMR | Method SM |
|---|---|---|---|---|---|
| I-319 | 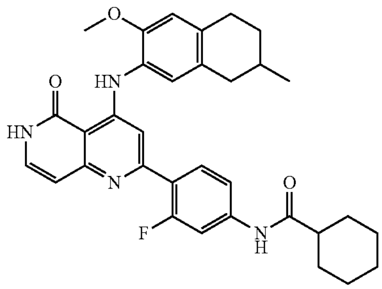 [SMILES: COc1cc2c(cc1Nc1cc(-c3ccc(NC(=O)C4CCCCC4)cc3F)nc3cc[nH]c(=O)c13)CC(C)CC2] | N-(3-fluoro-4-(4-((3-methoxy-7-methyl-5,6,7,8-tetrahydro-naphthalen-2-yl)amino)-5-oxo-5,6-dihydro-1,6-naphthyridin-2-yl)phenyl)cyclohexane | Method: J, m/z = 556.2 [M + H]+, Ret. time = 3.68 min. | 1H NMR (400 MHz, DMSO-d6) δ 1.15-1.45 (m, 6H), 1.68 (d, J = 11.1 Hz, 1H), 1.81 (t, J = 17.1 Hz, 2H), 2.37 (t, 2H), 2.94 (s, 3H), 3.13 (s, 2H), 3.36 (s, 2H), 3.87 (s, 3H), 4.26 (s, 1H), 4.46 (d, J = 15.2 Hz, 1H), 6.72 (s, 1H), 6.90 (s, 1H), 7.15 (s, 1H), 7.41 (s, 1H), 7.49 (d, J = 8.7 Hz, 1H), 7.84 (d, J = 14.0 Hz, 3H), 10.14 (s, 1H), 10.41 (s, 1H), 12.11 (s, 1H) | BP PA12 PB1 |
| I-320 | 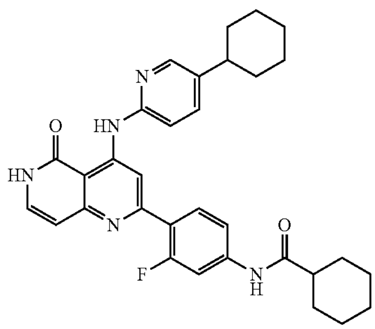 [SMILES: O=C(Nc1ccc(-c2cc(Nc3ccc(C4CCCCC4)cn3)c3c(=O)[nH]ccc3n2)c(F)c1)C1CCCCC1] | N-(4-(4-((5-cyclohexylpyridin-2-yl)amino)-5-oxo-5,6-dihydro-1,6-naphthyridin-2-yl)-3-fluorophenyl)cyclohexane-carboxamide | Method: H, m/z = 540.40 [M + H]+, Ret. time = 5.73 min. | 1H NMR (400 MHz, DMSO-d6) δ 1.23-1.43 (m, 11H), 1.69 (d, 2H), 1.80 (d, J = 12.0 Hz, 8H), 2.35 (t, 1H), 6.59 (d, J = 7.3 Hz, 1H), 7.02 (d, J = 8.4 Hz, 1H), 7.41-7.46 (m, 2H), 7.66 (dd, J = 8.5, 2.5 Hz, 1H), 7.75 (d, J = 14.0 Hz, 1H), 8.00 (t, J = 8.8 Hz, 1H), 8.24 (d, J = 2.4 Hz, 1H), 9.01 (s, 1H), 10.23 (s, 1H), 11.68 (s, 1H), 12.62 (s, 1H) | BP PA13 PB1 |
| I-321 | 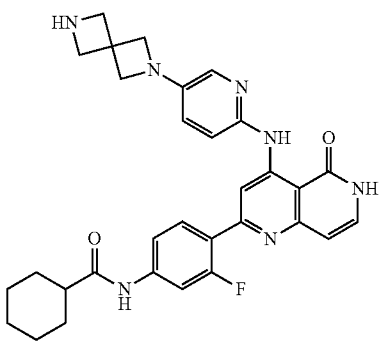 [SMILES: O=C(Nc1ccc(-c2cc(Nc3ccc(N4CC5(CNC5)C4)cn3)c3c(=O)[nH]ccc3n2)c(F)c1)C1CCCCC1] | N-(4-(4-((5-(2,6-diazaspiro[3.3]heptan-2-yl)pyridin-2-yl)amino)-5-oxo-5,6-dihydro-1,6-naphthyridin-2-yl)-2-fluorophenyl)cyclohexane-carboxamide | Method: C3, m/z = 554.98 [M + H]+, Ret. time = 1.39 min. | 1H NMR (400 MHz, DMSO-d6) δ 1.17-1.47 (m, 5H), 1.68 (d, J = 11.7 Hz, 1H), 1.77-1.86 (m, 4H), 2.34 (s, 1H), 3.64 (s, 5H), 4.08 (s, 4H), 4.19 (t, J = 6.2 Hz, 4H), 6.72 (d, J = 7.3 Hz, 1H), 7.08 (dd, J = 8.7, 3.0 Hz, 1H), 7.20 (d, J = 8.8 Hz, 1H), 7.53 (d, J = 8.6 Hz, 1H), 7.75 (d, J = 2.9 Hz, 2H), 7.86 (q, J = 9.5, 8.4 Hz, 2H), 8.60 (d, J = 17.7 Hz, 3H), 10.41 (s, 1H), 12.34 (s, 1H), 12.94 (s, 1H) | BP tert-butyl 6-(6-amino-pyridin-3-yl)-2,6-diazaspiro [3.3] heptane-2-carboxylate PB1 |
| I-322 | 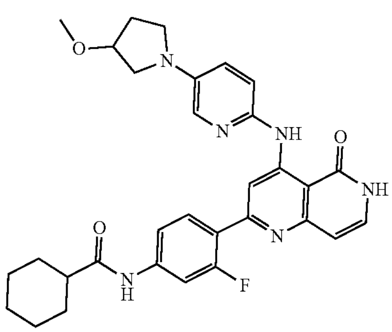 [SMILES: COC1CCN(c2ccc(Nc3cc(-c4ccc(NC(=O)C5CCCCC5)cc4F)nc4cc[nH]c(=O)c34)nc2)C1] | N-(3-fluoro-4-(4-((5-(3-methoxy-pyrrolidin-1-yl)pyridin-2-yl)amino)-5-oxo-5,6-dihydro-1,6-naphthyridin-2-yl)phenyl)cyclohexane-carboxamide | Method: C3, m/z = 557.83 [M + H]+, Ret. time = 1.65 min. | 1H NMR (400 MHz, DMSO-d6) δ 1.19-1.30 (m, 3H), 1.39-1.47 (m, 2H), 1.67 (d, J = 11.5 Hz, 1H), 1.76-1.85 (m, 3H), 2.06-2.11 (m, 2H), 2.37 (t, J = 11.5 Hz, 1H), 3.28 (s, 3H), 3.31-3.35 (m, 3H), 3.43-3.47 (m, 2H), 4.11 (s, 1H), 6.56 (d, J = 7.3 Hz, 1H), 7.03-7.11 (m, 2H), 7.37-7.46 (m, 2H), 7.73-7.76 (m, 2H), 8.00 (t, J = 8.8 Hz, 1H), 8.56 (s, 1H), 10.23 (s, 1H), 11.59 (d, J = 5.9 Hz, 1H), 12.23 (s, 1H) | BP 5-(3-methoxy pyrrolidin-1-yl) pyridin-2-amine PB1 |

TABLE 2-continued

| I-# | NAME | LCMS | HNMR | Method SM |
|---|---|---|---|---|
| I-323 | N-(3-fluoro-4-(4-((6-methoxy-1,2,3,4-tetrahydroisoquinolin-7-yl)amino)-5-oxo-5,6-dihydro-1,6-naphthyridin-2-yl)phenyl)cyclohexanecarboxamide | Method: C3, m/z = 542.4 [M + H]+, Ret. time = 1.48 min. | 1H NMR (400 MHz, DMSO-d6) δ 1.21-1.29 (m, 3H), 1.37-1.46 (q, J = 11.8 Hz, 2H), 1.67 (d, J = 10.9 Hz, 1H), 1.80 (t, J = 16.7 Hz, 4H), 2.34 (s, 1H), 2.77 (s, 3H), 3.05 (t, J = 5.8 Hz, 2H), 3.80 (s, 3H), 3.88 (s, 1H), 6.52 (d, J = 7.2 Hz, 1H), 6.89 (s, 1H), 7.16 (dd, 2H), 7.39 (dd, J = 12.2, 8.1 Hz, 2H), 7.72 (d, J = 14.4 Hz, 1H), 8.01 (t, J = 8.9 Hz, 1H), 10.21 (s, 1H), 11.27 (s, 1H), 11.48 (s, 1H) | BP PA14 PB1 |
| I-324 | N-(4-(4-((5-cyclopentylpyridin-2-yl)amino)-5-oxo-5,6-dihydro-1,6-naphthyridin-2-yl)-3-fluorophenyl)cyclohexanecarboxamide | Method: C3, m/z = 526.66 [M + H]+, Ret. time = 2.05 min. | 1H NMR (400 MHz, DMSO-d6) δ 1.17-1.32 (m, 3H), 1.38-1.46 (m, 2H), 1.53 (d, J = 9.7 Hz, 2H), 1.65 (t, 3H), 1.78-1.84 (m, 6H), 2.02 (s, 2H), 2.36 (t, J = 8.4 Hz, 1H), 2.98 (t, J = 8.3 Hz, 1H), 6.60 (d, J = 7.2 Hz, 1H), 7.04 (d, J = 8.4 Hz, 1H), 7.41-7.46 (q, 2H), 7.68-7.78 (dd, 2H), 8.00 (t, J = 8.8 Hz, 1H), 8.27 (s, 1H), 9.00 (s, 1H), 10.23 (s, 1H), 11.71 (s, 1H), 12.65 (s, 1H) | BP PA15 PB1 |
| I-325 | N-(4-(4-((5-(1-oxa-7-azaspiro[3.5]nonan-7-yl)pyridin-2-yl)amino)-5-oxo-5,6-dihydro-1,6-naphthyridin-2-yl)-3-fluorophenyl)cyclohexanecarboxamide | Method: C3, m/z = 583.88 [M + H]+, Ret. time = 1.53 min. | 1H NMR (400 MHz, DMSO-d6) δ 0.86 (s, 1H), 1.19-1.34 (m, 5H), 1.39-1.47 (m, 2H), 1.56 (s, 1H), 1.68 (d, J = 11.1 Hz, 1H), 1.77-1.86 (m, 4H), 2.19 (s, 3H), 3.47-3.54 (m, 2H), 3.67 (s, 2H), 4.50 (s, 1H), 5.54 (s, 1H), 6.61 (d, J = 7.4 Hz, 1H), 7.09 (d, J = 9.0 Hz, 1H), 7.48 (d, J = 9.1 Hz, 3H), 7.79 (d, J = 13.9 Hz, 1H), 7.95 (t, 1H), 8.10 (s, 1H), 8.70 (s, 1H), 10.29 (s, 1H), 11.79 (s, 1H), 12.56 (s, 1H) | BP 5-(1-oxa-7-azaspiro[3.5]nonan-7-yl)pyridin-2-amine PB1 |
| I-326 | (R)-N-(4-(4-((5-(3-aminopyrrolidin-1-yl)pyridin-2-yl)amino)-5-oxo-5,6-dihydro-1,6-naphthyridin-2-yl)-3-fluorophenyl)cyclohexanecarboxamide | Method: C3, m/z 542.73 [M + H]+, Ret. time = 1.36 min. | 1H NMR (400 MHz, DMSO-d6) δ 1.16-1.31 (m, 4H), 1.37-1.45 (m, 3H), 1.64-1.83 (m, 6H), 2.05 (m, 1H), 2.35 (t, 1H), 2.90 (t, 1H), 3.27 (t, 1H), 3.41 (t, 1H), 3.57 (d, 1H), 6.53 (d, J = 6.9 Hz, 1H), 7.08 (s, 2H), 7.37 (d, 1H), 7.43 (d, J = 7.3 Hz, 1H), 7.71 (t, 2H), 7.98 (t, 1H), 8.49 (s, 1H), 11.22 (s, 1H), 12.18 (s, 1H) | BP PA16 PB1 |

TABLE 2-continued

| I-# | STRUCTURE | NAME | LCMS | HNMR | Method SM |
|---|---|---|---|---|---|
| I-327 | 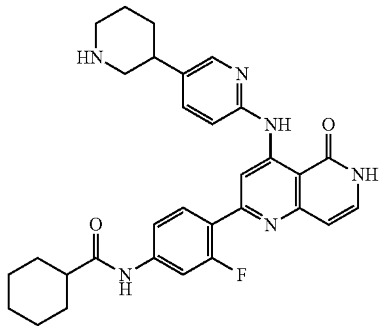 [SMILES: O=C(Nc1ccc(-c2cc(Nc3ccc(C4CCCNC4)cn3)c3c(=O)[nH]ccc3n2)c(F)c1)C1CCCCC1] | Synthesis of N-(3-fluoro-4-(5-oxo-4-((5-(piperidin-3-yl)pyridin-2-yl)amino)-5,6-dihydro-1,6-naphthyridin-2-yl)phenyl) cyclohexane-carboxamide | Method: C3, m/z = 541.7 [M + H]+, Ret. time = 1.36 min. | 1H NMR (400 MHz, DMSO-d6) δ 1.26-1.32 (m, 3H), 1.40-1.45 (m, 2H), 1.70-1.94 (m, 7H), 2.92-2.97 (m, 2H), 3.12 (d, J = 11.4 Hz, 1H), 3.38 (m, 5H merged with moisture), 6.70 (s, 1H), 7.23 (s, 1H), 7.48-7.60 (m, 2H), 7.84-7.98 (m, 2H), 8.40 (s, 1H), 8.47 (d, 1H), 8.80 (d, J = 11.1 Hz, 1H), 9.05 (s, 1H), 10.33 (s, 1H), 11.93 (s, 1H), 13.00 (s, 1H) | BP PA17 PB1 |
| I-328 | 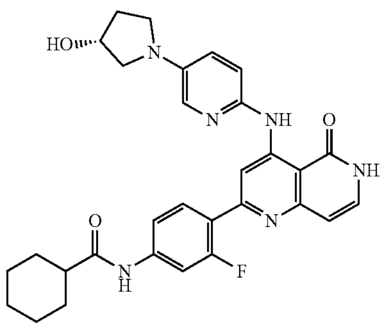 [SMILES: O=C(Nc1ccc(-c2cc(Nc3ccc(N4CC[C@@H](O)C4)cn3)c3c(=O)[nH]ccc3n2)c(F)c1)C1CCCCC1] | (R)-N-(3-fluoro-4-(4-((5-(3-hydroxy-pyrrolidin-1-yl)pyridin-2-yl)amino)-5-oxo-5,6-dihydro-1,6-naphthyridin-2-yl)phenyl) cyclohexane carboxamide | Method: C3, m/z = 543.90 [M + H]+, Ret. time = 1.515 min. | 1H NMR (400 MHz, DMSO-d6) δ 1.19-1.47 (m, 7H), 1.69 (d, 1H), 1.76-1.93 (m, 6H), 2.06 (m, 1H), 2.37 (m, 1H), 2.12 (d, 1H), 3.46 (m, 1H), 4.43 (s, 1H), 5.00 (s, 1H), 6.56 (d, J = 7.5 Hz, 1H), 7.06 (s, 2H), 7.45 (m, 2H), 7.75 (d, J = 13.0 Hz, 2H), 7.98 (s, 1H), 8.52 (s, 1H), 10.23 (s, 1H), 11.61 (s, 1H), 12.21 (s, 1H) | BP (R)-1-(6-amino-pyridin-3-yl) pyrrolidin-3-ol PB1 |
| I-329 | 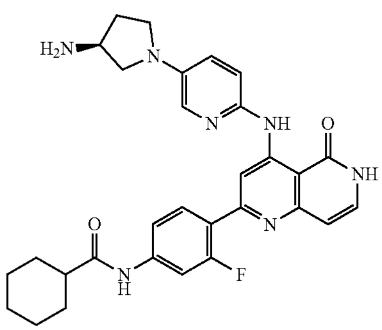 [SMILES: N[C@H]1CCN(c2ccc(Nc3cc(-c4ccc(NC(=O)C5CCCCC5)cc4F)nc4cc[nH]c(=O)c34)nc2)C1] | (S)-N-(4-(4-((5-(3-amino-pyrrolidin-1-yl)pyridin-2-yl)amino)-5-oxo-5,6-dihydro-1,6-naphthyridin-2-yl)-3-fluorophenyl) cyclohexane-carboxamide | Method: C3, m/z = 542.83 [M + H]+, Ret. time = 1.387 min. | 1H NMR (400 MHz, DMSO-d6) δ 0.86 (s, 1H), 1.24 (s, 4H), 1.29 (d, J = 11.9 Hz, 2H), 1.43 (d, J = 11.9 Hz, 2H), 1.67 (s, 1H), 1.82-1.92 (m, 6H), 2.08 (s, 1H), 3.16 (s, 1H), 3.54 (s, 2H), 6.55 (d, J = 7.2 Hz, 1H), 7.04 (s, 1H), 7.39 (d, 1H), 7.45 (d, 1H), 7.71-7.79 (m, 3H), 8.00 (t, J = 8.8 Hz, 1H), 8.52 (d, J = 10.3 Hz, 1H), 10.22 (s, 1H), 12.20 (d, J = 11.2 Hz, 1H) | BP tert-butyl (S)-(1-(6-amino-pyridin-3-yl) pyrrolidin-3-yl) carbamate PB1 |
| I-330 | 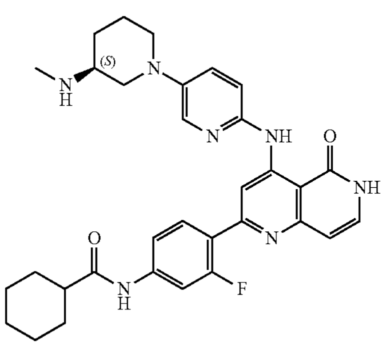 | (S)-N-(3-fluoro-4-(4-((5-(3-(methyl-amino) piperidin-1-yl)pyridin-2-yl)amino)-5-oxo-5,6-dihydro-1,6-naphthyridin-2-yl)phenyl) cyclohexane-carboxamide | Method: C3, m/z = 270.37 [M + H]+, Ret. time = 1.381 min. | 1H NMR (400 MHz, DMSO-d6) δ 1.10-1.29 (m, 4H), 1.37-1.66 (m, 2H), 1.75 (s, 2H), 1.54 (s, 2H), 1.81-1.88 (m, 6H), 2.33 (s, 4H), 2.69 (d, J = 11.0 Hz, 2H), 3.51 (d, J = 12.4 Hz, 2H), 3.66 (d, J = 10.5 H,z 1H), 6.56 (d, J = 7.3 Hz, 1H), 7.01 (d, J = 8.9 Hz, 2H), 7.38-7.45 (m, 3H), 7.75 (d, J = 13.9 Hz, 2H), 7.97-8.04 (m, 2H), 8.73 (s, 1H), 10.24 (s, 1H), 12.39 (s, 1H) | BP PA18 PB1 |

TABLE 2-continued

| I-# | STRUCTURE | NAME | LCMS | HNMR | Method SM |
|---|---|---|---|---|---|
| I-331 | 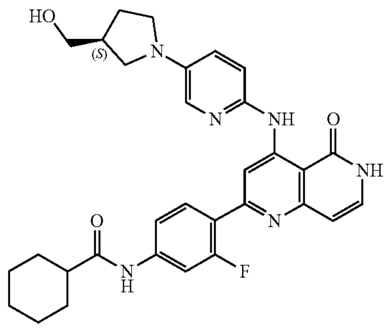 | (S)-N-(3-fluoro-4-(4-((5-(3-(hydroxymethyl)pyrrolidin-1-yl)pyridin-2-yl)amino)-5-oxo-5,6-dihydro-1,6-naphthyridin-2-yl)phenyl)cyclohexane-carboxamide | Method: C3, m/z = 577.78 [M + H]+, Ret. time = 1.519 min. | $^1$H NMR (400 MHz, DMSO-d$_6$) δ0 1.12-1.22 (m, 2H), 1.28-1.34 (m, 2H), 1.44 (q, J = 12.3 Hz, 2H), 1.59-1.86 (m, 4H), 2.02-2.08 (m, 1H), 2.34-2.43 (m, 2H), 3.04 (dd, J = 9.3, 6.1 Hz, 2H), 3.16-3.32 (m, 3H), 3.27-3.52 (m, 2H), 4.76 (s, 1H), 6.32 (d, J = 6.0 Hz, 1H), 6.87 (d, J = 8.8 Hz, 1H), 7.05 (dd, J = 8.8, 3.1 Hz, 1H), 7.41 (dd, J = 8.6, 2.0 Hz, 1H), 7.61 (d, J = 6.0 Hz, 1H), 7.65-7.75 (m, 2H), 7.90 (m, 1H), 8.34 (s, 2H), 10.18 (s, 1H), 14.64 (s, 1H) | BP PA19 PB1 |
| I-332 | 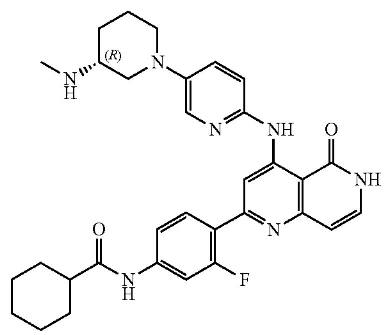 | (R)-N-(3-fluoro-4-(4-((5-(3-(methylamino)piperidin-1-yl)pyridin-2-yl)amino)-5-oxo-5,6-dihydro-1,6-naphthyridin-2-yl)phenyl)cyclohexane-carboxamide | Method: C3, m/z = 570.8 [M + H]+, Ret. time = 1.354 min. Chiral HPLC: Method A3 Ret time: 5.5 min. | $^1$H NMR (400 MHz, DMSO-d$_6$) δ0 1.21-1.29 (m, 4H), 1.40-1.43 (m, 2H), 1.54-1.57 (m, 2H), 1.64-1.75 (m, 2H), 1.81-1.90 (m, 5H), 2.36-2.71 (m, 5H), 3.34-3.43 (m, 2H), 3.66 (d, J = 11.6 Hz, 2H), 6.56 (d, J = 7.3 Hz, 1H), 7.02 (d, J = 8.9 Hz, 1H), 7.39-7.45 (m, 3H), 7.75 (d, J = 14.1 Hz, 1H), 7.97-8.06 (m, 3H), 8.74 (s, 1H), 10.23 (s, 1H), 12.39 (s, 1H) | BP PA20 PB1 |
| I-333 | 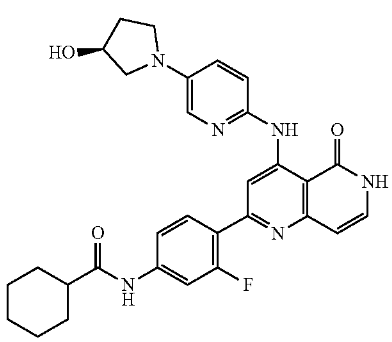 | (S)-N-(3-fluoro-4-(4-((5-(3-hydroxypyrrolidin-1-yl)pyridin-2-yl)amino)-5-oxo-5,6-dihydro-6H-naphthyridin-2-yl)phenyl)cyclohexane-carboxamide | Method: H, m/z = 543.40 [M + H]+, Ret. time = 3.668 min. | $^1$H NMR (400 MHz, DMSO-d$_6$) δ0 1.90-1.34 (m, 3H), 1.39-1.48 (m, 2H), 1.66-1.69 (d, J = 10.4 Hz, 1H), 1.72-1.93 (m, 6H), 2.02-2.08 (m, 1H), 2.34-2.40 (m, 2H), 3.11-3.13 (m, 1H), 3.46 (dd, J = 10.1, 4.9 Hz, 1H), 4.43 (s, 1H), 4.98-5.04 (m, 1H), 6.55 (d, J = 7.3 Hz, 1H), 7.42 (dd, J = 25.0, 7.9 Hz, 2H), 7.75 (d, J = 13.3 Hz, 2H), 8.00 (m, 1H), 8.53 (s, 1H), 10.23 (s, 1H), 11.58 (s, 1H), 12.21 (s, 1H). | BP (S)-1-(6-aminopyridin-3-yl)pyrrolidin-3-ol PB1 |
| I-334 | 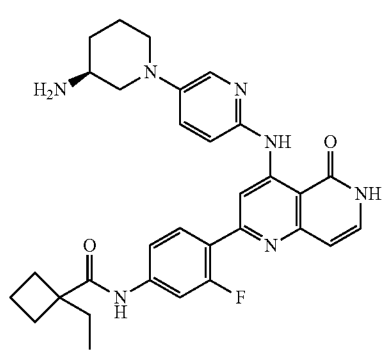 [SMILES: CCC1(C(=O)Nc2ccc(-c3cc(Nc4ccc(N5CCC[C@H](N)C5)cn4)c4c(=O)[nH]ccc4n3)c(F)c2)CCC1] | (S)-N-(4-(4-((5-(3-aminopiperidin-1-yl)pyridin-2-yl)amino)-5-oxo-5,6-dihydro-1,6-naphthyridin-2-yl)-3-fluorophenyl)cyclohexane)carboxamide | Method: C3, m/z = 556.78 [M + H]+, Ret. time = 1.372 min. | 1H NMR (400 MHz, DMSO-d6) δ 0.75-0.78 (m, 3H), 1.72 (s, 3H), 1.89 (dt, J = 11.8, 7.3 Hz, 6H), 2.33-2.41 (m, 5H), 2.62-2.66 (m, 3H), 2.78 (s, 2H), 6.57 (d, J = 7.3 Hz, 1H), 7.02 (d, J = 8.9 Hz, 1H), 7.39-7.45 (m, 2H), 7.55 (d, J = 8.5 Hz, 1H), 7.81 (d, J = 14.1 Hz, 1H), 7.97-8.04 (m, 2H), 8.74 (s, 1H), 9.74 (s, 1H), 12.38 (s, 1H) | BP PA23 PB4 |

TABLE 2-continued

| I-# | STRUCTURE | NAME | LCMS | HNMR | Method SM |
|---|---|---|---|---|---|
| I-335 | 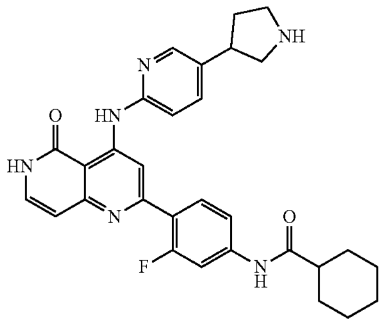 [SMILES: O=C(Nc1ccc(-c2cc(Nc3ccc(C4CCNC4)cn3)c3c(=O)[nH]ccc3n2)c(F)c1)C1CCCCC1] | N-(3-fluoro-4-(5-oxo-4-((5-(pyrrolidin-3-yl)pyridin-2-yl)amino)-5,6-dihydro-1,6-naphthyridin-2-yl)phenyl)cyclohexane-carboxamide | Method: C3, m/z = 527.3 [M + H]+, Ret. time = 1.359 min. | 1H NMR (400 MHz, DMSO-d6) δ 1.23-1.29 (m, 5H), 1.40-1.43 (m, 3H), 1.67-1.75 (m, 2H), 1.82-1.84 (m, 5H), 2.14-2.45 (m, 1H), 3.13-3.16 (m, 2H), 3.50-3.67 (m, 1H), 6.57 (d, J = 7.1 Hz, 1H), 7.02 (d, J = 8.5 Hz, 1H), 7.46 (s, 2H), 7.69 (d, J = 14.3 Hz, 1H), 7.97-7.99 (m, 1H), 8.27 (s, 1H), 8.99 (s, 1H), 10.32 (s, 1H), 12.95 (s, 1H) | BP tert-butyl 3-(6-amino-pyridin-3-yl)pyrrolidine-1-carboxylate PB1 |
| I-336 | 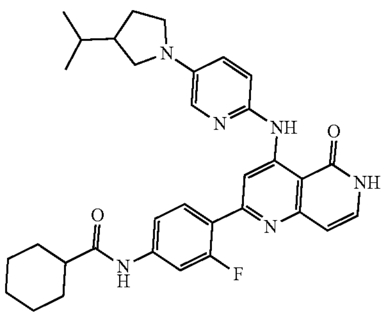 [SMILES: CC(C)C1CCN(c2ccc(Nc3cc(-c4ccc(NC(=O)C5CCCCC5)cc4F)nc4cc[nH]c(=O)c34)nc2)C1] | N-(3-fluoro-4-(4-((5-(3-isopropyl-pyrrolidin-1-yl)pyridin-2-yl)amino)-5-oxo-5,6-dihydro-1,6-naphthyridin-2-yl)phenyl)cyclohexane-carboxamide | Method: C3, m/z = 569.49 [M + H]+, Ret. time = 2.060 min. | 1H NMR (400 MHz, DMSO-d6) δ 0.97 (d, J = 6.6 Hz, 6H), 1.22-1.34 (m, 3H), 1.39-1.47 (m, 2H), 1.53-1.69 (m, 3H), 1.85 (d, J = 12.9 Hz, 4H), 1.91-2.03 (m, 1H), 2.09-2.17 (m, 1H), 2.38 (dd, J = 13.4, 9.7 Hz, 1H), 2.93 (t, J = 9.3 Hz, 1H), 3.16-3.32 (m, 1H), 3.45 (m, 2H), 6.62 (d, J = 7.2 Hz, 1H), 7.09 (s, 2H), 7.45-7.56 (m, 2H), 7.74-7.84 (m, 2H), 7.92 (t, J = 8.7 Hz, 1H), 8.52 (s, 1H), 10.30 (s, 1H), 11.91 (s, 1H), 12.54 (s, 1H) | BP PA24 PB1 |
| I-337 | 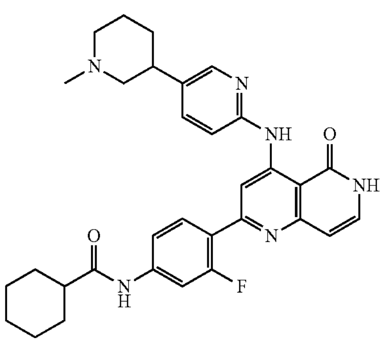 [SMILES: CN1CCCC(c2ccc(Nc3cc(-c4ccc(NC(=O)C5CCCCC5)cc4F)nc4cc[nH]c(=O)c34)nc2)C1] | N-(3-fluoro-4-(4-((5-(1-methyl-piperidin-3-yl)pyridin-2-yl)amino)-5-oxo-5,6-dihydro-1,6-naphthyridin-2-yl)phenyl)cyclohexane-carboxamide | Method: C3, m/z = 555.8 [M + H]+, Ret. time = 1.435 min. | $^1$H NMR (400 MHz, DMSO-$d_6$) δ0 1.25-1.30 (m, 5H), 1.39-1.51 (m, 3H), 1.69-1.77 (m, 2H), 1.78-1.86 (m, 6H), 2.40 (s, 3H), 2.87-3.01 (s, 3H), 6.62 (d, J = 7.2 Hz, 1H), 7.08 (d, J = 8.5 Hz, 1H), 7.40-7.50 (m, 2H), 7.71-7.81 (m, 2H), 8.01-8.05 (m, 1H), 8.32 (s, 1H), 9.06 (s, 1H), 10.26 (s, 1H), 11.71 (d, J = 6.0 Hz, 1H), 12.69 (s, 1H) | DP PA22 PB1 |
| I-338 | 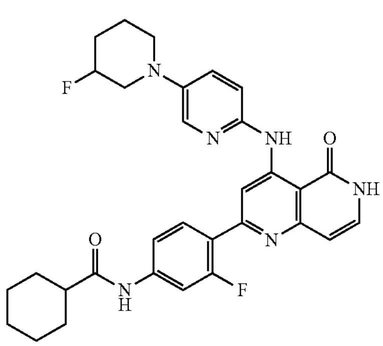 [SMILES: O=C(Nc1ccc(-c2cc(Nc3ccc(N4CCCC(F)C4)cn3)c3c(=O)[nH]ccc3n2)c(F)c1)C1CCCCC1] | N-(3-fluoro-4-(4-((5-(3-fluoro-piperidin-1-yl)pyridin-2-yl)amino)-5-oxo-5,6-dihydro-1,6-naphthyridin-2-yl)phenyl)cyclohexane-carboxamide | Method: C3, m/z 559.8 [M + H]+, Ret. time = 1.731 min. | $^1$H NMR (400 MHz, DMSO-$d_6$) δ0 1.18-1.32 (m, 3H), 1.38-1.46 (m, 2H), 1.62-1.67 (m, 2H), 1.75-1.85 (m, 6H), 1.90-1.93 (m, 1H), 2.33-2.37 (m, 1H), 3.16-3.17 (m, 3H), 3.39-3.45 (m, 1H), 4.75-4.87 (m, 1H), 6.56 (d, J = 7.2 Hz, 1H), 7.02 (d, J = 8.9 Hz, 1H), 7.38-7.51 (m, 3H), 7.75 (dd, J = 14.3, 2.0 Hz, 1H), 7.97-8.01 (m, 1H), 8.08 (d, J = 3.1 Hz, 1H), 8.75 (s, 1H), 10.22 (s, 1H), 11.62 (d, J = 5.7 Hz, 1H), 12.41 (s, 1H) | BP PA21 PB1 |

TABLE 2-continued

| I-# | STRUCTURE | NAME | LCMS | HNMR | Method SM |
|---|---|---|---|---|---|
| I-339 | 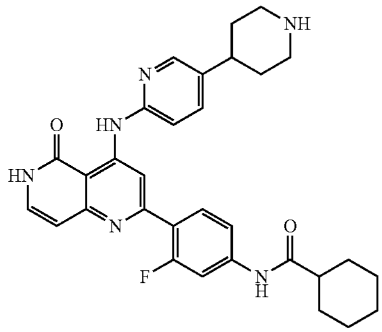 [SMILES: O=C(Nc1ccc(-c2cc(Nc3ccc(C4CCNCC4)cn3)c3c(=O)[nH]ccc3n2)c(F)c1)C1CCCCC1] | N-(3-fluoro-4-(5-oxo-4-((5-(piperidin-4-yl)pyridin-2-yl)amino)-5,6-dihydro-1,6-naphthyridin-2-yl)phenyl)cyclohexane-carboxamide | Method: H, m/z = 539.35 [M + H]+, Ret. time = 3.365 min. | 1H NMR (400 MHz, DMSO-d6) δ 1.12-1.29 (m, 3H), 1.37-1.54 (m, 4H), 1.67-1.84 (m, 7H), 2.38 (d, J = 11.7 Hz, 2H), 2.58 (d, J = 12.1 Hz, 2H), 3.02 (d, J = 12.0 Hz, 2H), 6.59 (d, J = 7.2 Hz, 1H), 7.03 (d, J = 8.4 Hz, 1H), 7.44 (dd, J = 13.5, 7.9 Hz, 2H), 7.66 (d, J = 8.5 Hz, 1H), 7.77 (d, J = 14.2 Hz, 1H), 8.00 (t, J = 8.8 Hz, 1H), 8.25 (s, 1H), 9.01 (s, 1H), 10.25 (s, 1H), 12.65 (s, 1H) | BP tert-butyl 4-(6-amino-pyridin-3-yl)piperidine-1-carboxylate PB1 |
| I-340 | 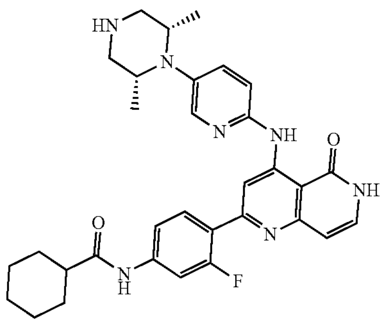 [SMILES: C[C@@H]1CNC[C@H](C)N1c1ccc(Nc2cc(-c3ccc(NC(=O)C4CCCCC4)cc3F)nc3cc[nH]c(=O)c23)nc1] | N-(4-(4-((5-((2S,6R)-2,6-dimethyl-piperazin-1-yl)pyridin-2-yl)amino)-5-oxo-5,6-dihydro-1,6-naphthyridin-2-yl)-3-fluorophenyl)cyclohexane-carboxamide | Method: H, m/z = 568.40 [M + H]+, Ret. time = 3.583 min. | 1H NMR (400 MHz, DMSO-d6) δ 0.75 (d, J = 6.0 Hz, 5H), 1.17-1.29 (m, 4H), 1.37-1.43 (m, 2H), 1.66 (d, J = 11.9 Hz, 1H), 1.75-1.84 (m, 3H), 2.72 (d, J = 11.0 Hz, 2H), 3.16 (d, J = 4.8 Hz, 4H), 4.09-4.17 (m, 2H), 6.61 (d, J = 7.2 Hz, 1H), 7.13 (d, J = 8.7 Hz, 1H), 7.45 (d, J = 8.4 Hz, 2H), 7.59-7.67 (m, 1H), 7.80 (d, J = 14.0 Hz, 1H), 8.01 (t, J = 8.8 Hz, 1H), 8.09 (s, 1H), 9.03 (s, 1H), 10.28 (s, 1H), 11.73 (s, 1H), 12.77 (s, 1H) | BP PA27 PB1 |
| I-341 | 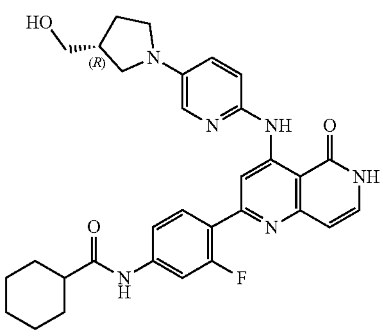 | (R)-N-(3-fluoro-4-(4-((5-(3-(hydroxy-methyl)pyrrolidin-1-yl)pyridin-2-yl)amino)-5-oxo-5,6-dihydro-1,6-naphthyridin-2-yl)phenyl)cyclohexane-carboxamide | Method: C3, m/z = 557.6 [M + H]+, Ret. time = 1.566 min. | 1H NMR (400 MHz, DMSO-d6) δ 1.17-1.32 (m, 3H), 1.37-1.45 (m, 2H), 1.67-1.84 (m, 6H), 2.04 (m, 1H), 2.38 (d, J = 11.7 Hz, 3H), 3.02 (d, J = 12.0 Hz, 1H), 3.16 (m, 2H), 3.04 (m, 2H), 4.74 (s, 1H), 6.59 (d, J = 7.2 Hz, 1H), 7.03 (d, J = 8.4 Hz, 2H), 7.44 (dd, J = 13.5, 7.9 Hz, 2H), 7.66 (d, J = 8.5 Hz, 1H), 7.77 (d, J = 14.2 Hz, 1H), 8.00 (t, J = 8.8 Hz, 1H), 8.51 (s, 1H), 10.22 (s, 1H), 11.58 (s, 1H), 12.23 (s, 1H) | BP PA26 PB1 |
| I-342 | 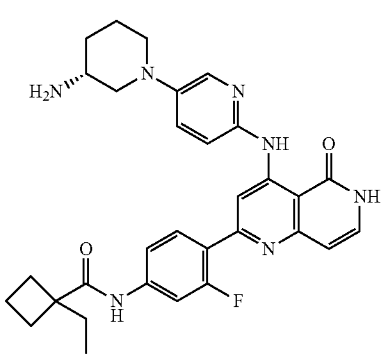 [SMILES: CCC1(C(=O)Nc2ccc(-c3cc(Nc4ccc(N5CCC[C@@H](N)C5)cn4)c4c(=O)[nH]ccc4n3)c(F)c2)CCC1] | (R)-N-(4-(4-((5-(3-amino-piperidin-1-yl)pyridin-2-yl)amino)-5-oxo-5,6-dihydro-1,6-naphthyridin-2-yl)-3-fluorophenyl)1-ethyl-cyclobutane-1-carboxamide | Method: C3, m/z = 556.78 [M + H]+, Ret. time = 1.399 min. | 1H NMR (400 MHz, DMSO-d6) δ 0.77 (t, J = 7.3 Hz, 3H), 1.13 (d, J = 12.3 Hz, 2H), 1.56 (s, 2H), 1.85-1.92 (m, 6H), 2.76 (s, 2H), 3.16 (m, 1H), 3.55 (dd, J = 30.8, 11.8 Hz, 3H), 6.57 (d, J = 7.2 Hz, 1H), 7.02 (d, J = 8.9 Hz, 1H), 7.42 (dd, J = 16.5, 7.6 Hz, 2H), 7.55 (d, J = 9.0 Hz, 1H), 7.81 (d, J = 14.7 Hz, 1H), 7.94-8.07 (m, 2H), 8.74 (s, 1H), 9.74 (s, 1H), 12.38 (s, 1H) | BP PA25 PB4 |

TABLE 2-continued

| I-# | STRUCTURE | NAME | LCMS | HNMR | Method SM |
|---|---|---|---|---|---|
| I-343 | 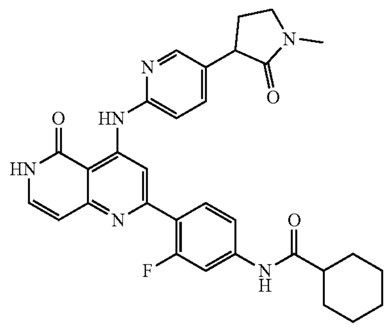 [SMILES: CN1CCC(c2ccc(Nc3cc(-c4ccc(NC(=O)C5CCCCC5)cc4F)nc4cc[nH]c(=O)c34)nc2)C1=O] | N-(3-fluoro-4-(4-((5-(1-methyl-2-oxo-pyrrolidin-3-yl)pyridin-2-yl)amino)-5-oxo-5,6-dihydro-1,6-naphthyridin-2-yl)phenyl)cyclohexane-carboxamide | Method: H, m/z = 555.40 [M + H]+, Ret. time = 3.749 min. | ¹H NMR (400 MHz, DMSO-d₆) δ0 1.19-1.34 (m, 3H), 1.37-1.43 (m, 2H), 1.56 (s, 1H), 1.68 (d, J = 11.1 Hz, 1H), 1.82 (dd, J = 25.9, 12.1 Hz, 4H), 2.07 (dq, J = 12.7, 8.7 Hz, 1H), 2.35-2.50 (m, 1H), 2.82 (s, 3H), 3.38-3.51 (m, 2H), 3.69 (t, J = 9.2 Hz, 1H), 6.63 (d, J = 7.2 Hz, 1H), 7.09 (d, J = 8.5 Hz, 1H), 7.41-7.52 (m, 2H), 7.67 (dd, J = 8.4, 2.5 Hz, 1H), 7.79 (dd, J = 14.3, 2.1 Hz, 1H), 8.03 (d, J = 2.4 Hz, 1H), 9.07 (s, 1H), 10.26 (s, 1H), 11.74 (s, 1H), 12.73 (s, 1H) | BP PA28 PB1 |
| I-344 | 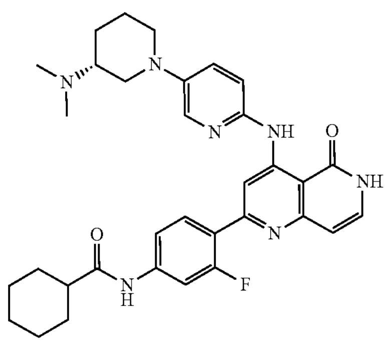 [SMILES: CN(C)[C@@H]1CCCN(c2ccc(Nc3cc(-c4ccc(NC(=O)C5CCCCC5)cc4F)nc4cc[nH]c(=O)c34)nc2)C1] | (R)-N-(4-(4-((5-(3-(dimethyl-amino)piperidin-1-yl)pyridin-2-yl)amino)-5-oxo-5,6-dihydro-1,6-naphthyridin-2-yl)-3-fluorophenyl)cyclohexane-carboxamide | Method: J, m/z = 584.4 [M + H]+, Ret. time = 3.710 min. | 1H NMR (400 MHz, DMSO-d6) δ 1.18-1.37 (m, 3H), 1.43 (q, J = 12.0 Hz, 2H), 1.56-1.59 (m, 1H), 1.67 (d, J = 10.8 Hz, 1H), 1.82-1.92 (m, 6H), 2.26 (s, 6H), 2.37 (d, J = 9.0 Hz, 3H), 2.55-2.66 (m, 2H), 3.61 (d, J = 12.2 Hz, 1H), 3.72 (d, J = 12.0 Hz, 1H), 6.58 (dd, J = 7.3, 1.8 Hz, 1H), 7.02 (d, J = 8.9 Hz, 1H), 7.38-7.53 (m, 3H), 7.77 (d, J = 14.2 Hz, 1H), 8.00 (t, J = 8.8 Hz, 1H), 8.08 (d, J = 2.8 Hz, 1H), 8.74 (s, 1H), 10.27 (s, 1H), 11.67 (s, 1H), 12.40 (s, 1H) | BP PA29 PB1 |
| I-345 | 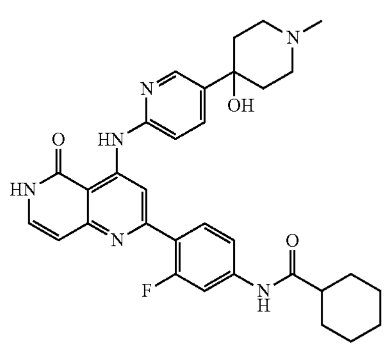 [SMILES: CN1CCC(O)(c2ccc(Nc3cc(-c4ccc(NC(=O)C5CCCCC5)cc4F)nc4cc[nH]c(=O)c34)nc2)CC1] | N-(3-fluoro-4-(4-((5-(4-hydroxy-1-methyl-piperidin-4-yl)pyridin-2-yl)amino)-5-oxo-5,6-dihydro-1,6-naphthyridin-2-yl)phenyl)cyclohexane-carboxamide | Method: C3, m/z = 571.6 [M + H]+, Ret. time = 1.458 min. | 1H NMR (400 MHz, DMSO-d6) δ 1.20-1.35 (m, 3H), 1.45 (q, J = 12.3, 11.5 Hz, 2H), 1.64-1.677 (m, 2H), 1.78-1.87 (m, 4H), 1.98 (dt, J = 12.7, 6.5 Hz, 2H), 2.23 (s, 3H), 2.38 (t, J = 11.5 Hz, 3H), 2.56-2.69 (m, 3H), 4.96 (s, 1H), 6.63 (d, J = 7.3 Hz, 1H), 7.07 (d, J = 8.6 Hz, 1H), 7.41-7.53 (m, 2H), 7.79 (dd, J = 14.2, 2.1 Hz, 1H), 7.88 (dd, J = 8.6, 2.6 Hz, 1H), 8.04 (t, J = 8.8 Hz, 1H), 8.49 (d, J = 2.5 Hz, 1H), 9.07 (s, 1H), 10.26 (s, 1H), 11.71 (s, 1H), 12.70 (s, 1H) | DP 4-(6-amino-pyridin-3-yl)-1-methyl-piperidin-4-ol PB1 |

TABLE 2-continued

| I-# | STRUCTURE | NAME | LCMS | HNMR | Method SM |
|---|---|---|---|---|---|
| I-346 | 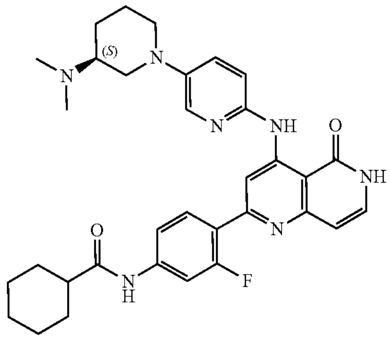 | (S)-N-(4-(4-((5-(3-(dimethyl-amino)piperidin-1-yl)pyridin-2-yl)amino)-5-oxo-5,6-dihydro-1,6-naphthyridin-2-yl)-3-fluorophenyl)cyclohexane-carboxamide | Method: C3, m/z = 584.9 [M + H]+, Ret. time = 1.400 min. | ¹H NMR (400 MHz, DMSO-d₆) δ0 1.19-1.34 (m, 3H), 1.44 (q, J = 11.6 Hz, 2H), 1.56-1.59 (m, 1H) 1.68 (d, J = 11.2 Hz, 1H), 1.77-1.92 (m, 6H), 2.26 (s, 6H), 2.32-2.43 (m, 3H), 2.53-2.66 (m, 2H), 3.61 (d, J = 12.3 Hz, 1H), 3.68-3.77 (m, 1H), 6.58 (dd, J = 7.3, 1.8 Hz, 1H), 7.03 (d, J = 8.9 Hz, 1H), 7.38-7.53 (m, 3H), 7.77 (d, J = 14.2 Hz, 1H), 8.00 (t, J = 8.8 Hz, 1H), 8.08 (d, J = 3.0 Hz, 1H), 8.75 (s, 1H), 10.27 (s, 1H), 11.67 (s, 1H), 12.41 (s, 1H). | BP PA30 PB1 |
| I-347 | 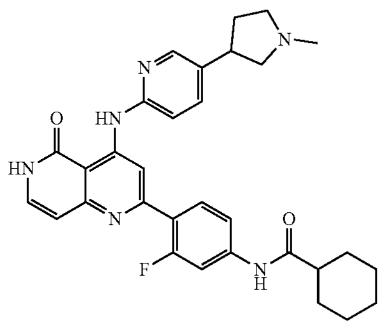 [SMILES: CN1CCC(c2ccc(Nc3cc(-c4ccc(NC(=O)C5CCCCC5)cc4F)nc4cc[nH]c(=O)c34)nc2)C1] | N-(3-fluoro-4-(4-((5-(1-methyl-pyrrolidin-3-yl)pyridin-2-yl)amino)-5-oxo-5,6-dihydro-1,6-naphthyridin-2-yl)phenyl)cyclohexane-carboxamide | Method: C3, m/z = 541.4 [M + H]+, Ret. time = 1.384 min.. | ¹H NMR (DMSO-d₆, 400 MHZ): 12.66 (s, 1H), 11.70 (s, 1H), 10.26 (s, 1H), 9.05 (s, 1H), 8.29 (s, 1H), 8.03 (t, J = 8.8, 1H), 7.80-7.74 (m, 2H), 7.48 (d, J = 14.4 Hz, 1H), 7.46 (d, J = 8.0 Hz, 1H), 7.06 (d, J = 8.4 Hz, 1H), 6.62 (d, J = 6.8 Hz, 1H), 2.85-2.8 (m, 1H), 2.69-2.65 (m, 2H), 2.46-2.42 (m, 2H), 2.38-2.34 (m, 2H), 2.31 (s, 3H), 1.86-1.78 (s, 4H), 1.69 (br s, 1H), 1.45-1.39 (m, 2H), 1.31-1.25 (m, 4H). | DP 5-(1-methyl-pyrrolidin-3-yl)pyridin-2-amine PB1 |
| I-348 | 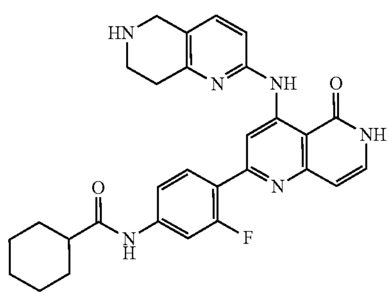 [SMILES: O=C(Nc1ccc(-c2cc(Nc3ccc4c(n3)CCNC4)c3c(=O)[nH]ccc3n2)c(F)c1)C1CCCCC1] | N-(3-fluoro-4-(5-oxo-4-((5,6,7,8-tetrahydro-1,6-naphthyridin-2-yl)amino)-5,6-dihydro-2-yl)phenyl)cyclohexane-carboxamide | Method: H, m/z = 513.55 [M + H]+, Ret. time = 3.603 min. | ¹H NMR (DMSO-d₆, 400 MHZ): 12.63 (s, 1H), 11.73 (s, 1H), 10.27 (s, 1H), 9.32 (s, 1H), 8.3 (s, 1H), 8.11 (t, J = 8.8, 1H), 7.86 (d, J = 14.4 Hz, 1H), 7.57 (d, J = 8.0 Hz, 1H), 7.43-7.38 (m, 2H), 6.89 (d, J = 8.4 Hz, 1H), 6.62 (d, J = 6.8 Hz, 1H), 3.96 (br s, 1H), 3.2 (s, 2H), 2.87 (s, 2H), 2.37 (m, 1H), 1.86-1.77 (m, 4H), 1.69-1.66 (m, 1H), 1.45-1.42 (m, 2H), 1.34-1.24 (m, 4H). | BP tert-butyl 2-amino-7,8-dihydro-1,6-naphthy-ridine-6(5H)-carboxylate PB1 |
| I-349 | 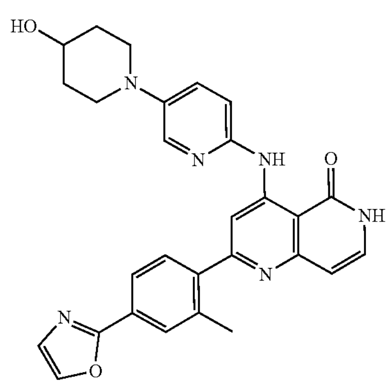 [SMILES: Cc1cc(-c2ncco2)ccc1-c1cc(Nc2ccc(N3CCC(O)CC3)cn2)c2c(=O)[nH]ccc2n1] | 4-((5-(4-hydroxy-piperidin-1-yl)pyridin-2-yl)amino)-2-(2-methyl-4-(oxazol-2-yl)phenyl)-1,6-naphthyridin-5(6H)-one | Method: C3 m/z = 495.47 [M + H]+, Ret. time = 1.321 min. | ¹H NMR (DMSO-d₆, 400 MHZ): 12.49 (s, 1H), 11.67 (s, 1H), 8.5 (s, 1H), 8.28 (s, 1H), 8.06-8.05 (d, J = 4.8 Hz, 1H), 7.96 (s, 1H), 7.93-7.91 (d, J = 4.0 Hz, 1H), 7.6 (d, J = 4.0 Hz, 1H), 7.48-7.42 (m, 3h), 7.01 c(d, J = 8.0 Hz, 1H), 6.57 (d, J = 7.8 Hz, 1H), 3.61 (br s, 1H), 3.51-3.48 (m, 1H), 2.84 (s, J = 10 Hz, 1H), 2.46 (s, 3H), 1.83-1.80 (br d, 2H), 1.51-1.47 (m, 2H). | CP 1-(6-amino-pyridin-3-yl)piperidin-4-ol 2-(3-methyl-4-(4,4,5,5-tetramethyl-1,3,2-dioxa-borolan-2-yl)phenyl)oxazole |

TABLE 2-continued

| I-# | STRUCTURE | NAME | LCMS | HNMR | Method SM |
|---|---|---|---|---|---|
| I-350 | 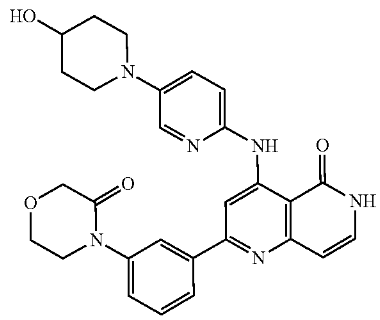 [SMILES: O=C1COCCN1c1cccc(-c2cc(Nc3ccc(N4CCC(O)CC4)cn3)c3c(=O)[nH]ccc3n2)c1] | 4-(3-(4-((5-(4-hydroxy-piperidin-1-yl)pyridin-2-yl)amino)-5-oxo-5,6-dihydro-1,6-naphthyridin-2-yl)phenyl)morpholin-3-one | Method: C3, m/z = 513.67 [M + H]+, Ret. time = 1.290 min. | $^1$H NMR (DMSO-d$_6$, 400 MHZ): 12.46 (s, 1H), 11.67 (s, 1H), 8.84 (s, 1H), 8.15-8.12 (m, 2H), 7.92 (d, J = 7.8 Hz, 1H), 7.61-7.57 (m, 1H), 7.54-7.48 (m, 1H), 7.43 (d, J = 7.2 Hz, 1H), 7.05 (d, J = 8.8 Hz, 1H), 6.62 (d, J = 7.2 Hz, 1H), 4.72 (d, J = 3.2 Hz, 1H), 4.27 (s, 2H), 4.39 (t, J = 4.4 Hz, 2H), 3.83 (t, J = 4.4 Hz, 2H), 3.66-3.65 (m, 1H), 3.56-3.53 (m, 2H), 2.89 (t, J = 10 Hz, 2H), 1.83-1.80 (br d, 2H), 1.51-1.47 (m, 2H). | CP 1-(6-amino-pyridin-3-yl) piperidin-4-ol PB2 |
| I-351 | 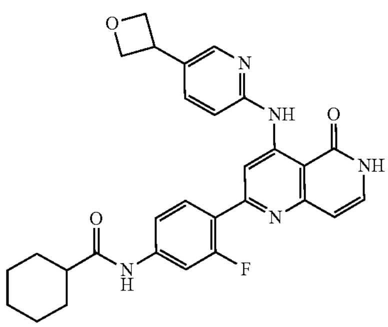 [SMILES: O=C(Nc1ccc(-c2cc(Nc3ccc(C4COC4)cn3)c3c(=O)[nH]ccc3n2)c(F)c1)C1CCCCC1] | N-(3-fluoro-4-(4-((5-(oxetan-3-yl)pyridin-2-yl)amino)-5-oxo-5,6-dihydro-1,6-naphthyridin-2-yl)phenyl)cyclohexane carboxamide | Method: C3, m/z = 514.57 [M + H]+, Ret. time = 1.539 min. | $^1$H NMR (DMSO-d$_6$, 400 MHZ): 12.73 (s, 1H), 11.73 (s, 1H), 10.25 (s, 1H), 9.015 (s, 1H), 8.37 (s, 1H), 8.02 (t, J = 8.4 Hz, 1H), 7.97-7.94 (m, 1H), 7.80-7.76 (m, 1H), 7.72-7.70 (m, 1H), 7.47-7.36 (m, 2H), 7.14 (d, J = 8.4 Hz, 1H), 6.62 (d, J = 7.2 Hz, 1H), 4.97-4.93 (m, 2H), 4.65 (t, J = 6.4 Hz, 2H), 4.33-4.25 (m, 1H), 1.86-1.77 (m, 4H), 1.66 (s, 1H), 1.45-1.38 (m, 2H), 1.34-1.24 (m, 4H) | BP PA31 PB1 |
| I-352 | 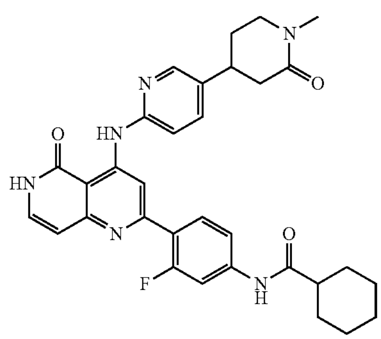 [SMILES: CN1CCC(c2ccc(Nc3cc(-c4ccc(NC(=O)C5CCCCC5)cc4F)nc4cc[nH]c(=O)c34)nc2)CC1=O] | N-(3-fluoro-4-(4-((5-(1-methyl-2-oxopiperidin-4-yl)pyridin-2-yl)amino)-5-oxo-5,6-dihydro-1,6-naphthyridin-2-yl)phenyl)cyclohexane carboxamide | Method: C3, m/z = 567.61 [M + H]+, Ret. time = 1.455 min. | $^1$H NMR (DMSO-d$_6$, 400 MHZ): 12.69 (s, 1H), 11.71 (s, 1H), 10.25 (s, 1H), 9.015 (s, 1H), 8.31 (s, 1H), 8.02 (t, J = 8.4 Hz, 1H), 7.79-7.37 (m, 2H), 7.48-7.43 (m, 2H), 7.07 (d, J = 8.4 Hz, 1H), 6.61 (d, J = 7.2 Hz, 1H), 3.38 3.3 (m, 2H), 3.08 (s, 1H), 2.83 (s, 3H), 2.37-2.33 (m, 3H), 2.01 (s, 2H), 1.86-1.77 (m, 4H), 1.66 (s, 1H), 1.45-1.38 (m, 2H), 1.34-1.24 (m, 4H) | BP PA32 PB1 |
| I-353 | 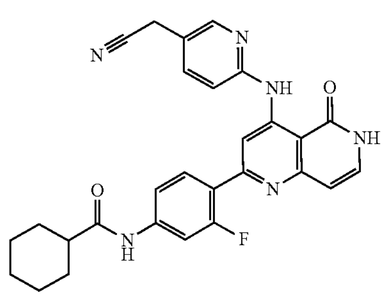 [SMILES: N#CCc1ccc(Nc2cc(-c3ccc(NC(=O)C4CCCCC4)cc3F)nc3cc[nH]c(=O)c23)nc1] | N-(4-(4-((5-(cyano-methyl)pyridin-2-yl)amino)-5-oxo-5,6-dihydro-1,6-naphthyridin-2-yl)-3-fluorophenyl)cyclohexane carboxamide | Method: C3, m/z = 597.39 [M + H]+, Ret. time = 1.580 min. | $^1$H NMR (DMSO-d$_6$, 400 MHZ): 13.26 (s, 1H), 12.41 (s, 1H), 10.40 (s, 1H), 8.96 (s, 1H), 8.43 (s, 1H), 7.89-7.85 (m, 3H), 7.47 (s, 1H), 7.55 (d, J = 8.0 Hz, 1H), 7.34 (s, 1H), 6.77 (d, J = 72 Hz, 1H), 4.21 (s, 2H), 2.42-2.36 (m, 1H), 1.87-1.77 (m, 4H), 1.69-1.67 (m, 1H), 1.48-1.39 (m, 2H), 1.34-1.25 (m, 4H). | EP 2-(6-bromo-pyridin-3-yl) acetonitrile PB1 |

TABLE 2-continued

| I-# | STRUCTURE | NAME | LCMS | HNMR | Method SM |
|---|---|---|---|---|---|
| I-354 | 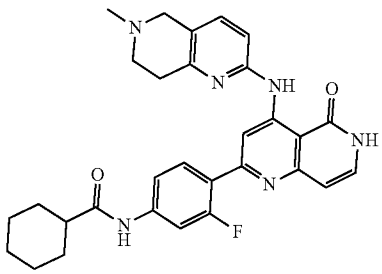 [SMILES: CN1CCc2nc(Nc3cc(-c4ccc(NC(=O)C5CCCCC5)cc4F)nc4cc[nH]c(=O)c34)ccc2C1] | N-(3-fluoro-4-(4-((6-methyl-5,6,7,8-tetrahydro-1,6-naphthyridin-2-yl)amino)-5-oxo-5,6-dihydro-1,6-naphthyridin-2-yl)phenyl)cyclohexane carboxamide | Method: C3 02, m/z = 527.5 [M + H]+, Ret. time = 1.421 min. | ¹H NMR (DMSO-d₆, 400 MHZ): 12.72 (s, 1H), 11.73 (s, 1H), 10.26 (s, 1H), 9.32 (s, 1H), 8.11 (t, J = 8.8, 1H), 7.87 (d, J = 14.4 Hz, 1H), 7.57 (d, J = 8.0 Hz, 1H), 7.43-7.38 (m, 2H), 6.95 (d, J = 8.4 Hz, 1H), 6.61 (d, J = 6.8 Hz, 1H), 4.06 (br s, 1H), 3.06 (s, 2H), 2.66 (s, 3H), 1.90-1.65 (m, 6H), 1.43-1.4 (m, 2H), 1.29-1.73 (m, 2H). | DP 6-methyl-5,6,7,8-tetrahydro-1,6-naphthyridin-2-amine PB1 |
| I-355 | 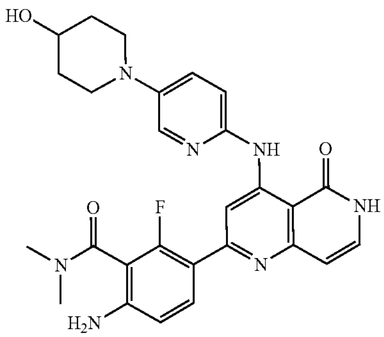 [SMILES: CN(C)C(=O)c1c(N)ccc(-c2cc(Nc3ccc(N4CCC(O)CC4)cn3)c3c(=O)[nH]ccc3n2)c1F] | 6-amino-2-fluoro-3-(4-((5-(4-hydroxy-piperidin-1-yl)pyridin-2-yl)amino)-5-oxo-5,6-dihydro-1,6-naphthyridin-2-yl)-N,N-dimethyl-benzamide | Method: C3 04, m/z = 518.44 [M + H]+, Ret. time = 1.333 min. | 1H NMR (400 MHz, DMSO-d6) δ 12.25 (s, 1H), 11.33 (s, 1H), 8.68 (s, 1H), 7.98 (d, J = 2.4 Hz, 1H), 7.7 (s, 1H), 7.6 (d, J = 8.0 Hz, 1H), 7.45-7.41 (m, 2H), 7.25 (t, J = 6.4 Hz, 1H), 7.00-6.93 (m, 2H), 6.23 (d, J = 6.8 Hz, 1H), 4.70 (d, 1H), 4.52 (t, J = 5.2 Hz, 1H), 3.62-3.61 (m, 1H), 3.49-3.42 (m, 4H), 2.9 (s, 3H), 2.88 (s, 3H), 2.83-2.80 (m, 1H), 1.84-1.81 (m, 2H), 1.50-1.48 (m, 2H). | EP 1-(6-amino-pyridin-3-yl)piperidin-4-ol PB3 |
| I-356 | 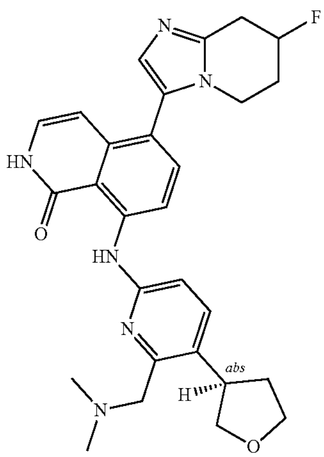 | (R)-8-((6-((dimethyl-amino)methyl)-5-(THF-3-yl)pyridin-2-yl)amino)-5-(7-fluoro-imidazo[1,2-a]pyridin-3-yl)isoquinolin-1(2H)-one | LCMS Method J m/z = 500.2 [M + H]+, Ret. time = 2.57 min Chiral HPLC method A1: Ret. time = 6.63 | 1H NMR (400 MHz, DMSO-d6) δ 12.81 (s, 1H), 11.61 (d, J = 6.0 Hz, 1H), 8.89 (d, J = 8.7 Hz, 1H), 7.93 (dd, J = 7.5, 5.8 Hz, 1H), 7.77-7.63 (m, 3H), 7.55 (dd, J = 10.2, 2.6 Hz, 1H), 7.15 (dd, J = 7.3, 5.8 Hz, 1H), 7.01-6.88 (m, 2H), 5.89 (dd, J = 7.3, 1.3 Hz, 1H), 4.05-3.93 (m, 2H), 3.81 (q, J = 7.7 Hz, 2H), 3.81 (q, J = 8.2, 6.8 Hz, 1H), 2.36-2.18 (m, 6H), 1.90 (dq, J = 12.1, 7.7 Hz, 1H). | FP PA35 3-bromo-7-fluoro-imidazo[1,2-a]pyridine |
| I-357 | 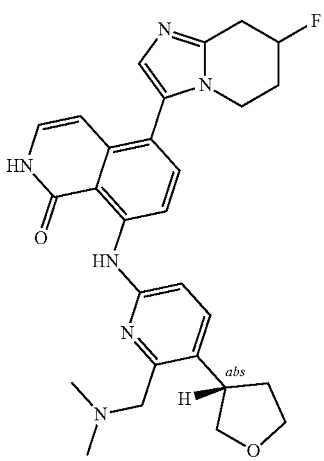 | (S)-8-((6-((dimethyl-amino)methyl)-5-(THF-3-yl)pyridin-2-yl)amino)-5-(7-fluoro-imidazo[1,2-a]pyridin-3-yl)isoquinolin-1(2H)-one | LCMS Method J m/z = 500.2 [M + H]+, Ret. time = 2.56 min Chiral HPLC method A1: Ret. time = 6.71 | 1H NMR (400 MHz, DMSO-d6) δ 12.81 (s, 1H), 11.63 (d, J = 5.8 Hz, 1H), 8.80 (s, 1H), 7.93 (dd, J = 7.6, 5.8 Hz, 1H), 7.77-7.63 (m, 3H), 7.56 (dd, J = 10.1, 2.6 Hz, 1H), 7.23-7.11 (m, 1H), 7.02 (d, J = 8.3 Hz, 1H), 6.93 (td, J = 7.6, 2.6 Hz, 1H), 5.97-5.81 (m, 1H), 4.15-3.93 (m, 3H), 3.82 (q, J = 7.7 Hz, 2H), 3.73 (s, 1H), 3.55 (t, J = 7.6 Hz, 1H), 3.49 (t, J = 5.3 Hz, 1H), 3.42 (t, J = 5.2 Hz, 1H), 2.31 (s, 2H), 1.96-1.86 (m, 1H), 1.25 (d, J = 8.0 Hz, 1H). | FP PA35 3-bromo-7-fluoro-imidazo[1,2-a]pyridine |

TABLE 2-continued

| I-# | STRUCTURE | NAME | LCMS | HNMR | Method SM |
|---|---|---|---|---|---|
| I-358 | 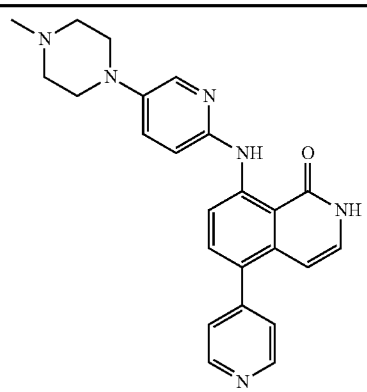 | 8-((5-(4-methyl-piperazin-1-yl)pyridin-2-yl)amino)-5-(pyridin-4-yl)isoquinolin-1(2H)-one | LCMS Method J m/z = 418.1 [M + H]+, Ret. time = 2.09 min | 1H NMR (400 MHz, DMSO-d6) δ 12.51 (s, 1H), 8.70-8.54 (m, 3H), 8.00 (d, J = 3.0 Hz, 1H), 7.54 (d, J = 8.7 Hz, 1H), 7.50-7.39 (m, 3H), 7.17 (d, J = 7.4 Hz, 1H), 6.96 (d, J = 8.9 Hz, 1H), 6.47 (d, J = 7.5 Hz, 1H), 3.13 (t, J = 5.0 Hz, 4H), 2.5 (s, 4H, murged in DMSO peak), 2.26 (s, 3H). | GP 5-(4-methyl-piperazin-1-yl)pyridin-2-amino Pyridine 4-boronic acid |
| I-359 | 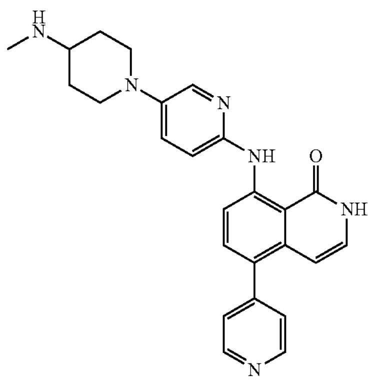 | 8-((5-(4-(methyl-amino)piperidin-1-yl)pyridin-2-yl)amino)-5-(pyridin-4-yl)isoquinolin-1(2H)-one | LCMS Method J m/z = 438.1 [M + H]+, Ret. time = 2.31 min | 1H NMR (400 MHz, DMSO-d6) δ 12.59 (s, 1H), 11.54 (s, 1H), 8.66 (t, J = 6.8 Hz, 3H), 8.35 (s, 1H), 8.04 (d, J = 3.0 Hz, 1H), 7.55 (d, J = 8.7 Hz, 1H), 7.50-7.38 (m, 3H), 7.18 (d, J = 7.4 Hz, 1H), 6.95 (d, J = 8.9 Hz, 1H), 6.46 (d, J = 7.4 Hz, 1H), 3.68 (d, J = 4.1 Hz, 2H), 2.85 (td, J = 10.2, 9.7, 5.2 Hz, 1H), 2.77-2.69 (m, 2H), 2.48 (s, 3H), 2.02 (d, J = 12.0 Hz, 2H), 1.56 (tt, J = 12.1, 6.2 Hz, 2H). | GP PA36 Pyridine 4-boronic acid |
| I-360 | 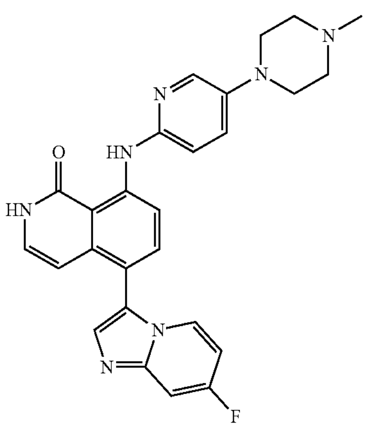 [SMILES: CN1CCN(c2ccc(Nc3ccc(-c4cnc5cc(F)ccn45)c4cc[nH]c(=O)c34)nc2)CC1] | 5-(7-fluoro-imidazo[1,2-a]pyridin-3-yl)-8-((5-(4-methyl-piperazin-1-yl)pyridin-2-yl)amino)isoquinolin-1(2H)-one | LCMS Method J m/z = 471.2 [M + H]+, Ret. time = 2.31 min | 1H NMR (400 MHz, DMSO-d6) δ 12.59 (s, 1H), 11.56 (s, 1H), 8.75-8.59 (m, 1H), 8.27 (s, 1H), 8.03 (d, J = 3.1 Hz, 1H), 7.97-7.86 (m, 1H), 7.71-7.60 (m, 2H), 7.56 (dd, J = 10.1, 2.8 Hz, 1H), 7.47 (dd, J = 9.0, 3.0 Hz, 1H), 7.14 (dd, J = 7.6, 3.3 Hz, 1H), 7.05-6.85 (m, 2H), 5.88 (d, J = 7.3 Hz, 1H), 3.14 (t, J = 4.9 Hz, 4H), 2.48 (d, J = 5.1 Hz, 3H), 2.25 (s, 3H). | FP 5-(4-methyl-piperazin-1-yl)pyridin-2-amine 3-bromo-7-fluoro-imidazo[1,2-a]pyridine |
| I-361 | 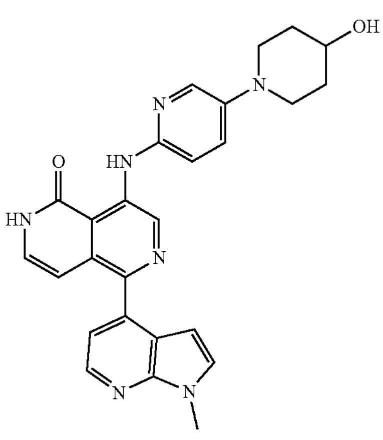 [SMILES: Cn1ccc2c(-c3ncc(Nc4ccc(N5CCC(O)CC5)cn4)c4c(=O)[nH]ccc34)ccnc21] | 8-((5-(4-hydroxy-piperidin-1-yl)pyridin-2-yl)amino)-5-(1-methyl-1H-pyrrolo[2,3-b]pyridin-4-yl)-2,6-naphthyridin-1(2H)-one | LCMS Method J m/z = 468.4 [M + H]+, Ret. time = 2.57 min | 1H NMR (400 MHz, DMSO-d6) δ 11.41 (s, 1H), 9.33 (s, 1H), 8.32-8.07 (m, 2H), 8.04 (d, J = 3.1 Hz, 1H), 7.97-7.77 (m, 2H), 7.51-7.37 (m, 2H), 7.32 (t, J = 6.4 Hz, 1H), 7.18 (d, J = 7.4 Hz, 1H), 6.92 (d, J = 4.9 Hz, 1H), 6.07 (d, J = 3.5 Hz, 1H), 4.70 (s, 1H), 3.84 (s, 3H), 3.71-3.58 (m, 1H), 3.49 (dd, J = 11.2, 6.2 Hz, 2H), 2.93-2.76 (m, 2H), 1.97-1.75 (m, 2H), 1.51 (q, J = 11.1, 9.7 Hz, 2H). | IP 1-(6-amino-pyridin-3-yl)piperidin-4-ol 1-methyl-4-(4,4,5,5-tetramethyl-1,3,2-dioxa-borolan-2-yl)-1H-pyrrolo[2,3-b]pyridine |

| I-# | STRUCTURE | NAME | LCMS | HNMR | Method SM |
|---|---|---|---|---|---|
| I-362 | 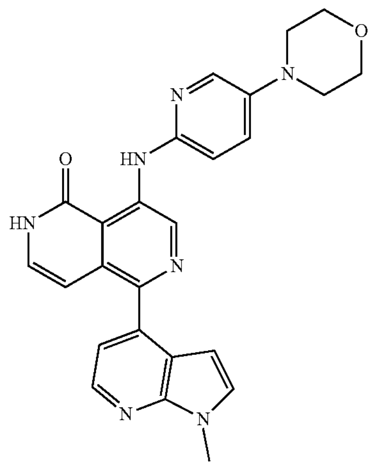 [SMILES: Cn1ccc2c(-c3ncc(Nc4ccc(N5CCOCC5)cn4)c4c(=O)[nH]ccc34)ccnc21] | 5-(1-methyl-1H-pyrrolo[2,3-b]pyridin-4-yl)-8-((5-morpholino pyridin-2-yl)amino)-2,6-naphthyridin-1(2H)-one | LCMS Method J m/z = 454.3 [M + H]+, Ret. time = 2.39 min | 1H NMR (400 MHz, DMSO-d6) δ 11.43 (s, 1H), 9.39 (s, 1H), 8.31-8.16 (m, 1H), 8.06 (d, J = 3.0 Hz, 1H), 7.99 (d, J = 9.1 Hz, 1H), 7.90 (s, 1H), 7.50-7.37 (m, 2H), 7.33 (t, J = 6.5 Hz, 1H), 7.19 (d, J = 7.3 Hz, 1H), 6.93 (d, J = 4.9 Hz, 1H), 6.08 (d, J = 3.5 Hz, 1H), 3.86 (s, 3H), 3.78 (t, J = 4.7 Hz, 3H), 3.13 (t, J = 4.8 Hz, 4H). | JP 5-morpholino-pyridin-2-amine 1-methyl-4-(4,4,5,5-tetramethyl-1,3,2-dioxa-borolan-2-yl)-1H-pyrrolo[2,3-b]pyridine |
| I-363 | 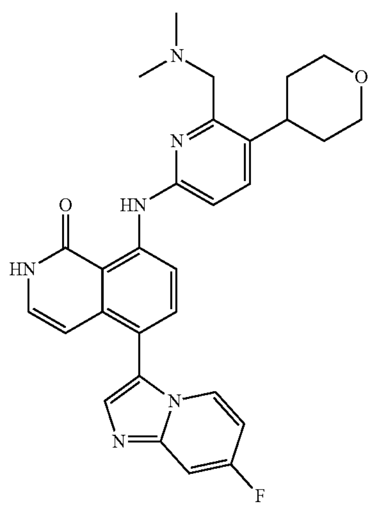 [SMILES: CN(C)Cc1nc(Nc2ccc(-c3cnc4cc(F)ccn34)c3cc[nH]c(=O)c23)ccc1C1CCOCC1] | 8-((6-((dimethyl-amino)methyl)-5-(tetrahydro-2H-pyran-4-yl)pyridin-2-yl)amino)-5-(7-fluoro-imidazo[1,2-a]pyridin-3-yl)isoquinolin-1(2H)-one | LCMS Method J m/z = 513.2 [M + H]+, Ret. time = 2.52 min | 1H NMR (400 MHz, DMSO-d6) δ 12.80 (s, 1H), 11.64 (s, 1H), 8.94 (d, J = 8.7 Hz, 1H), 8.41 (s, 2H), 7.94 (t, J = 6.6 Hz, 1H), 7.78-7.60 (m, 3H), 7.16 (d, J = 7.3 Hz, 1H), 6.94 (d, J = 8.4 Hz, 2H), 5.89 (d, J = 7.3 Hz, 1H), 3.98 (d, J = 11.1 Hz, 3H), 3.58 (s, 3H), 3.21 (s, 2H), 2.23 (s, 6H), 1.78-1.61 (m, 4H), 1.25 (s, 2H). | FP PA37 3-bromo-7-fluoro-imidazo[1,2-a]pyridine |
| I-364 | 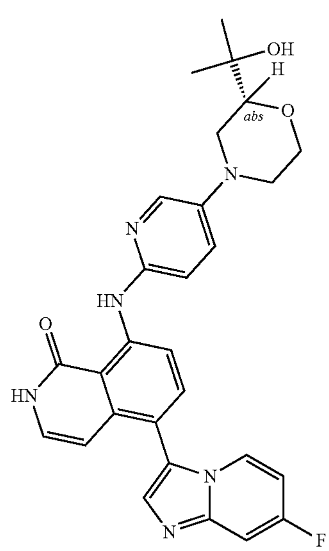 | (R)-5-(7-fluoro-imidazo[1,2-a]pyridin-3-yl)-8-((5-(2-(2-hydroxy-propan-2-yl)morpholino)pyridin-2-yl)amino)isoquinolin-1(2H)-one | LCMS Method J m/z = 545.2 [M + H]+, Ret. time = 2.89 min Chiral HPLC method A2: Ret. time = 19.69 | 1H NMR (400 MHz, DMSO-d6) δ 12.61 (d, J = 7.5 Hz, 1H), 11.56 (d, J = 5.6 Hz, 1H), 8.71 (dd, J = 24.1, 8.7 Hz, 1H), 8.05 (d, J = 3.3 Hz, 1H), 7.97-7.86 (m, 1H), 7.77-7.60 (m, 2H), 7.55 (dd, J = 10.2, 2.8 Hz, 1H), 7.47 (dt, J = 11.3, 5.6 Hz, 1H), 7.14 (t, J = 6.3 Hz, 1H), 7.01 (t, J = 8.2 Hz, 1H), 6.93 (td, J = 7.6, 2.7 Hz, 1H), 5.88 (d, J = 7.3 Hz, 1H), 4.49 (s, 1H), 4.07-3.96 (m, 1H), 3.75-3.59 (m, 2H), 3.49 (d, J = 11.7 Hz, 1H), 1.16 (d, J = 22.8 Hz, 6H). | FP PA38 3-bromo-7-fluoro-imidazo[1,2-a]pyridine |

TABLE 2-continued

| I-# | STRUCTURE | NAME | LCMS | HNMR | Method SM |
|---|---|---|---|---|---|
| I-365 | 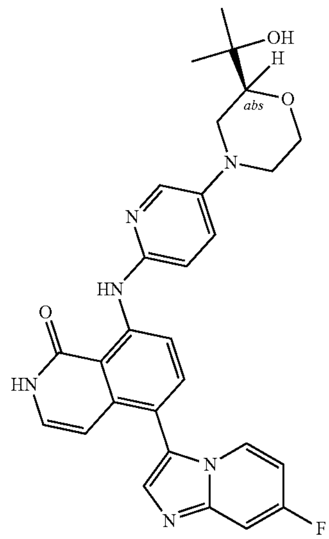 [SMILES: CC(C)(O)[C@@H]1CN(c2ccc(Nc3ccc(-c4cnc5cc(F)ccn45)c4cc[nH]c(=O)c34)nc2)CCO1] | (S)-5-(7-fluoro-imidazo[1,2-a]pyridin-3-yl)-8-((5-(2-(2-hydroxy-propan-2-yl)morpholino)pyridin-2-yl)amino)isoquinolin-1(2H)-one | LCMS Method J m/z = 515.1 [M + H]+, Ret. time = 2.87 min Chiral HPLC method A1: Ret. time = 8.42 | 1H NMR (400 MHz, DMSO-d6) δ 12.62 (s, 1H), 11.60 (s, 1H), 8.68 (d, J = 8.7 Hz, 1H), 8.51 (s, 2H), 8.05 (d, J = 3.0 Hz, 1H), 7.98-7.88 (m, 1H), 7.71-7.60 (m, 2H), 7.51 (ddd, J = 29.1, 9.6, 2.9 Hz, 2H), 7.13 (d, J = 5.7 Hz, 1H), 7.00 (d, J = 8.9 Hz, 1H), 6.93 (td, J = 7.5, 2.7 Hz, 1H), 5.88 (d, J = 7.3 Hz, 1H), 4.50 (s, 1H), 4.06-3.95 (m, 1H), 3.71-3.59 (m, 2H), 1.16 (d, J = 22.8 Hz, 6H). | FP PA38 3-bromo-7-fluoro-imidazo[1,2-a]pyridine |
| I-366 | 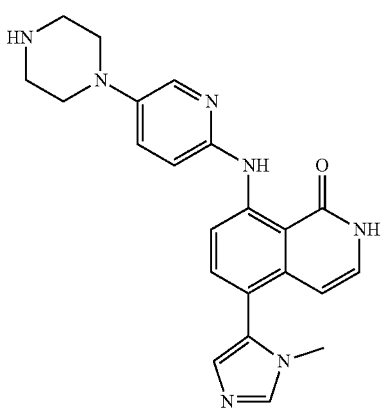 [SMILES: Cn1cncc1-c1ccc(Nc2ccc(N3CCNCC3)cn2)c2c(=O)[nH]ccc12] | 5-(1-methyl-1H-imidazol-5-yl)-8-((5-(piperazin-1-yl)pyridin-2-yl)amino)isoquinolin-1(2H)-one | LCMS Method J m/z = 402.21 [M + H]+, Ret. time = 2.14 min | 1H NMR (400 MHz, DMSO-d6) δ 12.52 (s, 1H), 11.50 (s, 1H), 8.60 (d, J = 8.7 Hz, 1H), 8.27 (s, 1H), 8.01 (d, J = 3.0 Hz, 1H), 7.76 (s, 1H), 7.51-7.43 (m, 2H), 7.15 (d, J = 5.7 Hz, 1H), 6.93 (d, J = 8.9 Hz, 1H), 6.91 (td, J = 7.5, 2.7 Hz, 1H), 6.14 (d, J = 7.2 Hz, 1H), 3.36 (s, 3H), 3.26 (s, 4H), 3.17 (s, 4H). | HP tert-butyl 4-(6-amino-pyridin-3-yl)piperazine-carboxylate 1-methyl-5-(4,4,5,5-tetramethyl-1,3,2-dioxaborolan-2-yl)-1H-imidazole |
| I-367 | 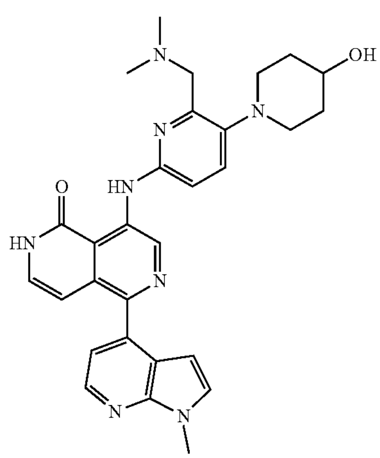 [SMILES: CN(C)Cc1nc(Nc2cnc(-c3ccnc4c3ccn4C)c3cc[nH]c(=O)c23)ccc1N1CCC(O)CC1] | 8-((6-((dimethylamino)methyl)-5-(4-hydroxy-piperidin-1-yl)pyridin-2-yl)amino)-5-(1-methyl-1H-pyrrolo[2,3-b]pyridin-4-yl)-2,6-naphthyridin-1(2H)-one | LCMS Method J m/z = 525.2 [M + H]+, Ret. time = 2.58 min | 1H NMR (400 MHz, DMSO-d6) δ 11.43 (d, J = 5.9 Hz, 1H), 9.33 (s, 2H), 8.28-8.13 (m, 2H), 7.89 (s, 1H), 7.84 (d, J = 8.8 Hz, 1H), 7.55 (d, J = 8.8 Hz, 1H), 7.41 (d, J = 3.5 Hz, 1H), 733 (t, J = 6.6 Hz, 1H), 7.17 (d, J = 7.3 Hz, 1H), 6.92 (d, J = 4.9 Hz, 1H), 6.06 (d, J = 3.5 Hz, 1H), 3.84 (s, 3H), 2.72 (d, J = 10.8 Hz, 3H), 2.31 (s, 6H), 1.86 (d, J = 13.6 Hz, 2H), 1.63-1.52 (m, 2H). | IP PA40 1-methyl-4-(4,4,5,5-tetramethyl-1,3,2-dioxaborolan-2-yl)-1H-pyrrolo[2,3-b]pyridine |

TABLE 2-continued

| I-# | STRUCTURE | NAME | LCMS | HNMR | Method SM |
|---|---|---|---|---|---|
| I-368 | 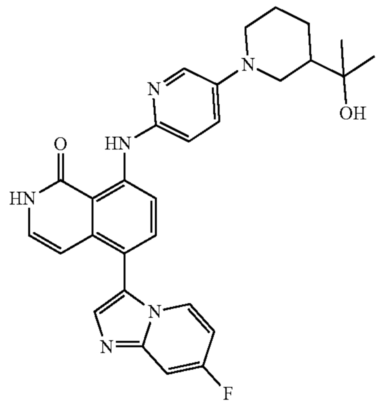 [SMILES: CC(C)(O)C1CCCN(c2ccc(Nc3ccc(-c4cnc5cc(F)ccn45)c4cc[nH]c(=O)c34)nc2)C1] | 5-(7-fluoro-imidazo[1,2-a]pyridin-3-yl)-8-((5-(3-(2-hydroxy-propan-2-yl)piperidin-1-yl)pyridin-2-yl)amino)isoquinolin-1(2H)-one | LCMS Method C m/z = 513.8 [M + H]+, Ret. time = 0.98 min | 1H NMR (400 MHz, DMSO-d6) δ 12.56 (s, 1H), 11.55 (s, 1H), 8.65 (d, J = 8.7 Hz, 1H), 8.01 (d, J = 3.0 Hz, 1H), 7.91 (dd, J = 7.6, 5.8 Hz, 1H), 7.72-7.58 (m, 2H), 7.55 (dd, J = 10.1, 2.7 Hz, 1H), 7.43 (dd, J = 8.9, 3.1 Hz, 1H), 7.13 (d, J = 7.3 Hz, 1H), 7.02-6.83 (m, 2H), 5.87 (d, J = 7.3 Hz, 1H), 4.28 (s, 1H), 3.76 (d, J = 12.3 Hz, 1H), 3.64 (d, J = 11.8 Hz, 1H), 3.17 (d, J = 5.0 Hz, 1H), 1.84 (d, J = 12.8 Hz, 1H), 1.75 (d, J = 13.1 Hz, 1H), 1.60-1.49 (m, 2H), 1.24 (s, 1H), 1.11 (d, J = 10.1 Hz, 6H). | FP PA39 3-bromo-7-fluoro-imidazo[1,2-a]pyridine |
| I-369 | 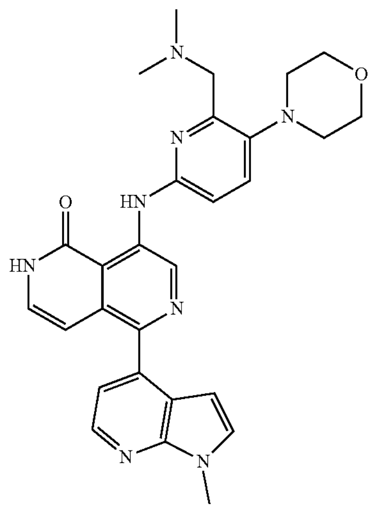 [SMILES: CN(C)Cc1nc(Nc2cnc(-c3ccnc4c3ccn4C)c3cc[nH]c(=O)c23)ccc1N1CCOCC1] | 8-((6-((dimethyl-amino)methyl)-5-morpholino pyridin-2-yl)amino)-5-(1-methyl-1H-pyrrolo[2,3-b]pyridin-4-yl)-2,6-naphthyridin-1(2H)-one | LCMS Method J m/z = 510.9 [M + H]+, Ret. time = 2.38 min | 1H NMR (400 MHz, DMSO-d6) δ 9.40 (s, 1H), 8.24 (d, J = 4.9 Hz, 1H), 7.91-7.74 (m, 2H), 7.45 (dd, J = 8.2, 4.9 Hz, 2H), 6.97 (dd, J = 16.2, 6.1 Hz, 2H), 4.51 (s, 1H), 3.86 (s, 2H), 3.81-3.74 (m, 2H), 2.95 (s, 2H), 2.85 (t, J = 4.5 Hz, 2H). | JP PA41 1-methyl-4-(4,4,5,5-tetramethyl-1,3,2-dioxaborolan-2-yl)-1H-pyrrolo[2,3-b]pyridine |
| I-370 | 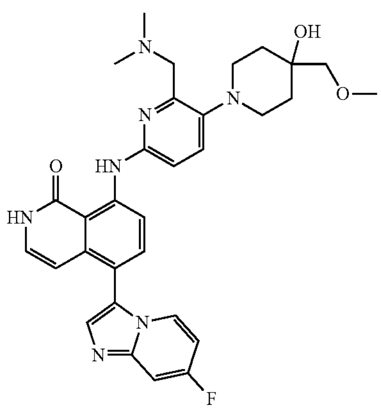 [SMILES: COCC1(O)CCN(c2ccc(Nc3ccc(-c4cnc5cc(F)ccn45)c4cc[nH]c(=O)c34)nc2CN(C)C)CC1] | 8-((6-((dimethyl-amino)methyl)-5-(4-hydroxy-4-(methoxy-methyl)piperidin-1-yl)pyridin-2-yl)amino)-5-(7-fluoro-imidazo[1,2-a]pyridin-3-yl)isoquinolin-1(2H)-one | LCMS Method J m/z = 572.2 [M + H]+, Ret. time = 2.55 min | 1H NMR (400 MHz, DMSO-d6) δ 12.72 (s, 1H), 11.57 (d, J = 5.6 Hz, 1H), 8.86 (d, J = 8.8 Hz, 1H), 7.92 (t, J = 6.8 Hz, 1H), 7.66-7.53 (m, 3H), 7.35 (t, J = 6.4 Hz, 1H), 6.96-6.90 (m, 2H), 5.86 (d, J = 7.2 Hz, 1H), 4.36 (s, 1H), 3.56 (s, 2H), 3.3 (s, 3H), 3.21 (s, 2H), 2.97 (d, J = 6.0 Hz, 2H), 2.33 (s, 6H), 3.81-3.74 (m, 2H), 1.80-1.76 (m, 2H), 1.54-1.51 (m, 2H) | FP PA42 3-bromo-7-fluoro-imidazo[1,2-a]pyridine |

HPLC Conditions

Chiral Analytical Method A1

| | |
|---|---|
| Instrumentation | Agilent 1260 Series HPLC and PDA detector |
| Column | Chiralpak IH (250*4.6 mm), 5 micron maintained at temp |
| Mobile Phase A | 0.1% DEA in n-Hexane |
| Mobile Phase B | 0.1% DEA in Propan-2-ol:Acetonitrile (70:30) |
| Flow | 1.0 ml/min |

Chiral Analytical Method A1

| | Time (mins) | % A | % B |
|---|---|---|---|
| Gradient Program | 0.01 | 65 | 35 |
| | 25 | 65 | 35 |

| | |
|---|---|
| UV | 308 nm |

Chiral Analytical Method A2

| | |
|---|---|
| Instrumentation | Agilent 1260 Series HPLC and PDA detector |
| Column | Chiralpak IC (250*4.6 mm), 5 micron maintained at temp |
| Mobile Phase A | 0.1% DEA in n-Hexane |
| Mobile Phase B | 0.1% DEA in Propan-2-ol:Acetonitrile (50:50) |
| Flow | 1.0 ml/min |

| | Time (mins) | % A | % B |
|---|---|---|---|
| Gradient Program | 0.01 | 80 | 20 |
| | 5 | 45 | 55 |
| | 10 | 30 | 70 |
| | 20 | 30 | 70 |

| | |
|---|---|
| UV | 276 nm |

Chiral Analytical Method A3

| | |
|---|---|
| Instrumentation | Waters SFC Investigator and PDA detector |
| Column | Chiralcel OJ-H (250*4.6 mm), 5 micron |
| Mobile Phase A | Liquid Carbon dioxide |
| Mobile Phase B | 0.1% DEA in Methanol |
| Flow | 4.0 ml/min |

| | Time (mins) | % A | % B |
|---|---|---|---|
| Gradient Program | 0.01 | 95 | 5 |
| | 6 | 50 | 50 |
| | 12 | 50 | 50 |

| | |
|---|---|
| UV | 290 nm |

LCMS Conditions

Method: AcHSSC18

| | |
|---|---|
| Instrumentation | UPLC + Waters DAD + Waters SQD2, single quadrapole UPLC-MS |
| Column | Acquity UPLC HSS C18 1.8 um 100 × 2.1 mm. (Plus guard cartridge), maintained at temp |
| Mobile Phase A | Water (High purity via PureLab Option unit) with 0.1% formic acid |
| Mobile Phase B | Acetonitrile (Far UV grade) with 0.1% (V/V) formic acid |
| Flow | 0.4 ml/min |

| | Time (mins) | % A | % B |
|---|---|---|---|
| Gradient Program | 0.0 | 95 | 05 |
| | 0.4 | 95 | 05 |
| | 6.0 | 05 | 95 |
| | 6.8 | 05 | 95 |
| | 7.0 | 95 | 05 |
| | 8.0 | 95 | 05 |

| | |
|---|---|
| Sample | 0.5-2 ul (concentration ~ 0.2-1 mg/ml). |
| Detectors | UV, diode array 210 nm-400 nm Resolution 1.2 nm Other wavelength traces are extracted from the DAD data MS, mass 100-700 (or –1500 for HM method) in ES+ & ES– 300 μl/min split to MS) |

Method: 10 cm_Formic_AQ

| | |
|---|---|
| Instrumentation | UPLC + Waters DAD + Waters SQD2, single quadrapole UPLC-MS |
| Column | Acquity UPLC HSS C18 1.8 um 100 × 2.1 mm. (Plus guard cartridge), maintained at temp |
| Mobile Phase A | Water (High purity via PureLab Option unit) with 0.1% formic acid |
| Mobile Phase B | Acetonitrile (Far UV grade) with 0.1% (V/V) formic acid |
| Flow | 0.5 ml/min |

| | Time (mins) | % A | % B |
|---|---|---|---|
| Gradient Program | 0.0 | 95 | 05 |
| | 1.2 | 95 | 05 |
| | 3.5 | 0 | 100 |
| | 4.9 | 0 | 100 |
| | 5 | 95 | 05 |
| | 6 | 95 | 05 |

| | |
|---|---|
| Sample | 0.5-2 ul (concentration ~ 0.2-1 mg/ml). |
| Detectors | UV, diode array 210 nm-400 nm Resolution 1.2 nm Other wavelength traces are extracted from the DAD data MS, mass 100-700 (or –1500 for HM method) in ES+ & ES– 300 μl/min split to MS) |

Method: 10 cm_Formic_ACE-AR_AQ

| | |
|---|---|
| Instrumentation | UPLC + Waters DAD + Waters SQD2, single quadrapole UPLC-MS |
| Column | ACE-AR ACE excel 2 um C18-AR, maintained at temp |
| Mobile Phase A | Water (High purity via PureLab Option unit) with 0.1% formic acid |
| Mobile Phase B | Acetonitrile (Far UV grade) with 0.1% (V/V) formic acid |
| Flow | 0.5 ml/min |

| | Time (mins) | % A | % B |
|---|---|---|---|
| Gradient Program | 0.0 | 95 | 05 |
| | 1.2 | 95 | 05 |
| | 3.5 | 0 | 100 |
| | 4.9 | 0 | 100 |
| | 5 | 95 | 05 |
| | 6 | 95 | 05 |

| | |
|---|---|
| Sample | 0.5-2 ul (concentration ~ 0.2-1 mg/ml). |
| Detectors | UV, diode array 210 nm-400 nm Resolution 1.2 nm Other wavelength traces are extracted from the DAD data MS, mass 100-700 (or –1500 for HM method) in ES+ & ES– 300 μl/min split to MS) |

Method: BicarbBEHC18

| | |
|---|---|
| Instrumentation | UPLC + Waters DAD + Waters SQD2, single quadrapole UPLC-MS |
| Column | Acquity UPLC BEH Shield RP18 1.7 um 100 × 2.1 mm. (Plus guard cartridge), maintained at temp |

Method: BicarbBEHC18

| | | | |
|---|---|---|---|
| Mobile Phase A | Water (High purity via PureLab Option unit) with 10 mM ammonium bicarbonate (ammonium hydrogen carbonate) | | |
| Mobile Phase B | Acetonitrile (Far UV grade) | | |
| Flow | 0.4 ml/min | | |

| | Time (mins) | % A | % B |
|---|---|---|---|
| Gradient Program | 0.0 | 95 | 05 |
| | 0.4 | 95 | 05 |
| | 6.0 | 05 | 95 |
| | 6.8 | 05 | 95 |
| | 7.0 | 95 | 05 |
| | 8.0 | 95 | 05 |

| | |
|---|---|
| Sample | 0.5-2 ul (concentration ~ 0.2-1 mg/ml). |
| Detectors | UV, diode array 210 nm-400 nm Resolution 1.2 nm<br>Other wavelength traces are extracted from the DAD data<br>MS, mass 100-700 (or −1500 for HM method)<br>in ES+ & ES− 300 μl/min split to MS) |

Method: 10 cm_Bicarb_AQ

| | |
|---|---|
| Instrumentation | UPLC + Waters DAD + Waters SQD2, single quadrapole UPLC-MS |
| Column | Acquity UPLC BEH Shield RP18 1.7 um 100 × 2.1 mm. (Plus guard cartridge), maintained at temp |
| Mobile Phase A | Water (High purity via PureLab Option unit) with 10 mM ammonium bicarbonate (ammonium hydrogen carbonate) |
| Mobile Phase B | Acetonitrile (Far UV grade) |
| Flow | 0.5 ml/min |

| | Time (mins) | % A | % B |
|---|---|---|---|
| Gradient Program | 0.0 | 95 | 05 |
| | 1.2 | 95 | 05 |
| | 3.5 | 0 | 100 |
| | 4.9 | 0 | 100 |
| | 5 | 95 | 05 |
| | 6 | 95 | 05 |

| | |
|---|---|
| Sample | 0.5-2 ul (concentration ~ 0.2-1 mg/ml). |
| Detectors | UV, diode array 210 nm-400 nm Resolution 1.2 nm<br>Other wavelength traces are extracted from the DAD data<br>MS, mass 100-700 (or −1500 for HM method)<br>in ES+ & ES− 300 μl/min split to MS) |

Method: CP

| | |
|---|---|
| Instrumentation | WATERS ACQUETY H Class with PDA and SQ DETECTOR |
| Column | BEH C18(50*2.1 mm)1.7 μm maintained at temp |
| Mobile Phase A | 2 mM ammonium acetate |
| Mobile Phase B | 0.1% formic acid in acetonitrile |
| Flow | 0.55 ml/min |

| | Time (mins) | % A | % B |
|---|---|---|---|
| Gradient Program | 0.0 | 98 | 02 |
| | 0.3 | 98 | 2 |
| | 0.6 | 50 | 50 |
| | 1.10 | 25 | 75 |
| | 2 | 0 | 100 |
| | 2.7 | 0 | 100 |

Method: CP

| | |
|---|---|
| Sample | 0.5-2 ul (concentration ~ 0.2-1 mg/ml). |
| Detectors | UV, diode array 210 nm-400 nm Resolution 1.2 nm<br>Other wavelength traces are extracted from the DAD data<br>MS, mass 100-700 (or −1500 for HM method)<br>in ES+ & ES− 300 μl/min split to MS) |

Method GP

| | |
|---|---|
| Instrumentation | Agilent 1290 Infinity RRLC attached with Agilent 6120 Mass detector and Diode array Detector |
| Column | YMC Triart C18 (150*4.6 mm),5 μm maintained at RT |
| Mobile Phase A | 10 mM ammonium acetate |
| Mobile Phase B | 100% acetonitrile |
| Flow | 1.0 ml/min |

| | Time (mins) | % A | % B |
|---|---|---|---|
| Gradient Program | 0.01 | 100 | 0 |
| | 7.0 | 50 | 50 |
| | 9.0 | 0 | 100 |
| | 11 | 0 | 100 |

| | |
|---|---|
| Sample | 0.5-2 ul (concentration ~ 0.2-1 mg/ml). |
| Detectors | UV, diode array 210 nm-400 nm Resolution 1.2 nm<br>Other wavelength traces are extracted from the DAD data<br>MS, mass 100-700 (or −1500 for HM method)<br>in ES+ & ES− 300 μl/min split to MS) |

Method FP

| | |
|---|---|
| Instrumentation | Agilent 1290 Infinity RRLC attached with Agilent 6120 Mass detector and Diode array Detector |
| Column | YMC Triart C18 (150*4.6 mm),5 μm maintained at RT |
| Mobile Phase A | 10 mM ammonium acetate |
| Mobile Phase B | 100% acetonitrile |
| Flow | 1.0 ml/min |

| | Time (mins) | % A | % B |
|---|---|---|---|
| Gradient Program | 0.01 | 90 | 10 |
| | 5.0 | 10 | 90 |
| | 7.0 | 0 | 100 |
| | 11 | 0 | 100 |

| | |
|---|---|
| Sample | 0.5-2 ul (concentration ~ 0.2-1 mg/ml). |
| Detectors | UV, diode array 210 nm-400 nm Resolution 1.2 nm<br>Other wavelength traces are extracted from the DAD data<br>MS, mass 100-700 (or −1500 for HM method)<br>in ES+ & ES− 300 μl/min split to MS) |

Method HP

| | |
|---|---|
| Instrumentation | Shimadzu Nexera High Pressure UHPLC and LCMS-2020 |
| Column | X-Bridge C18 (50*4.6 mm), 3.5 um maintained at temp |
| Mobile Phase A | 5 mM Ammonium bicarbonate |
| Mobile Phase B | 100% acetonitrile |
| Flow | 1.0 ml/min |

-continued

Method HP

| | Time (mins) | % A | % B |
|---|---|---|---|
| Gradient Program | 0.01 | 95 | 05 |
| | 5.0 | 10 | 90 |
| | 5.8 | 5 | 95 |
| | 7.2 | 5 | 95 |
| | 7.21 | 95 | 5 |
| | 10 | 95 | 5 |

| | |
|---|---|
| Sample | 0.5-2 ul (concentration ~ 0.2-1 mg/ml). |
| Detectors | UV, diode array 210 nm-400 nm Resolution 1.2 nm |
| | Other wavelength traces are extracted from the DAD data |
| | MS, mass 100-700 (or ~1500 for HM method) |
| | in ES+ & ES– 300 µl/min split to MS) |

Method JP

| | |
|---|---|
| Instrumentation | WATERS ACQUETY H Class with PDA and SQ DETECTOR |
| Column | BEH C18(50*2.1 mm)1.7 µm maintained at RT |
| Mobile Phase A | 2 mM ammonium acetate |
| Mobile Phase B | 0.1% formic acid in acetonitrile |
| Flow | 0.45 ml/min |

| | Time (mins) | % A | % B |
|---|---|---|---|
| Gradient Program | 0.01 | 98 | 2 |
| | 0.5 | 98 | 2 |
| | 5.0 | 10 | 90 |
| | 6.0 | 5 | 95 |
| | 7.0 | 5 | 95 |

| | |
|---|---|
| Sample | 0.5-2 ul (concentration ~ 0.2-1 mg/ml). |
| Detectors | UV, diode array 210 nm-400 nm Resolution 1.2 nm |
| | Other wavelength traces are extracted from the DAD data |
| | MS, mass 100-700 (or ~1500 for HM method) |
| | in ES+ & ES– 300 µl/min split to MS) |

Preparative HPLC Conditions

Post-synthesis all compounds were purified using reverse phase HPLC using a Waters Fractionlynx preparative HPLC system (2525 pump, 2996/2998 UV/VIS detector, 2767 liquid handler) or Gilson preparative HPLC system (322 pump, 155 UV/VIS detector, GX-281 liquid handler).

The column used for the preparative purification of the compounds was a Waters Sunfire OBD, Phenomenex Luna Phenyl Hexyl or Waters Xbridge Phenyl at 10 um 19×150 mm.

Appropriate focused gradients were selected based on acetonitrile and methanol solvent systems under either acidic or basic conditions. The standard gradient used was 5% ACN to 20% over 1 min, hold 2.5 min, to 80% ACN over 12.5 min, hold 7.5 min. Followed by 3 min re-equilibration at initial conditions. A flow rate of 20 ml/min is used.

All compounds were screened analytically prior to the purification step. Each sample was run under both acidic and basic conditions (2 ul injection, 5/95 gradient for 2.25 minutes). A decision was then made by the analyst as to what pH and which gradient to use depending on where the desired product elutes and the separation achieved.

The modifiers used under acidic/basic conditions were formic acid (0.1% V/V) and ammonium bicarbonate (10 mM) respectively or TFA (0.1% V/V) if Method Development was required.

The purification was controlled by Waters FractionLynx software through monitoring at 210-400 nm and triggered a threshold collection value at 260 nm and the presence of target molecular ion as observed under ESI conditions. Collected fractions were analysed by LCMS (Waters Acquity systems with Waters SQD). The fractions that contained the desired product were dried overnight by Genevac lypholisation, and further dried using BioPharma shelf freeze dryers. Some of the compounds may have gone through a second purification process in order to achieve the required purity due to complex mixtures. More focused gradient or isocratic conditions may have been used for the more challenging separations (e.g Method development).

Preparative SFC Conditions

Where indicated, post-synthesis compounds were purified using Supercritical Fluid Chromatography (SFC) using either Waters Thar Prep100 preparative SFC system (P200 CO2 pump, 2545 modifier pump, 2998 UV/VIS detector, 2767 liquid handler with Stacked Injection Module) or Waters Thar Investigator semi preparative system (Waters Fluid Delivery Module, 2998 UV/VIS detector, Waters Fraction Collection Module). Where the Waters 2767 liquid handler was used it acted as both auto-sampler and fraction collector.

The compounds were purified using an appropriate column (YMC Amylose-C, YMC Cellulose-C, YMC Cellulose-SC, Phenomenex LUX Cellulose-3 or Phenomenex LUX Cellulose-4) unless otherwise stated.

Appropriate isocratic methods were selected based on methanol, ethanol or isopropanol solvent systems under un-modified or basic conditions. The standard method used was modifier/CO2, 100 ml/min (or as appropriate), 120 Bar backpressure, 40° C. column temperature were the specific modifier composition was as stated by the method development.

All compounds were screened analytically prior to the purification step. Each sample was run under both un-modified and basic conditions (2.0 ul injection, 5/55 gradient for 2.25 minutes) across ethanol, methanol and isopropanol. If necessary, secondary screen across extended solvents such as acetonitrile, ethyl acetate and THF may also be reviewed. A decision was then made by the analyst as to what pH and which isocratic condition to use depending on where the desired product elutes and the separation achieved.

The modifier used under basic conditions was diethyl amine (0.1% V/V). Alternate modifiers such as formic acid (0.1% V/V), acetic acid (0.1% V/V), etc may be used as an acidic modifier.

The purification was controlled either by Waters FractionLynx or Waters ChromScope software through monitoring at 210-400 nm and triggered a threshold collection value at an appropriate wavelength. Collected fractions were analysed by SFC (Waters/Thar SFC systems with Waters SQD or Waters UPCC with Waters QDa). The fractions that contained the desired product were concentrated by vacuum centrifugation and further dried using Biopharma shelf freeze dryers.

All samples have been pre-purified by achiral systems and purity checked before SFC chiral purification.

Some of the compounds may have gone through a second purification process in order to achieve the required % ee or % de purity.

Example 33. HPK1 Biochemical Enzyme Assay

HPK1 biochemical enzyme assay: HPK1 enzyme inhibition was measured using a microfluidic mobility shift assay. Reactions were performed in a 384-well plate, containing 1.5 nM HPK1 (Invitrogen), in assay buffer (Carna Biosciences; pH 7.4). Test compounds were titrated in ten point curves (top final assay concentration 3 µM), and preincubated with enzyme/substrate mix for 30 min prior to initiation of the reaction by addition of ATP (1 mM final concentration) and substrate (1 µM final concentration; Carna Biosciences) diluted in assay buffer supplemented by MgCl$_2$ (final assay concentration of 5 mM). Following 60 min incubation at RT, the reaction was terminated by addition of 60 µl/well termination buffer (Carna Biosciences) and signal determination using a Caliper EZ Reader (Perkin Elmer, UK).

Table 3 shows the activity of selected compounds of this invention in the HPK1 biochemical enzyme assay. The compound numbers correspond to the compound numbers in Table 1. Compounds having an activity designated as "A" provided an IC$_{50}$≤100 nM; compounds having an activity designated as "B" provided an IC$_{50}$>100 nM and ≤1,000 nM; compounds having an activity designated as "C" provided an IC$_{50}$>1,000 nM. Table 3.

TABLE 3

| Compound | HPK1 1000UMATP caliper IC50 (nM) A < 100 nM B 100-1000 nM C > 1000 nM | Compound | HPK1 1000UMATP caliper IC50 (nM) A < 100 nM B 100-1000 nM C > 1000 nM |
|---|---|---|---|
| I-4 | A | I-5 | B |
| I-6 | A | I-7 | B |
| I-8 | B | I-9 | B |
| I-10 | B | I-11 | B |
| I-12 | B | I-13 | B |
| I-14 | A | I-15 | B |
| I-16 | B | I-17 | B |
| I-18 | C | I-19 | B |
| I-20 | B | I-21 | B |
| I-22 | A | I-23 | B |
| I-24 | B | I-25 | B |
| I-26 | C | I-28 | B |
| I-29 | B | I-30 | B |
| I-31 | B | I-32 | B |
| I-33 | B | I-34 | B |
| I-35 | B | I-36 | A |
| I-37 | B | I-38 | A |
| I-39 | C | I-40 | B |
| I-41 | C | I-42 | B |
| I-43 | A | I-44 | A |
| I-45 | A | I-46 | B |
| I-47 | A | I-48 | B |
| I-49 | B | I-50 | B |
| I-51 | B | I-52 | B |
| I-53 | A | I-54 | B |
| I-55 | B | I-56 | C |
| I-57 | A | I-58 | A |
| I-59 | B | I-60 | B |
| I-61 | B | I-62 | B |
| I-63 | B | I-64 | B |
| I-65 | B | I-66 | B |
| I-67 | B | I-68 | B |
| I-69 | B | I-70 | B |
| I-71 | B | I-72 | B |
| I-73 | B | I-74 | A |
| I-75 | A | I-76 | B |
| I-77 | B | I-78 | C |
| I-79 | B | I-80 | B |
| I-81 | A | I-82 | B |
| I-83 | B | I-84 | B |
| I-85 | B | I-86 | B |
| I-87 | B | I-88 | A |
| I-89 | C | I-90 | B |
| I-91 | A | I-92 | B |
| I-93 | A | I-94 | A |
| I-95 | B | I-96 | B |
| I-97 | B | I-98 | A |
| I-99 | B | I-100 | A |
| I-101 | A | I-102 | A |
| I-103 | A | I-104 | C |
| I-105 | C | I-106 | A |
| I-107 | B | I-108 | A |
| I-109 | A | I-110 | A |
| I-111 | C | I-112 | C |
| I-113 | B | I-114 | A |
| I-115 | A | I-116 | B |
| I-117 | B | I-118 | B |
| I-119 | B | I-120 | B |
| I-121 | A | I-122 | B |
| I-123 | A | I-124 | B |
| I-125 | A | I-126 | B |
| I-127 | B | I-128 | B |
| I-129 | B | I-130 | A |
| I-131 | B | I-132 | B |
| I-133 | A | I-134 | A |
| I-135 | A | I-136 | A |
| I-137 | A | I-138 | B |
| I-139 | A | I-140 | A |
| I-141 | C | I-142 | A |
| I-143 | C | I-144 | C |
| I-145 | C | I-146 | B |
| I-147 | B | I-148 | C |
| I-149 | B | I-150 | B |
| I-151 | A | I-152 | B |
| I-153 | B | I-154 | B |
| I-155 | C | I-156 | B |
| I-157 | C | I-158 | A |
| I-159 | A | I-160 | A |
| I-161 | A | I-162 | A |
| I-163 | C | I-164 | A |
| I-165 | B | I-166 | A |
| I-167 | A | I-168 | A |
| I-169 | B | I-170 | B |
| I-171 | B | I-172 | C |
| I-173 | B | I-174 | C |
| I-175 | B | I-176 | A |
| I-177 | A | I-178 | B |
| I-179 | B | I-180 | A |
| I-181 | C | I-182 | C |
| I-183 | A | I-184 | C |
| I-185 | B | I-186 | A |
| I-187 | B | I-188 | A |
| I-189 | B | I-190 | B |
| I-191 | A | I-192 | B |
| I-193 | B | I-194 | A |
| I-195 | C | I-196 | B |
| I-197 | B | I-198 | B |
| I-199 | B | I-200 | A |
| I-201 | A | I-202 | A |
| I-203 | A | I-204 | A |
| I-205 | A | I-206 | A |
| I-207 | A | I-208 | B |
| I-209 | B | I-210 | A |
| I-211 | C | I-212 | B |
| I-213 | B | I-214 | B |
| I-215 | B | I-216 | C |
| I-217 | B | I-218 | A |
| I-219 | A | I-220 | A |
| I-221 | B | I-222 | A |
| I-223 | A | I-224 | B |
| I-225 | C | I-226 | A |
| I-227 | A | I-228 | A |
| I-229 | B | I-230 | A |
| I-231 | B | I-232 | A |
| I-233 | A | I-234 | A |
| I-235 | A | I-236 | B |
| I-237 | B | I-238 | B |
| I-239 | B | I-240 | A |
| I-241 | B | I-242 | B |
| I-243 | B | I-244 | A |
| I-245 | A | I-247 | A |
| I-248 | A | I-249 | A |
| I-250 | A | I-251 | A |

TABLE 3-continued

| Compound | HPK1 1000UMATP caliper IC50 (nM) A < 100 nM B 100-1000 nM C > 1000 nM | Compound | HPK1 1000UMATP caliper IC50 (nM) A < 100 nM B 100-1000 nM C > 1000 nM |
|---|---|---|---|
| I-255 | C | I-256 | C |
| I-257 | C | I-258 | B |
| I-259 | A | I-260 | B |
| I-261 | A | I-262 | C |
| I-263 | A | I-264 | A |
| I-265 | A | I-266 | A |
| I-267 | A | I-268 | C |
| I-269 | B | I-270 | A |
| I-271 | A | I-273 | A |
| I-274 | A | I-275 | A |
| I-276 | C | I-277 | A |
| I-278 | B | I-279 | A |
| I-280 | C | I-281 | A |
| I-282 | C | I-283 | A |
| I-284 | C | | |

The invention claimed is:

1. A compound of formula I:

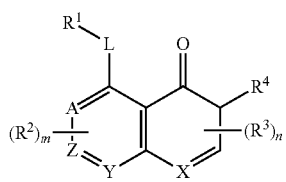

or a pharmaceutically acceptable salt thereof, wherein:
X is N or CR$^3$;
Y is N, CH or CR$^2$; Z is N, CH or CR$^2$; A is CH or CR$^2$;
L is —NR—;
R$^1$ is selected from phenyl and a 5-6 membered monocyclic heteroaryl ring having 1-4 heteroatoms independently selected from nitrogen, oxygen, and sulfur; each of which is substituted with q instances of R$^C$;
each R$^2$ is independently selected from phenyl; a 5-6 membered monocyclic heteroaryl ring having 1-4 heteroatoms independently selected from nitrogen, oxygen, and sulfur; a 5-8 membered saturated or partially unsaturated bridged bicyclic ring having 0-3 heteroatoms independently selected from nitrogen, oxygen, and sulfur; and a 6-11 membered saturated, partially unsaturated, or unsaturated fused, bridged, or spiro bicyclic ring having 0-3 heteroatoms independently selected from nitrogen, oxygen, and sulfur; each of which is substituted with r instances of R$^D$;
each R$^3$ is independently selected from H; C$_{1-6}$ aliphatic; and phenyl; each of which is substituted with s instances of R$^E$; or R$^3$ is halogen, —CN, or —C(O)OR;
R$^4$ is H;
each instance of R$^C$, R$^D$, R$^E$, and R$^F$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)NR$_2$, —N(R)S(O)$_2$NR$_2$, —N(R)S(O)$_2$R, —N=S(O)R$^2$, —S(NR)(O)R, —N(R)S(O)R, —N(R)CN, —P(O)(R)NR$_2$, —P(O)(R)OR, or —P(O)R$^2$; or each instance of R$^C$, R$^D$, R$^E$, and R$^F$ is independently an optionally substituted group selected from C$_{1-6}$ aliphatic; naphthyl; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, phosphorous, silicon, and sulfur; a 5-6 membered monocyclic heteroaryl ring having 1-4 heteroatoms independently selected from nitrogen, oxygen, and sulfur; an 8-10 membered bicyclic heteroaryl ring having 1-5 heteroatoms independently selected from nitrogen, oxygen, and sulfur; a 5-8 membered saturated or partially unsaturated bridged bicyclic ring having 0-3 heteroatoms independently selected from nitrogen, oxygen, and sulfur; a 6-10 membered saturated or partially unsaturated spirocyclic ring having 0-3 heteroatoms independently selected from nitrogen, oxygen, and sulfur; and a 6-11 membered saturated or partially unsaturated bicyclic heterocyclic ring having 1-2 heteroatoms independently selected from nitrogen, oxygen, and sulfur; each of which is substituted with u instances of R;

each R is independently hydrogen, —CN, halogen, or an optionally substituted group selected from C$_{1-6}$ aliphatic; phenyl; naphthyl; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, and sulfur; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 7-12 membered saturated or partially unsaturated bicyclic heterocyclic ring having 1-4 heteroatoms independently selected from nitrogen, oxygen, and sulfur; a 5-8 membered saturated or partially unsaturated bridged bicyclic ring having 0-3 heteroatoms independently selected from nitrogen, oxygen, and sulfur; a 6-10 membered saturated or partially unsaturated spirocyclic ring having 0-3 heteroatoms independently selected from nitrogen, oxygen, and sulfur; and a 6-11 membered saturated or partially unsaturated bicyclic heteroocyclic ring having 1-2 heteroatoms independently selected from nitrogen, oxygen, and sulfur; or:

two R groups on the same nitrogen are taken together with the nitrogen to form an optionally substituted 4-7 membered monocyclic saturated, partially unsaturated, or heteroaryl ring having, in addition to the nitrogen, 0-3 heteroatoms independently selected from nitrogen, oxygen, and sulfur; an 8-10 membered bicyclic heteroaryl ring having 1-4 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur;

m is 1, 2, or 3;

n is 0, 1, or 2;

each of q, r, s, and t is independently 0, 1, 2, 3, or 4; and u is 0, 1, 2, 3, or 4.

2. The compound of claim 1, wherein the compound is selected from any one of the following formulae:

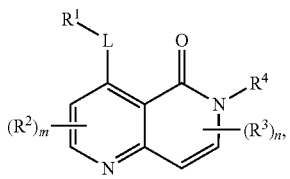

II

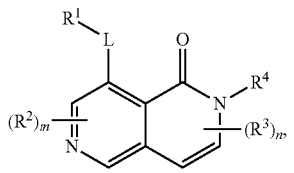

III

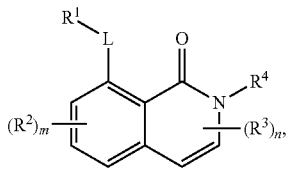

IV

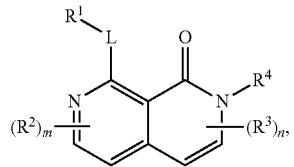

V

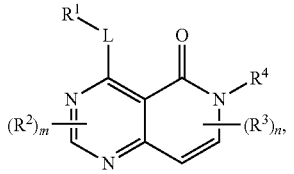

VI

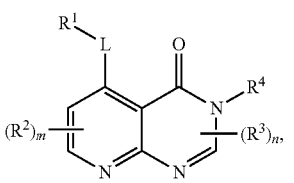

VII

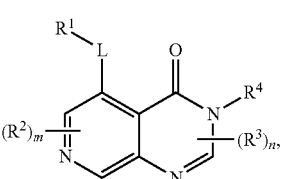

VIII

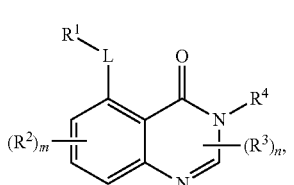

IX

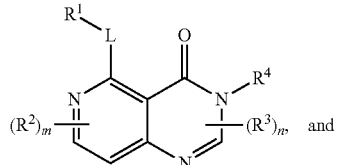

X

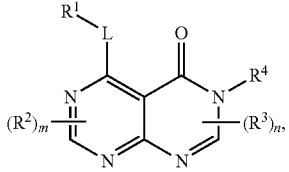

and

XI or a pharmaceutically acceptable salt thereof.

3. The compound of claim 1, wherein L is —NH—.

4. The compound of claim 1, wherein $R^1$ is a 5-6 membered monocyclic heteroaryl ring having 1-4 heteroatoms independently selected from nitrogen, oxygen, and sulfur, which is substituted with q instances of $R^C$.

5. The compound of claim 1, wherein $R^1$ is phenyl, imidazolyl, isothiazolyl, isoxazolyl, oxazolyl, pyrazolyl, pyridazinyl, pyridinyl, pyridyl, pyrimidinyl; each of which is substituted by q instances of $R^C$.

6. The compound of claim 1, wherein $R^1$ is

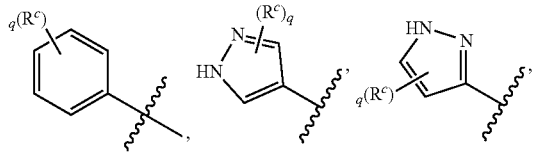

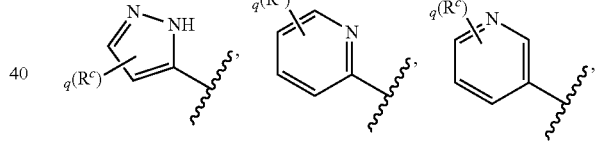

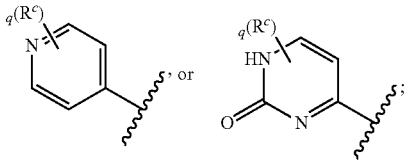

wherein each instance of $R^C$ is independently halogen, —CN, —OR, —S(O)$_2$R, —S(O)NR$_2$, —C(O)NR$_2$, an optionally substituted group selected from C$_{1-6}$ aliphatic; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, phosphorous, silicon, and sulfur; a 5-8 membered saturated or partially unsaturated bridged bicyclic ring having 0-3 heteroatoms independently selected from nitrogen, oxygen, and sulfur; a 6-10 membered saturated or partially unsaturated spirocyclic ring having 0-3 heteroatoms independently selected from nitrogen, oxygen, and sulfur; and a 6-11 membered saturated or partially unsaturated bicyclic heterocyclic ring having 1-2 heteroatoms independently selected from nitrogen, oxygen, and sulfur; each of which is substituted with r instances of R and s instances of $R^D$.

7. The compound of claim 1, wherein R¹ is
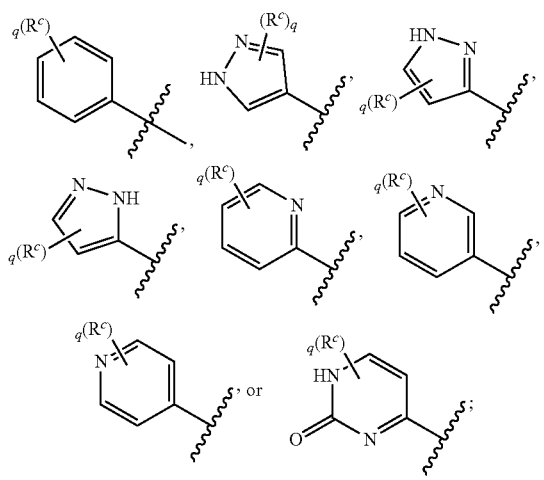
wherein each instance of $R^C$ is independently -Me, -Et, —CH$_2$N(CH$_3$)$_2$, —CN, —CH$_2$CN, —F, —OMe, —S(O)$_2$Me, —CH$_2$S(O)$_2$Me,
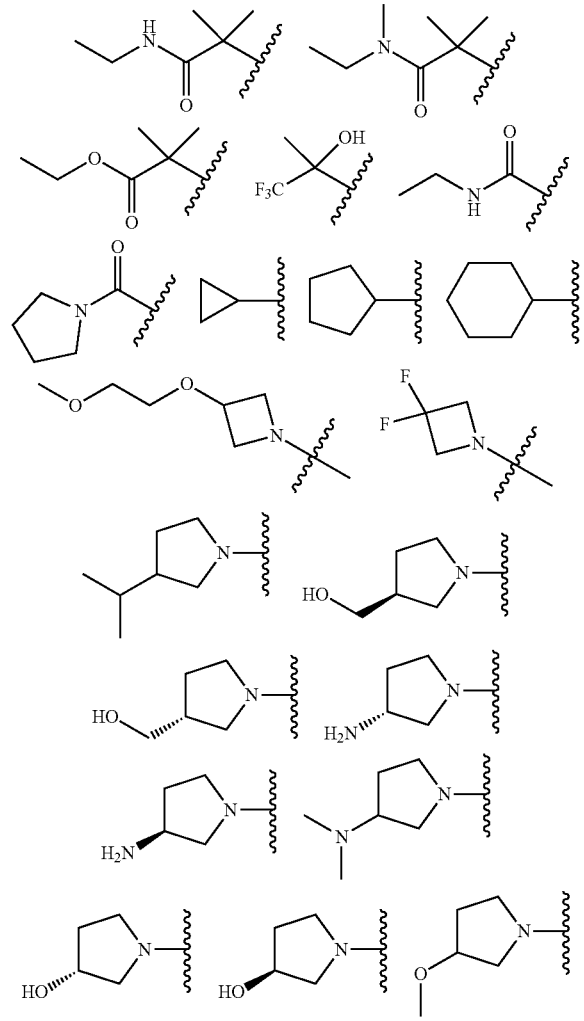
-continued
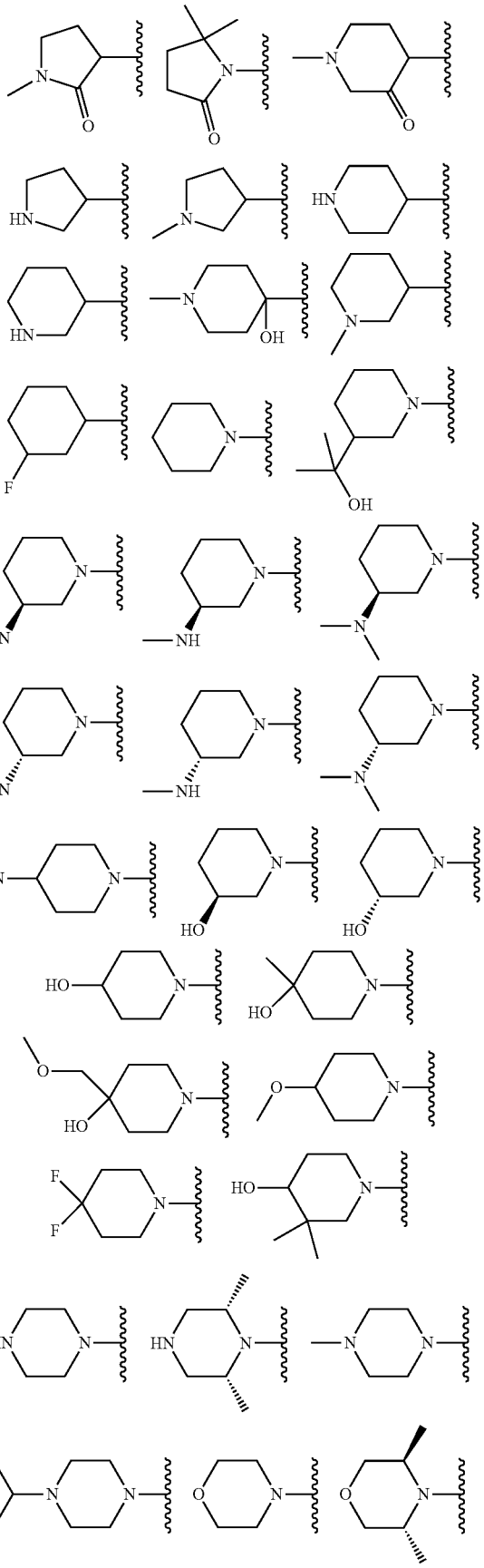

563
-continued
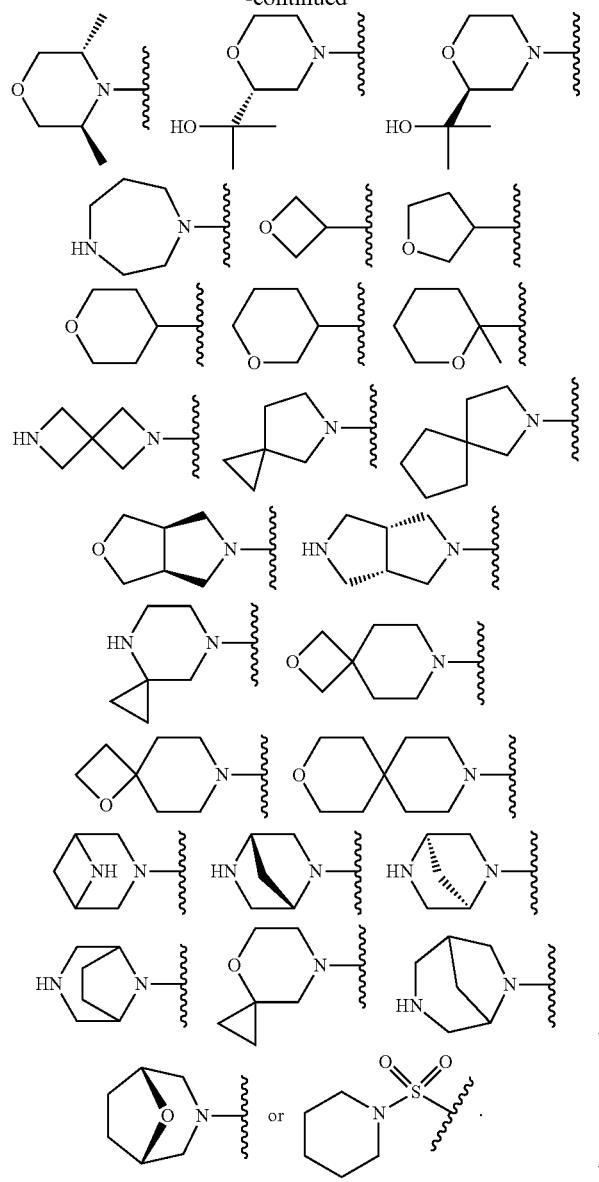
8. The compound of claim 1, wherein R¹ is
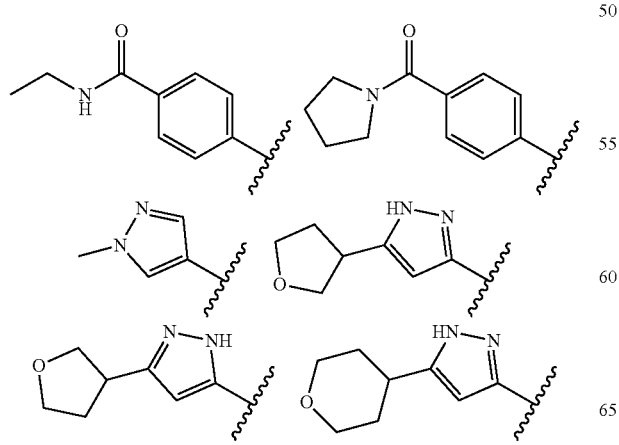
564
-continued
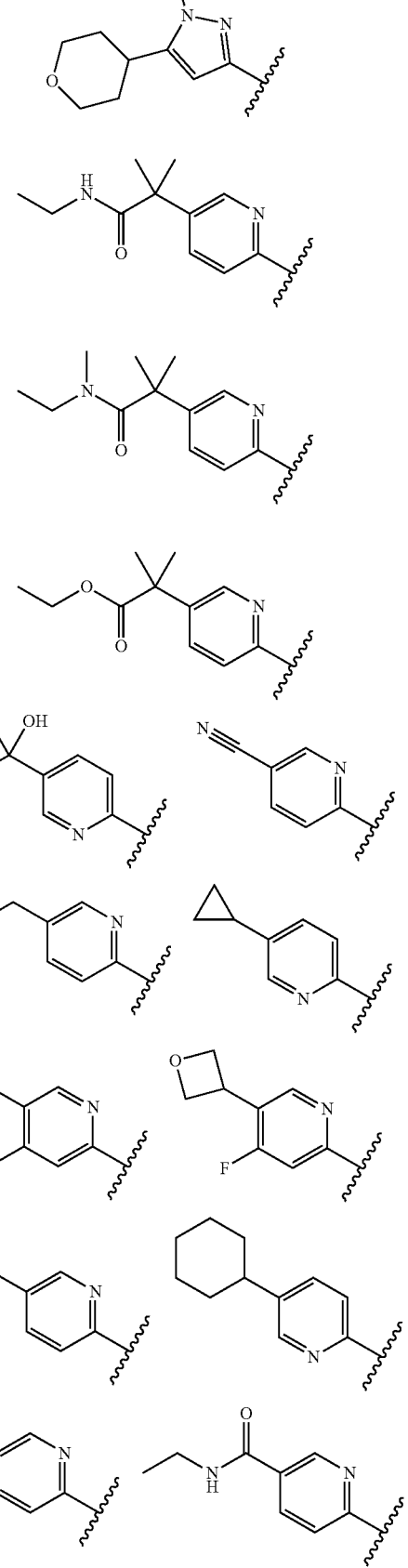

565
-continued
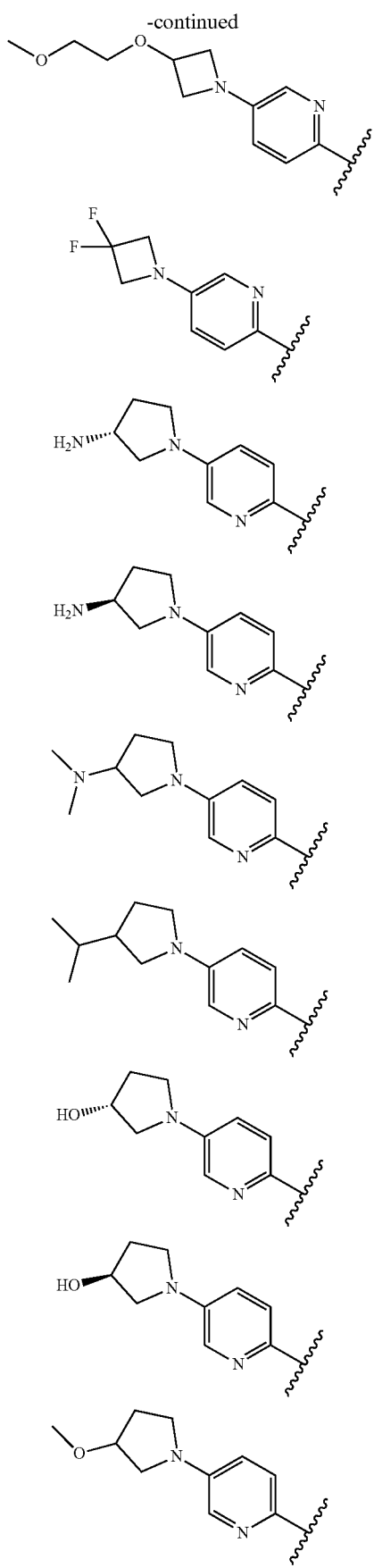
566
-continued
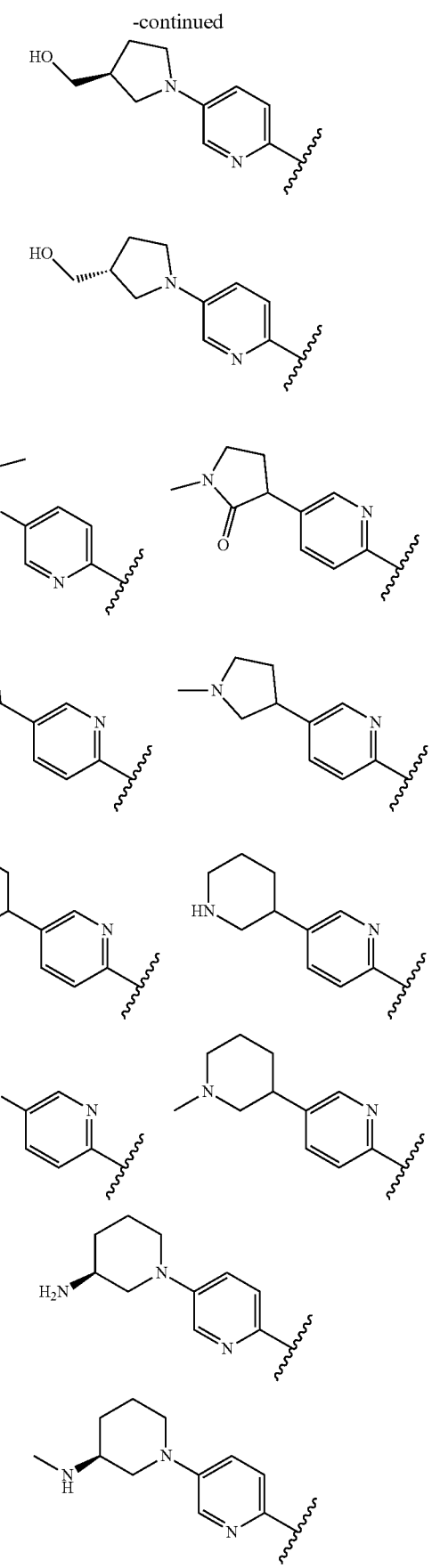

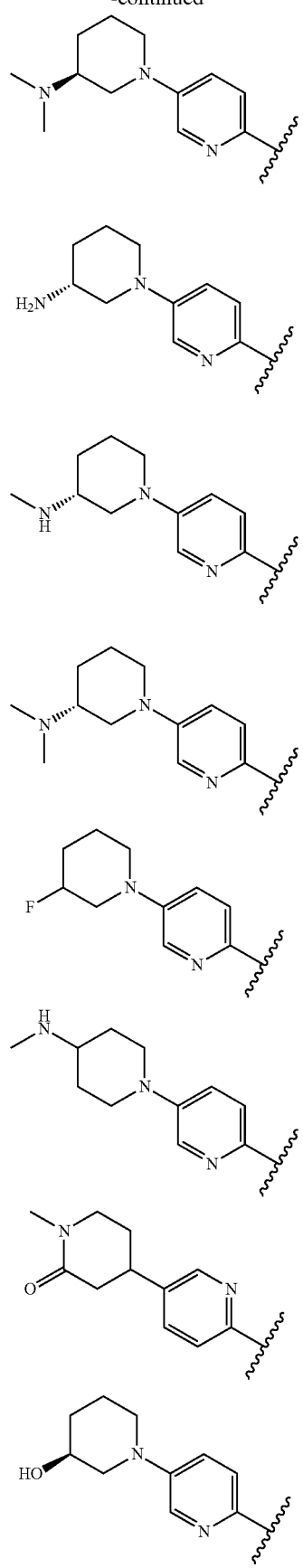
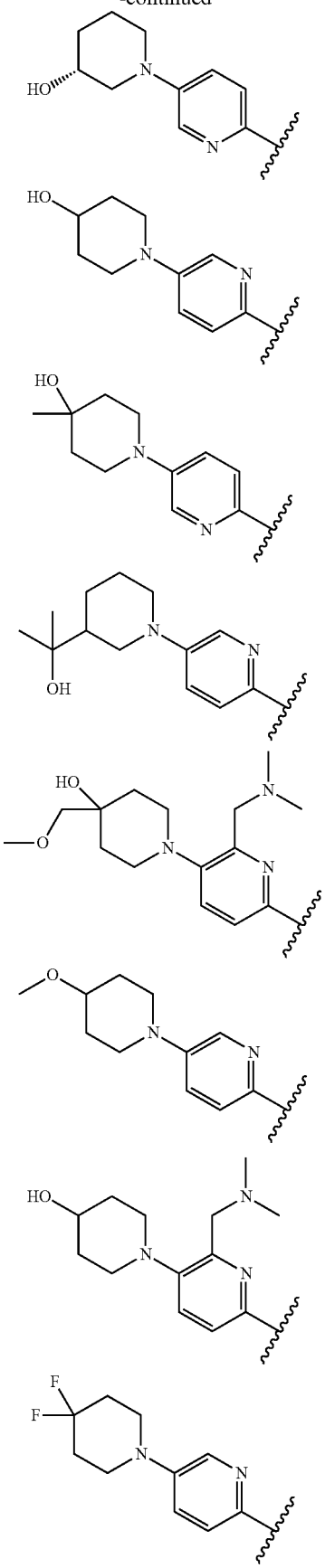

-continued
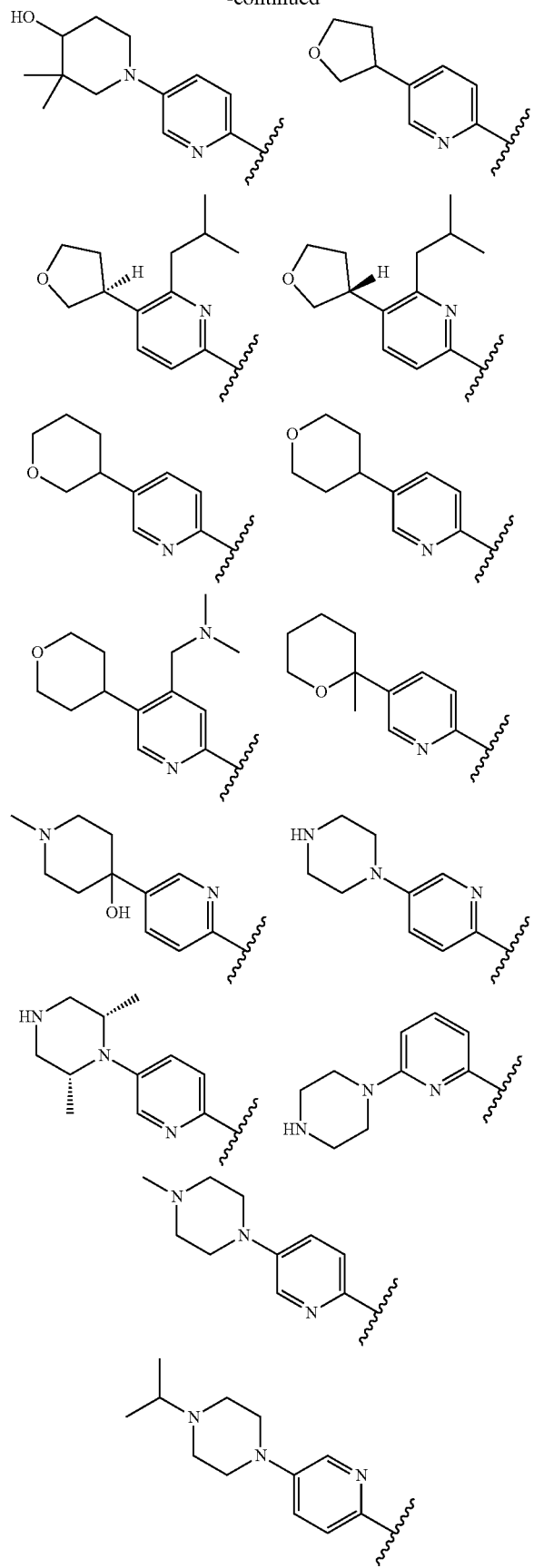
-continued
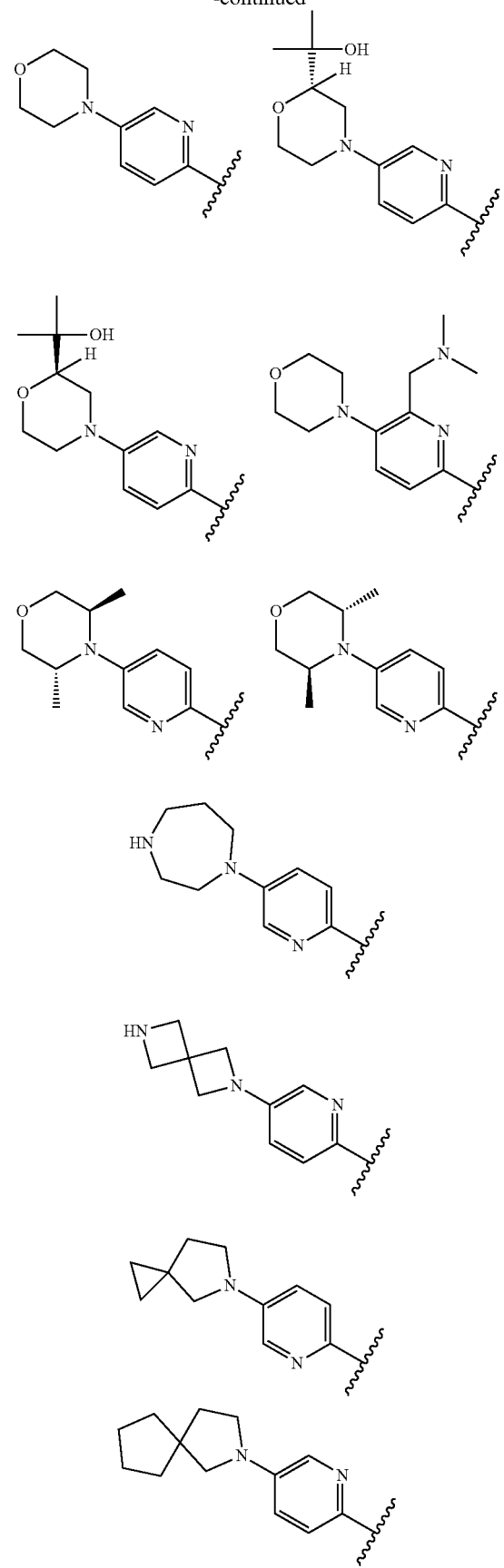

571
-continued

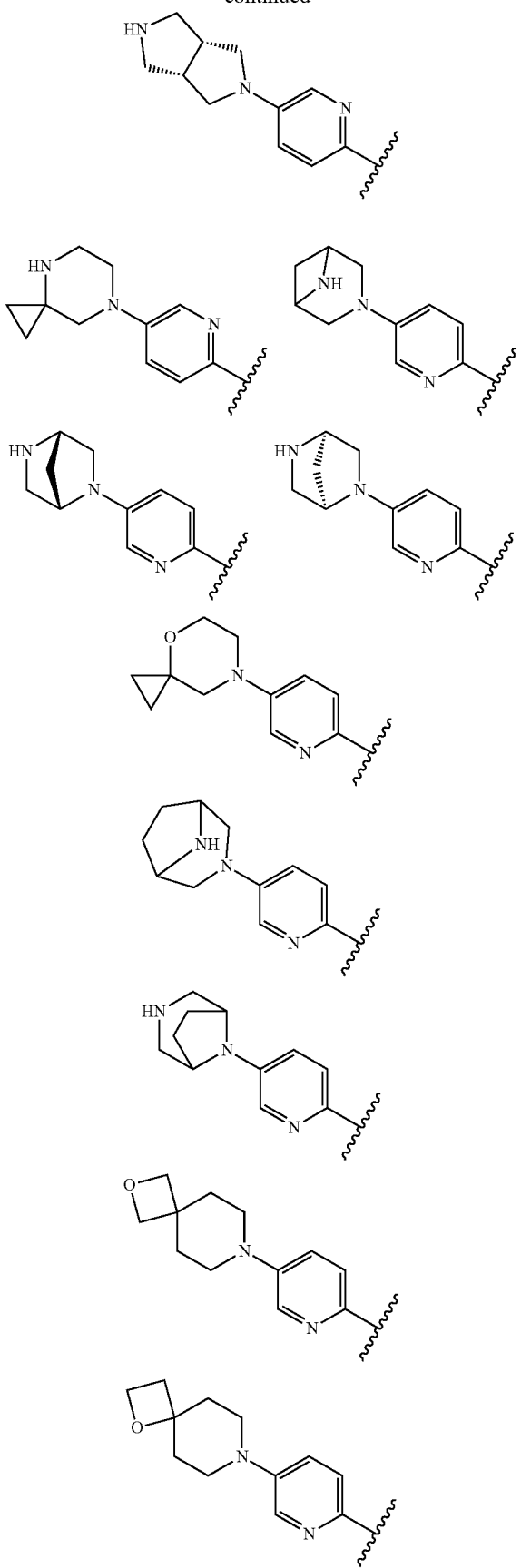

572
-continued

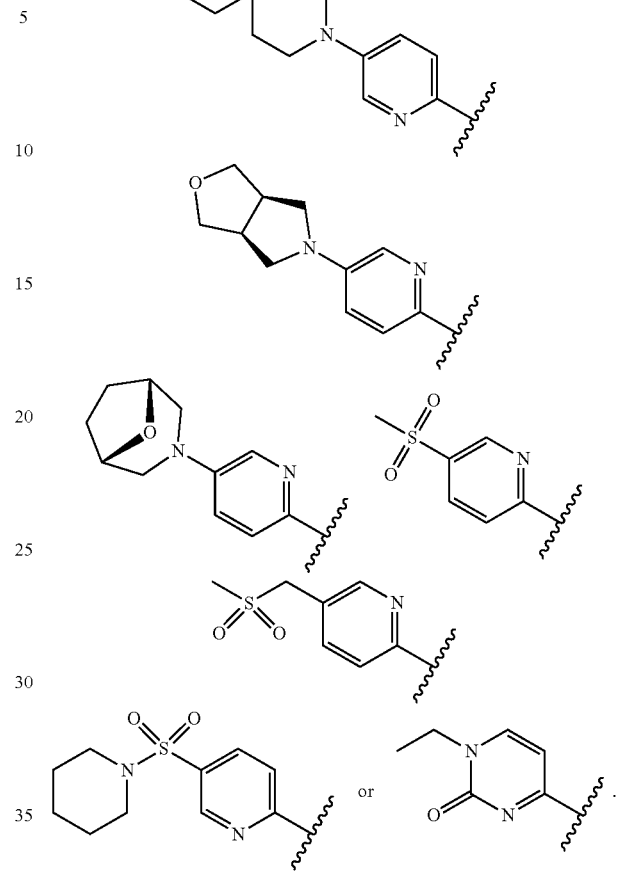

9. The compound of claim 1, wherein $R^2$ is selected from phenyl; and a 5-6 membered monocyclic heteroaryl ring having 1-4 heteroatoms independently selected from nitrogen, oxygen, and sulfur; each of which is substituted with r instances of $R^D$.

10. The compound of claim 1, wherein $R^2$ is phenyl; a 6-11 membered saturated, partially unsaturated, or unsaturated fused, bridged, or spiro bicyclic ring having 0-3 heteroatoms independently selected from nitrogen, oxygen, and sulfur; a 7-10-membered fused bicyclic ring having 1-3 nitrogen atoms; or a 9-membered fused bicyclic ring having 1-3 nitrogen atoms; each of which is substituted by r instances of $R^D$.

11. The compound of claim 1, wherein $R^2$ is

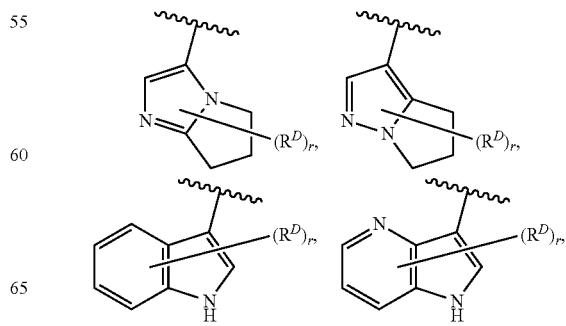

573
-continued
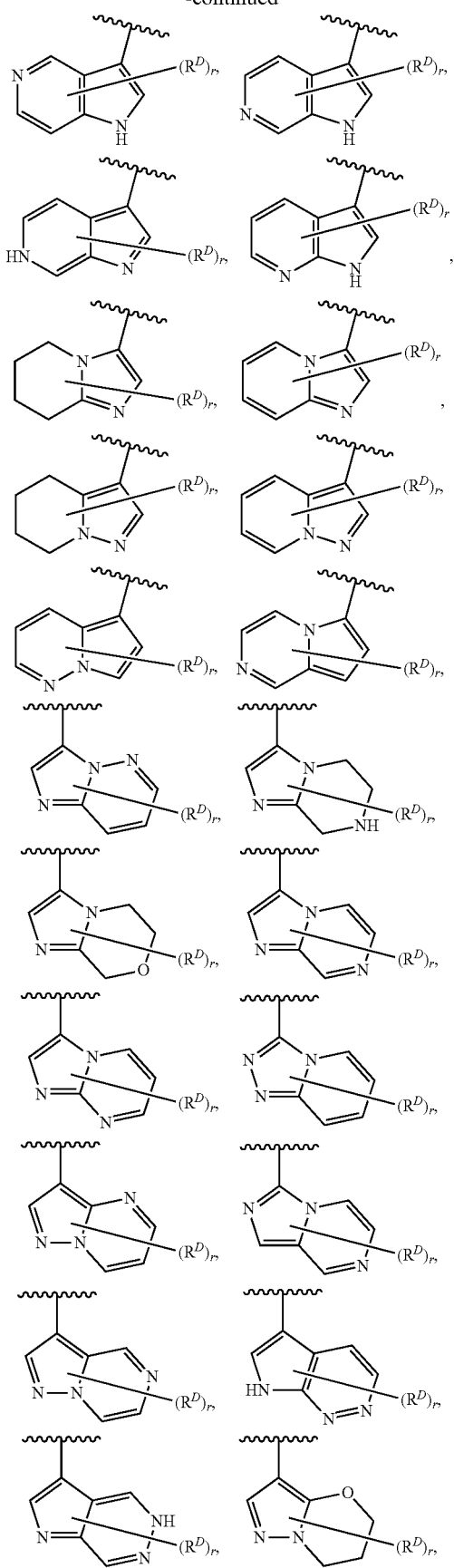
574
-continued
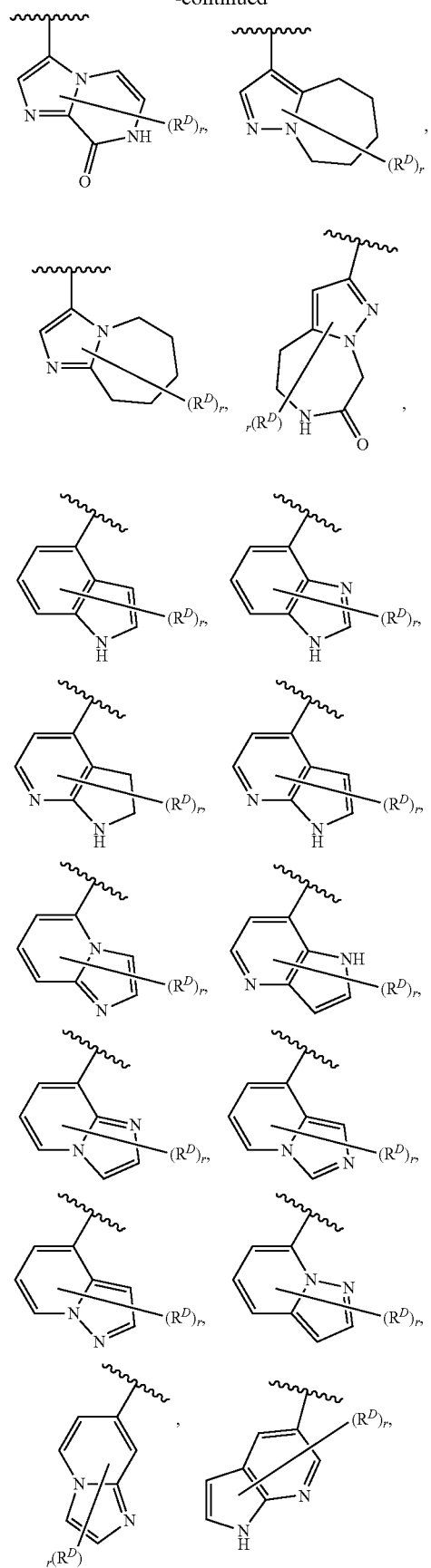

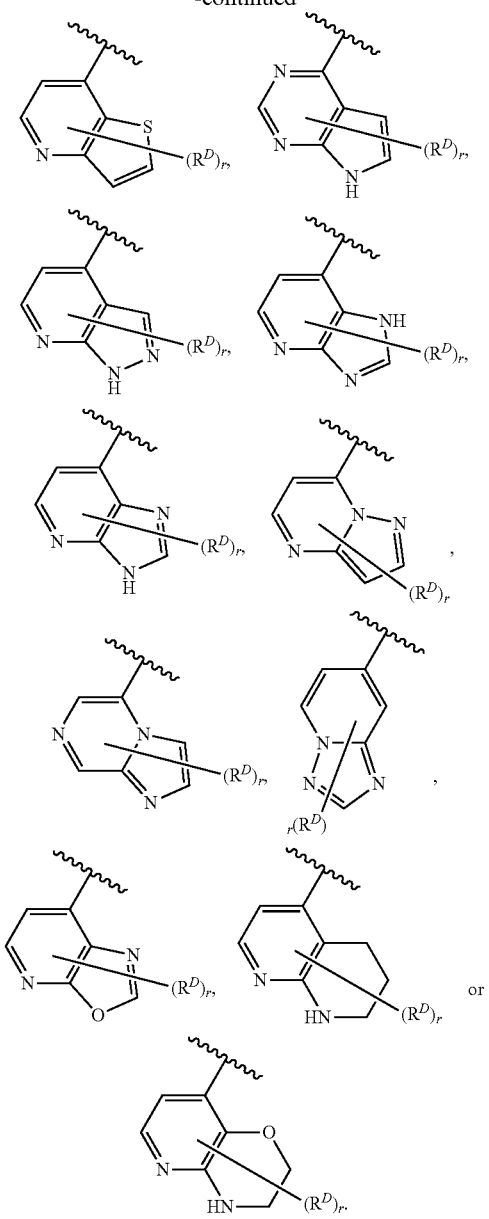

12. The compound of claim 1, wherein R² is

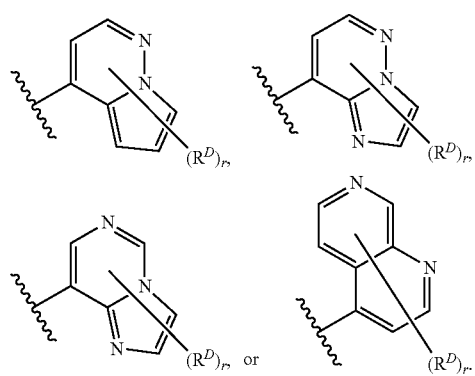

13. The compound of claim 1, wherein R² is

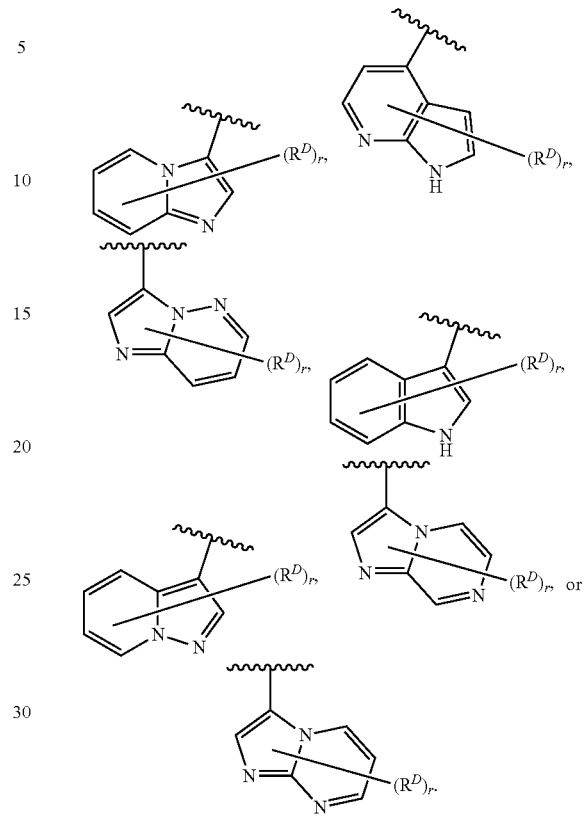

14. The compound of claim 1, wherein each instance of $R^D$ is independently oxo, halogen, —CN, —OR, —C(O)R, —C(O)OR, —C(O)NR₂, or —N(R)C(O)R; or each instance of $R^D$ is independently an optionally substituted group selected from $C_{1-6}$ aliphatic; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, phosphorous, silicon, and sulfur; and a 5-6 membered monocyclic heteroaryl ring having 1-4 heteroatoms independently selected from nitrogen, oxygen, and sulfur; wherein each instance of $R^D$ is independently optionally substituted by u instances of R.

15. The compound of claim 1, wherein each instance of $R^D$ is independently halogen, —CN, —OR, —C(O)NR₂, or —NR₂; or each instance of $R^D$ is independently an optionally substituted group selected from $C_{1-6}$ aliphatic; a 3-7 membered saturated or partially unsaturated monocyclic heterocyclic ring having 1-2 heteroatoms independently selected from nitrogen, oxygen, phosphorous, silicon, and sulfur; and a 6-11 membered saturated or partially unsaturated fused, bridged, or spiro bicyclic heterocyclic ring having 1-3 heteroatoms independently selected from nitrogen, oxygen, and sulfur; wherein each instance of $R^D$ is independently substituted by u instances of R.

16. The compound of claim 1, wherein R² is

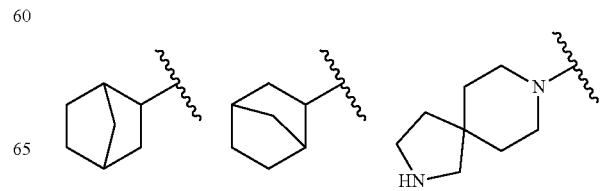

577
-continued
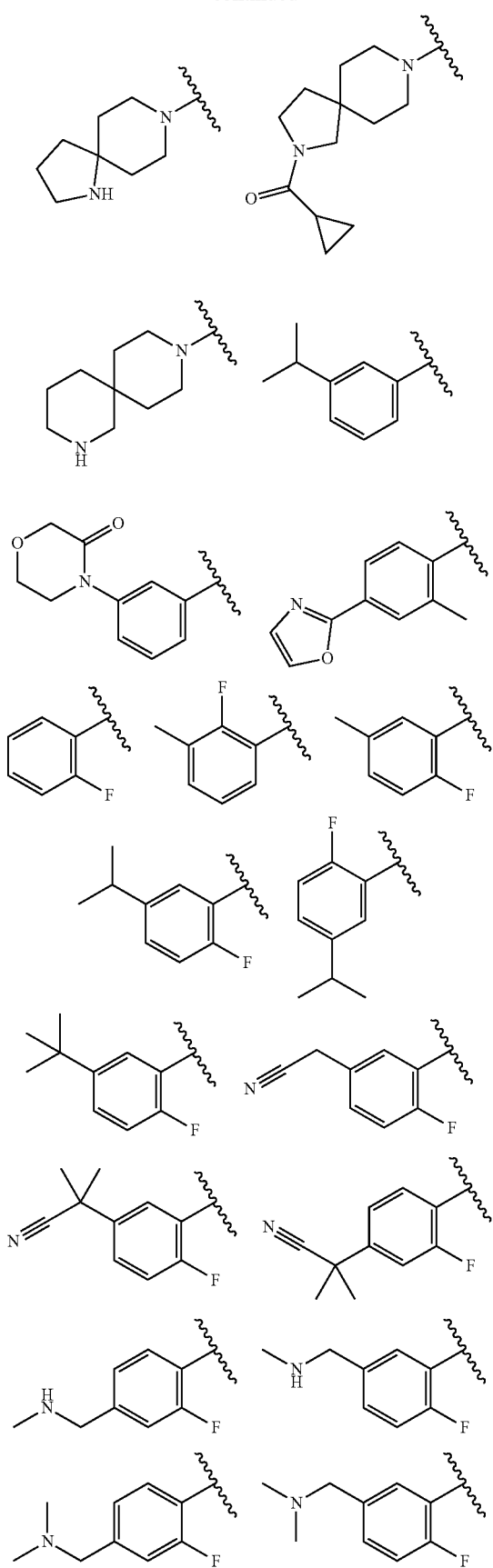
578
-continued
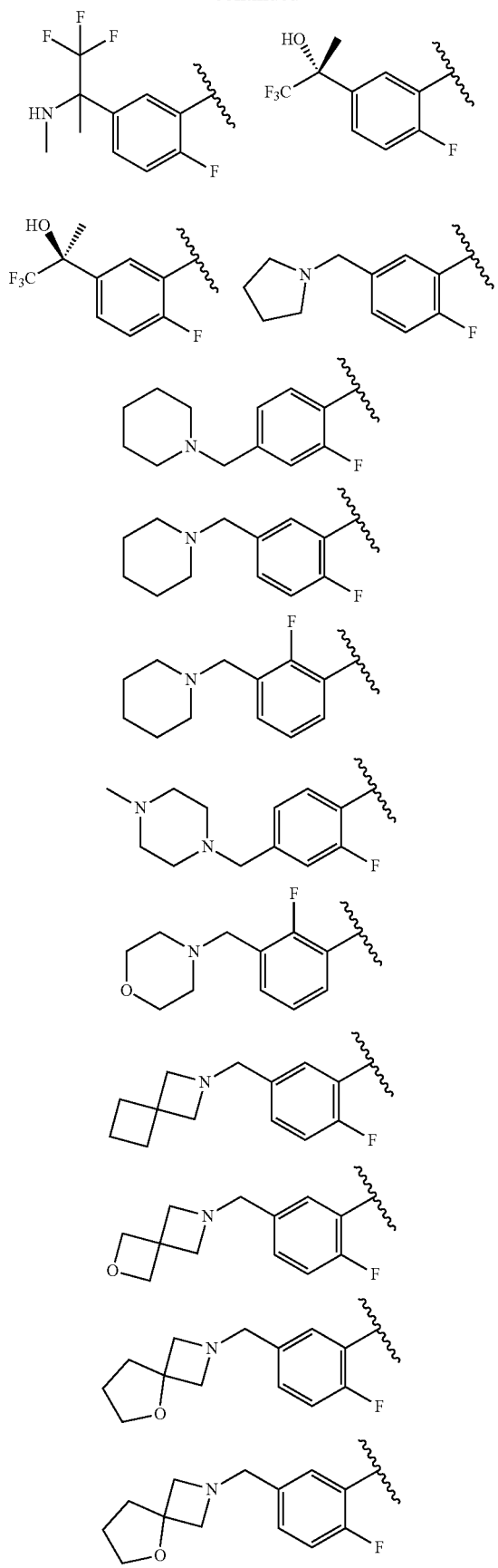

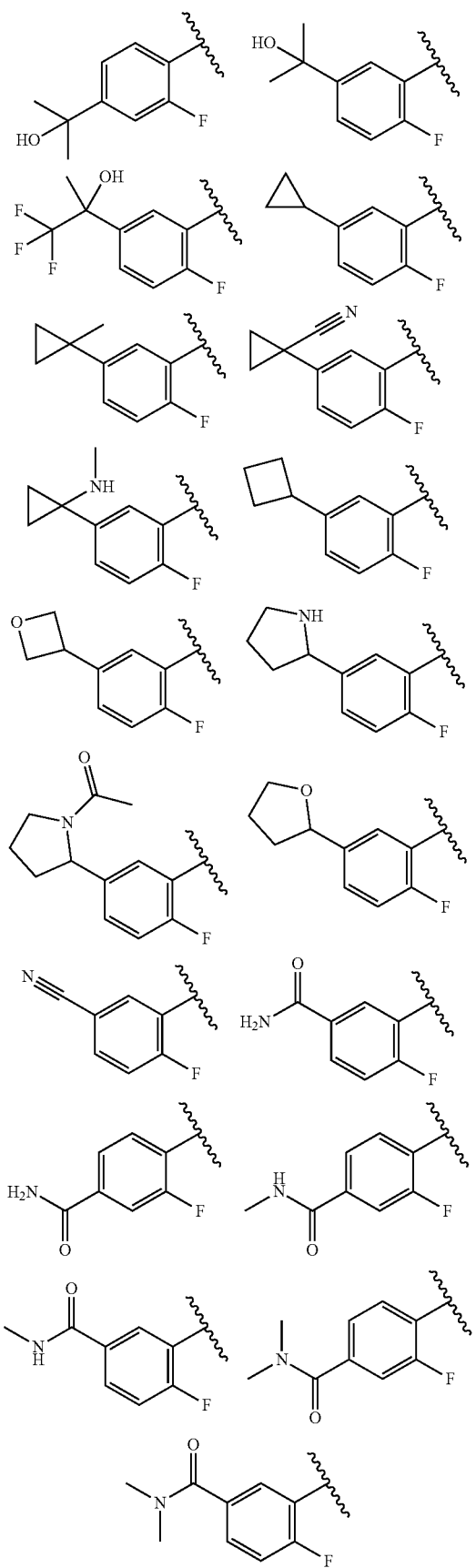
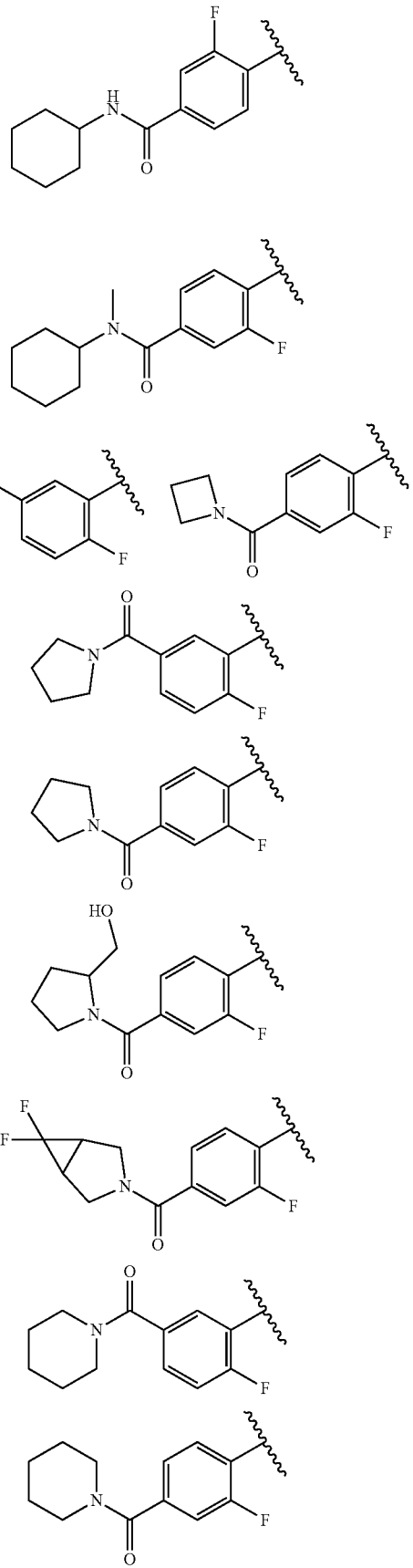

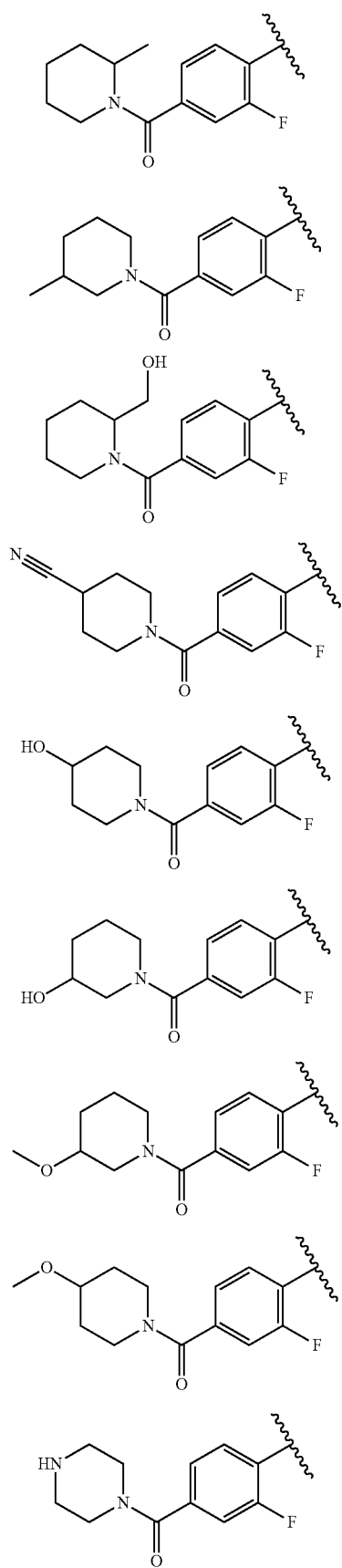
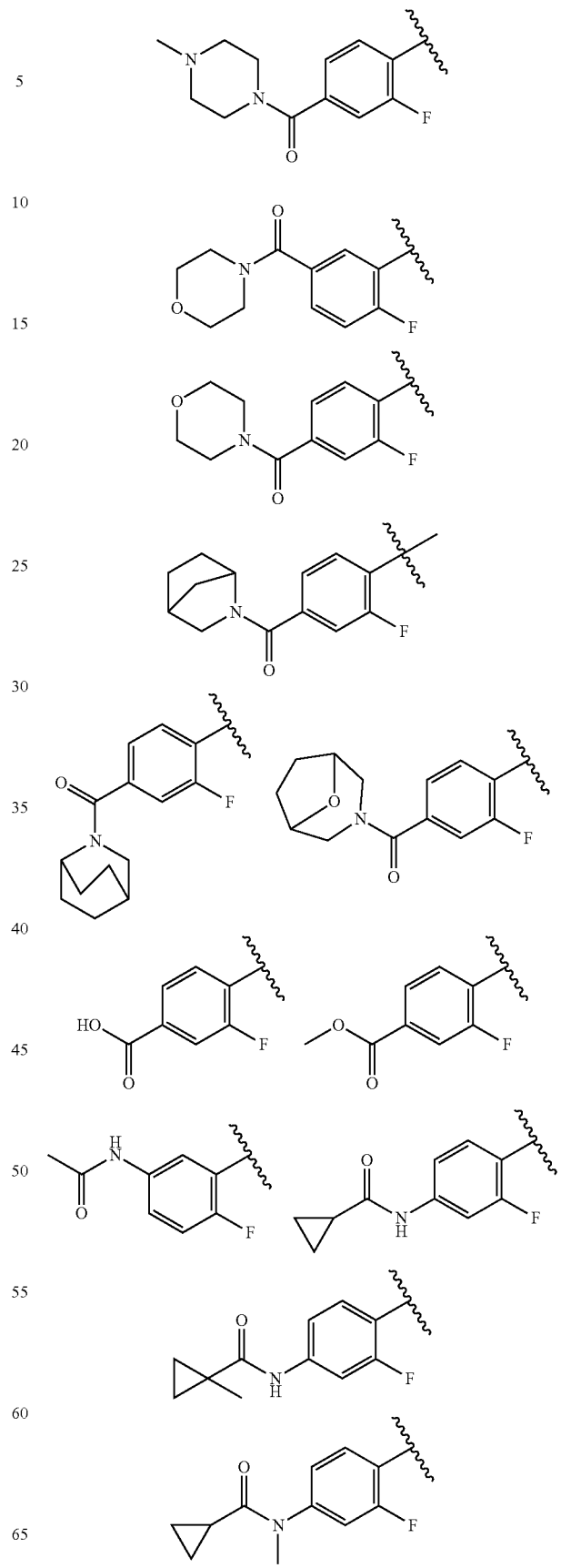

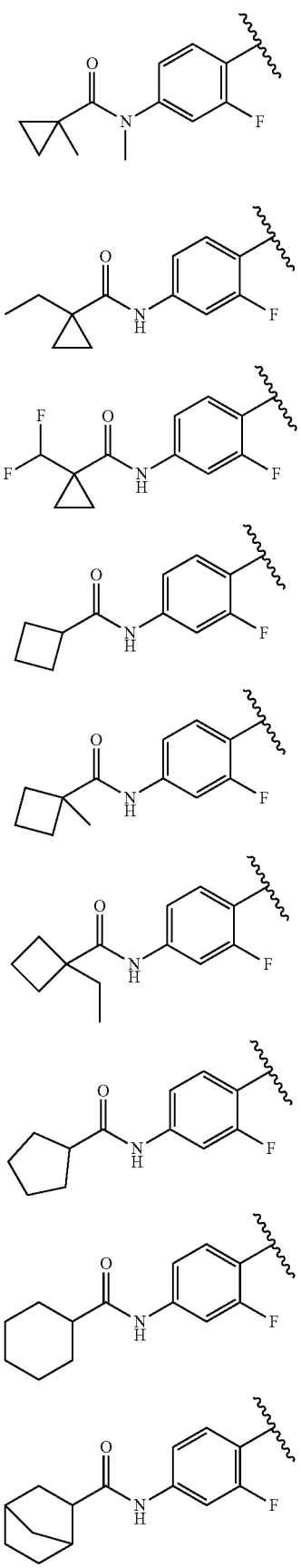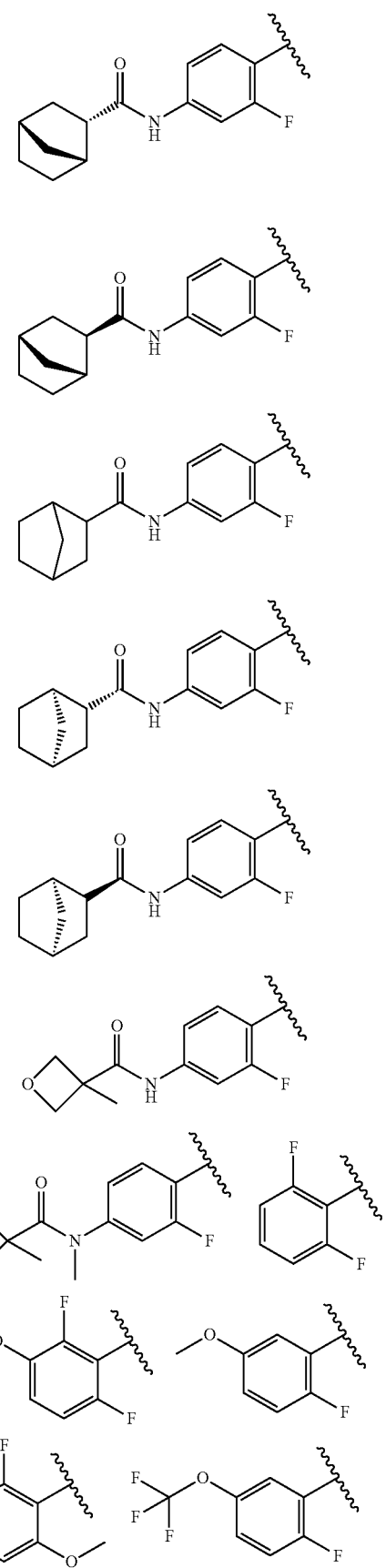

585
-continued
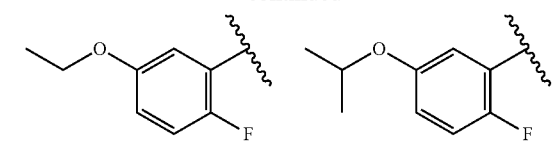
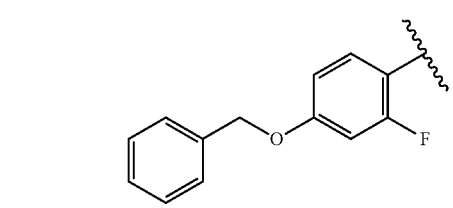
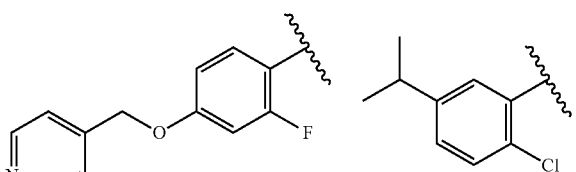
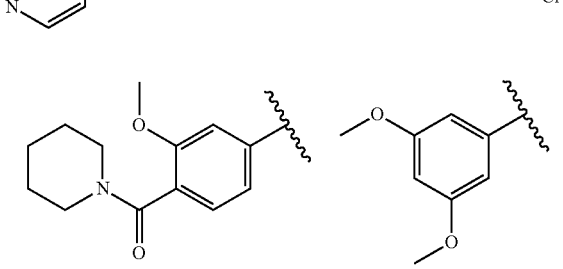
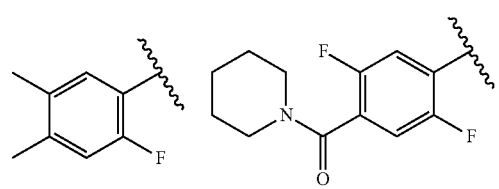
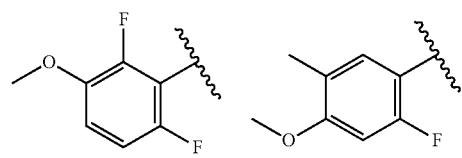
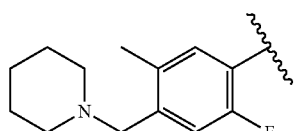
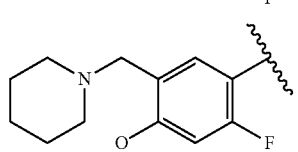
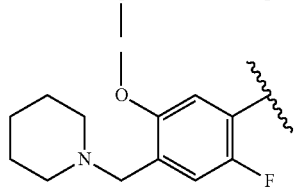
586
-continued
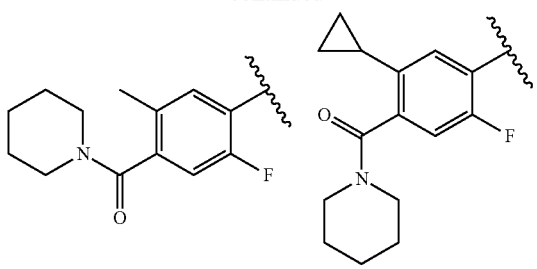
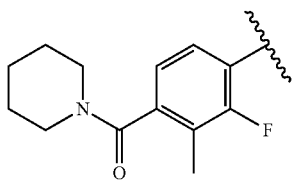
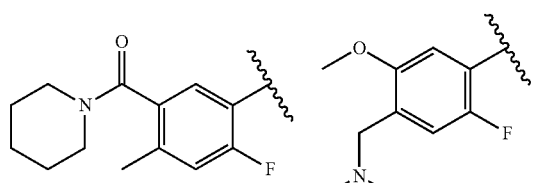
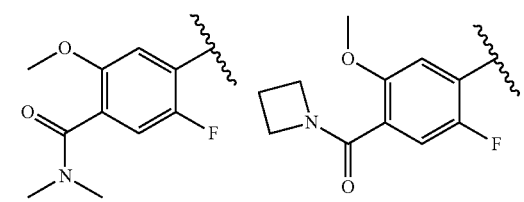
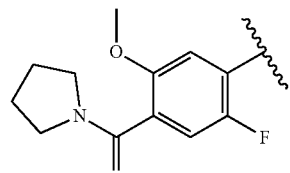
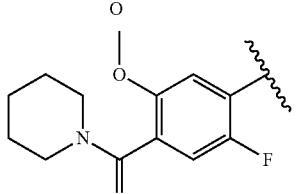
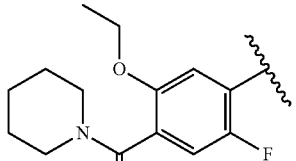
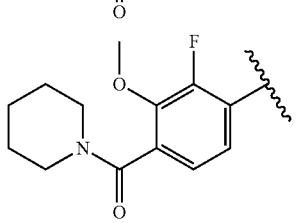

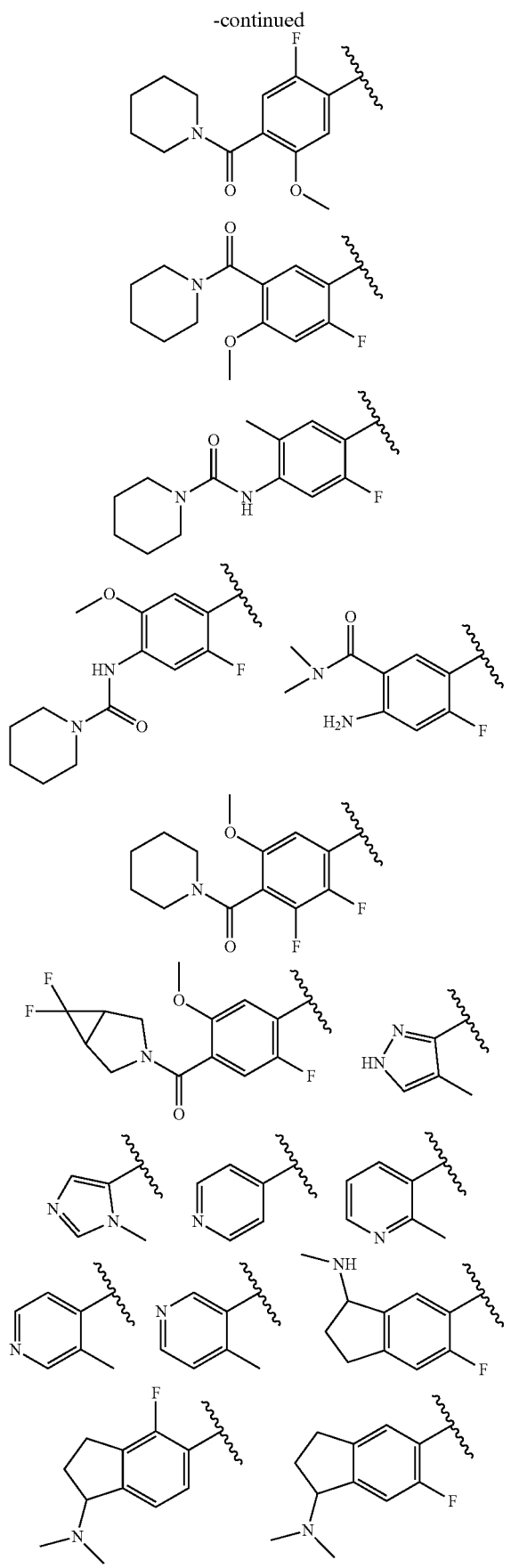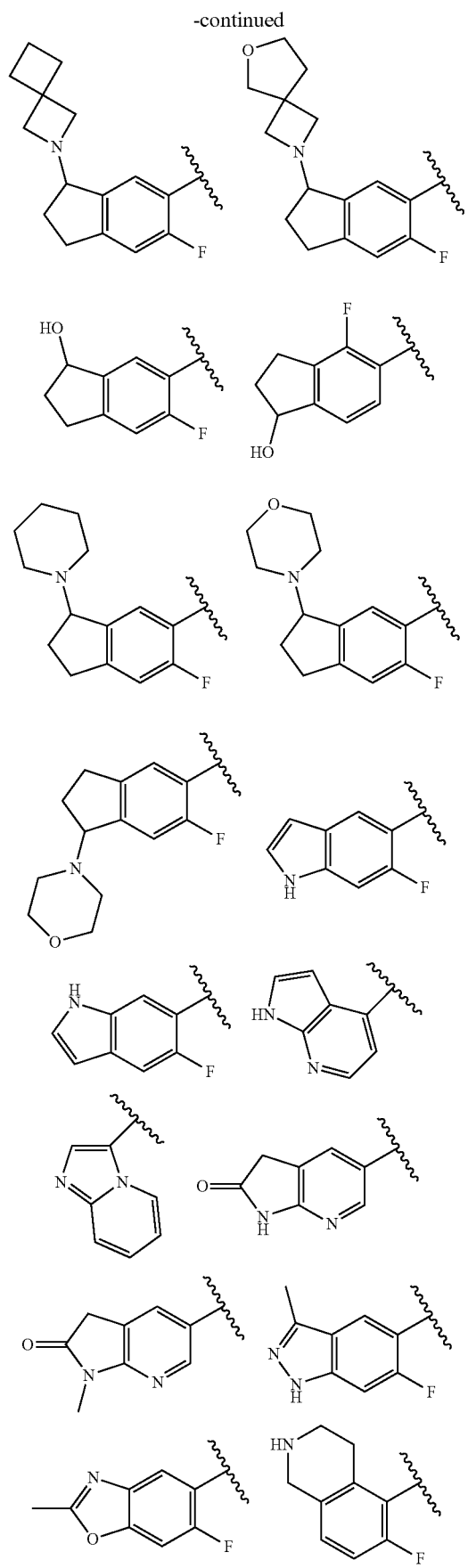

-continued

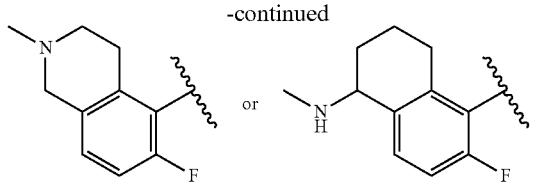

17. The compound of claim 1, wherein $R^3$ is H, $C_{1-6}$ aliphatic, or phenyl; each of which is substituted with s instances of $R^E$; or each $R^3$ is independently —CN, halogen, —C(O)R, —C(O)OR, —C(O)NR$_2$, or —C(O)N(R)OR.

18. The compound of claim 1, wherein $R^3$ is H, -Me, -Et, or phenyl; each of which is substituted with s instances of $R^E$; or each $R^3$ is independently —CN, halogen, or —C(O)OR.

19. The compound of claim 1, wherein the compound is selected from

I-1

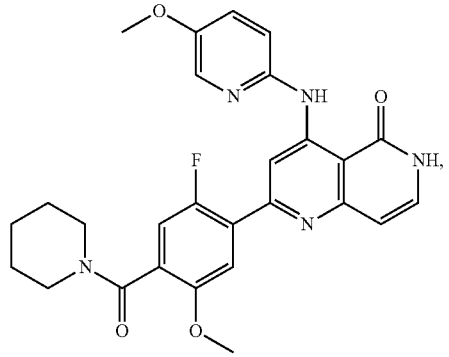

I-2

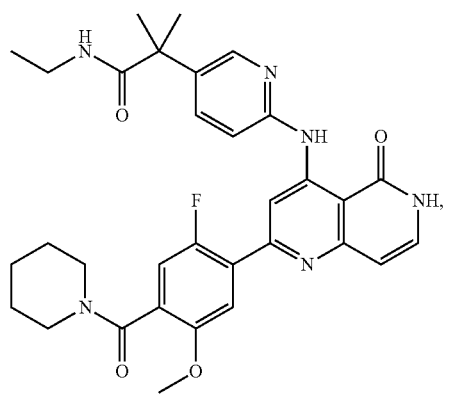

I-3

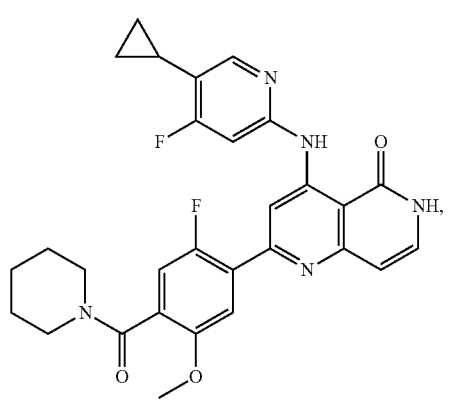

-continued

I-4

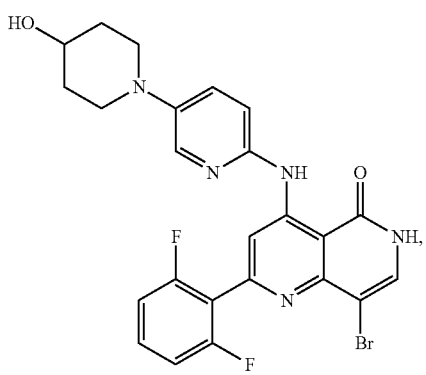

I-5

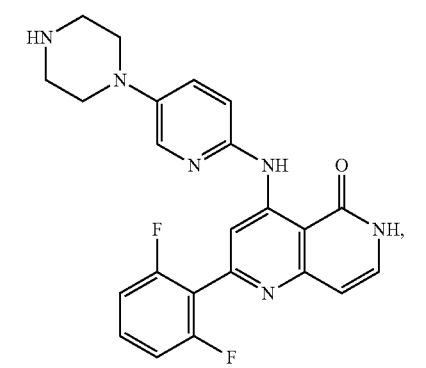

I-6

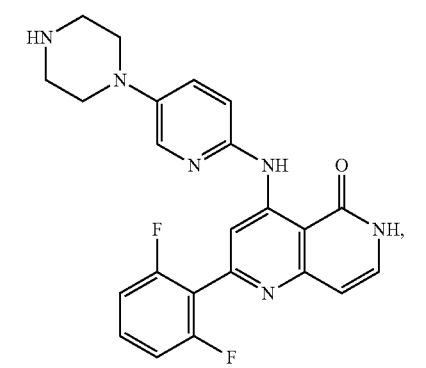

I-11

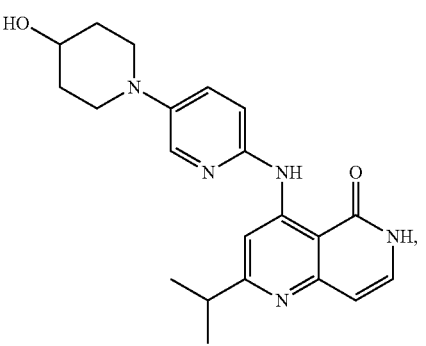

I-14
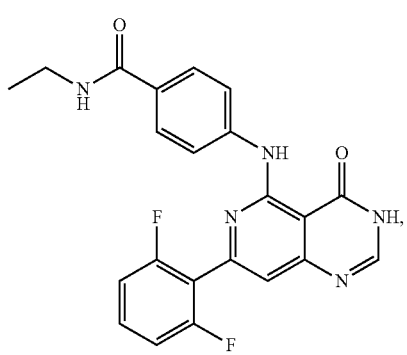
I-15
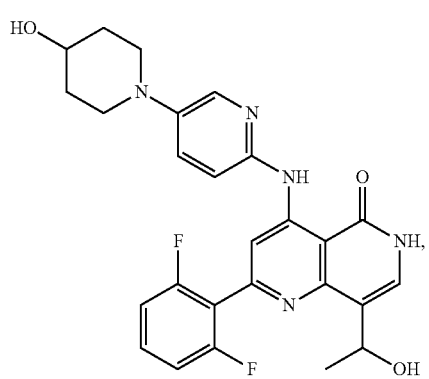
I-16
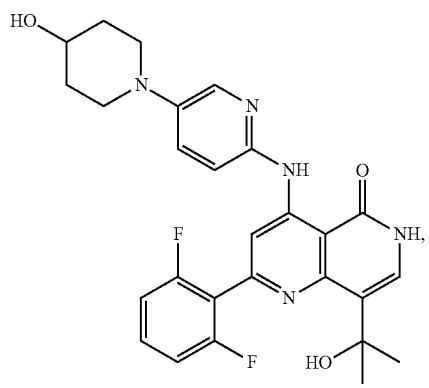
I-18
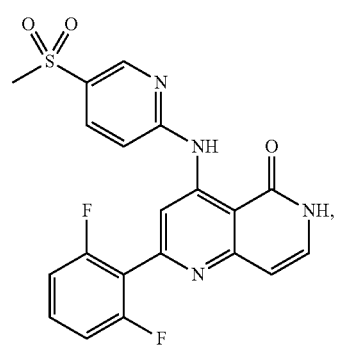
I-24
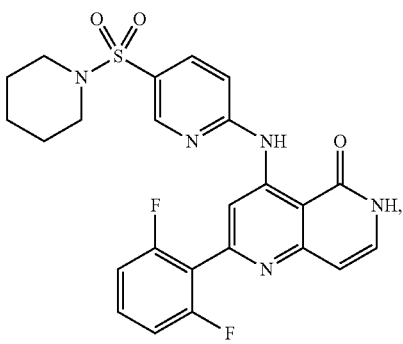
I-25
I-30
I-33
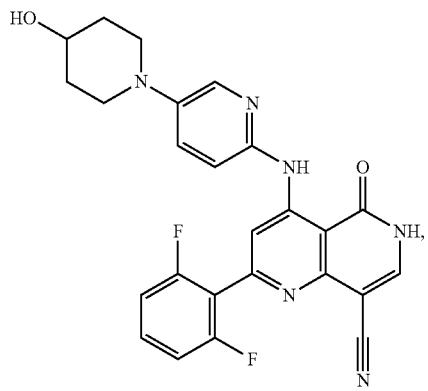

I-35
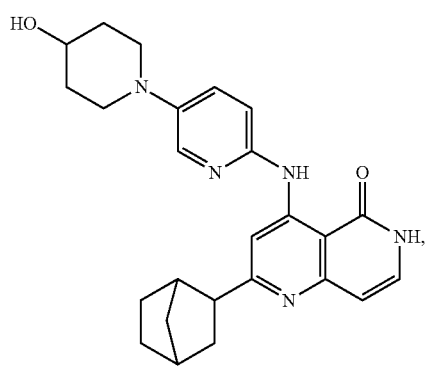
I-39
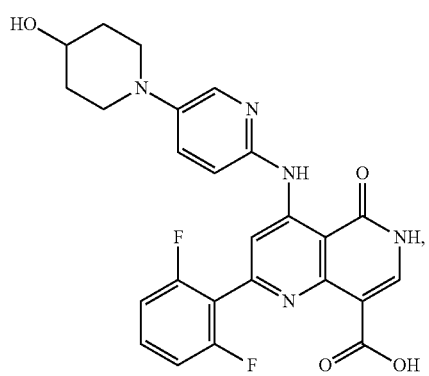
I-40
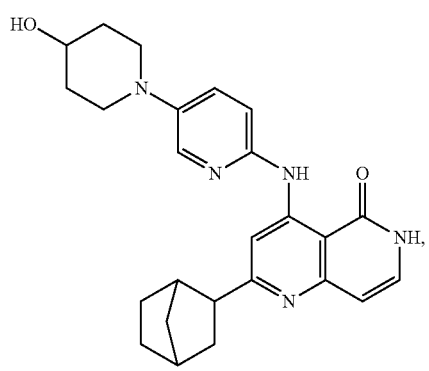
I-41
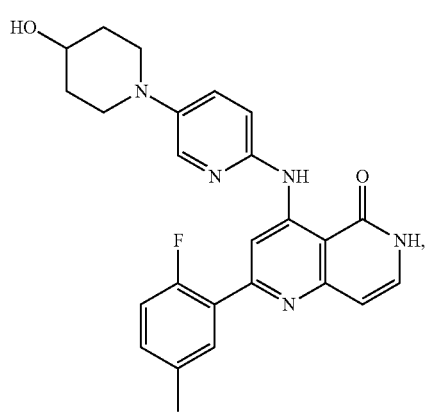
I-42
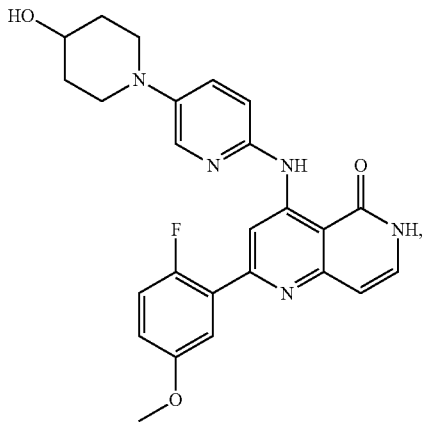
I-43
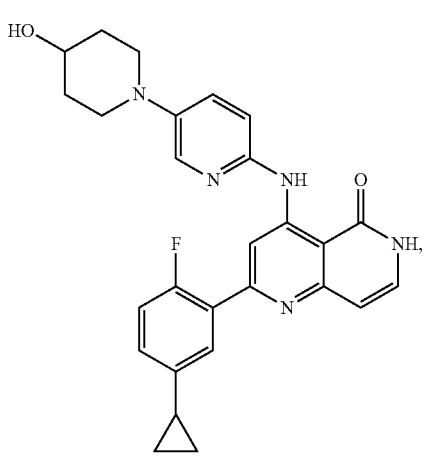
I-45
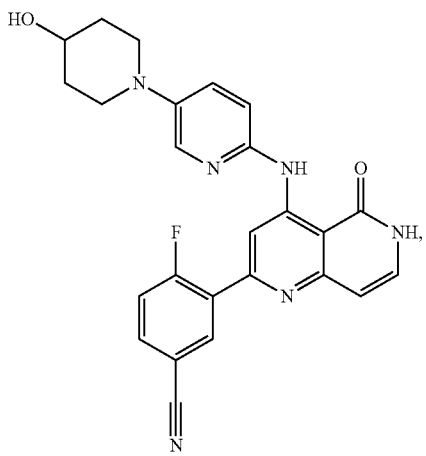
I-46
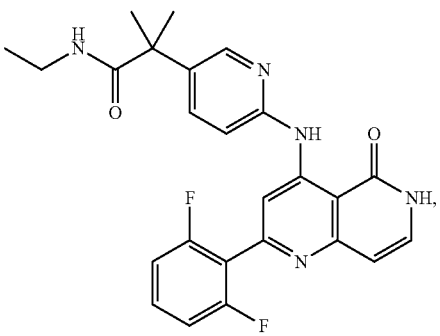

-continued
I-48
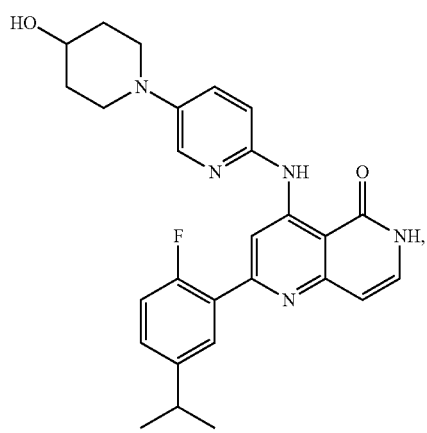
I-49
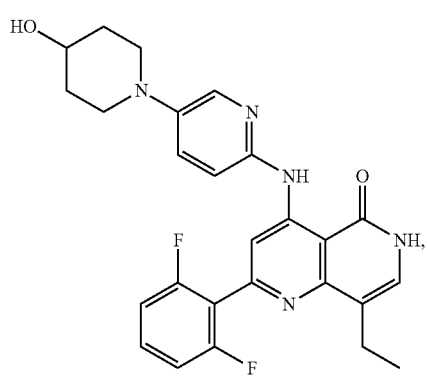
I-51
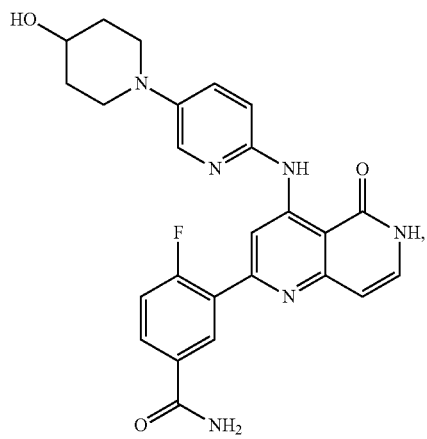
I-52
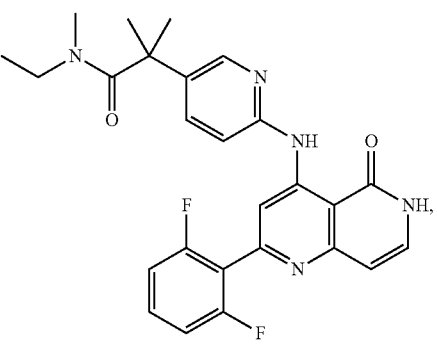
-continued
I-53
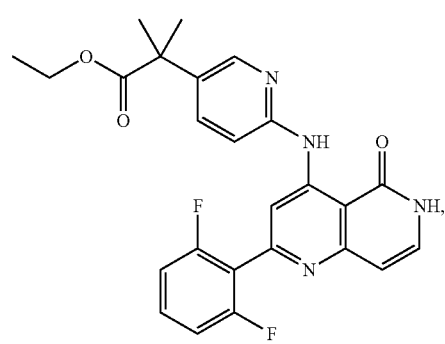
I-55
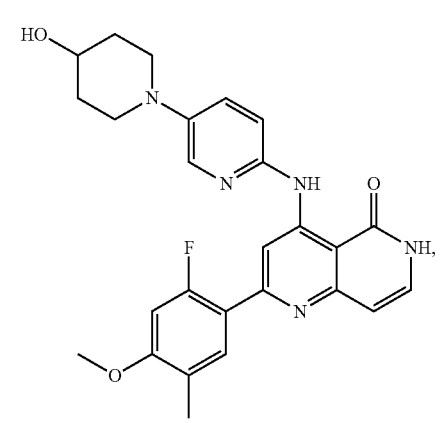
I-56
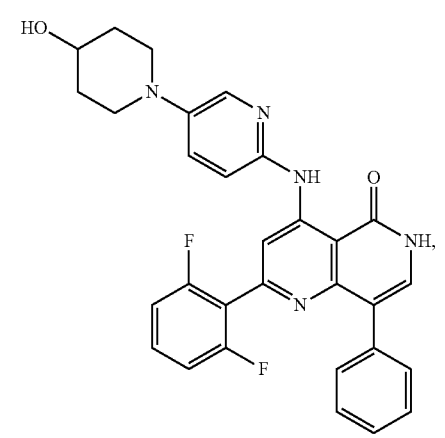
I-58
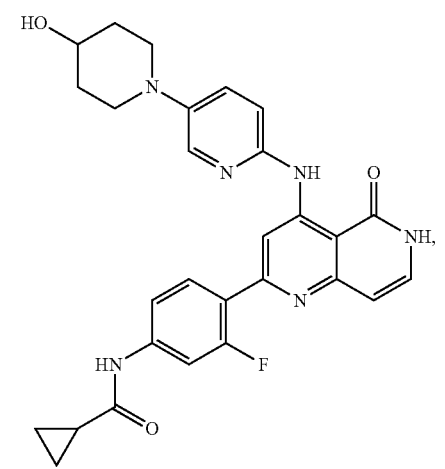

I-61
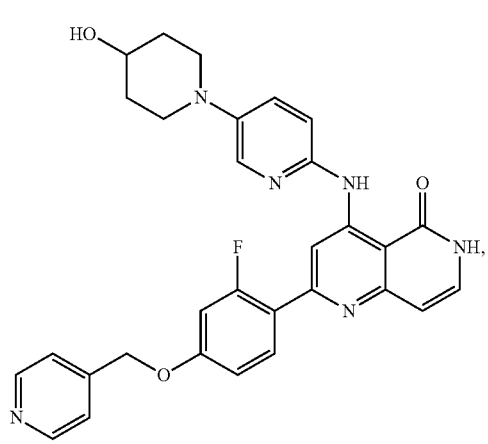
I-62
I-64
I-65
I-66
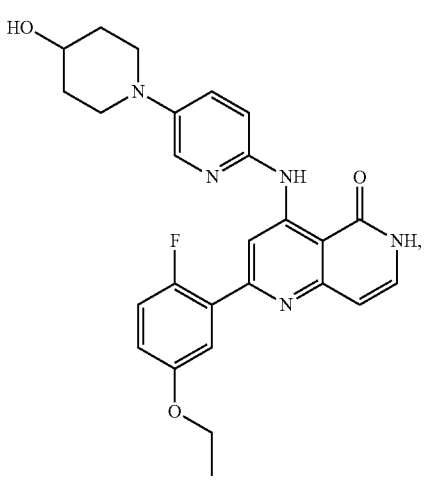
I-67
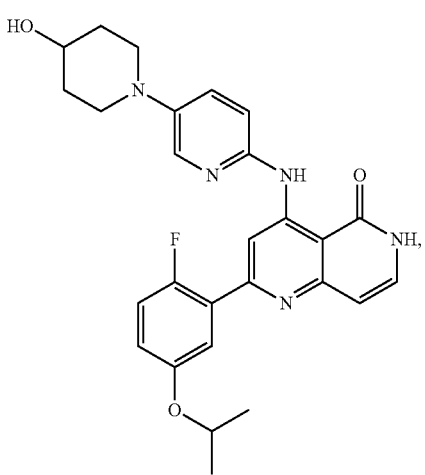
I-68
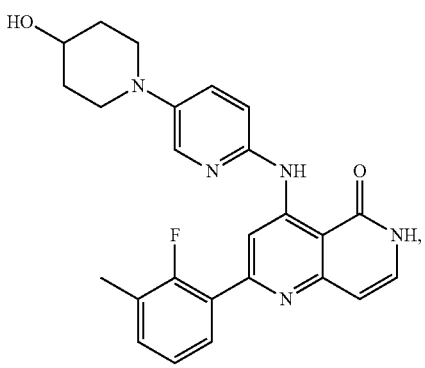

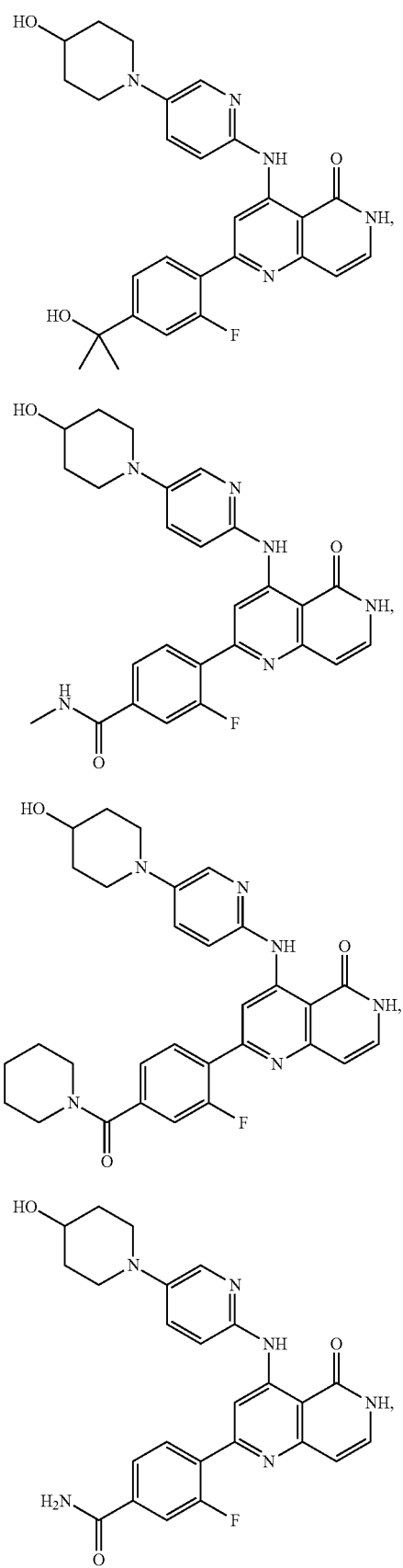
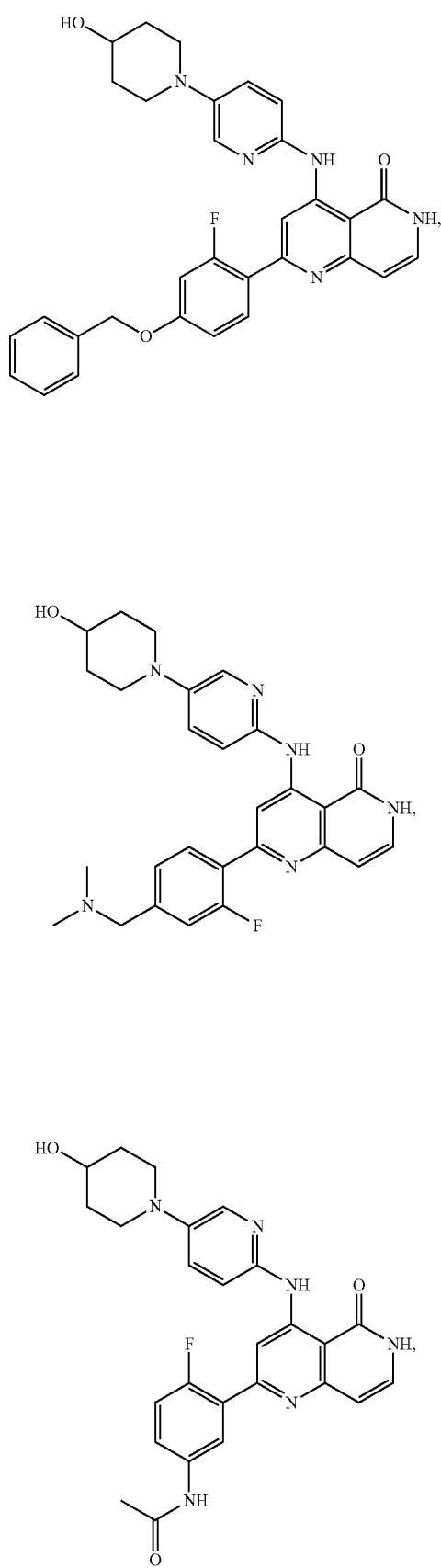

I-79
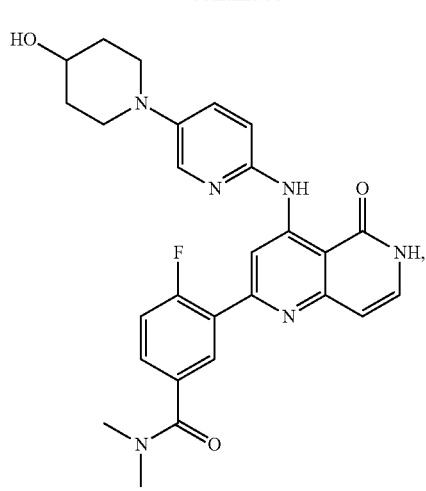
I-86
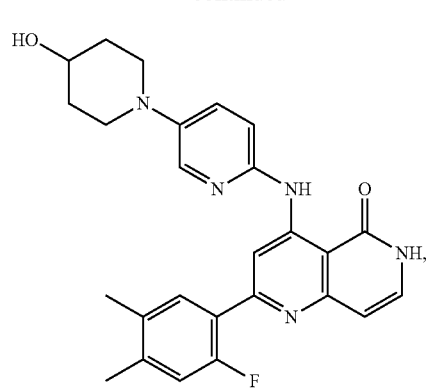
I-80
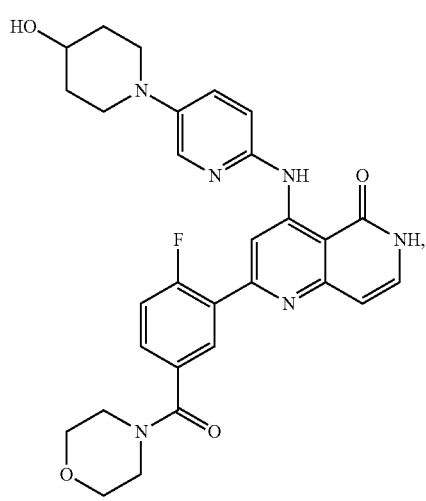
I-91
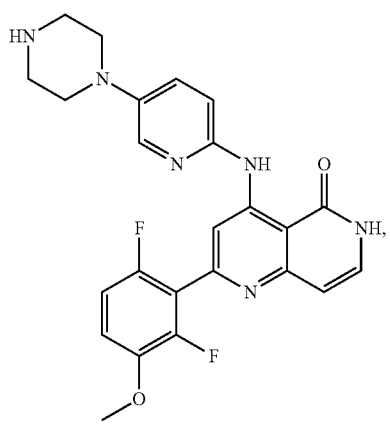
I-85
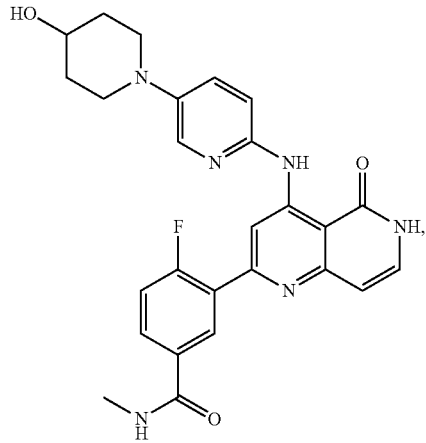
I-92
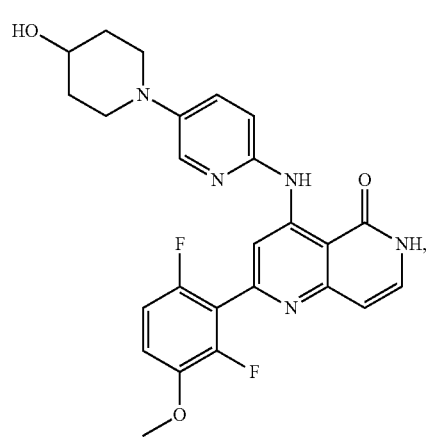

I-93
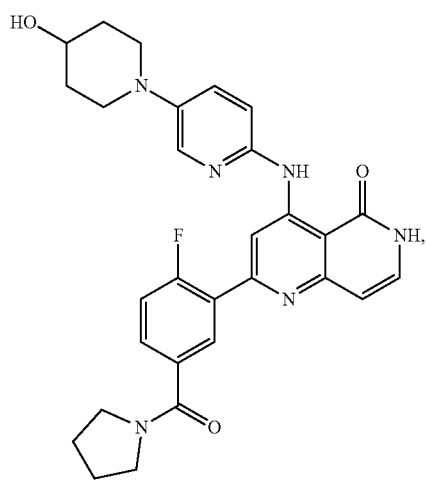
I-96
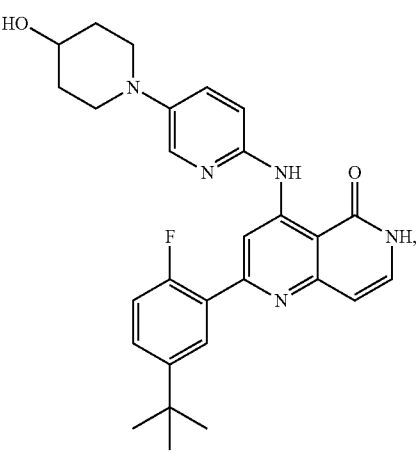
I-94
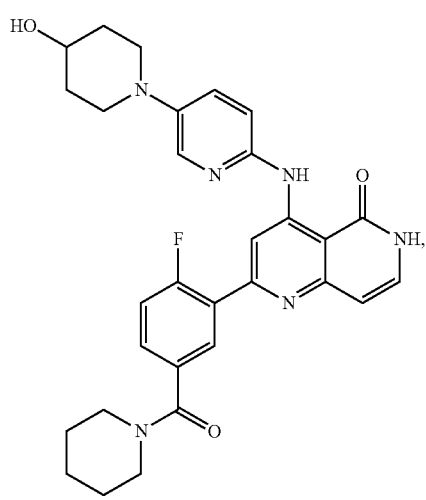
I-97
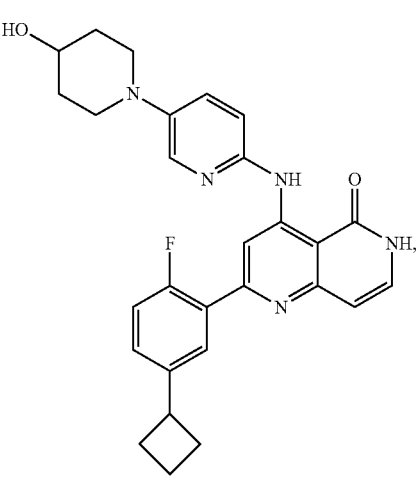
I-95
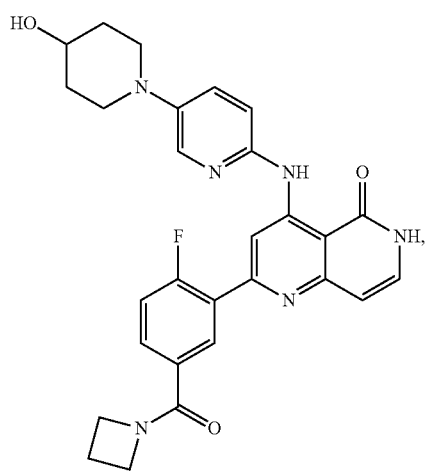
I-98
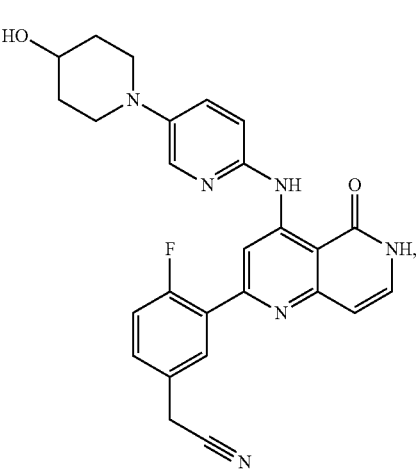

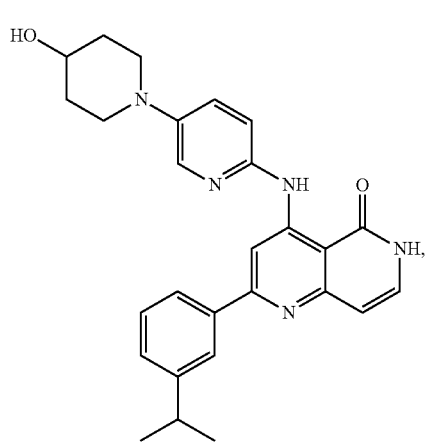
I-99
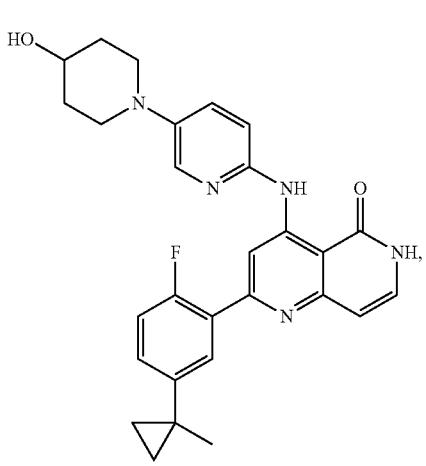
I-102
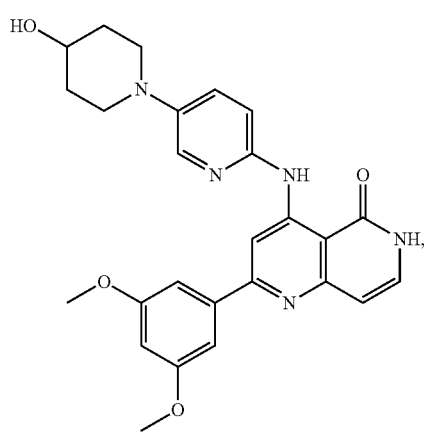
I-100
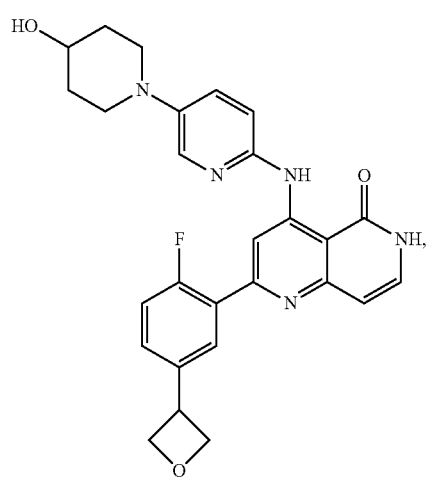
I-103
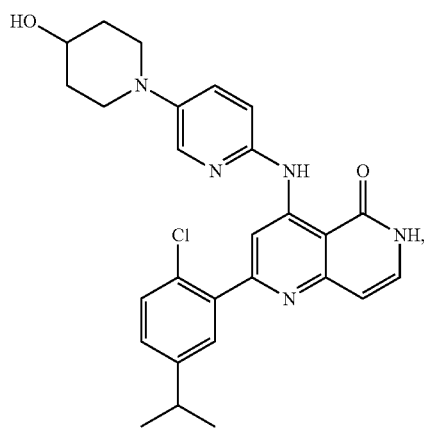
I-101
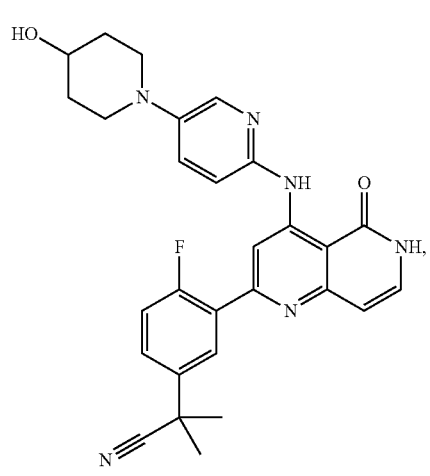
I-104

-continued

I-105

I-106

I-107

I-108

I-109

I-110

I-111
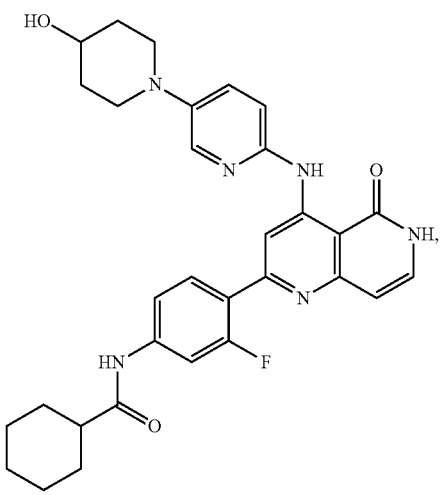
I-114
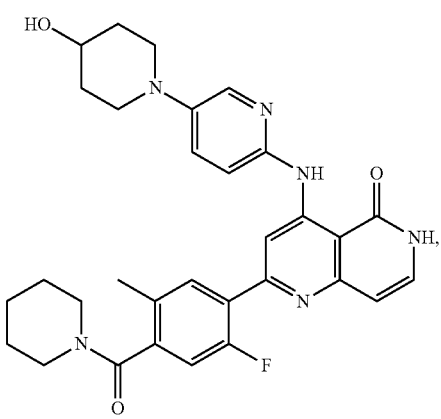
I-112
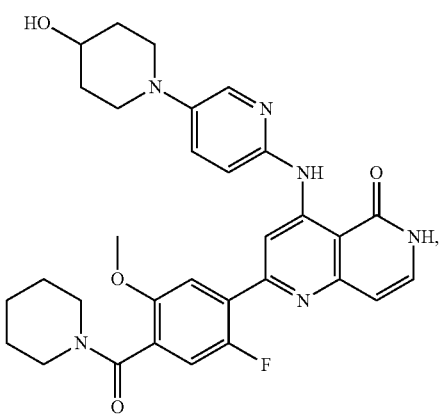
I-115
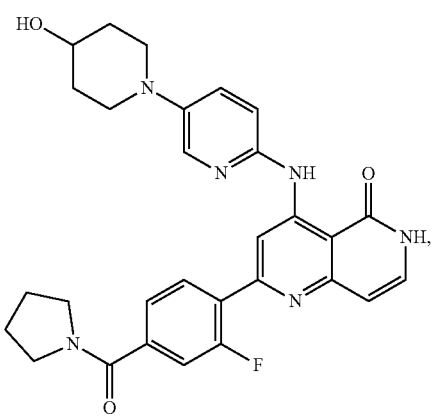
I-113
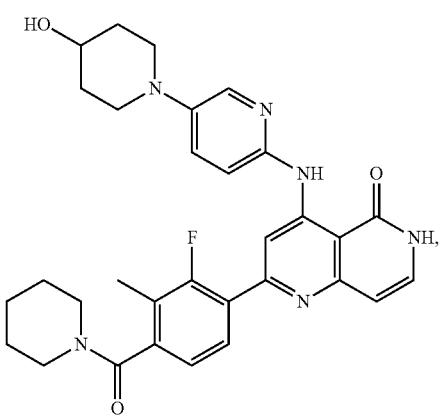
I-116
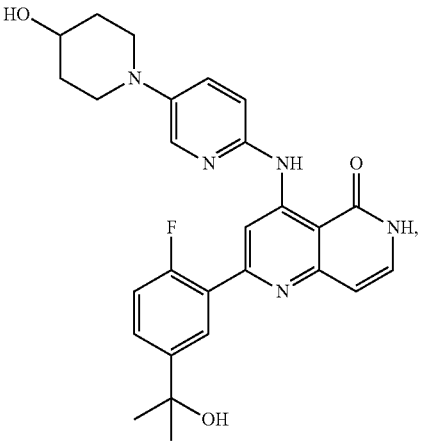

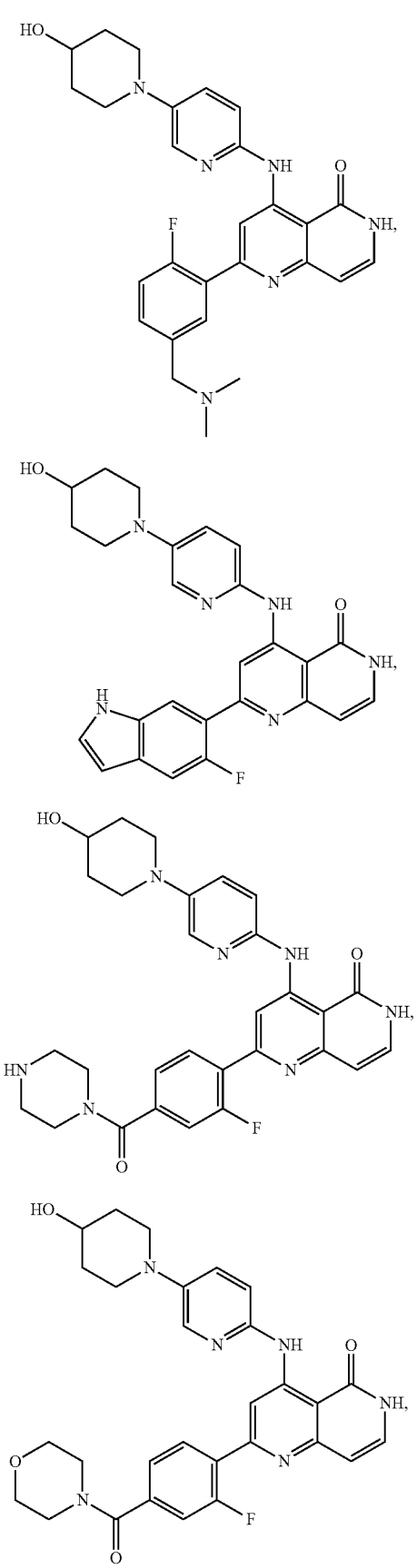
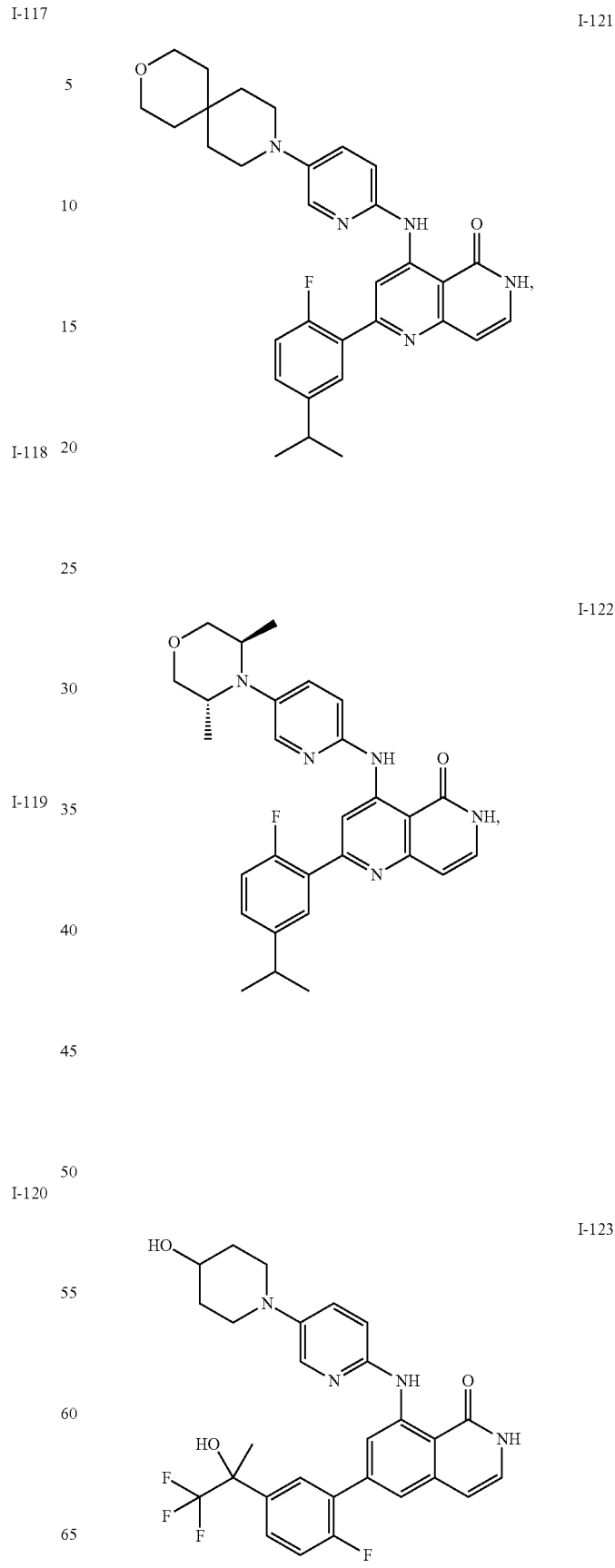

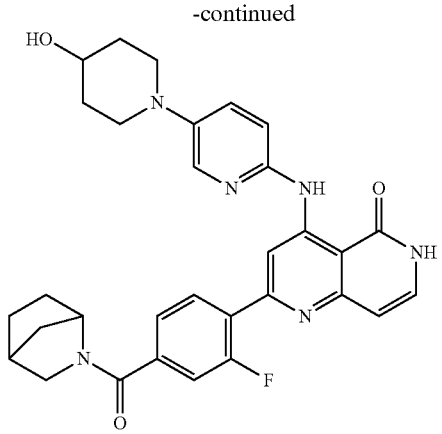
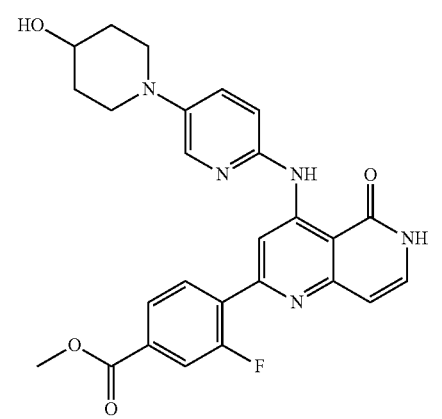
I-125
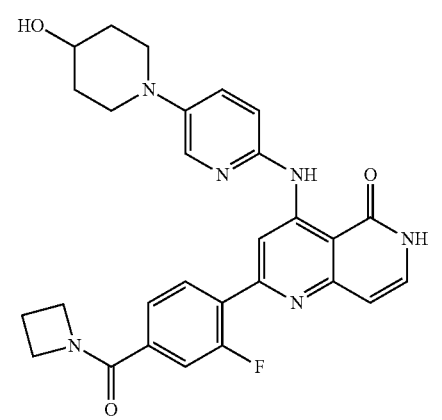
I-126
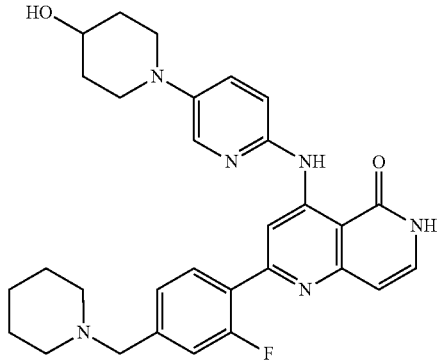
I-127
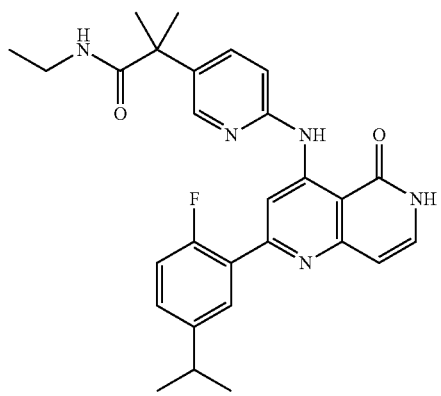
I-128
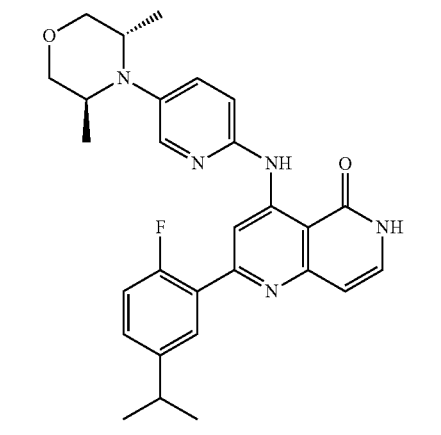
I-129
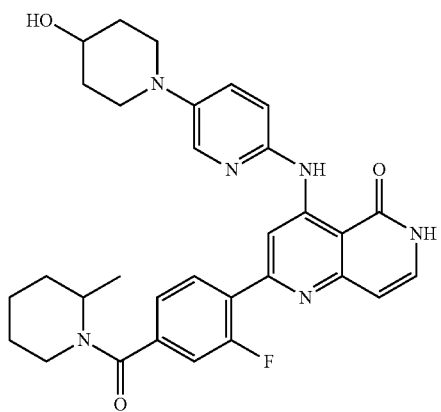
I-130
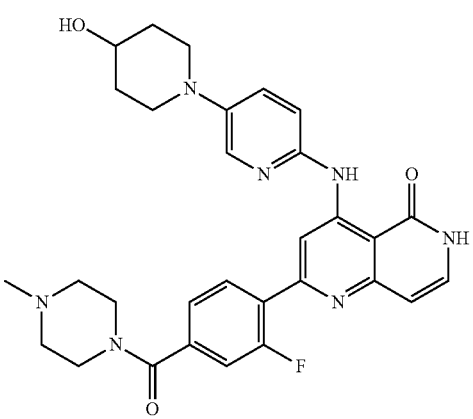
I-131

-continued
I-132
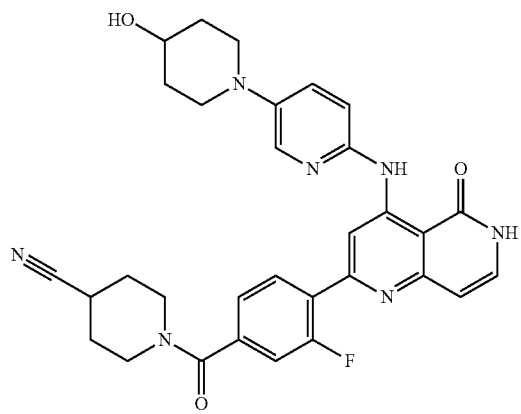
I-133
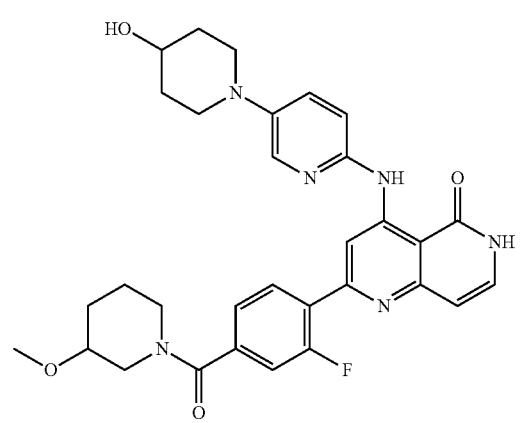
I-134
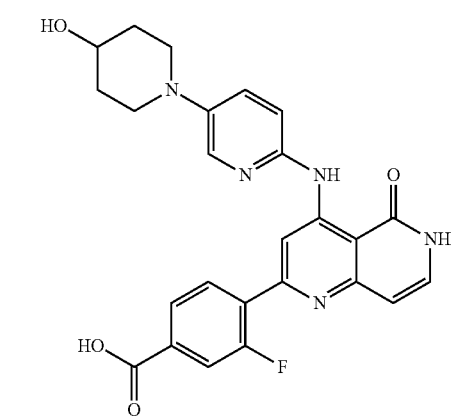
-continued
I-135
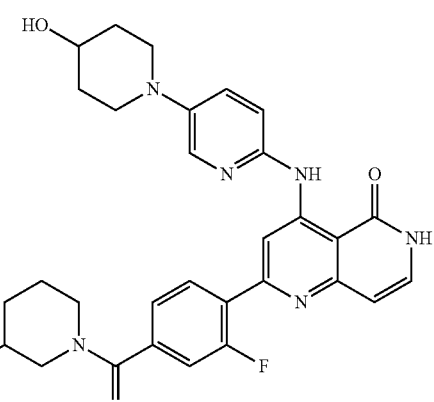
I-136
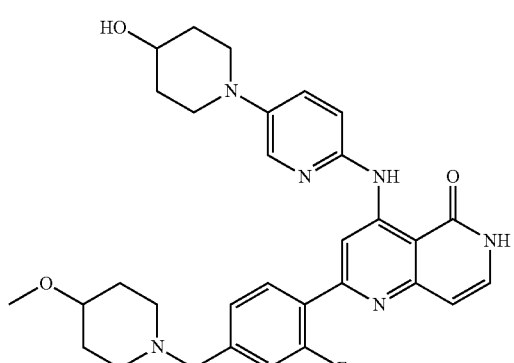
I-137
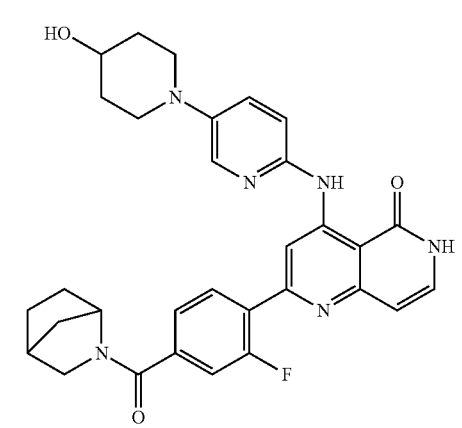
I-138
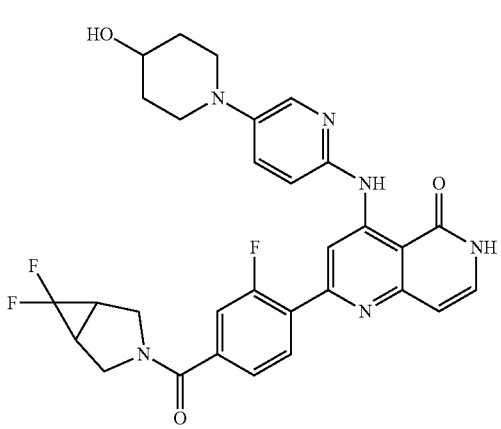

I-139
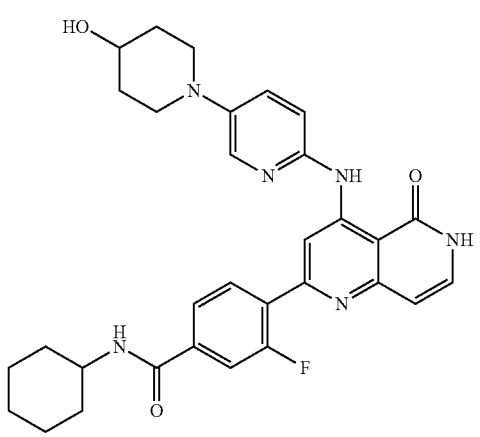
I-140
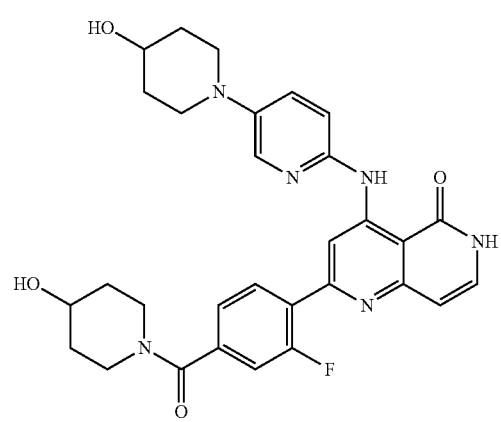
I-141
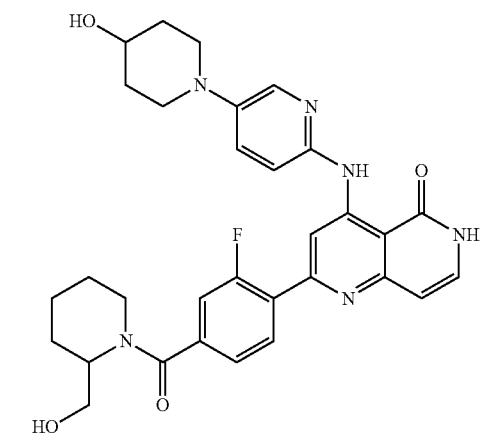
I-142
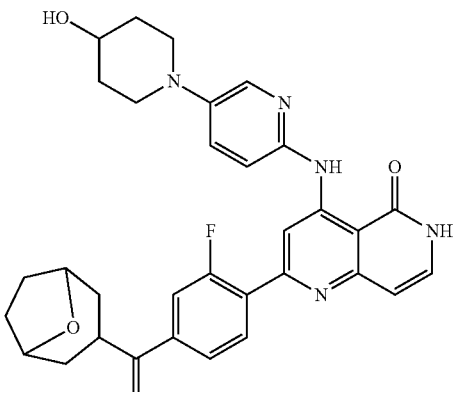
I-143
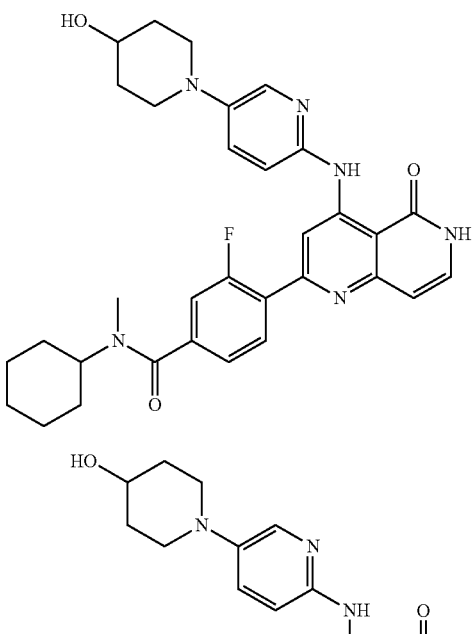
I-145
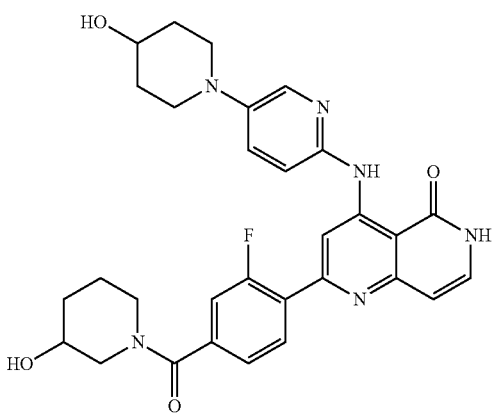
I-146
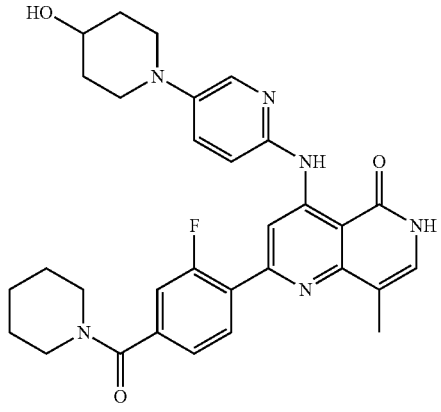

I-147 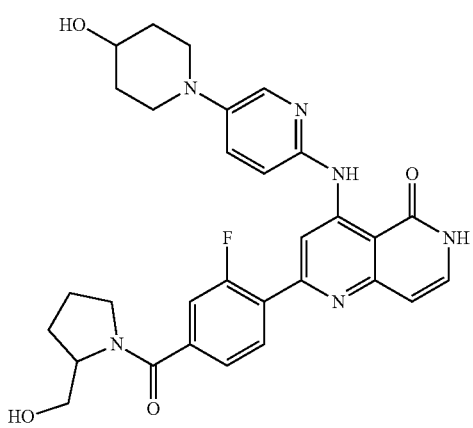
I-148 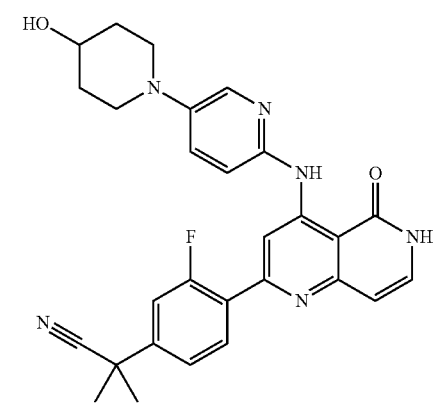
I-149
I-150 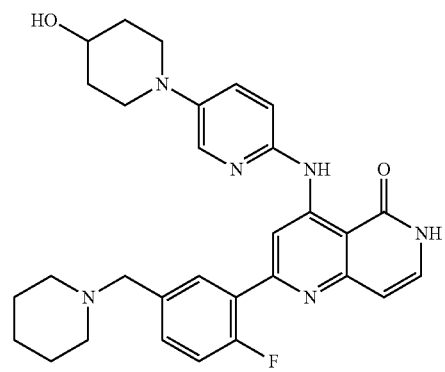
I-151 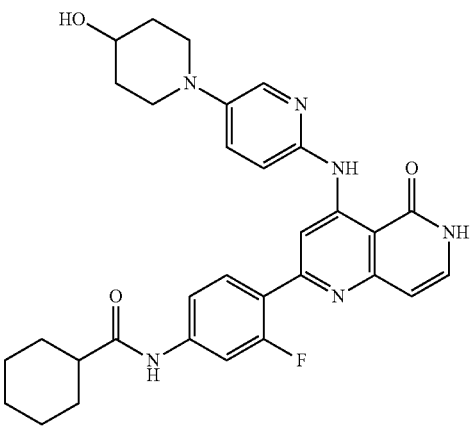
I-152 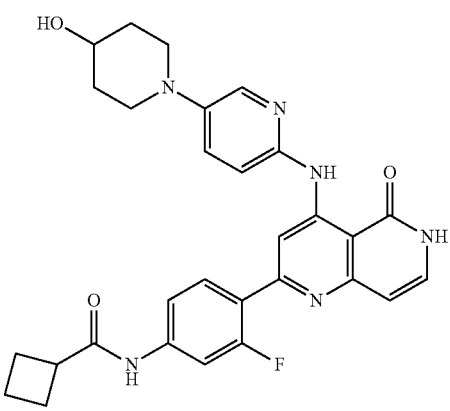
I-153

-continued
I-154
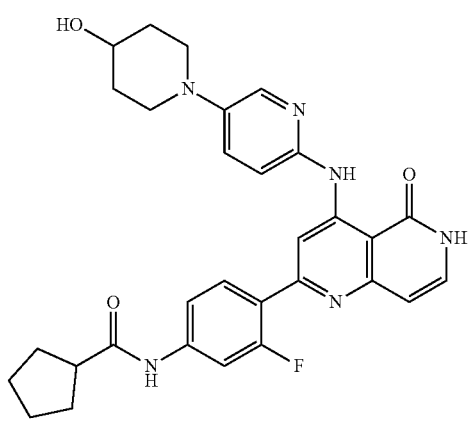
I-155
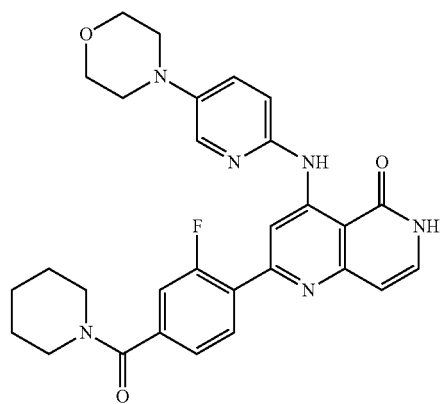
I-156
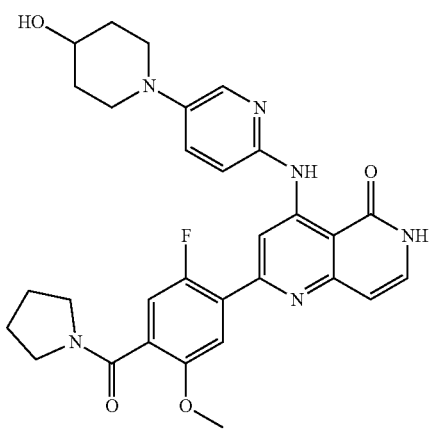
-continued
I-157
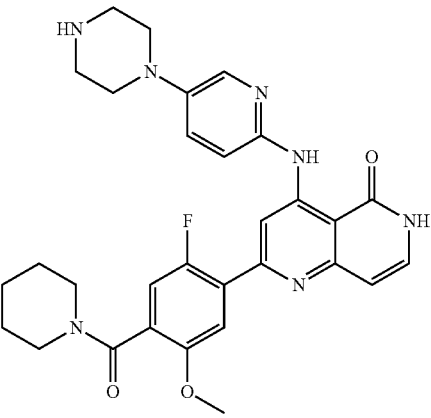
I-158
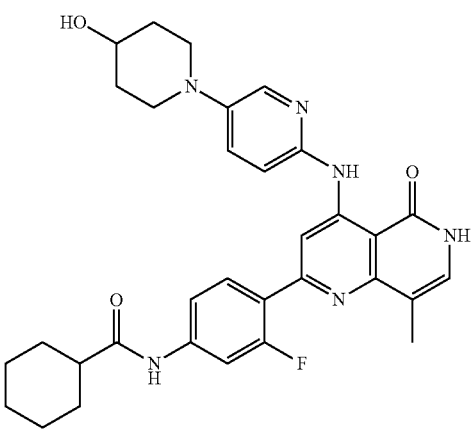
I-159
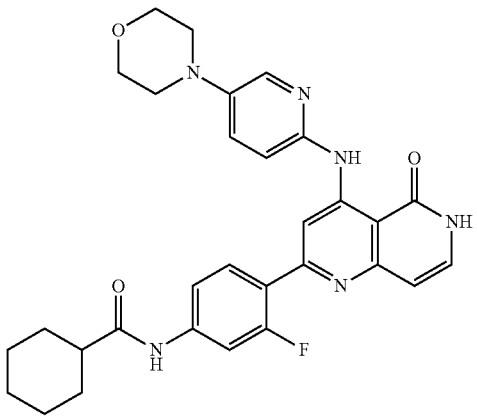

I-160
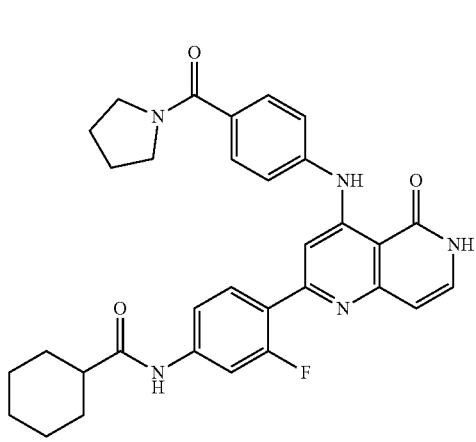
I-161
I-162
I-163
I-164
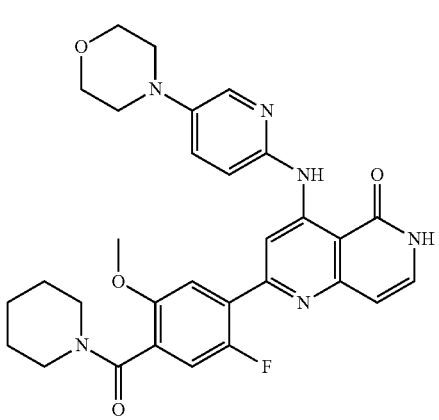
I-165
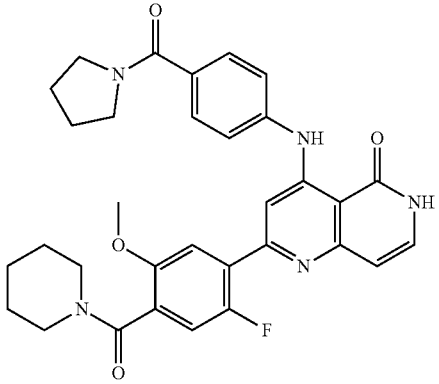
I-166
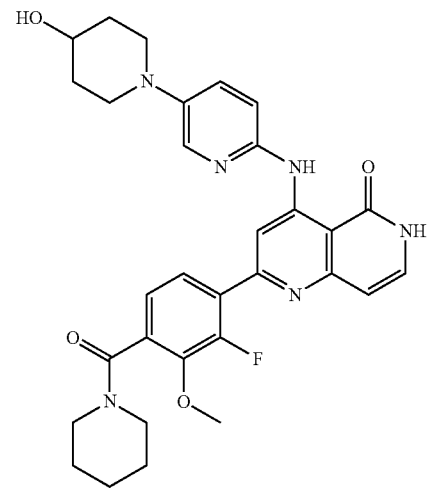
I-167
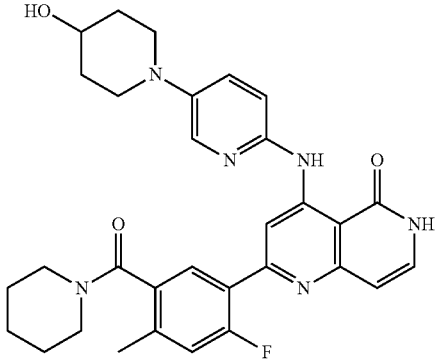

I-168
I-169
I-170
I-171
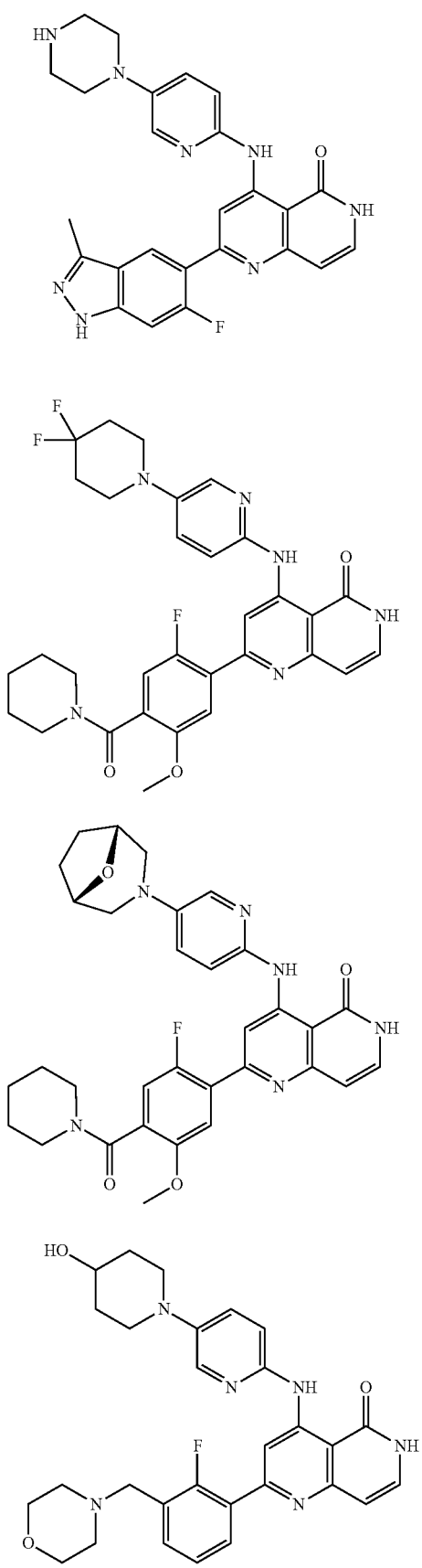
I-172
I-173
I-174
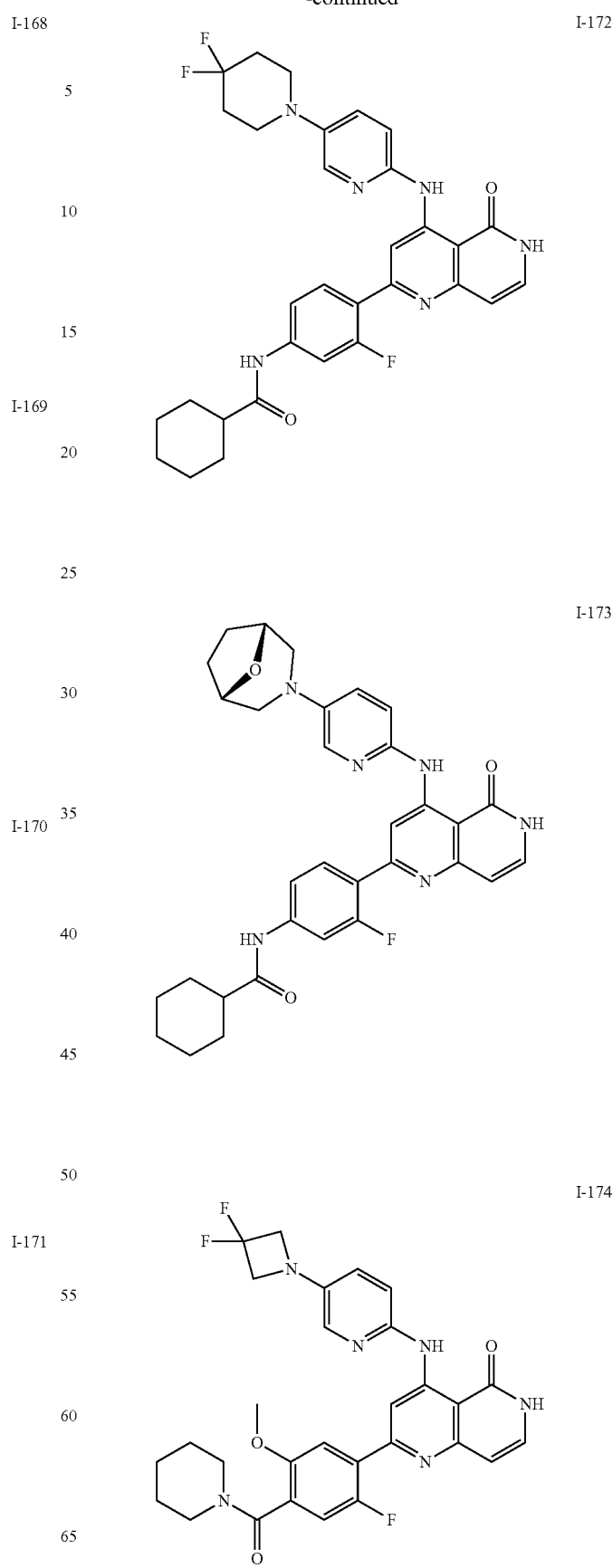

-continued
I-175
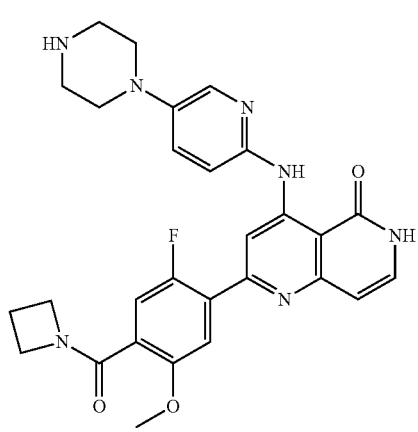
I-176
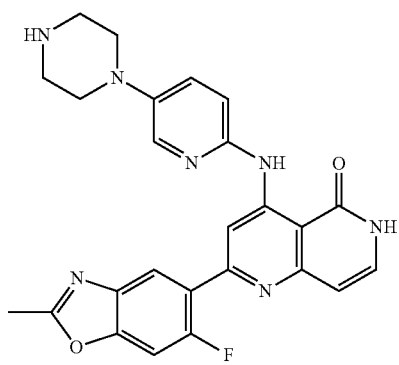
I-177
-continued
I-178
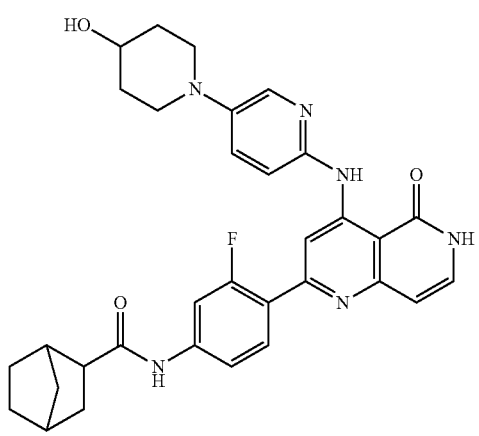
I-179
I-180
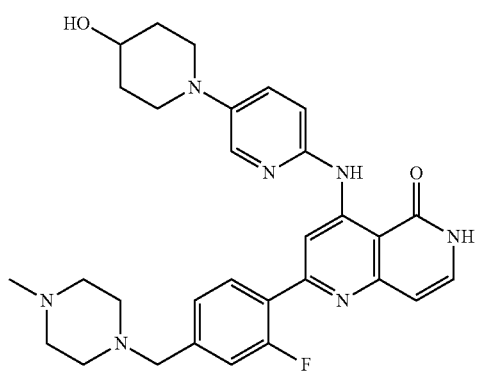
I-181
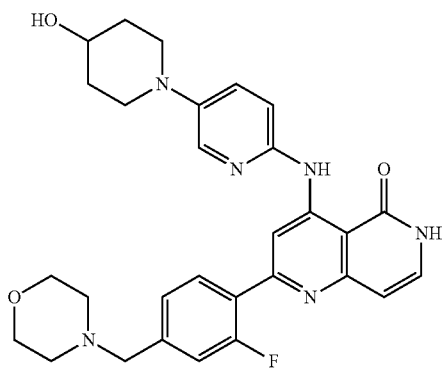

I-182
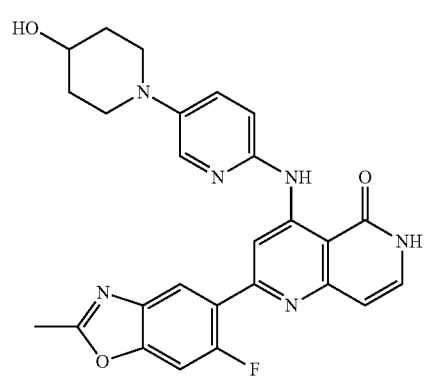
I-183
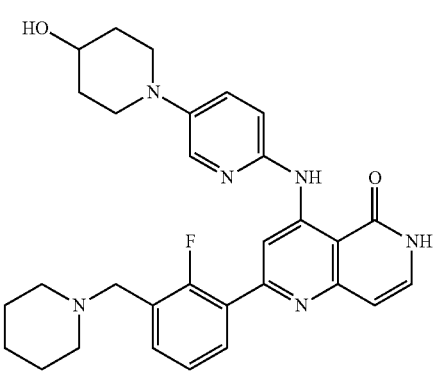
I-184
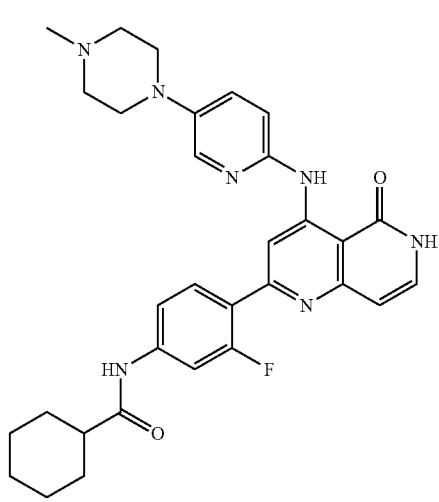
I-185
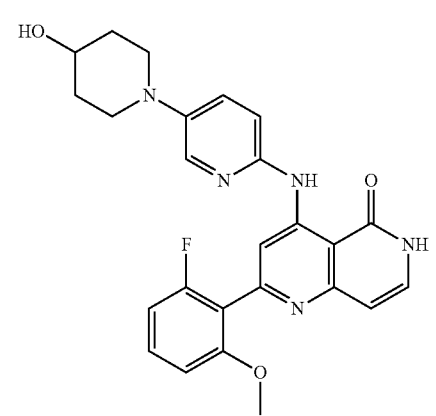
I-186
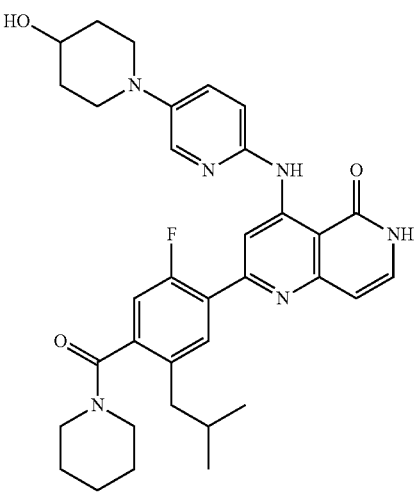
I-187
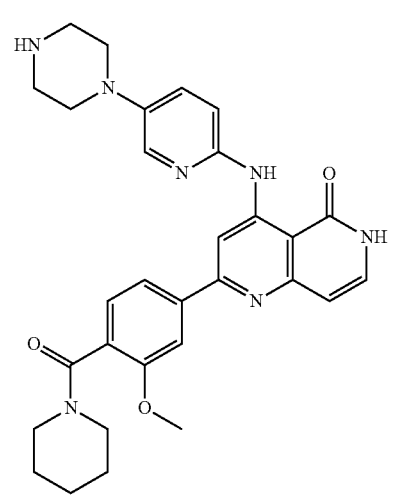
I-188
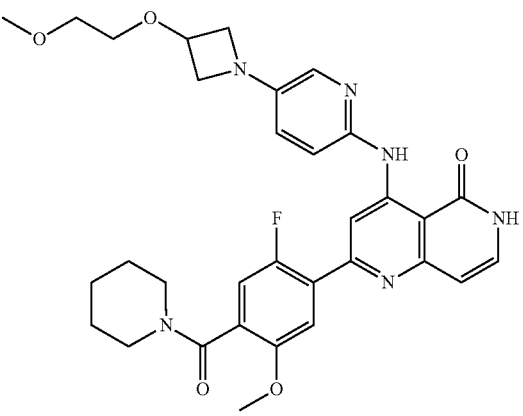

I-189
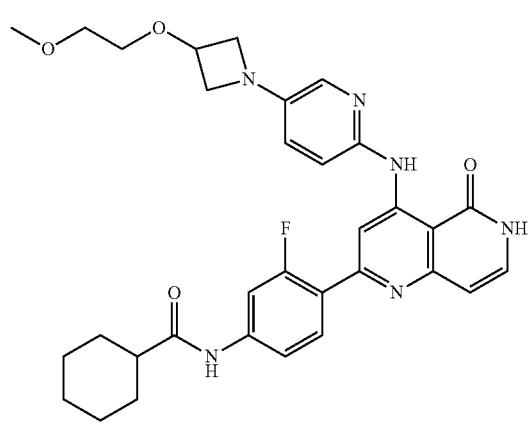
I-190
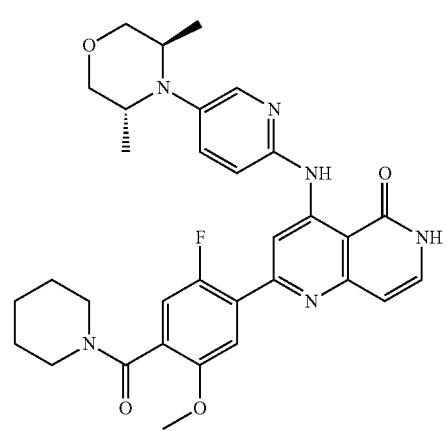
I-191
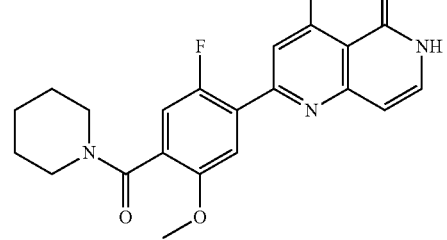
I-192
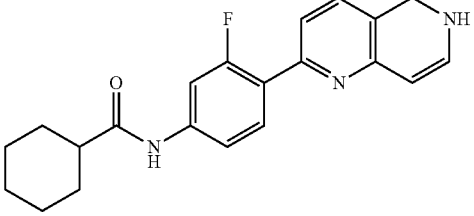
I-193
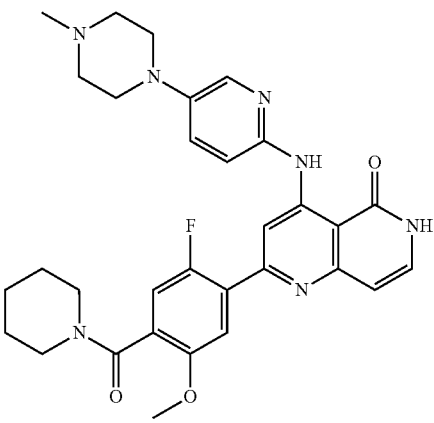
I-194
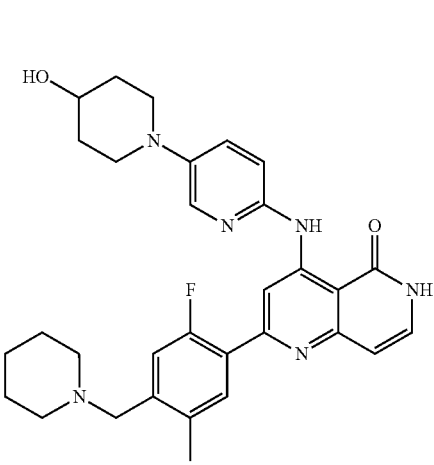
I-195
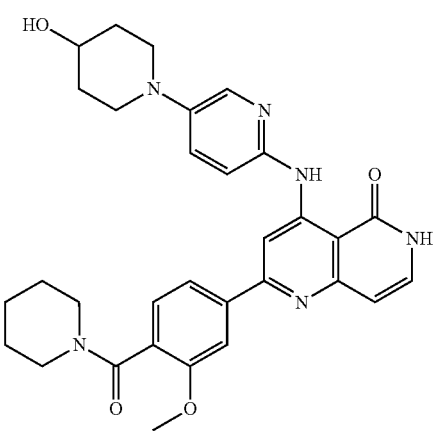

I-196
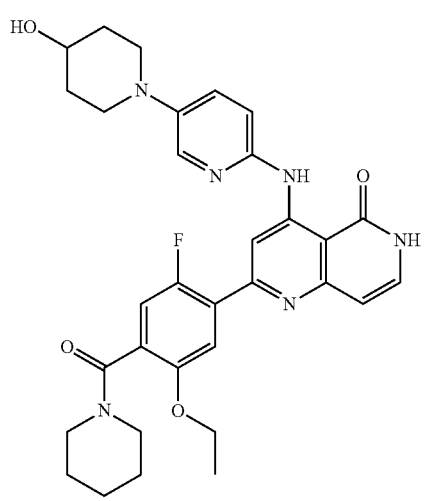
I-197
I-198
I-199
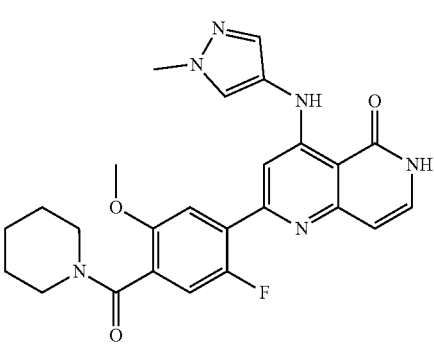
I-200
I-201
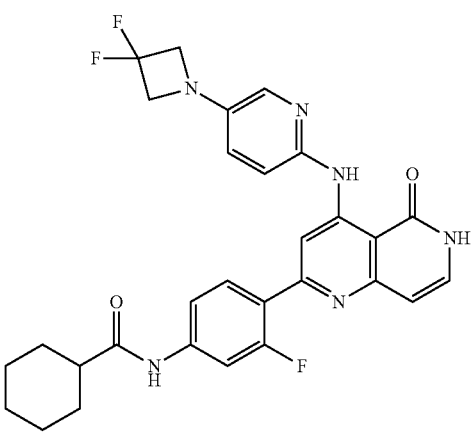
I-202
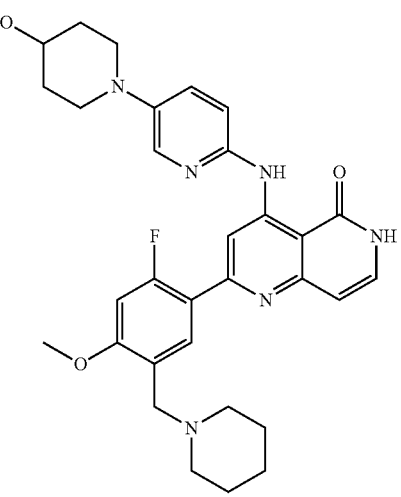

I-203
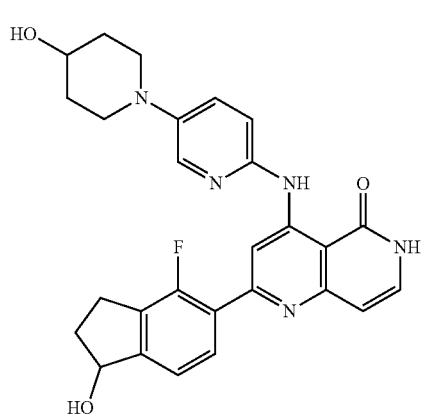
I-206
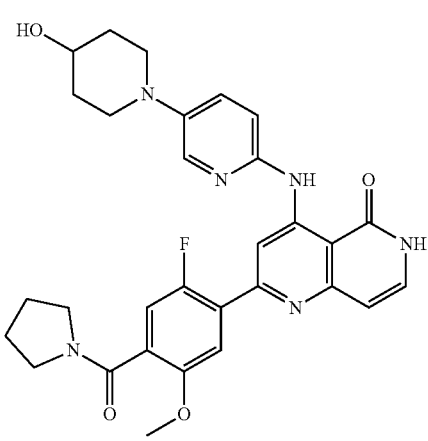
I-204
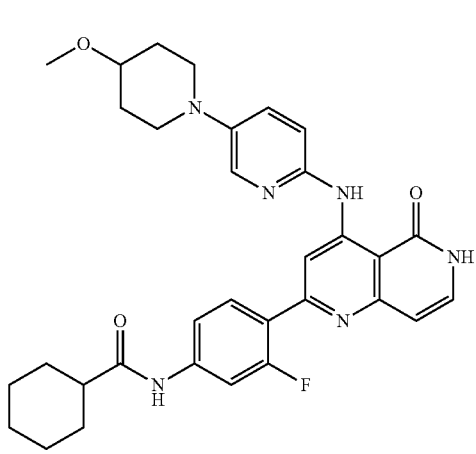
I-207
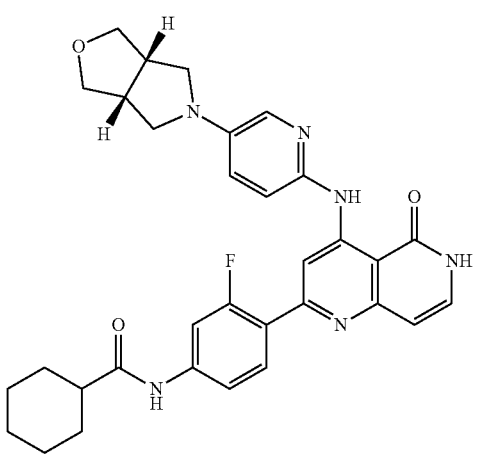
I-205
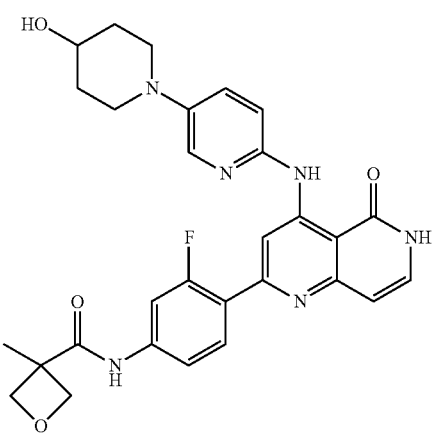
I-208
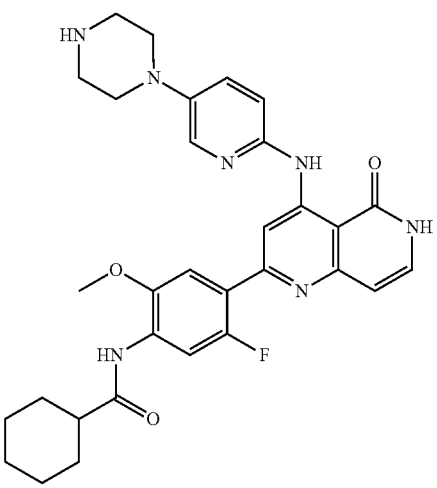

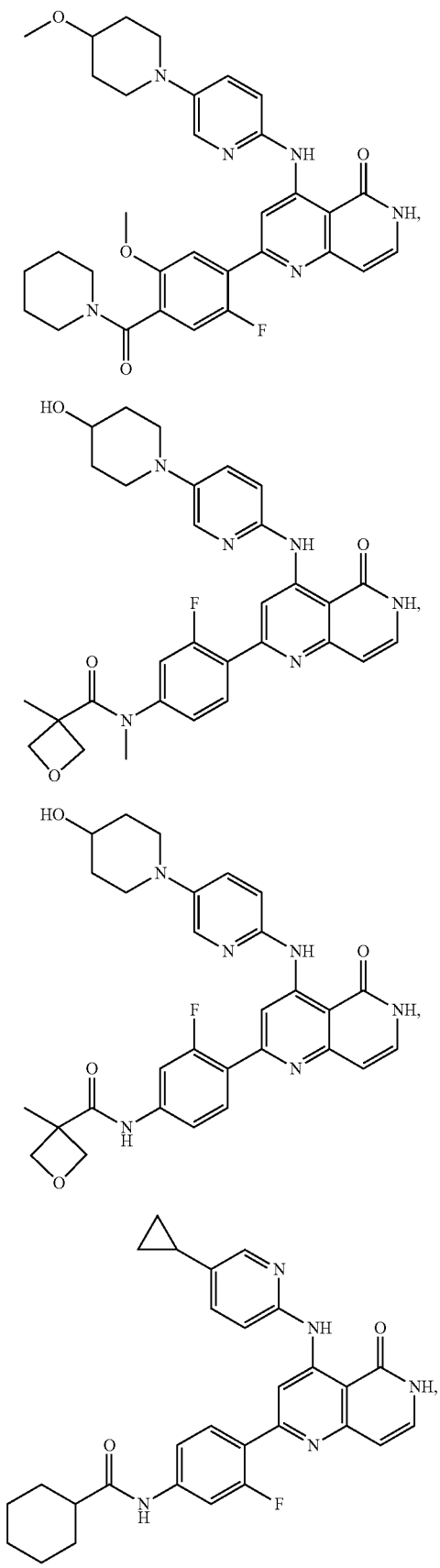
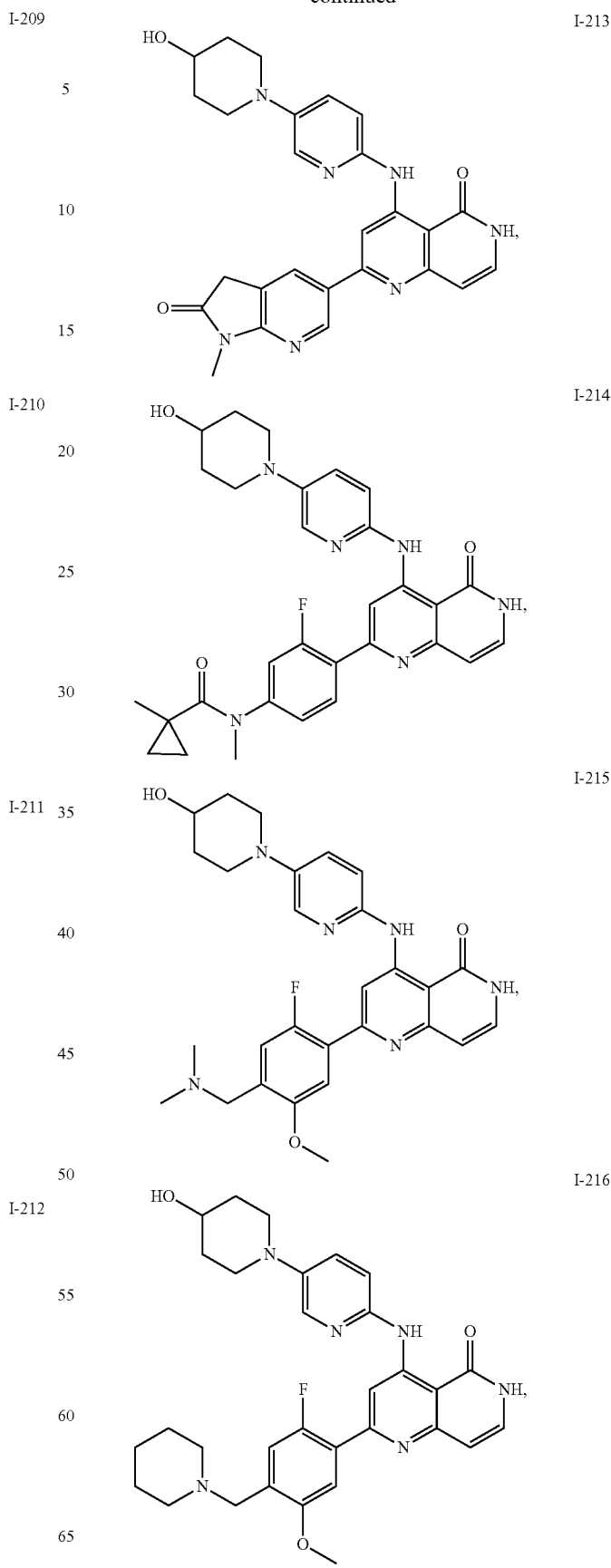

I-217
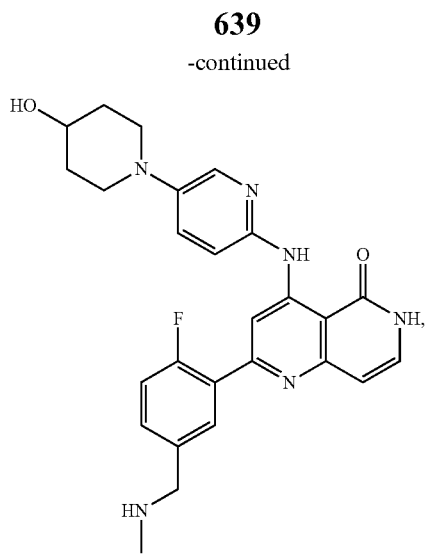
I-220
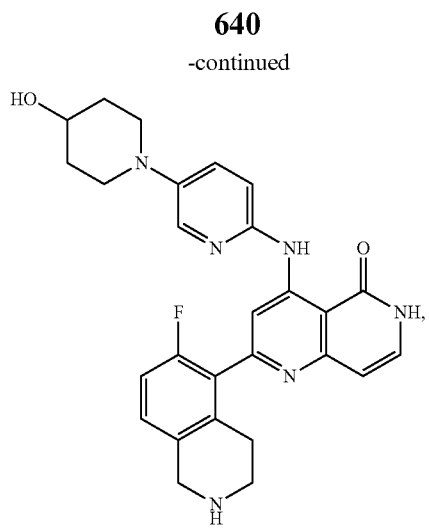
I-218
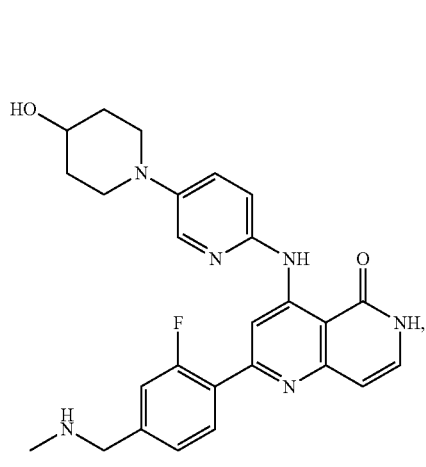
I-221
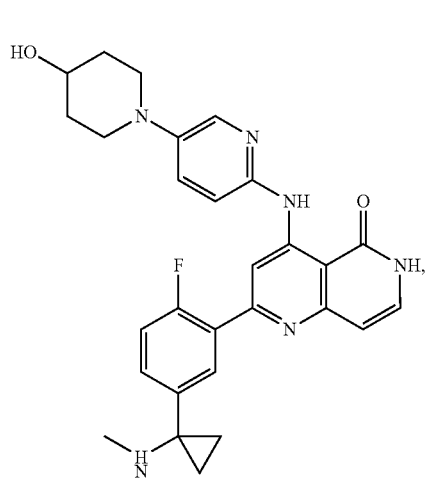
I-219
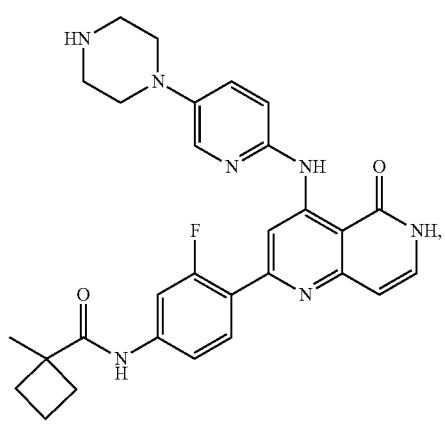
I-222
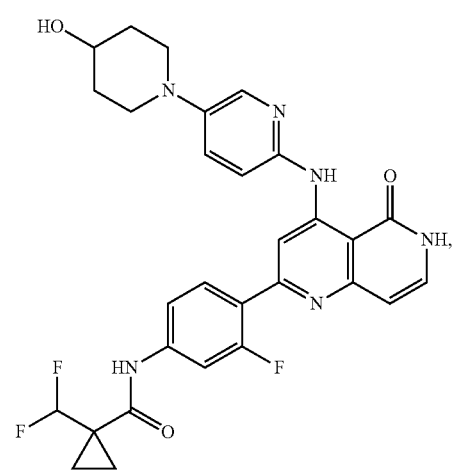

I-223
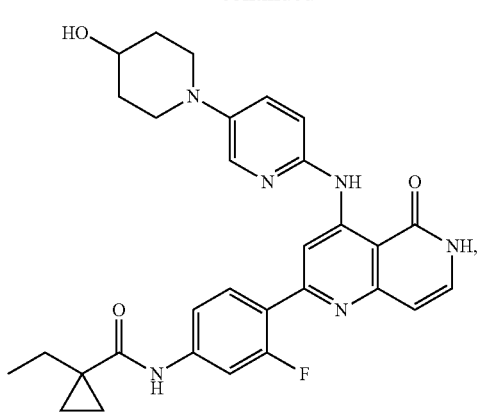
I-224
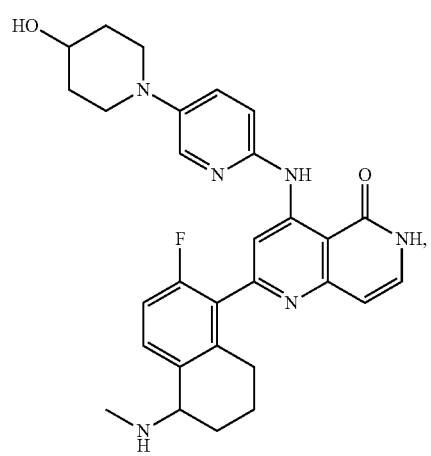
I-225
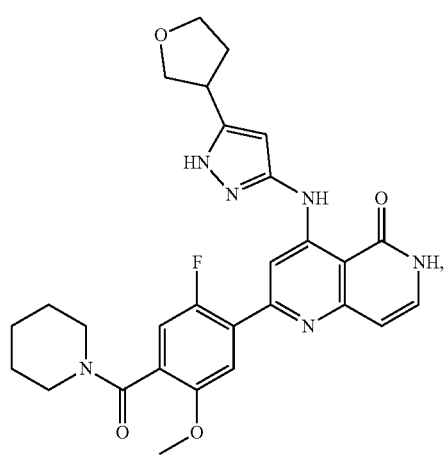
I-226
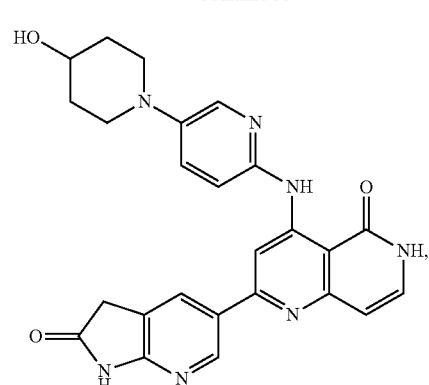
I-227
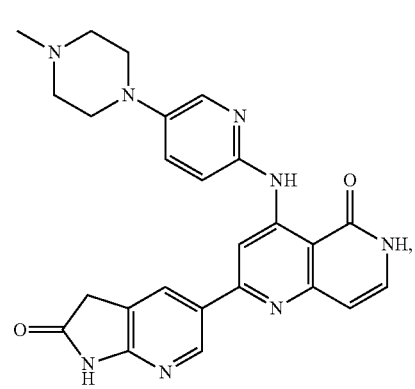
I-228
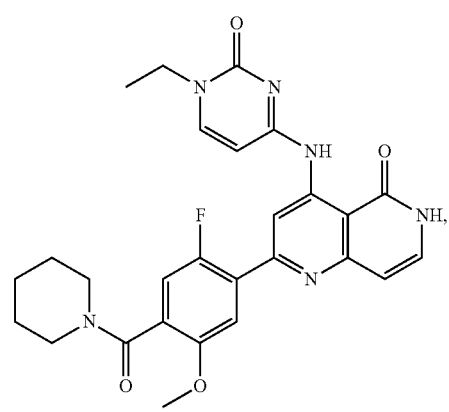
I-229
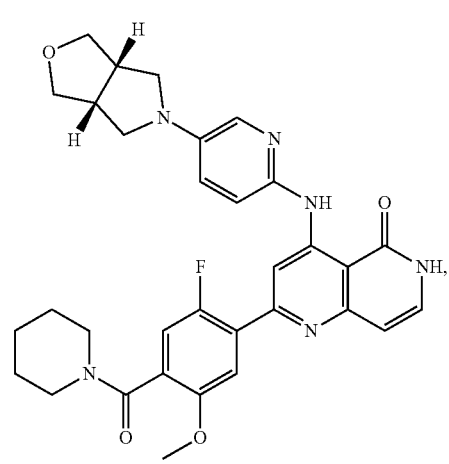

I-230

I-231

I-232

I-233

I-234

I-235

I-236

-continued
I-237
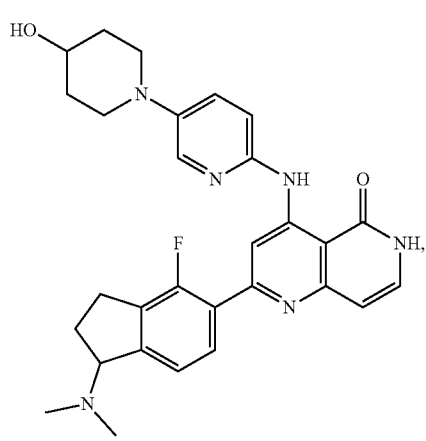
I-238
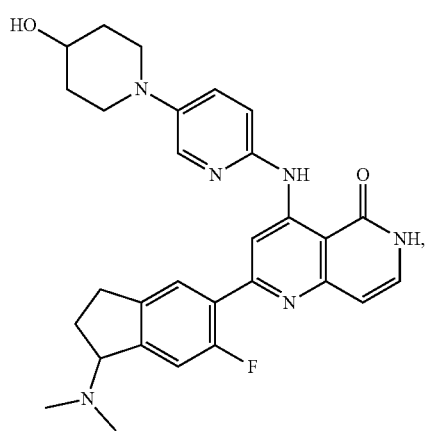
I-239
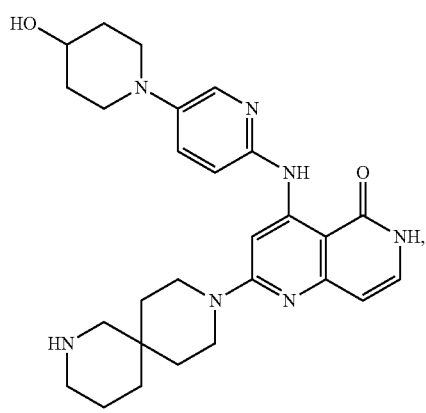
-continued
I-240
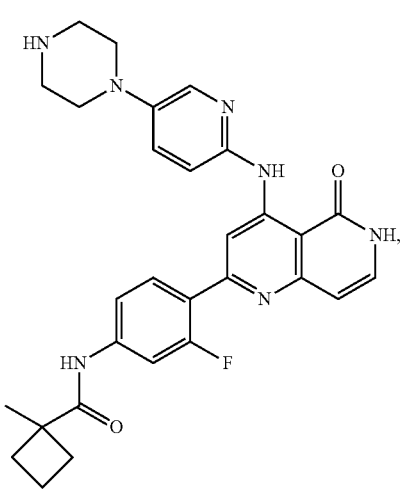
I-241
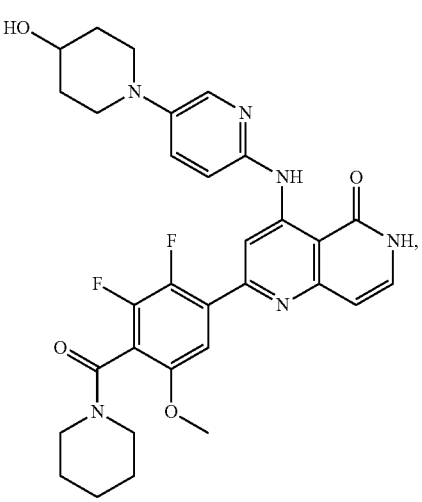
I-242
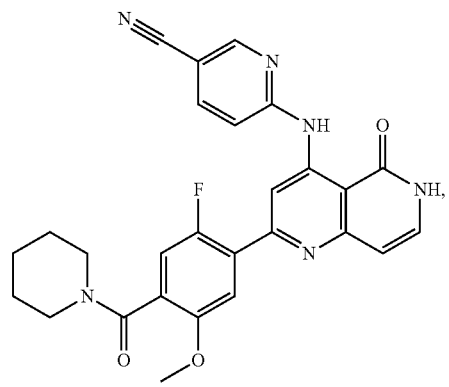

I-243
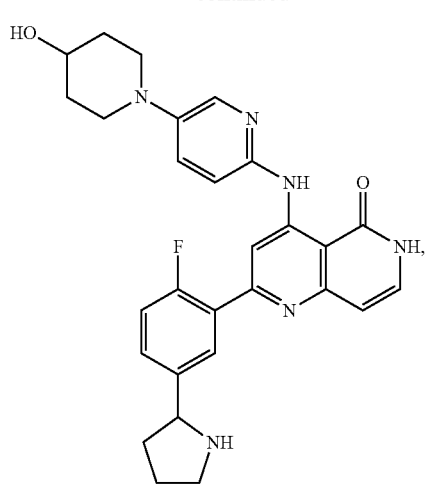
I-244
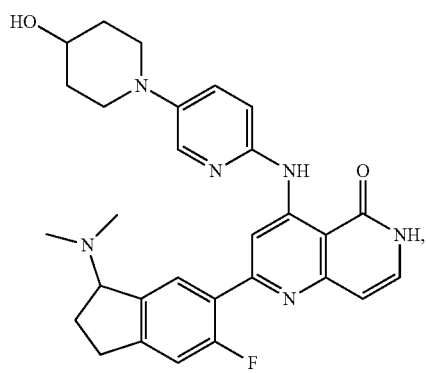
I-245
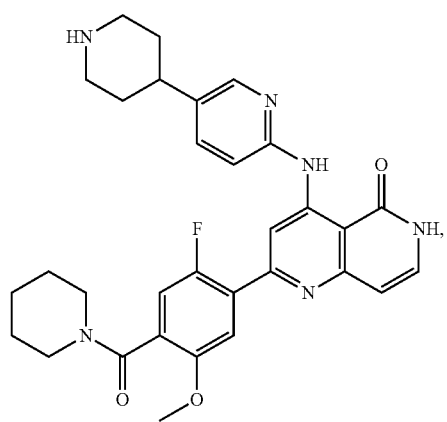
I-246
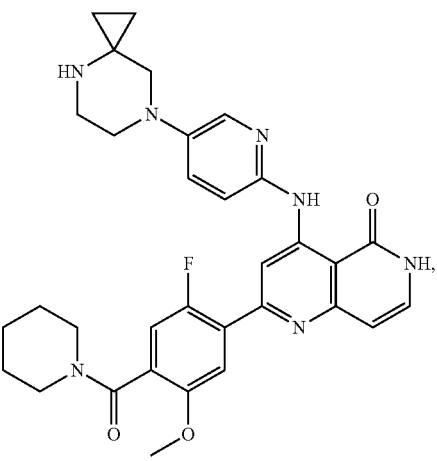
I-247
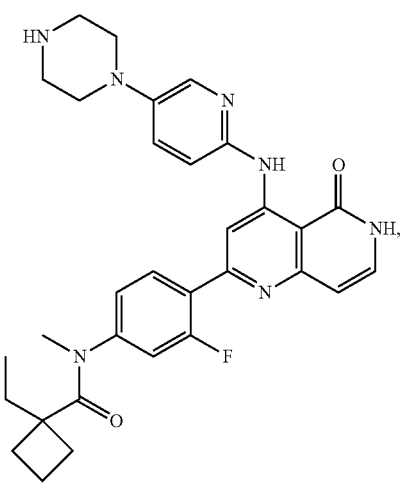
I-248
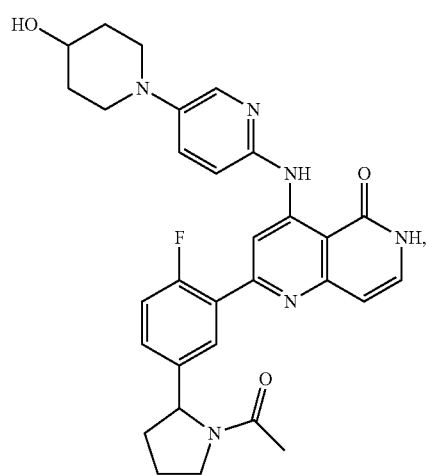

I-249
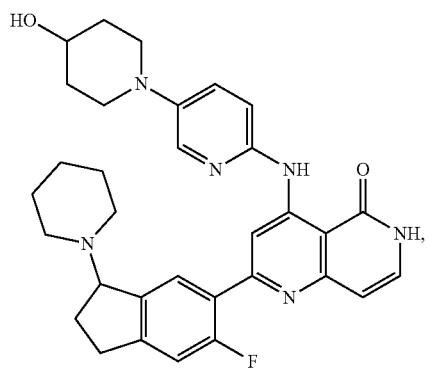
I-252
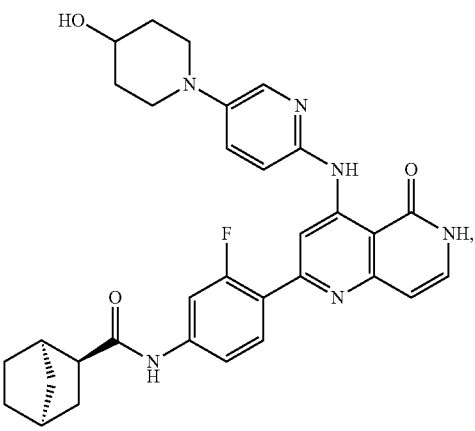
I-250
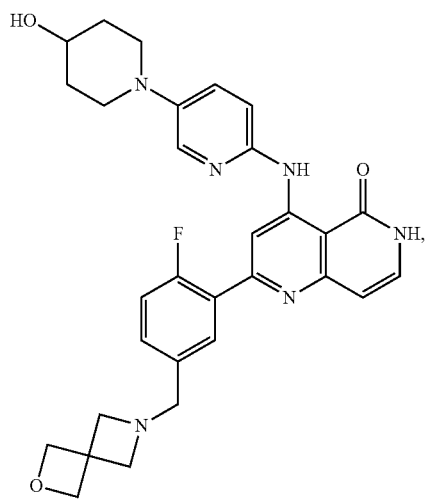
I-253
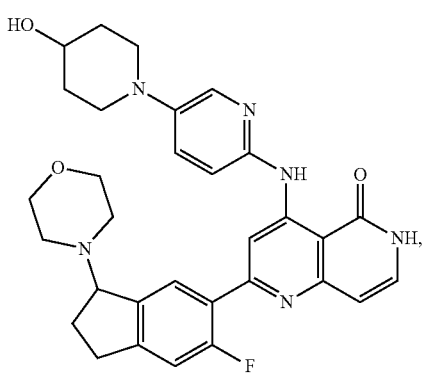
I-251
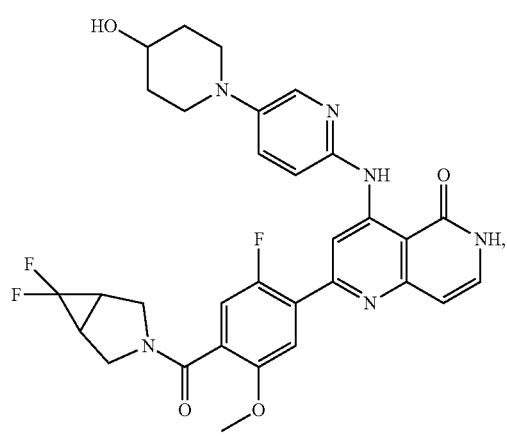
I-254
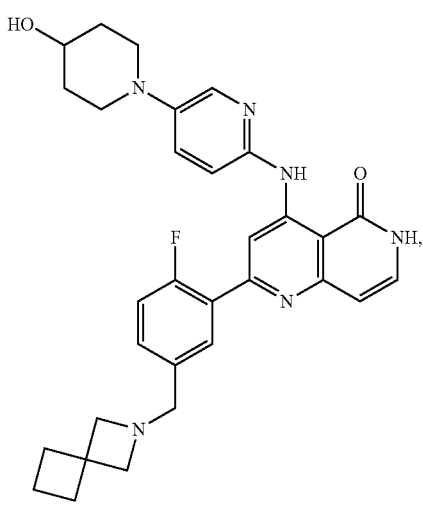

I-255
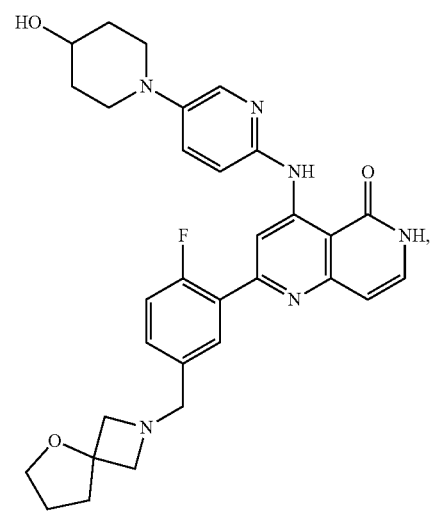
I-256
I-257
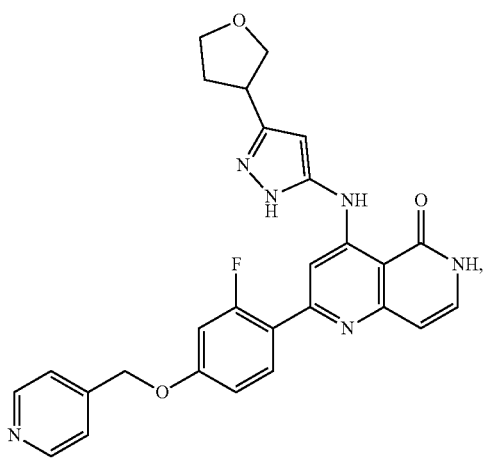
I-258
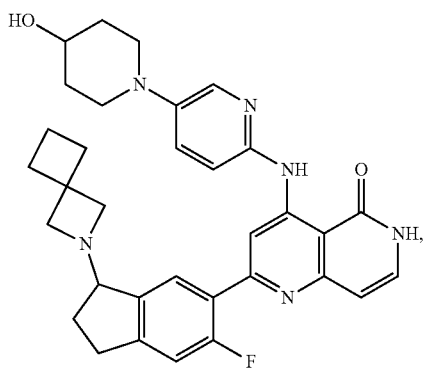
I-259
I-260
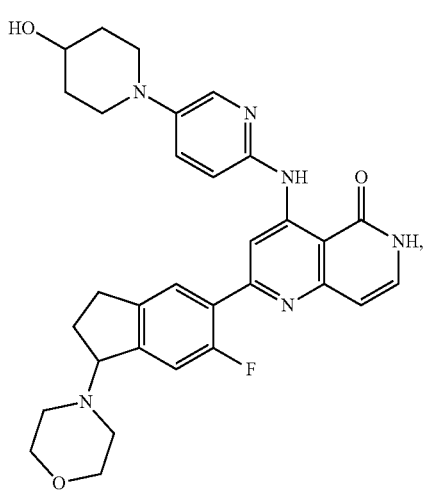
I-261
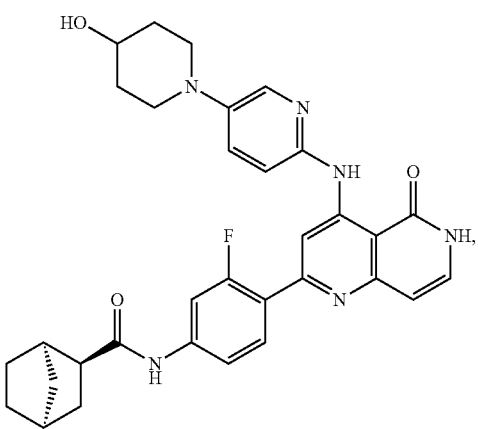

I-262 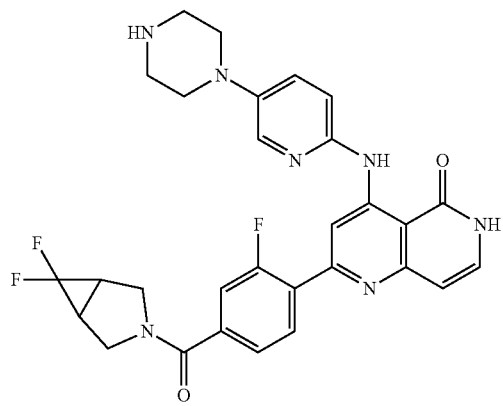
I-265 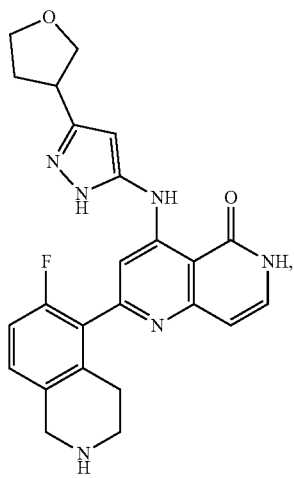
I-263 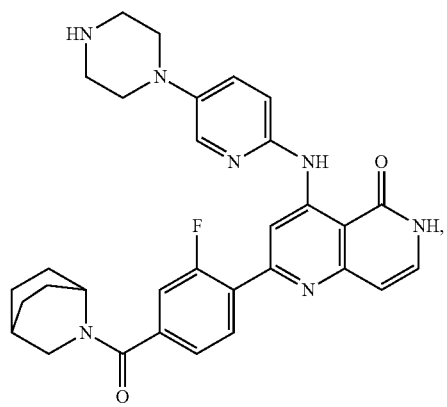
I-266 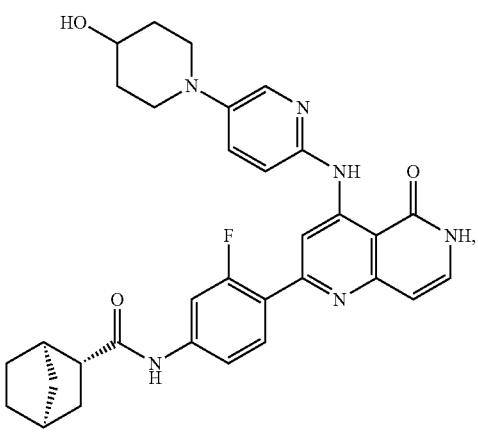
I-264 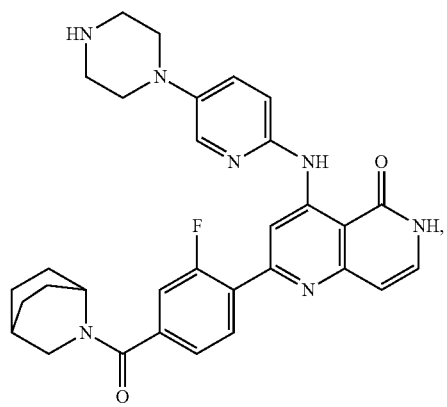
I-267 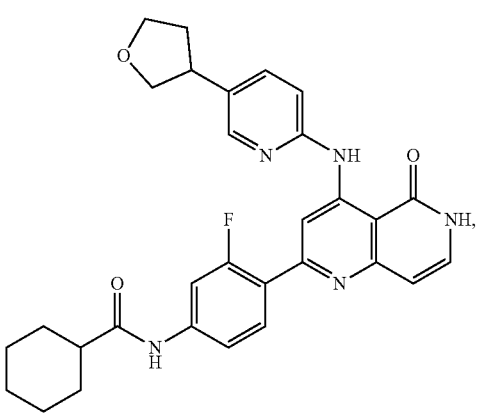

I-268
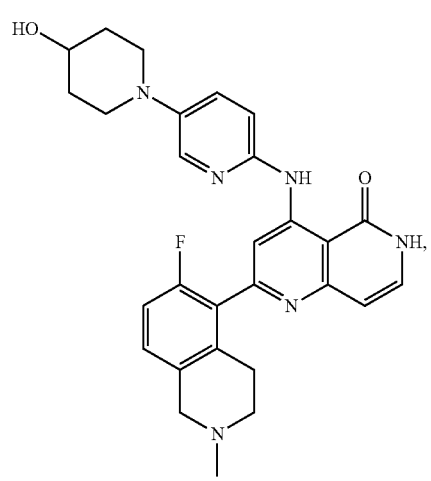
I-269
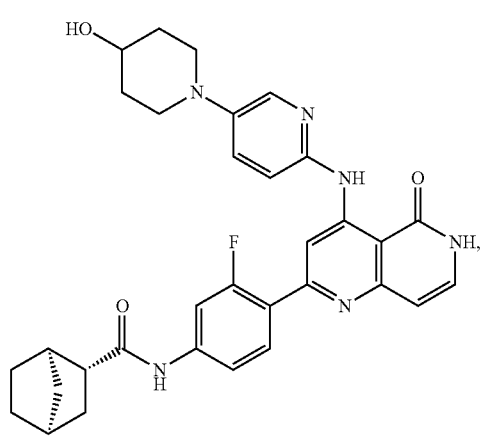
I-270
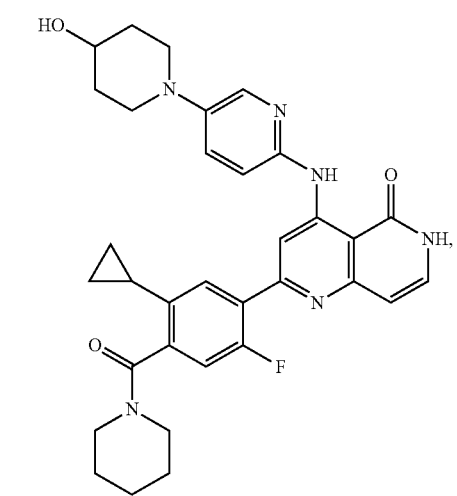
I-272
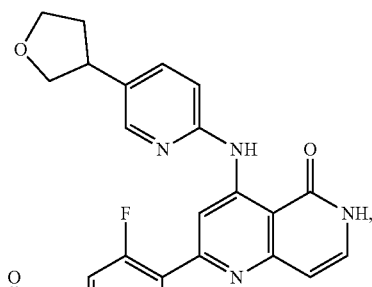
I-273
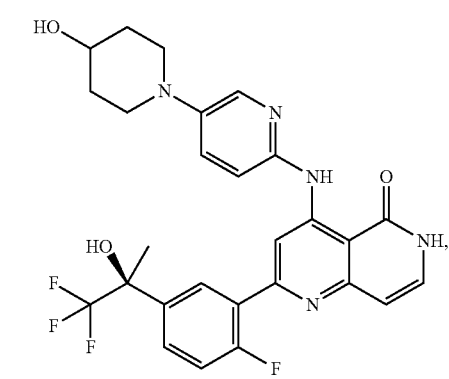
I-274
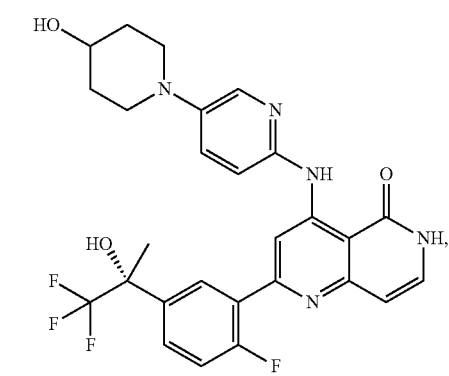
I-275
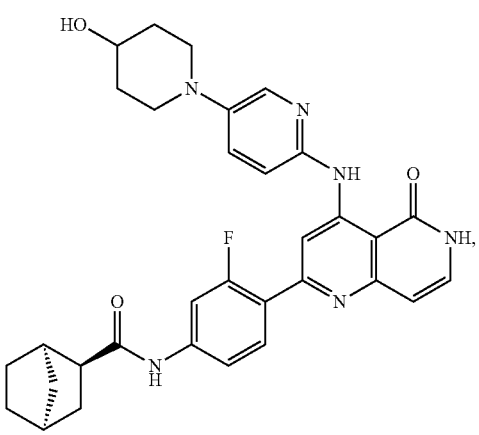

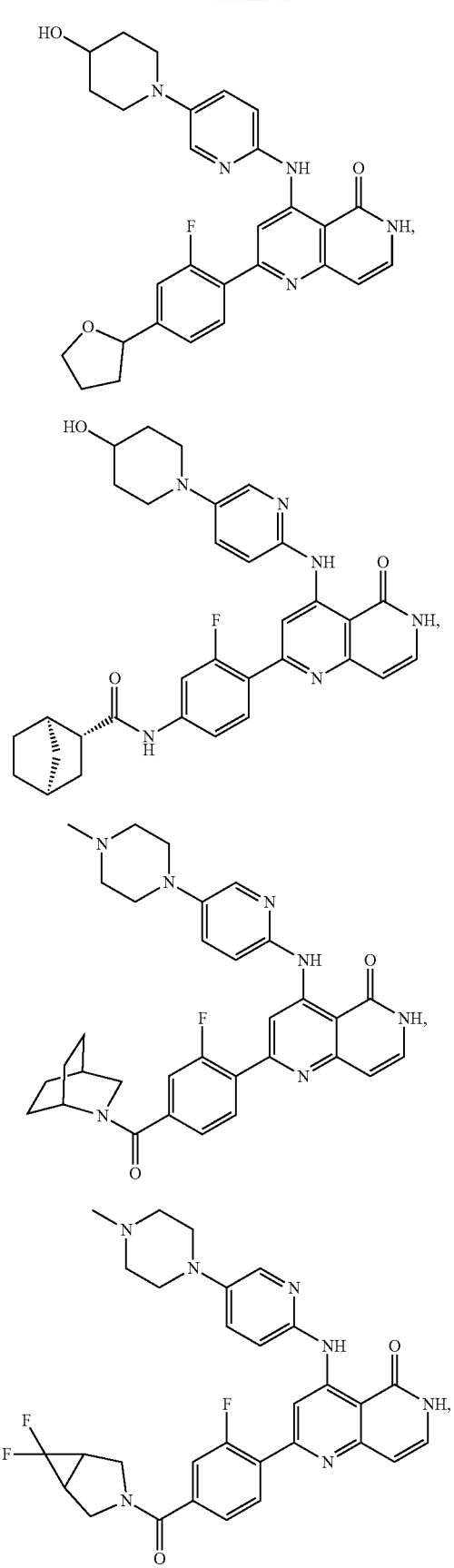
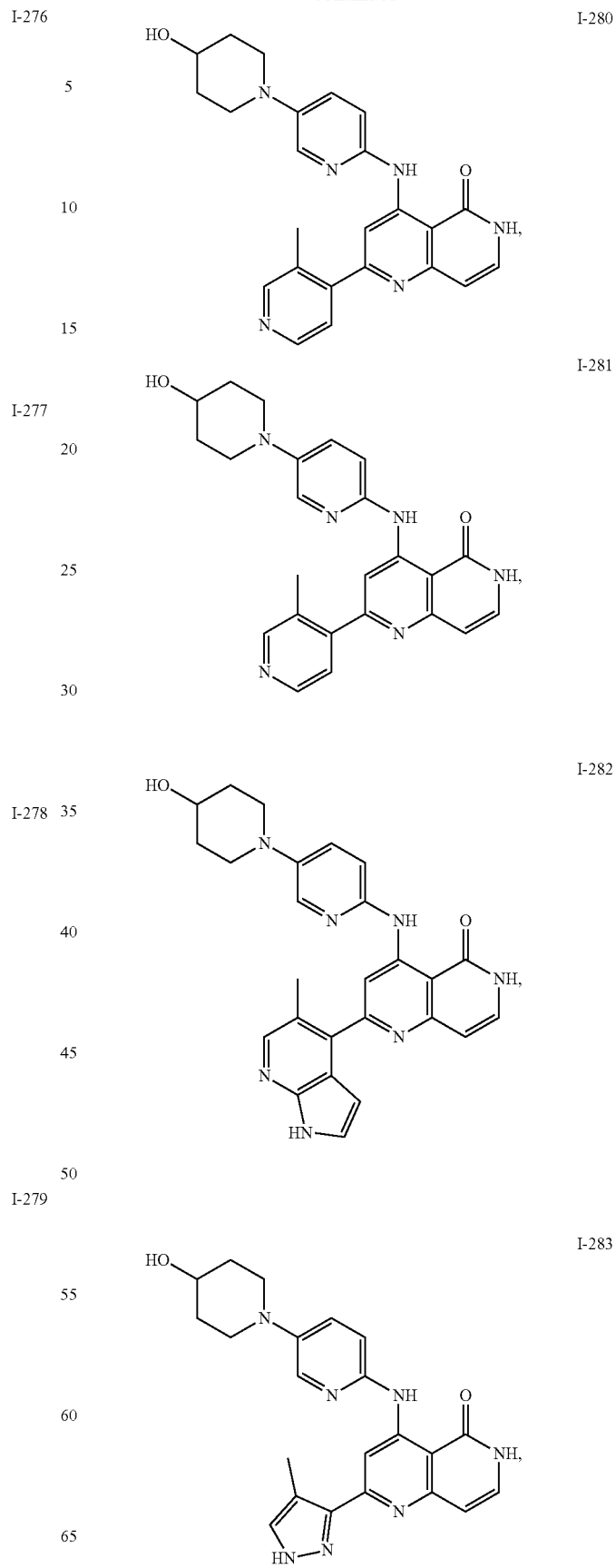

-continued
I-284
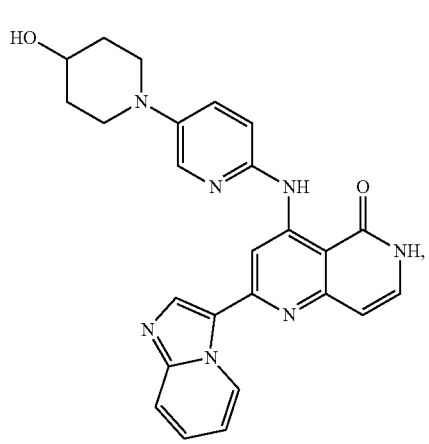
I-285
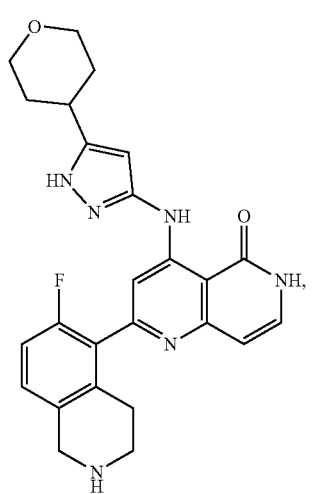
I-286
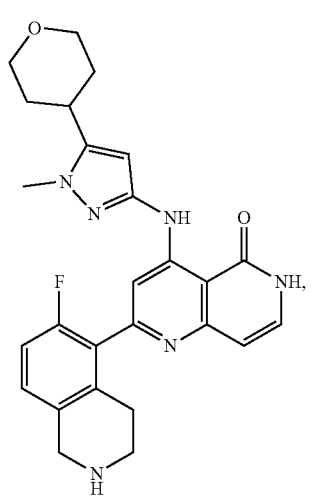
-continued
I-287
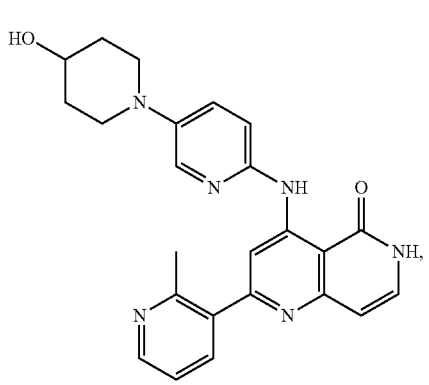
I-288
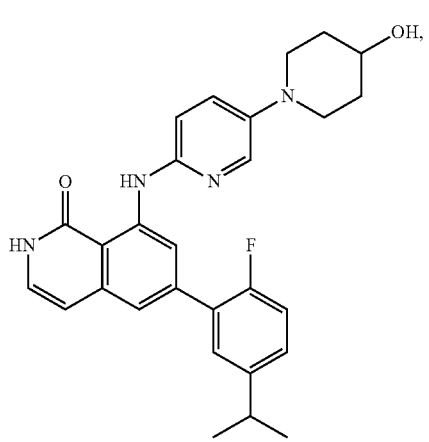
I-289
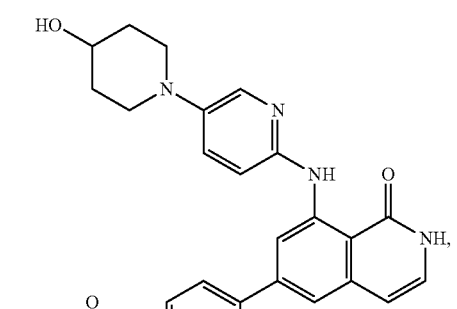
I-290
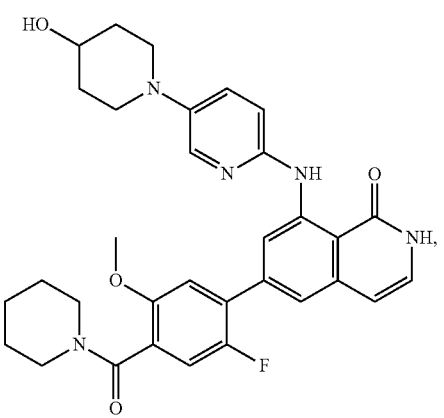

I-291
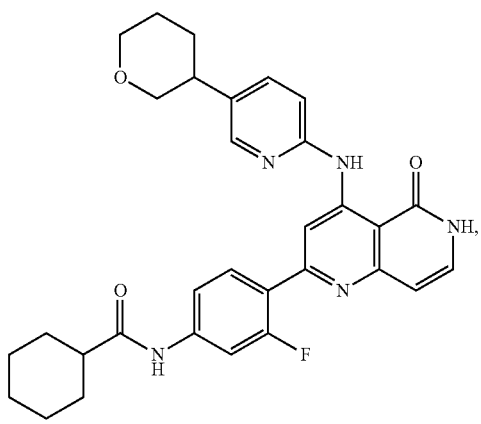
I-294
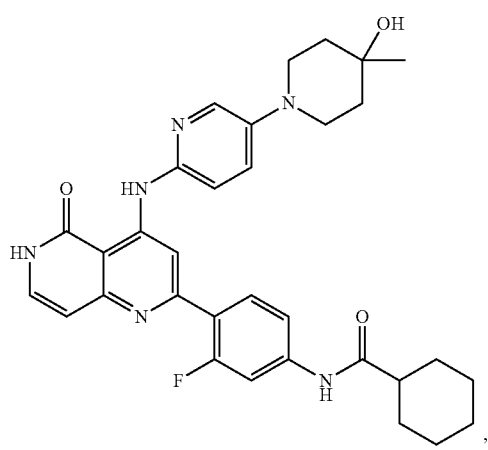
I-292
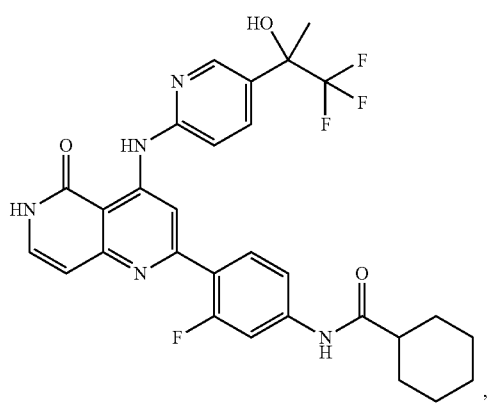
I-295
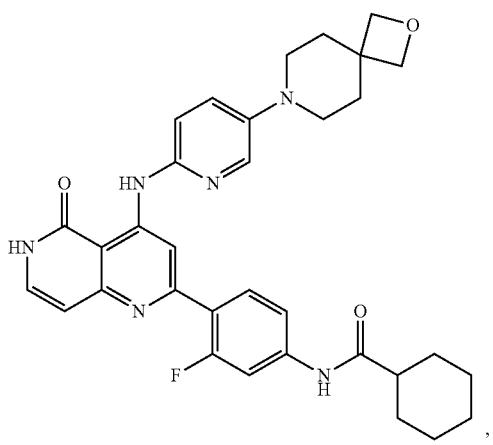
I-293
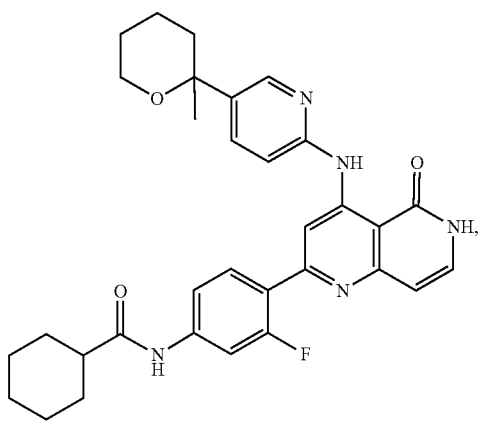
I-296
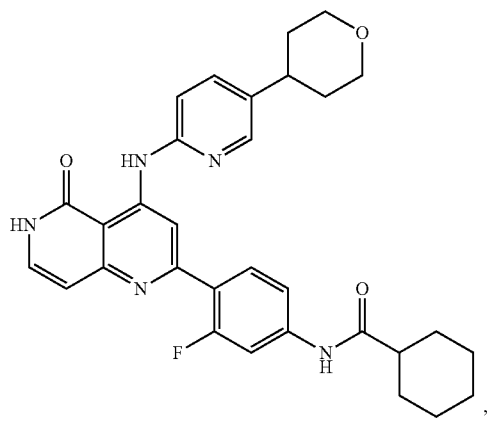

I-297
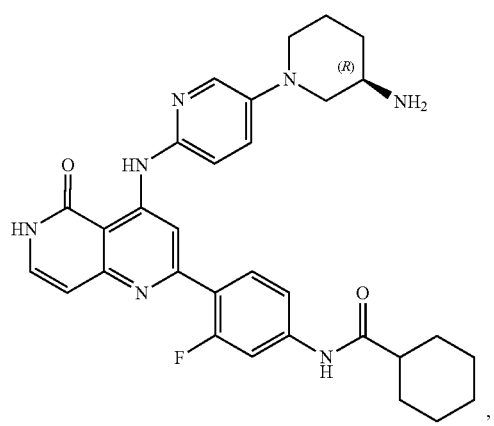
I-300
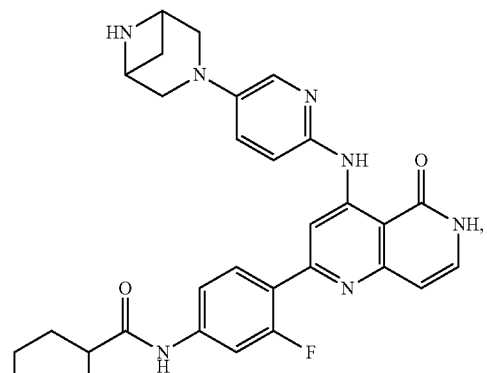
I-298
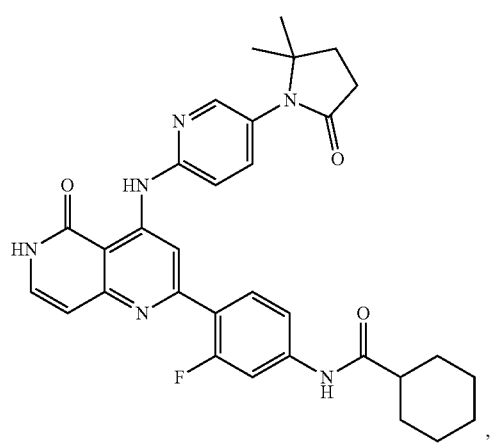
I-301
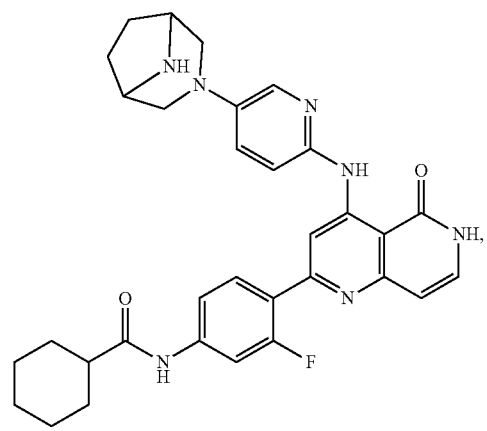
I-299
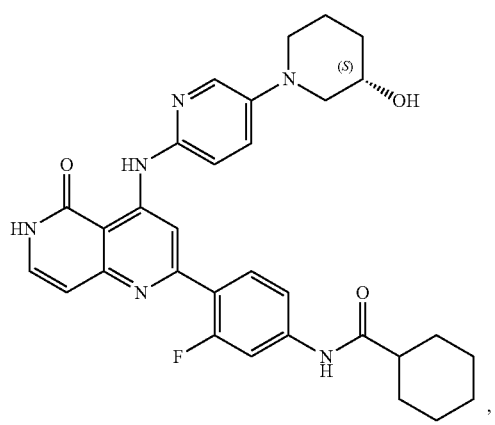
I-302
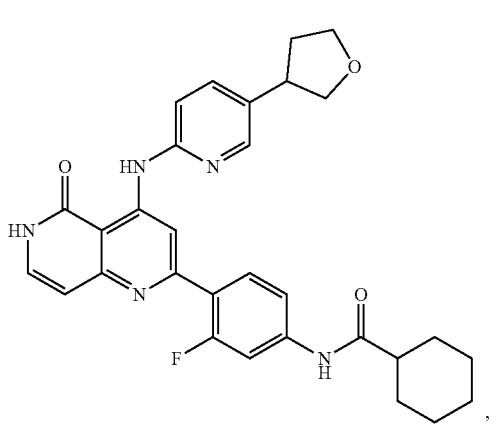

I-303
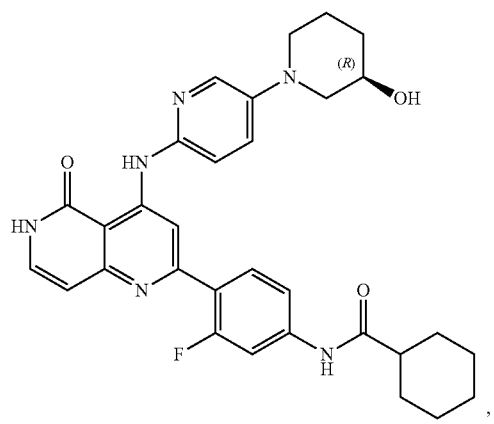
I-304
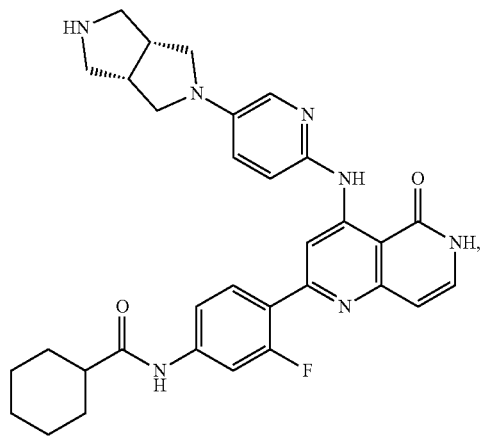
I-305
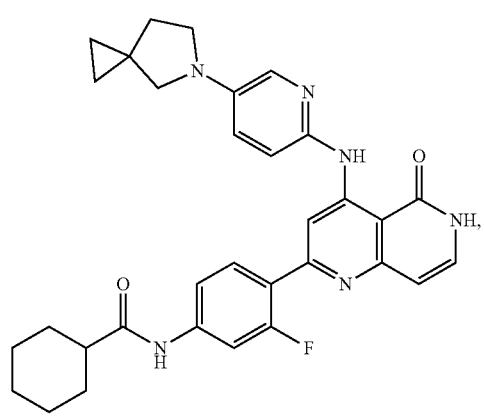
I-306
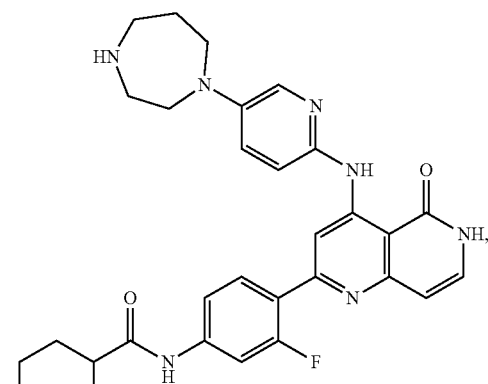
I-307
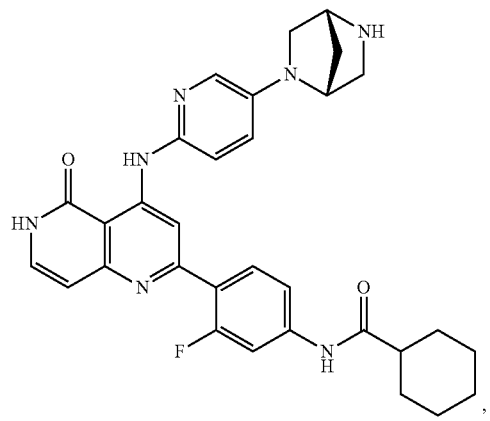
I-308
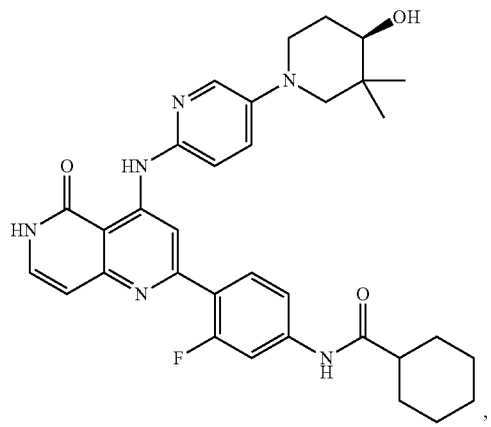

I-309
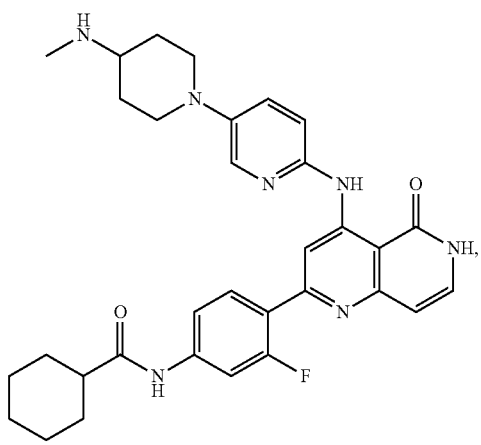
I-310
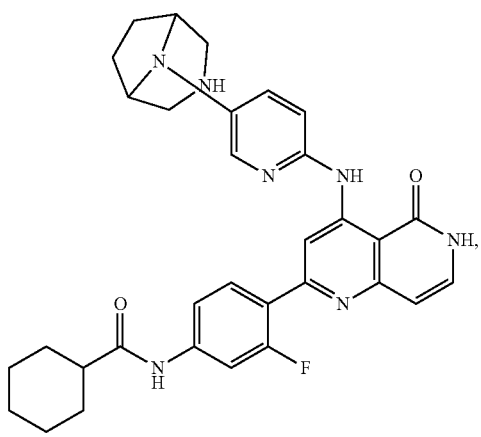
I-311
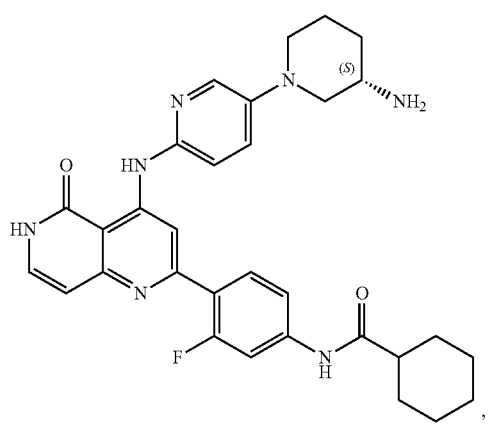
I-313
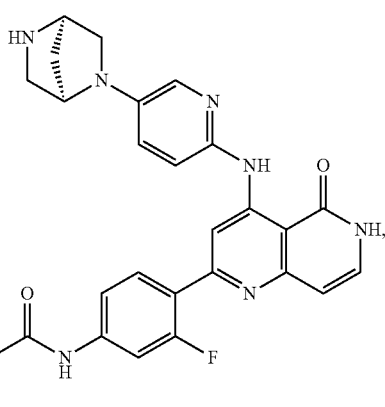
I-314
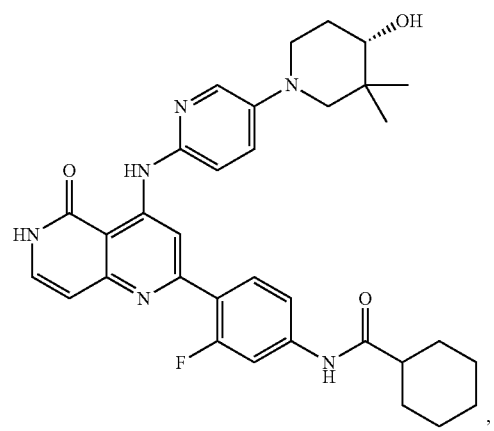
I-315
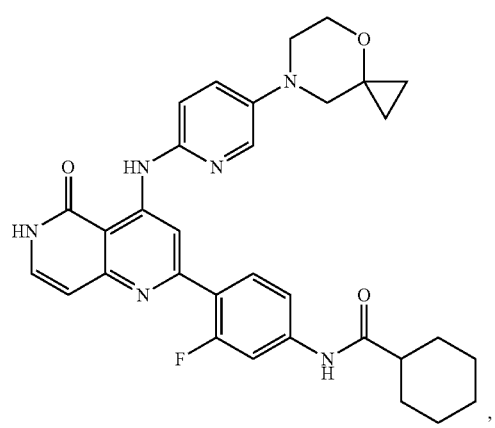

I-316
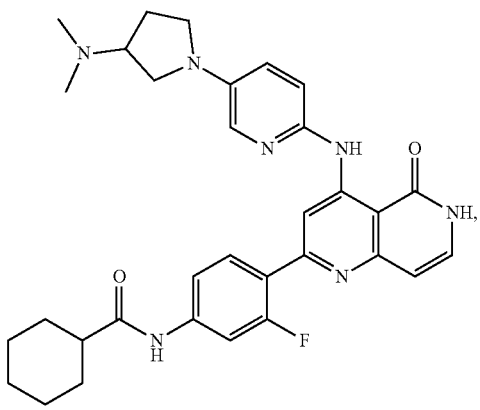
I-317
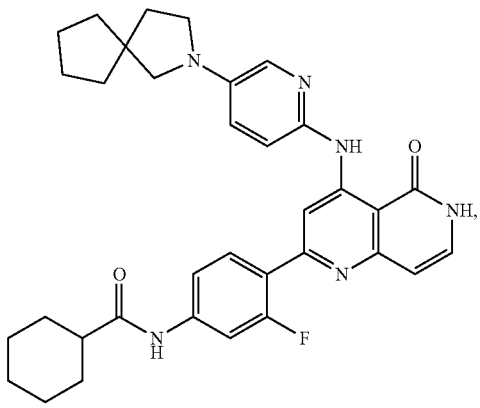
I-318
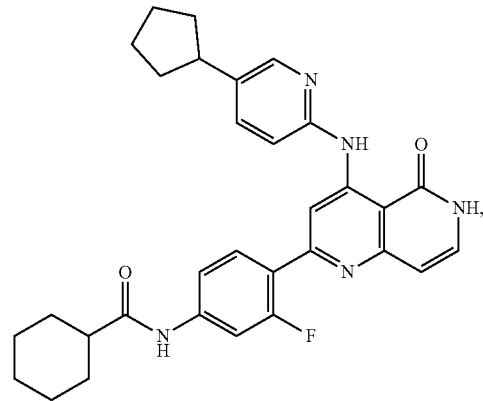
I-320
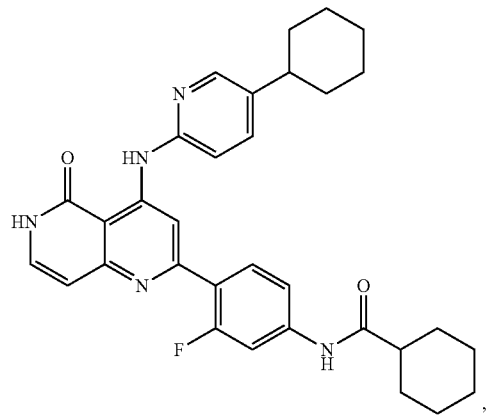
I-321
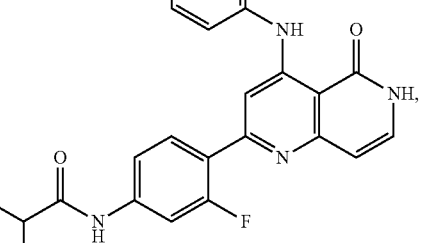
I-322
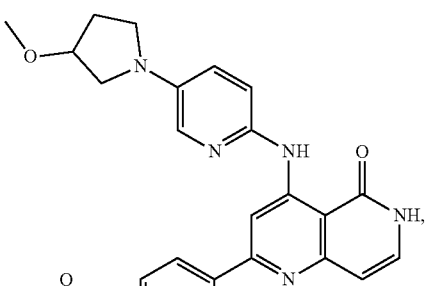
I-324

I-325
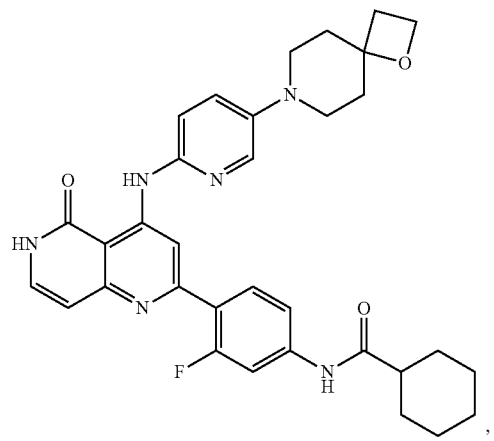
I-328
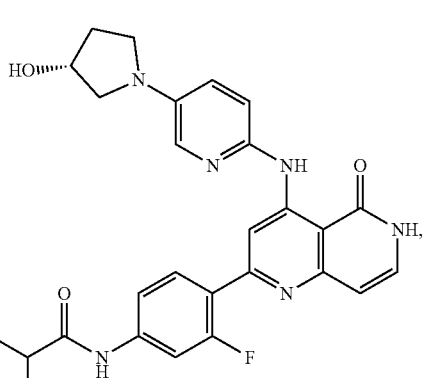
I-329
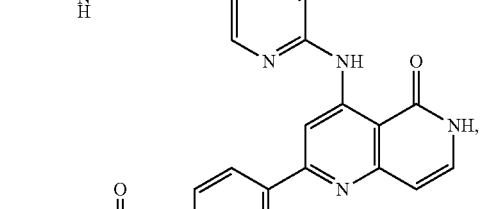
I-326
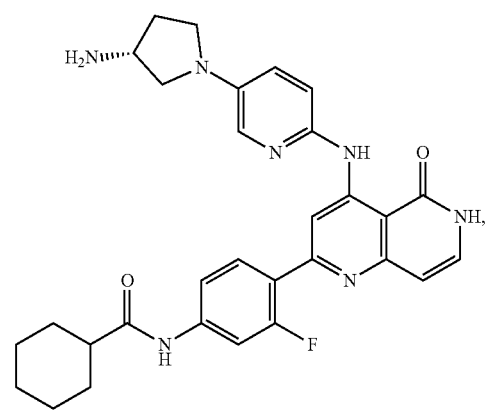
I-330
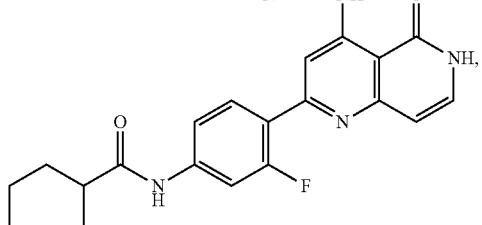
I-327
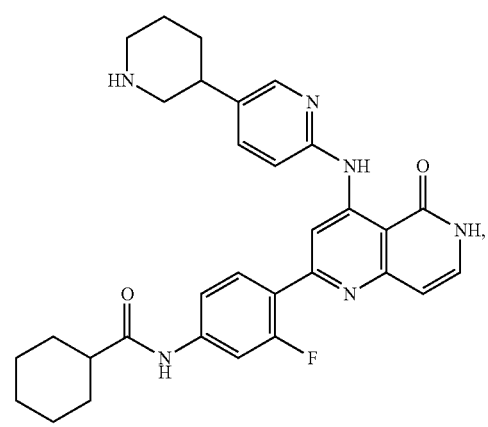
I-331
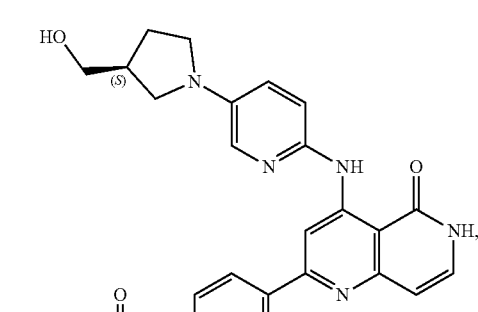

I-332
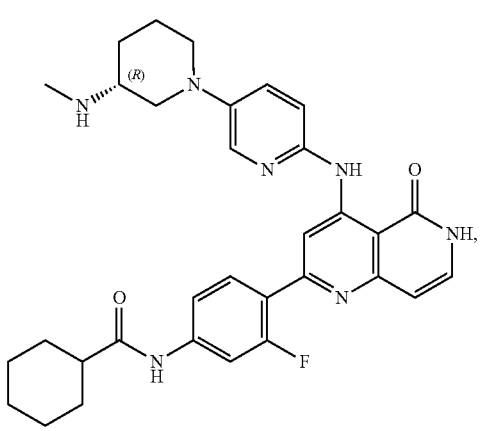
I-336
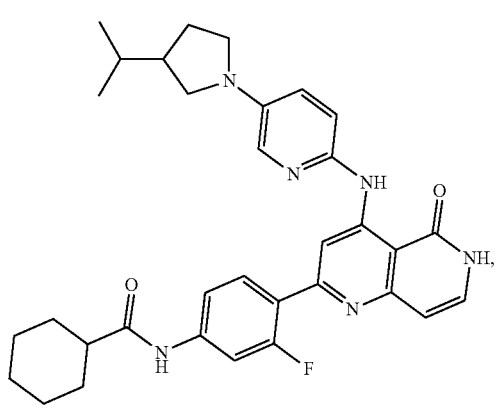
I-333
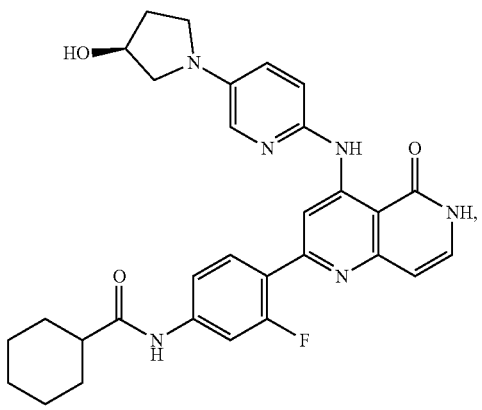
I-334
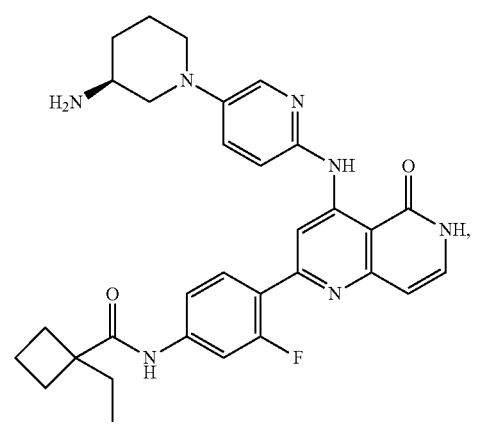
I-337
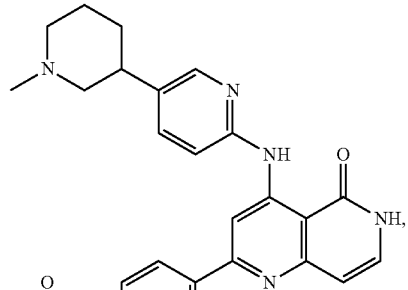
I-335
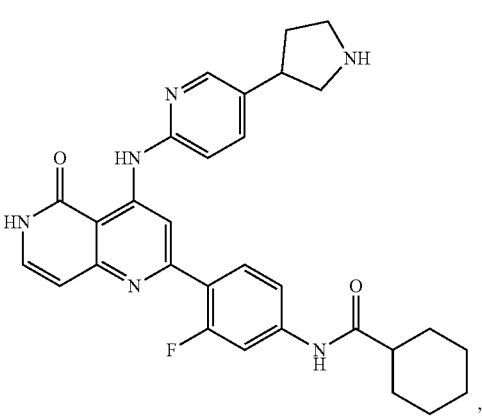
I-338
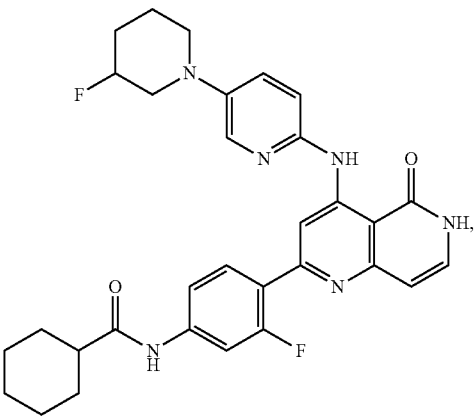

I-339
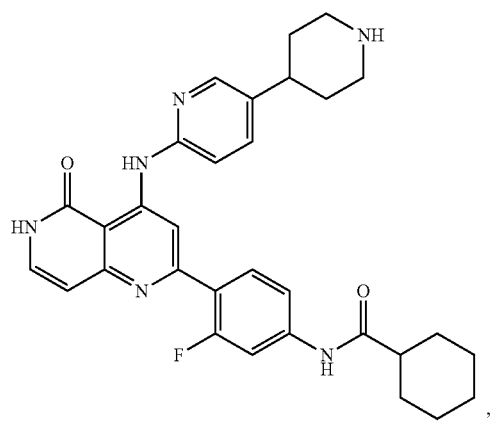
I-340
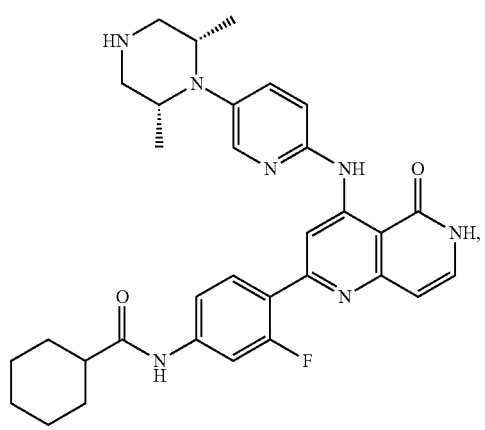
I-341
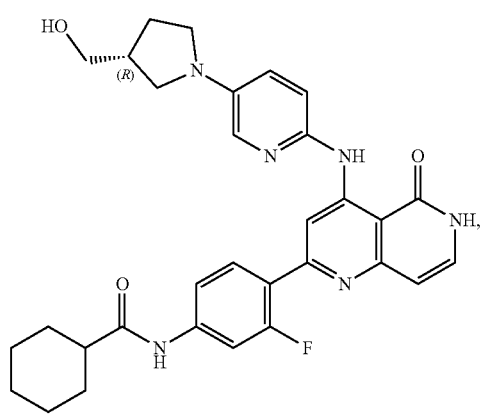
I-342
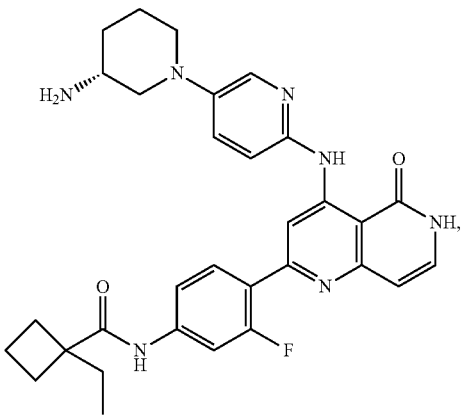
I-343
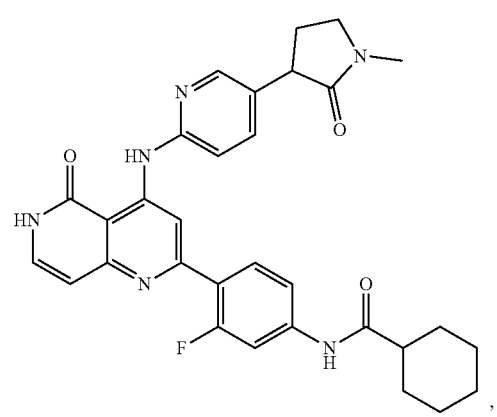
I-344
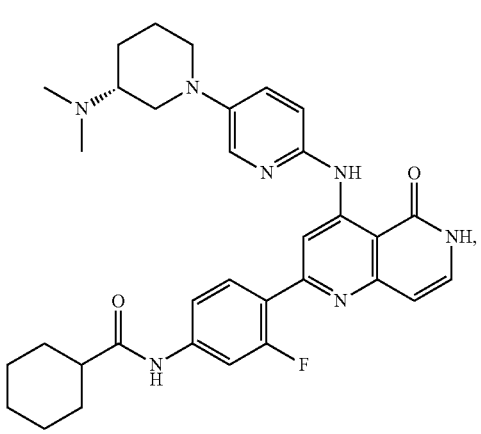

I-345
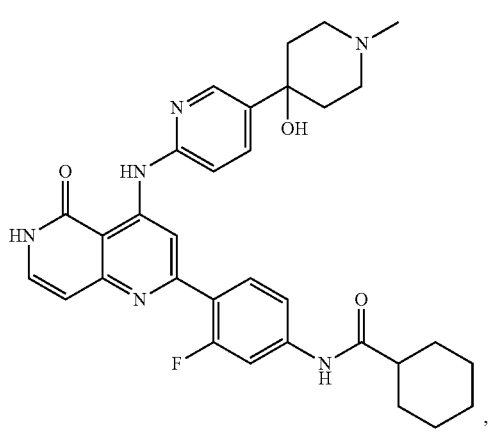
I-346
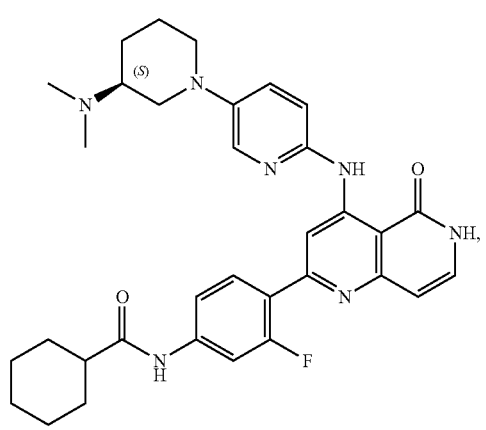
I-347
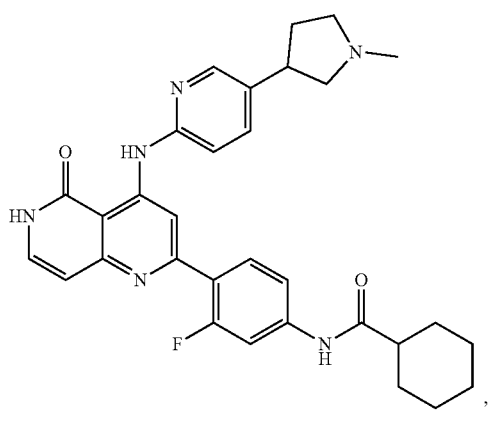
I-349
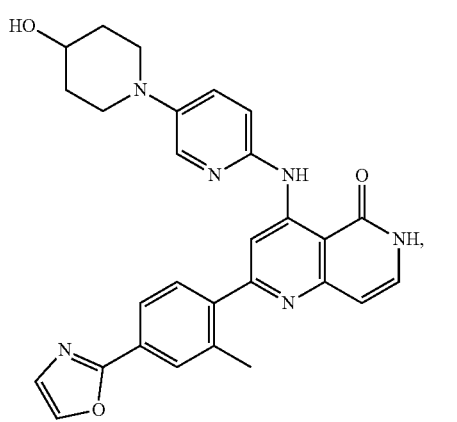
I-350
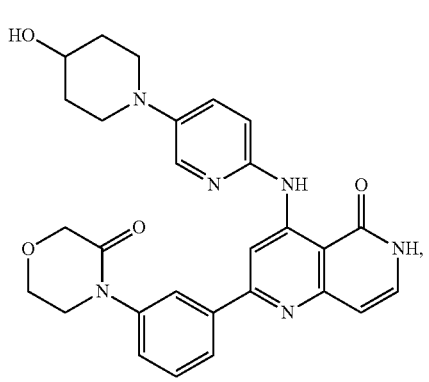
I-351
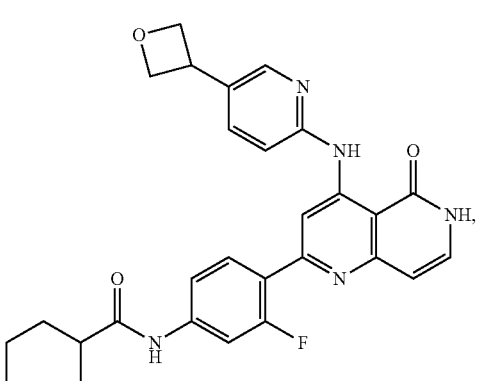
I-352
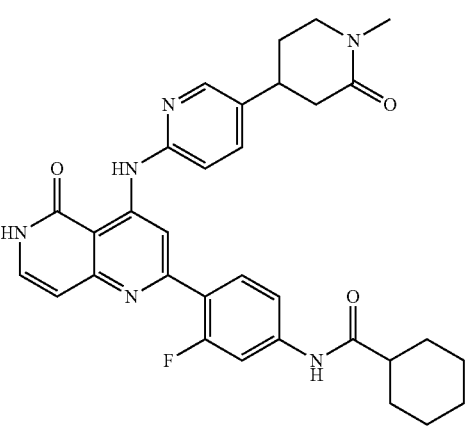
I-353
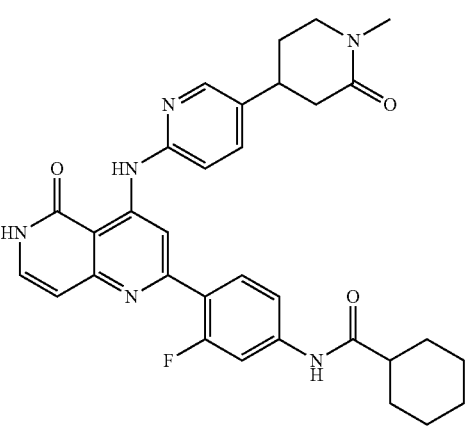

I-355
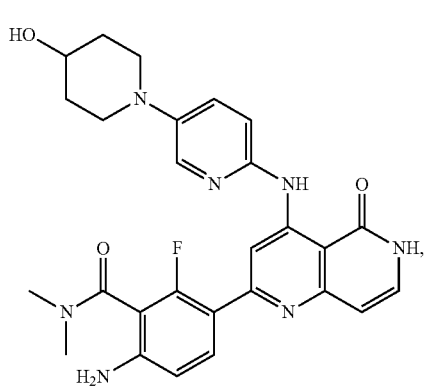
I-356
I-358
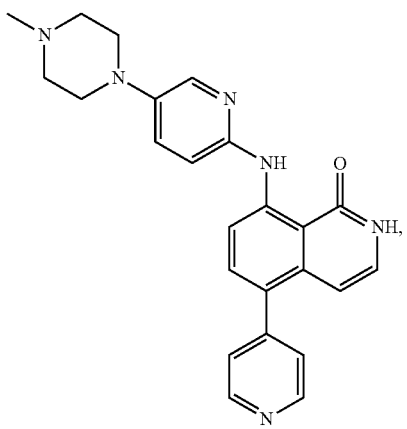
I-359
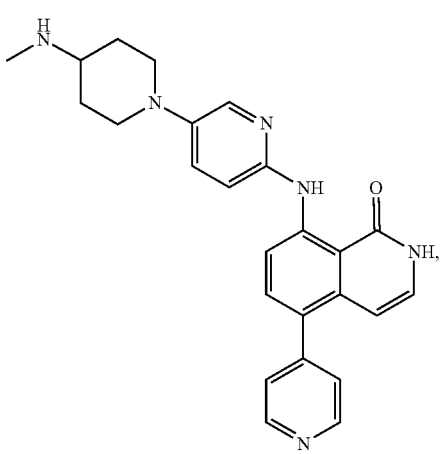
I-357
I-360
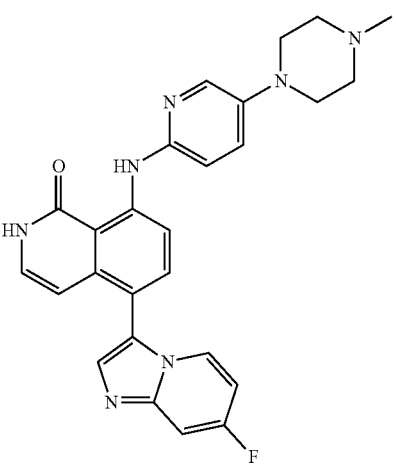

I-361
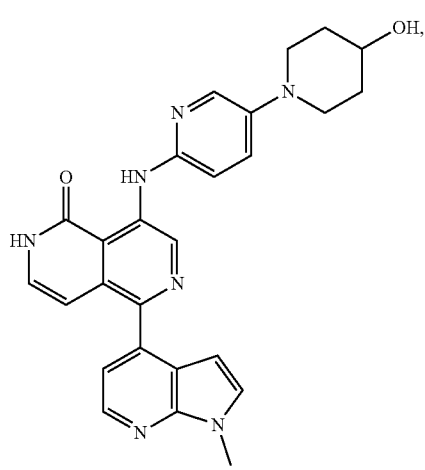
I-362
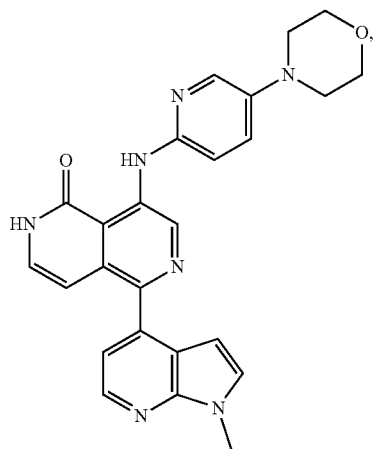
I-363
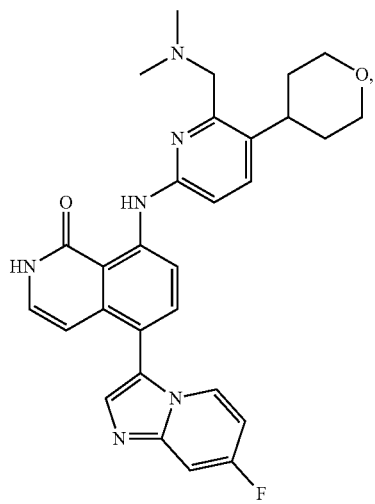
I-364
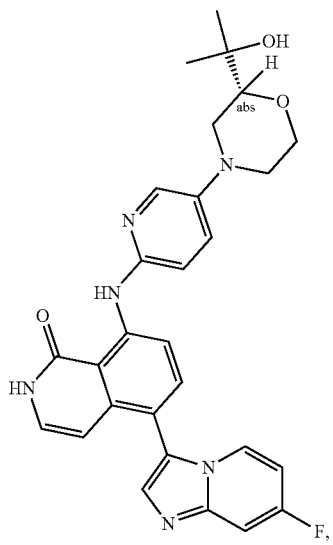
I-365
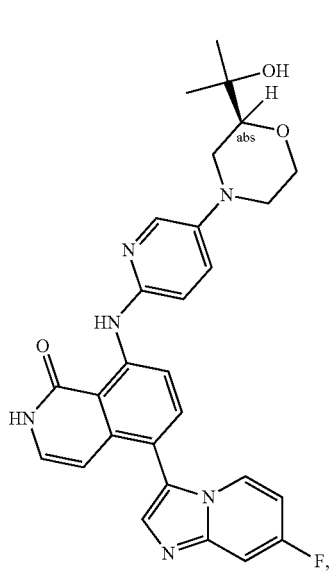
I-366
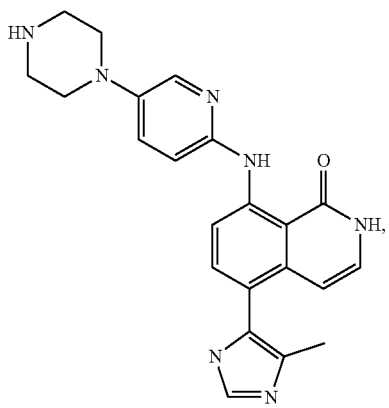

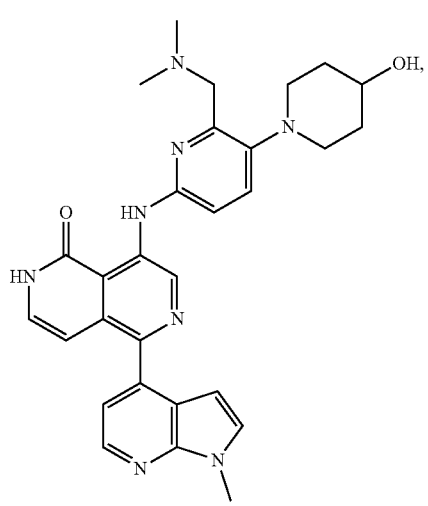

I-367

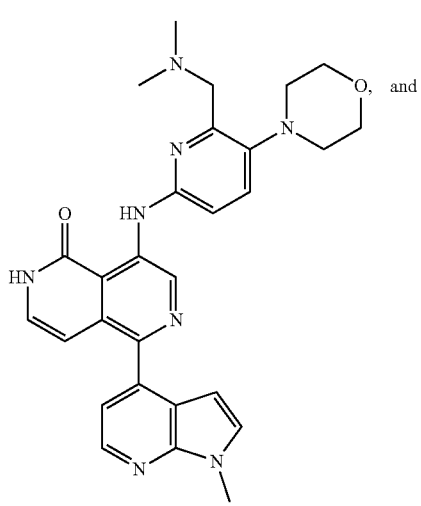

I-369

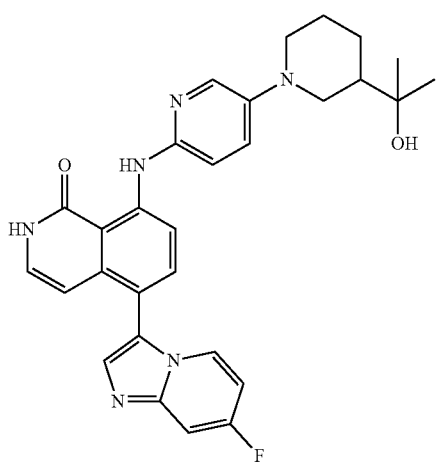

I-368

I-370 or a pharmaceutically acceptable salt thereof.

20. A pharmaceutical composition comprising a compound of claim 1, or a pharmaceutically acceptable salt thereof, and a pharmaceutically acceptable carrier, adjuvant, or vehicle.

21. A method of inhibiting HPK1 in a biological sample comprising contacting the sample with the compound of claim 1, or a pharmaceutically acceptable salt thereof, or a pharmaceutical composition thereof.

22. A method of treating an HPK1-mediated disorder, disease, or condition in a patient comprising administering to said patient the compound of claim 1, or a pharmaceutically acceptable salt thereof, or a pharmaceutical composition thereof.

* * * * *